(12) United States Patent
Scanlan et al.

(10) Patent No.: US 6,266,622 B1
(45) Date of Patent: Jul. 24, 2001

(54) NUCLEAR RECEPTOR LIGANDS AND LIGAND BINDING DOMAINS

(75) Inventors: Thomas S. Scanlan; John D. Baxter; Robert J. Fletterick; Richard L. Wagner; Peter J. Kushner, all of San Francisco; James J. Apriletti, Berkeley; Brian L. West, San Francisco; Andrew K. Shiau, San Francisco, all of CA (US)

(73) Assignee: Regents of the University of California, Oakland, CA (US)

(*) Notice: Subject to any disclaimer, the term of this patent is extended or adjusted under 35 U.S.C. 154(b) by 0 days.

(21) Appl. No.: 08/980,115

(22) Filed: Nov. 26, 1997

Related U.S. Application Data

(63) Continuation-in-part of application No. 08/764,870, filed on Dec. 13, 1996.
(60) Provisional application No. 60/008,540, filed on Dec. 13, 1995, provisional application No. 60/008,543, filed on Dec. 13, 1995, and provisional application No. 60/008,606, filed on Dec. 14, 1995.

(51) Int. Cl.[7] ............................ G06F 19/00; G06F 17/00; C07G 14/00
(52) U.S. Cl. ............................... 702/22; 702/19; 702/20; 530/350
(58) Field of Search .................................. 702/19, 21, 22; 530/350

(56) References Cited

U.S. PATENT DOCUMENTS

| | | | |
|---|---|---|---|
| 4,741,897 | * 5/1988 | Andrews et al. | 424/1.1 |
| 4,766,121 | * 8/1988 | Ellis et al. | 514/247 |
| 4,826,876 | * 5/1989 | Ellis et al. | 514/535 |
| 4,910,305 | * 3/1990 | Ellis et al. | 544/239 |
| 5,061,798 | * 10/1991 | Emmett et al. | 544/239 |
| 5,116,828 | * 5/1992 | Miura et al. | 514/171 |
| 5,171,671 | * 12/1992 | Evans et al. | 435/69.1 |
| 5,284,999 | * 2/1994 | Chin et al. | 435/252.3 |
| 5,312,732 | * 5/1994 | Evans | 435/69.1 |
| 5,322,933 | * 6/1994 | Davies et al. | 530/399 |
| 5,403,925 | * 4/1995 | Ozato | 536/23.5 |
| 5,438,126 | * 8/1995 | DeGroot et al. | 536/23.5 |
| 5,463,564 | * 10/1995 | Agrafiotis et al. | 364/496 |
| 5,466,861 | * 11/1995 | Dawson et al. | 560/100 |

FOREIGN PATENT DOCUMENTS

| | | | |
|---|---|---|---|
| 335628 | * 4/1989 | (EP) | . |
| WO 97/21993 | * 6/1997 | (WO) | . |
| WO 98/07435 | * 2/1998 | (WO) | . |
| WO 98/57919 | * 12/1998 | (WO) | . |

OTHER PUBLICATIONS

Andrea, T.A., et al., "A Model for Thyroid Hormone–Receptor Interactions", *J. Med.Chem.*, vol.22:221–232 (1979).*

Apriletti, J.W., et al., "Expression of the Rat α1 Thyroid Hormone Receptor Ligand Binding Domain in *Escherichia coli* and the Use of a Ligand–Induced Conformation Change as a Method for its Purification to Homogeneity", *Protein Expression and Purification*, vol.6:363–370 (1995).*

Apriletti, J.W., et al., "Large Scale Purification of the Nuclear Thyroid Hormone Receptor From Rat Liver and Sequence–specific Binding of the Receptor to DNA", *J. Biol.Chem.*, vol.263:9409–9417 (1988).*

Au–Fliegner, et al., "The Conserved Ninth C–Terminal Heptad in Thyroid Hormone and Retinoic Acid Receptors Mediates Diverse Responses by Affecting Heterodimer but Not Homodimer Formation", *Mol.Cell Biol.*, vol.13:5725–5737 (1993).*

Baniahmad, A., et al., "The τ4 Activation Domain of the Thyroid Hormone Receptor is Required for Release of a Putative Corepressor(s) Necessary for Transcriptional Silencing", *Mol.Cell Biol.*, vol.15,:76–86 (1995).*

Barettino, D., et al., "Characterization of the Ligand–dependent Transactivation Domain of Thyroid Hormone Receptor", *Embo.J.*, vol.13:3039–3049 (1994).*

Barker, et al., "Thyroxine Antagonism by Partially Iodinated Thyronines and Analogues", *Ann.N.Y.Acad.Sci.*, vol.86:545–562 (1960).*

Beck–Peccoz, P., et al., "Nomenclature of Thyroid Hormone Receptor β–Gene Mutations in Resistance to Thyroid Hormone: Consensus Statement from the First Workshop on Thyroid Hormone Resistance, Jul. 10–11, 1993 Cambridge, United Kingdom", *J.Clin.Endocrinol Metab.*, vol.78:990–993 (1994).*

Bhat, M.K., et al., "Interaction of Thyroid Hormone Nuclear Receptor With Antibody: Characterization of the Thyroid Hormone Binding Site", *Biochem.Biophys.Res.Commun.*, vol.210:464–471 (1995).*

Blake, C.C. & Oatley, S.J., "Protein–DNA and Protein–Hormone Interactions in prealbumin: a Model of the Thyroid Hormone Nuclear Receptor?", *Nature*, vol.268:115–120 (1977).*

Blake, C.C., et al., "Structure of Prealbumin: Secondary, Tertiary and Quarternary Interactions Determined by Fourier Refinement at 1 8 A", *J.Mol.Biol.*, vol.121:339–356 (1978).*

(List continued on next page.)

*Primary Examiner*—Elizabeth Kemmerer
*Assistant Examiner*—Nirmal S. Basi
(74) *Attorney, Agent, or Firm*—Cooley Godward LLP

(57) ABSTRACT

The present invention provides new methods, particularly computational methods, and compositions for the generation of nuclear receptor synthetic ligands based on the three dimensional structure of nuclear receptors, particularly the thyroid receptor (herein referred to as "TR"). Also provided are crystals, nuclear receptor synthetic ligands, and related methods.

28 Claims, 50 Drawing Sheets

(4 of 50 Drawing Sheet(s) Filed in Color)

OTHER PUBLICATIONS

Bourguet, W., et al., "Crystal Structure of the Ligand–Binding Domain of the Human Nuclear Receptor RXR–α", *Nature*, vol.375:377–382 (1995).*

Brent, G.A., "The Molecular Basis of Thyroid Hormone Action", *N.Engl.J.Med.*, vol.331:847–853 (1994).*

Brunger, A.T., et al., "Crystallographic R Factor Refinement by Molecular Dynamics", *Science*, vol.235:458–460 (1987).*

Casanova, J., et al., "Functional Evidence for Ligand–Dependent Dissociation of Thyroid Hormone and Retinoic Acid Receptors from an Inhibitory Cellular Factor", *Mol. Cell.Biol.*, vol.14:5756–5765 (1994).*

Cavailles, V. et al., "Nuclear Factor RIP140 Modulates Transcriptional Activation by the Estrogen Receptor", *Embo, J.*, vol.14:3741–3751 (1995).*

Chang, K.H., et al., "A Thyroid hormone receptor coativator negatively regulated by the retinoblastoma protein," *Proc. Natl.Acad.Sci.USA*, vol. 94(17):9040–9045 (1997).*

Collaborative Computational Project, N. 4., "The CCP4 Suite: Programs for Protein Crystallography", *Acta Crystallogr.*, vol.D50:760–763 (1994).*

Collingwood, T.N., et al., "Spectrum of Transcriptional, Dimerization, and Dominant Negative Properties of Twenty Different Mutant Thyroid Hormone β–Receptors Thyroid Hormone Resistance Syndrome", *Mol.Endocrinol.*, vol.8:1262–1277 (1994).*

Cowan, S.W., et al., "Improved Methods for Building Protein Models in Electron Density Maps and the Location of Errors in These Models", *Acta Crystallogr A*, vol.47:110–119 (1991).*

Cowtan, K., *Joint CCP4 and ESF–EACBM Newsletter on Protein Crystallography*, vol.31:34–38 (1994).*

Crowe et al., "6xHis–Ni–NTA Chromatography as a Superior Technique in Recombinant Protein Expression/Purification" *Methods in Molecular Biology*, vol.31:371–387 (1994).*

Damm, K. & Evans, R.M., "Identification of a Domain Required for Oncogenic Activity and Transcription suppression by v–erbA and Thyroid–Hormone receptor α", *Proc. Natl.Acad.Sci.USA*, vol.90:10668–10672 (1993).*

Danielian, P.S., et al., "Identification of a Conserved Region Required for Hormone Dependent Transcriptional Activation by Steroid Hormone Receptors", *Embo.J.*, vol.11:1025–1033 (1992).*

Dietrich, S.W., et al., "Thyroxine Analogues. 23. Quantitative Structure–Activity Correlation Studies of in Vivo and in Vitro Thyromimetric Activities", *J. Med.Chem.*, vol.20:863–880 (1977).*

Durand, B., et al., "Activation Function 2 (AF–2) of Retinoic Acid Receptor and 9–cis Retinoic Acid Receptor: Presence of a Conserved Autonomous Constitutive Activating Domain and Influence of the Nature of the Response Element on AF–2 Activity", *Embo.J.*, vol.13:5370–5382 (1994).*

Evans, R.M., "The Steroid and Thyroid Hormone Receptor Superfamily", *Science*, vol. 240:889–895 (1988).*

Fawell, S.E. et al., "Characterization and Colocalization of Steroid Binding and Dimerization Activities in the Mouse Estrogen Receptor", *Cell*, vol.60:953–962 (1990).*

Forman, B.M. & Samuels, H.H., "Interactions Among a Subfamily of Nuclear Hormone Receptors: The Regulatory Zipper Model", *Mol.Endocrinol.*, vol.4:1293–1301 (1990).*

Gewirth, D.T. & Sigler, P.B., "The Basis for Half–Site Specificity Explored Through a Non–Cognate Steroid Receptor–DNA Complex", *Nature Structural Biology*, vol.2:386–394 (1995).*

Glass, C.K., "Differential Recognition of Target Genes by Nuclear Receptor Monomers, Dimers, and Heterodimers", *Enocr.Rev.*, vol.15:391–407 (1994).*

Hajduk et al., "Discovering High Affinity Ligands for Proteins," *Science*, vol.278:497–499 (1997).*

Hayashi, Y. et al., "Mutations of CpG Dinucleotides Located in the Triiodothyronine ($T_3$)–Binding Domain of the Thyroid hormone Receptor (TR)β Gene That Appears to be Devoid of Natural Mutations may not be Detected Because They are Unlikely to Produce the Clinical Phenotype of Resistance to Thyroid Hormone", *J.Clin.Invest.*, vol.94:607–615 (1994).*

Heery, E., et al., "A signature motif in transcriptional co–activators mediates binding to nuclear receptors," *Nature*, vol.387:733–736 (1997).*

Hollenberg, et al., "Ligand–Independent and –Dependent Functions of Thyroid Hormone Receptor Isoforms Depend Upon Their Distinct Amino Termini", *J.Biol.Chem.*, vol.270(24):14274–14280 ((1995).*

Horwitz, K.B., "The Molecular Biology of RU486. Is There a Role for Antiprogestins in the Treatment for Breast Cancer?", *Endocrine Rev.*, vol.13:146–163 (1992).*

Jackson, R.C., "Contributions of protein structure–based drug design to cancer chemotherapy," *Seminars in Oncology*, vol.24(2)L164–172 (1997).*

Janknecht R., "Rapid and Efficient Purification of Native Histidine–Tagged Protein Expressed by Recombinant Vaccinia Virus", *Proc.Natl.Acad.Sci.USA*, vol.88:8972–8976 (1991).*

Jancarik & Kim, "Sparse Matrix Sampling: A Screening Method for Crystallization of Proteins", *J.Appl.Crystallogr.*, vol.24:409–411 (1991).*

Jones, T.A. et al., "Improved Methods for Building Protein Models in Electron Density Maps and the Location of Errord in these Models," *ACTA Cryst*, vol.47:110–119 (1991).*

Jones, T.R., et al., "Structure–Based Deisgn of Lipophilic Quinazoline Inhibitors of Thymidylate Synthase," *J.Med. Chem.*, vol.39(4):904–917 (1996).*

Jorgenson, "Thyroid Hormones and Analogs in 6 Hormonal Proteins and Peptides" *Thyroid Hormones*, 150–151 (1978).*

Jorgensen, E.C., "Thyroid Hormones and Analogs. II. Structure–Activity Relationships" *Hormonal Peptides and Proteins*, (eds. Li, C.H.) 107–204 (Academic Press, New York, 1978).*

Kabsch, W.J., "Automatic Processing of Rotation Diffraction Data From Crystals of Initially Unknown Symmetry and Cell Constants", *Appl.Crystallogr.*, vol.26:795–800 (1993).*

Kabsch, W. & Sander, C., "Dictionary of Protein Secondary Structure: Pattern Recognition of Hydrogen–Bonded and Geometrical Features", *Biopolymers*, vol.22:2577–2637 (1983).*

Kakizawa, T., et al., "Ligand–dependent Heterodimerization of Thyroid Hormone Receptor and Retinoid X Receptor," *J.Biol.Chem.* vol.272(38):23799–23804 (1997).*

Kediel S., et al., "Different Agonist–and Antagonist–Induced Conformational Changes in Retinoic Acid Receptors Analyzed by Protease Mapping", *Mol.Cell.Biol.*, vol.14:287–298 (1994).*

Laskowski, R.A., et al., "Procheck: a Program to Check the Stereochemical Quality of Protein Structures", *J.Appl.Crystallogr.*, vol.26:283–291 (1993).*

Latham, K.R., et al., "Development of Support Matrices for Affinity Chromatography of Thyroid Hormone Receptors", *J.Biol.Chem.*, vol.256:12088–12093 (1991).*

Laudet, V., "Evolution of the Nuclear Receptor Gene Superfamily" *Embo.J.*, vol.11:1003–1013 (1992).*

LeDouarin, B., et al., "The N–Terminal Part of TIF1, a Putative Mediator of the Ligand–Dependent Activiation Function (AF–2) of Nuclear Receptors, is fused to B–raf in the Oncogenic Protein T18", *Embo.J.*, vol.14:2020–2033 (1995).*

Lee, J.W., "Interaction of Thyroid–Hormone Receptor With a Conserved Tanscriptional Mediator", *Nature*, vol.374:91–94 (1995).*

Lee, J.W., et al., "Two Classes of Proteins Dependent on Either the Presence or Absence of Thyroid Hormone for Interaction With the Thyroid Hormone Receptor", *Molec.Endocrinol.*, vol.9:243–254 (1995).*

Leeson, P.D., et al., "Selective Thyromimetics. Cardiac-Sparing Thyroid Hormone Analogues Containing 3'-Arylmethyl Substituents", *J.Med.Chem.*, vol.32:320–336 (1989).*

Leeson, P.D., et al., "Thyroid Hormone Analogues. Synthesis of 3'-Substituted 3,5–Diiodo–L–Thyronines and Quantitiative Structure–Activity Studies of in Vitro and in Vivo Thyromimetic Activities in Rat Liver and Heart", *J.Med.Chem.*, vol.31:37–54 (1987).*

Leitman, D.C., et al., "Identification of a Tumor Necrosis Factor–Responsive Element in the Tumor Necrosis Factor α Gene", *J.Biol.Chem.*, vol.266:9343 (1991).*

Leng, X., et al., "Ligand–Dependent Conformational Changes in Thyroid Hormone and Retinoic Acid Receptors are Potentially Enhanced by Heterodimerization With Retinoic X. Receptor", *J.Steroid Biochem. Molec.Biol.*, vol.46:643–661 (1993).*

Leng, X., et al., "Mouse Retinoid X Receptor Contains a Separable Ligand–Binding and Transactivation Domain in its E Region", *Mol.and Cellular Biol.*, vol.15:255–263 (1995).*

Lewis, N. and Wallbank, P., "Formation of Quinol Ethers Using (Diacetoxyiodo) Benzene", *Synthesis*, 1103 (1987).*

Lin, B.C., et al., "A Conformational Switch in Nuclear Hormone Receptors is Involved in Coupling Hormone Binding to Corepressor Release," *Mol.Cell.Biol.*, vol.17(10):6131–6138 (1997).*

Lin, K.H., et al., "An Essential Role of Domain D in the Hormone–Binding Activity of Human β1 Thyroid Hormone Nuclear Receptor", *Mol.Endocrinol.*, vol.5:485–492 (1991).*

Lleywegt, G.J. et al., "OOPS–a–daisy" *ESF/CCP4 Newsletter*, Jun. 30, 1994, pp. 20–24.*

Luisi, B.F., et al., "Crystallographic Analysis of the Interaction of the Glucocorticoid Receptor with DNA", *Nature*, vol.352:497–505 (1991).*

McGrath et al., "Rapid Preparation of Proteins for Crystallization Tials," *Biotechniques*, vol.7:246–247 (1989).*

McGrath, M.E., et al., "Preliminary Crystallographic Studies of the Ligand–Binding Domain of the Thyroid Hormone Receptor Complexed With Triiodothyronine", *J.Mol.Biol.*, vol.237:236–239 (1994).*

McRee et al., *Practical Protein Crystallography*, Academic Press, N.Y., Chapters 1, 2 and 3 (1993).*

Meier, C.A., et al., "Variable Transcriptional Activity and Ligand Binding of Mutant β1 3,5,3'–Triiodothyronine Receptors From Four Families With Generalized Resistance to Thyroid Hormone", *Mol.Endocrinol.*, vol.6:248–258 (1992).*

Monaco, Hugo et al., "Structure of a Complex of Two Plasma Proteins: Transthyretin and Retinol–Binding Protein", *Science*, vol.268:1039–1041 (1995).*

Murshudov, et al., "Application of Maximum Likelihood Methods for Macromolecular Refinements," *Refinement of Protein Structures*, Proceedings of Daresbury Study Weekend, pp. 1–12 (1996).*

Navaza, J., "AmoRe: an Automated Package for Molecular Replacement", *Acta Crytallographica Section A—Fundamentals of Crystallography*, vol.50:157–63 (1994).*

Nicholls, A., et al., "Protein Folding and Association: Insights From the Interfacial and Thermodynamic Properties of Hydrocarbons", *Proteins*, vol.11:281–296 (1991).*

O'Donnell, A.L. et al. "Thyroid Hormone Receptor Mutations That Interfere With Transcriptional Activation Also Interface With Receptor", *Mol.Endocrinol.*, vol.5:94–99 (1991).*

Onate, S.A., et al., "Sequence and Characterization of a Coactivator for the Steroid Hormone Receptor Superfamily", *Science*, vol.270:1354–1357.*

Otwinoski, Z., "Oscillation Data Reduction Program", Proceedings of the CCP4 Study Weekend: Data Collection and Processing, 56–62 (1993).*

Otwinoski, Z., "Maximum Likelihood Refinement of Heavy Atom Parameters", Proceedings of the CCP4 Study Weekend:80–86 (1991).*

Rastinejad, R., et al., "Structural Determinants of Nuclear Receptor Assembly on DNA Direct Repeats", *Nature*, vol.375:203–211 (1995).*

Raynaud J.P. et al., "The Design and use of Sex–Steroid Antagonist", *J.Steroid Biochem.*, vol.25:811–833 (1986).*

Refetoff, S., et al., "The Syndromes of Resistance to Thyroid Hormone", *Endocr.Rev.*, vol.14:348–399 (1993).*

Ribeiro, R.C.J., et al., "The Molecular Biology of Thyroid Hormone Action", *Ann.N.Y.Acad.Sci.*, vol.758:366–389 (1995).*

Ribeiro, R.C.J., et al., "Thyroid Hormone Alters in Vitro DNA Binding of Monomers and Dimers of Thyroid Hormone Receptors", *Mol.Endocrinol.*, vol.6:1142–1152 (1992).*

Ribeiro, R.C.J., et al., "The Nuclear Hormone Receptor Gene Superfamily", *Annu.Rev.Med.*, vol.46:443–53 (1995).*

Robsseau, G.G., et al., "Glucocorticoid Receptors: Relations Between Steroid Binding and Biological Effects", *J.Mol.Biol.*, vol.67:99–115 (1972).*

Saatcioglu, F., et al., "A Conserved C–Terminal Sequence That is Deleted in v–ErbA is Essential for the Biological Activities of c–ErbA (the Thyroid Hormone Receptor)", *Mol.Cell Biol.*, vol.13:3675–3685 (1993).*

Schwabe, J.W., et al., "The Crystal Structure of the Estrogen Receptor DNA–Binding Domain Bound to DNA: How Receptors Discriminate Between Their Response Elements", *Cell*, vol.75:567–578 (1993).*

Seielstad, et al., "Molecular Characterization by Mass Spectrometry of the Human Estrogen Receptor Ligand–Binding Domain Expresses in *Escherichia coli*", *Molecular Endocrinology*, vol.9:647–658 (1995).*

Selmi, S. & Samuels, H.H., "Thyroid Hormone Receptor/and v–erbA", *J.Biol.Chem.*, vol.266:11589–11593 (1991).*

Shibata, H., et al., "Role of Co–activators and Co–repressors in the Mechanism of Steroid/Thyroid Receptor Action," *Recent Progress in Hormone Res.*, vol.52:141–164 (1997).*

Stephan et al., "Reduction of Cardiovascular and Thyroxine–Suppressing Activities of L–$T_3$ by Liver Targeting with Cholic Acid," *Biochem.Pharmacol.* vol.13:1969–1974 (1992).*

Swaffield, J.C., et al., "A Highly Conserved ATPase Protein as a Mediator Between Acidic Activation Domains and the TATA–Binding Protein", *Nature*, vol.374:88–91 (1995).*

Tagami, T., et al., "Nuclear Receptor Corepressors Activate Rather than Suppress Basal Transcription of Genes that are Negatively Regulated by Thyroid Hormone," *Mol.Cell. Biol.*, vol.17(5):2642–2648 (1997).*

Toney, J.H., et al., "Conformational Changes in Chicken Thyroid Hormone Receptor α1 Induced by Binding to Ligand or to DNA", *Biochemistry*, vol.32:2–6 (1993).*

Tsai, M.J. & O'Malley, B.W., "Molecular Mechanisms of Action of Steroid/Thyroid Receptor Superfamily Members", *Annu.Rev.Biochem.*, vol.63:451–486 (1994).*

Wagner, et al., "A Structural Role for Hormone in the Thyroid Hormone Receptor", *Nature*, vol.378(6558):670–697 (1995).*

Westerfield, W.W., et al., "New Assay Procedure for Thyroxine Analogs", *Endocrinolgoy*, vol.77:802 (1965).*

Yokoyama et al., "Synthesis and Structure–Activity Relationships of Oxamic Acid and Acetic Acid Derivatives Related to L–Thyronine", *J.Med.Chem.*, vol.38:695–707 (1995).*

Zenkie, M., et al., "v–erbA Oncogene Activation Entails the Loss of Hormone–Dependent Regulator Activity of c–erbA", *Cell*, vol.61:1035–1049 (1990).*

Zhu, XG., et al., "The Differentiation Hormone–dependent Transcriptional Activation of Thyroid Hormone Receptor Isoforms is Mediated by Interplay of their Domains," *J.Biol.Chem.*, vol.272(14):9048–9054 (1997).*

Bolger et al., "Molecular Interactions between Thyroid Hormone Analogs and the Rat Liver Nuclear Receptor," *Journal of Biological Chemistry*, 255(21):10271–10278, (1980).*

Chiellini, et al., "A High–Affinity Subtype–Selective Agonist for the Thyroid Hormone Receptor," *Chemistry and Biology*, 5(6):299–306, (1998).*

Jorgenson et al., "The Nature of the Thyroid Hormone Receptor," *Thyroid Research*, 378:303–306, (1976).*

Ribeiro et al., "Mechanism of Thyroid Hormone Action: Insights from X–ray Crystallographic and Functional Studies," *Recent Progress in Hormone Research*, 53:351–394, (1998).*

* cited by examiner

FIG.1

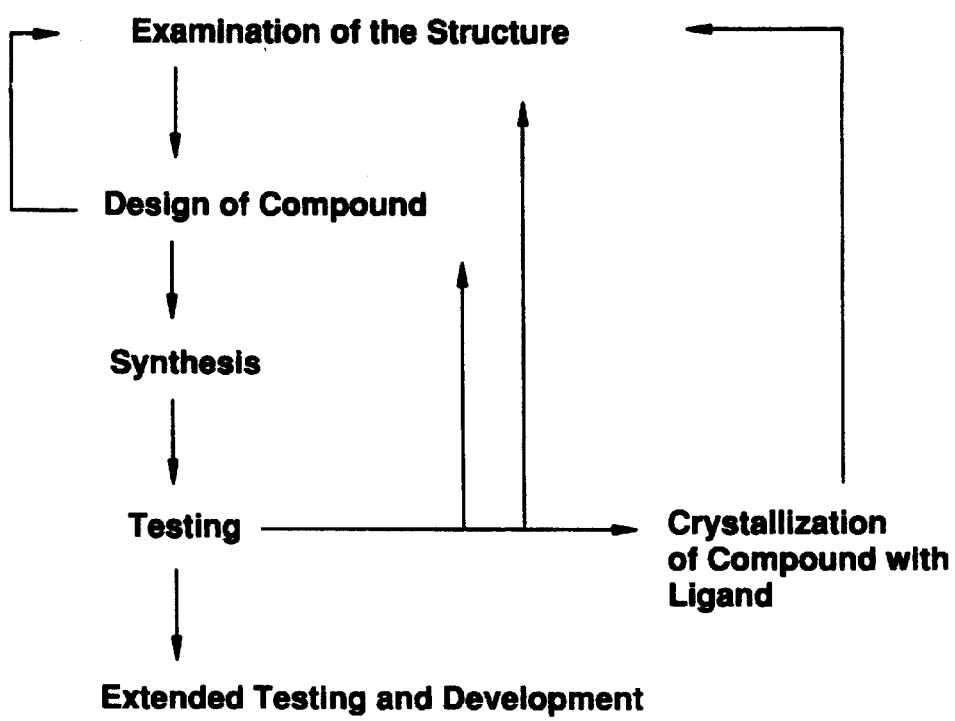

Examination of the Structure → Design of Compound → Synthesis → Testing → Extended Testing and Development Testing → Crystallization of Compound with Ligand → Examination of the Structure

FIG.2

| DOMAINS: | NH$_2$- TERMINAL | DNA BINDING | LIGAND BINDING |
|---|---|---|---|
| HOMOLOGY: | Hypervariable | > 40% | About 20% |
| FUNCTION: | Transactivation | DNA Binding<br>Dimerization | LIGAND Binding<br>Dimerization<br>Transactivation<br>Nuclear translocation<br>Hsp binding |

```
              1                                                              60
rTRalpha      ............ ............ ............ ............ ............
hTRalpha      ............ ............ ............ ............ ............
hTRbeta       ............ ............ ............ ............ ............
hRARalpha     ............ ............ ............ ............ ............
hRARgamma     ............ ............ ............ ............ ............
hRXRalpha     ............ ............ ............ ............ ............
hRXRbeta      ............ ............ ............ ............ ............
hPPARalpha    ............ ............ ............ ............ ............
hPPARbeta     ............ ............ ............ ............ ............
hPPARgamma    ............ ............ ............ ............ ............
hVDR          ............ ............ ............ ............ ............
hER           ............ ............ ............ ............ ............
hGR           ............ ............ ............ ............ ............
hPR           MTELKAKGPR  APHVAGGPPS  PEVGSPLLCR  PAAGPFPGSQ  TSDTLPEVSA  IPISLDGLLF
hMR           ...METKGYH  SLPEGLDMER  RWGQVSQAVE  RSSLGPTERT  DENNYMEIVN  VSCVSGAIPN
hAR           ............ ............ ............ ............ ............
```

FIG.3A

```
                61                                                              120
rTRalpha        ............ ............ ............ ............ ............
hTRalpha        ............ ............ ............ ............ ............
hTRbeta         ............ ............ ............ ............ ............
hRARalpha       ............ ............ ............ ............ ............
hRARgamma       ............ ............ ............ ............ ............
hRXRalpha       ............ ............ ............ ............ ............
hRXRbeta        ............ ............ ............ ............ ............
hPPARalpha      ............ ............ ............ ............ ............
hPPARbeta       ............ ............ ............ ............ ............
hPPARgamma      ............ ............ ............ ............ ............
hVDR            ............ ............ ............ ............ ............
hER             ............ ............ ............ ............ ............
hGR             ............ .....MDSKE   SLTPGREENP   SSVLAQERGD   VMDFYKTLRG
hPR             PRPCQGQDPS   DEKTQDQQSL   SDVEGAYSRA   EATRGAGGSS   SSPPEKDSGL LDSVLDTLLA
hMR             NSTQGSSKEK   QELLPCLQQD   NNRPGILTSD   IKTELESKEL   SATVAESMGL YHDSVRDADY
hAR             ............ ............ ............ ............ ............

FIG.3B
```

```
             121                                                                                         180
rTRalpha     ............ ............ ............ ............ ............ .............
hTRalpha     ............ ............ ............ ............ ............ .............
hTRbeta      ............ ............ ............ ............ ............ .............
hRARalpha    ............ ............ ............ ............ ............ .............
hRARgamma    ............ ............ ............ ............ ............ .............
hRXRalpha    ............ ............ ............ ............ ............ .............
hRXRbeta     ............ ............ ............ ............ ............ .............
hPPARalpha   ............ ............ ............ ............ ............ .............
hPPARbeta    ............ ............ ............ ............ ............ .............
hPPARgamma   ............ ............ ............ ............ ............ .............
hVDR         ............ ............ ............ ............ ............ .............
hER          ............ ............ ............ ............ ............ .............
hGR          GATVKVSASS   PSLAVASQS.   ..........   ..........   ..........   .............
hPR          PSGPGQSQPS   PPACEVTSSW   CLFGPELPED   PPAAPATQRV   .DSKQRRLLV   DFPKGSVSNA
hMR          SYEQQNQQGS   MSPAKIYQNV   EQLVKFYKGN   GHRPSTLSCV   NTPL..RSFM   SDSGSSVNGG
hAR          ............ ............ ............ ............ ............ .............
```

FIG. 3C

| | 181 | | | | 240 |
|---|---|---|---|---|---|
| rTRalpha | | | | | |
| hTRalpha | | | | | |
| hTRbeta | | | | | |
| hRARalpha | | | | | |
| hRARgamma | | | | | |
| hRXRalpha | | | | | |
| hRXRbeta | | | | | |
| hPPARalpha | | | | | |
| hPPARbeta | | | | | |
| hPPARgamma | | | | | |
| hVDR | | | | | |
| hER | ........ | ........ | ........ | SGETDLKLLE | ESIANLNRS. |
| hGR | QQPDLSKAVS | LSMGLYMGET | ETKVMGNDLG | FPQQGQISLS | |
| hPR | AHKVLPRGLS | PARQLLLPAS | ESPHWSGAPV | KPSPQAAAVE | VEEEDSSESE |
| hMR | VHRAIVK..S | PIMCHEKSPS | VCSPLNMTSS | VCSPAGINSV | SSTTASFGSF |
| hAR | | | | | |

| | | |
|---|---|---|
| | | |
| | | |
| | | |
| | | |
| | | |
| | | |
| | | |
| | | |
| | | |
| | | |
| | | |
| | | |
| | | |
| ESAGPLLKGK | | |
| PVHSPITQGT | | |
| | | |

FIG.3D

```
            241                                                              300
rTRalpha    ............ .......... .......... .......... .......... ..........
hTRalpha    ............ .......... .......... .......... .......... ..........
hTRbeta     ............ .......... .......... .......... .......... ..........
hRARalpha   ............ .......... .......... .......... .......... ..........
hRARgamma   ............ .......... .......... .......... .......... ..........
hRXRalpha   ............ .......... .......... .......... .......... ..........
hRXRbeta    ............ .......... .......... .......... .......... ..........
hPPARalpha  ............ .......... .......... .......... .......... ..........
hPPARbeta   ............ .......... .......... .......... .......... ..........
hPPARgamma  ............ .......... .......... .......... .......... ..........
hVDR        ............ .......... .......... .......... .......... ..........
hER         ............ .......... .......... .......... .......... ..........
hGR         ...TSVPEN    PKSSASTAVS AAPTEKEFPK THSDVSSEQQ HLKGQTGTNG GNVKLYTT..
hPR         PRALGGAAAG   GGAAACPPGA AAGGVALVPK EDSRFSAPRV ALVEQDAPMA PGRSPLATTV
hMR         PLTCSPNAEN   RGSRSHSPAH ASNVGSPLSS PLSSMKSSIS SPPSHCSVKS PVSSPNNVTL
hAR         ............ .......... .......... .......... .......... ..........
```

FIG. 3E

```
             301                                                         360
rTRalpha     ..........  ..........  ..........  ..........  ..........  ..........
hTRalpha     ..........  ..........  ..........  ..........  ..........  ..........
hTRbeta      ..........  ..........  ..........  ..........  ..........  ..........
hRARalpha    ..........  ..........  ..........  ..........  ..........  ..........
hRARgamma    ..........  ..........  ..........  ..........  ..........  ..........
hRXRalpha    ..........  ..........  ..........  ..........  ..........  ..........
hRXRbeta     ..........  ..........  ..........  ..........  ..........  ..........
hPPARalpha   ..........  ..........  ..........  ..........  ..........  ..........
hPPARbeta    ..........  ..........  ..........  ..........  ..........  ..........
hPPARgamma   ..........  ..........  ..........  ..........  ..........  ..........
hVDR         ..........  ..........  ..........  ..........  ..........  ..........
hER          ..........  ......DQST  FDILQDLEFS  SGSPGK....  ..........  ..........
hGR          ..........  ..........  ..........  ..........  ....ET  NESPWRSDLL
hPR          MDFIHVPILP  LNHALLAART  RQLLEDESYD  GGAGAA....  ......SA  FAPPRTSPCA
hMR          RSSVSSPANI  NNSRCSVSSP  SNTNNRSTLS  SPAASTVGSI  CSPVNNAFSY  TASGTSAGSS
hAR          ..........  ..........  ..........  ..........  ..........  ..........
```

FIG. 3F

```
                361                                                                                   420
rTRalpha        ....... .......... .......... .......... .......... .......... ..........
hTRalpha        ....... .......... .......... .......... .......... .......... ..........
hTRbeta         ....... .......... .......... .......... .......... .......... ..........
hRARalpha       ....... .......... .......... .......... .......... .......... ..........
hRARgamma       ....... .......... .......... .......... .......... .......... ..........
hRXRalpha       ....... .......... .......... .......... .......... .......... ..........
hRXRbeta        ....... .......... .......... .......... .......... ...MSW AARPPFLPQR HAEGSVGRWG
hPPARalpha      ....... .......... .......... .......... .......... .......... ..........
hPPARbeta       ....... .......... .......... .......... .......... .......... ..........
hPPARgamma      ....... .......... .......... .......... .......... .......... ..........
hVDR            ....... .......... .......... .......... .......... .......... ..........
hER             ....... .......... .......... .......... .......... .......... .......MTM
hGR             IDENCLLSPL AGEDDSFLLE GNSNEDCKPL ILPDTKPKIK DNGDLVLSSP SNVTLPQVKT
hPR             SSTPVAVGDF P..DCAYPPD AEPKDDAYPL YSDFQPPALK IKEEEGAEA SARSPRSYLV
hMR             TLRDVVPSPD TQEKGAQEVP FPKTEEVESA ISNGVTGQLN IVQYIKPEPD GAFSSSCLGG
hAR             ....... .......... .......... .......... .......... .......... ..........
```

FIG. 3G

```
              421                                                                                    480
rTRalpha      ..........  ..........  ..........  ..........  ..........  ..........  ..........  ..........
hTRalpha      ..........  ..........  ..........  ..........  ..........  ..........  ..........  ..........
hTRbeta       ..........  ..........  ..........  ..........  ..........  ..........  ..........  ..........
hRARalpha     ..........  ..........  ..........  ..........  ..........  ..........  ..........  ..........
hRARgamma     ..........  ..........  ..........  ..........  ..........  MDTKHFLPLD  FSTQVNSS..  ..........
hRXRalpha     .......M    AKECIVGSAT  ALAGSRSGGG  GGGGRRRTTN  PGAGARGWTG  RDGRH..GRD  SRSPDSSSPN  ..........
hRXRbeta      ..........  ..........  ..........  ..........  ..........  ..........  ..........  ..........
hPPARalpha    ..........  ..........  ..........  ..........  ..........  ..........  ..........  ..........
hPPARbeta     ..........  ..........  ..........  ..........  ..........  ..........  ..........  ..........
hPPARgamma    ..........  ..........  ..........  ..........  ..........  ..........  ..........  ..........
hVDR          .......M    DTEDLPANNA  PLTVNEQLLG  SCTLKFPAQD  AQVIVMSGQE  TIRVLEVEVD  ..........  ..........
hER           TLHTKASGMA  LLHQIQGNEL  EPLNRPQLKI  PLERPLGEVY  LDSSKPAVYN  YPEGAAYEFN  ..........  ..........
hGR           EKEDFIELCT  PGVIKQEKLG  TVYCQASFPG  ANIIG.....  ....NK      MSAISVHGVS  ..........  ..........
hPR           AGANPAAFPD  FPLGPPPPLP  PR.ATPSRPG  EAAVT.....  ......AA    PASASVSSAS  ..........  ..........
hMR           NSKINSDSSF  SVPIKQESTK  HSCSGTSFKG  NPTVNPFPFM  DGSYFSFMDD  KDYYSLSGIL  ..........  ..........
hAR           ..........  ..........  ......GG    GGGEA.....  ......GA    VAPYGYTRP.  ..........  ..........
```

FIG.3H

```
            481                                                         540
rTRalpha    ........... ........... ........... ........... ...........
hTRalpha    ........... ........... ........... ...MEQKPSK  VECGSDPEEN
hTRbeta     ........... ........... ........... ...MEQKPSK  VECGSDPEEN
hRARalpha   ........... ........... ..MTPNSMTE  NGLTAWDKPK  HCPDREHDWK  LVGMSEACLH
hRARgamma   ........... ........... ........... ........... ...........
hRXRalpha   .LTSPTGR.. GSMAAPSLHP  SLGPGIGSPG  .QLHSPISTL  SSPINGMGPP  FSVISSPMGP
hRXRbeta    PLPQGVPP.. PSPPGPPLPP  STAPTLGGSG  .APPPP....  PMPPPPLGSP  FPVISSSMGS
hPPARalpha  ..MVDTESPL CPLSPLEAGD  LESPLSEEFL  QEMGNIQEIS  QSIGEDSSGS  FGFTEYQYLG
hPPARbeta   ........... ...MEQPQ   EEAP......  .EVREEEEKE  EVAEAEGAPE  LNGGPQHALP
hPPARgamma  ........... ....MVD    TEMPFWPTNF  ....GISSVD  LSMMDDHSHS  FDIKPFTTVD
hVDR        TALSSAGAAE  SGGDEEGSGQ SLEATEEAQL  DGPVTTSSTT  AVTVEVSAPV  VQTVVSKAAI    M  ATNKERLFAA  GALGPGSGYP
hER         AAAAANAQVY  GQTGLPYGPG SEAAAFGSNG  LGGFPPLNSV  SPSPLMLLHP  PPQLSPFLQP
hGR         TSGGQMYHYD  MNTASLSQQQ DQ........  .KPIFNVIPP  IPVGSEN...  ...........
hPR         SSGSTLECIL  YKAEGAPPQQ GPFAPPPCKA  PGASGCLLPR  DGLPSTS...  ...........
hMR         GPPVPGFDGN  CEGSGFPVGI KQEPDDGSYY  PEASIPSSAI  VGVNSGGQSF  HYRIGAQGTI
hAR         ..PQGLAGQE  SDFTAPDVWY PGG...MVSR  VPYPSPT...  ...........
```

FIG. 31

```
            541                                                         600
rTRalpha    SARSPDGKRK RKN.GQCP.. .....LKSSM .......... .......... .....SGYI
hTRalpha    SARSPDGKRK RKN.GQCS.. .....LKTSM .......... .......... .....SGYI
hTRbeta     RKSHSERRST LKN.EQSSPH LIQTTWTSSI FHLDHDDVND QSVSSAQTFQ TEEKKCKGYI
hRARalpha   .......... .......... .......PN SNHVASGAGE AAIETQSSSS EEIVPSPPSP
hRARgamma   GAGFPFAFPG ALR.GSPPFE MLSPSFRGLG QPDLPKEMAS LSVETQSTSS EEMVPSSPSP
hRXRalpha   HSMSVP.... .TTPTLGFST GSPQLSS... .PMNPVSSSE DIKPPLGLNG VLKVPAHPSG
hRXRbeta    PGLPPP.... .APPGFSGPV SSPQINSTVS LPGGGSGPPE DVKPPVLGVR GLHCPPPPGG
hPPARalpha  SCPGSDGSVI TDTLSPA... .......... .......... .SSPS..SVT YPVVPGSVDE
hPPARbeta   SSSYTD.... ...LSRS... .......... .......... .SSPP..SLL DQLQMGC.DG
hPPARgamma  FSSISAPHYE DIPFTRADPM VADYKYDLKL QEYQSAIKVE PASPPYYSEK AQLYNRPHEE
hVDR        SVSPAQQTSV PITVQACPQV LTQDGLASLM TGMLAQQSSL GQPLLIPLSM AGSVGQGGL
hER         HGQQVPYYLE NEPSGYTVRE AGPP....AF YRPNSDNRRQ GGRERLASTN DKGSMAMESA
hGR         ..WNRCQGSG DDNLTSLGTL NFPGRTVFSN GYSSPSMRPD V......... .SSPPSSSST
hPR         ..ASAAAGA APALYPALGL NGLPQLGYQA AVLKEGLPQV YPPYLNYLRP DSEASQSPQY
hMR         SLSRSARDQS FQHLSSFPPV NTLVESWKSH GDLSSRRSDG YPVLEYIPEN VSSSTLRSVS
hAR         ..CVKSEMGP WMDSYSG... .......PYGD MRLETARDHV LP..IDYYFP ..........
```

FIG. 3J

```
             601                                                              660
rTRalpha     PSYLDKDEQC VVCGDKATGY HYRCITCEGC KGFFRRTIQK NLHPTYSCKY DS..........
hTRalpha     PSYLDKDEQC VVCGDKATGY HYRCITCEGC KGFFRRTIQK NLHPTYSCKY DS..........
hTRbeta      PSYLDKDELC VVCGDKATGY HYRCITCEGC KGFFRRTIQK NLHPSYSCKY EG..........
hRARalpha    PPLPRIYKPC FVCQDKSSGY HYGVSACEGC KGFFRRSIQK NM..VYTCHR DK..........
hRARgamma    PPPPRVYKPC FVCNDKSSGY HYGVSSCEGC KGFFRRSIQK NM..VYTCHR DK..........
hRXRalpha    NMASFTKHIC AICGDRSSGK HYGVYSCEGC KGFFKRTVRK DL..TYTCRD NK..........
hRXRbeta     PGAG..KRLC AICGDRSSGK HYGVYSCEGC KGFFKRTIRK DL..TYSCRD NK..........
hPPARalpha   SPSGALNIEC RICGDKASGY HYGVHACEGC KGFFRRTIRL KLVYD...KC DR..........
hPPARbeta    ASCGSLNMEC RVCGDKASGF HYGVHACEGC KGFFRRTIRM KLEYE...KC ER..........
hPPARgamma   PSNSLMAIEC RVCGDKASGF HYGVHACEGC KGFFRRTIRL KLIYD...RC DL..........
hVDR         AVLTLPTATV ATLPGLAAAS PAGGLLKLPF AGLQAATVLN SVQTQLQAPA QAVLQPQMSA
hER          KET....RYC AVCNDYASGY HYGVWSCEGC KAFFKRSIQG HN..DYMCPA TN..........
hGR          ATTGPPPKLC LVCSDEASGC HYGVLTCGSC KVFFKRAVEG QHNYLCAGRN D...........
hPR          SFESLPQKIC LICGDEASGC HYGVLTCGSC KVFFKRAMEG QHNYLCAGRN D...........
hMR          TGSSRPSKIC LVCGDEASGC HYGVVTCGSC KVFFKRAVEG QHNYLCAGRN D...........
hAR          .....PQKTC LICGDKASGC HYGALTCGSC KVFFKRAAEG KQKYLCASRN D...........
```

FIG.3K

```
           661                                                          720
rTRalpha   .CCVIDKITR NQCQLCRFKK CIAVGMAMDL VLDDSKRVAK RKLIEQNRER RRK..EEMIR
hTRalpha   .CCVIDKITR NQCQLCRFKK CIAVGMAMDL VLDDSKRVAK RKLIEQNRER RRK..EEMIR
hTRbeta    .KCVIDKVTR NQCQECRFKK CIYVGMATDL VLDDSKRLAK RKLIEENREK RRR..EELQK
hRARalpha  .NCIINKVTR NRCQYCRLQK CFEVGMSKES VRND...... ......RNK KKK..EVPKP
hRARgamma  .NCIINKVTR NRCQYCRLQK CFEVGMSKEA VRND...... ......RNK KKK..EVKEE
hRXRalpha  .DCLIDKRQR NRCQYCRYQK CLAMGMKREA VQEERQRG.. ....KDRNEN EVE..STSSA
hRXRbeta   .DCTVDKRQR NRCQYCRYQK CLATGMKREA VQEERQRG.. ....KDK.DG DGE..CAGGA
hPPARalpha .SCKIQKKNR NKCQYCRFHK CLSVGMSHNA IRFG...... .RMPRSEKAK LKA..EILTC
hPPARbeta  .SCKIQKKNR NKCQYCRFQK CLALGMSHNA IRFG...... .RMPEAEKRK LVA..GLTAN
hPPARgamma .NCRIHKKSR NKCQYCRFQK CLAVGMSHNA IRFG...... .RMPQAEKEK LLA..EI.SS
hVDR       LQAMQQTQTT AATTASIVQK ASEPSVSVAT LQTAGLSINP AIISAASLGA QPQFISSLTT
hER        .QCTIDKNRR KSCQACRLRK CYEVGMMKGG IRKDRRGGRM LKHKRQRDDG EGR..GEVGS
hGR        ..CIIDKIRR KNCPACRYRK CLQAGMNLEA .......... RKTKK..KIK GIQ..QATT.
hPR        ..CIVDKIRR KNCPACRLRK CCQAGMVLGG .......... RKFKKFNKVR VVR..ALDAV
hMR        ..CIIDKIRR KNCPACRLQK CLQAGMNLGA .......... RKSKKLGKLK GIH..EEQPQ
hAR        ..CTIDKFRR KNCPSCRLRK CYEAGMTLGA .......... RKLKKLGNLK LQE..EGEAS

FIG.3L
```

```
           721  ┌─ minimal start site 725                                                              780
rTRalpha        SLQQRPEPTP EEWDLIHVAT EAHRSTNAQG SHWKQRRKFL PDDIGQSPIV ..........
hTRalpha        SLQQRPEPTP EEWDLIHIAT EAHRSTNAQG SHWKQRRKFL PDDIGQSPIV ..........
hTRbeta         SIGHKPEPTD EEWELIKTVT EAHVATNAQG SHWKQPKFL  PEDIGQAPIV ..........
hRARalpha       ECSESYTLTP EVGELIEKVR KAHQETFPAL CQL...GKYT TNNSSEQRV. ..........
hRARgamma       GSPDSYELSP QLEELITKVS KAHQETFPSL CQL...GKYT TNSSADHRV. ..........
hRXRalpha       NEDMPVERIL EAELAVEPKT ETYVE..ANM GLNPS..... ......SP.. ..........
hRXRbeta        PEEMPVDRIL EAELAVEQKS DQGVEGPGGT GGSGS..... ......SP.. ..........
hPPARalpha      EHDIEDSETA DLKSLAKRIY EAYLKNFN.M NKVKARVILS GKASNNPPFV IHDMETLCMA
hPPARbeta       EGSQYNPQVA DLKAFSKHIY NAYLKNFN.M TKKKARSILT GKASHTAPFV IHDIETLWQA
hPPARgamma      DIDQLNPESA DLRALAKHLY DSYIKSFP.L TKAKARAILT GKTTDKSPFV IYDMNSLMMG
hVDR            TPIITSAMSN VAGLTSQLIT NAQGVIGTL  PLLVNPASLA GAAAASA... ......LPA
hER             AGDHRAANLW PSPLMIKRSK KNSLALSLTA DQMVSALLDA EPPILYSE.. ..........
hGR             ...GVSQ    ETSENPGNKT IVPATLPQLT PTLVS..... .......... LL........
hPR             ALPQPLGVPN ESQALSQRFT FSPGQDIQLI PPLIN..... .......... LL........
hMR             QQQPPPPPP  PQSPEEGTTY IAPAKEPSVN TALVPQLSTI SRALTPSPVM VL........
hAR             STTSP..... .TEETTQKLT VSHIEGYECQ PIFLN..... .......... VL........
```

FIG. 3M

```
            781                                                            840
rTRalpha     ........ ........ ........ ........ ........ ........
hTRalpha     ........ ........ ........ ........ ........ ........
hTRbeta      ........ ........ ........ ........ ........ ........

hRARalpha    ........ .SMPDGDKVD LEAFSEFTKI ITPAITRVVD FAKKLPMFSE LPCEDQILL
hRARgamma    ........ .SMPDGDKVD LEAFSEFTKI ITPAITRVVD FAKKLPMFSE LPCEDQILL
hRXRalpha    ........ .NAPEGGKVD LEAFSHFTKI ITPAITRVVD FAKKLPMFCE LPCEDQILL
hRXRbeta     ........ ......SLD IDLWDKFSEL STKCIIKTVE FAKQLPGFTT LTIADQITLL
hPPARalpha   ........ ......QLD LGLWDKFSEL ATKCIIKIVE FAKRLPGFTG LSIADQITLL
hPPARbeta    ........ .NDPVTNICQ A........ ADKQLFTLVE WAKRIPHFSE LPLDDQVILL
hPPARgamma   ........ .NDPVTNICQ A........ ADKQLFTLVE WAKRIPHFSS LPLDDQVILL
hVDR         EKTLVAKLVA NGIQN.KEVE VRIFHCCQCT SVETVELTE FAKAIPAFAN LDLNDQVTLL
hER          EKGLVWKQLV NGLPPYKEIS VHVFYRCQCT TVETVRELTE FAKSIPSFSS LFLNDQVTLL
hGR          EDKIKFKHIT PLQEQSKEVA IRIFQGCQFR SVEAVQEITE YAKNIPGFIN LDLNDQVTLL
hPR          QGLQVQTVAP QLLLNSQGQI IATIGNGPTA AIPSTASVLP KATVPLTLTK TTTQGPVGKV
hMR          ........ .YDPTRPFSE ASMMGLLTNL ADRELVHMIN WAKRVPGFVD LTLHDQVHLL
hAR          EVIEPEVLYA GYDSSVPDST WRIMTTLNML GGRQVIAAVK WAKAIPGFRN LHLDDQMTLL
             MSIEPDVIYA GHDNTKPDTS SSLLTSLNQL GERQLLSVVK WSKSLPGFRN LHIDDQITLI
             ENIEPEIVYA GYDSSKPDTA ENLLSTLNRL AGKQMIQVVK WAKVLPGFKN LPLEDQITLI
             EAIEPGVVCA GHDNNQPDSF AALLSSLNEL GERQLVHVVK WAKALPGFRN LHVDDQMAVI
```

FIG.3N

```
            841                                             900
rTRalpha    KGCCMEIMSL RAAVRY..DP ESDTLTLSGE MTVKRKQLK. ..N..GGLGV VSDAIFELGK
hTRalpha    KGCCMEIMSL RAAVRY..DP ESDTLTLSGE MAVKREQLK. ..N..GGLGV VSDAIFELGK
hTRbeta     KGCCMEIMSL RAAVRY..DP ESETLTLNGE MAVIRGQLK. ..N..GGLGV VSDAIFDLGM
hRARalpha   KAACLDILIL RICTRY..TP EQDTMTFSDG LTLNRTQMH. ..N..AGFGP LTDLVFAFAN
hRARgamma   KAACLDILML RICTRY..TP EQDTMTFSDG LTLNRTQMH. ..N..AGFGP LTDLVFAFAG
hRXRalpha   RAGWNELLIA SFSHRS...IA VKDGILLATG LHVHRNSAH. ..S.AGVGAI FDRVLTELVS
hRXRbeta    RAGWNELLIA SFSHRS...ID VRDGILLATG LHVHRNSAH. ..S.AGVGAI FDRVLTELVS
hPPARalpha  KYGVYEAIFA MLSSVM..NK DGMLVAYGNG F.ITREFLK. ..SLRKPFCD IMEPKFDFAM
hPPARbeta   KYGVHEAIFA MLASIV..NK DGLLVANGSG F.VTREFLR. ..SLRKPFSD IIEPKFEFAV
hPPARgamma  KYGVHEIIYT MLASLM..NK DGVLISEGQG F.MTREFLK. ..SLRKPFGD FMEPKFEFAV
hVDR        APSKVIIAPQ PSVVKPVTSL TAAGVIACGE MPTVGQLVNK PSAVKDEEAI NLEEIREFAK
hER         ECAWLEILMI GLVWRS..ME HPGKLLFAPN LLLDRNQGK. ..CVEGMVEI FDMLLAT.SS
hGR         ALGWRSYRQS SANLLCFAPD LIINEQRMT. .....LPCHYD QCKHMLYVSS
hPR         QYSWMFLMAF GLGWRSYKHV SGQMLYFAPD LILNEQRMK. .....ESSFYS LCLTMWQIPQ
hMR         QYSWMCLSSF ALSWRSYKHT NSQFLYFAPD LVFNEEKMH. ....QSAMYE LCQGMHQISL
hAR         QYSWMGLMVF AMGWRSFTNV NSRMLYFAPD LVFNEYRMH. ....KSRMYS QCVRMRHLSQ
```

FIG. 30

```
            901                                                              960
rTRalpha    SLSAFNLDDT EVALLQAVLL MSTD...... ..RSGLLCVD KIEKSQEAYL LA...FEHYV
hTRalpha    SLSAFNLDDT EVALLQAVLL MSTD...... ..RSGLLCVD KIEKSQEAYL LA...FEHYV
hTRbeta     SLSSFNLDDT EVALLQAVLL MSSD...... ..RPGLACVE RIEKYQDSFL LA...FEHYI
hRARalpha   QLLPLEMDDA ETGILSAICL ICGD...... ..RQDLEQPD RVDMLQEPLL EA...LKVYV
hRARgamma   QLLPLEMDDT ETGLLSAICL ICGD...... ..RMDLEEPE KVDKLQEPLL EA...LRLYA
hRXRalpha   KMRDMQMDKT ELGCLRAIVL FNPDS..... ...KGLSNPA EVEALREKVY AS...LEAYC
hRXRbeta    KMRDMRMDKT ELGCLRAIIL FNPDA..... ...KGLSNPS EVEVLREKVY AS...LETYC
hPPARalpha  KFNALELDDS DISLFVAAII CCGD...... ..RPGLLNVG HIEKMQEGIV HV...LRLHL
hPPARbeta   KFNALELDDS DLALFIAAII LCGD...... ..RPGLMNVP RVEAIQDTIL RA...LEFHL
hPPARgamma  KFNALELDDS DLAIFIAVII LSGD...... ..RPGLLNVK PIEDIQDNLL QA...LELQL
hVDR        NFKIRRLSLG LTQTQVGQAL TATEGPAYSQ SAICRFEKLD ITPKSAQKLK PVLERWLAEA
hER         RFRMMNLQGE EFVCLKSIIL LNSGVYTFLS STLKSLEEKD HIHRVLDKIT DTLIHLMAKA
hGR         ELHRLQVSYE EYLCMKTLLL LSS....... .......... VPKDGLKSQE LFDEIRMTYI KELGKAIVKR
hPR         EFVKLQVSQE EFLCMKVLLL LNT....... .......... IPLEGLRSQT QFEEMRSSYI RELIKAIGLR
hMR         QFVRLQLTFE EYTIMKVLLL LST....... .......... IPKDGLKSQA AFEEMRTNYI KELRKMVTKC
hAR         EFGWLQITPQ EFLCMKALLL FSI....... .......... IPVDGLKNQK FFDELRMNYI KELDRIIACK
```

FIG.3P

```
            961                                                                    1020
rTRalpha    NHRKHNIPHF WPKLL.....M KVTDLRMIGA CHASRFL..H MKVEC..PTE LFPPLFLEVF
hTRalpha    NHRKHNIPHF WPKLL.....M KVTDLRMIGA CHASRFL..H MKVEC..PTE LFPPLFLEVF
hTRbeta     NYRKHHVTHF WPKLL.....M KVTDLRMIGA CHASRFL..H MKVEC..PTE LLPPLFLEVF
hRARalpha   RKRRPSRPHM FPKML.....M KITDLRSISA KGAERVI..T LKMEI..PGS M.PPLIQEML
hRARgamma   RRRRPSQPYM FPRML.....M KITDLRGIST KGAERAI..T LKMEI..PGP M.PPLIREML
hRXRalpha   KHKYPEQPGR FAKLL.....L RLPALRSIGL KCLEHLF..F FKL.I..GDT PIDTFLMEML
hRXRbeta    KQKYPEQQGR FAKLL.....L RLPALRSIGL KCLEHLF..F FKL.I..GDT PIDTFLMEML
hPPARalpha  QSNHPDDIFL FPKLL.....Q KMADLRQLVT EHAQLVQ..I IKKTE..SDA ALHPLLQEIY
hPPARbeta   QANHPDAQYL FPKLL.....Q KMADLRQLVT EHAQMMQ..R IKKTE..TET SLHPLLQEIY
hPPARgamma  KLNHPESSQL FAKVL.....Q KMTDLRQIVT EHVQLLH..V IKKTE..TDM SLHPLLQEIY
hVDR        ELWNQKGQQN LMEFVGGEPS KKRKRRTSFT PQAIEVLNTY FEKNSLPTGQ EITEIAKELN
hER         GLTLQQQHQR LAQLL.....L ILSHIRHMSN KGMEHLY..S MKC.K..NVV PLYDLLLEML
hGR         EGNSSQNWQR FYQLT.....K LLDSMHEVVE NLLNYCFQTF LD.KT..MSI EFPEMLAEII
hPR         QKGVVSSSQR FYQLT.....K LLDSMHDLVK QLHLYCLNTF IQSRA..LSV EFPEMMSEVI
hMR         PNNSGQSWQR FYQLT.....K LLDSMHDLVS DLLEFCFYTF RESHA..LKV EFPAMLVEII
hAR         RKNPTSCSRR FYQLT.....K LLDSVQPIAR ELHQFTFDLL IKSHM..VSV DFPEMMAEII
```

FIG. 3Q

|            | 1021       | minimal end site 1025 |            |            |            | 1071 |
|------------|------------|------------------------|------------|------------|------------|------|
| rTRalpha   | EDQEV      |            |            |            |            |      |
| hTRalpha   | EDQEV      |            |            |            |            |      |
| hTRbeta    | ED         |            |            |            |            |      |
| hRARalpha  | ENSEGLDTLS | GQPGGGGRDG | GGLAPPPGSC | SPSLSPSSNR | SSPATHSP   |      |
| hRARgamma  | ENPEMFEDDS | SQPGPHPNAS | SEDEVPGGQG | KGGLKSPA   |            |      |
| hRXRalpha  | EAPHQMT    |            |            |            |            |      |
| hRXRbeta   | EAPHQLA    |            |            |            |            |      |
| hPPARalpha | RDMY       |            |            |            |            |      |
| hPPARbeta  | KDMY       |            |            |            |            |      |
| hPPARgamma | KDLY       |            |            |            |            |      |
| hVDR       | YDREVVRVWF | CNRRQTLKNT | SKINVFQSQ  |            |            |      |
| hER        | DAHRLHAPTS | RGGASVEETD | QSHLATAGST | SSHSLQKYYI | TGEAEGFPAT | V    |
| hGR        | TNQIPKYSNG | NIKKLLFHQK |            |            |            |      |
| hPR        | AAQLPKILAG | MVKPLLFHKK |            |            |            |      |
| hMR        | SDQLPKVESG | NAKPLYFHRK |            |            |            |      |
| hAR        | SVQVPKILSG | KVKPIYFHTQ |            |            |            |      | socr:<5>

FIG.3R

AGONISTS
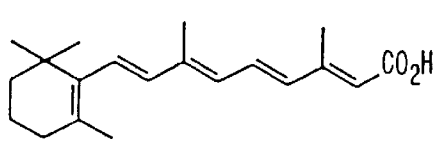
Retinoic Acid
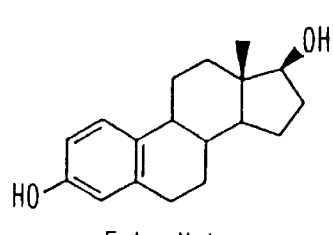
Estradiol
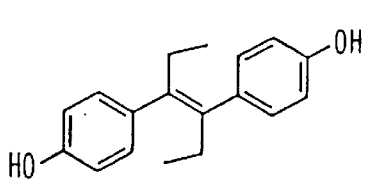
Diethylstilbestrol
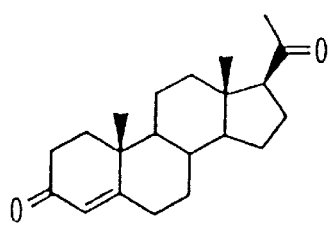
Progesterone
ANTAGONISTS
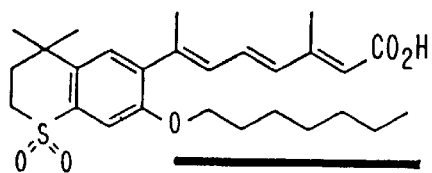
RO 46-8515
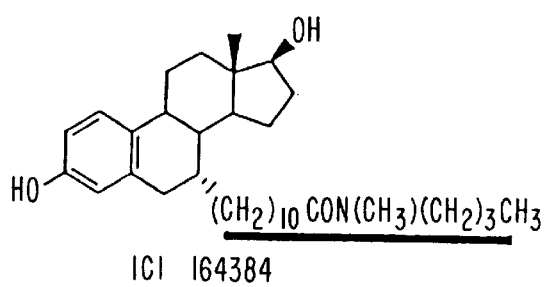
ICI 164384
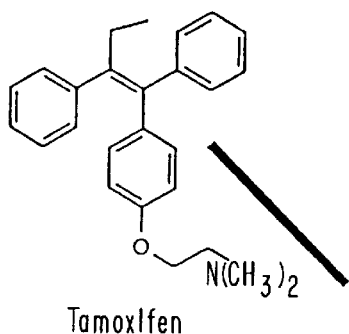
Tamoxifen
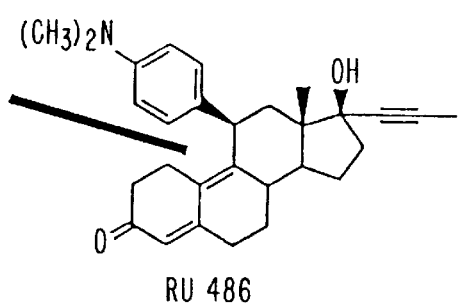
RU 486
FIG.10        ———  shows position of extension group

| Compound | RCOX |
|---|---|
| TS1 | Ph$_2$CHCO$_2$NHS |
| TS2 | C$_{16}$H$_{33}$CO$_2$NHS |
| TS3 | FMOC-Cl |
| TS4 | tBOC$_2$O |
| TS5 | tBOC$_2$O |

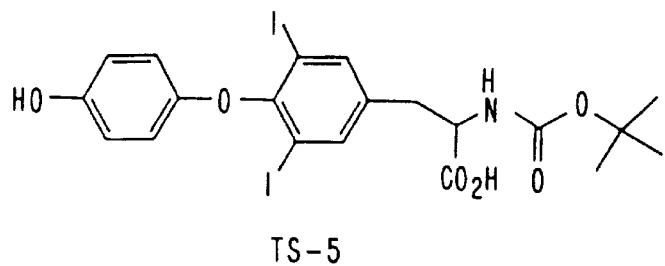
TS-5
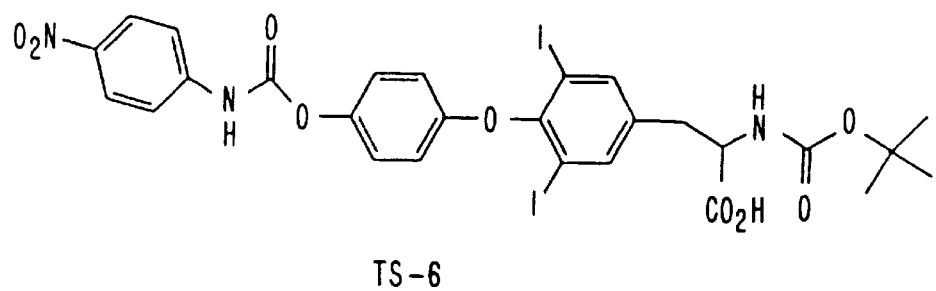
TS-6
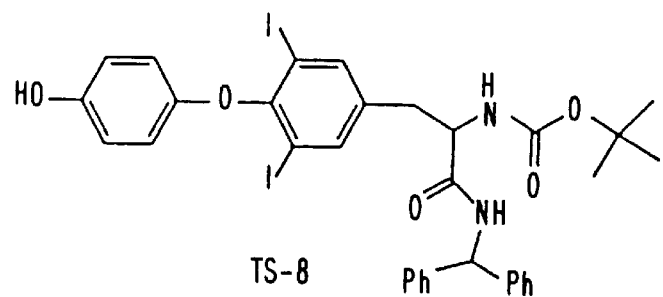
TS-8
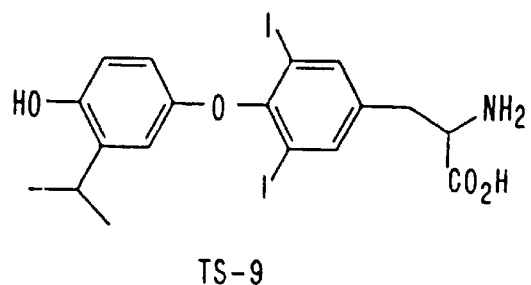
TS-9
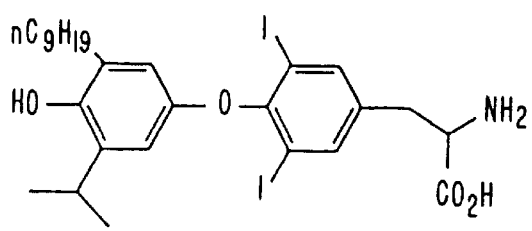
TS-10
FIG.15

Atomic Numbering for Thyronine-like Ligands
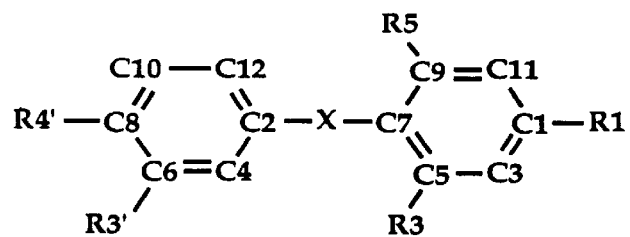
| Ligand | R1 | R3 | R5 | X | R3' | R4' |
|---|---|---|---|---|---|---|
| Dimit | amino propionic | C19 | C20 | O2 | iPr | O1 |
| IpBr$_2$ | amino propionic | BR1 | BR2 | O2 | iPr | O1 |
| T$_3$ | amino propionic | I1 | I3 | O2 | I2 | O1 |
| Triac | acetic acid | I1 | I3 | O2 | I2 | O1 |
| GC1 | oxyacetic acid | C19 | C20 | C21 | iPr | O1 |
amino propionic acid
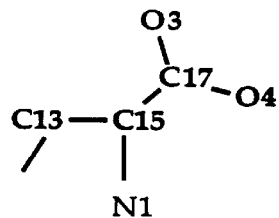
acetic acid
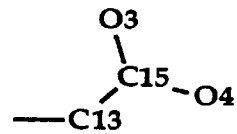
oxyacetic acid
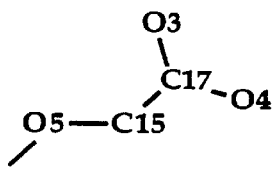
isopropyl
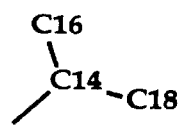
FIG. 32

NUCLEAR RECEPTOR LIGANDS AND LIGAND BINDING DOMAINS

CROSS-REFERENCE TO RELATED APPLICATIONS

This application claims the benefit of U.S. Provisional Applications 60/008,540, filed Dec. 13, 1995; U.S. Provisional Application 60/008,543, filed Dec. 13, 1995; and U.S. Provisional Application 60/008,606, filed Dec. 14, 1995. This application is a continuation-in-part of U.S. patent application Ser. No. 08/764,870 filed Dec. 13, 1996.

ACKNOWLEDGMENTS

This invention was supported in part by grants from the National Institutes of Health grant number 1 R01 DK43787, and 5 R01 DK 41842. The U.S. Government may have rights in this invention.

INTRODUCTION

1. Technical Field

This invention relates to computational methods for designing ligands that bind to nuclear receptors, crystals of nuclear receptors, synthetic ligands of nuclear receptors and methods of using synthetic ligands.

2. Background

Nuclear receptors represent a superfamily of proteins that specifically bind a physiologically relevant small molecule, such as hormone or vitamin. As a result of a molecule binding to a nuclear receptor, the nuclear receptor changes the ability of a cell to transcribe DNA, i.e. nuclear receptors modulate the transcription of DNA, although they may have transcription independent actions. Unlike integral membrane receptors and membrane associated receptors, the nuclear receptors reside in either the cytoplasm or nucleus of eukaryotic cells. Thus, nuclear receptors comprise a class of intracellular, soluble ligand-regulated transcription factors.

Nuclear receptors include receptors for glucocorticoids (GRs), androgens (ARs), mineralocorticoids (MRs), progestins (PRs), estrogens (ERs), thyroid hormones (TRs), vitamin D (VDRs), retinoids (RARs and RXRs), peroxisomes (XPARs and PPARs) and icosanoids (IRs). The so called "orphan receptors" are also part of the nuclear receptor superfamily, as they are structurally homologous to the classic nuclear receptors, such as steroid and thyroid receptors. To date, ligands have not been identified with orphan receptors but it is likely that small molecule ligands will be discovered in the near future for this class of transcription factors. Generally, nuclear receptors specifically bind physiologically relevant small molecules with high affinity and apparent Kd's are commonly in the 0.01–20 nM range, depending on the nuclear receptor/ligand pair.

Development of synthetic ligands that specifically bind to nuclear receptors has been largely guided by the trial and error method of drug design despite the importance of nuclear receptors in a myriad of physiological processes and medical conditions such as hypertension, inflammation, hormone dependent cancers (e.g. breast and prostate cancer), modulation of reproductive organ function, hyperthyroidism, hypercholesterolemia and obesity. Previously, new ligands specific for nuclear receptors were discovered in the absence of information on the three dimensional structure of a nuclear receptor with a bound ligand. Before the present invention, researchers were essentially discovering nuclear receptor ligands by probing in the dark and without the ability to visualize how the amino acids of a nuclear receptor held a ligand in its grasp.

Consequently, it would be advantageous to devise methods and compositions for reducing the time required to discover ligands to nuclear receptors, synthesize such compounds and administer such compounds to organisms to modulate physiological processes regulated by nuclear receptors.

SUMMARY OF THE INVENTION

The present invention provides for crystals of nuclear receptor ligand binding domains with a ligand bound to the ligand binding domain (LBD). The crystals of the present invention provide excellent atomic resolution of the amino acids that interact with nuclear receptor ligand, especially thyroid receptor ligands. The three dimensional model of a nuclear receptor LBD with a ligand bound reveals a previously unknown structure for nuclear receptors and shows that the ligand is bound in a water inaccessible binding cavity of the ligand binding domain of the nuclear receptor.

The present invention also provides for computational methods using three dimensional models of nuclear receptors that are based on crystals of nuclear receptor LBDs. Generally, the computational method of designing a nuclear receptor ligand determines which amino acid or amino acids of a nuclear receptor LBD interact with a chemical moiety (at least one) of the ligand using a three dimensional model of a crystallized protein comprising a nuclear receptor LBD with a bound ligand, and selecting a chemical modification (at least one) of the chemical moiety to produce a second chemical moiety with a structure that either decreases or increases an interaction between the interacting amino acid and the second chemical moiety compared to the interaction between the interacting amino acid and the corresponding chemical moiety on the natural hormone.

Also provided is a method of modulating the activity of a nuclear receptor. The method can be in vitro or in vivo. The method comprises administering in vitro or in vivo a sufficient amount of a compound of the following formula:

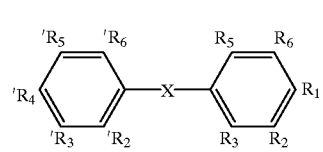

FORMULA I.

where the compound fits specially and preferentially into a nuclear hormone receptor LBD of interest. The method is exemplified by modulating the activity of a thyroid receptor (TR). For modulating TR activity, a compound of Formula I is employed that fits spacially and preferentially into a TR ligand binding domain (TR LBD), including compounds specific for a TR LBD isoform of interest. Of particular interest are the TR LBD isoforms α (TR-α) and β (TR-β). Additional compounds of interest include derivatives of Formula I, such as those compounds having the biphenyl (φ-X-φ) or single phenyl (φ-X or X-φ) nucleus of Formula I and its corresponding substituent groups described herein. Compounds that are interactively designed using structural information gleaned from these compounds and which modulate nuclear hormone receptor activity also are of interest.

The present invention also includes a method for identifying a compound capable of selectively modulating the activity of a nuclear receptor. This aspect of the invention is exemplified by a method for identifying a compound capable of selectively modulating the activity of a TR isoform. The method comprises modeling test compounds that fit spacially and preferentially into a TR LBD isoform of interest using an atomic structural model of a TR LBD isoform bound to a test compound, screening the test compounds in a biological assay for TR isoform activity characterized by binding of a test compound to a TR LBD isoform, and identifying a test compound that selectively modulates the activity of a TR isoform. The compounds may be those of Formula I or derivatives thereof, including compounds having a biphenyl or single phenyl nucleus of Formula I.

Further included is a method for identifying agonist or antagonist ligands of a nuclear receptor using the atomic coordinates of a LBD in conjunction with a computerized modeling system. This aspect of the invention is exemplified by identifying a TR agonist or antagonist ligand by providing the atomic coordinates of a TR LBD to a computerized modeling system, modeling ligands which fit spacially into the TR LBD, and identifying in a biological assay for TR activity a ligand which increases or decreases TR activity. The compounds can be those of Formula I or derivatives thereof, including compounds having a biphenyl or single phenyl nucleus of Formula I.

Also provided is a method of identifying a compound that selectively modulates the activity of one type of nuclear receptor compared to other nuclear hormone receptors. The method is exemplified by modeling test compounds which fit spacially into a TR LBD using an atomic structural model of a TR LBD, selecting a compound comprising conformationally constrained structural features that interact with conformationally constrained residues of a TR LBD, and identifying in a biological assay for TR activity a compound that selectively binds to a TR LBD compared to other nuclear receptors. The conformationally constrained features involved in receptor-selective ligand binding can be identified by comparing atomic models of receptor isoforms bound to the same and/or different ligands. The methods facilitate design and selection of compounds that have increased selectivity for a particular nuclear receptor. The compounds may be those of Formula I or derivatives thereof, including compounds having the biphenyl or single phenyl nucleus of Formula I.

Another aspect of the invention is a method for increasing the receptor selectivity of a compound for a particular type of nuclear receptor. This involves the chemical modification of a substituent group of a compound of Formula I to generate compounds which have increased selectivity for one type of receptor. For example, chemical modification of a substituent group of the compound of Formula I can be used to introduce additional constraints into a compound that modulates TR activity to increase its selectivity in vivo for TR-type receptors. Additional constraints also may be added for stability. The modified groups will preferably interact with a conformationally constrained structural feature of a TR LBD that is conserved among TR isoforms. A more preferred method comprises selecting compounds having conformationally constrained groups that interact with conformationally constrained residues of a TR LBD conserved among TR isoforms. The compounds can be those of Formula I or derivatives thereof, including compounds having the biphenyl or single phenyl nucleus of Formula I.

The invention finds use in the selection and characterization of peptide, peptidomimetic or synthetic compounds identified by the methods of the invention, particularly new lead compounds useful in treating disorders related to nuclear receptor-based deficiencies, including TR-related disorders. For TR-related disorders, the compounds and methods of the invention can be used to modulate TR activity by administering to a mammal in need thereof a sufficient amount of compound of Formula I or derivative thereof that fits spacially and preferentially into a TR LBD.

BRIEF DESCRIPTION OF THE DRAWINGS

The file of this patent contains at least one drawing executed in color. Copies of this patent with color drawings will be provided by the Patent and Trademark Office upon request and payment of necessary fee.

FIG. 1 is a diagram illustrating computational methods for designing ligands that interact with nuclear receptors of the nuclear receptor superfamily.

FIG. 2 is a schematic representation of nuclear receptor structures, indicating regions of homology within family members and functions of the various domains.

FIGS. 3A–3R shows the aligned amino acid sequences of the ligand binding domains of several members of the nuclear receptor superfamily SEQ ID NO: 1 rTRα; SEQ ID NO: 2 hTRα; SEQ ID NO: 3 hTRβ; SEQ ID NO: 4 hRARα; SEQ ID NO: 5 hRARγ; SEQ ID NO: 6 hRXRα; SEQ ID NO: 7 hRXRβ; SEQ ID NO: 8 hPPARα; SEQ ID NO: 9 hPPARβ; SEQ ID NO: 10 hPPARγ; SEQ ID NO: 11 hVDR; SEQ ID NO: 12 hER; SEQ ID NO: 13 hGR; SEQ ID NO: 14 hPR; SEQ ID NO: 15 hMR; and SEQ ID NO: 16 hAR.

FIG. 10 is a diagram comparing agonists and antagonists for several nuclear receptors.

FIG. 15 depicts the chemical structures of several TR ligands.

FIG. 32 shows atomic numbering for thyronine-like ligands.

Figure 4:
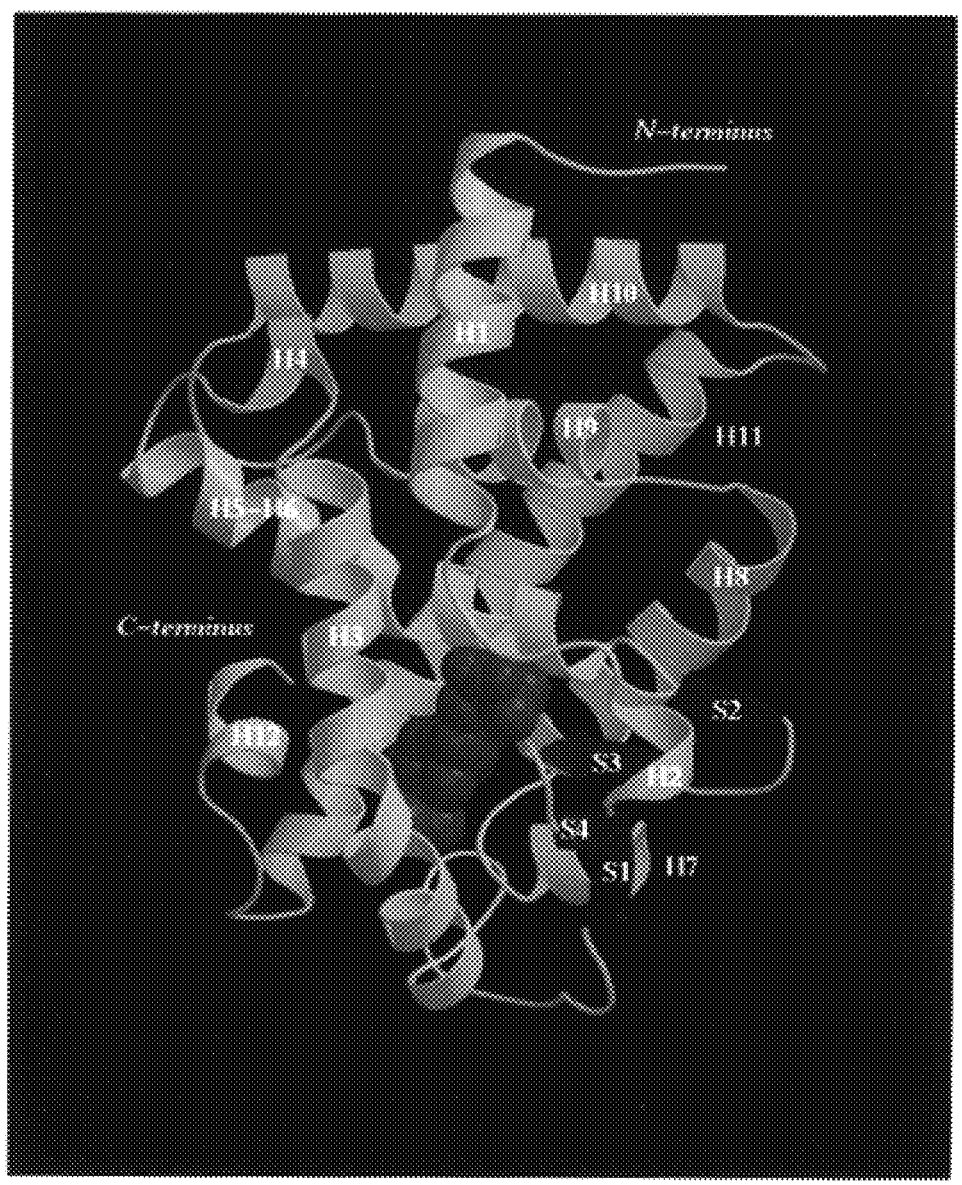
FIG. 4 is a ribbon drawing of the rat TR-α LBD with secondary structure elements labelled. The ligand is depicted as a space-filling model. Alpha helices, coil conformations, and beta strands are also shown.

APPENDIX 1 is an appendix of references.

APPENDIX 2 is a chart of amino acids that interact with a TR ligand, for TR complexed with Dimit, Triac, IpBr2, T3 and GC-1.

APPENDIX 3 is a chart of atomic coordinates for the crystal of rat TR-α LBD complexed with Dimit.

APPENDIX 4 is a chart of atomic coordinates for the crystal of rat TR-α LBD complexed with Triac.

APPENDIX 5 is a chart of atomic coordinates for the crystal of rat TR-α LBD complexed with $IpBr_2$.

APPENDIX 6 is a chart of atomic coordinates for the crystal of rat TR-α LBD complexed with $T_3$.

APPENDIX 7 is a chart of atomic coordinates for the crystal of human TR-β LBD complexed with Triac.

APPENDIX 8 is a chart of atomic coordinates for the crystal of human TR-β-LBD complexed with GC-1.

DETAILED DESCRIPTION OF THE INVENTION

INTRODUCTION

The present invention provides new methods, particularly computational methods, and compositions for the generation of nuclear receptor synthetic ligands based on the three dimensional structure of nuclear receptors, particularly the thyroid receptor (herein referred to as "TR"). Previously, the lack of three dimensional structural information about the ligand binding domain of a nuclear receptor thwarted the field of nuclear receptor drug discovery, especially the absence of three dimensional structural information relating to a nuclear receptor with a ligand bound.

Described herein for the first time are crystals and three dimensional structural information from a nuclear receptor's ligand binding domain (LBD) with a ligand bound. The structure of the TR LBD complexed with 3,5,3'-triiodothyronine ($T_3$), 3,5-dibromo-3'-isopropylthyronine ($IpBr_2$), 3,5-dimethyl-3'-isopropylthyronine (Dimit), and 3,5,3'-triiodothyroacetic acid (Triac), 3,5-dimethyl-4-(4'-hydroxy-3'isopropylbenzyl)-phenoxy acetic acid (GC1) are exemplified. Such crystals offer superior resolution at the atomic level and the ability to visualize the coordination of nuclear receptor ligands by amino acids that comprise the LBD. The present invention also provides computational methods for designing nuclear receptor synthetic ligands using such crystal and three dimensional structural information to generate synthetic ligands that modulate the conformational changes of a nuclear receptor's LBD. Such synthetic ligands can be designed using the computational methods described herein and shown, in part, in FIG. 1. These computational methods are particularly useful in designing an antagonist or partial agonist to a nuclear receptor, wherein the antagonist or partial agonist has an extended moiety that prevents any one of a number of ligand-induced molecular events that alter the receptor's influence on the regulation of gene expression, such as preventing the normal coordination of the activation domain observed for a naturally occurring ligand or other ligands that mimic the naturally occurring ligand, such as an agonist. As described herein, synthetic ligands of nuclear receptors will be useful in modulating nuclear receptor activity in a variety of medical conditions.

Of particular interest is use of such ligands in a method of modulating TR activity in a mammal by administering to a mammal in need thereof a sufficient amount of a compound of Formula I,

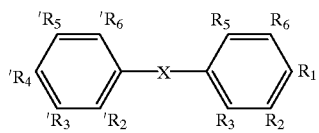

where the compound fits spatially and preferentially into a TR LBD. By "fits spacially" is intended that the three-dimensional structure of a compound is accommodated geometrically by a cavity or pocket of a TR LBD. By "TR LBD" is intended a structural segment or segments of thyroid hormone receptor polypeptide chain folded in such a way so as to give the proper geometry and amino acid residue configuration for ligand binding. This is the physical arrangement of protein atoms in three-dimensional space forming a ligand binding pocket or cavity. By "fits spacially and preferentially" is intended that a compound possesses a three-dimensional structure and conformation for selectively interacting with a TR LBD. Compounds of interest also include derivatives of Formula I. By "derivatives of Formula I" is intended compounds that comprise at least a single phenyl scaffold (φ-X or X-φ) of the biphenyl scaffold (φ-X-φ) of Formula I which comprise the corresponding substituents of Formula I described herein. Compounds that are interactively designed using structural information gleaned from these compounds and which modulate nuclear hormone receptor activity also are of interest. Preferred compounds of Formula I and its derivatives that fit spacially and preferentially into a TR LBD comprise the following substituents:

(i) an R1-substituent comprising an anionic group that interacts with a side chain nitrogen atom of an arginine corresponding to a residue from the group Arg228, Arg262, and Arg266 of human TR-α, and Arg282, Arg316 and Arg320 of human TR-β, where the anionic group is about 1.7–4.0 Å from the nitrogen atom;

(ii) an R2-substituent comprising a hydrophobic or hydrophilic group that fits spacially into the TR LBD;

(iii) an R3-substituent comprising a hydrophobic or hydrophilic group that interacts with a side chain atom of a serine, alanine and/or isoleucine corresponding to a residue from the group Ser260, Ala263 and Ile299 of human TR-α, and Ser314, Ala317 and Ile352 of human TR-β, where the hydrophobic or hydrophilic group is about 1.7–4.0 Å from the side chain atom;

(iv) an R5-substituent comprising a hydrophobic or hydrophilic group that interacts with a side chain atom of a phenylalanine and/or isoleucine corresponding to a residue from the group Phe218, Ile221 and Ile222 of human TR-α, and Phe272, Ile275 and Ile276 of human TR-β, where the hydrophobic or hydrophilic group is about 1.7–4.0 Å from the side chain atom;

(v) an R6-substituent comprising a hydrophobic or hydrophilic group that fits spacially into the TR LBD;

(vi) an X-substituent comprising a hydrophobic or hydrophilic group that interacts with a side chain atom of a leucine corresponding to a residue from the group Leu276 and Leu292 of human TR-α, and Leu 330 and Leu346 of human TR-β, where the hydrophobic or hydrophilic group is about 1.7–4.0 Å from the side chain atom;

(vii) an R2'-substituent comprising a hydrophobic or hydrophilic group that fits spacially into the TR LBD;

(viii) an R3'-substituent comprising a hydrophobic group that interacts with a side chain atom of a phenylalanine, glycine and/or methionine corresponding to a residue from the group Phe215, Gly290, and Met388 of human TR-α, and Phe269, Gly344, Met442 of human TR-β, where the hydrophobic group is about 1.7–4.0 Å from the side chain atom;

(ix) an R4'-substituent comprising an hydrogen bond donor or acceptor group that interacts with a side chain carbon or nitrogen atom of a histidine corresponding to residue His381 of human TR-α, and His435 of human TR-β, where the hydrogen bond donor or acceptor group is about 1.7–4.0 Å from the side chain atom;

(x) an R5'-substituent comprising a hydrophobic or hydrophilic group that fits spacially into the TR LBD;

(xi) and R6'-substituent comprising a hydrophobic or hydrophilic group that fits spacially into the TR LBD; and where the compound is other than thyronine (T3), tri-iodothyronine (T4) or other thyronine-like compounds previously known and used in a TR treatment method, such as those referenced in Appendix I.

Examples of such substituents include the following:

where $R_1$ is
—O—$CH_2CO_2H$, —$NHCH_2CO_2H$, —$CO_2H$, —$CH_2CO_2H$, —$CH_2CH_2CO_2H$, —$CH_2CH_2CH_2CO_2H$, —$CH_2CH(NH_2)CO_2H$, —$CH_2CH[NHCOCH\phi_2]CO_2H$, —$CH_2CH[NHCO(CH_2)_{15}CH_3]CO_2H$, —$CH_2CH[NH$—$FMOC]CO_2H$, —$CH_2CH[NH$-$tBOC]CO_2H$, or a carboxylate connected to the ring with a 0 to 3 carbon linker, —$PO_3H_2$, —$CH_2PO_3H_2$, —$CH_2CH_2PO_3H_2$, —$CH_2CHNH_2PO_3H_2$, —$CH_2CH[NHCOCH\phi_2]PO_3H_2$, —$CH_2CH[NHCO(CH_2)_{15}CH_3]PO_3H_2$, —$CH_2CH[NH$-$FMOC]PO_3H_2$, —$CH_2CH[NH$-$tBOC]PO_3H_2$, or a phosphate or phosphonate connected to the ring with a 0 to 3 carbon linker, —$SO_3H$, —$CH_2SO_3H$, —$CH_2CH_2SO_3H$, —$CH_2CHNH_2SO_3H$, —$CH_2CH[NHCOCH\phi_2]SO_3H$, —$CH_2CH[NHCO(CH_2)_{15}CH_3]SO_3H$, —$CH_2CH[NH$-$FMOC]SO_3H$, —$CH_2CH[NH$-$tBOC]SO3H$, or a sulfate or sulfite connected to the ring with a 0 to 3 carbon linker, or acts as the functional equivalent of $CH_2CH(NH_2)CO_2H$ of T3 in the molecular recognition domain when bound to a TR, wherein $R_1$ can be optionally substituted with an amine, where $R_2$ is
H, halogen, $CF_3$, OH, $NH_2$, SH, $CH_3$, —Et, or acts as the functional equivalent of H in the molecular recognition domain when bound to a TR, where $R_3$ is
—H, halogen, —$CF_3$, —OH, —$NH_2$, —$N_3$, —SH, —$CH_3$, —Et, or acts as the functional equivalent of I in the molecular recognition domain when bound to a TR, where $R_5$ is
—H, halogen, —$CF_3$, —OH, —$NH_2$, —$N_3$, —SH, —$CH_3$, —Et, or acts as the functional equivalent of I in the molecular recognition domain when bound to a TR, and $R_3$ can be identical to $R_5$, where $R_6$ is
—H, halogen, —$CF_3$, —OH, —$NH_2$, —SH, —$CH_3$, or acts as the functional equivalent of H in the molecular recognition domain when bound to a TR, and $R_2$ can be identical to $R_6$, where $R_2'$ is
—H, halogen, —$CF_3$, —OH, —$NH_2$, —$N_3$, —SH, —$CH_3$, —Et, or acts as the functional equivalent of H in the molecular recognition domain when bound to a TR, where $R_3'$ is any hydrophobic group, including halogen, —$CF_3$, —SH, alkyl, aryl, 5- or 6-membered heterocyclic, cyano, or acts as the functional equivalent of I in the molecular recognition domain when bound to a TR, where $R_4'$ is —H, halogen, —$CF_3$, —OH, —$NH_2$, $NH_3$, —$N(CH_3)_3$, carboxylate, phosphonate, phosphate or sulfate, —SH, —$CH_3$, —Et, or akyl, aryl or 5- or 6-membered heterocyclic aromatic attached through urea or carbamate linkages to O or N or S at the $R_4'$ position, or acts as the functional equivalent of OH in the molecular recognition domain when bound to a TR, where $R_5'$ is —H, —OH, —$NH_2$, —$N(CH_3)_2$ —SH —$NH_3$, —$N(CH_3)_3$, carboxylate, phosphonate, phosphate, sulfate, branched or straight chain alkyl having 1 to 9 carbons, substituted or unsubstituted aryl, wherein said substituted aryl is substituted with halogen or 1 to 5 carbon alkyl and wherein said aryl is optionally connected to the ring by a —$CH_2$—, aromatic heterocycle having 5 to 6 atoms, wherein said heterocycle may be substituted with one or more groups selected from —OH, —$NH_2$, —SH, —$NH_3$, —$N(CH_3)_3$, carboxylate, phosphonate, phosphate or sulfate, heteroalkyl, arylalkyl, heteroaryl alkyl, polyaromatic, or polyheteroaromatic, wherein said $R_5'$ may be substituted with polar or charged groups, where $R_6'$ is —H, halogen, —$CF_3$, —OH, —$NH_2$, —SH, —$CH_3$, —Et, or acts as the functional equivalent of H in the molecular recognition domain when bound to a TR, where X is O, S, $SO_2$, NH, $NR_7$, $CH_2$, $CHR_7$, $CR_7R_7$, wherein $R_7$ is alkyl, aryl or 5- or 6-membered heterocyclic aromatic, and where the TR LBD ligand has an apparent Kd for binding TR LBD of 1 $\mu$M or less.

Of particular interest are the class of compounds according to Formula I having the following substituents: where $R_1$ is carboxylate, phosphonate, phosphate or sulfite and is connected to the ring with a 0 to 3 carbon linker, $R_2$ is H, $R_3$ is —I, —Br, or —$CH_3$, $R_5$ is —I, —Br, or —$CH_3$, $R_6$ is H, $R_2'$ is H, $R_3'$ is —I, —Br, —$CH_3$, —iPr, -phenyl, benzyl, or 5- or 6-membered ring heterocycles, $R_4'$ is —OH, —$NH_2$, and —SH, $R_5'$ is —H, —OH, —$NH_2$, —$N(CH_3)_2$—SH—$NH_3$, —$N(CH_3)_3$, carboxylate, phosphonate, phosphate, sulfate, branched or straight chain alkyl having 1 to 9 carbons, substituted or unsubstituted aryl, wherein said substituted aryl is substituted with halogen or 1 to 5 carbon alkyl and wherein said aryl is optionally connected to the ring by a —$CH_2$—, aromatic heterocycle having 5 to 6 atoms, wherein said heterocycle may be substituted with one or more groups selected from —OH, —$NH_2$, —SH, —$NH_3$, —$N(CH_3)_3$, carboxylate, phosphonate, phosphate or sulfate, heteroalkyl, arylalkyl, heteroaryl alkyl, polyaromatic, or polyheteroaromatic, wherein said $R_5'$ may be substituted with polar or charged groups, and $R_6'$ is H.

The present invention also includes a method for identifying a compound capable of selectively modulating the activity of a TR isoform. By "modulating" is intended increasing or decreasing activity of a TR. By "TR isoform" is intended TR proteins encoded by subtype and variant TR genes. This includes TR-α and TR-β isoforms encoded by different genes (e.g., thra and thrb) and variants of the same genes (e.g., thrb1 and thrb2). The method comprises the steps of modeling test compounds that fit spacially and preferentially into a TR LBD isoform of interest using an atomic structural model of a TR LBD isoform bound to a test compound, screening the test compounds in a biological assay for TR isoform activity characterized by binding of a test compound to a TR LBD isoform, and identifying a test compound that selectively modulates the activity of a TR isoform. By "modeling" is intended quantitative and qualitative analysis of receptor-ligand structure/function based on three-dimensional structural information and receptor-ligand interaction models. This includes conventional numeric-based molecular dynamic and energy minimization models, interactive computer graphic models, modified molecular mechanics models, distance geometry and other structure-based constraint models. Modeling is preferably performed using a computer and may be further optimized using known methods.

For selectively modulating activity of a TR isoform, such as TR-α or TR-β, a sufficient amount of a compound that fits spatially and preferentially into TR LBD isoform is provided in vitro or in vivo to achieve the desired end result. TR-α isoform selectivity can be accomplished with a compound comprising an anionic group that interacts with an oxygen or carbon of a serine residue corresponding to Ser277 of human TR-α, where the anionic group is about 1.7–4.0 Å from the side chain atom. TR-β isoform selectivity can be accomplished with a compound comprising an anionic group that interacts with the side chain nitrogen of an asparagine corresponding to Asn331 of human TR-β, where the anionic group is about 1.7–4.0 Å from the side chain nitrogen atom.

The present invention further includes a method for identifying a TR agonist or antagonist ligand by providing the atomic coordinates of a TR LBD to a computerized modeling system, modeling ligands which fit spacially into the TR LBD, and identifying in a biological assay for TR activity a ligand which increases or decreases the activity of the TR.

The invention also involves a method for increasing receptor selectivity of a compound of Formula I or derivatives thereof for a TR-type receptor versus other nuclear receptors by selecting a compound that interacts with conformationally constrained residues of a TR LBD that are conserved among TR isoforms. "Conformationally constrained" is intended to refer to the three-dimensional structure of a chemical or moiety thereof having certain rotations about its bonds fixed by various local geometric and physical-chemical constraints. In designing and selecting compounds having increased specificity for TRs compared to other nuclear receptors, the following methods of the invention can be used. One method involves comparing atomic models of a first TR LBD isoform bound to a compound with a second TR LBD isoform bound to the same compound, identifying atoms of the TR LBD and compounds which interact, and designing or selecting a compound that interacts with TR LBD residues comprising a conformationally constrained structural feature that is conserved between the TR LBD isoforms. Another method relates to comparing a first TR LBD complexed with a first compound to a second TR LBD complexed with a second compound having one or more different substituents compared to the first compound, identifying atoms of the TR LBD and compounds which interact, and designing or selecting compounds that interact with TR LBD residues comprising a conformationally constrained structural feature that is conserved between the TR LBD isoforms. The methods also facilitate identification of structural and conformationally constrained interactions that are conserved between compounds that bind to a TR LBD. The methods are exemplified by comparing atomic models of a first TR LBD isoform complexed with a first compound of Formula I to a second TR LBD isoform complexed with the first compound, or a second compound of Formula I having different substituents than the first compound. For example, a TR-α LBD bound to a natural hormone such as T3 is compared to a TR-β LBD bound to an organic thyronine-like compound such as GC-1. Conserved contacts are identified which are made between atoms of the different compounds and atoms of the TR LBDs, and the fiducial and adjustable components identified. Compounds selective for TR are identified in a biological assay for TR activity that assays for selective binding to a TR and/or TR LBD compared to other nuclear receptors. Conventional assays for TR and other nuclear receptors may be conducted in parallel or serially, including those assays described herein. Automatable methods are preferred. The methods facilitate design and selection of compounds comprising cyclic carbon and substituent atoms that interact with a constrained side chain and/or main chain atom of a TR LBD residue.

In another aspect of the invention, the methods described herein are useful for selecting peptides, peptidomimetics or synthetic molecules that modulate TR activity. Methods of the invention also find use in characterizing structure/function relationships of natural and synthetic TR-ligands. Molecules of particular interest are new thyronine-like compounds other than T3, T4 and other thyronine-like compounds previously known and used for treating TR-related disorders. New compounds of the invention include those which bind to a TR LBD isoform with greater affinity than T3 or T4 and those which exhibit isoform-specific binding affinity.

APPLICABILITY TO NUCLEAR RECEPTORS

The present invention, particularly the computational methods, can be used to design drugs for a variety of nuclear receptors, such as receptors for glucocorticoids (GRs), androgens (ARs), mineralocorticoids (MRs), progestins (PRs), estrogens (ERs), thyroid hormones (TRs), vitamin D (VDRs), retinoid (RARs and RXRs), icosanoid (IRs), and peroxisomes (XPARS and peroxisomal proliferators (PPAP)). The present invention can also be applied to the "orphan receptors," as they are structurally homologous in terms of modular domains and primary structure to classic nuclear receptors, such as steroid and thyroid receptors. The amino acid homologies of orphan receptors with other nuclear receptors ranges from very low (<15%) to in the range of 35% when compared to rat RARα and human TR-β receptors, for example. In addition, as is revealed by the X-ray crystallographic structure of the TR and structural analysis disclosed herein, the overall folding of liganded superfamily members is likely to be similar. Although ligands have not been identified with orphan receptors, once such ligands are identified one skilled in the art will be able to apply the present invention to the design and use of such ligands, as their overall structural modular motif will be similar to other nuclear receptors described herein.

Modular Functional Domains of Nuclear Receptors

The present invention will usually be applicable to all nuclear receptors, as discussed herein, in part, to the patterns of nuclear receptor activation, structure and modulation that have emerged as a consequence of determining the three dimensional structures of nuclear receptors with different ligands bound, notably the three dimensional structures or crystallized protein structure of the ligand binding domains for TR-α and TR-β. Proteins of the nuclear receptor superfamily display substantial regions of amino acid homology, as described herein and known in the art see FIG. 2. Members of this family display an overall structural motif of three modular domains (which is similar to the TR three modular domain motif):

1) a variable amino-terminal domain;
2) a highly conserved DNA-binding domain (DBD); and
3) a less conserved carboxyl-terminal LBD. The modularity of this superfamily permits different domains of each protein to separately accomplish different functions, although the domains can influence each other. The separate function of a domain is usually preserved when a particular domain is isolated from the remainder of the protein. Using conventional protein chemistry techniques a modular domain can sometimes be separated from the parent protein. Using conventional molecular biology techniques each domain can usually be separately expressed with its original function intact or chimerics of two different nuclear receptors can be constructed, wherein the chimerics retain the properties of the individual functional domains of the respective nuclear receptors from which the chimerics were generated.

FIG. 2 provides a schematic representation of family member structures, indicating regions of homology within family members and functions of the various domains.

Amino Terminal Domain

The amino terminal domain is the least conserved of the three domains and varies markedly in size among nuclear receptor superfamily members. For example, this domain contains 24 amino acids in the VDR and 603 amino acids in the MR. This domain is involved in transcriptional activation and in some cases its uniqueness may dictate selective receptor-DNA binding and activation of target genes by specific receptor isoforms. This domain can display synergistic and antagonistic interactions with the domains of the LBD. For example, studies with mutated and/or deleted receptors show positive cooperativity of the amino and carboxy terminal domains. In some cases, deletion of either of these domains will abolish the receptor's transcriptional activation functions.

DNA-Binding Domain

The DBD is the most conserved structure in the nuclear receptor superfamily. It usually contains about 70 amino acids that fold into two zinc finger motifs, wherein a zinc ion coordinates four cysteines. DBDs contain two perpendicularly oriented α-helixes that extend from the base of the first and second zinc fingers. The two zinc fingers function in concert along with non-zinc finger residues to direct nuclear receptors to specific target sites on DNA and to align receptor homodimer or heterodimer interfaces. Various amino acids in DBD influence spacing between two half-sites (usually comprised of six nucleotides) for receptor dimer binding. For example, GR subfamily and ER homodimers bind to half-sites spaced by three nucleotides and oriented as palindromes. The optimal spacings facilitate cooperative interactions between DBDs, and D box residues are part of the dimerization interface. Other regions of the DBD facilitate DNA-protein and protein-protein interactions required for RXR homodimerization and heterodimerization on direct repeat elements.

The LBD may influence the DNA binding of the DBD, and the influence can also be regulated by ligand binding. For example, TR ligand binding influences the degree to which a TR binds to DNA as a monomer or dimer. Such dimerization also depends on the spacing and orientation of the DNA half sites. The receptors also can interact with other proteins and function to regulate gene expression.

The nuclear receptor superfamily has been subdivided into two subfamilies: 1) GR (GR, AR, MR and PR) and 2) TR (TR, VDR, RAR, RXR, and most orphan receptors) on the basis of DBD structures, interactions with heat shock proteins (hsp), and ability to form heterodimers. GR subgroup members are tightly bound by hsp in the absence of ligand, dimerize following ligand binding and dissociation of hsp, and show homology in the DNA half sites to which they bind. These half sites also tend to be arranged as palindromes. TR subgroup members tend to be bound to DNA or other chromatin molecules when unliganded, can bind to DNA as monomers and dimers, but tend to form heterodimers, and bind DNA elements with a variety of orientations and spacings of the half sites, and also show homology with respect to the nucleotide sequences of the half sites. By this classification, ER does not belong to either subfamily, since it resembles the GR subfamily in hsp interactions, and the TR subfamily in nuclear localization and DNA-binding properties.

Ligand Binding Domain

The LBD is the second most highly conserved domain in these receptors. Whereas integrity of several different LBD sub-domains is important for ligand binding, truncated molecules containing only the LBD retain normal ligand-binding activity. This domain also participates in other functions, including dimerization, nuclear translocation and transcriptional activation, as described herein. Importantly, this domain binds the ligand and undergoes ligand-induced conformational changes as detailed herein.

Most members of the superfamily, including orphan receptors, possess at least two transcription activation subdomains, one of which is constitutive and resides in the amino terminal domain (AF-1), and the other of which (AF-2 (also referenced as TAU 4)) resides in the ligand-binding domain whose activity is regulated by binding of an agonist ligand. The function of AF-2 requires an activation domain (also called trsactivation domain) that is highly conserved among the receptor superfamily (approximately amino acids 1005 to 1022). Most LBDs contain an activation domain. Some mutations in this domain abolish AF-2 function, but leave ligand binding and other functions unaffected. Ligand binding allows the activation domain to serve as an interaction site for essential co-activator proteins that function to stimulate (or in some cases, inhibit) transcription.

For example, Shibata, H., et al. (*Recent Progress in Hormone Res*. 52:141–164 (1997)) has; reviewed the role of co-activators and co-repressors in steroid/thyroid hormone receptor systems. Steroid receptor co-activator-one (SRC-1) appears to be a general co-activator for all AF-2 domain containing receptors tested. SRC-1 enhances transactivation of steroid hormone-dependent target genes. Other putative co-activators have been reported, including the SRC-1 related proteins, TIF-2 and GRIP-1, and other putative unrelated co-activators such as ARA-70, Trip 1, RIP-140, and TIF-1. In addition another co-activator CREB-binding protein (CBP) has been shown to enhance receptor-dependent target gene trascription. CBP and SRC-1 interact and synergistically enhance transcriptional activation by the ER and PR. A ternary complex of CBP, SRC-1, and liganded receptors-may form to increase the rate of hormone-responsive gene transcription. Co-repressors, such as SMRT and N-CoR, for TR and RAR, have been identified that also contribute to the silencing function of unliganded TR. The unliganded TR and RAR have been shown to inhibit basal promoter activity; this silencing of target gene transcription by unliganded receptors is mediated by these co-repressors.

The collective data suggests that upon binding of agonist, the receptor changes its conformation in the ligand-binding domain that enables recruitment of co-activators, which allows the receptor to interact with the basal transcriptional machinery more efficiently and to activate transcription. In contrast, binding of antagonists induces a different conformational change in the receptor. Although some antagonist-bound receptors can dimerize and bind to their cognate DNA elements, they fail to dislodge the associated co-repressors, which results in a nonproductive interaction with the basal transcriptional machinery. Similarly, the TR and RAR associate with co-repressors in the absence of ligand, thereby resulting in a negative interaction with the transcriptional machinery that silences target gene expression. In the case of mixed agonist/antagonists, such as 4-hydroxytamoxifen, activation of gene transcription may depend on the relative ratio of co-activators and co-repressors in the cell or cell-specific factors that determine the relative agonistic or antagonistic potential of different compounds. These co-activators and co-repressors appear to act as an accelerator and/or a brake that modulates transcriptional regulation of hormone-responsive target gene expression.

The carboxy-terminal activation subdomain, as described herein is in close three dimensional proximity in the LBD to the ligand, so as to allow for ligands bound to the LBD to coordinate (or interact) with amino acid(s) in the activation subdomain. As described herein, the LBD of a nuclear receptor can be expressed, crystallized, its three dimensional structure determined with a ligand bound (either using crystal data from the same receptor or a different receptor or a combination thereof), and computational methods used to design ligands to its LBD, including ligands that contain an extension moiety that coordinates the activation domain of the nuclear receptor.

Once a computationally designed ligand (CDL) is synthesized as described herein and known in the art, it can be tested using assays to establish its activity as an agonist, partial agonist or antagonist, and affinity, as described herein. After such testing, the CDLs can be further refined by generating LBD crystals with a CDL bound to the LBD. The structure of the CDL can then be further refined using the chemical modification methods described herein for three dimensional models to improve the activity or affinity of the CDL and make second generation CDLs with improved properties, such as that of a super agonist or antagonist described herein. Agonist and antagonist ligands also can be selected that modulate nuclear receptor responsive gene transcription through altering the interaction of co-activators and co-repressors with their cognate nuclear hormone receptor. For example, CDL agonists can be selected that block or dissociate the co-repressor from interaction with the receptor, and/or which promote binding or association of the co-activator. CDL antagonists can be selected that block co-activator interaction and/or promote co-repressor interaction with the target receptor. Selection can be done in binding assays that screen for CDLs having the desired agonist or antagonist properties. Suitable assays for such screening are described herein and in Shibata, H., et al. (*Recent Prog. Horm. Res*. 52:141–164 (1997)); Tagami, T., et al. (*Mol. Cell Biol*. 17(5):2642–2648 (1997)); Zhu, X G., et al. (*J. Biol. Chem*. 272(14):9048–9054 (1997)); Lin, B. C., et al. (*Mol. Cell Biol*. 17(10):6131–6138 (1997)); Kakizawa, T., et al. (*J. Biol. Chem*. 272(38):23799–23804 (1997)); and Chang, K. H., et al. (*Proc. Natl. Acad. Sci. USA* 94(17): 9040–9045 (1997)), which references are incorporated herein in their entirety by reference.

NUCLEAR RECEPTOR ISOFORMS

The present invention also is applicable to generating new synthetic ligands to distinguish nuclear receptor isoforms.

As described herein, CDLs can be generated that distinguish between binding isoforms, thereby allowing the generation of either tissue specific or function specific synthetic ligands. For instance, GR subfamily members have usually one receptor encoded by a single gene, although are exceptions. For example, there are two PR isoforms, A and B, translated from the same mRNA by alternate initiation from different AUG codons. There are two GR forms, one of which does not bind ligand. This method is especially applicable to the TR subfamily which usually has several receptors that are encoded by at least two (TR: α, β) or three (RAR, RXR, and PPAR: α, β, γ) genes or have alternate RNA splicing and such an example for TR is described herein.

NUCLEAR RECEPTOR CRYSTALS

The invention provides for crystals made from nuclear receptor ligand binding domains with the ligand bound to the receptor. As exemplified in the Examples, TRs are crystallized with a ligand bound to it. Crystals are made from purified nuclear receptor LBDs that are usually expressed by a cell culture, such as *E. coli*. Preferably, different crystals (cc-crystals) for the same nuclear receptor are separately made using different ligands, such as a naturally occurring ligand and at least one bromo- or iodo-substituted synthetic ligand that acts as an analog or antagonist of the naturally occurring ligand. Such bromo- and iodo-substitutions act as heavy atom substitutions in nuclear receptor ligands and crystals of nuclear receptor proteins. This method has the advantage for phasing of the crystal in that it bypasses the need for obtaining traditional heavy metal derivatives. After the three dimensional structure is determined for the nuclear receptor LBD with its ligand bound, the three dimensional structure can be used in computational methods to design a synthetic ligand for the nuclear receptor and further activity structure relationships can be determined through routine testing using the assays described herein and known in the art.

Expression and Purification of other Nuclear Receptor LBD Structures

High level expression of nuclear receptor LBDs can be obtained by the techniques described herein as well as others described in the literature. High level expression in *E. coli* of ligand binding domains of TR and other nuclear receptors, including members of the steroid/thyroid receptor superfamily, such as the receptors ER, AR, MR, PR, RAR, RXR and VDR can also be achieved. Yeast and other eukaryotic expression systems can be used with nuclear receptors that bind heat shock proteins as these nuclear receptors are generally more difficult to express in bacteria, with the exception of ER, which can be expressed in bacteria. Representative nuclear receptors or their ligand binding domains have been cloned and sequenced: human RAR-α, human RAR-γ, human RXR-α, human RXR-β, human PPAR-α, human PPAR-β, human PPAR-γ, human VDR, human ER (as described in Seielstad et al., *Molecular Endocrinology*, vol 9:647–658 (1995), incorporated herein by reference), human GR, human PR, human MR, and human AR. The ligand binding domain of each of these nuclear receptors has been identified and is shown in FIGS. 3A–3R. Using the information in FIGS. 3A–3R in conjunction with the methods described herein and known in the art, one of ordinary skill in the art could express and purify LBDs of any of the nuclear receptors, including those illustrated in FIGS. 3A–3R, bind it to an appropriate ligand, and crystallize the nuclear receptor's LBD with a bound ligand.

FIGS. 3A–3R is an alignment of several members of the steroid/thyroid hormone receptor superfamily that indicates the amino acids to be included in a suitable expression vector.

Extracts of expressing cells are a suitable source of receptor for purification and preparation of crystals of the chosen receptor. To obtain such expression, a vector is constructed in a manner similar to that employed for expression of the rat TR alpha (Apriletti et al. *Protein Expression and Purification*, 6:363–370 (1995), herein incorporated by reference). The nucleotides encoding the amino acids encompassing the ligand binding domain of the receptor to be expressed, for example the estrogen receptor ligand binding domain (hER-LBD) (corresponding to R at position 725 to L at position 1025 as standardly aligned as shown in the FIG. 3), are inserted into an expression vector such as the one employed by Apriletti et al (1995). For the purposes of obtaining material that will yield good crystals it is preferable to include at least the amino acids corresponding to human TR-β positions 725 to 1025. Stretches of adjacent amino acid sequences may be included if more structural information is desired. Thus, an expression vector for the human estrogen receptor can be made by inserting nucleotides encoding amino acids from position 700 to the c-terminus at position 1071. Such a vector gives high yield of receptor in *E. coli* that can bind hormone (Seielstad et al. *Molecular Endocrinology* 9:647–658 (1995)). However, the c-terminal region beyond position 1025 is subject to variable proteolysis and can advantageously be excluded from the construct, this technique of avoiding variable proteolysis can also be applied to other nuclear receptors.

TR-α And TR-β As Examples of Nuclear Receptor LBD Structure and Function TR Expression, Purification And Crystallization As an example of nuclear receptor structure of the ligand binding domain the α- and β-isoforms of TR are crystallized from proteins expressed from expression constructs, preferably constructs that can be expressed in *E. coli*. Other expression systems, such as yeast or other eukaryotic expression systems can be used. For the TR, the LBD can be expressed without any portion of the DBD or amino-terminal domain. Portions of the DBD or amino-terminus can be included if further structural information with amino acids adjacent the LBD is desired. Generally, for the TR the LBD used for crystals will be less than 300 amino acids in length. Preferably, the TR LBD will be at least 150 amino acids in length, more preferably at least 200 amino acids in length, and most preferably at least 250 amino acids in length. For example the LBD used for crystallization can comprise amino acids spanning from Met 122 to Val 410 of the rat TR-α, Glu 202 to Asp 461 of the human TR-β.

Typically TR LBDs are purified to homogeneity for crystallization. Purity of TR LBDs is measured with sodium dodecyl sulfate polyacrylamide gel electrophoresis (SDS-PAGE), mass spectrometry (MS) and hydrophobic high performance liquid chromatography (HPLC). The purified TR for crystallization should be at least 97.5% pure or 97.5%, preferably at least 99.0% pure or 99.0% pure, more preferably at least 99.5% pure or 99.5% pure.

Initially purification of the unliganded receptor can be obtained by conventional techniques, such as hydrophobic interaction chromatography (HPLC), ion exchange chromatography (HPLC), and heparin affinity chromatography.

To achieve higher purification for improved crystals of nuclear receptors, especially the TR subfamily and TR, it will be desirable to ligand shift purify the nuclear receptor using a column that separates the receptor according to charge, such as an ion exchange or hydrophobic interaction column, and then bind the eluted receptor with a ligand, especially an agonist. The ligand induces a change in the receptor's surface charge such that when re-chromatographed on the same column, the receptor then elutes at the position of the liganded receptor are removed by the original column run with the unliganded receptor. Usually saturating concentrations of ligand are used in the column and the protein can be preincubated with the ligand prior to passing it over the column. The structural studies detailed herein indicate the general applicability of this technique for obtaining super-pure nuclear receptor LBDs for crystallization.

More recently developed methods involve engineering a "tag" such as with histidine placed on the end of the protein, such as on the amino terminus, and then using a nickle chelation column for purification, Janknecht R., *Proc. Natl. Acad. Sci. USA*, 88:8972–8976 (1991) incorporated by reference.

To determine the three dimensional structure of a TR LBD, or a LBD from another member of the nuclear receptor superfamily, it is desirable to co-crystalize the LBD with a corresponding LBD ligand. In the case of TR LBD, it is preferable to separately co-crystalize it with ligands such as T3, IpBr and Dimit that differ in the heavy atoms which they contain. Other TR ligands such as those encompassed by Formula 1 described herein and known in the prior art, can also be used for the generation of co-crystals of TR LBD and TR ligands. Of the compounds encompassed by Formula 1 it is generally desirable to use at least one ligand that has at least one bromo- or iodo- substitution at the $R_3$, $R_5$, $R_3'$ or $R_5'$ position, preferably such compounds will be have at least two such substitutions and more preferably at least 3 such substitutions. As described herein, such substitutions are advantageously used as heavy atoms to help solve the phase problem for the three dimensional structure of the TR LBD and can be used as a generalized method of phasing using a halogen (e.g. I or Br) substituted ligand, especially for nuclear receptors.

Typically purified LBD, such as TR LBD, is equilibrated at a saturating concentration of ligand it a temperature that preserves the integrity of the protein. Ligand equilibration can be established between 2 and 37° C., although the receptor tends to be more stable in the 2–20° C. range.

Preferably crystals are made with the hanging drop methods detailed herein. Regulated temperature control is desirable to improve crystal stability and quality. Temperatures between 4 and 25° C. are generally used and it is often preferable to test crystallization over a range of temperatures. In the case of TR it is preferable to use crystallization temperatures from 18 to 25° C., more preferably 20 to 23° C., and most preferably 22° C.

Complexes of the TR-α LBD with a variety of agonists, including $T_3$, $IpBr_2$, Dimit, and Triac, are prepared with by methods described herein. For example, cocrystals of the rTR-α LBD, with ligand prebound, are prepared by vapor diffusion at ambient temperature from 15% 2-methyl-2,4-pentanediol (MPD). The crystals are radiation sensitive, and require freezing to measure complete diffraction data. On a rotating anode X-ray source, the crystals diffract to ~3 Å; synchrotron radiation extends the resolution limit significantly, to as high as 2.0 Å for $T_3$ cocrystals. The composition of the thyroid hormone, combined with the ability to prepare and cocrystallize the receptor complexed with a variety of analogs, permitted the unusual phasing strategy. This phasing strategy can be applied to the ligands of the nuclear receptors described therein by generating I and Br substitutions of such ligands. In this strategy, cocrystals of the TR LBD containing four hormone analogs that differ at the 3,5, and 3' positions ($T_3$, $IpBr_2$, Dimit, and Triac) provided isomorphous derivatives. For this set of analogs, the halogen substituents (2Br and 3I atoms) function as heavy atoms, while the Dimit cocrystal (3 alkyl groups) acts as the parent. The initial 2.5 Å multiple isomorphous replacement/anomalous scattering/density modified electron density map allowed the LBD to be traced from skeletons created in the molecular graphics program O5 (Jones, T. A. et al., *ACTA Cryst*, 47:110–119 (1991), incorporated by reference herein). A model of the LBD was built in four fragments, Arg157-Gly184, Trp186-Gly197, Ser199-Pro205, and Val210-Phe405, and refined in XPLOR using positional refinement and simulated annealing protocols. Missing residues were built with the aid of difference density. The final model was refined to $R_{cryst}$=21.8% and $R_{free}$=24.4% for data from 15.0 to 2.2 Å, see Table 6. The human TR-β LBD model was resolved by molecular replacement of the Tr-α LBD coordinates. The structure is based on E202 to D461 with a his-tag at the N-terminus. The final model was refined to $R_{cryst}$=25.3% and $R_{free}$=28.9% for data from 30.0 to 2.4 Å+, see Table 7.

This; phasing strategy can be applied to the ligands of the nuclear receptors described herein by generating I and Br substitutions of such ligands.

THREE DIMENSIONAL STRUCTURE OF TR LBD

Architecture of TR LBD

As an example of the three dimensional structure of a nuclear receptor, the folding of the TR-$α_1$ LBD is shown in FIG. 4. The TR-α LBD consists of a single structural domain packed in three layers, composed of twelve α-helices, H1–12, and four short β-strands, S1–4, forming a mixed β-sheet. The buried hormone and three antiparallel α-helices, H5–6, H9, and H10, form the central layer of the domain, as shown in FIG. 4. H1, H2, H3 and S1 form one face of the LBD, with the opposite face formed by H7, H8, H11, and H12. The first 35 amino acids of the N-terminus (Met122–Gln156) are not visible in the electron density maps. The three dimensional structure of the heterodimeric RXR:TR DNA-binding domains bound to DNA, amino acids Met 122–Gln151 of the TR DBD make extensive contacts with the minor groove of the DNA8. The five disordered amino acids (Arg152–Gln156), which reside between the last visible residue of the TR DBD and the first visible residue of ihe LBD likely represent the effective "hinge" linking the LBD and the DBD in the intact receptor.

The predominantly helical composition and the layered arrangement of secondary structure is identical to that of the unliganded hRXRα, confirming the existence of a common nuclear receptor fold between two nuclear receptors.

The TR LBD is visible beginning at Arg157, and continues in an extended coil conformation to the start of H1. A turn of α-helix, H2, covers the hormone binding cavity, immediately followed by short β-strand, S1, which forms the edge of the mixed β-sheet, parallel to S4, the outermost of the three antiparallel strands. The chain is mostly irregular until H3 begins, antiparallel to H1. H3 bends at Ile221 and Ile222, residues which contact the ligand. The chain turns almost 90° at the end of H3 to form an incomplete α-helix, H4. The first buried core helix, H5–6, follows, its axis altered by a kink near the ligand at Gly 253. The helix is composed of mostly hydrophobic sidechains interrupted by two striking exceptions: Arg262 is solvent inaccessible and interacts with the ligand carboxylate (1-substituent), and Glu256 meets Arg329 from H9 and Arg375 from H11 in a polar invagination. H5–6 terminates in a short β-strand, S2, of the four strand mixed sheet. S3 and S4 are joined through a left-handed turn, and further linked by a salt bridge between Lys284 and Asp272. Following S4, H7 and H8 form an L, stabilized by a salt bridge between Lys268 and Asp277. The turn between H7 and H8 adopts an unusual conformation, a result of interaction with ligand and its glycine rich sequence. H9 is the second core helix. antiparallel to the neighboring H5–6. Again, two buried polar sidechains are found, Glu315 and Gln320. Glu315 forms a buried salt bridge with His358 and Arg356. The oxygen of Gln320 forms a hydrogen bond with the buried sidechain of His 175. The chain then switches back again to form H10, also antiparallel to H9. H11 extends diagonally across the full length of the molecule. Immediately after H11, the chain forms a type II turn, at approximately 90° to H11. The chain then turns again to form H 12, which packs loosely against H3 and H11 as part of the hormone or ligand binding cavity. The final five amino acids at the C-terminus, Glu406–Val410, are disordered. The architecture of the TR-β, LBD is identical to that of the TR-α LBD, with two significant differences. An additional helix is present at the N-terminus (residues Glu202–Ile208), which is part of the DBD, and packs antiparallel to H10. Following the helix is a two residue turn (Gly209–His210) continuing into an extended coil to he start of H1, as seen in the TR-α LBD. A further difference occurs in the irregular conformation adopted between H2 and H3. In the TR-α LBD, residue Gly197–Asp211 form a loop that packs against the receptor, contacting helices H7, H8, H11, and the loop between H11 and H12. In the TR-β LBD, only the ends of the loop are ordered, with the stretch Ala253–Lys263 disordered. In addition to these residues, the residues of the His-tag at the N-terminus, and the final residue at the C-terninus, Asp461, are disordered.

TR LBD's Ligand Binding Cavity as an Example of a Nuclear Receptor's Buried Ligand Cavity The three dimensional structure of the TR LBD leads to the startling finding that ligand binding cavity of the LBD is solvent inaccessible when a T3 or its isostere is bound to the LBD. This surprising result leads to a new model of nuclear receptor three dimensional structure and function, as further described herein, particularly in the sections elucidating the computational methods of ligand design and the application of such methods to designing nuclear receptor synthetic ligands that contain extended positions that prevent normal activation of the activation domain.

Figure 5:
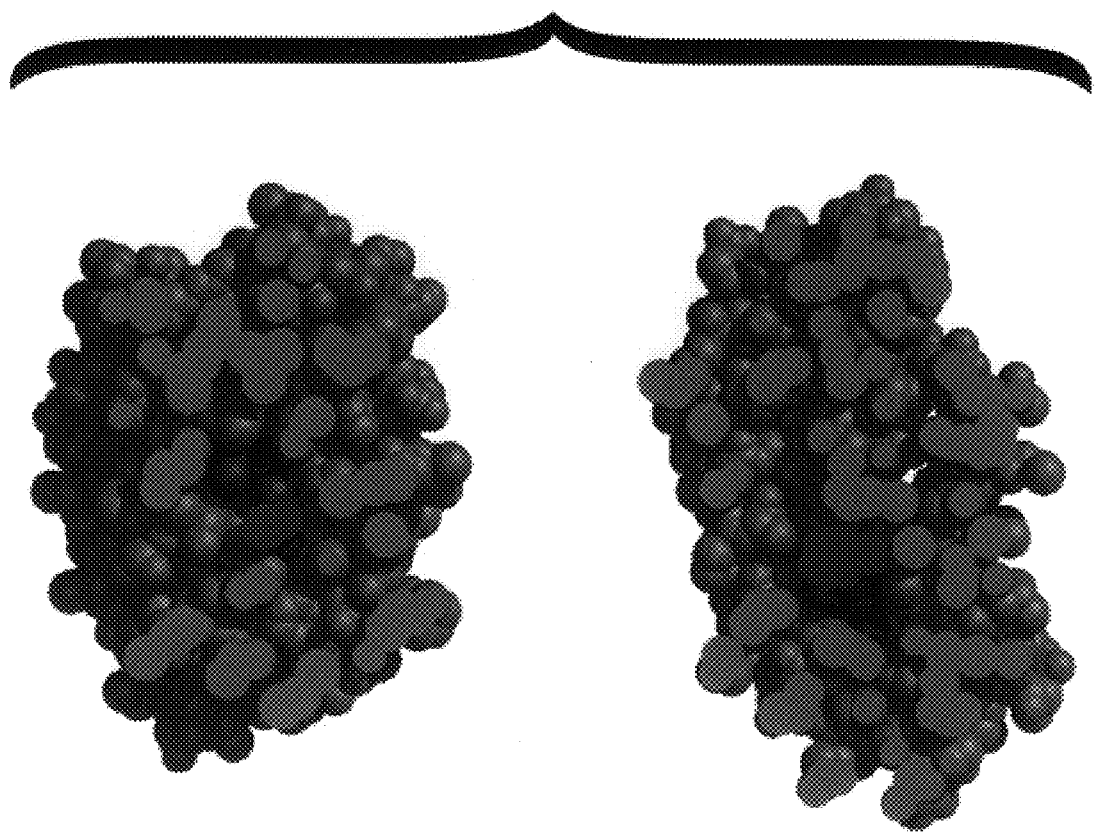
FIG. 5 shows two cross-sections of a space-filling model of rat TR-α exposing the ligand tightly packed within the receptor.

Dimit, the ligand bound to the receptor, is an isostere of $T_3$ and a thyroid hormone agonist. Therefore the binding of Dimit should reflect that of $T_3$, and the Dimit-bound receptor is expected to be the active conformation of TR. The ligand is buried within the receptor, providing the hydrophobic core for a subdomain of the protein, as shown in FIG. 5 a and b. H5–6 and H9 comprise the hydrophobic core for the rest of the receptor.

An extensive binding cavity is constructed from several structural elements. The cavity is enclosed from above by H5–6 (Met 256–Arg266), from below by H7 and H8 and the intervening loop (Leu287–Ile299), and along the sides by H2 (185–187), by the turn between S3 and S4 (Leu276–Ser277), by H3 (Phe215–Arg228), by H11 (His381–Met388) and by H12 (Phe401–Phe405). The volume of the cavity defined by these elements, calculated by GRASP (Columbia University, USA) (600 Å3), is essentially the volume of the hormone (530 Å). The change in volume can be exploited for ligand design as described herein. The remaining volume is occupied by water molecules surrounding the amino-propionic acid substituent.

Figure 6:
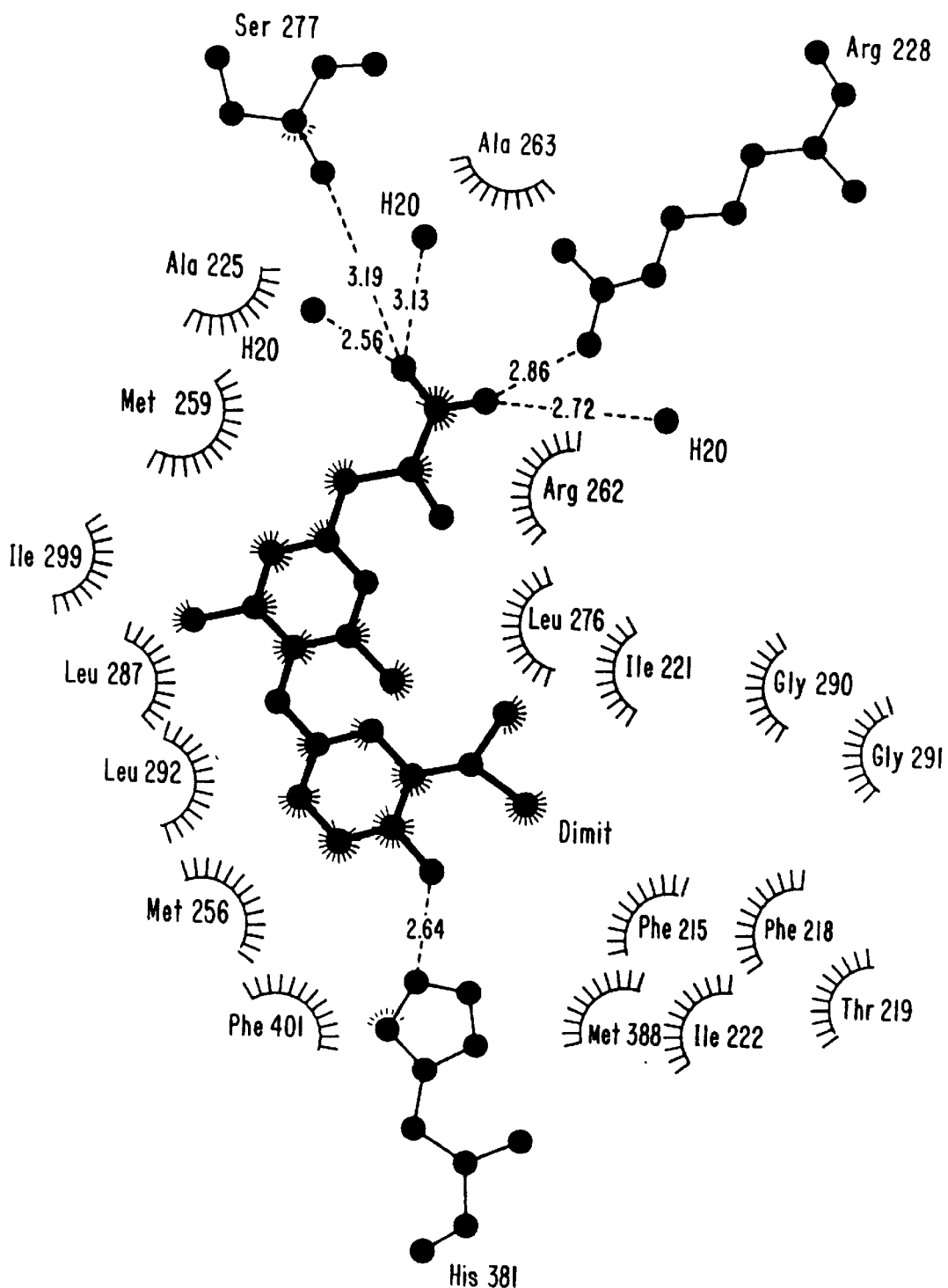
FIG. 6 is a schematic of the ligand binding cavity. Residues which interact with the ligand appear approximately at the site of interaction. Hydrogen bonds are shown as dashed lines between the bonding partners; distances for each bond are listed. Non-bonded contacts are shown as radial spokes which face toward interacting atoms.

FIG. 6 depicts various contacts (or interactions) between TR's LBD and the ligand.

The planes of the inner and outer (prime ring) rings of the ligand are rotated from planarity about 60° with respect to each other, adopting the 3'-distal conformation (in which the 3' substituent of the outer ring projects down and away from the inner ring). The amino-propionic acid and the outer phenolic ring assume the transoid conformation, each on opposite sides of the inner ring. The torsion angle $\lambda_1$ for the amino-propionic acid is 300°.

The amino-propionic acid substituent is packed loosely in a polar pocket formed by side chains from H2, H4 and S3. The carboxylate group forms direct hydrogen bonds with the guanidium group of Arg228 and the amino N of Ser277. In addition, Arg262, Arg266 and Asn179 interact with the carboxylate through water-mediated hydrogen bonds. The three arginine residues create a significantly positive local electrostatic potential, which may stabilize the negative charge of the carboxylate. No hydrogen bond is formed by the amino nitrogen. The interactions of the amino-propionic acid substituent are consistent with the fact that Triac, which lacks the amino nitrogen, has a binding affinity equal to that of $T_3$, indicating that the amino nitrogen and longer aliphatic chain of $T_3$ do not contribute greatly to binding affinity.

The biphenyl ether, in contrast, is found buried within the hydrophobic core. The inner ring packs in a hydrophobic pocket formed by H3, H5–6, and S3. Pockets for the 3- and 5-methyl substituents are not completely filled, as expected since the van der waals radius of methyl substituent for Dimit is smaller than the iodine substituent provided by the thyroid hormone $T_3$. Such pockets are typically 25 to 100 cubic angstroms (although smaller pocket for substitutes are contemplated in the 40 to 80 cubic angstrom range) and could be filled more tightly with better fitting chemical substitutions, as described herein.

The outer ring packed tightly in a pocket formed by H3, H5–6, H7, H8, H11 and H12, and the loop between H7 and H8. The ether oxygen is found in a hydrophobic environment defined by Phe218, Leu287, Leu276, and Leu292. The absence of a hydrogen bond to the ether oxygen is consistent with its role in establishing the correct stereochemistry of the phenyl rings, as suggested by potent binding of hormone analogs with structurally similar linkages possessing reduced or negligible hydrogen bonding capability. The 3'-isopropyl substituent contacts Gly290 and 291. The presence of glycine at this position in the pocket can explain the observed relationship between activity and the size of 3'-substituenls. Activity is highest for 3'-isopropyl, and decreases with added bulk. The only hydrogen bond in the hydrophobic cavity is formed between the phenolic hydroxyl and His381 Nε2. The conformation of His381 is stabilized by packing contacts provided by Phe405, and Met256.

The presence of a 5' substituent larger than hydrogen affects the binding affinity for hormone. The more abundant thyroid hormone, 3,5,3',5'-tetraiodo-L-thyronine ($T_4$), contains an iodine at this position, and binds the receptor with 2% of the affinity of $T_3$. The structure suggests that discrimination against $T_4$ is accomplished through the combination of steric conflict by Met256 and possibly the constraints imposed by the geometry of the hydrogen bond from His381 to the phenolic hydroxyl. The 5' position is a preferred location for introducing a chemical modification of C-H at the 5' of T3 or and TR agonist, as described herein, that produces an extension from the prime ring and results in the creation of an antagonist or partial agonist.

Deletion and antibody competition studies suggest the involvement of residues Pro162 to Val202 in ligand binding.

Figure 7:
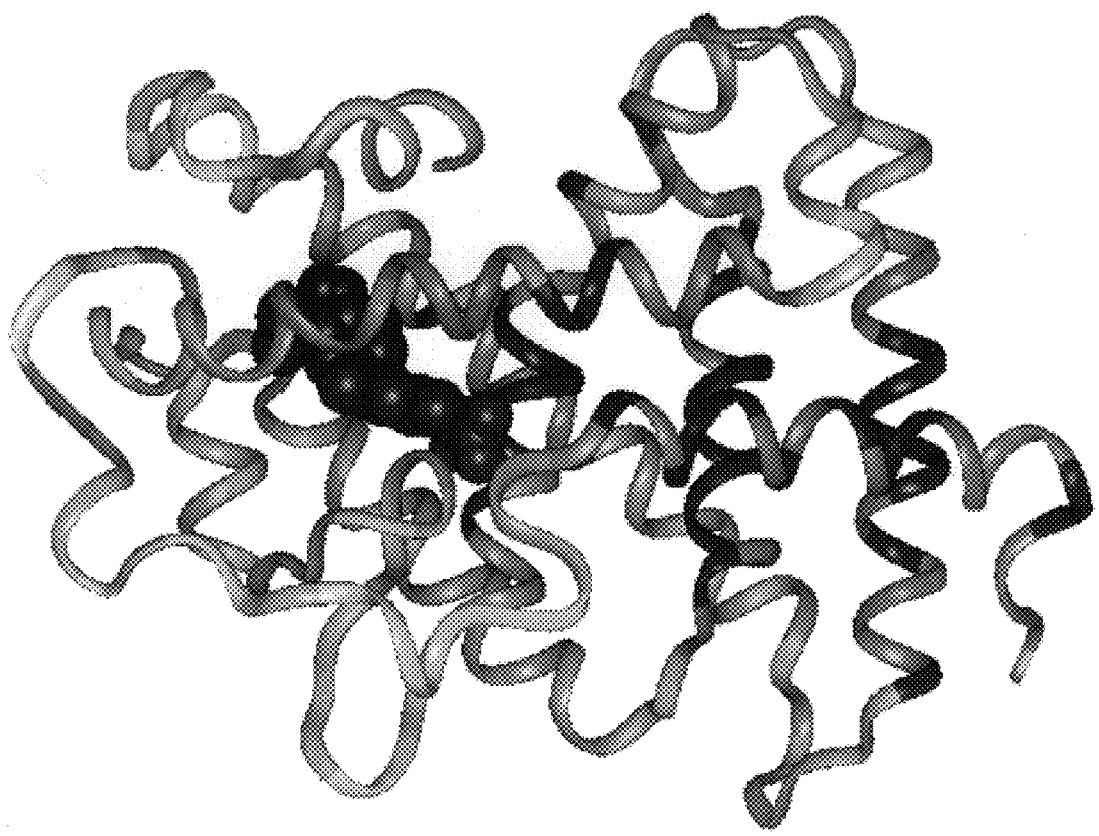
FIG. 7 is the distribution of crystallographic temperature factors in the refined rat TR-α LBD.

The region does not directly contact hormone in the bound structure, although H2 packs against residues forming the polar pocket that interacts with the amino-propionic acid group. One role for H2, then, is to stabilize these residues in the bound state, H2, with β-strands S3 and S4, might also represent a prevalent entry point for ligand, since the amino-propionic acid of the ligand is oriented toward this region. Studies of receptor binding to $T_3$ affinity matrices demonstrate that only a linkage to the amino-propionic acid is tolerated, suggesting that steric hindrance present in other linkages prevent binding. Furthermore, the crystallographic temperature factors suggest the coil and β-strand region is most flexible part of the domain FIG. 7. Participation of this region, part of the hinge domain between the DBD and LBD, in binding hormone may provide structural means for ligand binding to influence DNA binding, since parts of the Hinge domain contact DNA.

TR LBD Transcriptional Activation Helix as an Example of a Nuclear Receptor Activation Domain In addition to the startling finding that the ligand binding cavity is solvent inaccessible when loaded with a ligand, the activation helix of TR LBD presents a surface to the ligand cavity for interaction between at least one amino acid and the bound ligand. The C-terminal 17 amino acids of the TR, referred to as the activation helix or AF-2 (an example of an LBD activation domain), are implicated in mediating hormone-dependent transcriptional activation. Although, mutations of key residues within the domain decrease ligand-dependent activation it was unclear until the present invention whether such mutations directly affected ligand coordination. Although some mutations of this domain have been noted to reduce or abolish ligand binding, other mutations in more distant sites of the LBD have a similar effect.

Activation domains among nuclear receptors display an analogous three dimensional relationship to the binding cavity, which is a region of the LBD that binds the molecular recognition domain of a ligand, i.e. the activation domain presents a portion of itself to the binding cavity (but necessarily the molecular recognition domain of the ligand). Many nuclear receptors are expected to have such domains, including the retinoid receptors, RAR and RXR, the glucocorticoid receptor GR, and the estrogen receptor ER. Based upon the TR's sequence, the domain is proposed to adopt an amphipathic helical structure. β-sheet or mixed secondary structures, could be present as activation domains in less related nuclear receptors.

Within the activation domain, the highly conserved motif ΦΦXEΦΦ, where Φ represents a hydrophobic residue, is proposed to mediate interactions between the receptors and transcriptional coactivators. Several proteins have been identified which bind the TR in a hormone-dependent fashion. One of these, Trip1, is related to a putative yeast coactivator Sug1, and also interacts with both the C-terminal activation domain and a subset of the basal transcriptional machinery, suggesting a role in transactivation by the TR. Other proteins, such as RIP140, SRC1, (Onate, S. A. et. al., *Science* 270:1354–1357 (1995)) and TF-1 (see also Ledouarim, B., et. al., *EMBO J*. 14:2020–2033 (1995)), and GRIP-1 (Heery, E., et al., *Nature* 387:733–736 (1997)) also interact with other nuclear receptors in a ligand dependent manner through the C-terminal domain. Binding of these proteins can be modulated using the TR ligands described herein especially those TR ligands with extensions that sterically hinder the interaction between the highly conserved motif and other proteins.

Figure 8:
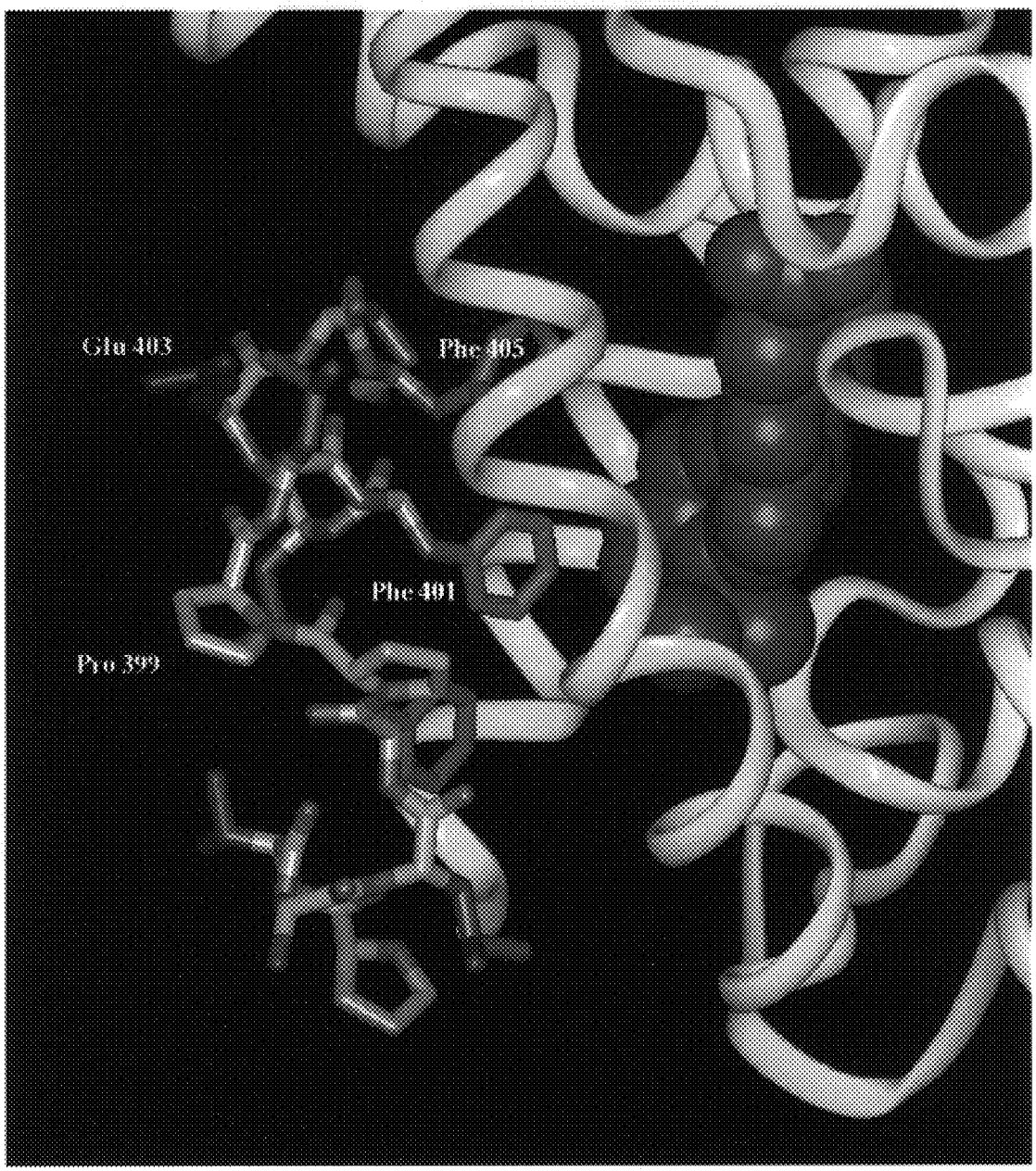
FIG. 8 is a ribbon drawing of the rat TR-α LBD showing the c-terminal activation domain to ligand. Residues which comprise the c-terminal activation domain (Pro393-Phe405) are depicted as a stick representation. Hydrophobic residues, particularly Phe401and Phe405 face inwards toward the ligand. Glu403 projects outward into the solvent.
Figure 9:
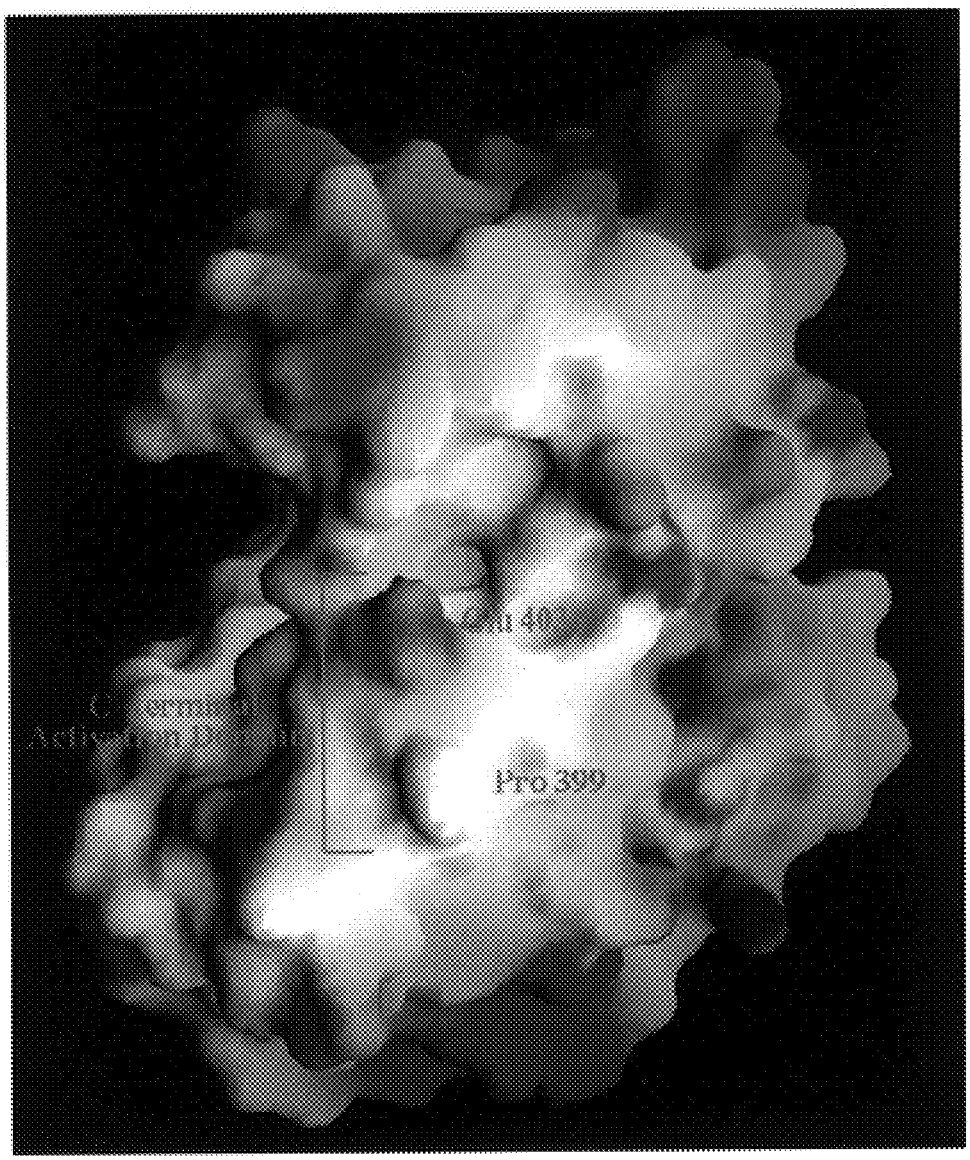
FIG. 9 is an electrostatic potential surface of the rat TR-α LBD, calculated using GRAPH.

The C-terminal activation domain of the TR forms an amphipathic helix, H12, which nestles loosely against the receptor to form part of the hormone binding cavity. The helix packs with the hydrophobic residues facing inward towards the hormone binding cavity, and the charged residues, including the highly-conserved glutamate, extending into the solvent, as shown in FIG. 8. The activation helix of TR LBD presents Phe 401 to the ligand binding cavity and permits direct coordination with the hormone i.e. such amino acids interact with the ligand forming a van der waals contact with the plane of the outer phenyl ring. Phe 405 also interacts with His 381, perhaps stabilizing its hydrogen bonding conformation, i.e. a favorable hydrogen bond interaction. Participation of Phe 401 and Phe 405 in binding hormone (explains how mutation of these residues decreases hormone binding affinity. Furthermore, the impact of these mutations on activation likely derives from a role in stabilizing the domain in the bound structure through increased hydrogen bond interaction of dipole interactions. Glu 403 extends into the solvent, emphasizing its critical role in transactivation. In its observed conformation, presented on the surface as an ordered residue, against a background of predominantly hydrophobic surface, Glu 403 is available to interact with activator proteins described herein, as shown in FIG. 9. The other charged residues, Glu 405 and Asp 406 are disordered, as the helix frays at Phe 405.

Two other sequences in the TR, τ2 and τ3, activate transcription when expressed as fusion proteins with a DNA-binding domain. The sequences, discovered in the TRB, correspond to TR-α residues Pro158–Ile168 in H1 (τ2), and Gly290–Leu3 19 in H8 and H9 (τ3). Unlike the C-terminal activation domain, τ2 and τ3 do not appear to represent modular structural units in the rat TR-α LBD, nor present a surface for protein-protein interactions: the critical aspartate/glutamate residues of τ3 are located on two separate helices, and do not form a single surface; the charged residues of τ2 are engaged in ion pair interactions with residues of the LBD. Thus, τ2 and τ3 may not function as activation domains in the context of the entire receptor.

Computational Methods for Designing a Nuclear Receptor LBD LIGAND

The elucidation of the three dimensional structure of a nuclear receptor ligand binding domain provides an important and useful approach for designing ligands to nuclear receptors using the computational methods described herein. By inspecting the FIGURES it can be determined that the nuclear receptor ligand is bound in a water inaccessible binding cavity in the LBD and that chemical moieties can be added to selected positions on the ligand. Such chemical modifications, usually extensions, can fill up the binding cavity represented in the FIGURES for a tighter fit (or less water) or can be used to disrupt or make contacts with amino acids not in contact with the ligand before the chemical modification was introduced or represented in a figure of the three dimensional model of the LBD. Ligands that interact with nuclear superfamily members can act as agonists, antagonists and partial agonists based on what ligand-induced conformational changes take place.

Agonists induce changes in receptors that place them in an active conformation that allows them to influence transcription, either positively or negatively. There may be several different ligand-induced changes in the receptor's conformation.

Antagonists, bind to receptors, but fail to induce conformational changes that alter the receptor's transcriptional regulatory properties or physiologically relevant conformations. Binding of an antagonist can also block the binding and therefore the actions of an agonist.

Partial agonists bind to receptors and induce only part of the changes in the receptors that are induced by agonists.

The differences can be qualitative or quantitative. Thus, a partial agonist may induce some of the conformation changes induced by agonists, but not others, or it may only induce certain changes to a limited extent.

Ligand-induced Conformational Changes

As described herein, the unliganded receptor is in a configuration that is either inactive, has some activity or has repressor activity. Binding of agonist ligands induces conformational changes in the receptor such that the receptor becomes more active, either to stimulate or repress the expression of genes. The receptors may also have nongenomic actions. Some of the known types of changes and/or the sequelae of these are listed herein.

Heat Shock Protein Binding

For many of the nuclear receptors ligand binding induces a dissociation of heat shock proteins such that the receptors can form dimers in most cases, after which the receptors bind to DNA and regulate transcription.

Nuclear receptors usually have heat shock protein binding domains that present a region for binding to the LBD and can be modulated by the binding of a ligand to the LBD. Consequently, an extended chemical moiety (or more) from the ligand that stabilizes the binding or contact of the heat shock protein binding domain with the LBD can be designed using the computational methods described herein to produce a partial agonist or antagonist. Typically such extended chemical moieties will extend past and away from the molecular recognition domain on the ligand and usually past the buried binding cavity of the ligand.

Dimerization and Heterodimerization

With the receptors that are associated with the hsp in the absence of the ligand, dissociation of the hsp results in dimerization of the receptors. Dimerization is due to receptor domains in both the DBD and the LBD. Although the main stimulus for dimerization is dissociation of the hsp, the ligand-induced conformational changes in the receptors may have an additional facilitative influence. With the receptors that are not associated with hsp in the absence of the ligand, particularly with the TR, ligand binding can affect the pattern of dimerization/heterodimerization. The influence depends on the DNA binding site context, and may also depend on the promoter context with respect to other proteins that may interact with the receptors. A common pattern is to discourage monomer formation, with a resulting preference for heterodimer formation over dimer formation on DNA.

Nuclear receptor LBDs usually have dimerization domains that present a region for binding to another nuclear receptor and can be modulated by the binding of a ligand to the LBD. Consequently, an extended chemical moiety (or more) from the ligand that disrupts the binding or contact of the dimerization domain can be designed using the computational methods described herein to produce a partial agonist or antagonist. Typically such extended chemical moieties will extend past and away from the molecular recognition domain on the ligand and usually past the buried binding cavity of the ligand.

DNA Binding

In nuclear receptors that bind to hsp, the ligand-induced dissociation of hsp with consequent dimer formation allows, and therefore, promotes DNA binding. With receptors that are not associated (as in the absence of ligand), ligand binding tends to stimulate DNA binding of heterodimers and dimers, and to discourage monomer binding to DNA. However, ligand binding to TR, for example, tends to decrease dimer binding on certain DNA elements and has minimal to no effect on increasing heterodimer binding. With DNA containing only a single half site, the ligand tends to stimulate the receptor's binding to DNA. The effects are modest and depend on the nature of the DNA site and probably on the presence of other proteins that may interact with the receptors. Nuclear receptors usually have DBDs that present a region for binding to DNA and this binding can be modulated by the binding of a ligand to the LBD. Consequently, an extended chemical moiety (or more) from the ligand that disrupts the binding or contact of the DBD can be designed using the computational methods described herein to produce a partial agonist or antagonist. Typically such extended chemical moieties will extend past and away from the molecular recognition domain on the ligand and usually past the buried binding cavity of the ligand.

Repressor Binding

Receptors that are not associated with hsp in the absence of ligand frequently act as transcriptional repressors in the absence of the ligand. This appears to be due, in part, to transcriptional repressor proteins that bind to the LBD of the receptors. Agonist binding induces a dissociation of these proteins from the receptors. This relieves the inhibition of transcription and allows the transcriptional transactivation functions of the receptors to become manifest.

Transcriptional Transactivation Functions

Ligand binding induces transcriptional activation functions in two basic ways. The first is through dissociation of the hsp from receptors. This dissociation, with consequent dimerization of the receptors and their binding to DNA or other proteins in the nuclear chromatin allows transcriptional regulatory properties of the receptors to be manifest. This may be especially true of such functions on the amino terminus of the receptors.

The second way is to alter the receptor to interact with other proteins involved in transcription. These could be proteins that interact directly or indirectly with elements of the proximal promoter or proteins of the proximal promoter. Alternatively, the interactions could be through other transcription factors that themselves interact directly or indirectly with proteins of the proximal promoter. Several different proteins have been described that bind to the receptors in a ligand-dependent manner. In addition, it is possible that in some cases, the ligand-induced conformational changes do not affect the binding of other proteins to the receptor, but do affect their abilities to regulate transcription.

Nuclear receptors or nuclear receptor LBDs usually have activation domains modulated in part by a co-activator/co-repressor system that coordinately functions to present a region for binding to DNA, and can be modulated by the binding of a ligand to the LBD. Consequently, an extended chemical moiety (or more) from the ligand that disrupts the binding or contact of the activation domain with co-activator and/or co-repressor can be designed using the computational methods described herein to produce a partial agonist or antagonist. For instance, an agonist can be designed and/or selected which (1) blocks binding and/or dissociates co-repressor, and/or (2) promotes binding and/or association of a co-activator. An antagonist can be designed which (1) promotes binding and/or association of co-repressor, and/or (2) promotes binding and/or association of co-activator. Ratios of agonists and antagonists may be used to modulate transcription of the gene of interest. Selection can be accomplished in binding assays that screen for ligands having the desired agonist or antagonist properties, including such ligands which induce conformational changes as described below. Suitable assays for such screening are described herein and in Shibata, H., et al. (*Recent Prog. Horm. Res.* 52:141–164 (1997)); Tagami, T., et al. (*Mol. Cell Biol.*

17(5):2642–2648 (1997)); Zhu, X G., et al. (*J. Biol. Chem.* 272(14):9048–9054 (1997)); Lin, B. C., et al. (*Mol. Cell Biol.* 17(10):6131–6138 (1997)); Kakizawa, T., et al. (*J. Biol. Chem.* 272(38):23799–23804 (1997)); and Chang, K. H., et al. (*Proc. Natl. Acad. Sci. USA* 94(17):9040–9045 (1997)). Typically such extended chemical moieties will extend past and away from the molecular recognition domain on the ligand and usually past the buried binding cavity of the ligand and in the direction of the activation domain, which is often a helix as seen in the three dimensional model shown in the FIGURES in two dimensions on paper or more conveniently on a computer screen.

Ligand-Induced Conformational Change

Plasma proteins bind hormones without undergoing a conformational change through a static binding pocket formed between monomers or domains. For example, the tetrameric thyroid-binding plasma protein transthyretin forms a solvent-accessible hormone-binding channel at the oligomer interface. The structure of the protein is unchanged upon binding hormone with respect to the appearance of a buried binding cavity with a ligand bound.

However, the structural role for a ligand bound to a nuclear receptor LBD, like rat TR-α LBD, predicts that the receptor would differ in the bound and unbound states. In the absence of hormone, the receptor would possess a cavity at its core, uncharacteristic of a globular protein. A ligand (e.g. hormone) completes the hydrophobic core of the active receptor after it binds to the nuclear receptor. Ligand binding by the receptor is a dynamic process, which regulates receptor function by inducing an altered conformation.

An exact description of the hormone-induced conformational changes requires comparison of the structures of the liganded and the unliganded TR. The structure of the unliganded human RXRα may substitute as a model for the unliganded TR. The rat TR-α LBD and human RXRα LBDs adopt a similar fold, and it is likely that the structural similarity extends to the conformational changes after ligand binding.

There are three major differences between the two structures, which indeed appear to be the result of ligand binding. First, the bound rat TR-α LBD structure is more compact, with the hormone tightly packed within the hydrophobic core of the receptor. By contrast, the unliganded human RXRα LBD contains several internal hydrophobic cavities. The presence of such cavities is unusual in folded proteins, and is likely a reflection of the unliganded state of the receptor. Two of these cavities were proposed as possible binding sites for 9-cis retinoic acid, though these multiple sites only partly overlap with the single buried binding cavity observed in the liganded rat TR-α LBD.

The second difference involves H11 in the rat TR-α LBD, which contributes part of the hormone binding cavity. H11, continuous in the rat TR-α LBD, is broken at Cys 432 in the RXR, forming a loop between H10 and H11 in the hRXRα. This residue corresponds to His381 in the TR, which provides a hydrogen bond to the outer ring hydroxyl of the ligand. Furthermore, the hormone binding cavity occupied by ligand in the rat TR-α LBD is interrupted in the hRXRα by the same loop, forming an isolated hydrophobic pocket in the RXR with H6 and H7. In the bound rat TR-α LBD, the corresponding helices H7 and H8 are contiguous with the binding pocket, and enclose the hormone binding cavity from below.

The third difference between the two receptors is the position of the C-terminal activation domain. While the C-terminal activation domain forms α-helices in both receptors, the domain in the rat TR-α LBD follows a proline-rich turn, and lies against the receptor to contribute part of the binding cavity. In contrast, the activation domain in the unliganded hRXRα, is part of a longer helix which projects into the solvent.

These differences lead to a model for an alternate conformation of the TR LBD assumed in the absence of ligand. In the unliganded TR, the subdomain of the receptor surrounding the hormone binding cavity is loosely packed, with the binding cavity occluded by a partly unstructured H11 providing a partial core for the receptor.

Upon binding hormone, residues which form a coil in the unbound receptor engage the ligand, and continues H11. The ordering of H11 could unblock the hydrophobic cavity, allowing H7 and H8 to interact with hormone. The extended hydrophobic cavity then collapses around the hormone, generating the compact bound structure.

It is possible to predict ligand-induced conformational changes in the C-terminal activation domain that rely, in part, on an extended structure in the unliganded TR that repacks upon ligand binding. The ligand-induced conformation change can be subtle since the amino acid sequence of the rat TR-α in the turn (393-PTELFPP-399) significantly reduces the propensity of the peptide chain of the rat TR-α to form an α-helix and therefore repacking can be accomplished with a minor change in volume.

After the ligand-induced conformational change occurs, it is likely that the conformation of the C-terminal activation domain in the bound structure changes packing compared to the unbound form of the receptor. Binding of the ligand improves the stability of the activation domain. The activation domain packs loosely even in the bound structure, as measured by the distribution of packing interactions for the entire LBD. The packing density for the activation domain, defined as the number of atoms within 4.5 Å, is 1.5 standard deviations below the mean. For comparison, another surface helix, H1, is 0.5 standard deviations below the mean and the most poorly packed part of the structure, the irregular coil from residues Ile196–Asp206, is 2.0 standard deviations below the mean. Moreover, the majority of packing contacts for the C-terminal domain in the bound receptor are provided either by residues which interact with ligand, such as His381, or by the ligand itself. The conformation of these residues can be expected to be different in the bound and unbound receptors, and by extension the conformation of C-terminal activation domain which relies upon these interactions. Without the stabilization provided by a bound ligand, it is likely that the C-terminal activation domain is disordered prior to hormone binding.

The interrelation of ligand-induced conformational changes is evident as described herein. For example, His381 from H11 and Phe405 from H12 interact in the bound structure to provide a specific hydrogen bond to the phenolic hydroxyl. The ligand-induced changes which affect H11 and H12 are reinforcing, and lead to the formation of the compact, bound state.

Comparison of the TR-α and TR-β LBD structures shows similar packing of the helices when complexed with the ligand Triac.

COMPUTATIONAL METHODS USING THREE DIMENSIONAL MODELS AND EXTENSIONS OF LIGANDS

The three-dimensional structure of the liganded TR receptor is unprecedented, and will greatly aid in the development of new nuclear receptor synthetic ligands, such as thyroid receptor antagonists and improved agonists, especially those that bind selectively to one of the two TR isoforms (α or β).

In addition, this receptor superfamily is overall well suited to modern methods including three-dimensional structure elucidation and combinatorial chemistry such as those disclosed in EP 335 628, U.S. Pat. No. 5,463,564, which are incorporated herein by reference. Structure determination using X-ray crystallography is possible because of the solubility properties of the receptors. Computer programs that use crystallography data when practicing the present invention will enable the rational design of ligand to these receptors. Programs such as RASMOL can be used with the atomic coordinates from crystals generated by practicing the invention or used to practice the invention by generating three dimensional models and/or determining the structures involved in ligand binding. Computer programs such as INSIGHT and GRASP allow for further manipulation and the ability to introduce new structures. In addition, high throughput binding and bioactivity assays can be devised using purified recombinant protein and modern reporter gene transcription assays described herein and known in the art in order to refine the activity of a CDL.

Generally the computational method of designing a nuclear receptor synthetic ligand comprises two steps:

1) determining which amino acid or amino acids of a nuclear receptor LBD interacts with a first chemical moiety (at least one) of the ligand using a three dimensional model of a crystallized protein comprising a nuclear receptor LBD with a bound ligand, and 2) selecting a chemical modification (at least one) of the first chemical moiety to produce a second chemical moiety with a structure to either decrease or increase an interaction between the interacting amino acid and the second chemical moiety compared to the interaction between the interacting amino acid and the first chemical moiety.

As shown herein, interacting amino acids form contacts with the ligand and the center of the atoms of the interacting amino acids are usually 2 to 4 angstroms away from the center of the atoms of the ligand. Generally these distances are determined by computer as discussed herein and in McRee 1993, however distances can be determined manually once the three dimensional model is made. Examples of interacting amino acids are described in Appendix 2. See also Wagner et al., Nature 378(6558):670–697 (1995) for stereochemical figures of three dimensional models. More commonly, the atoms of the ligand and the atoms of interacting amino acids are 3 to 4 angstroms apart. The invention can be practiced by repeating steps 1 and 2 to refine the fit of the ligand to the LBD and to determine a better ligand, such as an agonist. As shown in the FIGURES the three dimensional model of TR can be represented in two dimensions to determine which amino acids contact the ligand and to select a position on the ligand for chemical modification and changing the interaction with a particular amino acid compared to that before chemical modification. Structural comparison of LBD isoforms complexed with the same or similar ligand permit identification of fiducial and adjustable amino acids that can be exploited in designing isoform-specific ligands through chemical modification. "Fiducial" refers to amino acids that form rigid features of the ligand binding cavity. "Adjustable" refers to amino acids that form less rigid features of the ligand binding cavity. The chemical modification may be made using a computer, manually using a two dimensional representation of the three dimensional model or by chemically synthesizing the ligand. The three dimensional model may be made using Appendix 2 and the FIGURES. As an additional step, the three dimensional model may be made using atomic coordinates of nuclear receptor LBDs from crystallized protein as known in the art, see McRee 1993 referenced herein.

The ligand can also interact with distant amino acids after chemical modification of the ligand to create a new ligand. Distant amino acids are generally not in contact with the ligand before chemical modification. A chemical modification can change the structure of the ligand to make as new ligand that interacts with a distant amino acid usually at least 4.5 angstroms away from the ligand. Often distant amino acids will not line the surface of the binding cavity for the ligand, as they are too far away from the ligand to be part of a pocket or surface of the binding cavity.

The interaction between an atom of a LBD amino acid and an atom of an LBD ligand can be made by any force or attraction described in nature. Usually the interaction between the atom of the amino acid and the ligand will be the result of a hydrogen bonding interaction, charge interaction, hydrophobic interaction, van der waals interaction or dipole interaction. In the case of the hydrophobic interaction it is recognized that this is not a per se interaction between the amino acid and ligand, but rather the usual result, in part, of the repulsion of water or other hydrophilic group from a hydrophobic surface. Reduction or enhancement of the interaction of the LBD and a ligand can be measured by standard binding procedures, calculating or testing binding energies, computationally or using thermodynamic or kinetic methods as known in the art.

Chemical modifications will often enhance or reduce interactions of an atom of a LBD amino acid and an atom of an LBD ligand. Steric hinderance will be a common means of changing the interaction of the LBD binding cavity with the activation domain. Chemical modifications are preferably introduced at C—H, C— and C—OH position in ligands, where the carbon is part of the ligand structure which remains the same after modification is complete. In the case of C—H, C— could have 1, 2 or 3 hydrogens, but usually only one hydrogen will be replaced. The H or OH are removed after modification is complete and replaced with the desired chemical moiety.

Because the thyroid receptor is a member of the larger superfamily of hormone-binding nuclear receptors, the rules for agonist and antagonist development will be recognized by one skilled in the art as useful in designing ligands to the entire superfamily. Examining the structures of known agonists and antagonists of the estrogen and androgen receptors supports the generality of antagonist mechanism of action as shown in FIG. 10.

The overall folding of the receptor based on a comparison of the reported structure of the unliganded RXR and with amino acid sequences of other superfamily members reveals that the overall folding of receptors of the superfamily is similar. Thus, it is predicted from the structure that there is a general pattern of folding of the nuclear receptor around the agonist or antagonist ligand.

The three dimensional structure of a nuclear receptor with a ligand bound leads to the nonobvious observation that a nuclear receptor folds around agonist ligands, as the binding cavity fits the agonist, especially the agonist's molecular recognition domain, and antagonists commonly have chemical structures that extend beyond the ligand, especially the agonist, and would prohibit folding of the receptor around the ligand to form a buried binding cavity or other groups that have the same effect. The location of the extension could affect the folding in various ways as indicated by the structure. Such extensions on antagonists are shown in FIG. 10 for various receptors and compared to the corresponding agonist.

For example, an extension towards the carboxy-terminal activation helix affects the packing/folding of this helix into the body of the receptor. This in turn can affect the ability of this portion of the nuclear receptor to interact with other proteins or other portions of the receptor, including transcriptional transactivation functions on the opposite end of the linear receptor, or the receptor's amino terminus that may interact directly or indirectly with the carboxy-terminal transactivation domain (including helix 12). Extensions in this direction can also affect the packing of helix 11 of TR (or its analogous helix in nuclear receptors) into the body of the receptor and selectively affect dimerization and heterodimerization of receptors. An extension pointing towards helix 1 can affect the relationship of the DNA binding domain and hinge regions of the receptors with the ligand binding domain and selectively or in addition affect the receptors' binding to DNA and/or interactions of receptors with proteins that interact with this region of the receptor. Other extensions towards helix 11 can be made to affect the packing of this helix and helices 1 and 10 and thereby homo- and hetero-dimerization. Such chemical modifications can be assessed using the computational methods described herein. It is also possible that, in some cases, extensions may protrude through the receptor that is otherwise completely or incompletely folded around the ligand. Such protruding extensions could present a steric blockade to interactions with co-activators or other proteins.

The three dimensional structure with the ligand buried in the binding cavity immediately offers a simple description of a nuclear receptor that has a binding cavity that contains hinges and a lid, composed of one or more structural elements, that move to accommodate and surround the ligand. The ligand to TR can be modified on specific sites with specific classes of chemical groups that will serve to leave the lid and hinge region in open, partially open or closed states to achieve partial agonist or antagonist functions. In these states, the biological response of the TR is different and so the structure can be used to design particular compounds with desired effects.

Knowledge of the three-dimensional structure of the TR-T$_3$ complex leads to a general model for agonist and antagonist design. An important novel feature of the structural data is the fact that the T$_3$ ligand is completely buried within the central hydrophobic core of the protein. Other ligand-receptor complexes belonging to the nuclear receptor superfamily will have a similarly buried ligand binding site and therefore this model will be useful for agonist/antagonist design for the entire superfamily.

When design of an antagonist is desired, one needs either to preserve the important binding contacts of natural hormone agonist while incorporating an "extension group" that interferes with the normal operation of the ligand-receptor complex or to generate the requisite binding affinity through the interactions of the extensions with receptor domains.

The model applied to antagonist design and described herein is called the "Extension Model." Antagonist compounds for nuclear receptors should contain the same or similar groups that facilitate high-affinity binding to the receptor, and in addition, such compounds should contain a side chain which may be large and/or polar. This side chain could be an actual extension, giving it bulk, or it could be a side group with a charge function that differs from the agonist ligand. For example, substitution of a CH$_3$ for CH$_2$OH at the 21-position, and alteration at the 11-position from an OH group to a keto group of cortisol generates glucocorticoid antagonist activity (Robsseau, G. G., et. al., *J. Mol. Biol.* 67:99–115 (1972)). However, in most cases effective antagonists have more bulky extensions. Thus, the antiglucocorticoid (and antiprogestin) RU486 contains a bulky side group at the 11-position (Horwitz, K. B. *Endocrine Rev.* 13:146–163 (1992)). The antagonist compound will then bind within the buried ligand binding site of the receptor with reasonably high affinity (100 nM), but the extension function will prevent the receptor-ligand complex from adopting the necessary conformation needed for transcription factor function. The antagonism (which could be in an agonist or antagonist) may manifest itself at the molecular level in a number of ways, including by preventing receptor homo/heterodimer formation at the HRE, by preventing coactivator binding to receptor monomers, homodimers or homo/heterodimers, or by a combination of these effects which otherwise prevent transcription of hormone responsive genes mediated by ligand-induced effects on the HRE. There are several antagonist compounds for nuclear receptors in the prior art (see also Horwitz, K. B., *Endocrine Rev.* 13:146–163 (1992), Raunnaud J. P. et. al., *J. Steroid Biochem.* 25:811–833 (1986), Keiel S., et. al., *Mol. Cell. Biol.* 14:287–298 (1994) whose antagonist function can be explained by the extension hypothesis. These compounds are shown in FIG. 10 along with their agonist counterparts. Each of these antagonists contains a large extension group attached to an agonist or agonist analogue core structure. Importantly, these antagonist compounds, were discovered by chance and not designed with a structure-function hypothesis such as the extension principle.

One method of design of a thyroid antagonist using the extension hypothesis is provided below as a teaching example. The three-dimensional structure of the TR-α Dimit complex combined with structure-activity data published in the prior art, especially those reference herein, can be used to establish the following ligand-receptor interactions which are most critical for high-affinity ligand binding. A physical picture of these interactions is shown in FIG. 6. The figure describes the isolated essential contacts for ligand binding. Because the ligand is buried in the center of the receptor, the structural spacing between these isolated interactions is also important. Thus, our present knowledge of this system dictates that, for this example, a newly designed ligand for the receptor must contain a thyronine structural skeleton, or two substituted aryl groups joined by a one-atom spacer.

The general structure for an antagonist designed by the extension hypothesis is exemplified in the following general description of the substituents of a TR antagonist (referring to Formula 1): R1 can have anionic groups such as a carboxylate, phosphonate, phosphate, sulfate or sulfite and is connected to the ring with a 0 to 3 atom linker, comprising) one or more C, O, N, S atoms, and preferably a 2 carbon linker. Such R1 can be optionally substituted with an amine (e.g. —NH2). R3 and R5 are small hydrophobic groups such as —Br, —I, or —CH3. R3 and R5 can be the same substituents or different. R$_3$' can be a hydrophobic group that may be larger than those of R3 and R5, such as —I, —CH3, -isopropyl, -phenyl, -benzyl, 5 and 6 ring heterocycles. R$_4$' is a group that can participate in a hydrogen bond as either a donor or acceptor. Such groups include —OH, —NH$_2$, and —SH. R$_5$' is an important extension group that makes this compound an antagonist. R$_5$' can be a long chain alkyl (e.g. 1 to 9 carbons, straight chain or branched), aryl (benzyl, phenyl and substituted benzyl and phenyl rings (e.g with halogen, alkyl (1 and 5 carbons) and optionally connected to the ring by a —CH2—), heterocycle (e.g. 5 or 6 atoms, preferably 5 carbons and 1 nitrogen, or five carbons), which can optionally include polar (e.g. —OH, —NH$_2$, and —SH), cationic (e.g. —NH3, N(CH)3), or anionic (carboxylate, phosphonate, phosphate or sulfate) groups. $R_5'$ can also be a polar (e.g. —OH, —NH$_2$, and —SH), cationic (e.g. —NH3, —N(CH3)3), and anionic (carboxylate, phosphonate, phosphate or sulfate) groups. X is the spacer group that appropriately positions the two aromatic rings. This group is usually a one-atom spacer, such as O, S, SO, SO2, NH, NZ where Z is an alkyl, CH2, CHOH, CO, C(CH3)OH, and C(CH3)(CH3). X also may be NR$_7$, CHR$_7$, CR$_7$, R$_7$, where R$_7$, is an alkyl, aryl or 5- or 6-membered heterocyclic aromatic. R2, R6, R2' and R6' can be —F, and —Cl and are preferably H.

A TR ligand can also be described as a substituted phenylated 3,5 diiodo tyrosine with substituted R5' and R3' groups. R5' can be a long chain alkyl (e.g. 4 to 9 carbons, straight chain or branched), aryl (benzyl, phenyl and substituted benzyl and phenyl rings (e.g with halogen, alkyl (1 and 5 carbons) and optionally connected to the ring by a —CH2—), heterocycle (e.g. 5 or 6 atoms, preferably 5 carbons and 1 nitrogen, or five carbons), which can optionally include polar (e.g. —OH, —NH$_2$, and —SH), cationic (e.g. —NH3, N(CH)3), or anionic (carboxylate, phosphonate, phosphate or sulfate) groups. R5' can also be a polar (e.g. —OH, —NH$_2$, and —SH), cationic (e.g. —NH3, N(CH)3), and anionic (carboxylate, phosphonate, phosphate or sulfate) groups. R3' can be -IsoPr, halogen, —CH3, alkyl (1 to 6 carbons) or aryl (benzyl, phenyl and substituted benzyl and phenyl rings (e.g with halogen, alkyl (1 and 5 carbons) and optionally connected to the ring by a —CH2—), heterocycle (e.g. 5 or 6 atoms, preferably 5 carbons and 1 nitrogen, or five carbons), which can optionally include polar (e.g. —OH, —NH$_2$, and —SH), cationic (e.g. —NH3, N(CH)3), or anionic (carboxylate, phosphonate, phosphate or sulfate) groups.

A TR antagonist can also be a modified $T_3$ agonist (having a biphenyl structure) wherein $R_5'$ is alkyl, aryl, 5- or 6-membered heterocyclic aromatic, heteroalkyl, heteroaryl, arylalkyl, heteroaryl alkyl, polyaromatic, polyheteroaromatic, polar or charged groups, wherein said $R_5'$ may be substituted with polar or charged groups. The R5' groups are defined, as described herein.

Using these methods the ligands of this example preferably have the following properties:

1. The compounds should bind to the TR with high affinity (for example 100 nM).

2. The compounds should bind the receptor in the same basic orientation as the natural hormone.

3. The extension group R5' should project toward the activation helix (C-terminal helix) of the receptor.

4. The appropriate substituent at R5' should perturb the activation helix from its optimal local structure needed for mediating transcription.

Antagonists may also be designed with multiple extensions in order to block more than one aspect of the folding at any time.

TR ligands (e.g. super agonists) can be designed (and synthesized) to enhance the interaction of at least one amino acid with at least one chemical moiety on the ligand's molecular recognition domain. One method is to enhance the charge and polar interactions by replacing the carboxylate of $T_3$ (R1 position) with phosphonate, phosphate, sulfate or sulfite. This enhances the interaction with Arg 262, Arg 266 and Arg 228. The interaction of at least one amino acid with at least one chemical moiety on the ligand's molecular recognition domain can also be enhanced by increasing the size of R1 group to fill the space occupied by water when Dimit is bound (referring to R1). Preferably the group has a complementary charge and hydrophobicity to the binding cavity.

Another way of improving the interaction of at least one amino acid with at least one chemical moiety on the ligand's molecular recognition domain is to restrict the conformation of the dihedral angle between the two phenyl rings of the thyronine ligand in solution. In solution the planes of two phenyl rings are orthogonal where the dihedral angle is 90°. In the TR Dimit structure, the dihedral angle is close to 60°. A TR ligand design that fixes the angle between the two phenyl rings will lead to tighter binding. Such a ligand may be made by connecting the R6' and the R5 positions of a thyronine or a substituted thyronine-like biphenyl. The size of the cyclic connection can fix the angle between the two phenyl rings. Referring specifically to Formula 1, the following cyclic modifications are preferred: 1) $R_5$ is connected to $R_6'$, 2) $R_3$ is connected to $R_2'$ or 3) $R_5$ is connected to $R_6'$ and $R_3$ is connected to R2'. The connections can be made by an alkyl or heteroalkyl chain having between 1 to 6 atoms and preferably from 2 to 4 carbon atoms or other atoms. Any position of the heteroalkyl chain can be N, O, P or S. The S and P heteroatoms along said heteroalkyl chain are in any of their possible oxidative states. The N heteroatom or any carbon along the alkyl or heteroalkyl chain may have one or more Z substituents, wherein Z is alkyl, heteroalkyl, aryl, heteroaryl, 5- or 6-membered heterocyclic aromatic. These compounds can be claimed with the proviso that Formula 1 does not include any prior art compound as of the priority filing date of this application.

The interaction of at least one amino acid with at least one chemical moiety on the ligand's molecular recognition domain can also be enhanced by selecting a chemical modification that fills the unfilled space between a TR ligand and the LBD in the area of the bridging oxygen (such as in T3, Triac or Dimit). Thus, a slighter larger moiety that replaces the ether oxygen can enhance binding. Such a linker may be a mono- or geminal-disubstituted carbon group. A group approximately the same size as oxygen but with greater hydrophobicity is preferred as well as small, hydrophobic groups for the disubstituted carbon.

Compounds of Formula I or derivatives thereof that modulate TR activity also may be designed and selected to interact with a conformationally constrained structural feature of a TR LBD that is conserved among TR LBD isoforms to increase TR-specific selectivity. Conserved structural features of a TR LBD include residues found in equivalent positions of TR LBD isoforms which interact with a conserved structural feature of a compound comprising the biphenyl scaffold (φ-X-φ) or a single phenyl scaffold (φ-X or X-φ) of Formula I. Conformationally constrained structural features of a TR LBD include residues that have their natural flexible conformations fixed by various geometric and physical-chemical constraints, such as local backbone, local side chain, and topological constraints. These types of constraints are exploited to restrict positioning of atoms involved in receptor-ligand recognition and binding. For example, comparison of atomic models of TR LBD isoforms bound to thyronine and thyronine-like ligands reveal that certain residues which contact the ligands are restricted to particular topological shapes and angles of rotation about bonds. These include Met259, Leu276, Leu292, His381, Gly290, Ile221, and Phe401 of TR-α. The corresponding positions in TR-β include Met313, Leu330, Leu346, His435, Gly344, Ile275 and Phe455, respectively.

Selectivity imparted by conformationally constrained features of both the receptor and compound are of particular interest. For example, compounds of Formula I comprising constrained cyclic carbons and substituent groups that interact with a constrained feature of a TR LBD can be exploited to further increase binding specificity while reducing the potential for cross-over interaction with other receptors. These include hydrophobic and/or hydrophilic contacts between constrained residues of a TR LBD and atomic groups of the following constituents of the compound in reference to Formula I: (i) the biphenyl rings; (ii) the R3-substituent; (iii) the R3'-substituent; and (iv) the R4'-substituent.

For example, contacts to the phenyl moiety comprising the R1, R2, R3, R5 and R6 substituents, i.e., the ring proximal to the polar pocket (the "inner ring"), include a cycle carbon atom that interacts with an atom of a hydrophobic residue of a TR LBD, such as a carbon and oxygen atom of Met259 and a carbon atom of Leu276 of TR-α, or Met313 and Leu330 of TR-β, where the cycle carbon is about 3.0 to 4.0A from the atom of the hydrophobic group. For example, comparison of TR-α complexed with T3 and TR-β complexed with GC-1 reveals the following conserved inner ring contacts:

| Ligand | TR LBD | | |
|---|---|---|---|
| T3/Atom | TR-α Residue | Atom | Distance |
| C11 | Met259 | C | 3.95 |
| C11 | Met259 | O | 3.59 |
| C11 | Met259 | CB | 3.77 |
| C7 | Leu276 | CD2 | 3.80 |
| C9 | Leu276 | CD2 | 3.70 |
| GC1/Atom | TR-β Residue | Atom | Distance |
| C11 | Met313 | C | 3.85 |
| C11 | Met313 | O | 3.41 |
| C11 | Met313 | CB | 3.79 |
| C7 | Leu330 | CD2 | 3.56 |
| C9 | Leu330 | CD2 | 3.63 |

Contacts to the phenyl moiety comprising the R2', R3', R4', R5' and R6' substituents, i.e., the ring distal to the polar pocket (the "outer ring"), include a cyclic carbon atom that interacts with an atom of a hydrophobic residue of a TR LBD, such as a carbon atom of Leu292 of TR-α, or Leu346 of TR-β, where the cyclic carbon atom is about 3.0 to 4.0A from the atom of the hydrophobic residue. For example, comparison of TR-α complexed with T3 and TR-β complexed with GC-1 reveals the following conserved outer ring contacts:

| Ligand | TR LBD | | |
|---|---|---|---|
| T3/Atom | TR-α Residue | Atom | Distance |
| C6 | Leu292 | CD2 | 3.58 |
| C8 | Leu292 | CD2 | 3.50 |
| GC1/Atom | TR-β Residue | Atom | Distance |
| C6 | Leu346 | CD2 | 3.77 |
| C8 | Leu346 | CD2 | 3.80 |

Contacts to the R3-substituent include an atom that interacts with a carbon atom of a hydrophobic residue of a TR LBD, such as Ile221 of TR-α, or Ile275 of TR-β, where the R3-substituent atom is about 3.0 to 4.0A from the carbon atom of the hydrophobic residue. For example, comparison of TR-α complexed with T3 and TR-β complexed with GC-1 reveals the following conserved R3-substituent contacts:

| Ligand | TR LBD | | |
|---|---|---|---|
| T3/Atom | TR-α Residue | Atom | Distance |
| I1 | Ile221 | CG1 | 4.01 |
| GC1/Atom | TR-β Residue | Atom | Distance |
| C19 | Ile275 | CG1 | 3.98 |

Contacts to the R3'-substituent include an atom that interacts with an atom of a hydrophobic or hydrophilic residue of a TR LBD, such as an oxygen atom of Gly290 of TR-α, or Gly344 of TR-β, where the R3'-substituent atom is about 3.0 to 4.0A from the atom of the hydrophobic or hydrophilic residue. For example, comparison of TR-α complexed with T3 and TR-β complexed with GC-1 reveals the following conserved R4'-substituent, phenolic hydroxyl contacts:

| Ligand | TR LBD | | |
|---|---|---|---|
| T3/Atom | TR-α Residue | Atom | Distance |
| I2 | Gly290 | O | 3.50 |
| GC1/Atom | TR-β Residue | Atom | Distance |
| C18 | Gly344 | O | 3.60 |

Contacts to the R4'-substituent comprising a phenolic hydroxyl include carbon and oxygen atoms that interact with a hydrophobic or hydrophilic residue of a TR LBD, such as a carbon and nitrogen atom of His381 of TR-α, or His435 of TR-β, where the R4'-substituent atom is about 2.0 to 4.0A from an atom of the hydrophobic or hydrophilic residue. For example, comparison of TR-α complexed with T3 and TR-β complexed with GC-1 reveals the following conserved R4'-substituent, phenolic hydroxyl contacts:

| Ligand | TR LBD | | |
|---|---|---|---|
| T3/Atom | TR-α Residue | Atom | Distance |
| C10 | His381 | CD2 | 3.97 |
| O1 | His381 | CD2 | 3.39 |
| O1 | His381 | CE1 | 3.82 |
| C8 | His381 | NE2 | 3.47 |
| C10 | His381 | NE2 | 3.55 |
| O1 | His381 | NE2 | 2.70 |
| GC1/Atom | TR-β Residue | Atom | Distance |
| C10 | His435 | CD2 | 3.89 |
| O1 | His435 | CD2 | 3.64 |
| O1 | His435 | CE1 | 3.79 |
| C8 | His435 | NE2 | 3.44 |
| C10 | His435 | NE2 | 3.33 |
| O1 | His435 | NE2 | 2.77 |

Contacts to the R4'-substituent also may include an atom that interacts with a carbon atom of a hydrophobic residue of a TR LBD, such as Phe401 of TR-α, or Phe455 of TR-β, for defining agonist activity, i.e., proper presentation of helix-12 (H12) of the TR LBD following ligand binding. The R4'-substituent atom is about 3.0 to 4.0A from the carbon atom of the hydrophobic group. For example, comparison of TR-α complexed with T3 and TR-β complexed with GC-1 reveals the following conserved R4'-substituent contacts:

| Ligand | TR LBD | | |
|---|---|---|---|
| T3/Atom | TR-α Residue | Atom | Distance |
| O1 | Phe401 | CE1 | 3.52 |
| O1 | Phe401 | CZ | 3.32 |
| GC1/Atom | TR-β Residue | Atom | Distance |
| O1 | Phe455 | CE1 | 3.40 |
| O1 | Phe455 | CZ | 3.22 |

Comparison of atomic models of TR LBD isoforms complexed with the same and/or different ligands therefore facilitates the identification of new compounds that fit spacially and preferentially into a TR LBD. Modeling, comparison of TR-ligand overlays, and comparison of TR LBD isoforms also permit identification of conformationally conserved structural features of TR LBD/ligand contacts. Exploiting conformational constraints of the LBD-ligand interaction identified by such methods therefore improves the design and identification of new compounds having increased selectivity for binding a particular type of nuclear receptor, such as TR.

TR-α AND TR-β SELECTIVITY FOR THE THYROID HORMONE RECEPTOR

Using the method described herein ligands can be designed that selectively bind to the alpha more than the beta TR or vice versa. The X-ray crystallographic structure of the rat TR-α LBD provides insight into design of such ligands.

The three dimensional structure reveals that the major difference between the TR-α and TRβ in the ligand binding cavity resides in amino acid Ser 277 (with the side group —CH2OH) in the rat TR-α and whose corresponding residue is 331, asparagine (with the side group —CH2CONH2), in the human TR-β. The side chain in human TR-β is larger, charged and has a different hydrogen bonding potential, which would allow the synthesis of compound; that discriminate between this difference. The Ser277 (Asn331 in TR-β) forms part of the polar pocket of the TR LBD, indicating that for TR-α versus TR-β discrimination, ligands can be designed to contain chemical modification of the R1-substituent with reference to Formula I that exploit this difference.

For example, in the complex of TR-α with Triac, Ser277 does not participate in ligand binding. The absence of a role for Ser277 (Asn331 in beta) is consistent with the equal affinity of Triac for the alpha and beta isoforms, and indirectly supports the contention that alpha/beta selectivity resides in the amino acid substitution Ser277 to Asn331 and its interaction with Arg228. The effect of the amino acid substitution is further evident when the interactions of Asn331 and Arg282 in the structures of the TR-β LBD complexed with GC-1 or Triac are compared with those of Ser277 and Arg228 in the TR-α LBD. In the complex with GC-1, Asn331 forms a hydrogen bond to Arg282, which in turn forms a hydrogen bond with the carboxylate of GC-1, a pattern that resembles the interactions of Ser277 and Arg228 in the complexes of the TR-α LBD complexed with $T_3$ or Triac. However, in the complex of TR-β with Triac, Arg282 rotates away from Asn331 and the ligand, instead forming hydrogen bonds to residues Thr287 and Asp291 of H3. Therefore, differences exist between the two isoforms in the conformation of the polar pocket, depending on the nature of the ligand R1-substituent, indicating that certain substituents may interact preferentially with the conformation of a given isoform.

Comparing overlays of various ligands bound to the TR-α versus TR-β LBDs shows the positioning of the ligand to be very similar. Surprisingly, comparison of the volume and area for the TR-α and TR-β LBDs bound by the same or different ligands unexpectedly shows that the cubic space or volume available for accommodating ligand binding by the TR-β LBD (645±28.28 Å$^3$) is larger and more flexible than that of the TR-α LBD (596.25±7.97 Å$^3$) (Table 1). The volume of the ligand binding cavity for TR-α varies over a narrow range of about 8+, with a maximum difference of about 16+. In contrast, the volume of the ligand binding cavity for TR-β differs by nearly 40+ between the complexes with GC-1 and Triac. There also is a difference in the volume of the ligand binding cavity when comparing the same ligand bound to TR-α and TR-β. For example, TR-α and TR-β complexed with Triac differ in LBD volume by about 36 Å$^3$. Comparison of TR-α and TR-β bound to Dimit and GC-1, respectively, which ligands have similar volume/area and superpositioned architecture, show that the difference in LBD volume is about 75 Å$^3$. These differences are attributed primarily to variable movement and interaction of side chain groups with ligand substituents of the phenyl moiety (φ) of the biphenyl scaffold (φ-X-φ) located proximal to the polar pocket, e.g., R1-substituents in reference to Formula I. In contrast, the volume available in the hydrophobic pocket for both the TR-α and TR-β LBDs is substantially the same. For example, binding of Triac to the TR-β LBD displaces the side chain of Arg 282 providing approximately 60 Å$^3$ in the polar pocket cavity, exposing the polar pocket to bulk solvent exchange. For GC1 bound to the TR-β LBD, approximately 14 Å$^3$ is due to side chain motion of Met310, and approximately 44 Å$^3$ is due to side chain motion of Arg320, the combination of which increases the size of the polar pocket in the TR-β LBD. This extra pliability also may explain the absence of ordered water in the polar pocket of TR-β LBD bound to Triac or GC-1, which is in contrast to the ordered water found in the polar pocket of TR-α LBD bound to Dimit, IpBr2 or T3.

TABLE 1*

| | rTR-α | | | | hTR-β | |
|---|---|---|---|---|---|---|
| | Dimit | Triac | IpBr2 | T3 | GC-1 | Triac |
| TR LBD (vol Å$^3$/ area Å$^2$) | 590/456 | 589/440 | 601/474 | 605/472 | 665/575 | 625/474 |
| Ligand (vol Å$^3$/ area Å$^2$) | 303/314 | 333/326 | 326/330 | 355/346 | 294/310 | 333/326 |
| Complementarity | 0.65 | 0.68 | 0.66 | 0.71 | 0.61 | 0.67 |

*TR LBD volume and area are reported in Angstroms measured by GRASP. Complementarity is determined as defined in Lawrence et al., J. Mol. Biol. 234: 946–950 (1993).

Residue Ser277 in TR-α and the corresponding residue Asn331 of TR-β also contribute to the volumetric differences observed in the polar pockets of these two TR isoforms. And substitution of the Asn331 of hTR-β with serine has the affect of modifying ligand binding affinity of TR-β so that it resembles that of TR-α (See Example 5). Taken together, differences in hydrogen bonding of atoms of the side chain group of. Ser277 in TR-α and Asp331 in TR-β extending from the equivalent backbone position in these TR LBDs and the more restricted polar pocket of the TR-α LBD further supports the concept of designing TR LBD isoform-specific ligands having substituents that fit spacially and preferentially into the polar pocket of either the TR-α or TR-β LBDs. Exploitation of this difference provides an additional means for computational design of isoform-specific TR agonists and antagonists.

In terms of ligand design, these differences mean that for β-selective ligands, some or all of the following differences should be exploited:

1. The presence of a larger side chain asparagine.
2. The ability of the carbonyl group on the side chain to provide a strong hydrogen bond acceptor.
3. The ability of the amido group on the side chain to provide a two hydrogen bond donors.
4. Adjustment of polarity to reorganize the trapped water in the T3 pocket.
5. Greater size and flexibility of the polar pocket.

In terms of pharmaceutical design, these differences mean that for α-selective ligands, some or all of the following differences should be exploited:

1. The presence of a smaller side group.
2. The ability of the hydroxyl on the —$CH_2OH$ side group carbonyl group on the side chain to provide a weak hydrogen donor.
3. Adjustment of polarity to reorganize the trapped water in the T3 pocket.
4. Smaller size and limited flexibility of the polar pocket.

In both cases these differences can be exploited in a number of ways. For example, they can also be used with a software set for construction of novel organic molecules such as LUDI from Biosym-MSI. An example of designing TR-β selective ligands is increasing the polarity of a ligand substituent located in the polar pocket of a TR LBD through addition of one or more ligand groups having a formal negative charge and/or negative dipole charge that interacts with a formal positive charge and/or positive dipole charge of a group in the polar pocket of the LBD. This exploits preferential interactions, such as with the additional positive charge contributed by Asn 331 in TR-β. Another example of a TR-β selective ligand is one that comprises one or more groups which fit spacially into the TR-β LBD polar pocket. This exploits spacial differences between TR LBD isoforms, such as the larger and more flexible polar pocket of TR-β.

METHODS OF TREATMENT

The compounds of Formula 1 can be useful in medical treatments and exhibit biological activity which can be demonstrated in the following tests:

(i) the induction of mitochondrial α-glycerophosphate dehydrogenase (GPDH:EC 1.1.99.5). This assay is particularly useful since in certain species e.g. rats it is induced specifically by thyroid hormones and thyromimetics in a close-related manner in responsive tissues e.g. liver, kidney and the heart (Westerfield, W. W., Richert, D. A. and Ruegamer, W. R., *Endocrinology* (1965) 77:802). The assay allows direct measurement in rates of a thyroid hormone-like effect of compounds and in particular allows measurement of the direct thyroid hormone-like effect on the heart. Other measurements included parameters such as heart rate and cardiac enzymes including $Ca^{++}$ ATPase, $Na^{++}/K^+$ ATPase, myosin isoforms and specific liver enzymes;

(ii) the elevation of basal metabolic rate as measured by the increase in whole body oxygen consumption (see e.g., Barker et al., *Ann. N. Y. Acad. Sci.*, (1960) 86:545–562);

(iii) the stimulation of the rate of beating of atria isolated from animals previously dosed with thyromimetrics (see e.g., Stephan et al., *Biochem. Pharmacol.* (1992) 13:1969–1974; Yokoyama et al., *J. Med. Chem.*, (1995) 38:695–707);

(iv) the change in total plasma cholesterol levels as determined using a cholesterol oxidase kit (for example, the Merck CHOD iodine colorimetric kit. see also, Stephan et al. (1992));

(v) the measurement of LDL (low density lipoprotein) and HDL (high density lipoprotein) cholesterol in lipoprotein fractions separated by ultracentrifugation; and p (vi) the change in total plasma triglyceride levels as determined using enzymatic color tests, for example the Merck System GPO-PAP method.

The compounds of Formula 1 can be found to exhibit selective thyromimetic activity in these tests, (a) by increasing the metabolic rate of test animals, and raising hepatic GPDH levels at doses which do not significantly modify cardiac GPDH levels.

(b) by lowering plasma cholesterol and triglyceride levels, and the ratio of LDL to HDL cholesterol at doses which do not significantly modify cardiac GPDH levels.

The compounds of Formula 1 may therefore be used in therapy, in the treatment of conditions which can be alleviated by compounds which selectively mimic the effects of thyroid hormones in certain tissues whilst having little or no direct thyromimetic effect on the heart. For example, compounds of Formula 1 which raise hepatic GPDH levels and metabolic rate at doses which do not significantly modify cardiac GPDH levels are indicated in the treatment of obesity.

Agonists of Formula 1 will lower total plasma cholesterol, the ratio of LDL-cholesterol to HDL-cholesterol and triglyceride levels at doses which do not significantly modify cardiac GPDH levels are indicated for use as general anti-hyperlipidaemic (antihyperlipoproteinaemic) agents i.e. in the treatment of patients having elevated plasma lipid (cholesterol and triglyceride) levels. In addition, in view of this effect on plasma cholesterol and triglyceride, they are also indicated for use as specific anti-hypercholesterolemic and anti-hypertriglyceridaemic agents.

Patients having elevated plasma lipid levels are considered at risk of developing coronary heart disease or other manifestations of atherosclerosis as a result of their high plasma cholesterol and/or triglyceride concentrations. Further, since LDL-cholesterol is believed to be the lipoprotein which induces atherosclerosis, and HDL-cholesterol believed to transport cholesterol from blood vessel walls to the liver and to prevent the build up of atherosclerotic plaque, anti-hyperlipidemic agents which lower the ratio of LDL-cholesterol to HDL cholesterol are indicated as anti-atherosclerotic agents, herein incorporated by reference U.S. Pat. Nos. 4,826,876 and 5,466,861.

The present invention also provides a method of producing selective thyromimetic activity in certain tissues except the heart which comprises administering to an animal in need thereof an effective amount to produce said activity of a compound of Formula 1 or a pharmaceutically acceptable salt thereof.

The present invention also relates to a method of lowering plasma lipid levels and a method of lowering the ratio of LDL-cholesterol to HDL-cholesterol levels by suitably administering a compound of this invention or a pharmaceutically acceptable sale thereof.

In addition, compounds of Formula 1 may be indicated in thyroid hormone replacement therapy in patients with compromised cardiac function.

In therapeutic use the compounds of the present invention are usually administered in a standard pharmaceutical composition.

The present invention therefore provides in a further aspect pharmaceutical compositions comprising a compound of Formula 1 or a pharmaceutically acceptable salt thereof and a pharmaceutically acceptable carrier. Such compositions include those suitable for oral, parenteral or rectal administration.

PHARMACEUTICAL COMPOSITIONS

Compounds of Formula 1 and their pharmaceutically acceptable salts which are active when given orally can be formulated as liquids for example syrups, suspensions or emulsions, tablets, capsules and lozenges.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule. Compound of Formula 1 and their pharmaceutically acceptable salts which are active when given parenterally can be formulated for intramuscular or intravenous administration.

A typical composition for intramuscular administration will consist of a suspension or solution of active ingredient in an oil, for example arachis oil or sesame oil. A typical composition for intravenous administration will consist of a sterile isotonic aqueous solution containing, for example active ingredient, dextrose, sodium chloride, a co-solvent, for example polyethylene glycol and, optionally, a chelating agent, for example ethylenediamine tetracetic acid and an anti-oxidant, for example, sodium metabisulphite. Alternatively, the solution can be freeze dried and then reconstituted with a suitable solvent just prior to administration.

Compounds of structure (1) and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

Compounds of Formula 1 and their pharmaceutically acceptable salts which are active on topical administration can be formulated as transdermal compositions. Such compositions include, for example, a backing, active compound reservoir, a control membrane, liner and contact adhesive.

The typical daily dose of a compound of Formula 1 varies according to individual needs, the condition to be treated and with the route of administration. Suitable doses are in the general range of from 0.001 to 10 mg/kg bodyweight of the recipient per day.

Within this general dosage range, doses can be chosen at which the compounds of Formula 1 lower plasma cholesterol levels and raise metabolic rate with little or no direct effect on the heart. In general, but not exclusively, such doses will be in the range of from lower doses (0.001 to 0.5 mg/kg) to higher doses (0.5 to 10 mg/kg).

In addition, within the general dose range, doses can be chosen at which the compounds of Formula 1 lower plasma cholesterol levels and have little or no effect on the heart without raising metabolic rate. In general, but not exclusively, such doses will be in the range of from 0.001 to 0.5 mg/kg.

It is to be understood that the 2 sub ranges noted above are not mutually exclusive and that the particular activity encountered at a particular dose will depend on the nature of the compound of Formula 1 used.

Preferably, the compound of Formula 1 is in unit dosage form, for example, a tablet or a capsule so that the patient may self-administer a single dose. In general, unit doses contain in the range of from 0.05–100 mg of a compound of Formula 1. Preferred unit doses contain from 0.05 to 10 mg of a compound of Formula 1.

The active ingredient may be administered from 1 to 6 times a day. Thus daily doses are in general in the range of from 0.05 to 600 mg per day. Preferably, daily doses are in the range of from 0.05 to 100 mg per day. Most preferably from 0.05 to 5 mg per day.

EXAMPLES

EXAMPLE 1—SYNTHESIS OF TR LIGANDS

Many TR ligands are known in the art, including T4 (thyroxine), T3, T2 and TS-9. See Jorgensen, Thyroid Hormones and Analogs, in *Hormonal Proteins and Peptides, Thyroid Hormones* 107–204 (Choh Hao Li ed., 1978), incorporated by reference herein.

The syntheses of several TR ligands are described below. Synthesis of TS1, TS2, TS3, TS4, TS5

Figure 11:
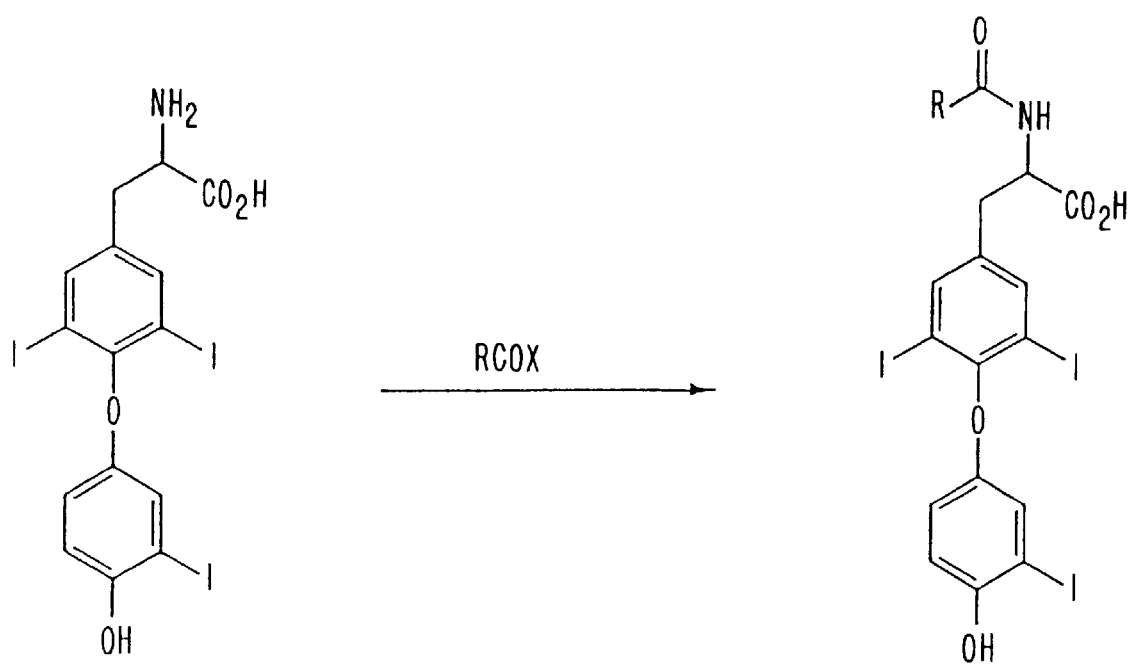
FIG. 11 is the synthetic scheme for preparation of TS1, TS2, TS3, TS4 and TS5.

TS1, TS2, TS3, TS4 and TS5 and analogs thereof can all be prepared by simple acylation of the nitrogen atom of any thyronine analog, including T3 (3,5,3'-triiodo-L-thyronine), T4 (thyroxine) and 3,5-diiodothyronine. TS1 and TS2 are synthesized by reacting T3 with $Ph_2CHCO_2NHS$ (N-hydroxy succinimide-2,2-diphenylacetate) and $C_{16}H_{33}CO_2NHS$, respectively. TS3 is synthesized by reacting T3 with FMOC-Cl (fluorenylmethyloxycarbonylchloride). TS4 is synthesized by reacting T3 with tBOC$_2$O (tBOC anhydride or di-t-butyldicarbonate). TS5, which differs from TS1–4 by having a —H instead of an —I at the $R_3^1$ position, is synthesized by reacting 3,5-diiodothyronine with tBOC$_2$O. The general reaction scheme for TS1, TS2, TS3, TS4 and TS5 is depicted in FIG. 11. It should be noted that in the reaction scheme, both TS5 and its precursor both have a hydrogen rather than an iodine at the $R_3^1$ position.

Synthesis of TS6 and TS7

Figure 12:
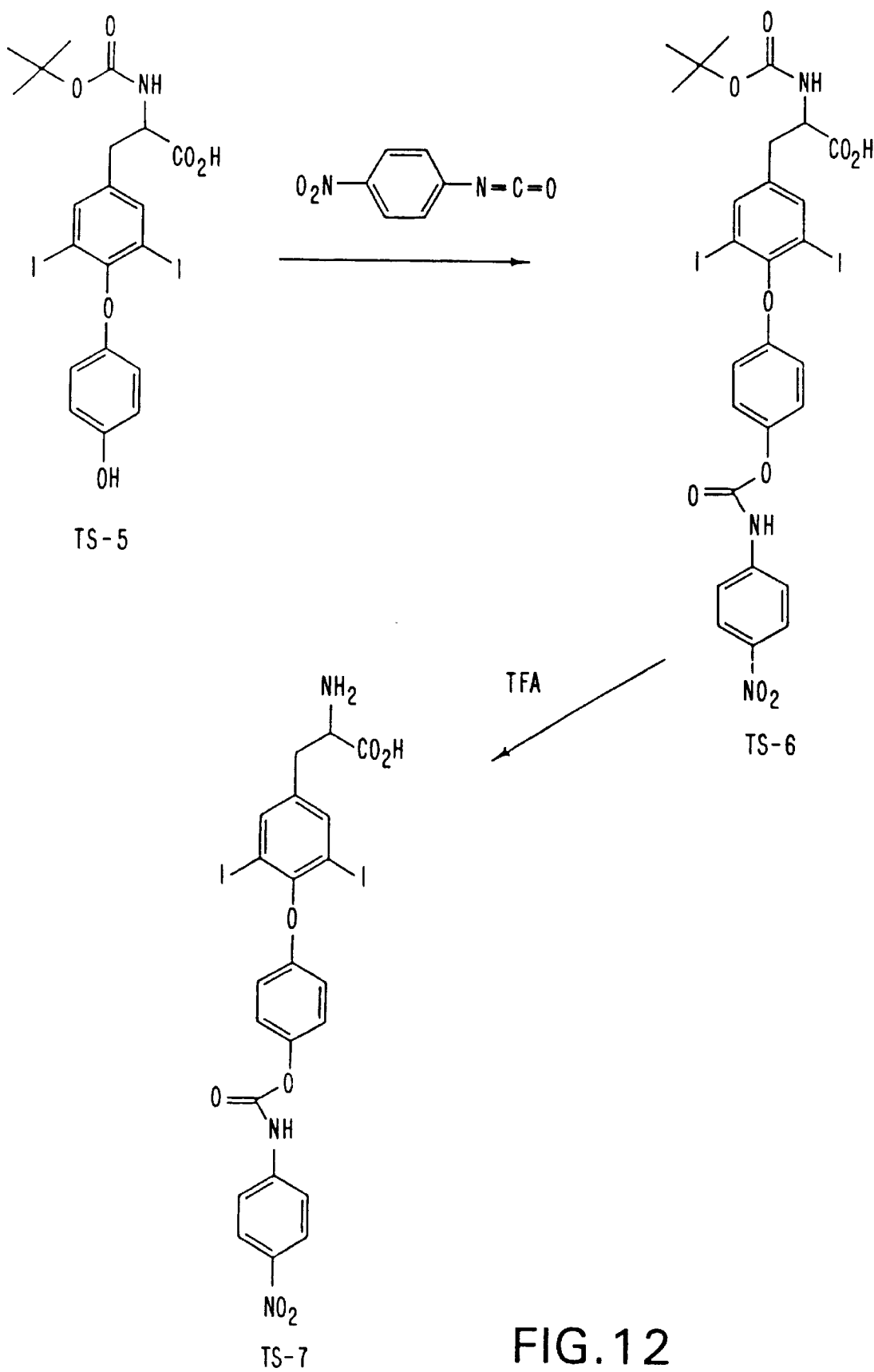
FIG. 12 is the synthetic scheme for preparation of TS6 and TS7.

TS6 is synthesized by reacting TS5 with paranitrophenylisocyanate. TS7 is synthesized by reacting TS6 with TFA (trifluoroacetic acid), which cleaves the tBOC group. These reactions are simple organic synthesis reactions that can be performed by anyone of ordinary skill in the art. The synthetic scheme for TS6 and TS7 is diagrammed in FIG. 12.

Synthesis of TS8

Figure 13:
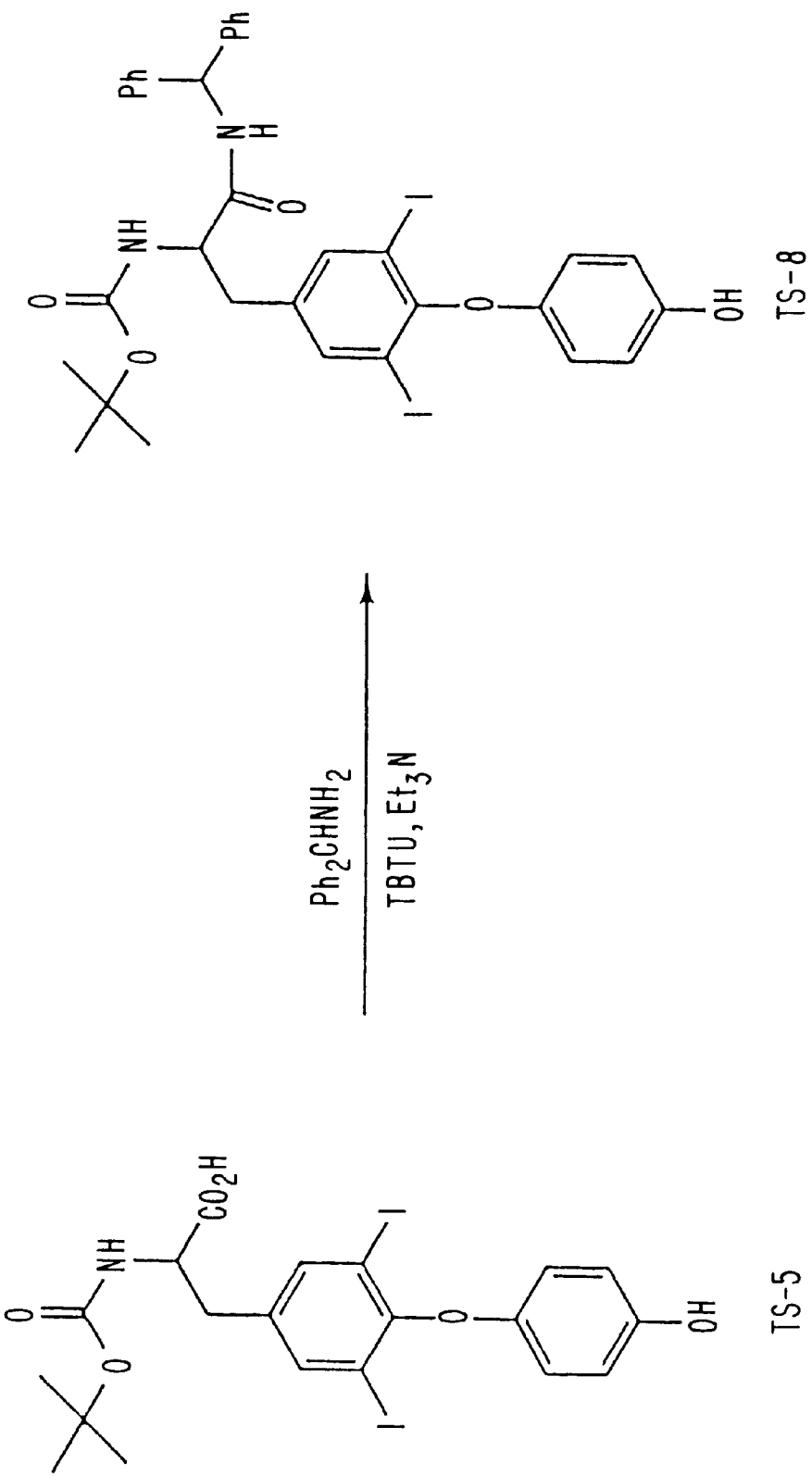
FIG. 13 is the synthetic scheme for preparation of TS8.

TS8 is synthesized by reacting TS5 with Ph$_2$CHNH$_2$ (diphenylmethylamine) in the presence of triethylamine and any amide forming condensing reagent, such as TBTU (hydroxybenztriazoleuronium tetrafluoroborate) or HBTU (hydroxybenztriazoleuronium hexafluorophosphate). The synthesis scheme for TS8 is depicted in FIG. 13.

SYNTHESIS OF 3,5-DIIODO-3'ISOPROPYLTHYRONINE DERIVATIVES

For designing a class of antagonists, it is important to have a hydrophobic group at the 3' position as well as an extension at the 5' position. Preferred hydrophobic groups at the 3' position include: methyl, benzyl, phenyl, iodo, and heterocyclic structures. The synthesis of a 3,5-diiodo-3'-isopropyl-5'-substituted thyronine is described below. The example provided describes the specific steps for synthesizing the TS10 compound, but this general reaction scheme can be used by one of ordinary skill in the art to synthesize any number of 3,5, -diiodo-3'-isopropyl-5'-substituted thyronine derivatives, which are characterized by having an extension at the 5' position. Additional compounds of this class can be synthesized using known organic synthesis techniques.

Figure 14A:
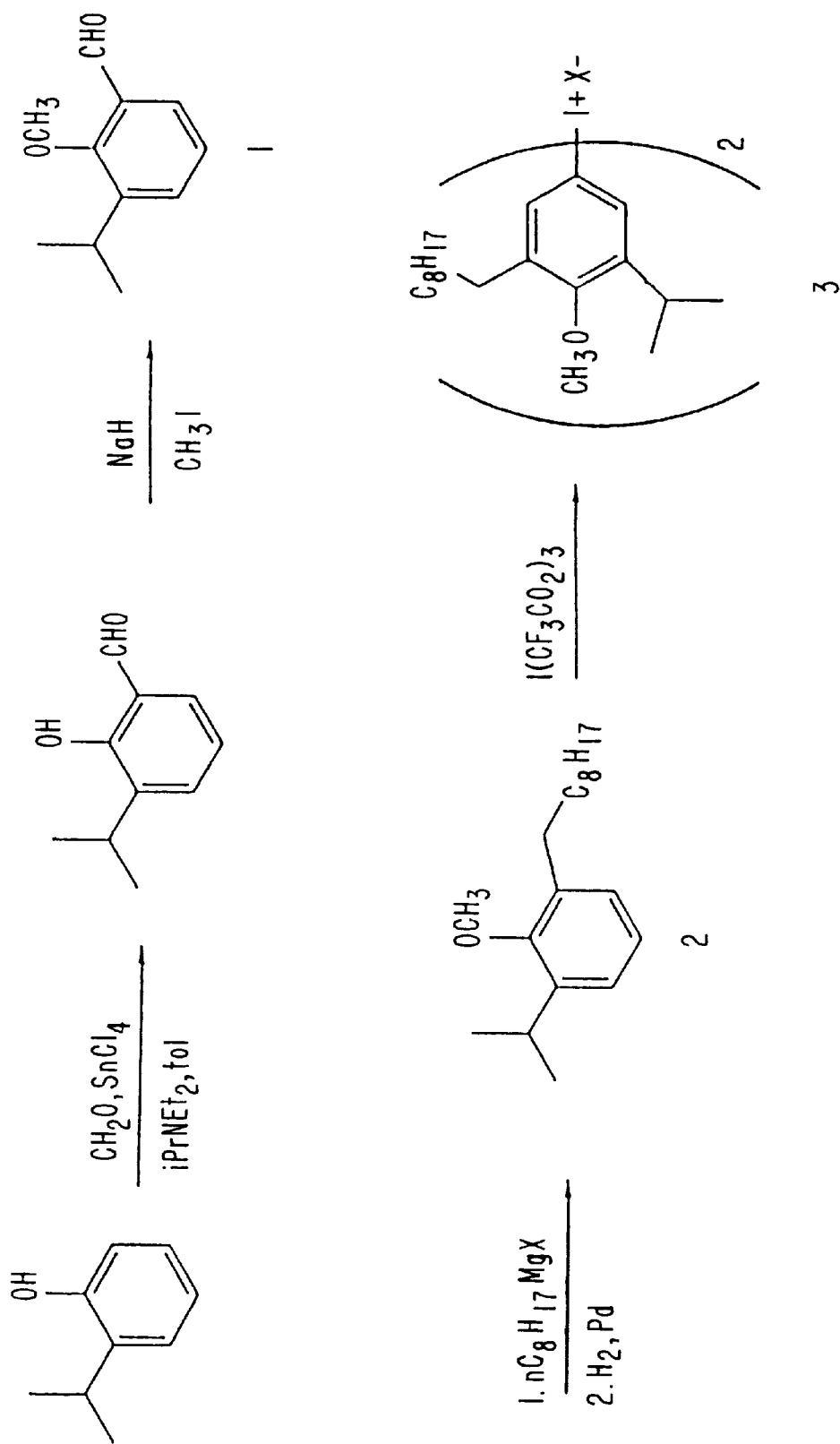
FIGS. 14A–14B is the synthetic scheme for preparation of TS10.
Figure 14B:
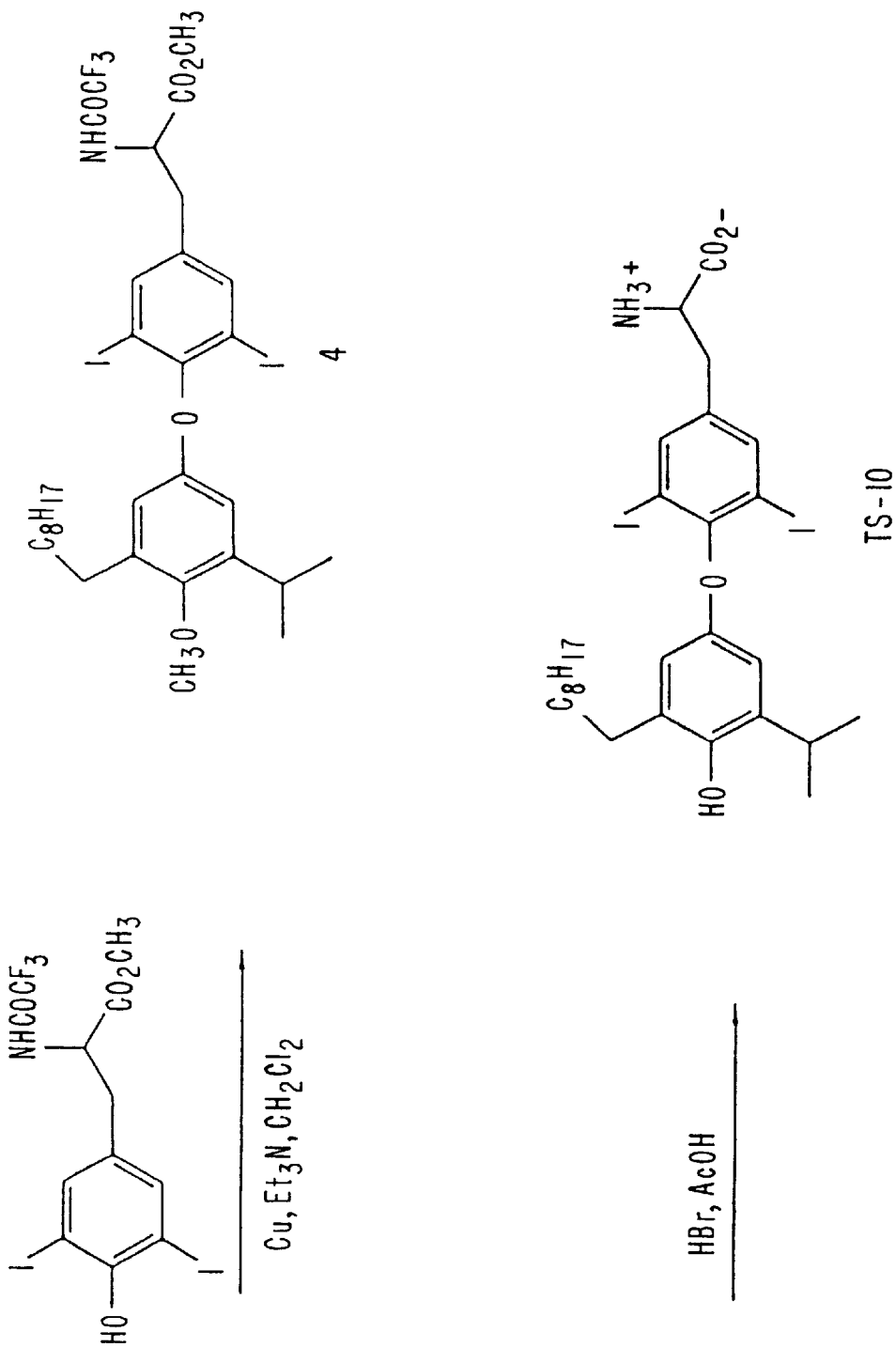

The synthesis of TS10 is described below and is depicted in FIG. 14. Numbers used in the reaction scheme for TS10 indicating the reaction product for each step are in parentheses.

2-Formyl-6-isopropylanisole (1): 2-formyl-6-isopropylanisole (10.0 g, 61 mmol), as made by Casiraghi, et al. JCS Perkin I, 1862 (1980) (incorporated by reference), is added dropwise to a suspension of sodium hydride (3.7 g, 153 mmol) in 50 mL THF and 50 mL of DMF in a round bottom flask. The addition generates an exothermic reaction and formation of a gray solid. Methyl iodide (26.0 g, 183 mmol) is then added dropwise and the reaction mixture is stirred at room temperature for 5 hours. The reaction mixture is quenched with 20 mL of water, then poured into 500 mL of water, and is extracted with ether (2×300 mL). The ether layers are combined, washed with water (5×1000 mL), dried over magnesium sulfate and concentrated in vacuo to provide 10.2 g (94%) of the title compound, with the following $^1$H NMR (CDCl$_3$) properties: d 10.30 (s, 1H), 7.63 (d, 1H, J=3 Hz), 7.50 (d, 1H, J=3 Hz), 7.13 (t, 1H, J=3 Hz), 3.81 (s, 3H), 3.31 (heptet, 1H, J=7.5 Hz), 1.19 (d, 6H, J=7.5 Hz).

2-(2-Hydroxynonyl)-6-isopropylanisole (not shown in scheme): Octylmagnesium chloride (8.4 mL, 16.9 mmol, 2.0 M) is added dropwise to a solution of 1 (1.5 g, 8.4 mmol) in 10 mL THF at −78° C. The reaction mixture is stirred for 2 hours with warming to room temperature. The reaction mixture is diluted with 50 mL ether and poured into 50 mL water. The ether layer is washed with brine (1×50 mL), dried over sodium sulfate, and concentrated in vacuo. Flash chromatography (silica gel, 10% ether/hexane→15% ether/hexane) provides 734 mg (30%) of the title compound with the following $^1$H NMR (CDCl$_3$) properties: d 7.33–7.10 (m, 3H), 5.00 (br. s, 1H), 3.81 (s, 3H), 3.33 (heptet, 1H, J=7 Hz) 1.90–1.19 (m, 14H), 0.86 (t, 3H, J=6.5 Hz); HRMS (EI), found: 292.2404; calc'd: 292.2402.

2-nonyl-6-isopropylanisole (2): Compound 2 (663 mg, 2.3 mmol) is dissolved in solution 5 mL ethanol and 5 mL acetic acid, and a spatula tip of palladium on carbon catalyst is added. The reaction mixture is then charged with hydrogen gas (using a simple balloon and needle) and the mixture is stirred at room temperature overnight. The next day, the reaction mixture is poured into ether (100 mL) and the ether layer is extracted with saturated sodium bicarbonate (3×100 mL). The ether layer is dried over sodium sulfate and concentrated in vacuo to provide 581 mg (91%) of (2) with the following $^1$H NMR (CDCl$_3$) properties: d 7.14–7.00 (m, 3H), 3.75 (s, 3H), 3.36 (heptet, 1H, J=6.8 Hz), 2.63 (t, 2H, J=7.5 Hz), 1.68–1.15 (m, 14H), 0.86 (t, 3H, J=5.5 Hz); HRMS (EI), mass found: 276.2459; calculated: 276.2453.

Thyronine adduct (4): Fuming nitric acid (0.071 mL) is added to 0.184 mL acetic anhydride chilled to −5° C. Iodine (66 mg) is added to this mixture followed by trifluoroacetic acid (0.124 mL). This mixture is stirred for 1 hour with warming to room temperature, at which point all of the iodine is dissolved. The reaction mixture was then concentrated in vacuo to provide an oily semi-solid material. The residue was dissolved in 0.7 mL of acetic anhydride and cooled to −20° C. A solution of anisole (2) (581 mg, 2.1 mmol) in 1.2 mL acetic anhydride and 0.58 mL TFA is added dropwise. The reaction mixture is stirred at −20° for 1 hour, then stirred overnight with warming to room temperature. The reaction mixture is partitioned between water and methylene chloride. The methylene chloride layer is dried over sodium sulfate and concentrated in vacuo to provide the iodonium salt (3) as an oil. This material is not purified or characterized, and is directly introduced into the coupling reaction.

N-Trifluoroacetyl-3,5-diiodotyrosine methyl ester (552 mg, 1.0 mmol) prepared according to the procedure of N. Lewis and P. Wallbank, *Synthesis* 1103 (1987) (incorporated by reference) and all of the crude iodonium salt (3) from above is dissolved in 5 mL of anhydrous methanol. Diazabicyclo[5.4.0]undecane (DBU) (183 mg, 1.2 mmol) and a spatula tip of copper-bronze are added and the resulting mixture is stirred at room temperature overnight. The next day, the reaction mixture is filtered, and the filtrate is concentrated in vacuo. The crude residue is purified by flash chromatography (silica gel, 10% ethyl acetate/hexane) to provide 30 mg (4%) of the protected thyronine adduct (4).

Deprotected thyronine (TS10): The protected thyronine 4 (30 mg, 0.04 mmol) is dissolved in a mixture of 2.25 mL acetic acid and 2.25 mL 49% hydrobromic acid. The reaction mixture is heated to reflux for 5 hours. The reaction mixture is cooled to room temperature, and the solvents are removed in vacuo. Water is added to triturate the oily residue into a gray solid. This solid material is filtered, washed with water, and dried over P$_2$O$_5$ in vacuo to provide 24 mg (81%) of the tide compound, TS10, with the following $^1$H NMR (CDCl$_3$) properties: d 7.57 (s, 1H), 6.86 (s, 1H), 6.45 (s, 1H), 6.34 (s, 1H), 4.81 (m, 1H), 3.86 (s, 3H), 3.71 (s, 3H), 3.33–3.05 (m, 3H), 2.58–2.47 (m, 2H), 1.62–0.76 (m, 23H); MS (LSIMS): M$^+$=817.0.

As mentioned above, this reaction scheme can be modified by one of ordinary skill in the art to synthesize a class of compounds characterized by 3,5-diiodo-3' isopropylthyronine derivatives, wherein (1) the 3' isopropyl group can be replaced with a hydrophobic group, including methyl, benzyl, phenyl, iodo, and heterocyclic structures, and (2) a wide variety of chemical structures can be incorporated at the 5' position, including alkyl groups, planar aryl, heterocyclic groups, or polar and/or charged groups.

The aldehyde (1) in the above reaction scheme is a versatile synthetic intermediate which allows for the attachment of a variety of chemical moieties to the 5' position of the final thyronine derivative. In addition, a variety of chemical reactions can be used to attach the chemical moieties. These reactions are well known in the art and include organometallic additions to the aldehyde (including Grignard reagents, organolithiums, etc.), reductive amination reactions of the aldehyde with a primary or secondary amine, and Wittig olefination reactions with a phosphorous ylid or stabilized phosphonate anion. Other possibilities include reduction of the aldehyde to a benzyl alcohol allowing for etherification reactions at the 5' position. As mentioned above, these methods allow for a wide variety of chemical structures to be incorporated at the 5' position of the final thyronine derivative, including alkyl groups, planar aryl, heterocyclic groups or polar and/or charged groups.

Synthesis of 3,5-dibromo-4-(3',5'-diisopropyl-4'-hydroxyphenoxy)benzoic acid (Compound 11).

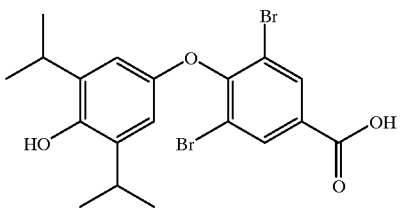

(a) A mixture of 2,6-diisopropyl phenol (20 g, 0.11 mol), potassium carbonate (62 g, 0.45 mol), acetone (160 ml) and methyl iodide (28 ml, 0.45 mole) is refluxed for three days. The reaction mixture is filtered through celite, evaporated, dissolved in ether, washed twice with 1M sodium hydroxide, dried over magnesium sulphate and concentrated to afford 15.1 g (0.08 mol, 70%) of 2,6-diisopropyl anisole as a slightly yellow oil.

(b) Fuming nitric acid (12.4 ml, 265 mmol) is added dropwise to 31.4 ml of acetic anhydride which is cooled in a dry ice/carbon tetrachloride bath. Iodine 11.3 g, 44.4 mmol) is added in one portion followed by dropwise addition of trifluoroacetic acid (20.5 ml, 266 mmole). The reaction mixture is stirred at room temperature until all the iodine is dissolved. Nitrogen oxides are removed by flushing nitrogen into the vessel. The reaction mixture is concentrated, the residue is dissolved in 126 ml of acetic anhydride and is cooled in a dry ice/carbon tetrachloride bath. To the stirred solution 2,6-diisopropylanisole (51 g, 266 mmol) in 150 ml of acetic anhydride and 22.6 ml of trifluoroacetic acid is added dropwise. The reaction mixture is left to stand at room temperature over night and then is concentrated. The residue is taken up in 150 ml of methanol and treated with 150 ml of 10% aqueous sodium bisulfite solution and 1 liter of 2M sodium borotetrafluoride solution. After the precipitate aggregates, petroleum ether is added and the supernatant is decanted. The precipitate is triturated with petroleum ether, filtered, washed with petroleum ether and dried at room temperature in vacuo. This affords 34 g (57 mmol, 65%) of bis(3,5-diisopropyl-4-methoxyphenyl)iodonium tetrafluoroborate as a white solid.

(c) To a stirred solution of 3,5-dibromo4-hydroxybenzoic acid (12 g, 40.5 mmol) in 250 ml of methanol, thionyl chloride (3 ml) is added dropwise. The reaction mixture is refluxed for five days, water is added and the precipitated product is filtered off. The residue is dissolved in ethyl acetate. From the aqueous phase, methanol is removed by concentration. The aqueous phase is then saturated with sodium chloride, and extracted with ethyl acetate. The combined organic phases are dried over magnesium sulphate, filtered and concentrated. This gives 12.5 g (40.5 mmol, 100%) of 3,5-dibromo-4-hydroxymethyl benzoate as a white crystalline solid.

(d) The products obtained in steps b and c are reacted with each other according to the following protocol. To bis(3,5-diisopropyl-4-methoxyphenyl)iodonium tetrafluoroborate (2.86 g, 4.8 mmole) and copper bronze (0.42 g, 6.4 mmole) in 7 ml. of dichloromethane at 0° C. is added dropwise a solution of 3,5-dibromo-4-hydroxymethyl benzoate (1.0 g, 3.2 mmole) and triethylamine (0.36 g, 3.5 mmole) in 5 ml of dichloromethane. The reaction mixture is stirred in the dark for eight days and then is filtered through celite. The filtrate is concentrated and the residue is purified by column chromatography (silica gel, 97:3 petroleum ether/ethyl acetate) to give 0.62 g (1.2 mmole, 39%) of 3,5-dibromo-4-(3',5'-diisopropyl-4'-methoxyphenoxy)methyl benzoate as a solid.

(e) The product from step d (0.2 g, 0.4 mmole) is dissolved in 2 ml. dichloromethane, is put under nitrogen and is cooled at −40° C. To the stirred solution is added 1M $BBr_3$ (1.2 ml, 1.2 mmole) dropwise. The reaction mixture is allowed to reach room temperature and then is left over night. It is cooled to 0° C. and then hydrolyzed with water. Dichloromethane is removed by concentration and the aqueous phase is extracted with ethyl acetate. The organic phase is washed with 1M hydrochloric acid and brine. Then it is dried over magnesium sulphate, filtered and concentrated. The residue is chromatographed (silica, 96:3.6:0.4 dichloromethane/methanol/acetic acid) producing 93 mg (0.2 mmole, 51%) of 3,5-dibromo-4-(3',5'-diisopropyl-4'-hydroxyphenoxy)benzoic acid as a white solid. $^1H$ nmr ($CDCl_3$) δ 1.23 (d, 12H, methyl), 3.11 (m, 2H, CH), 6.50 (s, 2H, 2,6-H) 8.33 (s, 2H, 2',6'-H).

Synthesis of addition ligands are described in U.S. Ser. No. 08/877,792, filed Jun. 18, 1997 which is herein incorporated in its entirety by reference.

TABLE 2 and FIG. 15 depict the structures of several TR ligands in reference to Formula I.

TABLE 2

| Cmpd | $R_3$ | $R_4$ | $R_5$ | $R'_3$ | $R'_4$ | $R'_5$ | $R_1$ |
|---|---|---|---|---|---|---|---|
| *$T_3$ | —I | —O— | —I | —I | —OH | —H | —$CH_2CH(NH_2)CO_2H$ |
| *$T_4$ | —I | —O— | —I | —I | —OH | —I | —$CH_2CH(NH_2)CO_2H$ |
| TS1 | —I | —O— | —I | —I | —OH | —H | —$CH_2CH[NHCOCH\phi_2]CO_2H$ |

TABLE 2-continued

| Cmpd | $R_3$ | $R_4$ | $R_5$ | $R'_3$ | $R'_4$ | $R'_5$ | $R_1$ |
|---|---|---|---|---|---|---|---|
| TS2 | —I | —O— | —I | —I | —OH | —H | —CH$_2$CH[NHCO(CH$_2$)$_{15}$CH$_3$]CO$_2$H |
| TS3 | —I | —O— | —I | —I | —OH | —H | —CH$_2$CH[NH-FMOC]CO$_2$H |
| TS4 | —I | —O— | —I | —I | —OH | —H | —CH$_2$CH[NH-tBOC]CO$_2$H |
| TS5 | —I | —O— | —I | —H | —OH | —H | —CH$_2$CH[NH-tBOC]CO$_2$H |
| TS6 | —I | —O— | —I | —H | —OC(O)NH—ØpNO$_2$ | —H | —CH$_2$CH[NH-tBOC]CO$_2$H |
| TS7 | —I | —O— | —I | —I | —OC(O)NH=NHØNO$_2$ | —H | —CH$_2$CH(NH$_2$)CO$_2$H |
| TS8 | —I | —O— | —I | —H | —NH—CHØØ | —H | —CH$_2$CH[NH-tBOC]CO$_2$H |
| TS9 | —I | —O— | —I | -IsoPr | —OH | —H | —CH$_2$CH(NH$_2$)CO$_2$H |
| TS10 | —I | —O— | —I | -IsoPr | —OH | —(CH)$_8$—CH$_3$ | —CH$_2$CH(NH$_2$)CO$_2$H |

*Prior Art Compound
—Ø: phenyl
—ØOpNO$_2$: para nitro phenyl

EXAMPLE 2—RECEPTOR BINDING ASSAYS OF TR LIGANDS

To test the ability of synthesized TR ligands to bind to a thyroid receptor (TR), the binding affinity of a TR ligand for TR is assayed using TR's prepared from rat liver nuclei and $125_I$T$_3$ as described in J. D. Apriletti, J. B. Baxter, and T. N. Lavin, *J. Biol. Chem.*, 263: 9409–9417 (1988). The apparent Kd's are calculated using the method described by Apriletti (1995) and Apriletti (1988). The apparent Kd's are presented in TABLE 3. The apparent Kd's (App.Kd) are determined in the presence of the sample to be assayed, 1 nM [$^{125}$I]T$_3$, and 50 μg/ml core histones, in buffer E (400 mM KCl, 200 mM potassium phosphate, pH 8.0, 0.5 mM EDTA, 1 mM MgCl$_2$, 10% glycerol, 1 mM DTT) in a volume of 0.21 ml. After incubation overnight at 4° C., 0.2 ml of the incubation mixture is loaded onto a Quick-Sep Sephadex G-25 column (2.7×0.9 cm, 1.7 ml bed volume) equilibrated with buffer E. The excluded peak of protein-bound [$^{125}$I]T$_3$ is eluted with 1 ml of buffer E, collected in a test tube, and counted. Specific T$_3$ binding is calculated by subtracting nonspecific binding from total binding.

TABLE 3

| Compound | App.Kd (nM) | Coactivation Assay RIP-140 | EC$_{50}$(M) |
|---|---|---|---|
| T$_3$ | 0.06 | + | 10$^{-10}$ |
| T$_4$ | 2 | + | 10$^{-9}$ |
| TS1 | 4 | + | 10$^{-7}$ |
| TS2 | 1400 | nd | nd |
| TS3 | 4 | + | 10$^{-8}$ |
| TS4 | 8 | + | nd |
| TS5 | 220 | + | 10$^{-6}$ |
| TS6 | >10000 | nd | nd |
| TS7 | 260 | + | 10$^{-7}$ |
| TS8 | 6000 | nd | nd |
| TS9 | 1 | + | 10$^{-10}$ |
| TS10 | 400 | + | 10$^{-6}$ |

+: RIP-140 Binding
−: RIP-140 Binding
nd: Not Determined

EXAMPLE 3—INCREASED NUCLEAR PROTEIN COACTIVATION BY TR LIGANDS

To test the ability of TR ligands to activate the binding of TR to the nuclear activation protein RIP-140 (a nuclear protein that can bind to nuclear receptors, such as the estrogen receptor), a TR ligand is liganded to TR and then incubated with RIP-140 as described in V. Cavailles, et al., EMBO J., 14(15):3741–3751 (1995), which is incorporated by reference herein. In this assay, 35$_s$-RIP-140 protein binds to liganded TR but not unliganded TR. Many TR 35$_s$ ligands can activate RIP-140 binding as shown in TABLE 3.

EXAMPLE 4—TR LIGAND BINDING AND TR ACTIVATION IN CULTURED CELLS

To test TR activation of transcription in a cellular environment, TR ligands are assayed for their ability to activate a reporter gene, chloramphenicol transferase ("CAT"), which has a TR DNA binding sequence operatively linked to it. Either GC or L937 cells (available from the ATCC) can be used, respectively). In such assays, a TR ligand crosses the cell membrane, binds to the TR, and activates the TR, which in turn activates gene transcription of the CAT by binding the TR DNA binding region upstream of the CAT gene. The effective concentration for half maximal gene activation (EC$_{50}$) is determined by assaying CAT gene activation at various concentrations as described herein and in the literature. The results of CAT gene activation experiments are shown in TABLE 3.

CAT GENE ACTIVATION ASSAYS

Functional response to thyroid hormone (3,5,3'-triiodo-L-thyronine, T$_3$) and TR ligands is assessed either in a rat pituitary cell line, GC cells, that contain endogenous thyroid hormone receptors (TRs) or U937 cells that contain exogenous TRs expressed as known in the art. GC cells are grown in 10-cm dishes in RPMI 1640 with 10% newborn bovine serum, 2 mM glutamine, 50 units/ml penicillin and 50 μg/ml streptomycin. For transfections, cells are trypsinized, resuspended in buffer (PBS, 0.1% glucose) and mixed with a TREtkCAT plasmid (10 mg) or phage in 0.5 ml buffer (15±5 million cells) and electroporated using a Bio-Rad gene pulser at 0.33 kvolts and 960 mF. The TREtkCAT plasmid contains two copies of a T$_3$ response element (AGGTCAcaggAGGTCA) cloned in the Hind III site of the pUC19 polylinker immediately upstream of a minimal (−32/+45) thymidine kinase promoter linked to CAT (tkCAT) coding sequences. After electroporation, cells are pooled in growth medium (RPMI with 10% charcoal-treated, hormone stripped, newborn bovine serum), plated in 6-well dishes and treated with either ethanol or hormone. CAT activity is determined 24 hours later as described D. C. Leitman, R. C. J. Ribeiro, E. R. Mackow, J. D. Baxter, B. L. West, *J. Biol. Chem.* 266, 9343 (1991), which is incorporated by reference herein.

EFFECT OF TS-10 ON THE TRANSCRIPTIONAL REGULATION OF THE DR4-ALP REPORTER GENE IN THE PRESENCE OR ABSENCE OF T3.

Characteristics of the TRAF cells: TRAFa1 are CHO K1 cells stably transformed with an expression vector encoding the human thyroid hormone receptor α 1 and a DR4,ALP reporter vector; TRAFb1 are CHO K1 cells stably transformed with an expression vector encoding the human thyroid hormone receptor β1 and a DR4-ALP reporter vector.

Interpretation of the Effect of Compound TS-10 on the Transcriptional Regulation of the DR4-ALP Reporter Gene in the Presence or Absence of T3.

TRAFa1 reporter cells: TS-10 alone (open circles) induces a partial activation of the expression of the ALP reporter protein amounting to approximately 27% of the maximal effect by the natural thyroid hormone T3. In the presence of T3 (filled circles), TS-10 has a weak antagonistic effect. The EC50 concentration for the agonistic effect of TS-10 and the EC50 concentration for its T3 antagonistic effect, respectively, is indicated in FIG. 18.

Figure 18:
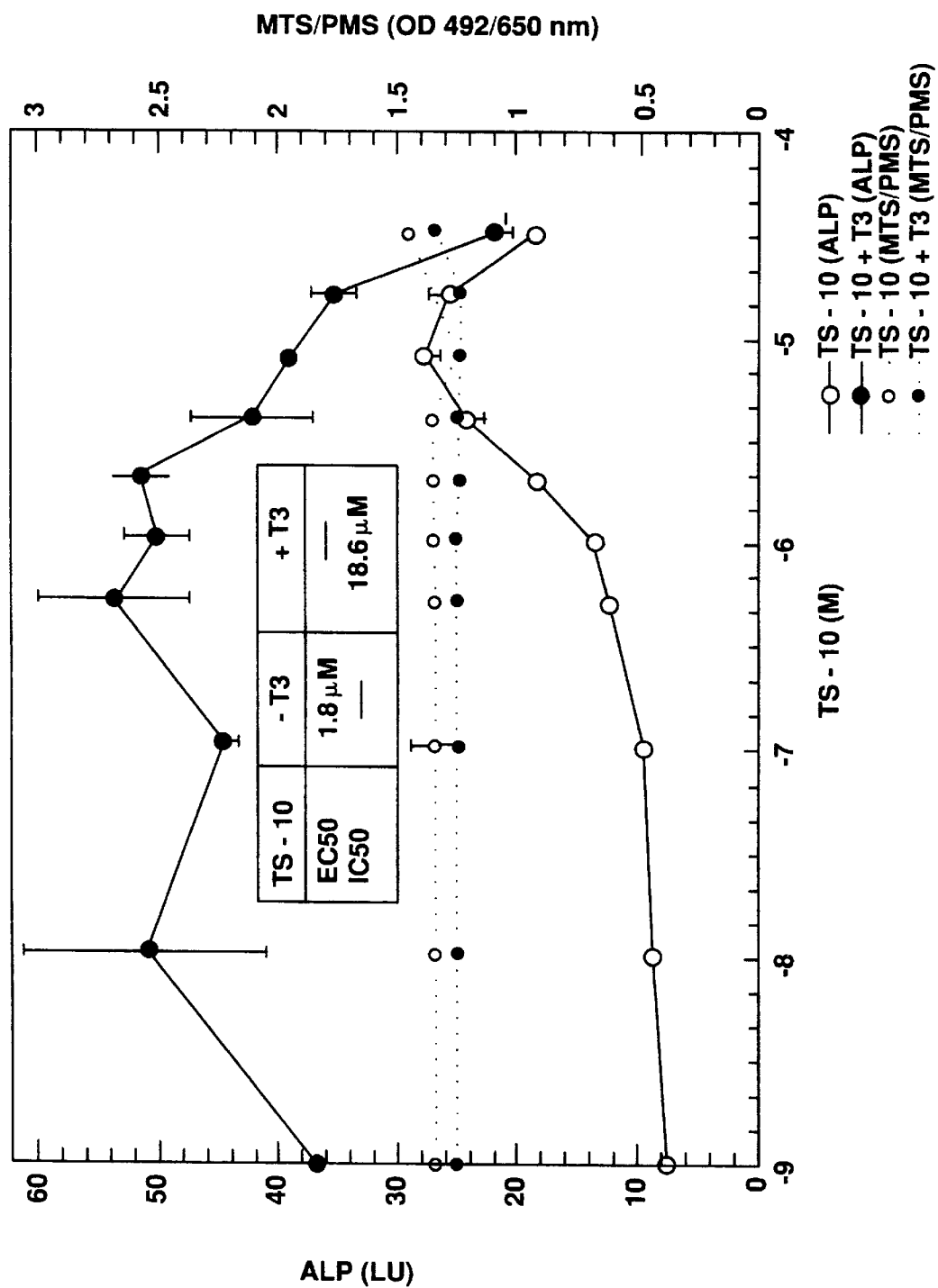
FIG. 18 is a chart showing the effect of TS-10 on the transcriptional regulation of the DR4-ALP reporter gene in the presence or absence of T3 as assayed in TRAFα1 reporter cells.

In FIG. 18, open and filled circles with dotted lines show the dose-dependent effect of TS-10/T3 on the toxicity marker (MTS/PMS), reduction of tetrazolium salt in the mitochondria, displayed on the right y-axis as optical density. There is no obvious toxic effect of TS-10 on the MTS-PMS marker but there is a clear effect on the morphology of the cells, as can be seen under the light microscope, at the highest concentration of TS-10 (32 mM) both in the absence and presence of T3, respectively (not shown in the figure).

Figure 19:
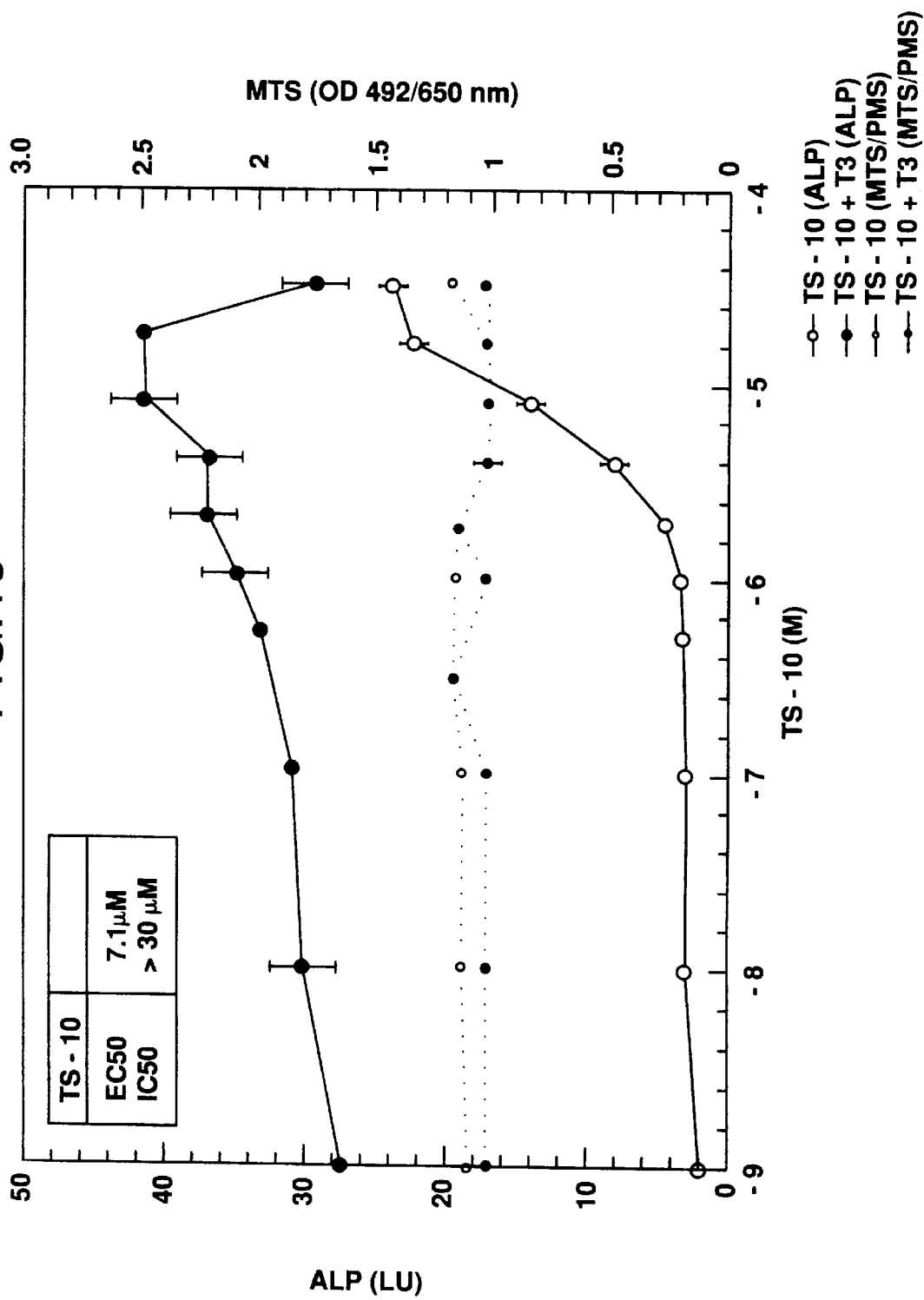
FIG. 19 is a chart showing the effect of TS-10 on the transcriptional regulation of the DR4-ALP reporter gene in the presence or absence of T3 as assayed in TRAFβ1 reporter cells.

TRAFb1 reporter cells: TS-10 alone (open circles) induces a partial activation of the expression of the ALP reporter protein amounting to approximately 35% of the maximal effect by 13. The EC50 concentration for the agonistic effect of TS-10 is indicated in FIG. 19. In the presence of T3 (filled circles), TS-10 shows, if anything, a slight potentiation of the T3 effect on the expression of the ALP reporter protein. The T3 inhibitory effect of TS-10 at its highest concentration used (32 mM) is a toxic effect rather than T3 antagonism.

In FIG. 19, open and filled circles with dotted lines show the dose-dependent effect of TS-10/T3 on the toxicity marker (MTS/PMS), reduction of tetrazolium salt in the mitochondria, displayed on the right y-axis as optical density. There is no obvious toxic effect of TS-10 on the MTS-PMS marker but a clear effect on the morphology of the cells can be observed, under the light microscope, at the highest concentration of TS-10 (32 mM) both in the absence and presence of T3, respectively (not shown in the figure).

Figure 20:
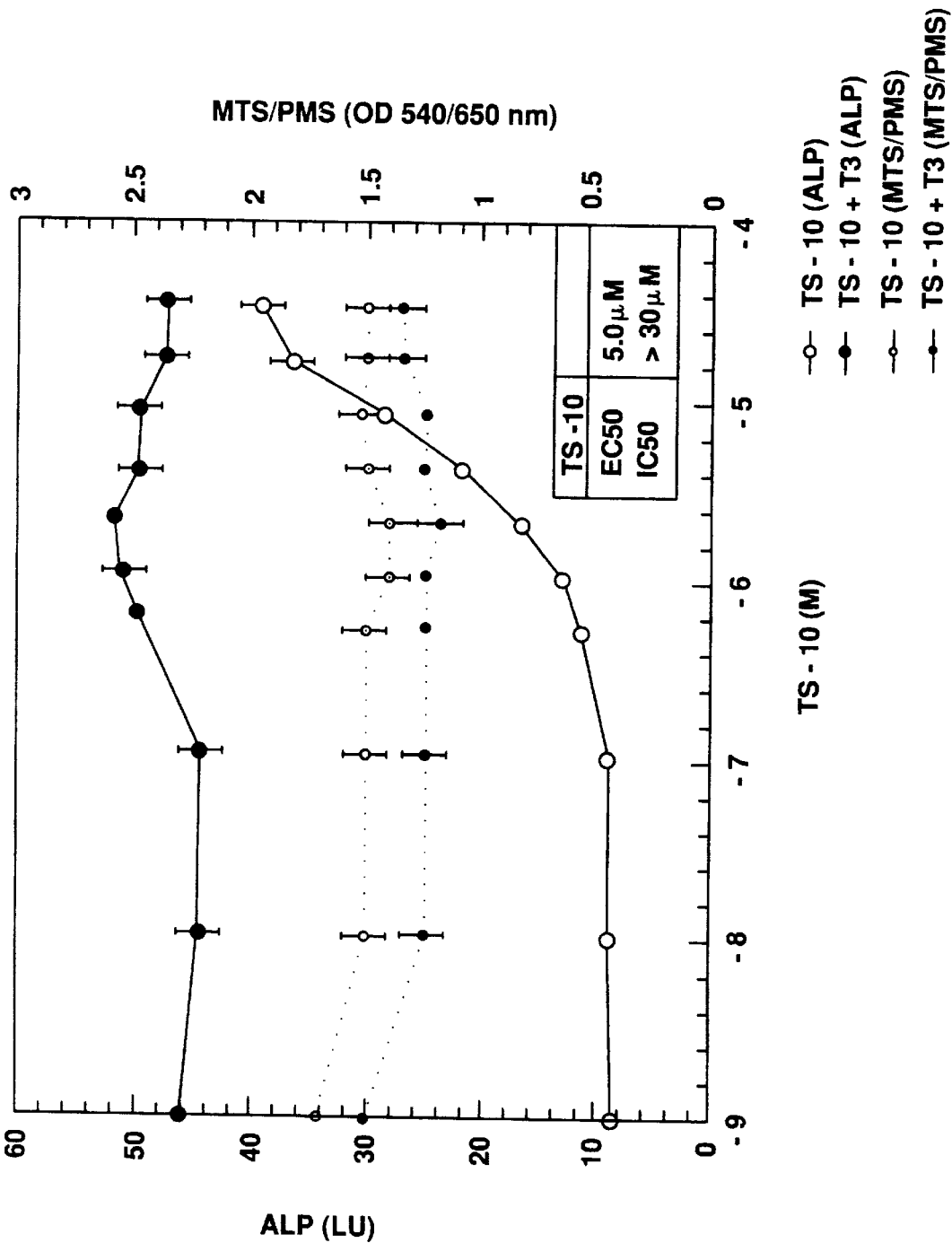
FIG. 20 is a chart showing the effect of TS-10 on the transcriptional regulation of the DR4-ALP reporter gene in the presence or absence of T3 as assayed in HepG2, a liver reporter cell line.

HepG2 (HAF18) reporter cells: TS-10 alone (open circles) induces a partial activation of the expression of the ALP reporter protein amounting to slightly more than 50% of the maximal effect by T3. The EC50 concentration for the agonistic effect of TS-10 is indicated in FIG. 20. In the presence of T3 (filled circles), TS-10 shows no effect i.e. no T3 antagonism nor potentiation/additive effect to T3. Open and filled circles with dotted lines show the dose-dependent effect of TS-10/T3 on the toxicity marker (MTS/PMS), reduction of tetrazolium salt in the mitochondria, displayed on the right y-axis as optical density. There is no obvious toxic effect of TS-10 on the MTS/PMS marker or on the morphology of the cells, as can be observed using a light microscope, at any concentration of TS-10/T3 used.

EXAMPLE 5—COMPARISONS OF HUMAN TR-α AND HUMAN TR-β

Competition for $[^{125}I]T_3$ binding to TR LBD by $T_3$ and Triac

Figure 16:
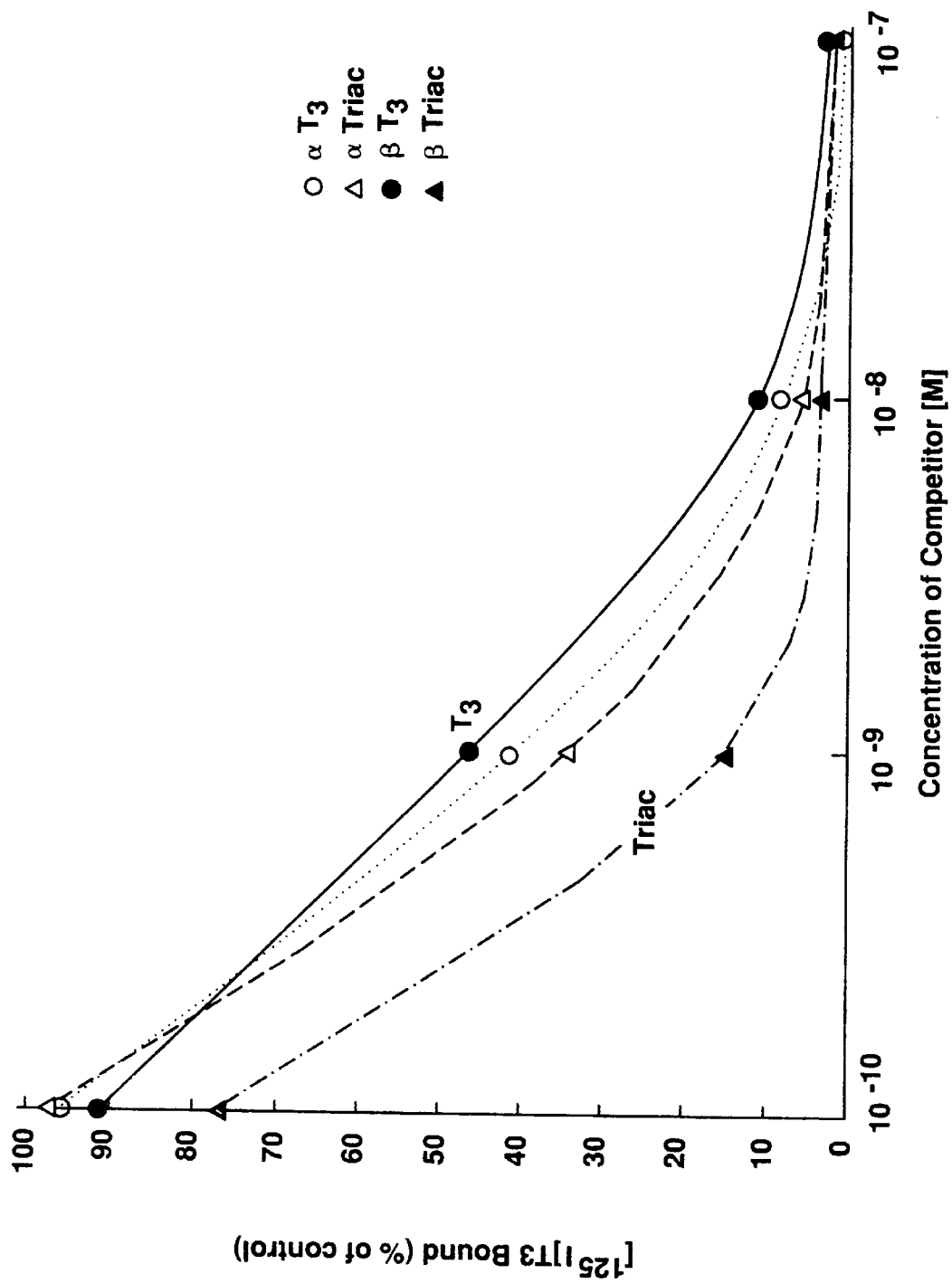
FIG. 16 is a graph illustrating competition assays in which $T_3$ and Triac compete with labeled $T_3$ for binding to human TR-α or human TR-β.

The drug, Triac, is a thyroid hormone agonist. Triac is 3,5,3'-triiodothyroacetic acid and is described in Jorgensen, Thyroid Hormones and Analogs in *Hormonal Proteins and Peptides, Thyroid Hormones* at 150–151 (1978). Another compound that can be used in place of Triac is 3,5-diiodo-3'-isopropylthyroacetic acid. Competition assays are performed to compare the displacement of $[^{125}I]T_3$ from binding with human TR-α LBD or human TR-β LBD by unlabeled $T_3$ or Triac. The results of such assays are depicted in FIG. 16.

Standard binding reactions are prepared containing 1 nM $[^{125}I]T_3$, 30 fmol of human TR-α (empty symbols) or β (solid symbols), and various concentrations of competing unlabeled $T_3$ (circles) or Triac (triangles). Assays are performed in duplicate.

Competition for $[^{125}I]T_3$ binding to variant TR LBD by $T_3$, Triac and GC-1

Figure 27:
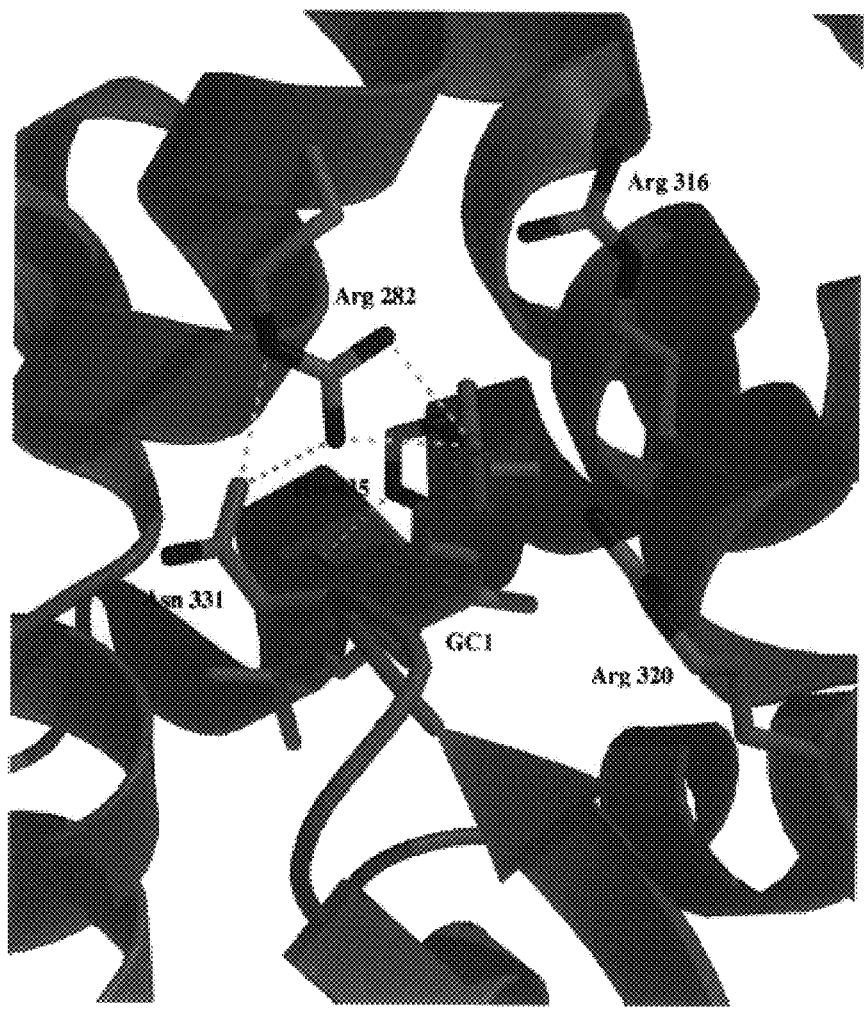
FIG. 27 is a partial ribbon drawing of TR-β LBD with GC-1 in the ligand binding cavity. Amino acids Arg282, Arg316, Arg320, Asn 331 and His435 are labelled.
Figure 28:
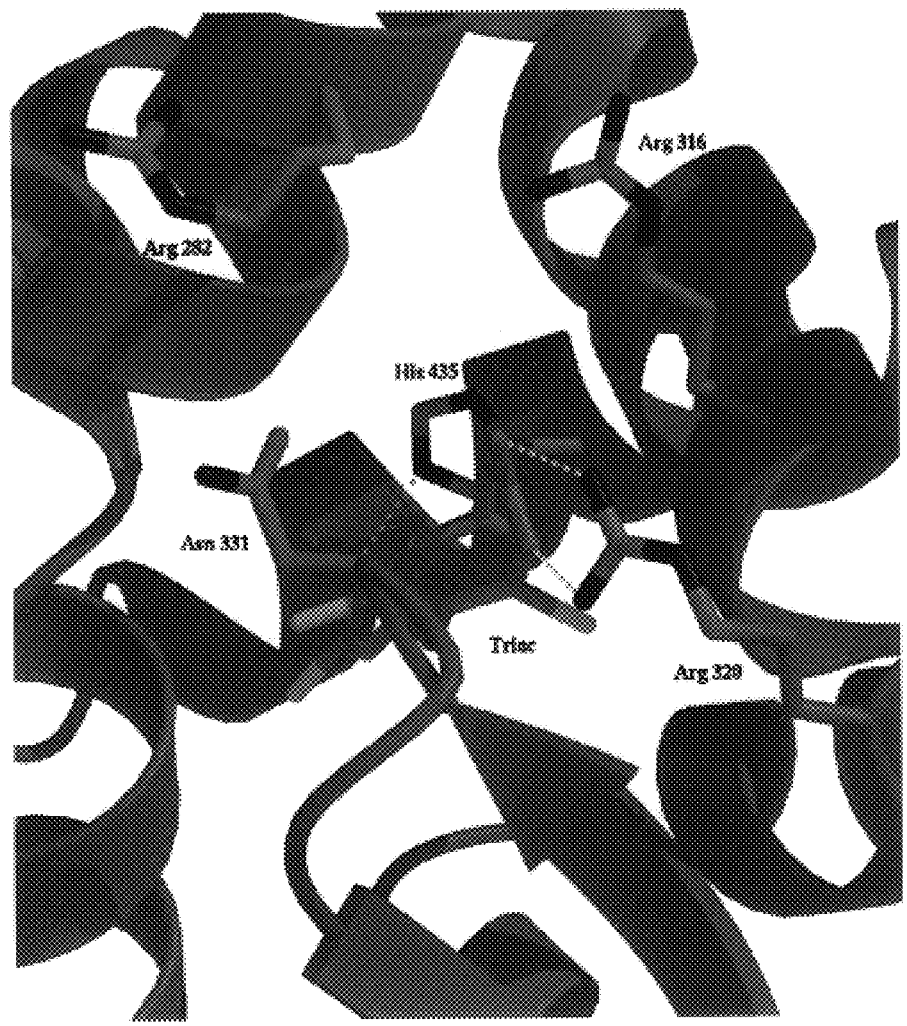
FIG. 28 is a partial ribbon drawing of TR-β LBD with Triac in the ligand binding cavity. Amino acids Arg282, Arg316, Arg320, Asn331 and His435 are labelled.
Figure 29:
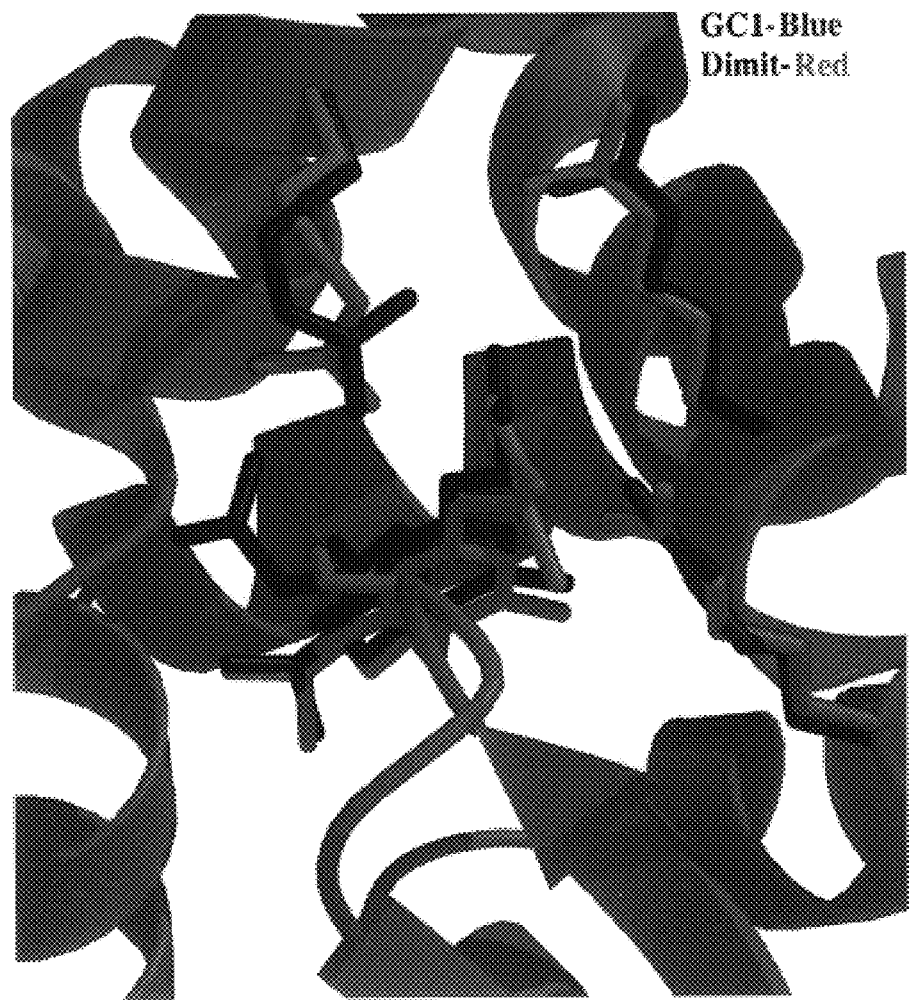
FIG. 29 is a partial ribbon drawing of TR-βLBD with GC-1 (Blue) overlayed with TR-α LBD with Dimit (Red) in the ligand binding cavities. Amino acids Arg228, Arg262, Arg266 and Ser277 (TR-α LBD), and Arg282, Arg316, Arg320 and Asn331 (TR-β LBD) are labelled.
Figure 30:
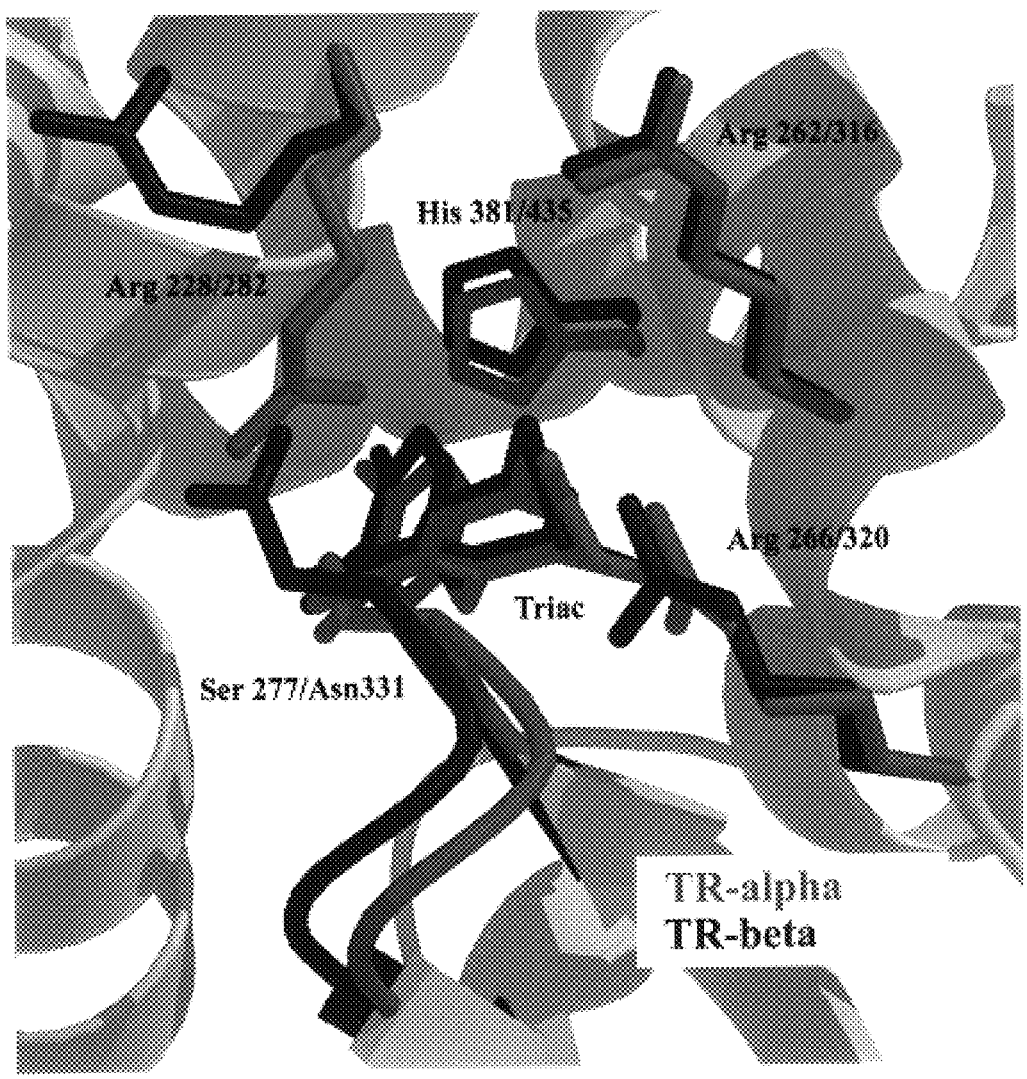
FIG. 30 is a partial ribbon drawing of TR-β LBD with Triac (Blue) overlayed with TR-α LBD with Triac (Red) in the ligand binding cavities. Amino acids Arg228, Arg262, Arg266, Ser277 and His381 (TR-α LBD), and Arg282, Arg316, Arg320 and His435 (TR-β LBD) are labelled.
Figure 31:
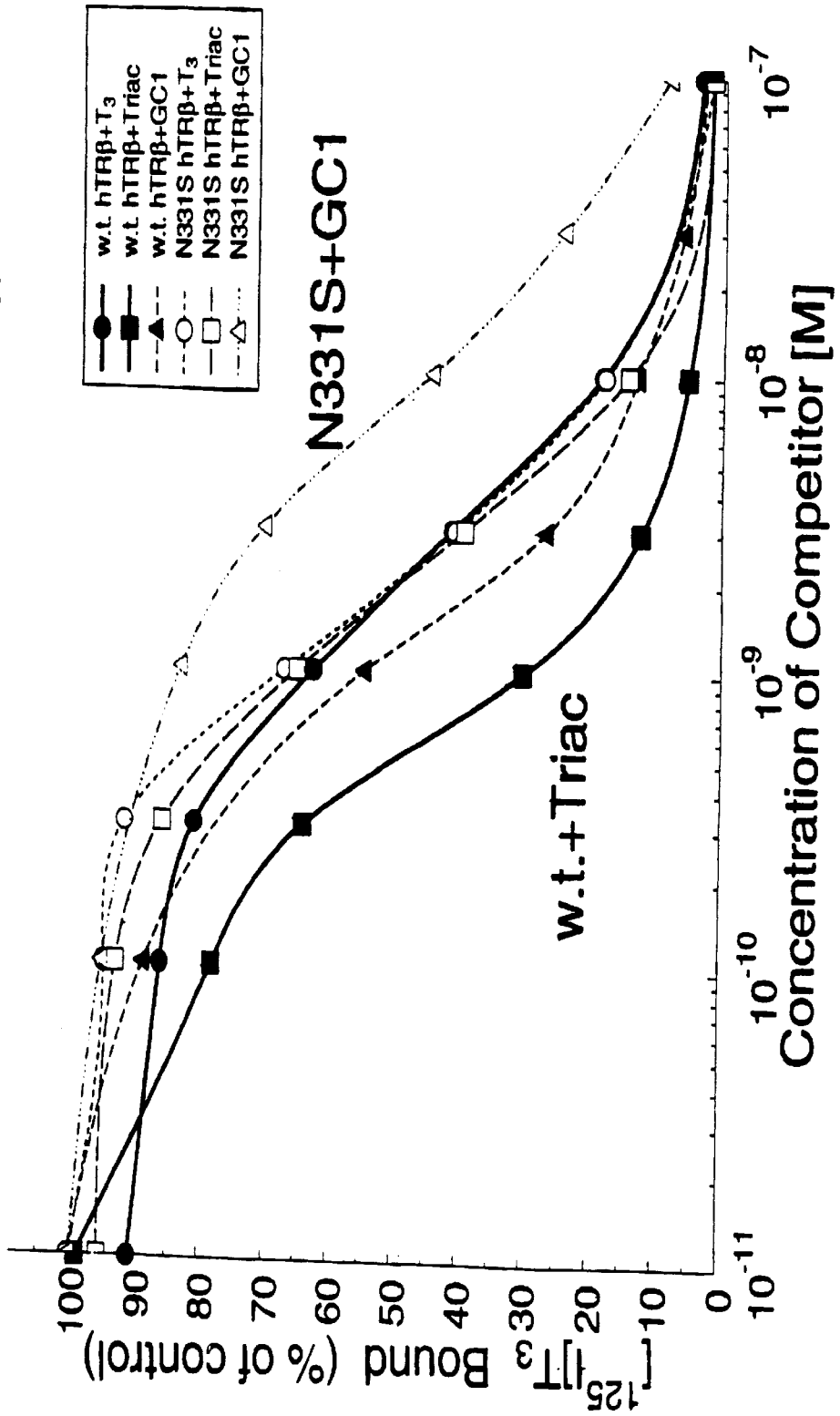
FIG. 31 is a graph showing competition curves comparing wildtype TR-α and TR-β to a variant TR-β having a single amino acid substitution in the ligand binding domain.

The following assays residues involved in selective binding among TR isoforms. Competition assays are performed to compare the displacement of $[^{125}I]T_3$ from binding with wild-type human TR-α LBD or human TR-β LBD, to a variant form of the TR LBDs by unlabeled $T_3$, Triac or GC-1. A variant TR-α or TRβ is constructed by substituting an amino acid found in the corresponding position of the other TR isoform. For example, asparagine 331 in human TRβ corresponds to serine 277 in human TRα. To test binding specificity contributed by this position, a variant human TR-β is constructed that contains asparagine 331 substituted with a serine residue (designated Asn331Ser or N331S). Binding assays are described in Apriletti et al. (Protein Expression and Purification 6:363–370 (1995)). The results of such assays are depicted in FIG. 27, and summarized in Table 4 below.

TABLE 4

Effect of TR-β Substitution N331S on Binding Affinity

| Ligand | Native TR-α | Native TR-β | Mutant TR-β |
|---|---|---|---|
| T3 | 20 pM | 60 pM | 100 pM |
| T4 | 600 | 3000 | ND |
| Triac | 20 | 20 | 100 |
| IpBr₂ | 17 | ND | ND |
| Dimit | 6000 | 8000 | ND |
| GC-1 | 200 | 40 | 400 |

Competition curves comparing wildtype TR-β versus the variant TR-β N331S for binding T3, Triac or GC-1 show that the affinity of the mutant receptor for Triac was reduced to approximately the same as for T3 (vs. 3-fold greater in wild type) so that the relative affinities are similar to wild-type TR-α. The affinity for GC-1 was also reduced to several fold less than T3, as is seen with TR-α.

Comparison of the affinity of TR-β variant N331S to the native TRs for selected ligands is as follows:

Native TR-α for various ligands (T3, T4, Triac, IpBr2, Dimit, GC-1):
  IpBr₂>Triac≈T3>GC-1>T4>Dimit Native TR-β (T3, T4, Triac, Dimit, GC-1)
  Triac>GC-1≧T3>T4>Dimit Variant TR-β (N331S) (T3, Triac, GC-1)
  Triac≈T3>GC-1.

Scatchard Analysis of $[^{125}I]T_3$ Binding to TR

Figure 17A:
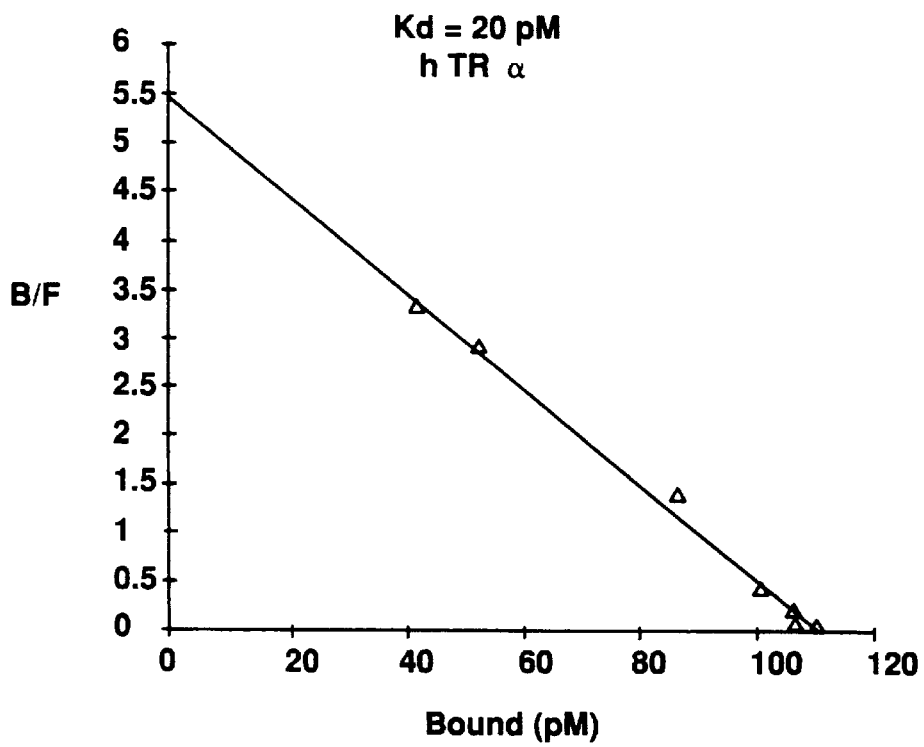
FIGS. 17A–17B depicts a Scatchard analysis of labelled $T_3$ binding to TR-α and TR-β.
Figure 17B:
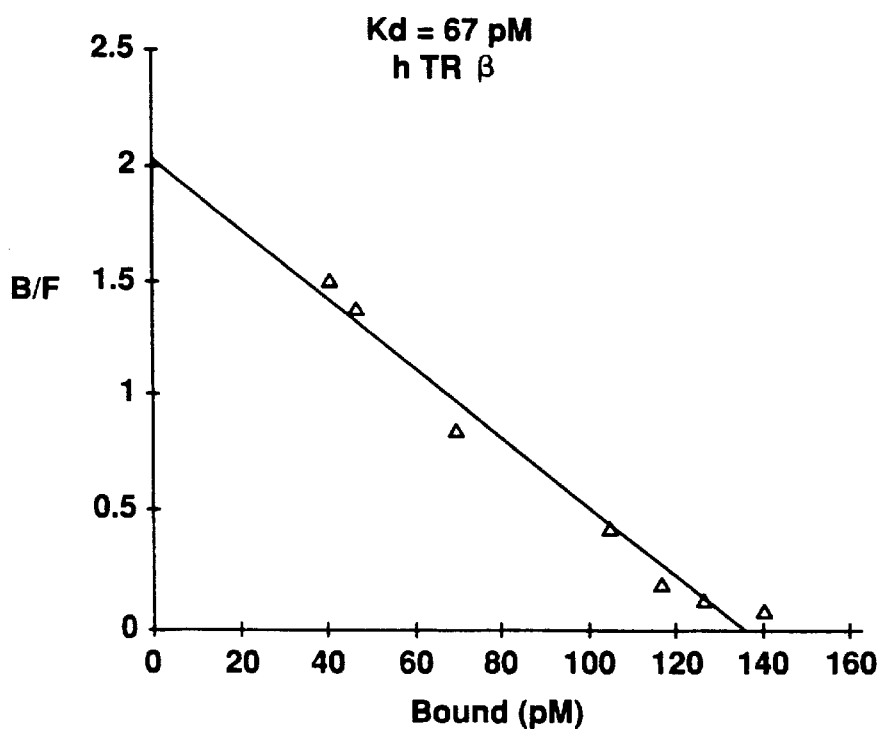

Human TR-α (left panel) or human TR-β (right panel) is assayed for $T_3$ binding in the presence of increasing concentrations of $[^{125}I]T_3$. The apparent equilibrium dissociation constant (20 pM for α and 67 pM for β) is calculated by linear regression analysis and is depicted in FIGS. 17A–17B.

3,5-DIBROMO-4-(3',5'-DIISOPROPYL-4'-HYDROXYPHENOXY) BENZOIC ACID IS A TR-α SELECTIVE SYNTHETIC LIGAND.

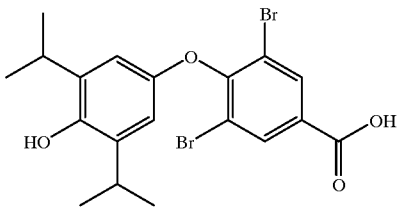

3,5-dibromo-4-(3',5'-diisopropyl-4'-hydroxyphenoxy) benzoic acid (Compound 11), the structures of which is drawn above, is assayed for binding to the two different isoforms of the TR, TR-α and TR-β. Compound 11 exhibits an IC50 of 1.6 μM for binding to TR-α and an IC50 of 0.91 μM for binding to TR-β. Assays for determining selective binding to the TR-α or TR-β LBD can include reporter assays, as described herein. See also Hollenberg, et al., *J. Biol. Chem.*, (1995) 270(24):14274–14280.

EXAMPLE 6—PREPARATION AND PURIFICATION OF A TR-α LBD

Rat TR-α LBD, residues Met122–Val410, is purified from *E. coli* ("LBD-122/410"). The expression vector encoding the rat TR-α LBD is freshly transfected into *E. coli* strain BL21(DE3) and grown at 22° C. in a 50-liter fermenter using 2× LB medium. At an $A_{600}$ of 2.5–3, IPTG is added to 0.5 mM and growth is continued for 3 h before harvesting. The bacterial pellet is quickly frozen in liquid nitrogen and stored at –70° C. until processed. Extraction and purification steps are carried out at 4° C. The bacteria are thawed in extraction buffer (20MM Hepes, pH 8.-, 1 mM EDTA, 0.1% MTG, 0.1 mM PMSF, and 10% glycerol) at a ratio of 10 ml buffer/g bacteria. Bacteria are lysed by incubation for 15 min. with 0.2 mg/ml lysozyme and sonicated at maximum power while simultaneously homogenized with a Brinkmann homogenizer (Model PT 10/35 with generator PTA 35/2) until the solution loses its viscosity. After centrifugation for 10 min at 10,000 g, the supernatant is adjusted to 0.4 M KCl, treated with 0.6% PEI to precipitate fragmented DNA, and centrifuged for 10 min at 10,000 g. The rat TR-α LBD in the supernatant is then precipitated with 50% ammonium sulfate and centrifuged for 10 min at 10,000 g. The precipitate is resuspended with buffer B (20 mM Hepes, pH 8.0, 1 mM EDTA, 1 mM DTT, 0.1 mM PMSF, 0.01% Lubrol, and 10% glycerol) to a final conductivity of 9 mS/cm (approx. 0.7 M ammonium sulfate) and centrifuged 1 h at 100,000 g. The supernatant is frozen in liquid nitrogen and stored at –70° C.

The crude extract is thawed, bound with a tracer amount of $[^{125}I]T_3$, and loaded directly onto a phenyl-Toyopearl hydrophobic interaction column (2.6×18 cm, 95 ml bed volume) at 1.5 ml/min. The column is eluted with a 2-h gradient from 0.7 ammonium sulfate, no glycerol to no salt, 20% glycerol in buffer C (20 mM Hepes, pH 8.0, 0.5 mM EDTA, 1 mM DTT, 0.2 mM PMSF). The rat TR-α LBD prebound to tracer $[^{125}I]T_3$ (less than 0.005% of total rat TR-α LBD) is detected using a flow-through gamma emission detector, whereas unliganded rat TR-α LBD is assayed by postcolumn $[^{125}I]T_3$ binding assays (described herein).

The phenyl-Toyopearl unliganded rat TR-α LBD peak fractions are pooled, diluted with buffer B to a conductivity of 0.5 mS/cm (equivalent to approx. 20 mM ammonium sulfate), loaded onto a TSK-DEAE anion-exchange column (2×15 cm, 47 ml bed volume) at 4 ml/min, and eluted with a 60-min gradient from 50 to 200 mM NaCl in buffer B.

The unliganded rat TR-α LBD peak fractions from TSK-DEAE are pooled, diluted twofold with buffer B, loaded at 0.75 ml/min on a TSK-heparin HPLC column (0.8×7.5 cm, 3 ml bed volume), and eluted with a 50 to 400 mM NaCl gradient in buffer B.

The pool of unliganded rat TR-α LBD peak fractions from the TSK-heparin column is adjusted to 0.7 M ammonium sulfate, loaded at 0.75 ml/min on a TSK-phenyl HPLC column (0.8×7.5 cm, 3 ml bed volume), and eluted with a 60-min gradient from 0.7 M ammonium sulfate without glycerol to no salt with 20% glycerol in buffer C. The fractions containing unliganded rat TR-α LBD are pooled and incubated with a five fold excess of hormone for 1 h, the salt concentration is adjusted to 0.7 M ammonium sulfate, and the sample is reloaded and chromatographed on the same column as described above.

EXAMPLE 7—CRYSTALLIZATION OF LIGANDED TR-α LBD

Material from a single LBD-122/410 preparation is divided into batches, and quantitatively bound with one of the following ligands: Dimit, $T_3$, or Triac IpBr$_2$ (3,5dibromo-3'isopropylthyronine) for the final purification step.

To maintain full saturation of rat TR-α LBD with a ligand, and to prepare the complex for crystallization, the ligand-bound rat TR-α LBD is concentrated and desalted in an Amicon Centricon-10 microconcentrator (McGrath et al, *Biotechniques*, (1989) 7:246–247, incorporated by reference herein), using 10 mM Hepes (pH 7.0), 3.0 mM DTT, and 1.0 nM to 10 nM ligand.

Factorial crystallization screening trials (Jancarik & Kim, *J. Appl. Crystallogr.* (1991) 24:409–411, incorporated by reference herein) are carried out for rat TR-α LBD bound to selected ligands using hanging-drop vapor diffusion at 17° C. (with 1 μl protein solution, 1 μl precipitant solution and a 0.5 ml reservoir using silanized coverslip: (McPherson, Preparation and Analysis of Protein Crystals (1982), incorporated by reference herein). Rat TR-α LBD is not stable at 4° C. and is stored at –80° C., where it maintains its avidity for hormone and its crystallizability for approximately two to three months. These procedures are carried out as described in McGrath, M. E. et al., *J. Mol. Biol.* (1994) 237:236–239 (incorporated by reference,. Crystals are obtained in condition 21 of the screening trials (Jancarik & Kim 1991) and conditions are then optimized. Wedge-shaped crystals are reproducibly obtained with hanging-drop vapor fusion at 22° C. with 15% 2-methyl-2,4-pentanediol (MPD), 0.2 M ammonium acetate and 0.1 M sodium cacodylate (pH 6.7), 3 mM DTT, with 2 μl protein solution, 1 μl precipitant solution and a 0.6 ml reservoir using silanized coverslip, and with 8.7 mg/ml (Dimit), 5.5 mg/ml (IpBr$_2$), 5 mg/ml (Triac), or 2.3 mg/ml ($T_3$) over a period of three days. Under these conditions, diffraction quality crystals (dimension 0.5×0.2×0.0075 mm$^3$) can be grown at ambient temperature (22° C.). The best crystals have a limiting dimension of approximately 100 μm and are obtained at a protein concentration between 2.3 and 8.7 mg/ml in the presence of 3 mM DTT. The crystals are of the monoclinic space group C2, with one monomer in the asymmetric unit.

EXAMPLE 8—CRYSTALLIZATION OF HUMAN TR-β LBD COMPLEXED WITH T3, TRIAC, OR GC-1

Human TR-β LBD complexed with $T_3$, Triac, or GC-1 are purified according to the same procedures described above for the rat TR-α LBD, with the following modifications.

The expression of human TR-β LBD differs from the rat TR-α LBD in that the human TR-β LBD residues extend from the amino acid at position 716 through the amino acid at position 1022, according to the amino acid numbering scheme for the various nuclear receptor LBDs depicted in illustrates a numbering scheme applicable to all of the nuclear receptors listed as well as to any additional homologous nuclear receptors. The vertical lines on FIGS. 3A–3R at position 725 and at position 1025 delineate the preferred minimum amino acid sequence necessary to obtain adequate binding of ligand. The amino acid sequence from position 716 to position 1022 according to the numbering scheme of FIGS. 3A–3R corresponds to the amino acid positions 202 to 461 according to the conventional numbering of the amino acid sequence of human TR-β which is publicly available. Also, the human TR-β LBD is expressed with a histidine tag, as described in Crowe et al., *Methods in Molecular Biology* (1994) 31:371–387, incorporated by reference herein.

The purification of human TR-β LBD is the same as that described above for the rat TR-α LBD with the following exceptions. First, before the purification step using the hydrophobic interaction column, a step is added in which the expressed human TR-β LBD is purified using a nickel NTA column (commercially available from Qiagen, Chatsworth, Calif.) according to manufacturer's instructions, and eluted with 200 mM imidazole. The second difference is that in the purification of the human TR-β LBD, the purification step using a heparin column is omitted.

The crystallization of human TR-β LBD bound to $T_3$, Triac or GC-1 is as follows. Crystals are obtained in condition 7 of the factorial screen using hanging drops as before at ambient temperature (22° C.) using the factorial crystallization screening trials of Jancarik & Kim (1991) and using the commercially available product from Hampton Research, Riverside). The following are optimum conditions: hexagonal bipyrimidal crystals are grown at 4° C. for 2–3 days from hanging drops containing 1.0–1.2 M sodium acetate (pH unadjusted) and 0.1 M sodium cacodylate (pH 7.4), 3 mM DTT, with either a 1 μl protein solution, 1 μl precipitant solution or 2 μl protein solution, 1 μl precipitant solution and a 0.6 ml reservoir using silanized coverslip, at a protein concentration of 7–10 mg/ml. The best crystals have a limiting dimension of 200 μm. The following are optimum conditions for crystallization of the TR-β LBD with GC-1: hexagonal bipyrimidal crystals are grown at 4° C. for 2–3 days from hanging drops containing 0.8–1.0M sodium acetate (pH unadjusted), 50–200 nM sodium succinate, and 0.1M sodium cacodylate (pH 7.2), 3 mM DTT, 1 μl protein solution, 1 μl precipitant solution and a 0.6 ml reservoir using silanized coverslip, at a protein concentration of 7–10 mg/ml. The best crystals have a limiting dimension of 200 μM. The unit cell dimensions are cell length a=b=68.73, cell length c=130.09. The unit cell angles are α=90°, β=90°, γ=120°.

The crystal system for human TR-β LBD bound to $T_3$, Triac or GC-1 is trigonal with the space group p3$_1$21. The unit cell dimensions are cell length a=cell length b=68.448 angstroms, cell length c=130.559 angstroms. The angles are α=90°, β=90°, gamma=120°.

EXAMPLE 9—DETERMINATION OF LIGANDED TR-α LBD AND TR-β CRYSTAL STRUCTURES

Data from each cocrystal (Rat TR-α LBD with Dimit, T3 and IpBr2; Human TR-β LBD with Triac and GC-1) is measured on a Mar area detector at Stanford Synchrotron Radiation Laboratory beamline 7-1 (λ=1.08 angstroms) using 1.2° oscillations. Data from the cocrystal of the hTR-β LBD with Triac is measured on a Mar area detector at Stanford Synchrotron Radiations Laboratory beamline 7-1 (λ=1.08 angstroms) using 1.0 oscillations. Data from the cocrystal of the hTR-β LBd with GC-1 is measured on a R-axis II area detector on a Rigaku rotating Cu anode (50 kV, 300 mA). The crystals are transferred into a cryosolvent containing 1.2M sodium acetate, 0.1M sodium cacodylate, and 15% glycerol followed by a second transfer into 30% glycerol, then flash frozen in liquid nitrogen. An orientation matrix for each crystal is obtained using DENZO. The reflections are integrated with DENZO (commercially available from Molecular Structure Corp., The Woodlands., Tex.) and are scaled with SCALEPACK (as described in Otwinowski, Z, *Proceedings of the CCP4 Study Weekend: "Data Collection and Processing,"* 56–62 (SERC Daresbury Laboratory, Warrington, UK 1993) incorporated by reference).

For rTR-α cocrystals, data from the $T_3$ cocrystal is measured with the b* axis approximately parallel with the spindle. The crystals are flash frozen at −178° C. in a nitrogen gas stream with the MPD mother liquor serving as the cryosolvent. An orientation matrix for each crystal is determined using REFIX (Kabsch, W., *J. Appl. Crystallogr.* (1993) 26:795–800 incorporated by reference). Reflections are integrated with DENZO, and are scaled with SCALEPACK.

For the $T_3$ data set, Bijvoet pairs are kept separate, and are locally scaled using MADSYS (W. Hendrickson (Columbia University) and W. Weis (Stanford University)).

Cocrystals prepared from the three isosteric ligands are isomorphous. MIR analysis is performed using programs from the CCP4 suite (Collaborative Computational Project, N.R. *Acta Crystallogr.* (1994) D50:760–763, incorporated by reference herein). Difference Pattersons is calculated for both $T_3$ and IpBr$_2$, taking the Dimit cocrystal as the parent. The positions of the three iodine atoms in the $T_3$ difference Patterson are unambiguously determined from the Harker section of the density map as peaks of 11σ above background. The positions for the two bromine atoms in the IpBr$_2$ cocrystals, are located independently, as peaks 8σ above the noise level. Phases for the LBD-122/410 are calculated from the solution to the IpBr$_2$ difference Patterson, and are used to confirm the location of the unique third iodine of the $T_3$ cocrystal. Halogen positions are refined with MLPHARE, including the anomalous contributions from the iodine atoms (Otwinowski, Z, *Proceedings of the CCPR Study Weekend* 80–86 (SERC Daresbury Laboratory, Warrington, UK 1991)). The MIRAS phases are improved through solvent flattening/histogram matching using DM (Cowtan, K., *Joint CCP4 and ESF-EACBM Newsletter on Protein Crystallography* (1994) 31: 34–38, incorporated by reference herein).

A model of the LBD-122/410 with Dimit bound is built with the program O from the solvent flattened MIRAS 2.5 angstrom electron density map (Jones et al., *Acta Crystallogr.* (1991) A 47:110–119, incorporated by reference herein). The initial model, without ligand, (Rcryst=40.1%), is refined using least-squares protocols with XPLOR. The Dimit ligand is built into unambiguous Fo-Fc difference density during the following round. Subsequent refinement employs both least-squares and simulated annealing protocols with XPLOR (Brunger et al., *Science* (1987) 235:458–460), incorporated by reference herein). Individual atomic B-factors are refined isotropically. As defined in PROCHECK, all residues are in allowed main-chain torsion angle regions as described in Laskowski et al., *J. Appl. Crystallogr.*, (1993) 26:283–291, incorporated by reference herein. The current model is missing 34 residues ($Met_{122}$–$Gln_{156}$) at the N-terminus, and 5 residues ($Glu_{406}$–$Val_{410}$) at the C-terminus.

In addition, the following residues are not modeled beyond Cβ due to poor density: 184, 186, 190, 198, 206, 209, 240, 301, 330, 337, 340, 343, 359, and 395. The average B-value for protein atoms is 34.5 $Å^2$. The final model consists of the LBD-122/410, residues $Arg_{157}$–$Ser_{183}$, $Trp_{185}$–$Gly_{197}$, $Ser_{199}$–$Asp_{206}$ and $Asp_{208}$–$Phe_{405}$; three cacodylate-modified cysteines: $Cys_{334}$, $Cys_{380}$ and $Cys_{392}$; and 73 solvent molecules modeled as water (2003 atoms).

$$*R_{sym}=100\times\Sigma_{hkl}\Sigma_i|I_i-I|/\Sigma_{hkl}\Sigma_i I_i$$

$$\dagger R_{der}=100\times\Sigma_{hkl}|F_{PH}-F_H|/\Sigma_{hkl}|F_P|$$

The occupancy for the two bromine sites is set to 35 electrons. The occupancies of the iodine sites are relative to this value. §Phasing power=<FH>/<ε>, where <FH> is the mean calculated heavy atom structure factor amplitude and <ε> is the mean estimated lack of closure. ‖Rcullis=<ε>/<iso>, where <ε> is the mean estimated lack of closure and (iso) is the isomorphous difference. ¶Rcryst=$100\times\Sigma_{hkl}|F_o-Fc|/\Sigma_{hkl}|F_o|$ where $F_o$ and $F_c$ are the observed and calculated structure factor amplitudes (for data F/σ>2). The Rfree was calculated using 3% of the data, chosen randomly, and omitted from the refinement. § Correlation coefficient=$\Sigma_{hkl}(|F_o|-|\overline{F_o}|)\times(|F_c|-|\overline{F_c}|)/\Sigma_{hkl}(|F_o|-|\overline{F_o}|)^2\times\Sigma_{hkl}(|F_c|-|\overline{F_c}|)^2$ EXAMPLE 10 PHASING OF THE rTR-α LBD AND hTR-β LBD COMPLEX WITH TRIAC Due to the possible non-isomorphism of the rTRα LBD complex with Triac, a molecular replacement solution is determined using AMORE (Navaza, *J., Acta Crystallographica Section A-Fundamentals of Crystallography* (1994) 50:157–63 from a starting model consisting of rTRα LBD complex with $T_3$, but with the ligand, all water molecules, and the following residues omitted: Asn 179, Arg228, Arg262, Arg266, and Ser 277. Strong peaks are obtained in both the rotation and translation searches, with no significant (>0.5 times the top peak) false solutions observed (Table 6). Strong positive density present in both the anomalous and conventional difference Fourier maps confirm the solution. Maps are calculated using sigma-A weighted coefficients output by REFMAC (Murshudov, et al. "Application of Maximum Likelihood Refinements," in *Refinement of Protein Structures, Proceedings of Daresbury Study Weekend* (1996)) after 15 cycles of maximum likelihood refinement. Triac, the omitted residues, and water molecules 503, 504, 534 (following the numbering convention for the TR complex with T3) are built into the resulting difference density using O (Jones et. al.); the conformations of these residues are further confirmed in a simulated-annealing omit map (Brunger et. al.). The complete model is then refined using positional least-squares, simulated annealing, and restrained, grouped B factor refinement in XPLOR to an Rcryst of 23.6% and an Rfree of 24.1%

Phasing of a related LBD using the structure of the rTR-α LBD is conducted as follows. A molecular replacement solution for the hTR-β LBD complex with Triac is determined using AMORE from a starting model consisting of the rTR-α LBD complexed with T3, but with the ligand and all water molecules omitted. Strong peaks are obtained in both the rotation and translation searches, with no significant (>0.5 times the top peak) false solutions (Table 7). Strong positive density present in both the anomalous and conventional difference Fourier maps confirm the solution. Initial maps are calculated using sigma-A weighted (coefficients output by REFMAC after 9 cycles of maximum likelihood refinement. The real-space fit for each residues was calculated using OOPS (Kleywegt, GJ and Jones, TA, OOPS-a-daisy, ESF/CCP4 Newsletter Jun. 30, 1994, pp. 20–24) and the residues with a real-space fit less than 2 standard deviations below the mean removed: Ala253–Lys263; Glu245–Leu250. To reduce bias, the following residues were modeled as alanine: Arg282, Arg316, Arg 320, Asn 331. Cycles of rebuilding and positional least-squares, simulated annealing, and restrained, grouped B factor refinement with XPLOR produce a model with an $R_{cryst}$ of 25.3 and an $R_{free}$ of 28.9%. The final model consists of hTR-β LBD residues Glu202–Gln252, Val264–Glu460; three cacodylate-modified cysteines with the cacodylate moeity modeled as free arsenic: Cys294, Cys298, Cys388, and Cys434; and 35 solvent molecules in modeled as water.

EXAMPLE 11 CONNECTING QSAR WITH STRUCTURE IN THE THYROID HORMONE RECEPTOR

The conclusions of classic thyroid hormone receptor quantitative structure-activity relationships may be summarized as follows:

1) the $R_4$'-hydroxyl group functions as a hydrogen bond donor;
2) the amino-propionic acid interacts electrostatically through the carboxylate anion with a positively charged residue from the receptor;
3) the preferences of $R_3/R_5$, substituent are I>Br>Me>>H;
4) the preferences of the $R_3$'-substituent are Ipr>I>Br>Me>>H.

The structure of the thyroid hormone receptor ligand binding domain complexed with the agonists T3, $IpBr_2$, Dimit, Triac, and GC1 as provided herein, permits:

1) the identification of receptor determinants of binding at the level of the hydrogen bond;
2) the association of these determinants with the predictions of classic thyroid hormone receptor QSAR; and
3) prediction as to which determinants of binding are rigid, and which are flexible, for both the ligand and the receptor.

This classification for the agonists of the type ($R_1$=amino-propionic, acetic acid; $R_3,R_5$=I,Br,Me; $R_3$'=Ipr,I) is given below (for the representative ligand $T_3$);
F=Fiducial (always satisfied)
A=Adjustable

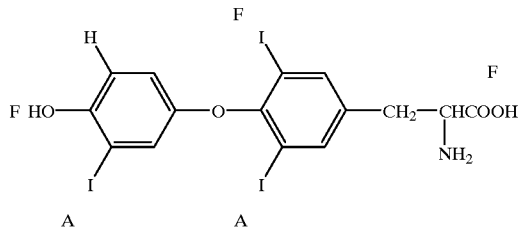

Figure 23:
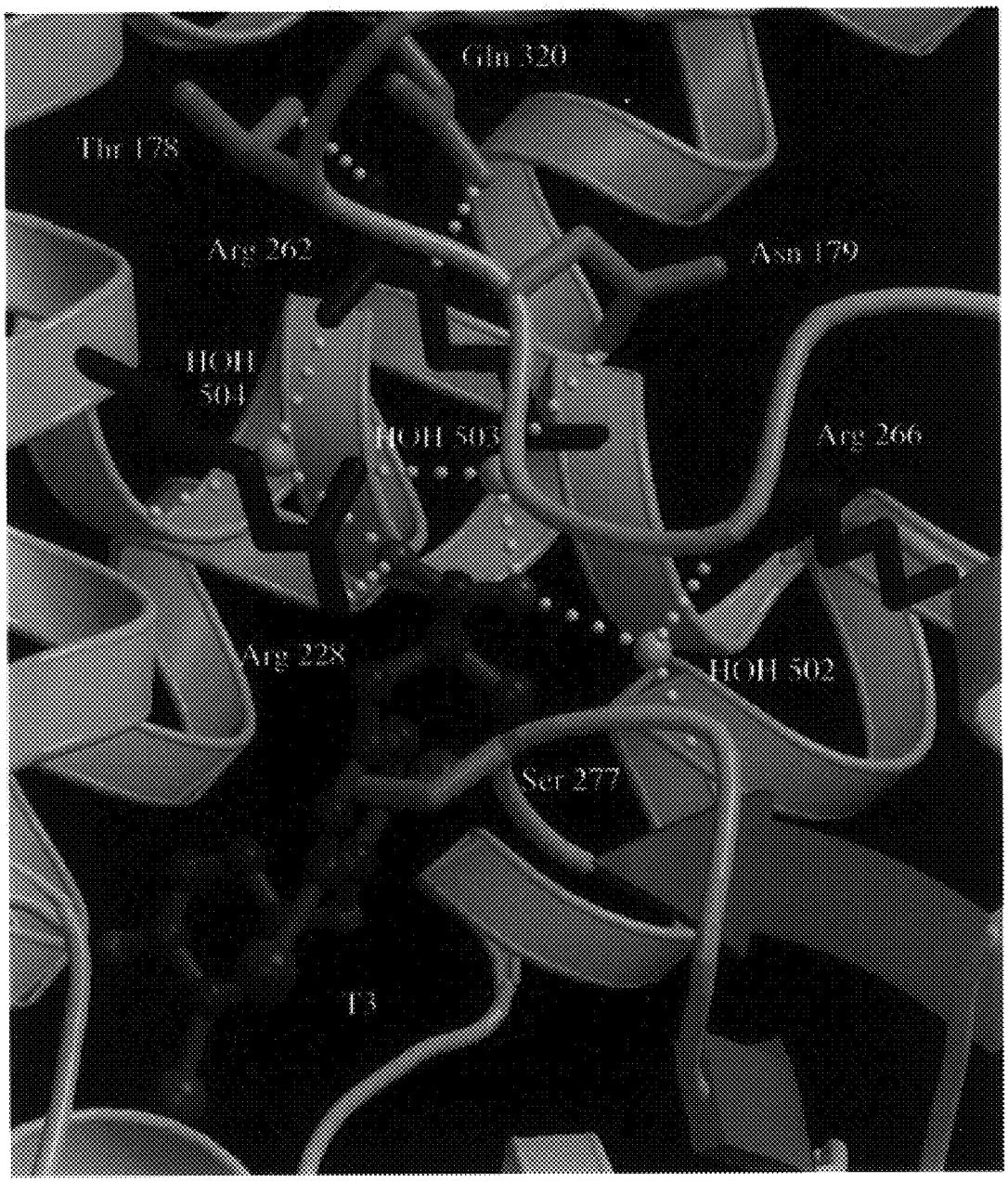
FIG. 23 is a partial ribbon drawing of TR-α LBD with T3, illustrating the three Arginine residues (Arg228, Arg262 and Arg 266 (dark stick figures)) of the polar pocket, three water molecules HOH502, HOH503 and HOH504, with hydrogen bonds indicated by dotted lines.
Figure 24:
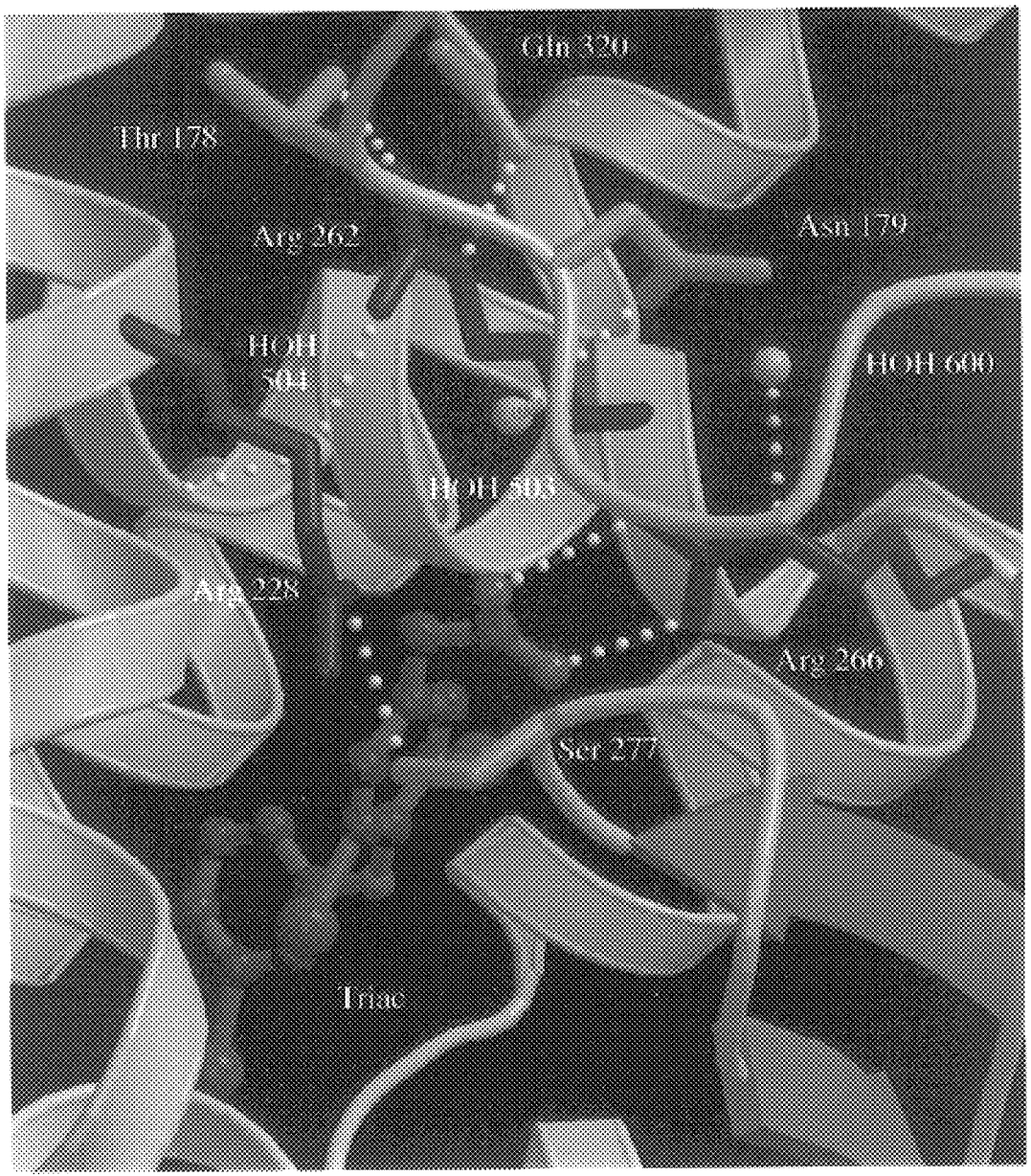
FIG. 24 is a partial ribbon drawing of TR-α LBD with Triac, illustrating the three Arginine residues (dark stick figures) of the polar pocket, water molecules (HOH503, HOH504 and HOH600), with hydrogen bonds indicated by dotted lines.
Figure 25:
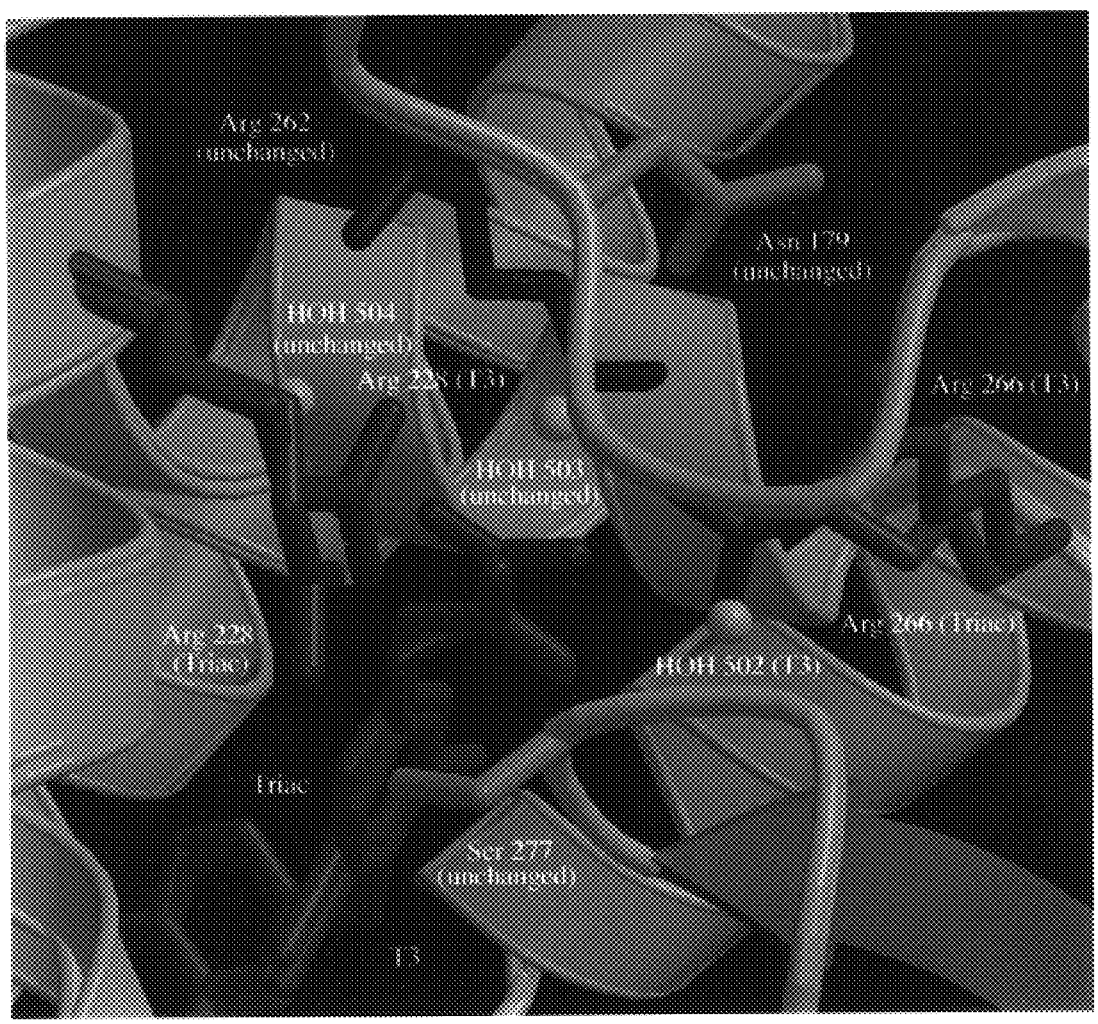
FIG. 25 is a partial ribbon drawing of the TR-α LBD with T3 and Triac superimposed in the ligand binding cavity. The drawing shows several interacting amino acid residues in the polar pocket that remain unchanged whether T3 or Triac occupies the ligand binding cavity: Arg262, Asn179, HOH503 and HOH504, and Ser277. Both Arg228 and Arg 266 occupy two different positions, depending on whether T3 or Triac is bound.
Figure 26A:
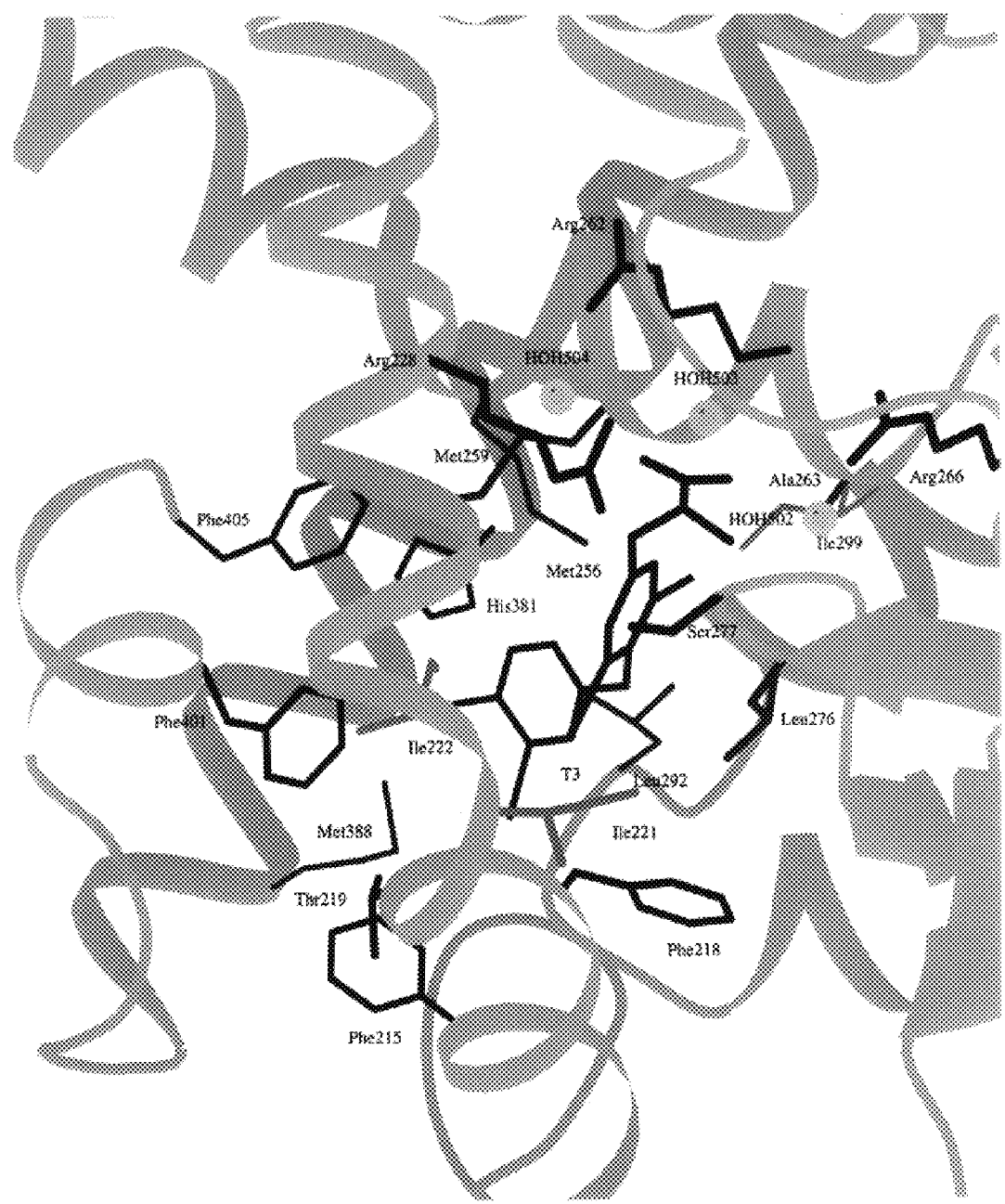
FIGS. 26A and 26B are stereochemical representations of the TR-α LBD with Dimit bound.
Figure 26B:
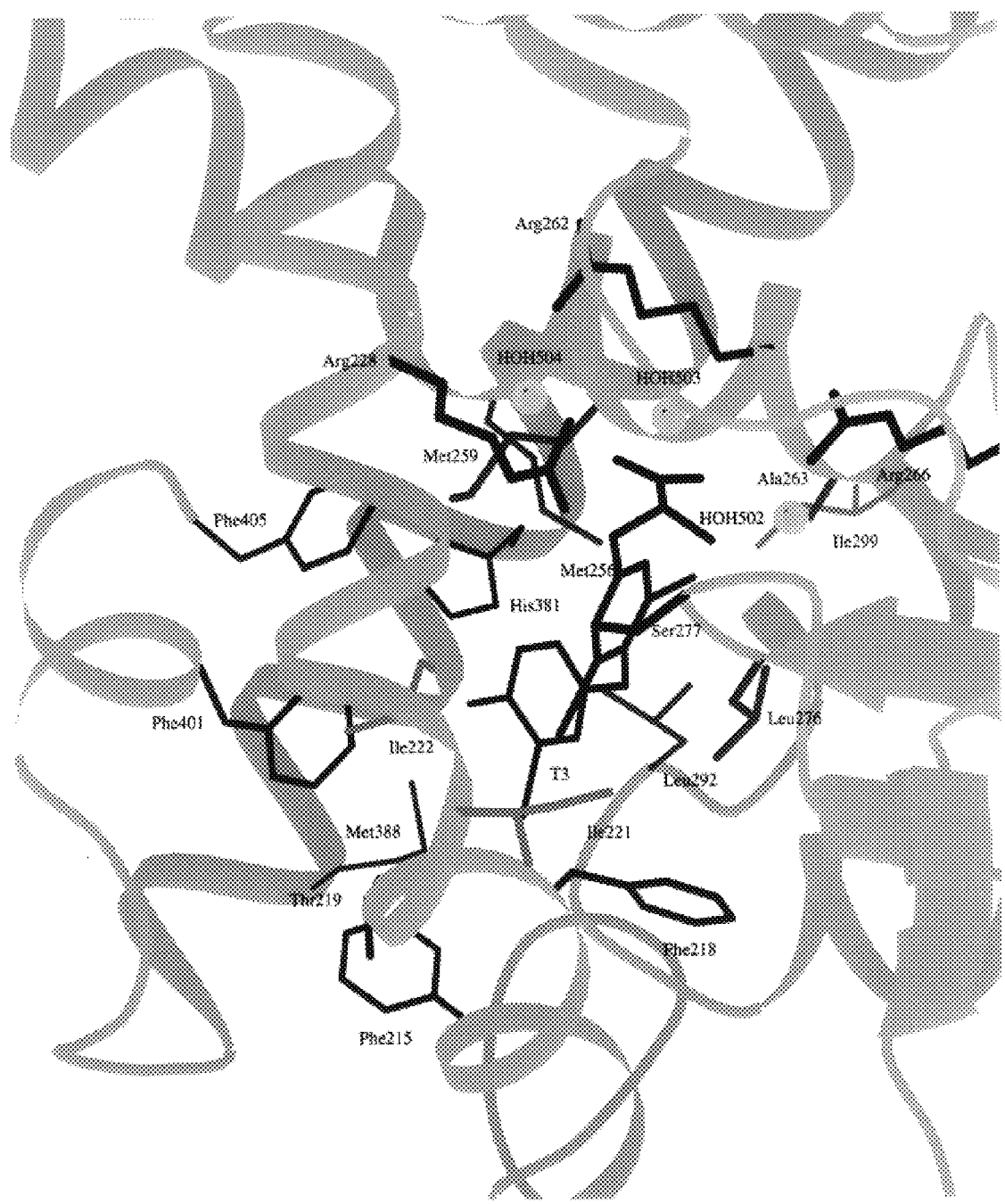

Based upon the methods and data described herein, the following is an embodiment of the computational methods of the invention, which permit design of nuclear receptor ligands based upon interactions between the structure of the amino acid residues of the receptor LBD and the four different ligands described herein. The small molecule structures for the ligands can be obtained from Cambridge Structural Database (CSD), and three dimensional models can be constructed using the methods described throughout the specification. The following are factors to consider in designing synthetic ligands:

1) Histidine 381 acts as a hydrogen bond acceptor for the $R_4'$ hydroxyl, with the optimal taulomer maintained by water molecules. See FIG. 23 and FIG. 24. Histidine is the only hydrophilic residue in this hydrophobic pocket that surrounds the $R_4'$ substituent. Histidine can be either a hydrogen bond acceptor or donor, depending on its tautomeric state. It is preferably a hydrogen bond donor, but can tolerate being a hydrogen bond acceptor, as for example, when there is a methoxy at the $R_4'$ position of the ligand;

2) Arginines 228, 262, and 266 interact directly and through water-mediated hydrogen bonds with the $R_1$-substituent, with the electrostatic interaction provided by Arginine 266 (as in the Triac complex). This polar pocket is illustrated by FIG. 23–FIG. 25. FIG. 23 depicts $T_3$ in the TRα ligand binding cavity, where T3's amino-propionic R1-substituent interacts with Arg 228, HOH502, H9H503 and HOH504 via hydrogen bonds. FIG. 24 depicts Triac in the ligand binding cavity, with its —COOH $R_1$ substituent in the polar pocket. In FIG. 24, Arg 228 no longer shares a hydrogen bond with the ligand, but the —COOH $R_1$ substituent forms hydrogen bonds with Arg 266. FIG. 25 superimposes $T_3$ and Triac in the ligand binding cavity and shows several positionally unchanged amino acids and water molecules, and selected changed interacting amino acids and water molecules. The three figures illustrate parts of the polar pocket that can change and those parts that do not move upon binding of different ligands. For example, the Arg 262 at the top of the polar pocket does not move, even when the $R_1$ substituent has changed from a —COOH to an aminopropionic acid group. However, the other two Arginines, Arg 228 and Arg 266, demonstrate flexibility in the polar pocket to respond to the change in the size or chemical nature of the $R_1$ substituent.

Figure 21:
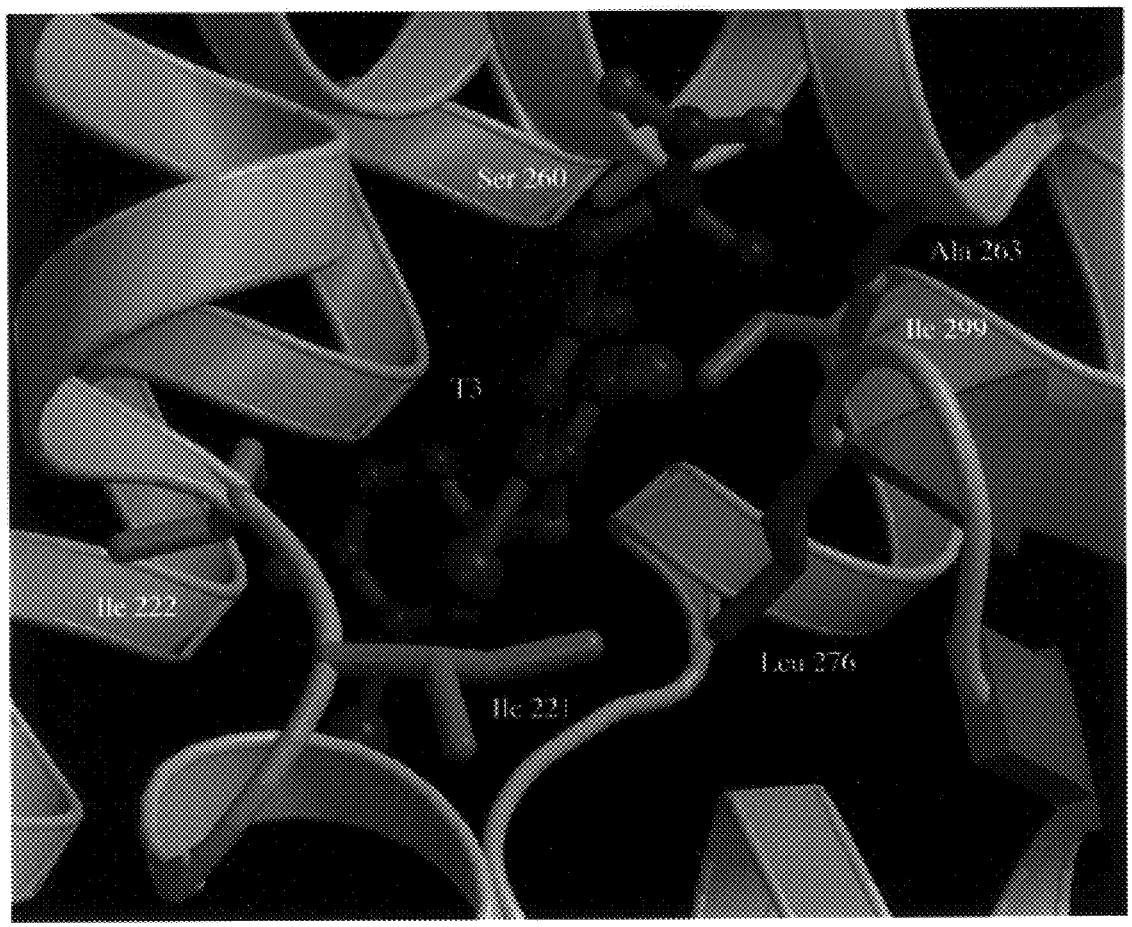
FIG. 21 is a partial ribbon drawing of TR-α LBD with T3 in the ligand binding cavity. Selected interacting amino acids are labelled, including Ile221, Ile222 and Ser260, Ala263, Ile299 and Leu 276.
Figure 22:
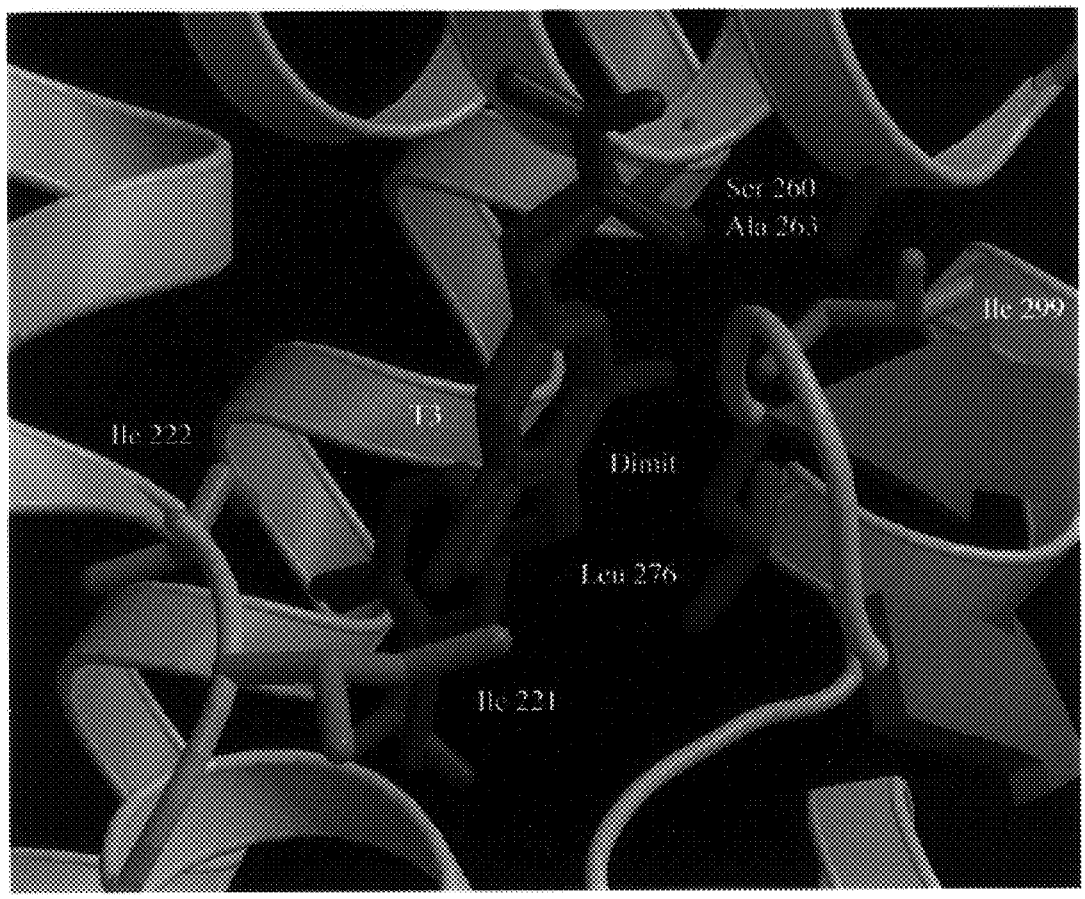
FIG. 22 is a partial ribbon drawing of TR-α LBD with T3 and Dimit superimposed in the ligand binding cavity. Interactions with Ile221, Ile222, Ala260, Ile 299 and Leu276 are labelled.

3) Inner and outer pockets for the $R_3/R_5$ substituents are formed by Ser260, Ala263, Ile299; and Phe 218, Ile221, Ile222, respectively. See FIGS. 21 and 22. The inner pocket is filled by either the $R_3$ or the $R_5$ substituent, regardless of the size of the substituent, and may act as a binding determinant by positioning the ligand in the receptor. Optimally, the inner pocket amino acids interact with an R3 or R5 substituent that is no larger than an iodo group. If the inner pocket is filled by the $R_3$ substituent, then the outer pocket interacts with the $R_5$ substituent and vice versa. The outer pocket can adjust to the size of its substituent through main chain motion centered at the break in helix 3 (Lys220–Ile221), suggesting that the bending of H3, and motion of the N-terminal portion of H3, may represent a conformational change induced on ligand binding. The outer pocket has greater flexibility than does the inner pocket in terms of accommodating a larger substituent group.

4) A pocket for the $R_3'$-substituent is formed by Phe 215, Gly290, Met388. The pocket is incompletely filled by the $R_3'$-iodo substituent, and accommodates the slightly larger 3'-isopropyl substituent by movement of the flexible Met388 side chain and the H7/H8 loop. This pocket can accommodate $R_3'$ substituents that are even larger than isopropyl, for example, a phenyl group.

The above information will facilitate the design of high affinity agonists and antagonists by improving automated QSAR methodologies and informing manual modeling of pharmaceutical lead compounds. For example, the inclusion of discrete water molecules provides a complete description of hydrogen bonding in the polar pocket for use with pharmacophore development: also, the identification of mobile and immobile residues within the receptor suggests physically reasonable constraints for use in molecular mechanics/dynamics calculations.

EXAMPLE 12 DESIGN OF AN INCREASED AFFINITY LIGAND

Direct interaction between the receptor and the ligand is limited in the polar pocket, which interacts with the $R_1$ substituent. While the lack of complementarity may contain implications for biological regulation, it also provides an opportunity for increasing affinity by optimizing the interaction between the amino acids of the polar pocket and the $R_1$ substituent of a synthetic ligand. The structure of the receptor-ligand interactions described herein enables design of an increased affinity synthetic ligand having two complementary modifications:

1) Remove the positively charged amine. The strongly positive electrostatic potential predicted for the polar pocket suggests that the positively charged amine of the aminopropionic acid $R_1$ substituent may be detrimental to binding. Suitable groups for substitution are suggested by the nature of nearby hydrogen bond partners: for example, Thr 275 O or Ser 277 N. See e.g. Tables in Appendix 2. For example, any any negatively charged substituent would be compatible for interacting with the amino acids of the polar pocket, including carboxylates, carbonyl, phosphonates, and sulfates, comprising 0 to 4 carbons. Another example of an $R_1$ substitution is an oxamic acid that replaces the amine of the naturally occurring ligand with one or more carbonyl groups.

2) Incorporate hydrogen bond acceptor and donor groups into the $R_1$-substituent to provide broader interactions with the polar pocket scaffold. Such hydrogen bond acceptor and donor groups incorporated into the $R_1$-substituent will allow interactions that would otherwise occur with water molecules in the polar pocket. Specific waters include HOH 504 (hydrogen bonds with Ala 225 O and Arg 262 NH); and HOH 503 hydrogen bonds with Asn 179 OD1, Ala 180 N), both of which are present in all four complexes (TR LBD complexed with T3, TR LBD complexed with $IpBr_2$, TR LBD complexed with Dimit and TR LBD complexed with Triac). Analysis of the hydrogen bonding network in the polar pocket suggests replacement of HOH 504 with a hydrogen bond acceptor, and HOH 503 with an hydrogen bond donor (although the chemical nature of asparagine probably permits flexibility at this site). Thus, incorporating a hydrogen bond acceptor in an R1 substituent that could take the place of the HOH504 or incorporating a hydrogen bond acceptor in an R1 substituent that could positionally replace the HOH503, or a combination thereof, are methods of designing novel synthetic TR ligands.

These two design approaches can be used separately or in combination to design synthetic ligands, including those in Table 5 (below).

A corollary to this approach is to design specific interactions to the residues Arg262 and Asn 179. The goal is to build in interactions to these residues by designing ligands that have $R_1$ substituents that form hydrogen bonds with water molecules or charged residues in the polar pocket.

High-affinity ligands also may be designed and selected using small molecules that bind to proximal subsites of the target nuclear hormone receptor that are identified in a structure-based screen and then linked together in their experimentally determined bound orientations. Such a method has been described in design of high-affinity ligands for the FK506 binding protein (FKBP), stromelysin, gelatinase A, and human papillomavirus E2 (Hajduk et al., *Science* 278:497–499 (1997)), which reference and its references are incorporated herein by reference. The preferred small molecules for screening are compounds of Formula I or derivatives thereof. For example, a compound of Formula I (φ-X-φ) or a derivative thereof (φ-X or X-φ) is screened for binding a target nuclear hormone receptor LBD. Proximal subsites of the nuclear hormone receptor include the hydrophobic and polar pockets of the LBD, and subsites extended therefrom. As an example, Fourier transformation or nuclear magnetic resonance (NMR)-based structure screens can be used. When a NMR-based screen is used, binding can be detected from the amide chemical shift changes observed in two-dimensional heteronuclear single quantum correlation (HSQC) spectra acquired in the presence and absence of added compound. Once two ligands are identified that bind to the receptor, the crystal or solution structure of the ternary complex is determined. From the structural information, a compound is synthesized which links the two ligands, where the linker is selected based on structural information. The new compound is then screened for binding affinity, for example, using a binding assay as described herein. Only a few linked ligands need to synthesized and screened when using this approach.

Compounds of the invention also may be interactively designed from structural information of the compounds described above using other structure-based design/ modeling techniques (Jackson, R. C., *Contributions of protein structure-based drug design to cancer chemotherapy.*

*Seminars in Oncology*, 1997, 24(2)L164–172; and Jones, T. R., et al., *J. Med. Chem.*, 1996 39(4):904–917).

TABLE 5

Synthetic TR Ligands

| R1 | R2 | R3 | R5 | R6 | X | R'2 | R'3 | R'4 | R'5 | R'6 |
|---|---|---|---|---|---|---|---|---|---|---|
| $CO_2H$ | H | Me | Me | H | O | H | Me | OH | Me | H |
| $CH_2CO_2H$ | | I | I | | S | | Et | SH | Et | |
| $CH_2CH_2CO_2H$ | | Br | Br | | | | nPr | $NH_2$ | nPr | |
| $CH_2CH(NH_2)CO_2H$ | | Cl | Cl | | | | iPr | | iPr | |
| $OCH_2CO_2H$ | | Et | Et | | | | Ph | | nBu | |
| $OCH_2CH_2CO_2H$ | | OH | OH | | | | I | | nPen | |
| $NHCH_2CO_2H$ | | $NH_2$ | $NH_2$ | | | | Br | | nHex | |
| $NHCH_2CH_2CO_2H$ | | SH | SH | | | | Cl | | Ph | |
| $CH_2COCOCO_2H$ | | | | | | | | | hetero cycle | |
| $NHCOCOCO_2H$ | | | | | | | | | aryl | |
| $COCO_2H$ | | | | | | | | | | |
| $CF_2CO_2H$ | | | | | | | | | | |
| $COCH_2CO_2H$ | | | | | | | | | | |

Any combination of the above substituents in the biphenyl ether scaffold structure shown above may result in a potentially pharmacologically useful ligand for the thyroid hormone receptor. These novel ligands may be antagonists of the thyroid receptor.

TABLE 6

| TR-α LBD-122/410 | | | | |
|---|---|---|---|---|
| | Dimit | T3 | $IpBr_2$ | Triac |
| Data collection | | | | |
| Cell dimensions | | | | |
| a (Å) | 117.16 | 117.19 | 117.18 | 118.19 |
| b (Å) | 80.52 | 80.20 | 80.12 | 81.37 |
| c (Å) | 63.21 | 63.23 | 63.13 | 63.73 |
| β (°) | 120.58 | 120.60 | 120.69 | 121.00 |
| Resolution (Å) | 2.2 | 2.0 | 2.1 | 2.45 |
| Obs. Reflections, (no.) | 57031 | 64424 | 66877 | 83573 |
| Unique Reflections, (no.) | 22327 | 21023 | 23966 | 18453 |
| Completeness, (%) | 87.0 | 82.4 | 93.7 | 96.0 |
| *$R_{sym}$ (%) | 3.9 | 3.5 | 4.5 | 7.5 |
| Phasing (15.0–2.5 Å) | | | | |
| †$R_{der}$ (%) | — | 19.6 | 11.6 | |
| No. of sites | — | 3 | 2 | |
| ‡Occupancy | — | 44.6 (19.8) | 35.0 | |
| (Anomalous) | — | 50.2 (23.7) | 35.0 | |
| | | 39.2 (22.3) | | |
| §$F_H$/E | | | | |
| centric (acentric) | | | | |
| 15.0–5.0 Å | — | 3.67 (4.61) | 2.25 (3.09) | |
| 5.0–3.0 Å | — | 2.23 (2.75) | 1.25 (1.85) | |
| 3.0–2.5 Å | — | 1.64 (1.99) | 1.15 (1.57) | |
| ‖$R_{cullis}$ (%) | | | | |
| 15.0–5.0 Å | — | 33 | 44 | |
| 5.0–3.0 Å | — | 45 | 63 | |

TABLE 6-continued

TR-α LBD-122/410

|  | Dimit | T3 | IpBr$_2$ | Triac |
|---|---|---|---|---|
| 3.0–2.5 Å | — | 60 | 65 |  |
| Mean figure of merit MR Phasing (10–3.5 Å) | 0.62 | — | — |  |
| Rotation Search: Euler Angles (°) |  |  |  | θ$_1$ = 309.37 θ$_2$ = 48.96 θ$_3$ = 127.28 |
| § correlation coefficient |  |  |  | 34.3 |
| Translation Search: Fractional coordinates |  |  |  | x = 0.1571 y = 0.000 z = 0.3421 |
| § correlation Coefficient |  |  |  | 65.8 |
| ¹R factor |  |  |  | 31.2 |
| Refinement Resolution (Å) | 15.0–2.2 | 5.0–2.0 | 15.0–2.2 | 25–2.5 |
| ¶R$_{cryst}$ (%) | 20.5 | 22.1 | 21.4 | 23.6 |
| R$_{free}$ (%) | 22.7 | 24.0 | 22.4 | 24.1 |

TABLE 7

TR-β LBD-202/461

|  | Triac | T3 | GC1 |
|---|---|---|---|
| Data collection |  |  |  |
| Space Group |  | P3121 |  |
| Cell dimensions |  |  |  |
| a (Å) | 68.9 | 68.45 | 68.73 |
| c (Å) | 131.5 | 130.56 | 130.09 |
| Resolution (Å) | 2.4 | 3.1 | 2.8 |
| Obs. Reflections, (no.) | 80196 | 55103 | 54104 |
| Unique Reflections, (no.) | 14277 | 6847 | 8987 |
| Coverage (%) | 97.0 | 95.7 | 97.1 |
| *R$_{sym}$ (%) | 5.1 | 4.6 | 5.5 |
| MR Phasing (15.0–3.5 Å) |  |  |  |
| Rotation Search Euler Angles (°) | θ$_1$ = 39.13 θ$_2$ = 68.00 θ$_3$ = 323.6 |  |  |
| § correlation coefficient (Highest false peak) | 21.6 (10.8) |  |  |
| Translation Search Fractional Coordinates | x = 0.748 y = 0.158 z = 0.167 |  |  |
| § correlation coefficient (Highest false peak) | 57.5 (38.7) 0.612 |  |  |
| *R factor | 40.7 |  | 40.8 |
| Refinement Resolution (Å) | 30–2.4 |  | 30–2.9 |
| ¶R$_{cryst}$ (%) | 25.3 |  | 27.3 |
| R$_{free}$ (%) | 28.9 |  | 33.4 |

All publications and patent applications mentioned in this specification are herein incorporated by reference to the same extent as if each individual publication or patent application was specifically and individually indicated to be incorporated by reference. The nuclear receptor ligands, particularly the TR ligands, of these references are herein incorporated by reference and can be optionally excluded from the claimed compounds with a proviso.

Headings and subheadings are presented only for the convenience of the reader and should not be used to construe the meaning of terms used within such headings and subheadings.

The invention now being fully described, it will be apparent to one of ordinary skill in the art that many changes and modifications can be made thereto without departing from the spirit or scope of the appended claims.

APPENDIX 1

Andrea, T. A., et al. *J Med Chem* 22, 221–232 (1979).
Andrews et al, U.S. Pat. No. 4,741,897, issued May 3, 1989.
Apriletti, J. W., Baxter, J. D., Lau, K. H & West, B. L. *Protein Expression and Purification* 6, 363–370 (1995).
Apriletti, J. W., Baxter, J. D. & Lavin, T. N. *J. Biol. Chem.* 263, 9409–9417 (1988).
Au-Fliegner, M., Helmer, E., Casanova, J., Raaka, B. M. & Samuels, H. H. *Mol Cell Biol* 13, 5725–5737 (1993).
Baniahmad, A., et al. Mol Cell Biol 15, 76–86 (1995).
Barettino, D., Vivanco Ruiz, M. M. & Stunnenberg, H. G. *Embo J* 13, 3039–3049 (1994).
Beck-Peccoz, P., et al. J Clin Endocrinol Metab 78, 990–993 (1994).
Bhat, M. K., McPhie, P. & Cheng, S. Y. *Biochem Biophys Res Commun* 210, 464–471 (1995).
Blake, C. C. & Oatley, S. J. *Nature* 268, 115–120 (1977).
Blake, C. C., Geisow, M. J., Oatley, S. J., Rerat, B. & Rerat, C. *J Mol Biol* 121, 339–356 (1978).
Bourguet, W., Ruff, M., Chambon, P., Gronemeyer, H. & Moras, D. *Nature* 375, 377–382 (1995).
Brent, G. A. *N Engl J Med* 331, 847–853 (1994).
Brunger, A. T., Kuriyan, J. & Karplus, M. *Science* 235, 458–460 (1987).
Casanova, J., et al. Mol Cell Biol 14, 5756–5765 (1994).
Cavailles, V., et al. Embo J 14, 3741–3751 (1995).
Chin et al, U.S. Pat. No. 5,284,999, issued Feb. 8, 1994.
Collaborative Computational Project, N.4. *Acta Crystallogr.* D50, 760–763 (1994).
Collingwood, T. N., Adams, M., Tone, Y & Chatterjee, V. K. *Mol Endocrinol* 8, 1262–1277 (1994).
Cowtan, K. *Joint CCP4 and ESF-EACBM Newsletter on Protein Crystallography* 31, 34–38 (1994).
Damm, K. & Evans, R. M. *Proc Natl Acad Sci USA* 90, 10668–10672 (1993).
Danielian, P. S., White, R., Lees, J. A. & Parker, M. G. *Embo J* 11, 1025–1033 (1992).
Davies et al, U.S. Pat. No. 5,322,933, issued Jun. 21, 1994.
Dawson et al, U.S. Pat. No. 5,466,861, issued Nov. 14, 1995.
DeGroot et al, U.S. Pat. No. 5,438,126, issued Aug. 1, 1995.
Dietrich, S. W., Bolger, M. B., Kollman, P. A. & Jorgensen, E. C. *J Med Chem* 20, 863–880 (1977).
Durand, B., et al. Embo J 13, 5370–5382 (1994).
Ellis et al, U.S. Pat. No. 4,766,121, issued Aug. 23, 1988.
Ellis et al, U.S. Pat. No. 4,826,876, issued May 2, 1989.
Ellis et al, U.S. Pat. No. 4,910,305, issued Mar. 20, 1990.
Emmett et al, U.S. Pat. No. 5,061,798, issued Oct. 29, 1991.
Evans, R. M. *Science* 240, 889–895 (1988).
Evans et al, U.S. Pat. No. 5,171,671, issued Dec. 15, 1992.
Evans et al, U.S. Pat. No. 5,312,732, issued May 17, 1994.
Fawell, S. E., Lees, J. A., White, R. & Parker, M. G. *Cell* 60, 953–962 (1990).
Forman, B. M. & Samuels, H. H. *Mol. Endocrinol.* 4, 1293–1301 (1990).
Gewirth, D. T. & Sigler, P. B. *Nature Structural Biology* 2, 386–394 (1995).
Glass, C. K. *Endocr Rev* 15, 391–407 (1994).
Hayashi, Y. Sunthornthepvarakul, T. & Refetoff, S. *J Clin Invest* 94, 607–615 (1994).
Jones, T. A., Zou, J. Y., Cowan, S. W. & Kjeldgaard. *Acta Crystallogr* A 47, 110–119 (1991).
Jorgensen, E. C. in *Hormonal Peptides and Proteins* (eds. Li, C. H.) 107–204 (Academic Press, New York, 1978).

Kabsch, W. *J. Appl. Crystallogr.* 26, 795–800 (1993).
Kabsch, W. & Sander, C. *Biopolymers* 22, 2577–2637 (1983).
Laskowski, R. A., Macarthur, M. W., Moss, D. S. & Thornton, J. M. *J. Appl. Crystallogr.* 26, 283–291 (1993).
Latham, K. R., Apriletti, J. W., Eberhardt, N. L. & Baxter, J. D. *J Biol Chem* 256, 12088–12093 (1981).
Laudet, V., Hanni, C., Coll, J., Catzeflis, F. & Stehelin, D. *Embo J* 11, 1003–1013 (1992).
LeDouarin, B., et al. Embo J 14, 2020–2033 (1995).
Lee, J. W., Ryan, F., Swaffield, J. C., Johnston, S. A. & Moore, D. D. *Nature* 374, 91–94 (1995).
Lee, J. W., Choi, H. S., Gyuris, J., Brent, R. & Moore, D. D. *Molec. Endocrinol.* 9, 243–254 (1995).
Leeson, P. D., Emmett, J. C., Shah, V. P., Showell, G. A., Novelli, R., Prain, H. D.,
Benson, M. G., Ellis, D., Pearce, N. J. & Underwood, A. H. *J. Med. Chem.* 32, 320–336 (1989).
Leeson, P. D., Ellis, D., Emmett, J. D., Shah, V. P., Showell, G. A. & Underwood, A. H. *J. Leng*, X., et al. Mol Cell Biol 15, 255–263 (1995).
Leng, X., Tsai, S. Y., O'Malley, B. W. & Tsai, M. J. J Steroid Biochem Mol Biol 46, 643–661 (1993).
Lin, K. H., Parkison, C., McPhie, P. & Cheng, S. Y. *Mol. Endocrinol.* 5, 485–492 (1991).
Luisi, B. F., et al. Nature 352, 497–505 (1991).
McGrath, M. E., et al. J. Mol. Biol. 237, 236–239 (1994).
McRee, D. E., *Practical Protein Crystallography*, Academic Press, N.Y. (1993), especially chapters 1, 2 and 3.
Meier, C. A., et al. Mol. Endocrinol. 6, 248–258 (1992).
Miura et al, U.S. Pat. No. 5,116,828, issued May 26, 1992.
Monaco, H. L., Rizzi, M. & Coda, A. *Science* 268, 1039–1041 (1995).
Nicholls, A., Sharp, K. A. & Honig, B. *Proteins* 11, 281–296 (1991).
O'Donnell, A. L., Rosen, E. D., Darling, D. S. & Koenig, R. J. *Mol. Endocrinol.* 5, 94–99 (1991).
Otwinowski, Z. Proceedings of the CCP4 Study Weekend 80–86 (*SERC Daresbury Laboratory, Warrington*, U.K., 1991).
Otwinowski, Z. Proceedings of the CCP4 Study Weekend: "Data Collection and Processing" 56–62 (SERC Daresbury Laboratory, Warrington, U.K., 1993).
Ozato, U.S. Pat. No. 5,403,925, issued Apr. 4, 1995.
Rastinejad, R., Perlmann, T., Evans, R. M. & Sigler, P. B. *Nature* 375, 203–211 (1995).
Refetoff, S., Weiss, R. E. & Usala, S. J. *Endocr. Rev.* 14, 348–399 (1993).
Ribeiro, R. C. J., Kushner, P. J. & Baxter, J. D. *Annu. Rev. Med.* 46, 443–453 (1995).
Ribeiro, R. C. J., et al. Ann. N. Y. Acad. Sci. 758, 366–389 (1995).
Ribeiro, R. C., Kushner, P. J., Apriletti, J. W., West, B. L. & Baxter, J. D. *Mol. Endocrinol.* 6, 1142–1152 (1992).
Saatcioglu, F., Bartunek, P., Deng, T., Zenke, M. & Karin, M. Mol. *Cell Biol.* 13, 3675–3685 (1993).
Schwabe, J. W., Chapman, L., Finch, J. T. & Rhodes, D. *Cell* 75, 567–578 (1993).
Selmi, S. & Samuels, H. H. *J. Biol. Chem.* 266, 11589–11593 (1991).
Swaffield, J. C., Melcher, K. & Johnston, S. A. *Nature* 374, 88–91 (1995).
Toney, J. H. et al. Biochemistry 32, 2–6 (1993).
Tsai, M. J. & O'Malley, B. W. *Annu. Rev. Biochem.* 63, 451–486 (1994).
Zenke, M., Munoz, A., Sap, J., Vennstrom, B. & Beug, H. *Cell* 61, 1035–1049 (1990).

TABLE 8

APPENDIX 2

| Dimit Atom | Amino Acid in full length α | Amino Acid Atom | Distance Å |
|---|---|---|---|
| C16 | 215-PHE | CD1 | 3.98 |
| C16 | 215-PHE | CE1 | 3.86 |
| C19 | 218-PHE | O | 3.69 |
| C16 | 218-PHE | CB | 3.89 |
| C18 | 218-PHE | CB | 3.92 |
| C19 | 218-PHE | CB | 4.13 |
| C18 | 218-PHE | CD2 | 3.77 |
| C16 | 219-THR | CG2 | 3.68 |
| C19 | 221-ILE | CG1 | 4.11 |
| C6 | 222-ILE | CD1 | 4.18 |
| C8 | 222-ILE | CD1 | 3.72 |
| C10 | 222-ILE | CD1 | 3.53 |
| C12 | 222-ILE | CD1 | 3.85 |
| O1 | 222-ILE | CD1 | 4.13 |
| C13 | 225-ALA | C8 | 3.64 |
| O4 | 225-ALA | C8 | 4.02 |
| O4 | 228-ARG | CZ | 3.96 |
| C17 | 228-ARG | NH2 | 3.36 |
| O3 | 228-ARG | NH2 | 3.58 |
| O4 | 228-ARG | NH2 | 2.86 |
| C10 | 256-MET | SD | 3.70 |
| C12 | 256-MET | SD | 3.89 |
| C10 | 256-MET | CE | 3.88 |
| C12 | 256-MET | CE | 3.83 |
| C11 | 259-MET | C | 4.03 |
| C11 | 259-MET | O | 3.66 |
| C15 | 259-MET | O | 3.42 |
| N1 | 259-MET | O | 3.71 |
| C1 | 259-MET | C8 | 4.20 |
| C11 | 259-MET | C8 | 3.87 |
| C13 | 259-MET | C8 | 4.09 |
| C15 | 262-ARG | C8 | 4.03 |
| C17 | 262-ARG | C8 | 3.58 |
| O3 | 262-ARG | C8 | 3.62 |
| O4 | 262-ARG | C8 | 3.85 |
| C17 | 262-ARG | CD | 4.10 |
| O4 | 262-ARG | CD | 3.61 |
| N1 | 263-ALA | N | 3.71 |
| C17 | 263-ALA | CA | 3.69 |
| N1 | 263-ALA | CB | 3.46 |
| O3 | 266-ARG | NH1 | 3.93 |
| N1 | 275-THR | O | 3.62 |
| N1 | 276-LEU | CA | 3.51 |
| N1 | 276-LEU | C | 3.92 |
| C5 | 276-LEU | CD1 | 4.05 |
| C19 | 276-LEU | CD1 | 4.04 |
| C7 | 276-LEU | CD2 | 4.09 |
| C9 | 276-LEU | CD2 | 3.95 |
| C11 | 276-LEU | CD2 | 4.13 |
| N1 | 276-LEU | CD2 | 4.17 |
| C13 | 277-SER | N | 4.14 |
| C15 | 277-SER | N | 3.79 |

| Dimit Atom | Amino Acid in full length α | Atom | Distance Å |
|---|---|---|---|
| C17 | 277-SER | N | 3.69 |
| N1 | 277-SER | N | 3.30 |
| O3 | 277-SER | N | 3.19 |
| C17 | 277-SER | CA | 3.92 |
| O3 | 277-SER | CA | 3.35 |
| C13 | 277-SER | OG | 3.92 |
| C7 | 287-LEU | CD2 | 3.90 |
| C18 | 290-GLY | C | 4.04 |
| C18 | 290-GLY | O | 3.54 |
| C18 | 291-GLY | CA | 4.04 |
| C18 | 292-LEU | N | 4.20 |
| C2 | 292-LEU | CG | 4.18 |
| C4 | 292-LEU | CG | 3.86 |
| C6 | 292-LEU | CG | 4.01 |
| C2 | 292-LEU | CD1 | 3.88 |
| C4 | 292-LEU | CD1 | 4.02 |
| O2 | 292-LEU | CD1 | 4.07 |
| C4 | 292-LEU | CD2 | 4.05 |

TABLE 8-continued

APPENDIX 2

| | | | |
|---|---|---|---|
| C6 | 292-LEU | CD2 | 3.72 |
| C8 | 292-LEU | CD2 | 3.69 |
| C10 | 292-LEU | CD2 | 3.98 |
| O1 | 292-LEU | CD2 | 4.16 |
| C20 | 299-ILE | CD1 | 3.87 |
| C8 | 381-HIS | CD2 | 3.90 |
| C10 | 381-HIS | CD2 | 3.84 |
| O1 | 381-HIS | GO2 | 3.40 |
| O1 | 381-HIS | CE1 | 3.72 |
| C8 | 381-HIS | NE2 | 3.47 |
| C10 | 381-HIS | NE2 | 3.51 |
| O1 | 381-HIS | NE2 | 2.64 |
| C6 | 388-MET | CE | 3.90 |
| C8 | 401-PHE | CE1 | 4.19 |
| O1 | 401-PHE | CE1 | 3.37 |
| C16 | 401-PHE | CZ | 3.97 |
| O1 | 401-PHE | CZ | 3.28 |
| N1 | 502-H$_2$O | O1 | 3.35 |
| O3 | 502-H$_2$O | O1 | 2.56 |
| O3 | 503-H$_2$O | O1 | 3.13 |
| O4 | 503-H$_2$O | O1 | 3.72 |
| O4 | 504-H$_2$O | O1 | 2.72 |

Legend to Table 8.
The table lists the interactions with Dimit (DMT). The column headings are as follows:
1 The atom of Dimit that interacts with the amino acid of the receptor. These are also numbered in FIG. 32.
2 The amino acid in the full length rTRα that interacts with the ligand.
3 The name of the atom in the amino acid (standard nomenclature) where the interaction occurs.
4 The distance in A between Dimit and the protein atom.

TABLE 9

| Triac Atom | Amino Acid in full length α | Amino Acid Atom | Distance A |
|---|---|---|---|
| I1 | 218-PHE | O | 3.52 |
| I1 | 221-ILE | CD1 | 4.16 |
| I1 | 221-ILE | CG1 | 3.92 |
| I1 | 222-ILE | CA | 4.15 |
| I1 | 222-ILE | CB | 4.03 |
| I1 | 222-ILE | CG1 | 3.92 |
| C8 | 222-ILE | CD1 | 4.12 |
| C10 | 222-ILE | CD1 | 3.77 |
| C12 | 222-ILE | CD1 | 3.79 |
| C13 | 225-ALA | CB | 4.17 |
| C3 | 225-ALA | CB | 3.86 |
| C10 | 256-MET | SD | 3.45 |
| C12 | 256-MET | SD | 3.73 |
| C10 | 256-MET | CE | 3.66 |
| C12 | 256-MET | CE | 3.77 |
| I3 | 256-MET | CE | 3.89 |
| C1 | 259-MET | O | 3.93 |
| C11 | 259-MET | O | 3.24 |
| O3 | 259-MET | O | 4.09 |
| C1 | 259-MET | CB | 3.89 |
| C13 | 259-MET | O | 3.74 |
| C14 | 259-MET | O | 3.96 |
| C1 | 259-MET | CB | 3.89 |
| C11 | 259-MET | CB | 3.68 |
| C13 | 259-MET | CB | 4.01 |
| C11 | 259-MET | CA | 4.13 |
| C13 | 259-MET | CA | 4.20 |
| I3 | 260-SER | CA | 4.10 |
| I3 | 260-SER | OG | 4.19 |
| C14 | 262-ARG | CB | 4.07 |
| O4 | 262-ARG | CB | 3.60 |
| O3 | 263-ALA | N | 3.79 |
| C14 | 263-ALA | N | 4.12 |
| O3 | 263-ALA | CA | 3.67 |
| O3 | 263-ALA | CB | 3.49 |
| C11 | 263-ALA | CB | 4.00 |
| C14 | 266-ARG | CZ | 3.89 |
| O3 | 266-ARG | CZ | 4.01 |

TABLE 9-continued

| Triac Atom | Amino Acid in full length α | Amino Acid Atom | Distance A |
|---|---|---|---|
| O4 | 266-ARG | CZ | 3.03 |
| C14 | 266-ARG | NH1 | 3.25 |
| O3 | 266-ARG | NH1 | 3.00 |
| O4 | 266-ARG | NH1 | 2.82 |
| C14 | 266-ARG | NH2 | 3.48 |
| O3 | 266-ARG | NH2 | 4.01 |
| O4 | 266-ARG | NH2 | 2.34 |
| O3 | 275-THR | C | 4.02 |
| C14 | 275-THR | O | 4.20 |
| O3 | 275-THR | O | 3.20 |
| O3 | 278-LEU | CA | 3.11 |
| O3 | 276-LEU | C | 3.52 |
| O3 | 276-LEU | N | 4.04 |
| C14 | 276-LEU | CA | 3.98 |
| O3 | 276-LEU | CA | 3.11 |
| C14 | 276-LEU | C | 3.98 |
| O3 | 276-LEU | CB | 3.95 |
| O2 | 276-LEU | CD1 | 4.03 |
| I1 | 276-LEU | CD1 | 4.10 |
| C7 | 276-LEU | CD2 | 3.84 |
| C9 | 276-LEU | CD2 | 3.73 |
| CII | 276-LEU | CD2 | 4.06 |
| O2 | 276-LEU | CD2 | 4.10 |
| O3 | 276-LEU | CD2 | 3.91 |
| C13 | 277-SER | N | 4.06 |
| C14 | 277-SER | N | 3.13 |
| O4 | 277-SER | N | 3.28 |
| O3 | 277-SER | N | 3.05 |
| C14 | 277-SER | CA | 3.76 |
| O4 | 277-SER | CA | 3.52 |
| C3 | 277-SER | OG | 3.87 |
| C13 | 277-SER | OG | 4.02 |
| C14 | 277-SER | OG | 4.14 |
| I2 | 290-GLY | O | 3.57 |
| I2 | 292-LEU | CG | 3.94 |
| C4 | 292-LEU | CG | 3.95 |
| C6 | 292-LEU | CG | 3.65 |
| C8 | 292-LEU | CG | 4.02 |
| C2 | 292-LEU | CD1 | 4.11 |
| C4 | 292-LEU | CD1 | 3.85 |
| C6 | 292-LEU | CD1 | 4.02 |
| I2 | 292-LEU | CD2 | 3.98 |
| C4 | 292-LEU | CD2 | 4.11 |
| C6 | 292-LEU | CD2 | 3.44 |
| C8 | 292-LEU | CD2 | 3.28 |
| C10 | 292-LEU | CD2 | 3.88 |
| O1 | 292-LEU | CD2 | 3.35 |
| I3 | 299-ILE | CD1 | 3.77 |
| C8 | 381-HIS | CD2 | 3.87 |
| C10 | 381-HIS | CD2 | 3.90 |
| O1 | 381-HIS | GO2 | 3.20 |
| O1 | 381-HIS | CE1 | 3.82 |
| C8 | 381-HIS | NE2 | 3.57 |
| C10 | 381-HIS | NE2 | 3.52 |
| O1 | 381-HIS | NE2 | 2.64 |
| O1 | 388-MET | CE | 4.03 |
| O1 | 401-PHE | CE1 | 3.86 |
| O1 | 401-PHE | CZ | 3.70 |
| C13 | 460-H$_2$O | O1 | 4.00 |

Legend to Table 9.
The table lists the interactions with Triac. The column headings are as follows:
1 The atom of Triac that interacts with the amino acid of the receptor. These are also numbered in FIG. 32.
2 The amino acid in the full length rTRα that interacts with the ligand.
3 The name of the atom in the amino acid (standard nomenclature) where the interaction occurs.
4 The distance in A between Triac and the protein atom.

TABLE 10

| IpBR₂ Atom | Amino Acid in full length α | Amino Acid Atom | Distance Å |
|---|---|---|---|
| C16 | 215-PHE | CD1 | 4.01 |
| C16 | 215-PHE | CE1 | 3.78 |
| BR1 | 218-PHE | O | 3.24 |
| BR1 | 218-PHE | C | 3.98 |
| C16 | 218-PHE | CB | 3.81 |
| C18 | 218-PHE | CB | 3.92 |
| BR1 | 218-PHE | CB | 4.08 |
| C18 | 218-PHE | CD2 | 3.92 |
| C16 | 219-THR | CG2 | 3.45 |
| BR1 | 221-ILE | CG1 | 3.81 |
| BR1 | 221-ILE | CD1 | 4.07 |
| BR1 | 222-ILE | CB | 3.81 |
| BR1 | 222-ILE | CG1 | 3.97 |
| C6 | 222-ILE | CD1 | 4.07 |
| C8 | 222-ILE | CD1 | 3.64 |
| C10 | 222-ILE | CD1 | 3.50 |
| C12 | 222-ILE | CD1 | 3.82 |
| O1 | 222-ILE | CD1 | 4.08 |
| C13 | 225-ALA | CB | 3.76 |
| O4 | 225-ALA | CB | 4.01 |
| O4 | 228-ARG | CZ | 3.92 |
| C17 | 228-ARG | NH2 | 3.26 |
| O3 | 228-ARG | NH2 | 3.43 |
| O4 | 228-ARG | NH2 | 2.79 |
| C10 | 256-MET | SD | 3.65 |
| C12 | 256-MET | SD | 3.71 |
| C10 | 256-MET | CE | 3.90 |
| C12 | 256-MET | CE | 3.75 |
| BR2 | 256-MET | CE | 4.03 |
| C11 | 259-MET | C | 3.98 |
| C11 | 259-MET | O | 3.52 |
| C15 | 259-MET | O | 3.44 |
| N1 | 259-MET | O | 3.76 |
| C11 | 259-MET | CB | 3.87 |
| N1 | 262-ARG | C | 4.03 |
| C15 | 262-ARG | CB | 4.03 |
| C17 | 262-ARG | CB | 3.56 |
| O3 | 262-ARG | CB | 3.55 |
| O4 | 262-ARG | CB | 3.91 |
| C17 | 262-ARG | CD | 4.09 |
| O4 | 262-ARG | CD | 3.71 |
| N1 | 263-ALA | N | 3.61 |
| N1 | 263-ALA | CA | 3.59 |
| N1 | 263-ALA | CB | 3.54 |
| O3 | 266-ARG | NH1 | 3.93 |
| N1 | 275-THR | O | 3.43 |
| N1 | 276-LEU | CA | 3.46 |
| N1 | 276-LEU | C | 3.83 |
| C5 | 276-LEU | CD1 | 4.02 |
| C7 | 276-LEU | CD2 | 4.00 |
| C9 | 276-LEU | CD2 | 3.81 |
| C11 | 276-LEU | CD2 | 3.91 |
| C13 | 277-SER | N | 3.79 |
| C15 | 277-SER | N | 3.63 |
| C17 | 277-SER | N | 3.70 |
| N1 | 277-SER | N | 3.17 |
| O3 | 277-SER | N | 3.37 |
| C17 | 277-SER | CA | 3.89 |
| O3 | 277-SER | CA | 3.43 |
| C13 | 277-SER | OG | 3.66 |
| O2 | 287-LEU | CD1 | 4.05 |
| C18 | 290-GLY | C | 4.04 |
| C18 | 290-GLY | O | 3.48 |
| C18 | 291-GLY | CA | 4.02 |
| C4 | 292-LEU | CG | 3.89 |
| C6 | 292-LEU | CG | 4.02 |
| C2 | 292-LEU | CD1 | 3.79 |
| C4 | 292-LEU | CD1 | 3.96 |
| O2 | 292-LEU | CD1 | 3.97 |
| C4 | 292-LEU | CD2 | 4.07 |
| C6 | 292-LEU | CD2 | 3.75 |
| C8 | 292-LEU | CD2 | 3.67 |
| C10 | 292-LEU | CD2 | 3.92 |
| BR2 | 299-ILE | CD1 | 3.68 |
| C8 | 381-HIS | CD2 | 3.92 |
| C10 | 381-HIS | CD2 | 3.78 |
| O1 | 381-HIS | GD2 | 3.50 |
| O1 | 381-HIS | CE1 | 3.62 |
| C8 | 381-HIS | NE2 | 3.36 |
| C10 | 381-HIS | NE2 | 3.34 |
| O1 | 381-HIS | NE2 | 2.62 |
| C8 | 401-PHE | CE1 | 4.02 |
| O1 | 401-PHE | CE1 | 3.19 |
| C16 | 401-PHE | CZ | 4.03 |
| O1 | 401-PHE | CZ | 3.06 |
| O3 | 502-H₂O | O1 | 3.40 |
| N1 | 502-H2O | O1 | 3.12 |
| O4 | 503-H₂O | O1 | 3.20 |
| C17 | 503-H₂O | O1 | 3.04 |
| O3 | 503-H₂O | O1 | 2.27 |
| C15 | 504-H₂O | O1 | 4.01 |
| C17 | 504-H₂O | O1 | 2.99 |
| O3 | 504-H₂O | O1 | 3.80 |
| O4 | 504-H₂O | O1 | 1.78 |

Legend to Table 10.
The table lists the interactions with IpBr2. The column headings are as follows:
1 The atom of IpBr2 that interacts with the amino acid of the receptor. These are also numbered in FIG. 32.
2 The amino acid in the full length rTRα that interacts with the ligand.
3 The name of the atom in the amino acid (standard nomenclature) where the interaction occurs.
4 The distance in Å between IpBr2 and the protein atom.

TABLE 11

| T3 Atom | Amino Acid in full length α | Amino Acid Atom | Distance Å |
|---|---|---|---|
| I2 | 215-PHE | CD1 | 4.08 |
| I1 | 218-PHE | O | 3.19 |
| I1 | 218-PHE | CB | 3.99 |
| C4 | 218-PHE | CB | 4.04 |
| I1 | 218-PHE | C | 3.79 |
| I1 | 218-PHE | CB | 3.99 |
| I1 | 221-ILE | CG1 | 4.01 |
| I1 | 222-ILE | CB | 3.95 |
| I1 | 222-ILE | CG1 | 3.91 |
| C8 | 222-ILE | CD1 | 3.99 |
| C10 | 222-ILE | CD1 | 3.57 |
| C12 | 222-ILE | CD1 | 3.68 |
| C13 | 225-ALA | CB | 3.66 |
| C3 | 225-ALA | CB | 4.04 |
| O4 | 228-ARG | NH1 | 3.23 |
| O4 | 228-ARG | CZ | 3.45 |
| C15 | 228-ARG | NH2 | 3.54 |
| O3 | 228-ARG | NH2 | 3.90 |
| O4 | 228-ARG | NH2 | 2.86 |
| C10 | 256-MET | SD | 3.73 |
| C12 | 256-MET | SD | 3.90 |
| C10 | 256-MET | CE | 3.97 |
| C12 | 256-MET | CE | 3.92 |
| I3 | 256-MET | CE | 3.89 |
| C11 | 259-MET | C | 3.95 |
| C11 | 259-MET | O | 3.59 |
| C14 | 259-MET | O | 3.51 |
| N1 | 259-MET | O | 3.88 |
| C1 | 259-MET | CB | 4.06 |
| C11 | 259-MET | CB | 3.77 |
| C13 | 259-MET | CB | 3.96 |
| C15 | 262-ARG | CB | 3.61 |
| C14 | 262-ARG | CB | 4.02 |
| O3 | 262-ARG | CB | 3.65 |
| O4 | 262-ARG | CB | 3.92 |
| O4 | 262-ARG | CD | 3.72 |
| N1 | 263-ALA | N | 3.81 |
| N1 | 263-ALA | CA | 3.81 |
| N1 | 263-ALA | CB | 3.63 |
| N1 | 275-THR | O | 3.54 |
| N1 | 276-LEU | CA | 3.38 |

TABLE 11-continued

| T3 Atom | Amino Acid in full length α | Amino Acid Atom | Distance A |
|---|---|---|---|
| N1 | 276-LEU | C | 3.73 |
| C5 | 276-LEU | CD1 | 4.00 |
| C7 | 276-LEU | CD1 | 4.05 |
| O2 | 276-LEU | CD1 | 4.03 |
| C7 | 276-LEU | CD2 | 3.80 |
| C9 | 276-LEU | CD2 | 3.70 |
| C11 | 276-LEU | CD2 | 4.01 |
| C14 | 277-SER | N | 3.67 |
| C15 | 277-SER | N | 3.62 |
| N1 | 277-SER | N | 3.07 |
| O3 | 277-SER | N | 3.24 |
| C15 | 277-SER | CA | 3.77 |
| O3 | 277-SER | CA | 3.34 |
| C13 | 277-SER | OG | 3.92 |
| I2 | 290-GLY | O | 3.50 |
| C4 | 292-LEU | CG | 3.95 |
| C8 | 292-LEU | CG | 3.83 |
| C2 | 292-LEU | CD1 | 4.07 |
| C4 | 292-LEU | CD1 | 3.99 |
| C4 | 292-LEU | CD2 | 4.09 |
| C6 | 292-LEU | CD2 | 3.58 |
| C8 | 292-LEU | CD2 | 3.50 |
| C10 | 292-LEU | CD2 | 3.96 |
| O1 | 292-LEU | CD2 | 3.71 |
| I3 | 299-ILE | CD1 | 3.74 |
| C8 | 381-HIS | CD2 | 3.94 |
| C10 | 381-HIS | CD2 | 3.97 |
| O1 | 381-HIS | CD2 | 3.39 |
| O1 | 381-HIS | CD1 | 3.82 |
| C8 | 381-HIS | NE2 | 3.47 |
| C10 | 381-HIS | NE2 | 3.55 |
| O1 | 381-HIS | NE2 | 2.70 |
| O1 | 388-MET | CE | 3.88 |
| O1 | 401-PHE | CE1 | 3.52 |
| O1 | 401-PHE | CZ | 3.32 |
| C14 | 502-H2O | O1 | 4.01 |
| C15 | 502-H2O | O1 | 3.61 |
| O3 | 502-H2O | O1 | 2.51 |
| C15 | 503-H2O | O1 | 3.31 |
| O4 | 503-H$_2$O | O1 | 3.10 |
| N1 | 502-H$_2$O | O1 | 3.27 |
| O3 | 503-H2O | O1 | 2.81 |
| C15 | 504-H2O | O1 | 3.92 |
| O4 | 504-H2O | O1 | 2.73 |

Legend to Table 11. The table lists the interactions with T3. The column headings are as follows:
1 The atom of T3 that interacts with the amino acid of the receptor. These are also numbered in FIG 32.
2 The amino acid in the full length rTRα that interacts with the ligand.
3 The name of the atom in the amino acid (standard nomenclature) where the interaction occurs.
4 The distance in A between T3 and the protein atom.

TABLE 12

| Triac Atom | Amino Acid in full length hTR β | Amino Acid Atom | Distance A |
|---|---|---|---|
| I2 | 269-PHE | CD1 | 3.75 |
| I2 | 269-PHE | CE1 | 3.88 |
| I1 | 272-PHE | C | 4.03 |
| I1 | 272-PHE | O | 3.54 |
| I1 | 275-ILE | CG1 | 3.93 |
| I1 | 276-ILE | CG1 | 4.02 |
| C3 | 279-ALA | CB | 3.81 |
| C13 | 279-ALA | CB | 3.87 |
| C10 | 310-MET | SD | 3.72 |
| C12 | 310-MET | SD | 3.78 |
| C10 | 310-MET | CE | 4.02 |
| C12 | 310-MET | CE | 3.92 |
| I3 | 310-MET | CE | 3.93 |
| C13 | 313-MET | CA | 3.94 |
| C11 | 313-MET | C | 3.72 |
| C1 | 313-MET | O | 3.79 |
| C11 | 313-MET | O | 3.12 |
| C13 | 313-MET | O | 3.55 |
| C1 | 313-MET | CB | 4.00 |
| C11 | 313-MET | CB | 3.82 |
| C13 | 313-MET | CB | 3.76 |
| O3 | 316-ARG | CB | 3.99 |
| O4 | 317-ALA | CA | 4.08 |
| O4 | 317-ALA | CA | 4.10 |
| C11 | 317-ALA | CB | 3.70 |
| I3 | 317-ALA | CB | 4.10 |
| O4 | 317-ALA | CB | 4.06 |
| O4 | 320-ARG | NH1 | 3.58 |
| O3 | 320-ARG | NH2 | 3.55 |
| O4 | 320-ARG | NH2 | 4.04 |
| O4 | 329-THR | O | 3.55 |
| O4 | 330-LEU | CA | 3.42 |
| O4 | 330-LEU | C | 3.77 |
| C3 | 330-LEU | CB | 4.06 |
| C5 | 330-LEU | CB | 4.08 |
| C1 | 330-LEU | CD2 | 4.07 |
| C3 | 330-LEU | CD2 | 4.00 |
| C5 | 330-LEU | CD2 | 3.73 |
| C7 | 330-LEU | CD2 | 3.51 |
| C9 | 330-LEU | CD2 | 3.54 |
| C11 | 330-LEU | CD2 | 3.86 |
| C15 | 331-ASN | N | 3.55 |
| O3 | 331-ASN | N | 3.74 |
| O4 | 331-ASN | N | 3.12 |
| O3 | 331-ASN | CA | 4.02 |
| I2 | 344-GLY | O | 3.87 |
| C6 | 346-LEU | CD2 | 3.87 |
| C8 | 346-LEU | CD2 | 3.84 |
| O1 | 346-LEU | CD2 | 3.91 |
| I3 | 353-ILE | CD1 | 3.51 |
| C8 | 435-HIS | CD2 | 3.93 |
| C10 | 435-HIS | CD2 | 3.79 |
| O1 | 435-HIS | CD2 | 3.33 |
| O1 | 435-HIS | CE1 | 3.81 |
| C8 | 435-HIS | NE2 | 3.42 |
| C10 | 435-HIS | NE2 | 3.33 |
| O1 | 435-HIS | NE2 | 2.67 |
| O1 | 442-MET | SD | 3.96 |
| O1 | 442-MET | CE | 3.72 |
| I2 | 442-MET | SD | 4.01 |
| O1 | 455-PHE | CE1 | 3.92 |
| O1 | 455-PHE | CZ | 3.50 |

Legend to Table 12. The table lists the interactions with Triac. The column headings are as follows:
1 The atom of Triac that interacts with the amino acid of the receptor. These are also numbered in FIG 32.
2 The amino acid in the full length hTRβ that interacts with the ligand.
3 The name of the atom in the amino acid (standard nomenclature) where the interaction occurs.
4 The distance in A between Triac and the protein atom.

TABLE 13

| GC1 Atom | Amino Acid in full length TR β | Amino Acid Atom | Distance A |
|---|---|---|---|
| C16 | 269-PHE | CE1 | 3.99 |
| C19 | 272-PHE | O | 3.85 |
| C16 | 272-PHE | CB | 3.98 |
| C16 | 273-THR | CG2 | 3.76 |
| C19 | 275-ILE | CG1 | 3.98 |
| C19 | 276-ILE | CA | 3.98 |
| C2 | 276-ILE | CD1 | 3.88 |
| C8 | 276-ILE | CD1 | 3.77 |
| C10 | 276-ILE | CD1 | 3.58 |
| C12 | 276-ILE | CD1 | 3.62 |
| C19 | 276-ILE | CD1 | 3.56 |
| C1 | 279-ALA | CB | 3.68 |
| C3 | 279-ALA | CB | 3.56 |

TABLE 13-continued

| GC1 Atom | Amino Acid in full length TR β | Amino Acid Atom | Distance A |
|---|---|---|---|
| O5 | 279-ALA | CB | 3.11 |
| O4 | 279-ALA | CB | 3.90 |
| O3 | 282-ARG | CZ | 3.53 |
| C17 | 282-ARG | NH1 | 3.87 |
| O3 | 282-ARG | NH1 | 3.20 |
| O4 | 282-ARG | NH1 | 3.85 |
| C17 | 282-ARG | NH2 | 3.63 |
| O3 | 282-ARG | NH2 | 3.00 |
| C10 | 310-MET | SD | 3.86 |
| C12 | 310-MET | SD | 3.91 |
| C11 | 313-MET | C | 3.85 |
| C11 | 313-MET | O | 3.41 |
| C15 | 313-MET | O | 3.87 |
| C20 | 313-MET | O | 3.99 |
| C11 | 313-MET | CB | 3.79 |
| C1 | 313-MET | CG | 3.94 |
| C11 | 313-MET | CG | 3.91 |
| O5 | 313-MET | CG | 3.87 |
| O4 | 313-MET | CG | 3.79 |
| C20 | 314-SER | CA | 4.00 |
| C17 | 316-ARG | CB | 3.95 |
| C17 | 316-ARG | CD | 3.80 |
| O3 | 316-ARG | CD | 3.83 |
| O4 | 316-ARG | CD | 3.51 |
| C20 | 317-ALA | CB | 3.93 |
| C7 | 330-LEU | CD2 | 3.56 |
| C9 | 330-LEU | CD2 | 3.63 |
| C21 | 330-LEU | CD2 | 3.90 |
| O5 | 331-ASN | N | 3.62 |
| C15 | 331-ASN | N | 3.67 |
| C18 | 344-GLY | O | 3.60 |
| C18 | 346-LEU | CG | 3.89 |
| C6 | 346-LEU | CD2 | 3.77 |
| C8 | 346-LEU | CD2 | 3.80 |
| C10 | 435-HIS | CD2 | 3.89 |
| O1 | 435-HIS | CD2 | 3.64 |
| O1 | 435-HIS | CE1 | 3.79 |
| C8 | 435-HIS | NE2 | 3.44 |
| C10 | 435-HIS | NE2 | 3.33 |
| O1 | 435-HIS | NE2 | 2.77 |
| O1 | 455-PHE | CE1 | 3.40 |
| O1 | 455-PHE | CZ | 3.22 |

Legend to Table 13. The table lists the interactions with GC1. The column headings are as follows:

1 The atom of GC1 that interacts with the amino acid of the receptor. These are also numbered in FIG 32.
2 The amino acid in the full length hTRβ that interacts with the ligand.
3 The name of the atom in the amino acid (standard nomenclature) where the interaction occurs.
4 The distance in A between GC1 and the protein atom.

TABLE 14

Coordination Structure of TR-α and Dimit

| Coordination Structure | $R_1$ —$CH_2$— $CH(NH_2)(CO_2)H$ | $R_2$ —H | $R_3$ —$CH_3$ | $R_5$ —$CH_3$ | $R_6$ —H | $R'_2$ —H | $R'_3$ —$CH(CH_3)_2$ | $R'_4$ —OH | $R'_5$ —H | $R'_6$ —H | X O |
|---|---|---|---|---|---|---|---|---|---|---|---|
| AA |  |  |  |  |  |  | 215 |  |  |  |  |
| SS |  |  |  |  |  |  | H3 |  |  |  |  |
| AA |  |  | 218 |  |  |  | 218 |  |  |  |  |
| SS |  |  | H3 |  |  |  | H3 |  |  |  |  |
| AA |  |  |  |  |  |  | 219 |  |  |  |  |
| SS |  |  |  |  |  |  | H3 |  |  |  |  |
| AA |  |  | 221 |  |  |  |  |  |  |  |  |
| SS |  |  | H3 |  |  |  |  |  |  |  |  |
| AA |  |  |  |  |  |  | 222 | 222 | 222 | 222 |  |
| SS |  |  |  |  |  |  | H3 | H3 | H3 | H3 |  |
| AA | 225 |  |  |  |  |  |  |  |  |  |  |
| SS | H3 |  |  |  |  |  |  |  |  |  |  |
| AA | 228 |  |  |  |  |  |  |  |  |  |  |
| SS | H3 |  |  |  |  |  |  |  |  |  |  |
| AA |  |  |  |  |  |  |  |  | 256 | 256 |  |
| SS |  |  |  |  |  |  |  |  | H5–H6 | H5–H6 |  |
| AA | 259 |  |  |  | 259 |  |  |  |  |  |  |
| SS | H5–H6 |  |  |  | H5–H6 |  |  |  |  |  |  |
| AA | 262 |  |  |  |  |  |  |  |  |  |  |
| SS | H5–H6 |  |  |  |  |  |  |  |  |  |  |
| AA | 263 |  |  |  |  |  |  |  |  |  |  |
| SS | H5–H6 |  |  |  |  |  |  |  |  |  |  |
| AA | 266 |  |  |  |  |  |  |  |  |  |  |
| SS | loop |  |  |  |  |  |  |  |  |  |  |
| AA | 275 |  |  |  |  |  |  |  |  |  |  |
| SS | S3 |  |  |  |  |  |  |  |  |  |  |
| AA | 276 | 276 | 276 | 276 |  |  |  |  |  |  |  |
| SS | S3 | S3 | S3 | S3 |  |  |  |  |  |  |  |
| AA | 277 |  |  |  |  |  |  |  |  |  |  |
| SS | loop |  |  |  |  |  |  |  |  |  |  |
| AA |  |  |  |  |  |  | 290–291 |  |  |  |  |
| SS |  |  |  |  |  |  | loop |  |  |  |  |
| AA |  |  |  |  |  |  | 292 | 292 | 292 | 292 | 292 |

TABLE 14-continued

Coordination Structure of TR-α and Dimit

| Coordination Structure | R₁ —CH₂—CH(NH₂)(CO₂)H | R₂ —H | R₃ —CH₃ | R₅ —CH₃ | R₆ —H | R'₂ —H | R'₃ —CH(CH₃)₂ | R'₄ —OH | R'₅ —H | R'₆ —H | X O |
|---|---|---|---|---|---|---|---|---|---|---|---|
| SS |  |  |  |  |  | loop | loop | loop | loop |  | loop |
| AA |  |  |  | 299 |  |  |  |  |  |  |  |
| SS |  |  |  | H8 |  |  |  |  |  |  |  |
| AA |  |  |  |  |  |  |  | 381 | 381 |  |  |
| SS |  |  |  |  |  |  |  | H11 | H11 |  |  |
| AA |  |  |  |  |  |  | 388 |  |  |  |  |
| SS |  |  |  |  |  |  | H11 |  |  |  |  |
| AA |  |  |  |  |  |  | 401 | 401 |  |  |  |
| SS |  |  |  |  |  |  | H12 | H12 |  |  |  |
| AA | H0H502/H0H503/H0H504 |  |  |  |  |  |  |  |  |  |  |
| SS |  |  |  |  |  |  |  |  |  |  |  |

AA = Amino Acid
SS = Secondary Structure

TABLE 15

Coordination Structure of TR-α and Triac

| Coordination Structure | R₁ —CH₂—COOH | R₂ —H | R₃ —I | R₅ —I | R₆ —H | R'₂ —H | R'₃ —I | R'₄ —OH | R'₅ —H | R'₆ —H | X O |
|---|---|---|---|---|---|---|---|---|---|---|---|
| AA |  |  | 218 |  |  |  |  |  |  |  |  |
| SS |  |  | H3 |  |  |  |  |  |  |  |  |
| AA |  |  | 221 |  |  |  |  |  |  |  |  |
| SS |  |  | H3 |  |  |  |  |  |  |  |  |
| AA |  |  |  |  |  |  | 222 | 222 | 222 | 222 |  |
| SS |  |  |  |  |  |  | H3 | H3 | H3 | H3 |  |
| AA | 225 |  |  |  |  |  |  |  |  |  |  |
| SS | H3 |  |  |  |  |  |  |  |  |  |  |
| AA |  |  |  | 256 |  |  |  | 256 | 256 |  |  |
| SS |  |  |  | H5–H6 |  |  |  | H5–H6 | H5–H6 |  |  |
| AA | 259 |  |  |  | 259 |  |  |  |  |  |  |
| SS | H5–H6 |  |  |  | H5–H6 |  |  |  |  |  |  |
| AA | 262 |  |  |  |  |  |  |  |  |  |  |
| SS | H5–H6 |  |  |  |  |  |  |  |  |  |  |
| AA | 263 |  |  |  |  |  |  |  |  |  |  |
| SS | H5–H6 |  |  |  |  |  |  |  |  |  |  |
| AA | 266 |  |  |  |  |  |  |  |  |  |  |
| SS | loop |  |  |  |  |  |  |  |  |  |  |
| AA | 275 |  |  |  |  |  |  |  |  |  |  |
| SS | S3 |  |  |  |  |  |  |  |  |  |  |
| AA | 276 |  | 276 | 276 | 276 |  |  |  |  |  |  |
| SS | S3 |  | S3 | S3 | S3 |  |  |  |  |  |  |
| AA | 277 |  |  |  |  |  |  |  |  |  |  |
| SS | loop |  |  |  |  |  |  |  |  |  |  |
| AA |  |  |  |  |  |  |  | 290 |  |  |  |
| SS |  |  |  |  |  |  |  | loop |  |  |  |
| AA |  |  |  |  |  | 292 | 292 | 292 | 292 |  | 292 |
| SS |  |  |  |  |  | loop | loop | loop | loop |  | loop |
| AA |  |  |  | 299 |  |  |  |  |  |  |  |
| SS |  |  |  | H8 |  |  |  |  |  |  |  |
| AA |  |  |  |  |  |  |  | 381 | 381 |  |  |
| SS |  |  |  |  |  |  |  | H11 | H11 |  |  |
| AA |  |  |  |  |  |  | 388 |  |  |  |  |
| SS |  |  |  |  |  |  | H11 |  |  |  |  |
| AA |  |  |  |  |  |  | 401 | 401 |  |  |  |
| SS |  |  |  |  |  |  | H12 | H12 |  |  |  |

AA = Amino Acid
SS = Secondary Structure

TABLE 16

Coordination Structure of TR-α and IpBr2

| Coordination Structure | R$_1$ —CH$_2$—CH(NH$_2$)(CO$_2$)H | R$_2$ —H | R$_3$ —Br | R$_5$ —Br | R$_6$ —H | R'$_2$ —H | R'$_3$ —CH(CH$_3$)$_2$ | R'$_4$ —OH | R'$_5$ —H | R'$_6$ —H | X O |
|---|---|---|---|---|---|---|---|---|---|---|---|
| AA |  |  |  |  |  |  | 215 |  |  |  |  |
| SS |  |  |  |  |  |  | H3 |  |  |  |  |
| AA |  |  | 218 |  |  |  | 218 |  |  |  |  |
| SS |  |  | H3 |  |  |  | H3 |  |  |  |  |
| AA |  |  |  |  |  |  | 219 |  |  |  |  |
| SS |  |  |  |  |  |  | H3 |  |  |  |  |
| AA |  |  | 221 |  |  |  |  |  |  |  |  |
| SS |  |  | H3 |  |  |  |  |  |  |  |  |
| AA |  |  |  |  |  |  | 222 | 222 | 222 | 222 |  |
| SS |  |  |  |  |  |  | H3 | H3 | H3 | H3 |  |
| AA |  | 225 |  |  |  |  |  |  |  |  |  |
| SS |  | H3 |  |  |  |  |  |  |  |  |  |
| AA |  | 228 |  |  |  |  |  |  |  |  |  |
| SS |  | H3 |  |  |  |  |  |  |  |  |  |
| AA |  |  |  |  | 256 |  |  |  | 256 | 256 |  |
| SS |  |  |  |  | H5–H6 |  |  |  | H5–H6 | H5–H6 |  |
| AA |  | 259 |  |  | 259 |  |  |  |  |  |  |
| SS |  | H5–H6 |  |  | H5–H6 |  |  |  |  |  |  |
| AA |  | 262 |  |  |  |  |  |  |  |  |  |
| SS |  | H5–H6 |  |  |  |  |  |  |  |  |  |
| AA |  | 263 |  |  |  |  |  |  |  |  |  |
| SS |  | H5–H6 |  |  |  |  |  |  |  |  |  |
| AA |  | 266 |  |  |  |  |  |  |  |  |  |
| SS |  | loop |  |  |  |  |  |  |  |  |  |
| AA |  | 275 |  |  |  |  |  |  |  |  |  |
| SS |  | S3 |  |  |  |  |  |  |  |  |  |
| AA |  | 276 | 276 | 276 | 276 |  |  |  |  |  |  |
| SS |  | S3 | S3 | S3 | S3 |  |  |  |  |  |  |
| AA |  | 277 |  |  |  |  |  |  |  |  |  |
| SS |  |  |  |  |  |  |  |  |  |  |  |
| AA |  |  |  |  |  |  | 290–291 |  |  |  |  |
| SS |  |  |  |  |  |  | loop |  |  |  |  |
| AA |  |  |  |  |  | 292 | 292 | 292 | 292 |  | 292 |
| SS |  |  |  |  |  | loop | loop | loop | loop |  | loop |
| AA |  |  |  |  | 299 |  |  |  |  |  |  |
| SS |  |  |  |  | H8 |  |  |  |  |  |  |
| AA |  |  |  |  |  |  |  | 381 | 381 |  |  |
| SS |  |  |  |  |  |  |  | H11 | H11 |  |  |
| AA |  |  |  |  |  |  | 401 | 401 |  |  |  |
| SS |  |  |  |  |  |  | H12 | H12 |  |  |  |
| AA | H0H502/H0H503/H0H504 |  |  |  |  |  |  |  |  |  |  |
| SS |  |  |  |  |  |  |  |  |  |  |  |

AA = Amino Acid
SS = Secondary Structure

TABLE 17

Coordination Structure of TR-α and Dimit

| Coordination Structure | R$_1$ —CH$_2$—CH(NH$_2$)(CO$_2$)H | R$_2$ —H | R$_3$ —I | R$_5$ —I | R$_6$ —H | R'$_2$ —H | R'$_3$ —I | R'$_4$ —OH | R'$_5$ —H | R'$_6$ —H | X O |
|---|---|---|---|---|---|---|---|---|---|---|---|
| AA |  |  |  |  |  |  | 215 |  |  |  |  |
| SS |  |  |  |  |  |  | H3 |  |  |  |  |
| AA |  |  | 218 |  | 218 |  |  |  |  |  |  |
| SS |  |  | H3 |  | H3 |  |  |  |  |  |  |
| AA |  |  | 221 |  |  |  |  |  |  |  |  |
| SS |  |  | H3 |  |  |  |  |  |  |  |  |
| AA |  |  |  |  |  |  | 222 | 222 | 222 | 222 |  |
| SS |  |  |  |  |  |  | H3 | H3 | H3 | H3 |  |
| AA |  | 225 |  |  |  |  |  |  |  |  |  |
| SS |  | H3 |  |  |  |  |  |  |  |  |  |
| AA |  | 228 |  |  |  |  |  |  |  |  |  |
| SS |  | H3 |  |  |  |  |  |  |  |  |  |
| AA |  |  |  |  | 256 |  |  |  | 256 | 256 |  |
| SS |  |  |  |  | H5–H6 |  |  |  | H5–H6 | H5–H6 |  |

TABLE 17-continued

Coordination Structure of TR-α and Dimit

| Coordination Structure | R₁ —CH₂— CH(NH₂)(CO₂)H | R₂ —H | R₃ —I | R₅ —I | R₆ —H | R'₂ —H | R'₃ —I | R'₄ —OH | R'₅ —H | R'₆ —H | X O |
|---|---|---|---|---|---|---|---|---|---|---|---|
| AA | 259 | | | | 259 | | | | | | |
| SS | H5–H6 | | | | H5–H6 | | | | | | |
| AA | 262 | | | | | | | | | | |
| SS | H5–H6 | | | | | | | | | | |
| AA | 263 | | | | | | | | | | |
| SS | H5–H6 | | | | | | | | | | |
| AA | 275 | | | | | | | | | | |
| SS | S3 | | | | | | | | | | |
| AA | 276 | | 276 | 276 | 276 | | | | | | |
| SS | S3 | | S3 | S3 | S3 | | | | | | |
| AA | 277 | | | | | | | | | | |
| SS | | | | | | | | | | | |
| AA | | | | | | | 290 | | | | |
| SS | | | | | | | loop | | | | |
| AA | | | | | | 292 | 292 | 292 | 292 | | 292 |
| SS | | | | | | loop | loop | loop | loop | | loop |
| AA | | | | 299 | | | | | | | |
| SS | | | | H8 | | | | | | | |
| AA | | | | | | | | 381 | 381 | | |
| SS | | | | | | | | H11 | H11 | | |
| AA | | | | | | | | 388 | | | |
| SS | | | | | | | | H11 | | | |
| AA | | | | | | | | 401 | 401 | | |
| SS | | | | | | | | H12 | H12 | | |
| AA | H0H502/H0H 503/H0H504 | | | | | | | | | | |
| SS | | | | | | | | | | | |

AA = Amino Acid
SS = Secondary Structure

TABLE 18

Coordination Structure of TR-β and Triac

| Coordination Structure | R1 —CH₂CO₂H | R2 H | R3 I | R5 I | R6 H | R2' H | R3' I | R4' OH | R5' H | R6' H | X O |
|---|---|---|---|---|---|---|---|---|---|---|---|
| AA | | | | | | | | 269 | | | |
| SS | | | | | | | | H3 | | | |
| AA | | | 272 | | | | | | | | |
| SS | | | H3 | | | | | | | | |
| AA | | | 275 | | | | | | | | |
| SS | | | H3 | | | | | | | | |
| AA | | | 276 | | | | | | | | |
| SS | | | H3 | | | | | | | | |
| AA | 279 | 279 | | | | | | | | | |
| SS | H3 | H3 | | | | | | | | | |
| AA | | | | 310 | | | | | 310 | 310 | |
| SS | | | | H5–H6 | | | | | H5–H6 | H5–H6 | |
| AA | 313 | | | | 313 | | | | | | |
| SS | H5–H6 | | | | H5–H6 | | | | | | |
| AA | 316 | | | | | | | | | | |
| SS | H5–H6 | | | | | | | | | | |
| AA | 317 | | | | 317 | | 317 | | | | |
| SS | H5–H6 | | | | H5–H6 | | H5–H6 | | | | |
| AA | 320 | | | | | | | | | | |
| SS | H5–H6 | | | | | | | | | | |
| AA | 329 | | | | | | | | | | |
| SS | S3 | | | | | | | | | | |
| AA | 330 | 330 | 330 | 330 | 330 | | | | | | |
| SS | S3 | S3 | S3 | S3 | S3 | | | | | | |
| AA | 331 | | | | | | | | | | |
| SS | loop | | | | | | | | | | |
| AA | | | | | | | | 344 | | | |

TABLE 18-continued

Coordination Structure of TR-β and Triac

| Coordination Structure | R1 —CH$_2$CO$_2$H | R2 H | R3 I | R5 I | R6 H | R2' H | R3' I | R4' OH | R5' H | R6' H | X O |
|---|---|---|---|---|---|---|---|---|---|---|---|
| SS |  |  |  |  |  |  | loop |  |  |  |  |
| AA |  |  |  |  |  |  | 346 | 346 |  |  |  |
| SS |  |  |  |  |  |  | loop | loop |  |  |  |
| AA |  |  |  | 353 |  |  |  |  |  |  |  |
| SS |  |  |  | H8 |  |  |  |  |  |  |  |
| AA |  |  |  |  |  |  |  | 435 | 435 |  |  |
| SS |  |  |  |  |  |  |  | H11 | H11 |  |  |
| AA |  |  |  |  |  |  |  | 442 | 442 |  |  |
| SS |  |  |  |  |  |  |  | H11 | H11 |  |  |
| AA |  |  |  |  |  |  |  | 455 |  |  |  |
| SS |  |  |  |  |  |  |  | H12 |  |  |  |

AA = Amino Acid
SS = Secondary Structure

TABLE 19

Coordination Structure of TR-β and GC1

| Coordination Structure | R$_1$ —O—CH$_2$CO$_2$H | R$_2$ H | R$_3$ CH$_3$ | R$_5$ CH$_3$ | R$_6$ H | R2' H | R3' CH(CH$_3$) | R4' OH | R5' H | R6' H | X CH$_2$ |
|---|---|---|---|---|---|---|---|---|---|---|---|
| AA |  |  |  |  |  |  |  | 269 |  |  |  |
| SS |  |  |  |  |  |  |  | H3 |  |  |  |
| AA |  |  | 272 |  |  |  |  |  |  |  |  |
| SS |  |  | H3 |  |  |  |  |  |  |  |  |
| AA |  |  | 273 |  |  |  |  | 273 |  |  |  |
| SS |  |  | H3 |  |  |  |  | H3 |  |  |  |
| AA |  |  | 275 |  |  |  |  |  |  |  |  |
| SS |  |  | H3 |  |  |  |  |  |  |  |  |
| AA |  |  | 276 |  |  |  |  | 276 | 276 | 276 |  |
| SS |  |  | H3 |  |  |  |  | H3 | H3 | H3 |  |
| AA | 279 | 279 |  |  |  |  |  |  |  |  |  |
| SS | H3 | H3 |  |  |  |  |  |  |  |  |  |
| AA | 282 |  |  |  |  |  |  |  |  |  |  |
| SS | H3 |  |  |  |  |  |  |  |  |  |  |
| AA |  |  |  | 310 |  |  |  |  | 310 | 310 |  |
| SS |  |  |  | H5–H6 |  |  |  |  | H5–H6 | H5–H6 |  |
| AA | 313 |  |  |  | 313 |  |  |  |  |  |  |
| SS | H5–H6 |  |  |  | H5–H6 |  |  |  |  |  |  |
| AA |  |  |  |  |  |  |  | 314 |  |  |  |
| SS |  |  |  |  |  |  |  | H5–H6 |  |  |  |
| AA | 316 |  |  |  |  |  |  |  |  |  |  |
| SS | H5–H6 |  |  |  |  |  |  |  |  |  |  |
| AA |  |  |  |  |  |  |  | 317 |  |  |  |
| SS |  |  |  |  |  |  |  | H5–H6 |  |  |  |
| AA | 320 |  |  |  |  |  |  |  |  |  |  |
| SS | H5–H6 |  |  |  |  |  |  |  |  |  |  |
| AA | 329 |  |  |  |  |  |  |  |  |  |  |
| SS | S3 |  |  |  |  |  |  |  |  |  |  |
| AA | 330 |  |  |  | 330 |  |  |  |  |  |  |
| SS | S3 |  |  |  | S3 |  |  |  |  |  |  |
| AA | 331 |  |  |  |  |  |  |  |  |  |  |
| SS | loop |  |  |  |  |  |  |  |  |  |  |
| AA |  |  |  |  |  |  |  | 344 |  |  |  |
| SS |  |  |  |  |  |  |  | loop |  |  |  |
| AA |  |  |  |  |  |  |  | 346 | 346 |  |  |
| SS |  |  |  |  |  |  |  | loop | loop |  |  |
| AA |  |  |  | 353 |  |  |  |  |  |  |  |
| SS |  |  |  | H8 |  |  |  |  |  |  |  |
| AA |  |  |  |  |  |  |  | 435 | 435 |  |  |
|  |  |  |  |  |  |  |  | H11 | H11 |  |  |
|  |  |  |  |  |  |  |  | 455 |  |  |  |
| SS |  |  |  |  |  |  |  | H12 |  |  |  |

AA = Amino Acid
SS = Secondary Structure

APPENDIX 3

TR_DMT.PDB

REMARK TR_full length numbering
REMARK
REMARK Rfactor 0.205 Rfree 0.227
REMARK Resolution 15. 2.2 all reflections
REMARK
REMARK Three cacodylate-modified cysteines (CYA)
REMARK Cya334, Cya380, Cya392
REMARK cacodylate modeled as single arsenic atom
REMARK
REMARK side chain of certain residues modeled as ALA due to poor density;
REMARK however, residue name reflects true residue for clarity
REMARK
REMARK clone obtained from Murray et. al.
REMARK deposited sequence confirmed,
REMARK differing from that reported by Thompson et. al.
REMARK in the following codons:
REMARK 281 Thr—Ala
REMARK 285 Lys—Glu
REMARK identical to that reported by Mitsuhashi et. al.
REMARK gb:RNTRAVI X07409

| | | | | | | | | |
|---|---|---|---|---|---|---|---|---|
| JRNL | | AUTH | M. B. MURRAY, N. D. ZILZ, N. L. MCCREARY, M. J. MACDONALD | | | | | |
| JRNL | | AUTH 2 | H. C. TOWLE | | | | | |
| JRNL | | TITL | ISOLATION AND CHARACTERIZATION OF RAT CDNA CLONES FOR TWO | | | | | |
| JRNL | | TITL 2 | DISTINCT THYROID HORMONE RECPTORS | | | | | |
| JRNL | | REF | JBC V. 263 25 1988 | | | | | |
| JRNL | | AUTH | C. C. THOMPSON, C. WEINBERGER, R. LEBO, R. M. EVANS | | | | | |
| JRNL | | TITL | IDENTIFICATION OF A NOVEL THYROID HORMONE RECEPTOR EXPRESSED | | | | | |
| JRNL | | TITL 2 | IN THE MAMMALIAN CENTRAL NERVOUS SYSTEM | | | | | |
| JRNL | | REF | SCIENCE V. 237 1987 | | | | | |
| JRNL | | AUTH | T. MITSUHASHI, G. TENNYSON, V. NIKODEM | | | | | |
| JRNL | | TITL | NUCLEOTIDE SEQUENCE OF NOVEL CDNAS GENERATED BY ALTERNATIVE | | | | | |
| JRNL | | TITL 2 | SPLICING OF A RAT THYROID HORMONE RECEPTOR GENE TRANSCRIPT | | | | | |
| JRNL | | REF | NUC. ACIDS. RES. V. 16 12 1988 | | | | | |
| ATOM | 1 | N | ARG | 157 | 68.504 | 8.445 | 5.651 | 1.00 | 68.93 |
| ATOM | 2 | CA | ARG | 157 | 67.886 | 9.543 | 6.398 | 1.00 | 56.98 |
| ATOM | 3 | CB | ARG | 157 | 68.769 | 10.789 | 6.324 | 1.00 | 59.25 |
| ATOM | 4 | CG | ARG | 157 | 70.147 | 10.632 | 6.932 | 1.00 | 58.90 |
| ATOM | 5 | CD | ARG | 157 | 70.068 | 10.422 | 8.425 | 1.00 | 59.37 |
| ATOM | 6 | NE | ARG | 157 | 71.392 | 10.446 | 9.036 | 1.00 | 63.94 |
| ATOM | 7 | CZ | ARG | 157 | 71.613 | 10.329 | 10.341 | 1.00 | 64.39 |
| ATOM | 8 | NH1 | ARG | 157 | 70.596 | 10.182 | 11.179 | 1.00 | 62.14 |
| ATOM | 9 | NH2 | ARG | 157 | 72.855 | 10.365 | 10.808 | 1.00 | 65.56 |
| ATOM | 10 | C | ARG | 157 | 66.500 | 9.881 | 5.854 | 1.00 | 48.97 |
| ATOM | 11 | O | ARG | 157 | 66.351 | 10.203 | 4.674 | 1.00 | 48.61 |
| ATOM | 12 | N | PRO | 158 | 65.469 | 9.818 | 6.712 | 1.00 | 41.90 |
| ATOM | 13 | CD | PRO | 158 | 65.550 | 9.366 | 8.112 | 1.00 | 41.06 |
| ATOM | 14 | CA | PRO | 158 | 64.083 | 10.114 | 6.333 | 1.00 | 39.34 |
| ATOM | 15 | CB | PRO | 158 | 63.286 | 9.704 | 7.576 | 1.00 | 37.89 |
| ATOM | 16 | CG | PRO | 158 | 64.260 | 9.883 | 8.693 | 1.00 | 42.40 |
| ATOM | 17 | C | PRO | 158 | 63.814 | 11.573 | 5.930 | 1.00 | 37.10 |
| ATOM | 18 | O | PRO | 158 | 64.189 | 12.517 | 6.636 | 1.00 | 33.31 |
| ATOM | 19 | N | GLU | 159 | 63.171 | 11.733 | 4.778 | 1.00 | 30.56 |
| ATOM | 20 | CA | GLU | 159 | 62.821 | 13.038 | 4.231 | 1.00 | 24.26 |
| ATOM | 21 | CB | GLU | 159 | 62.553 | 12.904 | 2.727 | 1.00 | 19.19 |
| ATOM | 22 | CG | GLU | 159 | 63.788 | 12.677 | 1.874 | 1.00 | 20.60 |
| ATOM | 23 | CD | GLU | 159 | 64.407 | 13.971 | 1.390 | 1.00 | 26.54 |
| ATOM | 24 | OE1 | GLU | 159 | 63.649 | 14.929 | 1.115 | 1.00 | 30.85 |
| ATOM | 25 | OE2 | GLU | 159 | 65.649 | 14.027 | 1.268 | 1.00 | 28.35 |
| ATOM | 26 | C | GLU | 159 | 61.549 | 13.520 | 4.909 | 1.00 | 23.26 |
| ATOM | 27 | O | GLU | 159 | 60.906 | 12.765 | 5.643 | 1.00 | 26.86 |
| ATOM | 28 | N | PRO | 160 | 61.200 | 14.806 | 4.729 | 1.00 | 22.72 |
| ATOM | 29 | CD | PRO | 160 | 61.981 | 15.916 | 4.153 | 1.00 | 17.87 |
| ATOM | 30 | CA | PRO | 160 | 59.969 | 15.292 | 5.359 | 1.00 | 19.90 |
| ATOM | 31 | CB | PRO | 160 | 60.004 | 16.799 | 5.070 | 1.00 | 14.42 |
| ATOM | 32 | CG | PRO | 160 | 61.465 | 17.109 | 4.919 | 1.00 | 12.87 |
| ATOM | 33 | C | PRO | 160 | 58.747 | 14.623 | 4.701 | 1.00 | 23.68 |
| ATOM | 34 | O | PRO | 160 | 58.730 | 14.383 | 3.491 | 1.00 | 24.72 |
| ATOM | 35 | N | THR | 161 | 57.749 | 14.281 | 5.506 | 1.00 | 22.19 |
| ATOM | 36 | CA | THR | 161 | 56.542 | 13.660 | 4.985 | 1.00 | 19.50 |
| ATOM | 37 | CB | THR | 161 | 55.691 | 13.031 | 6.125 | 1.00 | 21.50 |
| ATOM | 38 | OG1 | THR | 161 | 55.163 | 14.062 | 6.972 | 1.00 | 20.33 |
| ATOM | 39 | CG2 | THR | 161 | 56.537 | 12.078 | 6.959 | 1.00 | 19.48 |
| ATOM | 40 | C | THR | 161 | 55.744 | 14.765 | 4.298 | 1.00 | 22.86 |

APPENDIX 3-continued

TR_DMT.PDB

| ATOM | 41  | O   | THR | 161 | 56.040 | 15.949 | 4.481  | 1.00 | 27.68 |
|------|-----|-----|-----|-----|--------|--------|--------|------|-------|
| ATOM | 42  | N   | PRO | 162 | 54.720 | 14.403 | 3.504  | 1.00 | 20.36 |
| ATOM | 43  | CD  | PRO | 162 | 54.280 | 13.050 | 3.113  | 1.00 | 16.55 |
| ATOM | 44  | CA  | PRO | 162 | 53.924 | 15.435 | 2.830  | 1.00 | 21.97 |
| ATOM | 45  | CB  | PRO | 162 | 52.780 | 14.633 | 2.210  | 1.00 | 18.17 |
| ATOM | 46  | CG  | PRO | 162 | 53.422 | 13.316 | 1.905  | 1.00 | 18.01 |
| ATOM | 47  | C   | PRO | 162 | 53.399 | 16.467 | 3.826  | 1.00 | 22.56 |
| ATOM | 48  | O   | PRO | 162 | 53.461 | 17.675 | 3.567  | 1.00 | 21.73 |
| ATOM | 49  | N   | GLU | 163 | 52.912 | 15.976 | 4.967  | 1.00 | 25.28 |
| ATOM | 50  | CA  | GLU | 163 | 52.357 | 16.816 | 6.030  | 1.00 | 26.64 |
| ATOM | 51  | CB  | GLU | 163 | 51.743 | 15.962 | 7.144  | 1.00 | 30.22 |
| ATOM | 52  | CG  | GLU | 163 | 50.514 | 15.131 | 6.748  | 1.00 | 44.99 |
| ATOM | 53  | CD  | GLU | 163 | 50.836 | 13.950 | 5.831  | 1.00 | 48.88 |
| ATOM | 54  | OE1 | GLU | 163 | 50.016 | 13.660 | 4.929  | 1.00 | 52.48 |
| ATOM | 55  | OE2 | GLU | 163 | 51.895 | 13.309 | 6.015  | 1.00 | 44.23 |
| ATOM | 56  | C   | GLU | 163 | 53.414 | 17.731 | 6.634  | 1.00 | 27.65 |
| ATOM | 57  | O   | GLU | 163 | 53.114 | 18.862 | 7.034  | 1.00 | 29.30 |
| ATOM | 58  | N   | GLU | 164 | 54.646 | 17.235 | 6.712  | 1.00 | 21.89 |
| ATOM | 59  | CA  | GLU | 164 | 55.741 | 18.015 | 7.265  | 1.00 | 18.29 |
| ATOM | 60  | CB  | GLU | 164 | 56.901 | 17.109 | 7.657  | 1.00 | 14.78 |
| ATOM | 61  | CG  | GLU | 164 | 56.552 | 16.196 | 8.825  | 1.00 | 21.11 |
| ATOM | 62  | CD  | GLU | 164 | 57.669 | 15.249 | 9.198  | 1.00 | 20.35 |
| ATOM | 63  | OE1 | GLU | 164 | 58.605 | 15.071 | 8.392  | 1.00 | 28.55 |
| ATOM | 64  | OE2 | GLU | 164 | 57.610 | 14.677 | 10.302 | 1.00 | 28.25 |
| ATOM | 65  | C   | GLU | 164 | 56.200 | 19.097 | 6.306  | 1.00 | 24.62 |
| ATOM | 66  | O   | GLU | 164 | 56.574 | 20.183 | 6.741  | 1.00 | 32.05 |
| ATOM | 67  | N   | TRP | 165 | 56.174 | 18.817 | 5.003  | 1.00 | 28.22 |
| ATOM | 68  | CA  | TRP | 165 | 56.576 | 19.825 | 4.021  | 1.00 | 22.99 |
| ATOM | 69  | CB  | TRP | 165 | 56.575 | 19.262 | 2.605  | 1.00 | 17.37 |
| ATOM | 70  | CG  | TRP | 165 | 57.876 | 18.633 | 2.210  | 1.00 | 10.74 |
| ATOM | 71  | CD2 | TRP | 165 | 59.153 | 19.283 | 2.109  | 1.00 | 11.74 |
| ATOM | 72  | CE2 | TRP | 165 | 60.075 | 18.319 | 1.648  | 1.00 | 9.97  |
| ATOM | 73  | CE3 | TRP | 165 | 59.606 | 20.583 | 2.365  | 1.00 | 13.88 |
| ATOM | 74  | CD1 | TRP | 165 | 58.074 | 17.343 | 1.832  | 1.00 | 9.17  |
| ATOM | 75  | NE1 | TRP | 165 | 59.390 | 17.145 | 1.486  | 1.00 | 16.55 |
| ATOM | 76  | CZ2 | TRP | 165 | 61.427 | 18.613 | 1.436  | 1.00 | 13.37 |
| ATOM | 77  | CZ3 | TRP | 165 | 60.954 | 20.874 | 2.156  | 1.00 | 16.15 |
| ATOM | 78  | CH2 | TRP | 165 | 61.846 | 19.892 | 1.696  | 1.00 | 17.42 |
| ATOM | 79  | C   | TRP | 165 | 55.634 | 21.015 | 4.115  | 1.00 | 21.44 |
| ATOM | 80  | O   | TRP | 165 | 56.041 | 22.149 | 3.865  | 1.00 | 22.12 |
| ATOM | 81  | N   | ASP | 166 | 54.373 | 20.747 | 4.456  | 1.00 | 21.29 |
| ATOM | 82  | CA  | ASP | 166 | 53.369 | 21.796 | 4.621  | 1.00 | 25.77 |
| ATOM | 83  | CB  | ASP | 166 | 51.972 | 21.196 | 4.808  | 1.00 | 26.02 |
| ATOM | 84  | CG  | ASP | 166 | 51.428 | 20.559 | 3.539  | 1.00 | 33.01 |
| ATOM | 85  | OD1 | ASP | 166 | 51.874 | 20.932 | 2.434  | 1.00 | 29.48 |
| ATOM | 86  | OD2 | ASP | 166 | 50.537 | 19.692 | 3.649  | 1.00 | 34.47 |
| ATOM | 87  | C   | ASP | 166 | 53.732 | 22.637 | 5.842  | 1.00 | 27.91 |
| ATOM | 88  | O   | ASP | 166 | 53.744 | 23.865 | 5.767  | 1.00 | 31.28 |
| ATOM | 89  | N   | LEU | 167 | 54.046 | 21.966 | 6.951  | 1.00 | 25.57 |
| ATOM | 90  | CA  | LEU | 167 | 54.439 | 22.640 | 8.187  | 1.00 | 28.28 |
| ATOM | 91  | CB  | LEU | 167 | 54.854 | 21.624 | 9.256  | 1.00 | 32.80 |
| ATOM | 92  | CG  | LEU | 167 | 53.945 | 21.347 | 10.455 | 1.00 | 41.75 |
| ATOM | 93  | CD1 | LEU | 167 | 54.765 | 20.640 | 11.532 | 1.00 | 39.15 |
| ATOM | 94  | CD2 | LEU | 167 | 53.374 | 22.647 | 11.008 | 1.00 | 39.20 |
| ATOM | 95  | C   | LEU | 167 | 55.636 | 23.532 | 7.902  | 1.00 | 22.19 |
| ATOM | 96  | O   | LEU | 167 | 55.671 | 24.700 | 8.302  | 1.00 | 29.51 |
| ATOM | 97  | N   | ILE | 168 | 56.610 | 22.957 | 7.206  | 1.00 | 15.01 |
| ATOM | 98  | CA  | ILE | 168 | 57.846 | 23.632 | 6.833  | 1.00 | 18.03 |
| ATOM | 99  | CB  | ILE | 168 | 58.756 | 22.668 | 6.040  | 1.00 | 11.37 |
| ATOM | 100 | CG2 | ILE | 168 | 59.890 | 23.413 | 5.367  | 1.00 | 16.36 |
| ATOM | 101 | CG1 | ILE | 168 | 59.289 | 21.580 | 6.975  | 1.00 | 21.63 |
| ATOM | 102 | CD1 | ILE | 168 | 60.095 | 20.501 | 6.287  | 1.00 | 21.03 |
| ATOM | 103 | C   | ILE | 168 | 57.579 | 24.897 | 6.022  | 1.00 | 22.54 |
| ATOM | 104 | O   | ILE | 168 | 58.155 | 25.948 | 6.300  | 1.00 | 24.88 |
| ATOM | 105 | N   | HIS | 169 | 56.682 | 24.800 | 5.045  | 1.00 | 25.70 |
| ATOM | 106 | CA  | HIS | 169 | 56.337 | 25.934 | 4.190  | 1.00 | 21.28 |
| ATOM | 107 | CB  | HIS | 169 | 55.411 | 25.493 | 3.057  | 1.00 | 22.29 |
| ATOM | 108 | CG  | HIS | 169 | 56.047 | 24.543 | 2.091  | 1.00 | 23.11 |
| ATOM | 109 | CD2 | HIS | 169 | 57.348 | 24.265 | 1.839  | 1.00 | 16.86 |
| ATOM | 110 | ND1 | HIS | 169 | 55.312 | 23.721 | 1.263  | 1.00 | 25.30 |
| ATOM | 111 | CE1 | HIS | 169 | 56.130 | 22.974 | 0.546  | 1.00 | 15.89 |
| ATOM | 112 | NE2 | HIS | 169 | 57.371 | 23.283 | 0.878  | 1.00 | 25.38 |
| ATOM | 113 | C   | HIS | 169 | 55.664 | 27.048 | 4.976  | 1.00 | 18.32 |
| ATOM | 114 | O   | HIS | 169 | 56.033 | 28.215 | 4.842  | 1.00 | 21.53 |
| ATOM | 115 | N   | VAL | 170 | 54.679 | 26.685 | 5.795  | 1.00 | 17.13 |
| ATOM | 116 | CA  | VAL | 170 | 53.957 | 27.661 | 6.607  | 1.00 | 21.29 |
| ATOM | 117 | CB  | VAL | 170 | 52.808 | 26.991 | 7.399  | 1.00 | 24.33 |

APPENDIX 3-continued

TR_DMT.PDB

| ATOM | 118 | CG1 | VAL | 170 | 52.164 | 27.985 | 8.354 | 1.00 | 23.78 |
|---|---|---|---|---|---|---|---|---|---|
| ATOM | 119 | CG2 | VAL | 170 | 51.760 | 26.439 | 6.435 | 1.00 | 18.87 |
| ATOM | 120 | C | VAL | 170 | 54.910 | 28.382 | 7.567 | 1.00 | 24.69 |
| ATOM | 121 | O | VAL | 170 | 54.912 | 29.616 | 7.637 | 1.00 | 28.77 |
| ATOM | 122 | N | ALA | 171 | 55.759 | 27.609 | 8.245 | 1.00 | 20.35 |
| ATOM | 123 | CA | ALA | 171 | 56.722 | 28.148 | 9.202 | 1.00 | 19.61 |
| ATOM | 124 | CB | ALA | 171 | 57.393 | 27.013 | 9.977 | 1.00 | 17.52 |
| ATOM | 125 | C | ALA | 171 | 57.775 | 29.026 | 8.531 | 1.00 | 20.91 |
| ATOM | 126 | O | ALA | 171 | 58.102 | 30.105 | 9.041 | 1.00 | 21.98 |
| ATOM | 127 | N | THR | 172 | 58.308 | 28.571 | 7.398 | 1.00 | 18.94 |
| ATOM | 128 | CA | THR | 172 | 59.313 | 29.342 | 6.668 | 1.00 | 19.55 |
| ATOM | 129 | CB | THR | 172 | 59.820 | 28.594 | 5.413 | 1.00 | 20.49 |
| ATOM | 130 | OG1 | THR | 172 | 60.394 | 27.336 | 5.795 | 1.00 | 20.66 |
| ATOM | 131 | CG2 | THR | 172 | 60.894 | 29.418 | 4.702 | 1.00 | 20.44 |
| ATOM | 132 | C | THR | 172 | 58.730 | 30.697 | 6.254 | 1.00 | 23.26 |
| ATOM | 133 | O | THR | 172 | 59.403 | 31.724 | 6.334 | 1.00 | 24.32 |
| ATOM | 134 | N | GLU | 173 | 57.468 | 30.694 | 5.836 | 1.00 | 27.42 |
| ATOM | 135 | CA | GLU | 173 | 56.797 | 31.922 | 5.434 | 1.00 | 27.68 |
| ATOM | 136 | CB | GLU | 173 | 55.477 | 31.605 | 4.728 | 1.00 | 24.51 |
| ATOM | 137 | CG | GLU | 173 | 54.652 | 32.836 | 4.338 | 1.00 | 39.69 |
| ATOM | 138 | CD | GLU | 173 | 55.396 | 33.814 | 3.426 | 1.00 | 47.72 |
| ATOM | 139 | OE1 | GLU | 173 | 55.019 | 35.009 | 3.417 | 1.00 | 48.26 |
| ATOM | 140 | OE2 | GLU | 173 | 56.344 | 33.398 | 2.717 | 1.00 | 49.61 |
| ATOM | 141 | C | GLU | 173 | 56.557 | 32.834 | 6.641 | 1.00 | 25.68 |
| ATOM | 142 | O | GLU | 173 | 56.773 | 34.046 | 6.559 | 1.00 | 23.39 |
| ATOM | 143 | N | ALA | 174 | 56.119 | 32.245 | 7.755 | 1.00 | 25.19 |
| ATOM | 144 | CA | ALA | 174 | 55.863 | 32.989 | 8.993 | 1.00 | 22.25 |
| ATOM | 145 | CB | ALA | 174 | 55.450 | 32.030 | 10.111 | 1.00 | 15.95 |
| ATOM | 146 | C | ALA | 174 | 57.125 | 33.747 | 9.391 | 1.00 | 23.22 |
| ATOM | 147 | O | ALA | 174 | 57.076 | 34.918 | 9.768 | 1.00 | 24.52 |
| ATOM | 148 | N | HIS | 175 | 58.261 | 33.073 | 9.275 | 1.00 | 20.97 |
| ATOM | 149 | CA | HIS | 175 | 59.544 | 33.665 | 9.606 | 1.00 | 19.55 |
| ATOM | 150 | CB | HIS | 175 | 60.625 | 32.577 | 9.649 | 1.00 | 16.19 |
| ATOM | 151 | CG | HIS | 175 | 62.016 | 33.104 | 9.835 | 1.00 | 18.89 |
| ATOM | 152 | CD2 | HIS | 175 | 63.148 | 32.901 | 9.119 | 1.00 | 16.05 |
| ATOM | 153 | ND1 | HIS | 175 | 62.359 | 33.962 | 10.859 | 1.00 | 13.83 |
| ATOM | 154 | CE1 | HIS | 175 | 63.642 | 34.265 | 10.765 | 1.00 | 15.87 |
| ATOM | 155 | NE2 | HIS | 175 | 64.143 | 33.635 | 9.718 | 1.00 | 19.19 |
| ATOM | 156 | C | HIS | 175 | 59.934 | 34.757 | 8.617 | 1.00 | 21.28 |
| ATOM | 157 | O | HIS | 175 | 60.274 | 35.869 | 9.014 | 1.00 | 25.12 |
| ATOM | 158 | N | ARG | 176 | 59.891 | 34.436 | 7.329 | 1.00 | 26.73 |
| ATOM | 159 | CA | ARG | 176 | 60.266 | 35.387 | 6.292 | 1.00 | 27.13 |
| ATOM | 160 | CB | ARG | 176 | 60.156 | 34.748 | 4.914 | 1.00 | 36.00 |
| ATOM | 161 | CG | ARG | 176 | 61.286 | 33.795 | 4.602 | 1.00 | 43.20 |
| ATOM | 162 | CD | ARG | 176 | 61.197 | 33.334 | 3.170 | 1.00 | 50.07 |
| ATOM | 163 | NE | ARG | 176 | 62.316 | 32.477 | 2.813 | 1.00 | 58.20 |
| ATOM | 164 | CZ | ARG | 176 | 62.266 | 31.548 | 1.867 | 1.00 | 67.22 |
| ATOM | 165 | NH | ARG | 176 | 61.143 | 31.358 | 1.182 | 1.00 | 67.62 |
| ATOM | 166 | NH2 | ARG | 176 | 63.336 | 30.806 | 1.612 | 1.00 | 70.56 |
| ATOM | 167 | C | ARG | 176 | 59.487 | 36.688 | 6.325 | 1.00 | 23.97 |
| ATOM | 168 | O | ARG | 176 | 60.073 | 37.760 | 6.209 | 1.00 | 24.52 |
| ATOM | 169 | N | SER | 177 | 58.177 | 36.598 | 6.515 | 1.00 | 23.60 |
| ATOM | 170 | CA | SER | 177 | 57.341 | 37.789 | 6.565 | 1.00 | 26.36 |
| ATOM | 171 | CB | SER | 177 | 55.865 | 37.407 | 6.439 | 1.00 | 21.93 |
| ATOM | 172 | OG | SER | 177 | 55.495 | 36.459 | 7.423 | 1.00 | 25.97 |
| ATOM | 173 | C | SER | 177 | 57.557 | 38.623 | 7.829 | 1.00 | 28.76 |
| ATOM | 174 | O | SER | 177 | 57.084 | 39.761 | 7.907 | 1.00 | 33.09 |
| ATOM | 175 | N | THR | 178 | 58.257 | 38.062 | 8.815 | 1.00 | 25.52 |
| ATOM | 176 | CA | THR | 178 | 58.508 | 38.772 | 10.064 | 1.00 | 18.93 |
| ATOM | 177 | CB | THR | 178 | 57.828 | 38.064 | 11.258 | 1.00 | 21.81 |
| ATOM | 178 | OG1 | THR | 178 | 58.348 | 36.736 | 11.394 | 1.00 | 24.18 |
| ATOM | 179 | CG2 | THR | 178 | 56.330 | 37.971 | 11.032 | 1.00 | 13.81 |
| ATOM | 180 | C | THR | 178 | 59.993 | 38.967 | 10.358 | 1.00 | 20.69 |
| ATOM | 181 | O | THR | 178 | 60.373 | 39.407 | 11.448 | 1.00 | 20.56 |
| ATOM | 182 | N | ASN | 179 | 60.837 | 38.645 | 9.385 | 1.00 | 23.68 |
| ATOM | 183 | CA | ASN | 179 | 62.275 | 38.802 | 9.555 | 1.00 | 28.22 |
| ATOM | 184 | CB | ASN | 179 | 63.022 | 37.627 | 8.927 | 1.00 | 27.45 |
| ATOM | 185 | CG | ASN | 179 | 64.460 | 37.529 | 9.402 | 1.00 | 33.98 |
| ATOM | 186 | OD1 | ASN | 179 | 65.342 | 37.131 | 8.644 | 1.00 | 42.72 |
| ATOM | 187 | ND2 | ASN | 179 | 64.702 | 37.865 | 10.667 | 1.00 | 31.14 |
| ATOM | 188 | C | ASN | 179 | 62.689 | 40.115 | 8.902 | 1.00 | 34.47 |
| ATOM | 189 | O | ASN | 179 | 62.832 | 40.200 | 7.678 | 1.00 | 36.54 |
| ATOM | 190 | N | ALA | 180 | 62.874 | 41.135 | 9.735 | 1.00 | 37.39 |
| ATOM | 191 | CA | ALA | 180 | 63.235 | 42.479 | 9.292 | 1.00 | 33.71 |
| ATOM | 192 | CB | ALA | 180 | 63.555 | 43.352 | 10.494 | 1.00 | 31.57 |
| ATOM | 193 | C | ALA | 180 | 64.375 | 42.545 | 8.284 | 1.00 | 37.87 |
| ATOM | 194 | O | ALA | 180 | 65.458 | 42.018 | 8.525 | 1.00 | 35.26 |

APPENDIX 3-continued

TR_DMT.PDB

| ATOM | 195 | N   | GLN | 181 | 64.095 | 43.187 | 7.150  | 1.00 | 40.55 |
|------|-----|-----|-----|-----|--------|--------|--------|------|-------|
| ATOM | 196 | CA  | GLN | 181 | 65.049 | 43.391 | 6.057  | 1.00 | 42.95 |
| ATOM | 197 | CB  | GLN | 181 | 66.344 | 44.043 | 6.570  | 1.00 | 45.47 |
| ATOM | 198 | CG  | GLN | 181 | 66.144 | 45.326 | 7.383  | 1.00 | 52.70 |
| ATOM | 199 | CD  | GLN | 181 | 65.351 | 46.399 | 6.650  | 1.00 | 55.03 |
| ATOM | 200 | OE1 | GLN | 181 | 65.270 | 46.412 | 5.421  | 1.00 | 59.56 |
| ATOM | 201 | NE2 | GLN | 181 | 64.757 | 47.308 | 7.411  | 1.00 | 54.39 |
| ATOM | 202 | C   | GLN | 181 | 65.391 | 42.176 | 5.197  | 1.00 | 44.27 |
| ATOM | 203 | O   | GLN | 181 | 66.181 | 42.291 | 4.251  | 1.00 | 46.47 |
| ATOM | 204 | N   | GLY | 182 | 64.797 | 41.025 | 5.508  | 1.00 | 42.17 |
| ATOM | 205 | CA  | GLY | 182 | 65.054 | 39.815 | 4.742  | 1.00 | 42.63 |
| ATOM | 206 | C   | GLY | 182 | 66.522 | 39.584 | 4.427  | 1.00 | 47.40 |
| ATOM | 207 | O   | GLY | 182 | 67.382 | 39.691 | 5.306  | 1.00 | 49.38 |
| ATOM | 208 | N   | SER | 183 | 66.816 | 39.297 | 3.163  | 1.00 | 49.46 |
| ATOM | 209 | CA  | SER | 183 | 68.189 | 39.061 | 2.733  | 1.00 | 54.13 |
| ATOM | 210 | CB  | SER | 183 | 68.208 | 38.225 | 1.449  | 1.00 | 55.08 |
| ATOM | 211 | OG  | SER | 183 | 67.197 | 38.647 | 0.546  | 1.00 | 63.54 |
| ATOM | 212 | C   | SER | 183 | 68.949 | 40.369 | 2.532  | 1.00 | 54.84 |
| ATOM | 213 | O   | SER | 183 | 70.175 | 40.373 | 2.407  | 1.00 | 56.90 |
| ATOM | 214 | N   | HIS | 184 | 68.223 | 41.482 | 2.535  | 1.00 | 55.77 |
| ATOM | 215 | CA  | HIS | 184 | 68.854 | 42.775 | 2.342  | 1.00 | 57.78 |
| ATOM | 216 | C   | HIS | 184 | 69.605 | 43.296 | 3.556  | 1.00 | 59.09 |
| ATOM | 217 | O   | HIS | 184 | 70.312 | 44.301 | 3.454  | 1.00 | 60.34 |
| ATOM | 218 | N   | TRP | 185 | 69.502 | 42.597 | 4.686  | 1.00 | 55.60 |
| ATOM | 219 | CA  | TRP | 185 | 70.159 | 43.020 | 5.923  | 1.00 | 53.73 |
| ATOM | 220 | CB  | TRP | 185 | 69.973 | 41.973 | 7.030  | 1.00 | 50.40 |
| ATOM | 221 | CG  | TRP | 185 | 70.746 | 40.694 | 6.837  | 1.00 | 48.09 |
| ATOM | 222 | CD2 | TRP | 185 | 72.091 | 40.419 | 7.269  | 1.00 | 47.38 |
| ATOM | 223 | CE2 | TRP | 185 | 72.390 | 39.094 | 6.888  | 1.00 | 40.29 |
| ATOM | 224 | CE3 | TRP | 185 | 73.071 | 41.169 | 7.937  | 1.00 | 45.43 |
| ATOM | 225 | CD1 | TRP | 185 | 70.301 | 39.554 | 6.234  | 1.00 | 49.87 |
| ATOM | 226 | NE1 | TRP | 185 | 71.280 | 38.589 | 6.262  | 1.00 | 48.02 |
| ATOM | 227 | CZ2 | TRP | 185 | 73.628 | 38.496 | 7.154  | 1.00 | 38.65 |
| ATOM | 228 | CZ3 | TRP | 185 | 74.304 | 40.573 | 8.201  | 1.00 | 43.26 |
| ATOM | 229 | CH2 | TRP | 185 | 74.570 | 39.250 | 7.807  | 1.00 | 40.00 |
| ATOM | 230 | C   | TRP | 185 | 71.638 | 43.386 | 5.800  | 1.00 | 55.99 |
| ATOM | 231 | O   | TRP | 185 | 72.089 | 44.359 | 6.401  | 1.00 | 52.84 |
| ATOM | 232 | N   | LYS | 186 | 72.389 | 42.614 | 5.021  | 1.00 | 59.15 |
| ATOM | 233 | CA  | LYS | 186 | 73.818 | 42.863 | 4.843  | 1.00 | 64.01 |
| ATOM | 234 | CB  | LYS | 186 | 74.466 | 41.688 | 4.091  | 1.00 | 64.67 |
| ATOM | 235 | CG  | LYS | 186 | 75.943 | 41.868 | 3.729  | 1.00 | 65.58 |
| ATOM | 236 | CD  | LYS | 186 | 76.817 | 42.181 | 4.946  | 1.00 | 62.03 |
| ATOM | 237 | CE  | LYS | 186 | 78.238 | 42.512 | 4.515  | 1.00 | 61.52 |
| ATOM | 238 | NZ  | LYS | 186 | 78.988 | 43.243 | 5.579  | 1.00 | 61.67 |
| ATOM | 239 | C   | LYS | 186 | 74.131 | 44.203 | 4.160  | 1.00 | 67.49 |
| ATOM | 240 | O   | LYS | 186 | 75.164 | 44.816 | 4.432  | 1.00 | 68.66 |
| ATOM | 241 | N   | GLN | 187 | 73.221 | 44.678 | 3.316  | 1.00 | 68.99 |
| ATOM | 242 | CA  | GLN | 187 | 73.431 | 45.939 | 2.612  | 1.00 | 69.65 |
| ATOM | 243 | CB  | GLN | 187 | 72.880 | 45.867 | 1.180  | 1.00 | 73.76 |
| ATOM | 244 | CG  | GLN | 187 | 73.632 | 44.935 | 0.237  | 1.00 | 78.61 |
| ATOM | 245 | CD  | GLN | 187 | 73.368 | 43.471 | 0.525  | 1.00 | 84.96 |
| ATOM | 246 | OE1 | GLN | 187 | 74.203 | 42.782 | 1.109  | 1.00 | 87.73 |
| ATOM | 247 | NE2 | GLN | 187 | 72.197 | 42.989 | 0.122  | 1.00 | 84.98 |
| ATOM | 248 | C   | GLN | 187 | 72.817 | 47.141 | 3.323  | 1.00 | 69.16 |
| ATOM | 249 | O   | GLN | 187 | 73.379 | 48.235 | 3.299  | 1.00 | 71.39 |
| ATOM | 250 | N   | ARG | 188 | 71.666 | 46.936 | 3.953  | 1.00 | 65.82 |
| ATOM | 251 | CA  | ARG | 188 | 70.961 | 48.014 | 4.639  | 1.00 | 65.00 |
| ATOM | 252 | CB  | ARG | 188 | 69.458 | 47.739 | 4.591  | 1.00 | 66.20 |
| ATOM | 253 | CG  | ARG | 188 | 68.957 | 47.483 | 3.181  | 1.00 | 70.30 |
| ATOM | 254 | CD  | ARG | 188 | 67.463 | 47.212 | 3.132  | 1.00 | 78.59 |
| ATOM | 255 | NE  | ARG | 188 | 67.003 | 47.008 | 1.760  | 1.00 | 87.71 |
| ATOM | 256 | CZ  | ARG | 188 | 67.011 | 47.946 | 0.814  | 1.00 | 94.10 |
| ATOM | 257 | NH1 | ARG | 188 | 67.453 | 49.171 | 1.081  | 1.00 | 97.26 |
| ATOM | 258 | NH2 | ARG | 188 | 66.589 | 47.657 | −0.409 | 1.00 | 94.07 |
| ATOM | 259 | C   | ARG | 188 | 71.409 | 48.286 | 6.077  | 1.00 | 65.39 |
| ATOM | 260 | O   | ARG | 188 | 70.900 | 49.201 | 6.727  | 1.00 | 65.20 |
| ATOM | 261 | N   | ARG | 189 | 72.372 | 47.506 | 6.561  | 1.00 | 64.28 |
| ATOM | 262 | CA  | ARG | 189 | 72.882 | 47.654 | 7.922  | 1.00 | 60.75 |
| ATOM | 263 | CB  | ARG | 189 | 73.691 | 46.409 | 8.321  | 1.00 | 56.87 |
| ATOM | 264 | CG  | ARG | 189 | 75.050 | 46.308 | 7.630  | 1.00 | 59.52 |
| ATOM | 265 | CD  | ARG | 189 | 75.580 | 44.891 | 7.589  | 1.00 | 55.86 |
| ATOM | 266 | NE  | ARG | 189 | 75.874 | 44.348 | 8.907  | 1.00 | 55.48 |
| ATOM | 267 | CZ  | ARG | 189 | 77.055 | 43.849 | 9.257  | 1.00 | 61.38 |
| ATOM | 268 | NH1 | ARG | 189 | 78.057 | 43.832 | 8.388  | 1.00 | 62.54 |
| ATOM | 269 | NH2 | ARG | 189 | 77.225 | 43.328 | 10.465 | 1.00 | 62.20 |
| ATOM | 270 | C   | ARG | 189 | 73.747 | 48.907 | 8.082  | 1.00 | 60.91 |
| ATOM | 271 | O   | ARG | 189 | 74.548 | 49.245 | 7.207  | 1.00 | 60.67 |

APPENDIX 3-continued

TR_DMT.PDB

| ATOM | 272 | N | LYS | 190 | 73.575 | 49.591 | 9.207 | 1.00 | 59.06 |
|---|---|---|---|---|---|---|---|---|---|
| ATOM | 273 | CA | LYS | 190 | 74.340 | 50.790 | 9.521 | 1.00 | 55.00 |
| ATOM | 274 | CB | LYS | 190 | 73.423 | 52.008 | 9.582 | 1.00 | 55.45 |
| ATOM | 275 | C | LYS | 190 | 74.991 | 50.542 | 10.875 | 1.00 | 51.52 |
| ATOM | 276 | O | LYS | 190 | 74.320 | 50.144 | 11.830 | 1.00 | 51.68 |
| ATOM | 277 | N | PHE | 191 | 76.304 | 50.721 | 10.944 | 1.00 | 50.49 |
| ATOM | 278 | CA | PHE | 191 | 77.037 | 50.508 | 12.186 | 1.00 | 50.17 |
| ATOM | 279 | CB | PHE | 191 | 78.546 | 50.571 | 11.943 | 1.00 | 48.38 |
| ATOM | 280 | CG | PHE | 191 | 79.090 | 49.423 | 11.142 | 1.00 | 49.66 |
| ATOM | 281 | CD1 | PHE | 191 | 78.873 | 49.348 | 9.768 | 1.00 | 51.03 |
| ATOM | 282 | CD2 | PHE | 191 | 79.845 | 48.429 | 11.759 | 1.00 | 46.28 |
| ATOM | 283 | CE1 | PHE | 191 | 79.403 | 48.298 | 9.018 | 1.00 | 51.35 |
| ATOM | 284 | CE2 | PHE | 191 | 80.379 | 47.377 | 11.021 | 1.00 | 47.26 |
| ATOM | 285 | CZ | PHE | 191 | 80.158 | 47.311 | 9.646 | 1.00 | 48.48 |
| ATOM | 286 | C | PHE | 191 | 76.663 | 51.534 | 13.248 | 1.00 | 48.61 |
| ATOM | 287 | O | PHE | 191 | 76.507 | 52.720 | 12.952 | 1.00 | 50.38 |
| ATOM | 288 | N | LEU | 192 | 76.488 | 51.068 | 14.479 | 1.00 | 47.31 |
| ATOM | 289 | CA | LEU | 192 | 76.169 | 51.958 | 15.584 | 1.00 | 42.72 |
| ATOM | 290 | CB | LEU | 192 | 75.845 | 51.151 | 16.844 | 1.00 | 36.66 |
| ATOM | 291 | CG | LEU | 192 | 75.397 | 51.949 | 18.068 | 1.00 | 31.01 |
| ATOM | 292 | CD1 | LEU | 192 | 74.048 | 52.590 | 17.786 | 1.00 | 28.37 |
| ATOM | 293 | CD2 | LEU | 192 | 75.318 | 51.043 | 19.289 | 1.00 | 29.60 |
| ATOM | 294 | C | LEU | 192 | 77.447 | 52.760 | 15.800 | 1.00 | 42.28 |
| ATOM | 295 | O | LEU | 192 | 78.528 | 52.179 | 15.932 | 1.00 | 39.71 |
| ATOM | 296 | N | PRO | 193 | 77.350 | 54.104 | 15.781 | 1.00 | 45.15 |
| ATOM | 297 | CD | PRO | 193 | 76.095 | 54.865 | 15.617 | 1.00 | 43.82 |
| ATOM | 298 | CA | PRO | 193 | 78.493 | 55.006 | 15.973 | 1.00 | 43.14 |
| ATOM | 299 | CB | PRO | 193 | 77.820 | 56.306 | 16.400 | 1.00 | 44.37 |
| ATOM | 300 | CG | PRO | 193 | 76.571 | 56.308 | 15.565 | 1.00 | 41.66 |
| ATOM | 301 | C | PRO | 193 | 79.476 | 54.498 | 17.028 | 1.00 | 43.34 |
| ATOM | 302 | O | PRO | 193 | 79.103 | 54.296 | 18.182 | 1.00 | 45.18 |
| ATOM | 303 | N | ASP | 194 | 80.732 | 54.317 | 16.628 | 1.00 | 44.22 |
| ATOM | 304 | CA | ASP | 194 | 81.781 | 53.804 | 17.512 | 1.00 | 47.20 |
| ATOM | 305 | CB | ASP | 194 | 83.108 | 53.732 | 16.761 | 1.00 | 41.89 |
| ATOM | 306 | C | ASP | 194 | 81.962 | 54.511 | 18.866 | 1.00 | 51.99 |
| ATOM | 307 | O | ASP | 194 | 82.636 | 53.986 | 19.752 | 1.00 | 54.04 |
| ATOM | 308 | N | ASP | 195 | 81.381 | 55.698 | 19.025 | 1.00 | 55.21 |
| ATOM | 309 | CA | ASP | 195 | 81.489 | 56.428 | 20.288 | 1.00 | 57.50 |
| ATOM | 310 | CB | ASP | 195 | 81.423 | 57.948 | 20.061 | 1.00 | 60.04 |
| ATOM | 311 | CG | ASP | 195 | 80.123 | 58.398 | 19.406 | 1.00 | 68.39 |
| ATOM | 312 | OD1 | ASP | 195 | 79.211 | 58.847 | 20.136 | 1.00 | 69.46 |
| ATOM | 313 | OD2 | ASP | 195 | 80.020 | 58.322 | 18.162 | 1.00 | 72.91 |
| ATOM | 314 | C | ASP | 195 | 80.410 | 55.976 | 21.280 | 1.00 | 58.05 |
| ATOM | 315 | O | ASP | 195 | 80.540 | 56.180 | 22.491 | 1.00 | 58.97 |
| ATOM | 316 | N | ILE | 196 | 79.349 | 55.363 | 20.759 | 1.00 | 56.06 |
| ATOM | 317 | CA | ILE | 196 | 78.247 | 54.863 | 21.580 | 1.00 | 50.48 |
| ATOM | 318 | CB | ILE | 196 | 76.930 | 54.762 | 20.766 | 1.00 | 45.82 |
| ATOM | 319 | CG2 | ILE | 196 | 75.818 | 54.166 | 21.621 | 1.00 | 44.04 |
| ATOM | 320 | CG1 | ILE | 196 | 76.517 | 56.147 | 20.261 | 1.00 | 44.27 |
| ATOM | 321 | CD1 | ILE | 196 | 75.179 | 56.171 | 19.541 | 1.00 | 45.25 |
| ATOM | 322 | C | ILE | 196 | 78.603 | 53.484 | 22.435 | 1.00 | 47.66 |
| ATOM | 323 | O | ILE | 196 | 79.138 | 52.636 | 21.419 | 1.00 | 43.96 |
| ATOM | 324 | N | GLY | 197 | 78.309 | 53.269 | 23.414 | 1.00 | 46.29 |
| ATOM | 325 | CA | GLY | 197 | 78.608 | 51.995 | 24.045 | 1.00 | 48.03 |
| ATOM | 326 | C | GLY | 197 | 79.978 | 51.963 | 24.692 | 1.00 | 50.42 |
| ATOM | 327 | O | GLY | 197 | 80.463 | 50.902 | 25.070 | 1.00 | 46.66 |
| ATOM | 328 | N | GLN | 198 | 80.583 | 53.137 | 24.854 | 1.00 | 56.94 |
| ATOM | 329 | CA | GLN | 198 | 81.910 | 53.259 | 25.454 | 1.00 | 59.51 |
| ATOM | 330 | CB | GLN | 198 | 82.751 | 54.257 | 24.649 | 1.00 | 62.53 |
| ATOM | 331 | CG | GLN | 198 | 83.232 | 53.718 | 23.316 | 1.00 | 69.39 |
| ATOM | 332 | CD | GLN | 198 | 84.088 | 52.484 | 23.483 | 1.00 | 76.76 |
| ATOM | 333 | OE1 | GLN | 198 | 83.745 | 51.399 | 22.996 | 1.00 | 81.73 |
| ATOM | 334 | NE2 | GLN | 198 | 85.205 | 52.632 | 24.192 | 1.00 | 78.09 |
| ATOM | 335 | C | GLN | 198 | 81.915 | 53.678 | 26.922 | 1.00 | 57.56 |
| ATOM | 336 | O | GLN | 198 | 82.946 | 53.584 | 27.588 | 1.00 | 57.71 |
| ATOM | 337 | N | SER | 199 | 80.770 | 54.128 | 27.425 | 1.00 | 54.11 |
| ATOM | 338 | CA | SER | 199 | 80.676 | 54.600 | 28.800 | 1.00 | 46.28 |
| ATOM | 339 | CB | SER | 199 | 80.243 | 56.067 | 28.777 | 1.00 | 50.28 |
| ATOM | 340 | OG | SER | 199 | 80.935 | 56.776 | 27.757 | 1.00 | 50.95 |
| ATOM | 341 | C | SER | 199 | 79.776 | 53.805 | 29.757 | 1.00 | 40.19 |
| ATOM | 342 | O | SER | 199 | 78.680 | 54.252 | 30.102 | 1.00 | 39.26 |
| ATOM | 343 | N | PRO | 200 | 80.236 | 52.629 | 30.214 | 1.00 | 35.63 |
| ATOM | 344 | CD | PRO | 200 | 81.530 | 52.011 | 29.904 | 1.00 | 34.88 |
| ATOM | 345 | CA | PRO | 200 | 79.464 | 51.789 | 31.139 | 1.00 | 37.54 |
| ATOM | 346 | CB | PRO | 200 | 80.223 | 50.457 | 31.124 | 1.00 | 29.86 |
| ATOM | 347 | CG | PRO | 200 | 81.207 | 50.570 | 29.995 | 1.00 | 34.29 |
| ATOM | 348 | C | PRO | 200 | 79.521 | 52.416 | 32.532 | 1.00 | 44.63 |

APPENDIX 3-continued

TR_DMT.PDB

| ATOM | 349 | O | PRO | 200 | 80.443 | 52.137 | 33.300 | 1.00 | 47.80 |
|---|---|---|---|---|---|---|---|---|---|
| ATOM | 350 | N | ILE | 201 | 78.532 | 53.241 | 32.867 | 1.00 | 49.57 |
| ATOM | 351 | CA | ILE | 201 | 78.525 | 53.924 | 34.158 | 1.00 | 49.15 |
| ATOM | 352 | CB | ILE | 201 | 78.213 | 55.426 | 33.990 | 1.00 | 49.19 |
| ATOM | 353 | CG2 | ILE | 201 | 78.429 | 56.150 | 35.306 | 1.00 | 53.37 |
| ATOM | 354 | CG1 | ILE | 201 | 79.137 | 56.037 | 32.934 | 1.00 | 52.55 |
| ATOM | 355 | CD1 | ILE | 201 | 78.811 | 57.471 | 32.586 | 1.00 | 55.26 |
| ATOM | 356 | C | ILE | 201 | 77.625 | 53.352 | 35.254 | 1.00 | 49.88 |
| ATOM | 357 | O | ILE | 201 | 78.044 | 53.250 | 36.408 | 1.00 | 50.20 |
| ATOM | 358 | N | VAL | 202 | 76.384 | 53.014 | 34.920 | 1.00 | 47.85 |
| ATOM | 359 | CA | VAL | 202 | 75.468 | 52.474 | 35.927 | 1.00 | 45.76 |
| ATOM | 360 | CB | VAL | 202 | 74.015 | 52.415 | 35.400 | 1.00 | 39.98 |
| ATOM | 361 | CG1 | VAL | 202 | 73.072 | 51.896 | 36.482 | 1.00 | 35.94 |
| ATOM | 362 | CG2 | VAL | 202 | 73.574 | 53.799 | 34.944 | 1.00 | 29.43 |
| ATOM | 363 | C | VAL | 202 | 75.954 | 51.093 | 36.373 | 1.00 | 50.57 |
| ATOM | 364 | O | VAL | 202 | 76.296 | 50.249 | 35.545 | 1.00 | 49.50 |
| ATOM | 365 | N | SER | 203 | 76.009 | 50.876 | 37.683 | 1.00 | 54.82 |
| ATOM | 366 | CA | SER | 203 | 76.490 | 49.609 | 38.223 | 1.00 | 59.26 |
| ATOM | 367 | CB | SER | 203 | 77.067 | 49.809 | 39.628 | 1.00 | 64.88 |
| ATOM | 368 | OG | SER | 203 | 76.127 | 50.428 | 40.492 | 1.00 | 75.47 |
| ATOM | 369 | C | SER | 203 | 75.457 | 48.491 | 38.244 | 1.00 | 55.78 |
| ATOM | 370 | O | SER | 203 | 74.285 | 48.712 | 38.544 | 1.00 | 57.50 |
| ATOM | 371 | N | MET | 204 | 75.923 | 47.283 | 37.958 | 1.00 | 52.29 |
| ATOM | 372 | CA | MET | 204 | 75.076 | 46.103 | 37.948 | 1.00 | 50.42 |
| ATOM | 373 | CB | MET | 204 | 75.032 | 45.487 | 36.548 | 1.00 | 47.74 |
| ATOM | 374 | CG | MET | 204 | 74.243 | 46.297 | 35.541 | 1.00 | 43.40 |
| ATOM | 375 | SD | MET | 204 | 72.491 | 46.348 | 35.953 | 1.00 | 40.93 |
| ATOM | 376 | CE | MET | 204 | 71.947 | 44.785 | 35.241 | 1.00 | 39.19 |
| ATOM | 377 | C | MET | 204 | 75.670 | 45.107 | 38.925 | 1.00 | 49.42 |
| ATOM | 378 | O | MET | 204 | 76.892 | 45.020 | 39.062 | 1.00 | 52.25 |
| ATOM | 379 | N | PRO | 205 | 74.816 | 44.329 | 39.605 | 1.00 | 47.73 |
| ATOM | 380 | CD | PRO | 205 | 73.344 | 44.414 | 39.549 | 1.00 | 48.94 |
| ATOM | 381 | CA | PRO | 205 | 75.250 | 43.326 | 40.580 | 1.00 | 47.34 |
| ATOM | 382 | CB | PRO | 205 | 73.982 | 42.513 | 40.810 | 1.00 | 49.44 |
| ATOM | 383 | CG | PRO | 205 | 72.907 | 43.562 | 40.725 | 1.00 | 50.62 |
| ATOM | 384 | C | PRO | 205 | 76.431 | 42.442 | 40.168 | 1.00 | 47.12 |
| ATOM | 385 | O | PRO | 205 | 77.299 | 42.160 | 40.990 | 1.00 | 51.21 |
| ATOM | 386 | N | ASP | 206 | 76.487 | 42.023 | 38.909 | 1.00 | 48.81 |
| ATOM | 387 | CA | ASP | 206 | 77.583 | 41.160 | 38.465 | 1.00 | 49.88 |
| ATOM | 388 | CB | ASP | 206 | 77.128 | 40.223 | 37.330 | 1.00 | 54.06 |
| ATOM | 389 | CG | ASP | 206 | 76.598 | 40.967 | 36.107 | 1.00 | 57.34 |
| ATOM | 390 | OD1 | ASP | 206 | 77.056 | 42.095 | 35.811 | 1.00 | 52.21 |
| ATOM | 391 | OD2 | ASP | 206 | 75.719 | 40.397 | 35.423 | 1.00 | 59.16 |
| ATOM | 392 | C | ASP | 206 | 78.902 | 41.843 | 38.093 | 1.00 | 48.70 |
| ATOM | 393 | O | ASP | 206 | 79.862 | 41.171 | 37.715 | 1.00 | 49.75 |
| ATOM | 394 | N | GLY | 207 | 78.946 | 43.168 | 38.161 | 1.00 | 47.54 |
| ATOM | 395 | CA | GLY | 207 | 80.174 | 43.869 | 37.820 | 1.00 | 49.23 |
| ATOM | 396 | C | GLY | 207 | 80.169 | 44.585 | 36.482 | 1.00 | 51.96 |
| ATOM | 397 | O | GLY | 207 | 80.783 | 45.645 | 36.348 | 1.00 | 56.32 |
| ATOM | 398 | N | ASP | 208 | 79.510 | 44.005 | 35.481 | 1.00 | 52.50 |
| ATOM | 399 | CA | ASP | 208 | 79.435 | 44.624 | 34.157 | 1.00 | 48.00 |
| ATOM | 400 | CB | ASP | 208 | 78.968 | 43.609 | 33.115 | 1.00 | 53.23 |
| ATOM | 401 | CG | ASP | 208 | 80.038 | 42.592 | 32.774 | 1.00 | 53.17 |
| ATOM | 402 | OD1 | ASP | 208 | 81.130 | 43.006 | 32.335 | 1.00 | 57.42 |
| ATOM | 403 | OD2 | ASP | 208 | 79.787 | 41.380 | 32.942 | 1.00 | 55.64 |
| ATOM | 404 | C | ASP | 208 | 78.497 | 45.823 | 34.187 | 1.00 | 46.68 |
| ATOM | 405 | O | ASP | 208 | 77.283 | 45.671 | 34.332 | 1.00 | 45.81 |
| ATOM | 406 | N | LYS | 209 | 79.075 | 47.014 | 34.077 | 1.00 | 45.95 |
| ATOM | 407 | CA | LYS | 209 | 78.313 | 48.257 | 34.115 | 1.00 | 45.87 |
| ATOM | 408 | CB | LYS | 209 | 79.235 | 49.418 | 34.478 | 1.00 | 46.90 |
| ATOM | 409 | C | LYS | 209 | 77.561 | 48.546 | 32.812 | 1.00 | 41.17 |
| ATOM | 410 | O | LYS | 209 | 77.951 | 48.074 | 31.745 | 1.00 | 39.51 |
| ATOM | 411 | N | VAL | 210 | 76.500 | 49.344 | 32.916 | 1.00 | 39.35 |
| ATOM | 412 | CA | VAL | 210 | 75.652 | 49.713 | 31.782 | 1.00 | 38.03 |
| ATOM | 413 | CB | VAL | 210 | 74.136 | 49.584 | 32.140 | 1.00 | 32.13 |
| ATOM | 414 | CG1 | VAL | 210 | 73.269 | 49.926 | 30.937 | 1.00 | 27.92 |
| ATOM | 415 | CG2 | VAL | 210 | 73.818 | 48.183 | 32.627 | 1.00 | 29.43 |
| ATOM | 416 | C | VAL | 210 | 75.895 | 51.134 | 31.263 | 1.00 | 38.68 |
| ATOM | 417 | O | VAL | 210 | 76.090 | 52.079 | 32.038 | 1.00 | 39.57 |
| ATOM | 418 | N | ASP | 211 | 75.848 | 51.272 | 29.942 | 1.00 | 39.19 |
| ATOM | 419 | CA | ASP | 211 | 76.019 | 52.544 | 29.254 | 1.00 | 38.39 |
| ATOM | 420 | CB | ASP | 211 | 76.794 | 52.327 | 27.946 | 1.00 | 40.36 |
| ATOM | 421 | CG | ASP | 211 | 77.051 | 53.620 | 27.177 | 1.00 | 36.85 |
| ATOM | 422 | OD4 | ASP | 211 | 76.193 | 54.528 | 27.167 | 1.00 | 37.95 |
| ATOM | 423 | OD2 | ASP | 211 | 78.121 | 53.716 | 26.553 | 1.00 | 33.87 |
| ATOM | 424 | C | ASP | 211 | 74.601 | 53.040 | 28.958 | 1.00 | 40.60 |
| ATOM | 425 | O | ASP | 211 | 73.919 | 52.517 | 28.073 | 1.00 | 40.36 |

APPENDIX 3-continued

TR_DMT.PDB

| ATOM | 426 | N | LEU | 212 | 74.185 | 54.074 | 29.680 | 1.00 | 41.55 |
|---|---|---|---|---|---|---|---|---|---|
| ATOM | 427 | CA | LEU | 212 | 72.854 | 54.664 | 29.552 | 1.00 | 38.39 |
| ATOM | 428 | CB | LEU | 212 | 72.759 | 55.883 | 30.467 | 1.00 | 40.93 |
| ATOM | 429 | CG | LEU | 212 | 71.575 | 55.979 | 31.428 | 1.00 | 45.32 |
| ATOM | 430 | CD1 | LEU | 212 | 71.271 | 54.626 | 32.047 | 1.00 | 43.83 |
| ATOM | 431 | CD2 | LEU | 212 | 71.900 | 57.007 | 32.502 | 1.00 | 44.93 |
| ATOM | 432 | C | LEU | 212 | 72.448 | 55.050 | 28.133 | 1.00 | 37.61 |
| ATOM | 433 | O | LEU | 212 | 71.318 | 54.805 | 27.719 | 1.00 | 33.71 |
| ATOM | 434 | N | GLU | 213 | 73.360 | 55.670 | 27.393 | 1.00 | 41.23 |
| ATOM | 435 | CA | GLU | 213 | 73.068 | 56.984 | 26.023 | 1.00 | 43.48 |
| ATOM | 436 | CB | GLU | 213 | 74.181 | 56.986 | 25.481 | 1.00 | 47.66 |
| ATOM | 437 | CG | GLU | 213 | 73.919 | 57.494 | 24.065 | 1.00 | 56.87 |
| ATOM | 438 | CD | GLU | 213 | 75.121 | 58.180 | 23.433 | 1.00 | 60.87 |
| ATOM | 439 | OE1 | GLU | 213 | 76.258 | 57.996 | 23.924 | 1.00 | 60.37 |
| ATOM | 440 | OE2 | GLU | 213 | 74.921 | 58.894 | 22.423 | 1.00 | 61.13 |
| ATOM | 441 | C | GLU | 213 | 72.889 | 54.880 | 25.102 | 1.00 | 39.29 |
| ATOM | 442 | O | GLU | 213 | 71.965 | 54.841 | 24.290 | 1.00 | 36.66 |
| ATOM | 443 | N | ALA | 214 | 73.785 | 53.906 | 25.233 | 1.00 | 36.33 |
| ATOM | 444 | CA | ALA | 214 | 73.739 | 52.693 | 24.422 | 1.00 | 34.89 |
| ATOM | 445 | CB | ALA | 214 | 74.946 | 51.817 | 24.711 | 1.00 | 30.70 |
| ATOM | 446 | C | ALA | 214 | 72.454 | 51.938 | 24.718 | 1.00 | 31.96 |
| ATOM | 447 | O | ALA | 214 | 71.739 | 51.523 | 23.804 | 1.00 | 33.93 |
| ATOM | 448 | N | PHE | 215 | 72.151 | 51.798 | 26.003 | 1.00 | 28.47 |
| ATOM | 449 | CA | PHE | 215 | 70.947 | 51.116 | 26.445 | 1.00 | 29.74 |
| ATOM | 450 | CB | PHE | 215 | 70.819 | 51.223 | 27.962 | 1.00 | 23.73 |
| ATOM | 451 | CG | PHE | 215 | 69.589 | 50.568 | 28.515 | 1.00 | 22.71 |
| ATOM | 452 | CD1 | PHE | 215 | 69.603 | 49.220 | 28.858 | 1.00 | 22.53 |
| ATOM | 453 | CD2 | PHE | 215 | 68.423 | 51.301 | 28.712 | 1.00 | 19.74 |
| ATOM | 454 | CE1 | PHE | 215 | 68.477 | 48.606 | 29.391 | 1.00 | 20.75 |
| ATOM | 455 | CE2 | PHE | 215 | 67.290 | 50.698 | 29.245 | 1.00 | 21.02 |
| ATOM | 456 | CZ | PHE | 215 | 67.318 | 49.346 | 29.586 | 1.00 | 19.50 |
| ATOM | 457 | C | PHE | 215 | 69.730 | 51.742 | 25.771 | 1.00 | 34.64 |
| ATOM | 458 | O | PHE | 215 | 68.872 | 51.034 | 25.239 | 1.00 | 39.86 |
| ATOM | 459 | N | SER | 216 | 69.677 | 53.071 | 25.771 | 1.00 | 34.78 |
| ATOM | 460 | CA | SER | 216 | 68.572 | 53.801 | 25.160 | 1.00 | 36.01 |
| ATOM | 461 | CB | SER | 216 | 68.762 | 55.302 | 25.366 | 1.00 | 37.36 |
| ATOM | 462 | OG | SER | 216 | 67.537 | 55.987 | 25.193 | 1.00 | 48.33 |
| ATOM | 463 | C | SER | 216 | 68.458 | 53.475 | 23.664 | 1.00 | 37.06 |
| ATOM | 464 | O | SER | 216 | 67.358 | 53.250 | 23.148 | 1.00 | 33.23 |
| ATOM | 465 | N | GLU | 217 | 69.601 | 53.410 | 22.986 | 1.00 | 36.25 |
| ATOM | 466 | CA | GLU | 217 | 69.645 | 53.091 | 21.562 | 1.00 | 36.99 |
| ATOM | 467 | CB | GLU | 217 | 71.092 | 53.104 | 21.064 | 1.00 | 37.10 |
| ATOM | 468 | CG | GLU | 217 | 71.682 | 54.491 | 20.912 | 1.00 | 44.30 |
| ATOM | 469 | CD | GLU | 217 | 71.016 | 55.284 | 19.802 | 1.00 | 51.30 |
| ATOM | 470 | OE1 | GLU | 217 | 71.439 | 55.142 | 18.633 | 1.00 | 57.25 |
| ATOM | 471 | OE2 | GLU | 217 | 70.070 | 56.046 | 20.096 | 1.00 | 52.50 |
| ATOM | 472 | C | GLU | 217 | 69.019 | 51.726 | 21.286 | 1.00 | 36.93 |
| ATOM | 473 | O | GLU | 217 | 68.191 | 51.577 | 20.381 | 1.00 | 41.06 |
| ATOM | 474 | N | PHE | 218 | 69.395 | 50.740 | 22.093 | 1.00 | 30.27 |
| ATOM | 475 | CA | PHE | 218 | 68.875 | 49.388 | 21.947 | 1.00 | 27.20 |
| ATOM | 476 | CB | PHE | 218 | 69.679 | 48.421 | 22.814 | 1.00 | 28.10 |
| ATOM | 477 | CG | PHE | 218 | 71.124 | 48.330 | 22.428 | 1.00 | 24.84 |
| ATOM | 478 | CD1 | PHE | 218 | 72.117 | 48.286 | 23.398 | 1.00 | 21.78 |
| ATOM | 479 | CD2 | PHE | 218 | 71.495 | 48.301 | 21.087 | 1.00 | 24.78 |
| ATOM | 480 | CE1 | PHE | 218 | 73.458 | 48.215 | 23.040 | 1.00 | 24.08 |
| ATOM | 481 | CE2 | PHE | 218 | 72.834 | 48.230 | 20.719 | 1.00 | 25.33 |
| ATOM | 482 | CZ | PHE | 218 | 73.818 | 48.187 | 21.697 | 1.00 | 25.04 |
| ATOM | 483 | C | PHE | 218 | 67.381 | 49.281 | 22.261 | 1.00 | 28.23 |
| ATOM | 484 | O | PHE | 218 | 66.639 | 48.605 | 21.543 | 1.00 | 33.52 |
| ATOM | 485 | N | THR | 219 | 66.927 | 49.961 | 23.310 | 1.00 | 27.24 |
| ATOM | 486 | CA | THR | 219 | 65.515 | 49.913 | 23.666 | 1.00 | 29.28 |
| ATOM | 487 | CB | THR | 219 | 65.238 | 50.533 | 25.052 | 1.00 | 30.97 |
| ATOM | 488 | OG1 | THR | 219 | 65.724 | 51.880 | 25.090 | 1.00 | 35.50 |
| ATOM | 489 | CG2 | THR | 219 | 65.901 | 49.712 | 26.149 | 1.00 | 30.78 |
| ATOM | 490 | C | THR | 219 | 64.660 | 50.612 | 22.615 | 1.00 | 33.29 |
| ATOM | 491 | O | THR | 219 | 63.473 | 50.317 | 22.474 | 1.00 | 36.85 |
| ATOM | 492 | N | LYS | 220 | 65.276 | 51.515 | 21.860 | 1.00 | 35.23 |
| ATOM | 493 | CA | LYS | 220 | 64.579 | 52.253 | 20.816 | 1.00 | 38.97 |
| ATOM | 494 | CB | LYS | 220 | 65.506 | 53.334 | 20.236 | 1.00 | 44.67 |
| ATOM | 495 | CG | LYS | 220 | 64.805 | 54.491 | 19.513 | 1.00 | 58.02 |
| ATOM | 496 | CD | LYS | 220 | 64.406 | 54.130 | 18.079 | 1.00 | 68.57 |
| ATOM | 497 | CE | LYS | 220 | 63.732 | 55.296 | 17.347 | 1.00 | 70.50 |
| ATOM | 498 | NZ | LYS | 220 | 62.395 | 55.668 | 17.905 | 1.00 | 66.08 |
| ATOM | 499 | C | LYS | 220 | 64.112 | 51.289 | 19.721 | 1.00 | 38.48 |
| ATOM | 500 | O | LYS | 220 | 63.021 | 51.446 | 19.173 | 1.00 | 37.18 |
| ATOM | 501 | N | ILE | 221 | 64.917 | 50.270 | 19.432 | 1.00 | 36.19 |
| ATOM | 502 | CA | ILE | 221 | 64.563 | 49.305 | 18.394 | 1.00 | 36.77 |

APPENDIX 3-continued

TR_DMT.PDB

| ATOM | 503 | CB  | ILE | 221 | 65.756 | 48.996 | 17.457 | 1.00 | 34.41 |
|------|-----|-----|-----|-----|--------|--------|--------|------|-------|
| ATOM | 504 | CG2 | ILE | 221 | 66.270 | 50.276 | 16.814 | 1.00 | 38.54 |
| ATOM | 505 | CG1 | ILE | 221 | 66.864 | 48.267 | 18.221 | 1.00 | 32.93 |
| ATOM | 506 | CD1 | ILE | 221 | 67.984 | 47.752 | 17.338 | 1.00 | 31.12 |
| ATOM | 507 | C   | ILE | 221 | 64.002 | 47.971 | 18.888 | 1.00 | 38.22 |
| ATOM | 508 | O   | ILE | 221 | 63.499 | 47.181 | 18.089 | 1.00 | 38.90 |
| ATOM | 509 | N   | ILE | 222 | 64.048 | 47.719 | 20.191 | 1.00 | 35.75 |
| ATOM | 510 | CA  | ILE | 222 | 63.557 | 46.446 | 20.702 | 1.00 | 31.77 |
| ATOM | 511 | CB  | ILE | 222 | 64.086 | 46.152 | 22.130 | 1.00 | 33.14 |
| ATOM | 512 | CG2 | ILE | 222 | 63.203 | 46.813 | 23.183 | 1.00 | 24.60 |
| ATOM | 513 | CG1 | ILE | 222 | 64.147 | 44.638 | 22.350 | 1.00 | 32.60 |
| ATOM | 514 | CD1 | ILE | 222 | 64.860 | 44.226 | 23.609 | 1.00 | 34.52 |
| ATOM | 515 | C   | ILE | 222 | 62.042 | 46.240 | 20.624 | 1.00 | 32.56 |
| ATOM | 516 | O   | ILE | 222 | 61.581 | 45.109 | 20.452 | 1.00 | 35.74 |
| ATOM | 517 | N   | THR | 223 | 61.262 | 47.313 | 20.720 | 1.00 | 29.43 |
| ATOM | 518 | CA  | THR | 223 | 59.806 | 47.170 | 20.651 | 1.00 | 33.57 |
| ATOM | 519 | CB  | THR | 223 | 59.075 | 48.514 | 20.903 | 1.00 | 38.99 |
| ATOM | 520 | OG1 | THR | 223 | 59.422 | 49.010 | 22.205 | 1.00 | 41.23 |
| ATOM | 521 | CG2 | THR | 223 | 57.558 | 48.325 | 20.836 | 1.00 | 36.98 |
| ATOM | 522 | C   | THR | 223 | 59.355 | 46.528 | 19.325 | 1.00 | 31.45 |
| ATOM | 523 | O   | THR | 223 | 58.571 | 45.571 | 19.334 | 1.00 | 26.77 |
| ATOM | 524 | N   | PRO | 224 | 59.824 | 47.054 | 18.173 | 1.00 | 31.35 |
| ATOM | 525 | CD  | PRO | 224 | 60.570 | 48.306 | 17.950 | 1.00 | 30.11 |
| ATOM | 526 | CA  | PRO | 224 | 59.424 | 46.462 | 16.891 | 1.00 | 30.38 |
| ATOM | 527 | CB  | PRO | 224 | 60.149 | 47.336 | 15.865 | 1.00 | 30.09 |
| ATOM | 528 | CG  | PRO | 224 | 60.200 | 48.659 | 16.530 | 1.00 | 31.86 |
| ATOM | 529 | C   | PRO | 224 | 59.882 | 45.007 | 16.795 | 1.00 | 29.51 |
| ATOM | 530 | O   | PRO | 224 | 59.147 | 44.153 | 16.295 | 1.00 | 32.52 |
| ATOM | 531 | N   | ALA | 225 | 61.090 | 44.734 | 17.285 | 1.00 | 22.63 |
| ATOM | 532 | CA  | ALA | 225 | 61.650 | 43.385 | 17.268 | 1.00 | 20.88 |
| ATOM | 533 | CB  | ALA | 225 | 63.046 | 43.386 | 17.862 | 1.00 | 20.57 |
| ATOM | 534 | C   | ALA | 225 | 60.752 | 42.416 | 18.026 | 1.00 | 23.53 |
| ATOM | 535 | O   | ALA | 225 | 60.455 | 41.323 | 17.544 | 1.00 | 25.07 |
| ATOM | 536 | N   | ILE | 226 | 60.296 | 42.828 | 19.202 | 1.00 | 22.61 |
| ATOM | 537 | CA  | ILE | 226 | 59.420 | 41.989 | 20.007 | 1.00 | 19.46 |
| ATOM | 538 | CB  | ILE | 226 | 59.120 | 42.644 | 21.360 | 1.00 | 20.25 |
| ATOM | 539 | CG2 | ILE | 226 | 58.071 | 41.843 | 22.105 | 1.00 | 16.75 |
| ATOM | 540 | CG1 | ILE | 226 | 60.401 | 42.772 | 22.182 | 1.00 | 19.30 |
| ATOM | 541 | CD1 | ILE | 226 | 60.240 | 43.645 | 23.413 | 1.00 | 20.92 |
| ATOM | 542 | C   | ILE | 226 | 58.112 | 41.768 | 19.251 | 1.00 | 21.28 |
| ATOM | 543 | O   | ILE | 226 | 57.553 | 40.670 | 19.256 | 1.00 | 23.75 |
| ATOM | 544 | N   | THR | 227 | 57.629 | 42.821 | 18.598 | 1.00 | 24.46 |
| ATOM | 545 | CA  | THR | 227 | 56.393 | 42.752 | 17.826 | 1.00 | 25.81 |
| ATOM | 546 | CB  | THR | 227 | 56.020 | 44.136 | 17.260 | 1.00 | 31.00 |
| ATOM | 547 | OG1 | THR | 227 | 55.772 | 45.039 | 18.345 | 1.00 | 35.43 |
| ATOM | 548 | CG2 | THR | 227 | 54.776 | 44.049 | 16.388 | 1.00 | 29.01 |
| ATOM | 549 | C   | THR | 227 | 56.508 | 41.728 | 16.691 | 1.00 | 22.85 |
| ATOM | 550 | O   | THR | 227 | 55.589 | 40.939 | 16.469 | 1.00 | 22.84 |
| ATOM | 551 | N   | ARG | 228 | 57.647 | 41.713 | 16.004 | 1.00 | 16.09 |
| ATOM | 552 | CA  | ARG | 228 | 57.862 | 40.765 | 14.919 | 1.00 | 16.97 |
| ATOM | 553 | CB  | ARG | 228 | 59.161 | 41.064 | 14.174 | 1.00 | 14.71 |
| ATOM | 554 | CG  | ARG | 228 | 59.137 | 42.369 | 13.391 | 1.00 | 16.22 |
| ATOM | 555 | CD  | ARG | 228 | 60.309 | 42.447 | 12.422 | 1.00 | 20.90 |
| ATOM | 556 | NE  | ARG | 228 | 61.595 | 42.207 | 13.078 | 1.00 | 24.94 |
| ATOM | 557 | CZ  | ARG | 228 | 62.243 | 43.113 | 13.805 | 1.00 | 35.06 |
| ATOM | 558 | NH1 | ARG | 228 | 61.729 | 44.328 | 13.973 | 1.00 | 36.35 |
| ATOM | 559 | NH2 | ARG | 228 | 63.404 | 42.807 | 14.370 | 1.00 | 32.78 |
| ATOM | 560 | C   | ARG | 228 | 57.866 | 39.326 | 15.431 | 1.00 | 21.63 |
| ATOM | 561 | O   | ARG | 228 | 57.477 | 38.407 | 14.704 | 1.00 | 24.47 |
| ATOM | 562 | N   | VAL | 229 | 58.304 | 39.128 | 16.675 | 1.00 | 20.00 |
| ATOM | 563 | CA  | VAL | 229 | 58.319 | 37.793 | 17.266 | 1.00 | 18.39 |
| ATOM | 564 | CB  | VAL | 229 | 59.103 | 37.745 | 18.606 | 1.00 | 19.20 |
| ATOM | 565 | CG1 | VAL | 229 | 58.938 | 36.382 | 19.265 | 1.00 | 14.19 |
| ATOM | 566 | CG2 | VAL | 229 | 60.581 | 38.001 | 18.356 | 1.00 | 14.81 |
| ATOM | 567 | C   | VAL | 229 | 56.875 | 37.367 | 17.501 | 1.00 | 20.00 |
| ATOM | 568 | O   | VAL | 229 | 56.499 | 36.227 | 17.212 | 1.00 | 20.04 |
| ATOM | 569 | N   | VAL | 230 | 56.058 | 38.291 | 18.003 | 1.00 | 19.60 |
| ATOM | 570 | CA  | VAL | 230 | 54.651 | 37.996 | 18.247 | 1.00 | 18.72 |
| ATOM | 571 | CB  | VAL | 230 | 53.930 | 39.185 | 18.912 | 1.00 | 22.15 |
| ATOM | 572 | CG1 | VAL | 230 | 52.452 | 38.862 | 19.113 | 1.00 | 15.66 |
| ATOM | 573 | CG2 | VAL | 230 | 54.592 | 39.522 | 20.248 | 1.00 | 21.05 |
| ATOM | 574 | C   | VAL | 230 | 53.967 | 37.660 | 16.917 | 1.00 | 26.17 |
| ATOM | 575 | O   | VAL | 230 | 53.188 | 36.704 | 16.836 | 1.00 | 28.01 |
| ATOM | 576 | N   | ASP | 231 | 54.288 | 38.426 | 15.873 | 1.00 | 25.07 |
| ATOM | 577 | CA  | ASP | 231 | 53.714 | 38.216 | 14.542 | 1.00 | 26.10 |
| ATOM | 578 | CB  | ASP | 231 | 54.169 | 39.309 | 13.568 | 1.00 | 22.15 |
| ATOM | 579 | CG  | ASP | 231 | 53.620 | 40.684 | 13.921 | 1.00 | 29.49 |

APPENDIX 3-continued

TR_DMT.PDB

| ATOM | 580 | OD1 | ASP | 231 | 52.587 | 40.767 | 14.624 | 1.00 | 30.93 |
|---|---|---|---|---|---|---|---|---|---|
| ATOM | 581 | OD2 | ASP | 231 | 54.223 | 41.687 | 13.481 | 1.00 | 31.74 |
| ATOM | 582 | C | ASP | 231 | 54.087 | 36.842 | 13.989 | 1.00 | 27.35 |
| ATOM | 583 | O | ASP | 231 | 53.245 | 36.154 | 13.408 | 1.00 | 25.89 |
| ATOM | 584 | N | PHE | 232 | 55.347 | 36.451 | 14.175 | 1.00 | 24.29 |
| ATOM | 585 | CA | PHE | 232 | 55.825 | 35.154 | 13.714 | 1.00 | 22.90 |
| ATOM | 586 | CB | PHE | 232 | 57.302 | 34.956 | 14.090 | 1.00 | 20.56 |
| ATOM | 587 | CG | PHE | 232 | 57.762 | 33.525 | 14.007 | 1.00 | 24.20 |
| ATOM | 588 | CD1 | PHE | 232 | 57.952 | 32.910 | 12.772 | 1.00 | 23.44 |
| ATOM | 589 | CD2 | PHE | 232 | 57.959 | 32.776 | 15.167 | 1.00 | 19.41 |
| ATOM | 590 | CE1 | PHE | 232 | 58.329 | 31.567 | 12.689 | 1.00 | 19.53 |
| ATOM | 591 | CE2 | PHE | 232 | 58.336 | 31.431 | 15.100 | 1.00 | 21.09 |
| ATOM | 592 | CZ | PHE | 232 | 58.520 | 30.824 | 13.858 | 1.00 | 21.61 |
| ATOM | 593 | C | PHE | 232 | 54.984 | 34.047 | 14.341 | 1.00 | 24.18 |
| ATOM | 594 | O | PHE | 232 | 54.481 | 33.160 | 13.645 | 1.00 | 22.26 |
| ATOM | 595 | N | ALA | 233 | 54.810 | 34.127 | 15.656 | 1.00 | 23.90 |
| ATOM | 596 | CA | ALA | 233 | 54.048 | 33.128 | 16.397 | 1.00 | 22.60 |
| ATOM | 597 | CB | ALA | 233 | 54.088 | 33.435 | 17.890 | 1.00 | 15.34 |
| ATOM | 598 | C | ALA | 233 | 52.609 | 33.040 | 15.917 | 1.00 | 22.04 |
| ATOM | 599 | O | ALA | 233 | 52.084 | 31.948 | 15.697 | 1.00 | 22.86 |
| ATOM | 600 | N | LYS | 234 | 51.978 | 34.195 | 15.743 | 1.00 | 25.04 |
| ATOM | 601 | CA | LYS | 234 | 50.593 | 34.248 | 15.298 | 1.00 | 27.68 |
| ATOM | 602 | CB | LYS | 234 | 50.096 | 35.691 | 15.292 | 1.00 | 31.41 |
| ATOM | 603 | CG | LYS | 234 | 49.845 | 36.248 | 16.682 | 1.00 | 40.37 |
| ATOM | 604 | CD | LYS | 234 | 49.212 | 37.626 | 16.604 | 1.00 | 57.53 |
| ATOM | 605 | CE | LYS | 234 | 48.772 | 38.112 | 17.974 | 1.00 | 64.28 |
| ATOM | 606 | NZ | LYS | 234 | 48.164 | 39.473 | 17.904 | 1.00 | 67.19 |
| ATOM | 607 | C | LYS | 234 | 50.358 | 33.588 | 13.939 | 1.00 | 26.42 |
| ATOM | 608 | O | LYS | 234 | 49.269 | 33.067 | 13.674 | 1.00 | 31.34 |
| ATOM | 609 | N | LYS | 235 | 51.382 | 33.588 | 13.093 | 1.00 | 24.38 |
| ATOM | 610 | CA | LYS | 235 | 51.278 | 32.985 | 11.770 | 1.00 | 26.42 |
| ATOM | 611 | CB | LYS | 235 | 52.244 | 33.664 | 10.805 | 1.00 | 24.92 |
| ATOM | 612 | CG | LYS | 235 | 51.908 | 35.127 | 10.583 | 1.00 | 22.41 |
| ATOM | 613 | CD | LYS | 235 | 52.843 | 35.775 | 9.588 | 1.00 | 29.38 |
| ATOM | 614 | CE | LYS | 235 | 52.481 | 37.234 | 9.395 | 1.00 | 33.49 |
| ATOM | 615 | NZ | LYS | 235 | 53.354 | 37.869 | 8.376 | 1.00 | 40.13 |
| ATOM | 616 | C | LYS | 235 | 51.470 | 31.469 | 11.759 | 1.00 | 30.02 |
| ATOM | 617 | O | LYS | 235 | 51.417 | 30.838 | 10.699 | 1.00 | 30.37 |
| ATOM | 618 | N | LEU | 236 | 51.722 | 30.889 | 12.930 | 1.00 | 32.39 |
| ATOM | 619 | CA | LEU | 236 | 51.878 | 29.443 | 13.053 | 1.00 | 36.24 |
| ATOM | 620 | CB | LEU | 236 | 52.944 | 29.080 | 14.089 | 1.00 | 29.91 |
| ATOM | 621 | CG | LEU | 236 | 54.373 | 29.516 | 13.765 | 1.00 | 24.69 |
| ATOM | 622 | CD1 | LEU | 236 | 55.299 | 29.054 | 14.877 | 1.00 | 22.71 |
| ATOM | 623 | CD2 | LEU | 236 | 54.811 | 28.942 | 12.427 | 1.00 | 24.48 |
| ATOM | 624 | C | LEU | 236 | 50.520 | 28.891 | 13.470 | 1.00 | 41.22 |
| ATOM | 625 | O | LEU | 236 | 49.936 | 29.333 | 14.467 | 1.00 | 41.45 |
| ATOM | 626 | N | PRO | 237 | 50.012 | 27.895 | 12.729 | 1.00 | 47.86 |
| ATOM | 627 | CD | PRO | 237 | 50.739 | 27.190 | 11.657 | 1.00 | 49.32 |
| ATOM | 628 | CA | PRO | 237 | 48.713 | 27.262 | 12.992 | 1.00 | 50.28 |
| ATOM | 629 | CB | PRO | 237 | 48.669 | 26.128 | 11.962 | 1.00 | 55.25 |
| ATOM | 630 | CG | PRO | 237 | 50.135 | 25.818 | 11.706 | 1.00 | 54.08 |
| ATOM | 631 | C | PRO | 237 | 48.495 | 26.751 | 14.422 | 1.00 | 47.94 |
| ATOM | 632 | O | PRO | 237 | 47.533 | 27.134 | 15.087 | 1.00 | 42.48 |
| ATOM | 633 | N | MET | 238 | 49.415 | 25.927 | 14.906 | 1.00 | 49.51 |
| ATOM | 634 | CA | MET | 238 | 49.306 | 25.354 | 16.245 | 1.00 | 53.49 |
| ATOM | 635 | CB | MET | 238 | 50.379 | 24.275 | 16.424 | 1.00 | 52.52 |
| ATOM | 636 | CG | MET | 238 | 50.028 | 22.959 | 15.728 | 1.00 | 56.00 |
| ATOM | 637 | SD | MET | 238 | 51.443 | 21.961 | 15.204 | 1.00 | 50.16 |
| ATOM | 638 | CE | MET | 238 | 50.896 | 21.440 | 13.552 | 1.00 | 55.71 |
| ATOM | 639 | C | MET | 238 | 49.352 | 26.362 | 17.395 | 1.00 | 54.20 |
| ATOM | 640 | O | MET | 238 | 48.930 | 26.058 | 18.515 | 1.00 | 54.72 |
| ATOM | 641 | N | PHE | 239 | 49.803 | 27.578 | 17.101 | 1.00 | 50.11 |
| ATOM | 642 | CA | PHE | 239 | 49.917 | 28.619 | 18.117 | 1.00 | 41.11 |
| ATOM | 643 | CB | PHE | 239 | 51.089 | 29.552 | 17.788 | 1.00 | 34.80 |
| ATOM | 644 | CG | PHE | 239 | 51.336 | 30.607 | 18.826 | 1.00 | 30.25 |
| ATOM | 645 | CD1 | PHE | 239 | 52.127 | 30.332 | 19.937 | 1.00 | 25.66 |
| ATOM | 646 | CD2 | PHE | 239 | 50.786 | 31.878 | 18.690 | 1.00 | 26.30 |
| ATOM | 647 | CE1 | PHE | 239 | 52.368 | 31.307 | 20.896 | 1.00 | 30.28 |
| ATOM | 648 | CE2 | PHE | 239 | 51.019 | 32.862 | 19.644 | 1.00 | 30.49 |
| ATOM | 649 | CZ | PHE | 239 | 51.813 | 32.576 | 20.750 | 1.00 | 29.00 |
| ATOM | 650 | C | PHE | 239 | 48.647 | 29.434 | 18.337 | 1.00 | 35.65 |
| ATOM | 651 | O | PHE | 239 | 48.151 | 29.521 | 19.457 | 1.00 | 30.27 |
| ATOM | 652 | N | SER | 240 | 48.133 | 30.037 | 17.272 | 1.00 | 36.49 |
| ATOM | 653 | CA | SER | 240 | 46.936 | 30.866 | 17.359 | 1.00 | 36.37 |
| ATOM | 654 | CB | SER | 240 | 46.622 | 31.466 | 15.994 | 1.00 | 35.87 |
| ATOM | 655 | C | SER | 240 | 45.707 | 30.145 | 17.936 | 1.00 | 40.37 |
| ATOM | 656 | O | SER | 240 | 44.784 | 30.789 | 18.438 | 1.00 | 37.47 |

APPENDIX 3-continued

TR_DMT.PDB

| ATOM | 657 | N | GLU | 241 | 45.713 | 28.814 | 17.889 | 1.00 | 43.00 |
|---|---|---|---|---|---|---|---|---|---|
| ATOM | 658 | CA | GLU | 241 | 44.605 | 28.004 | 18.404 | 1.00 | 46.31 |
| ATOM | 659 | CB | GLU | 241 | 44.714 | 26.566 | 17.881 | 1.00 | 55.84 |
| ATOM | 660 | CG | GLU | 241 | 44.750 | 26.422 | 16.360 | 1.00 | 69.03 |
| ATOM | 661 | CD | GLU | 241 | 45.141 | 25.015 | 15.900 | 1.00 | 74.99 |
| ATOM | 662 | OE1 | GLU | 241 | 45.835 | 24.299 | 16.658 | 1.00 | 77.81 |
| ATOM | 663 | OE2 | GLU | 241 | 44.765 | 24.629 | 14.770 | 1.00 | 70.58 |
| ATOM | 664 | C | GLU | 241 | 44.587 | 27.961 | 19.933 | 1.00 | 42.60 |
| ATOM | 665 | O | GLU | 241 | 43.541 | 27.740 | 20.545 | 1.00 | 43.23 |
| ATOM | 666 | N | LEU | 242 | 45.762 | 28.125 | 20.535 | 1.00 | 39.31 |
| ATOM | 667 | CA | LEU | 242 | 45.926 | 28.086 | 21.987 | 1.00 | 34.54 |
| ATOM | 668 | CB | LEU | 242 | 47.417 | 28.109 | 22.344 | 1.00 | 28.35 |
| ATOM | 669 | CG | LEU | 242 | 48.311 | 26.974 | 21.853 | 1.00 | 27.59 |
| ATOM | 670 | CD1 | LEU | 242 | 49.750 | 27.307 | 22.180 | 1.00 | 20.72 |
| ATOM | 671 | CD2 | LEU | 242 | 47.902 | 25.661 | 22.500 | 1.00 | 24.97 |
| ATOM | 672 | C | LEU | 242 | 45.242 | 29.240 | 22.711 | 1.00 | 32.23 |
| ATOM | 673 | O | LEU | 242 | 44.956 | 30.282 | 22.119 | 1.00 | 31.50 |
| ATOM | 674 | N | PRO | 243 | 44.954 | 29.060 | 24.010 | 1.00 | 34.39 |
| ATOM | 675 | CD | PRO | 243 | 45.118 | 27.843 | 24.827 | 1.00 | 31.68 |
| ATOM | 676 | CA | PRO | 243 | 44.309 | 30.134 | 24.773 | 1.00 | 34.39 |
| ATOM | 677 | CB | PRO | 243 | 44.092 | 29.498 | 26.154 | 1.00 | 32.34 |
| ATOM | 678 | CG | PRO | 243 | 44.081 | 28.026 | 25.892 | 1.00 | 33.80 |
| ATOM | 679 | C | PRO | 243 | 45.300 | 31.303 | 24.873 | 1.00 | 35.56 |
| ATOM | 680 | O | PRO | 243 | 46.517 | 31.082 | 24.897 | 1.00 | 34.99 |
| ATOM | 681 | N | CYS | 244 | 44.791 | 32.532 | 24.946 | 1.00 | 34.23 |
| ATOM | 682 | CA | CYS | 244 | 45.648 | 33.714 | 25.062 | 1.00 | 37.03 |
| ATOM | 683 | CB | CYS | 244 | 44.820 | 34.960 | 25.376 | 1.00 | 43.49 |
| ATOM | 684 | SG | CYS | 244 | 43.820 | 35.531 | 24.007 | 1.00 | 71.28 |
| ATOM | 685 | C | CYS | 244 | 46.716 | 33.555 | 26.135 | 1.00 | 34.99 |
| ATOM | 686 | O | CYS | 244 | 47.894 | 33.802 | 25.882 | 1.00 | 37.49 |
| ATOM | 687 | N | GLU | 245 | 46.305 | 33.125 | 27.326 | 1.00 | 33.03 |
| ATOM | 688 | CA | GLU | 245 | 47.249 | 32.944 | 28.424 | 1.00 | 35.72 |
| ATOM | 689 | CB | GLU | 245 | 46.559 | 32.469 | 29.716 | 1.00 | 37.85 |
| ATOM | 690 | CG | GLU | 245 | 45.294 | 31.633 | 29.549 | 1.00 | 46.81 |
| ATOM | 691 | CD | GLU | 245 | 44.029 | 32.478 | 29.480 | 1.00 | 44.81 |
| ATOM | 692 | OE1 | GLU | 245 | 43.606 | 33.012 | 30.527 | 1.00 | 33.05 |
| ATOM | 693 | OE2 | GLU | 245 | 43.454 | 32.599 | 28.377 | 1.00 | 48.22 |
| ATOM | 694 | C | GLU | 245 | 48.414 | 32.035 | 28.047 | 1.00 | 32.29 |
| ATOM | 695 | O | GLU | 245 | 49.558 | 32.319 | 28.399 | 1.00 | 35.92 |
| ATOM | 696 | N | ASP | 246 | 48.134 | 30.975 | 27.295 | 1.00 | 30.64 |
| ATOM | 697 | CA | ASP | 246 | 49.182 | 30.058 | 26.855 | 1.00 | 28.23 |
| ATOM | 698 | CB | ASP | 246 | 48.575 | 28.809 | 26.208 | 1.00 | 30.51 |
| ATOM | 699 | CG | ASP | 246 | 48.213 | 27.737 | 27.222 | 1.00 | 33.18 |
| ATOM | 700 | OD1 | ASP | 246 | 48.265 | 28.006 | 28.439 | 1.00 | 31.26 |
| ATOM | 701 | OD2 | ASP | 246 | 47.884 | 26.613 | 26.796 | 1.00 | 33.85 |
| ATOM | 702 | C | ASP | 246 | 50.104 | 30.757 | 25.860 | 1.00 | 30.10 |
| ATOM | 703 | O | ASP | 246 | 51.330 | 30.651 | 25.950 | 1.00 | 27.08 |
| ATOM | 704 | N | GLN | 247 | 49.500 | 31.477 | 24.918 | 1.00 | 30.39 |
| ATOM | 705 | CA | GLN | 247 | 50.249 | 32.208 | 23.901 | 1.00 | 29.08 |
| ATOM | 706 | CB | GLN | 247 | 49.295 | 32.949 | 22.964 | 1.00 | 27.34 |
| ATOM | 707 | CG | GLN | 247 | 48.390 | 32.034 | 22.147 | 1.00 | 28.95 |
| ATOM | 708 | CD | GLN | 247 | 47.531 | 32.796 | 21.153 | 1.00 | 30.74 |
| ATOM | 709 | OE1 | GLN | 247 | 47.850 | 33.918 | 20.767 | 1.00 | 33.23 |
| ATOM | 710 | NE2 | GLN | 247 | 46.439 | 32.185 | 20.729 | 1.00 | 35.19 |
| ATOM | 711 | C | GLN | 247 | 51.190 | 33.196 | 24.575 | 1.00 | 27.51 |
| ATOM | 712 | O | GLN | 247 | 52.377 | 33.261 | 24.256 | 1.00 | 28.70 |
| ATOM | 713 | N | ILE | 248 | 50.661 | 33.921 | 25.552 | 1.00 | 27.81 |
| ATOM | 714 | CA | ILE | 248 | 51.431 | 34.908 | 26.295 | 1.00 | 29.41 |
| ATOM | 715 | CB | ILE | 248 | 50.525 | 35.662 | 27.303 | 1.00 | 28.96 |
| ATOM | 716 | CG2 | ILE | 248 | 51.356 | 36.476 | 28.279 | 1.00 | 28.67 |
| ATOM | 717 | CG1 | ILE | 248 | 49.555 | 36.571 | 26.543 | 1.00 | 28.83 |
| ATOM | 718 | CD1 | ILE | 248 | 48.514 | 37.236 | 27.420 | 1.00 | 30.76 |
| ATOM | 719 | C | ILE | 248 | 52.618 | 34.259 | 27.006 | 1.00 | 28.39 |
| ATOM | 720 | O | ILE | 248 | 53.759 | 34.715 | 26.869 | 1.00 | 27.88 |
| ATOM | 721 | N | ILE | 249 | 52.356 | 33.177 | 27.732 | 1.00 | 26.07 |
| ATOM | 722 | CA | ILE | 249 | 53.413 | 32.474 | 28.454 | 1.00 | 27.37 |
| ATOM | 723 | CB | ILE | 249 | 52.839 | 31.294 | 29.281 | 1.00 | 30.32 |
| ATOM | 724 | CG2 | ILE | 249 | 53.958 | 30.425 | 29.840 | 1.00 | 31.29 |
| ATOM | 725 | CG1 | ILE | 249 | 51.987 | 31.831 | 30.429 | 1.00 | 30.31 |
| ATOM | 726 | CD1 | ILE | 249 | 51.295 | 30.753 | 31.230 | 1.00 | 31.30 |
| ATOM | 727 | C | ILE | 249 | 54.510 | 31.974 | 27.509 | 1.00 | 28.63 |
| ATOM | 728 | O | ILE | 249 | 55.701 | 32.100 | 27.808 | 1.00 | 29.59 |
| ATOM | 729 | N | LEU | 250 | 54.110 | 31.442 | 26.357 | 1.00 | 29.03 |
| ATOM | 730 | CA | LEU | 250 | 55.068 | 30.934 | 25.380 | 1.00 | 22.44 |
| ATOM | 731 | CB | LEU | 250 | 54.351 | 30.166 | 24.266 | 1.00 | 24.30 |
| ATOM | 732 | CG | LEU | 250 | 53.665 | 28.866 | 24.687 | 1.00 | 23.20 |
| ATOM | 733 | CD1 | LEU | 250 | 52.951 | 28.273 | 23.502 | 1.00 | 20.36 |

APPENDIX 3-continued

TR_DMT.PDB

| ATOM | 734 | CD2 | LEU | 250 | 54.685 | 27.880 | 25.238 | 1.00 | 19.45 |
|---|---|---|---|---|---|---|---|---|---|
| ATOM | 735 | C | LEU | 250 | 55.919 | 32.055 | 24.794 | 1.00 | 18.97 |
| ATOM | 736 | O | LEU | 250 | 57.133 | 31.903 | 24.648 | 1.00 | 18.37 |
| ATOM | 737 | N | LEU | 251 | 55.291 | 33.180 | 24.468 | 1.00 | 20.63 |
| ATOM | 738 | CA | LEU | 251 | 56.026 | 34.3.18 | 23.915 | 1.00 | 27.43 |
| ATOM | 739 | CB | LEU | 251 | 55.065 | 35.412 | 23.449 | 1.00 | 22.92 |
| ATOM | 740 | CG | LEU | 251 | 54.364 | 35.093 | 22.128 | 1.00 | 24.72 |
| ATOM | 741 | CD1 | LEU | 251 | 53.342 | 36.167 | 21.821 | 1.00 | 32.13 |
| ATOM | 742 | CD2 | LEU | 251 | 55.389 | 34.981 | 21.009 | 1.00 | 22.46 |
| ATOM | 743 | C | LEU | 251 | 57.026 | 34.875 | 24.930 | 1.00 | 27.23 |
| ATOM | 744 | O | LEU | 251 | 58.202 | 35.078 | 24.614 | 1.00 | 26.48 |
| ATOM | 745 | N | LYS | 252 | 56.561 | 35.094 | 26.156 | 1.00 | 27.34 |
| ATOM | 746 | CA | LYS | 252 | 57.425 | 35.598 | 27.215 | 1.00 | 28.95 |
| ATOM | 747 | CB | LYS | 252 | 56.649 | 35.715 | 28.527 | 1.00 | 32.89 |
| ATOM | 748 | CG | LYS | 252 | 55.570 | 36.783 | 28.530 | 1.00 | 35.06 |
| ATOM | 749 | CD | LYS | 252 | 55.084 | 37.028 | 29.943 | 1.00 | 42.82 |
| ATOM | 750 | CE | LYS | 252 | 54.124 | 38.191 | 30.003 | 1.00 | 53.05 |
| ATOM | 751 | NZ | LYS | 252 | 53.677 | 38.451 | 31.398 | 1.00 | 64.03 |
| ATOM | 752 | C | LYS | 252 | 58.605 | 34.647 | 27.405 | 1.00 | 27.66 |
| ATOM | 753 | O | LYS | 252 | 59.734 | 35.076 | 27.646 | 1.00 | 33.16 |
| ATOM | 754 | N | GLY | 253 | 58.344 | 33.357 | 27.243 | 1.00 | 24.50 |
| ATOM | 755 | CA | GLY | 253 | 59.386 | 32.364 | 27.402 | 1.00 | 22.33 |
| ATOM | 756 | C | GLY | 253 | 60.423 | 32.273 | 26.297 | 1.00 | 23.99 |
| ATOM | 757 | O | GLY | 253 | 61.589 | 32.016 | 26.581 | 1.00 | 30.77 |
| ATOM | 758 | N | CYS | 254 | 60.041 | 32.526 | 25.049 | 1.00 | 22.66 |
| ATOM | 759 | CA | CYS | 254 | 60.986 | 32.405 | 23.934 | 1.00 | 20.75 |
| ATOM | 760 | CB | CYS | 254 | 60.386 | 31.494 | 22.868 | 1.00 | 24.86 |
| ATOM | 761 | SG | CYS | 254 | 58.996 | 32.276 | 22.014 | 1.00 | 25.55 |
| ATOM | 762 | C | CYS | 254 | 61.399 | 33.702 | 23.242 | 1.00 | 23.79 |
| ATOM | 763 | O | CYS | 254 | 62.262 | 33.685 | 22.357 | 1.00 | 22.18 |
| ATOM | 764 | N | CYS | 255 | 60.788 | 34.814 | 23.625 | 1.00 | 19.49 |
| ATOM | 765 | CA | CYS | 255 | 61.084 | 36.085 | 22.981 | 1.00 | 21.08 |
| ATOM | 766 | CB | CYS | 255 | 60.336 | 37.220 | 23.669 | 1.00 | 18.21 |
| ATOM | 767 | SG | CYS | 255 | 60.264 | 38.713 | 22.677 | 1.00 | 22.96 |
| ATOM | 768 | C | CYS | 255 | 62.570 | 36.413 | 22.842 | 1.00 | 21.87 |
| ATOM | 769 | O | CYS | 255 | 63.050 | 36.641 | 21.729 | 1.00 | 22.23 |
| ATOM | 770 | N | MET | 256 | 63.310 | 36.397 | 23.947 | 1.00 | 20.82 |
| ATOM | 771 | CA | MET | 256 | 64.741 | 36.706 | 23.895 | 1.00 | 20.50 |
| ATOM | 772 | CB | MET | 256 | 65.322 | 36.801 | 25.312 | 1.00 | 22.50 |
| ATOM | 773 | CG | MET | 256 | 66.808 | 37.139 | 25.354 | 1.00 | 16.67 |
| ATOM | 774 | SD | MET | 256 | 67.205 | 38.732 | 24.605 | 1.00 | 24.46 |
| ATOM | 775 | CE | MET | 256 | 69.027 | 38.764 | 24.791 | 1.00 | 19.21 |
| ATOM | 776 | C | MET | 256 | 65.510 | 35.667 | 23.072 | 1.00 | 18.38 |
| ATOM | 777 | O | MET | 256 | 66.401 | 36.005 | 22.293 | 1.00 | 17.68 |
| ATOM | 778 | N | GLU | 257 | 65.149 | 34.404 | 23.248 | 1.00 | 20.33 |
| ATOM | 779 | CA | GLU | 257 | 65.779 | 33.308 | 22.526 | 1.00 | 21.08 |
| ATOM | 780 | CB | GLU | 257 | 65.148 | 31.982 | 22.943 | 1.00 | 22.28 |
| ATOM | 781 | CG | GLU | 257 | 65.374 | 31.640 | 24.411 | 1.00 | 34.68 |
| ATOM | 782 | CD | GLU | 257 | 64.515 | 30.486 | 24.907 | 1.00 | 43.20 |
| ATOM | 783 | OE1 | GLU | 257 | 63.823 | 29.836 | 24.091 | 1.00 | 42.14 |
| ATOM | 784 | OE2 | GLU | 257 | 64.530 | 30.230 | 26.128 | 1.00 | 50.15 |
| ATOM | 785 | C | GLU | 257 | 65.650 | 33.503 | 21.018 | 1.00 | 19.26 |
| ATOM | 786 | O | GLU | 257 | 66.632 | 33.360 | 20.276 | 1.00 | 18.09 |
| ATOM | 787 | N | ILE | 258 | 64.446 | 33.850 | 20.566 | 1.00 | 16.30 |
| ATOM | 788 | CA | ILE | 258 | 64.199 | 34.065 | 19.141 | 1.00 | 18.09 |
| ATOM | 789 | CB | ILE | 258 | 62.677 | 34.150 | 18.825 | 1.00 | 18.61 |
| ATOM | 790 | CG2 | ILE | 258 | 62.441 | 34.653 | 17.395 | 1.00 | 16.23 |
| ATOM | 791 | CG1 | ILE | 258 | 62.032 | 32.771 | 19.021 | 1.00 | 13.80 |
| ATOM | 792 | CD1 | ILE | 258 | 60.544 | 32.714 | 18.695 | 1.00 | 13.21 |
| ATOM | 793 | C | ILE | 258 | 64.948 | 35.297 | 18.638 | 1.00 | 20.12 |
| ATOM | 794 | O | ILE | 258 | 65.605 | 35.242 | 17.593 | 1.00 | 19.17 |
| ATOM | 795 | N | MET | 259 | 64.903 | 36.387 | 19.404 | 1.00 | 22.71 |
| ATOM | 796 | CA | MET | 259 | 65.602 | 37.611 | 19.015 | 1.00 | 17.09 |
| ATOM | 797 | CB | MET | 259 | 65.249 | 38.772 | 19.941 | 1.00 | 18.80 |
| ATOM | 798 | CG | MET | 259 | 63.782 | 39.159 | 19.894 | 1.00 | 17.66 |
| ATOM | 799 | SD | MET | 259 | 63.457 | 40.748 | 20.678 | 1.00 | 25.77 |
| ATOM | 800 | CE | MET | 259 | 63.774 | 40.377 | 22.374 | 1.00 | 16.65 |
| ATOM | 801 | C | MET | 259 | 67.111 | 37.397 | 18.973 | 1.00 | 19.51 |
| ATOM | 802 | O | MET | 259 | 67.797 | 37.913 | 18.080 | 1.00 | 25.53 |
| ATOM | 803 | N | SER | 260 | 67.625 | 36.605 | 19.908 | 1.00 | 19.58 |
| ATOM | 804 | CA | SER | 260 | 69.056 | 36.324 | 19.947 | 1.00 | 16.90 |
| ATOM | 805 | CB | SER | 260 | 69.434 | 35.631 | 21.251 | 1.00 | 15.56 |
| ATOM | 806 | OG | SER | 260 | 69.093 | 36.455 | 22.352 | 1.00 | 22.98 |
| ATOM | 807 | C | SER | 260 | 69.471 | 35.487 | 18.746 | 1.00 | 14.52 |
| ATOM | 808 | O | SER | 260 | 70.496 | 35.761 | 18.129 | 1.00 | 22.82 |
| ATOM | 809 | N | LEU | 261 | 68.663 | 34.490 | 18.397 | 1.00 | 16.50 |
| ATOM | 810 | CA | LEU | 261 | 68.948 | 33.642 | 17.241 | 1.00 | 17.78 |

APPENDIX 3-continued

TR_DMT.PDB

| ATOM | 811 | CB | LEU | 261 | 67.878 | 32.552 | 17.092 | 1.00 | 18.38 |
|---|---|---|---|---|---|---|---|---|---|
| ATOM | 812 | CG | LEU | 261 | 67.890 | 31.708 | 15.812 | 1.00 | 14.47 |
| ATOM | 813 | CD1 | LEU | 261 | 69.159 | 30.877 | 15.728 | 1.00 | 16.76 |
| ATOM | 814 | CD2 | LEU | 261 | 66.672 | 30.806 | 15.793 | 1.00 | 14.06 |
| ATOM | 815 | C | LEU | 261 | 68.959 | 34.519 | 15.992 | 1.00 | 20.40 |
| ATOM | 816 | O | LEU | 261 | 69.885 | 34.450 | 15.181 | 1.00 | 22.00 |
| ATOM | 817 | N | ARG | 262 | 67.934 | 35.356 | 15.854 | 1.00 | 21.02 |
| ATOM | 818 | CA | ARG | 262 | 67.821 | 36.249 | 14.705 | 1.00 | 22.84 |
| ATOM | 819 | CB | ARG | 262 | 66.530 | 37.067 | 14.782 | 1.00 | 20.29 |
| ATOM | 820 | CG | ARG | 262 | 65.311 | 36.267 | 14.364 | 1.00 | 23.33 |
| ATOM | 821 | CD | ARG | 262 | 64.007 | 37.026 | 14.509 | 1.00 | 19.05 |
| ATOM | 822 | NE | ARG | 262 | 62.959 | 36.321 | 13.775 | 1.00 | 21.32 |
| ATOM | 823 | CZ | ARG | 262 | 61.780 | 36.837 | 13.441 | 1.00 | 23.44 |
| ATOM | 824 | NH1 | ARG | 262 | 61.465 | 38.081 | 13.780 | 1.00 | 22.99 |
| ATOM | 825 | NH2 | ARG | 262 | 60.933 | 36.116 | 12.713 | 1.00 | 22.09 |
| ATOM | 826 | C | ARG | 262 | 69.035 | 37.154 | 14.561 | 1.00 | 22.66 |
| ATOM | 827 | O | ARG | 262 | 69.434 | 37.483 | 13.445 | 1.00 | 22.41 |
| ATOM | 828 | N | ALA | 263 | 69.625 | 37.545 | 15.689 | 1.00 | 23.52 |
| ATOM | 829 | CA | ALA | 263 | 70.820 | 38.386 | 15.677 | 1.00 | 22.37 |
| ATOM | 830 | CB | ALA | 263 | 70.986 | 39.089 | 17.018 | 1.00 | 22.76 |
| ATOM | 831 | C | ALA | 263 | 72.052 | 37.530 | 15.366 | 1.00 | 22.85 |
| ATOM | 832 | O | ALA | 263 | 72.882 | 37.897 | 14.529 | 1.00 | 25.50 |
| ATOM | 833 | N | ALA | 264 | 72.131 | 36.365 | 16.005 | 1.00 | 21.68 |
| ATOM | 834 | CA | ALA | 264 | 73.242 | 35.438 | 15.826 | 1.00 | 20.26 |
| ATOM | 835 | CB | ALA | 264 | 73.092 | 34.256 | 16.763 | 1.00 | 15.97 |
| ATOM | 836 | C | ALA | 264 | 73.401 | 34.957 | 14.382 | 1.00 | 23.11 |
| ATOM | 837 | O | ALA | 264 | 74.523 | 34.831 | 13.892 | 1.00 | 24.87 |
| ATOM | 838 | N | VAL | 265 | 72.293 | 34.679 | 13.697 | 1.00 | 22.94 |
| ATOM | 839 | CA | VAL | 265 | 72.380 | 34.226 | 12.306 | 1.00 | 28.98 |
| ATOM | 840 | CB | VAL | 265 | 71.072 | 33.547 | 11.797 | 1.00 | 25.97 |
| ATOM | 841 | CG1 | VAL | 265 | 70.751 | 32.330 | 12.638 | 1.00 | 26.27 |
| ATOM | 842 | CG2 | VAL | 265 | 69.907 | 34.527 | 11.797 | 1.00 | 26.64 |
| ATOM | 843 | C | VAL | 265 | 72.761 | 35.373 | 11.369 | 1.00 | 28.81 |
| ATOM | 844 | O | VAL | 265 | 72.966 | 35.160 | 10.176 | 1.00 | 31.92 |
| ATOM | 845 | N | ARG | 266 | 72.830 | 36.587 | 11.915 | 1.00 | 31.83 |
| ATOM | 846 | CA | ARG | 266 | 73.210 | 37.774 | 11.150 | 1.00 | 33.19 |
| ATOM | 847 | CB | ARG | 266 | 72.141 | 38.861 | 11.258 | 1.00 | 31.67 |
| ATOM | 848 | CG | ARG | 266 | 70.986 | 38.623 | 10.320 | 1.00 | 26.82 |
| ATOM | 849 | CD | ARG | 266 | 69.913 | 39.668 | 10.454 | 1.00 | 33.95 |
| ATOM | 850 | NE | ARG | 266 | 68.955 | 39.532 | 9.361 | 1.00 | 38.15 |
| ATOM | 851 | CZ | ARG | 26.6 | 67.688 | 39.927 | 9.410 | 1.00 | 37.39 |
| ATOM | 852 | NH1 | ARG | 266 | 67.198 | 40.491 | 10.509 | 1.00 | 29.92 |
| ATOM | 853 | NH2 | ARG | 266 | 66.918 | 39.770 | 8.340 | 1.00 | 31.24 |
| ATOM | 854 | C | ARG | 266 | 74.565 | 38.307 | 11.604 | 1.00 | 36.31 |
| ATOM | 855 | O | ARG | 266 | 74.821 | 39.516 | 11.575 | 1.00 | 38.56 |
| ATOM | 856 | N | TYR | 267 | 75.416 | 37.393 | 12.056 | 1.00 | 34.21 |
| ATOM | 857 | CA | TYR | 267 | 76.755 | 37.733 | 12.502 | 1.00 | 35.24 |
| ATOM | 858 | CB | TYR | 267 | 77.283 | 36.640 | 13.440 | 1.00 | 32.37 |
| ATOM | 859 | CG | TYR | 267 | 78.774 | 36.699 | 13.703 | 1.00 | 35.07 |
| ATOM | 860 | CD1 | TYR | 267 | 79.303 | 37.555 | 14.669 | 1.00 | 33.94 |
| ATOM | 861 | CE1 | TYR | 267 | 80.677 | 37.609 | 14.905 | 1.00 | 36.60 |
| ATOM | 862 | CD2 | TYR | 267 | 79.658 | 35.894 | 12.979 | 1.00 | 34.68 |
| ATOM | 863 | CE2 | TYR | 267 | 81.029 | 35.940 | 13.208 | 1.00 | 36.07 |
| ATOM | 864 | CZ | TYR | 267 | 81.533 | 36.797 | 14.170 | 1.00 | 37.14 |
| ATOM | 865 | OH | TYR | 267 | 82.889 | 36.835 | 14.396 | 1.00 | 41.52 |
| ATOM | 866 | C | TYR | 267 | 77.639 | 37.831 | 11.263 | 1.00 | 37.68 |
| ATOM | 867 | O | TYR | 267 | 77.609 | 36.943 | 10.410 | 1.00 | 36.48 |
| ATOM | 868 | N | ASP | 268 | 78.400 | 38.915 | 11.150 | 1.00 | 39.58 |
| ATOM | 869 | CA | ASP | 268 | 79.301 | 39.096 | 10.016 | 1.00 | 42.77 |
| ATOM | 870 | CB | ASP | 268 | 79.170 | 40.511 | 9.434 | 1.00 | 44.38 |
| ATOM | 871 | CG | ASP | 268 | 80.145 | 40.770 | 8.290 | 1.00 | 50.31 |
| ATOM | 872 | OD1 | ASP | 268 | 80.290 | 39.901 | 7.400 | 1.00 | 55.79 |
| ATOM | 873 | OD2 | ASP | 268 | 80.773 | 41.847 | 8.280 | 1.00 | 50.24 |
| ATOM | 874 | C | ASP | 268 | 80.737 | 38.846 | 10.466 | 1.00 | 42.51 |
| ATOM | 875 | O | ASP | 268 | 81.305 | 39.645 | 11.208 | 1.00 | 42.7S |
| ATOM | 876 | N | PRO | 269 | 81.346 | 37.733 | 10.020 | 1.00 | 44.56 |
| ATOM | 877 | CD | PRO | 269 | 80.770 | 36.697 | 9.146 | 1.00 | 42.66 |
| ATOM | 878 | CA | PRO | 269 | 82.725 | 37.395 | 10.393 | 1.00 | 45.98 |
| ATOM | 879 | CB | PRO | 269 | 82.991 | 36.111 | 9.607 | 1.00 | 44.04 |
| ATOM | 880 | CG | PRO | 269 | 81.631 | 35.506 | 9.4S8 | 1.00 | 43.33 |
| ATOM | 881 | C | PRO | 269 | 83.710 | 38.492 | 10.004 | 1.00 | 50.31 |
| ATOM | 882 | O | PRO | 269 | 84.630 | 38.800 | 10.761 | 1.00 | 49.83 |
| ATOM | 883 | N | ALA | 270 | 83.486 | 39.100 | 8.840 | 1.00 | 53.62 |
| ATOM | 884 | CA | ALA | 270 | 84.348 | 40.165 | 8.329 | 1.00 | 54.54 |
| ATOM | 885 | CB | ALA | 270 | 83.892 | 40.585 | 6.929 | 1.00 | 51.24 |
| ATOM | 886 | C | ALA | 270 | 84.449 | 41.389 | 9.248 | 1.00 | 55.69 |
| ATOM | 887 | O | ALA | 270 | 85.488 | 42.045 | 9.294 | 1.00 | 57.92 |

APPENDIX 3-continued

TR_DMT.PDB

| ATOM | 888 | N | SER | 271 | 83.384 | 41.685 | 9.989 | 1.00 | 54.71 |
|---|---|---|---|---|---|---|---|---|---|
| ATOM | 889 | CA | SER | 271 | 83.378 | 42.838 | 10.889 | 1.00 | 51.26 |
| ATOM | 890 | CB | SER | 271 | 82.182 | 43.740 | 10.575 | 1.00 | 49.92 |
| ATOM | 891 | OG | SER | 271 | 82.065 | 43.976 | 9.183 | 1.00 | 60.09 |
| ATOM | 892 | C | SER | 271 | 83.305 | 42.443 | 12.360 | 1.00 | 50.78 |
| ATOM | 893 | O | SER | 271 | 83.482 | 43.288 | 13.240 | 1.00 | 52.11 |
| ATOM | 894 | N | ASP | 272 | 83.051 | 41.162 | 12.619 | 1.00 | 48.96 |
| ATOM | 895 | CA | ASP | 272 | 82.898 | 40.643 | 13.978 | 1.00 | 45.53 |
| ATOM | 896 | CB | ASP | 272 | 84.206 | 40.765 | 14.776 | 1.00 | 44.82 |
| ATOM | 897 | CG | ASP | 272 | 84.142 | 40.064 | 16.131 | 1.00 | 47.66 |
| ATOM | 898 | OD1 | ASP | 272 | 84.750 | 40.581 | 17.091 | 1.00 | 48.64 |
| ATOM | 899 | OD2 | ASP | 272 | 83.495 | 38.999 | 16.238 | 1.00 | 43.85 |
| ATOM | 900 | C | ASP | 272 | 81.765 | 41.437 | 14.636 | 1.00 | 44.46 |
| ATOM | 901 | O | ASP | 272 | 81.904 | 41.958 | 15.747 | 1.00 | 42.41 |
| ATOM | 902 | N | THR | 273 | 80.652 | 41.551 | 13.915 | 1.00 | 39.79 |
| ATOM | 903 | CA | THR | 273 | 79.492 | 42.282 | 14.401 | 1.00 | 38.82 |
| ATOM | 904 | CB | THR | 273 | 79.334 | 43.648 | 13.670 | 1.00 | 39.73 |
| ATOM | 905 | OG1 | THR | 273 | 79.288 | 43.439 | 12.254 | 1.00 | 39.36 |
| ATOM | 906 | CG2 | THR | 273 | 80.496 | 44.578 | 13.991 | 1.00 | 41.31 |
| ATOM | 907 | C | THR | 273 | 78.203 | 41.485 | 14.211 | 1.00 | 38.36 |
| ATOM | 908 | O | THR | 273 | 78.151 | 40.546 | 13.408 | 1.00 | 33.79 |
| ATOM | 909 | N | LEU | 274 | 77.187 | 41.835 | 14.995 | 1.00 | 36.91 |
| ATOM | 910 | CA | LEU | 274 | 75.869 | 41.212 | 14.912 | 1.00 | 34.49 |
| ATOM | 911 | CB | LEU | 274 | 75.342 | 40.822 | 16.297 | 1.00 | 30.37 |
| ATOM | 912 | CG | LEU | 274 | 75.948 | 39.651 | 17.069 | 1.00 | 32.97 |
| ATOM | 913 | CD1 | LEU | 274 | 75.297 | 39.593 | 18.440 | 1.00 | 28.23 |
| ATOM | 914 | CD2 | LEU | 274 | 75.749 | 38.341 | 16.318 | 1.00 | 26.86 |
| ATOM | 915 | C | LEU | 274 | 74.956 | 42.289 | 14.352 | 1.00 | 35.35 |
| ATOM | 916 | O | LEU | 274 | 75.171 | 43.478 | 14.601 | 1.00 | 37.47 |
| ATOM | 917 | N | THR | 275 | 73.942 | 41.890 | 13.599 | 1.00 | 34.05 |
| ATOM | 918 | CA | THR | 275 | 73.020 | 42.868 | 13.052 | 1.00 | 32.62 |
| ATOM | 919 | CB | THR | 275 | 72.824 | 42.674 | 11.542 | 1.00 | 35.14 |
| ATOM | 920 | OG1 | THR | 275 | 74.108 | 42.590 | 10.909 | 1.00 | 39.50 |
| ATOM | 921 | CG2 | THR | 275 | 72.064 | 43.851 | 10.952 | 1.00 | 30.94 |
| ATOM | 922 | C | THR | 275 | 71.699 | 42.746 | 13.793 | 1.00 | 30.92 |
| ATOM | 923 | O | THR | 275 | 71.100 | 41.670 | 13.845 | 1.00 | 36.53 |
| ATOM | 924 | N | LEU | 276 | 71.291 | 43.835 | 14.434 | 1.00 | 28.10 |
| ATOM | 925 | CA | LEU | 276 | 70.051 | 43.868 | 15.192 | 1.00 | 27.78 |
| ATOM | 926 | CB | LEU | 276 | 70.205 | 44.780 | 16.420 | 1.00 | 22.51 |
| ATOM | 927 | CG | LEU | 276 | 71.383 | 44.532 | 17.373 | 1.00 | 25.89 |
| ATOM | 928 | CD1 | LEU | 276 | 71.225 | 45.408 | 18.608 | 1.00 | 20.70 |
| ATOM | 929 | CD2 | LEU | 276 | 71.456 | 43.069 | 17.782 | 1.00 | 20.79 |
| ATOM | 930 | C | LEU | 276 | 68.930 | 44.376 | 14.296 | 1.00 | 27.27 |
| ATOM | 931 | O | LEU | 276 | 69.068 | 45.430 | 13.672 | 1.00 | 29.06 |
| ATOM | 932 | N | SER | 277 | 67.854 | 43.598 | 14.187 | 1.00 | 25.97 |
| ATOM | 933 | CA | SER | 277 | 66.697 | 43.957 | 13.366 | 1.00 | 28.63 |
| ATOM | 934 | CB | SER | 277 | 65.990 | 45.177 | 13.967 | 1.00 | 27.78 |
| ATOM | 935 | OG | SER | 277 | 65.561 | 44.905 | 15.290 | 1.00 | 22.65 |
| ATOM | 936 | C | SER | 277 | 67.067 | 44.209 | 11.897 | 1.00 | 30.31 |
| ATOM | 937 | O | SER | 277 | 66.374 | 44.939 | 11.181 | 1.00 | 28.52 |
| ATOM | 938 | N | GLY | 278 | 68.168 | 43.597 | 11.465 | 1.00 | 31.24 |
| ATOM | 939 | CA | GLY | 278 | 68.638 | 43.754 | 10.101 | 1.00 | 39.59 |
| ATOM | 940 | C | GLY | 278 | 68.999 | 45.178 | 9.706 | 1.00 | 44.55 |
| ATOM | 941 | O | GLY | 278 | 69.104 | 45.479 | 8.517 | 1.00 | 46.66 |
| ATOM | 942 | N | GLU | 279 | 69.234 | 46.046 | 10.686 | 1.00 | 43.47 |
| ATOM | 943 | CA | GLU | 279 | 69.566 | 47.435 | 10.387 | 1.00 | 43.87 |
| ATOM | 944 | CB | GLU | 279 | 68.314 | 48.312 | 10.515 | 1.00 | 44.28 |
| ATOM | 945 | CG | GLU | 279 | 67.703 | 48.322 | 11.908 | 1.00 | 52.30 |
| ATOM | 946 | CD | GLU | 279 | 66.440 | 49.159 | 12.001 | 1.00 | 60.23 |
| ATOM | 947 | OE1 | GLU | 279 | 66.398 | 50.074 | 12.853 | 1.00 | 63.06 |
| ATOM | 948 | OE2 | GLU | 279 | 65.485 | 48.894 | 11.238 | 1.00 | 65.67 |
| ATOM | 949 | C | GLU | 279 | 70.700 | 48.038 | 11.216 | 1.00 | 42.40 |
| ATOM | 950 | O | GLU | 279 | 71.330 | 49.001 | 10.787 | 1.00 | 43.89 |
| ATOM | 951 | N | MET | 280 | 70.977 | 47.472 | 12.388 | 1.00 | 40.86 |
| ATOM | 952 | CA | MET | 280 | 72.027 | 48.009 | 13.248 | 1.00 | 32.80 |
| ATOM | 953 | CB | MET | 280 | 71.435 | 48.415 | 14.603 | 1.00 | 29.25 |
| ATOM | 954 | CG | MET | 280 | 72.384 | 49.193 | 15.506 | 1.00 | 31.64 |
| ATOM | 955 | SD | MET | 280 | 71.830 | 49.235 | 17.232 | 1.00 | 34.02 |
| ATOM | 956 | CE | MET | 280 | 70.566 | 50.495 | 17.197 | 1.00 | 26.56 |
| ATOM | 957 | C | MET | 280 | 73.172 | 47.033 | 13.465 | 1.00 | 32.77 |
| ATOM | 958 | O | MET | 280 | 72.983 | 45.971 | 14.058 | 1.D0 | 34.61 |
| ATOM | 959 | N | ALA | 281 | 74.351 | 47.375 | 12.959 | 1.00 | 31.87 |
| ATOM | 960 | CA | ALA | 281 | 75.523 | 46.526 | 13.147 | 1.00 | 34.71 |
| ATOM | 961 | CB | ALA | 281 | 76.519 | 46.727 | 12.023 | 1.00 | 34.42 |
| ATOM | 962 | C | ALA | 281 | 76.125 | 46.950 | 14.482 | 1.00 | 36.76 |
| ATOM | 963 | O | ALA | 281 | 76.416 | 48.129 | 14.693 | 1.00 | 34.59 |
| ATOM | 964 | N | VAL | 282 | 76.275 | 45.993 | 15.390 | 1.00 | 37.16 |

APPENDIX 3-continued

TR_DMT.PDB

| ATOM | 965 | CA | VAL | 282 | 76.798 | 46.263 | 16.721 | 1.00 | 37.83 |
|---|---|---|---|---|---|---|---|---|---|
| ATOM | 966 | CB | VAL | 282 | 75.692 | 46.023 | 17.780 | 1.00 | 37.58 |
| ATOM | 967 | CG1 | VAL | 282 | 76.219 | 46.271 | 19.175 | 1.00 | 48.99 |
| ATOM | 968 | CG2 | VAL | 282 | 74.514 | 46.939 | 17.514 | 1.00 | 43.59 |
| ATOM | 969 | C | VAL | 282 | 78.017 | 45.400 | 17.046 | 1.00 | 39.04 |
| ATOM | 970 | O | VAL | 282 | 78.081 | 44.230 | 16.660 | 1.00 | 39.16 |
| ATOM | 971 | N | LYS | 283 | 78.989 | 45.993 | 17.735 | 1.00 | 38.75 |
| ATOM | 972 | CA | LYS | 283 | 80.205 | 45.287 | 18.136 | 1.00 | 42.18 |
| ATOM | 973 | CB | LYS | 283 | 81.428 | 46.208 | 18.045 | 1.00 | 47.46 |
| ATOM | 974 | CG | LYS | 283 | 81.803 | 46.617 | 16.632 | 1.00 | 51.71 |
| ATOM | 975 | CD | LYS | 283 | 83.092 | 47.416 | 16.618 | 1.00 | 59.26 |
| ATOM | 976 | CE | LYS | 283 | 83.481 | 47.813 | 15.202 | 1.00 | 62.52 |
| ATOM | 977 | NZ | LYS | 283 | 82.492 | 48.742 | 14.588 | 1.00 | 66.27 |
| ATOM | 978 | C | LYS | 283 | 80.075 | 44.746 | 19.559 | 1.00 | 38.78 |
| ATOM | 979 | O | LYS | 283 | 79.283 | 45.257 | 20.356 | 1.00 | 40.63 |
| ATOM | 980 | N | ARG | 284 | 80.900 | 43.753 | 19.881 | 1.00 | 36.01 |
| ATOM | 981 | CA | ARG | 284 | 80.908 | 43.104 | 21.189 | 1.00 | 38.62 |
| ATOM | 982 | CB | ARG | 284 | 82.150 | 42.224 | 21.327 | 1.00 | 38.83 |
| ATOM | 983 | CG | ARG | 284 | 82.220 | 41.091 | 20.333 | 1.00 | 41.87 |
| ATOM | 984 | CD | ARG | 284 | 83.521 | 40.335 | 20.451 | 1.00 | 39.60 |
| ATOM | 985 | NE | ARG | 284 | 83.506 | 39.120 | 19.644 | 1.00 | 45.18 |
| ATOM | 986 | CZ | ARG | 284 | 83.259 | 37.905 | 20.128 | 1.00 | 44.79 |
| ATOM | 987 | NH1 | ARG | 284 | 83.005 | 37.739 | 21.421 | 1.00 | 41.84 |
| ATOM | 988 | NH2 | ARG | 284 | 83.271 | 36.852 | 19.319 | 1.00 | 42.27 |
| ATOM | 989 | C | ARG | 284 | 80.829 | 44.051 | 22.385 | 1.00 | 41.18 |
| ATOM | 990 | O | ARG | 284 | 79.995 | 43.867 | 23.274 | 1.00 | 44.38 |
| ATOM | 991 | N | GLU | 285 | 81.703 | 45.052 | 22.416 | 1.00 | 38.71 |
| ATOM | 992 | CA | GLU | 285 | 81.724 | 46.002 | 23.525 | 1.00 | 37.18 |
| ATOM | 993 | CB | GLU | 285 | 82.950 | 46.906 | 23.422 | 1.00 | 36.65 |
| ATOM | 994 | C | GLU | 285 | 80.444 | 46.838 | 23.614 | 1.00 | 35.71 |
| ATOM | 995 | O | GLU | 285 | 79.921 | 47.074 | 24.704 | 1.00 | 33.00 |
| ATOM | 996 | N | GLN | 286 | 79.920 | 47.245 | 22.463 | 1.00 | 32.01 |
| ATOM | 997 | CA | GLN | 286 | 78.714 | 48.061 | 22.425 | 1.00 | 32.31 |
| ATOM | 998 | CB | GLN | 286 | 78.440 | 48.525 | 20.997 | 1.00 | 38.24 |
| ATOM | 999 | CG | GLN | 286 | 79.565 | 49.352 | 20.392 | 1.00 | 42.42 |
| ATOM | 1000 | CD | GLN | 286 | 79.277 | 49.761 | 18.964 | 1.00 | 44.79 |
| ATOM | 1001 | OE1 | GLN | 286 | 79.103 | 48.910 | 18.089 | 1.00 | 42.21 |
| ATOM | 1002 | NE2 | GLN | 286 | 79.215 | 51.063 | 18.719 | 1.00 | 47.53 |
| ATOM | 1003 | C | GLN | 286 | 77.484 | 47.355 | 23.002 | 1.00 | 33.08 |
| ATOM | 1004 | O | GLN | 286 | 76.770 | 47.929 | 23.827 | 1.00 | 30.95 |
| ATOM | 1005 | N | LEU | 287 | 77.245 | 46.114 | 22.579 | 1.00 | 31.49 |
| ATOM | 1006 | CA | LEU | 287 | 76.095 | 45.350 | 23.068 | 1.00 | 31.01 |
| ATOM | 1007 | CB | LEU | 287 | 75.892 | 44.073 | 22.242 | 1.00 | 24.63 |
| ATOM | 1008 | CG | LEU | 287 | 74.498 | 43.780 | 21.661 | 1.00 | 27.34 |
| ATOM | 1009 | CD1 | LEU | 287 | 74.382 | 42.282 | 21.359 | 1.00 | 20.50 |
| ATOM | 1010 | CD2 | LEU | 287 | 73.393 | 44.205 | 22.616 | 1.00 | 14.41 |
| ATOM | 1011 | C | LEU | 287 | 76.298 | 44.986 | 24.538 | 1.00 | 32.80 |
| ATOM | 1012 | O | LEU | 287 | 75.351 | 45.014 | 25.334 | 1.00 | 32.10 |
| ATOM | 1013 | N | LYS | 288 | 77.536 | 44.641 | 24.885 | 1.00 | 32.54 |
| ATOM | 1014 | CA | LYS | 288 | 77.897 | 44.280 | 26.251 | 1.00 | 30.70 |
| ATOM | 1015 | CB | LYS | 288 | 79.376 | 43.893 | 26.315 | 1.00 | 31.24 |
| ATOM | 1016 | CG | LYS | 288 | 79.834 | 43.382 | 27.662 | 1.00 | 34.69 |
| ATOM | 1017 | CD | LYS | 288 | 81.227 | 42.784 | 27.574 | 1.00 | 37.69 |
| ATOM | 1018 | CE | LYS | 288 | 81.638 | 42.177 | 28.904 | 1.00 | 42.86 |
| ATOM | 1019 | NZ | LYS | 288 | 82.883 | 41.369 | 28.786 | 1.00 | 49.63 |
| ATOM | 1020 | C | LYS | 288 | 77.611 | 45.448 | 27.189 | 1.00 | 28.74 |
| ATOM | 1021 | O | LYS | 288 | 76.827 | 45.319 | 28.129 | 1.00 | 34.45 |
| ATOM | 1022 | N | ASN | 289 | 78.190 | 46.602 | 26.882 | 1.00 | 26.57 |
| ATOM | 1023 | CA | ASN | 289 | 78.011 | 47.803 | 27.691 | 1.00 | 30.84 |
| ATOM | 1024 | CB | ASN | 289 | 79.012 | 48.819 | 27.274 | 1.00 | 26.04 |
| ATOM | 1025 | CG | ASN | 289 | 80.437 | 48.485 | 27.570 | 1.00 | 35.16 |
| ATOM | 1026 | OD1 | ASN | 289 | 80.700 | 47.718 | 28.499 | 1.00 | 42.54 |
| ATOM | 1027 | ND2 | ASN | 289 | 81.371 | 48.998 | 26.784 | 1.00 | 32.82 |
| ATOM | 1028 | C | ASN | 289 | 76.602 | 48.371 | 27.620 | 1.00 | 35.05 |
| ATOM | 1029 | O | ASN | 289 | 76.154 | 49.039 | 28.550 | 1.00 | 36.94 |
| ATOM | 1030 | N | GLY | 290 | 75.909 | 48.113 | 26.515 | 1.00 | 32.43 |
| ATOM | 1031 | CA | GLY | 290 | 74.556 | 48.614 | 26.345 | 1.00 | 28.66 |
| ATOM | 1032 | C | GLY | 290 | 73.525 | 48.024 | 27.289 | 1.00 | 28.48 |
| ATOM | 1033 | O | GLY | 290 | 72.377 | 48.467 | 27.308 | 1.00 | 28.17 |
| ATOM | 1034 | N | GLY | 291 | 73.908 | 47.002 | 28.047 | 1.00 | 28.66 |
| ATOM | 1035 | CA | GLY | 291 | 72.969 | 46.408 | 28.980 | 1.00 | 29.19 |
| ATOM | 1036 | C | GLY | 291 | 72.976 | 44.894 | 29.075 | 1.00 | 29.76 |
| ATOM | 1037 | O | GLY | 291 | 72.595 | 44.340 | 30.105 | 1.00 | 34.44 |
| ATOM | 1038 | N | LEU | 292 | 73.399 | 44.213 | 28.017 | 1.00 | 29.69 |
| ATOM | 1039 | CA | LEU | 292 | 73.410 | 42.755 | 28.036 | 1.00 | 30.64 |
| ATOM | 1040 | CB | LEU | 292 | 73.421 | 42.194 | 26.611 | 1.00 | 27.07 |
| ATOM | 1041 | CG | LEU | 292 | 72.113 | 42.348 | 25.833 | 1.00 | 23.27 |

APPENDIX 3-continued

TR_DMT.PDB

| ATOM | 1042 | CD1 | LEU | 292 | 72.202 | 41.580 | 24.532 | 1.00 | 22.24 |
|------|------|-----|-----|-----|--------|--------|--------|------|-------|
| ATOM | 1043 | CD2 | LEU | 292 | 70.950 | 41.827 | 26.661 | 1.00 | 23.80 |
| ATOM | 1044 | C | LEU | 292 | 74.530 | 42.125 | 28.861 | 1.00 | 29.22 |
| ATOM | 1045 | O | LEU | 292 | 74.365 | 41.033 | 29.404 | 1.00 | 31.02 |
| ATOM | 1046 | N | GLY | 293 | 75.671 | 42.800 | 28.945 | 1.00 | 30.26 |
| ATOM | 1047 | CA | GLY | 293 | 76.788 | 42.259 | 29.700 | 1.00 | 28.37 |
| ATOM | 1048 | C | GLY | 293 | 77.307 | 40.995 | 29.040 | 1.00 | 29.85 |
| ATOM | 1049 | O | GLY | 293 | 77.460 | 40.951 | 27.820 | 1.00 | 32.37 |
| ATOM | 1050 | N | VAL | 294 | 77.537 | 39.953 | 29.832 | 1.00 | 30.08 |
| ATOM | 1051 | CA | VAL | 294 | 78.041 | 38.687 | 29.308 | 1.00 | 31.62 |
| ATOM | 1052 | CB | VAL | 294 | 78.466 | 37.716 | 30.442 | 1.00 | 29.11 |
| ATOM | 1053 | CG1 | VAL | 294 | 79.649 | 38.292 | 31.191 | 1.00 | 31.37 |
| ATOM | 1054 | CG2 | VAL | 294 | 77.304 | 37.443 | 31.396 | 1.00 | 26.69 |
| ATOM | 1055 | C | VAL | 294 | 77.079 | 37.978 | 28.351 | 1.00 | 32.81 |
| ATOM | 1056 | O | VAL | 294 | 77.496 | 37.095 | 27.591 | 1.00 | 33.00 |
| ATOM | 1057 | N | VAL | 295 | 75.801 | 38.356 | 28.380 | 1.00 | 30.45 |
| ATOM | 1058 | CA | VAL | 295 | 74.814 | 37.752 | 27.487 | 1.00 | 28.02 |
| ATOM | 1059 | CB | VAL | 295 | 73.378 | 38.232 | 27.793 | 1.00 | 29.96 |
| ATOM | 1060 | CG1 | VAL | 295 | 72.380 | 37.575 | 26.838 | 1.00 | 22.55 |
| ATOM | 1061 | CG2 | VAL | 295 | 73.016 | 37.903 | 29.232 | 1.00 | 20.10 |
| ATOM | 1062 | C | VAL | 295 | 75.203 | 38.115 | 26.057 | 1.00 | 29.90 |
| ATOM | 1063 | O | VAL | 295 | 75.047 | 37.312 | 25.140 | 1.00 | 34.47 |
| ATOM | 1064 | N | SER | 296 | 75.762 | 39.309 | 25.886 | 1.00 | 29.11 |
| ATOM | 1065 | CA | SER | 296 | 76.215 | 39.771 | 24.581 | 1.00 | 30.96 |
| ATOM | 1066 | CB | SER | 296 | 76.785 | 41.184 | 24.702 | 1.00 | 27.26 |
| ATOM | 1067 | OG | SER | 296 | 77.300 | 41.648 | 23.469 | 1.00 | 22.93 |
| ATOM | 1068 | C | SER | 296 | 77.294 | 38.811 | 24.080 | 1.00 | 36.41 |
| ATOM | 1069 | O | SER | 296 | 77.238 | 38.341 | 22.939 | 1.00 | 38.84 |
| ATOM | 1070 | N | ASP | 297 | 78.254 | 38.501 | 24.954 | 1.00 | 35.29 |
| ATOM | 1071 | CA | ASP | 297 | 79.346 | 37.585 | 24.629 | 1.00 | 32.14 |
| ATOM | 1072 | CB | ASP | 297 | 80.245 | 37.356 | 25.851 | 1.00 | 36.57 |
| ATOM | 1073 | CG | ASP | 297 | 80.958 | 38.616 | 26.307 | 1.00 | 41.75 |
| ATOM | 1074 | OD1 | ASP | 29T | 81.492 | 39.352 | 25.447 | 1.00 | 45.45 |
| ATOM | 1075 | OD2 | ASP | 297 | 80.999 | 38.861 | 27.532 | 1.00 | 45.15 |
| ATOM | 1076 | C | ASP | 297 | 78.768 | 36.249 | 24.191 | 1.00 | 29.61 |
| ATOM | 1077 | O | ASP | 297 | 79.242 | 35.644 | 23.231 | 1.00 | 32.90 |
| ATOM | 1078 | N | ALA | 298 | 77.738 | 35.804 | 24.903 | 1.00 | 27.85 |
| ATOM | 1079 | CA | ALA | 298 | 77.071 | 34.544 | 24.608 | 1.00 | 27.89 |
| ATOM | 1080 | CB | ALA | 298 | 75.998 | 34.258 | 25.657 | 1.00 | 21.67 |
| ATOM | 1081 | C | ALA | 298 | 76.462 | 34.539 | 23.202 | 1.00 | 28.26 |
| ATOM | 1082 | O | ALA | 298 | 76.648 | 33.579 | 22.446 | 1.00 | 30.19 |
| ATOM | 1083 | N | ILE | 299 | 75.744 | 35.606 | 22.853 | 1.00 | 25.20 |
| ATOM | 1084 | CA | ILE | 299 | 75.119 | 35.708 | 21.537 | 1.00 | 23.46 |
| ATOM | 1085 | CB | ILE | 299 | 74.200 | 36.944 | 21.427 | 1.00 | 21.63 |
| ATOM | 1086 | C | 2ILE | 299 | 73.491 | 36.946 | 20.078 | 1.00 | 22.20 |
| ATOM | 1087 | CG1 | ILE | 299 | 73.145 | 36.914 | 22.536 | 1.00 | 19.79 |
| ATOM | 1088 | CD1 | ILE | 299 | 72.245 | 38.139 | 22.578 | 1.00 | 18.33 |
| ATOM | 1089 | C | ILE | 299 | 76.181 | 35.752 | 20.444 | 1.00 | 26.28 |
| ATOM | 1090 | O | ILE | 299 | 76.043 | 35.095 | 19.414 | 1.00 | 31.72 |
| ATOM | 1091 | N | PHE | 300 | 77.247 | 36.512 | 20.675 | 1.00 | 29.35 |
| ATOM | 1092 | A | PHE | 300 | 78.338 | 36.613 | 19.709 | 1.00 | 29.01 |
| ATOM | 1093 | CB | PHE | 300 | 79.386 | 37.622 | 20.182 | 1.00 | 29.53 |
| ATOM | 1094 | CG | PHE | 300 | 79.239 | 38.978 | 19.562 | 1.00 | 27.60 |
| ATOM | 1095 | CD1 | PHE | 300 | 78.481 | 39.964 | 20.179 | 1.00 | 24.86 |
| ATOM | 1096 | CD2 | PHE | 300 | 79.853 | 39.266 | 18.350 | 1.00 | 27.39 |
| ATOM | 1097 | CE1 | PHE | 300 | 78.337 | 41.218 | 19.597 | 1.00 | 25.66 |
| ATOM | 1098 | CE2 | PHE | 300 | 79.715 | 40.518 | 17.761 | 1.00 | 25.97 |
| ATOM | 1099 | CZ | PHE | 300 | 78.956 | 41.495 | 18.384 | 1.00 | 21.03 |
| ATOM | 1100 | C | PHE | 300 | 78.988 | 35.248 | 19.496 | 1.00 | 30.34 |
| ATOM | 1101 | O | PHE | 300 | 79.309 | 34.873 | 18.367 | 1.00 | 29.35 |
| ATOM | 1102 | N | GLU | 301 | 79.181 | 34.507 | 20.582 | 1.00 | 31.04 |
| ATOM | 1103 | CA | GLU | 301 | 79.775 | 33.178 | 20.499 | 1.00 | 33.60 |
| ATOM | 1104 | CB | GLU | 301 | 80.012 | 32.607 | 21.898 | 1.00 | 31.64 |
| ATOM | 1105 | C | GLU | 301 | 78.851 | 32.265 | 19.696 | 1.00 | 33.90 |
| ATOM | 1106 | O | GLU | 301 | 79.315 | 31.473 | 18.872 | 1.00 | 33.33 |
| ATOM | 1107 | N | LEU | 302 | 77.546 | 32.386 | 19.935 | 1.00 | 31.13 |
| ATOM | 1108 | CA | LEU | 302 | 76.556 | 31.581 | 19.227 | 1.00 | 27.57 |
| ATOM | 1109 | CB | LEU | 302 | 75.150 | 31.842 | 19.776 | 1.00 | 25.24 |
| ATOM | 1110 | CG | LEU | 302 | 73.994 | 31.131 | 19.059 | 1.00 | 28.59 |
| ATOM | 1111 | CD1 | LEU | 302 | 74.066 | 29.634 | 19.299 | 1.00 | 25.52 |
| ATOM | 1112 | CD2 | LEU | 302 | 72.660 | 31.682 | 19.532 | 1.00 | 19.30 |
| ATOM | 1113 | C | LEU | 302 | 76.601 | 31.904 | 17.739 | 1.00 | 26.80 |
| ATOM | 1114 | O | LEU | 302 | 76.682 | 31.003 | 16.904 | 1.00 | 27.81 |
| ATOM | 1115 | N | GLY | 303 | 76.576 | 33.195 | 17.416 | 1.00 | 26.47 |
| ATOM | 1116 | CA | GLY | 303 | 76.611 | 33.624 | 16.030 | 1.00 | 26.99 |
| ATOM | 1117 | C | GLY | 303 | 77.845 | 33.133 | 15.295 | 1.00 | 33.46 |
| ATOM | 1118 | O | GLY | 303 | 77.757 | 32.646 | 14.164 | 1.00 | 32.33 |

APPENDIX 3-continued

TR_DMT.PDB

| ATOM | 1119 | N   | LYS | 304 | 78.994 | 33.232 | 15.956 | 1.00 | 34.63 |
|------|------|-----|-----|-----|--------|--------|--------|------|-------|
| ATOM | 1120 | CA  | LYS | 304 | 80.269 | 32.813 | 15.383 | 1.00 | 36.20 |
| ATOM | 1121 | CB  | LYS | 304 | 81.399 | 33.115 | 16.372 | 1.00 | 41.96 |
| ATOM | 1122 | CG  | LYS | 304 | 82.779 | 33.179 | 15.757 | 1.00 | 47.05 |
| ATOM | 1123 | CD  | LYS | 304 | 83.800 | 33.610 | 16.796 | 1.00 | 59.47 |
| ATOM | 1124 | CE  | LYS | 304 | 85.179 | 33.791 | 16.181 | 1.00 | 65.89 |
| ATOM | 1125 | NZ  | LYS | 304 | 85.182 | 34.863 | 15.144 | 1.00 | 71.01 |
| ATOM | 1126 | C   | LYS | 304 | 80.276 | 31.332 | 14.992 | 1.00 | 33.17 |
| ATOM | 1127 | O   | LYS | 304 | 80.752 | 30.974 | 13.913 | 1.00 | 34.44 |
| ATOM | 1128 | N   | SER | 305 | 79.739 | 30.482 | 15.861 | 1.00 | 31.40 |
| ATOM | 1129 | CA  | SER | 305 | 79.687 | 29.048 | 15.594 | 1.00 | 33.10 |
| ATOM | 1130 | CB  | SER | 305 | 79.513 | 28.266 | 16.900 | 1.00 | 34.10 |
| ATOM | 1131 | OG  | SER | 305 | 78.391 | 28.727 | 17.633 | 1.00 | 40.61 |
| ATOM | 1132 | C   | SER | 305 | 78.597 | 28.664 | 14.589 | 1.00 | 33.02 |
| ATOM | 1133 | O   | SER | 305 | 78.771 | 27.718 | 13.816 | 1.00 | 35.32 |
| ATOM | 1134 | N   | LEU | 306 | 77.488 | 29.404 | 14.580 | 1.00 | 32.14 |
| ATOM | 1135 | CA  | LEU | 306 | 76.391 | 29.121 | 13.653 | 1.00 | 31.02 |
| ATOM | 1136 | CB  | LEU | 306 | 75.138 | 29.936 | 13.996 | 1.00 | 22.76 |
| ATOM | 1137 | CG  | LEU | 306 | 74.361 | 29.487 | 15.235 | 1.00 | 24.42 |
| ATOM | 1138 | CD1 | LEU | 306 | 73.094 | 30.311 | 15.380 | 1.00 | 23.13 |
| ATOM | 1139 | CD2 | LEU | 306 | 74.016 | 28.009 | 15.126 | 1.00 | 25.53 |
| ATOM | 1140 | C   | LEU | 306 | 76.780 | 29.354 | 12.198 | 1.00 | 33.11 |
| ATOM | 1141 | O   | LEU | 306 | 76.161 | 28.796 | 11.293 | 1.00 | 32.60 |
| ATOM | 1142 | N   | SER | 307 | 77.821 | 30.153 | 11.975 | 1.00 | 36.12 |
| ATOM | 1143 | CA  | SER | 307 | 78.296 | 30.448 | 10.624 | 1.00 | 38.80 |
| ATOM | 1144 | CB  | SER | 307 | 79.514 | 31.373 | 10.677 | 1.00 | 41.64 |
| ATOM | 1145 | OG  | SER | 307 | 79.224 | 32.556 | 11.401 | 1.00 | 54.66 |
| ATOM | 1146 | C   | SER | 307 | 78.650 | 29.182 | 9.845  | 1.00 | 36.98 |
| ATOM | 1147 | O   | SER | 307 | 78.302 | 29.055 | 8.669  | 1.00 | 42.87 |
| ATOM | 1148 | N   | ALA | 308 | 79.315 | 28.239 | 10.509 | 1.00 | 35.72 |
| ATOM | 1149 | CA  | ALA | 308 | 79.719 | 26.983 | 9.879  | 1.00 | 32.70 |
| ATOM | 1150 | CB  | ALA | 308 | 80.683 | 26.227 | 10.782 | 1.00 | 33.88 |
| ATOM | 1151 | C   | ALN | 308 | 78.531 | 26.093 | 9.521  | 1.00 | 34.83 |
| ATOM | 1152 | O   | ALA | 308 | 78.620 | 25.278 | 8.600  | 1.00 | 39.61 |
| ATOM | 1153 | N   | PHE | 309 | 77.424 | 26.250 | 10.244 | 1.00 | 31.54 |
| ATOM | 1154 | CA  | PHE | 309 | 76.226 | 25.453 | 9.999  | 1.00 | 32.43 |
| ATOM | 1155 | CB  | PHE | 309 | 75.259 | 25.558 | 11.182 | 1.00 | 30.89 |
| ATOM | 1156 | CG  | PHE | 309 | 75.718 | 24.826 | 12.415 | 1.00 | 33.73 |
| ATOM | 1157 | CD1 | PHE | 309 | 76.769 | 25.314 | 13.183 | 1.00 | 40.48 |
| ATOM | 1158 | CD2 | PHE | 309 | 75.091 | 23.654 | 12.816 | 1.00 | 35.96 |
| ATOM | 1159 | CE1 | PHE | 309 | 77.189 | 24.643 | 14.334 | 1.00 | 37.87 |
| ATOM | 1160 | CE2 | PHE | 309 | 75.502 | 22.975 | 13.962 | 1.00 | 38.44 |
| ATOM | 1161 | CZ  | PHE | 309 | 76.553 | 23.471 | 14.722 | 1.00 | 37.34 |
| ATOM | 1162 | C   | PHE | 309 | 75.507 | 25.809 | 8.693  | 1.00 | 34.76 |
| ATOM | 1163 | O   | PHE | 309 | 74.810 | 24.969 | 8.118  | 1.00 | 36.18 |
| ATOM | 1164 | N   | ASN | 310 | 75.693 | 27.040 | 8.218  | 1.00 | 35.80 |
| ATOM | 1165 | CA  | ASN | 310 | 75.060 | 27.506 | 6.980  | 1.00 | 41.00 |
| ATOM | 1166 | CB  | ASN | 310 | 75.705 | 26.852 | 5.755  | 1.00 | 51.94 |
| ATOM | 1167 | CG  | ASN | 310 | 77.053 | 27.452 | 5.419  | 1.00 | 67.92 |
| ATOM | 1168 | OD1 | ASN | 310 | 77.139 | 28.439 | 4.687  | 1.00 | 77.32 |
| ATOM | 1169 | ND2 | ASN | 310 | 78.116 | 26.869 | 5.962  | 1.00 | 72.62 |
| ATOM | 1170 | C   | ASN | 310 | 73.560 | 27.245 | 6.985  | 1.00 | 38.15 |
| ATOM | 1171 | O   | ASN | 310 | 73.034 | 26.515 | 6.141  | 1.00 | 35.87 |
| ATOM | 1172 | N   | LEU | 311 | 72.885 | 27.819 | 7.971  | 1.00 | 33.94 |
| ATOM | 1173 | CA  | LEU | 311 | 71.450 | 27.651 | 8.111  | 1.00 | 32.09 |
| ATOM | 1174 | CB  | LEU | 311 | 71.011 | 28.009 | 9.533  | 1.00 | 28.06 |
| ATOM | 1175 | CG  | LEU | 311 | 71.656 | 27.301 | 10.724 | 1.00 | 26.38 |
| ATOM | 1176 | CD1 | LEU | 311 | 71.092 | 27.883 | 12.012 | 1.00 | 23.56 |
| ATOM | 1177 | CD2 | LEU | 311 | 71.409 | 25.801 | 10.651 | 1.00 | 21.24 |
| ATOM | 1178 | C   | LEU | 311 | 70.705 | 28.542 | 7.124  | 1.00 | 33.00 |
| ATOM | 1179 | O   | LEU | 311 | 71.173 | 29.630 | 6.782  | 1.00 | 35.47 |
| ATOM | 1180 | N   | ASP | 312 | 69.569 | 28.057 | 6.638  | 1.00 | 27.78 |
| ATOM | 1181 | CA  | ASP | 312 | 68.749 | 28.841 | 5.733  | 1.00 | 27.06 |
| ATOM | 1182 | CB  | ASP | 312 | 68.385 | 28.049 | 4.456  | 1.00 | 25.84 |
| ATOM | 1183 | CG  | ASP | 312 | 67.580 | 26.778 | 4.724  | 1.00 | 25.67 |
| ATOM | 1184 | OD1 | ASP | 312 | 67.124 | 26.541 | 5.860  | 1.00 | 28.20 |
| ATOM | 1185 | OD2 | ASP | 312 | 67.387 | 26.008 | 3.762  | 1.00 | 27.62 |
| ATOM | 1186 | C   | ASP | 312 | 67.517 | 29.314 | 6.514  | 1.00 | 28.51 |
| ATOM | 1187 | O   | ASP | 312 | 67.371 | 28.990 | 7.703  | 1.00 | 25.35 |
| ATOM | 1188 | N   | ASP | 313 | 66.633 | 30.060 | 5.855  | 1.00 | 22.16 |
| ATOM | 1189 | CA  | ASP | 313 | 65.430 | 30.589 | 6.494  | 1.00 | 21.37 |
| ATOM | 1190 | CB  | ASP | 313 | 64.625 | 31.431 | 5.499  | 1.00 | 25.11 |
| ATOM | 1191 | CG  | ASP | 313 | 65.380 | 32.666 | 5.025  | 1.00 | 31.54 |
| ATOM | 1192 | OD1 | ASP | 313 | 65.119 | 33.115 | 3.890  | 1.00 | 35.35 |
| ATOM | 1193 | OD2 | ASP | 313 | 66.225 | 33.193 | 5.783  | 1.00 | 35.37 |
| ATOM | 1194 | C   | ASP | 313 | 64.524 | 29.535 | 7.120  | 1.00 | 21.11 |
| ATOM | 1195 | O   | ASP | 313 | 63.904 | 29.783 | 8.158  | 1.00 | 23.68 |

APPENDIX 3-continued

TR_DMT.PDB

| ATOM | 1196 | N   | THR | 314 | 64.440 | 28.367 | 6.489  | 1.00 | 22.88 |
|------|------|-----|-----|-----|--------|--------|--------|------|-------|
| ATOM | 1197 | CA  | THR | 314 | 63.591 | 27.281 | 6.981  | 1.00 | 22.81 |
| ATOM | 1198 | CB  | THR | 314 | 63.472 | 26.155 | 5.927  | 1.00 | 26.00 |
| ATOM | 1199 | OG1 | THR | 314 | 62.873 | 26.679 | 4.732  | 1.00 | 20.14 |
| ATOM | 1200 | CG2 | THR | 314 | 62.629 | 25.010 | 6.457  | 1.00 | 17.51 |
| ATOM | 1201 | C   | THR | 314 | 64.086 | 26.706 | 8.310  | 1.00 | 19.46 |
| ATOM | 1202 | O   | THR | 314 | 63.312 | 26.529 | 9.247  | 1.00 | 19.33 |
| ATOM | 1203 | N   | GLU | 315 | 65.381 | 26.431 | 8.392  | 1.00 | 17.49 |
| ATOM | 1204 | CA  | GLU | 315 | 65.965 | 25.885 | 9.611  | 1.00 | 20.62 |
| ATOM | 1205 | CB  | GLU | 315 | 67.426 | 25.514 | 9.358  | 1.00 | 14.39 |
| ATOM | 1206 | CG  | GLU | 315 | 67.539 | 24.339 | 8.400  | 1.00 | 13.07 |
| ATOM | 1207 | CD  | GLU | 315 | 68.923 | 24.125 | 7.835  | 1.00 | 14.98 |
| ATOM | 1208 | OE1 | GLU | 315 | 69.634 | 25.116 | 7.552  | 1.00 | 17.71 |
| ATOM | 1209 | OE2 | GLU | 315 | 69.287 | 22.948 | 7.651  | 1.00 | 17.88 |
| ATOM | 1210 | C   | GLU | 315 | 65.810 | 26.883 | 10.762 | 1.00 | 20.57 |
| ATOM | 1211 | O   | GLU | 315 | 65.368 | 26.518 | 11.854 | 1.00 | 18.43 |
| ATOM | 1212 | N   | VAL | 316 | 66.096 | 28.154 | 10.488 | 1.00 | 19.19 |
| ATOM | 1213 | CA  | VAL | 316 | 65.955 | 29.203 | 11.490 | 1.00 | 16.53 |
| ATOM | 1214 | CB  | VAL | 316 | 66.418 | 30.567 | 10.933 | 1.00 | 17.42 |
| ATOM | 1215 | CG1 | VAL | 316 | 66.149 | 31.687 | 11.940 | 1.00 | 13.89 |
| ATOM | 1216 | CG2 | VAL | 316 | 67.900 | 30.506 | 10.594 | 1.00 | 14.31 |
| ATOM | 1217 | C   | VAL | 316 | 64.488 | 29.291 | 11.927 | 1.00 | 19.53 |
| ATOM | 1218 | O   | VAL | 316 | 64.191 | 29.448 | 13.110 | 1.00 | 19.86 |
| ATOM | 1219 | N   | ALA | 317 | 63.575 | 29.159 | 10.970 | 1.00 | 19.02 |
| ATOM | 1220 | CA  | ALA | 317 | 62.145 | 29.215 | 11.254 | 1.00 | 16.95 |
| ATOM | 1221 | CB  | ALA | 317 | 61.357 | 29.239 | 9.951  | 1.00 | 17.68 |
| ATOM | 1222 | C   | ALA | 317 | 61.674 | 28.047 | 12.126 | 1.00 | 14.13 |
| ATOM | 1223 | O   | ALA | 317 | 60.875 | 28.228 | 13.045 | 1.00 | 15.34 |
| ATOM | 1224 | N   | LEU | 318 | 62.154 | 26.847 | 11.819 | 1.00 | 17.41 |
| ATOM | 1225 | CA  | LEU | 318 | 61.769 | 25.653 | 12.569 | 1.00 | 19.10 |
| ATOM | 1226 | CB  | LEU | 318 | 62.186 | 24.398 | 11.802 | 1.00 | 18.21 |
| ATOM | 1227 | CG  | LEU | 318 | 61.443 | 24.209 | 10.473 | 1.00 | 19.02 |
| ATOM | 1228 | CD1 | LEU | 318 | 62.105 | 23.128 | 9.646  | 1.00 | 16.10 |
| ATOM | 1229 | CD2 | LEU | 318 | 59.987 | 23.875 | 10.735 | 1.00 | 11.32 |
| ATOM | 1230 | C   | LEU | 318 | 62.399 | 25.685 | 13.954 | 1.00 | 22.38 |
| ATOM | 1231 | O   | LEU | 318 | 61.782 | 25.278 | 14.945 | 1.00 | 21.64 |
| ATOM | 1232 | N   | LEU | 319 | 63.619 | 26.207 | 14.016 | 1.00 | 20.97 |
| ATOM | 1233 | CA  | LEU | 319 | 64.338 | 26.344 | 15.270 | 1.00 | 19.71 |
| ATOM | 1234 | CB  | LEU | 319 | 65.715 | 26.951 | 15.005 | 1.00 | 20.56 |
| ATOM | 1235 | CG  | LEU | 319 | 66.722 | 27.036 | 16.152 | 1.00 | 32.05 |
| ATOM | 1236 | CD1 | LEU | 319 | 66.704 | 25.760 | 16.963 | 1.00 | 33.15 |
| ATOM | 1237 | CD2 | LEU | 319 | 68.109 | 27.303 | 15.590 | 1.00 | 28.25 |
| ATOM | 1238 | C   | LEU | 319 | 63.496 | 27.254 | 16.164 | 1.00 | 20.66 |
| ATOM | 1239 | O   | LEU | 319 | 63.215 | 26.920 | 17.313 | 1.00 | 24.47 |
| ATOM | 1240 | N   | GLN | 320 | 63.026 | 28.365 | 15.604 | 1.00 | 19.25 |
| ATOM | 1241 | CA  | GLN | 320 | 62.191 | 29.307 | 16.346 | 1.00 | 19.02 |
| ATOM | 1242 | CB  | GLN | 320 | 61.842 | 30.526 | 15.488 | 1.00 | 19.11 |
| ATOM | 1243 | CG  | GLN | 320 | 63.032 | 31.377 | 15.101 | 1.00 | 20.02 |
| ATOM | 1244 | CD  | GLN | 320 | 62.665 | 32.562 | 14.224 | 1.00 | 23.65 |
| ATOM | 1245 | OE1 | GLN | 320 | 63.487 | 33.445 | 13.997 | 1.00 | 22.68 |
| ATOM | 1246 | NE2 | GLN | 320 | 61.440 | 32.574 | 13.704 | 1.00 | 20.77 |
| ATOM | 1247 | C   | GLN | 320 | 60.905 | 28.635 | 16.811 | 1.00 | 20.52 |
| ATOM | 1248 | O   | GLN | 320 | 60.465 | 28.845 | 17.938 | 1.00 | 22.04 |
| ATOM | 1249 | N   | ALA | 321 | 60.306 | 27.825 | 15.942 | 1.00 | 21.01 |
| ATOM | 1250 | CA  | ALA | 321 | 59.069 | 27.128 | 16.280 | 1.00 | 16.83 |
| ATOM | 1251 | CB  | ALA | 321 | 58.556 | 26.358 | 15.079 | 1.00 | 16.58 |
| ATOM | 1252 | C   | ALA | 321 | 59.288 | 26.185 | 17.462 | 1.00 | 18.15 |
| ATOM | 1253 | O   | ALA | 321 | 58.427 | 26.069 | 18.344 | 1.00 | 13.03 |
| ATOM | 1254 | N   | VAL | 322 | 60.442 | 25.523 | 17.481 | 1.00 | 14.89 |
| ATOM | 1255 | CA  | VAL | 322 | 60.774 | 24.599 | 18.559 | 1.00 | 19.05 |
| ATOM | 1256 | CB  | VAL | 322 | 62.051 | 23.779 | 18.233 | 1.00 | 21.50 |
| ATOM | 1257 | CG1 | VAL | 322 | 62.510 | 22.990 | 19.457 | 1.00 | 21.49 |
| ATOM | 1258 | CG2 | VAL | 322 | 61.773 | 22.819 | 17.073 | 1.00 | 15.42 |
| ATOM | 1259 | C   | VAL | 322 | 60.947 | 25.375 | 19.867 | 1.00 | 19.89 |
| ATOM | 1260 | O   | VAL | 322 | 60.478 | 24.940 | 20.919 | 1.00 | 21.58 |
| ATOM | 1261 | N   | LEU | 323 | 61.591 | 26.537 | 19.788 | 1.00 | 20.25 |
| ATOM | 1262 | CA  | LEU | 323 | 61.804 | 27.387 | 20.959 | 1.00 | 19.32 |
| ATOM | 1263 | CB  | LEU | 323 | 62.683 | 28.586 | 20.597 | 1.00 | 12.95 |
| ATOM | 1264 | CG  | LEU | 323 | 64.129 | 28.273 | 20.217 | 1.00 | 20.70 |
| ATOM | 1265 | CD1 | LEU | 323 | 64.805 | 29.503 | 19.641 | 1.00 | 13.23 |
| ATOM | 1266 | CD2 | LEU | 323 | 64.883 | 27.767 | 21.438 | 1.00 | 22.91 |
| ATOM | 1267 | C   | LEU | 323 | 60.468 | 27.884 | 21.497 | 1.00 | 20.25 |
| ATOM | 1268 | O   | LEU | 323 | 60.251 | 27.918 | 22.706 | 1.00 | 25.88 |
| ATOM | 1269 | N   | LEU | 324 | 59.571 | 28.251 | 20.587 | 1.00 | 23.08 |
| ATOM | 1270 | CA  | LEU | 324 | 58.248 | 28.753 | 20.944 | 1.00 | 21.24 |
| ATOM | 1271 | CB  | LEU | 324 | 57.555 | 29.333 | 19.707 | 1.00 | 18.45 |
| ATOM | 1272 | CG  | LEU | 324 | 56.119 | 29.847 | 19.868 | 1.00 | 17.07 |

APPENDIX 3-continued

TR_DMT.PDB

| ATOM | 1273 | CD1 | LEU | 324 | 56.083 | 31.092 | 20.752 | 1.00 | 15.39 |
|---|---|---|---|---|---|---|---|---|---|
| ATOM | 1274 | CD2 | LEU | 324 | 55.545 | 30.162 | 18.498 | 1.06 | 17.90 |
| ATOM | 1275 | C | LEU | 324 | 57.342 | 27.706 | 21.598 | 1.00 | 21.54 |
| ATOM | 1276 | O | LEU | 324 | 56.742 | 27.967 | 22.642 | 1.00 | 23.41 |
| ATOM | 1277 | N | MET | 325 | 57.249 | 26.521 | 21.003 | 1.00 | 24.63 |
| ATOM | 1278 | CA | MET | 325 | 56.380 | 25.476 | 21.545 | 1.00 | 25.35 |
| ATOM | 1279 | CB | MET | 325 | 55.901 | 24.536 | 20.430 | 1.00 | 25.53 |
| ATOM | 1280 | CG | MET | 325 | 55.235 | 25.220 | 19.232 | 1.00 | 21.89 |
| ATOM | 1281 | SD | MET | 325 | 53.871 | 26.337 | 19.649 | 1.00 | 25.50 |
| ATOM | 1282 | CE | MET | 325 | 52.705 | 25.250 | 20.397 | 1.00 | 17.66 |
| ATOM | 1283 | C | MET | 325 | 57.031 | 24.676 | 22.675 | 1.00 | 27.58 |
| ATOM | 1284 | O | MET | 325 | 56.988 | 23.450 | 22.690 | 1.00 | 28.61 |
| ATOM | 1285 | N | SER | 326 | 57.613 | 25.376 | 23.638 | 1.00 | 27.98 |
| ATOM | 1286 | CA | SER | 326 | 58.265 | 24.718 | 24.757 | 1.00 | 31.60 |
| ATOM | 1287 | CB | SER | 326 | 59.527 | 25.493 | 25.155 | 1.00 | 35.80 |
| ATOM | 1288 | OG | SER | 326 | 60.123 | 24.966 | 26.327 | 1.00 | 43.74 |
| ATOM | 1289 | C | SER | 326 | 57.313 | 24.624 | 25.939 | 1.00 | 32.12 |
| ATOM | 1290 | O | SER | 326 | 56.590 | 25.574 | 26.240 | 1.00 | 30.94 |
| ATOM | 1291 | N | THR | 327 | 57.276 | 23.464 | 26.583 | 1.00 | 35.41 |
| ATOM | 1292 | CA | THR | 327 | 56.420 | 23.278 | 27.747 | 1.00 | 39.61 |
| ATOM | 1293 | CB | THR | 327 | 55.777 | 21.890 | 27.758 | 1.00 | 38.84 |
| ATOM | 1294 | OG1 | THR | 327 | 56.784 | 20.890 | 27.538 | 1.00 | 42.53 |
| ATOM | 1295 | CG2 | THR | 327 | 54.716 | 21.802 | 26.679 | 1.00 | 40.78 |
| ATOM | 1296 | C | THR | 327 | 57.232 | 23.471 | 29.022 | 1.00 | 43.86 |
| ATOM | 1297 | O | THR | 327 | 56.785 | 23.133 | 30.118 | 1.00 | 42.40 |
| ATOM | 1298 | N | ASP | 328 | 58.417 | 24.054 | 28.869 | 1.00 | 47.35 |
| ATOM | 1299 | CA | ASP | 328 | 59.309 | 24.308 | 29.987 | 1.00 | 49.43 |
| ATOM | 1300 | CB | ASP | 328 | 60.750 | 24.358 | 29.482 | 1.00 | 58.03 |
| ATOM | 1301 | CG | ASP | 328 | 61.718 | 23.687 | 30.425 | 1.00 | 72.16 |
| ATOM | 1302 | OD1 | ASP | 328 | 61.816 | 24.117 | 31.595 | 1.00 | 82.32 |
| ATOM | 1303 | OD2 | ASP | 328 | 62.378 | 22.720 | 29.994 | 1.00 | 81.63 |
| ATOM | 1304 | C | ASP | 328 | 58.951 | 25.625 | 30.676 | 1.00 | 47.99 |
| ATOM | 1305 | O | ASP | 328 | 59.830 | 26.373 | 31.093 | 1.00 | 53.33 |
| ATOM | 1306 | N | ARG | 329 | 57.657 | 25.910 | 30.780 | 1.00 | 48.33 |
| ATOM | 1307 | CA | ARG | 329 | 57.177 | 27.135 | 31.413 | 1.00 | 47.67 |
| ATOM | 1308 | CB | ARG | 329 | 56.562 | 28.091 | 30.379 | 1.00 | 47.64 |
| ATOM | 1309 | CG | ARG | 329 | 57.550 | 28.802 | 29.450 | 1.00 | 47.87 |
| ATOM | 1310 | CD | ARG | 329 | 57.893 | 27.968 | 28.226 | 1.00 | 44.00 |
| ATOM | 1311 | NE | ARG | 329 | 58.759 | 28.682 | 27.288 | 1.00 | 41.17 |
| ATOM | 1312 | CZ | ARG | 329 | 60.087 | 28.605 | 27.283 | 1.00 | 48.58 |
| ATOM | 1313 | NH1 | ARG | 329 | 60.719 | 27.848 | 28.172 | 1.00 | 52.94 |
| ATOM | 1314 | NH2 | ARG | 329 | 60.784 | 29.257 | 26.362 | 1.00 | 43.16 |
| ATOM | 1315 | C | ARG | 329 | 56.126 | 26.778 | 32.457 | 1.00 | 48.01 |
| ATOM | 1316 | O | ARG | 329 | 55.573 | 25.677 | 32.437 | 1.00 | 50.22 |
| ATOM | 1317 | N | SER | 330 | 55.832 | 27.716 | 33.351 | 1.00 | 47.37 |
| ATOM | 1318 | CA | SER | 330 | 54.848 | 27.490 | 34.402 | 1.00 | 47.64 |
| ATOM | 1319 | CB | SER | 330 | 55.376 | 28.021 | 35.736 | 1.00 | 46.62 |
| ATOM | 1320 | C | SER | 330 | 53.506 | 28.139 | 34.074 | 1.00 | 46.40 |
| ATOM | 1321 | O | SER | 330 | 53.460 | 29.252 | 33.548 | 1.00 | 48.49 |
| ATOM | 1322 | N | GLY | 331 | 52.421 | 27.424 | 34.359 | 1.00 | 44.16 |
| ATOM | 1323 | CA | GLY | 331 | 51.090 | 27.956 | 34.123 | 1.00 | 41.44 |
| ATOM | 1324 | C | GLY | 331 | 50.424 | 27.660 | 32.790 | 1.00 | 42.83 |
| ATOM | 1325 | O | GLY | 331 | 49.478 | 28.351 | 32.413 | 1.00 | 45.88 |
| ATOM | 1326 | N | LEU | 332 | 50.889 | 26.643 | 32.075 | 1.00 | 40.10 |
| ATOM | 1327 | CA | LEU | 332 | 50.288 | 26.300 | 30.789 | 1.00 | 39.27 |
| ATOM | 1328 | CB | LEU | 332 | 51.301 | 25.596 | 29.885 | 1.00 | 37.42 |
| ATOM | 1329 | CG | LEU | 332 | 52.436 | 26.426 | 29.291 | 1.00 | 35.35 |
| ATOM | 1330 | CD1 | LEU | 332 | 53.374 | 25.505 | 28.530 | 1.00 | 31.61 |
| ATOM | 1331 | CD2 | LEU | 332 | 51.875 | 27.511 | 28.376 | 1.00 | 31.82 |
| ATOM | 1332 | C | LEU | 332 | 49.058 | 25.415 | 30.951 | 1.00 | 39.32 |
| ATOM | 1333 | O | LEU | 332 | 49.060 | 24.467 | 31.738 | 1.00 | 42.74 |
| ATOM | 1334 | N | LEU | 333 | 48.009 | 25.730 | 30.202 | 1.00 | 37.62 |
| ATOM | 1335 | CA | LEU | 333 | 46.778 | 24.953 | 30.241 | 1.00 | 41.30 |
| ATOM | 1336 | CB | LEU | 333 | 45.586 | 25.835 | 29.852 | 1.00 | 43.52 |
| ATOM | 1337 | CG | LEU | 333 | 45.125 | 26.904 | 30.848 | 1.00 | 49.39 |
| ATOM | 1338 | CD1 | LEU | 333 | 44.296 | 27.970 | 30.142 | 1.00 | 46.19 |
| ATOM | 1339 | CD2 | LEU | 333 | 44.330 | 26.248 | 31.968 | 1.00 | 51.29 |
| ATOM | 1340 | C | LEU | 333 | 46.859 | 23.762 | 29.285 | 1.00 | 41.39 |
| ATOM | 1341 | O | LEU | 333 | 46.565 | 22.628 | 29.657 | 1.00 | 43.41 |
| ATOM | 1342 | N | CYA | 334 | 47.3.17 | 24.024 | 28.067 | 1.00 | 42.18 |
| ATOM | 1343 | CA | CYA | 334 | 47.409 | 23.003 | 27.029 | 1.00 | 39.56 |
| ATOM | 1344 | CB | CYA | 334 | 47.004 | 23.616 | 25.691 | 1.00 | 45.48 |
| ATOM | 1345 | SG | CYA | 334 | 45.517 | 24.616 | 25.785 | 1.00 | 51.57 |
| ATOM | 1346 | AS | CYA | 334 | 44.187 | 22.808 | 25.555 | 1.00 | 90.90 |
| ATOM | 1347 | C | CYA | 334 | 48.776 | 22.347 | 26.891 | 1.00 | 38.28 |
| ATOM | 1348 | O | CYA | 334 | 49.273 | 22.178 | 25.778 | 1.00 | 40.95 |
| ATOM | 1349 | N | VAL | 335 | 49.345 | 21.913 | 28.009 | 1.00 | 36.05 |

APPENDIX 3-continued

TR_DMT.PDB

| ATOM | 1350 | CA | VAL | 335 | 50.661 | 21.278 | 28.006 | 1.00 | 35.78 |
|---|---|---|---|---|---|---|---|---|---|
| ATOM | 1351 | CB | VAL | 335 | 50.996 | 20.679 | 29.399 | 1.00 | 35.53 |
| ATOM | 1352 | CG1 | VAL | 335 | 52.413 | 20.123 | 29.407 | 1.00 | 32.76 |
| ATOM | 1353 | CG2 | VAL | 335 | 50.822 | 21.729 | 30.490 | 1.00 | 28.87 |
| ATOM | 1354 | C | VAL | 335 | 50.776 | 20.170 | 26.950 | 1.00 | 36.41 |
| ATOM | 1355 | O | VAL | 335 | 51.756 | 20.104 | 26.202 | 1.00 | 34.26 |
| ATOM | 1356 | N | ASP | 336 | 49.756 | 19.323 | 26.880 | 1.00 | 38.42 |
| ATOM | 1357 | CA | ASP | 336 | 49.736 | 18.209 | 25.942 | 1.00 | 39.71 |
| ATOM | 1358 | CB | ASP | 336 | 48.485 | 17.359 | 26.179 | 1.00 | 51.53 |
| ATOM | 1359 | CG | ASP | 336 | 48.534 | 16.028 | 25.452 | 1.00 | 65.98 |
| ATOM | 1360 | OD1 | ASP | 336 | 49.240 | 15.114 | 25.934 | 1.00 | 70.75 |
| ATOM | 1361 | OD2 | ASP | 336 | 47.858 | 15.891 | 24.406 | 1.00 | 72.15 |
| ATOM | 1362 | C | ASP | 336 | 49.794 | 18.668 | 24.486 | 1.00 | 37.72 |
| ATOM | 1363 | O | ASP | 336 | 50.686 | 18.259 | 23.733 | 1.00 | 32.08 |
| ATOM | 1364 | N | LYS | 337 | 48.858 | 19.532 | 24.100 | 1.00 | 33.78 |
| ATOM | 1365 | CA | LYS | 337 | 48.797 | 20.040 | 22.731 | 1.00 | 28.00 |
| ATOM | 1366 | CB | LYS | 337 | 47.626 | 21.022 | 22.574 | 1.00 | 22.46 |
| ATOM | 1367 | C | LYS | 337 | 50.116 | 20.704 | 22.334 | 1.00 | 29.06 |
| ATOM | 1368 | O | LYS | 337 | 50.607 | 20.512 | 21.220 | 1.00 | 28.41 |
| ATOM | 1369 | N | ILE | 338 | 50.705 | 21.449 | 23.267 | 1.00 | 27.56 |
| ATOM | 1370 | CA | ILE | 338 | 51.964 | 22.138 | 23.022 | 1.00 | 25.03 |
| ATOM | 1371 | CB | ILE | 338 | 52.274 | 23.149 | 24.144 | 1.00 | 19.49 |
| ATOM | 1372 | CG2 | ILE | 338 | 53.577 | 23.876 | 23.859 | 1.00 | 19.00 |
| ATOM | 1373 | CG1 | ILE | 338 | 51.135 | 24.167 | 24.232 | 1.00 | 21.97 |
| ATOM | 1374 | CD1 | ILE | 338 | 51.277 | 25.175 | 25.348 | 1.00 | 26.67 |
| ATOM | 1375 | C | ILE | 338 | 53.119 | 21.153 | 22.826 | 1.00 | 29.97 |
| ATOM | 1376 | O | ILE | 338 | 53.935 | 21.328 | 21.914 | 1.00 | 31.00 |
| ATOM | 1377 | N | GLU | 339 | 53.165 | 20.100 | 23.642 | 1.00 | 33.52 |
| ATOM | 1378 | CA | GLU | 339 | 54.213 | 19.080 | 23.516 | 1.00 | 35.34 |
| ATOM | 1379 | CB | GLU | 339 | 54.136 | 18.062 | 24.659 | 1.00 | 39.97 |
| ATOM | 1380 | CG | GLU | 339 | 54.653 | 18.585 | 25.986 | 1.00 | 53.23 |
| ATOM | 1381 | CD | GLU | 339 | 54.549 | 17.579 | 27.126 | 1.00 | 61.16 |
| ATOM | 1382 | OE1 | GLU | 339 | 53.602 | 16.759 | 27.131 | 1.00 | 64.30 |
| ATOM | 1383 | OE2 | GLU | 339 | 55.412 | 17.622 | 28.031 | 1.00 | 57.76 |
| ATOM | 1384 | C | GLU | 339 | 54.091 | 18.353 | 22.178 | 1.00 | 31.63 |
| ATOM | 1385 | O | GLU | 339 | 55.086 | 18.123 | 21.491 | 1.00 | 28.96 |
| ATOM | 1386 | N | LYS | 340 | 52.861 | 18.006 | 21.810 | 1.00 | 30.95 |
| ATOM | 1387 | CA | LYS | 340 | 52.602 | 17.313 | 20.554 | 1.00 | 31.58 |
| ATOM | 1388 | CB | LYS | 340 | 51.121 | 16.966 | 20.438 | 1.00 | 31.83 |
| ATOM | 1389 | C | LYS | 340 | 53.057 | 18.159 | 19.358 | 1.00 | 29.84 |
| ATOM | 1390 | O | LYS | 340 | 53.696 | 17.640 | 18.438 | 1.00 | 31.58 |
| ATOM | 1391 | N | SER | 341 | 52.765 | 19.460 | 19.388 | 1.00 | 25.33 |
| ATOM | 1392 | CA | SER | 341 | 53.165 | 20.351 | 18.297 | 1.00 | 23.92 |
| ATOM | 1393 | CB | SER | 341 | 52.468 | 21.707 | 18.400 | 1.00 | 24.02 |
| ATOM | 1394 | OG | SER | 341 | 52.700 | 22.302 | 19.657 | 1.00 | 48.88 |
| ATOM | 1395 | C | SER | 341 | 54.677 | 20.533 | 18.240 | 1.00 | 24.39 |
| ATOM | 1396 | O | SER | 341 | 55.254 | 20.593 | 17.150 | 1.00 | 24.71 |
| ATOM | 1397 | N | GLN | 342 | 55.324 | 20.606 | 19.405 | 1.00 | 25.45 |
| ATOM | 1398 | CA | GLN | 342 | 56.777 | 20.751 | 19.437 | 1.00 | 26.66 |
| ATOM | 1399 | CB | GLN | 342 | 57.311 | 20.975 | 20.853 | 1.00 | 22.77 |
| ATOM | 1400 | CG | GLN | 342 | 58.805 | 21.307 | 20.840 | 1.00 | 25.76 |
| ATOM | 1401 | CD | GLN | 342 | 59.427 | 21.371 | 22.214 | 1.00 | 28.46 |
| ATOM | 1402 | OE1 | GLN | 342 | 59.342 | 20.422 | 22.990 | 1.00 | 34.22 |
| ATOM | 1403 | NE2 | GLN | 342 | 60.080 | 22.483 | 22.517 | 1.00 | 30.01 |
| ATOM | 1404 | C | GLN | 342 | 57.425 | 19.504 | 18.843 | 1.00 | 23.37 |
| ATOM | 1405 | O | GLN | 342 | 58.414 | 19.598 | 18.106 | 1.00 | 23.65 |
| ATOM | 1406 | N | GLU | 343 | 56.864 | 18.340 | 19.162 | 1.00 | 21.48 |
| ATOM | 1407 | CA | GLU | 343 | 57.370 | 17.076 | 18.641 | 1.00 | 20.74 |
| ATOM | 1408 | CB | GLU | 343 | 56.599 | 15.902 | 19.247 | 1.00 | 22.09 |
| ATOM | 1409 | C | GLU | 343 | 57.225 | 17.094 | 17.119 | 1.00 | 19.18 |
| ATOM | 1410 | O | GLU | 343 | 58.156 | 16.743 | 16.393 | 1.00 | 21.11 |
| ATOM | 1411 | N | ALA | 344 | 56.077 | 17.570 | 16.648 | 1.00 | 19.93 |
| ATOM | 1412 | CA | ALA | 344 | 55.803 | 17.662 | 15.217 | 1.00 | 20.20 |
| ATOM | 1413 | CB | ALA | 344 | 54.411 | 18.216 | 14.989 | 1.00 | 16.46 |
| ATOM | 1414 | C | ALA | 344 | 56.850 | 18.539 | 14.528 | 1.00 | 20.75 |
| ATOM | 1415 | O | ALA | 344 | 57.432 | 18.140 | 13.514 | 1.00 | 25.13 |
| ATOM | 1416 | N | TYR | 345 | 57.105 | 19.722 | 15.088 | 1.00 | 21.31 |
| ATOM | 1417 | CA | TYR | 345 | 58.107 | 20.631 | 14.531 | 1.00 | 15.93 |
| ATOM | 1418 | CB | TYR | 345 | 58.127 | 21.969 | 15.282 | 1.00 | 17.29 |
| ATOM | 1419 | CG | TYR | 345 | 57.049 | 22.927 | 14.833 | 1.00 | 16.11 |
| ATOM | 1420 | CD1 | TYR | 345 | 56.017 | 23.296 | 15.689 | 1.00 | 9.93 |
| ATOM | 1421 | CE1 | TYR | 345 | 54.999 | 24.138 | 15.263 | 1.00 | 16.95 |
| ATOM | 1422 | CD2 | TYR | 345 | 57.041 | 23.431 | 13.531 | 1.00 | 19.84 |
| ATOM | 1423 | CE2 | TYR | 345 | 56.026 | 24.276 | 13.094 | 1.00 | 17.13 |
| ATOM | 1424 | CZ | TYR | 345 | 5S.005 | 24.622 | 13.963 | 1.00 | 18.12 |
| ATOM | 1425 | OH | TYR | 345 | 53.980 | 25.430 | 13.530 | 1.00 | 26.25 |
| ATOM | 1426 | C | TYR | 345 | 59.493 | 20.008 | 14.554 | 1.00 | 20.65 |

APPENDIX 3-continued

TR_DMT.PDB

| ATOM | 1427 | O | TYR | 345 | 60.240 | 20.129 | 13.583 | 1.00 | 20.75 |
|---|---|---|---|---|---|---|---|---|---|
| ATOM | 1428 | N | LEU | 346 | 59.832 | 19.337 | 15.655 | 1.00 | 22.14 |
| ATOM | 1429 | CA | LEU | 346 | 61.134 | 18.684 | 15.803 | 1.00 | 19.43 |
| ATOM | 1430 | CB | LEU | 346 | 61.267 | 18.041 | 17.186 | 1.00 | 19.92 |
| ATOM | 1431 | CG | LEU | 346 | 61.683 | 18.945 | 18.347 | 1.00 | 25.56 |
| ATOM | 1432 | CD1 | LEU | 346 | 61.440 | 18.244 | 19.677 | 1.00 | 22.06 |
| ATOM | 1433 | CD2 | LEU | 346 | 63.147 | 19.332 | 18.197 | 1.00 | 17.62 |
| ATOM | 1434 | C | LEU | 346 | 61.359 | 17.635 | 14.723 | 1.00 | 19.30 |
| ATOM | 1435 | O | LEU | 346 | 62.441 | 17.560 | 14.142 | 1.00 | 22.84 |
| ATOM | 1436 | N | LEU | 347 | 60.337 | 16.826 | 14.456 | 1.00 | 25.17 |
| ATOM | 1437 | CA | LEU | 347 | 60.423 | 15.790 | 13.427 | 1.00 | 24.55 |
| ATOM | 1438 | CB | LEU | 347 | 59.187 | 14.892 | 13.453 | 1.00 | 25.47 |
| ATOM | 1439 | CG | LEU | 347 | 59.2S6 | 13.654 | 14.345 | 1.00 | 30.65 |
| ATOM | 1440 | CD1 | LEU | 347 | 57.941 | 12.890 | 14.258 | 1.00 | 34.28 |
| ATOM | 1441 | CD2 | LEU | 347 | 60.416 | 12.765 | 13.908 | 1.00 | 28.26 |
| ATOM | 1442 | C | LEU | 347 | 60.584 | 16.400 | 12.042 | 1.00 | 24.00 |
| ATOM | 1443 | O | LEU | 347 | 61.399 | 15.932 | 11.245 | 1.00 | 29.74 |
| ATOM | 1444 | N | ALA | 348 | 59.809 | 17.443 | 11.761 | 1.00 | 22.72 |
| ATOM | 1445 | CA | ALA | 348 | 59.875 | 18.125 | 10.475 | 1.00 | 19.19 |
| ATOM | 1446 | CB | ALA | 348 | 58.789 | 19.188 | 10.388 | 1.00 | 22.73 |
| ATOM | 1447 | C | ALA | 348 | 61.246 | 18.762 | 10.316 | 1.00 | 20.34 |
| ATOM | 1448 | O | ALA | 348 | 61.881 | 18.633 | 9.274 | 1.00 | 23.94 |
| ATOM | 1449 | N | PHE | 349 | 61.707 | 19.402 | 11.388 | 1.00 | 22.19 |
| ATOM | 1450 | CA | PHE | 349 | 63.001 | 20.078 | 11.435 | 1.00 | 19.41 |
| ATOM | 1451 | CB | PHE | 349 | 63.185 | 20.701 | 12.832 | 1.00 | 17.45 |
| ATOM | 1452 | CG | PHE | 349 | 64.371 | 21.632 | 12.963 | 1.00 | 18.70 |
| ATOM | 1453 | CD1 | PHE | 349 | 65.183 | 21.943 | 11.874 | 1.00 | 19.09 |
| ATOM | 1454 | CD2 | PHE | 349 | 64.669 | 22.203 | 14.199 | 1.00 | 21.81 |
| ATOM | 1455 | CE1 | PHE | 349 | 66.270 | 22.811 | 12.012 | 1.00 | 21.49 |
| ATOM | 1456 | CE2 | PHE | 349 | 65.753 | 23.072 | 14.351 | 1.00 | 18.58 |
| ATOM | 1457 | CZ | PHE | 349 | 66.555 | 23.376 | 13.256 | 1.00 | 18.67 |
| ATOM | 1458 | C | PHE | 349 | 64.110 | 19.071 | 11.136 | 1.00 | 20.96 |
| ATOM | 1459 | O | PHE | 349 | 64.961 | 19.311 | 10.283 | 1.00 | 25.19 |
| ATOM | 1460 | N | GLU | 350 | 64.076 | 17.935 | 11.824 | 1.00 | 23.96 |
| ATOM | 1461 | CA | GLU | 350 | 65.077 | 16.888 | 11.642 | 1.00 | 27.98 |
| ATOM | 1462 | CB | GLU | 350 | 64.794 | 15.721 | 12.591 | 1.00 | 28.90 |
| ATOM | 1463 | CG | GLU | 350 | 65.738 | 14.542 | 12.413 | 1.00 | 39.36 |
| ATOM | 1464 | CD | GLU | 350 | 65.603 | 13.497 | 13.505 | 1.00 | 41.62 |
| ATOM | 1465 | OE1 | GLU | 350 | 64.475 | 13.260 | 13.988 | 1.00 | 43.67 |
| ATOM | 1466 | OE2 | GLU | 350 | 66.636 | 12.908 | 13.876 | 1.00 | 49.64 |
| ATOM | 1467 | C | GLU | 350 | 65.100 | 16.385 | 10.203 | 1.00 | 27.12 |
| ATOM | 1468 | O | GLU | 350 | 66.158 | 16.288 | 9.577 | 1.00 | 27.44 |
| ATOM | 1469 | N | HIS | 351 | 63.918 | 16.088 | 9.678 | 1.00 | 27.36 |
| ATOM | 1470 | CA | HIS | 351 | 63.787 | 15.591 | 8.318 | 1.00 | 23.97 |
| ATOM | 1471 | CB | HIS | 351 | 62.366 | 15.087 | 8.090 | 1.00 | 22.89 |
| ATOM | 1472 | CG | HIS | 351 | 61.991 | 13.945 | 8.986 | 1.00 | 24.58 |
| ATOM | 1473 | CD2 | HIS | 351 | 62.736 | 13.209 | 9.846 | 1.00 | 25.83 |
| ATOM | 1474 | ND1 | HIS | 351 | 60.709 | 13.448 | 9.073 | 1.00 | 26.50 |
| ATOM | 1475 | CE1 | HIS | 351 | 60.677 | 12.460 | 9.948 | 1.00 | 24.81 |
| ATOM | 1476 | NE2 | HIS | 351 | 61.896 | 12.295 | 10.431 | 1.00 | 28.42 |
| ATOM | 1477 | C | HIS | 351 | 64.200 | 16.635 | 7.278 | 1.00 | 24.22 |
| ATOM | 1478 | O | HIS | 351 | 64.757 | 16.287 | 6.236 | 1.00 | 25.79 |
| ATOM | 1479 | N | TYR | 352 | 63.969 | 17.912 | 7.572 | 1.00 | 21.04 |
| ATOM | 1480 | CA | TYR | 352 | 64.363 | 18.974 | 6.654 | 1.00 | 18.98 |
| ATOM | 1481 | CB | TYR | 352 | 63.770 | 20.321 | 7.067 | 1.00 | 17.08 |
| ATOM | 1482 | CG | TYR | 352 | 64.127 | 21.413 | 6.090 | 1.00 | 21.83 |
| ATOM | 1483 | CD1 | TYR | 352 | 63.537 | 21.467 | 4.828 | 1.00 | 20.07 |
| ATOM | 1484 | CE1 | TYR | 352 | 63.941 | 22.411 | 3.883 | 1.00 | 23.51 |
| ATOM | 1485 | CD2 | TYR | 352 | 65.121 | 22.339 | 6.388 | 1.00 | 19.94 |
| ATOM | 1486 | CE2 | TYR | 352 | 65.531 | 23.284 | 5.452 | 1.00 | 20.85 |
| ATOM | 1487 | CZ | TYR | 352 | 64.942 | 23.313 | 4.203 | 1.00 | 24.80 |
| ATOM | 1488 | OH | TYR | 352 | 65.380 | 24.221 | 3.269 | 1.00 | 26.74 |
| ATOM | 1489 | C | TYR | 352 | 65.889 | 19.055 | 6.624 | 1.00 | 20.58 |
| ATOM | 1490 | O | TYR | 352 | 66.492 | 19.276 | 5.570 | 1.00 | 22.72 |
| ATOM | 1491 | N | VAL | 353 | 66.508 | 18.877 | 7.789 | 1.00 | 28.34 |
| ATOM | 1492 | CA | VAL | 353 | 67.967 | 18.892 | 7.904 | 1.00 | 22.38 |
| ATOM | 1493 | CB | VAL | 353 | 68.419 | 18.755 | 9.389 | 1.00 | 26.46 |
| ATOM | 1494 | CG1 | VAL | 353 | 69.915 | 18.527 | 9.478 | 1.00 | 20.92 |
| ATOM | 1495 | CG2 | VAL | 353 | 68.053 | 20.009 | 10.165 | 1.00 | 22.46 |
| ATOM | 1496 | C | VAL | 353 | 68.518 | 17.725 | 7.078 | 1.00 | 23.51 |
| ATOM | 1497 | O | VAL | 353 | 69.535 | 17.865 | 6.391 | 1.00 | 24.73 |
| ATOM | 1498 | N | ASN | 354 | 67.850 | 16.575 | 7.158 | 1.00 | 20.93 |
| ATOM | 1499 | CA | ASN | 354 | 68.252 | 15.392 | 6.397 | 1.00 | 27.25 |
| ATOM | 1500 | CB | ASN | 354 | 67.320 | 14.210 | 6.680 | 1.00 | 28.43 |
| ATOM | 1501 | CG | ASN | 354 | 67.521 | 13.607 | 8.058 | 1.00 | 31.50 |
| ATOM | 1502 | OD1 | ASN | 354 | 68.565 | 13.787 | 8.692 | 1.00 | 37.79 |
| ATOM | 1503 | ND2 | ASN | 354 | 66.521 | 12.867 | 8.524 | 1.00 | 26.44 |

APPENDIX 3-continued

TR_DMT.PDB

| ATOM | 1504 | C   | ASN | 354 | 68.182 | 15.721 | 4.908  | 1.00 | 31.27 |
| ---- | ---- | --- | --- | --- | ------ | ------ | ------ | ---- | ----- |
| ATOM | 1505 | O   | ASN | 354 | 69.066 | 15.347 | 4.134  | 1.00 | 34.22 |
| ATOM | 1506 | N   | HIS | 355 | 67.124 | 16.429 | 4.520  | 1.00 | 30.49 |
| ATOM | 1507 | CA  | HIS | 355 | 66.917 | 16.826 | 3.132  | 1.00 | 26.88 |
| ATOM | 1508 | CB  | HIS | 355 | 65.548 | 17.494 | 2.975  | 1.00 | 27.27 |
| ATOM | 1509 | CG  | HIS | 355 | 65.319 | 18.103 | 1.625  | 1.00 | 37.76 |
| ATOM | 1510 | CD2 | HIS | 355 | 65.439 | 19.382 | 1.196  | 1.00 | 35.28 |
| ATOM | 1511 | ND1 | HIS | 355 | 64.913 | 17.369 | 0.532  | 1.00 | 34.93 |
| ATOM | 1512 | CE1 | HIS | 355 | 64.789 | 18.169 | −0.513 | 1.00 | 34.84 |
| ATOM | 1513 | NE2 | HIS | 355 | 65.104 | 19.394 | −0.135 | 1.00 | 33.13 |
| ATOM | 1514 | C   | HIS | 355 | 68.016 | 17.748 | 2.610  | 1.00 | 24.66 |
| ATOM | 1515 | O   | HIS | 355 | 68.420 | 17.630 | 1.456  | 1.00 | 26.62 |
| ATOM | 1516 | N   | ARG | 356 | 68.487 | 18.670 | 3.448  | 1.00 | 25.86 |
| ATOM | 1517 | CA  | ARG | 356 | 69.536 | 19.608 | 3.040  | 1.00 | 26.94 |
| ATOM | 1518 | CB  | ARG | 356 | 69.620 | 20.791 | 3.996  | 1.00 | 20.57 |
| ATOM | 1519 | CG  | ARG | 356 | 68.453 | 21.727 | 3.899  | 1.00 | 19.69 |
| ATOM | 1520 | CD  | ARG | 356 | 68.866 | 23.110 | 4.340  | 1.00 | 23.81 |
| ATOM | 1521 | NE  | ARG | 356 | 69.768 | 23.746 | 3.388  | 1.00 | 23.14 |
| ATOM | 1522 | CZ  | ARG | 356 | 70.641 | 24.697 | 3.702  | 1.00 | 24.11 |
| ATOM | 1523 | NH1 | ARG | 356 | 70.755 | 25.129 | 4.949  | 1.00 | 26.29 |
| ATOM | 1524 | NH2 | ARG | 356 | 71.384 | 25.242 | 2.754  | 1.00 | 32.79 |
| ATOM | 1525 | C   | ARG | 356 | 70.921 | 19.002 | 2.875  | 1.00 | 29.38 |
| ATOM | 1526 | O   | ARG | 356 | 71.795 | 19.607 | 2.257  | 1.00 | 32.91 |
| ATOM | 1527 | N   | LYS | 357 | 71.133 | 17.848 | 3.498  | 1.00 | 33.39 |
| ATOM | 1528 | CA  | LYS | 357 | 72.401 | 17.128 | 3.417  | 1.00 | 35.97 |
| ATOM | 1529 | CB  | LYS | 357 | 72.479 | 16.363 | 2.089  | 1.00 | 40.55 |
| ATOM | 1530 | CG  | LYS | 357 | 71.327 | 15.381 | 1.891  | 1.00 | 44.03 |
| ATOM | 1531 | CD  | LYS | 357 | 71.360 | 14.722 | 0.523  | 1.00 | 52.31 |
| ATOM | 1532 | CE  | LYS | 357 | 70.171 | 13.787 | 0.343  | 1.00 | 56.99 |
| ATOM | 1533 | NZ  | LYS | 357 | 70.208 | 13.085 | −0.970 | 1.00 | 64.78 |
| ATOM | 1534 | C   | LYS | 357 | 73.657 | 17.981 | 3.629  | 1.00 | 38.55 |
| ATOM | 1535 | O   | LYS | 357 | 74.518 | 18.079 | 2.748  | 1.00 | 42.50 |
| ATOM | 1536 | N   | HIS | 358 | 73.751 | 18.601 | 4.802  | 1.00 | 35.00 |
| ATOM | 1537 | CA  | HIS | 358 | 74.906 | 19.418 | 5.155  | 1.00 | 32.94 |
| ATOM | 1538 | CB  | HIS | 358 | 74.732 | 20.018 | 6.552  | 1.00 | 27.62 |
| ATOM | 1539 | CG  | HIS | 358 | 73.669 | 21.067 | 6.643  | 1.00 | 26.64 |
| ATOM | 1540 | CD2 | HIS | 358 | 72.330 | 20.968 | 6.819  | 1.00 | 20.85 |
| ATOM | 1541 | ND1 | HIS | 358 | 73.950 | 22.416 | 6.587  | 1.00 | 24.71 |
| ATOM | 1542 | CE1 | HIS | 358 | 72.831 | 23.103 | 6.724  | 1.00 | 21.02 |
| ATOM | 1543 | NE2 | HIS | 358 | 71.834 | 22.248 | 6.865  | 1.00 | 21.42 |
| ATOM | 1544 | C   | HIS | 358 | 76.140 | 18.520 | 5.176  | 1.00 | 36.60 |
| ATOM | 1545 | O   | HIS | 358 | 76.072 | 17.379 | 5.635  | 1.00 | 38.73 |
| ATOM | 1546 | N   | ASN | 359 | 77.267 | 19.037 | 4.702  | 1.00 | 41.40 |
| ATOM | 1547 | CA  | ASN | 359 | 78.515 | 18.277 | 4.689  | 1.00 | 45.02 |
| ATOM | 1548 | CB  | ASN | 359 | 79.441 | 18.799 | 3.587  | 1.00 | 42.57 |
| ATOM | 1549 | C   | ASN | 359 | 79.193 | 18.386 | 6.058  | 1.00 | 46.59 |
| ATOM | 1550 | O   | ASN | 359 | 80.405 | 18.588 | 6.150  | 1.00 | 52.31 |
| ATOM | 1551 | N   | ILE | 360 | 78.400 | 18.254 | 7.117  | 1.00 | 45.14 |
| ATOM | 1552 | CA  | ILE | 360 | 78.896 | 18.348 | 8.487  | 1.00 | 43.69 |
| ATOM | 1553 | CB  | ILE | 360 | 78.330 | 19.597 | 9.207  | 1.00 | 40.08 |
| ATOM | 1554 | CG2 | ILE | 360 | 78.824 | 19.657 | 10.645 | 1.00 | 32.11 |
| ATOM | 1555 | CG1 | ILE | 360 | 78.733 | 20.864 | 8.452  | 1.00 | 41.47 |
| ATOM | 1556 | CD1 | ILE | 360 | 78.057 | 22.115 | 8.954  | 1.00 | 44.93 |
| ATOM | 1557 | C   | ILE | 360 | 78.452 | 17.101 | 9.242  | 1.00 | 43.63 |
| ATOM | 1558 | O   | ILE | 360 | 77.257 | 16.797 | 9.313  | 1.00 | 45.20 |
| ATOM | 1559 | N   | PRO | 361 | 79.413 | 16.337 | 9.780  | 1.00 | 43.91 |
| ATOM | 1560 | CD  | PRO | 361 | 80.871 | 16.540 | 9.699  | 1.00 | 47.07 |
| ATOM | 1561 | CA  | PRO | 361 | 79.087 | 15.118 | 10.526 | 1.00 | 41.66 |
| ATOM | 1562 | CB  | PRO | 361 | 80.462 | 14.495 | 10.782 | 1.00 | 43.73 |
| ATOM | 1563 | CG  | PRO | 361 | 81.383 | 15.679 | 10.830 | 1.00 | 45.45 |
| ATOM | 1564 | C   | PRO | 361 | 78.332 | 15.403 | 11.832 | 1.00 | 36.42 |
| ATOM | 1565 | O   | PRO | 361 | 78.679 | 16.325 | 12.572 | 1.00 | 35.74 |
| ATOM | 1566 | N   | HIS | 362 | 77.291 | 14.610 | 12.088 | 1.00 | 33.14 |
| ATOM | 1567 | CA  | HIS | 362 | 76.462 | 14.726 | 13.292 | 1.00 | 34.09 |
| ATOM | 1568 | CB  | HIS | 362 | 77.288 | 14.413 | 14.547 | 1.00 | 33.82 |
| ATOM | 1569 | CG  | HIS | 362 | 78.132 | 13.18  | 14.424 | 1.00 | 36.04 |
| ATOM | 1570 | CD2 | HIS | 362 | 77.793 | 11.885 | 14.224 | 1.00 | 34.77 |
| ATOM | 1571 | ND1 | HIS | 362 | 79.509 | 13.212 | 14.482 | 1.00 | 37.16 |
| ATOM | 1572 | CE1 | HIS | 362 | 79.983 | 11.990 | 14.325 | 1.00 | 37.16 |
| ATOM | 1573 | NE2 | HIS | 362 | 78.962 | 11.165 | 14.167 | 1.00 | 40.13 |
| ATOM | 1574 | C   | HIS | 362 | 75.829 | 16.110 | 13.417 | 1.00 | 31.00 |
| ATOM | 1575 | O   | HIS | 362 | 75.617 | 16.608 | 14.525 | 1.00 | 30.22 |
| ATOM | 1576 | N   | PHE | 363 | 75.478 | 16.690 | 12.272 | 1.00 | 33.06 |
| ATOM | 1577 | CA  | PHE | 363 | 74.878 | 18.021 | 12.200 | 1.00 | 28.08 |
| ATOM | 1578 | CB  | PHE | 363 | 74.503 | 18.355 | 10.747 | 1.00 | 25.26 |
| ATOM | 1579 | CG  | PHE | 363 | 73.923 | 19.733 | 10.567 | 1.00 | 24.91 |
| ATOM | 1580 | CD1 | PHE | 363 | 74.750 | 20.817 | 10.320 | 1.00 | 27.60 |

APPENDIX 3-continued

TR_DMT.PDB

| ATOM | 1581 | CD2 | PHE | 363 | 72.552 | 19.948 | 10.664 | 1.00 | 25.52 |
|------|------|-----|-----|-----|--------|--------|--------|------|-------|
| ATOM | 1582 | CE1 | PHE | 363 | 74.221 | 22.1.00 | 10.175 | 1.00 | 29.70 |
| ATOM | 1583 | CE2 | PHE | 363 | 72.014 | 21.227 | 10.522 | 1.00 | 25.88 |
| ATOM | 1584 | CZ  | PHE | 363 | 72.850 | 22.304 | 10.278 | 1.00 | 21.49 |
| ATOM | 1585 | C   | PHE | 363 | 73.659 | 18.201 | 13.099 | 1.00 | 23.79 |
| ATOM | 1586 | O   | PHE | 363 | 73.587 | 19.164 | 13.863 | 1.00 | 24.48 |
| ATOM | 1587 | N   | TRP | 364 | 72.707 | 17.277 | 13.012 | 1.00 | 23.13 |
| ATOM | 1588 | CA  | TRP | 364 | 71.484 | 17.369 | 13.805 | 1.00 | 25.06 |
| ATOM | 1589 | CB  | TRP | 364 | 70.536 | 16.201 | 13.494 | 1.00 | 21.17 |
| ATOM | 1590 | CG  | TRP | 364 | 69.247 | 16.220 | 14.271 | 1.00 | 23.14 |
| ATOM | 1591 | CD2 | TRP | 364 | 68.261 | 17.266 | 14.296 | 1.00 | 27.68 |
| ATOM | 1592 | CE2 | TRP | 364 | 67.229 | 16.845 | 15.165 | 1.00 | 28.31 |
| ATOM | 1593 | CE3 | TRP | 364 | 68.149 | 18.517 | 13.671 | 1.00 | 26.46 |
| ATOM | 1594 | CD1 | TRP | 364 | 68.784 | 15.241 | 15.096 | 1.00 | 23.76 |
| ATOM | 1595 | NE1 | TRP | 364 | 67.576 | 15.607 | 15.637 | 1.00 | 32.12 |
| ATOM | 1596 | CZ2 | TRP | 364 | 66.100 | 17.628 | 15.427 | 1.00 | 25.63 |
| ATOM | 1597 | CZ3 | TRP | 364 | 67.028 | 19.294 | 13.931 | 1.00 | 25.55 |
| ATOM | 1598 | CH2 | TRP | 364 | 66.017 | 18.845 | 14.803 | 1.00 | 29.79 |
| ATOM | 1599 | C   | TRP | 364 | 71.715 | 17.531 | 15.312 | 1.00 | 27.80 |
| ATOM | 1600 | O   | TRP | 364 | 71.212 | 18.486 | 15.904 | 1.00 | 26.96 |
| ATOM | 1601 | N   | PRO | 365 | 72.458 | 16.605 | 15.955 | 1.00 | 30.69 |
| ATOM | 1602 | CD  | PRO | 365 | 72.974 | 15.308 | 15.481 | 1.00 | 31.45 |
| ATOM | 1603 | CA  | PRO | 365 | 72.687 | 16.757 | 17.397 | 1.00 | 27.97 |
| ATOM | 1604 | CB  | PRO | 365 | 73.506 | 15.512 | 17.752 | 1.00 | 26.50 |
| ATOM | 1605 | CG  | PRO | 365 | 73.057 | 14.509 | 16.757 | 1.00 | 33.47 |
| ATOM | 1606 | C   | PRO | 365 | 73.457 | 18.043 | 17.709 | 1.00 | 27.10 |
| ATOM | 1607 | O   | PRO | 365 | 73.154 | 18.736 | 18.681 | 1.00 | 26.88 |
| ATOM | 1608 | N   | LYS | 366 | 74.440 | 18.365 | 16.873 | 1.00 | 26.99 |
| ATOM | 1609 | CA  | LYS | 366 | 75.230 | 19.577 | 17.061 | 1.00 | 30.69 |
| ATOM | 1610 | CB  | LYS | 366 | 76.275 | 19.708 | 15.957 | 1.00 | 28.53 |
| ATOM | 1611 | CG  | LYS | 366 | 77.481 | 18.804 | 16.106 | 1.00 | 28.89 |
| ATOM | 1612 | CD  | LYS | 366 | 78.430 | 19.027 | 14.939 | 1.00 | 32.51 |
| ATOM | 1613 | CE  | LYS | 366 | 79.743 | 18.294 | 15.116 | 1.00 | 38.52 |
| ATOM | 1614 | NZ  | LYS | 366 | 80.632 | 18.506 | 13.939 | 1.00 | 45.28 |
| ATOM | 1615 | C   | LYS | 366 | 74.349 | 20.831 | 17.079 | 1.00 | 36.18 |
| ATOM | 1616 | O   | LYS | 366 | 74.472 | 21.672 | 17.972 | 1.00 | 39.82 |
| ATOM | 1617 | N   | LEU | 367 | 73.464 | 20.950 | 16.091 | 1.00 | 37.54 |
| ATOM | 1618 | CA  | LEU | 367 | 72.557 | 22.092 | 15.994 | 1.00 | 36.14 |
| ATOM | 1619 | CB  | LEU | 367 | 71.803 | 22.070 | 14.659 | 1.00 | 32.20 |
| ATOM | 1620 | CG  | LEU | 367 | 70.764 | 23.179 | 14.447 | 1.00 | 36.16 |
| ATOM | 1621 | CD1 | LEU | 367 | 71.402 | 24.567 | 14.618 | 1.00 | 20.60 |
| ATOM | 1622 | CD2 | LEU | 367 | 70.139 | 23.030 | 13.065 | 1.00 | 34.30 |
| ATOM | 1623 | C   | LEU | 367 | 71.561 | 22.060 | 17.143 | 1.00 | 36.84 |
| ATOM | 1624 | O   | LEU | 367 | 71.231 | 23.091 | 17.729 | 1.00 | 36.94 |
| ATOM | 1625 | N   | LEU | 368 | 71.083 | 20.866 | 17.459 | 1.00 | 37.81 |
| ATOM | 1626 | CA  | LEU | 368 | 70.130 | 20.683 | 18.536 | 1.00 | 34.83 |
| ATOM | 1627 | CB  | LEU | 368 | 69.763 | 19.205 | 18.622 | 1.00 | 36.98 |
| ATOM | 1628 | CG  | LEU | 368 | 68.421 | 18.777 | 19.205 | 1.00 | 40.34 |
| ATOM | 1629 | CD1 | LEU | 368 | 67.276 | 19.595 | 18.619 | 1.00 | 36.28 |
| ATOM | 1630 | CD2 | LEU | 368 | 68.241 | 17.299 | 18.908 | 1.00 | 39.39 |
| ATOM | 1631 | C   | LEU | 368 | 70.755 | 21.182 | 19.843 | 1.00 | 38.32 |
| ATOM | 1632 | O   | LEU | 368 | 70.059 | 21.711 | 20.707 | 1.00 | 41.87 |
| ATOM | 1633 | N   | MET | 369 | 72.075 | 21.057 | 19.962 | 1.00 | 39.46 |
| ATOM | 1634 | CA  | MET | 369 | 72.790 | 21.515 | 21.154 | 1.00 | 40.12 |
| ATOM | 1635 | CB  | MET | 369 | 74.219 | 20.971 | 21.168 | 1.00 | 41.26 |
| ATOM | 1636 | CG  | MET | 369 | 74.307 | 19.493 | 21.521 | 1.00 | 47.83 |
| ATOM | 1637 | SD  | MET | 369 | 75.961 | 18.810 | 21.289 | 1.00 | 55.72 |
| ATOM | 1638 | CE  | MET | 369 | 76.809 | 19.474 | 22.727 | 1.00 | 54.37 |
| ATOM | 1639 | C   | MET | 369 | 72.805 | 23.039 | 21.251 | 1.00 | 42.81 |
| ATOM | 1640 | O   | MET | 369 | 72.990 | 23.601 | 22.335 | 1.00 | 47.81 |
| ATOM | 1641 | N   | LYS | 370 | 72.622 | 23.708 | 20.115 | 1.00 | 40.09 |
| ATOM | 1642 | CA  | LYS | 370 | 72.588 | 25.165 | 20.080 | 1.00 | 33.65 |
| ATOM | 1643 | CB  | LYS | 370 | 72.751 | 25.677 | 18.650 | 1.00 | 30.83 |
| ATOM | 1644 | CG  | LYS | 370 | 74.138 | 25.435 | 18.078 | 1.00 | 30.98 |
| ATOM | 1645 | CD  | LYS | 370 | 75.188 | 26.198 | 18.867 | 1.00 | 37.82 |
| ATOM | 1646 | CE  | LYS | 370 | 76.591 | 2S.938 | 18.351 | 1.00 | 36.05 |
| ATOM | 1647 | NZ  | LYS | 370 | 77.034 | 24.562 | 18.667 | 1.00 | 48.68 |
| ATOM | 1648 | C   | LYS | 370 | 71.293 | 25.684 | 20.702 | 1.00 | 33.32 |
| ATOM | 1649 | O   | LYS | 370 | 71.218 | 26.842 | 21.112 | 1.00 | 34.75 |
| ATOM | 1650 | N   | VAL | 371 | 70.277 | 24.826 | 20.779 | 1.00 | 31.90 |
| ATOM | 1651 | CA  | VAL | 371 | 69.006 | 25.197 | 21.395 | 1.00 | 31.77 |
| ATOM | 1652 | CB  | VAL | 371 | 67.933 | 24.092 | 21.214 | 1.00 | 30.28 |
| ATOM | 1653 | CG1 | VAL | 371 | 66.673 | 24.429 | 21.995 | 1.00 | 30.02 |
| ATOM | 1654 | CG2 | VAL | 371 | 67.596 | 23.933 | 19.746 | 1.00 | 32.23 |
| ATOM | 1655 | C   | VAL | 371 | 69.277 | 25.417 | 22.885 | 1.00 | 34.44 |
| ATOM | 1656 | O   | VAL | 37L | 68.722 | 26.331 | 23.499 | 1.00 | 33.35 |
| ATOM | 1657 | N   | THR | 372 | 70.161 | 24.590 | 23.443 | 1.00 | 33.1S |

APPENDIX 3-continued

TR_DMT.PDB

| | | | | | | | | |
|---|---|---|---|---|---|---|---|---|
| ATOM | 1658 | CA | THR | 372 | 70.551 | 24.675 | 24.847 | 1.00 | 32.47 |
| ATOM | 1659 | CB | THR | 372 | 71.541 | 23.556 | 25.207 | 1.00 | 32.11 |
| ATOM | 1660 | OG1 | THR | 372 | 70.955 | 22.288 | 24.891 | 1.00 | 35.33 |
| ATOM | 1661 | CG2 | THR | 372 | 71.894 | 23.603 | 26.688 | 1.00 | 32.54 |
| ATOM | 1662 | C | THR | 372 | 71.226 | 26.020 | 25.108 | 1.00 | 34.49 |
| ATOM | 1663 | O | THR | 372 | 70.936 | 26.696 | 26.099 | 1.00 | 34.07 |
| ATOM | 1664 | N | ASP | 373 | 72.120 | 26.405 | 24.202 | 1.00 | 32.77 |
| ATOM | 1665 | CA | ASP | 373 | 72.830 | 27.671 | 24.315 | 1.00 | 28.08 |
| ATOM | 1666 | CB | ASP | 373 | 73.803 | 27.841 | 23.147 | 1.00 | 31.59 |
| ATOM | 1667 | CG | ASP | 373 | 74.910 | 26.789 | 23.142 | 1.00 | ,37.29 |
| ATOM | 1668 | OD1 | ASP | 373 | 75.170 | 26.169 | 24.196 | 1.00 | 40.82 |
| ATOM | 1669 | OD2 | ASP | 373 | 75.531 | 26.586 | 22.079 | 1.00 | 40.81 |
| ATOM | 1670 | C | ASP | 373 | 71.830 | 28.821 | 24.353 | 1.00 | 29.21 |
| ATOM | 1671 | O | ASP | 373 | 71.931 | 29.709 | 25.200 | 1.00 | 31.85 |
| ATOM | 1672 | N | LEU | 374 | 70.843 | 28.775 | 23.463 | 1.00 | 24.71 |
| ATOM | 1673 | CA | LEU | 374 | 69.813 | 29.802 | 23.403 | 1.00 | 25.25 |
| ATOM | 1674 | CB | LEU | 374 | 68.906 | 29.587 | 22.188 | 1.00 | 25.61 |
| ATOM | 1675 | CG | LEU | 374 | 69.480 | 30.084 | 20.858 | 1.00 | 25.51 |
| ATOM | 1676 | CD1 | LEU | 374 | 68.741 | 29.469 | 19.677 | 1.00 | 23.53 |
| ATOM | 1677 | CD2 | LEU | 374 | 69.405 | 31.596 | 20.820 | 1.00 | 21.92 |
| ATOM | 1678 | C | LEU | 374 | 68.994 | 29.827 | 24.686 | 1.00 | 26.84 |
| ATOM | 1679 | O | LEU | 374 | 68.591 | 30.895 | 25.151 | 1.00 | 28.96 |
| ATOM | 1680 | N | ARG | 375 | 68.746 | 28.651 | 25.254 | 1.00 | 31.00 |
| ATOM | 1681 | CA | ARG | 375 | 67.996 | 28.554 | 26.502 | 1.00 | 32.86 |
| ATOM | 1682 | CB | ARG | 375 | 67.831 | 27.090 | 26.924 | 1.00 | 36.80 |
| ATOM | 1683 | CG | ARG | 375 | 66.861 | 26.297 | 26.071 | 1.00 | 44.91 |
| ATOM | 1684 | CD | ARG | 375 | 65.433 | 26.731 | 26.338 | 1.00 | 58.99 |
| ATOM | 1685 | NE | ARG | 375 | 64.501 | 26.210 | 25.342 | 1.00 | 72.26 |
| ATOM | 1686 | CZ | ARG | 375 | 63.909 | 25.020 | 25.404 | 1.00 | 77.46 |
| ATOM | 1687 | NH1 | ARG | 375 | 64.147 | 24.201 | 26.422 | 1.00 | 80.94 |
| ATOM | 1688 | NH2 | ARG | 375 | 63.062 | 24.657 | 24.447 | 1.00 | 75.58 |
| ATOM | 1689 | C | ARG | 375 | 68.771 | 29.317 | 27.570 | 1.00 | 32.27 |
| ATOM | 1690 | O | ARG | 375 | 68.199 | 30.125 | 28.304 | 1.00 | 33.75 |
| ATOM | 1691 | N | MET | 376 | 70.084 | 29.098 | 27.602 | 1.00 | 32.65 |
| ATOM | 1692 | CA | MET | 376 | 70.967 | 29.753 | 28.560 | 1.00 | 35.83 |
| ATOM | 1693 | CB | MET | 376 | 72.392 | 29.210 | 28.434 | 1.00 | 39.25 |
| ATOM | 1694 | CG | MET | 376 | 72.526 | 27.751 | 28.839 | 1.00 | 54.45 |
| ATOM | 1695 | SD | MET | 376 | 74.245 | 27.212 | 28.944 | 1.00 | 73.93 |
| ATOM | 1696 | CE | MET | 376 | 74.421 | 26.270 | 27.434 | 1.00 | 67.01 |
| ATOM | 1697 | C | MET | 376 | 70.960 | 31.267 | 28.378 | 1.00 | 35.38 |
| ATOM | 1698 | O | MET | 376 | 70.882 | 32.015 | 29.353 | 1.00 | 34.73 |
| ATOM | 1699 | N | ILE | 377 | 71.038 | 31.716 | 27.129 | 1.00 | 32.51 |
| ATOM | 1700 | CA | ILE | 377 | 71.016 | 33.142 | 26.816 | 1.00 | 26.55 |
| ATOM | 1701 | CB | ILE | 377 | 71.182 | 33.370 | 25.299 | 1.00 | 24.84 |
| ATOM | 1702 | CG2 | ILE | 377 | 70.817 | 34.797 | 24.923 | 1.00 | 26.63 |
| ATOM | 1703 | CG1 | ILE | 377 | 72.616 | 33.038 | 24.890 | 1.00 | 20.66 |
| ATOM | 1704 | CD1 | ILE | 377 | 72.872 | 33.104 | 23.409 | 1.00 | 20.74 |
| ATOM | 1705 | C | ILE | 377 | 69.706 | 33.755 | 27.313 | 1.00 | 25.47 |
| ATOM | 1706 | O | ILE | 377 | 69.696 | 34.848 | 27.881 | 1.00 | 29.99 |
| ATOM | 1707 | N | GLY | 378 | 68.608 | 33.033 | 27.127 | 1.00 | 25.11 |
| ATOM | 1708 | CA | GLY | 378 | 67.321 | 33.522 | 27.580 | 1.00 | 27.82 |
| ATOM | 1709 | C | GLY | 378 | 67.279 | 33.613 | 29.095 | 1.00 | 30.90 |
| ATOM | 1710 | O | GLY | 378 | 66.740 | 34.5.79 | 29.651 | 1.00 | 31.19 |
| ATOM | 1711 | N | ALA | 379 | 67.851 | 32.611 | 29.761 | 1.00 | 31.62 |
| ATOM | 1712 | CA | ALA | 379 | 67.896 | 32.547 | 31.223 | 1.00 | 30.74 |
| ATOM | 1713 | CB | ALA | 379 | 68.433 | 31.198 | 31.671 | 1.00 | 30.82 |
| ATOM | 1714 | C | ALA | 379 | 68.756 | 33.668 | 31.801 | 1.00 | 30.07 |
| ATOM | 1715 | O | ALA | 379 | 68.327 | 34.384 | 32.708 | 1.00 | 31.05 |
| ATOM | 1716 | N | CYA | 380 | 69.966 | 33.817 | 31.273 | 1.00 | 29.72 |
| ATOM | 1717 | CA | CYA | 380 | 70.873 | 34.866 | 31.723 | 1.00 | 33.36 |
| ATOM | 1718 | CB | CYA | 380 | 72.201 | 34.809 | 30.963 | 1.00 | 38.31 |
| ATOM | 1719 | SG | CYA | 380 | 73.249 | 33.407 | 31.386 | 1.00 | 50.99 |
| ATOM | 1720 | AS | CYA | 380 | 74.982 | 33.655 | 29.929 | 1.00 | 70.37 |
| ATOM | 1721 | C | CYA | 380 | 70.226 | 36.232 | 31.535 | 1.00 | 33.40 |
| ATOM | 1722 | O | CYA | 380 | 70.246 | 37.062 | 32.442 | 1.00 | 36.41 |
| ATOM | 1723 | N | HIS | 381 | 69.615 | 36.456 | 30.374 | 1.00 | 32.55 |
| ATOM | 1724 | CA | HIS | 381 | 68.965 | 37.734 | 30.114 | 1.00 | 26.41 |
| ATOM | 1725 | CB | HIS | 381 | 68.434 | 37.811 | 28.681 | 1.00 | 20.89 |
| ATOM | 1726 | CG | HIS | 381 | 67.593 | 39.023 | 28.423 | 1.00 | 15.78 |
| ATOM | 1727 | CD2 | HIS | 381 | 67.928 | 40.277 | 28.041 | 1.00 | 12.67 |
| ATOM | 1728 | ND1 | HIS | 381 | 66.226 | 39.031 | 28.605 | 1.00 | 17.88 |
| ATOM | 1729 | CE1 | HIS | 381 | 65.756 | 40.239 | 28.353 | 1.00 | 16.27 |
| ATOM | 1730 | NE2 | HIS | 381 | 66.768 | 41.013 | 28.008 | 1.00 | 17.18 |
| ATOM | 1731 | C | HIS | 381 | 67.839 | 38.023 | 31.102 | 1.00 | 26.73 |
| ATOM | 1732 | O | HIS | 381 | 67.621 | 39.176 | 31.464 | 1.00 | 30.46 |
| ATOM | 1733 | N | ALA | 382 | 67.111 | 36.991 | 31.521 | 1.00 | 26.68 |
| ATOM | 1734 | CA | ALA | 382 | 66.010 | 37.176 | 32.464 | 1.00 | 27.90 |

APPENDIX 3-continued

TR_DMT.PDB

| ATOM | 1735 | CB | ALA | 382 | 65.237 | 35.878 | 32.642 | 1.00 | 25.29 |
|---|---|---|---|---|---|---|---|---|---|
| ATOM | 1736 | C | ALA | 382 | 66.511 | 37.697 | 33.810 | 1.00 | 31.23 |
| ATOM | 1737 | O | ALA | 382 | 65.927 | 38.617 | 34.378 | 1.00 | 37.67 |
| ATOM | 1738 | N | SER | 383 | 67.596 | 37.114 | 34.316 | 1.00 | 34.15 |
| ATOM | 1739 | CA | SER | 383 | 68.174 | 37.550 | 35.588 | 1.00 | 37.23 |
| ATOM | 1740 | CB | SER | 383 | 69.294 | 36.605 | 36.027 | 1.00 | 40.21 |
| ATOM | 1741 | OG | SER | 383 | 68.785 | 35.324 | 36.361 | 1.00 | 53.99 |
| ATOM | 1742 | C | SER | 383 | 68.727 | 38.958 | 35.417 | 1.00 | 33.67 |
| ATOM | 1743 | O | SER | 383 | 68.532 | 39.827 | 36.268 | 1.00 | 40.73 |
| ATOM | 1744 | N | ARG | 384 | 69.411 | 39.171 | 34.298 | 1.00 | 29.95 |
| ATOM | 1745 | CA | ARG | 384 | 70.000 | 40.458 | 33.957 | 1.00 | 29.77 |
| ATOM | 1746 | CB | ARG | 384 | 70.684 | 40.350 | 32.594 | 1.00 | 30.79 |
| ATOM | 1747 | CG | ARG | 384 | 71.481 | 41.558 | 32.167 | 1.00 | 31.34 |
| ATOM | 1748 | CD | ARG | 384 | 72.781 | 41.638 | 32.918 | 1.00 | 33.62 |
| ATOM | 1749 | NE | ARG | 384 | 73.657 | 42.660 | 32.358 | 1.00 | 41.68 |
| ATOM | 1750 | CZ | ARG | 384 | 74.584 | 43.310 | 33.052 | 1.00 | 41.20 |
| ATOM | 1751 | NH1 | ARG | 384 | 74.756 | 43.047 | 34.339 | 1.00 | 42.11 |
| ATOM | 1752 | NH2 | ARG | 384 | 75.349 | 44.213 | 32.455 | 1.00 | 37.27 |
| ATOM | 1753 | C | ARG | 384 | 68.910 | 41.536 | 33.911 | 1.00 | 35.72 |
| ATOM | 1754 | O | ARG | 384 | 69.090 | 42.635 | 34.439 | 1.00 | 41.66 |
| ATOM | 1755 | N | PHE | 385 | 67.768 | 41.196 | 33.318 | 1.00 | 34.30 |
| ATOM | 1756 | CA | PHE | 385 | 66.646 | 42.119 | 33.199 | 1.00 | 32.40 |
| ATOM | 1757 | CB | PHE | 385 | 65.527 | 41.502 | 32.356 | 1.00 | 29.02 |
| ATOM | 1758 | CG | PHE | 385 | 64.344 | 42.407 | 32.163 | 1.00 | 26.56 |
| ATOM | 1759 | CD1 | PHE | 385 | 64.317 | 43.320 | 31.119 | 1.00 | 26.59 |
| ATOM | 1760 | CD2 | PHE | 385 | 63.263 | 42.355 | 33.037 | 1.00 | 24.69 |
| ATOM | 1761 | CE1 | PHE | 385 | 63.231 | 44.173 | 30.947 | 1.00 | 31.70 |
| ATOM | 1762 | CE2 | PHE | 385 | 62.174 | 43.202 | 32.875 | 1.00 | 26.79 |
| ATOM | 1763 | CZ | PHE | 385 | 62.158 | 44.115 | 31.827 | 1.00 | 31.59 |
| ATOM | 1764 | C | PHE | 385 | 66.121 | 42.492 | 34.578 | 1.00 | 32.98 |
| ATOM | 1765 | O | PHE | 385 | 65.822 | 43.659 | 34.839 | 1.00 | 33.91 |
| ATOM | 1766 | N | LEU | 386 | 66.003 | 41.499 | 35.456 | 1.00 | 33.91 |
| ATOM | 1767 | CA | LEU | 386 | 65.533 | 41.736 | 36.818 | 1.00 | 38.66 |
| ATOM | 1768 | CB | LEU | 386 | 65.547 | 40.440 | 37.633 | 1.00 | 43.79 |
| ATOM | 1769 | CG | LEU | 386 | 64.327 | 39.521 | 37.525 | 1.00 | 49.81 |
| ATOM | 1770 | CD1 | LEU | 386 | 64.652 | 38.147 | 38.099 | 1.00 | 51.12 |
| ATOM | 1771 | CD2 | LEU | 386 | 63.135 | 40.148 | 38.246 | 1.00 | 49.17 |
| ATOM | 1772 | C | LEU | 386 | 66.445 | 42.761 | 37.475 | 1.00 | 38.95 |
| ATOM | 1773 | O | LEU | 386 | 65.979 | 43.682 | 38.146 | 1.00 | 42.16 |
| ATOM | 1774 | N | HIS | 387 | 67.745 | 42.613 | 37.248 | 1.00 | 33.62 |
| ATOM | 1775 | CA | HIS | 387 | 68.723 | 43.531 | 37.808 | 1.00 | 39.73 |
| ATOM | 1776 | CB | HIS | 387 | 70.138 | 42.980 | 37.639 | 1.00 | 40.71 |
| ATOM | 1777 | CG | HIS | 387 | 70.403 | 41.749 | 38.449 | 1.00 | 52.03 |
| ATOM | 1778 | CD2 | HIS | 387 | 69.573 | 40.967 | 39.181 | 1.00 | 53.85 |
| ATOM | 1779 | ND1 | HIS | 387 | 71.657 | 41.189 | 38.566 | 1.00 | 54.79 |
| ATOM | 1780 | CE1 | HIS | 387 | 71.590 | 40.114 | 39.334 | 1.00 | 56.55 |
| ATOM | 1781 | NE2 | HIS | 387 | 70.336 | 39.958 | 39.720 | 1.00 | 57.48 |
| ATOM | 1782 | C | HIS | 387 | 68.594 | 44.913 | 37.175 | 1.00 | 42.08 |
| ATOM | 1783 | O | HIS | 387 | 68.712 | 45.926 | 37.865 | 1.00 | 44.12 |
| ATOM | 1784 | N | MET | 388 | 68.318 | 44.957 | 35.874 | 1.00 | 42.38 |
| ATOM | 1785 | CA | MET | 388 | 68.154 | 46.229 | 35.175 | 1.00 | 38.00 |
| ATOM | 1786 | CB | MET | 388 | 67.840 | 46.006 | 33.692 | 1.00 | 40.21 |
| ATOM | 1787 | CG | MET | 388 | 69.009 | 45.555 | 32.829 | 1.00 | 41.26 |
| ATOM | 1788 | SD | MET | 388 | 68.500 | 45.427 | 31.089 | 1.00 | 45.51 |
| ATOM | 1789 | CE | MET | 388 | 69.089 | 43.802 | 30.645 | 1.00 | 42.40 |
| ATOM | 1790 | C | MET | 388 | 67.025 | 47.044 | 35.810 | 1.00 | 38.11 |
| ATOM | 1791 | O | MET | 388 | 67.155 | 48.255 | 35.997 | 1.00 | 38.41 |
| ATOM | 1792 | N | LYS | 389 | 65.926 | 46.374 | 36.144 | 1.00 | 39.67 |
| ATOM | 1793 | CA | LYS | 389 | 64.773 | 47.036 | 36.750 | 1.00 | 44.96 |
| ATOM | 1794 | CB | LYS | 389 | 63.570 | 46.087 | 36.818 | 1.00 | 49.52 |
| ATOM | 1795 | CG | LYS | 389 | 62.674 | 46.102 | 35.588 | 1.00 | 56.74 |
| ATOM | 1796 | CD | LYS | 389 | 62.145 | 47.509 | 35.278 | 1.00 | 68.05 |
| ATOM | 1797 | CE | LYS | 389 | 61.287 | 48.100 | 36.403 | 1.00 | 71.47 |
| ATOM | 1798 | NZ | LYS | 389 | 60.038 | 47.330 | 36.661 | 1.00 | 71.98 |
| ATOM | 1799 | C | LYS | 389 | 65.041 | 47.604 | 38.141 | 1.00 | 46.60 |
| ATOM | 1800 | O | LYS | 389 | 64.516 | 48.661 | 38.499 | 1.00 | 47.25 |
| ATOM | 1801 | N | VAL | 390 | 65.832 | 46.893 | 38.935 | 1.00 | 47.15 |
| ATOM | 1802 | CA | VAL | 390 | 66.129 | 47.353 | 40.284 | 1.00 | 50.75 |
| ATOM | 1803 | CB | VAL | 390 | 66.686 | 46.202 | 41.182 | 1.00 | 50.42 |
| ATOM | 1804 | CG1 | VAL | 390 | 68.095 | 45.802 | 40.770 | 1.00 | 47.93 |
| ATOM | 1805 | CG2 | VAL | 390 | 66.650 | 46.612 | 42.640 | 1.00 | 56.67 |
| ATOM | 1806 | C | VAL | 390 | 67.072 | 48.558 | 40.286 | 1.00 | 49.82 |
| ATOM | 1807 | O | VAL | 390 | 66.971 | 49.426 | 41.152 | 1.00 | 52.44 |
| ATOM | 1808 | N | GLU | 391 | 67.926 | 48.651 | 39.272 | 1.00 | 46.14 |
| ATOM | 1809 | CA | GLU | 391 | 68.888 | 49.741 | 39.173 | 1.00 | 43.84 |
| ATOM | 1810 | CB | GLU | 391 | 70.150 | 49.268 | 38.449 | 1.00 | 41.44 |
| ATOM | 1811 | CG | GLU | 391 | 70.837 | 48.074 | 39.095 | 1.00 | 51.12 |

APPENDIX 3-continued

TR_DMT.PDB

| ATOM | 1812 | CD | GLU | 391 | 71.218 | 48.325 | 40.540 | 1.00 | 57.29 |
|---|---|---|---|---|---|---|---|---|---|
| ATOM | 1813 | OE1 | GLU | 391 | 71.970 | 49.287 | 40.802 | 1.00 | 58.15 |
| ATOM | 1814 | OE2 | GLU | 391 | 70.764 | 47.559 | 41.416 | 1.00 | 62.51 |
| ATOM | 1815 | C | GLU | 391 | 68.386 | 51.015 | 38.501 | 1.00 | 45.94 |
| ATOM | 1816 | O | GLU | 391 | 68.567 | 52.114 | 39.033 | 1.00 | 51.14 |
| ATOM | 1817 | N | CYA | 392 | 67.727 | 50.872 | 37.354 | 1.00 | 45.84 |
| ATOM | 1818 | CA | CYA | 392 | 67.255 | 52.029 | 36.598 | 1.00 | 41.60 |
| ATOM | 1819 | CB | CYA | 392 | 67.681 | 51.889 | 35.140 | 1.00 | 42.06 |
| ATOM | 1820 | SG | CYA | 392 | 69.452 | 52.008 | 34.968 | 1.00 | 44.47 |
| ATOM | 1821 | AS | CYA | 392 | 69.867 | 50.812 | 33.150 | 1.00 | 54.22 |
| ATOM | 1822 | C | CYA | 392 | 65.779 | 52.395 | 36.683 | 1.00 | 42.27 |
| ATOM | 1823 | O | CYA | 392 | 64.937 | 51.564 | 37.029 | 1.00 | 43.91 |
| ATOM | 1824 | N | PRO | 393 | 65.451 | 53.674 | 36.414 | 1.00 | 42.79 |
| ATOM | 1825 | CD | PRO | 393 | 66.384 | 54.774 | 36.106 | 1.00 | 38.59 |
| ATOM | 1826 | CA | PRO | 393 | 64.067 | 54.159 | 36.459 | 1.00 | 44.20 |
| ATOM | 1827 | CB | PRO | 393 | 64.218 | 55.667 | 36.238 | 1.00 | 39.88 |
| ATOM | 1828 | CG | PRO | 393 | 65.487 | 55.789 | 35.459 | 1.00 | 35.88 |
| ATOM | 1829 | C | PRO | 393 | 63.178 | 53.513 | 35.398 | 1.00 | 45.29 |
| ATOM | 1830 | O | PRO | 393 | 63.600 | 53.308 | 34.257 | 1.00 | 43.97 |
| ATOM | 1831 | N | THR | 394 | 61.935 | 53.238 | 35.782 | 1.00 | 48.20 |
| ATOM | 1832 | CA | THR | 394 | 60.959 | 52.607 | 34.901 | 1.00 | 53.71 |
| ATOM | 1833 | CB | THR | 394 | 59.605 | 52.429 | 35.629 | 1.00 | 59.59 |
| ATOM | 1834 | OG1 | THR | 394 | 58.690 | 51.717 | 34.787 | 1.00 | 66.50 |
| ATOM | 1835 | CG2 | THR | 394 | 59.013 | 53.787 | 36.004 | 1.00 | 61.00 |
| ATOM | 1836 | C | THR | 394 | 60.752 | 53.358 | 33.581 | 1.00 | 51.35 |
| ATOM | 1837 | O | THR | 394 | 60.419 | 52.751 | 32.563 | 1.00 | 54.39 |
| ATOM | 1838 | N | GLU | 395 | 61.008 | 54.664 | 33.595 | 1.00 | 47.65 |
| ATOM | 1839 | CA | GLU | 395 | 60.845 | 55.509 | 32.414 | 1.00 | 44.43 |
| ATOM | 1840 | CB | GLU | 395 | 60.988 | 56.978 | 32.804 | 1.00 | 43.85 |
| ATOM | 1841 | C | GLU | 395 | 61.788 | 55.175 | 31.250 | 1.00 | 42.93 |
| ATOM | 1842 | O | GLU | 395 | 61.589 | 55.649 | 30.129 | 1.00 | 41.39 |
| ATOM | 1843 | N | LEU | 396 | 62.818 | 54.375 | 31.517 | 1.00 | 39.38 |
| ATOM | 1844 | CA | LEU | 396 | 63.782 | 53.989 | 30.486 | 1.00 | 35.70 |
| ATOM | 1845 | CB | LEU | 396 | 65.185 | 53.867 | 31.090 | 1.00 | 34.96 |
| ATOM | 1846 | CG | LEU | 396 | 65.854 | 55.141 | 31.609 | 1.00 | 36.47 |
| ATOM | 1847 | CD1 | LEU | 396 | 67.234 | 54.807 | 32.150 | 1.00 | 34.21 |
| ATOM | 1848 | CD2 | LEU | 396 | 65.959 | 56.164 | 30.491 | 1.00 | 32.74 |
| ATOM | 1849 | C | LEU | 396 | 63.407 | 52.671 | 29.803 | 1.00 | 34.60 |
| ATOM | 1850 | O | LEU | 396 | 64.086 | 52.223 | 28.873 | 1.00 | 30.36 |
| ATOM | 1851 | N | PHE | 397 | 62.325 | 52.059 | 30.269 | 1.00 | 33.02 |
| ATOM | 1852 | CA | PHE | 397 | 61.868 | 50.792 | 29.725 | 1.00 | 33.39 |
| ATOM | 1853 | CB | PHE | 397 | 61.615 | 49.782 | 30.852 | 1.00 | 34.30 |
| ATOM | 1854 | CG | PHE | 397 | 62.834 | 49.439 | 31.665 | 1.00 | 32.62 |
| ATOM | 1855 | CD1 | PHE | 397 | 63.296 | 50.301 | 32.654 | 1.00 | 32.35 |
| ATOM | 1856 | CD2 | PHE | 397 | 63.504 | 48.241 | 31.461 | 1.00 | 31.28 |
| ATOM | 1857 | CE1 | PHE | 397 | 64.407 | 49.976 | 33.426 | 1.00 | 27.01 |
| ATOM | 1858 | CE2 | PHE | 397 | 64.616 | 47.905 | 32.229 | 1.00 | 33.34 |
| ATOM | 1859 | CZ | PHE | 397 | 65.067 | 48.775 | 33.213 | 1.00 | 31.29 |
| ATOM | 1860 | C | PHE | 397 | 60.580 | 50.961 | 28.934 | 1.00 | 33.17 |
| ATOM | 1861 | O | PHE | 397 | 59.540 | 51.318 | 29.498 | 1.00 | 31.99 |
| ATOM | 1862 | N | PRO | 398 | 60.636 | 50.752 | 27.606 | 1.00 | 32.45 |
| ATOM | 1863 | CD | PRO | 398 | 61.821 | 50.493 | 26.768 | 1.00 | 28.15 |
| ATOM | 1864 | CA | PRO | 398 | 59.429 | 50.885 | 26.786 | 1.00 | 30.02 |
| ATOM | 1865 | CB | PRO | 398 | 59.921 | 50.483 | 25.394 | 1.00 | 28.15 |
| ATOM | 1866 | CG | PRO | 398 | 61.352 | 50.923 | 25.397 | 1.00 | 24.89 |
| ATOM | 1867 | C | PRO | 398 | 58.384 | 49.900 | 27.326 | 1.00 | 28.39 |
| ATOM | 1868 | O | PRO | 398 | 58.735 | 48.810 | 27.789 | 1.00 | 28.00 |
| ATOM | 1869 | N | PRO | 399 | 57.092 | 50.262 | 27.267 | 1.00 | 32.45 |
| ATOM | 1870 | CD | PRO | 399 | 56.577 | 51.511 | 26.672 | 1.00 | 34.93 |
| ATOM | 1871 | CA | PRO | 399 | 55.989 | 49.421 | 27.753 | 1.00 | 32.54 |
| ATOM | 1872 | CB | PRO | 399 | 54.755 | 50.122 | 27.188 | 1.00 | 34.47 |
| ATOM | 1873 | CG | PRO | 399 | 55.159 | 51.564 | 27.196 | 1.00 | 31.37 |
| ATOM | 1874 | C | PRO | 399 | 56.044 | 47.946 | 27.338 | 1.00 | 32.18 |
| ATOM | 1875 | O | PRO | 399 | 55.950 | 47.054 | 28.188 | 1.00 | 32.58 |
| ATOM | 1876 | N | LEU | 400 | 56.195 | 47.689 | 26.041 | 1.00 | 30.15 |
| ATOM | 1877 | CA | LEU | 400 | 56.259 | 46.314 | 25.541 | 1.00 | 32.32 |
| ATOM | 1878 | CB | LEU | 400 | 56.211 | 46.297 | 24.011 | 1.00 | 28.67 |
| ATOM | 1879 | CG | LEU | 400 | 56.028 | 44.927 | 23.351 | 1.00 | 28.77 |
| ATOM | 1880 | CD1 | LEU | 400 | 54.802 | 44.234 | 23.919 | 1.00 | 22.73 |
| ATOM | 1881 | CD2 | LEU | 400 | 55.897 | 45.096 | 21.846 | 1.00 | 27.89 |
| ATOM | 1882 | C | LEU | 400 | 57.496 | 45.561 | 26.051 | 1.00 | 32.27 |
| ATOM | 1883 | O | LEU | 400 | 57.437 | 44.358 | 26.307 | 1.00 | 32.87 |
| ATOM | 1884 | N | PHE | 401 | 58.602 | 46.279 | 26.215 | 1.00 | 32.27 |
| ATOM | 1885 | CA | PHE | 401 | 59.847 | 45.695 | 26.710 | 1.00 | 32.39 |
| ATOM | 1886 | CB | PHE | 401 | 60.946 | 46.769 | 26.711 | 1.00 | 31.38 |
| ATOM | 1887 | CG | PHE | 401 | 62.290 | 46.286 | 27.194 | 1.00 | 35.12 |
| ATOM | 1888 | CD1 | PHE | 401 | 62.835 | 45.089 | 26.729 | 1.00 | 34.68 |

APPENDIX 3-continued

TR_DMT.PDB

| ATOM | 1889 | CD2 | PHE | 401 | 63.030 | 47.051 | 28.097 | 1.00 | 34.57 |
|---|---|---|---|---|---|---|---|---|---|
| ATOM | 1890 | CE1 | PHE | 401 | 64.100 | 44.662 | 27.155 | 1.00 | 30.27 |
| ATOM | 1891 | CE2 | PHE | 401 | 64.291 | 46.635 | 28.526 | 1.00 | 33.57 |
| ATOM | 1892 | CZ | PHE | 401 | 64.828 | 45.438 | 28.054 | 1.00 | 35.74 |
| ATOM | 1893 | C | PHE | 401 | 59.599 | 45.169 | 28.129 | 1.00 | 32.21 |
| ATOM | 1894 | O | PHE | 401 | 60.002 | 44.056 | 28.478 | 1.00 | 33.36 |
| ATOM | 1895 | N | LEU | 402 | 58.902 | 45.967 | 28.929 | 1.00 | 31.85 |
| ATOM | 1896 | CA | LEU | 402 | 58.582 | 45.602 | 30.302 | 1.00 | 35.06 |
| ATOM | 1897 | CB | LEU | 402 | 57.948 | 46.789 | 31.029 | 1.00 | 34.76 |
| ATOM | 1898 | CG | LEU | 402 | 58.878 | 47.852 | 31.591 | 1.00 | 33.48 |
| ATOM | 1899 | CD1 | LEU | 402 | 58.060 | 49.010 | 32.152 | 1.00 | 32.58 |
| ATOM | 1900 | CD2 | LEU | 402 | 59.753 | 47.217 | 32.662 | 1.00 | 26.27 |
| ATOM | 1901 | C | LEU | 402 | 57.626 | 44.426 | 30.393 | 1.00 | 36.80 |
| ATOM | 1902 | O | LEU | 402 | 57.793 | 43.545 | 31.239 | 1.00 | 35.43 |
| ATOM | 1903 | N | GLU | 403 | 56.600 | 44.443 | 29.547 | 1.00 | 38.50 |
| ATOM | 1904 | CA | GLU | 403 | 55.581 | 43.401 | 29.540 | 1.00 | 40.24 |
| ATOM | 1905 | CB | GLU | 403 | 54.435 | 43.792 | 28.605 | 1.00 | 44.03 |
| ATOM | 1906 | CG | GLU | 403 | 53.239 | 42.850 | 28.666 | 1.00 | 55.53 |
| ATOM | 1907 | CD | GLU | 403 | 52.180 | 43.159 | 27.618 | 1.00 | 66.67 |
| ATOM | 1908 | OE1 | GLU | 403 | 52.151 | 44.299 | 27.095 | 1.00 | 70.81 |
| ATOM | 1909 | OE2 | GLU | 403 | 51.370 | 42.255 | 27.315 | 1.00 | 73.80 |
| ATOM | 1910 | C | GLU | 403 | 56.096 | 42.018 | 29.162 | 1.00 | 38.00 |
| ATOM | 1911 | O | GLU | 403 | 55.745 | 41.029 | 29.805 | 1.00 | 38.78 |
| ATOM | 1912 | N | VAL | 404 | 56.934 | 41.955 | 28.132 | 1.00 | 37.39 |
| ATOM | 1913 | CA | VAL | 404 | 57.475 | 40.686 | 27.652 | 1.00 | 37.05 |
| ATOM | 1914 | CB | VAL | 404 | 58.180 | 40.855 | 26.286 | 1.00 | 35.57 |
| ATOM | 1915 | CG1 | VAL | 404 | 58.677 | 39.513 | 25.776 | 1.00 | 36.85 |
| ATOM | 1916 | CG2 | VAL | 404 | 57.222 | 41.451 | 25.287 | 1.00 | 42.03 |
| ATOM | 1917 | C | VAL | 404 | 58.438 | 40.000 | 28.609 | 1.00 | 38.69 |
| ATOM | 1918 | O | VAL | 404 | 58.436 | 38.774 | 28.727 | 1.00 | 40.71 |
| ATOM | 1919 | N | PHE | 405 | 59.267 | 40.785 | 29.286 | 1.00 | 39.34 |
| ATOM | 1920 | CA | PHE | 405 | 60.250 | 40.221 | 30.198 | 1.00 | 39.33 |
| ATOM | 1921 | CB | PHE | 405 | 61.620 | 40.840 | 29.913 | 1.00 | 33.87 |
| ATOM | 1922 | CG | PHE | 405 | 62.107 | 40.609 | 28.509 | 1.00 | 32.17 |
| ATOM | 1923 | CD1 | PHE | 405 | 62.355 | 41.683 | 27.660 | 1.00 | 31.34 |
| ATOM | 1924 | CD2 | PHE | 405 | 62.315 | 39.317 | 28.032 | 1.00 | 31.98 |
| ATOM | 1925 | CE1 | PHE | 405 | 62.801 | 41.476 | 26.352 | 1.00 | 30.79 |
| ATOM | 1926 | CE2 | PHE | 405 | 62.759 | 39.099 | 26.730 | 1.00 | 26.06 |
| ATOM | 1927 | CZ | PHE | 405 | 63.004 | 40.182 | 25.889 | 1.00 | 27.98 |
| ATOM | 1928 | C | PHE | 405 | 59.905 | 40.322 | 31.682 | 1.00 | 42.64 |
| ATOM | 1929 | O | PHE | 405 | 60.785 | 40.188 | 32.534 | 1.00 | 45.10 |
| ATOM | 1930 | N | GLU | 406 | 58.630 | 40.536 | 31.988 | 1.00 | 48.95 |
| ATOM | 1931 | CA | GLU | 406 | 58.181 | 40.641 | 33.373 | 1.00 | 56.93 |
| ATOM | 1932 | CB | GLU | 406 | 56.820 | 41.324 | 33.432 | 1.00 | 56.94 |
| ATOM | 1933 | C | GLU | 406 | 58.116 | 39.263 | 34.040 | 1.00 | 61.92 |
| ATOM | 1934 | O | GLU | 406 | 57.988 | 38.256 | 33.308 | 1.00 | 67.61 |
| ATOM | 1 | O1 | HOH | 501 | 67.588 | 36.828 | 11.225 | 1.00 | 27.32 |
| ATOM | 2 | O1 | HOH | 502 | 68.647 | 41.203 | 12.940 | 1.00 | 39.54 |
| ATOM | 3 | O1 | HOH | 503 | 64.072 | 40.115 | 12.407 | 1.00 | 32.47 |
| ATOM | 4 | O1 | HOH | 504 | 62.312 | 39.659 | 16.075 | 1.00 | 17.39 |
| ATOM | 5 | O1 | HOH | 505 | 63.449 | 46.468 | 15.530 | 1.00 | 30.46 |
| ATOM | 6 | O1 | HOH | 506 | 67.191 | 15.561 | −0.279 | 1.00 | 35.96 |
| ATOM | 7 | O1 | HOH | 507 | 67.100 | 11.855 | 0.295 | 1.00 | 20.00 |
| ATOM | 8 | O1 | HOH | 508 | 61.004 | 15.510 | 0.047 | 1.00 | 20.00 |
| ATOM | 9 | O1 | HOH | 509 | 59.851 | 10.761 | 6.050 | 1.00 | 20.00 |
| ATOM | 10 | O1 | HOH | 510 | 57.553 | 11.824 | 10.360 | 1.00 | 44.63 |
| ATOM | 11 | O1 | HOH | 511 | 54.101 | 13.545 | 8.720 | 1.00 | 20.00 |
| ATOM | 12 | O1 | HOH | 512 | 55.923 | 15.916 | 12.205 | 1.00 | 29.31 |
| ATOM | 13 | O1 | HOH | 513 | 50.900 | 19.934 | 8.193 | 1.00 | 20.00 |
| ATOM | 14 | O1 | HOH | 514 | 50.474 | 22.912 | 7.942 | 1.00 | 45.34 |
| ATOM | 15 | O1 | HOH | 515 | 49.737 | 20.631 | 11.530 | 1.00 | 20.00 |
| ATOM | 16 | O1 | HOH | 516 | 50.829 | 25.467 | 13.330 | 1.00 | 20.00 |
| ATOM | 17 | O1 | HOH | 517 | 53.818 | 25.833 | 10.682 | 1.00 | 42.12 |
| ATOM | 18 | O1 | HOH | 518 | 52.591 | 31.216 | 7.313 | 1.00 | 35.55 |
| ATOM | 19 | O1 | HOH | 519 | 58.510 | 31.667 | 2.158 | 1.00 | 20.00 |
| ATOM | 20 | O1 | HOH | 520 | 58.235 | 36.751 | 2.232 | 1.00 | 20.00 |
| ATOM | 21 | O1 | HOH | 521 | 62.484 | 37.992 | 5.537 | 1.00 | 20.00 |
| ATOM | 22 | O1 | HOH | 522 | 68.184 | 36.969 | 5.889 | 1.00 | 50.08 |
| ATOM | 23 | O1 | HOH | 523 | 66.889 | 33.781 | 8.584 | 1.00 | 20.00 |
| ATOM | 24 | O1 | HOH | 524 | 67.217 | 30.836 | 3.085 | 1.00 | 34.44 |
| ATOM | 25 | O1 | HOH | 525 | 64.336 | 28.325 | 3.098 | 1.00 | 20.00 |
| ATOM | 26 | O1 | HOH | 526 | 67.667 | 26.625 | 1.519 | 1.00 | 20.00 |
| ATOM | 27 | O1 | HOH | 527 | 76.757 | 22.883 | 5.467 | 1.00 | 36.94 |
| ATOM | 28 | O1 | HOH | 528 | 72.250 | 17.936 | 6.950 | 1.00 | 36.00 |
| ATOM | 29 | O1 | HOH | 529 | 71.760 | 14.791 | 8.058 | 1.00 | 40.18 |
| ATOM | 30 | O1 | HOH | 530 | 72.884 | 14.751 | 11.484 | 1.00 | 41.44 |
| ATOM | 31 | O1 | HOH | 531 | 69.235 | 12.986 | 11.709 | 1.00 | 39.38 |

APPENDIX 3-continued

TR_DMT.PDB

| ATOM | 32 | O1 | HOH | 532 | 69.402 | 12.036 | 14.891 | 1.00 | 40.68 |
|---|---|---|---|---|---|---|---|---|---|
| ATOM | 33 | O1 | HOH | 533 | 64.560 | 10.910 | 15.076 | 1.00 | 20.00 |
| ATOM | 34 | O1 | HOH | 534 | 63.169 | 10.413 | 11.722 | 1.00 | 20.00 |
| ATOM | 35 | O1 | HOH | 535 | 66.042 | 11.455 | 11.077 | 1.00 | 41.05 |
| ATOM | 36 | O1 | HOH | 536 | 76.285 | 12.458 | 10.677 | 1.00 | 20.00 |
| ATOM | 37 | O1 | HOH | 537 | 81.094 | 22.520 | 13.435 | 1.00 | 48.70 |
| ATOM | 38 | O1 | HOH | 538 | 80.505 | 25.457 | 14.849 | 1.00 | 46.30 |
| ATOM | 39 | O1 | HOH | 539 | 77.669 | 21.932 | 18.119 | 1.00 | 43.79 |
| ATOM | 40 | O1 | HOH | 540 | 77.187 | 28.903 | 21.137 | 1.00 | 40.22 |
| ATOM | 41 | O1 | HOH | 541 | 76.420 | 30.760 | 23.658 | 1.00 | 29.63 |
| ATOM | 42 | O1 | HOH | 542 | 83.028 | 32.743 | 20.922 | 1.00 | 38.14 |
| ATOM | 43 | O1 | HOH | 543 | 82.842 | 43.133 | 17.983 | 1.00 | 39.36 |
| ATOM | 44 | O1 | HOH | 544 | 77.484 | 34.040 | 9.664 | 1.00 | 36.37 |
| ATOM | 45 | O1 | HOH | 545 | 75.904 | 32.986 | 12.256 | 1.00 | 34.93 |
| ATOM | 46 | O1 | HOH | 546 | 74.185 | 29.689 | 9.761 | 1.00 | 38.60 |
| ATOM | 47 | O1 | HOH | 547 | 64.936 | 20.644 | 23.365 | 1.00 | 36.83 |
| ATOM | 48 | O1 | HOH | 548 | 61.750 | 22.313 | 25.288 | 1.00 | 34.81 |
| ATOM | 49 | O1 | HOH | 549 | 59.544 | 21.463 | 26.162 | 1.00 | 20.00 |
| ATOM | 50 | O1 | HOH | 550 | 62.300 | 27.528 | 24.386 | 1.00 | 35.89 |
| ATOM | 51 | O1 | HOH | 551 | 58.228 | 29.424 | 24.603 | 1.00 | 25.47 |
| ATOM | 52 | O1 | HOH | 552 | 57.368 | 32.196 | 30.527 | 1.00 | 45.27 |
| ATOM | 53 | O1 | HOH | 553 | 62.063 | 36.304 | 30.245 | 1.00 | 42.26 |
| ATOM | 54 | O1 | HOH | 554 | 64.722 | 36.725 | 28.906 | 1.00 | 24.66 |
| ATOM | 55 | O1 | HOH | 555 | 62.207 | 35.851 | 26.642 | 1.00 | 30.36 |
| ATOM | 56 | O1 | HOH | 556 | 63.608 | 33.715 | 25.707 | 1.00 | 42.74 |
| ATOM | 57 | O1 | HOH | 557 | 62.979 | 38.422 | 32.977 | 1.00 | 49.93 |
| ATOM | 58 | O1 | HOH | 558 | 66.911 | 33.364 | 34.901 | 1.00 | 50.02 |
| ATOM | 59 | O1 | HOH | 559 | 72.608 | 29.636 | 31.674 | 1.00 | 37.60 |
| ATOM | 60 | O1 | HOH | 560 | 76.967 | 40.633 | 32.514 | 1.00 | 44.81 |
| ATOM | 61 | O1 | HOH | 561 | 73.613 | 41.817 | 36.847 | 1.00 | 31.79 |
| ATOM | 62 | O1 | HOH | 562 | 75.773 | 46.227 | 30.514 | 1.00 | 29.06 |
| ATOM | 63 | O1 | HOH | 563 | 79.903 | 46.178 | 30.800 | 1.00 | 41.67 |
| ATOM | 64 | O1 | HOH | 564 | 69.746 | 51.175 | 33.564 | 1.00 | 20.00 |
| ATOM | 65 | O1 | HOH | 565 | 74.320 | 52.047 | 39.438 | 1.00 | 20.00 |
| ATOM | 66 | O1 | HOH | 566 | 65.900 | 53.647 | 27.404 | 1.00 | 40.45 |
| ATOM | 67 | O1 | HOH | 567 | 68.848 | 53.076 | 17.895 | 1.00 | 39.25 |
| ATOM | 68 | O1 | HOH | 568 | 63.507 | 48.672 | 13.581 | 1.00 | 43.77 |
| ATOM | 69 | O1 | HOH | 569 | 64.625 | 46.825 | 10.331 | 1.00 | 20.00 |
| ATOM | 70 | O1 | HOH | 570 | 55.882 | 41.431 | 11.148 | 1.00 | 20.00 |
| ATOM | 71 | O1 | HOH | 571 | 52.830 | 43.513 | 20.032 | 1.00 | 35.18 |
| ATOM | 72 | O1 | HOH | 572 | 56.990 | 49.485 | 24.052 | 1.00 | 37.30 |
| ATOM | 73 | O1 | HOH | 573 | 54.188 | 47.024 | 30.900 | 1.00 | 52.93 |
| ATOM | 74 | O1 | HOH | 574 | 57.823 | 44.590 | 34.025 | 1.00 | 53.64 |
| ATOM | 75 | O1 | HOH | 575 | 47.827 | 29.597 | 30.690 | 1.00 | 37.61 |
| ATOM | 76 | O1 | HOH | 576 | 53.030 | 24.901 | 32.732 | 1.00 | 45.06 |
| ATOM | 77 | O1 | HOH | 577 | 47.569 | 19.105 | 28.647 | 1.00 | 38.88 |
| ATOM | 78 | O1 | HOH | 578 | 47.232 | 20.282 | 25.561 | 1.00 | 20.00 |
| ATOM | 79 | O1 | HOH | 579 | 51.960 | 14.869 | 25.534 | 1.00 | 49.45 |
| ATOM | 80 | O1 | HOH | 580 | 52.831 | 23.395 | 1.634 | 1.00 | 20.00 |
| ATOM | 81 | O1 | HOH | 581 | 51.472 | 22.968 | −0.900 | 1.00 | 25.10 |
| ATOM | 82 | O1 | HOH | 582 | 77.238 | 52.503 | 8.906 | 1.00 | 47.05 |
| ATOM | 2004 | C1 | DMT | 1 | 67.320 | 42.326 | 18.648 | 1.00 | 28.58 |
| ATOM | 2005 | C2 | DMT | 1 | 68.927 | 43.263 | 23.318 | 1.00 | 29.26 |
| ATOM | 2006 | C3 | DMT | 1 | 67.236 | 43.583 | 19.236 | 1.00 | 24.54 |
| ATOM | 2007 | C4 | DMT | 1 | 69.268 | 44.313 | 24.111 | 1.00 | 28.48 |
| ATOM | 2008 | C5 | DMT | 1 | 68.003 | 43.859 | 20.363 | 1.00 | 28.76 |
| ATOM | 2009 | C6 | DMT | 1 | 68.654 | 44.389 | 25.458 | 1.00 | 28.16 |
| ATOM | 2010 | C7 | DMT | 1 | 68.811 | 42.902 | 20.875 | 1.00 | 26.80 |
| ATOM | 2011 | C8 | DMT | 1 | 67.803 | 43.410 | 25.793 | 1.00 | 29.83 |
| ATOM | 2012 | C9 | DMT | 1 | 68.921 | 41.665 | 20.324 | 1.00 | 26.77 |
| ATOM | 2013 | C10 | DMT | 1 | 67.464 | 42.358 | 24.989 | 1.00 | 28.60 |
| ATOM | 2014 | C11 | DMT | 1 | 68.165 | 41.349 | 19.185 | 1.00 | 25.29 |
| ATOM | 2015 | C12 | DMT | 1 | 68.059 | 42.281 | 23.675 | 1.00 | 26.74 |
| ATOM | 2016 | C13 | DMT | 1 | 66.475 | 42.038 | 17.456 | 1.00 | 21.51 |
| ATOM | 2017 | C14 | DMT | 1 | 68.916 | 45.478 | 26.380 | 1.00 | 21.05 |
| ATOM | 2018 | C15 | DMT | 1 | 66.989 | 40.910 | 16.417 | 1.00 | 22.84 |
| ATOM | 2019 | C16 | DMT | 1 | 68.090 | 46.870 | 26.009 | 1.00 | 19.41 |
| ATOM | 2020 | C17 | DMT | 1 | 65.982 | 40.730 | 15.243 | 1.00 | 27.07 |
| ATOM | 2021 | C18 | DMT | 1 | 70.279 | 46.131 | 26.085 | 1.00 | 16.03 |
| ATOM | 2022 | C19 | DMT | 1 | 67.903 | 45.249 | 20.974 | 1.00 | 19.56 |
| ATOM | 2023 | C20 | DMT | 1 | 69.853 | 40.599 | 20.901 | 1.00 | 4.52 |
| ATOM | 2024 | N1 | DMT | 1 | 68.280 | 41.070 | 16.042 | 1.00 | 17.57 |
| ATOM | 2025 | O1 | DMT | 1 | 67.209 | 43.465 | 27.087 | 1.00 | 25.94 |
| ATOM | 2026 | O2 | DMT | 1 | 69.547 | 43.191 | 22.015 | 1.00 | 30.23 |
| ATOM | 2027 | O3 | DMT | 1 | 66.449 | 40.778 | 14.118 | 1.00 | 29.45 |

APPENDIX 3-continued

TR_DMT.PDB

| ATOM | 2028 | O4 | DMT | 1 | 64.820 | 40.564 | 15.546 | 1.00 | 26.46 |
|------|------|----|-----|---|--------|--------|--------|------|-------|

END

APPENDIX 4

TR_TRIAC.PDB

REMARK
REMARK TR_triac full length numbering
REMARK Rfactor 0.236 Rfree 0.241
REMARK Resolution 25. 2.5 all reflections
REMARK
REMARK Three cacodylate-modified cysteines:
REMARK Cys334, Cys380, Cys392
REMARK modeled as free arsenic atoms
REMARK
REMARK conserved polar HOH numbered as in TR_t3.pdb
REMARK rearrangements start 600
REMARK
REMARK side chain of certain residues modeled as ALA due to poor density;
REMARK however, residue name reflects true residue for clarity
REMARK
REMARK clone obtained from Murray et. al.
REMARK deposited sequence confirmed,
REMARK differing from that reported by Thompson et. al.
REMARK in the following codons:
REMARK 281 Thr—Ala
REMARK 285 Lys—Glu
REMARK identical to that reported by Mitsuhashi et. al.
REMARK gb:RNTRAVI X07409
JRNL      AUTH   M. B. MURRAY, N. D. ZILZ, N. L. MCCREARY, M. J. MACDONALD
JRNL      AUTH 2 H. C. TOWLE
JRNL      TITL   ISOLATION AND CHARACTERIZATION OF RAT CDNA CLONES FOR TWO
JRNL      TITL 2 DISTINCT THYROID HORMONE RECPTORS
JRNL      REF    JBC          V. 263 25 1988
JRNL      AUTH   C. C. THOMPSON, C. WEINBERGER, R. LEBO, R. M. EVANS
JRNL      TITL   IDENTIFICATION OF A NOVEL THYROID HORMONE RECEPTOR EXPRESSED
JRNL      TITL 2 IN THE MAMMALIAN CENTRAL NERVOUS SYSTEM
JRNL      REF    SCIENCE      V. 237 1987
JRNL      AUTH   T. MITSUHASHI, G. TENNYSON, V. NIKODEM
JRNL      TITL   NUCLEOTIDE SEQUENCE OF NOVEL CDNAS GENERATED BY ALTERNATIVE
JRNL      TITL 2 SPLICING OF A RAT THYROID HORMONE RECEPTOR GENE TRANSCRIPT
JRNL      REF    NUC. ACIDS. RES.       V. 16 12 1988
REMARK

| ATOM | 1  | CB  | ARG | 157 | 9.880  | −24.199 | 7.196  | 1.00 | 57.79 |
|------|----|-----|-----|-----|--------|---------|--------|------|-------|
| ATOM | 2  | CG  | ARG | 157 | 11.380 | −24.411 | 7.340  | 1.00 | 57.79 |
| ATOM | 3  | CD  | ARG | 157 | 11.960 | −23.602 | 8.486  | 1.00 | 57.79 |
| ATOM | 4  | NE  | ARG | 157 | 11.492 | −24.098 | 9.778  | 1.00 | 57.79 |
| ATOM | 5  | CZ  | ARG | 157 | 12.284 | −24.379 | 10.809 | 1.00 | 57.79 |
| ATOM | 6  | NH1 | ARG | 157 | 13.598 | −24.212 | 10.714 | 1.00 | 57.79 |
| ATOM | 7  | NH2 | ARG | 157 | 11.762 | −24.854 | 11.932 | 1.00 | 57.79 |
| ATOM | 8  | C   | ARG | 157 | 7.774  | −24.838 | 5.974  | 1.00 | 38.50 |
| ATOM | 9  | O   | ARG | 157 | 7.553  | −24.416 | 4.840  | 1.00 | 57.79 |
| ATOM | 10 | N   | ARG | 157 | 9.929  | −25.500 | 5.089  | 1.00 | 38.50 |
| ATOM | 11 | CA  | ARG | 157 | 9.183  | −25.276 | 6.360  | 1.00 | 38.50 |
| ATOM | 12 | N   | PRO | 158 | 6.802  | −24.951 | 6.895  | 1.00 | 23.08 |
| ATOM | 13 | CD  | PRO | 158 | 6.945  | −25.424 | 8.282  | 1.00 | 28.38 |
| ATOM | 14 | CA  | PRO | 158 | 5.415  | −24.562 | 6.617  | 1.00 | 23.08 |
| ATOM | 15 | CB  | PRO | 158 | 4.704  | −24.824 | 7.948  | 1.00 | 28.38 |
| ATOM | 16 | CG  | PRO | 158 | 5.801  | −24.735 | 8.966  | 1.00 | 28.38 |
| ATOM | 17 | C   | PRO | 158 | 5.210  | −23.124 | 6.132  | 1.00 | 23.08 |
| ATOM | 18 | O   | PRO | 158 | 5.678  | −22.167 | 6.753  | 1.00 | 28.38 |
| ATOM | 19 | N   | GLU | 159 | 4.504  | −23.000 | 5.012  | 1.00 | 19.26 |
| ATOM | 20 | CA  | GLU | 159 | 4.191  | −21.717 | 4.389  | 1.00 | 19.26 |
| ATOM | 21 | CB  | GLU | 159 | 4.022  | −21.912 | 2.878  | 1.00 | 24.58 |
| ATOM | 22 | CG  | GLU | 159 | 5.317  | −22.009 | 2.086  | 1.00 | 24.58 |
| ATOM | 23 | CD  | GLU | 159 | 5.849  | −20.651 | 1.659  | 1.00 | 24.58 |
| ATOM | 24 | OE1 | GLU | 159 | 5.034  | −19.722 | 1.476  | 1.00 | 24.58 |
| ATOM | 25 | OE2 | GLU | 159 | 7.080  | −20.513 | 1.490  | 1.00 | 24.58 |
| ATOM | 26 | C   | GLU | 159 | 2.879  | −21.193 | 4.968  | 1.00 | 19.26 |

APPENDIX 4-continued

TR_TRIAC.PDB

| ATOM | 27 | O | GLU | 159 | 2.152 | −21.931 | 5.636 | 1.00 | 24.58 |
|---|---|---|---|---|---|---|---|---|---|
| ATOM | 28 | N | PRO | 160 | 2.579 | −19.899 | 4.765 | 1.00 | 17.44 |
| ATOM | 29 | CD | PRO | 160 | 3.442 | −18.817 | 4.259 | 1.00 | 13.94 |
| ATOM | 30 | CA | PRO | 160 | 1.323 | −19.360 | 5.299 | 1.00 | 17.44 |
| ATOM | 31 | CB | PRO | 160 | 1.414 | −17.872 | 4.956 | 1.00 | 13.94 |
| ATOM | 32 | CG | PRO | 160 | 2.880 | −17.604 | 4.952 | 1.00 | 13.94 |
| ATOM | 33 | C | PRO | 160 | 0.098 | −20.006 | 4.639 | 1.00 | 17.44 |
| ATOM | 34 | O | PRO | 160 | 0.067 | −20.207 | 3.423 | 1.00 | 13.94 |
| ATOM | 35 | N | THR | 161 | −0.895 | −20.352 | 5.450 | 1.00 | 17.00 |
| ATOM | 36 | CA | THR | 161 | −2.119 | −20.957 | 4.941 | 1.00 | 17.00 |
| ATOM | 37 | CB | THR | 161 | −2.958 | −21.587 | 6.086 | 1.00 | 20.43 |
| ATOM | 38 | OG1 | THR | 161 | −3.441 | −20.557 | 6.959 | 1.00 | 20.43 |
| ATOM | 39 | CG2 | THR | 161 | −2.121 | −22.576 | 6.888 | 1.00 | 20.43 |
| ATOM | 40 | C | THR | 161 | −2.929 | −19.843 | 4.284 | 1.00 | 17.00 |
| ATOM | 41 | O | THR | 161 | −2.691 | −18.660 | 4.547 | 1.00 | 20.43 |
| ATOM | 42 | N | PRO | 162 | −3.918 | −20.200 | 3.449 | 1.00 | 12.94 |
| ATOM | 43 | CD | PRO | 162 | −4.311 | −21.559 | 3.038 | 1.00 | 17.56 |
| ATOM | 44 | CA | PRO | 162 | −4.743 | −19.190 | 2.780 | 1.00 | 12.94 |
| ATOM | 45 | CB | PRO | 162 | −5.846 | −20.029 | 2.143 | 1.00 | 17.56 |
| ATOM | 46 | CG | PRO | 162 | −5.147 | −21.303 | 1.816 | 1.00 | 17.56 |
| ATOM | 47 | C | PRO | 162 | −5.317 | −18.171 | 3.763 | 1.00 | 12.94 |
| ATOM | 48 | O | PRO | 162 | −5.305 | −16.964 | 3.503 | 1.00 | 17.56 |
| ATOM | 49 | N | GLU | 163 | −5.790 | −18.668 | 4.903 | 1.00 | 19.45 |
| ATOM | 50 | CA | GLU | 163 | −6.374 | −17.828 | 5.943 | 1.00 | 19.45 |
| ATOM | 51 | CB | GLU | 163 | −6.994 | −18.690 | 7.047 | 1.00 | 49.96 |
| ATOM | 52 | CG | GLU | 163 | −8.178 | −19.558 | 6.606 | 1.00 | 49.96 |
| ATOM | 53 | CD | GLU | 163 | −7.782 | −20.720 | 5.697 | 1.00 | 49.96 |
| ATOM | 54 | OE1 | GLU | 163 | −6.735 | −21.361 | 5.951 | 1.00 | 49.96 |
| ATOM | 55 | OE2 | GLU | 163 | −8.527 | −20.999 | 4.731 | 1.00 | 49.96 |
| ATOM | 56 | C | GLU | 163 | −5.330 | −16.897 | 6.548 | 1.00 | 19.45 |
| ATOM | 57 | O | GLU | 163 | −5.614 | −15.731 | 6.832 | 1.00 | 49.96 |
| ATOM | 58 | N | GLU | 164 | −4.120 | −17.417 | 6.734 | 1.00 | 22.03 |
| ATOM | 59 | CA | GLU | 164 | −3.033 | −16.634 | 7.305 | 1.00 | 22.03 |
| ATOM | 60 | CB | GLU | 164 | −1.875 | −17.541 | 7.725 | 1.00 | 17.15 |
| ATOM | 61 | CG | GLU | 164 | −2.198 | −18.414 | 8.937 | 1.00 | 17.15 |
| ATOM | 62 | CD | GLU | 164 | −1.114 | −19.434 | 9.249 | 1.00 | 17.15 |
| ATOM | 63 | OE1 | GLU | 164 | −0.283 | −19.710 | 8.361 | 1.00 | 17.15 |
| ATOM | 64 | OE2 | GLU | 164 | −1.099 | −19.968 | 10.379 | 1.00 | 17.15 |
| ATOM | 65 | C | GLU | 164 | −2.559 | −15.542 | 6.354 | 1.00 | 22.03 |
| ATOM | 66 | O | GLU | 164 | −2.160 | −14.470 | 6.802 | 1.00 | 17.15 |
| ATOM | 67 | N | TRP | 165 | −2.607 | −15.805 | 5.048 | 1.00 | 10.72 |
| ATOM | 68 | CA | TRP | 165 | −2.205 | −14.803 | 4.063 | 1.00 | 10.72 |
| ATOM | 69 | CB | TRP | 165 | −2.223 | −15.377 | 2.644 | 1.00 | 2.00 |
| ATOM | 70 | CG | TRP | 165 | −0.928 | −16.003 | 2.227 | 1.00 | 2.00 |
| ATOM | 71 | CD2 | TRP | 165 | 0.350 | −15.358 | 2.131 | 1.00 | 2.00 |
| ATOM | 72 | CE2 | TRP | 165 | 1.275 | −16.326 | 1.685 | 1.00 | 2.00 |
| ATOM | 73 | CE3 | TRP | 165 | 0.804 | −14.054 | 2.379 | 1.00 | 2.00 |
| ATOM | 74 | CD1 | TRP | 165 | −0.731 | −17.298 | 1.848 | 1.00 | 2.00 |
| ATOM | 75 | NE1 | TRP | 165 | 0.587 | −17.500 | 1.521 | 1.00 | 2.00 |
| ATOM | 76 | CZ2 | TRP | 165 | 2.627 | −16.036 | 1.479 | 1.00 | 2.00 |
| ATOM | 77 | CZ3 | TRP | 165 | 2.152 | −13.764 | 2.174 | 1.00 | 2.00 |
| ATOM | 78 | CH2 | TRP | 165 | 3.046 | −14.754 | 1.729 | 1.00 | 2.00 |
| ATOM | 79 | C | TRP | 165 | −3.137 | −13.601 | 4.149 | 1.00 | 10.72 |
| ATOM | 80 | O | TRP | 165 | −2.717 | −12.463 | 3.925 | 1.00 | 2.00 |
| ATOM | 81 | N | ASP | 166 | −4.408 | −13.861 | 4.441 | 1.00 | 14.80 |
| ATOM | 82 | CA | ASP | 166 | −5.397 | −12.796 | 4.580 | 1.00 | 14.80 |
| ATOM | 83 | CB | ASP | 166 | −6.812 | −13.370 | 4.698 | 1.00 | 28.74 |
| ATOM | 84 | CG | ASP | 166 | −7.298 | −13.999 | 3.403 | 1.00 | 28.74 |
| ATOM | 85 | OD1 | ASP | 166 | −6.909 | −13.511 | 2.320 | 1.00 | 28.74 |
| ATOM | 86 | OD2 | ASP | 166 | −8.071 | −14.978 | 3.466 | 1.00 | 28.74 |
| ATOM | 87 | C | ASP | 166 | −5.063 | −11.981 | 5.819 | 1.00 | 14.80 |
| ATOM | 88 | O | ASP | 166 | −5.056 | −10.749 | 5.775 | 1.00 | 28.74 |
| ATOM | 89 | N | LEU | 167 | −4.745 | −12.682 | 6.906 | 1.00 | 11.01 |
| ATOM | 90 | CA | LEU | 167 | −4.383 | −12.044 | 8.166 | 1.00 | 11.01 |
| ATOM | 91 | CB | LEU | 167 | −4.036 | −13.103 | 9.214 | 1.00 | 31.53 |
| ATOM | 92 | CG | LEU | 167 | −4.672 | −12.975 | 10.601 | 1.00 | 31.53 |
| ATOM | 93 | CD1 | LEU | 167 | −3.806 | −13.709 | 11.619 | 1.00 | 31.53 |
| ATOM | 94 | CD2 | LEU | 167 | −4.820 | −11.507 | 10.989 | 1.00 | 31.53 |
| ATOM | 95 | C | LEU | 167 | −3.161 | −11.159 | 7.933 | 1.00 | 11.01 |
| ATOM | 96 | O | LEU | 167 | −3.120 | −10.006 | 8.367 | 1.00 | 31.53 |
| ATOM | 97 | N | ILE | 168 | −2.180 | −11.714 | 7.228 | 1.00 | 13.18 |
| ATOM | 98 | CA | ILE | 168 | −0.937 | −11.027 | 6.900 | 1.00 | 13.18 |
| ATOM | 99 | CB | ILE | 168 | 0.015 | −11.968 | 6.113 | 1.00 | 18.30 |
| ATOM | 100 | CG2 | ILE | 168 | 1.118 | −11.182 | 5.414 | 1.00 | 18.30 |
| ATOM | 101 | CG1 | ILE | 168 | 0.604 | −13.013 | 7.063 | 1.00 | 18.30 |
| ATOM | 102 | CD1 | ILE | 168 | 1.379 | −14.111 | 6.373 | 1.00 | 18.30 |
| ATOM | 103 | C | ILE | 168 | −1.185 | −9.747 | 6.107 | 1.00 | 13.18 |

APPENDIX 4-continued

TR_TRIAC.PDB

| ATOM | 104 | O | ILE | 168 | −0.637 | −8.697 | 6.437 | 1.00 | 18.30 |
|---|---|---|---|---|---|---|---|---|---|
| ATOM | 105 | N | HIS | 169 | −2.032 | −9.831 | 5.084 | 1.00 | 12.99 |
| ATOM | 106 | CA | HIS | 169 | −2.342 | −8.674 | 4.245 | 1.00 | 12.99 |
| ATOM | 107 | CB | HIS | 169 | −3.218 | −9.087 | 3.062 | 1.00 | 13.09 |
| ATOM | 108 | CG | HIS | 169 | −2.553 | −10.045 | 2.126 | 1.00 | 13.09 |
| ATOM | 109 | CD2 | HIS | 169 | −1.247 | −10.223 | 1.811 | 1.00 | 13.09 |
| ATOM | 110 | ND1 | HIS | 169 | −3.249 | −11.000 | 1.416 | 1.00 | 13.09 |
| ATOM | 111 | CE1 | HIS | 169 | −2.403 | −11.728 | 0.710 | 1.00 | 13.09 |
| ATOM | 112 | NE2 | HIS | 169 | −1.181 | −11.277 | 0.936 | 1.00 | 13.09 |
| ATOM | 113 | C | HIS | 169 | −3.017 | −7.550 | 5.017 | 1.00 | 12.99 |
| ATOM | 114 | O | HIS | 169 | −2.680 | −6.377 | 4.839 | 1.00 | 13.09 |
| ATOM | 115 | N | VAL | 170 | −3.978 | −7.909 | 5.862 | 1.00 | 13.36 |
| ATOM | 116 | CA | VAL | 170 | −4.696 | −6.926 | 6.664 | 1.00 | 13.36 |
| ATOM | 117 | CB | VAL | 110 | −5.863 | −7.572 | 7.443 | 1.00 | 20.12 |
| ATOM | 118 | CG1 | VAL | 170 | −6.541 | −6.540 | 8.340 | 1.00 | 20.12 |
| ATOM | 119 | CG2 | VAL | 170 | −6.869 | −8.165 | 6.471 | 1.00 | 20.12 |
| ATOM | 120 | C | VAL | 170 | −3.741 | −6.246 | 7.639 | 1.00 | 13.36 |
| ATOM | 121 | O | VAL | 170 | −3.728 | −5.019 | 7.744 | 1.00 | 20.12 |
| ATOM | 122 | N | ALA | 171 | −2.920 | −7.043 | 8.320 | 1.00 | 11.04 |
| ATOM | 123 | CA | ALA | 171 | −1.953 | −6.515 | 9.277 | 1.00 | 11.04 |
| ATOM | 124 | CB | ALA | 171 | −1.249 | −7.653 | 10.005 | 1.00 | 13.43 |
| ATOM | 125 | C | ALA | 171 | −0.931 | −5.613 | 8.588 | 1.00 | 11.04 |
| ATOM | 126 | O | ALA | 171 | −0.658 | −4.507 | 9.058 | 1.00 | 13.43 |
| ATOM | 127 | N | THR | 172 | −0.382 | −6.076 | 7.469 | 1.00 | 12.51 |
| ATOM | 128 | CA | THR | 172 | 0.606 | −5.301 | 6.723 | 1.00 | 12.51 |
| ATOM | 129 | CB | THR | 172 | 1.062 | −6.032 | 5.445 | 1.00 | 14.17 |
| ATOM | 130 | OG1 | THR | 172 | 1.548 | −7.338 | 5.782 | 1.00 | 14.17 |
| ATOM | 131 | CG2 | THR | 172 | 2.175 | −5.255 | 4.756 | 1.00 | 14.17 |
| ATOM | 132 | C | THR | 172 | 0.045 | −3.936 | 6.337 | 1.00 | 12.51 |
| ATOM | 133 | O | THR | 172 | 0.701 | −2.910 | 6.537 | 1.00 | 14.17 |
| ATOM | 134 | N | GLU | 173 | −1.178 | −3.921 | 5.815 | 1.00 | 17.79 |
| ATOM | 135 | CA | GLU | 173 | −1.818 | −2.675 | 5.421 | 1.00 | 17.79 |
| ATOM | 136 | CB | GLU | 173 | −3.130 | −2.946 | 4.682 | 1.00 | 49.44 |
| ATOM | 137 | CG | GLU | 173 | −3.823 | −1.679 | 4.171 | 1.00 | 49.44 |
| ATOM | 138 | CD | GLU | 173 | −2.930 | −0.835 | 3.266 | 1.00 | 49.44 |
| ATOM | 139 | OE1 | GLU | 173 | −2.075 | −1.408 | 2.552 | 1.00 | 49.44 |
| ATOM | 140 | OE2 | GLU | 173 | −3.085 | 0.404 | 3.269 | 1.00 | 49.44 |
| ATOM | 141 | C | GLU | 173 | −2.072 | −1.780 | 6.628 | 1.00 | 17.79 |
| ATOM | 142 | O | GLU | 173 | −1.854 | −0.568 | 6.557 | 1.00 | 49.44 |
| ATOM | 143 | N | ALA | 174 | −2.525 | −2.375 | 7.731 | 1.00 | 13.12 |
| ATOM | 144 | CA | ALA | 174 | −2.798 | −1.631 | 8.957 | 1.00 | 13.12 |
| ATOM | 145 | CB | ALA | 174 | −3.226 | −2.576 | 10.068 | 1.00 | 17.51 |
| ATOM | 146 | C | ALA | 174 | −1.556 | −0.856 | 9.375 | 1.00 | 13.12 |
| ATOM | 147 | O | ALA | 174 | −1.634 | 0.319 | 9.735 | 1.00 | 17.51 |
| ATOM | 148 | N | HIS | 175 | −0.409 | −1.521 | 9.317 | 1.00 | 12.20 |
| ATOM | 149 | CA | HIS | 175 | 0.851 | −0.895 | 9.679 | 1.00 | 12.20 |
| ATOM | 150 | CB | HIS | 175 | 1.944 | −1.949 | 9.886 | 1.00 | 17.52 |
| ATOM | 151 | CG | HIS | 175 | 3.302 | −1.365 | 10.136 | 1.00 | 17.52 |
| ATOM | 152 | CD2 | HIS | 175 | 3.733 | −0.468 | 11.055 | 1.00 | 17.52 |
| ATOM | 153 | ND1 | HIS | 175 | 4.400 | −1.679 | 9.364 | 1.00 | 17.52 |
| ATOM | 154 | CE1 | HIS | 175 | 5.447 | −0.999 | 9.793 | 1.00 | 17.52 |
| ATOM | 155 | NE2 | HIS | 175 | 5.070 | −0.258 | 10.818 | 1.00 | 17.52 |
| ATOM | 156 | C | HIS | 175 | 1.311 | 0.133 | 8.654 | 1.00 | 12.20 |
| ATOM | 157 | O | HIS | 175 | 1.700 | 1.240 | 9.024 | 1.00 | 17.52 |
| ATOM | 158 | N | ARG | 176 | 1.291 | −0.233 | 7.375 | 1.00 | 12.54 |
| ATOM | 159 | CA | ARG | 176 | 1.735 | 0.677 | 6.328 | 1.00 | 12.54 |
| ATOM | 160 | CB | ARG | 176 | 1.662 | 0.017 | 4.950 | 1.00 | 50.41 |
| ATOM | 161 | CG | ARG | 176 | 2.683 | −1.088 | 4.730 | 1.00 | 50.41 |
| ATOM | 162 | CD | ARG | 176 | 2.666 | −1.565 | 3.299 | 1.00 | 50.41 |
| ATOM | 163 | NE | ARG | 176 | 3.682 | −2.571 | 2.989 | 1.00 | 50.41 |
| ATOM | 164 | CZ | ARG | 176 | 3.577 | −3.472 | 2.012 | 1.00 | 50.41 |
| ATOM | 165 | NH1 | ARG | 176 | 2.496 | −3.513 | 1.236 | 1.00 | 50.41 |
| ATOM | 166 | NH2 | ARG | 176 | 4.536 | −4.376 | 1.841 | 1.00 | 50.41 |
| ATOM | 167 | C | ARG | 176 | 0.972 | 1.988 | 6.306 | 1.00 | 12.54 |
| ATOM | 168 | O | ARG | 176 | 1.561 | 3.040 | 6.087 | 1.00 | 50.41 |
| ATOM | 169 | N | SER | 177 | −0.326 | 1.935 | 6.581 | 1.00 | 24.74 |
| ATOM | 170 | CA | SER | 177 | −1.147 | 3.145 | 6.584 | 1.00 | 24.74 |
| ATOM | 171 | CB | SER | 177 | −2.622 | 2.792 | 6.414 | 1.00 | 21.56 |
| ATOM | 172 | OG | SER | 177 | −3.069 | 1.913 | 7.436 | 1.00 | 21.56 |
| ATOM | 173 | C | SER | 177 | −0.960 | 4.013 | 7.832 | 1.00 | 24.74 |
| ATOM | 174 | O | SER | 177 | −1.401 | 5.159 | 7.863 | 1.00 | 21.56 |
| ATOM | 175 | N | THR | 178 | −0.347 | 3.453 | 8.870 | 1.00 | 17.96 |
| ATOM | 176 | CA | THR | 178 | −0.104 | 4.181 | 10.115 | 1.00 | 17.96 |
| ATOM | 177 | CB | THR | 178 | −0.736 | 3.440 | 11.323 | 1.00 | 19.76 |
| ATOM | 178 | OG1 | THR | 178 | −0.265 | 2.091 | 11.361 | 1.00 | 19.76 |
| ATOM | 179 | CG2 | THR | 178 | −2.253 | 3.443 | 11.211 | 1.00 | 19.76 |
| ATOM | 180 | C | THR | 178 | 1.376 | 4.395 | 10.382 | 1.00 | 17.96 |

APPENDIX 4-continued

TR_TRIAC.PDB

| ATOM | 181 | O | THR | 178 | 1.760 | 4.880 | 11.445 | 1.00 | 19.76 |
|---|---|---|---|---|---|---|---|---|---|
| ATOM | 182 | N | ASN | 179 | 2.207 | 4.024 | 9.417 | 1.00 | 25.88 |
| ATOM | 183 | CA | ASN | 179 | 3.654 | 4.180 | 9.546 | 1.00 | 25.88 |
| ATOM | 184 | CB | ASN | 179 | 4.362 | 2.974 | 8.943 | 1.00 | 44.29 |
| ATOM | 185 | CG | ASN | 179 | 5.817 | 2.871 | 9.368 | 1.00 | 44.29 |
| ATOM | 186 | OD1 | ASN | 179 | 6.129 | 2.768 | 10.564 | 1.00 | 44.29 |
| ATOM | 187 | ND2 | ASN | 179 | 6.719 | 2.830 | 8.391 | 1.00 | 44.29 |
| ATOM | 188 | C | ASN | 179 | 4.078 | 5.458 | 8.823 | 1.00 | 25.88 |
| ATOM | 189 | O | ASN | 179 | 4.150 | 5.495 | 7.590 | 1.00 | 44.29 |
| ATOM | 190 | N | ALA | 180 | 4.332 | 6.502 | 9.604 | 1.00 | 45.20 |
| ATOM | 191 | CA | ALA | 180 | 4.740 | 7.818 | 9.126 | 1.00 | 45.20 |
| ATOM | 192 | CB | ALA | 180 | 5.026 | 8.743 | 10.313 | 1.00 | 36.14 |
| ATOM | 193 | C | ALA | 180 | 5.931 | 7.808 | 8.170 | 1.00 | 45.20 |
| ATOM | 194 | O | ALA | 180 | 6.918 | 7.097 | 8.372 | 1.00 | 36.14 |
| ATOM | 195 | N | ALA | 181 | 5.784 | 8.552 | 7.086 | 1.00 | 44.05 |
| ATOM | 196 | CA | ALA | 181 | 6.834 | 8.661 | 6.072 | 1.00 | 44.05 |
| ATOM | 197 | CB | ALA | 181 | 8.170 | 9.116 | 6.722 | 1.00 | 50.21 |
| ATOM | 198 | C | ALA | 181 | 7.069 | 7.427 | 5.196 | 1.00 | 44.05 |
| ATOM | 199 | O | ALA | 181 | 7.663 | 7.550 | 4.118 | 1.00 | 50.21 |
| ATOM | 200 | N | GLY | 182 | 6.567 | 6.268 | 5.622 | 1.00 | 39.06 |
| ATOM | 201 | CA | GLY | 182 | 6.756 | 5.040 | 4.867 | 1.00 | 39.06 |
| ATOM | 202 | C | GLY | 182 | 8.202 | 4.769 | 4.482 | 1.00 | 39.06 |
| ATOM | 203 | O | GLY | 182 | 9.096 | 4.785 | 5.334 | 1.00 | 48.58 |
| ATOM | 204 | N | SER | 183 | 8.438 | 4.564 | 3.189 | 1.00 | 64.55 |
| ATOM | 205 | CA | SER | 183 | 9.781 | 4.270 | 2.693 | 1.00 | 64.55 |
| ATOM | 206 | CB | SER | 183 | 9.690 | 3.402 | 1.430 | 1.00 | 67.68 |
| ATOM | 207 | OG | SER | 183 | 8.822 | 3.978 | 0.467 | 1.00 | 67.68 |
| ATOM | 208 | C | SER | 183 | 10.643 | 5.510 | 2.437 | 1.00 | 64.55 |
| ATOM | 209 | O | SER | 183 | 11.839 | 5.407 | 2.158 | 1.00 | 67.68 |
| ATOM | 210 | N | HIS | 184 | 10.035 | 6.683 | 2.579 | 1.00 | 52.73 |
| ATOM | 211 | CA | HIS | 184 | 10.725 | 7.953 | 2.352 | 1.00 | 52.73 |
| ATOM | 212 | CB | HIS | 184 | 9.772 | 8.955 | 1.698 | 1.00 | 44.77 |
| ATOM | 213 | C | HIS | 184 | 11.364 | 8.582 | 3.595 | 1.00 | 52.73 |
| ATOM | 214 | O | HIS | 184 | 11.837 | 9.722 | 3.540 | 1.00 | 44.77 |
| ATOM | 215 | N | TRP | 185 | 11.420 | 7.842 | 4.699 | 1.00 | 54.14 |
| ATOM | 216 | CA | TRP | 185 | 11.977 | 8.389 | 5.940 | 1.00 | 54.14 |
| ATOM | 217 | CB | TRP | 185 | 11.813 | 7.395 | 7.104 | 1.00 | 40.24 |
| ATOM | 218 | CG | TRP | 185 | 12.605 | 6.123 | 6.991 | 1.00 | 40.24 |
| ATOM | 219 | CD2 | TRP | 185 | 13.894 | 5.873 | 7.551 | 1.00 | 40.24 |
| ATOM | 220 | CE2 | TRP | 185 | 14.245 | 4.543 | 7.221 | 1.00 | 40.24 |
| ATOM | 221 | CE3 | TRP | 185 | 14.791 | 6.641 | 8.300 | 1.00 | 40.24 |
| ATOM | 222 | CD1 | TRP | 185 | 12.227 | 4.973 | 6.359 | 1.00 | 40.24 |
| ATOM | 223 | NE1 | TRP | 185 | 13.210 | 4.015 | 6.496 | 1.00 | 40.24 |
| ATOM | 224 | CZ2 | TRP | 185 | 15.461 | 3.968 | 7.619 | 1.00 | 40.24 |
| ATOM | 225 | CZ3 | TRP | 185 | 15.996 | 6.073 | 8.696 | 1.00 | 40.24 |
| ATOM | 226 | CH2 | TRP | 185 | 16.319 | 4.747 | 8.353 | 1.00 | 40.24 |
| ATOM | 227 | C | TRP | 185 | 13.432 | 8.870 | 5.819 | 1.00 | 54.14 |
| ATOM | 228 | O | TRP | 185 | 13.759 | 10.008 | 6.168 | 1.00 | 40.24 |
| ATOM | 229 | N | LYS | 186 | 14.277 | 8.032 | 5.232 | 1.00 | 43.72 |
| ATOM | 230 | CA | LYS | 186 | 15.694 | 8.329 | 5.035 | 1.00 | 43.72 |
| ATOM | 231 | CB | LYS | 186 | 16.353 | 7.168 | 4.282 | 1.00 | 64.14 |
| ATOM | 232 | CG | LYS | 186 | 17.830 | 7.355 | 3.945 | 1.00 | 64.14 |
| ATOM | 233 | CD | LYS | 186 | 18.758 | 7.175 | 5.139 | 1.00 | 64.14 |
| ATOM | 234 | CE | LYS | 186 | 20.195 | 7.060 | 4.652 | 1.00 | 64.14 |
| ATOM | 235 | NZ | LYS | 186 | 20.348 | 5.838 | 3.805 | 1.00 | 64.14 |
| ATOM | 236 | C | LYS | 186 | 15.900 | 9.634 | 4.263 | 1.00 | 43.72 |
| ATOM | 237 | O | LYS | 186 | 16.948 | 10.256 | 4.366 | 1.00 | 64.14 |
| ATOM | 238 | N | GLN | 187 | 14.892 | 10.032 | 3.491 | 1.00 | 58.06 |
| ATOM | 239 | CA | GLN | 187 | 14.958 | 11.244 | 2.682 | 1.00 | 58.06 |
| ATOM | 240 | CB | GLN | 187 | 14.288 | 10.997 | 1.321 | 1.00 | 74.68 |
| ATOM | 241 | CG | GLN | 187 | 14.639 | 9.662 | 0.667 | 1.00 | 74.68 |
| ATOM | 242 | CD | GLN | 187 | 16.133 | 9.397 | 0.607 | 1.00 | 74.68 |
| ATOM | 243 | OE1 | GLN | 187 | 16.926 | 10.312 | 0.381 | 1.00 | 74.68 |
| ATOM | 244 | NE2 | GLN | 187 | 16.528 | 8.156 | 0.855 | 1.00 | 74.68 |
| ATOM | 245 | C | GLN | 187 | 14.322 | 12.466 | 3.342 | 1.00 | 58.06 |
| ATOM | 246 | O | GLN | 187 | 14.897 | 13.551 | 3.358 | 1.00 | 74.68 |
| ATOM | 247 | N | ARG | 188 | 13.117 | 12.280 | 3.866 | 1.00 | 54.11 |
| ATOM | 248 | CA | ARG | 188 | 12.363 | 13.360 | 4.505 | 1.00 | 54.11 |
| ATOM | 249 | CB | ARG | 188 | 10.889 | 13.115 | 4.334 | 1.00 | 53.33 |
| ATOM | 250 | C | ARG | 188 | 12.654 | 13.626 | 5.977 | 1.00 | 54.11 |
| ATOM | 251 | O | ARG | 188 | 11.879 | 14.298 | 6.659 | 1.00 | 53.33 |
| ATOM | 252 | N | ARG | 189 | 13.754 | 13.090 | 6.473 | 1.00 | 39.52 |
| ATOM | 253 | CA | ARG | 189 | 14.089 | 13.271 | 7.875 | 1.00 | 39.52 |
| ATOM | 254 | CB | ARG | 189 | 14.594 | 11.959 | 8.482 | 1.00 | 60.85 |
| ATOM | 255 | CG | ARG | 189 | 15.969 | 11.555 | 7.991 | 1.00 | 60.85 |
| ATOM | 256 | CD | ARG | 189 | 16.442 | 10.298 | 8.693 | 1.00 | 60.85 |
| ATOM | 257 | NE | ARG | 189 | 17.833 | 9.963 | 8.385 | 1.00 | 60.85 |

APPENDIX 4-continued

TR_TRIAC.PDB

| ATOM | 258 | CZ  | ARG | 189  | 18.627 | 9.261  | 9.190  | 1.00 | 60.85 |
| ATOM | 259 | NH1 | ARG | 189  | 18.178 | 8.805  | 10.356 | 1.00 | 60.85 |
| ATOM | 260 | NH2 | ARG | 189  | 19.882 | 9.021  | 8.841  | 1.00 | 60.85 |
| ATOM | 261 | C   | ARG | 189  | 15.109 | 14.378 | 8.109  | 1.00 | 39.52 |
| ATOM | 262 | O   | ARG | 189  | 16.037 | 14.565 | 7.320  | 1.00 | 60.85 |
| ATOM | 263 | N   | LYS | 190  | 14.934 | 15.100 | 9.212  | 1.00 | 44.13 |
| ATOM | 264 | CA  | LYS | 190  | 15.834 | 16.183 | 9.586  | 1.00 | 44.13 |
| ATOM | 265 | CB  | LYS | 190  | 15.068 | 17.500 | 9.680  | 1.00 | 45.33 |
| ATOM | 266 | C   | LYS | 190  | 16.472 | 15.846 | 10.928 | 1.00 | 44.13 |
| ATOM | 267 | O   | LYS | 190  | 15.827 | 15.272 | 11.805 | 1.00 | 45.33 |
| ATOM | 268 | N   | PHE | 191  | 17.748 | 16.184 | 11.067 | 1.00 | 35.64 |
| ATOM | 269 | CA  | PHE | 191  | 18.489 | 15.928 | 12.291 | 1.00 | 35.64 |
| ATOM | 270 | CB  | PHE | 191  | 19.993 | 16.008 | 12.025 | 1.00 | 53.94 |
| ATOM | 271 | CG  | PHE | 191  | 20.550 | 14.827 | 11.286 | 1.00 | 53.94 |
| ATOM | 272 | CD1 | PHE | 191  | 20.209 | 14.596 | 9.958  | 1.00 | 53.94 |
| ATOM | 273 | CD2 | PHE | 191  | 21.430 | 13.949 | 11.915 | 1.00 | 53.94 |
| ATOM | 274 | CE1 | PHE | 191  | 20.735 | 13.510 | 9.265  | 1.00 | 53.94 |
| ATOM | 275 | CE2 | PHE | 191  | 21.964 | 12.859 | 11.230 | 1.00 | 53.94 |
| ATOM | 276 | CZ  | PHE | 191  | 21.615 | 12.639 | 9.900  | 1.00 | 53.94 |
| ATOM | 277 | C   | PHE | 191  | 18.135 | 16.928 | 13.384 | 1.00 | 35.64 |
| ATOM | 278 | O   | PHE | 191  | 17.997 | 18.127 | 13.120 | 1.00 | 53.94 |
| ATOM | 279 | N   | LEU | 192  | 17.978 | 16.439 | 14.610 | 1.00 | 44.53 |
| ATOM | 280 | CA  | LEU | 192  | 17.683 | 17.315 | 15.736 | 1.00 | 44.53 |
| ATOM | 281 | CB  | LEU | 192  | 17.326 | 16.493 | 16.980 | 1.00 | 22.94 |
| ATOM | 282 | CG  | LEU | 192  | 16.931 | 17.259 | 18.246 | 1.00 | 22.94 |
| ATOM | 283 | CD1 | LEU | 192  | 15.568 | 17.906 | 18.064 | 1.00 | 22.94 |
| ATOM | 284 | CD2 | LEU | 192  | 16.909 | 16.308 | 19.427 | 1.00 | 22.94 |
| ATOM | 285 | C   | LEU | 192  | 18.974 | 18.101 | 15.980 | 1.00 | 44.53 |
| ATOM | 286 | O   | LEU | 192  | 20.049 | 17.507 | 16.129 | 1.00 | 22.94 |
| ATOM | 287 | N   | PRO | 193  | 18.895 | 19.444 | 15.977 | 1.00 | 34.26 |
| ATOM | 288 | CD  | PRO | 193  | 17.670 | 20.241 | 15.781 | 1.00 | 46.23 |
| ATOM | 289 | CA  | PRO | 193  | 20.058 | 20.311 | 16.198 | 1.00 | 34.26 |
| ATOM | 290 | CB  | PRO | 193  | 19.417 | 21.670 | 16.465 | 1.00 | 46.23 |
| ATOM | 291 | CG  | PRO | 193  | 18.213 | 21.641 | 15.579 | 1.00 | 46.23 |
| ATOM | 292 | C   | PRO | 193  | 20.917 | 19.844 | 17.372 | 1.00 | 34.26 |
| ATOM | 293 | O   | PRO | 193  | 20.413 | 19.614 | 18.471 | 1.00 | 46.23 |
| ATOM | 294 | N   | ASP | 194  | 22.217 | 19.716 | 17.125 | 1.00 | 42.67 |
| ATOM | 295 | CA  | ASP | 194  | 23.174 | 19.254 | 18.128 | 1.00 | 42.67 |
| ATOM | 296 | CB  | ASP | 194  | 24.583 | 19.226 | 17.536 | 1.00 | 68.50 |
| ATOM | 297 | CG  | ASP | 194  | 24.731 | 18.185 | 16.450 | 1.00 | 68.50 |
| ATOM | 298 | OD1 | ASP | 194  | 25.066 | 17.027 | 16.782 | 1.00 | 68.50 |
| ATOM | 299 | OD2 | ASP | 194  | 24.498 | 18.518 | 15.269 | 1.00 | 68.50 |
| ATOM | 300 | C   | ASP | 194  | 23.187 | 20.003 | 19.457 | 1.00 | 42.67 |
| ATOM | 301 | O   | ASP | 194  | 23.545 | 19.432 | 20.486 | 1.00 | 68.50 |
| ATOM | 302 | N   | ASP | 195  | 22.817 | 21.280 | 19.438 | 1.00 | 47.52 |
| ATOM | 303 | CA  | ASP | 195  | 22.793 | 22.070 | 20.666 | 1.00 | 47.52 |
| ATOM | 304 | CB  | ASP | 195  | 22.586 | 23.559 | 20.351 | 1.00 | 85.02 |
| ATOM | 305 | CG  | ASP | 195  | 21.327 | 23.824 | 19.537 | 1.00 | 85.02 |
| ATOM | 306 | OD1 | ASP | 195  | 20.291 | 24.188 | 20.138 | 1.00 | 85.02 |
| ATOM | 307 | OD2 | ASP | 195  | 21.377 | 23.683 | 18.294 | 1.00 | 85.02 |
| ATOM | 308 | C   | ASP | 195  | 21.715 | 21.561 | 21.627 | 1.00 | 47.52 |
| ATOM | 309 | O   | ASP | 195  | 21.762 | 21.826 | 22.831 | 1.00 | 85.02 |
| ATOM | 310 | N   | ILE | 196  | 20.760 | 20.810 | 21.089 | 1.00 | 44.54 |
| ATOM | 311 | CA  | ILE | 196  | 19.663 | 20.259 | 21.875 | 1.00 | 44.54 |
| ATOM | 312 | CB  | ILE | 196  | 18.379 | 20.137 | 21.023 | 1.00 | 39.66 |
| ATOM | 313 | CG2 | ILE | 196  | 17.223 | 19.627 | 21.874 | 1.00 | 39.66 |
| ATOM | 314 | CG1 | ILE | 196  | 18.031 | 21.496 | 20.407 | 1.00 | 39.66 |
| ATOM | 315 | CD1 | ILE | 196  | 16.816 | 21.475 | 19.503 | 1.00 | 39.66 |
| ATOM | 316 | C   | ILE | 196  | 20.030 | 18.882 | 22.420 | 1.00 | 44.54 |
| ATOM | 317 | O   | ILE | 196  | 20.582 | 18.046 | 21.705 | 1.00 | 39.66 |
| ATOM | 318 | N   | GLY | 197  | 19.714 | 18.652 | 23.690 | 1.00 | 42.85 |
| ATOM | 319 | CA  | GLY | 1.97 | 20.006 | 17.372 | 24.307 | 1.00 | 42.85 |
| ATOM | 320 | C   | GLY | 197  | 21.371 | 17.285 | 24.956 | 1.00 | 42.85 |
| ATOM | 321 | O   | GLY | 197  | 21.815 | 16.198 | 25.318 | 1.00 | 40.22 |
| ATOM | 322 | N   | GLN | 198  | 22.029 | 18.425 | 25.137 | 1.00 | 53.07 |
| ATOM | 323 | CA  | GLN | 198  | 23.351 | 18.444 | 25.754 | 1.00 | 53.07 |
| ATOM | 324 | CB  | GLN | 198  | 24.357 | 19.103 | 24.810 | 1.00 | 44.23 |
| ATOM | 325 | C   | GLN | 198  | 23.344 | 19.153 | 27.110 | 1.00 | 53.07 |
| ATOM | 326 | O   | GLN | 198  | 24.396 | 19.545 | 27.616 | 1.00 | 44.23 |
| ATOM | 327 | N   | SER | 199  | 22.170 | 19.244 | 27.729 | 1.00 | 35.30 |
| ATOM | 328 | CA  | SER | 199  | 22.037 | 19.918 | 29.019 | 1.00 | 35.30 |
| ATOM | 329 | CB  | SER | 199  | 21.472 | 21.328 | 28.806 | 1.00 | 58.72 |
| ATOM | 330 | OG  | SER | 199  | 22.093 | 21.971 | 27.704 | 1.00 | 58.72 |
| ATOM | 331 | C   | SER | 199  | 21.168 | 19.169 | 30.036 | 1.00 | 35.30 |
| ATOM | 332 | O   | SER | 199  | 20.135 | 19.681 | 30.482 | 1.00 | 58.72 |
| ATOM | 333 | N   | PRO | 200  | 21.544 | 17.928 | 30.387 | 1.00 | 34.70 |
| ATOM | 334 | CD  | PRO | 200  | 22.656 | 17.108 | 29.872 | 1.00 | 38.71 |

APPENDIX 4-continued

TR_TRIAC.PDB

| ATOM | 335 | CA | PRO | 200 | 20.740 | 17.184 | 31.362 | 1.00 | 34.70 |
|------|-----|-----|-----|-----|--------|--------|--------|------|-------|
| ATOM | 336 | CB | PRO | 200 | 21.311 | 15.769 | 31.266 | 1.00 | 38.71 |
| ATOM | 337 | CG | PRO | 200 | 22.737 | 15.992 | 30.878 | 1.00 | 38.71 |
| ATOM | 338 | C | PRO | 200 | 20.923 | 17.784 | 32.759 | 1.00 | 34.70 |
| ATOM | 339 | O | PRO | 200 | 22.006 | 17.692 | 33.341 | 1.00 | 38.71 |
| ATOM | 340 | N | ILE | 201 | 19.876 | 18.413 | 33.286 | 1.00 | 42.94 |
| ATOM | 341 | CA | ILE | 201 | 19.961 | 19.041 | 34.604 | 1.00 | 42.94 |
| ATOM | 342 | CB | ILE | 201 | 20.059 | 20.582 | 34.491 | 1.00 | 51.32 |
| ATOM | 343 | CG2 | ILE | 201 | 21.468 | 20.991 | 34.078 | 1.00 | 51.32 |
| ATOM | 344 | CG1 | ILE | 201 | 19.009 | 21.111 | 33.510 | 1.00 | 51.32 |
| ATOM | 345 | CD1 | ILE | 201 | 19.169 | 22.582 | 33.164 | 1.00 | 51.32 |
| ATOM | 346 | C | ILE | 201 | 18.871 | 18.676 | 35.610 | 1.00 | 42.94 |
| ATOM | 347 | O | ILE | 201 | 19.049 | 18.875 | 36.814 | 1.00 | 51.32 |
| ATOM | 348 | N | VAL | 202 | 17.737 | 18.172 | 35.133 | 1.00 | 50.33 |
| ATOM | 349 | CA | VAL | 202 | 16.661 | 17.787 | 36.043 | 1.00 | 50.33 |
| ATOM | 350 | CB | VAL | 202 | 15.296 | 17.722 | 35.326 | 1.00 | 36.59 |
| ATOM | 351 | CG1 | VAL | 202 | 14.202 | 17.311 | 36.304 | 1.00 | 36.59 |
| ATOM | 352 | CG2 | VAL | 202 | 14.968 | 19.074 | 34.714 | 1.00 | 36.59 |
| ATOM | 353 | C | VAL | 202 | 17.007 | 16.435 | 36.665 | 1.00 | 50.33 |
| ATOM | 354 | O | VAL | 202 | 17.335 | 15.481 | 35.955 | 1.00 | 36.59 |
| ATOM | 355 | N | SER | 203 | 16.960 | 16.375 | 37.991 | 1.00 | 49.46 |
| ATOM | 356 | CA | SER | 203 | 17.289 | 15.166 | 38.736 | 1.00 | 49.46 |
| ATOM | 357 | CB | SER | 203 | 17.298 | 15.467 | 40.241 | 1.00 | 64.20 |
| ATOM | 358 | OG | SER | 203 | 17.673 | 14.330 | 41.003 | 1.00 | 64.20 |
| ATOM | 359 | C | SER | 203 | 16.356 | 13.992 | 38.463 | 1.00 | 49.46 |
| ATOM | 360 | O | SER | 203 | 15.147 | 14.166 | 38.310 | 1.00 | 64.20 |
| ATOM | 361 | N | MET | 204 | 16.944 | 12.800 | 38.419 | 1.00 | 41.99 |
| ATOM | 362 | CA | MET | 204 | 16.223 | 11.551 | 38.205 | 1.00 | 41.99 |
| ATOM | 363 | CB | MET | 204 | 16.320 | 11.096 | 36.746 | 1.00 | 48.64 |
| ATOM | 364 | CG | MET | 204 | 15.470 | 11.895 | 35.771 | 1.00 | 48.64 |
| ATOM | 365 | SD | MET | 204 | 13.702 | 11.783 | 36.114 | 1.00 | 48.64 |
| ATOM | 366 | CE | MET | 204 | 13.284 | 10.257 | 35.264 | 1.00 | 48.64 |
| ATOM | 367 | C | MET | 204 | 16.900 | 10.528 | 39.109 | 1.00 | 41.99 |
| ATOM | 368 | O | MET | 204 | 18.127 | 10.417 | 39.121 | 1.00 | 48.64 |
| ATOM | 369 | N | PRO | 205 | 16.108 | 9.754 | 39.869 | 1.00 | 38.42 |
| ATOM | 370 | CD | PRO | 205 | 14.633 | 9.815 | 39.866 | 1.00 | 52.20 |
| ATOM | 371 | CA | PRO | 205 | 16.586 | 8.724 | 40.797 | 1.00 | 38.42 |
| ATOM | 372 | CB | PRO | 205 | 15.334 | 7.888 | 41.041 | 1.00 | 52.20 |
| ATOM | 373 | CG | PRO | 205 | 14.254 | 8.919 | 41.028 | 1.00 | 52.20 |
| ATOM | 374 | C | PRO | 205 | 17.769 | 7.858 | 40.340 | 1.00 | 38.42 |
| ATOM | 375 | O | PRO | 205 | 18.724 | 7.675 | 41.092 | 1.00 | 52.20 |
| ATOM | 376 | N | ASP | 206 | 17.720 | 7.349 | 39.111 | 1.00 | 49.06 |
| ATOM | 377 | CA | ASP | 206 | 18.791 | 6.490 | 38.601 | 1.00 | 49.06 |
| ATOM | 378 | CB | ASP | 206 | 18.282 | 5.627 | 37.437 | 1.00 | 74.42 |
| ATOM | 379 | CG | ASP | 206 | 17.690 | 6.450 | 36.305 | 1.00 | 74.42 |
| ATOM | 380 | OD1 | ASP | 206 | 18.397 | 7.335 | 35.770 | 1.00 | 74.42 |
| ATOM | 381 | OD2 | ASP | 206 | 16.516 | 6.199 | 35.948 | 1.00 | 74.42 |
| ATOM | 382 | C | ASP | 206 | 20.106 | 7.177 | 38.214 | 1.00 | 49.06 |
| ATOM | 383 | O | ASP | 206 | 21.069 | 6.506 | 37.838 | 1.00 | 74.42 |
| ATOM | 384 | N | GLY | 207 | 20.139 | 8.505 | 38.272 | 1.00 | 42.48 |
| ATOM | 385 | CA | GLY | 207 | 21.355 | 9.225 | 37.928 | 1.00 | 42.48 |
| ATOM | 386 | C | GLY | 207 | 21.330 | 9.965 | 36.601 | 1.00 | 42.48 |
| ATOM | 387 | O | GLY | 207 | 21.890 | 11.058 | 36.494 | 1.00 | 42.50 |
| ATOM | 388 | N | ASP | 208 | 20.725 | 9.365 | 35.581 | 1.00 | 46.70 |
| ATOM | 389 | CA | ASP | 208 | 20.636 | 9.999 | 34.266 | 1.00 | 46.70 |
| ATOM | 390 | CB | ASP | 208 | 20.162 | 8.994 | 33.212 | 1.00 | 61.56 |
| ATOM | 391 | CG | ASP | 208 | 21.143 | 7.856 | 33.006 | 1.00 | 61.56 |
| ATOM | 392 | OD1 | ASP | 208 | 20.723 | 6.684 | 33.122 | 1.00 | 61.56 |
| ATOM | 393 | OD2 | ASP | 208 | 22.330 | 8.134 | 32.724 | 1.00 | 61.56 |
| ATOM | 394 | C | ASP | 208 | 19.666 | 11.176 | 34.339 | 1.00 | 46.70 |
| ATOM | 395 | O | ASP | 208 | 18.462 | 10.983 | 34.506 | 1.00 | 61.56 |
| ATOM | 396 | N | LYS | 209 | 20.200 | 12.389 | 34.238 | 1.00 | 41.30 |
| ATOM | 397 | CA | LYS | 209 | 19.389 | 13.602 | 34.308 | 1.00 | 41.30 |
| ATOM | 398 | CB | LYS | 209 | 20.254 | 14.782 | 34.732 | 1.00 | 41.38 |
| ATOM | 399 | C | LYS | 209 | 18.657 | 13.916 | 33.004 | 1.00 | 41.30 |
| ATOM | 400 | O | LYS | 209 | 19.052 | 13.458 | 31.930 | 1.00 | 41.38 |
| ATOM | 401 | N | VAL | 210 | 17.603 | 14.723 | 33.109 | 1.00 | 43.36 |
| ATOM | 402 | CA | VAL | 210 | 16.792 | 15.107 | 31.954 | 1.00 | 43.36 |
| ATOM | 403 | CB | VAL | 210 | 15.275 | 15.014 | 32.282 | 1.00 | 30.23 |
| ATOM | 404 | CG1 | VAL | 210 | 14.440 | 15.358 | 31.055 | 1.00 | 30.23 |
| ATOM | 405 | CG2 | VAL | 210 | 14.923 | 13.624 | 32.782 | 1.00 | 30.23 |
| ATOM | 406 | C | VAL | 210 | 17.088 | 16.522 | 31.442 | 1.00 | 43.36 |
| ATOM | 407 | O | VAL | 210 | 17.395 | 17.430 | 32.221 | 1.00 | 30.23 |
| ATOM | 408 | N | ASP | 211 | 17.004 | 16.685 | 30.125 | 1.00 | 27.49 |
| ATOM | 409 | CA | ASP | 211 | 17.217 | 17.966 | 29.458 | 1.00 | 27.49 |
| ATOM | 410 | CB | ASP | 211 | 18.073 | 17.765 | 28.198 | 1.00 | 30.75 |
| ATOM | 411 | CG | ASP | 211 | 18.360 | 19.068 | 27.447 | 1.00 | 30.75 |

APPENDIX 4-continued

TR_TRIAC.PDB

| ATOM | 412 | OD1 | ASP | 211 | 19.473 | 19.196 | 26.900 | 1.00 | 30.75 |
|------|-----|-----|-----|-----|--------|--------|--------|------|-------|
| ATOM | 413 | OD2 | ASP | 211 | 17.484 | 19.955 | 27.370 | 1.00 | 30.75 |
| ATOM | 414 | C | ASP | 211 | 15.819 | 18.445 | 29.073 | 1.00 | 27.49 |
| ATOM | 415 | O | ASP | 211 | 15.197 | 17.892 | 28.166 | 1.00 | 30.75 |
| ATOM | 416 | N | LEU | 212 | 15.343 | 19.488 | 29.745 | 1.00 | 31.99 |
| ATOM | 417 | CA | LEU | 212 | 14.013 | 20.042 | 29.492 | 1.00 | 31.99 |
| ATOM | 418 | CB | LEU | 212 | 13.778 | 21.274 | 30.369 | 1.00 | 35.19 |
| ATOM | 419 | CG | LEU | 212 | 13.606 | 20.997 | 31.864 | 1.00 | 35.19 |
| ATOM | 420 | CD1 | LEU | 212 | 13.621 | 22.298 | 32.652 | 1.00 | 35.19 |
| ATOM | 421 | CD2 | LEU | 212 | 12.309 | 20.237 | 32.098 | 1.00 | 35.19 |
| ATOM | 422 | C | LEU | 212 | 13.713 | 20.377 | 28.032 | 1.00 | 31.99 |
| ATOM | 423 | O | LEU | 212 | 12.625 | 20.083 | 27.539 | 1.00 | 35.19 |
| ATOM | 424 | N | GLU | 213 | 14.672 | 20.981 | 27.338 | 1.00 | 28.70 |
| ATOM | 425 | CA | GLU | 213 | 14.468 | 21.345 | 25.940 | 1.00 | 28.70 |
| ATOM | 426 | CB | GLU | 213 | 15.623 | 22.209 | 25.428 | 1.00 | 62.21 |
| ATOM | 427 | CG | GLU | 213 | 15.434 | 22.707 | 23.997 | 1.00 | 62.21 |
| ATOM | 428 | CD | GLU | 213 | 16.651 | 23.440 | 23.446 | 1.00 | 62.21 |
| ATOM | 429 | OE1 | GLU | 213 | 17.778 | 23.214 | 23.945 | 1.00 | 62.21 |
| ATOM | 430 | OE2 | GLU | 213 | 16.478 | 24.237 | 22.498 | 1.00 | 62.21 |
| ATOM | 431 | C | GLU | 213 | 14.317 | 20.104 | 25.067 | 1.00 | 28.70 |
| ATOM | 432 | O | GLU | 213 | 13.403 | 20.024 | 24.247 | 1.00 | 62.21 |
| ATOM | 433 | N | ALA | 214 | 15.201 | 19.130 | 25.262 | 1.00 | 28.17 |
| ATOM | 434 | CA | ALA | 214 | 15.162 | 17.890 | 24.494 | 1.00 | 28.17 |
| ATOM | 435 | CB | ALA | 214 | 16.330 | 16.998 | 24.872 | 1.00 | 42.74 |
| ATOM | 436 | C | ALA | 214 | 13.844 | 17.176 | 24.759 | 1.00 | 28.17 |
| ATOM | 437 | O | ALA | 214 | 13.174 | 16.726 | 23.829 | 1.00 | 42.74 |
| ATOM | 438 | N | PHE | 215 | 13.468 | 17.104 | 26.032 | 1.00 | 21.66 |
| ATOM | 439 | CA | PHE | 215 | 12.222 | 16.471 | 26.444 | 1.00 | 21.66 |
| ATOM | 440 | CB | PHE | 215 | 12.033 | 16.628 | 27.958 | 1.00 | 28.76 |
| ATOM | 441 | CG | PHE | 215 | 10.751 | 16.038 | 28.481 | 1.00 | 28.76 |
| ATOM | 442 | CD1 | PHE | 215 | 10.675 | 14.689 | 28.815 | 1.00 | 28.76 |
| ATOM | 443 | CD2 | PHE | 215 | 9.623 | 16.835 | 28.653 | 1.00 | 28.76 |
| ATOM | 444 | CE1 | PHE | 215 | 9.493 | 14.143 | 29.315 | 1.00 | 28.76 |
| ATOM | 445 | CE2 | PHE | 215 | 8.438 | 16.300 | 29.150 | 1.00 | 28.76 |
| ATOM | 446 | CZ | PHE | 215 | 8.373 | 14.951 | 29.482 | 1.00 | 28.76 |
| ATOM | 447 | C | PHE | 215 | 11.068 | 17.132 | 25.696 | 1.00 | 21.66 |
| ATOM | 448 | O | PHE | 215 | 10.215 | 16.451 | 25.122 | 1.00 | 28.76 |
| ATOM | 449 | N | SER | 216 | 11.073 | 18.462 | 25.680 | 1.00 | 28.03 |
| ATOM | 450 | CA | SER | 216 | 10.043 | 19.242 | 25.007 | 1.00 | 28.03 |
| ATOM | 451 | CB | SER | 216 | 10.349 | 20.734 | 25.146 | 1.00 | 33.85 |
| ATOM | 452 | OG | SER | 216 | 9.300 | 21.529 | 24.624 | 1.00 | 33.85 |
| ATOM | 453 | C | SER | 216 | 9.945 | 18.857 | 23.532 | 1.00 | 28.03 |
| ATOM | 454 | O | SER | 216 | 8.852 | 18.613 | 23.019 | 1.00 | 33.85 |
| ATOM | 455 | N | GLU | 217 | 11.092 | 18.761 | 22.868 | 1.00 | 28.84 |
| ATOM | 456 | CA | GLU | 217 | 11.138 | 18.402 | 21.454 | 1.00 | 28.84 |
| ATOM | 457 | CB | GLU | 217 | 12.581 | 18.420 | 20.943 | 1.00 | 47.68 |
| ATOM | 458 | CG | GLU | 217 | 13.174 | 19.815 | 20.811 | 1.00 | 47.68 |
| ATOM | 459 | CD | GLU | 217 | 12.405 | 20.684 | 19.829 | 1.00 | 47.68 |
| ATOM | 460 | OE1 | GLU | 217 | 11.660 | 21.581 | 20.281 | 1.00 | 47.68 |
| ATOM | 461 | OE2 | GLU | 217 | 12.542 | 20.465 | 18.606 | 1.00 | 47.68 |
| ATOM | 462 | C | GLU | 217 | 10.505 | 17.044 | 21.179 | 1.00 | 28.84 |
| ATOM | 463 | O | GLU | 217 | 9.751 | 16.886 | 20.217 | 1.00 | 47.68 |
| ATOM | 464 | N | PHE | 218 | 10.799 | 16.071 | 22.036 | 1.00 | 21.49 |
| ATOM | 465 | CA | PHE | 218 | 10.259 | 14.725 | 21.883 | 1.00 | 21.49 |
| ATOM | 466 | CB | PHE | 218 | 11.020 | 13.746 | 22.781 | 1.00 | 24.12 |
| ATOM | 467 | CG | PHE | 218 | 12.489 | 13.652 | 22.464 | 1.00 | 24.12 |
| ATOM | 468 | CD1 | PHE | 218 | 13.431 | 13.554 | 23.481 | 1.00 | 24.12 |
| ATOM | 469 | CD2 | PHE | 218 | 12.932 | 13.677 | 21.144 | 1.00 | 24.12 |
| ATOM | 470 | CE1 | PHE | 218 | 14.793 | 13.484 | 23.187 | 1.00 | 24.12 |
| ATOM | 471 | CE2 | PHE | 218 | 14.290 | 13.607 | 20.843 | 1.00 | 24.12 |
| ATOM | 472 | CZ | PHE | 218 | 15.221 | 13.511 | 21.867 | 1.00 | 24.12 |
| ATOM | 473 | C | PHE | 218 | 8.765 | 14.675 | 22.176 | 1.00 | 21.49 |
| ATOM | 474 | O | PHE | 218 | 7.985 | 14.166 | 21.369 | 1.00 | 24.12 |
| ATOM | 475 | N | THR | 219 | 8.358 | 15.227 | 23.312 | 1.00 | 20.07 |
| ATOM | 476 | CA | THR | 219 | 6.949 | 15.231 | 23.685 | 1.00 | 20.07 |
| ATOM | 477 | CB | THR | 219 | 6.741 | 15.766 | 25.118 | 1.00 | 28.98 |
| ATOM | 478 | OG1 | THR | 219 | 7.418 | 17.021 | 25.274 | 1.00 | 28.98 |
| ATOM | 479 | CG2 | THR | 219 | 7.275 | 14.767 | 26.132 | 1.00 | 28.98 |
| ATOM | 480 | C | THR | 219 | 6.080 | 16.011 | 22.696 | 1.00 | 20.07 |
| ATOM | 481 | O | THR | 219 | 4.914 | 15.670 | 22.482 | 1.00 | 28.98 |
| ATOM | 482 | N | LYS | 220 | 6.662 | 17.022 | 22.060 | 1.00 | 25.35 |
| ATOM | 483 | CA | LYS | 220 | 5.943 | 17.840 | 21.088 | 1.00 | 25.35 |
| ATOM | 484 | CB | LYS | 220 | 6.842 | 18.965 | 20.577 | 1.00 | 29.07 |
| ATOM | 485 | C | LYS | 220 | 5.414 | 17.015 | 19.916 | 1.00 | 25.35 |
| ATOM | 486 | O | LYS | 220 | 4.376 | 17.343 | 19.339 | 1.00 | 29.07 |
| ATOM | 487 | N | ILE | 221 | 6.122 | 15.943 | 19.569 | 1.00 | 31.43 |
| ATOM | 488 | CA | ILE | 221 | 5.708 | 15.089 | 18.458 | 1.00 | 31.43 |

APPENDIX 4-continued

TR_TRIAC.PDB

| ATOM | 489 | CB | ILE | 221 | 6.842 | 14.915 | 17.413 | 1.00 | 25.19 |
|---|---|---|---|---|---|---|---|---|---|
| ATOM | 490 | CG2 | ILE | 221 | 7.240 | 16.264 | 16.838 | 1.00 | 25.19 |
| ATOM | 491 | CG1 | ILE | 221 | 8.050 | 14.215 | 18.043 | 1.00 | 25.19 |
| ATOM | 492 | CD1 | ILE | 221 | 9.113 | 13.799 | 17.044 | 1.00 | 25.19 |
| ATOM | 493 | C | ILE | 221 | 5.240 | 13.700 | 18.892 | 1.00 | 31.43 |
| ATOM | 494 | O | ILE | 221 | 4.930 | 12.857 | 18.046 | 1.00 | 25.19 |
| ATOM | 495 | N | ILE | 222 | 5.129 | 13.474 | 20.198 | 1.00 | 24.41 |
| ATOM | 496 | CA | ILE | 222 | 4.720 | 12.162 | 20.687 | 1.00 | 24.41 |
| ATOM | 497 | CB | ILE | 222 | 5.189 | 11.916 | 22.147 | 1.00 | 27.10 |
| ATOM | 498 | CG2 | ILE | 222 | 4.221 | 12.545 | 23.145 | 1.00 | 27.10 |
| ATOM | 499 | CG1 | ILE | 222 | 5.302 | 10.410 | 22.400 | 1.00 | 27.10 |
| ATOM | 500 | CD1 | ILE | 222 | 6.062 | 10.053 | 23.646 | 1.00 | 27.10 |
| ATOM | 501 | C | ILE | 222 | 3.231 | 11.845 | 20.541 | 1.00 | 24.41 |
| ATOM | 502 | O | ILE | 222 | 2.864 | 10.691 | 20.307 | 1.00 | 27.10 |
| ATOM | 503 | N | THR | 223 | 2.378 | 12.861 | 20.642 | 1.00 | 33.16 |
| ATOM | 504 | CA | THR | 223 | 0.936 | 12.653 | 20.520 | 1.00 | 33.16 |
| ATOM | 505 | CB | THR | 223 | 0.150 | 13.974 | 20.721 | 1.00 | 36.84 |
| ATOM | 506 | OG1 | THR | 223 | 0.352 | 14.442 | 22.063 | 1.00 | 36.84 |
| ATOM | 507 | CG2 | THR | 223 | −1.346 | 13.764 | 20.484 | 1.00 | 36.84 |
| ATOM | 508 | C | THR | 223 | 0.536 | 11.954 | 19.212 | 1.00 | 33.16 |
| ATOM | 509 | O | THR | 223 | −0.156 | 10.932 | 19.242 | 1.00 | 36.84 |
| ATOM | 510 | N | PRO | 224 | 0.968 | 12.482 | 18.048 | 1.00 | 18.75 |
| ATOM | 511 | CD | PRO | 224 | 1.691 | 13.735 | 17.770 | 1.00 | 26.12 |
| ATOM | 512 | CA | PRO | 224 | 0.590 | 11.805 | 16.802 | 1.00 | 18.75 |
| ATOM | 513 | CB | PRO | 224 | 1.117 | 12.747 | 15.715 | 1.00 | 26.12 |
| ATOM | 514 | CG | PRO | 224 | 2.221 | 13.497 | 16.386 | 1.00 | 26.12 |
| ATOM | 515 | C | PRO | 224 | 1.200 | 10.402 | 16.701 | 1.00 | 18.75 |
| ATOM | 516 | O | PRO | 224 | 0.606 | 9.502 | 16.101 | 1.00 | 26.12 |
| ATOM | 517 | N | ALA | 225 | 2.368 | 10.213 | 17.312 | 1.00 | 12.19 |
| ATOM | 518 | CA | ALA | 225 | 3.040 | 8.916 | 17.300 | 1.00 | 12.19 |
| ATOM | 519 | CB | ALA | 225 | 4.415 | 9.021 | 17.943 | 1.00 | 20.39 |
| ATOM | 520 | C | ALA | 225 | 2.187 | 7.881 | 18.030 | 1.00 | 12.19 |
| ATOM | 521 | O | ALA | 225 | 1.998 | 6.764 | 17.545 | 1.00 | 20.39 |
| ATOM | 522 | N | ILE | 226 | 1.645 | 8.271 | 19.179 | 1.00 | 14.61 |
| ATOM | 523 | CA | ILE | 226 | 0.798 | 7.385 | 19.971 | 1.00 | 14.61 |
| ATOM | 524 | CB | ILE | 226 | 0.450 | 8.025 | 21.332 | 1.00 | 16.10 |
| ATOM | 525 | CG2 | ILE | 226 | −0.508 | 7.132 | 22.108 | 1.00 | 16.10 |
| ATOM | 526 | CG1 | ILE | 226 | 1.729 | 8.293 | 22.132 | 1.00 | 16.10 |
| ATOM | 527 | CD1 | ILE | 226 | 1.509 | 9.113 | 23.387 | 1.00 | 16.10 |
| ATOM | 528 | C | ILE | 226 | −0.499 | 7.094 | 19.213 | 1.00 | 14.61 |
| ATOM | 529 | O | ILE | 226 | −0.986 | 5.961 | 19.200 | 1.00 | 16.10 |
| ATOM | 530 | N | THR | 227 | −1.042 | 8.123 | 18.569 | 1.00 | 15.93 |
| ATOM | 531 | CA | THR | 227 | −2.278 | 7.997 | 17.800 | 1.00 | 15.93 |
| ATOM | 532 | CB | THR | 227 | −2.706 | 9.360 | 17.207 | 1.00 | 22.37 |
| ATOM | 533 | OG1 | THR | 227 | −2.890 | 10.301 | 18.273 | 1.00 | 22.37 |
| ATOM | 534 | CG2 | THR | 227 | −4.014 | 9.232 | 16.434 | 1.00 | 22.37 |
| ATOM | 535 | C | THR | 227 | −2.149 | 6.964 | 16.680 | 1.00 | 15.93 |
| ATOM | 536 | O | THR | 227 | −3.091 | 6.217 | 16.402 | 1.00 | 22.37 |
| ATOM | 537 | N | ARG | 228 | −0.982 | 6.916 | 16.045 | 1.00 | 14.49 |
| ATOM | 538 | CA | ARG | 228 | −0.750 | 5.956 | 14.975 | 1.00 | 14.49 |
| ATOM | 539 | CB | ARG | 228 | 0.602 | 6.188 | 14.307 | 1.00 | 33.87 |
| ATOM | 540 | CG | ARG | 228 | 0.701 | 7.482 | 13.540 | 1.00 | 33.87 |
| ATOM | 541 | CD | ARG | 228 | 2.053 | 7.572 | 12.868 | 1.00 | 33.87 |
| ATOM | 542 | NE | ARG | 228 | 2.510 | 8.952 | 12.793 | 1.00 | 33.87 |
| ATOM | 543 | CZ | ARG | 228 | 3.551 | 9.431 | 13.469 | 1.00 | 33.87 |
| ATOM | 544 | NH1 | ARG | 228 | 4.256 | 8.634 | 14.270 | 1.00 | 33.87 |
| ATOM | 545 | NH2 | ARG | 228 | 3.864 | 10.716 | 13.374 | 1.00 | 33.87 |
| ATOM | 546 | C | ARG | 228 | −0.813 | 4.531 | 15.516 | 1.00 | 14.49 |
| ATOM | 547 | O | ARG | 228 | −1.309 | 3.632 | 14.839 | 1.00 | 33.87 |
| ATOM | 548 | N | VAL | 229 | −0.313 | 4.327 | 16.735 | 1.00 | 14.80 |
| ATOM | 549 | CA | VAL | 229 | −0.333 | 3.002 | 17.352 | 1.00 | 14.80 |
| ATOM | 550 | CB | VAL | 229 | 0.456 | 2.979 | 18.683 | 1.00 | 13.78 |
| ATOM | 551 | CG1 | VAL | 229 | 0.339 | 1.612 | 19.350 | 1.00 | 13.78 |
| ATOM | 552 | CG2 | VAL | 229 | 1.915 | 3.312 | 18.430 | 1.00 | 13.78 |
| ATOM | 553 | C | VAL | 229 | −1.788 | 2.602 | 17.591 | 1.00 | 14.80 |
| ATOM | 554 | O | VAL | 229 | −2.185 | 1.465 | 17.323 | 1.00 | 13.78 |
| ATOM | 555 | N | VAL | 230 | −2.588 | 3.561 | 18.047 | 1.00 | 9.33 |
| ATOM | 556 | CA | VAL | 230 | −4.005 | 3.327 | 18.292 | 1.00 | 9.33 |
| ATOM | 557 | CB | VAL | 230 | −4.679 | 4.564 | 18.909 | 1.00 | 16.07 |
| ATOM | 558 | CG1 | VAL | 230 | −6.168 | 4.319 | 19.076 | 1.00 | 16.07 |
| ATOM | 559 | CG2 | VAL | 230 | −4.038 | 4.896 | 20.253 | 1.00 | 16.07 |
| ATOM | 560 | C | VAL | 230 | −4.700 | 2.982 | 16.981 | 1.00 | 9.33 |
| ATOM | 561 | O | VAL | 230 | −5.504 | 2.049 | 16.929 | 1.00 | 16.07 |
| ATOM | 562 | N | ASP | 231 | −4.364 | 3.719 | 15.922 | 1.00 | 12.71 |
| ATOM | 563 | CA | ASP | 231 | −4.951 | 3.496 | 14.603 | 1.00 | 12.71 |
| ATOM | 564 | CB | ASP | 231 | −4.529 | 4.596 | 13.624 | 1.00 | 27.08 |
| ATOM | 565 | CG | ASP | 231 | −5.053 | 5.967 | 14.020 | 1.00 | 27.08 |

APPENDIX 4-continued

TR_TRIAC.PDB

| ATOM | 566 | OD1 | ASP | 231 | −6.144 | 6.047 | 14.624 | 1.00 | 27.08 |
|---|---|---|---|---|---|---|---|---|---|
| ATOM | 567 | OD2 | ASP | 231 | −4.370 | 6.969 | 13.723 | 1.00 | 27.08 |
| ATOM | 568 | C | ASP | 231 | −4.570 | 2.132 | 14.049 | 1.00 | 12.71 |
| ATOM | 569 | O | ASP | 231 | −5.413 | 1.436 | 13.483 | 1.00 | 27.08 |
| ATOM | 570 | N | PHE | 232 | −3.305 | 1.755 | 14.215 | 1.00 | 14.33 |
| ATOM | 571 | CA | PHE | 232 | −2.823 | 0.461 | 13.748 | 1.00 | 14.33 |
| ATOM | 572 | CB | PHE | 232 | −1.351 | 0.257 | 14.134 | 1.00 | 16.35 |
| ATOM | 573 | CG | PHE | 232 | −0.911 | −1.184 | 14.097 | 1.00 | 16.35 |
| ATOM | 574 | CD1 | PHE | 232 | −0.789 | −1.862 | 12.887 | 1.00 | 16.35 |
| ATOM | 575 | CD2 | PHE | 232 | −0.661 | −1.879 | 15.280 | 1.00 | 16.35 |
| ATOM | 576 | CE1 | PHE | 232 | −0.430 | −3.208 | 12.851 | 1.00 | 16.35 |
| ATOM | 577 | CE2 | PHE | 232 | −0.302 | −3.224 | 15.255 | 1.00 | 16.35 |
| ATOM | 578 | CZ | PHE | 232 | −0.187 | −3.890 | 14.038 | 1.00 | 16.35 |
| ATOM | 579 | C | PHE | 232 | −3.670 | −0.642 | 14.368 | 1.00 | 14.33 |
| ATOM | 580 | O | PHE | 232 | −4.226 | −1.482 | 13.661 | 1.00 | 16.35 |
| ATOM | 581 | N | ALA | 233 | −3.769 | −0.619 | 15.695 | 1.00 | 15.30 |
| ATOM | 582 | CA | ALA | 233 | −4.537 | −1.607 | 16.444 | 1.00 | 15.30 |
| ATOM | 583 | CB | ALA | 233 | −4.413 | −1.335 | 17.938 | 1.00 | 12.88 |
| ATOM | 584 | C | ALA | 233 | −6.005 | −1.609 | 16.030 | 1.00 | 15.30 |
| ATOM | 585 | O | ALA | 233 | −6.627 | −2.663 | 15.902 | 1.00 | 12.88 |
| ATOM | 586 | N | LYS | 234 | −6.542 | −0.419 | 15.795 | 1.00 | 25.69 |
| ATOM | 587 | CA | LYS | 234 | −7.933 | −0.256 | 15.401 | 1.00 | 25.69 |
| ATOM | 588 | CB | LYS | 234 | −8.270 | 1.234 | 15.318 | 1.00 | 45.91 |
| ATOM | 589 | CG | LYS | 234 | −9.574 | 1.595 | 15.979 | 1.00 | 45.91 |
| ATOM | 590 | CD | LYS | 234 | −9.535 | 1.268 | 17.463 | 1.00 | 45.91 |
| ATOM | 591 | CE | LYS | 234 | −10.938 | 1.047 | 18.006 | 1.00 | 45.91 |
| ATOM | 592 | NZ | LYS | 234 | −11.605 | −0.106 | 17.327 | 1.00 | 45.91 |
| ATOM | 593 | C | LYS | 234 | −8.240 | −0.931 | 14.067 | 1.00 | 25.69 |
| ATOM | 594 | O | LYS | 234 | −9.368 | −1.368 | 13.827 | 1.00 | 45.91 |
| ATOM | 595 | N | LYS | 235 | −7.234 | −1.019 | 13.204 | 1.00 | 17.44 |
| ATOM | 596 | CA | LYS | 235 | −7.406 | −1.627 | 11.892 | 1.00 | 17.44 |
| ATOM | 597 | CB | LYS | 235 | −6.459 | −0.975 | 10.884 | 1.00 | 26.26 |
| ATOM | 598 | CG | LYS | 235 | −6.757 | 0.499 | 10.669 | 1.00 | 26.26 |
| ATOM | 599 | CD | LYS | 235 | −5.785 | 1.141 | 9.706 | 1.00 | 26.26 |
| ATOM | 600 | CE | LYS | 235 | −6.154 | 2.593 | 9.460 | 1.00 | 26.26 |
| ATOM | 601 | NZ | LYS | 235 | −5.231 | 3.230 | 8.484 | 1.00 | 26.26 |
| ATOM | 602 | C | LYS | 235 | −7.258 | −3.146 | 11.875 | 1.00 | 17.44 |
| ATOM | 603 | O | LYS | 235 | −7.365 | −3.773 | 10.817 | 1.00 | 26.26 |
| ATOM | 604 | N | LEU | 236 | −7.015 | −3.738 | 13.040 | 1.00 | 21.99 |
| ATOM | 605 | CA | LEU | 236 | −6.880 | −5.187 | 13.144 | 1.00 | 21.99 |
| ATOM | 606 | CB | LEU | 236 | −5.792 | −5.564 | 14.154 | 1.00 | 25.38 |
| ATOM | 607 | CG | LEU | 236 | −4.362 | −5.127 | 13.818 | 1.00 | 25.38 |
| ATOM | 608 | CD1 | LEU | 236 | −3.415 | −5.555 | 14.929 | 1.00 | 25.38 |
| ATOM | 609 | CD2 | LEU | 236 | −3.931 | −5.725 | 12.491 | 1.00 | 25.38 |
| ATOM | 610 | C | LEU | 236 | −8.219 | −5.796 | 13.556 | 1.00 | 21.99 |
| ATOM | 611 | O | LEU | 236 | −8.821 | −5.386 | 14.553 | 1.00 | 25.38 |
| ATOM | 612 | N | PRO | 237 | −8.682 | −6.819 | 12.817 | 1.00 | 34.89 |
| ATOM | 613 | CD | PRO | 237 | −7.936 | −7.474 | 11.730 | 1.00 | 42.99 |
| ATOM | 614 | CA | PRO | 237 | −9.953 | −7.513 | 13.071 | 1.00 | 34.89 |
| ATOM | 615 | CB | PRO | 237 | −9.911 | −8.687 | 12.084 | 1.00 | 42.99 |
| ATOM | 616 | CG | PRO | 237 | −8.433 | −8.887 | 11.816 | 1.00 | 42.99 |
| ATOM | 617 | C | PRO | 237 | −10.184 | −7.986 | 14.513 | 1.00 | 34.89 |
| ATOM | 618 | O | PRO | 237 | −11.142 | −7.563 | 15.159 | 1.00 | 42.99 |
| ATOM | 619 | N | MET | 238 | −9.301 | −8.843 | 15.021 | 1.00 | 40.45 |
| ATOM | 620 | CA | MET | 238 | −9.433 | −9.364 | 16.382 | 1.00 | 40.45 |
| ATOM | 621 | CB | MET | 238 | −8.360 | −10.423 | 16.671 | 1.00 | 59.70 |
| ATOM | 622 | CG | MET | 238 | −8.689 | −11.839 | 16.195 | 1.00 | 59.70 |
| ATOM | 623 | SD | MET | 238 | −8.013 | −12.275 | 14.573 | 1.00 | 59.70 |
| ATOM | 624 | CE | MET | 238 | −6.482 | −13.074 | 15.032 | 1.00 | 59.70 |
| ATOM | 625 | C | MET | 238 | −9.395 | −8.305 | 17.486 | 1.00 | 40.45 |
| ATOM | 626 | O | MET | 238 | −9.801 | −8.574 | 18.617 | 1.00 | 59.70 |
| ATOM | 627 | N | PHE | 239 | −8.928 | −7.103 | 17.160 | 1.00 | 33.70 |
| ATOM | 628 | CA | PHE | 239 | −8.829 | −6.037 | 18.152 | 1.00 | 33.70 |
| ATOM | 629 | CB | PHE | 239 | −7.651 | −5.113 | 17.829 | 1.00 | 22.27 |
| ATOM | 630 | CG | PHE | 239 | −7.386 | −4.079 | 18.885 | 1.00 | 22.27 |
| ATOM | 631 | CD1 | PHE | 239 | −6.602 | −4.385 | 19.990 | 1.00 | 22.27 |
| ATOM | 632 | CD2 | PHE | 239 | −7.926 | −2.802 | 18.778 | 1.00 | 22.27 |
| ATOM | 633 | CE1 | PHE | 239 | −6.358 | −3.436 | 20.974 | 1.00 | 22.27 |
| ATOM | 634 | CE2 | PHE | 239 | −7.688 | −1.846 | 19.757 | 1.00 | 22.27 |
| ATOM | 635 | CZ | PHE | 239 | −6.901 | −2.163 | 20.857 | 1.00 | 22.27 |
| ATOM | 636 | C | PHE | 239 | −10.103 | −5.213 | 18.329 | 1.00 | 33.70 |
| ATOM | 637 | O | PHE | 239 | −10.594 | −5.059 | 19.446 | 1.00 | 22.27 |
| ATOM | 638 | N | SER | 240 | −10.629 | −4.679 | 17.232 | 1.00 | 23.42 |
| ATOM | 639 | CA | SER | 240 | −11.837 | −3.857 | 17.278 | 1.00 | 23.42 |
| ATOM | 640 | CB | SER | 240 | −12.175 | −3.352 | 15.884 | 1.00 | 26.21 |
| ATOM | 641 | C | SER | 240 | −13.046 | −4.562 | 17.899 | 1.00 | 23.42 |
| ATOM | 642 | O | SER | 240 | −13.976 | −3.909 | 18.369 | 1.00 | 26.21 |

APPENDIX 4-continued

TR_TRIAC.PDB

| ATOM | 643 | N   | GLU | 241 | -13.028 | -5.891  | 17.893 | 1.00 | 26.54 |
| ---- | --- | --- | --- | --- | ------- | ------- | ------ | ---- | ----- |
| ATOM | 644 | CA  | GLU | 241 | -14.116 | -6.695  | 18.450 | 1.00 | 26.54 |
| ATOM | 645 | CB  | GLU | 241 | -14.007 | -8.139  | 17.957 | 1.00 | 67.32 |
| ATOM | 646 | CG  | GLU | 241 | -14.241 | -8.322  | 16.467 | 1.00 | 67.32 |
| ATOM | 647 | CD  | GLU | 241 | -13.979 | -9.748  | 16.001 | 1.00 | 67.32 |
| ATOM | 648 | OE1 | GLU | 241 | -14.161 | -10.691 | 16.803 | 1.00 | 67.32 |
| ATOM | 649 | OE2 | GLU | 241 | -13.584 | -9.924  | 14.828 | 1.00 | 67.32 |
| ATOM | 650 | C   | GLU | 241 | -14.137 | -6.706  | 19.975 | 1.00 | 26.54 |
| ATOM | 651 | O   | GLU | 241 | -15.182 | -6.924  | 20.589 | 1.00 | 67.32 |
| ATOM | 652 | N   | LEU | 242 | -12.972 | -6.506  | 20.579 | 1.00 | 26.16 |
| ATOM | 653 | CA  | LEU | 242 | -12.835 | -6.514  | 22.030 | 1.00 | 26.16 |
| ATOM | 654 | CB  | LEU | 242 | -11.352 | -6.473  | 22.412 | 1.00 | 19.79 |
| ATOM | 655 | CG  | LEU | 242 | -10.461 | -7.627  | 21.956 | 1.00 | 19.79 |
| ATOM | 656 | CD1 | LEU | 242 | -9.014  | -7.309  | 22.264 | 1.00 | 19.79 |
| ATOM | 657 | CD2 | LEU | 242 | -10.888 | -8.912  | 22.640 | 1.00 | 19.79 |
| ATOM | 658 | C   | LEU | 242 | -13.547 | -5.351  | 22.711 | 1.00 | 26.16 |
| ATOM | 659 | O   | LEU | 242 | -13.738 | -4.290  | 22.115 | 1.00 | 19.79 |
| ATOM | 660 | N   | PRO | 243 | -13.980 | -5.547  | 23.968 | 1.00 | 17.98 |
| ATOM | 661 | CD  | PRO | 243 | -13.996 | -6.785  | 24.764 | 1.00 | 19.17 |
| ATOM | 662 | CA  | PRO | 243 | -14.657 | -4.454  | 24.671 | 1.00 | 17.98 |
| ATOM | 663 | CB  | PRO | 243 | -15.095 | -5.105  | 25.988 | 1.00 | 19.17 |
| ATOM | 664 | CG  | PRO | 243 | -14.155 | -6.263  | 26.161 | 1.00 | 19.17 |
| ATOM | 665 | C   | PRO | 243 | -13.652 | -3.323  | 24.898 | 1.00 | 17.98 |
| ATOM | 666 | O   | PRO | 243 | -12.458 | -3.572  | 25.081 | 1.00 | 19.17 |
| ATOM | 667 | N   | CYS | 244 | -14.142 | -2.088  | 24.880 | 1.00 | 20.08 |
| ATOM | 668 | CA  | CYS | 244 | -13.310 | -0.900  | 25.059 | 1.00 | 20.08 |
| ATOM | 669 | CB  | CYS | 244 | -14.194 | 0.329   | 25.278 | 1.00 | 61.80 |
| ATOM | 670 | SG  | CYS | 244 | -13.674 | 1.784   | 24.340 | 1.00 | 61.80 |
| ATOM | 671 | C   | CYS | 244 | -12.286 | -1.017  | 26.189 | 1.00 | 20.08 |
| ATOM | 672 | O   | CYS | 244 | -11.141 | -0.590  | 26.040 | 1.00 | 61.80 |
| ATOM | 673 | N   | GLU | 245 | -12.691 | -1.630  | 27.299 | 1.00 | 21.05 |
| ATOM | 674 | CA  | GLU | 245 | -11.814 | -1.811  | 28.454 | 1.00 | 21.05 |
| ATOM | 675 | CB  | GLU | 245 | -12.541 | -2.560  | 29.578 | 1.00 | 40.41 |
| ATOM | 676 | CG  | GLU | 245 | -13.510 | -1.705  | 30.393 | 1.00 | 40.41 |
| ATOM | 677 | CD  | GLU | 245 | -14.953 | -1.773  | 29.910 | 1.00 | 40.41 |
| ATOM | 678 | OE1 | GLU | 245 | -15.854 | -1.761  | 30.775 | 1.00 | 40.41 |
| ATOM | 679 | OE2 | GLU | 245 | -15.197 | -1.824  | 28.683 | 1.00 | 40.41 |
| ATOM | 680 | C   | GLU | 245 | -10.541 | -2.558  | 28.084 | 1.00 | 21.05 |
| ATOM | 681 | O   | GLU | 245 | -9.439  | -2.138  | 28.440 | 1.00 | 40.41 |
| ATOM | 682 | N   | ASP | 246 | -10.698 | -3.654  | 27.351 | 1.00 | 17.22 |
| ATOM | 683 | CA  | ASP | 246 | -9.564  | -4.463  | 26.924 | 1.00 | 17.22 |
| ATOM | 684 | CB  | ASP | 246 | -10.044 | -5.774  | 26.303 | 1.00 | 30.41 |
| ATOM | 685 | CG  | ASP | 246 | -10.634 | -6.727  | 27.327 | 1.00 | 30.41 |
| ATOM | 686 | OD1 | ASP | 246 | -10.755 | -6.349  | 28.512 | 1.00 | 30.41 |
| ATOM | 687 | OD2 | ASP | 246 | -10.975 | -7.864  | 26.946 | 1.00 | 30.41 |
| ATOM | 688 | C   | ASP | 246 | -8.693  | -3.705  | 25.936 | 1.00 | 17.22 |
| ATOM | 689 | O   | ASP | 246 | -7.467  | -3.713  | 26.050 | 1.00 | 30.41 |
| ATOM | 690 | N   | GLN | 247 | -9.332  | -3.045  | 24.973 | 1.00 | 17.12 |
| ATOM | 691 | CA  | GLN | 247 | -8.615  | -2.272  | 23.966 | 1.00 | 17.12 |
| ATOM | 692 | CB  | GLN | 247 | -9.594  | -1.494  | 23.088 | 1.00 | 16.72 |
| ATOM | 693 | CG  | GLN | 247 | -10.504 | -2.365  | 22.242 | 1.00 | 16.72 |
| ATOM | 694 | CD  | GLN | 247 | -11.352 | -1.553  | 21.290 | 1.00 | 16.72 |
| ATOM | 695 | OE1 | GLN | 247 | -10.925 | -0.515  | 20.790 | 1.00 | 16.72 |
| ATOM | 696 | NE2 | GLN | 247 | -12.560 | -2.018  | 21.033 | 1.00 | 16.72 |
| ATOM | 697 | C   | GLN | 247 | -7.650  | -1.303  | 24.637 | 1.00 | 17.12 |
| ATOM | 698 | O   | GLN | 247 | -6.476  | -1.228  | 24.273 | 1.00 | 16.72 |
| ATOM | 699 | N   | ILE | 248 | -8.152  | -0.591  | 25.640 | 1.00 | 19.19 |
| ATOM | 700 | CA  | ILE | 248 | -7.358  | 0.377   | 26.387 | 1.00 | 19.19 |
| ATOM | 701 | CB  | ILE | 248 | -8.238  | 1.137   | 27.410 | 1.00 | 24.32 |
| ATOM | 702 | CG2 | ILE | 248 | -7.385  | 2.055   | 28.282 | 1.00 | 24.32 |
| ATOM | 703 | CG1 | ILE | 248 | -9.312  | 1.942   | 26.668 | 1.00 | 24.32 |
| ATOM | 704 | CD1 | ILE | 248 | -10.327 | 2.618   | 27.573 | 1.00 | 24.32 |
| ATOM | 705 | C   | ILE | 248 | -6.180  | -0.297  | 27.093 | 1.00 | 19.19 |
| ATOM | 706 | O   | ILE | 248 | -5.035  | 0.131   | 26.943 | 1.00 | 24.32 |
| ATOM | 707 | N   | ILE | 249 | -6.457  | -1.367  | 27.830 | 1.00 | 12.09 |
| ATOM | 708 | CA  | ILE | 249 | -5.409  | -2.090  | 28.547 | 1.00 | 12.09 |
| ATOM | 709 | CB  | ILE | 249 | -5.996  | -3.295  | 29.322 | 1.00 | 30.01 |
| ATOM | 710 | CG2 | ILE | 249 | -4.884  | -4.168  | 29.885 | 1.00 | 30.01 |
| ATOM | 711 | CG1 | ILE | 249 | -6.899  | -2.794  | 30.451 | 1.00 | 30.01 |
| ATOM | 712 | CD1 | ILE | 249 | -7.598  | -3.893  | 31.215 | 1.00 | 30.01 |
| ATOM | 713 | C   | ILE | 249 | -4.299  | -2.561  | 27.602 | 1.00 | 12.09 |
| ATOM | 714 | O   | ILE | 249 | -3.115  | -2.339  | 27.866 | 1.00 | 30.01 |
| ATOM | 715 | N   | LEU | 250 | -4.691  | -3.168  | 26.486 | 1.00 | 20.87 |
| ATOM | 716 | CA  | LEU | 250 | -3.740  | -3.669  | 25.498 | 1.00 | 20.87 |
| ATOM | 717 | CB  | LEU | 250 | -4.474  | 4.410   | 24.376 | 1.00 | 15.15 |
| ATOM | 718 | CG  | LEU | 250 | -5.252  | -5.669  | 24.761 | 1.00 | 15.15 |
| ATOM | 719 | CD1 | LEU | 250 | -5.907  | -6.256  | 23.533 | 1.00 | 15.15 |

APPENDIX 4-continued

TR_TRIAC.PDB

| ATOM | 720 | CD2 | LEU | 250 | −4.325 | −6.686 | 25.400 | 1.00 | 15.15 |
|---|---|---|---|---|---|---|---|---|---|
| ATOM | 721 | C | LEU | 250 | −2.900 | −2.548 | 24.902 | 1.00 | 20.87 |
| ATOM | 722 | O | LEU | 250 | −1.680 | −2.667 | 24.792 | 1.00 | 15.15 |
| ATOM | 723 | N | LEU | 251 | −3.559 | −1.455 | 24.532 | 1.00 | 9.31 |
| ATOM | 724 | CA | LEU | 251 | −2.887 | −0.301 | 23.945 | 1.00 | 9.31 |
| ATOM | 725 | CB | LEU | 251 | −3.920 | 0.760 | 23.553 | 1.00 | 19.90 |
| ATOM | 726 | CG | LEU | 251 | −4.075 | 1.127 | 22.073 | 1.00 | 19.90 |
| ATOM | 727 | CD1 | LEU | 251 | −3.281 | 0.190 | 21.180 | 1.00 | 19.90 |
| ATOM | 728 | CD2 | LEU | 251 | −5.550 | 1.113 | 21.699 | 1.00 | 19.90 |
| ATOM | 729 | C | LEU | 251 | −1.851 | 0.307 | 24.887 | 1.00 | 9.31 |
| ATOM | 730 | O | LEU | 251 | −0.699 | 0.521 | 24.507 | 1.00 | 19.90 |
| ATOM | 731 | N | LYS | 252 | −2.253 | 0.545 | 26.127 | 1.00 | 18.83 |
| ATOM | 732 | CA | LYS | 252 | −1.362 | 1.132 | 27.114 | 1.00 | 18.83 |
| ATOM | 733 | CB | LYS | 252 | −2.138 | 1.455 | 28.395 | 1.00 | 42.69 |
| ATOM | 734 | CG | LYS | 252 | −3.395 | 2.274 | 28.130 | 1.00 | 42.69 |
| ATOM | 735 | CD | LYS | 252 | −3.588 | 3.412 | 29.115 | 1.00 | 42.69 |
| ATOM | 736 | CE | LYS | 252 | −3.998 | 2.934 | 30.493 | 1.00 | 42.69 |
| ATOM | 737 | NZ | LYS | 252 | 4.300 | 4.109 | 31.361 | 1.00 | 42.69 |
| ATOM | 738 | C | LYS | 252 | −0.171 | 0.222 | 27.408 | 1.00 | 18.83 |
| ATOM | 739 | O | LYS | 252 | 0.942 | 0.700 | 27.646 | 1.00 | 42.69 |
| ATOM | 740 | N | GLY | 253 | −0.392 | −1.086 | 27.328 | 1.00 | 16.16 |
| ATOM | 741 | CA | GLY | 253 | 0.676 | −2.031 | 27.595 | 1.00 | 16.16 |
| ATOM | 742 | C | GLY | 253 | 1.688 | −2.232 | 26.479 | 1.00 | 16.16 |
| ATOM | 743 | O | GLY | 253 | 2.836 | −2.587 | 26.747 | 1.00 | 34.57 |
| ATOM | 744 | N | CYS | 254 | 1.286 | −1.999 | 25.233 | 1.00 | 21.81 |
| ATOM | 745 | CA | CYS | 254 | 2.194 | −2.203 | 24.108 | 1.00 | 21.81 |
| ATOM | 746 | CB | CYS | 254 | 1.563 | −3.151 | 23.093 | 1.00 | 23.60 |
| ATOM | 747 | SG | CYS | 254 | 0.211 | −2.387 | 22.179 | 1.00 | 23.60 |
| ATOM | 748 | C | CYS | 254 | 2.616 | −0.935 | 23.380 | 1.00 | 21.81 |
| ATOM | 749 | O | CYS | 254 | 3.499 | −0.983 | 22.521 | 1.00 | 23.60 |
| ATOM | 750 | N | CYS | 255 | 2.004 | 0.193 | 23.724 | 1.00 | 14.98 |
| ATOM | 751 | CA | CYS | 255 | 2.309 | 1.461 | 23.066 | 1.00 | 14.98 |
| ATOM | 752 | CB | CYS | 255 | 1.611 | 2.616 | 23.781 | 1.00 | 24.32 |
| ATOM | 753 | SG | CYS | 255 | 1.602 | 4.153 | 22.841 | 1.00 | 24.32 |
| ATOM | 754 | C | CYS | 255 | 3.804 | 1.750 | 22.922 | 1.00 | 14.98 |
| ATOM | 755 | O | CYS | 255 | 4.305 | 1.895 | 21.805 | 1.00 | 24.32 |
| ATOM | 756 | N | MET | 256 | 4.525 | 1.777 | 24.037 | 1.00 | 13.77 |
| ATOM | 757 | CA | MET | 256 | 5.959 | 2.056 | 24.003 | 1.00 | 13.77 |
| ATOM | 758 | CB | MET | 256 | 6.515 | 2.218 | 25.423 | 1.00 | 19.23 |
| ATOM | 759 | CG | MET | 256 | 7.988 | 2.607 | 25.477 | 1.00 | 19.23 |
| ATOM | 760 | SD | MET | 256 | 8.344 | 4.132 | 24.571 | 1.00 | 19.23 |
| ATOM | 761 | CE | MET | 256 | 10.127 | 4.254 | 24.782 | 1.00 | 19.23 |
| ATOM | 762 | C | MET | 256 | 6.734 | 0.978 | 23.246 | 1.00 | 13.77 |
| ATOM | 763 | O | MET | 256 | 7.672 | 1.284 | 22.516 | 1.00 | 19.23 |
| ATOM | 764 | N | GLU | 257 | 6.316 | −0.275 | 23.400 | 1.00 | 12.57 |
| ATOM | 765 | CA | GLU | 257 | 6.971 | −1.397 | 22.730 | 1.00 | 12.57 |
| ATOM | 766 | CB | GLU | 257 | 6.342 | −2.716 | 23.182 | 1.00 | 31.54 |
| ATOM | 767 | CG | GLU | 257 | 6.497 | −2.982 | 24.677 | 1.00 | 31.54 |
| ATOM | 768 | CD | GLU | 257 | 5.720 | −4.196 | 25.167 | 1.00 | 31.54 |
| ATOM | 769 | OE1 | GLU | 257 | 5.220 | −4.983 | 24.334 | 1.00 | 31.54 |
| ATOM | 770 | OE2 | GLU | 257 | 5.607 | −4.361 | 26.400 | 1.00 | 31.54 |
| ATOM | 771 | C | GLU | 257 | 6.889 | −1.254 | 21.211 | 1.00 | 12.57 |
| ATOM | 772 | O | GLU | 257 | 7.881 | −1.452 | 20.505 | 1.00 | 31.54 |
| ATOM | 773 | N | ILE | 258 | 5.712 | −0.881 | 20.717 | 1.00 | 17.89 |
| ATOM | 774 | CA | ILE | 258 | 5.508 | −0.692 | 19.288 | 1.00 | 17.89 |
| ATOM | 775 | CB | ILE | 258 | 4.001 | −0.555 | 18.946 | 1.00 | 15.57 |
| ATOM | 776 | CG2 | ILE | 258 | 3.813 | −0.129 | 17.493 | 1.00 | 15.57 |
| ATOM | 777 | CG1 | ILE | 258 | 3.288 | −1.886 | 19.211 | 1.00 | 15.57 |
| ATOM | 778 | CD1 | ILE | 258 | 1.798 | −1.872 | 18.922 | 1.00 | 15.57 |
| ATOM | 779 | C | ILE | 258 | 6.289 | 0.535 | 18.811 | 1.00 | 17.89 |
| ATOM | 780 | O | ILE | 258 | 7.000 | 0.468 | 17.805 | 1.00 | 15.57 |
| ATOM | 781 | N | MET | 259 | 6.196 | 1.636 | 19.556 | 1.00 | 11.23 |
| ATOM | 782 | CA | MET | 259 | 6.907 | 2.861 | 19.201 | 1.00 | 11.23 |
| ATOM | 783 | CB | MET | 259 | 6.568 | 3.995 | 20.175 | 1.00 | 22.19 |
| ATOM | 784 | CG | MET | 259 | 5.112 | 4.439 | 20.117 | 1.00 | 22.19 |
| ATOM | 785 | SD | MET | 259 | 4.828 | 6.033 | 20.915 | 1.00 | 22.19 |
| ATOM | 786 | CE | MET | 259 | 5.038 | 5.606 | 22.621 | 1.00 | 22.19 |
| ATOM | 787 | C | MET | 259 | 8.415 | 2.637 | 19.131 | 1.00 | 11.23 |
| ATOM | 788 | O | MET | 259 | 9.060 | 3.008 | 18.145 | 1.00 | 22.19 |
| ATOM | 789 | N | SER | 260 | 8.974 | 1.994 | 20.153 | 1.00 | 8.59 |
| ATOM | 790 | CA | SER | 260 | 10.408 | 1.706 | 20.195 | 1.00 | 8.59 |
| ATOM | 791 | CB | SER | 260 | 10.763 | 0.939 | 21.472 | 1.00 | 23.39 |
| ATOM | 792 | OG | SER | 260 | 10.430 | 1.685 | 22.623 | 1.00 | 23.39 |
| ATOM | 793 | C | SER | 260 | 10.793 | 0.864 | 18.977 | 1.00 | 8.59 |
| ATOM | 794 | O | SER | 260 | 11.824 | 1.100 | 18.350 | 1.00 | 23.39 |
| ATOM | 795 | N | LEU | 261 | 9.952 | −0.111 | 18.644 | 1.00 | 13.26 |
| ATOM | 796 | CA | LEU | 261 | 10.194 | −0.992 | 17.507 | 1.00 | 13.26 |

APPENDIX 4-continued

TR_TRIAC.PDB

| | | | | | | | | |
|---|---|---|---|---|---|---|---|---|
| ATOM | 797 | CB | LEU | 261 | 9.076 | −2.035 | 17.401 | 1.00 | 14.32 |
| ATOM | 798 | CG | LEU | 261 | 9.019 | −2.894 | 16.134 | 1.00 | 14.32 |
| ATOM | 799 | CD1 | LEU | 261 | 10.278 | −3.733 | 15.999 | 1.00 | 14.32 |
| ATOM | 800 | CD2 | LEU | 261 | 7.785 | −3.772 | 16.174 | 1.00 | 14.32 |
| ATOM | 801 | C | LEU | 261 | 10.276 | −0.170 | 16.220 | 1.00 | 13.26 |
| ATOM | 802 | O | LEU | 261 | 11.213 | −0.313 | 15.432 | 1.00 | 14.32 |
| ATOM | 803 | N | ARG | 262 | 9.330 | 0.744 | 16.043 | 1.00 | 10.57 |
| ATOM | 804 | CA | ARG | 262 | 9.278 | 1.598 | 14.861 | 1.00 | 10.57 |
| ATOM | 805 | CB | ARG | 262 | 8.018 | 2.454 | 14.917 | 1.00 | 16.08 |
| ATOM | 806 | CG | ARG | 262 | 6.755 | 1.647 | 14.728 | 1.00 | 16.08 |
| ATOM | 807 | CD | ARG | 262 | 5.540 | 2.525 | 14.614 | 1.00 | 16.08 |
| ATOM | 808 | NE | ARG | 262 | 4.418 | 1.765 | 14.076 | 1.00 | 16.08 |
| ATOM | 809 | CZ | ARG | 262 | 3.260 | 2.289 | 13.689 | 1.00 | 16.08 |
| ATOM | 810 | NH1 | ARG | 262 | 3.050 | 3.596 | 13.780 | 1.00 | 16.08 |
| ATOM | 811 | NH2 | ARG | 262 | 2.322 | 1.497 | 13.183 | 1.00 | 16.08 |
| ATOM | 812 | C | ARG | 262 | 10.530 | 2.471 | 14.704 | 1.00 | 10.57 |
| ATOM | 813 | O | ARG | 262 | 11.038 | 2.649 | 13.589 | 1.00 | 16.08 |
| ATOM | 814 | N | ALA | 263 | 11.016 | 3.014 | 15.820 | 1.00 | 13.37 |
| ATOM | 815 | CA | ALA | 263 | 12.221 | 3.842 | 15.831 | 1.00 | 13.37 |
| ATOM | 816 | CB | ALA | 263 | 12.363 | 4.516 | 17.172 | 1.00 | 17.12 |
| ATOM | 817 | C | ALA | 263 | 13.443 | 2.964 | 15.561 | 1.00 | 13.37 |
| ATOM | 818 | O | ALA | 263 | 14.313 | 3.316 | 14.762 | 1.00 | 17.12 |
| ATOM | 819 | N | ALA | 264 | 13.474 | 1.802 | 16.207 | 1.00 | 16.55 |
| ATOM | 820 | CA | ALA | 264 | 14.514 | 0.855 | 16.072 | 1.00 | 16.55 |
| ATOM | 821 | CB | ALA | 264 | 14.375 | −0.327 | 17.019 | 1.00 | 24.62 |
| ATOM | 822 | C | ALA | 264 | 14.770 | 0.364 | 14.642 | 1.00 | 16.55 |
| ATOM | 823 | O | ALA | 264 | 15.904 | 0.244 | 14.169 | 1.00 | 24.62 |
| ATOM | 824 | N | VAL | 265 | 13.670 | 0.073 | 13.955 | 1.00 | 22.25 |
| ATOM | 825 | CA | VAL | 265 | 13.754 | −0.401 | 12.583 | 1.00 | 22.25 |
| ATOM | 826 | CB | VAL | 265 | 12.428 | −1.038 | 12.086 | 1.00 | 25.31 |
| ATOM | 827 | CG1 | VAL | 265 | 12.079 | −2.239 | 12.936 | 1.00 | 25.31 |
| ATOM | 828 | CG2 | VAL | 265 | 11.302 | −0.030 | 12.091 | 1.00 | 25.31 |
| ATOM | 829 | C | VAL | 265 | 14.208 | 0.707 | 11.639 | 1.00 | 22.25 |
| ATOM | 830 | O | VAL | 265 | 14.615 | 0.434 | 10.513 | 1.00 | 25.31 |
| ATOM | 831 | N | ARG | 266 | 14.124 | 1.955 | 12.092 | 1.00 | 26.45 |
| ATOM | 832 | CA | ARG | 266 | 14.567 | 3.086 | 11.283 | 1.00 | 26.45 |
| ATOM | 833 | CB | ARG | 266 | 13.596 | 4.261 | 11.399 | 1.00 | 38.04 |
| ATOM | 834 | CG | ARG | 266 | 12.232 | 4.019 | 10.807 | 1.00 | 38.04 |
| ATOM | 835 | CD | ARG | 266 | 11.503 | 5.339 | 10.651 | 1.00 | 38.04 |
| ATOM | 836 | NE | ARG | 266 | 10.074 | 5.216 | 10.925 | 1.00 | 38.04 |
| ATOM | 837 | CZ | ARG | 266 | 9.504 | 5.551 | 12.079 | 1.00 | 38.04 |
| ATOM | 838 | NH1 | ARG | 266 | 10.237 | 6.038 | 13.075 | 1.00 | 38.04 |
| ATOM | 839 | NH2 | ARG | 266 | 8.196 | 5.411 | 12.240 | 1.00 | 38.04 |
| ATOM | 840 | C | ARG | 266 | 15.957 | 3.531 | 11.729 | 1.00 | 26.45 |
| ATOM | 841 | O | ARG | 266 | 16.296 | 4.717 | 11.660 | 1.00 | 38.04 |
| ATOM | 842 | N | TYR | 267 | 16.733 | 2.590 | 12.251 | 1.00 | 24.87 |
| ATOM | 843 | CA | TYR | 267 | 18.083 | 2.888 | 12.700 | 1.00 | 24.87 |
| ATOM | 844 | CB | TYR | 267 | 18.592 | 1.788 | 13.639 | 1.00 | 25.84 |
| ATOM | 845 | CG | TYR | 267 | 20.073 | 1.865 | 13.931 | 1.00 | 25.84 |
| ATOM | 846 | CD1 | TYR | 267 | 20.579 | 2.789 | 14.844 | 1.00 | 25.84 |
| ATOM | 847 | CE1 | TYR | 267 | 21.940 | 2.865 | 15.103 | 1.00 | 25.84 |
| ATOM | 848 | CD2 | TYR | 267 | 20.971 | 1.017 | 13.284 | 1.00 | 25.84 |
| ATOM | 849 | CE2 | TYR | 267 | 22.331 | 1.085 | 13.536 | 1.00 | 25.84 |
| ATOM | 850 | CZ | TYR | 267 | 22.810 | 2.011 | 14.444 | 1.00 | 25.84 |
| ATOM | 851 | OH | TYR | 267 | 24.162 | 2.078 | 14.683 | 1.00 | 25.84 |
| ATOM | 852 | C | TYR | 267 | 18.999 | 3.009 | 11.488 | 1.00 | 24.87 |
| ATOM | 853 | O | TYR | 267 | 19.019 | 2.130 | 10.625 | 1.00 | 25.84 |
| ATOM | 854 | N | ASP | 268 | 19.751 | 4.102 | 11.423 | 1.00 | 28.13 |
| ATOM | 855 | CA | ASP | 268 | 20.666 | 4.320 | 10.313 | 1.00 | 28.13 |
| ATOM | 856 | CB | ASP | 268 | 20.524 | 5.744 | 9.773 | 1.00 | 51.63 |
| ATOM | 857 | CG | ASP | 268 | 21.339 | 5.973 | 8.517 | 1.00 | 51.63 |
| ATOM | 858 | OD1 | ASP | 268 | 21.060 | 5.305 | 7.498 | 1.00 | 51.63 |
| ATOM | 859 | OD2 | ASP | 268 | 22.262 | 6.814 | 8.547 | 1.00 | 51.63 |
| ATOM | 860 | C | ASP | 268 | 22.105 | 4.068 | 10.749 | 1.00 | 28.13 |
| ATOM | 861 | O | ASP | 268 | 22.683 | 4.854 | 11.500 | 1.00 | 51.63 |
| ATOM | 862 | N | PRO | 269 | 22.707 | 2.964 | 10.276 | 1.00 | 37.07 |
| ATOM | 863 | CD | PRO | 269 | 22.103 | 1.938 | 9.410 | 1.00 | 39.18 |
| ATOM | 864 | CA | PRO | 269 | 24.086 | 2.612 | 10.623 | 1.00 | 37.07 |
| ATOM | 865 | CB | PRO | 269 | 24.319 | 1.324 | 9.832 | 1.00 | 39.18 |
| ATOM | 866 | CG | PRO | 269 | 22.950 | 0.735 | 9.706 | 1.00 | 39.18 |
| ATOM | 867 | C | PRO | 269 | 25.079 | 3.698 | 10.216 | 1.00 | 37.07 |
| ATOM | 868 | O | PRO | 269 | 26.003 | 4.006 | 10.964 | 1.00 | 39.18 |
| ATOM | 869 | N | ALA | 270 | 24.855 | 4.295 | 9.047 | 1.00 | 46.88 |
| ATOM | 870 | CA | ALA | 279 | 25.730 | 5.340 | 8.519 | 1.00 | 46.88 |
| ATOM | 871 | CB | ALA | 270 | 25.177 | 5.873 | 7.198 | 1.00 | 41.71 |
| ATOM | 872 | C | ALA | 270 | 25.974 | 6.493 | 9.492 | 1.00 | 46.88 |
| ATOM | 873 | O | ALA | 270 | 27.121 | 6.844 | 9.763 | 1.00 | 41.71 |

APPENDIX 4-continued

TR_TRIAC.PDB

| ATOM | 874 | N   | SER | 271 | 24.899 | 7.081  | 10.009 | 1.00 | 34.54 |
| ---- | --- | --- | --- | --- | ------ | ------ | ------ | ---- | ----- |
| ATOM | 875 | CA  | SER | 271 | 25.013 | 8.198  | 10.941 | 1.00 | 34.54 |
| ATOM | 876 | CB  | SER | 271 | 23.959 | 9.259  | 10.618 | 1.00 | 42.29 |
| ATOM | 877 | OG  | SER | 271 | 22.686 | 8.668  | 10.422 | 1.00 | 42.29 |
| ATOM | 878 | C   | SER | 271 | 24.910 | 7.793  | 12.408 | 1.00 | 34.54 |
| ATOM | 879 | O   | SER | 271 | 25.169 | 8.607  | 13.297 | 1.00 | 42.29 |
| ATOM | 880 | N   | ASP | 272 | 24.546 | 6.535  | 12.653 | 1.00 | 41.05 |
| ATOM | 881 | CA  | ASP | 272 | 24.388 | 6.005  | 14.007 | 1.00 | 41.05 |
| ATOM | 882 | CB  | ASP | 272 | 25.720 | 6.078  | 14.772 | 1.00 | 47.32 |
| ATOM | 883 | CG  | ASP | 272 | 25.653 | 5.428  | 16.147 | 1.00 | 47.32 |
| ATOM | 884 | OD1 | ASP | 272 | 24.981 | 4.384  | 16.299 | 1.00 | 47.32 |
| ATOM | 885 | OD2 | ASP | 272 | 26.284 | 5.967  | 17.081 | 1.00 | 47.32 |
| ATOM | 886 | C   | ASP | 272 | 23.279 | 6.777  | 14.730 | 1.00 | 41.05 |
| ATOM | 887 | O   | ASP | 272 | 23.444 | 7.233  | 15.866 | 1.00 | 47.32 |
| ATOM | 888 | N   | THR | 273 | 22.139 | 6.905  | 14.058 | 1.00 | 27.60 |
| ATOM | 889 | CA  | THR | 273 | 20.996 | 7.618  | 14.608 | 1.00 | 27.60 |
| ATOM | 890 | CB  | THR | 273 | 20.808 | 8.991  | 13.911 | 1.00 | 30.96 |
| ATOM | 891 | OG1 | THR | 273 | 20.723 | 8.808  | 12.491 | 1.00 | 30.96 |
| ATOM | 892 | CG2 | THR | 273 | 21.967 | 9.924  | 14.228 | 1.00 | 30.96 |
| ATOM | 893 | C   | THR | 273 | 19.701 | 6.829  | 14.442 | 1.00 | 27.60 |
| ATOM | 894 | O   | THR | 273 | 19.633 | 5.883  | 13.650 | 1.00 | 30.96 |
| ATOM | 895 | N   | LEU | 274 | 18.696 | 7.192  | 15.232 | 1.00 | 20.89 |
| ATOM | 896 | CA  | LEU | 274 | 17.374 | 6.574  | 15.161 | 1.00 | 20.89 |
| ATOM | 897 | CB  | LEU | 274 | 16.862 | 6.193  | 16.555 | 1.00 | 22.48 |
| ATOM | 898 | CG  | LEU | 274 | 17.480 | 5.009  | 17.301 | 1.00 | 22.48 |
| ATOM | 899 | CD1 | LEU | 274 | 16.798 | 4.866  | 18.650 | 1.00 | 22.48 |
| ATOM | 900 | CD2 | LEU | 274 | 17.317 | 3.736  | 16.497 | 1.00 | 22.48 |
| ATOM | 901 | C   | LEU | 274 | 16.470 | 7.654  | 14.586 | 1.00 | 20.89 |
| ATOM | 902 | O   | LEU | 274 | 16.753 | 8.842  | 14.744 | 1.00 | 22.48 |
| ATOM | 903 | N   | THR | 275 | 15.393 | 7.258  | 13.922 | 1.00 | 27.89 |
| ATOM | 904 | CA  | THR | 275 | 14.478 | 8.235  | 13.354 | 1.00 | 27.89 |
| ATOM | 905 | CB  | THR | 275 | 14.325 | 8.045  | 11.832 | 1.00 | 37.64 |
| ATOM | 906 | OG1 | THR | 275 | 15.622 | 7.983  | 11.228 | 1.00 | 37.64 |
| ATOM | 907 | CG2 | THR | 275 | 13.570 | 9.215  | 11.222 | 1.00 | 37.64 |
| ATOM | 908 | C   | THR | 275 | 13.120 | 8.135  | 14.032 | 1.00 | 27.89 |
| ATOM | 909 | O   | THR | 275 | 12.493 | 7.081  | 14.019 | 1.00 | 37.64 |
| ATOM | 910 | N   | LEU | 276 | 12.700 | 9.226  | 14.667 | 1.00 | 28.07 |
| ATOM | 911 | CA  | LEU | 276 | 11.418 | 9.275  | 15.358 | 1.00 | 28.07 |
| ATOM | 912 | CB  | LEU | 276 | 11.497 | 10.214 | 16.572 | 1.00 | 24.81 |
| ATOM | 913 | CG  | LEU | 276 | 12.639 | 10.005 | 17.577 | 1.00 | 24.81 |
| ATOM | 914 | CD1 | LEU | 276 | 12.459 | 10.929 | 18.769 | 1.00 | 24.81 |
| ATOM | 915 | CD2 | LEU | 276 | 12.692 | 8.558  | 18.038 | 1.00 | 24.81 |
| ATOM | 916 | C   | LEU | 276 | 10.339 | 9.761  | 14.395 | 1.00 | 28.07 |
| ATOM | 917 | O   | LEU | 276 | 10.533 | 10.760 | 13.691 | 1.00 | 24.81 |
| ATOM | 918 | N   | SER | 277 | 9.232  | 9.027  | 14.331 | 1.00 | 29.24 |
| ATOM | 919 | CA  | SER | 277 | 8.106  | 9.357  | 13.458 | 1.00 | 29.24 |
| ATOM | 920 | CB  | SER | 277 | 7.369  | 10.594 | 13.985 | 1.00 | 30.56 |
| ATOM | 921 | OG  | SER | 277 | 6.845  | 10.358 | 15.283 | 1.00 | 30.56 |
| ATOM | 922 | C   | SER | 277 | 8.533  | 9.569  | 12.005 | 1.00 | 29.24 |
| ATOM | 923 | O   | SER | 277 | 7.902  | 10.326 | 11.263 | 1.00 | 30.56 |
| ATOM | 924 | N   | GLY | 278 | 9.619  | 8.908  | 11.618 | 1.00 | 34.41 |
| ATOM | 925 | CA  | GLY | 278 | 10.135 | 9.024  | 10.263 | 1.00 | 34.41 |
| ATOM | 926 | C   | GLY | 278 | 10.472 | 10.442 | 9.830  | 1.00 | 34.41 |
| ATOM | 927 | O   | GLY | 278 | 10.516 | 10.725 | 8.631  | 1.00 | 44.04 |
| ATOM | 928 | N   | GLU | 279 | 10.733 | 11.326 | 10.791 | 1.00 | 37.82 |
| ATOM | 929 | CA  | GLU | 279 | 11.056 | 12.717 | 10.479 | 1.00 | 37.82 |
| ATOM | 930 | CB  | GLU | 279 | 9.808  | 13.600 | 10.612 | 1.00 | 70.24 |
| ATOM | 931 | CG  | GLU | 279 | 9.202  | 13.631 | 12.014 | 1.00 | 70.24 |
| ATOM | 932 | CD  | GLU | 279 | 8.028  | 14.593 | 12.141 | 1.00 | 70.24 |
| ATOM | 933 | OE1 | GLU | 279 | 8.028  | 15.406 | 13.093 | 1.00 | 70.24 |
| ATOM | 934 | OE2 | GLU | 279 | 7.103  | 14.535 | 11.301 | 1.00 | 70.24 |
| ATOM | 935 | C   | GLU | 279 | 12.192 | 13.321 | 11.300 | 1.00 | 37.82 |
| ATOM | 936 | O   | GLU | 279 | 12.857 | 14.248 | 10.841 | 1.00 | 70.24 |
| ATOM | 937 | N   | MET | 280 | 12.424 | 12.811 | 12.505 | 1.00 | 33.77 |
| ATOM | 938 | CA  | MET | 280 | 13.482 | 13.360 | 13.344 | 1.00 | 33.77 |
| ATOM | 939 | CB  | MET | 280 | 12.903 | 13.848 | 14.674 | 1.00 | 33.89 |
| ATOM | 940 | CG  | MET | 280 | 13.898 | 14.595 | 15.545 | 1.00 | 33.89 |
| ATOM | 941 | SD  | MET | 280 | 13.350 | 14.740 | 17.256 | 1.00 | 33.89 |
| ATOM | 942 | CE  | MET | 280 | 12.100 | 16.017 | 17.121 | 1.00 | 33.89 |
| ATOM | 943 | C   | MET | 280 | 14.620 | 12.383 | 13.613 | 1.00 | 33.77 |
| ATOM | 944 | O   | MET | 280 | 14.432 | 11.366 | 14.282 | 1.00 | 33.89 |
| ATOM | 945 | N   | ALA | 281 | 15.797 | 12.690 | 13.080 | 1.00 | 30.24 |
| ATOM | 946 | CA  | ALA | 281 | 16.972 | 11.852 | 13.287 | 1.00 | 30.24 |
| ATOM | 947 | CB  | ALA | 281 | 17.937 | 11.998 | 12.120 | 1.00 | 25.10 |
| ATOM | 948 | C   | ALA | 281 | 17.631 | 12.309 | 14.587 | 1.00 | 30.24 |
| ATOM | 949 | O   | ALA | 281 | 18.008 | 13.477 | 14.718 | 1.00 | 25.10 |
| ATOM | 950 | N   | VAL | 282 | 17.743 | 11.401 | 15.551 | 1.00 | 32.12 |

APPENDIX 4-continued

TR_TRIAC.PDB

| | | | | | | | | |
|---|---|---|---|---|---|---|---|---|
| ATOM | 951 | CA | VAL | 282 | 18.339 | 11.726 | 16.844 | 1.00 | 32.12 |
| ATOM | 952 | CB | VAL | 282 | 17.303 | 11.606 | 17.991 | 1.00 | 37.75 |
| ATOM | 953 | CG1 | VAL | 282 | 16.184 | 12.615 | 17.799 | 1.00 | 37.75 |
| ATOM | 954 | CG2 | VAL | 282 | 16.739 | 10.193 | 18.055 | 1.00 | 37.75 |
| ATOM | 955 | C | VAL | 282 | 19.543 | 10.852 | 17.181 | 1.00 | 32.12 |
| ATOM | 956 | O | VAL | 282 | 19.614 | 9.690 | 16.778 | 1.00 | 37.75 |
| ATOM | 957 | N | LYS | 283 | 20.491 | 11.428 | 17.913 | 1.00 | 26.82 |
| ATOM | 958 | CA | LYS | 283 | 21.700 | 10.722 | 18.328 | 1.00 | 26.82 |
| ATOM | 959 | CB | LYS | 283 | 22.894 | 11.679 | 18.342 | 1.00 | 57.25 |
| ATOM | 960 | CG | LYS | 283 | 23.258 | 12.245 | 16.979 | 1.00 | 57.25 |
| ATOM | 961 | CD | LYS | 283 | 24.282 | 13.361 | 17.105 | 1.00 | 57.25 |
| ATOM | 962 | CE | LYS | 283 | 24.752 | 13.836 | 15.741 | 1.00 | 57.25 |
| ATOM | 963 | NZ | LYS | 283 | 25.518 | 12.772 | 15.033 | 1.00 | 57.25 |
| ATOM | 964 | C | LYS | 283 | 21.509 | 10.120 | 19.717 | 1.00 | 26.82 |
| ATOM | 965 | O | LYS | 283 | 20.648 | 10.566 | 20.477 | 1.00 | 57.25 |
| ATOM | 966 | N | ARG | 284 | 22.351 | 9.146 | 20.058 | 1.00 | 26.41 |
| ATOM | 967 | CA | ARG | 284 | 22.297 | 8.457 | 21.351 | 1.00 | 26.41 |
| ATOM | 968 | CB | ARG | 284 | 23.527 | 7.566 | 21.528 | 1.00 | 41.02 |
| ATOM | 969 | CG | ARG | 284 | 23.715 | 6.539 | 20.440 | 1.00 | 41.02 |
| ATOM | 970 | CD | ARG | 284 | 25.016 | 5.794 | 20.616 | 1.00 | 41.02 |
| ATOM | 971 | NE | ARG | 284 | 25.145 | 4.730 | 19.630 | 1.00 | 41.02 |
| ATOM | 972 | CZ | ARG | 284 | 24.759 | 3.475 | 19.831 | 1.00 | 41.02 |
| ATOM | 973 | NH1 | ARG | 284 | 24.221 | 3.117 | 20.990 | 1.00 | 41.02 |
| ATOM | 974 | NH2 | ARG | 284 | 24.886 | 2.584 | 18.859 | 1.00 | 41.02 |
| ATOM | 975 | C | ARG | 284 | 22.200 | 9.399 | 22.543 | 1.00 | 26.41 |
| ATOM | 976 | O | ARG | 284 | 21.296 | 9.278 | 23.370 | 1.00 | 41.02 |
| ATOM | 977 | N | GLU | 285 | 23.152 | 10.321 | 22.634 | 1.00 | 33.23 |
| ATOM | 978 | CA | GLU | 285 | 23.201 | 11.292 | 23.721 | 1.00 | 33.23 |
| ATOM | 979 | CB | GLU | 285 | 24.366 | 12.258 | 23.492 | 1.00 | 69.82 |
| ATOM | 980 | CG | GLU | 285 | 24.485 | 13.359 | 24.533 | 1.00 | 69.82 |
| ATOM | 981 | CD | GLU | 285 | 25.079 | 14.636 | 23.964 | 1.00 | 69.82 |
| ATOM | 982 | OE1 | GLU | 285 | 26.309 | 14.826 | 24.070 | 1.00 | 69.82 |
| ATOM | 983 | OE2 | GLU | 285 | 24.309 | 15.453 | 23.409 | 1.00 | 69.82 |
| ATOM | 984 | C | GLU | 285 | 21.898 | 12.082 | 23.823 | 1.00 | 33.23 |
| ATOM | 985 | O | GLU | 285 | 21.336 | 12.239 | 24.907 | 1.00 | 69.82 |
| ATOM | 986 | N | GLN | 286 | 21.414 | 12.551 | 22.677 | 1.00 | 28.07 |
| ATOM | 987 | CA | GLN | 286 | 20.194 | 13.346 | 22.614 | 1.00 | 28.07 |
| ATOM | 988 | CB | GLN | 286 | 19.948 | 13.824 | 21.181 | 1.00 | 41.05 |
| ATOM | 989 | CG | GLN | 286 | 21.051 | 14.726 | 20.639 | 1.00 | 41.05 |
| ATOM | 990 | CD | GLN | 286 | 20.808 | 15.154 | 19.202 | 1.00 | 41.05 |
| ATOM | 991 | OE1 | GLN | 286 | 20.783 | 14.322 | 18.293 | 1.00 | 41.05 |
| ATOM | 992 | NE2 | GLN | 286 | 20.635 | 16.452 | 18.990 | 1.00 | 41.05 |
| ATOM | 993 | C | GLN | 286 | 18.955 | 12.642 | 23.162 | 1.00 | 28.07 |
| ATOM | 994 | O | GLN | 286 | 18.281 | 13.174 | 24.048 | 1.00 | 41.05 |
| ATOM | 995 | N | LEU | 287 | 18.663 | 11.447 | 22.658 | 1.00 | 30.11 |
| ATOM | 996 | CN | LEU | 287 | 17.492 | 10.705 | 23.116 | 1.00 | 30.11 |
| ATOM | 997 | CB | LEU | 287 | 17.232 | 9.489 | 22.219 | 1.00 | 21.70 |
| ATOM | 998 | CG | LEU | 287 | 15.859 | 8.821 | 22.357 | 1.00 | 21.70 |
| ATOM | 999 | CD1 | LEU | 287 | 14.748 | 9.818 | 22.061 | 1.00 | 21.70 |
| ATOM | 1000 | CD2 | LEU | 287 | 15.763 | 7.628 | 21.421 | 1.00 | 21.70 |
| ATOM | 1001 | C | LEU | 287 | 17.641 | 10.277 | 24.577 | 1.00 | 30.11 |
| ATOM | 1002 | O | LEU | 287 | 16.655 | 10.212 | 25.320 | 1.00 | 21.70 |
| ATOM | 1003 | N | LYS | 288 | 18.878 | 10.015 | 24.992 | 1.00 | 20.72 |
| ATOM | 1004 | CA | LYS | 288 | 19.156 | 9.611 | 26.365 | 1.00 | 20.72 |
| ATOM | 1005 | CB | LYS | 288 | 20.626 | 9.213 | 26.514 | 1.00 | 43.14 |
| ATOM | 1006 | CG | LYS | 288 | 20.991 | 8.721 | 27.903 | 1.00 | 43.14 |
| ATOM | 1007 | CD | LYS | 288 | 22.374 | 8.102 | 27.931 | 1.00 | 43.14 |
| ATOM | 1008 | CE | LYS | 288 | 22.615 | 7.379 | 29.250 | 1.00 | 43.14 |
| ATOM | 1009 | NZ | LYS | 288 | 23.866 | 6.568 | 29.224 | 1.00 | 43.14 |
| ATOM | 1010 | C | LYS | 288 | 18.819 | 10.742 | 27.331 | 1.00 | 20.72 |
| ATOM | 1011 | O | LYS | 288 | 18.027 | 10.566 | 28.261 | 1.00 | 43.14 |
| ATOM | 1012 | N | ASN | 289 | 19.380 | 11.917 | 27.067 | 1.00 | 33.64 |
| ATOM | 1013 | CA | ASN | 289 | 19.156 | 13.090 | 27.906 | 1.00 | 33.64 |
| ATOM | 1014 | CB | ASN | 289 | 20.190 | 14.173 | 27.590 | 1.00 | 35.61 |
| ATOM | 1015 | CG | ASN | 289 | 21.607 | 13.730 | 27.898 | 1.00 | 35.61 |
| ATOM | 1016 | OD1 | ASN | 289 | 21.835 | 12.920 | 28.797 | 1.00 | 35.61 |
| ATOM | 1017 | ND2 | ASN | 289 | 22.566 | 14.253 | 27.149 | 1.00 | 35.61 |
| ATOM | 1018 | C | ASN | 289 | 17.747 | 13.654 | 27.757 | 1.00 | 33.64 |
| ATOM | 1019 | O | ASN | 289 | 17.276 | 14.399 | 28.616 | 1.00 | 35.61 |
| ATOM | 1020 | N | GLY | 290 | 17.072 | 13.287 | 26.672 | 1.00 | 22.05 |
| ATOM | 1021 | CA | GLY | 290 | 15.722 | 13.767 | 26.435 | 1.00 | 22.05 |
| ATOM | 1022 | C | GLY | 290 | 14.688 | 13.247 | 27.416 | 1.00 | 22.05 |
| ATOM | 1023 | O | GLY | 290 | 13.550 | 13.710 | 27.420 | 1.00 | 29.95 |
| ATOM | 1024 | N | GLY | 291 | 15.072 | 12.276 | 28.239 | 1.00 | 24.91 |
| ATOM | 1025 | CA | GLY | 291 | 14.142 | 11.732 | 29.211 | 1.00 | 24.91 |
| ATOM | 1026 | C | GLY | 291 | 14.093 | 10.217 | 29.248 | 1.00 | 24.91 |
| ATOM | 1027 | O | GLY | 291 | 13.536 | 9.640 | 30.179 | 1.00 | 29.39 |

APPENDIX 4-continued

TR_TRIAC.PDB

| ATOM | 1028 | N | LEU | 292 | 14.676 | 9.567 | 28.246 | 1.00 | 30.21 |
|---|---|---|---|---|---|---|---|---|---|
| ATOM | 1029 | CA | LEU | 292 | 14.675 | 8.110 | 28.189 | 1.00 | 30.21 |
| ATOM | 1030 | CB | LEU | 292 | 14.732 | 7.626 | 26.734 | 1.00 | 21.45 |
| ATOM | 1031 | CG | LEU | 292 | 13.439 | 7.795 | 25.928 | 1.00 | 21.45 |
| ATOM | 1032 | CD1 | LEU | 292 | 13.612 | 7.225 | 24.542 | 1.00 | 21.45 |
| ATOM | 1033 | CD2 | LEU | 292 | 12.296 | 7.087 | 26.630 | 1.00 | 21.45 |
| ATOM | 1034 | C | LEU | 292 | 15.785 | 7.461 | 29.013 | 1.00 | 30.21 |
| ATOM | 1035 | O | LEU | 292 | 15.645 | 6.324 | 29.473 | 1.00 | 21.45 |
| ATOM | 1036 | N | GLY | 293 | 16.885 | 8.180 | 29.205 | 1.00 | 16.29 |
| ATOM | 1037 | CA | GLY | 293 | 17.992 | 7.638 | 29.970 | 1.00 | 16.29 |
| ATOM | 1038 | C | GLY | 293 | 18.534 | 6.374 | 29.332 | 1.00 | 16.29 |
| ATOM | 1039 | O | GLY | 293 | 18.763 | 6.334 | 28.122 | 1.00 | 25.88 |
| ATOM | 1040 | N | VAL | 294 | 18.689 | 5.322 | 30.130 | 1.00 | 33.05 |
| ATOM | 1041 | CA | VAL | 294 | 19.211 | 4.050 | 29.635 | 1.00 | 33.05 |
| ATOM | 1042 | CB | VAL | 294 | 19.530 | 3.069 | 30.788 | 1.00 | 30.11 |
| ATOM | 1043 | CG1 | VAL | 294 | 20.718 | 3.577 | 31.582 | 1.00 | 30.11 |
| ATOM | 1044 | CG2 | VAL | 294 | 18.315 | 2.887 | 31.697 | 1.00 | 30.11 |
| ATOM | 1045 | C | VAL | 294 | 18.302 | 3.361 | 28.617 | 1.00 | 33.05 |
| ATOM | 1046 | O | VAL | 294 | 18.768 | 2.545 | 27.817 | 1.00 | 30.11 |
| ATOM | 1047 | N | VAL | 295 | 17.014 | 3.699 | 28.635 | 1.00 | 18.14 |
| ATOM | 1048 | CA | VAL | 295 | 16.056 | 3.118 | 27.698 | 1.00 | 18.14 |
| ATOM | 1049 | CB | VAL | 295 | 14.638 | 3.698 | 27.902 | 1.00 | 28.34 |
| ATOM | 1050 | CG1 | VAL | 295 | 13.668 | 3.099 | 26.893 | 1.00 | 28.34 |
| ATOM | 1051 | CG2 | VAL | 295 | 14.159 | 3.431 | 29.317 | 1.00 | 28.34 |
| ATOM | 1052 | C | VAL | 295 | 16.521 | 3.415 | 26.275 | 1.00 | 18.14 |
| ATOM | 1053 | O | VAL | 295 | 16.395 | 2.577 | 25.383 | 1.00 | 28.34 |
| ATOM | 1054 | N | SER | 296 | 17.091 | 4.601 | 26.085 | 1.00 | 20.84 |
| ATOM | 1055 | CA | SER | 296 | 17.596 | 5.028 | 24.785 | 1.00 | 20.84 |
| ATOM | 1056 | CB | SER | 296 | 18.160 | 6.446 | 24.884 | 1.00 | 25.61 |
| ATOM | 1057 | OG | SER | 296 | 18.615 | 6.911 | 23.627 | 1.00 | 25.61 |
| ATOM | 1058 | C | SER | 296 | 18.687 | 4.074 | 24.307 | 1.00 | 20.84 |
| ATOM | 1059 | O | SER | 296 | 18.723 | 3.691 | 23.133 | 1.00 | 25.61 |
| ATOM | 1060 | N | ASP | 297 | 19.571 | 3.691 | 25.224 | 1.00 | 28.08 |
| ATOM | 1061 | CA | ASP | 297 | 20.660 | 2.777 | 24.904 | 1.00 | 28.08 |
| ATOM | 1062 | CB | ASP | 297 | 21.555 | 2.552 | 26.129 | 1.00 | 51.15 |
| ATOM | 1063 | CG | ASP | 297 | 22.207 | 3.835 | 26.629 | 1.00 | 51.15 |
| ATOM | 1064 | OD1 | ASP | 297 | 22.508 | 4.725 | 25.804 | 1.00 | 51.15 |
| ATOM | 1065 | OD2 | ASP | 297 | 22.425 | 3.948 | 27.855 | 1.00 | 51.15 |
| ATOM | 1066 | C | ASP | 297 | 20.079 | 1.450 | 24.434 | 1.00 | 28.08 |
| ATOM | 1067 | O | ASP | 297 | 20.549 | 0.869 | 23.456 | 1.00 | 51.15 |
| ATOM | 1068 | N | ALA | 298 | 19.024 | 1.006 | 25.111 | 1.00 | 26.12 |
| ATOM | 1069 | CA | ALA | 298 | 18.357 | −0.245 | 24.778 | 1.00 | 26.12 |
| ATOM | 1070 | CB | ALA | 298 | 17.253 | −0.530 | 25.787 | 1.00 | 18.80 |
| ATOM | 1071 | C | ALA | 298 | 17.790 | −0.223 | 23.356 | 1.00 | 26.12 |
| ATOM | 1072 | O | ALA | 298 | 18.014 | −1.154 | 22.575 | 1.00 | 18.80 |
| ATOM | 1073 | N | ILE | 299 | 17.078 | 0.848 | 23.013 | 1.00 | 17.42 |
| ATOM | 1074 | CA | ILE | 299 | 16.483 | 0.979 | 21.686 | 1.00 | 17.42 |
| ATOM | 1075 | CB | ILE | 299 | 15.559 | 2.211 | 21.597 | 1.00 | 16.69 |
| ATOM | 1076 | CG2 | ILE | 299 | 14.845 | 2.238 | 20.253 | 1.00 | 16.69 |
| ATOM | 1077 | CG1 | ILE | 299 | 14.515 | 2.149 | 22.712 | 1.00 | 16.69 |
| ATOM | 1078 | CD1 | ILE | 299 | 13.713 | 3.406 | 22.872 | 1.00 | 16.69 |
| ATOM | 1079 | C | ILE | 299 | 17.563 | 1.042 | 20.609 | 1.00 | 17.42 |
| ATOM | 1080 | O | ILE | 299 | 17.416 | 0.443 | 19.542 | 1.00 | 16.69 |
| ATOM | 1081 | N | PHE | 300 | 18.652 | 1.752 | 20.889 | 1.00 | 14.46 |
| ATOM | 1082 | CA | PHE | 300 | 19.751 | 1.851 | 19.935 | 1.00 | 14.46 |
| ATOM | 1083 | CB | PHE | 300 | 20.804 | 2.854 | 20.409 | 1.00 | 24.01 |
| ATOM | 1084 | CG | PHE | 300 | 20.656 | 4.221 | 19.801 | 1.00 | 24.01 |
| ATOM | 1085 | CD1 | PHE | 300 | 19.904 | 5.204 | 20.435 | 1.00 | 24.01 |
| ATOM | 1086 | CD2 | PHE | 300 | 21.271 | 4.526 | 18.591 | 1.00 | 24.01 |
| ATOM | 1087 | CE1 | PHE | 300 | 19.766 | 6.472 | 19.873 | 1.00 | 24.01 |
| ATOM | 1088 | CE2 | PHE | 300 | 21.140 | 5.791 | 18.020 | 1.00 | 24.01 |
| ATOM | 1089 | CZ | PHE | 300 | 20.385 | 6.765 | 18.663 | 1.00 | 24.01 |
| ATOM | 1090 | C | PHE | 300 | 20.383 | 0.480 | 19.726 | 1.00 | 14.46 |
| ATOM | 1091 | O | PHE | 300 | 20.696 | 0.102 | 18.596 | 1.00 | 24.01 |
| ATOM | 1092 | N | GLU | 301 | 20.547 | −0.270 | 20.813 | 1.00 | 21.61 |
| ATOM | 1093 | CA | GLU | 301 | 21.123 | −1.609 | 20.744 | 1.00 | 21.61 |
| ATOM | 1094 | CB | GLU | 301 | 21.289 | −2.192 | 22.143 | 1.00 | 23.89 |
| ATOM | 1095 | C | GLU | 301 | 20.211 | −2.498 | 19.904 | 1.00 | 21.61 |
| ATOM | 1096 | O | GLU | 301 | 20.681 | −3.251 | 19.043 | 1.00 | 23.89 |
| ATOM | 1097 | N | LEU | 302 | 18.906 | −2.390 | 20.140 | 1.00 | 14.43 |
| ATOM | 1098 | CA | LEU | 302 | 17.922 | −3.168 | 19.399 | 1.00 | 14.43 |
| ATOM | 1099 | CB | LEU | 302 | 16.512 | −2.872 | 19.912 | 1.00 | 23.43 |
| ATOM | 1100 | CG | LEU | 302 | 15.350 | −3.669 | 19.312 | 1.00 | 23.43 |
| ATOM | 1101 | CD1 | LEU | 302 | 15.459 | −5.140 | 19.688 | 1.00 | 23.43 |
| ATOM | 1102 | CD2 | LEU | 302 | 14.035 | −3.094 | 19.804 | 1.00 | 23.43 |
| ATOM | 1103 | C | LEU | 302 | 18.027 | −2.812 | 17.917 | 1.00 | 14.43 |
| ATOM | 1104 | O | LEU | 302 | 18.089 | −3.697 | 17.066 | 1.00 | 23.43 |

APPENDIX 4-continued

TR_TRIAC.PDB

| ATOM | 1105 | N   | GLY | 303 | 18.098 | −1.515  | 17.625 | 1.00 | 15.17 |
|------|------|-----|-----|-----|--------|---------|--------|------|-------|
| ATOM | 1106 | CA  | GLY | 303 | 18.208 | −1.056  | 16.251 | 1.00 | 15.17 |
| ATOM | 1107 | C   | GLY | 303 | 19.411 | −1.640  | 15.530 | 1.00 | 15.17 |
| ATOM | 1108 | O   | GLY | 303 | 19.290 | −2.137  | 14.406 | 1.00 | 27.67 |
| ATOM | 1109 | N   | LYS | 304 | 20.570 | −1.594  | 16.182 | 1.00 | 19.04 |
| ATOM | 1110 | CA  | LYS | 304 | 21.802 | −2.127  | 15.605 | 1.00 | 19.04 |
| ATOM | 1111 | CB  | LYS | 304 | 22.979 | −1.975  | 16.577 | 1.00 | 56.94 |
| ATOM | 1112 | CG  | LYS | 304 | 23.496 | −0.556  | 16.741 | 1.00 | 56.94 |
| ATOM | 1113 | CD  | LYS | 304 | 24.811 | −0.524  | 17.516 | 1.00 | 56.94 |
| ATOM | 1114 | CE  | LYS | 304 | 24.634 | −0.965  | 18.968 | 1.00 | 56.94 |
| ATOM | 1115 | NZ  | LYS | 304 | 23.838 | 0.008   | 19.778 | 1.00 | 56.94 |
| ATOM | 1116 | C   | LYS | 304 | 21.653 | −3.596  | 15.229 | 1.00 | 19.04 |
| ATOM | 1117 | O   | LYS | 304 | 21.974 | −3.993  | 14.107 | 1.00 | 56.94 |
| ATOM | 1118 | N   | SER | 305 | 21.146 | −4.394  | 16.164 | 1.00 | 24.46 |
| ATOM | 1119 | CA  | SER | 305 | 20.965 | −5.822  | 15.932 | 1.00 | 24.46 |
| ATOM | 1120 | CB  | SER | 305 | 20.610 | −6.533  | 17.240 | 1.00 | 37.46 |
| ATOM | 1121 | OG  | SER | 305 | 19.444 | −5.984  | 17.827 | 1.00 | 37.46 |
| ATOM | 1122 | C   | SER | 305 | 19.926 | −6.128  | 14.853 | 1.00 | 24.46 |
| ATOM | 1123 | O   | SER | 305 | 20.146 | −6.996  | 14.006 | 1.00 | 37.46 |
| ATOM | 1124 | N   | LEU | 306 | 18.819 | −5.390  | 14.858 | 1.00 | 25.47 |
| ATOM | 1125 | CA  | LEU | 306 | 17.753 | −5.592  | 13.881 | 1.00 | 25.47 |
| ATOM | 1126 | CB  | LEU | 306 | 16.525 | −4.746  | 14.224 | 1.00 | 15.99 |
| ATOM | 1127 | CG  | LEU | 306 | 15.700 | −5.190  | 15.432 | 1.00 | 15.99 |
| ATOM | 1128 | CD1 | LEU | 306 | 14.504 | −4.271  | 15.600 | 1.00 | 15.99 |
| ATOM | 1129 | CD2 | LEU | 306 | 15.244 | −6.624  | 15.247 | 1.00 | 15.99 |
| ATOM | 1130 | C   | LEU | 306 | 18.174 | −5.330  | 12.439 | 1.00 | 25.47 |
| ATOM | 1131 | O   | LEU | 306 | 17.596 | −5.902  | 11.513 | 1.00 | 15.99 |
| ATOM | 1132 | N   | SER | 307 | 19.182 | −4.482  | 12.247 | 1.00 | 24.28 |
| ATOM | 1133 | CA  | SER | 307 | 19.670 | −4.160  | 10.907 | 1.00 | 24.28 |
| ATOM | 1134 | CB  | SER | 307 | 20.910 | −3.263  | 10.989 | 1.00 | 40.92 |
| ATOM | 1135 | OG  | SER | 307 | 20.617 | −2.028  | 11.622 | 1.00 | 40.92 |
| ATOM | 1136 | C   | SER | 307 | 19.995 | −5.422  | 10.107 | 1.00 | 24.28 |
| ATOM | 1137 | O   | SER | 307 | 19.625 | −5.535  | 8.936  | 1.00 | 40.92 |
| ATOM | 1138 | N   | ALA | 308 | 20.644 | −6.383  | 10.761 | 1.00 | 30.97 |
| ATOM | 1139 | CA  | ALA | 308 | 21.027 | −7.640  | 10.124 | 1.00 | 30.97 |
| ATOM | 1140 | CB  | ALA | 308 | 22.004 | −8.399  | 11.013 | 1.00 | 37.84 |
| ATOM | 1141 | C   | ALA | 308 | 19.830 | −8.528  | 9.779  | 1.00 | 30.97 |
| ATOM | 1142 | O   | ALA | 308 | 19.897 | −9.336  | 8.853  | 1.00 | 37.84 |
| ATOM | 1143 | N   | PHE | 309 | 18.737 | −8.372  | 10.520 | 1.00 | 22.78 |
| ATOM | 1144 | CA  | PHE | 309 | 17.533 | −9.166  | 10.292 | 1.00 | 22.78 |
| ATOM | 1145 | CB  | PHE | 309 | 16.571 | −9.037  | 11.477 | 1.00 | 30.14 |
| ATOM | 1146 | CG  | PHE | 309 | 17.032 | −9.751  | 12.716 | 1.00 | 30.14 |
| ATOM | 1147 | CD1 | PHE | 309 | 16.299 | −10.809 | 13.236 | 1.00 | 30.14 |
| ATOM | 1148 | CD2 | PHE | 309 | 18.204 | −9.372  | 13.359 | 1.00 | 30.14 |
| ATOM | 1149 | CE1 | PHE | 309 | 16.725 | −11.481 | 14.378 | 1.00 | 30.14 |
| ATOM | 1150 | CE2 | PHE | 309 | 18.640 | −10.038 | 14.503 | 1.00 | 30.14 |
| ATOM | 1151 | CZ  | PHE | 309 | 17.896 | −11.094 | 15.013 | 1.00 | 30.14 |
| ATOM | 1152 | C   | PHE | 309 | 16.818 | −8.813  | 8.990  | 1.00 | 22.78 |
| ATOM | 1153 | O   | PHE | 309 | 16.068 | −9.631  | 8.451  | 1.00 | 30.14 |
| ATOM | 1154 | N   | ASN | 310 | 17.051 | −7.598  | 8.496  | 1.00 | 35.30 |
| ATOM | 1155 | CA  | ASN | 310 | 16.441 | −7.109  | 7.255  | 1.00 | 35.30 |
| ATOM | 1156 | CB  | ASN | 310 | 17.109 | −7.760  | 6.037  | 1.00 | 28.28 |
| ATOM | 1157 | C   | ASN | 310 | 14.929 | −7.339  | 7.229  | 1.00 | 35.30 |
| ATOM | 1158 | O   | ASN | 310 | 14.395 | −7.970  | 6.312  | 1.00 | 28.28 |
| ATOM | 1159 | N   | LEU | 311 | 14.249 | −6.831  | 8.251  | 1.00 | 27.52 |
| ATOM | 1160 | CA  | LEU | 311 | 12.803 | −6.979  | 8.369  | 1.00 | 27.52 |
| ATOM | 1161 | CB  | LEU | 311 | 12.351 | −6.630  | 9.788  | 1.00 | 22.62 |
| ATOM | 1162 | CG  | LEU | 311 | 12.950 | −7.396  | 10.968 | 1.00 | 22.62 |
| ATOM | 1163 | CD1 | LEU | 311 | 12.360 | −6.864  | 12.268 | 1.00 | 22.62 |
| ATOM | 1164 | CD2 | LEU | 311 | 12.672 | −8.881  | 10.821 | 1.00 | 22.62 |
| ATOM | 1165 | C   | LEU | 311 | 12.060 | −6.085  | 7.382  | 1.00 | 27.52 |
| ATOM | 1166 | O   | LEU | 311 | 12.519 | −4.986  | 7.067  | 1.00 | 22.62 |
| ATOM | 1167 | N   | ASP | 312 | 10.918 | −6.563  | 6.892  | 1.00 | 16.74 |
| ATOM | 1168 | CA  | ASP | 312 | 10.095 | −5.789  | 5.968  | 1.00 | 16.74 |
| ATOM | 1169 | CB  | ASP | 312 | 9.803  | −6.578  | 4.673  | 1.00 | 16.35 |
| ATOM | 1170 | CG  | ASP | 312 | 8.924  | −7.814  | 4.888  | 1.00 | 16.35 |
| ATOM | 1171 | OD1 | ASP | 312 | 8.591  | −8.168  | 6.037  | 1.00 | 16.35 |
| ATOM | 1172 | OD2 | ASP | 312 | 8.559  | −8.446  | 3.876  | 1.00 | 16.35 |
| ATOM | 1173 | C   | ASP | 312 | 8.808  | −5.354  | 6.678  | 1.00 | 16.74 |
| ATOM | 1174 | O   | ASP | 312 | 8.535  | −5.798  | 7.797  | 1.00 | 16.35 |
| ATOM | 1175 | N   | ASP | 313 | 8.007  | −4.520  | 6.019  | 1.00 | 5.43  |
| ATOM | 1176 | CA  | ASP | 313 | 6.758  | −4.016  | 6.592  | 1.00 | 5.43  |
| ATOM | 1177 | CB  | ASP | 313 | 5.974  | −3.201  | 5.559  | 1.00 | 31.80 |
| ATOM | 1178 | CG  | ASP | 313 | 6.670  | −1.906  | 5.183  | 1.00 | 31.80 |
| ATOM | 1179 | OD1 | ASP | 313 | 7.392  | −1.340  | 6.033  | 1.00 | 31.80 |
| ATOM | 1180 | OD2 | ASP | 313 | 6.493  | −1.452  | 4.032  | 1.00 | 31.80 |
| ATOM | 1181 | C   | ASP | 313 | 5.849  | −5.081  | 7.189  | 1.00 | 5.43  |

APPENDIX 4-continued

TR_TRIAC.PDB

| ATOM | 1182 | O | ASP | 313 | 5.216 | −4.849 | 8.221 | 1.00 | 31.80 |
|---|---|---|---|---|---|---|---|---|---|
| ATOM | 1183 | N | THR | 314 | 5.777 | −6.238 | 6.543 | 1.00 | 12.98 |
| ATOM | 1184 | CA | THR | 314 | 4.934 | −7.327 | 7.022 | 1.00 | 12.98 |
| ATOM | 1185 | CB | THR | 314 | 4.825 | −8.441 | 5.968 | 1.00 | 18.90 |
| ATOM | 1186 | OG1 | THR | 314 | 4.249 | −7.904 | 4.769 | 1.00 | 18.90 |
| ATOM | 1187 | CG2 | THR | 314 | 3.960 | −9.578 | 6.477 | 1.00 | 18.90 |
| ATOM | 1188 | C | THR | 314 | 5.426 | −7.910 | 8.349 | 1.00 | 12.98 |
| ATOM | 1189 | O | THR | 314 | 4.636 | −8.124 | 9.268 | 1.00 | 18.90 |
| ATOM | 1190 | N | GLU | 315 | 6.731 | −8.135 | 8.457 | 1.00 | 9.13 |
| ATOM | 1191 | CA | GLU | 315 | 7.316 | −8.685 | 9.675 | 1.00 | 9.13 |
| ATOM | 1192 | CB | GLU | 315 | 8.771 | −9.078 | 9.427 | 1.00 | 11.49 |
| ATOM | 1193 | CG | GLU | 315 | 8.870 | −10.323 | 8.562 | 1.00 | 11.49 |
| ATOM | 1194 | CD | GLU | 315 | 10.233 | −10.544 | 7.945 | 1.00 | 11.49 |
| ATOM | 1195 | OE1 | GLU | 315 | 10.964 | −9.561 | 7.705 | 1.00 | 11.49 |
| ATOM | 1196 | OE2 | GLU | 315 | 10.558 | −11.715 | 7.669 | 1.00 | 11.49 |
| ATOM | 1197 | C | GLU | 315 | 7.180 | −7.720 | 10.847 | 1.00 | 9.13 |
| ATOM | 1198 | O | GLU | 315 | 6.863 | −8.131 | 11.967 | 1.00 | 11.49 |
| ATOM | 1199 | N | VAL | 316 | 7.376 | −6.433 | 10.575 | 1.00 | 9.46 |
| ATOM | 1200 | CA | VAL | 316 | 7.240 | −5.406 | 11.602 | 1.00 | 9.46 |
| ATOM | 1201 | CB | VAL | 316 | 7.655 | −4.015 | 11.063 | 1.00 | 7.95 |
| ATOM | 1202 | CG1 | VAL | 316 | 7.434 | −2.941 | 12.124 | 1.00 | 7.95 |
| ATOM | 1203 | CG2 | VAL | 316 | 9.112 | −4.037 | 10.625 | 1.00 | 7.95 |
| ATOM | 1204 | C | VAL | 316 | 5.777 | −5.365 | 12.051 | 1.00 | 9.46 |
| ATOM | 1205 | O | VAL | 316 | 5.484 | −5.300 | 13.247 | 1.00 | 7.95 |
| ATOM | 1206 | N | ALA | 317 | 4.866 | −5.438 | 11.083 | 1.00 | 5.52 |
| ATOM | 1207 | CA | ALA | 317 | 3.434 | −5.417 | 11.355 | 1.00 | 5.52 |
| ATOM | 1208 | CB | ALA | 317 | 2.656 | −5.415 | 10.054 | 1.00 | 10.98 |
| ATOM | 1209 | C | ALA | 317 | 3.002 | −6.595 | 12.225 | 1.00 | 5.52 |
| ATOM | 1210 | O | ALA | 317 | 2.317 | −6.412 | 13.230 | 1.00 | 10.98 |
| ATOM | 1211 | N | LEU | 318 | 3.411 | −7.799 | 11.838 | 1.00 | 8.62 |
| ATOM | 1212 | CA | LEU | 318 | 3.067 | −9.003 | 12.584 | 1.00 | 8.62 |
| ATOM | 1213 | CB | LEU | 318 | 3.523 | −10.249 | 11.825 | 1.00 | 10.49 |
| ATOM | 1214 | CG | LEU | 318 | 2.770 | −10.494 | 10.514 | 1.00 | 10.49 |
| ATOM | 1215 | CD1 | LEU | 318 | 3.376 | −11.664 | 9.769 | 1.00 | 10.49 |
| ATOM | 1216 | CD2 | LEU | 318 | 1.297 | −10.741 | 10.799 | 1.00 | 10.49 |
| ATOM | 1217 | C | LEU | 318 | 3.674 | −8.971 | 13.978 | 1.00 | 8.62 |
| ATOM | 1218 | O | LEU | 318 | 3.047 | −9.407 | 14.945 | 1.00 | 10.49 |
| ATOM | 1219 | N | LEU | 319 | 4.885 | −8.435 | 14.082 | 1.00 | 9.43 |
| ATOM | 1220 | CA | LEU | 319 | 5.560 | −8.325 | 15.366 | 1.00 | 9.43 |
| ATOM | 1221 | CB | LEU | 319 | 6.975 | −7.773 | 15.173 | 1.00 | 24.05 |
| ATOM | 1222 | CG | LEU | 319 | 7.901 | −7.680 | 16.389 | 1.00 | 24.05 |
| ATOM | 1223 | CD1 | LEU | 319 | 7.889 | −8.977 | 17.182 | 1.00 | 24.05 |
| ATOM | 1224 | CD2 | LEU | 319 | 9.310 | −7.356 | 15.922 | 1.00 | 24.05 |
| ATOM | 1225 | C | LEU | 319 | 4.731 | −7.404 | 16.259 | 1.00 | 9.43 |
| ATOM | 1226 | O | LEU | 319 | 4.456 | −7.731 | 17.416 | 1.00 | 24.05 |
| ATOM | 1227 | N | GLN | 320 | 4.287 | −6.282 | 15.699 | 1.00 | 8.67 |
| ATOM | 1228 | CA | GLN | 320 | 3.467 | −5.325 | 16.437 | 1.00 | 8.67 |
| ATOM | 1229 | CB | GLN | 320 | 3.151 | −4.102 | 15.573 | 1.00 | 10.94 |
| ATOM | 1230 | CG | GLN | 320 | 4.361 | −3.256 | 15.218 | 1.00 | 10.94 |
| ATOM | 1231 | CD | GLN | 320 | 4.025 | −2.045 | 14.359 | 1.00 | 10.94 |
| ATOM | 1232 | OE1 | GLN | 320 | 4.889 | −1.217 | 14.082 | 1.00 | 10.94 |
| ATOM | 1233 | NE2 | GLN | 320 | 2.773 | −1.940 | 13.924 | 1.00 | 10.94 |
| ATOM | 1234 | C | GLN | 320 | 2.169 | −5.984 | 16.895 | 1.00 | 8.67 |
| ATOM | 1235 | O | GLN | 320 | 1.708 | −5.751 | 18.013 | 1.00 | 10.94 |
| ATOM | 1236 | N | ALA | 321 | 1.586 | −6.806 | 16.028 | 1.00 | 9.21 |
| ATOM | 1237 | CA | ALA | 321 | 0.349 | −7.513 | 16.342 | 1.00 | 9.21 |
| ATOM | 1238 | CB | ALA | 321 | −0.136 | −8.283 | 15.129 | 1.00 | 12.83 |
| ATOM | 1239 | C | ALA | 321 | 0.558 | −8.460 | 17.523 | 1.00 | 9.21 |
| ATOM | 1240 | O | ALA | 321 | −0.315 | −8.591 | 18.382 | 1.00 | 12.83 |
| ATOM | 1241 | N | VAL | 322 | 1.718 | −9.111 | 17.566 | 1.00 | 9.10 |
| ATOM | 1242 | CA | VAL | 322 | 2.043 | −10.030 | 18.651 | 1.00 | 9.10 |
| ATOM | 1243 | CB | VAL | 322 | 3.340 | −10.827 | 18.352 | 1.00 | 15.92 |
| ATOM | 1244 | CG1 | VAL | 322 | 3.783 | −11.614 | 19.575 | 1.00 | 15.92 |
| ATOM | 1245 | CG2 | VAL | 322 | 3.106 | −11.780 | 17.194 | 1.00 | 15.92 |
| ATOM | 1246 | C | VAL | 322 | 2.192 | −9.256 | 19.960 | 1.00 | 9.10 |
| ATOM | 1247 | O | VAL | 322 | 1.707 | −9.691 | 21.003 | 1.00 | 15.92 |
| ATOM | 1248 | N | LEU | 323 | 2.856 | −8.106 | 19.893 | 1.00 | 11.07 |
| ATOM | 1249 | CA | LEU | 323 | 3.062 | −7.257 | 21.064 | 1.00 | 11.07 |
| ATOM | 1250 | CB | LEU | 323 | 3.959 | −6.070 | 20.705 | 1.00 | 16.31 |
| ATOM | 1251 | CG | LEU | 323 | 5.377 | −6.393 | 20.229 | 1.00 | 16.31 |
| ATOM | 1252 | CD1 | LEU | 323 | 6.039 | −5.149 | 19.669 | 1.00 | 16.31 |
| ATOM | 1253 | CD2 | LEU | 323 | 6.187 | −6.966 | 21.375 | 1.00 | 16.31 |
| ATOM | 1254 | C | LEU | 323 | 1.729 | −6.742 | 21.595 | 1.00 | 11.07 |
| ATOM | 1255 | O | LEU | 323 | 1.523 | −6.650 | 22.803 | 1.00 | 16.31 |
| ATOM | 1256 | N | LEU | 324 | 0.827 | −6.413 | 20.677 | 1.00 | 13.48 |
| ATOM | 1257 | CA | LEU | 324 | −0.494 | −5.900 | 21.015 | 1.00 | 13.48 |
| ATOM | 1258 | CB | LEU | 324 | −1.185 | −5.383 | 19.752 | 1.00 | 15.92 |

APPENDIX 4-continued

TR_TRIAC.PDB

| ATOM | 1259 | CG | LEU | 324 | −2.607 | −4.837 | 19.889 | 1.00 | 15.92 |
|------|------|-----|-----|-----|--------|--------|--------|------|-------|
| ATOM | 1260 | CD1 | LEU | 324 | −2.602 | −3.547 | 20.692 | 1.00 | 15.92 |
| ATOM | 1261 | CD2 | LEU | 324 | −3.182 | −4.598 | 18.511 | 1.00 | 15.92 |
| ATOM | 1262 | C | LEU | 324 | −1.393 | −6.924 | 21.707 | 1.00 | 13.48 |
| ATOM | 1263 | O | LEU | 324 | −1.896 | −6.678 | 22.802 | 1.00 | 15.92 |
| ATOM | 1264 | N | MET | 325 | −1.593 | −8.074 | 21.072 | 1.00 | 11.47 |
| ATOM | 1265 | CA | MET | 325 | −2.458 | −9.111 | 21.631 | 1.00 | 11.47 |
| ATOM | 1266 | CB | MET | 325 | −2.959 | −10.043 | 20.520 | 1.00 | 22.90 |
| ATOM | 1267 | CG | MET | 325 | −3.689 | −9.347 | 19.375 | 1.00 | 22.90 |
| ATOM | 1268 | SD | MET | 325 | −5.052 | −8.287 | 19.908 | 1.00 | 22.90 |
| ATOM | 1269 | CE | MET | 325 | −6.284 | −9.475 | 20.353 | 1.00 | 22.90 |
| ATOM | 1270 | C | MET | 325 | −1.814 | −9.932 | 22.752 | 1.00 | 11.47 |
| ATOM | 1271 | O | MET | 325 | −1.899 | −11.160 | 22.758 | 1.00 | 22.90 |
| ATOM | 1272 | N | SER | 326 | −1.193 | −9.256 | 23.711 | 1.00 | 30.07 |
| ATOM | 1273 | CA | SER | 326 | −0.543 | −9.936 | 24.826 | 1.00 | 30.07 |
| ATOM | 1274 | CB | SER | 326 | 0.723 | −9.175 | 25.239 | 1.00 | 32.79 |
| ATOM | 1275 | OG | SER | 326 | 1.283 | −9.699 | 26.433 | 1.00 | 32.79 |
| ATOM | 1276 | C | SER | 326 | −1.492 | −10.061 | 26.014 | 1.00 | 30.07 |
| ATOM | 1277 | O | SER | 326 | −2.343 | −9.198 | 26.235 | 1.00 | 32.79 |
| ATOM | 1278 | N | THR | 327 | −1.347 | −11.143 | 26.773 | 1.00 | 29.08 |
| ATOM | 1279 | CA | THR | 327 | −2.179 | −11.368 | 27.948 | 1.00 | 29.08 |
| ATOM | 1280 | CB | THR | 327 | −2.705 | −12.817 | 27.998 | 1.00 | 36.96 |
| ATOM | 1281 | OG1 | THR | 327 | −1.612 | −13.734 | 27.856 | 1.00 | 36.96 |
| ATOM | 1282 | CG2 | THR | 327 | −3.716 | −13.055 | 26.890 | 1.00 | 36.96 |
| ATOM | 1283 | C | THR | 327 | −1.426 | −11.049 | 29.239 | 1.00 | 29.08 |
| ATOM | 1284 | O | THR | 327 | −1.930 | −11.295 | 30.333 | 1.00 | 36.96 |
| ATOM | 1285 | N | ASP | 328 | −0.214 | −10.513 | 29.111 | 1.00 | 38.93 |
| ATOM | 1286 | CA | ASP | 328 | 0.596 | −10.152 | 30.273 | 1.00 | 38.93 |
| ATOM | 1287 | CB | ASP | 328 | 2.082 | −10.089 | 29.899 | 1.00 | 85.70 |
| ATOM | 1288 | CG | ASP | 328 | 2.660 | −11.451 | 29.556 | 1.00 | 85.70 |
| ATOM | 1289 | OD1 | ASP | 328 | 3.388 | −11.554 | 28.542 | 1.00 | 85.70 |
| ATOM | 1290 | OD2 | ASP | 328 | 2.393 | −12.418 | 30.303 | 1.00 | 85.70 |
| ATOM | 1291 | C | ASP | 328 | 0.148 | −8.810 | 30.845 | 1.00 | 38.93 |
| ATOM | 1292 | O | ASP | 328 | 0.962 | −7.911 | 31.061 | 1.00 | 85.70 |
| ATOM | 1293 | N | ARG | 329 | −1.154 | −8.673 | 31.070 | 1.00 | 28.95 |
| ATOM | 1294 | CA | ARG | 329 | −1.716 | −7.445 | 31.608 | 1.00 | 28.95 |
| ATOM | 1295 | CB | ARG | 329 | −2.390 | −6.612 | 30.509 | 1.00 | 38.88 |
| ATOM | 1296 | CG | ARG | 329 | −1.449 | −5.887 | 29.554 | 1.00 | 38.88 |
| ATOM | 1297 | CD | ARG | 329 | −1.107 | −6.739 | 28.347 | 1.00 | 38.88 |
| ATOM | 1298 | NE | ARG | 329 | −0.322 | −6.005 | 27.356 | 1.00 | 38.88 |
| ATOM | 1299 | CZ | ARG | 329 | 1.006 | −5.936 | 27.351 | 1.00 | 38.88 |
| ATOM | 1300 | NH1 | ARG | 329 | 1.713 | −6.552 | 28.290 | 1.00 | 38.88 |
| ATOM | 1301 | NH2 | ARG | 329 | 1.631 | −5.270 | 26.391 | 1.00 | 38.88 |
| ATOM | 1302 | C | ARG | 329 | −2.745 | −7.790 | 32.672 | 1.00 | 28.95 |
| ATOM | 1303 | O | ARG | 329 | −3.279 | −8.898 | 32.696 | 1.00 | 38.88 |
| ATOM | 1304 | N | SER | 330 | −3.029 | −6.829 | 33.542 | 1.00 | 42.07 |
| ATOM | 1305 | CA | SER | 330 | −3.999 | −7.025 | 34.607 | 1.00 | 42.07 |
| ATOM | 1306 | CB | SER | 330 | −3.488 | −6.399 | 35.899 | 1.00 | 37.35 |
| ATOM | 1307 | C | SER | 330 | −5.340 | −6.413 | 34.220 | 1.00 | 42.07 |
| ATOM | 1308 | O | SER | 330 | −5.386 | −5.382 | 33.550 | 1.00 | 37.35 |
| ATOM | 1309 | N | GLY | 331 | −6.424 | −7.085 | 34.598 | 1.00 | 26.57 |
| ATOM | 1310 | CA | GLY | 331 | −7.754 | −6.572 | 34.318 | 1.00 | 26.57 |
| ATOM | 1311 | C | GLY | 331 | −8.404 | −6.915 | 32.991 | 1.00 | 26.57 |
| ATOM | 1312 | O | GLY | 331 | −9.462 | −6.371 | 32.671 | 1.00 | 30.06 |
| ATOM | 1313 | N | LEU | 332 | −7.797 | −7.807 | 32.214 | 1.00 | 31.47 |
| ATOM | 1314 | CA | LEU | 332 | −8.374 | −8.189 | 30.928 | 1.00 | 31.47 |
| ATOM | 1315 | CB | LEU | 332 | −7.351 | −8.933 | 30.065 | 1.00 | 23.83 |
| ATOM | 1316 | CG | LEU | 332 | −6.261 | −8.076 | 29.425 | 1.00 | 23.83 |
| ATOM | 1317 | CD1 | LEU | 332 | −5.296 | −8.960 | 28.652 | 1.00 | 23.83 |
| ATOM | 1318 | CD2 | LEU | 332 | −6.897 | −7.041 | 28.509 | 1.00 | 23.83 |
| ATOM | 1319 | C | LEU | 332 | −9.630 | −9.039 | 31.091 | 1.00 | 31.47 |
| ATOM | 1320 | O | LEU | 332 | −9.665 | −9.969 | 31.895 | 1.00 | 23.83 |
| ATOM | 1321 | N | LEU | 333 | −10.659 | −8.702 | 30.321 | 1.00 | 27.66 |
| ATOM | 1322 | CA | LEU | 333 | −11.927 | −9.422 | 30.351 | 1.00 | 27.66 |
| ATOM | 1323 | CB | LEU | 333 | −13.072 | −8.500 | 29.918 | 1.00 | 49.79 |
| ATOM | 1324 | CG | LEU | 333 | −13.416 | −7.312 | 30.820 | 1.00 | 49.79 |
| ATOM | 1325 | CD1 | LEU | 333 | −14.328 | −6.339 | 30.083 | 1.00 | 49.79 |
| ATOM | 1326 | CD2 | LEU | 333 | −14.072 | −7.803 | 32.104 | 1.00 | 49.79 |
| ATOM | 1327 | C | LEU | 333 | −11.904 | −10.663 | 29.456 | 1.00 | 27.66 |
| ATOM | 1328 | O | LEU | 333 | −12.117 | −11.780 | 29.919 | 1.00 | 49.79 |
| ATOM | 1329 | N | CYS | 334 | −11.616 | −10.464 | 28.174 | 1.00 | 29.56 |
| ATOM | 1330 | CA | CYS | 334 | −11.583 | −11.566 | 27.220 | 1.00 | 29.56 |
| ATOM | 1331 | CB | CYS | 334 | −12.134 | −11.106 | 25.865 | 1.00 | 47.01 |
| ATOM | 1332 | SG | CYS | 334 | −13.888 | −10.657 | 25.883 | 1.00 | 47.01 |
| ATOM | 1333 | C | CYS | 334 | −10.187 | −12.161 | 27.050 | 1.00 | 29.56 |
| ATOM | 1334 | O | CYS | 334 | −9.652 | −12.202 | 25.942 | 1.00 | 47.01 |
| ATOM | 1335 | N | VAL | 335 | −9.617 | −12.655 | 28.147 | 1.00 | 30.69 |

APPENDIX 4-continued

TR_TRIAC.PDB

| ATOM | 1336 | CA | VAL | 335 | -8.280 | -13.250 | 28.132 | 1.00 | 30.69 |
|---|---|---|---|---|---|---|---|---|---|
| ATOM | 1337 | CB | VAL | 335 | -7.913 | -13.844 | 29.514 | 1.00 | 32.18 |
| ATOM | 1338 | CG1 | VAL | 335 | -6.517 | -14.456 | 29.480 | 1.00 | 32.18 |
| ATOM | 1339 | CG2 | VAL | 335 | -7.988 | -12.768 | 30.584 | 1.00 | 32.18 |
| ATOM | 1340 | C | VAL | 335 | -8.120 | -14.340 | 27.068 | 1.00 | 30.69 |
| ATOM | 1341 | O | VAL | 335 | -7.149 | -14.337 | 26.309 | 1.00 | 32.18 |
| ATOM | 1342 | N | ASP | 336 | -9.079 | -15.260 | 27.012 | 1.00 | 30.13 |
| ATOM | 1343 | CA | ASP | 336 | -9.040 | -16.360 | 26.052 | 1.00 | 30.13 |
| ATOM | 1344 | CB | ASP | 336 | -10.218 | -17.311 | 26.284 | 1.00 | 63.22 |
| ATOM | 1345 | CG | ASP | 336 | -10.178 | -18.528 | 25.370 | 1.00 | 63.22 |
| ATOM | 1346 | OD1 | ASP | 336 | -11.119 | -18.700 | 24.565 | 1.00 | 63.22 |
| ATOM | 1347 | OD2 | ASP | 336 | -9.205 | -19.311 | 25.452 | 1.00 | 63.22 |
| ATOM | 1348 | C | ASP | 336 | -9.012 | -15.903 | 24.594 | 1.00 | 30.13 |
| ATOM | 1349 | O | ASP | 336 | -8.156 | -16.339 | 23.823 | 1.00 | 63.22 |
| ATOM | 1350 | N | LYS | 337 | -9.944 | -15.027 | 24.223 | 1.00 | 26.63 |
| ATOM | 1351 | CA | LYS | 337 | -10.024 | -14.515 | 22.856 | 1.00 | 26.63 |
| ATOM | 1352 | CB | LYS | 337 | -11.172 | -13.516 | 22.729 | 1.00 | 21.38 |
| ATOM | 1353 | C | LYS | 337 | -8.706 | -13.865 | 22.438 | 1.00 | 26.63 |
| ATOM | 1354 | O | LYS | 337 | -8.204 | -14.110 | 21.338 | 1.00 | 21.38 |
| ATOM | 1355 | N | ILE | 338 | -8.141 | -13.060 | 23.334 | 1.00 | 24.65 |
| ATOM | 1356 | CA | ILE | 338 | -6.879 | -12.376 | 23.078 | 1.00 | 24.65 |
| ATOM | 1357 | CB | ILE | 338 | -6.543 | -11.380 | 24.215 | 1.00 | 20.45 |
| ATOM | 1358 | CG2 | ILE | 338 | -5.198 | -10.719 | 23.966 | 1.00 | 20.45 |
| ATOM | 1359 | CG1 | ILE | 338 | -7.632 | -10.308 | 24.308 | 1.00 | 20.45 |
| ATOM | 1360 | CD1 | ILE | 338 | -7.479 | -9.374 | 25.486 | 1.00 | 20.45 |
| ATOM | 1361 | C | ILE | 338 | -5.744 | -13.388 | 22.911 | 1.00 | 24.65 |
| ATOM | 1362 | O | ILE | 338 | -4.948 | -13.288 | 21.974 | 1.00 | 20.45 |
| ATOM | 1363 | N | GLU | 339 | -5.700 | -14.383 | 23.795 | 1.00 | 35.34 |
| ATOM | 1364 | CA | GLU | 339 | -4.673 | -15.422 | 23.745 | 1.00 | 35.34 |
| ATOM | 1365 | CB | GLU | 339 | -4.836 | -16.388 | 24.916 | 1.00 | 29.51 |
| ATOM | 1366 | C | GLU | 339 | -4.744 | -16.180 | 22.421 | 1.00 | 35.34 |
| ATOM | 1367 | O | GLU | 339 | -3.720 | -16.421 | 21.777 | 1.00 | 29.51 |
| ATOM | 1368 | N | LYS | 340 | -5.959 | -16.536 | 22.009 | 1.00 | 24.19 |
| ATOM | 1369 | CA | LYS | 340 | -6.168 | -17.256 | 20.755 | 1.00 | 24.19 |
| ATOM | 1370 | CB | LYS | 340 | -7.627 | -17.671 | 20.624 | 1.00 | 23.97 |
| ATOM | 1371 | C | LYS | 340 | -5.754 | -16.377 | 19.576 | 1.00 | 24.19 |
| ATOM | 1372 | O | LYS | 340 | -5.197 | -16.860 | 18.586 | 1.00 | 23.97 |
| ATOM | 1373 | N | SER | 341 | -6.000 | -15.079 | 19.708 | 1.00 | 16.85 |
| ATOM | 1374 | CA | SER | 341 | -5.651 | -14.115 | 18.676 | 1.00 | 16.85 |
| ATOM | 1375 | CB | SER | 341 | -6.223 | -12.744 | 19.033 | 1.00 | 26.59 |
| ATOM | 1376 | OG | SER | 341 | -5.852 | -11.765 | 18.080 | 1.00 | 26.59 |
| ATOM | 1377 | C | SER | 341 | -4.137 | -14.026 | 18.500 | 1.00 | 16.85 |
| ATOM | 1378 | O | SER | 341 | -3.638 | -14.042 | 17.374 | 1.00 | 26.59 |
| ATOM | 1379 | N | GLN | 342 | -3.406 | -13.932 | 19.608 | 1.00 | 17.35 |
| ATOM | 1380 | CA | GLN | 342 | -1.952 | -13.845 | 19.537 | 1.00 | 17.35 |
| ATOM | 1381 | CB | GLN | 342 | -1.337 | -13.597 | 20.913 | 1.00 | 30.07 |
| ATOM | 1382 | CG | GLN | 342 | 0.140 | -13.245 | 20.832 | 1.00 | 30.07 |
| ATOM | 1383 | CD | GLN | 342 | 0.811 | -13.196 | 22.182 | 1.00 | 30.07 |
| ATOM | 1384 | OE1 | GLN | 342 | 0.884 | -14.201 | 22.884 | 1.00 | 30.07 |
| ATOM | 1385 | NE2 | GLN | 342 | 1.318 | -12.030 | 22.548 | 1.00 | 30.07 |
| ATOM | 1386 | C | GLN | 342 | -1.368 | -15.118 | 18.944 | 1.00 | 17.35 |
| ATOM | 1387 | O | GLN | 342 | -0.405 | -15.066 | 18.178 | 1.00 | 30.07 |
| ATOM | 1388 | N | GLU | 343 | -1.949 | -16.260 | 19.303 | 1.00 | 18.35 |
| ATOM | 1389 | CA | GLU | 343 | -1.489 | -17.546 | 18.791 | 1.00 | 18.35 |
| ATOM | 1390 | CB | GLU | 343 | -2.308 | -18.676 | 19.394 | 1.00 | 16.98 |
| ATOM | 1391 | C | GLU | 343 | -1.603 | -17.560 | 17.267 | 1.00 | 18.35 |
| ATOM | 1392 | O | GLU | 343 | -0.699 | -18.026 | 16.568 | 1.00 | 16.98 |
| ATOM | 1393 | N | ALA | 344 | -2.706 | -17.017 | 16.761 | 1.00 | 14.83 |
| ATOM | 1394 | CA | ALA | 344 | -2.946 | -16.948 | 15.324 | 1.00 | 14.83 |
| ATOM | 1395 | CB | ALA | 344 | -4.327 | -16.376 | 15.049 | 1.00 | 19.42 |
| ATOM | 1396 | C | ALA | 344 | -1.872 | -16.102 | 14.640 | 1.00 | 14.83 |
| ATOM | 1397 | O | ALA | 344 | -1.311 | -16.507 | 13.619 | 1.00 | 19.42 |
| ATOM | 1398 | N | TYR | 345 | -1.586 | -14.934 | 15.211 | 1.00 | 13.10 |
| ATOM | 1399 | CA | TYR | 345 | -0.569 | -14.041 | 14.665 | 1.00 | 13.10 |
| ATOM | 1400 | CB | TYR | 345 | -0.573 | -12.697 | 15.393 | 1.00 | 2.00 |
| ATOM | 1401 | CG | TYR | 345 | -1.670 | -11.767 | 14.938 | 1.00 | 2.00 |
| ATOM | 1402 | CD1 | TYR | 345 | -2.707 | -11.409 | 15.794 | 1.00 | 2.00 |
| ATOM | 1403 | CE1 | TYR | 345 | -3.722 | -10.562 | 15.377 | 1.00 | 2.00 |
| ATOM | 1404 | CD2 | TYR | 345 | -1.674 | -11.248 | 13.647 | 1.00 | 2.00 |
| ATOM | 1405 | CE2 | TYR | 345 | -2.683 | -10.398 | 13.219 | 1.00 | 2.00 |
| ATOM | 1406 | CZ | TYR | 345 | -3.706 | -10.061 | 14.087 | 1.00 | 2.00 |
| ATOM | 1407 | OH | TYR | 345 | -4.722 | -9.233 | 13.669 | 1.00 | 2.00 |
| ATOM | 1408 | C | TYR | 345 | 0.818 | -14.666 | 14.732 | 1.00 | 13.10 |
| ATOM | 1409 | O | TYR | 345 | 1.614 | -14.504 | 13.811 | 1.00 | 2.00 |
| ATOM | 1410 | N | LEU | 346 | 1.101 | -15.387 | 15.813 | 1.00 | 12.59 |
| ATOM | 1411 | CA | LEU | 346 | 2.396 | -16.041 | 15.976 | 1.00 | 12.59 |
| ATOM | 1412 | CB | LEU | 346 | 2.498 | -16.715 | 17.347 | 1.00 | 22.61 |

APPENDIX 4-continued

TR_TRIAC.PDB

| ATOM | 1413 | CG | LEU | 346 | 2.899 | −15.799 | 18.504 | 1.00 | 22.61 |
|---|---|---|---|---|---|---|---|---|---|
| ATOM | 1414 | CD1 | LEU | 346 | 2.717 | −16.511 | 19.830 | 1.00 | 22.61 |
| ATOM | 1415 | CD2 | LEU | 346 | 4.341 | −15.357 | 18.324 | 1.00 | 22.61 |
| ATOM | 1416 | C | LEU | 346 | 2.629 | −17.057 | 14.865 | 1.00 | 12.59 |
| ATOM | 1417 | O | LEU | 346 | 3.706 | −17.099 | 14.272 | 1.00 | 22.61 |
| ATOM | 1418 | N | LEU | 347 | 1.612 | −17.862 | 14.574 | 1.00 | 18.42 |
| ATOM | 1419 | CA | LEU | 347 | 1.706 | −18.863 | 13.517 | 1.00 | 18.42 |
| ATOM | 1420 | CB | LEU | 347 | 0.471 | −19.762 | 13.512 | 1.00 | 23.56 |
| ATOM | 1421 | CG | LEU | 347 | 0.509 | −20.965 | 14.456 | 1.00 | 23.56 |
| ATOM | 1422 | CD1 | LEU | 347 | −0.819 | −21.702 | 14.398 | 1.00 | 23.56 |
| ATOM | 1423 | CD2 | LEU | 347 | 1.659 | −21.890 | 14.068 | 1.00 | 23.56 |
| ATOM | 1424 | C | LEU | 347 | 1.870 | −18.201 | 12.154 | 1.00 | 18.42 |
| ATOM | 1425 | O | LEU | 347 | 2.672 | −18.651 | 11.330 | 1.00 | 23.56 |
| ATOM | 1426 | N | ALA | 348 | 1.099 | −17.144 | 11.917 | 1.00 | 12.49 |
| ATOM | 1427 | CA | ALA | 348 | 1.157 | −16.403 | 10.663 | 1.00 | 12.49 |
| ATOM | 1428 | CB | ALA | 348 | 0.098 | −15.302 | 10.654 | 1.00 | 14.77 |
| ATOM | 1429 | C | ALA | 348 | 2.545 | −15.798 | 10.504 | 1.00 | 12.49 |
| ATOM | 1430 | O | ALA | 348 | 3.154 | −15.874 | 9.436 | 1.00 | 14.77 |
| ATOM | 1431 | N | PHE | 349 | 3.048 | −15.246 | 11.602 | 1.00 | 15.52 |
| ATOM | 1432 | CA | PHE | 349 | 4.357 | −14.613 | 11.664 | 1.00 | 15.52 |
| ATOM | 1433 | CB | PHE | 349 | 4.566 | −14.049 | 13.076 | 1.00 | 14.41 |
| ATOM | 1434 | CG | PHE | 349 | 5.714 | −13.085 | 13.203 | 1.00 | 14.41 |
| ATOM | 1435 | CD1 | PHE | 349 | 6.473 | −12.712 | 12.099 | 1.00 | 14.41 |
| ATOM | 1436 | CD2 | PHE | 349 | 6.027 | −12.540 | 14.443 | 1.00 | 14.41 |
| ATOM | 1437 | CE1 | PHE | 349 | 7.523 | −11.813 | 12.230 | 1.00 | 14.41 |
| ATOM | 1438 | CE2 | PHE | 349 | 7.075 | −11.640 | 14.584 | 1.00 | 14.41 |
| ATOM | 1439 | CZ | PHE | 349 | 7.825 | −11.275 | 13.475 | 1.00 | 14.41 |
| ATOM | 1440 | C | PHE | 349 | 5.444 | −15.633 | 11.324 | 1.00 | 15.52 |
| ATOM | 1441 | O | PHE | 349 | 6.252 | −15.413 | 10.422 | 1.00 | 14.41 |
| ATOM | 1442 | N | GLU | 350 | 5.439 | −16.760 | 12.026 | 1.00 | 13.20 |
| ATOM | 1443 | CA | GLU | 350 | 6.424 | −17.811 | 11.801 | 1.00 | 13.20 |
| ATOM | 1444 | CB | GLU | 350 | 6.152 | −18.995 | 12.734 | 1.00 | 33.43 |
| ATOM | 1445 | CG | GLU | 350 | 7.068 | −20.193 | 12.519 | 1.00 | 33.43 |
| ATOM | 1446 | CD | GLU | 350 | 6.786 | −21.331 | 13.482 | 1.00 | 33.43 |
| ATOM | 1447 | OE1 | GLU | 350 | 7.746 | −22.035 | 13.857 | 1.00 | 33.43 |
| ATOM | 1448 | OE2 | GLU | 350 | 5.611 | −21.525 | 13.865 | 1.00 | 33.43 |
| ATOM | 1449 | C | GLU | 350 | 6.409 | −18.283 | 10.352 | 1.00 | 13.20 |
| ATOM | 1450 | O | GLU | 350 | 7.449 | −18.355 | 9.694 | 1.00 | 33.43 |
| ATOM | 1451 | N | HIS | 351 | 5.217 | −18.573 | 9.850 | 1.00 | 19.10 |
| ATOM | 1452 | CA | HIS | 351 | 5.062 | −19.051 | 8.485 | 1.00 | 19.10 |
| ATOM | 1453 | CB | HIS | 351 | 3.632 | −19.536 | 8.256 | 1.00 | 18.97 |
| ATOM | 1454 | CG | HIS | 351 | 3.249 | −20.700 | 9.117 | 1.00 | 18.97 |
| ATOM | 1455 | CD2 | HIS | 351 | 3.987 | −21.474 | 9.948 | 1.00 | 18.97 |
| ATOM | 1456 | ND1 | HIS | 351 | 1.960 | −21.180 | 9.194 | 1.00 | 18.97 |
| ATOM | 1457 | CE1 | HIS | 351 | 1.918 | −22.195 | 10.039 | 1.00 | 18.97 |
| ATOM | 1458 | NE2 | HIS | 351 | 3.134 | −22.394 | 10.509 | 1.00 | 18.97 |
| ATOM | 1459 | C | HIS | 351 | 5.477 | −18.011 | 7.449 | 1.00 | 19.10 |
| ATOM | 1460 | O | HIS | 351 | 5.955 | −18.366 | 6.371 | 1.00 | 18.97 |
| ATOM | 1461 | N | TYR | 352 | 5.304 | −16.732 | 7.767 | 1.00 | 9.38 |
| ATOM | 1462 | CA | TYR | 352 | 5.711 | −15.683 | 6.843 | 1.00 | 9.38 |
| ATOM | 1463 | CB | TYR | 352 | 5.168 | −14.317 | 7.257 | 1.00 | 16.06 |
| ATOM | 1464 | CG | TYR | 352 | 5.539 | −13.238 | 6.268 | 1.00 | 16.06 |
| ATOM | 1465 | CD1 | TYR | 352 | 4.939 | −13.190 | 5.008 | 1.00 | 16.06 |
| ATOM | 1466 | CE1 | TYR | 352 | 5.321 | −12.242 | 4.060 | 1.00 | 16.06 |
| ATOM | 1467 | CD2 | TYR | 352 | 6.531 | −12.303 | 6.562 | 1.00 | 16.06 |
| ATOM | 1468 | CE2 | TYR | 352 | 6.923 | −11.349 | 5.620 | 1.00 | 16.06 |
| ATOM | 1469 | CZ | TYR | 352 | 6.313 | −11.326 | 4.371 | 1.00 | 16.06 |
| ATOM | 1470 | OH | TYR | 352 | 6.710 | −10.401 | 3.431 | 1.00 | 16.06 |
| ATOM | 1471 | C | TYR | 352 | 7.234 | −15.639 | 6.812 | 1.00 | 9.38 |
| ATOM | 1472 | O | TYR | 352 | 7.838 | −15.475 | 5.751 | 1.00 | 16.06 |
| ATOM | 1473 | N | VAL | 353 | 7.851 | −15.789 | 7.980 | 1.00 | 15.38 |
| ATOM | 1474 | CA | VAL | 353 | 9.305 | −15.790 | 8.087 | 1.00 | 15.38 |
| ATOM | 1475 | CB | VAL | 353 | 9.761 | −15.945 | 9.558 | 1.00 | 18.40 |
| ATOM | 1476 | CG1 | VAL | 353 | 11.262 | −16.163 | 9.633 | 1.00 | 18.40 |
| ATOM | 1477 | CG2 | VAL | 353 | 9.384 | −14.703 | 10.349 | 1.00 | 18.40 |
| ATOM | 1478 | C | VAL | 353 | 9.853 | −16.938 | 7.237 | 1.00 | 15.38 |
| ATOM | 1479 | O | VAL | 353 | 10.850 | −16.773 | 6.525 | 1.00 | 18.40 |
| ATOM | 1480 | N | ASN | 354 | 9.183 | −18.086 | 7.298 | 1.00 | 14.74 |
| ATOM | 1481 | CA | ASN | 354 | 9.578 | −19.259 | 6.521 | 1.00 | 14.74 |
| ATOM | 1482 | CB | ASN | 354 | 8.640 | −20.435 | 6.799 | 1.00 | 19.97 |
| ATOM | 1483 | CG | ASN | 354 | 8.832 | −21.020 | 8.180 | 1.00 | 19.97 |
| ATOM | 1484 | OD1 | ASN | 354 | 9.879 | −20.848 | 8.799 | 1.00 | 19.97 |
| ATOM | 1485 | ND2 | ASN | 354 | 7.826 | −21.734 | 8.664 | 1.00 | 19.97 |
| ATOM | 1486 | C | ASN | 354 | 9.550 | −18.939 | 5.034 | 1.00 | 14.74 |
| ATOM | 1487 | O | ASN | 354 | 10.452 | −19.319 | 4.290 | 1.00 | 19.97 |
| ATOM | 1488 | N | HIS | 355 | 8.507 | −18.230 | 4.613 | 1.00 | 13.03 |
| ATOM | 1489 | CA | HIS | 355 | 8.329 | −17.837 | 3.220 | 1.00 | 13.03 |

APPENDIX 4-continued

TR_TRIAC.PDB

| ATOM | 1490 | CB  | HIS | 355 | 6.960  | −17.164 | 3.042  | 1.00 | 24.39 |
|------|------|-----|-----|-----|--------|---------|--------|------|-------|
| ATOM | 1491 | CG  | HIS | 355 | 6.753  | −16.541 | 1.695  | 1.00 | 24.39 |
| ATOM | 1492 | CD2 | HIS | 355 | 7.195  | −15.370 | 1.176  | 1.00 | 24.39 |
| ATOM | 1493 | ND1 | HIS | 355 | 6.009  | −17.138 | 0.701  | 1.00 | 24.39 |
| ATOM | 1494 | CE1 | HIS | 355 | 6.005  | −16.368 | −0.372 | 1.00 | 24.39 |
| ATOM | 1495 | NE2 | HIS | 355 | 6.720  | −15.289 | −0.107 | 1.00 | 24.39 |
| ATOM | 1496 | C   | HIS | 355 | 9.434  | −16.894 | 2.758  | 1.00 | 13.03 |
| ATOM | 1497 | O   | HIS | 355 | 9.834  | −16.920 | 1.595  | 1.00 | 24.39 |
| ATOM | 1498 | N   | ARG | 356 | 9.878  | −16.027 | 3.660  | 1.00 | 19.55 |
| ATOM | 1499 | CA  | ARG | 356 | 10.920 | −15.054 | 3.358  | 1.00 | 19.55 |
| ATOM | 1500 | CB  | ARG | 356 | 10.970 | −14.001 | 4.460  | 1.00 | 22.01 |
| ATOM | 1501 | CG  | ARG | 356 | 9.772  | −13.081 | 4.454  | 1.00 | 22.01 |
| ATOM | 1502 | CD  | ARG | 356 | 10.097 | −11.784 | 3.750  | 1.00 | 22.01 |
| ATOM | 1503 | NE  | ARG | 356 | 10.932 | −10.934 | 4.592  | 1.00 | 22.01 |
| ATOM | 1504 | CZ  | ARG | 356 | 11.822 | −10.059 | 4.137  | 1.00 | 22.01 |
| ATOM | 1505 | NH1 | ARG | 356 | 12.010 | −9.907  | 2.833  | 1.00 | 22.01 |
| ATOM | 1506 | NH2 | ARG | 356 | 12.519 | −9.325  | 4.992  | 1.00 | 22.01 |
| ATOM | 1507 | C   | ARG | 356 | 12.297 | −15.675 | 3.158  | 1.00 | 19.55 |
| ATOM | 1508 | O   | ARG | 356 | 13.127 | −15.126 | 2.434  | 1.00 | 22.01 |
| ATOM | 1509 | N   | LYS | 357 | 12.547 | −16.788 | 3.841  | 1.00 | 23.18 |
| ATOM | 1510 | CA  | LYS | 357 | 13.815 | −17.504 | 3.739  | 1.00 | 23.18 |
| ATOM | 1511 | CB  | LYS | 357 | 13.879 | −18.273 | 2.415  | 1.00 | 42.91 |
| ATOM | 1512 | CG  | LYS | 357 | 12.750 | −19.277 | 2.274  | 1.00 | 42.91 |
| ATOM | 1513 | CD  | LYS | 357 | 12.773 | −20.021 | 0.960  | 1.00 | 42.91 |
| ATOM | 1514 | CE  | LYS | 357 | 11.619 | −21.011 | 0.913  | 1.00 | 42.91 |
| ATOM | 1515 | NZ  | LYS | 357 | 11.629 | −21.845 | −0.316 | 1.00 | 42.91 |
| ATOM | 1516 | C   | LYS | 357 | 15.047 | −16.619 | 3.918  | 1.00 | 23.18 |
| ATOM | 1517 | O   | LYS | 357 | 15.816 | −16.396 | 2.982  | 1.00 | 42.91 |
| ATOM | 1518 | N   | HIS | 358 | 15.228 | −16.122 | 5.137  | 1.00 | 32.39 |
| ATOM | 1519 | CA  | HIS | 358 | 16.367 | −15.272 | 5.460  | 1.00 | 32.39 |
| ATOM | 1520 | CB  | HIS | 358 | 16.181 | −14.626 | 6.835  | 1.00 | 26.77 |
| ATOM | 1521 | CG  | HIS | 358 | 15.232 | −13.468 | 6.841  | 1.00 | 26.77 |
| ATOM | 1522 | CD2 | HIS | 358 | 15.452 | −12.138 | 6.709  | 1.00 | 26.77 |
| ATOM | 1523 | ND1 | HIS | 358 | 13.875 | −13.615 | 7.028  | 1.00 | 26.77 |
| ATOM | 1524 | CE1 | HIS | 358 | 13.300 | −12.426 | 7.012  | 1.00 | 26.77 |
| ATOM | 1525 | NE2 | HIS | 358 | 14.234 | −11.513 | 6.821  | 1.00 | 26.77 |
| ATOM | 1526 | C   | HIS | 358 | 17.633 | −16.115 | 5.480  | 1.00 | 32.39 |
| ATOM | 1527 | O   | HIS | 358 | 17.618 | −17.248 | 5.961  | 1.00 | 26.77 |
| ATOM | 1528 | N   | ASN | 359 | 18.728 | −15.561 | 4.972  | 1.00 | 41.97 |
| ATOM | 1529 | CA  | ASN | 359 | 20.000 | −16.273 | 4.959  | 1.00 | 41.97 |
| ATOM | 1530 | CB  | ASN | 359 | 20.909 | −15.716 | 3.863  | 1.00 | 46.84 |
| ATOM | 1531 | C   | ASN | 359 | 20.663 | −16.134 | 6.331  | 1.00 | 41.97 |
| ATOM | 1532 | O   | ASN | 359 | 21.821 | −15.731 | 6.436  | 1.00 | 46.84 |
| ATOM | 1533 | N   | ILE | 360 | 19.908 | −16.450 | 7.379  | 1.00 | 35.72 |
| ATOM | 1534 | CA  | ILE | 360 | 20.394 | −16.359 | 8.753  | 1.00 | 35.72 |
| ATOM | 1535 | CB  | ILE | 360 | 19.819 | −15.113 | 9.480  | 1.00 | 36.14 |
| ATOM | 1536 | CG2 | ILE | 360 | 20.327 | −15.050 | 10.918 | 1.00 | 36.14 |
| ATOM | 1537 | CG1 | ILE | 360 | 20.204 | −13.833 | 8.734  | 1.00 | 36.14 |
| ATOM | 1538 | CD1 | ILE | 360 | 19.526 | −12.591 | 9.265  | 1.00 | 36.14 |
| ATOM | 1539 | C   | ILE | 360 | 19.935 | −17.611 | 9.493  | 1.00 | 35.72 |
| ATOM | 1540 | O   | ILE | 360 | 18.748 | −17.953 | 9.479  | 1.00 | 36.14 |
| ATOM | 1541 | N   | PRO | 361 | 20.877 | −18.338 | 10.109 | 1.00 | 31.56 |
| ATOM | 1542 | CD  | PRO | 361 | 22.334 | −18.114 | 10.100 | 1.00 | 33.50 |
| ATOM | 1543 | CA  | PRO | 361 | 20.532 | −19.556 | 10.847 | 1.00 | 31.56 |
| ATOM | 1544 | CB  | PRO | 361 | 21.901 | −20.163 | 11.161 | 1.00 | 33.50 |
| ATOM | 1545 | CG  | PRO | 361 | 22.801 | −18.967 | 11.249 | 1.00 | 33.50 |
| ATOM | 1546 | C   | PRO | 361 | 19.743 | −19.256 | 12.121 | 1.00 | 31.56 |
| ATOM | 1547 | O   | PRO | 361 | 20.080 | −18.338 | 12.867 | 1.00 | 33.50 |
| ATOM | 1548 | N   | HIS | 362 | 18.688 | −20.034 | 12.355 | 1.00 | 18.84 |
| ATOM | 1549 | CA  | HIS | 362 | 17.840 | −19.887 | 13.541 | 1.00 | 18.84 |
| ATOM | 1550 | CB  | HIS | 362 | 18.656 | −20.151 | 14.812 | 1.00 | 31.38 |
| ATOM | 1551 | CG  | HIS | 362 | 19.540 | −21.357 | 14.731 | 1.00 | 31.38 |
| ATOM | 1552 | CD2 | HIS | 362 | 19.250 | −22.667 | 14.537 | 1.00 | 31.38 |
| ATOM | 1553 | ND1 | HIS | 362 | 20.910 | −21.286 | 14.860 | 1.00 | 31.38 |
| ATOM | 1554 | CE1 | HIS | 362 | 21.427 | −22.497 | 14.754 | 1.00 | 31.38 |
| ATOM | 1555 | NE2 | HIS | 362 | 20.439 | −23.353 | 14.558 | 1.00 | 31.38 |
| ATOM | 1556 | C   | HIS | 362 | 17.189 | −18.506 | 13.628 | 1.00 | 18.84 |
| ATOM | 1557 | O   | HIS | 362 | 16.980 | −17.979 | 14.723 | 1.00 | 31.38 |
| ATOM | 1558 | N   | PHE | 363 | 16.825 | −17.950 | 12.476 | 1.00 | 18.69 |
| ATOM | 1559 | CA  | PHE | 363 | 16.209 | −16.630 | 12.408 | 1.00 | 18.69 |
| ATOM | 1560 | CB  | PHE | 363 | 15.825 | −16.302 | 10.962 | 1.00 | 19.25 |
| ATOM | 1561 | CG  | PHE | 363 | 15.339 | −14.894 | 10.765 | 1.00 | 19.25 |
| ATOM | 1562 | CD1 | PHE | 363 | 16.239 | −13.862 | 10.530 | 1.00 | 19.25 |
| ATOM | 1563 | CD2 | PHE | 363 | 13.981 | −14.598 | 10.819 | 1.00 | 19.25 |
| ATOM | 1564 | CE1 | PHE | 363 | 15.794 | −12.556 | 10.351 | 1.00 | 19.25 |
| ATOM | 1565 | CE2 | PHE | 363 | 13.527 | −13.296 | 10.642 | 1.00 | 19.25 |
| ATOM | 1566 | CZ  | PHE | 363 | 14.435 | −12.273 | 10.407 | 1.00 | 19.25 |

APPENDIX 4-continued

TR_TRIAC.PDB

| ATOM | 1567 | C | PHE | 363 | 14.995 | −16.461 | 13.323 | 1.00 | 18.69 |
|------|------|------|-----|-----|--------|---------|--------|------|-------|
| ATOM | 1568 | O | PHE | 363 | 14.955 | −15.540 | 14.138 | 1.00 | 19.25 |
| ATOM | 1569 | N | TRP | 364 | 14.016 | −17.351 | 13.191 | 1.00 | 16.46 |
| ATOM | 1570 | CA | TRP | 364 | 12.797 | −17.280 | 13.995 | 1.00 | 16.46 |
| ATOM | 1571 | CB | TRP | 364 | 11.882 | −18.482 | 13.706 | 1.00 | 17.81 |
| ATOM | 1572 | CG | TRP | 364 | 10.588 | −18.488 | 14.481 | 1.00 | 17.81 |
| ATOM | 1573 | CD2 | TRP | 364 | 9.586 | −17.458 | 14.504 | 1.00 | 17.81 |
| ATOM | 1574 | CE2 | TRP | 364 | 8.547 | −17.905 | 15.350 | 1.00 | 17.81 |
| ATOM | 1575 | CE3 | TRP | 364 | 9.467 | −16.202 | 13.894 | 1.00 | 17.81 |
| ATOM | 1576 | CD1 | TRP | 364 | 10.126 | −19.486 | 15.290 | 1.00 | 17.81 |
| ATOM | 1577 | NE1 | TRP | 364 | 8.902 | −19.144 | 15.814 | 1.00 | 17.81 |
| ATOM | 1578 | CZ2 | TRP | 364 | 7.403 | −17.142 | 15.602 | 1.00 | 17.81 |
| ATOM | 1579 | CZ3 | TRP | 364 | 8.329 | −15.444 | 14.145 | 1.00 | 17.81 |
| ATOM | 1580 | CH2 | TRP | 364 | 7.312 | −15.919 | 14.992 | 1.00 | 17.81 |
| ATOM | 1581 | C | TRP | 364 | 13.046 | −17.114 | 15.500 | 1.00 | 16.46 |
| ATOM | 1582 | O | TRP | 364 | 12.595 | −16.133 | 16.087 | 1.00 | 17.81 |
| ATOM | 1583 | N | PRO | 365 | 13.779 | −18.051 | 16.137 | 1.00 | 18.31 |
| ATOM | 1584 | CD | PRO | 365 | 14.342 | −19.314 | 15.625 | 1.00 | 25.61 |
| ATOM | 1585 | CA | PRO | 365 | 14.038 | −17.920 | 17.577 | 1.00 | 18.31 |
| ATOM | 1586 | CB | PRO | 365 | 14.939 | −19.118 | 17.874 | 1.00 | 25.61 |
| ATOM | 1587 | CG | PRO | 365 | 14.500 | −20.130 | 16.882 | 1.00 | 25.61 |
| ATOM | 1588 | C | PRO | 365 | 14.732 | −16.606 | 17.933 | 1.00 | 18.31 |
| ATOM | 1589 | O | PRO | 365 | 14.387 | −15.963 | 18.926 | 1.00 | 25.61 |
| ATOM | 1590 | N | LYS | 366 | 15.699 | −16.207 | 17.112 | 1.00 | 25.16 |
| ATOM | 1591 | CA | LYS | 366 | 16.439 | −14.968 | 17.338 | 1.00 | 25.16 |
| ATOM | 1592 | CB | LYS | 366 | 17.537 | −14.805 | 16.289 | 1.00 | 40.51 |
| ATOM | 1593 | CG | LYS | 366 | 18.679 | −15.792 | 16.417 | 1.00 | 40.51 |
| ATOM | 1594 | CD | LYS | 366 | 19.664 | −15.607 | 15.278 | 1.00 | 40.51 |
| ATOM | 1595 | CE | LYS | 366 | 20.884 | −16.492 | 15.440 | 1.00 | 40.51 |
| ATOM | 1596 | NZ | LYS | 366 | 21.800 | −16.360 | 14.275 | 1.00 | 40.51 |
| ATOM | 1597 | C | LYS | 366 | 15.521 | −13.747 | 17.317 | 1.00 | 25.16 |
| ATOM | 1598 | O | LYS | 366 | 15.593 | −12.893 | 18.202 | 1.00 | 49.51 |
| ATOM | 1599 | N | LEU | 367 | 14.661 | −13.666 | 16.307 | 1.00 | 25.30 |
| ATOM | 1600 | CA | LEU | 367 | 13.729 | −12.551 | 16.184 | 1.00 | 25.30 |
| ATOM | 1601 | CB | LEU | 367 | 12.989 | −12.620 | 14.845 | 1.00 | 27.80 |
| ATOM | 1602 | CG | LEU | 367 | 11.964 | −11.519 | 14.561 | 1.00 | 27.80 |
| ATOM | 1603 | CD1 | LEU | 367 | 12.621 | −10.147 | 14.679 | 1.00 | 27.80 |
| ATOM | 1604 | CD2 | LEU | 367 | 11.367 | −11.724 | 13.175 | 1.00 | 27.80 |
| ATOM | 1605 | C | LEU | 367 | 12.730 | −12.596 | 17.332 | 1.00 | 25.30 |
| ATOM | 1606 | O | LEU | 367 | 12.337 | −11.563 | 17.877 | 1.00 | 27.80 |
| ATOM | 1607 | N | LEU | 368 | 12.345 | −13.807 | 17.712 | 1.00 | 26.12 |
| ATOM | 1608 | CA | LEU | 368 | 11.396 | −14.019 | 18.793 | 1.00 | 26.12 |
| ATOM | 1609 | CB | LEU | 368 | 11.105 | −15.515 | 18.919 | 1.00 | 33.27 |
| ATOM | 1610 | CG | LEU | 368 | 9.696 | −15.976 | 19.289 | 1.00 | 33.27 |
| ATOM | 1611 | CD1 | LEU | 368 | 8.640 | −15.182 | 18.529 | 1.00 | 33.27 |
| ATOM | 1612 | CD2 | LEU | 368 | 9.582 | −17.460 | 18.976 | 1.00 | 33.27 |
| ATOM | 1613 | C | LEU | 368 | 11.973 | −13.466 | 20.096 | 1.00 | 26.12 |
| ATOM | 1614 | O | LEU | 368 | 11.249 | −12.920 | 20.930 | 1.00 | 33.27 |
| ATOM | 1615 | N | MET | 369 | 13.289 | −13.571 | 20.244 | 1.00 | 24.39 |
| ATOM | 1616 | CA | MET | 369 | 13.971 | −13.076 | 21.432 | 1.00 | 24.39 |
| ATOM | 1617 | CB | MET | 369 | 15.382 | −13.656 | 21.511 | 1.00 | 47.44 |
| ATOM | 1618 | CG | MET | 369 | 15.407 | −15.096 | 22.009 | 1.00 | 47.44 |
| ATOM | 1619 | SD | MET | 369 | 16.850 | −16.029 | 21.464 | 1.00 | 47.44 |
| ATOM | 1620 | CE | MET | 369 | 18.186 | −15.114 | 22.246 | 1.00 | 47.44 |
| ATOM | 1621 | C | MET | 369 | 13.996 | −11.552 | 21.491 | 1.00 | 24.39 |
| ATOM | 1622 | O | MET | 369 | 14.212 | −10.971 | 22.557 | 1.00 | 47.44 |
| ATOM | 1623 | N | LYS | 370 | 13.749 | −10.904 | 20.354 | 1.00 | 27.31 |
| ATOM | 1624 | CA | LYS | 370 | 13.713 | −9.445 | 20.297 | 1.00 | 27.31 |
| ATOM | 1625 | CB | LYS | 370 | 13.739 | −8.951 | 18.847 | 1.00 | 28.20 |
| ATOM | 1626 | CG | LYS | 370 | 15.004 | −9.312 | 18.090 | 1.00 | 28.20 |
| ATOM | 1627 | CD | LYS | 370 | 16.231 | −8.810 | 18.824 | 1.00 | 28.20 |
| ATOM | 1628 | CE | LYS | 370 | 17.512 | −9.244 | 18.142 | 1.00 | 28.20 |
| ATOM | 1629 | NZ | LYS | 370 | 18.696 | −8.851 | 18.952 | 1.00 | 28.20 |
| ATOM | 1630 | C | LYS | 370 | 12.453 | −8.945 | 21.002 | 1.00 | 27.31 |
| ATOM | 1631 | O | LYS | 370 | 12.424 | −7.835 | 21.535 | 1.00 | 28.20 |
| ATOM | 1632 | N | VAL | 371 | 11.413 | −9.776 | 21.009 | 1.00 | 26.41 |
| ATOM | 1633 | CA | VAL | 371 | 10.157 | −9.432 | 21.668 | 1.00 | 26.41 |
| ATOM | 1634 | CB | VAL | 371 | 9.109 | −10.561 | 21.512 | 1.00 | 25.61 |
| ATOM | 1635 | CG1 | VAL | 371 | 7.825 | −10.205 | 22.245 | 1.00 | 25.61 |
| ATOM | 1636 | CG2 | VAL | 371 | 8.819 | −10.805 | 20.044 | 1.00 | 25.61 |
| ATOM | 1637 | C | VAL | 371 | 10.450 | −9.205 | 23.151 | 1.00 | 26.41 |
| ATOM | 1638 | O | VAL | 371 | 9.962 | −8.248 | 23.752 | 1.00 | 25.61 |
| ATOM | 1639 | N | THR | 372 | 11.294 | −10.065 | 23.713 | 1.00 | 26.28 |
| ATOM | 1640 | CA | THR | 372 | 11.683 | −9.972 | 25.116 | 1.00 | 26.28 |
| ATOM | 1641 | CB | THR | 372 | 12.656 | −11.109 | 25.500 | 1.00 | 28.14 |
| ATOM | 1642 | OG1 | THR | 372 | 12.025 | −12.377 | 25.275 | 1.00 | 28.14 |
| ATOM | 1643 | CG2 | THR | 372 | 13.055 | −11.001 | 26.965 | 1.00 | 28.14 |

APPENDIX 4-continued

TR_TRIAC.PDB

| ATOM | 1644 | C   | THR | 372 | 12.358 | −8.624  | 25.372 | 1.00 | 26.28 |
|------|------|-----|-----|-----|--------|---------|--------|------|-------|
| ATOM | 1645 | O   | THR | 372 | 12.047 | −7.937  | 26.350 | 1.00 | 28.14 |
| ATOM | 1646 | N   | ASP | 373 | 13.269 | −8.247  | 24.478 | 1.00 | 15.09 |
| ATOM | 1647 | CA  | ASP | 373 | 13.977 | −6.979  | 24.588 | 1.00 | 15.09 |
| ATOM | 1648 | CB  | ASP | 373 | 14.976 | −6.822  | 23.435 | 1.00 | 37.94 |
| ATOM | 1649 | CG  | ASP | 373 | 16.065 | −7.893  | 23.445 | 1.00 | 37.94 |
| ATOM | 1650 | OD1 | ASP | 373 | 16.248 | −8.571  | 24.483 | 1.00 | 37.94 |
| ATOM | 1651 | OD2 | ASP | 373 | 16.750 | −8.052  | 22.410 | 1.00 | 37.94 |
| ATOM | 1652 | C   | ASP | 373 | 12.969 | −5.833  | 24.577 | 1.00 | 15.09 |
| ATOM | 1653 | O   | ASP | 373 | 13.040 | −4.928  | 25.407 | 1.00 | 37.94 |
| ATOM | 1654 | N   | LEU | 374 | 12.008 | −5.901  | 23.659 | 1.00 | 17.04 |
| ATOM | 1655 | CA  | LEU | 374 | 10.974 | −4.880  | 23.549 | 1.00 | 17.04 |
| ATOM | 1656 | CB  | LEU | 374 | 10.071 | −5.155  | 22.344 | 1.00 | 20.58 |
| ATOM | 1657 | CG  | LEU | 374 | 10.624 | −4.720  | 20.985 | 1.00 | 20.58 |
| ATOM | 1658 | CD1 | LEU | 374 | 9.826  | −5.352  | 19.862 | 1.00 | 20.58 |
| ATOM | 1659 | CD2 | LEU | 374 | 10.599 | −3.202  | 20.882 | 1.00 | 20.58 |
| ATOM | 1660 | C   | LEU | 374 | 10.145 | −4.786  | 24.825 | 1.00 | 17.04 |
| ATOM | 1661 | O   | LEU | 374 | 9.783  | −3.688  | 25.256 | 1.00 | 20.58 |
| ATOM | 1662 | N   | ARG | 375 | 9.850  | −5.935  | 25.430 | 1.00 | 20.46 |
| ATOM | 1663 | CA  | ARG | 375 | 9.080  | −5.977  | 26.673 | 1.00 | 20.46 |
| ATOM | 1664 | CB  | ARG | 375 | 8.873  | −7.422  | 27.140 | 1.00 | 55.89 |
| ATOM | 1665 | CG  | ARG | 375 | 8.180  | −8.354  | 26.152 | 1.00 | 55.89 |
| ATOM | 1666 | CD  | ARG | 375 | 6.692  | −8.084  | 26.027 | 1.00 | 55.89 |
| ATOM | 1667 | NE  | ARG | 375 | 5.943  | −9.338  | 25.968 | 1.00 | 55.89 |
| ATOM | 1668 | CZ  | ARG | 375 | 5.054  | −9.654  | 25.028 | 1.00 | 55.89 |
| ATOM | 1669 | NH1 | ARG | 375 | 4.782  | −8.808  | 24.040 | 1.00 | 55.89 |
| ATOM | 1670 | NH2 | ARG | 375 | 4.438  | −10.829 | 25.073 | 1.00 | 55.89 |
| ATOM | 1671 | C   | ARG | 375 | 9.874  | −5.221  | 27.735 | 1.00 | 20.46 |
| ATOM | 1672 | O   | ARG | 375 | 9.328  | −4.391  | 28.463 | 1.00 | 55.89 |
| ATOM | 1673 | N   | MET | 376 | 11.174 | −5.502  | 27.794 | 1.00 | 20.10 |
| ATOM | 1674 | CA  | MET | 376 | 12.076 | −4.863  | 28.744 | 1.00 | 20.10 |
| ATOM | 1675 | CB  | MET | 376 | 13.493 | −5.417  | 28.580 | 1.00 | 63.73 |
| ATOM | 1676 | CG  | MET | 376 | 13.956 | −6.310  | 29.722 | 1.00 | 63.73 |
| ATOM | 1677 | SD  | MET | 376 | 14.494 | −5.373  | 31.182 | 1.00 | 63.73 |
| ATOM | 1678 | CE  | MET | 376 | 12.934 | −5.151  | 32.087 | 1.00 | 63.73 |
| ATOM | 1679 | C   | MET | 376 | 12.081 | −3.347  | 28.566 | 1.00 | 20.10 |
| ATOM | 1680 | O   | MET | 376 | 11.973 | −2.602  | 29.539 | 1.00 | 63.73 |
| ATOM | 1681 | N   | ILE | 377 | 12.194 | −2.896  | 27.321 | 1.00 | 30.02 |
| ATOM | 1682 | CA  | ILE | 377 | 12.198 | −1.469  | 27.014 | 1.00 | 30.02 |
| ATOM | 1683 | CB  | ILE | 377 | 12.329 | −1.228  | 25.488 | 1.00 | 19.31 |
| ATOM | 1684 | CG2 | ILE | 377 | 12.088 | 0.242   | 25.152 | 1.00 | 19.31 |
| ATOM | 1685 | CG1 | ILE | 377 | 13.711 | −1.685  | 25.011 | 1.00 | 19.31 |
| ATOM | 1686 | CD1 | ILE | 377 | 13.906 | −1.634  | 23.507 | 1.00 | 19.31 |
| ATOM | 1687 | C   | ILE | 377 | 10.915 | −0.821  | 27.542 | 1.00 | 30.02 |
| ATOM | 1688 | O   | ILE | 377 | 10.962 | 0.216   | 28.211 | 1.00 | 19.31 |
| ATOM | 1689 | N   | GLY | 378 | 9.779  | −1.455  | 27.266 | 1.00 | 21.85 |
| ATOM | 1690 | CA  | GLY | 378 | 8.505  | −0.936  | 27.729 | 1.00 | 21.85 |
| ATOM | 1691 | C   | GLY | 378 | 8.459  | −0.821  | 29.243 | 1.00 | 21.85 |
| ATOM | 1692 | O   | GLY | 378 | 7.990  | 0.185   | 29.779 | 1.00 | 34.01 |
| ATOM | 1693 | N   | ALA | 379 | 8.967  | −1.842  | 29.928 | 1.00 | 31.30 |
| ATOM | 1694 | CA  | ALA | 379 | 8.996  | −1.870  | 31.388 | 1.00 | 31.30 |
| ATOM | 1695 | CB  | ALA | 379 | 9.471  | −3.231  | 31.880 | 1.00 | 30.06 |
| ATOM | 1696 | C   | ALA | 379 | 9.895  | −0.763  | 31.938 | 1.00 | 31.30 |
| ATOM | 1697 | O   | ALA | 379 | 9.482  | 0.002   | 32.810 | 1.00 | 30.06 |
| ATOM | 1698 | N   | CYS | 380 | 11.117 | −0.677  | 31.418 | 1.00 | 28.61 |
| ATOM | 1699 | CA  | CYS | 380 | 12.067 | 0.349   | 31.841 | 1.00 | 28.61 |
| ATOM | 1700 | CB  | CYS | 380 | 13.360 | 0.268   | 31.025 | 1.00 | 60.26 |
| ATOM | 1701 | SG  | CYS | 380 | 14.499 | −1.067  | 31.470 | 1.00 | 60.26 |
| ATOM | 1702 | C   | CYS | 380 | 11.449 | 1.730   | 31.658 | 1.00 | 28.61 |
| ATOM | 1703 | O   | CYS | 380 | 11.516 | 2.573   | 32.554 | 1.00 | 60.26 |
| ATOM | 1704 | N   | HIS | 381 | 10.840 | 1.957   | 30.498 | 1.00 | 30.42 |
| ATOM | 1705 | CA  | HIS | 381 | 10.212 | 3.243   | 30.216 | 1.00 | 30.42 |
| ATOM | 1706 | CB  | HIS | 381 | 9.696  | 3.306   | 28.779 | 1.00 | 16.49 |
| ATOM | 1707 | CG  | HIS | 381 | 8.942  | 4.562   | 28.472 | 1.00 | 16.49 |
| ATOM | 1708 | CD2 | HIS | 381 | 9.370  | 5.805   | 28.151 | 1.00 | 16.49 |
| ATOM | 1709 | ND1 | HIS | 381 | 7.566  | 4.633   | 28.524 | 1.00 | 16.49 |
| ATOM | 1710 | CE1 | HIS | 381 | 7.180  | 5.866   | 28.251 | 1.00 | 16.49 |
| ATOM | 1711 | NE2 | HIS | 381 | 8.255  | 6.596   | 28.021 | 1.00 | 16.49 |
| ATOM | 1712 | C   | HIS | 381 | 9.073  | 3.539   | 31.182 | 1.00 | 30.42 |
| ATOM | 1713 | O   | HIS | 381 | 8.856  | 4.690   | 31.552 | 1.00 | 16.49 |
| ATOM | 1714 | N   | ALA | 382 | 8.330  | 2.506   | 31.564 | 1.00 | 22.89 |
| ATOM | 1715 | CA  | ALA | 382 | 7.218  | 2.666   | 32.493 | 1.00 | 22.89 |
| ATOM | 1716 | CB  | ALA | 382 | 6.520  | 1.336   | 32.708 | 1.00 | 34.50 |
| ATOM | 1717 | C   | ALA | 382 | 7.738  | 3.213   | 33.819 | 1.00 | 22.89 |
| ATOM | 1718 | O   | ALA | 382 | 7.219  | 4.200   | 34.343 | 1.00 | 34.50 |
| ATOM | 1719 | N   | SER | 383 | 8.789  | 2.586   | 34.336 | 1.00 | 26.39 |
| ATOM | 1720 | CA  | SER | 383 | 9.400  | 3.006   | 35.591 | 1.00 | 26.39 |

APPENDIX 4-continued

TR_TRIAC.PDB

| ATOM | 1721 | CB | SER | 383 | 10.510 | 2.030 | 35.985 | 1.00 | 52.94 |
|---|---|---|---|---|---|---|---|---|---|
| ATOM | 1722 | OG | SER | 383 | 10.015 | 0.702 | 36.046 | 1.00 | 52.94 |
| ATOM | 1723 | C | SER | 383 | 9.966 | 4.418 | 35.470 | 1.00 | 26.39 |
| ATOM | 1724 | O | SER | 383 | 9.772 | 5.253 | 36.357 | 1.00 | 52.94 |
| ATOM | 1725 | N | ARG | 384 | 10.662 | 4.683 | 34.368 | 1.00 | 30.36 |
| ATOM | 1726 | CA | ARG | 384 | 11.249 | 5.995 | 34.134 | 1.00 | 30.36 |
| ATOM | 1727 | CB | ARG | 384 | 12.116 | 5.977 | 32.874 | 1.00 | 37.39 |
| ATOM | 1728 | CG | ARG | 384 | 12.601 | 7.344 | 32.431 | 1.00 | 37.39 |
| ATOM | 1729 | CD | ARG | 384 | 14.070 | 7.321 | 32.060 | 1.00 | 37.39 |
| ATOM | 1730 | NE | ARG | 384 | 14.935 | 7.597 | 33.204 | 1.00 | 37.39 |
| ATOM | 1731 | CZ | ARG | 384 | 15.750 | 8.646 | 33.291 | 1.00 | 37.39 |
| ATOM | 1732 | NH1 | ARG | 384 | 15.824 | 9.529 | 32.303 | 1.00 | 37.39 |
| ATOM | 1733 | NH2 | ARG | 384 | 16.488 | 8.819 | 34.376 | 1.00 | 37.39 |
| ATOM | 1734 | C | ARG | 384 | 10.169 | 7.067 | 34.030 | 1.00 | 30.36 |
| ATOM | 1735 | O | ARG | 384 | 10.301 | 8.144 | 34.616 | 1.00 | 37.39 |
| ATOM | 1736 | N | PHE | 385 | 9.078 | 6.749 | 33.338 | 1.00 | 24.47 |
| ATOM | 1737 | CA | PHE | 385 | 7.980 | 7.693 | 33.171 | 1.00 | 24.47 |
| ATOM | 1738 | CB | PHE | 385 | 6.859 | 7.092 | 32.319 | 1.00 | 28.70 |
| ATOM | 1739 | CG | PHE | 385 | 5.710 | 8.036 | 32.075 | 1.00 | 28.70 |
| ATOM | 1740 | CD1 | PHE | 385 | 5.795 | 9.017 | 31.092 | 1.00 | 28.70 |
| ATOM | 1741 | CD2 | PHE | 385 | 4.549 | 7.954 | 32.836 | 1.00 | 28.70 |
| ATOM | 1742 | CE1 | PHE | 385 | 4.740 | 9.903 | 30.874 | 1.00 | 28.70 |
| ATOM | 1743 | CE2 | PHE | 385 | 3.491 | 8.835 | 32.624 | 1.00 | 28.70 |
| ATOM | 1744 | CZ | PHE | 385 | 3.587 | 9.812 | 31.641 | 1.00 | 28.70 |
| ATOM | 1745 | C | PHE | 385 | 7.436 | 8.097 | 34.533 | 1.00 | 24.47 |
| ATOM | 1746 | O | PHE | 385 | 7.250 | 9.285 | 34.805 | 1.00 | 28.70 |
| ATOM | 1747 | N | LEU | 386 | 7.208 | 7.107 | 35.391 | 1.00 | 31.13 |
| ATOM | 1748 | CA | LEU | 386 | 6.690 | 7.352 | 36.734 | 1.00 | 31.13 |
| ATOM | 1749 | CB | LEU | 386 | 6.596 | 6.044 | 37.513 | 1.00 | 39.10 |
| ATOM | 1750 | C | LEU | 386 | 7.577 | 8.348 | 37.474 | 1.00 | 31.13 |
| ATOM | 1751 | O | LEU | 386 | 7.085 | 9.201 | 38.217 | 1.00 | 39.10 |
| ATOM | 1752 | N | HIS | 387 | 8.884 | 8.254 | 37.243 | 1.00 | 36.46 |
| ATOM | 1753 | CA | HIS | 387 | 9.837 | 9.152 | 37.881 | 1.00 | 36.46 |
| ATOM | 1754 | CB | HIS | 387 | 11.258 | 8.589 | 37.794 | 1.00 | 62.78 |
| ATOM | 1755 | CG | HIS | 387 | 11.459 | 7.338 | 38.590 | 1.00 | 62.78 |
| ATOM | 1756 | CD2 | HIS | 387 | 10.601 | 6.614 | 39.346 | 1.00 | 62.78 |
| ATOM | 1757 | ND1 | HIS | 387 | 12.675 | 6.689 | 38.663 | 1.00 | 62.78 |
| ATOM | 1758 | CE1 | HIS | 387 | 12.554 | 5.620 | 39.431 | 1.00 | 62.78 |
| ATOM | 1759 | NE2 | HIS | 387 | 11.309 | 5.550 | 39.856 | 1.00 | 62.78 |
| ATOM | 1760 | C | HIS | 387 | 9.778 | 10.544 | 37.266 | 1.00 | 36.46 |
| ATOM | 1761 | O | HIS | 387 | 9.885 | 11.543 | 37.979 | 1.00 | 62.78 |
| ATOM | 1762 | N | MET | 388 | 9.587 | 10.612 | 35.950 | 1.00 | 33.41 |
| ATOM | 1763 | CA | MET | 388 | 9.505 | 11.894 | 35.258 | 1.00 | 33.41 |
| ATOM | 1764 | CB | MET | 388 | 9.269 | 11.703 | 33.755 | 1.00 | 42.63 |
| ATOM | 1765 | CG | MET | 388 | 10.456 | 11.144 | 32.982 | 1.00 | 42.63 |
| ATOM | 1766 | SD | MET | 388 | 10.253 | 11.325 | 31.192 | 1.00 | 42.63 |
| ATOM | 1767 | CE | MET | 388 | 9.501 | 9.772 | 30.748 | 1.00 | 42.63 |
| ATOM | 1768 | C | MET | 388 | 8.385 | 12.746 | 35.849 | 1.00 | 33.41 |
| ATOM | 1769 | O | MET | 388 | 8.573 | 13.934 | 36.103 | 1.00 | 42.63 |
| ATOM | 1770 | N | LYS | 389 | 7.235 | 12.126 | 36.092 | 1.00 | 39.26 |
| ATOM | 1771 | CA | LYS | 389 | 6.082 | 12.825 | 36.659 | 1.00 | 39.26 |
| ATOM | 1772 | CB | LYS | 389 | 4.867 | 11.900 | 36.719 | 1.00 | 52.87 |
| ATOM | 1773 | CG | LYS | 389 | 4.237 | 11.594 | 35.379 | 1.00 | 52.87 |
| ATOM | 1774 | CD | LYS | 389 | 3.048 | 10.667 | 35.553 | 1.00 | 52.87 |
| ATOM | 1775 | CE | LYS | 389 | 3.482 | 9.321 | 36.125 | 1.00 | 52.87 |
| ATOM | 1776 | NZ | LYS | 389 | 2.335 | 8.407 | 36.326 | 1.00 | 52.87 |
| ATOM | 1777 | C | LYS | 389 | 6.363 | 13.360 | 38.056 | 1.00 | 39.26 |
| ATOM | 1778 | O | LYS | 389 | 5.837 | 14.404 | 38.452 | 1.00 | 52.87 |
| ATOM | 1779 | N | VAL | 390 | 7.156 | 12.614 | 38.818 | 1.00 | 44.18 |
| ATOM | 1780 | CA | VAL | 390 | 7.508 | 13.016 | 40.172 | 1.00 | 44.18 |
| ATOM | 1781 | CB | VAL | 390 | 8.299 | 11.898 | 40.905 | 1.00 | 50.50 |
| ATOM | 1782 | CG1 | VAL | 390 | 8.718 | 12.362 | 42.293 | 1.00 | 50.50 |
| ATOM | 1783 | CG2 | VAL | 390 | 7.455 | 10.640 | 41.012 | 1.00 | 50.50 |
| ATOM | 1784 | C | VAL | 390 | 8.352 | 14.288 | 40.145 | 1.00 | 44.18 |
| ATOM | 1785 | O | VAL | 390 | 8.144 | 15.198 | 40.948 | 1.00 | 50.50 |
| ATOM | 1786 | N | GLU | 391 | 9.261 | 14.368 | 39.179 | 1.00 | 38.64 |
| ATOM | 1787 | CA | GLU | 391 | 10.161 | 15.509 | 39.056 | 1.00 | 38.64 |
| ATOM | 1788 | CB | GLU | 391 | 11.483 | 15.060 | 38.424 | 1.00 | 64.18 |
| ATOM | 1789 | CG | GLU | 391 | 12.065 | 13.766 | 39.009 | 1.00 | 64.18 |
| ATOM | 1790 | CD | GLU | 391 | 12.662 | 13.922 | 40.405 | 1.00 | 64.18 |
| ATOM | 1791 | OE1 | GLU | 391 | 12.190 | 14.773 | 41.192 | 1.00 | 64.18 |
| ATOM | 1792 | OE2 | GLU | 391 | 13.611 | 13.173 | 40.721 | 1.00 | 64.18 |
| ATOM | 1793 | C | GLU | 391 | 9.623 | 16.737 | 38.314 | 1.00 | 38.64 |
| ATOM | 1794 | O | GLU | 391 | 9.656 | 17.850 | 38.849 | 1.00 | 64.18 |
| ATOM | 1795 | N | CYS | 392 | 9.125 | 16.539 | 37.096 | 1.00 | 37.24 |
| ATOM | 1796 | CA | CYS | 392 | 8.611 | 17.635 | 36.271 | 1.00 | 37.24 |
| ATOM | 1797 | CB | CYS | 392 | 8.879 | 17.345 | 34.784 | 1.00 | 30.64 |

APPENDIX 4-continued

TR_TRIAC.PDB

| ATOM | 1798 | SG  | CYS | 392 | 10.634 | 17.137 | 34.283 | 1.00 | 30.64 |
|------|------|-----|-----|-----|--------|--------|--------|------|-------|
| ATOM | 1799 | C   | CYS | 392 | 7.110  | 17.882 | 36.496 | 1.00 | 37.24 |
| ATOM | 1800 | O   | CYS | 392 | 6.403  | 17.011 | 37.006 | 1.00 | 30.64 |
| ATOM | 1801 | N   | PRO | 393 | 6.625  | 19.107 | 36.199 | 1.00 | 40.56 |
| ATOM | 1802 | CD  | PRO | 393 | 7.444  | 20.297 | 35.904 | 1.00 | 33.41 |
| ATOM | 1803 | CA  | PRO | 393 | 5.209  | 19.473 | 36.358 | 1.00 | 40.56 |
| ATOM | 1804 | CB  | PRO | 393 | 5.253  | 21.001 | 36.404 | 1.00 | 33.41 |
| ATOM | 1805 | CG  | PRO | 393 | 6.409  | 21.332 | 35.527 | 1.00 | 33.41 |
| ATOM | 1806 | C   | PRO | 393 | 4.330  | 18.975 | 35.207 | 1.00 | 40.56 |
| ATOM | 1807 | O   | PRO | 393 | 4.776  | 18.907 | 34.057 | 1.00 | 33.41 |
| ATOM | 1808 | N   | THR | 394 | 3.067  | 18.691 | 35.516 | 1.00 | 41.91 |
| ATOM | 1809 | CA  | THR | 394 | 2.101  | 18.186 | 34.540 | 1.00 | 41.91 |
| ATOM | 1810 | CB  | THR | 394 | 0.691  | 18.075 | 35.156 | 1.00 | 62.04 |
| ATOM | 1811 | OG1 | THR | 394 | 0.706  | 18.582 | 36.497 | 1.00 | 62.04 |
| ATOM | 1812 | CG2 | THR | 394 | 0.232  | 16.626 | 35.168 | 1.00 | 62.04 |
| ATOM | 1813 | C   | THR | 394 | 1.995  | 18.984 | 33.242 | 1.00 | 41.91 |
| ATOM | 1814 | O   | THR | 394 | 1.758  | 18.411 | 32.181 | 1.00 | 62.04 |
| ATOM | 1815 | N   | GLU | 395 | 2.191  | 20.297 | 33.327 | 1.00 | 43.92 |
| ATOM | 1816 | CA  | GLU | 395 | 2.104  | 21.176 | 32.160 | 1.00 | 43.92 |
| ATOM | 1817 | CB  | GLU | 395 | 2.313  | 22.626 | 32.585 | 1.00 | 34.22 |
| ATOM | 1818 | C   | GLU | 395 | 3.071  | 20.814 | 31.031 | 1.00 | 43.92 |
| ATOM | 1819 | O   | GLU | 395 | 2.887  | 21.243 | 29.891 | 1.00 | 34.22 |
| ATOM | 1820 | N   | LEU | 396 | 4.104  | 20.041 | 31.350 | 1.00 | 34.92 |
| ATOM | 1821 | CA  | LEU | 396 | 5.096  | 19.634 | 30.359 | 1.00 | 34.92 |
| ATOM | 1822 | CB  | LEU | 396 | 6.473  | 19.495 | 31.017 | 1.00 | 35.81 |
| ATOM | 1823 | CG  | LEU | 396 | 7.074  | 20.747 | 31.662 | 1.00 | 35.81 |
| ATOM | 1824 | CD1 | LEU | 396 | 8.427  | 20.410 | 32.263 | 1.00 | 35.81 |
| ATOM | 1825 | CD2 | LEU | 396 | 7.209  | 21.857 | 30.629 | 1.00 | 35.81 |
| ATOM | 1826 | C   | LEU | 396 | 4.731  | 18.324 | 29.661 | 1.00 | 34.92 |
| ATOM | 1827 | O   | LEU | 396 | 5.343  | 17.954 | 28.659 | 1.00 | 35.81 |
| ATOM | 1828 | N   | PHE | 397 | 3.734  | 17.627 | 30.197 | 1.00 | 35.28 |
| ATOM | 1829 | CA  | PHE | 397 | 3.302  | 16.352 | 29.640 | 1.00 | 35.28 |
| ATOM | 1830 | CB  | PHE | 397 | 3.059  | 15.341 | 30.764 | 1.00 | 27.13 |
| ATOM | 1831 | CG  | PHE | 397 | 4.285  | 15.004 | 31.561 | 1.00 | 27.13 |
| ATOM | 1832 | CD1 | PHE | 397 | 4.700  | 15.824 | 32.604 | 1.00 | 27.13 |
| ATOM | 1833 | CD2 | PHE | 397 | 5.021  | 13.860 | 31.273 | 1.00 | 27.13 |
| ATOM | 1834 | CE1 | PHE | 397 | 5.831  | 15.510 | 33.349 | 1.00 | 27.13 |
| ATOM | 1835 | CE2 | PHE | 397 | 6.155  | 13.537 | 32.013 | 1.00 | 27.13 |
| ATOM | 1836 | CZ  | PHE | 397 | 6.561  | 14.364 | 33.052 | 1.00 | 27.13 |
| ATOM | 1837 | C   | PHE | 397 | 2.027  | 16.474 | 28.812 | 1.00 | 35.28 |
| ATOM | 1838 | O   | PHE | 397 | 0.977  | 16.861 | 29.331 | 1.00 | 27.13 |
| ATOM | 1839 | N   | PRO | 398 | 2.102  | 16.164 | 27.505 | 1.00 | 26.41 |
| ATOM | 1840 | CD  | PRO | 398 | 3.305  | 15.850 | 26.713 | 1.00 | 19.32 |
| ATOM | 1841 | CA  | PRO | 398 | 0.917  | 16.247 | 26.647 | 1.00 | 26.41 |
| ATOM | 1842 | CB  | PRO | 398 | 1.439  | 15.752 | 25.300 | 1.00 | 19.32 |
| ATOM | 1843 | CG  | PRO | 398 | 2.867  | 16.193 | 25.312 | 1.00 | 19.32 |
| ATOM | 1844 | C   | PRO | 398 | −0.157 | 15.313 | 27.206 | 1.00 | 26.41 |
| ATOM | 1845 | O   | PRO | 398 | 0.160  | 14.232 | 27.710 | 1.00 | 19.32 |
| ATOM | 1846 | N   | PRO | 399 | −1.439 | 15.702 | 27.104 | 1.00 | 25.12 |
| ATOM | 1847 | CD  | PRO | 399 | −1.935 | 16.929 | 26.454 | 1.00 | 24.32 |
| ATOM | 1848 | CA  | PRO | 399 | −2.554 | 14.894 | 27.612 | 1.00 | 25.12 |
| ATOM | 1849 | CB  | PRO | 399 | −3.777 | 15.594 | 27.022 | 1.00 | 24.32 |
| ATOM | 1850 | CG  | PRO | 399 | −3.349 | 17.026 | 26.974 | 1.00 | 24.32 |
| ATOM | 1851 | C   | PRO | 399 | −2.502 | 13.416 | 27.222 | 1.00 | 25.12 |
| ATOM | 1852 | O   | PRO | 399 | −2.599 | 12.540 | 28.085 | 1.00 | 24.32 |
| ATOM | 1853 | N   | LEU | 400 | −2.322 | 13.139 | 25.933 | 1.00 | 23.10 |
| ATOM | 1854 | CA  | LEU | 400 | −2.265 | 11.759 | 25.454 | 1.00 | 23.10 |
| ATOM | 1855 | CB  | LEU | 400 | −2.230 | 11.720 | 23.923 | 1.00 | 22.35 |
| ATOM | 1856 | CG  | LEU | 400 | −2.485 | 10.354 | 23.276 | 1.00 | 22.35 |
| ATOM | 1857 | CD1 | LEU | 400 | −3.792 | 9.765  | 23.792 | 1.00 | 22.35 |
| ATOM | 1858 | CD2 | LEU | 400 | −2.523 | 10.494 | 21.763 | 1.00 | 22.35 |
| ATOM | 1859 | C   | LEU | 400 | −1.066 | 11.012 | 26.032 | 1.00 | 23.10 |
| ATOM | 1860 | O   | LEU | 400 | −1.160 | 9.825  | 26.345 | 1.00 | 22.35 |
| ATOM | 1861 | N   | PHE | 401 | 0.044  | 11.723 | 26.202 | 1.00 | 13.85 |
| ATOM | 1862 | CA  | PHE | 401 | 1.269  | 11.150 | 26.755 | 1.00 | 13.85 |
| ATOM | 1863 | CB  | PHE | 401 | 2.374  | 12.213 | 26.753 | 1.00 | 26.97 |
| ATOM | 1864 | CG  | PHE | 401 | 3.729  | 11.702 | 27.164 | 1.00 | 26.97 |
| ATOM | 1865 | CD1 | PHE | 401 | 4.189  | 10.461 | 26.732 | 1.00 | 26.97 |
| ATOM | 1866 | CD2 | PHE | 401 | 4.561  | 12.481 | 27.963 | 1.00 | 26.97 |
| ATOM | 1867 | CE1 | PHE | 401 | 5.459  | 10.005 | 27.091 | 1.00 | 26.97 |
| ATOM | 1868 | CE2 | PHE | 401 | 5.830  | 12.035 | 28.327 | 1.00 | 26.97 |
| ATOM | 1869 | CZ  | PHE | 401 | 6.280  | 10.795 | 27.889 | 1.00 | 26.97 |
| ATOM | 1870 | C   | PHE | 401 | 0.993  | 10.659 | 28.179 | 1.00 | 13.85 |
| ATOM | 1871 | O   | PHE | 401 | 1.393  | 9.558  | 28.555 | 1.00 | 26.97 |
| ATOM | 1872 | N   | LEU | 402 | 0.274  | 11.473 | 28.947 | 1.00 | 25.21 |
| ATOM | 1873 | CA  | LEU | 402 | −0.080 | 11.145 | 30.325 | 1.00 | 25.21 |
| ATOM | 1874 | CB  | LEU | 402 | −0.640 | 12.380 | 31.035 | 1.00 | 29.34 |

APPENDIX 4-continued

TR_TRIAC.PDB

| ATOM | 1875 | CG | LEU | 402 | 0.334 | 13.411 | 31.600 | 1.00 | 29.34 | |
|------|------|------|-----|-----|---------|---------|---------|------|-------|----|
| ATOM | 1876 | CD1 | LEU | 402 | −0.430 | 14.658 | 32.018 | 1.00 | 29.34 | |
| ATOM | 1877 | CD2 | LEU | 402 | 1.090 | 12.814 | 32.775 | 1.00 | 29.34 | |
| ATOM | 1878 | C | LEU | 402 | −1.109 | 10.025 | 30.425 | 1.00 | 25.21 | |
| ATOM | 1879 | O | LEU | 402 | −1.034 | 9.189 | 31.320 | 1.00 | 29.34 | |
| ATOM | 1880 | N | GLU | 403 | −2.090 | 10.043 | 29.529 | 1.00 | 23.54 | |
| ATOM | 1881 | CA | GLU | 403 | −3.159 | 9.046 | 29.521 | 1.00 | 23.54 | |
| ATOM | 1882 | CB | GLU | 403 | −4.274 | 9.482 | 28.562 | 1.00 | 63.22 | |
| ATOM | 1883 | CG | GLU | 403 | −5.469 | 8.531 | 28.506 | 1.00 | 63.22 | |
| ATOM | 1884 | CD | GLU | 403 | −6.530 | 8.952 | 27.498 | 1.00 | 63.22 | |
| ATOM | 1885 | OE1 | GLU | 403 | −6.237 | 9.786 | 26.613 | 1.00 | 63.22 | |
| ATOM | 1886 | OE2 | GLU | 403 | −7.666 | 8.436 | 27.589 | 1.00 | 63.22 | |
| ATOM | 1887 | C | GLU | 403 | −2.708 | 7.629 | 29.170 | 1.00 | 23.54 | |
| ATOM | 1888 | O | GLU | 403 | −3.210 | 6.656 | 29.735 | 1.00 | 63.22 | |
| ATOM | 1889 | N | VAL | 404 | −1.787 | 7.515 | 28.221 | 1.00 | 33.24 | |
| ATOM | 1890 | CA | VAL | 404 | −1.297 | 6.213 | 27.782 | 1.00 | 33.24 | |
| ATOM | 1891 | CB | VAL | 404 | −0.621 | 6.314 | 26.390 | 1.00 | 30.71 | |
| ATOM | 1892 | CG1 | VAL | 404 | −0.097 | 4.957 | 25.947 | 1.00 | 30.71 | |
| ATOM | 1893 | CG2 | VAL | 404 | −1.611 | 6.841 | 25.371 | 1.00 | 30.71 | |
| ATOM | 1894 | C | VAL | 404 | −0.338 | 5.528 | 28.752 | 1.00 | 33.24 | |
| ATOM | 1895 | O | VAL | 404 | −0.386 | 4.305 | 28.914 | 1.00 | 30.71 | |
| ATOM | 1896 | N | PHE | 405 | 0.526 | 6.309 | 29.392 | 1.00 | 33.66 | |
| ATOM | 1897 | CA | PHE | 405 | 1.516 | 5.752 | 30.308 | 1.00 | 33.66 | |
| ATOM | 1898 | CB | PHE | 405 | 2.901 | 6.326 | 29.984 | 1.00 | 34.35 | |
| ATOM | 1899 | CG | PHE | 405 | 3.343 | 6.076 | 28.568 | 1.00 | 34.35 | |
| ATOM | 1900 | CD1 | PHE | 405 | 3.519 | 7.134 | 27.683 | 1.00 | 34.35 | |
| ATOM | 1901 | CD2 | PHE | 405 | 3.569 | 4.782 | 28.114 | 1.00 | 34.35 | |
| ATOM | 1902 | CE1 | PHE | 405 | 3.911 | 6.906 | 26.365 | 1.00 | 34.35 | |
| ATOM | 1903 | CE2 | PHE | 405 | 3.960 | 4.545 | 26.798 | 1.00 | 34.35 | |
| ATOM | 1904 | CZ | PHE | 405 | 4.131 | 5.610 | 25.922 | 1.00 | 34.35 | |
| ATOM | 1905 | C | PHE | 405 | 1.189 | 5.931 | 31.790 | 1.00 | 33.66 | |
| ATOM | 1906 | O | PHE | 405 | 2.036 | 5.539 | 32.623 | 1.00 | 34.35 | |
| ATOM | 1907 | OXT | PHE | 405 | 0.090 | 6.434 | 32.107 | 1.00 | 34.35 | |
| ATOM | 1908 | C1 | TRI | 1 | 8.375 | 7.063 | 18.475 | 1.00 | 34.21 | |
| ATOM | 1909 | C2 | TRI | 1 | 10.048 | 8.688 | 23.016 | 1.00 | 33.36 | |
| ATOM | 1910 | C3 | TRI | 1 | 8.104 | 8.391 | 18.941 | 1.00 | 34.21 | |
| ATOM | 1911 | C4 | TRI | 1 | 10.496 | 9.696 | 23.813 | 1.00 | 33.36 | |
| ATOM | 1912 | C5 | TRI | 1 | 8.916 | 8.943 | 19.927 | 1.00 | 34.21 | |
| ATOM | 1913 | C6 | TRI | 1 | 10.152 | 9.772 | 25.121 | 1.00 | 33.36 | |
| ATOM | 1914 | C7 | TRI | 1 | 9.862 | 8.178 | 20.609 | 1.00 | 34.21 | |
| ATOM | 1915 | C8 | TRI | 1 | 9.246 | 8.821 | 25.653 | 1.00 | 33.36 | |
| ATOM | 1916 | C9 | TRI | 1 | 10.117 | 6.865 | 20.147 | 1.00 | 34.21 | |
| ATOM | 1917 | C10 | TRI | 1 | 8.805 | 7.754 | 24.847 | 1.00 | 33.36 | |
| ATOM | 1918 | C11 | TRI | 1 | 9.375 | 6.339 | 19.026 | 1.00 | 34.21 | |
| ATOM | 1919 | C12 | TRI | 1 | 9.125 | 7.756 | 23.490 | 1.00 | 33.36 | |
| ATOM | 1920 | C13 | TRI | 1 | 7.540 | 6.470 | 17.383 | 1.00 | 35.85 | |
| ATOM | 1921 | C15 | TRI | 1 | 8.158 | 6.555 | 15.938 | 1.00 | 35.85 | |
| ATOM | 1922 | I1 | TRI | 1 | 8.713 | 10.990 | 20.395 | 1.00 | 34.21 | |
| ATOM | 1923 | I2 | TRI | 1 | 10.951 | 11.289 | 26.315 | 1.00 | 33.36 | |
| ATOM | 1924 | I3 | TRI | 1 | 11.592 | 5.685 | 21.118 | 1.00 | 34.21 | |
| ATOM | 1925 | O3 | TRI | 1 | 9.407 | 6.654 | 15.852 | 1.00 | 35.85 | |
| ATOM | 1926 | O2 | TRI | 1 | 10.570 | 8.649 | 21.717 | 1.00 | 33.36 | |
| ATOM | 1927 | O1 | TRI | 1 | 8.798 | 8.969 | 26.979 | 1.00 | 33.36 | |
| ATOM | 1928 | O4 | TRI | 1 | 7.352 | 6.522 | 14.973 | 1.00 | 35.85 | |
| ATOM | 1929 | O1 | HOH | 501 | 9.189 | 2.098 | 11.091 | 1.00 | 33.36 | |
| ATOM | 1930 | O1 | HOH | 503 | 5.152 | 5.261 | 12.137 | 1.00 | 33.36 | |
| ATOM | 1931 | O1 | HOH | 504 | 3.970 | 5.057 | 16.390 | 1.00 | 33.36 | |
| ATOM | 1932 | O1 | HOH | 534 | 8.296 | −0.941 | 8.998 | 1.00 | 33.36 | |
| ATOM | 1933 | O1 | HOH | 538 | 4.845 | 14.369 | 13.635 | 1.00 | 33.36 | |
| ATOM | 1934 | O1 | HOH | 540 | 5.789 | 12.049 | 10.352 | 1.00 | 33.36 | |
| ATOM | 1936 | O1 | HOH | 555 | 5.721 | 2.525 | 28.939 | 1.00 | 33.36 | |
| ATOM | 1937 | O1 | HOH | 556 | 3.732 | 1.273 | 26.724 | 1.00 | 33.36 | |
| ATOM | 1935 | O1 | HOH | 600 | 8.767 | 4.847 | 8.517 | 1.00 | 33.36 | |
| ATOM | 1938 | AS1 | CAD | 701 | 1.863 | 1.579 | 0.837 | 1.00 | 37.00 | |
| ATOM | 1939 | C2 | CAD | 701 | 1.760 | −0.100 | 0.335 | 1.00 | 33.36 | |
| ATOM | 1940 | C3 | CAD | 701 | 3.511 | 1.872 | 1.858 | 1.00 | 28.02 | |
| ATOM | 1941 | O4 | CAD | 701 | 1.785 | 2.506 | −0.433 | 1.00 | 28.02 | |
| ATOM | 1942 | O5 | CAD | 701 | 0.592 | 2.019 | 1.654 | 1.00 | 28.02 | |
| ATOM | 1943 | AS | AS | 801 | 11.254 | 16.718 | 33.126 | 1.00 | 37.00 | AS |
| ATOM | 1944 | AS | AS | 802 | 16.338 | −1.161 | 29.914 | 1.00 | 37.00 | AS |
| ATOM | 1945 | AS | AS | 803 | −14.931 | −11.763 | 25.324 | 1.00 | 37.00 | AS |
| END | | | | | | | | | | |

APPENDIX 5

TR_IPBR2.PDB

REMARK rTR_ipbr2 full length numbering
REMARK
REMARK Rfactor 0.214 Rfree 0.224
REMARK Resolution 15. 2.2 all reflections
REMARK
REMARK Three cacodylate-modified cysteines (CYA)
REMARK Cya334, Cya380, Cya392
REMARK cacodylate modeled as single arsenic atom
REMARK
REMARK side chain of certain residues modeled as ALA due to poor
density;
REMARK however, residue name reflects true residue for clarity
REMARK
REMARK clone obtained from Murray et. al.
REMARK deposited sequence confirmed,
REMARK differing from that reported by Thompson et. al.
REMARK in the following codons:
REMARK 281 Thr—Ala
REMARK 285 Lys—Glu
REMARK identical to that reported by Mitsuhashi et. al.
REMARK gb:RNTRAVI X07409
JRNL      AUTH   M. B. MURRAY, N. D. ZILZ, N. L. MCCREARY, M. J. MACDONALD
JRNL      AUTH 2 H. C. TOWLE
JRNL      TITL   ISOLATION AND CHARACTERIZATION OF RAT CDNA CLONES FOR TWO
JRNL      TITL 2 DISTINCT THYROID HORMONE RECPTORS
JRNL      REF    JBC         V. 263 25 1988
JRNL      AUTH   C. C. THOMPSON, C. WEINBERGER, R. LEBO, R. M. EVANS
JRNL      TITL   IDENTIFICATION OF A NOVEL THYROID HORMONE RECEPTOR EXPRESSED
JRNL      TITL 2 IN THE MAMMALIAN CENTRAL NERVOUS SYSTEM
JRNL      REF    SCIENCE     V. 237 1987
JRNL      AUTH   T. MITSUHASHI, G. TENNYSON, V. NIKODEM
JRNL      TITL   NUCLEOTIDE SEQUENCE OF NOVEL CDNAS GENERATED BY ALTERNATIVE
JRNL      TITL 2 SPLICING OF A RAT THYROID HORMONE RECEPTOR GENE TRANSCRIPT
JRNL      REF    NUC. ACIDS. RES.      V. 16 12 1988
REMARK

| | | | | | | | | | |
|---|---|---|---|---|---|---|---|---|---|
| ATOM | 1 | CB | ARG | 157 | 68.481 | 10.663 | 6.906 | 1.00 | 57.50 |
| ATOM | 2 | CG | ARG | 157 | 69.793 | 10.213 | 7.512 | 1.00 | 59.93 |
| ATOM | 3 | CD | ARG | 157 | 70.510 | 11.365 | 8.189 | 1.00 | 70.24 |
| ATOM | 4 | NE | ARG | 157 | 71.661 | 10.906 | 8.961 | 1.00 | 77.62 |
| ATOM | 5 | CZ | ARG | 157 | 11.599 | 10.492 | 10.224 | 1.00 | 78.75 |
| ATOM | 6 | NH1 | ARG | 157 | 70.440 | 10.480 | 10.870 | 1.00 | 74.33 |
| ATOM | 7 | NH2 | ARG | 157 | 72.697 | 10.075 | 10.839 | 1.00 | 83.44 |
| ATOM | 8 | C | ARG | 157 | 66.314 | 10.014 | 5.809 | 1.00 | 46.84 |
| ATOM | 9 | O | ARG | 157 | 66.109 | 10.397 | 4.659 | 1.00 | 54.49 |
| ATOM | 10 | N | ARG | 157 | 68.442 | 9.069 | 5.013 | 1.00 | 56.54 |
| ATOM | 11 | CA | ARG | 157 | 67.704 | 9.537 | 6.222 | 1.00 | 52.92 |
| ATOM | 12 | N | PRO | 158 | 65.335 | 9.953 | 6.727 | 1.00 | 39.44 |
| ATOM | 13 | CD | PRO | 158 | 65.503 | 9.448 | 8.099 | 1.00 | 41.72 |
| ATOM | 14 | CA | PRO | 158 | 63.946 | 10.368 | 6.487 | 1.00 | 34.98 |
| ATOM | 15 | CB | PRO | 158 | 63.282 | 10.172 | 7.854 | 1.00 | 34.92 |
| ATOM | 16 | CG | PRO | 158 | 64.096 | 9.096 | 8.487 | 1.00 | 45.83 |
| ATOM | 17 | C | PRO | 158 | 63.765 | 11.804 | 5.992 | 1.00 | 34.13 |
| ATOM | 18 | O | PRO | 158 | 64.223 | 12.757 | 6.621 | 1.00 | 31.07 |
| ATOM | 19 | N | GLU | 159 | 63.110 | 11.932 | 4.841 | 1.00 | 31.36 |
| ATOM | 20 | CA | GLU | 159 | 62.814 | 13.220 | 4.228 | 1.00 | 27.34 |
| ATOM | 21 | CB | GLU | 159 | 62.569 | 13.041 | 2.726 | 1.00 | 24.27 |
| ATOM | 22 | CG | GLU | 159 | 63.814 | 12.866 | 1.887 | 1.00 | 24.85 |
| ATOM | 23 | CD | GLU | 159 | 64.409 | 14.188 | 1.454 | 1.00 | 28.12 |
| ATOM | 24 | OE1 | GLU | 159 | 63.642 | 15.144 | 1.224 | 1.00 | 29.26 |
| ATOM | 25 | OE2 | GLU | 159 | 65.646 | 14.269 | 1.326 | 1.00 | 29.52 |
| ATOM | 26 | C | GLU | 159 | 61.528 | 13.707 | 4.870 | 1.00 | 24.30 |
| ATOM | 27 | O | GLU | 159 | 60.855 | 12.934 | 5.566 | 1.00 | 29.01 |
| ATOM | 28 | N | PRO | 160 | 61.192 | 14.989 | 4.718 | 1.00 | 24.62 |
| ATOM | 29 | CD | PRO | 160 | 61.979 | 16.126 | 4.188 | 1.00 | 18.72 |
| ATOM | 30 | CA | PRO | 160 | 59.947 | 15.451 | 5.330 | 1.00 | 21.62 |
| ATOM | 31 | CB | PRO | 160 | 59.945 | 16.955 | 5.048 | 1.00 | 12.71 |
| ATOM | 32 | CG | PRO | 160 | 61.394 | 17.297 | 4.930 | 1.00 | 15.12 |
| ATOM | 33 | C | PRO | 160 | 58.743 | 14.752 | 4.671 | 1.00 | 24.61 |
| ATOM | 34 | O | PRO | 160 | 58.789 | 14.384 | 3.490 | 1.00 | 22.63 |
| ATOM | 35 | N | THR | 161 | 57.705 | 14.504 | 5.450 | 1.00 | 25.86 |
| ATOM | 36 | CA | THR | 161 | 56.515 | 13.864 | 4.921 | 1.00 | 23.77 |
| ATOM | 37 | CB | THR | 161 | 55.689 | 13.201 | 6.048 | 1.00 | 21.75 |

APPENDIX 5-continued

TR_IPBR2.PDB

| ATOM | 38 | OG1 | THR | 161 | 55.178 | 14.210 | 6.926 | 1.00 | 20.78 |
|---|---|---|---|---|---|---|---|---|---|
| ATOM | 39 | CG2 | THR | 161 | 56.549 | 12.227 | 6.847 | 1.00 | 18.44 |
| ATOM | 40 | C | THR | 161 | 55.680 | 14.967 | 4.269 | 1.00 | 28.67 |
| ATOM | 41 | O | THR | 161 | 55.917 | 16.151 | 4.510 | 1.00 | 29.90 |
| ATOM | 42 | N | PRO | 162 | 54.685 | 14.597 | 3.448 | 1.00 | 27.79 |
| ATOM | 43 | CD | PRO | 162 | 54.313 | 13.237 | 3.019 | 1.00 | 23.25 |
| ATOM | 44 | CA | PRO | 162 | 53.843 | 15.603 | 2.795 | 1.00 | 26.19 |
| ATOM | 45 | CB | PRO | 162 | 52.699 | 14.766 | 2.227 | 1.00 | 19.89 |
| ATOM | 46 | CG | PRO | 162 | 53.394 | 13.492 | 1.848 | 1.00 | 20.63 |
| ATOM | 47 | C | PRO | 162 | 53.334 | 16.661 | 3.775 | 1.00 | 24.81 |
| ATOM | 48 | O | PRO | 162 | 53.477 | 17.863 | 3.526 | 1.00 | 21.10 |
| ATOM | 49 | N | GLU | 163 | 52.812 | 16.198 | 4.911 | 1.00 | 26.34 |
| ATOM | 50 | CA | GLU | 163 | 52.266 | 17.065 | 5.959 | 1.00 | 30.38 |
| ATOM | 51 | CB | GLU | 163 | 51.640 | 16.231 | 7.086 | 1.00 | 29.46 |
| ATOM | 52 | CG | GLU | 163 | 50.482 | 15.321 | 6.666 | 1.00 | 48.37 |
| ATOM | 53 | CD | GLU | 163 | 50.918 | 14.132 | 5.816 | 1.00 | 53.12 |
| ATOM | 54 | OE1 | GLU | 163 | 51.890 | 13.441 | 6.194 | 1.00 | 52.22 |
| ATOM | 55 | OE2 | GLU | 163 | 50.282 | 13.886 | 4.766 | 1.00 | 59.14 |
| ATOM | 56 | C | GLU | 163 | 53.353 | 17.949 | 6.552 | 1.00 | 26.74 |
| ATOM | 57 | O | GLU | 163 | 53.109 | 19.107 | 6.898 | 1.00 | 27.03 |
| ATOM | 58 | N | GLU | 164 | 54.553 | 17.389 | 6.677 | 1.00 | 26.74 |
| ATOM | 59 | CA | GLU | 164 | 55.679 | 18.124 | 7.221 | 1.00 | 23.65 |
| ATOM | 60 | CB | GLU | 164 | 56.805 | 17.174 | 7.609 | 1.00 | 18.85 |
| ATOM | 61 | CG | GLU | 164 | 56.441 | 16.306 | 8.804 | 1.00 | 26.81 |
| ATOM | 62 | CD | GLU | 164 | 57.536 | 15.334 | 9.188 | 1.00 | 31.06 |
| ATOM | 63 | OE1 | GLU | 164 | 58.404 | 15.050 | 8.340 | 1.00 | 29.21 |
| ATOM | 64 | OE2 | GLU | 164 | 57.524 | 14.848 | 10.340 | 1.00 | 31.39 |
| ATOM | 65 | C | GLU | 164 | 56.165 | 19.204 | 6.276 | 1.00 | 26.54 |
| ATOM | 66 | O | GLU | 164 | 56.609 | 20.258 | 6.724 | 1.00 | 32.48 |
| ATOM | 67 | N | TRP | 165 | 56.075 | 18.957 | 4.971 | 1.00 | 23.41 |
| ATOM | 68 | CA | TRP | 165 | 56.488 | 19.962 | 3.998 | 1.00 | 20.81 |
| ATOM | 69 | CB | TRP | 165 | 56.462 | 19.405 | 2.573 | 1.00 | 18.15 |
| ATOM | 70 | CG | TRP | 165 | 57.762 | 18.747 | 2.164 | 1.00 | 15.80 |
| ATOM | 71 | CD2 | TRP | 165 | 59.058 | 19.377 | 2.064 | 1.00 | 15.35 |
| ATOM | 72 | CE2 | TRP | 165 | 59.959 | 18.392 | 1.628 | 1.00 | 12.14 |
| ATOM | 73 | CE3 | TRP | 165 | 59.527 | 20.676 | 2.287 | 1.00 | 17.56 |
| ATOM | 74 | CD1 | TRP | 165 | 57.939 | 17.449 | 1.804 | 1.00 | 12.78 |
| ATOM | 75 | NE1 | TRP | 165 | 59.253 | 17.230 | 1.484 | 1.00 | 16.10 |
| ATOM | 76 | CZ2 | TRP | 165 | 61.318 | 18.657 | 1.419 | 1.00 | 16.26 |
| ATOM | 77 | CZ3 | TRP | 165 | 60.879 | 20.944 | 2.079 | 1.00 | 19.52 |
| ATOM | 78 | CH2 | TRP | 165 | 61.760 | 19.933 | 1.642 | 1.00 | 16.48 |
| ATOM | 79 | C | TRP | 165 | 55.547 | 21.151 | 4.109 | 1.00 | 19.66 |
| ATOM | 80 | O | TRP | 165 | 55.975 | 22.295 | 3.960 | 1.00 | 23.61 |
| ATOM | 81 | N | ASP | 166 | 54.269 | 20.882 | 4.376 | 1.00 | 22.66 |
| ATOM | 82 | CA | ASP | 166 | 53.269 | 21.943 | 4.537 | 1.00 | 23.35 |
| ATOM | 83 | CB | ASP | 166 | 51.863 | 21.359 | 4.716 | 1.00 | 22.61 |
| ATOM | 84 | CG | ASP | 166 | 51.347 | 20.681 | 3.458 | 1.00 | 31.41 |
| ATOM | 85 | OD1 | ASP | 166 | 51.816 | 21.028 | 2.360 | 1.00 | 26.38 |
| ATOM | 86 | OD2 | ASP | 166 | 50.464 | 19.803 | 3.570 | 1.00 | 32.25 |
| ATOM | 87 | C | ASP | 166 | 53.631 | 22.760 | 5.773 | 1.00 | 26.47 |
| ATOM | 88 | O | ASP | 166 | 53.694 | 23.991 | 5.718 | 1.00 | 30.25 |
| ATOM | 89 | N | LEU | 167 | 53.887 | 22.054 | 6.872 | 1.00 | 24.12 |
| ATOM | 90 | CA | LEU | 167 | 54.268 | 22.663 | 8.139 | 1.00 | 26.44 |
| ATOM | 91 | CB | LEU | 167 | 54.596 | 21.557 | 9.148 | 1.00 | 32.57 |
| ATOM | 92 | CG | LEU | 167 | 54.659 | 21.919 | 10.629 | 1.00 | 36.97 |
| ATOM | 93 | CD1 | LEU | 167 | 53.289 | 22.402 | 11.080 | 1.00 | 43.83 |
| ATOM | 94 | CD2 | LEU | 167 | 55.096 | 20.712 | 11.448 | 1.00 | 34.75 |
| ATOM | 95 | C | LEU | 167 | 55.501 | 23.533 | 7.904 | 1.00 | 23.19 |
| ATOM | 96 | O | LEU | 167 | 55.570 | 24.670 | 8.368 | 1.00 | 28.18 |
| ATOM | 97 | N | ILE | 168 | 56.450 | 22.988 | 7.147 | 1.00 | 19.25 |
| ATOM | 98 | CA | ILE | 168 | 57.703 | 23.651 | 6.801 | 1.00 | 17.71 |
| ATOM | 99 | CB | ILE | 168 | 58.632 | 22.693 | 6.006 | 1.00 | 14.43 |
| ATOM | 100 | CG2 | ILE | 168 | 59.740 | 23.451 | 5.304 | 1.00 | 16.71 |
| ATOM | 101 | CG1 | ILE | 168 | 59.219 | 21.644 | 6.948 | 1.00 | 21.24 |
| ATOM | 102 | CD1 | ILE | 168 | 60.063 | 20.588 | 6.264 | 1.00 | 18.18 |
| ATOM | 103 | C | ILE | 168 | 57.475 | 24.931 | 6.002 | 1.00 | 28.73 |
| ATOM | 104 | O | ILE | 168 | 58.064 | 25.977 | 6.307 | 1.00 | 29.36 |
| ATOM | 105 | N | HIS | 169 | 56.601 | 24.866 | 5.005 | 1.00 | 24.43 |
| ATOM | 106 | CA | HIS | 169 | 56.319 | 26.027 | 4.169 | 1.00 | 23.64 |
| ATOM | 107 | CB | HIS | 169 | 55.459 | 25.631 | 2.971 | 1.00 | 23.55 |
| ATOM | 108 | CG | HIS | 169 | 56.140 | 24.683 | 2.034 | 1.00 | 23.82 |
| ATOM | 109 | CD2 | HIS | 169 | 57.455 | 24.429 | 1.824 | 1.00 | 19.23 |
| ATOM | 110 | ND1 | HIS | 169 | 55.450 | 23.833 | 1.199 | 1.00 | 22.92 |
| ATOM | 111 | CE1 | HIS | 169 | 56.302 | 23.089 | 0.522 | 1.00 | 19.56 |
| ATOM | 112 | NE2 | HIS | 169 | 57.527 | 23.431 | 0.883 | 1.00 | 26.00 |
| ATOM | 113 | C | HIS | 169 | 55.653 | 27.135 | 4.962 | 1.00 | 19.37 |
| ATOM | 114 | O | HIS | 169 | 56.069 | 28.288 | 4.880 | 1.00 | 25.64 |

APPENDIX 5-continued

TR_IPBR2.PDB

| ATOM | 115 | N   | VAL | 170 | 54.638 | 26.782 | 5.745  | 1.00 | 19.88 |
|------|-----|-----|-----|-----|--------|--------|--------|------|-------|
| ATOM | 116 | CA  | VAL | 170 | 53.925 | 27.758 | 6.555  | 1.00 | 20.28 |
| ATOM | 117 | CB  | VAL | 170 | 52.755 | 27.100 | 7.330  | 1.00 | 26.06 |
| ATOM | 118 | CG1 | VAL | 170 | 52.093 | 28.109 | 8.259  | 1.00 | 20.15 |
| ATOM | 119 | CG2 | VAL | 170 | 51.725 | 26.541 | 6.352  | 1.00 | 18.69 |
| ATOM | 120 | C   | VAL | 170 | 54.886 | 28.442 | 7.532  | 1.00 | 23.11 |
| ATOM | 121 | O   | VAL | 170 | 54.907 | 29.672 | 7.625  | 1.00 | 28.86 |
| ATOM | 122 | N   | ALA | 171 | 55.716 | 27.644 | 8.203  | 1.00 | 20.48 |
| ATOM | 123 | CA  | ALA | 171 | 56.686 | 28.146 | 9.173  | 1.00 | 19.84 |
| ATOM | 124 | CB  | ALA | 171 | 57.365 | 26.985 | 9.902  | 1.00 | 18.07 |
| ATOM | 125 | C   | ALA | 171 | 57.728 | 29.049 | 8.512  | 1.00 | 20.62 |
| ATOM | 126 | O   | ALA | 171 | 58.033 | 30.127 | 9.037  | 1.00 | 24.67 |
| ATOM | 127 | N   | THR | 172 | 58.251 | 28.632 | 7.359  | 1.00 | 20.65 |
| ATOM | 128 | CA  | THR | 172 | 59.247 | 29.428 | 6.640  | 1.00 | 18.91 |
| ATOM | 129 | CB  | THR | 172 | 59.755 | 28.709 | 5.380  | 1.00 | 20.06 |
| ATOM | 130 | OG1 | THR | 172 | 60.267 | 27.417 | 5.734  | 1.00 | 20.30 |
| ATOM | 131 | CG2 | THR | 172 | 60.877 | 29.516 | 4.726  | 1.00 | 18.38 |
| ATOM | 132 | C   | THR | 172 | 58.675 | 30.786 | 6.235  | 1.00 | 24.43 |
| ATOM | 133 | O   | THR | 172 | 59.346 | 31.815 | 6.360  | 1.00 | 23.54 |
| ATOM | 134 | N   | GLU | 173 | 57.430 | 30.792 | 5.766  | 1.00 | 24.33 |
| ATOM | 135 | CA  | GLU | 173 | 56.783 | 32.031 | 5.361  | 1.00 | 25.98 |
| ATOM | 136 | CB  | GLU | 173 | 55.460 | 31.734 | 4.651  | 1.00 | 28.39 |
| ATOM | 137 | CG  | GLU | 173 | 54.679 | 32.974 | 4.207  | 1.00 | 40.39 |
| ATOM | 138 | CD  | GLU | 173 | 55.487 | 33.951 | 3.347  | 1.00 | 48.33 |
| ATOM | 139 | OE1 | GLU | 173 | 55.261 | 35.172 | 3.478  | 1.00 | 51.86 |
| ATOM | 140 | OE2 | GLU | 173 | 56.334 | 33.513 | 2.533  | 1.00 | 46.92 |
| ATOM | 141 | C   | GLU | 173 | 56.564 | 32.953 | 6.562  | 1.00 | 25.57 |
| ATOM | 142 | O   | GLU | 173 | 56.877 | 34.141 | 6.498  | 1.00 | 27.76 |
| ATOM | 143 | N   | ALA | 174 | 56.071 | 32.383 | 7.664  | 1.00 | 25.31 |
| ATOM | 144 | CA  | ALA | 174 | 55.823 | 33.128 | 8.900  | 1.00 | 22.66 |
| ATOM | 145 | CB  | ALA | 174 | 55.340 | 32.183 | 10.000 | 1.00 | 18.21 |
| ATOM | 146 | C   | ALA | 174 | 57.097 | 33.847 | 9.338  | 1.00 | 23.47 |
| ATOM | 147 | O   | ALA | 174 | 57.056 | 35.003 | 9.755  | 1.00 | 23.76 |
| ATOM | 148 | N   | HIS | 175 | 58.233 | 33.168 | 9.226  | 1.00 | 22.22 |
| ATOM | 149 | CA  | HIS | 175 | 59.503 | 33.769 | 9.592  | 1.00 | 20.21 |
| ATOM | 150 | CB  | HIS | 175 | 60.586 | 32.700 | 9.738  | 1.00 | 13.82 |
| ATOM | 151 | CG  | HIS | 175 | 61.950 | 33.261 | 9.984  | 1.00 | 20.53 |
| ATOM | 152 | CD2 | HIS | 175 | 62.378 | 34.221 | 10.843 | 1.00 | 10.04 |
| ATOM | 153 | ND1 | HIS | 175 | 63.054 | 32.890 | 9.249  | 1.00 | 22.39 |
| ATOM | 154 | CE1 | HIS | 175 | 64.103 | 33.596 | 9.640  | 1.00 | 13.46 |
| ATOM | 155 | NE2 | HIS | 175 | 63.715 | 34.410 | 10.605 | 1.00 | 20.86 |
| ATOM | 156 | C   | HIS | 175 | 59.949 | 34.822 | 8.571  | 1.00 | 25.39 |
| ATOM | 157 | O   | HIS | 175 | 60.370 | 35.920 | 8.949  | 1.00 | 26.31 |
| ATOM | 158 | N   | ARG | 176 | 59.868 | 34.494 | 7.284  | 1.00 | 23.17 |
| ATOM | 159 | CA  | ARG | 176 | 60.292 | 35.423 | 6.239  | 1.00 | 24.26 |
| ATOM | 160 | CB  | ARG | 176 | 60.168 | 34.767 | 4.872  | 1.00 | 30.31 |
| ATOM | 161 | CG  | ARG | 176 | 61.286 | 33.793 | 4.576  | 1.00 | 39.36 |
| ATOM | 162 | CD  | ARG | 176 | 61.049 | 33.139 | 3.243  | 1.00 | 49.23 |
| ATOM | 163 | NE  | ARG | 176 | 62.188 | 32.346 | 2.808  | 1.00 | 60.62 |
| ATOM | 164 | CZ  | ARG | 176 | 62.230 | 31.688 | 1.653  | 1.00 | 67.96 |
| ATOM | 165 | NH1 | ARG | 176 | 61.192 | 31.731 | 0.823  | 1.00 | 68.84 |
| ATOM | 166 | NH2 | ARG | 176 | 63.313 | 30.999 | 1.321  | 1.00 | 67.97 |
| ATOM | 167 | C   | ARG | 176 | 59.548 | 36.749 | 6.267  | 1.00 | 23.09 |
| ATOM | 168 | O   | ARG | 176 | 60.163 | 37.807 | 6.173  | 1.00 | 30.71 |
| ATOM | 169 | N   | SER | 177 | 58.240 | 36.686 | 6.488  | 1.00 | 22.69 |
| ATOM | 170 | CA  | SER | 177 | 57.416 | 37.885 | 6.536  | 1.00 | 26.50 |
| ATOM | 171 | CB  | SER | 177 | 55.946 | 37.520 | 6.341  | 1.00 | 19.42 |
| ATOM | 172 | OG  | SER | 177 | 55.507 | 36.611 | 7.331  | 1.00 | 27.68 |
| ATOM | 173 | C   | SER | 177 | 57.574 | 38.695 | 7.821  | 1.00 | 28.70 |
| ATOM | 174 | O   | SER | 177 | 56.986 | 39.772 | 7.948  | 1.00 | 34.31 |
| ATOM | 175 | N   | THR | 178 | 58.327 | 38.165 | 8.786  | 1.00 | 27.42 |
| ATOM | 176 | CA  | THR | 178 | 58.540 | 38.850 | 10.060 | 1.00 | 21.88 |
| ATOM | 177 | CB  | THR | 178 | 57.842 | 38.107 | 11.228 | 1.00 | 23.73 |
| ATOM | 178 | OG1 | THR | 178 | 58.354 | 36.776 | 11.337 | 1.00 | 24.26 |
| ATOM | 179 | CG2 | THR | 178 | 56.344 | 38.037 | 10.994 | 1.00 | 16.77 |
| ATOM | 180 | C   | THR | 178 | 60.027 | 39.018 | 10.375 | 1.00 | 23.86 |
| ATOM | 181 | O   | THR | 178 | 60.399 | 39.439 | 11.474 | 1.00 | 24.64 |
| ATOM | 182 | N   | ASN | 179 | 60.873 | 38.690 | 9.402  | 1.00 | 23.79 |
| ATOM | 183 | CA  | ASN | 179 | 62.315 | 38.813 | 9.563  | 1.00 | 26.01 |
| ATOM | 184 | CB  | ASN | 179 | 63.018 | 37.607 | 8.947  | 1.00 | 23.77 |
| ATOM | 185 | CG  | ASN | 179 | 64.451 | 37.495 | 9.386  | 1.00 | 30.79 |
| ATOM | 186 | OD1 | ASN | 179 | 64.737 | 37.376 | 10.575 | 1.00 | 36.19 |
| ATOM | 187 | ND2 | ASN | 179 | 65.364 | 37.516 | 8.432  | 1.00 | 35.34 |
| ATOM | 188 | C   | ASN | 179 | 62.767 | 40.101 | 8.875  | 1.00 | 32.11 |
| ATOM | 189 | O   | ASN | 179 | 62.947 | 40.136 | 7.652  | 1.00 | 36.36 |
| ATOM | 190 | N   | ALA | 180 | 62.945 | 41.153 | 9.670  | 1.00 | 34.40 |
| ATOM | 191 | CA  | ALA | 180 | 63.333 | 42.473 | 9.179  | 1.00 | 28.75 |

APPENDIX 5-continued

TR_IPBR2.PDB

| ATOM | 192 | CB | ALA | 180 | 63.653 | 43.390 | 10.346 | 1.00 | 29.96 |
|---|---|---|---|---|---|---|---|---|---|
| ATOM | 193 | C | ALA | 180 | 64.481 | 42.481 | 8.182 | 1.00 | 37.02 |
| ATOM | 194 | O | ALA | 180 | 65.518 | 41.866 | 8.414 | 1.00 | 41.85 |
| ATOM | 195 | N | GLN | 181 | 64.266 | 43.163 | 7.057 | 1.00 | 37.15 |
| ATOM | 196 | CA | GLN | 181 | 65.261 | 43.306 | 5.995 | 1.00 | 39.33 |
| ATOM | 197 | CB | GLN | 181 | 66.572 | 43.877 | 6.552 | 1.00 | 37.42 |
| ATOM | 198 | CG | GLN | 181 | 66.420 | 45.190 | 7.309 | 1.00 | 44.86 |
| ATOM | 199 | CD | GLN | 181 | 65.779 | 46.285 | 6.479 | 1.00 | 53.60 |
| ATOM | 200 | OE1 | GLN | 181 | 64.712 | 46.793 | 6.821 | 1.00 | 58.51 |
| ATOM | 201 | NE2 | GLN | 181 | 66.422 | 46.650 | 5.378 | 1.00 | 63.36 |
| ATOM | 202 | C | GLN | 181 | 65.549 | 42.053 | 5.164 | 1.00 | 44.18 |
| ATOM | 203 | O | GLN | 181 | 66.367 | 42.102 | 4.239 | 1.00 | 46.35 |
| ATOM | 204 | N | GLY | 182 | 64.873 | 40.949 | 5.474 | 1.00 | 43.76 |
| ATOM | 205 | CA | GLY | 182 | 65.074 | 39.713 | 4.732 | 1.00 | 46.26 |
| ATOM | 206 | C | GLY | 182 | 66.531 | 39.363 | 4.477 | 1.00 | 49.98 |
| ATOM | 207 | O | GLY | 182 | 67.309 | 39.175 | 5.419 | 1.00 | 56.26 |
| ATOM | 208 | N | SER | 183 | 66.907 | 39.274 | 3.205 | 1.00 | 50.96 |
| ATOM | 209 | CA | SER | 183 | 68.281 | 38.947 | 2.830 | 1.00 | 55.69 |
| ATOM | 210 | CB | SER | 183 | 68.284 | 38.024 | 1.608 | 1.00 | 56.52 |
| ATOM | 211 | OG | SER | 183 | 67.398 | 38.497 | 0.609 | 1.00 | 60.82 |
| ATOM | 212 | C | SER | 183 | 69.121 | 40.197 | 2.558 | 1.00 | 59.84 |
| ATOM | 213 | O | SER | 183 | 70.352 | 40.138 | 2.540 | 1.00 | 66.02 |
| ATOM | 214 | N | HIS | 184 | 68.453 | 41.338 | 2.413 | 1.00 | 60.68 |
| ATOM | 215 | CA | HIS | 184 | 69.131 | 42.600 | 2.139 | 1.00 | 60.01 |
| ATOM | 216 | CB | HIS | 184 | 68.150 | 43.596 | 1.517 | 1.00 | 53.49 |
| ATOM | 217 | C | HIS | 184 | 69.798 | 43.209 | 3.380 | 1.00 | 59.43 |
| ATOM | 218 | O | HIS | 184 | 70.373 | 44.300 | 3.303 | 1.00 | 59.56 |
| ATOM | 219 | N | TRP | 185 | 69.753 | 42.500 | 4.508 | 1.00 | 57.54 |
| ATOM | 220 | CA | TRP | 185 | 70.343 | 42.995 | 5.754 | 1.00 | 54.25 |
| ATOM | 221 | CB | TRP | 185 | 70.147 | 41.988 | 6.899 | 1.00 | 47.54 |
| ATOM | 222 | CG | TRP | 185 | 70.905 | 40.692 | 6.752 | 1.00 | 41.08 |
| ATOM | 223 | CD2 | TRP | 185 | 72.233 | 40.404 | 7.230 | 1.00 | 39.59 |
| ATOM | 224 | CE2 | TRP | 185 | 72.522 | 39.070 | 6.874 | 1.00 | 30.27 |
| ATOM | 225 | CE3 | TRP | 185 | 73.202 | 41.146 | 7.919 | 1.00 | 35.23 |
| ATOM | 226 | CD1 | TRP | 185 | 70.462 | 39.553 | 6.149 | 1.00 | 39.73 |
| ATOM | 227 | NE1 | TRP | 185 | 71.427 | 38.577 | 6.219 | 1.00 | 40.01 |
| ATOM | 228 | CZ2 | TRP | 185 | 73.740 | 38.457 | 7.188 | 1.00 | 31.35 |
| ATOM | 229 | CZ3 | TRP | 185 | 74.416 | 40.535 | 8.230 | 1.00 | 32.76 |
| ATOM | 230 | CH2 | TRP | 185 | 74.673 | 39.203 | 7.861 | 1.00 | 31.71 |
| ATOM | 231 | C | TRP | 185 | 71.818 | 43.382 | 5.655 | 1.00 | 54.21 |
| ATOM | 232 | O | TRP | 185 | 72.229 | 44.403 | 6.200 | 1.00 | 52.82 |
| ATOM | 233 | N | LYS | 186 | 72.605 | 42.584 | 4.938 | 1.00 | 54.57 |
| ATOM | 234 | CA | LYS | 186 | 74.034 | 42.848 | 4.788 | 1.00 | 55.46 |
| ATOM | 235 | CB | LYS | 186 | 74.712 | 41.682 | 4.080 | 1.00 | 53.31 |
| ATOM | 236 | C | LYS | 186 | 74.338 | 44.160 | 4.061 | 1.00 | 58.96 |
| ATOM | 237 | O | LYS | 186 | 75.417 | 44.731 | 4.226 | 1.00 | 62.57 |
| ATOM | 238 | N | GLN | 187 | 73.382 | 44.640 | 3.268 | 1.00 | 60.12 |
| ATOM | 239 | CA | GLN | 187 | 73.563 | 45.873 | 2.512 | 1.00 | 60.15 |
| ATOM | 240 | CB | GLN | 187 | 73.157 | 45.653 | 1.050 | 1.00 | 57.00 |
| ATOM | 241 | C | GLN | 187 | 72.809 | 47.064 | 3.101 | 1.00 | 60.91 |
| ATOM | 242 | O | GLN | 187 | 73.149 | 48.213 | 2.822 | 1.00 | 66.50 |
| ATOM | 243 | N | ARG | 188 | 71.795 | 46.790 | 3.919 | 1.00 | 59.55 |
| ATOM | 244 | CA | ARG | 188 | 70.983 | 47.847 | 4.525 | 1.00 | 59.26 |
| ATOM | 245 | CB | ARG | 188 | 69.504 | 47.462 | 4.466 | 1.00 | 55.21 |
| ATOM | 246 | C | ARG | 188 | 71.372 | 48.243 | 5.959 | 1.00 | 58.97 |
| ATOM | 247 | O | ARG | 188 | 70.914 | 49.269 | 6.469 | 1.00 | 58.54 |
| ATOM | 248 | N | ARG | 189 | 72.202 | 47.432 | 6.607 | 1.00 | 55.46 |
| ATOM | 249 | CA | ARG | 189 | 72.630 | 47.704 | 7.979 | 1.00 | 52.98 |
| ATOM | 250 | CB | ARG | 189 | 73.211 | 46.437 | 8.619 | 1.00 | 47.73 |
| ATOM | 251 | CG | ARG | 189 | 74.509 | 45.985 | 7.989 | 1.00 | 47.88 |
| ATOM | 252 | CD | ARG | 189 | 75.080 | 44.763 | 8.654 | 1.00 | 46.96 |
| ATOM | 253 | NE | ARG | 189 | 76.377 | 44.441 | 8.068 | 1.00 | 57.93 |
| ATOM | 254 | CZ | ARG | 189 | 77.450 | 44.090 | 8.768 | 1.00 | 64.81 |
| ATOM | 255 | NH1 | ARG | 189 | 77.385 | 44.005 | 10.087 | 1.00 | 67.27 |
| ATOM | 256 | NH2 | ARG | 189 | 78.600 | 43.860 | 8.148 | 1.00 | 67.84 |
| ATOM | 257 | C | ARG | 189 | 73.650 | 48.838 | 8.091 | 1.00 | 53.48 |
| ATOM | 258 | O | ARG | 189 | 74.513 | 49.004 | 7.227 | 1.00 | 57.14 |
| ATOM | 259 | N | LYS | 190 | 73.533 | 49.617 | 9.161 | 1.00 | 51.31 |
| ATOM | 260 | CA | LYS | 190 | 74.444 | 50.722 | 9.435 | 1.00 | 48.83 |
| ATOM | 261 | CB | LYS | 190 | 73.682 | 52.036 | 9.516 | 1.00 | 45.36 |
| ATOM | 262 | C | LYS | 190 | 75.101 | 50.411 | 10.773 | 1.00 | 46.88 |
| ATOM | 263 | O | LYS | 190 | 74.454 | 49.872 | 11.675 | 1.00 | 48.81 |
| ATOM | 264 | N | PHE | 191 | 76.385 | 50.724 | 10.894 | 1.00 | 46.98 |
| ATOM | 265 | CA | PHE | 191 | 77.123 | 50.462 | 12.125 | 1.00 | 44.38 |
| ATOM | 266 | CB | PHE | 191 | 78.630 | 50.520 | 11.873 | 1.00 | 44.25 |
| ATOM | 267 | CG | PHE | 191 | 79.170 | 49.336 | 11.123 | 1.00 | 49.51 |
| ATOM | 268 | CD1 | PHE | 191 | 78.828 | 49.124 | 9.791 | 1.00 | 52.20 |

APPENDIX 5-continued

TR_IPBR2.PDB

| ATOM | 269 | CD2 | PHE | 191 | 80.029 | 48.437 | 11.748 | 1.00 | 47.25 |
|---|---|---|---|---|---|---|---|---|---|
| ATOM | 270 | CE1 | PHE | 191 | 79.335 | 48.031 | 9.090 | 1.00 | 55.86 |
| ATOM | 271 | CE2 | PHE | 191 | 80.542 | 47.343 | 11.059 | 1.00 | 49.73 |
| ATOM | 272 | CZ | PHE | 191 | 80.195 | 47.139 | 9.727 | 1.00 | 51.55 |
| ATOM | 273 | C | PHE | 191 | 76.764 | 51.443 | 13.233 | 1.00 | 46.44 |
| ATOM | 274 | O | PHE | 191 | 76.647 | 52.645 | 12.996 | 1.00 | 51.28 |
| ATOM | 275 | N | LEU | 192 | 76.567 | 50.924 | 14.439 | 1.00 | 47.66 |
| ATOM | 276 | CA | LEU | 192 | 76.256 | 51.776 | 15.577 | 1.00 | 46.44 |
| ATOM | 277 | CB | LEU | 192 | 75.930 | 50.924 | 16.808 | 1.00 | 38.06 |
| ATOM | 278 | CG | LEU | 192 | 75.527 | 51.672 | 18.082 | 1.00 | 33.55 |
| ATOM | 279 | CD1 | LEU | 192 | 74.180 | 52.339 | 17.871 | 1.00 | 28.17 |
| ATOM | 280 | CD2 | LEU | 192 | 75.476 | 50.717 | 19.268 | 1.00 | 26.95 |
| ATOM | 281 | C | LEU | 192 | 77.524 | 52.595 | 15.824 | 1.00 | 45.82 |
| ATOM | 282 | O | LEU | 192 | 78.604 | 52.024 | 16.008 | 1.00 | 41.65 |
| ATOM | 283 | N | PRO | 193 | 77.422 | 53.936 | 15.782 | 1.00 | 48.88 |
| ATOM | 284 | CD | PRO | 193 | 76.176 | 54.701 | 15.577 | 1.00 | 47.51 |
| ATOM | 285 | CA | PRO | 193 | 78.560 | 54.836 | 15.999 | 1.00 | 47.34 |
| ATOM | 286 | CB | PRO | 193 | 77.879 | 56.162 | 16.319 | 1.00 | 46.04 |
| ATOM | 287 | CG | PRO | 193 | 76.675 | 56.126 | 15.438 | 1.00 | 46.24 |
| ATOM | 288 | C | PRO | 193 | 79.475 | 54.377 | 17.137 | 1.00 | 49.60 |
| ATOM | 289 | O | PRO | 193 | 79.000 | 54.033 | 18.218 | 1.00 | 54.05 |
| ATOM | 290 | N | ASP | 194 | 80.783 | 54.383 | 16.891 | 1.00 | 50.63 |
| ATOM | 291 | CA | ASP | 194 | 81.769 | 53.951 | 17.885 | 1.00 | 54.57 |
| ATOM | 292 | CB | ASP | 194 | 83.164 | 53.965 | 17.272 | 1.00 | 59.28 |
| ATOM | 293 | CG | ASP | 194 | 83.309 | 52.952 | 16.170 | 1.00 | 66.39 |
| ATOM | 294 | OD1 | ASP | 194 | 83.057 | 53.311 | 14.998 | 1.00 | 72.95 |
| ATOM | 295 | OD2 | ASP | 194 | 83.640 | 51.787 | 16.486 | 1.00 | 69.00 |
| ATOM | 296 | C | ASP | 194 | 81.769 | 54.726 | 19.198 | 1.00 | 54.41 |
| ATOM | 297 | O | ASP | 194 | 82.229 | 54.221 | 20.222 | 1.00 | 55.27 |
| ATOM | 298 | N | ASP | 195 | 81.268 | 55.956 | 19.168 | 1.00 | 57.20 |
| ATOM | 299 | CA | ASP | 195 | 81.206 | 56.775 | 20.371 | 1.00 | 59.68 |
| ATOM | 300 | CB | ASP | 195 | 81.017 | 58.261 | 20.006 | 1.00 | 62.99 |
| ATOM | 301 | CG | ASP | 195 | 79.747 | 58.526 | 19.187 | 1.00 | 71.67 |
| ATOM | 302 | OD1 | ASP | 195 | 78.734 | 58.956 | 19.796 | 1.00 | 70.17 |
| ATOM | 303 | OD2 | ASP | 195 | 79.782 | 58.311 | 17.951 | 1.00 | 75.23 |
| ATOM | 304 | C | ASP | 195 | 80.092 | 56.289 | 21.306 | 1.00 | 58.39 |
| ATOM | 305 | O | ASP | 195 | 80.032 | 56.676 | 22.474 | 1.00 | 59.81 |
| ATOM | 306 | N | ILE | 196 | 79.245 | 55.399 | 20.794 | 1.00 | 54.47 |
| ATOM | 307 | CA | ILE | 196 | 78.141 | 54.840 | 21.568 | 1.00 | 49.00 |
| ATOM | 308 | CB | ILE | 196 | 76.839 | 54.780 | 20.731 | 1.00 | 46.64 |
| ATOM | 309 | CG2 | ILE | 196 | 75.701 | 54.195 | 21.560 | 1.00 | 42.11 |
| ATOM | 310 | CG1 | ILE | 196 | 76.467 | 56.184 | 20.241 | 1.00 | 44.23 |
| ATOM | 311 | CD1 | ILE | 196 | 75.214 | 56.238 | 19.373 | 1.00 | 48.45 |
| ATOM | 312 | C | ILE | 196 | 78.497 | 53.436 | 22.068 | 1.00 | 46.22 |
| ATOM | 313 | O | ILE | 196 | 78.912 | 52.570 | 21.298 | 1.00 | 42.07 |
| ATOM | 314 | N | GLY | 197 | 78.357 | 53.228 | 23.370 | 1.00 | 45.62 |
| ATOM | 315 | CA | GLY | 197 | 78.658 | 51.930 | 23.941 | 1.00 | 51.49 |
| ATOM | 316 | C | GLY | 197 | 80.005 | 51.832 | 24.625 | 1.00 | 54.64 |
| ATOM | 317 | O | GLY | 197 | 80.377 | 50.759 | 25.092 | 1.00 | 49.98 |
| ATOM | 318 | N | GLN | 198 | 80.726 | 52.946 | 24.725 | 1.00 | 60.08 |
| ATOM | 319 | CA | GLN | 198 | 82.039 | 52.939 | 25.366 | 1.00 | 61.01 |
| ATOM | 320 | CB | GLN | 198 | 83.082 | 53.568 | 24.441 | 1.00 | 55.55 |
| ATOM | 321 | C | GLN | 198 | 82.044 | 53.633 | 26.733 | 1.00 | 59.57 |
| ATOM | 322 | O | GLN | 198 | 83.103 | 54.016 | 27.232 | 1.00 | 61.30 |
| ATOM | 323 | N | SER | 199 | 80.875 | 53.738 | 27.362 | 1.00 | 57.27 |
| ATOM | 324 | CA | SER | 199 | 80.758 | 54.397 | 28.665 | 1.00 | 50.61 |
| ATOM | 325 | CB | SER | 199 | 80.276 | 55.842 | 28.478 | 1.00 | 53.70 |
| ATOM | 326 | OG | SER | 199 | 81.010 | 56.508 | 27.463 | 1.00 | 61.92 |
| ATOM | 327 | C | SER | 199 | 79.848 | 53.684 | 29.675 | 1.00 | 46.41 |
| ATOM | 328 | O | SER | 199 | 78.798 | 54.210 | 30.060 | 1.00 | 41.16 |
| ATOM | 329 | N | PRO | 200 | 80.222 | 52.466 | 30.096 | 1.00 | 42.08 |
| ATOM | 330 | CD | PRO | 200 | 81.349 | 51.648 | 29.605 | 1.00 | 38.31 |
| ATOM | 331 | CA | PRO | 200 | 79.409 | 51.722 | 31.065 | 1.00 | 44.04 |
| ATOM | 332 | CB | PRO | 200 | 79.941 | 50.297 | 30.925 | 1.00 | 36.06 |
| ATOM | 333 | CG | PRO | 200 | 81.377 | 50.504 | 30.583 | 1.00 | 37.43 |
| ATOM | 334 | C | PRO | 200 | 79.615 | 52.270 | 32.485 | 1.00 | 50.91 |
| ATOM | 335 | O | PRO | 200 | 80.629 | 51.980 | 33.123 | 1.00 | 55.65 |
| ATOM | 336 | N | ILE | 201 | 78.663 | 53.060 | 32.975 | 1.00 | 55.81 |
| ATOM | 337 | CA | ILE | 201 | 78.781 | 53.651 | 34.311 | 1.00 | 57.24 |
| ATOM | 338 | CB | ILE | 201 | 78.861 | 55.192 | 34.250 | 1.00 | 58.40 |
| ATOM | 339 | CG2 | ILE | 201 | 80.218 | 55.622 | 33.709 | 1.00 | 60.49 |
| ATOM | 340 | CG1 | ILE | 201 | 77.716 | 55.751 | 33.404 | 1.00 | 62.42 |
| ATOM | 341 | CD1 | ILE | 201 | 77.819 | 57.234 | 33.137 | 1.00 | 61.68 |
| ATOM | 342 | C | ILE | 201 | 77.728 | 53.241 | 35.332 | 1.00 | 56.52 |
| ATOM | 343 | O | ILE | 201 | 77.961 | 53.352 | 36.537 | 1.00 | 60.89 |
| ATOM | 344 | N | VAL | 202 | 76.564 | 52.794 | 34.871 | 1.00 | 52.76 |
| ATOM | 345 | CA | VAL | 202 | 75.522 | 52.366 | 35.802 | 1.00 | 47.37 |

APPENDIX 5-continued

TR_IPBR2.PDB

| ATOM | 346 | CB  | VAL | 202 | 74.117 | 52.377 | 35.153 | 1.00 | 38.14 |
|------|-----|-----|-----|-----|--------|--------|--------|------|-------|
| ATOM | 347 | CG1 | VAL | 202 | 73.092 | 51.804 | 36.117 | 1.00 | 30.35 |
| ATOM | 348 | CG2 | VAL | 202 | 73.730 | 53.798 | 34.763 | 1.00 | 26.69 |
| ATOM | 349 | C   | VAL | 202 | 75.885 | 50.958 | 36.285 | 1.00 | 53.65 |
| ATOM | 350 | O   | VAL | 202 | 75.914 | 50.010 | 35.500 | 1.00 | 55.10 |
| ATOM | 351 | N   | SER | 203 | 76.226 | 50.839 | 37.561 | 1.00 | 59.85 |
| ATOM | 352 | CA  | SER | 203 | 76.614 | 49.556 | 38.132 | 1.00 | 64.58 |
| ATOM | 353 | CB  | SER | 203 | 77.209 | 49.749 | 39.532 | 1.00 | 68.95 |
| ATOM | 354 | OG  | SER | 203 | 78.396 | 50.523 | 39.483 | 1.00 | 74.02 |
| ATOM | 355 | C   | SER | 203 | 75.493 | 48.528 | 38.197 | 1.00 | 61.69 |
| ATOM | 356 | O   | SER | 203 | 74.351 | 48.846 | 38.535 | 1.00 | 63.63 |
| ATOM | 357 | N   | MET | 204 | 75.848 | 47.295 | 37.859 | 1.00 | 57.37 |
| ATOM | 358 | CA  | MET | 204 | 74.932 | 46.162 | 37.885 | 1.00 | 57.54 |
| ATOM | 359 | CB  | MET | 204 | 74.847 | 45.505 | 36.501 | 1.00 | 56.59 |
| ATOM | 360 | CG  | MET | 204 | 74.012 | 46.270 | 35.489 | 1.00 | 44.08 |
| ATOM | 361 | SD  | MET | 204 | 72.255 | 46.228 | 35.884 | 1.00 | 46.62 |
| ATOM | 362 | CE  | MET | 204 | 71.775 | 44.758 | 35.013 | 1.00 | 48.37 |
| ATOM | 363 | C   | MET | 204 | 75.522 | 45.178 | 38.888 | 1.00 | 55.86 |
| ATOM | 364 | O   | MET | 204 | 76.746 | 45.089 | 39.027 | 1.00 | 58.94 |
| ATOM | 365 | N   | PRO | 205 | 74.671 | 44.432 | 39.607 | 1.00 | 55.36 |
| ATOM | 366 | CD  | PRO | 205 | 73.203 | 44.570 | 39.625 | 1.00 | 57.73 |
| ATOM | 367 | CA  | PRO | 205 | 75.119 | 43.453 | 40.604 | 1.00 | 56.82 |
| ATOM | 368 | CB  | PRO | 205 | 73.814 | 43.042 | 41.295 | 1.00 | 59.79 |
| ATOM | 369 | CG  | PRO | 205 | 72.769 | 43.281 | 40.255 | 1.00 | 57.85 |
| ATOM | 370 | C   | PRO | 205 | 75.902 | 42.239 | 40.083 | 1.00 | 57.25 |
| ATOM | 371 | O   | PRO | 205 | 75.683 | 41.118 | 40.541 | 1.00 | 66.28 |
| ATOM | 372 | N   | ASP | 206 | 76.822 | 42.462 | 39.147 | 1.00 | 58.75 |
| ATOM | 373 | CA  | ASP | 206 | 77.639 | 41.389 | 38.586 | 1.00 | 61.09 |
| ATOM | 374 | CB  | ASP | 206 | 76.802 | 40.462 | 37.685 | 1.00 | 66.07 |
| ATOM | 375 | CG  | ASP | 206 | 76.158 | 41.190 | 36.521 | 1.00 | 70.97 |
| ATOM | 376 | OD1 | ASP | 206 | 74.989 | 41.613 | 36.662 | 1.00 | 76.97 |
| ATOM | 377 | OD2 | ASP | 206 | 76.813 | 41.322 | 35.465 | 1.00 | 61.12 |
| ATOM | 378 | C   | ASP | 206 | 78.865 | 41.910 | 37.832 | 1.00 | 61.96 |
| ATOM | 379 | O   | ASP | 206 | 79.406 | 41.230 | 36.957 | 1.00 | 65.14 |
| ATOM | 380 | N   | GLY | 207 | 79.282 | 43.130 | 38.158 | 1.00 | 63.00 |
| ATOM | 381 | CA  | GLY | 207 | 80.455 | 43.709 | 37.522 | 1.00 | 64.43 |
| ATOM | 382 | C   | GLY | 207 | 80.224 | 44.467 | 36.229 | 1.00 | 64.81 |
| ATOM | 383 | O   | GLY | 207 | 80.649 | 45.619 | 36.110 | 1.00 | 68.76 |
| ATOM | 384 | N   | ASP | 208 | 79.584 | 43.827 | 35.253 | 1.00 | 63.53 |
| ATOM | 385 | CA  | ASP | 208 | 79.316 | 44.459 | 33.962 | 1.00 | 58.96 |
| ATOM | 386 | CB  | ASP | 208 | 78.746 | 43.434 | 32.974 | 1.00 | 62.84 |
| ATOM | 387 | CG  | ASP | 208 | 79.743 | 42.336 | 32.633 | 1.00 | 64.73 |
| ATOM | 388 | OD1 | ASP | 208 | 79.575 | 41.200 | 33.121 | 1.00 | 66.65 |
| ATOM | 389 | OD2 | ASP | 208 | 80.701 | 42.610 | 31.878 | 1.00 | 68.91 |
| ATOM | 390 | C   | ASP | 208 | 78.368 | 45.646 | 34.110 | 1.00 | 56.65 |
| ATOM | 391 | O   | ASP | 208 | 77.182 | 45.473 | 34.392 | 1.00 | 55.79 |
| ATOM | 392 | N   | LYS | 209 | 78.911 | 46.852 | 33.953 | 1.00 | 54.66 |
| ATOM | 393 | CA  | LYS | 209 | 78.132 | 48.081 | 34.082 | 1.00 | 53.92 |
| ATOM | 394 | CB  | LYS | 209 | 79.034 | 49.236 | 34.515 | 1.00 | 49.71 |
| ATOM | 395 | C   | LYS | 209 | 77.395 | 48.420 | 32.785 | 1.00 | 48.30 |
| ATOM | 396 | O   | LYS | 209 | 77.767 | 47.945 | 31.711 | 1.00 | 45.62 |
| ATOM | 397 | N   | VAL | 210 | 76.367 | 49.258 | 32.894 | 1.00 | 43.87 |
| ATOM | 398 | CA  | VAL | 210 | 75.539 | 49.662 | 31.757 | 1.00 | 41.25 |
| ATOM | 399 | CB  | VAL | 210 | 74.020 | 49.624 | 32.125 | 1.00 | 32.99 |
| ATOM | 400 | CG1 | VAL | 210 | 73.153 | 50.029 | 30.937 | 1.00 | 31.44 |
| ATOM | 401 | CG2 | VAL | 210 | 73.626 | 48.239 | 32.604 | 1.00 | 27.57 |
| ATOM | 402 | C   | VAL | 210 | 75.868 | 51.061 | 31.234 | 1.00 | 43.30 |
| ATOM | 403 | O   | VAL | 210 | 76.261 | 51.951 | 31.994 | 1.00 | 44.65 |
| ATOM | 404 | N   | ASP | 211 | 75.688 | 51.235 | 29.931 | 1.00 | 43.23 |
| ATOM | 405 | CA  | ASP | 211 | 75.906 | 52.498 | 29.240 | 1.00 | 40.62 |
| ATOM | 406 | CB  | ASP | 211 | 76.686 | 52.232 | 27.943 | 1.00 | 43.49 |
| ATOM | 407 | CG  | ASP | 211 | 77.014 | 53.499 | 27.161 | 1.00 | 40.77 |
| ATOM | 408 | OD1 | ASP | 211 | 76.180 | 54.427 | 27.092 | 1.00 | 42.13 |
| ATOM | 409 | OD2 | ASP | 211 | 78.111 | 53.549 | 26.574 | 1.00 | 37.49 |
| ATOM | 410 | C   | ASP | 211 | 74.491 | 53.001 | 28.921 | 1.00 | 44.56 |
| ATOM | 411 | O   | ASP | 211 | 73.849 | 52.500 | 27.998 | 1.00 | 46.44 |
| ATOM | 412 | N   | LEU | 212 | 74.006 | 53.982 | 29.684 | 1.00 | 43.76 |
| ATOM | 413 | CA  | LEU | 212 | 72.662 | 54.538 | 29.494 | 1.00 | 41.47 |
| ATOM | 414 | CB  | LEU | 212 | 72.473 | 55.785 | 30.359 | 1.00 | 40.45 |
| ATOM | 415 | CG  | LEU | 212 | 72.360 | 55.585 | 31.867 | 1.00 | 44.47 |
| ATOM | 416 | CD1 | LEU | 212 | 72.127 | 56.923 | 32.551 | 1.00 | 40.49 |
| ATOM | 417 | CD2 | LEU | 212 | 71.217 | 54.634 | 32.153 | 1.00 | 45.94 |
| ATOM | 418 | C   | LEU | 242 | 72.325 | 54.886 | 28.049 | 1.00 | 40.77 |
| ATOM | 419 | O   | LEU | 212 | 71.254 | 54.540 | 27.548 | 1.00 | 42.25 |
| ATOM | 420 | N   | GLU | 213 | 73.241 | 55.588 | 27.394 | 1.00 | 42.53 |
| ATOM | 421 | CA  | GLU | 213 | 73.068 | 56.008 | 26.009 | 1.00 | 43.60 |
| ATOM | 422 | CB  | GLU | 213 | 74.267 | 56.860 | 25.598 | 1.00 | 43.84 |

APPENDIX 5-continued

TR_IPBR2.PDB

| ATOM | 423 | CG  | GLU | 213 | 74.246 | 57.334 | 24.167 | 1.00 | 51.70 |
| ---- | --- | --- | --- | --- | ------ | ------ | ------ | ---- | ----- |
| ATOM | 424 | CD  | GLU | 213 | 75.598 | 57.848 | 23.722 | 1.00 | 59.23 |
| ATOM | 425 | OE1 | GLU | 213 | 75.655 | 58.939 | 23.121 | 1.00 | 60.14 |
| ATOM | 426 | OE2 | GLU | 213 | 76.611 | 57.158 | 23.980 | 1.00 | 64.78 |
| ATOM | 427 | C   | GLU | 213 | 72.913 | 54.810 | 25.066 | 1.00 | 42.63 |
| ATOM | 428 | O   | GLU | 213 | 72.008 | 54.779 | 24.226 | 1.00 | 37.04 |
| ATOM | 429 | N   | ALA | 214 | 73.775 | 53.814 | 25.245 | 1.00 | 39.28 |
| ATOM | 430 | CA  | ALA | 214 | 73.753 | 52.605 | 24.424 | 1.00 | 39.52 |
| ATOM | 431 | CB  | ALA | 214 | 74.952 | 51.726 | 24.740 | 1.00 | 35.16 |
| ATOM | 432 | C   | ALA | 214 | 72.460 | 51.852 | 24.694 | 1.00 | 37.14 |
| ATOM | 433 | O   | ALA | 214 | 71.795 | 51.390 | 23.767 | 1.00 | 42.29 |
| ATOM | 434 | N   | PHE | 215 | 72.098 | 51.773 | 25.970 | 1.00 | 31.60 |
| ATOM | 435 | CA  | PHE | 215 | 70.883 | 51.102 | 26.404 | 1.00 | 31.67 |
| ATOM | 436 | CB  | PHE | 215 | 70.728 | 51.217 | 27.922 | 1.00 | 24.80 |
| ATOM | 437 | CG  | PHE | 215 | 69.512 | 50.522 | 28.458 | 1.00 | 21.78 |
| ATOM | 438 | CD1 | PHE | 215 | 69.553 | 49.171 | 28.771 | 1.00 | 24.64 |
| ATOM | 439 | CD2 | PHE | 215 | 68.328 | 51.223 | 28.658 | 1.00 | 21.53 |
| ATOM | 440 | CE1 | PHE | 215 | 68.429 | 48.528 | 29.277 | 1.00 | 27.63 |
| ATOM | 441 | CE2 | PHE | 215 | 67.200 | 50.591 | 29.163 | 1.00 | 21.60 |
| ATOM | 442 | CZ  | PHE | 215 | 67.249 | 49.242 | 29.472 | 1.00 | 21.35 |
| ATOM | 443 | C   | PHE | 215 | 69.675 | 51.706 | 25.694 | 1.00 | 35.75 |
| ATOM | 444 | O   | PHE | 215 | 68.838 | 50.975 | 25.161 | 1.00 | 34.84 |
| ATOM | 445 | N   | SER | 216 | 69.604 | 53.035 | 25.665 | 1.00 | 39.09 |
| ATOM | 446 | CA  | SER | 216 | 68.506 | 53.739 | 25.001 | 1.00 | 40.61 |
| ATOM | 447 | CB  | SER | 216 | 68.668 | 55.249 | 25.165 | 1.00 | 43.86 |
| ATOM | 448 | OG  | SER | 216 | 68.616 | 55.603 | 26.537 | 1.00 | 68.66 |
| ATOM | 449 | C   | SER | 216 | 68.444 | 53.380 | 23.518 | 1.00 | 40.76 |
| ATOM | 450 | O   | SER | 216 | 67.362 | 53.161 | 22.969 | 1.00 | 35.50 |
| ATOM | 451 | N   | GLU | 217 | 69.611 | 53.332 | 22.878 | 1.00 | 38.37 |
| ATOM | 452 | CA  | GLU | 217 | 69.709 | 52.989 | 21.462 | 1.00 | 37.80 |
| ATOM | 453 | CB  | GLU | 217 | 71.164 | 53.049 | 20.997 | 1.00 | 39.67 |
| ATOM | 454 | CG  | GLU | 217 | 71.701 | 54.461 | 20.880 | 1.00 | 46.65 |
| ATOM | 455 | CD  | GLU | 217 | 70.881 | 55.315 | 19.925 | 1.00 | 53.25 |
| ATOM | 456 | OE1 | GLU | 217 | 70.920 | 55.056 | 18.702 | 1.00 | 57.12 |
| ATOM | 457 | OE2 | GLU | 217 | 70.189 | 56.240 | 20.400 | 1.00 | 54.13 |
| ATOM | 458 | C   | GLU | 217 | 69.135 | 51.598 | 21.209 | 1.00 | 38.48 |
| ATOM | 459 | O   | GLU | 217 | 68.416 | 51.378 | 20.228 | 1.00 | 43.00 |
| ATOM | 460 | N   | PHE | 218 | 69.426 | 50.677 | 22.120 | 1.00 | 35.49 |
| ATOM | 461 | CA  | PHE | 218 | 68.934 | 49.313 | 22.018 | 1.00 | 31.76 |
| ATOM | 462 | CB  | PHE | 218 | 69.743 | 48.392 | 22.925 | 1.00 | 29.10 |
| ATOM | 463 | CG  | PHE | 218 | 71.169 | 48.260 | 22.510 | 1.00 | 26.25 |
| ATOM | 464 | CD1 | PHE | 218 | 72.176 | 48.177 | 23.459 | 1.00 | 24.59 |
| ATOM | 465 | CD2 | PHE | 218 | 71.510 | 48.233 | 21.163 | 1.00 | 23.53 |
| ATOM | 466 | CE1 | PHE | 218 | 73.504 | 48.072 | 23.073 | 1.00 | 27.68 |
| ATOM | 467 | CE2 | PHE | 218 | 72.832 | 48.128 | 20.765 | 1.00 | 25.37 |
| ATOM | 468 | CZ  | PHE | 218 | 73.834 | 48.047 | 21.721 | 1.00 | 28.43 |
| ATOM | 469 | C   | PHE | 218 | 67.445 | 49.202 | 22.321 | 1.00 | 31.30 |
| ATOM | 470 | O   | PHE | 218 | 66.726 | 48.496 | 21.621 | 1.00 | 35.18 |
| ATOM | 471 | N   | THR | 219 | 66.967 | 49.915 | 23.333 | 1.00 | 30.54 |
| ATOM | 472 | CA  | THR | 219 | 65.552 | 49.853 | 23.675 | 1.00 | 33.53 |
| ATOM | 473 | CB  | THR | 219 | 65.269 | 50.467 | 25.057 | 1.00 | 36.07 |
| ATOM | 474 | OG1 | THR | 219 | 65.903 | 51.746 | 25.157 | 1.00 | 42.99 |
| ATOM | 475 | CG2 | THR | 219 | 65.797 | 49.562 | 26.145 | 1.00 | 34.32 |
| ATOM | 476 | C   | THR | 219 | 64.680 | 50.514 | 22.609 | 1.00 | 34.53 |
| ATOM | 477 | O   | THR | 219 | 63.507 | 50.162 | 22.450 | 1.00 | 36.57 |
| ATOM | 478 | N   | LYS | 220 | 65.267 | 51.457 | 21.873 | 1.00 | 38.13 |
| ATOM | 479 | CA  | LYS | 220 | 64.563 | 52.158 | 20.806 | 1.00 | 41.42 |
| ATOM | 480 | CB  | LYS | 220 | 65.452 | 53.257 | 20.208 | 1.00 | 41.62 |
| ATOM | 481 | C   | LYS | 220 | 64.140 | 51.182 | 19.716 | 1.00 | 41.80 |
| ATOM | 482 | O   | LYS | 220 | 63.032 | 51.274 | 19.192 | 1.00 | 43.29 |
| ATOM | 483 | N   | ILE | 221 | 65.018 | 50.234 | 19.393 | 1.00 | 36.93 |
| ATOM | 484 | CA  | ILE | 221 | 64.726 | 49.250 | 18.355 | 1.00 | 37.33 |
| ATOM | 485 | CB  | ILE | 221 | 65.965 | 48.932 | 17.482 | 1.00 | 33.71 |
| ATOM | 486 | CG2 | ILE | 221 | 66.491 | 50.202 | 16.826 | 1.00 | 41.26 |
| ATOM | 487 | CG1 | ILE | 221 | 67.042 | 48.235 | 18.309 | 1.00 | 30.36 |
| ATOM | 488 | CD1 | ILE | 221 | 68.178 | 47.687 | 17.472 | 1.00 | 26.28 |
| ATOM | 489 | C   | ILE | 221 | 64.141 | 47.922 | 18.845 | 1.00 | 40.49 |
| ATOM | 490 | O   | ILE | 221 | 63.593 | 47.159 | 18.048 | 1.00 | 43.43 |
| ATOM | 491 | N   | ILE | 222 | 64.219 | 47.651 | 20.144 | 1.00 | 39.43 |
| ATOM | 492 | CA  | ILE | 222 | 63.703 | 46.394 | 20.667 | 1.00 | 35.49 |
| ATOM | 493 | CB  | ILE | 222 | 64.169 | 46.133 | 22.130 | 1.00 | 34.06 |
| ATOM | 494 | CG2 | ILE | 222 | 63.287 | 46.881 | 23.130 | 1.00 | 26.15 |
| ATOM | 495 | CG1 | ILE | 222 | 64.155 | 44.627 | 22.405 | 1.00 | 34.08 |
| ATOM | 496 | CD1 | ILE | 222 | 64.760 | 44.220 | 23.719 | 1.00 | 33.67 |
| ATOM | 497 | C   | ILE | 222 | 62.186 | 46.230 | 20.539 | 1.00 | 37.60 |
| ATOM | 498 | O   | ILE | 222 | 61.703 | 45.127 | 20.279 | 1.00 | 42.14 |
| ATOM | 499 | N   | THR | 223 | 61.438 | 47.324 | 20.665 | 1.00 | 34.60 |

APPENDIX 5-continued

TR_IPBR2.PDB

| | | | | | | | | |
|---|---|---|---|---|---|---|---|---|
| ATOM | 500 | CA | THR | 223 | 59.979 | 47.257 | 20.562 | 1.00 | 35.96 |
| ATOM | 501 | CB | THR | 223 | 59.323 | 48.645 | 20.799 | 1.00 | 41.70 |
| ATOM | 502 | OG1 | THR | 223 | 59.681 | 49.119 | 22.106 | 1.00 | 44.59 |
| ATOM | 503 | CG2 | THR | 223 | 57.796 | 48.548 | 20.706 | 1.00 | 42.58 |
| ATOM | 504 | C | THR | 223 | 59.478 | 46.614 | 19.252 | 1.00 | 34.77 |
| ATOM | 505 | O | THR | 223 | 58.671 | 45.680 | 19.289 | 1.00 | 30.60 |
| ATOM | 506 | N | PRO | 224 | 59.942 | 47.103 | 18.084 | 1.00 | 31.99 |
| ATOM | 507 | CD | PRO | 224 | 60.784 | 48.288 | 17.839 | 1.00 | 30.37 |
| ATOM | 508 | CA | PRO | 224 | 59.496 | 46.517 | 16.815 | 1.00 | 29.25 |
| ATOM | 509 | CB | PRO | 224 | 60.225 | 47.366 | 15.769 | 1.00 | 29.27 |
| ATOM | 510 | CG | PRO | 224 | 60.393 | 48.677 | 16.441 | 1.00 | 36.31 |
| ATOM | 511 | C | PRO | 224 | 59.913 | 45.050 | 16.723 | 1.00 | 29.20 |
| ATOM | 512 | O | PRO | 224 | 59.146 | 44.209 | 16.251 | 1.00 | 33.73 |
| ATOM | 513 | N | ALA | 225 | 61.124 | 44.754 | 17.192 | 1.00 | 19.86 |
| ATOM | 514 | CA | ALA | 225 | 61.663 | 43.395 | 17.175 | 1.00 | 19.61 |
| ATOM | 515 | CB | ALA | 225 | 63.086 | 43.388 | 17.730 | 1.00 | 19.08 |
| ATOM | 516 | C | ALA | 225 | 60.777 | 42.428 | 17.960 | 1.00 | 20.48 |
| ATOM | 517 | O | ALA | 225 | 60.474 | 41.331 | 17.489 | 1.00 | 24.33 |
| ATOM | 518 | N | ILE | 226 | 60.330 | 42.847 | 19.141 | 1.00 | 23.72 |
| ATOM | 519 | CA | ILE | 226 | 59.471 | 42.001 | 19.972 | 1.00 | 21.94 |
| ATOM | 520 | CB | ILE | 226 | 59.152 | 42.667 | 21.333 | 1.00 | 21.01 |
| ATOM | 521 | CG2 | ILE | 226 | 58.118 | 41.846 | 22.095 | 1.00 | 15.14 |
| ATOM | 522 | CG1 | ILE | 226 | 60.425 | 42.841 | 22.163 | 1.00 | 20.45 |
| ATOM | 523 | CD1 | ILE | 226 | 60.216 | 43.741 | 23.358 | 1.00 | 17.65 |
| ATOM | 524 | C | ILE | 226 | 58.165 | 41.758 | 19.228 | 1.00 | 24.04 |
| ATOM | 525 | O | ILE | 226 | 57.640 | 40.642 | 19.220 | 1.00 | 26.92 |
| ATOM | 526 | N | THR | 227 | 57.653 | 42.811 | 18.596 | 1.00 | 25.22 |
| ATOM | 527 | CA | THR | 227 | 56.410 | 42.730 | 17.836 | 1.00 | 27.92 |
| ATOM | 528 | CB | THR | 227 | 55.984 | 44.132 | 17.333 | 1.00 | 34.33 |
| ATOM | 529 | OG1 | THR | 227 | 55.823 | 45.007 | 18.458 | 1.00 | 33.62 |
| ATOM | 530 | CG2 | THR | 227 | 54.669 | 44.061 | 16.563 | 1.00 | 39.18 |
| ATOM | 531 | C | THR | 227 | 56.524 | 41.733 | 16.671 | 1.00 | 23.61 |
| ATOM | 532 | O | THR | 227 | 55.587 | 40.977 | 16.413 | 1.00 | 24.41 |
| ATOM | 533 | N | ARG | 228 | 57.670 | 41.704 | 15.995 | 1.00 | 15.49 |
| ATOM | 534 | CA | ARG | 228 | 57.872 | 40.773 | 14.885 | 1.00 | 17.92 |
| ATOM | 535 | CB | ARG | 228 | 59.174 | 41.075 | 14.137 | 1.00 | 19.84 |
| ATOM | 536 | CG | ARG | 228 | 59.203 | 42.437 | 13.452 | 1.00 | 20.62 |
| ATOM | 537 | CD | ARG | 228 | 60.351 | 42.523 | 12.453 | 1.00 | 24.29 |
| ATOM | 538 | NE | ARG | 228 | 61.641 | 42.168 | 13.047 | 1.00 | 27.04 |
| ATOM | 539 | CZ | ARG | 228 | 62.452 | 43.039 | 13.642 | 1.00 | 37.92 |
| ATOM | 540 | NH1 | ARG | 228 | 62.113 | 44.327 | 13.725 | 1.00 | 42.82 |
| ATOM | 541 | NH2 | ARG | 228 | 63.618 | 42.634 | 14.136 | 1.00 | 34.80 |
| ATOM | 542 | C | ARG | 228 | 57.870 | 39.323 | 15.387 | 1.00 | 22.51 |
| ATOM | 543 | O | ARG | 228 | 57.402 | 38.421 | 14.686 | 1.00 | 28.49 |
| ATOM | 544 | N | VAL | 229 | 58.362 | 39.104 | 16.607 | 1.00 | 21.46 |
| ATOM | 545 | CA | VAL | 229 | 58.372 | 37.762 | 17.187 | 1.00 | 20.12 |
| ATOM | 546 | CB | VAL | 229 | 59.149 | 37.707 | 18.524 | 1.00 | 17.21 |
| ATOM | 547 | CG1 | VAL | 229 | 59.023 | 36.322 | 19.152 | 1.00 | 13.73 |
| ATOM | 548 | CG2 | VAL | 229 | 60.611 | 38.019 | 18.287 | 1.00 | 15.80 |
| ATOM | 549 | C | VAL | 229 | 56.926 | 37.348 | 17.421 | 1.00 | 19.19 |
| ATOM | 550 | O | VAL | 229 | 56.528 | 36.224 | 17.089 | 1.00 | 19.86 |
| ATOM | 551 | N | VAL | 230 | 56.134 | 38.275 | 17.953 | 1.00 | 21.49 |
| ATOM | 552 | CA | VAL | 230 | 54.721 | 38.023 | 18.217 | 1.00 | 17.69 |
| ATOM | 553 | CB | VAL | 230 | 54.041 | 39.239 | 18.881 | 1.00 | 21.30 |
| ATOM | 554 | CG1 | VAL | 230 | 52.568 | 38.952 | 19.090 | 1.00 | 17.26 |
| ATOM | 555 | CG2 | VAL | 230 | 54.706 | 39.572 | 20.218 | 1.00 | 17.13 |
| ATOM | 556 | C | VAL | 230 | 54.003 | 37.707 | 16.902 | 1.00 | 26.39 |
| ATOM | 557 | O | VAL | 230 | 53.180 | 36.790 | 16.843 | 1.00 | 29.63 |
| ATOM | 558 | N | ASP | 231 | 54.333 | 38.451 | 15.848 | 1.00 | 25.52 |
| ATOM | 559 | CA | ASP | 231 | 53.724 | 38.242 | 14.537 | 1.00 | 26.78 |
| ATOM | 560 | CB | ASP | 231 | 54.132 | 39.353 | 13.571 | 1.00 | 23.70 |
| ATOM | 561 | CG | ASP | 231 | 53.649 | 40.728 | 14.012 | 1.00 | 31.60 |
| ATOM | 562 | OD1 | ASP | 231 | 52.656 | 40.820 | 14.771 | 1.00 | 31.79 |
| ATOM | 563 | OD2 | ASP | 231 | 54.271 | 41.727 | 13.593 | 1.00 | 35.74 |
| ATOM | 564 | C | ASP | 231 | 54.108 | 36.879 | 13.970 | 1.00 | 27.69 |
| ATOM | 565 | O | ASP | 231 | 53.279 | 36.196 | 13.366 | 1.00 | 25.15 |
| ATOM | 566 | N | PHE | 232 | 55.364 | 36.490 | 14.170 | 1.00 | 22.29 |
| ATOM | 567 | CA | PHE | 232 | 55.858 | 35.200 | 13.703 | 1.00 | 23.78 |
| ATOM | 568 | CB | PHE | 232 | 57.328 | 35.008 | 14.097 | 1.00 | 24.76 |
| ATOM | 569 | CG | PHE | 232 | 57.794 | 33.581 | 14.017 | 1.00 | 25.63 |
| ATOM | 570 | CD1 | PHE | 232 | 58.000 | 32.967 | 12.785 | 1.00 | 24.50 |
| ATOM | 571 | CD2 | PHE | 232 | 57.980 | 32.830 | 15.181 | 1.00 | 19.35 |
| ATOM | 572 | CE1 | PHE | 232 | 58.381 | 31.630 | 12.705 | 1.00 | 22.27 |
| ATOM | 573 | CE2 | PHE | 232 | 58.359 | 31.496 | 15.114 | 1.00 | 20.63 |
| ATOM | 574 | CZ | PHE | 232 | 58.561 | 30.893 | 13.873 | 1.00 | 26.10 |
| ATOM | 575 | C | PHE | 232 | 55.018 | 34.093 | 14.328 | 1.00 | 23.51 |
| ATOM | 576 | O | PHE | 232 | 54.541 | 33.189 | 13.637 | 1.00 | 22.39 |

APPENDIX 5-continued

TR_IPBR2.PDB

| ATOM | 577 | N | ALA | 233 | 54.837 | 34.182 | 15.644 | 1.00 | 24.55 |
|---|---|---|---|---|---|---|---|---|---|
| ATOM | 578 | CA | ALA | 233 | 54.070 | 33.192 | 16.387 | 1.00 | 23.10 |
| ATOM | 579 | CB | ALA | 233 | 54.145 | 33.490 | 17.869 | 1.00 | 17.99 |
| ATOM | 580 | C | ALA | 233 | 52.616 | 33.137 | 15.929 | 1.00 | 27.99 |
| ATOM | 581 | O | ALA | 233 | 52.063 | 32.051 | 15.744 | 1.00 | 25.71 |
| ATOM | 582 | N | LYS | 234 | 51.997 | 34.305 | 15.760 | 1.00 | 30.19 |
| ATOM | 583 | CA | LYS | 234 | 50.601 | 34.380 | 15.325 | 1.00 | 31.58 |
| ATOM | 584 | CB | LYS | 234 | 50.136 | 35.838 | 15.229 | 1.00 | 30.40 |
| ATOM | 585 | CG | LYS | 234 | 50.100 | 36.593 | 16.555 | 1.00 | 37.97 |
| ATOM | 586 | CD | LYS | 234 | 49.151 | 35.947 | 17.569 | 1.00 | 53.64 |
| ATOM | 587 | CE | LYS | 234 | 47.694 | 35.958 | 17.101 | 1.00 | 59.60 |
| ATOM | 588 | NZ | LYS | 234 | 46.773 | 35.268 | 18.060 | 1.00 | 54.22 |
| ATOM | 589 | C | LYS | 234 | 50.388 | 33.686 | 13.978 | 1.00 | 30.35 |
| ATOM | 590 | O | LYS | 234 | 49.318 | 33.142 | 13.716 | 1.00 | 32.50 |
| ATOM | 591 | N | LYS | 235 | 51.425 | 33.687 | 13.144 | 1.00 | 23.98 |
| ATOM | 592 | CA | LYS | 235 | 51.351 | 33.071 | 11.828 | 1.00 | 22.75 |
| ATOM | 593 | CB | LYS | 235 | 52.353 | 33.737 | 10.896 | 1.00 | 23.12 |
| ATOM | 594 | CG | LYS | 235 | 51.997 | 35.181 | 10.631 | 1.00 | 20.88 |
| ATOM | 595 | CD | LYS | 235 | 52.982 | 35.836 | 9.688 | 1.00 | 26.50 |
| ATOM | 596 | CE | LYS | 235 | 52.512 | 37.227 | 9.310 | 1.00 | 31.33 |
| ATOM | 597 | NZ | LYS | 235 | 53.439 | 37.862 | 8.341 | 1.00 | 36.51 |
| ATOM | 598 | C | LYS | 235 | 51.508 | 31.554 | 11.791 | 1.00 | 28.37 |
| ATOM | 599 | O | LYS | 235 | 51.491 | 30.948 | 10.721 | 1.00 | 29.62 |
| ATOM | 600 | N | LEU | 236 | 51.700 | 30.943 | 12.954 | 1.00 | 33.22 |
| ATOM | 601 | CA | LEU | 236 | 51.828 | 29.494 | 13.036 | 1.00 | 32.24 |
| ATOM | 602 | CB | LEU | 236 | 52.911 | 29.101 | 14.043 | 1.00 | 26.25 |
| ATOM | 603 | CG | LEU | 236 | 54.327 | 29.582 | 13.730 | 1.00 | 23.40 |
| ATOM | 604 | CD1 | LEU | 236 | 55.289 | 29.113 | 14.806 | 1.00 | 20.52 |
| ATOM | 605 | CD2 | LEU | 236 | 54.750 | 29.054 | 12.374 | 1.00 | 20.29 |
| ATOM | 606 | C | LEU | 236 | 50.470 | 28.984 | 13.502 | 1.00 | 37.08 |
| ATOM | 607 | O | LEU | 236 | 50.013 | 29.342 | 14.588 | 1.00 | 34.23 |
| ATOM | 608 | N | PRO | 237 | 49.811 | 28.134 | 12.695 | 1.00 | 44.89 |
| ATOM | 609 | CD | PRO | 237 | 50.351 | 27.597 | 11.432 | 1.00 | 42.95 |
| ATOM | 610 | CA | PRO | 237 | 48.491 | 27.556 | 12.990 | 1.00 | 48.88 |
| ATOM | 611 | CB | PRO | 237 | 48.396 | 26.406 | 11.987 | 1.00 | 51.40 |
| ATOM | 612 | CG | PRO | 237 | 49.142 | 26.931 | 10.813 | 1.00 | 53.54 |
| ATOM | 613 | C | PRO | 237 | 48.278 | 27.072 | 14.430 | 1.00 | 49.12 |
| ATOM | 614 | O | PRO | 237 | 47.387 | 27.551 | 15.133 | 1.00 | 48.18 |
| ATOM | 615 | N | MET | 238 | 49.104 | 26.126 | 14.860 | 1.00 | 45.79 |
| ATOM | 616 | CA | MET | 238 | 49.029 | 25.558 | 16.200 | 1.00 | 52.79 |
| ATOM | 617 | CB | MET | 238 | 50.133 | 24.505 | 16.378 | 1.00 | 49.72 |
| ATOM | 618 | CG | MET | 238 | 49.861 | 23.195 | 15.637 | 1.00 | 58.16 |
| ATOM | 619 | SD | MET | 238 | 51.342 | 22.205 | 15.284 | 1.00 | 60.11 |
| ATOM | 620 | CE | MET | 238 | 50.993 | 21.626 | 13.625 | 1.00 | 53.03 |
| ATOM | 621 | C | MET | 238 | 49.103 | 26.593 | 17.324 | 1.00 | 53.36 |
| ATOM | 622 | O | MET | 238 | 48.583 | 26.365 | 18.420 | 1.00 | 58.87 |
| ATOM | 623 | N | PHE | 239 | 49.713 | 27.742 | 17.043 | 1.00 | 48.09 |
| ATOM | 624 | CA | PHE | 239 | 49.861 | 28.793 | 18.045 | 1.00 | 41.38 |
| ATOM | 625 | CB | PHE | 239 | 51.011 | 29.736 | 17.677 | 1.00 | 32.92 |
| ATOM | 626 | CG | PHE | 239 | 51.307 | 30.763 | 18.734 | 1.00 | 31.32 |
| ATOM | 627 | CD1 | PHE | 239 | 52.162 | 30.462 | 19.790 | 1.00 | 28.28 |
| ATOM | 628 | CD2 | PHE | 239 | 50.715 | 32.024 | 18.689 | 1.00 | 24.80 |
| ATOM | 629 | CE1 | PHE | 239 | 52.425 | 31.402 | 20.790 | 1.00 | 29.45 |
| ATOM | 630 | CE2 | PHE | 239 | 50.970 | 32.973 | 19.682 | 1.00 | 32.29 |
| ATOM | 631 | CZ | PHE | 239 | 51.828 | 32.659 | 20.737 | 1.00 | 26.00 |
| ATOM | 632 | C | PHE | 239 | 48.590 | 29.592 | 18.344 | 1.00 | 37.40 |
| ATOM | 633 | O | PHE | 239 | 48.194 | 29.696 | 19.501 | 1.00 | 33.32 |
| ATOM | 634 | N | SER | 240 | 47.958 | 30.166 | 17.321 | 1.00 | 36.32 |
| ATOM | 635 | CA | SER | 240 | 46.745 | 30.959 | 17.529 | 1.00 | 39.00 |
| ATOM | 636 | CB | SER | 240 | 46.385 | 31.724 | 16.258 | 1.00 | 47.52 |
| ATOM | 637 | OG | SER | 240 | 47.390 | 32.671 | 15.947 | 1.00 | 52.67 |
| ATOM | 638 | C | SER | 240 | 45.539 | 30.158 | 18.032 | 1.00 | 36.82 |
| ATOM | 639 | O | SER | 240 | 44.548 | 30.743 | 18.485 | 1.00 | 43.02 |
| ATOM | 640 | N | GLU | 241 | 45.617 | 28.833 | 17.931 | 1.00 | 38.98 |
| ATOM | 641 | CA | GLU | 241 | 44.554 | 27.954 | 18.408 | 1.00 | 40.35 |
| ATOM | 642 | CB | GLU | 241 | 44.788 | 26.521 | 17.926 | 1.00 | 49.38 |
| ATOM | 643 | CG | GLU | 241 | 44.541 | 26.287 | 16.452 | 1.00 | 65.25 |
| ATOM | 644 | CD | GLU | 241 | 44.873 | 24.856 | 16.002 | 1.00 | 70.72 |
| ATOM | 645 | OE1 | GLU | 241 | 44.806 | 23.923 | 16.845 | 1.00 | 73.36 |
| ATOM | 646 | OE2 | GLU | 241 | 45.211 | 24.679 | 14.805 | 1.00 | 68.60 |
| ATOM | 647 | C | GLU | 241 | 44.550 | 27.968 | 19.934 | 1.00 | 37.83 |
| ATOM | 648 | O | GLU | 241 | 43.504 | 27.857 | 20.570 | 1.00 | 40.77 |
| ATOM | 649 | N | LEU | 242 | 45.747 | 28.103 | 20.498 | 1.00 | 34.71 |
| ATOM | 650 | CA | LEU | 242 | 45.974 | 28.132 | 21.944 | 1.00 | 31.77 |
| ATOM | 651 | CB | LEU | 242 | 47.478 | 28.240 | 22.215 | 1.00 | 24.87 |
| ATOM | 652 | CG | LEU | 242 | 48.345 | 27.006 | 22.455 | 1.00 | 30.51 |
| ATOM | 653 | CD1 | LEU | 242 | 47.814 | 25.763 | 21.772 | 1.00 | 31.72 |

APPENDIX 5-continued

TR_IPBR2.PDB

| ATOM | 654 | CD2 | LEU | 242 | 49.743 | 27.328 | 21.996 | 1.00 | 24.25 |
|---|---|---|---|---|---|---|---|---|---|
| ATOM | 655 | C | LEU | 242 | 45.274 | 29.287 | 22.657 | 1.00 | 29.41 |
| ATOM | 656 | O | LEU | 242 | 45.029 | 30.339 | 22.071 | 1.00 | 28.12 |
| ATOM | 657 | N | PRO | 243 | 44.913 | 29.089 | 23.938 | 1.00 | 32.37 |
| ATOM | 658 | CD | PRO | 243 | 44.976 | 27.849 | 24.728 | 1.00 | 27.94 |
| ATOM | 659 | CA | PRO | 243 | 44.253 | 30.165 | 24.685 | 1.00 | 33.92 |
| ATOM | 660 | CB | PRO | 243 | 44.041 | 29.537 | 26.065 | 1.00 | 29.41 |
| ATOM | 661 | CG | PRO | 243 | 43.929 | 28.072 | 25.775 | 1.00 | 30.77 |
| ATOM | 662 | C | PRO | 243 | 45.246 | 31.334 | 24.775 | 1.00 | 35.86 |
| ATOM | 663 | O | PRO | 243 | 46.461 | 31.110 | 24.809 | 1.00 | 38.79 |
| ATOM | 664 | N | CYS | 244 | 44.751 | 32.570 | 24.834 | 1.00 | 39.67 |
| ATOM | 665 | CA | CYS | 244 | 45.621 | 33.749 | 24.931 | 1.00 | 45.78 |
| ATOM | 666 | CB | CYS | 244 | 44.788 | 35.028 | 25.102 | 1.00 | 71.13 |
| ATOM | 667 | SG | CYS | 244 | 44.068 | 35.680 | 23.580 | 1.00 | 100.76 |
| ATOM | 669 | C | CYS | 244 | 46.660 | 33.665 | 26.051 | 1.00 | 40.08 |
| ATOM | 670 | O | CYS | 244 | 47.797 | 34.096 | 25.879 | 1.00 | 35.68 |
| ATOM | 671 | N | GLU | 245 | 46.265 | 33.088 | 27.184 | 1.00 | 34.25 |
| ATOM | 672 | CA | GLU | 245 | 47.156 | 32.939 | 28.337 | 1.00 | 34.60 |
| ATOM | 673 | CB | GLU | 245 | 46.426 | 32.296 | 29.524 | 1.00 | 42.20 |
| ATOM | 674 | CG | GLU | 245 | 45.356 | 33.171 | 30.160 | 1.00 | 41.92 |
| ATOM | 675 | CD | GLU | 245 | 43.947 | 32.808 | 29.730 | 1.00 | 39.68 |
| ATOM | 676 | OE1 | GLU | 245 | 43.080 | 32.693 | 30.618 | 1.00 | 38.31 |
| ATOM | 677 | OE2 | GLU | 245 | 43.697 | 32.644 | 28.516 | 1.00 | 48.13 |
| ATOM | 678 | C | GLU | 245 | 48.376 | 32.109 | 27.984 | 1.00 | 29.54 |
| ATOM | 679 | O | GLU | 245 | 49.497 | 32.437 | 28.381 | 1.00 | 33.54 |
| ATOM | 680 | N | ASP | 246 | 48.146 | 31.034 | 27.236 | 1.00 | 26.40 |
| ATOM | 681 | CA | ASP | 246 | 49.219 | 30.154 | 26.794 | 1.00 | 26.99 |
| ATOM | 682 | CB | ASP | 246 | 48.650 | 28.887 | 26.153 | 1.00 | 29.86 |
| ATOM | 683 | CG | ASP | 246 | 48.184 | 27.876 | 27.175 | 1.00 | 34.10 |
| ATOM | 684 | OD1 | ASP | 246 | 48.149 | 28.199 | 28.381 | 1.00 | 31.83 |
| ATOM | 685 | OD2 | ASP | 246 | 47.863 | 26.742 | 26.772 | 1.00 | 35.79 |
| ATOM | 686 | C | ASP | 246 | 50.103 | 30.875 | 25.790 | 1.00 | 28.07 |
| ATOM | 687 | O | ASP | 246 | 51.331 | 30.789 | 25.863 | 1.00 | 27.35 |
| ATOM | 688 | N | GLN | 247 | 49.472 | 31.577 | 24.851 | 1.00 | 25.53 |
| ATOM | 689 | CA | GLN | 247 | 50.198 | 32.327 | 23.829 | 1.00 | 26.08 |
| ATOM | 690 | CB | GLN | 247 | 49.228 | 33.089 | 22.924 | 1.00 | 23.38 |
| ATOM | 691 | CG | GLN | 247 | 48.303 | 32.213 | 22.091 | 1.00 | 23.76 |
| ATOM | 692 | CD | GLN | 247 | 47.429 | 33.029 | 21.151 | 1.00 | 26.89 |
| ATOM | 693 | OE1 | GLN | 247 | 47.853 | 34.054 | 20.628 | 1.00 | 33.51 |
| ATOM | 694 | NE2 | GLN | 247 | 46.198 | 32.593 | 20.957 | 1.00 | 27.44 |
| ATOM | 695 | C | GLN | 247 | 51.133 | 33.313 | 24.511 | 1.00 | 22.74 |
| ATOM | 696 | O | GLN | 247 | 52.326 | 33.373 | 24.205 | 1.00 | 27.63 |
| ATOM | 697 | N | ILE | 248 | 50.588 | 34.047 | 25.473 | 1.00 | 25.03 |
| ATOM | 698 | CA | ILE | 248 | 51.353 | 35.035 | 26.220 | 1.00 | 25.94 |
| ATOM | 699 | CB | ILE | 248 | 50.436 | 35.781 | 27.226 | 1.00 | 24.84 |
| ATOM | 700 | CG2 | ILE | 248 | 51.251 | 36.633 | 28.179 | 1.00 | 21.87 |
| ATOM | 701 | CG1 | ILE | 248 | 49.430 | 36.652 | 26.459 | 1.00 | 27.98 |
| ATOM | 702 | CD1 | ILE | 248 | 48.359 | 37.298 | 27.328 | 1.00 | 29.90 |
| ATOM | 703 | C | ILE | 248 | 52.535 | 34.382 | 26.939 | 1.00 | 27.53 |
| ATOM | 704 | O | ILE | 248 | 53.671 | 34.847 | 26.833 | 1.00 | 29.35 |
| ATOM | 705 | N | ILE | 249 | 52.279 | 33.274 | 27.622 | 1.00 | 24.38 |
| ATOM | 706 | CA | ILE | 249 | 53.334 | 32.582 | 28.354 | 1.00 | 26.26 |
| ATOM | 707 | CB | ILE | 249 | 52.759 | 31.395 | 29.166 | 1.00 | 29.81 |
| ATOM | 708 | CG2 | ILE | 249 | 53.874 | 30.521 | 29.726 | 1.00 | 29.16 |
| ATOM | 709 | CG1 | ILE | 249 | 51.883 | 31.923 | 30.300 | 1.00 | 27.15 |
| ATOM | 710 | CD1 | ILE | 249 | 51.173 | 30.838 | 31.076 | 1.00 | 32.35 |
| ATOM | 711 | C | ILE | 249 | 54.448 | 32.103 | 27.422 | 1.00 | 27.78 |
| ATOM | 712 | O | ILE | 249 | 55.634 | 32.297 | 27.708 | 1.00 | 29.37 |
| ATOM | 713 | N | LEU | 250 | 54.061 | 31.516 | 26.289 | 1.00 | 29.25 |
| ATOM | 714 | CA | LEU | 250 | 55.021 | 31.005 | 25.319 | 1.00 | 24.49 |
| ATOM | 715 | CB | LEU | 250 | 54.303 | 30.224 | 24.214 | 1.00 | 23.75 |
| ATOM | 716 | CG | LEU | 250 | 53.541 | 28.962 | 24.629 | 1.00 | 23.18 |
| ATOM | 717 | CD1 | LEU | 250 | 52.886 | 28.353 | 23.416 | 1.00 | 19.94 |
| ATOM | 718 | CD2 | LEU | 250 | 54.475 | 27.960 | 25.278 | 1.00 | 20.76 |
| ATOM | 719 | C | LEU | 250 | 55.878 | 32.116 | 24.714 | 1.00 | 22.20 |
| ATOM | 720 | O | LEU | 250 | 57.082 | 31.940 | 24.528 | 1.00 | 23.49 |
| ATOM | 721 | N | LEU | 251 | 55.256 | 33.249 | 24.399 | 1.00 | 24.21 |
| ATOM | 722 | CA | LEU | 251 | 55.980 | 34.384 | 23.831 | 1.00 | 27.98 |
| ATOM | 723 | CB | LEU | 251 | 55.010 | 35.488 | 23.408 | 1.00 | 25.91 |
| ATOM | 724 | CG | LEU | 251 | 54.287 | 35.245 | 22.085 | 1.00 | 29.46 |
| ATOM | 725 | CD1 | LEU | 251 | 53.121 | 36.217 | 21.939 | 1.00 | 35.03 |
| ATOM | 726 | CD2 | LEU | 251 | 55.268 | 35.364 | 20.924 | 1.00 | 23.65 |
| ATOM | 727 | C | LEU | 251 | 56.998 | 34.931 | 24.828 | 1.00 | 26.85 |
| ATOM | 728 | O | LEU | 251 | 58.165 | 35.143 | 24.484 | 1.00 | 23.12 |
| ATOM | 729 | N | LYS | 252 | 56.556 | 35.145 | 26.063 | 1.00 | 25.33 |
| ATOM | 730 | CA | LYS | 252 | 57.427 | 35.644 | 27.119 | 1.00 | 31.33 |
| ATOM | 731 | CB | LYS | 252 | 56.659 | 35.723 | 28.437 | 1.00 | 37.06 |

APPENDIX 5-continued

TR_IPBR2.PDB

| ATOM | 732 | CG | LYS | 252 | 55.593 | 36.805 | 28.511 | 1.00 | 41.75 |
|------|-----|-----|-----|-----|--------|--------|--------|------|-------|
| ATOM | 733 | CD | LYS | 252 | 54.779 | 36.619 | 29.783 | 1.00 | 52.64 |
| ATOM | 734 | CE | LYS | 252 | 53.822 | 37.767 | 30.057 | 1.00 | 62.60 |
| ATOM | 735 | NZ | LYS | 252 | 54.503 | 39.005 | 30.520 | 1.00 | 71.68 |
| ATOM | 736 | C | LYS | 252 | 58.622 | 34.705 | 27.293 | 1.00 | 29.08 |
| ATOM | 737 | O | LYS | 252 | 59.758 | 35.150 | 27.460 | 1.00 | 35.24 |
| ATOM | 738 | N | GLY | 253 | 58.355 | 33.403 | 27.211 | 1.00 | 24.98 |
| ATOM | 739 | CA | GLY | 253 | 59.407 | 32.416 | 27.369 | 1.00 | 22.80 |
| ATOM | 740 | C | GLY | 253 | 60.413 | 32.282 | 26.235 | 1.00 | 26.90 |
| ATOM | 741 | O | GLY | 253 | 61.572 | 31.948 | 26.489 | 1.00 | 31.90 |
| ATOM | 742 | N | CYS | 254 | 60.013 | 32.574 | 24.997 | 1.00 | 25.42 |
| ATOM | 743 | CA | CYS | 254 | 60.932 | 32.427 | 23.863 | 1.00 | 20.71 |
| ATOM | 744 | CB | CYS | 254 | 60.314 | 31.509 | 22.811 | 1.00 | 24.98 |
| ATOM | 745 | SG | CYS | 254 | 58.976 | 32.310 | 21.909 | 1.00 | 24.24 |
| ATOM | 746 | C | CYS | 254 | 61.353 | 33.716 | 23.164 | 1.00 | 22.79 |
| ATOM | 747 | O | CYS | 254 | 62.217 | 33.683 | 22.282 | 1.00 | 23.23 |
| ATOM | 748 | N | CYS | 255 | 60.757 | 34.842 | 23.539 | 1.00 | 21.47 |
| ATOM | 749 | CA | CYS | 255 | 61.061 | 36.114 | 22.884 | 1.00 | 22.50 |
| ATOM | 750 | CB | CYS | 255 | 60.318 | 37.262 | 23.567 | 1.00 | 21.72 |
| ATOM | 751 | SG | CYS | 255 | 60.353 | 38.768 | 22.597 | 1.00 | 24.73 |
| ATOM | 752 | C | CYS | 255 | 62.547 | 36.457 | 22.738 | 1.00 | 23.81 |
| ATOM | 753 | O | CYS | 255 | 63.015 | 36.746 | 21.632 | 1.00 | 23.48 |
| ATOM | 754 | N | MET | 256 | 63.294 | 36.402 | 23.838 | 1.00 | 22.13 |
| ATOM | 755 | CA | MET | 256 | 64.719 | 36.713 | 23.792 | 1.00 | 22.91 |
| ATOM | 756 | CB | MET | 256 | 65.286 | 36.810 | 25.213 | 1.00 | 23.78 |
| ATOM | 757 | CG | MET | 256 | 66.781 | 37.094 | 25.272 | 1.00 | 17.41 |
| ATOM | 758 | SD | MET | 256 | 67.196 | 38.632 | 24.415 | 1.00 | 23.65 |
| ATOM | 759 | CE | MET | 256 | 69.010 | 38.715 | 24.624 | 1.00 | 18.57 |
| ATOM | 760 | C | MET | 256 | 65.487 | 35.671 | 22.980 | 1.00 | 21.41 |
| ATOM | 761 | O | MET | 256 | 66.432 | 36.005 | 22.260 | 1.00 | 22.01 |
| ATOM | 762 | N | GLU | 257 | 65.058 | 34.415 | 23.068 | 1.00 | 23.18 |
| ATOM | 763 | CA | GLU | 257 | 65.705 | 33.323 | 22.345 | 1.00 | 22.90 |
| ATOM | 764 | CB | GLU | 257 | 65.085 | 31.989 | 22.753 | 1.00 | 24.00 |
| ATOM | 765 | CG | GLU | 257 | 65.522 | 31.521 | 24.125 | 1.00 | 33.44 |
| ATOM | 766 | CD | GLU | 257 | 64.564 | 30.527 | 24.735 | 1.00 | 38.03 |
| ATOM | 767 | OE1 | GLU | 257 | 63.977 | 29.705 | 24.000 | 1.00 | 45.59 |
| ATOM | 768 | OE2 | GLU | 257 | 64.385 | 30.577 | 25.965 | 1.00 | 45.75 |
| ATOM | 769 | C | GLU | 257 | 65.595 | 33.526 | 20.840 | 1.00 | 21.68 |
| ATOM | 770 | O | GLU | 257 | 66.586 | 33.421 | 20.107 | 1.00 | 20.02 |
| ATOM | 771 | N | ILE | 258 | 64.383 | 33.852 | 20.391 | 1.00 | 17.07 |
| ATOM | 772 | CA | ILE | 258 | 64.135 | 34.090 | 18.973 | 1.00 | 17.01 |
| ATOM | 773 | CB | ILE | 258 | 62.613 | 34.207 | 18.684 | 1.00 | 17.33 |
| ATOM | 774 | CG2 | ILE | 258 | 62.369 | 34.758 | 17.276 | 1.00 | 15.91 |
| ATOM | 775 | CG1 | ILE | 258 | 61.952 | 32.831 | 18.885 | 1.00 | 16.69 |
| ATOM | 776 | CD1 | ILE | 258 | 60.450 | 32.783 | 18.632 | 1.00 | 16.31 |
| ATOM | 777 | C | ILE | 258 | 64.911 | 35.324 | 18.501 | 1.00 | 17.65 |
| ATOM | 778 | O | ILE | 258 | 65.605 | 35.263 | 17.484 | 1.00 | 22.58 |
| ATOM | 779 | N | MET | 259 | 64.865 | 36.410 | 19.274 | 1.00 | 20.17 |
| ATOM | 780 | CA | MET | 259 | 65.584 | 37.628 | 18.909 | 1.00 | 15.03 |
| ATOM | 781 | CB | MET | 259 | 65.234 | 38.771 | 19.856 | 1.00 | 20.12 |
| ATOM | 782 | CG | MET | 259 | 63.791 | 39.191 | 19.775 | 1.00 | 17.19 |
| ATOM | 783 | SD | MET | 259 | 63.523 | 40.795 | 20.524 | 1.00 | 28.92 |
| ATOM | 784 | CE | MET | 259 | 63.718 | 40.406 | 22.261 | 1.00 | 19.58 |
| ATOM | 785 | C | MET | 259 | 67.090 | 37.402 | 18.884 | 1.00 | 18.84 |
| ATOM | 786 | O | MET | 259 | 67.783 | 37.912 | 17.996 | 1.00 | 29.07 |
| ATOM | 787 | N | SER | 260 | 67.590 | 36.618 | 19.837 | 1.00 | 21.45 |
| ATOM | 788 | CA | SER | 260 | 69.019 | 36.319 | 19.906 | 1.00 | 18.71 |
| ATOM | 789 | CB | SER | 260 | 69.367 | 35.595 | 21.207 | 1.00 | 18.35 |
| ATOM | 790 | OG | SER | 260 | 69.128 | 36.421 | 22.329 | 1.00 | 25.42 |
| ATOM | 791 | C | SER | 260 | 69.430 | 35.469 | 18.709 | 1.00 | 17.83 |
| ATOM | 792 | O | SER | 260 | 70.497 | 35.673 | 18.131 | 1.00 | 22.97 |
| ATOM | 793 | N | LEU | 261 | 68.572 | 34.522 | 18.331 | 1.00 | 21.66 |
| ATOM | 794 | CA | LEU | 261 | 68.837 | 33.663 | 17.179 | 1.00 | 20.98 |
| ATOM | 795 | CB | LEU | 261 | 67.739 | 32.608 | 17.053 | 1.00 | 22.66 |
| ATOM | 796 | CG | LEU | 261 | 67.719 | 31.759 | 15.781 | 1.00 | 22.12 |
| ATOM | 797 | CD1 | LEU | 261 | 68.998 | 30.938 | 15.665 | 1.00 | 18.51 |
| ATOM | 798 | CD2 | LEU | 261 | 66.498 | 30.851 | 15.800 | 1.00 | 19.60 |
| ATOM | 799 | C | LEU | 261 | 68.873 | 34.527 | 15.920 | 1.00 | 22.95 |
| ATOM | 800 | O | LEU | 261 | 69.779 | 34.402 | 15.091 | 1.00 | 22.62 |
| ATOM | 801 | N | ARG | 262 | 67.892 | 35.418 | 15.798 | 1.00 | 22.12 |
| ATOM | 802 | CA | ARG | 262 | 67.816 | 36.301 | 14.643 | 1.00 | 25.32 |
| ATOM | 803 | CB | ARG | 262 | 66.525 | 37.115 | 14.677 | 1.00 | 21.95 |
| ATOM | 804 | CG | ARG | 262 | 65.304 | 36.268 | 14.362 | 1.00 | 21.48 |
| ATOM | 805 | CD | ARG | 262 | 64.026 | 37.077 | 14.345 | 1.00 | 19.12 |
| ATOM | 806 | NE | ARG | 262 | 62.990 | 36.377 | 13.599 | 1.00 | 22.18 |
| ATOM | 807 | CZ | ARG | 262 | 61.780 | 36.862 | 13.333 | 1.00 | 22.88 |
| ATOM | 808 | NH1 | ARG | 262 | 61.429 | 38.075 | 13.752 | 1.00 | 20.81 |

APPENDIX 5-continued

TR_IPBR2.PDB

| ATOM | 809 | NH2 | ARG | 262 | 60.912 | 36.129 | 12.648 | 1.00 | 20.26 |
|---|---|---|---|---|---|---|---|---|---|
| ATOM | 810 | C | ARG | 262 | 69.044 | 37.196 | 14.531 | 1.00 | 25.05 |
| ATOM | 811 | O | ARG | 262 | 69.485 | 37.513 | 13.427 | 1.00 | 22.98 |
| ATOM | 812 | N | ALA | 263 | 69.608 | 37.579 | 15.676 | 1.00 | 26.36 |
| ATOM | 813 | CA | ALA | 263 | 70.818 | 38.400 | 15.705 | 1.00 | 27.02 |
| ATOM | 814 | CB | ALA | 263 | 70.997 | 39.045 | 17.087 | 1.00 | 25.80 |
| ATOM | 815 | C | ALA | 263 | 72.026 | 37.514 | 15.368 | 1.00 | 25.21 |
| ATOM | 816 | O | ALA | 263 | 72.825 | 37.844 | 14.492 | 1.00 | 31.14 |
| ATOM | 817 | N | ALA | 264 | 72.109 | 36.358 | 16.027 | 1.00 | 25.62 |
| ATOM | 818 | CA | ALA | 264 | 73.203 | 35.408 | 15.828 | 1.00 | 23.85 |
| ATOM | 819 | CB | ALA | 264 | 73.062 | 34.237 | 16.794 | 1.00 | 17.15 |
| ATOM | 820 | C | ALA | 264 | 73.345 | 34.901 | 14.391 | 1.00 | 26.03 |
| ATOM | 821 | O | ALA | 264 | 74.460 | 34.773 | 13.886 | 1.00 | 25.66 |
| ATOM | 822 | N | VAL | 265 | 72.234 | 34.615 | 13.723 | 1.00 | 25.22 |
| ATOM | 823 | CA | VAL | 265 | 72.327 | 34.128 | 12.350 | 1.00 | 28.38 |
| ATOM | 824 | CB | VAL | 265 | 71.028 | 33.451 | 11.857 | 1.00 | 24.59 |
| ATOM | 825 | CG1 | VAL | 265 | 70.707 | 32.264 | 12.719 | 1.00 | 25.53 |
| ATOM | 826 | CG2 | VAL | 265 | 69.881 | 34.440 | 11.853 | 1.00 | 20.86 |
| ATOM | 827 | C | VAL | 265 | 72.747 | 35.235 | 11.393 | 1.00 | 31.46 |
| ATOM | 828 | O | VAL | 265 | 73.024 | 34.973 | 10.222 | 1.00 | 34.75 |
| ATOM | 829 | N | ARG | 266 | 72.795 | 36.464 | 11.896 | 1.00 | 30.10 |
| ATOM | 830 | CA | ARG | 266 | 73.211 | 37.602 | 11.089 | 1.00 | 30.69 |
| ATOM | 831 | CB | ARG | 266 | 72.170 | 38.713 | 11.148 | 1.00 | 25.13 |
| ATOM | 832 | CG | ARG | 266 | 70.976 | 38.406 | 10.299 | 1.00 | 25.43 |
| ATOM | 833 | CD | ARG | 266 | 69.999 | 39.537 | 10.277 | 1.00 | 29.56 |
| ATOM | 834 | NE | ARG | 266 | 69.032 | 39.340 | 9.205 | 1.00 | 31.59 |
| ATOM | 835 | CZ | ARG | 266 | 67.814 | 39.861 | 9.197 | 1.00 | 31.18 |
| ATOM | 836 | NH1 | ARG | 266 | 67.408 | 40.611 | 10.215 | 1.00 | 31.01 |
| ATOM | 837 | NH2 | ARG | 266 | 67.012 | 39.648 | 8.163 | 1.00 | 28.21 |
| ATOM | 838 | C | ARG | 266 | 74.568 | 38.111 | 11.544 | 1.00 | 34.28 |
| ATOM | 839 | O | ARG | 266 | 74.877 | 39.300 | 11.423 | 1.00 | 41.19 |
| ATOM | 840 | N | TYR | 267 | 75.362 | 37.207 | 12.108 | 1.00 | 30.80 |
| ATOM | 841 | CA | TYR | 267 | 76.694 | 37.544 | 12.573 | 1.00 | 33.84 |
| ATOM | 842 | CB | TYR | 267 | 77.202 | 36.461 | 13.534 | 1.00 | 32.56 |
| ATOM | 843 | CG | TYR | 267 | 78.674 | 36.570 | 13.867 | 1.00 | 34.23 |
| ATOM | 844 | CD1 | TYR | 267 | 79.131 | 37.465 | 14.835 | 1.00 | 32.60 |
| ATOM | 845 | CE1 | TYR | 267 | 80.491 | 37.593 | 15.106 | 1.00 | 34.90 |
| ATOM | 846 | CD2 | TYR | 267 | 79.615 | 35.801 | 13.184 | 1.00 | 32.84 |
| ATOM | 847 | CE2 | TYR | 267 | 80.972 | 35.920 | 13.446 | 1.00 | 34.70 |
| ATOM | 848 | CZ | TYR | 267 | 81.404 | 36.816 | 14.405 | 1.00 | 36.21 |
| ATOM | 849 | OH | TYR | 267 | 82.749 | 36.940 | 14.651 | 1.00 | 39.48 |
| ATOM | 850 | C | TYR | 267 | 77.615 | 37.649 | 11.360 | 1.00 | 37.82 |
| ATOM | 851 | O | TYR | 267 | 77.648 | 36.749 | 10.517 | 1.00 | 39.45 |
| ATOM | 852 | N | ASP | 268 | 78.319 | 38.769 | 11.239 | 1.00 | 44.62 |
| ATOM | 853 | CA | ASP | 268 | 79.248 | 38.963 | 10.133 | 1.00 | 45.56 |
| ATOM | 854 | CB | ASP | 268 | 79.096 | 40.366 | 9.533 | 1.00 | 46.62 |
| ATOM | 855 | CG | ASP | 268 | 80.068 | 40.624 | 8.391 | 1.00 | 50.96 |
| ATOM | 856 | OD1 | ASP | 268 | 80.204 | 39.755 | 7.502 | 1.00 | 55.65 |
| ATOM | 857 | OD2 | ASP | 268 | 80.700 | 41.699 | 8.384 | 1.00 | 52.09 |
| ATOM | 858 | C | ASP | 268 | 80.675 | 38.751 | 10.630 | 1.00 | 44.44 |
| ATOM | 859 | O | ASP | 268 | 81.242 | 39.614 | 11.304 | 1.00 | 45.68 |
| ATOM | 860 | N | PRO | 269 | 81.281 | 37.600 | 10.296 | 1.00 | 45.94 |
| ATOM | 861 | CD | PRO | 269 | 80.739 | 36.503 | 9.476 | 1.00 | 43.72 |
| ATOM | 862 | CA | PRO | 269 | 82.651 | 37.309 | 10.730 | 1.00 | 46.63 |
| ATOM | 863 | CB | PRO | 269 | 82.884 | 35.889 | 10.208 | 1.00 | 43.88 |
| ATOM | 864 | CG | PRO | 269 | 81.983 | 35.797 | 9.018 | 1.00 | 44.66 |
| ATOM | 865 | C | PRO | 269 | 83.682 | 38.298 | 10.190 | 1.00 | 50.80 |
| ATOM | 866 | O | PRO | 269 | 84.681 | 38.578 | 10.854 | 1.00 | 48.56 |
| ATOM | 867 | N | ALA | 270 | 83.407 | 38.858 | 9.012 | 1.00 | 55.09 |
| ATOM | 868 | CA | ALA | 270 | 84.306 | 39.820 | 8.374 | 1.00 | 55.68 |
| ATOM | 869 | CB | ALA | 270 | 83.799 | 40.168 | 6.974 | 1.90 | 53.64 |
| ATOM | 870 | C | ALA | 270 | 84.528 | 41.096 | 9.196 | 1.00 | 56.18 |
| ATOM | 871 | O | ALA | 270 | 85.577 | 41.729 | 9.082 | 1.00 | 61.07 |
| ATOM | 872 | N | SER | 271 | 83.543 | 41.479 | 10.006 | 1.00 | 51.38 |
| ATOM | 873 | CA | SER | 271 | 83.661 | 42.678 | 10.836 | 1.00 | 45.90 |
| ATOM | 874 | CB | SER | 271 | 82.710 | 43.774 | 10.346 | 1.00 | 44.49 |
| ATOM | 875 | OG | SER | 271 | 81.360 | 43.358 | 10.404 | 1.00 | 45.26 |
| ATOM | 876 | C | SER | 271 | 83.409 | 42.395 | 12.317 | 1.00 | 46.61 |
| ATOM | 877 | O | SER | 271 | 83.431 | 43.309 | 13.143 | 1.00 | 48.31 |
| ATOM | 878 | N | ASP | 272 | 83.172 | 41.126 | 12.642 | 1.00 | 46.73 |
| ATOM | 879 | CA | ASP | 272 | 82.920 | 40.689 | 14.013 | 1.00 | 42.49 |
| ATOM | 880 | CB | ASP | 272 | 84.200 | 40.807 | 14.849 | 1.00 | 42.12 |
| ATOM | 881 | CG | ASP | 272 | 84.103 | 40.072 | 16.169 | 1.00 | 50.30 |
| ATOM | 882 | OD1 | ASP | 272 | 83.417 | 39.028 | 16.218 | 1.00 | 45.10 |
| ATOM | 883 | OD2 | ASP | 272 | 84.708 | 40.537 | 17.160 | 1.00 | 57.61 |
| ATOM | 884 | C | ASP | 272 | 81.769 | 41.465 | 14.658 | 1.00 | 40.95 |
| ATOM | 885 | O | ASP | 272 | 81.885 | 41.975 | 15.779 | 1.00 | 42.93 |

APPENDIX 5-continued

TR_IPBR2.PDB

| ATOM | 886 | N   | THR | 273 | 80.651 | 41.531 | 13.945 | 1.00 | 38.57 |
| ---- | --- | --- | --- | --- | ------ | ------ | ------ | ---- | ----- |
| ATOM | 887 | CA  | THR | 273 | 79.473 | 42.239 | 14.425 | 1.00 | 40.99 |
| ATOM | 888 | CB  | THR | 273 | 79.262 | 43.574 | 13.656 | 1.00 | 40.76 |
| ATOM | 889 | OG1 | THR | 273 | 79.240 | 43.318 | 12.248 | 1.00 | 42.61 |
| ATOM | 890 | CG2 | THR | 273 | 80.373 | 44.574 | 13.965 | 1.00 | 39.67 |
| ATOM | 891 | C   | THR | 273 | 78.210 | 41.397 | 14.251 | 1.00 | 39.94 |
| ATOM | 892 | O   | THR | 273 | 78.202 | 40.419 | 13.494 | 1.00 | 36.66 |
| ATOM | 893 | N   | LEU | 274 | 77.168 | 41.757 | 14.993 | 1.00 | 36.08 |
| ATOM | 894 | CA  | LEU | 274 | 75.867 | 41.096 | 14.907 | 1.00 | 34.28 |
| ATOM | 895 | CB  | LEU | 274 | 75.343 | 40.699 | 16.292 | 1.00 | 30.96 |
| ATOM | 896 | CG  | LEU | 274 | 75.952 | 39.536 | 17.068 | 1.00 | 30.19 |
| ATOM | 897 | CD1 | LEU | 274 | 75.310 | 39.472 | 18.444 | 1.00 | 26.29 |
| ATOM | 898 | CD2 | LEU | 274 | 75.744 | 38.237 | 16.309 | 1.00 | 27.43 |
| ATOM | 899 | C   | LEU | 274 | 74.943 | 42.163 | 14.347 | 1.00 | 36.49 |
| ATOM | 900 | O   | LEU | 274 | 75.152 | 43.354 | 14.596 | 1.00 | 40.27 |
| ATOM | 901 | N   | THR | 275 | 73.923 | 41.758 | 13.606 | 1.00 | 36.42 |
| ATOM | 902 | CA  | THR | 275 | 72.994 | 42.731 | 13.062 | 1.00 | 35.07 |
| ATOM | 903 | CB  | THR | 275 | 72.773 | 42.522 | 11.556 | 1.00 | 36.04 |
| ATOM | 904 | OG1 | THR | 275 | 74.028 | 42.625 | 10.875 | 1.00 | 41.52 |
| ATOM | 905 | CG2 | THR | 275 | 71.852 | 43.583 | 11.008 | 1.00 | 36.47 |
| ATOM | 906 | C   | THR | 275 | 71.673 | 42.655 | 13.814 | 1.00 | 34.32 |
| ATOM | 907 | O   | THR | 275 | 71.055 | 41.590 | 13.907 | 1.00 | 34.96 |
| ATOM | 908 | N   | LEU | 276 | 71.292 | 43.767 | 14.432 | 1.00 | 31.79 |
| ATOM | 909 | CA  | LEU | 276 | 70.044 | 43.840 | 15.173 | 1.00 | 29.47 |
| ATOM | 910 | CB  | LEU | 276 | 70.181 | 44.766 | 16.389 | 1.00 | 25.29 |
| ATOM | 911 | CG  | LEU | 276 | 71.328 | 44.501 | 17.383 | 1.00 | 29.01 |
| ATOM | 912 | CD1 | LEU | 276 | 71.179 | 45.410 | 18.594 | 1.00 | 20.92 |
| ATOM | 913 | CD2 | LEU | 276 | 71.358 | 43.042 | 17.834 | 1.00 | 22.79 |
| ATOM | 914 | C   | LEU | 276 | 68.966 | 44.350 | 14.228 | 1.00 | 31.69 |
| ATOM | 915 | O   | LEU | 276 | 69.175 | 45.335 | 13.510 | 1.00 | 33.87 |
| ATOM | 916 | N   | SER | 277 | 67.862 | 43.608 | 14.162 | 1.00 | 33.07 |
| ATOM | 917 | CA  | SER | 277 | 66.721 | 43.935 | 13.315 | 1.00 | 30.61 |
| ATOM | 918 | CB  | SER | 277 | 65.949 | 45.111 | 13.909 | 1.00 | 22.87 |
| ATOM | 919 | OG  | SER | 277 | 65.587 | 44.822 | 15.250 | 1.00 | 23.35 |
| ATOM | 920 | C   | SER | 277 | 67.103 | 44.200 | 11.860 | 1.00 | 31.85 |
| ATOM | 921 | O   | SER | 277 | 66.433 | 44.958 | 11.158 | 1.00 | 32.13 |
| ATOM | 922 | N   | GLY | 278 | 68.188 | 43.566 | 11.421 | 1.00 | 32.29 |
| ATOM | 923 | CA  | GLY | 278 | 68.664 | 43.716 | 10.058 | 1.00 | 37.59 |
| ATOM | 924 | C   | GLY | 278 | 69.063 | 45.122 |  9.639 | 1.00 | 43.26 |
| ATOM | 925 | O   | GLY | 278 | 69.313 | 45.358 |  8.455 | 1.00 | 42.60 |
| ATOM | 926 | N   | GLU | 279 | 69.177 | 46.938 | 10.599 | 1.00 | 43.42 |
| ATOM | 927 | CA  | GLU | 279 | 69.532 | 47.420 | 10.291 | 1.00 | 44.55 |
| ATOM | 928 | CB  | GLU | 279 | 68.292 | 48.310 | 10.394 | 1.00 | 44.66 |
| ATOM | 929 | CG  | GLU | 279 | 67.671 | 48.344 | 11.783 | 1.00 | 54.19 |
| ATOM | 930 | CD  | GLU | 279 | 66.400 | 49.171 | 11.845 | 1.00 | 64.96 |
| ATOM | 931 | OE1 | GLU | 279 | 65.627 | 49.174 | 10.859 | 1.00 | 71.43 |
| ATOM | 932 | OE2 | GLU | 279 | 66.167 | 49.814 | 12.891 | 1.00 | 66.65 |
| ATOM | 933 | C   | GLU | 279 | 70.654 | 48.019 | 11.133 | 1.00 | 45.52 |
| ATOM | 934 | O   | GLU | 279 | 71.207 | 49.057 | 10.772 | 1.00 | 51.83 |
| ATOM | 935 | N   | MET | 280 | 71.007 | 47.373 | 12.242 | 1.00 | 44.66 |
| ATOM | 936 | CA  | MET | 280 | 72.060 | 47.904 | 13.105 | 1.00 | 34.22 |
| ATOM | 937 | CB  | MET | 280 | 71.470 | 48.382 | 14.433 | 1.00 | 32.38 |
| ATOM | 938 | CG  | MET | 280 | 72.479 | 49.058 | 15.345 | 1.00 | 37.87 |
| ATOM | 939 | SD  | MET | 280 | 71.912 | 49.201 | 17.052 | 1.00 | 41.78 |
| ATOM | 940 | CE  | MET | 280 | 70.650 | 50.495 | 16.911 | 1.00 | 37.01 |
| ATOM | 941 | C   | MET | 280 | 73.183 | 46.920 | 13.386 | 1.00 | 35.70 |
| ATOM | 942 | O   | MET | 280 | 72.976 | 45.900 | 14.044 | 1.00 | 36.99 |
| ATOM | 943 | N   | ALA | 281 | 74.366 | 47.221 | 12.867 | 1.00 | 34.80 |
| ATOM | 944 | CA  | ALA | 281 | 75.535 | 46.377 | 13.091 | 1.00 | 35.11 |
| ATOM | 945 | CB  | ALA | 281 | 76.529 | 46.527 | 11.955 | 1.00 | 31.27 |
| ATOM | 946 | C   | ALA | 281 | 76.155 | 46.837 | 14.406 | 1.00 | 35.96 |
| ATOM | 947 | O   | ALA | 281 | 76.478 | 48.015 | 14.570 | 1.00 | 39.10 |
| ATOM | 948 | N   | VAL | 282 | 76.285 | 45.916 | 15.353 | 1.00 | 36.46 |
| ATOM | 949 | CA  | VAL | 282 | 76.839 | 46.246 | 16.655 | 1.00 | 36.05 |
| ATOM | 950 | CB  | VAL | 282 | 75.783 | 46.090 | 17.783 | 1.00 | 35.60 |
| ATOM | 951 | CG1 | VAL | 282 | 74.633 | 47.069 | 17.568 | 1.00 | 38.73 |
| ATOM | 952 | CG2 | VAL | 282 | 75.262 | 44.660 | 17.844 | 1.00 | 33.27 |
| ATOM | 953 | C   | VAL | 282 | 78.062 | 45.408 | 16.996 | 1.00 | 37.70 |
| ATOM | 954 | O   | VAL | 282 | 78.137 | 44.223 | 16.660 | 1.00 | 37.45 |
| ATOM | 955 | N   | ALA | 283 | 79.032 | 46.047 | 17.637 | 1.00 | 39.21 |
| ATOM | 956 | CA  | ALA | 283 | 80.254 | 45.375 | 18.048 | 1.00 | 43.73 |
| ATOM | 957 | CB  | ALA | 283 | 81.433 | 46.352 | 18.047 | 1.00 | 42.04 |
| ATOM | 958 | C   | ALA | 283 | 80.060 | 44.752 | 19.435 | 1.00 | 43.28 |
| ATOM | 959 | O   | ALA | 283 | 79.179 | 45.157 | 20.203 | 1.00 | 45.77 |
| ATOM | 960 | N   | ARG | 284 | 80.903 | 43.774 | 19.744 | 1.00 | 41.96 |
| ATOM | 961 | CA  | ARG | 284 | 80.866 | 43.044 | 21.004 | 1.00 | 44.87 |
| ATOM | 962 | CB  | ARG | 284 | 82.084 | 42.125 | 21.087 | 1.00 | 46.34 |

APPENDIX 5-continued

TR_IPBR2.PDB

| ATOM | 963 | CG | ARG | 284 | 81.930 | 40.947 | 22.017 | 1.00 | 51.85 |
|---|---|---|---|---|---|---|---|---|---|
| ATOM | 964 | CD | ARG | 284 | 83.107 | 40.010 | 21.844 | 1.00 | 60.73 |
| ATOM | 965 | NE | ARG | 284 | 83.262 | 39.571 | 20.455 | 1.00 | 54.30 |
| ATOM | 966 | CZ | ARG | 284 | 83.221 | 38.300 | 20.074 | 1.00 | 53.66 |
| ATOM | 967 | NH1 | ARG | 284 | 83.032 | 37.343 | 20.973 | 1.00 | 49.99 |
| ATOM | 968 | NH2 | ARG | 284 | 83.379 | 37.984 | 18.797 | 1.00 | 47.31 |
| ATOM | 969 | C | ARG | 284 | 80.803 | 43.945 | 22.237 | 1.00 | 44.85 |
| ATOM | 970 | O | ARG | 284 | 79.896 | 43.806 | 23.062 | 1.00 | 48.26 |
| ATOM | 971 | N | GLU | 285 | 81.750 | 44.873 | 22.349 | 1.00 | 41.60 |
| ATOM | 972 | CA | GLU | 285 | 81.802 | 45.787 | 23.484 | 1.00 | 41.17 |
| ATOM | 973 | CB | GLU | 285 | 83.043 | 46.675 | 23.392 | 1.00 | 39.97 |
| ATOM | 974 | C | GLU | 285 | 80.538 | 46.640 | 23.603 | 1.00 | 40.08 |
| ATOM | 975 | O | GLU | 285 | 80.023 | 46.849 | 24.703 | 1.00 | 41.16 |
| ATOM | 976 | N | GLN | 286 | 80.017 | 47.088 | 22.463 | 1.00 | 38.49 |
| ATOM | 977 | CA | GLN | 286 | 78.818 | 47.926 | 22.425 | 1.00 | 36.25 |
| ATOM | 978 | CB | GLN | 286 | 78.549 | 48.401 | 20.997 | 1.00 | 39.50 |
| ATOM | 979 | CG | GLN | 286 | 79.619 | 49.311 | 20.424 | 1.00 | 43.62 |
| ATOM | 980 | CD | GLN | 286 | 79.324 | 49.710 | 18.987 | 1.00 | 49.48 |
| ATOM | 981 | OE1 | GLN | 286 | 79.253 | 48.856 | 18.097 | 1.00 | 48.41 |
| ATOM | 982 | NE2 | GLN | 286 | 79.125 | 51.000 | 18.755 | 1.00 | 47.15 |
| ATOM | 983 | C | GLN | 286 | 77.563 | 47.255 | 22.988 | 1.00 | 35.40 |
| ATOM | 984 | O | GLN | 286 | 76.903 | 47.806 | 23.871 | 1.00 | 31.24 |
| ATOM | 985 | N | LEU | 287 | 77.234 | 46.071 | 22.480 | 1.00 | 32.96 |
| ATOM | 986 | CA | LEU | 287 | 76.055 | 45.349 | 22.950 | 1.00 | 33.40 |
| ATOM | 987 | CB | LEU | 287 | 75.767 | 44.138 | 22.054 | 1.00 | 28.67 |
| ATOM | 988 | CG | LEU | 287 | 74.466 | 43.375 | 22.342 | 1.00 | 26.66 |
| ATOM | 989 | CD1 | LEU | 287 | 73.263 | 44.305 | 22.244 | 1.00 | 19.41 |
| ATOM | 990 | CD2 | LEU | 287 | 74.325 | 42.221 | 21.368 | 1.00 | 24.84 |
| ATOM | 991 | C | LEU | 287 | 76.234 | 44.914 | 24.406 | 1.00 | 34.81 |
| ATOM | 992 | O | LEU | 287 | 75.265 | 44.857 | 25.175 | 1.00 | 33.92 |
| ATOM | 993 | N | LYS | 288 | 77.476 | 44.621 | 24.781 | 1.00 | 31.38 |
| ATOM | 994 | CA | LYS | 288 | 77.814 | 44.204 | 26.140 | 1.00 | 36.12 |
| ATOM | 995 | CB | LYS | 288 | 79.296 | 43.839 | 26.210 | 1.00 | 37.13 |
| ATOM | 996 | CG | LYS | 288 | 79.762 | 43.280 | 27.533 | 1.00 | 44.61 |
| ATOM | 997 | CD | LYS | 288 | 81.256 | 43.018 | 27.494 | 1.00 | 54.07 |
| ATOM | 998 | CE | LYS | 288 | 81.757 | 42.435 | 28.801 | 1.00 | 60.87 |
| ATOM | 999 | NZ | LYS | 288 | 81.291 | 41.041 | 29.039 | 1.00 | 61.53 |
| ATOM | 1000 | C | LYS | 288 | 77.510 | 45.345 | 27.109 | 1.00 | 36.90 |
| ATOM | 1001 | O | LYS | 288 | 76.684 | 45.206 | 28.013 | 1.00 | 40.68 |
| ATOM | 1002 | N | ASN | 289 | 78.129 | 46.495 | 26.863 | 1.00 | 35.94 |
| ATOM | 1003 | CA | ASN | 289 | 77.947 | 47.680 | 27.695 | 1.00 | 36.12 |
| ATOM | 1004 | CB | ASN | 289 | 78.982 | 48.738 | 27.332 | 1.00 | 31.78 |
| ATOM | 1005 | CG | ASN | 289 | 80.388 | 48.263 | 27.569 | 1.00 | 40.31 |
| ATOM | 1006 | OD1 | ASN | 289 | 80.627 | 47.422 | 28.440 | 1.00 | 43.12 |
| ATOM | 1007 | ND2 | ASN | 289 | 81.326 | 48.758 | 26.775 | 1.00 | 35.36 |
| ATOM | 1008 | C | ASN | 289 | 76.553 | 48.277 | 27.590 | 1.00 | 36.98 |
| ATOM | 1009 | O | ASN | 289 | 76.099 | 48.959 | 28.509 | 1.00 | 34.29 |
| ATOM | 1010 | N | GLY | 290 | 75.883 | 48.032 | 26.466 | 1.00 | 32.65 |
| ATOM | 1011 | CA | GLY | 290 | 74.541 | 48.550 | 26.256 | 1.00 | 28.61 |
| ATOM | 1012 | C | GLY | 290 | 73.497 | 48.001 | 27.210 | 1.00 | 26.54 |
| ATOM | 1013 | O | GLY | 290 | 72.362 | 48.480 | 27.234 | 1.00 | 31.06 |
| ATOM | 1014 | N | GLY | 291 | 73.861 | 46.978 | 27.977 | 1.00 | 28.89 |
| ATOM | 1015 | CA | GLY | 291 | 72.929 | 46.413 | 28.937 | 1.00 | 25.24 |
| ATOM | 1016 | C | GLY | 291 | 72.872 | 44.900 | 28.997 | 1.00 | 28.12 |
| ATOM | 1017 | O | GLY | 291 | 72.335 | 44.345 | 29.955 | 1.00 | 31.16 |
| ATOM | 1018 | N | LEU | 292 | 73.406 | 44.223 | 27.985 | 1.00 | 29.51 |
| ATOM | 1019 | CA | LEU | 292 | 73.361 | 42.766 | 27.969 | 1.00 | 32.79 |
| ATOM | 1020 | CB | LEU | 292 | 73.304 | 42.240 | 26.531 | 1.00 | 28.00 |
| ATOM | 1021 | CG | LEU | 292 | 71.948 | 42.355 | 25.827 | 1.00 | 23.68 |
| ATOM | 1022 | CD1 | LEU | 292 | 72.004 | 41.626 | 24.509 | 1.00 | 26.12 |
| ATOM | 1023 | CD2 | LEU | 292 | 70.851 | 41.764 | 26.694 | 1.00 | 23.36 |
| ATOM | 1024 | C | LEU | 292 | 74.484 | 42.085 | 28.742 | 1.00 | 32.33 |
| ATOM | 1025 | O | LEU | 292 | 74.312 | 40.967 | 29.232 | 1.00 | 33.22 |
| ATOM | 1026 | N | GLY | 293 | 75.627 | 42.750 | 28.846 | 1.00 | 30.31 |
| ATOM | 1027 | CA | GLY | 293 | 76.751 | 42.176 | 29.561 | 1.00 | 28.82 |
| ATOM | 1028 | C | GLY | 293 | 77.238 | 40.894 | 28.913 | 1.00 | 29.87 |
| ATOM | 1029 | O | GLY | 293 | 77.432 | 40.843 | 27.698 | 1.00 | 35.43 |
| ATOM | 1030 | N | VAL | 294 | 77.392 | 39.848 | 29.714 | 1.00 | 31.88 |
| ATOM | 1031 | CA | VAL | 294 | 77.866 | 38.561 | 29.217 | 1.00 | 35.77 |
| ATOM | 1032 | CB | VAL | 294 | 78.232 | 37.590 | 30.363 | 1.00 | 34.29 |
| ATOM | 1033 | CG1 | VAL | 294 | 79.462 | 38.092 | 31.095 | 1.00 | 37.54 |
| ATOM | 1034 | CG2 | VAL | 294 | 77.065 | 37.425 | 31.322 | 1.00 | 25.62 |
| ATOM | 1035 | C | VAL | 294 | 76.882 | 37.879 | 28.274 | 1.00 | 35.89 |
| ATOM | 1036 | O | VAL | 294 | 77.263 | 36.960 | 27.541 | 1.00 | 37.99 |
| ATOM | 1037 | N | VAL | 295 | 75.619 | 38.304 | 28.305 | 1.00 | 34.41 |
| ATOM | 1038 | CA | VAL | 295 | 74.616 | 37.728 | 27.413 | 1.00 | 32.98 |
| ATOM | 1039 | CB | VAL | 295 | 73.208 | 38.298 | 27.677 | 1.00 | 31.25 |

APPENDIX 5-continued

TR_IPBR2.PDB

| ATOM | 1040 | CG1 | VAL | 295 | 72.208 | 37.706 | 26.694 | 1.00 | 23.54 |
|------|------|-----|-----|-----|--------|--------|--------|------|-------|
| ATOM | 1041 | CG2 | VAL | 295 | 72.783 | 37.993 | 29.101 | 1.00 | 23.07 |
| ATOM | 1042 | C   | VAL | 295 | 75.057 | 38.062 | 25.993 | 1.00 | 33.92 |
| ATOM | 1043 | O   | VAL | 295 | 74.932 | 37.238 | 25.090 | 1.00 | 36.95 |
| ATOM | 1044 | N   | SER | 296 | 75.625 | 39.253 | 25.820 | 1.00 | 31.27 |
| ATOM | 1045 | CA  | SER | 296 | 76.118 | 39.695 | 24.521 | 1.00 | 33.38 |
| ATOM | 1046 | CB  | SER | 296 | 76.667 | 41.115 | 24.620 | 1.00 | 24.78 |
| ATOM | 1047 | OG  | SER | 296 | 77.368 | 41.478 | 23.449 | 1.00 | 25.43 |
| ATOM | 1048 | C   | SER | 296 | 77.216 | 38.748 | 24.045 | 1.00 | 35.86 |
| ATOM | 1049 | O   | SER | 296 | 77.220 | 38.324 | 22.886 | 1.00 | 39.60 |
| ATOM | 1050 | N   | ASP | 297 | 78.135 | 38.402 | 24.943 | 1.00 | 37.41 |
| ATOM | 1051 | CA  | ASP | 297 | 79.227 | 37.490 | 24.602 | 1.00 | 35.39 |
| ATOM | 1052 | CB  | ASP | 297 | 80.147 | 37.269 | 25.808 | 1.00 | 43.07 |
| ATOM | 1053 | CG  | ASP | 297 | 80.839 | 38.540 | 26.266 | 1.00 | 45.07 |
| ATOM | 1054 | OD1 | ASP | 297 | 81.175 | 39.398 | 25.419 | 1.00 | 48.02 |
| ATOM | 1055 | OD2 | ASP | 297 | 81.064 | 38.670 | 27.485 | 1.00 | 50.13 |
| ATOM | 1056 | C   | ASP | 297 | 78.662 | 36.145 | 24.161 | 1.00 | 30.87 |
| ATOM | 1057 | O   | ASP | 297 | 79.155 | 35.534 | 23.213 | 1.00 | 33.92 |
| ATOM | 1058 | N   | ALA | 298 | 77.625 | 35.698 | 24.861 | 1.00 | 28.96 |
| ATOM | 1059 | CA  | ALA | 298 | 76.971 | 34.428 | 24.574 | 1.00 | 30.60 |
| ATOM | 1060 | CB  | ALA | 298 | 75.889 | 34.157 | 25.610 | 1.00 | 27.56 |
| ATOM | 1061 | C   | ALA | 298 | 76.377 | 34.408 | 23.163 | 1.00 | 33.04 |
| ATOM | 1062 | O   | ALA | 298 | 76.538 | 33.426 | 22.426 | 1.00 | 32.48 |
| ATOM | 1063 | N   | ILE | 299 | 75.706 | 35.493 | 22.786 | 1.00 | 30.92 |
| ATOM | 1064 | CA  | ILE | 299 | 75.091 | 35.588 | 21.468 | 1.00 | 24.71 |
| ATOM | 1065 | CB  | ILE | 299 | 74.138 | 36.789 | 21.368 | 1.00 | 22.98 |
| ATOM | 1066 | CG2 | ILE | 299 | 73.430 | 36.786 | 20.018 | 1.00 | 21.90 |
| ATOM | 1067 | CG1 | ILE | 299 | 73.091 | 36.707 | 22.477 | 1.00 | 20.91 |
| ATOM | 1068 | CD1 | ILE | 299 | 72.266 | 37.951 | 22.634 | 1.00 | 19.86 |
| ATOM | 1069 | C   | ILE | 299 | 76.168 | 35.680 | 20.395 | 1.00 | 26.77 |
| ATOM | 1070 | O   | ILE | 299 | 76.036 | 35.069 | 19.335 | 1.00 | 30.21 |
| ATOM | 1071 | N   | PHE | 300 | 77.238 | 36.428 | 20.673 | 1.00 | 29.08 |
| ATOM | 1072 | CA  | PHE | 300 | 78.345 | 36.562 | 19.726 | 1.00 | 28.06 |
| ATOM | 1073 | CB  | PHE | 300 | 79.386 | 37.565 | 20.235 | 1.00 | 29.06 |
| ATOM | 1074 | CG  | PHE | 300 | 79.289 | 38.920 | 19.590 | 1.00 | 28.14 |
| ATOM | 1075 | CD1 | PHE | 300 | 78.449 | 39.896 | 20.113 | 1.00 | 27.20 |
| ATOM | 1076 | CD2 | PHE | 300 | 80.017 | 39.209 | 18.437 | 1.00 | 29.11 |
| ATOM | 1077 | CE1 | PHE | 300 | 78.332 | 41.139 | 19.499 | 1.00 | 28.18 |
| ATOM | 1078 | CE2 | PHE | 300 | 79.908 | 40.450 | 17.815 | 1.00 | 29.07 |
| ATOM | 1079 | CZ  | PHE | 300 | 79.064 | 41.416 | 18.348 | 1.00 | 22.61 |
| ATOM | 1080 | C   | PHE | 300 | 78.991 | 35.201 | 19.485 | 1.00 | 29.00 |
| ATOM | 1081 | O   | PHE | 300 | 79.278 | 34.833 | 18.344 | 1.00 | 30.35 |
| ATOM | 1082 | N   | GLU | 301 | 79.183 | 34.442 | 20.560 | 1.00 | 31.81 |
| ATOM | 1083 | CA  | GLU | 301 | 79.767 | 33.111 | 20.470 | 1.00 | 34.96 |
| ATOM | 1084 | CB  | GLU | 301 | 79.962 | 32.528 | 21.865 | 1.00 | 30.78 |
| ATOM | 1085 | C   | GLU | 301 | 78.850 | 32.210 | 19.634 | 1.00 | 35.49 |
| ATOM | 1086 | O   | GLU | 301 | 79.322 | 31.438 | 18.793 | 1.00 | 35.76 |
| ATOM | 1087 | N   | LEU | 302 | 77.543 | 32.313 | 19.869 | 1.00 | 32.14 |
| ATOM | 1088 | CA  | LEU | 302 | 76.559 | 31.522 | 19.132 | 1.00 | 25.56 |
| ATOM | 1089 | CB  | LEU | 302 | 75.147 | 31.760 | 19.682 | 1.00 | 23.33 |
| ATOM | 1090 | CG  | LEU | 302 | 73.992 | 31.006 | 19.010 | 1.00 | 28.73 |
| ATOM | 1091 | CD1 | LEU | 302 | 74.093 | 29.509 | 19.270 | 1.00 | 23.93 |
| ATOM | 1092 | CD2 | LEU | 302 | 72.667 | 31.551 | 19.514 | 1.00 | 21.32 |
| ATOM | 1093 | C   | LEU | 302 | 76.617 | 31.885 | 17.650 | 1.00 | 23.10 |
| ATOM | 1094 | O   | LEU | 302 | 76.664 | 31.001 | 16.796 | 1.00 | 26.79 |
| ATOM | 1095 | N   | GLY | 303 | 76.672 | 33.181 | 17.353 | 1.00 | 22.79 |
| ATOM | 1096 | CA  | GLY | 303 | 76.745 | 33.631 | 15.974 | 1.00 | 21.60 |
| ATOM | 1097 | C   | GLY | 303 | 77.978 | 33.104 | 15.256 | 1.00 | 30.42 |
| ATOM | 1098 | O   | GLY | 303 | 77.889 | 32.619 | 14.125 | 1.00 | 29.18 |
| ATOM | 1099 | N   | ALA | 304 | 79.132 | 33.182 | 15.912 | 1.00 | 31.15 |
| ATOM | 1100 | CA  | ALA | 304 | 80.375 | 32.703 | 15.313 | 1.00 | 35.44 |
| ATOM | 1101 | CB  | ALA | 304 | 81.562 | 32.995 | 16.235 | 1.00 | 29.16 |
| ATOM | 1102 | C   | ALA | 304 | 80.300 | 31.208 | 14.978 | 1.00 | 35.15 |
| ATOM | 1103 | O   | ALA | 304 | 80.705 | 30.785 | 13.891 | 1.00 | 37.13 |
| ATOM | 1104 | N   | SER | 305 | 79.753 | 30.414 | 15.892 | 1.00 | 33.91 |
| ATOM | 1105 | CA  | SER | 305 | 79.638 | 28.979 | 15.663 | 1.00 | 36.39 |
| ATOM | 1106 | CB  | SER | 305 | 79.395 | 28.237 | 16.980 | 1.00 | 32.71 |
| ATOM | 1107 | OG  | SER | 305 | 78.265 | 28.749 | 17.663 | 1.00 | 48.66 |
| ATOM | 1108 | C   | SER | 305 | 78.558 | 28.619 | 14.641 | 1.00 | 37.61 |
| ATOM | 1109 | O   | SER | 305 | 78.747 | 27.697 | 13.845 | 1.00 | 39.92 |
| ATOM | 1110 | N   | LEU | 306 | 77.443 | 29.349 | 14.651 | 1.00 | 38.21 |
| ATOM | 1111 | CA  | LEU | 306 | 76.350 | 29.092 | 13.714 | 1.00 | 35.65 |
| ATOM | 1112 | CB  | LEU | 306 | 75.094 | 29.894 | 14.077 | 1.00 | 25.49 |
| ATOM | 1113 | CG  | LEU | 306 | 74.209 | 29.374 | 15.212 | 1.00 | 26.18 |
| ATOM | 1114 | CD1 | LEU | 306 | 72.988 | 30.262 | 15.361 | 1.00 | 23.40 |
| ATOM | 1115 | CD2 | LEU | 306 | 73.777 | 27.952 | 14.921 | 1.00 | 23.57 |
| ATOM | 1116 | C   | LEU | 306 | 76.123 | 29.356 | 12.258 | 1.00 | 38.05 |

APPENDIX 5-continued

TR_IPBR2.PDB

| ATOM | 1117 | O | LEU | 306 | 76.092 | 28.809 | 11.353 | 1.00 | 37.22 |
|---|---|---|---|---|---|---|---|---|---|
| ATOM | 1118 | N | SER | 307 | 77.743 | 30.185 | 12.030 | 1.00 | 40.41 |
| ATOM | 1119 | CA | SER | 307 | 78.199 | 30.511 | 10.677 | 1.00 | 40.85 |
| ATOM | 1120 | CB | SER | 307 | 79.415 | 31.442 | 10.736 | 1.00 | 37.32 |
| ATOM | 1121 | OG | SER | 307 | 79.086 | 32.678 | 11.344 | 1.00 | 56.20 |
| ATOM | 1122 | C | SER | 307 | 78.550 | 29.270 | 9.852 | 1.00 | 39.87 |
| ATOM | 1123 | O | SER | 307 | 78.221 | 29.191 | 8.670 | 1.00 | 44.27 |
| ATOM | 1124 | N | ALA | 308 | 79.207 | 28.305 | 10.487 | 1.00 | 39.29 |
| ATOM | 1125 | CA | ALA | 308 | 79.609 | 27.066 | 9.826 | 1.00 | 33.10 |
| ATOM | 1126 | CB | ALA | 308 | 80.607 | 26.310 | 10.696 | 1.00 | 33.37 |
| ATOM | 1127 | C | ALA | 308 | 78.403 | 26.177 | 9.502 | 1.00 | 34.07 |
| ATOM | 1128 | O | ALA | 308 | 78.467 | 25.340 | 8.600 | 1.00 | 40.61 |
| ATOM | 1129 | N | PHE | 309 | 77.305 | 26.368 | 10.230 | 1.00 | 31.85 |
| ATOM | 1130 | CA | PHE | 309 | 76.095 | 25.581 | 10.015 | 1.00 | 35.24 |
| ATOM | 1131 | CB | PHE | 309 | 75.149 | 25.698 | 11.219 | 1.00 | 33.69 |
| ATOM | 1132 | CG | PHE | 309 | 75.618 | 24.954 | 12.437 | 1.00 | 36.16 |
| ATOM | 1133 | CD1 | PHE | 309 | 76.785 | 25.327 | 13.090 | 1.00 | 43.79 |
| ATOM | 1134 | CD2 | PHE | 309 | 74.903 | 23.867 | 12.922 | 1.00 | 38.03 |
| ATOM | 1135 | CE1 | PHE | 309 | 77.237 | 24.627 | 14.210 | 1.00 | 41.12 |
| ATOM | 1136 | CE2 | PHE | 309 | 75.346 | 23.161 | 14.040 | 1.00 | 41.08 |
| ATOM | 1137 | CZ | PHE | 309 | 76.514 | 23.543 | 14.683 | 1.00 | 38.37 |
| ATOM | 1138 | C | PHE | 309 | 75.361 | 25.934 | 8.720 | 1.00 | 36.31 |
| ATOM | 1139 | O | PHE | 309 | 74.633 | 25.095 | 8.173 | 1.00 | 37.84 |
| ATOM | 1140 | N | ASN | 310 | 75.567 | 27.155 | 8.225 | 1.00 | 35.22 |
| ATOM | 1141 | CA | ASN | 310 | 74.933 | 27.625 | 6.988 | 1.00 | 43.66 |
| ATOM | 1142 | CB | ASN | 310 | 15.536 | 26.930 | 5.760 | 1.00 | 54.13 |
| ATOM | 1143 | CG | ASN | 310 | 76.980 | 27.339 | 5.501 | 1.00 | 68.29 |
| ATOM | 1144 | OD1 | ASN | 310 | 77.297 | 28.527 | 5.412 | 1.00 | 74.62 |
| ATOM | 1145 | ND2 | ASN | 310 | 77.859 | 26.348 | 5.352 | 1.00 | 68.85 |
| ATOM | 1146 | C | ASN | 310 | 73.430 | 27.385 | 7.013 | 1.00 | 38.37 |
| ATOM | 1147 | O | ASN | 310 | 72.882 | 26.735 | 6.123 | 1.00 | 36.70 |
| ATOM | 1148 | N | LEU | 311 | 72.780 | 27.865 | 8.062 | 1.00 | 35.22 |
| ATOM | 1149 | CA | LEU | 311 | 71.345 | 27.690 | 8.206 | 1.00 | 34.32 |
| ATOM | 1150 | CB | LEU | 311 | 70.895 | 28.054 | 9.630 | 1.00 | 30.19 |
| ATOM | 1151 | CG | LEU | 311 | 71.458 | 27.306 | 10.845 | 1.00 | 26.76 |
| ATOM | 1152 | CD1 | LEU | 311 | 70.792 | 27.847 | 12.104 | 1.00 | 21.37 |
| ATOM | 1153 | CD2 | LEU | 311 | 71.217 | 25.813 | 10.722 | 1.00 | 22.95 |
| ATOM | 1154 | C | LEU | 311 | 70.601 | 28.561 | 7.206 | 1.00 | 34.64 |
| ATOM | 1155 | O | LEU | 311 | 71.087 | 29.625 | 6.820 | 1.00 | 37.70 |
| ATOM | 1156 | N | ASP | 312 | 69.444 | 28.091 | 6.752 | 1.00 | 29.40 |
| ATOM | 1157 | CA | ASP | 312 | 68.634 | 28.867 | 5.823 | 1.00 | 28.65 |
| ATOM | 1158 | CB | ASP | 312 | 68.302 | 28.061 | 4.545 | 1.00 | 24.79 |
| ATOM | 1159 | CG | ASP | 312 | 67.459 | 26.804 | 4.804 | 1.00 | 21.47 |
| ATOM | 1160 | OD1 | ASP | 312 | 66.994 | 26.549 | 5.932 | 1.00 | 27.92 |
| ATOM | 1161 | OD2 | ASP | 312 | 67.250 | 26.057 | 3.832 | 1.00 | 27.53 |
| ATOM | 1162 | C | ASP | 312 | 67.380 | 29.346 | 6.557 | 1.00 | 25.92 |
| ATOM | 1163 | O | ASP | 312 | 67.167 | 28.985 | 7.717 | 1.00 | 26.98 |
| ATOM | 1164 | N | ASP | 313 | 66.540 | 30.122 | 5.878 | 1.00 | 21.78 |
| ATOM | 1165 | CA | ASP | 313 | 65.315 | 30.653 | 6.471 | 1.00 | 22.89 |
| ATOM | 1166 | CB | ASP | 313 | 64.517 | 31.458 | 5.439 | 1.00 | 29.19 |
| ATOM | 1167 | CG | ASP | 313 | 65.216 | 32.739 | 5.025 | 1.00 | 36.82 |
| ATOM | 1168 | OD1 | ASP | 313 | 65.985 | 33.285 | 5.845 | 1.00 | 41.51 |
| ATOM | 1169 | OD2 | ASP | 313 | 64.997 | 33.203 | 3.883 | 1.00 | 44.19 |
| ATOM | 1170 | C | ASP | 313 | 64.421 | 29.587 | 7.085 | 1.00 | 25.09 |
| ATOM | 1171 | O | ASP | 313 | 63.778 | 29.829 | 8.110 | 1.00 | 27.60 |
| ATOM | 1172 | N | THR | 314 | 64.363 | 28.420 | 6.449 | 1.00 | 20.90 |
| ATOM | 1173 | CA | THR | 314 | 63.538 | 27.322 | 6.942 | 1.00 | 22.71 |
| ATOM | 1174 | CB | THR | 314 | 63.408 | 26.208 | 5.884 | 1.00 | 22.07 |
| ATOM | 1175 | OG1 | THR | 314 | 62.825 | 26.746 | 4.693 | 1.00 | 23.15 |
| ATOM | 1176 | CG2 | THR | 314 | 62.542 | 25.079 | 6.401 | 1.00 | 18.17 |
| ATOM | 1177 | C | THR | 314 | 64.080 | 26.734 | 8.249 | 1.00 | 19.95 |
| ATOM | 1178 | O | THR | 314 | 63.326 | 26.477 | 9.182 | 1.00 | 22.40 |
| ATOM | 1179 | N | GLU | 315 | 65.391 | 26.536 | 8.318 | 1.00 | 20.01 |
| ATOM | 1180 | CA | GLU | 315 | 65.997 | 25.987 | 9.523 | 1.00 | 19.40 |
| ATOM | 1181 | CB | GLU | 315 | 67.454 | 25.626 | 9.254 | 1.00 | 11.72 |
| ATOM | 1182 | CG | GLU | 315 | 67.544 | 24.440 | 8.322 | 1.00 | 13.43 |
| ATOM | 1183 | CD | GLU | 315 | 68.925 | 24.157 | 7.791 | 1.00 | 18.51 |
| ATOM | 1184 | OE1 | GLU | 315 | 69.666 | 25.107 | 7.451 | 1.00 | 23.24 |
| ATOM | 1185 | OE2 | GLU | 315 | 69.254 | 22.962 | 7.673 | 1.00 | 24.23 |
| ATOM | 1186 | C | GLU | 315 | 65.833 | 26.960 | 10.681 | 1.00 | 20.12 |
| ATOM | 1187 | O | GLU | 315 | 65.425 | 26.570 | 11.777 | 1.00 | 20.53 |
| ATOM | 1188 | N | VAL | 316 | 66.055 | 28.240 | 10.406 | 1.00 | 21.79 |
| ATOM | 1189 | CA | VAL | 316 | 65.898 | 29.270 | 11.425 | 1.00 | 18.14 |
| ATOM | 1190 | CB | VAL | 316 | 66.346 | 30.659 | 10.898 | 1.00 | 18.97 |
| ATOM | 1191 | CG1 | VAL | 316 | 66.040 | 31.741 | 11.929 | 1.00 | 19.08 |
| ATOM | 1192 | CG2 | VAL | 316 | 67.840 | 30.641 | 10.537 | 1.00 | 17.97 |
| ATOM | 1193 | C | VAL | 316 | 64.430 | 29.332 | 11.880 | 1.00 | 22.54 |

APPENDIX 5-continued

TR_IPBR2.PDB

| ATOM | 1194 | O   | VAL | 316 | 64.146 | 29.433 | 13.072 | 1.00 | 26.47 |
|------|------|-----|-----|-----|--------|--------|--------|------|-------|
| ATOM | 1195 | N   | ALA | 317 | 63.505 | 29.242 | 10.924 | 1.00 | 19.66 |
| ATOM | 1196 | CA  | ALA | 317 | 62.076 | 29.286 | 11.216 | 1.00 | 16.99 |
| ATOM | 1197 | CB  | ALA | 317 | 61.279 | 29.329 | 9.926  | 1.00 | 17.79 |
| ATOM | 1198 | C   | ALA | 317 | 61.619 | 28.105 | 12.063 | 1.00 | 14.12 |
| ATOM | 1199 | O   | ALA | 317 | 60.808 | 28.263 | 12.970 | 1.00 | 17.04 |
| ATOM | 1200 | N   | LEU | 318 | 62.104 | 26.911 | 11.740 | 1.00 | 20.37 |
| ATOM | 1201 | CA  | LEU | 318 | 61.725 | 25.714 | 12.485 | 1.00 | 21.12 |
| ATOM | 1202 | CB  | LEU | 318 | 62.131 | 24.448 | 11.718 | 1.00 | 21.80 |
| ATOM | 1203 | CG  | LEU | 318 | 61.364 | 24.265 | 10.398 | 1.00 | 18.11 |
| ATOM | 1204 | CD1 | LEU | 318 | 61.946 | 23.125 | 9.594  | 1.00 | 16.79 |
| ATOM | 1205 | CD2 | LEU | 318 | 59.891 | 24.024 | 10.676 | 1.00 | 12.66 |
| ATOM | 1206 | C   | LEU | 318 | 62.335 | 25.752 | 13.880 | 1.00 | 22.03 |
| ATOM | 1207 | O   | LEU | 318 | 61.688 | 25.373 | 14.858 | 1.00 | 21.35 |
| ATOM | 1208 | N   | LEU | 319 | 63.564 | 26.257 | 13.964 | 1.00 | 20.03 |
| ATOM | 1209 | CA  | LEU | 319 | 64.260 | 26.395 | 15.236 | 1.00 | 20.24 |
| ATOM | 1210 | CB  | LEU | 319 | 65.657 | 26.960 | 15.001 | 1.00 | 19.07 |
| ATOM | 1211 | CG  | LEU | 319 | 66.594 | 27.108 | 16.196 | 1.00 | 27.61 |
| ATOM | 1212 | CD1 | LEU | 319 | 66.518 | 25.883 | 17.083 | 1.00 | 29.73 |
| ATOM | 1213 | CD2 | LEU | 319 | 68.012 | 27.326 | 15.699 | 1.00 | 20.98 |
| ATOM | 1214 | C   | LEU | 319 | 63.422 | 27.334 | 16.118 | 1.00 | 21.16 |
| ATOM | 1215 | O   | LEU | 319 | 63.144 | 27.032 | 17.279 | 1.00 | 26.65 |
| ATOM | 1216 | N   | GLN | 320 | 62.958 | 28.439 | 15.539 | 1.00 | 20.77 |
| ATOM | 1217 | CA  | GLN | 320 | 62.119 | 29.390 | 16.265 | 1.00 | 17.87 |
| ATOM | 1218 | CB  | GLN | 320 | 61.781 | 30.594 | 15.388 | 1.00 | 18.74 |
| ATOM | 1219 | CG  | GLN | 320 | 62.957 | 31.496 | 15.111 | 1.00 | 21.07 |
| ATOM | 1220 | CD  | GLN | 320 | 62.637 | 32.617 | 14.150 | 1.00 | 22.88 |
| ATOM | 1221 | OE1 | GLN | 320 | 61.571 | 32.653 | 13.528 | 1.00 | 26.07 |
| ATOM | 1222 | NE2 | GLN | 320 | 63.574 | 33.537 | 14.006 | 1.00 | 20.11 |
| ATOM | 1223 | C   | GLN | 320 | 60.829 | 28.728 | 16.730 | 1.00 | 19.08 |
| ATOM | 1224 | O   | GLN | 320 | 60.368 | 28.976 | 17.844 | 1.00 | 23.39 |
| ATOM | 1225 | N   | ALA | 321 | 60.251 | 27.886 | 15.876 | 1.00 | 22.71 |
| ATOM | 1226 | CA  | ALA | 321 | 59.010 | 27.187 | 16.201 | 1.00 | 18.86 |
| ATOM | 1227 | CB  | ALA | 321 | 58.495 | 26.422 | 14.993 | 1.00 | 17.22 |
| ATOM | 1228 | C   | ALA | 321 | 59.220 | 26.235 | 17.376 | 1.00 | 19.85 |
| ATOM | 1229 | O   | ALA | 321 | 58.362 | 26.119 | 18.250 | 1.00 | 19.60 |
| ATOM | 1230 | N   | VAL | 322 | 60.368 | 25.561 | 17.396 | 1.00 | 20.25 |
| ATOM | 1231 | CA  | VAL | 322 | 60.693 | 24.628 | 18.469 | 1.00 | 21.32 |
| ATOM | 1232 | CB  | VAL | 322 | 61.956 | 23.800 | 18.116 | 1.00 | 20.46 |
| ATOM | 1233 | CG1 | VAL | 322 | 62.418 | 22.971 | 19.304 | 1.00 | 20.39 |
| ATOM | 1234 | CG2 | VAL | 322 | 61.662 | 22.890 | 16.930 | 1.00 | 16.83 |
| ATOM | 1235 | C   | VAL | 322 | 60.880 | 25.393 | 19.785 | 1.00 | 20.67 |
| ATOM | 1236 | O   | VAL | 322 | 60.444 | 24.941 | 20.850 | 1.00 | 21.28 |
| ATOM | 1237 | N   | LEU | 323 | 61.492 | 26.574 | 19.701 | 1.00 | 21.14 |
| ATOM | 1238 | CA  | LEU | 323 | 61.722 | 27.417 | 20.869 | 1.00 | 22.94 |
| ATOM | 1239 | CB  | LEU | 323 | 62.610 | 28.608 | 20.511 | 1.00 | 16.12 |
| ATOM | 1240 | CG  | LEU | 323 | 64.051 | 28.291 | 20.115 | 1.00 | 22.28 |
| ATOM | 1241 | CD1 | LEU | 323 | 64.719 | 29.532 | 19.528 | 1.00 | 14.87 |
| ATOM | 1242 | CD2 | LEU | 323 | 64.816 | 27.750 | 21.320 | 1.00 | 21.55 |
| ATOM | 1243 | C   | LEU | 323 | 60.398 | 27.932 | 21.410 | 1.00 | 22.55 |
| ATOM | 1244 | O   | LEU | 323 | 60.185 | 27.986 | 22.615 | 1.00 | 25.21 |
| ATOM | 1245 | N   | LEU | 324 | 59.507 | 28.300 | 20.502 | 1.00 | 24.15 |
| ATOM | 1246 | CA  | LEU | 324 | 58.200 | 28.827 | 20.855 | 1.00 | 19.88 |
| ATOM | 1247 | CB  | LEU | 324 | 57.499 | 29.384 | 19.608 | 1.00 | 15.20 |
| ATOM | 1248 | CG  | LEU | 324 | 56.067 | 29.908 | 19.767 | 1.00 | 17.21 |
| ATOM | 1249 | CD1 | LEU | 324 | 56.021 | 31.161 | 20.637 | 1.00 | 15.99 |
| ATOM | 1250 | CD2 | LEU | 324 | 55.496 | 30.268 | 18.395 | 1.00 | 20.03 |
| ATOM | 1251 | C   | LEU | 324 | 57.311 | 27.795 | 21.536 | 1.00 | 19.83 |
| ATOM | 1252 | O   | LEU | 324 | 56.767 | 28.064 | 22.609 | 1.00 | 24.47 |
| ATOM | 1253 | N   | MET | 325 | 57.197 | 26.603 | 20.956 | 1.00 | 25.02 |
| ATOM | 1254 | CA  | MET | 325 | 56.339 | 25.563 | 21.522 | 1.00 | 26.72 |
| ATOM | 1255 | CB  | MET | 325 | 55.823 | 24.644 | 20.410 | 1.00 | 30.03 |
| ATOM | 1256 | CG  | MET | 325 | 55.129 | 25.358 | 19.241 | 1.00 | 25.09 |
| ATOM | 1257 | SD  | MET | 325 | 53.714 | 26.409 | 19.672 | 1.00 | 27.29 |
| ATOM | 1258 | CE  | MET | 325 | 52.503 | 25.220 | 20.084 | 1.00 | 20.67 |
| ATOM | 1259 | C   | MET | 325 | 56.995 | 24.736 | 22.635 | 1.00 | 28.94 |
| ATOM | 1260 | O   | MET | 325 | 56.881 | 23.510 | 22.672 | 1.00 | 32.94 |
| ATOM | 1261 | N   | SER | 326 | 57.642 | 25.418 | 23.569 | 1.00 | 29.36 |
| ATOM | 1262 | CA  | SER | 326 | 58.311 | 24.759 | 24.680 | 1.00 | 31.62 |
| ATOM | 1263 | CB  | SER | 326 | 59.554 | 25.559 | 25.064 | 1.00 | 38.13 |
| ATOM | 1264 | OG  | SER | 326 | 60.277 | 24.949 | 26.119 | 1.00 | 48.99 |
| ATOM | 1265 | C   | SER | 326 | 57.361 | 24.653 | 25.871 | 1.00 | 33.69 |
| ATOM | 1266 | O   | SER | 326 | 56.620 | 25.594 | 26.166 | 1.00 | 33.66 |
| ATOM | 1267 | N   | THR | 327 | 57.356 | 23.499 | 26.536 | 1.00 | 38.27 |
| ATOM | 1268 | CA  | THR | 327 | 56.497 | 23.306 | 27.701 | 1.00 | 38.98 |
| ATOM | 1269 | CB  | THR | 327 | 55.875 | 21.896 | 27.730 | 1.00 | 33.30 |
| ATOM | 1270 | OG1 | THR | 327 | 56.908 | 20.911 | 27.627 | 1.00 | 44.01 |

APPENDIX 5-continued

TR_IPBR2.PDB

| ATOM | 1271 | CG2 | THR | 327 | 54.888 | 21.722 | 26.587 | 1.00 | 38.09 |
|---|---|---|---|---|---|---|---|---|---|
| ATOM | 1272 | C | THR | 327 | 57.239 | 23.570 | 29.018 | 1.00 | 42.88 |
| ATOM | 1273 | O | THR | 327 | 56.702 | 23.325 | 30.099 | 1.00 | 43.36 |
| ATOM | 1274 | N | ASP | 328 | 58.462 | 24.091 | 28.924 | 1.00 | 45.92 |
| ATOM | 1275 | CA | ASP | 328 | 59.268 | 24.410 | 30.104 | 1.00 | 49.59 |
| ATOM | 1276 | CB | ASP | 328 | 60.760 | 24.411 | 29.760 | 1.00 | 59.87 |
| ATOM | 1277 | CG | ASP | 328 | 61.273 | 23.040 | 29.387 | 1.00 | 75.73 |
| ATOM | 1278 | OD1 | ASP | 328 | 62.008 | 22.939 | 28.382 | 1.00 | 85.81 |
| ATOM | 1279 | OD2 | ASP | 328 | 60.946 | 22.063 | 30.098 | 1.00 | 85.56 |
| ATOM | 1280 | C | ASP | 328 | 58.873 | 25.767 | 30.673 | 1.00 | 48.50 |
| ATOM | 1281 | O | ASP | 328 | 59.725 | 26.609 | 30.961 | 1.00 | 57.50 |
| ATOM | 1282 | N | ARG | 329 | 57.569 | 25.980 | 30.805 | 1.00 | 49.62 |
| ATOM | 1283 | CA | ARG | 329 | 57.032 | 27.222 | 31.340 | 1.00 | 50.52 |
| ATOM | 1284 | CB | ARG | 329 | 56.400 | 28.080 | 30.230 | 1.00 | 53.57 |
| ATOM | 1285 | CG | ARG | 329 | 57.376 | 28.828 | 29.324 | 1.00 | 51.09 |
| ATOM | 1286 | CD | ARG | 329 | 57.897 | 27.951 | 28.204 | 1.00 | 49.73 |
| ATOM | 1287 | NE | ARG | 329 | 58.692 | 28.699 | 27.233 | 1.00 | 47.44 |
| ATOM | 1288 | CZ | ARG | 329 | 60.005 | 28.569 | 27.080 | 1.00 | 54.28 |
| ATOM | 1289 | NH1 | ARG | 329 | 60.688 | 27.722 | 27.839 | 1.00 | 58.35 |
| ATOM | 1290 | NH2 | ARG | 329 | 60.631 | 29.256 | 26.136 | 1.00 | 51.92 |
| ATOM | 1291 | C | ARG | 329 | 55.970 | 26.870 | 32.375 | 1.00 | 51.90 |
| ATOM | 1292 | O | ARG | 329 | 55.378 | 25.790 | 32.324 | 1.00 | 50.77 |
| ATOM | 1293 | N | SER | 330 | 55.728 | 27.784 | 33.303 | 1.00 | 50.56 |
| ATOM | 1294 | CA | SER | 330 | 54.744 | 27.564 | 34.349 | 1.00 | 50.67 |
| ATOM | 1295 | CB | SER | 330 | 55.271 | 28.108 | 35.678 | 1.00 | 46.64 |
| ATOM | 1296 | C | SER | 330 | 53.404 | 28.213 | 34.004 | 1.00 | 47.63 |
| ATOM | 1297 | O | SER | 330 | 53.371 | 29.309 | 33.440 | 1.00 | 48.02 |
| ATOM | 1298 | N | GLY | 331 | 52.314 | 27.496 | 34.277 | 1.00 | 44.44 |
| ATOM | 1299 | CA | GLY | 331 | 50.977 | 28.023 | 34.044 | 1.00 | 38.77 |
| ATOM | 1300 | C | GLY | 331 | 50.236 | 27.710 | 32.756 | 1.00 | 41.74 |
| ATOM | 1301 | O | GLY | 331 | 49.147 | 28.246 | 32.537 | 1.00 | 49.57 |
| ATOM | 1302 | N | LEU | 332 | 50.783 | 26.841 | 31.912 | 1.00 | 39.75 |
| ATOM | 1303 | CA | LEU | 332 | 50.123 | 26.502 | 30.651 | 1.00 | 37.55 |
| ATOM | 1304 | CB | LEU | 332 | 51.107 | 25.829 | 29.694 | 1.00 | 32.36 |
| ATOM | 1305 | CG | LEU | 332 | 52.268 | 26.659 | 29.153 | 1.00 | 34.40 |
| ATOM | 1306 | CD1 | LEU | 332 | 53.207 | 25.749 | 28.379 | 1.00 | 30.22 |
| ATOM | 1307 | CD2 | LEU | 332 | 51.742 | 27.786 | 28.277 | 1.00 | 23.33 |
| ATOM | 1308 | C | LEU | 332 | 48.921 | 25.589 | 30.834 | 1.00 | 36.73 |
| ATOM | 1309 | O | LEU | 332 | 48.987 | 24.608 | 31.577 | 1.00 | 39.29 |
| ATOM | 1310 | N | LEU | 333 | 47.822 | 25.925 | 30.168 | 1.00 | 36.07 |
| ATOM | 1311 | CA | LEU | 333 | 46.615 | 25.107 | 30.215 | 1.00 | 39.58 |
| ATOM | 1312 | CB | LEU | 333 | 45.384 | 25.906 | 29.754 | 1.00 | 41.08 |
| ATOM | 1313 | CG | LEU | 333 | 44.601 | 26.883 | 30.644 | 1.00 | 47.59 |
| ATOM | 1314 | CD1 | LEU | 333 | 44.268 | 26.213 | 31.961 | 1.00 | 45.65 |
| ATOM | 1315 | CD2 | LEU | 333 | 45.366 | 28.171 | 30.874 | 1.00 | 47.42 |
| ATOM | 1316 | C | LEU | 333 | 46.791 | 23.911 | 29.278 | 1.00 | 40.00 |
| ATOM | 1317 | O | LEU | 333 | 46.690 | 22.754 | 29.689 | 1.00 | 44.77 |
| ATOM | 1318 | N | CYA | 334 | 47.102 | 24.213 | 28.022 | 1.00 | 37.70 |
| ATOM | 1319 | CA | CYA | 334 | 47.265 | 23.209 | 26.968 | 1.00 | 36.04 |
| ATOM | 1320 | CB | CYA | 334 | 46.815 | 23.808 | 25.635 | 1.00 | 40.64 |
| ATOM | 1321 | SG | CYA | 334 | 45.280 | 24.738 | 25.758 | 1.00 | 44.31 |
| ATOM | 1322 | AS | CYA | 334 | 43.972 | 22.946 | 25.380 | 1.00 | 76.30 |
| ATOM | 1323 | C | CYA | 334 | 48.668 | 22.617 | 26.815 | 1.00 | 34.91 |
| ATOM | 1324 | O | CYA | 334 | 49.237 | 22.615 | 25.722 | 1.00 | 37.63 |
| ATOM | 1325 | N | VAL | 335 | 49.189 | 22.056 | 27.903 | 1.00 | 35.43 |
| ATOM | 1326 | CA | VAL | 335 | 50.518 | 21.452 | 27.909 | 1.00 | 34.27 |
| ATOM | 1327 | CB | VAL | 335 | 50.861 | 20.868 | 29.298 | 1.00 | 34.21 |
| ATOM | 1328 | CG1 | VAL | 335 | 52.261 | 20.258 | 29.292 | 1.00 | 33.66 |
| ATOM | 1329 | CG2 | VAL | 335 | 50.755 | 21.945 | 30.362 | 1.00 | 31.77 |
| ATOM | 1330 | C | VAL | 335 | 50.662 | 20.349 | 26.865 | 1.00 | 37.14 |
| ATOM | 1331 | O | VAL | 335 | 51.639 | 20.320 | 26.114 | 1.00 | 37.59 |
| ATOM | 1332 | N | ASP | 336 | 49.683 | 19.451 | 26.813 | 1.00 | 39.99 |
| ATOM | 1333 | CA | ASP | 336 | 49.705 | 18.339 | 25.866 | 1.00 | 41.64 |
| ATOM | 1334 | CB | ASP | 336 | 48.532 | 17.392 | 26.146 | 1.00 | 54.27 |
| ATOM | 1335 | CG | ASP | 336 | 48.596 | 16.118 | 25.322 | 1.00 | 67.42 |
| ATOM | 1336 | OD1 | ASP | 336 | 47.915 | 16.049 | 24.274 | 1.00 | 70.98 |
| ATOM | 1337 | OD2 | ASP | 336 | 49.337 | 15.191 | 25.717 | 1.00 | 76.88 |
| ATOM | 1338 | C | ASP | 336 | 49.702 | 18.762 | 24.393 | 1.00 | 38.31 |
| ATOM | 1339 | O | ASP | 336 | 50.469 | 18.229 | 23.586 | 1.00 | 37.46 |
| ATOM | 1340 | N | LYS | 337 | 48.853 | 19.729 | 24.052 | 1.00 | 30.23 |
| ATOM | 1341 | CA | LYS | 337 | 48.740 | 20.211 | 22.676 | 1.00 | 29.21 |
| ATOM | 1342 | CB | LYS | 337 | 47.561 | 21.189 | 22.559 | 1.00 | 30.53 |
| ATOM | 1343 | CG | LYS | 337 | 47.012 | 21.360 | 21.162 | 1.00 | 51.63 |
| ATOM | 1344 | CD | LYS | 337 | 45.636 | 21.997 | 21.186 | 1.00 | 59.57 |
| ATOM | 1345 | CE | LYS | 337 | 45.066 | 22.115 | 19.774 | 1.00 | 66.05 |
| ATOM | 1346 | NZ | LYS | 337 | 43.673 | 22.693 | 19.776 | 1.00 | 67.20 |
| ATOM | 1347 | C | LYS | 337 | 50.054 | 20.873 | 22.249 | 1.00 | 28.33 |

APPENDIX 5-continued

TR_IPBR2.PDB

| ATOM | 1348 | O   | LYS | 337 | 50.581 | 20.594 | 21.170 | 1.00 | 26.08 |
|------|------|-----|-----|-----|--------|--------|--------|------|-------|
| ATOM | 1349 | N   | ILE | 338 | 50.609 | 21.696 | 23.141 | 1.00 | 26.74 |
| ATOM | 1350 | CA  | ILE | 338 | 51.873 | 22.390 | 22.902 | 1.00 | 25.42 |
| ATOM | 1351 | CB  | ILE | 338 | 52.177 | 23.379 | 24.052 | 1.00 | 23.57 |
| ATOM | 1352 | CG2 | ILE | 338 | 53.559 | 23.991 | 23.874 | 1.00 | 22.59 |
| ATOM | 1353 | CG1 | ILE | 338 | 51.105 | 24.471 | 24.096 | 1.00 | 23.57 |
| ATOM | 1354 | CD1 | ILE | 338 | 51.157 | 25.362 | 25.333 | 1.00 | 24.30 |
| ATOM | 1355 | C   | ILE | 338 | 53.018 | 21.382 | 22.768 | 1.00 | 29.20 |
| ATOM | 1356 | O   | ILE | 338 | 53.905 | 21.537 | 21.916 | 1.00 | 31.59 |
| ATOM | 1357 | N   | GLU | 339 | 52.977 | 20.340 | 23.595 | 1.00 | 34.82 |
| ATOM | 1358 | CA  | GLU | 339 | 53.980 | 19.277 | 23.597 | 1.00 | 34.23 |
| ATOM | 1359 | CB  | GLU | 339 | 53.639 | 18.256 | 24.681 | 1.00 | 40.38 |
| ATOM | 1360 | CG  | GLU | 339 | 54.785 | 17.354 | 25.072 | 1.00 | 54.98 |
| ATOM | 1361 | CD  | GLU | 339 | 55.644 | 17.964 | 26.178 | 1.00 | 71.26 |
| ATOM | 1362 | OE1 | GLU | 339 | 56.766 | 18.444 | 25.858 | 1.00 | 77.82 |
| ATOM | 1363 | OE2 | GLU | 339 | 55.170 | 17.985 | 27.349 | 1.00 | 65.14 |
| ATOM | 1364 | C   | GLU | 339 | 53.972 | 18.582 | 22.231 | 1.00 | 34.42 |
| ATOM | 1365 | O   | GLU | 339 | 55.018 | 18.431 | 21.590 | 1.00 | 29.41 |
| ATOM | 1366 | N   | LYS | 340 | 52.778 | 18.189 | 21.786 | 1.00 | 34.13 |
| ATOM | 1367 | CA  | LYS | 340 | 52.592 | 17.513 | 20.502 | 1.00 | 32.05 |
| ATOM | 1368 | CB  | LYS | 340 | 51.121 | 17.105 | 20.325 | 1.00 | 34.59 |
| ATOM | 1369 | C   | LYS | 340 | 53.064 | 18.390 | 19.337 | 1.00 | 32.56 |
| ATOM | 1370 | O   | LYS | 340 | 53.762 | 17.913 | 18.441 | 1.00 | 32.93 |
| ATOM | 1371 | N   | SER | 341 | 52.725 | 19.677 | 19.374 | 1.00 | 31.42 |
| ATOM | 1372 | CA  | SER | 341 | 53.134 | 20.621 | 18.334 | 1.00 | 27.79 |
| ATOM | 1373 | CB  | SER | 341 | 52.559 | 22.009 | 18.601 | 1.00 | 27.85 |
| ATOM | 1374 | OG  | SER | 341 | 51.149 | 21.966 | 18.579 | 1.00 | 47.20 |
| ATOM | 1375 | C   | SER | 341 | 54.647 | 20.713 | 18.240 | 1.00 | 26.01 |
| ATOM | 1376 | O   | SER | 341 | 55.205 | 20.706 | 17.139 | 1.00 | 27.10 |
| ATOM | 1377 | N   | GLN | 342 | 55.318 | 20.794 | 19.389 | 1.00 | 24.25 |
| ATOM | 1378 | CA  | GLN | 342 | 56.771 | 20.875 | 19.392 | 1.00 | 27.16 |
| ATOM | 1379 | CB  | GLN | 342 | 57.309 | 21.089 | 20.799 | 1.00 | 25.60 |
| ATOM | 1380 | CG  | GLN | 342 | 58.768 | 21.466 | 20.777 | 1.00 | 27.99 |
| ATOM | 1381 | CD  | GLN | 342 | 59.407 | 21.429 | 22.133 | 1.00 | 29.58 |
| ATOM | 1382 | OE1 | GLN | 342 | 60.123 | 22.356 | 22.513 | 1.00 | 31.18 |
| ATOM | 1383 | NE2 | GLN | 342 | 59.184 | 20.345 | 22.868 | 1.00 | 29.17 |
| ATOM | 1384 | C   | GLN | 342 | 57.377 | 19.609 | 18.786 | 1.00 | 28.45 |
| ATOM | 1385 | O   | GLN | 342 | 58.378 | 19.675 | 18.062 | 1.00 | 29.79 |
| ATOM | 1386 | N   | GLU | 343 | 56.777 | 18.458 | 19.078 | 1.00 | 26.58 |
| ATOM | 1387 | CA  | GLU | 343 | 57.251 | 17.190 | 18.525 | 1.00 | 30.07 |
| ATOM | 1388 | CB  | GLU | 343 | 56.462 | 16.016 | 19.114 | 1.00 | 40.79 |
| ATOM | 1389 | CG  | GLU | 343 | 56.812 | 15.700 | 20.568 | 1.00 | 61.22 |
| ATOM | 1390 | CD  | GLU | 343 | 55.951 | 14.594 | 21.166 | 1.00 | 71.76 |
| ATOM | 1391 | OE1 | GLU | 343 | 55.472 | 13.719 | 20.405 | 1.00 | 76.73 |
| ATOM | 1392 | OE2 | GLU | 343 | 55.758 | 14.601 | 22.403 | 1.00 | 74.09 |
| ATOM | 1393 | C   | GLU | 343 | 57.097 | 17.225 | 17.001 | 1.00 | 25.87 |
| ATOM | 1394 | O   | GLU | 343 | 58.008 | 16.842 | 16.260 | 1.00 | 27.26 |
| ATOM | 1395 | N   | ALA | 344 | 55.947 | 17.727 | 16.550 | 1.00 | 23.70 |
| ATOM | 1396 | CA  | ALA | 344 | 55.647 | 17.853 | 15.124 | 1.00 | 22.16 |
| ATOM | 1397 | CB  | ALA | 344 | 54.275 | 18.489 | 14.927 | 1.00 | 21.18 |
| ATOM | 1398 | C   | ALA | 344 | 56.729 | 18.694 | 14.454 | 1.00 | 21.24 |
| ATOM | 1399 | O   | ALA | 344 | 57.303 | 18.284 | 13.438 | 1.00 | 26.47 |
| ATOM | 1400 | N   | TYR | 345 | 57.048 | 19.840 | 15.055 | 1.00 | 22.48 |
| ATOM | 1401 | CA  | TYR | 345 | 58.073 | 20.738 | 14.531 | 1.00 | 21.41 |
| ATOM | 1402 | CB  | TYR | 345 | 58.085 | 22.059 | 15.304 | 1.00 | 20.10 |
| ATOM | 1403 | CG  | TYR | 345 | 57.023 | 23.015 | 14.830 | 1.00 | 15.87 |
| ATOM | 1404 | CD1 | TYR | 345 | 56.004 | 23.434 | 15.682 | 1.00 | 10.54 |
| ATOM | 1405 | CE1 | TYR | 345 | 54.983 | 24.259 | 15.225 | 1.00 | 17.09 |
| ATOM | 1406 | CD2 | TYR | 345 | 57.003 | 23.448 | 13.505 | 1.60 | 16.86 |
| ATOM | 1407 | CE2 | TYR | 345 | 55.991 | 24.269 | 13.036 | 1.00 | 16.84 |
| ATOM | 1408 | CZ  | TYR | 345 | 54.984 | 24.668 | 13.896 | 1.00 | 17.97 |
| ATOM | 1409 | OH  | TYR | 345 | 53.963 | 25.455 | 13.406 | 1.00 | 27.11 |
| ATOM | 1410 | C   | TYR | 345 | 59.465 | 20.120 | 14.548 | 1.00 | 24.43 |
| ATOM | 1411 | O   | TYR | 345 | 60.238 | 20.291 | 13.597 | 1.00 | 24.69 |
| ATOM | 1412 | N   | LEU | 346 | 59.777 | 19.401 | 15.621 | 1.00 | 26.75 |
| ATOM | 1413 | CA  | LEU | 346 | 61.074 | 18.746 | 15.767 | 1.00 | 25.06 |
| ATOM | 1414 | CB  | LEU | 346 | 61.207 | 18.108 | 17.150 | 1.00 | 24.59 |
| ATOM | 1415 | CG  | LEU | 346 | 61.637 | 19.076 | 18.252 | 1.00 | 26.46 |
| ATOM | 1416 | CD1 | LEU | 346 | 61.387 | 18.468 | 19.610 | 1.00 | 26.46 |
| ATOM | 1417 | CD2 | LEU | 346 | 63.101 | 19.437 | 18.076 | 1.00 | 21.78 |
| ATOM | 1418 | C   | LEU | 346 | 61.322 | 17.713 | 14.683 | 1.00 | 23.24 |
| ATOM | 1419 | O   | LEU | 346 | 62.416 | 17.645 | 14.127 | 1.00 | 27.54 |
| ATOM | 1420 | N   | LEU | 347 | 60.314 | 16.900 | 14.395 | 1.00 | 25.75 |
| ATOM | 1421 | CA  | LEU | 347 | 60.437 | 15.881 | 13.356 | 1.00 | 25.41 |
| ATOM | 1422 | CB  | LEU | 347 | 59.208 | 14.970 | 13.330 | 1.00 | 23.78 |
| ATOM | 1423 | CG  | LEU | 347 | 59.302 | 17.713 | 14.190 | 1.00 | 31.85 |
| ATOM | 1424 | CD1 | LEU | 347 | 58.004 | 12.928 | 14.089 | 1.00 | 39.88 |

APPENDIX 5-continued

TR_IPBR2.PDB

| ATOM | 1425 | CD2 | LEU | 347 | 60.483 | 12.864 | 13.738 | 1.00 | 27.65 |
|------|------|-----|-----|-----|--------|--------|--------|------|-------|
| ATOM | 1426 | C   | LEU | 347 | 60.611 | 16.535 | 11.998 | 1.00 | 23.22 |
| ATOM | 1427 | O   | LEU | 347 | 61.468 | 16.133 | 11.211 | 1.00 | 28.58 |
| ATOM | 1428 | N   | ALA | 348 | 59.784 | 17.542 | 11.731 | 1.00 | 26.40 |
| ATOM | 1429 | CA  | ALA | 348 | 59.840 | 18.273 | 10.474 | 1.00 | 23.85 |
| ATOM | 1430 | CB  | ALA | 348 | 58.732 | 19.324 | 10.433 | 1.00 | 25.27 |
| ATOM | 1431 | C   | ALA | 348 | 61.210 | 18.924 | 10.337 | 1.00 | 23.69 |
| ATOM | 1432 | O   | ALA | 348 | 61.847 | 18.835 | 9.288  | 1.00 | 29.11 |
| ATOM | 1433 | N   | PHE | 349 | 61.678 | 19.506 | 11.438 | 1.00 | 24.71 |
| ATOM | 1434 | CA  | PHE | 349 | 62.973 | 20.181 | 11.493 | 1.00 | 20.48 |
| ATOM | 1435 | CB  | PHE | 349 | 63.164 | 20.772 | 12.900 | 1.00 | 17.84 |
| ATOM | 1436 | CG  | PHE | 349 | 64.334 | 21.721 | 13.031 | 1.00 | 14.90 |
| ATOM | 1437 | CD1 | PHE | 349 | 65.109 | 22.069 | 11.933 | 1.00 | 17.58 |
| ATOM | 1438 | CD2 | PHE | 349 | 64.651 | 22.269 | 14.271 | 1.00 | 24.77 |
| ATOM | 1439 | CE1 | PHE | 349 | 66.185 | 22.944 | 12.063 | 1.00 | 20.26 |
| ATOM | 1440 | CE2 | PHE | 349 | 65.727 | 23.147 | 14.413 | 1.00 | 23.83 |
| ATOM | 1441 | CZ  | PHE | 349 | 66.494 | 23.486 | 13.299 | 1.00 | 20.36 |
| ATOM | 1442 | C   | PHE | 349 | 64.084 | 19.181 | 11.159 | 1.00 | 23.43 |
| ATOM | 1443 | O   | PHE | 349 | 64.916 | 19.427 | 10.278 | 1.00 | 24.35 |
| ATOM | 1444 | N   | GLU | 350 | 64.057 | 18.028 | 11.820 | 1.00 | 25.79 |
| ATOM | 1445 | CA  | GLU | 350 | 65.060 | 16.991 | 11.606 | 1.00 | 26.75 |
| ATOM | 1446 | CB  | GLU | 350 | 64.813 | 15.822 | 12.567 | 1.00 | 29.56 |
| ATOM | 1447 | CG  | GLU | 350 | 65.774 | 14.661 | 12.391 | 1.00 | 39.94 |
| ATOM | 1448 | CD  | GLU | 350 | 65.574 | 13.549 | 13.407 | 1.00 | 45.06 |
| ATOM | 1449 | OE1 | GLU | 350 | 64.413 | 13.192 | 13.715 | 1.00 | 49.26 |
| ATOM | 1450 | OE2 | GLU | 350 | 66.593 | 13.017 | 13.887 | 1.00 | 56.67 |
| ATOM | 1451 | C   | GLU | 350 | 65.051 | 16.494 | 10.162 | 1.00 | 26.95 |
| ATOM | 1452 | O   | GLU | 350 | 66.096 | 16.398 | 9.513  | 1.00 | 28.77 |
| ATOM | 1453 | N   | HIS | 351 | 63.858 | 16.219 | 9.652  | 1.00 | 22.56 |
| ATOM | 1454 | CA  | HIS | 351 | 63.699 | 15.728 | 8.294  | 1.00 | 22.20 |
| ATOM | 1455 | CB  | HIS | 351 | 62.263 | 15.265 | 8.083  | 1.00 | 22.47 |
| ATOM | 1456 | CG  | HIS | 351 | 61.881 | 14.106 | 8.947  | 1.00 | 23.61 |
| ATOM | 1457 | CD2 | HIS | 351 | 62.633 | 13.300 | 9.739  | 1.00 | 27.65 |
| ATOM | 1458 | ND1 | HIS | 351 | 60.585 | 13.653 | 9.069  | 1.00 | 26.13 |
| ATOM | 1459 | CE1 | HIS | 351 | 60.548 | 12.629 | 9.898  | 1.00 | 22.87 |
| ATOM | 1460 | NE2 | HIS | 351 | 61.779 | 12.393 | 10.319 | 1.00 | 27.53 |
| ATOM | 1461 | C   | HIS | 351 | 64.135 | 16.764 | 7.259  | 1.00 | 21.76 |
| ATOM | 1462 | O   | HIS | 351 | 64.708 | 16.419 | 6.226  | 1.00 | 27.02 |
| ATOM | 1463 | N   | TYR | 352 | 63.909 | 18.041 | 7.555  | 1.00 | 18.26 |
| ATOM | 1464 | CA  | TYR | 352 | 64.327 | 19.101 | 6.649  | 1.00 | 16.94 |
| ATOM | 1465 | CB  | TYR | 352 | 63.749 | 20.455 | 7.066  | 1.00 | 19.07 |
| ATOM | 1466 | CG  | TYR | 352 | 64.107 | 21.534 | 6.081  | 1.00 | 21.11 |
| ATOM | 1467 | CD1 | TYR | 352 | 63.518 | 21.564 | 4.819  | 1.00 | 21.33 |
| ATOM | 1468 | CE1 | TYR | 352 | 63.921 | 22.482 | 3.859  | 1.00 | 21.06 |
| ATOM | 1469 | CD2 | TYR | 352 | 65.105 | 22.462 | 6.367  | 1.00 | 22.07 |
| ATOM | 1470 | CE2 | TYR | 352 | 65.515 | 23.388 | 5.412  | 1.00 | 25.40 |
| ATOM | 1471 | CZ  | TYR | 352 | 64.921 | 23.384 | 4.161  | 1.00 | 21.90 |
| ATOM | 1472 | OH  | TYR | 352 | 65.334 | 24.268 | 3.197  | 1.00 | 23.57 |
| ATOM | 1473 | C   | TYR | 352 | 65.853 | 19.156 | 6.657  | 1.00 | 18.49 |
| ATOM | 1474 | O   | TYR | 352 | 66.487 | 19.323 | 5.609  | 1.00 | 24.99 |
| ATOM | 1475 | N   | VAL | 353 | 66.451 | 19.008 | 7.836  | 1.00 | 24.64 |
| ATOM | 1476 | CA  | VAL | 353 | 67.904 | 19.011 | 7.955  | 1.00 | 22.20 |
| ATOM | 1477 | CB  | VAL | 353 | 68.350 | 18.925 | 9.440  | 1.00 | 23.72 |
| ATOM | 1478 | CG1 | VAL | 353 | 69.838 | 18.597 | 9.546  | 1.00 | 21.24 |
| ATOM | 1479 | CG2 | VAL | 353 | 68.063 | 20.245 | 10.142 | 1.00 | 20.07 |
| ATOM | 1480 | C   | VAL | 353 | 68.452 | 17.829 | 7.146  | 1.00 | 25.07 |
| ATOM | 1481 | O   | VAL | 353 | 69.467 | 17.955 | 6.457  | 1.00 | 24.75 |
| ATOM | 1482 | N   | ASN | 354 | 67.768 | 16.690 | 7.221  | 1.00 | 24.59 |
| ATOM | 1483 | CA  | ASN | 354 | 68.171 | 15.502 | 6.474  | 1.00 | 25.64 |
| ATOM | 1484 | CB  | ASN | 354 | 67.223 | 14.331 | 6.751  | 1.00 | 26.05 |
| ATOM | 1485 | CG  | ASN | 354 | 67.368 | 13.763 | 8.151  | 1.00 | 30.27 |
| ATOM | 1486 | OD1 | ASN | 354 | 66.443 | 13.139 | 8.672  | 1.00 | 33.71 |
| ATOM | 1487 | ND2 | ASN | 354 | 68.529 | 13.959 | 8.765  | 1.00 | 34.78 |
| ATOM | 1488 | C   | ASN | 354 | 68.143 | 15.813 | 4.981  | 1.00 | 30.50 |
| ATOM | 1489 | O   | ASN | 354 | 69.042 | 15.423 | 4.233  | 1.00 | 33.73 |
| ATOM | 1490 | N   | HIS | 355 | 67.098 | 16.519 | 4.555  | 1.00 | 30.54 |
| ATOM | 1491 | CA  | HIS | 355 | 66.926 | 16.901 | 3.157  | 1.00 | 26.02 |
| ATOM | 1492 | CB  | HIS | 355 | 65.535 | 17.521 | 2.953  | 1.00 | 29.93 |
| ATOM | 1493 | CG  | HIS | 355 | 65.367 | 18.217 | 1.638  | 1.00 | 37.91 |
| ATOM | 1494 | CD2 | HIS | 355 | 65.654 | 19.486 | 1.264  | 1.00 | 31.26 |
| ATOM | 1495 | ND1 | HIS | 355 | 64.861 | 17.593 | 0.518  | 1.00 | 32.67 |
| ATOM | 1496 | CE1 | HIS | 355 | 64.843 | 18.447 | −0.488 | 1.00 | 33.22 |
| ATOM | 1497 | NE2 | HIS | 355 | 65.322 | 19.601 | −0.061 | 1.00 | 32.69 |
| ATOM | 1498 | C   | HIS | 355 | 68.009 | 17.851 | 2.652  | 1.00 | 24.29 |
| ATOM | 1499 | O   | HIS | 355 | 68.381 | 17.798 | 1.484  | 1.00 | 26.82 |
| ATOM | 1500 | N   | ARG | 356 | 68.484 | 18.735 | 3.526  | 1.00 | 29.72 |
| ATOM | 1501 | CA  | ARG | 356 | 69.516 | 19.711 | 3.167  | 1.00 | 26.65 |

APPENDIX 5-continued

TR_IPBR2.PDB

| ATOM | 1502 | CB   | ARG | 356 | 69.593 | 20.804 | 4.225  | 1.00 | 22.74 |
|------|------|------|-----|-----|--------|--------|--------|------|-------|
| ATOM | 1503 | CG   | ARG | 356 | 68.409 | 21.735 | 4.222  | 1.00 | 21.64 |
| ATOM | 1504 | CD   | ARG | 356 | 68.757 | 23.024 | 3.524  | 1.00 | 28.04 |
| ATOM | 1505 | NE   | ARG | 356 | 69.550 | 23.900 | 4.380  | 1.00 | 33.79 |
| ATOM | 1506 | CZ   | ARG | 356 | 70.508 | 24.716 | 3.952  | 1.00 | 29.26 |
| ATOM | 1507 | NH1  | ARG | 356 | 70.814 | 24.776 | 2.667  | 1.00 | 29.08 |
| ATOM | 1508 | NH2  | ARG | 356 | 71.136 | 25.493 | 4.816  | 1.00 | 33.61 |
| ATOM | 1509 | C    | ARG | 356 | 70.904 | 19.115 | 2.950  | 1.00 | 27.58 |
| ATOM | 1510 | O    | ARG | 356 | 71.757 | 19.740 | 2.312  | 1.00 | 31.44 |
| ATOM | 1511 | N    | LYS | 357 | 71.140 | 17.937 | 3.519  | 1.00 | 30.56 |
| ATOM | 1512 | CA   | LYS | 357 | 72.422 | 17.244 | 3.390  | 1.00 | 34.56 |
| ATOM | 1513 | CB   | LYS | 357 | 72.500 | 16.518 | 2.043  | 1.00 | 39.66 |
| ATOM | 1514 | CG   | LYS | 357 | 71.476 | 15.402 | 1.871  | 1.00 | 42.16 |
| ATOM | 1515 | CD   | LYS | 357 | 71.674 | 14.676 | 0.550  | 1.00 | 54.23 |
| ATOM | 1516 | CE   | LYS | 357 | 70.691 | 13.523 | 0.371  | 1.00 | 61.97 |
| ATOM | 1517 | NZ   | LYS | 357 | 69.288 | 13.974 | 0.162  | 1.00 | 65.88 |
| ATOM | 1518 | C    | LYS | 357 | 73.665 | 18.119 | 3.606  | 1.00 | 36.73 |
| ATOM | 1519 | O    | LYS | 357 | 74.522 | 18.248 | 2.728  | 1.00 | 40.70 |
| ATOM | 1520 | N    | HIS | 358 | 73.738 | 18.732 | 4.786  | 1.00 | 33.69 |
| ATOM | 1521 | CA   | HIS | 358 | 74.863 | 19.581 | 5.163  | 1.00 | 33.59 |
| ATOM | 1522 | CB   | HIS | 358 | 74.660 | 20.155 | 6.571  | 1.00 | 32.07 |
| ATOM | 1523 | CG   | HIS | 358 | 73.593 | 21.200 | 6.666  | 1.00 | 29.74 |
| ATOM | 1524 | CD2  | HIS | 358 | 72.245 | 21.098 | 6.736  | 1.00 | 23.35 |
| ATOM | 1525 | ND1  | HIS | 358 | 73.876 | 22.547 | 6.731  | 1.00 | 28.13 |
| ATOM | 1526 | CE1  | HIS | 358 | 72.752 | 23.231 | 6.834  | 1.00 | 26.94 |
| ATOM | 1527 | NE2  | HIS | 358 | 71.747 | 22.373 | 6.838  | 1.00 | 23.32 |
| ATOM | 1528 | C    | HIS | 358 | 76.121 | 18.720 | 5.180  | 1.00 | 37.98 |
| ATOM | 1529 | O    | HIS | 358 | 76.087 | 17.581 | 5.654  | 1.00 | 41.07 |
| ATOM | 1530 | N    | ASN | 359 | 77.231 | 19.261 | 4.690  | 1.00 | 44.20 |
| ATOM | 1531 | CA   | ASN | 359 | 78.492 | 18.523 | 4.676  | 1.00 | 49.72 |
| ATOM | 1532 | CB   | ASN | 359 | 79.406 | 19.053 | 3.572  | 1.00 | 46.66 |
| ATOM | 1533 | C    | ASN | 359 | 79.174 | 18.648 | 6.039  | 1.00 | 51.77 |
| ATOM | 1534 | O    | ASN | 359 | 80.356 | 18.985 | 6.122  | 1.00 | 57.32 |
| ATOM | 1535 | N    | ILE | 360 | 78.414 | 18.383 | 7.101  | 1.00 | 51.04 |
| ATOM | 1536 | CA   | ILE | 360 | 78.906 | 18.471 | 8.477  | 1.00 | 48.24 |
| ATOM | 1537 | CB   | ILE | 360 | 78.340 | 19.721 | 9.207  | 1.00 | 47.20 |
| ATOM | 1538 | CG2  | ILE | 360 | 78.781 | 19.741 | 10.673 | 1.00 | 43.50 |
| ATOM | 1539 | CG1  | ILE | 360 | 78.777 | 21.005 | 8.491  | 1.00 | 45.94 |
| ATOM | 1540 | CD1  | ILE | 360 | 78.157 | 22.262 | 9.050  | 1.00 | 43.00 |
| ATOM | 1541 | C    | ILE | 360 | 78.462 | 17.222 | 9.239  | 1.00 | 47.23 |
| ATOM | 1542 | O    | ILE | 360 | 77.272 | 16.901 | 9.278  | 1.00 | 45.13 |
| ATOM | 1543 | N    | PRO | 361 | 79.416 | 16.490 | 9.838  | 1.00 | 48.61 |
| ATOM | 1544 | CD   | PRO | 361 | 80.869 | 16.705 | 9.729  | 1.00 | 50.93 |
| ATOM | 1545 | CA   | PRO | 361 | 79.129 | 15.270 | 10.599 | 1.00 | 45.46 |
| ATOM | 1546 | CB   | PRO | 361 | 80.524 | 14.725 | 10.927 | 1.00 | 49.01 |
| ATOM | 1547 | CG   | PRO | 361 | 81.402 | 15.307 | 9.862  | 1.00 | 54.41 |
| ATOM | 1548 | C    | PRO | 361 | 78.330 | 15.514 | 11.879 | 1.00 | 36.54 |
| ATOM | 1549 | O    | PRO | 361 | 78.666 | 16.394 | 12.672 | 1.00 | 39.83 |
| ATOM | 1550 | N    | HIS | 362 | 77.282 | 14.716 | 12.075 | 1.00 | 31.35 |
| ATOM | 1551 | CA   | HIS | 362 | 76.430 | 14.798 | 13.264 | 1.00 | 33.34 |
| ATOM | 1552 | CB   | HIS | 362 | 77.246 | 14.495 | 14.524 | 1.00 | 33.77 |
| ATOM | 1553 | CG   | HIS | 362 | 78.129 | 13.292 | 14.397 | 1.00 | 34.40 |
| ATOM | 1554 | CD2  | HIS | 362 | 77.837 | 11.999 | 14.130 | 1.00 | 32.60 |
| ATOM | 1555 | ND1  | HIS | 362 | 79.501 | 13.362 | 14.506 | 1.00 | 36.14 |
| ATOM | 1556 | CE1  | HIS | 362 | 80.017 | 12.160 | 14.311 | 1.00 | 36.26 |
| ATOM | 1557 | NE2  | HIS | 362 | 79.029 | 11.316 | 14.080 | 1.00 | 35.73 |
| ATOM | 1558 | C    | HIS | 362 | 75.778 | 16.164 | 13.389 | 1.00 | 33.55 |
| ATOM | 1559 | O    | HIS | 362 | 75.539 | 16.652 | 14.495 | 1.00 | 31.93 |
| ATOM | 1560 | N    | PHE | 363 | 75.449 | 16.748 | 12.240 | 1.00 | 35.83 |
| ATOM | 1561 | CA   | PHE | 363 | 74.834 | 18.067 | 12.166 | 1.00 | 30.93 |
| ATOM | 1562 | CB   | PHE | 363 | 74.464 | 18.394 | 10.712 | 1.00 | 28.82 |
| ATOM | 1563 | CG   | PHE | 363 | 73.959 | 19.797 | 10.514 | 1.00 | 26.59 |
| ATOM | 1564 | CD1  | PHE | 363 | 74.846 | 20.843 | 10.301 | 1.00 | 26.96 |
| ATOM | 1565 | CD2  | PHE | 363 | 72.596 | 20.076 | 10.575 | 1.00 | 27.51 |
| ATOM | 1566 | CE1  | PHE | 363 | 74.384 | 22.151 | 10.155 | 1.00 | 31.83 |
| ATOM | 1567 | CE2  | PHE | 363 | 72.124 | 21.378 | 10.433 | 1.00 | 26.65 |
| ATOM | 1568 | CZ   | PHE | 363 | 73.019 | 22.417 | 10.223 | 1.00 | 24.42 |
| ATOM | 1569 | C    | PHE | 363 | 73.613 | 18.235 | 13.063 | 1.00 | 28.73 |
| ATOM | 1570 | O    | PHE | 363 | 73.550 | 19.174 | 13.848 | 1.00 | 25.33 |
| ATOM | 1571 | N    | TRP | 364 | 72.663 | 17.310 | 12.969 | 1.00 | 22.89 |
| ATOM | 1572 | CA   | TRP | 364 | 71.443 | 17.405 | 13.760 | 1.00 | 24.19 |
| ATOM | 1573 | CB   | TRP | 364 | 70.481 | 16.254 | 13.439 | 1.00 | 26.31 |
| ATOM | 1574 | CG   | TRP | 364 | 69.198 | 16.275 | 14.228 | 1.00 | 20.24 |
| ATOM | 1575 | CD2  | TRP | 364 | 68.213 | 17.325 | 14.262 | 1.00 | 24.50 |
| ATOM | 1576 | CE2  | TRP | 364 | 67.175 | 16.894 | 15.120 | 1.00 | 25.84 |
| ATOM | 1577 | CE3  | TRP | 364 | 68.106 | 18.583 | 13.652 | 1.00 | 25.83 |
| ATOM | 1578 | CD1  | TRP | 364 | 68.731 | 15.289 | 15.040 | 1.00 | 23.61 |

APPENDIX 5-continued

TR_IPBR2.PDB

| | | | | | | | | |
|---|---|---|---|---|---|---|---|---|
| ATOM | 1579 | NE1 | TRP | 364 | 67.515 | 15.648 | 15.579 | 1.00 | 32.26 |
| ATOM | 1580 | CZ2 | TRP | 364 | 66.048 | 17.674 | 15.386 | 1.00 | 21.95 |
| ATOM | 1581 | CZ3 | TRP | 364 | 66.979 | 19.360 | 13.919 | 1.00 | 20.73 |
| ATOM | 1582 | CH2 | TRP | 364 | 65.967 | 18.899 | 14.779 | 1.00 | 22.37 |
| ATOM | 1583 | C | TRP | 364 | 71.663 | 17.551 | 15.267 | 1.00 | 28.84 |
| ATOM | 1584 | O | TRP | 364 | 71.246 | 18.554 | 15.839 | 1.00 | 31.25 |
| ATOM | 1585 | N | PRO | 365 | 72.305 | 16.568 | 15.932 | 1.00 | 29.69 |
| ATOM | 1586 | CD | PRO | 365 | 72.790 | 15.245 | 15.497 | 1.00 | 30.89 |
| ATOM | 1587 | CA | PRO | 365 | 72.499 | 16.748 | 17.373 | 1.00 | 25.62 |
| ATOM | 1588 | CB | PRO | 365 | 73.195 | 15.451 | 17.810 | 1.00 | 25.50 |
| ATOM | 1589 | CG | PRO | 365 | 73.804 | 14.915 | 16.560 | 1.00 | 34.15 |
| ATOM | 1590 | C | PRO | 365 | 73.320 | 18.002 | 17.698 | 1.00 | 24.07 |
| ATOM | 1591 | O | PRO | 365 | 73.079 | 18.654 | 18.711 | 1.00 | 23.58 |
| ATOM | 1592 | N | LYS | 366 | 74.250 | 18.365 | 16.820 | 1.00 | 24.09 |
| ATOM | 1593 | CA | LYS | 366 | 75.063 | 19.562 | 17.027 | 1.00 | 29.44 |
| ATOM | 1594 | CB | LYS | 366 | 76.131 | 19.681 | 15.945 | 1.00 | 27.18 |
| ATOM | 1595 | CG | LYS | 366 | 77.341 | 18.802 | 16.149 | 1.00 | 23.71 |
| ATOM | 1596 | CD | LYS | 366 | 78.304 | 19.019 | 15.001 | 1.00 | 27.50 |
| ATOM | 1597 | CE | LYS | 366 | 79.624 | 18.329 | 15.231 | 1.00 | 35.88 |
| ATOM | 1598 | NZ | LYS | 366 | 80.550 | 18.591 | 14.097 | 1.00 | 41.92 |
| ATOM | 1599 | C | LYS | 366 | 74.195 | 20.820 | 17.012 | 1.00 | 32.76 |
| ATOM | 1600 | O | LYS | 366 | 74.326 | 21.694 | 17.873 | 1.00 | 36.13 |
| ATOM | 1601 | N | LEU | 367 | 73.307 | 20.907 | 16.028 | 1.00 | 33.70 |
| ATOM | 1602 | CA | LEU | 367 | 72.409 | 22.041 | 15.905 | 1.00 | 30.60 |
| ATOM | 1603 | CB | LEU | 367 | 71.636 | 21.955 | 14.587 | 1.00 | 24.26 |
| ATOM | 1604 | CG | LEU | 367 | 70.675 | 23.103 | 14.274 | 1.00 | 32.42 |
| ATOM | 1605 | CD1 | LEU | 367 | 71.394 | 24.440 | 14.404 | 1.00 | 24.78 |
| ATOM | 1606 | CD2 | LEU | 367 | 70.098 | 22.924 | 12.878 | 1.00 | 28.84 |
| ATOM | 1607 | C | LEU | 367 | 71.450 | 22.015 | 17.087 | 1.00 | 31.90 |
| ATOM | 1608 | O | LEU | 367 | 71.113 | 23.052 | 17.655 | 1.00 | 39.20 |
| ATOM | 1609 | N | LEU | 368 | 71.051 | 20.812 | 17.485 | 1.00 | 33.86 |
| ATOM | 1610 | CA | LEU | 368 | 70.144 | 20.617 | 18.608 | 1.00 | 32.97 |
| ATOM | 1611 | CB | LEU | 368 | 69.866 | 19.123 | 18.759 | 1.00 | 34.22 |
| ATOM | 1612 | CG | LEU | 368 | 68.458 | 18.633 | 19.084 | 1.00 | 38.15 |
| ATOM | 1613 | CD1 | LEU | 368 | 67.400 | 19.449 | 18.345 | 1.00 | 27.75 |
| ATOM | 1614 | CD2 | LEU | 368 | 68.374 | 17.154 | 18.733 | 1.00 | 31.51 |
| ATOM | 1615 | C | LEU | 368 | 70.793 | 21.181 | 19.875 | 1.00 | 35.29 |
| ATOM | 1616 | O | LEU | 368 | 70.128 | 21.806 | 20.703 | 1.00 | 36.16 |
| ATOM | 1617 | N | MET | 369 | 72.106 | 21.001 | 19.994 | 1.00 | 41.13 |
| ATOM | 1618 | CA | MET | 369 | 72.857 | 21.504 | 21.139 | 1.00 | 40.92 |
| ATOM | 1619 | CB | MET | 369 | 74.283 | 20.955 | 21.115 | 1.00 | 43.32 |
| ATOM | 1620 | CG | MET | 369 | 74.383 | 19.497 | 21.545 | 1.00 | 50.01 |
| ATOM | 1621 | SD | MET | 369 | 75.997 | 18.770 | 21.190 | 1.00 | 56.63 |
| ATOM | 1622 | CE | MET | 369 | 77.032 | 19.596 | 22.409 | 1.00 | 62.26 |
| ATOM | 1623 | C | MET | 369 | 72.872 | 23.032 | 21.186 | 1.00 | 43.46 |
| ATOM | 1624 | O | MET | 369 | 73.137 | 23.619 | 22.233 | 1.00 | 47.51 |
| ATOM | 1625 | N | LYS | 370 | 72.594 | 23.673 | 20.053 | 1.00 | 41.60 |
| ATOM | 1626 | CA | LYS | 370 | 72.561 | 25.131 | 19.988 | 1.00 | 34.48 |
| ATOM | 1627 | CB | LYS | 370 | 72.689 | 25.623 | 18.546 | 1.00 | 31.53 |
| ATOM | 1628 | CG | LYS | 370 | 74.012 | 25.278 | 17.896 | 1.00 | 30.76 |
| ATOM | 1629 | CD | LYS | 370 | 75.168 | 25.774 | 18.731 | 1.00 | 32.16 |
| ATOM | 1630 | CE | LYS | 370 | 76.488 | 25.388 | 18.116 | 1.00 | 31.08 |
| ATOM | 1631 | NZ | LYS | 370 | 77.604 | 25.822 | 18.993 | 1.00 | 51.52 |
| ATOM | 1632 | C | LYS | 370 | 71.269 | 25.652 | 20.606 | 1.00 | 36.35 |
| ATOM | 1633 | O | LYS | 370 | 71.197 | 26.806 | 21.032 | 1.00 | 39.02 |
| ATOM | 1634 | N | VAL | 371 | 70.248 | 24.804 | 20.652 | 1.00 | 34.33 |
| ATOM | 1635 | CA | VAL | 371 | 68.975 | 25.186 | 21.249 | 1.00 | 36.27 |
| ATOM | 1636 | CB | VAL | 371 | 67.885 | 24.097 | 21.046 | 1.00 | 36.15 |
| ATOM | 1637 | CG1 | VAL | 371 | 66.600 | 24.487 | 21.758 | 1.00 | 32.69 |
| ATOM | 1638 | CG2 | VAL | 371 | 67.612 | 23.892 | 19.567 | 1.00 | 33.75 |
| ATOM | 1639 | C | VAL | 371 | 69.196 | 25.423 | 22.745 | 1.00 | 41.55 |
| ATOM | 1640 | O | VAL | 371 | 68.638 | 26.367 | 23.316 | 1.00 | 40.82 |
| ATOM | 1641 | N | THR | 372 | 70.018 | 24.581 | 23.378 | 1.00 | 40.42 |
| ATOM | 1642 | CA | THR | 372 | 70.300 | 24.733 | 24.804 | 1.00 | 41.69 |
| ATOM | 1643 | CB | THR | 372 | 71.037 | 23.499 | 25.397 | 1.00 | 42.36 |
| ATOM | 1644 | OG1 | THR | 372 | 72.125 | 23.133 | 24.548 | 1.00 | 53.57 |
| ATOM | 1645 | CG2 | THR | 372 | 70.090 | 22.313 | 25.523 | 1.00 | 43.54 |
| ATOM | 1646 | C | THR | 372 | 71.090 | 26.021 | 25.048 | 1.00 | 38.75 |
| ATOM | 1647 | O | THR | 372 | 70.858 | 26.714 | 26.042 | 1.00 | 37.51 |
| ATOM | 1648 | N | ASP | 373 | 71.987 | 26.360 | 24.122 | 1.00 | 36.73 |
| ATOM | 1649 | CA | ASP | 373 | 72.768 | 27.594 | 24.223 | 1.00 | 30.96 |
| ATOM | 1650 | CB | ASP | 373 | 73.741 | 27.732 | 23.047 | 1.00 | 31.26 |
| ATOM | 1651 | CG | ASP | 373 | 74.865 | 26.707 | 23.085 | 1.00 | 35.85 |
| ATOM | 1652 | OD1 | ASP | 373 | 75.523 | 26.508 | 22.042 | 1.00 | 36.73 |
| ATOM | 1653 | OD2 | ASP | 373 | 75.102 | 26.103 | 24.153 | 1.00 | 39.92 |
| ATOM | 1654 | C | ASP | 373 | 71.797 | 28.769 | 24.230 | 1.00 | 31.30 |
| ATOM | 1655 | O | ASP | 373 | 71.926 | 29.689 | 25.039 | 1.00 | 35.37 |

APPENDIX 5-continued

TR_IPBR2.PDB

| ATOM | 1656 | N | LEU | 374 | 70.804 | 28.711 | 23.348 | 1.00 | 27.72 |
|---|---|---|---|---|---|---|---|---|---|
| ATOM | 1657 | CA | LEU | 374 | 69.783 | 29.751 | 23.257 | 1.00 | 28.18 |
| ATOM | 1658 | CB | LEU | 374 | 68.881 | 29.521 | 22.042 | 1.00 | 28.41 |
| ATOM | 1659 | CG | LEU | 374 | 69.391 | 30.055 | 20.703 | 1.00 | 29.87 |
| ATOM | 1660 | CD1 | LEU | 374 | 68.533 | 29.520 | 19.563 | 1.00 | 25.44 |
| ATOM | 1661 | CD2 | LEU | 374 | 69.385 | 31.581 | 20.728 | 1.00 | 23.74 |
| ATOM | 1662 | C | LEU | 374 | 68.946 | 29.786 | 24.527 | 1.00 | 28.61 |
| ATOM | 1663 | O | LEU | 374 | 68.516 | 30.859 | 24.968 | 1.00 | 29.51 |
| ATOM | 1664 | N | ARG | 375 | 68.690 | 28.615 | 25.105 | 1.00 | 32.32 |
| ATOM | 1665 | CA | ARG | 375 | 67.925 | 28.532 | 26.345 | 1.00 | 33.19 |
| ATOM | 1666 | CB | ARG | 375 | 67.758 | 27.074 | 26.776 | 1.00 | 41.70 |
| ATOM | 1667 | CG | ARG | 375 | 66.360 | 26.524 | 26.609 | 1.00 | 51.03 |
| ATOM | 1668 | CD | ARG | 375 | 65.979 | 26.416 | 25.153 | 1.00 | 60.16 |
| ATOM | 1669 | NE | ARG | 375 | 64.648 | 25.840 | 24.987 | 1.00 | 74.28 |
| ATOM | 1670 | CZ | ARG | 375 | 64.324 | 24.587 | 25.296 | 1.00 | 79.34 |
| ATOM | 1671 | NH1 | ARG | 375 | 65.233 | 23.756 | 25.796 | 1.00 | 80.84 |
| ATOM | 1672 | NH2 | ARG | 375 | 63.084 | 24.157 | 25.092 | 1.00 | 77.44 |
| ATOM | 1673 | C | ARG | 375 | 68.692 | 29.296 | 27.423 | 1.00 | 32.02 |
| ATOM | 1674 | O | ARG | 375 | 68.132 | 30.150 | 28.108 | 1.00 | 30.42 |
| ATOM | 1675 | N | MET | 376 | 69.993 | 29.020 | 27.521 | 1.00 | 32.30 |
| ATOM | 1676 | CA | MET | 376 | 70.860 | 29.668 | 28.499 | 1.00 | 36.82 |
| ATOM | 1677 | CB | MET | 376 | 72.278 | 29.097 | 28.433 | 1.00 | 45.36 |
| ATOM | 1678 | CG | MET | 376 | 72.375 | 27.645 | 28.866 | 1.00 | 66.71 |
| ATOM | 1679 | SD | MET | 376 | 74.078 | 27.057 | 28.966 | 1.00 | 89.64 |
| ATOM | 1680 | CE | MET | 376 | 74.256 | 26.229 | 27.400 | 1.00 | 85.51 |
| ATOM | 1681 | C | MET | 376 | 70.880 | 31.182 | 28.310 | 1.00 | 37.49 |
| ATOM | 1682 | O | MET | 376 | 70.780 | 31.928 | 29.281 | 1.00 | 39.99 |
| ATOM | 1683 | N | ILE | 377 | 71.008 | 31.630 | 27.060 | 1.00 | 33.14 |
| ATOM | 1684 | CA | ILE | 377 | 71.009 | 33.057 | 26.740 | 1.00 | 25.98 |
| ATOM | 1685 | CB | ILE | 377 | 71.181 | 33.291 | 25.211 | 1.00 | 22.79 |
| ATOM | 1686 | CG2 | ILE | 377 | 70.838 | 34.727 | 24.834 | 1.00 | 25.29 |
| ATOM | 1687 | CG1 | ILE | 377 | 72.606 | 32.947 | 24.785 | 1.00 | 21.42 |
| ATOM | 1688 | CD1 | ILE | 377 | 72.816 | 32.971 | 23.282 | 1.00 | 19.37 |
| ATOM | 1689 | C | ILE | 377 | 69.690 | 33.664 | 27.228 | 1.00 | 27.11 |
| ATOM | 1690 | O | ILE | 377 | 69.676 | 34.727 | 27.856 | 1.00 | 28.09 |
| ATOM | 1691 | N | GLY | 378 | 68.584 | 32.969 | 26.975 | 1.00 | 29.34 |
| ATOM | 1692 | CA | GLY | 378 | 67.292 | 33.457 | 27.418 | 1.00 | 30.41 |
| ATOM | 1693 | C | GLY | 378 | 67.233 | 33.532 | 28.934 | 1.00 | 36.85 |
| ATOM | 1694 | O | GLY | 378 | 66.672 | 34.481 | 29.489 | 1.00 | 36.44 |
| ATOM | 1695 | N | ALA | 379 | 67.837 | 32.547 | 29.603 | 1.00 | 37.98 |
| ATOM | 1696 | CA | ALA | 379 | 67.869 | 32.483 | 31.066 | 1.00 | 36.44 |
| ATOM | 1697 | CB | ALA | 379 | 68.415 | 31.133 | 31.528 | 1.00 | 35.63 |
| ATOM | 1698 | C | ALA | 379 | 68.712 | 33.613 | 31.642 | 1.00 | 34.14 |
| ATOM | 1699 | O | ALA | 379 | 68.259 | 34.343 | 32.523 | 1.00 | 35.15 |
| ATOM | 1700 | N | CYA | 380 | 69.941 | 33.747 | 31.144 | 1.00 | 36.66 |
| ATOM | 1701 | CA | CYA | 380 | 70.860 | 34.795 | 31.587 | 1.00 | 37.27 |
| ATOM | 1702 | CB | CYA | 380 | 72.172 | 34.728 | 30.810 | 1.00 | 36.85 |
| ATOM | 1703 | SG | CYA | 380 | 73.201 | 33.338 | 31.250 | 1.00 | 52.80 |
| ATOM | 1704 | AS | CYA | 380 | 74.942 | 33.593 | 29.823 | 1.00 | 65.79 |
| ATOM | 1705 | C | CYA | 380 | 70.230 | 36.165 | 31.398 | 1.00 | 38.70 |
| ATOM | 1706 | O | CYA | 380 | 70.337 | 37.033 | 32.270 | 1.00 | 45.73 |
| ATOM | 1707 | N | HIS | 381 | 69.555 | 36.354 | 30.265 | 1.00 | 37.32 |
| ATOM | 1708 | CA | HIS | 381 | 68.906 | 37.623 | 29.994 | 1.00 | 32.11 |
| ATOM | 1709 | CB | HIS | 381 | 68.377 | 37.687 | 28.565 | 1.00 | 25.76 |
| ATOM | 1710 | CG | HIS | 381 | 67.596 | 38.932 | 28.285 | 1.00 | 20.30 |
| ATOM | 1711 | CD2 | HIS | 381 | 67.998 | 40.200 | 28.044 | 1.00 | 16.31 |
| ATOM | 1712 | ND1 | HIS | 381 | 66.218 | 38.971 | 28.336 | 1.00 | 22.06 |
| ATOM | 1713 | CE1 | HIS | 381 | 65.807 | 40.210 | 28.146 | 1.00 | 21.20 |
| ATOM | 1714 | NE2 | HIS | 381 | 66.869 | 40.976 | 27.968 | 1.00 | 22.58 |
| ATOM | 1715 | C | HIS | 381 | 67.773 | 37.893 | 30.980 | 1.00 | 32.68 |
| ATOM | 1716 | O | HIS | 381 | 67.602 | 39.024 | 31.431 | 1.00 | 33.38 |
| ATOM | 1717 | N | ALA | 382 | 66.982 | 36.873 | 31.296 | 1.00 | 31.27 |
| ATOM | 1718 | CA | ALA | 382 | 65.884 | 37.045 | 32.243 | 1.00 | 29.39 |
| ATOM | 1719 | CB | ALA | 382 | 65.121 | 35.742 | 32.409 | 1.00 | 25.18 |
| ATOM | 1720 | C | ALA | 382 | 66.420 | 37.531 | 33.596 | 1.00 | 34.32 |
| ATOM | 1721 | O | ALA | 382 | 65.902 | 38.501 | 34.160 | 1.00 | 37.79 |
| ATOM | 1722 | N | SER | 383 | 67.483 | 36.893 | 34.085 | 1.00 | 36.88 |
| ATOM | 1723 | CA | SER | 383 | 68.100 | 37.268 | 35.361 | 1.00 | 39.74 |
| ATOM | 1724 | CB | SER | 383 | 69.233 | 36.297 | 35.719 | 1.00 | 42.58 |
| ATOM | 1725 | OG | SER | 383 | 68.734 | 35.010 | 36.049 | 1.00 | 61.85 |
| ATOM | 1726 | C | SER | 383 | 68.638 | 38.697 | 35.311 | 1.00 | 36.49 |
| ATOM | 1727 | O | SER | 383 | 68.443 | 39.480 | 36.243 | 1.00 | 43.81 |
| ATOM | 1728 | N | ARG | 384 | 69.305 | 39.036 | 34.213 | 1.00 | 33.66 |
| ATOM | 1729 | CA | ARG | 384 | 69.866 | 40.367 | 34.043 | 1.00 | 35.39 |
| ATOM | 1730 | CB | ARG | 384 | 70.800 | 40.404 | 32.835 | 1.00 | 29.29 |
| ATOM | 1731 | CG | ARG | 384 | 71.590 | 41.679 | 32.731 | 1.00 | 29.20 |
| ATOM | 1732 | CD | ARG | 384 | 72.881 | 41.435 | 31.995 | 1.00 | 37.73 |

APPENDIX 5-continued

TR_IPBR2.PDB

| | | | | | | | | |
|---|---|---|---|---|---|---|---|---|
| ATOM | 1733 | NE | ARG | 384 | 73.657 | 42.663 | 31.850 | 1.00 | 48.97 |
| ATOM | 1734 | CZ | ARG | 384 | 74.346 | 43.245 | 32.826 | 1.00 | 45.41 |
| ATOM | 1735 | NH1 | ARG | 384 | 74.371 | 42.715 | 34.038 | 1.00 | 44.51 |
| ATOM | 1736 | NH2 | ARG | 384 | 75.008 | 44.368 | 32.584 | 1.00 | 41.43 |
| ATOM | 1737 | C | ARG | 384 | 68.777 | 41.431 | 33.916 | 1.00 | 39.45 |
| ATOM | 1738 | O | ARG | 384 | 68.913 | 42.537 | 34.444 | 1.00 | 44.47 |
| ATOM | 1739 | N | PHE | 385 | 67.673 | 41.077 | 33.270 | 1.00 | 36.42 |
| ATOM | 1740 | CA | PHE | 385 | 66.568 | 42.007 | 33.099 | 1.00 | 34.68 |
| ATOM | 1741 | CB | PHE | 385 | 65.444 | 41.393 | 32.262 | 1.00 | 30.21 |
| ATOM | 1742 | CG | PHE | 385 | 64.263 | 42.304 | 32.081 | 1.00 | 29.48 |
| ATOM | 1743 | CD1 | PHE | 385 | 64.289 | 43.313 | 31.127 | 1.00 | 29.70 |
| ATOM | 1744 | CD2 | PHE | 385 | 63.130 | 42.161 | 32.873 | 1.00 | 28.04 |
| ATOM | 1745 | CE1 | PHE | 385 | 63.203 | 44.169 | 30.966 | 1.00 | 33.50 |
| ATOM | 1746 | CE2 | PHE | 385 | 62.040 | 43.012 | 32.718 | 1.00 | 31.35 |
| ATOM | 1747 | CZ | PHE | 385 | 62.077 | 44.017 | 31.763 | 1.00 | 32.08 |
| ATOM | 1748 | C | PHE | 385 | 66.040 | 42.412 | 34.468 | 1.00 | 35.76 |
| ATOM | 1749 | O | PHE | 385 | 65.761 | 43.590 | 34.693 | 1.00 | 40.58 |
| ATOM | 1750 | N | LEU | 386 | 65.906 | 41.441 | 35.373 | 1.00 | 37.55 |
| ATOM | 1751 | CA | LEU | 386 | 65.429 | 41.706 | 36.735 | 1.00 | 41.01 |
| ATOM | 1752 | CB | LEU | 386 | 65.394 | 40.413 | 37.563 | 1.00 | 42.30 |
| ATOM | 1753 | CG | LEU | 386 | 64.240 | 39.434 | 37.317 | 1.00 | 43.34 |
| ATOM | 1754 | CD1 | LEU | 386 | 64.559 | 38.066 | 37.912 | 1.00 | 43.50 |
| ATOM | 1755 | CD2 | LEU | 386 | 62.946 | 39.992 | 37.899 | 1.00 | 44.01 |
| ATOM | 1756 | C | LEU | 386 | 66.342 | 42.735 | 37.405 | 1.00 | 40.08 |
| ATOM | 1757 | O | LEU | 386 | 65.875 | 43.632 | 38.112 | 1.00 | 42.08 |
| ATOM | 1758 | N | HIS | 387 | 67.643 | 42.613 | 37.153 | 1.00 | 34.86 |
| ATOM | 1759 | CA | HIS | 387 | 68.631 | 43.537 | 37.700 | 1.00 | 39.09 |
| ATOM | 1760 | CB | HIS | 387 | 70.046 | 43.034 | 37.421 | 1.00 | 39.99 |
| ATOM | 1761 | CG | HIS | 387 | 70.402 | 41.791 | 38.172 | 1.00 | 56.37 |
| ATOM | 1762 | CD2 | HIS | 387 | 71.384 | 40.881 | 37.974 | 1.00 | 60.11 |
| ATOM | 1763 | ND1 | HIS | 387 | 69.711 | 41.370 | 39.290 | 1.00 | 60.40 |
| ATOM | 1764 | CE1 | HIS | 387 | 70.252 | 40.255 | 39.746 | 1.00 | 61.89 |
| ATOM | 1765 | NE2 | HIS | 387 | 71.269 | 39.937 | 38.966 | 1.00 | 63.96 |
| ATOM | 1766 | C | HIS | 387 | 68.446 | 44.928 | 37.401 | 1.00 | 41.00 |
| ATOM | 1767 | O | HIS | 387 | 68.492 | 45.927 | 37.817 | 1.00 | 46.99 |
| ATOM | 1768 | N | MET | 388 | 68.213 | 44.982 | 35.792 | 1.00 | 39.15 |
| ATOM | 1769 | CA | MET | 388 | 68.011 | 46.243 | 35.088 | 1.00 | 35.32 |
| ATOM | 1770 | CB | MET | 388 | 67.676 | 45.992 | 33.612 | 1.00 | 35.12 |
| ATOM | 1771 | CG | MET | 388 | 68.810 | 45.442 | 32.753 | 1.00 | 37.24 |
| ATOM | 1772 | SD | MET | 388 | 68.259 | 45.150 | 31.051 | 1.00 | 41.75 |
| ATOM | 1773 | CE | MET | 388 | 69.274 | 43.748 | 30.573 | 1.00 | 35.23 |
| ATOM | 1774 | C | MET | 388 | 66.880 | 47.048 | 35.733 | 1.00 | 36.52 |
| ATOM | 1775 | O | MET | 388 | 66.994 | 48.265 | 35.888 | 1.00 | 43.39 |
| ATOM | 1776 | N | LYS | 389 | 65.792 | 46.371 | 36.103 | 1.00 | 38.05 |
| ATOM | 1777 | CA | LYS | 389 | 64.637 | 47.025 | 36.729 | 1.00 | 42.88 |
| ATOM | 1778 | CB | LYS | 389 | 63.481 | 46.035 | 36.866 | 1.00 | 47.83 |
| ATOM | 1779 | CG | LYS | 389 | 62.835 | 45.627 | 35.560 | 1.00 | 52.36 |
| ATOM | 1780 | CD | LYS | 389 | 62.040 | 44.340 | 35.731 | 1.00 | 61.84 |
| ATOM | 1781 | CE | LYS | 389 | 60.978 | 44.451 | 36.814 | 1.00 | 69.04 |
| ATOM | 1782 | NZ | LYS | 389 | 60.254 | 43.162 | 36.987 | 1.00 | 70.00 |
| ATOM | 1783 | C | LYS | 389 | 64.983 | 47.587 | 38.107 | 1.00 | 43.99 |
| ATOM | 1784 | O | LYS | 389 | 64.455 | 48.621 | 38.525 | 1.00 | 44.22 |
| ATOM | 1785 | N | VAL | 390 | 65.851 | 46.878 | 38.816 | 1.00 | 45.50 |
| ATOM | 1786 | CA | VAL | 390 | 66.290 | 47.286 | 40.142 | 1.00 | 47.76 |
| ATOM | 1787 | CB | VAL | 390 | 67.152 | 46.186 | 40.804 | 1.00 | 46.30 |
| ATOM | 1788 | CG1 | VAL | 390 | 67.796 | 46.706 | 42.079 | 1.00 | 49.20 |
| ATOM | 1789 | CG2 | VAL | 390 | 66.305 | 44.962 | 41.097 | 1.00 | 42.69 |
| ATOM | 1790 | C | VAL | 390 | 67.109 | 48.571 | 40.070 | 1.00 | 47.25 |
| ATOM | 1791 | O | VAL | 390 | 66.811 | 49.540 | 40.760 | 1.00 | 48.67 |
| ATOM | 1792 | N | GLU | 391 | 68.115 | 48.580 | 39.199 | 1.00 | 44.11 |
| ATOM | 1793 | CA | GLU | 391 | 69.009 | 49.721 | 39.047 | 1.00 | 45.79 |
| ATOM | 1794 | CB | GLU | 391 | 70.266 | 49.311 | 38.273 | 1.00 | 45.78 |
| ATOM | 1795 | CG | GLU | 391 | 70.998 | 48.091 | 38.830 | 1.00 | 57.29 |
| ATOM | 1796 | CD | GLU | 391 | 71.479 | 48.268 | 40.261 | 1.00 | 61.20 |
| ATOM | 1797 | OE1 | GLU | 391 | 71.845 | 49.400 | 40.646 | 1.00 | 57.29 |
| ATOM | 1798 | OE2 | GLU | 391 | 71.496 | 47.263 | 41.001 | 1.00 | 63.69 |
| ATOM | 1799 | C | GLU | 391 | 68.410 | 50.959 | 38.391 | 1.00 | 49.16 |
| ATOM | 1800 | O | GLU | 391 | 68.463 | 52.055 | 38.956 | 1.00 | 58.82 |
| ATOM | 1801 | N | CYA | 392 | 67.802 | 50.782 | 37.224 | 1.00 | 49.75 |
| ATOM | 1802 | CA | CYA | 392 | 67.255 | 51.908 | 36.475 | 1.00 | 45.56 |
| ATOM | 1803 | CB | CYA | 392 | 67.667 | 51.768 | 35.016 | 1.00 | 44.82 |
| ATOM | 1804 | SG | CYA | 392 | 69.443 | 51.771 | 34.913 | 1.00 | 50.78 |
| ATOM | 1805 | AS | CYA | 392 | 69.929 | 50.778 | 33.022 | 1.00 | 53.29 |
| ATOM | 1806 | C | CYA | 392 | 65.771 | 52.200 | 36.601 | 1.00 | 44.35 |
| ATOM | 1807 | O | CYA | 392 | 64.988 | 51.324 | 36.962 | 1.00 | 44.10 |
| ATOM | 1808 | N | PRO | 393 | 65.378 | 53.469 | 36.365 | 1.00 | 45.52 |
| ATOM | 1809 | CD | PRO | 393 | 66.275 | 54.603 | 36.075 | 1.00 | 37.38 |

APPENDIX 5-continued

TR_IPBR2.PDB

| ATOM | 1810 | CA  | PRO | 393 | 63.982 | 53.916 | 36.444 | 1.00 | 45.41 |
|------|------|-----|-----|-----|--------|--------|--------|------|-------|
| ATOM | 1811 | CB  | PRO | 393 | 64.105 | 55.438 | 36.376 | 1.00 | 43.33 |
| ATOM | 1812 | CG  | PRO | 393 | 65.329 | 55.644 | 35.542 | 1.00 | 39.89 |
| ATOM | 1813 | C   | PRO | 393 | 63.108 | 53.376 | 35.318 | 1.00 | 44.89 |
| ATOM | 1814 | O   | PRO | 393 | 63.556 | 53.239 | 34.175 | 1.00 | 45.60 |
| ATOM | 1815 | N   | THR | 394 | 61.843 | 53.135 | 35.647 | 1.00 | 47.52 |
| ATOM | 1816 | CA  | THR | 394 | 60.853 | 52.603 | 34.713 | 1.00 | 53.06 |
| ATOM | 1817 | CB  | THR | 394 | 59.459 | 52.583 | 35.371 | 1.00 | 61.06 |
| ATOM | 1818 | OG1 | THR | 394 | 59.609 | 52.470 | 36.794 | 1.00 | 72.44 |
| ATOM | 1819 | CG2 | THR | 394 | 58.640 | 51.401 | 34.860 | 1.00 | 61.05 |
| ATOM | 1820 | C   | THR | 394 | 60.767 | 53.373 | 33.392 | 1.00 | 49.98 |
| ATOM | 1821 | O   | THR | 394 | 60.507 | 52.786 | 32.339 | 1.00 | 51.06 |
| ATOM | 1822 | N   | GLU | 395 | 61.024 | 54.676 | 33.452 | 1.00 | 48.55 |
| ATOM | 1823 | CA  | GLU | 395 | 60.970 | 55.548 | 32.282 | 1.00 | 44.21 |
| ATOM | 1824 | CB  | GLU | 395 | 61.258 | 56.987 | 32.697 | 1.00 | 41.66 |
| ATOM | 1825 | C   | GLU | 395 | 61.899 | 55.134 | 31.134 | 1.00 | 43.46 |
| ATOM | 1826 | O   | GLU | 395 | 61.684 | 55.527 | 29.988 | 1.00 | 44.17 |
| ATOM | 1827 | N   | LEU | 396 | 62.934 | 54.359 | 31.449 | 1.00 | 41.05 |
| ATOM | 1828 | CA  | LEU | 396 | 63.898 | 53.899 | 30.448 | 1.00 | 39.55 |
| ATOM | 1829 | CB  | LEU | 396 | 65.270 | 53.708 | 31.106 | 1.00 | 35.03 |
| ATOM | 1830 | CG  | LEU | 396 | 66.296 | 54.834 | 30.945 | 1.00 | 40.06 |
| ATOM | 1831 | CD1 | LEU | 396 | 65.638 | 56.200 | 31.055 | 1.00 | 39.06 |
| ATOM | 1832 | CD2 | LEU | 396 | 67.398 | 54.669 | 31.978 | 1.00 | 32.78 |
| ATOM | 1833 | C   | LEU | 396 | 63.468 | 52.602 | 29.757 | 1.00 | 38.50 |
| ATOM | 1834 | O   | LEU | 396 | 64.106 | 52.150 | 28.804 | 1.00 | 34.72 |
| ATOM | 1835 | N   | PHE | 397 | 62.364 | 52.028 | 30.225 | 1.00 | 38.76 |
| ATOM | 1836 | CA  | PHE | 397 | 61.860 | 50.774 | 29.683 | 1.00 | 36.57 |
| ATOM | 1837 | CB  | PHE | 397 | 61.610 | 49.775 | 30.819 | 1.00 | 33.96 |
| ATOM | 1838 | CG  | PHE | 397 | 62.842 | 49.421 | 31.607 | 1.00 | 36.95 |
| ATOM | 1839 | CD1 | PHE | 397 | 63.331 | 50.280 | 32.587 | 1.00 | 34.61 |
| ATOM | 1840 | CD2 | PHE | 397 | 63.523 | 48.234 | 31.362 | 1.00 | 37.14 |
| ATOM | 1841 | CE1 | PHE | 397 | 64.481 | 49.964 | 33.310 | 1.00 | 31.57 |
| ATOM | 1842 | CE2 | PHE | 397 | 64.675 | 47.908 | 32.082 | 1.00 | 37.85 |
| ATOM | 1843 | CZ  | PHE | 397 | 65.153 | 48.776 | 33.056 | 1.00 | 33.08 |
| ATOM | 1844 | C   | PHE | 397 | 60.584 | 50.921 | 28.858 | 1.00 | 35.65 |
| ATOM | 1845 | O   | PHE | 397 | 59.519 | 51.249 | 29.399 | 1.00 | 35.75 |
| ATOM | 1846 | N   | PRO | 398 | 60.672 | 50.685 | 27.536 | 1.00 | 35.78 |
| ATOM | 1847 | CD  | PRO | 398 | 61.891 | 50.367 | 26.767 | 1.00 | 32.81 |
| ATOM | 1848 | CA  | PRO | 398 | 59.503 | 50.786 | 26.658 | 1.00 | 33.94 |
| ATOM | 1849 | CB  | PRO | 398 | 60.041 | 50.297 | 25.315 | 1.00 | 33.91 |
| ATOM | 1850 | CG  | PRO | 398 | 61.488 | 50.707 | 25.356 | 1.00 | 33.09 |
| ATOM | 1851 | C   | PRO | 398 | 58.434 | 49.840 | 27.210 | 1.00 | 34.98 |
| ATOM | 1852 | O   | PRO | 398 | 58.753 | 48.729 | 27.654 | 1.00 | 35.76 |
| ATOM | 1853 | N   | PRO | 399 | 57.163 | 50.267 | 27.219 | 1.00 | 37.67 |
| ATOM | 1854 | CD  | PRO | 399 | 56.661 | 51.578 | 26.776 | 1.00 | 38.02 |
| ATOM | 1855 | CA  | PRO | 399 | 56.070 | 49.433 | 27.733 | 1.00 | 36.86 |
| ATOM | 1856 | CB  | PRO | 399 | 54.803 | 50.183 | 27.291 | 1.00 | 34.14 |
| ATOM | 1857 | CG  | PRO | 399 | 55.282 | 51.240 | 26.310 | 1.00 | 37.00 |
| ATOM | 1858 | C   | PRO | 399 | 56.085 | 47.970 | 27.273 | 1.00 | 37.06 |
| ATOM | 1859 | O   | PRO | 399 | 55.967 | 47.063 | 28.099 | 1.00 | 37.07 |
| ATOM | 1860 | N   | LEU | 400 | 56.299 | 47.738 | 25.980 | 1.00 | 35.13 |
| ATOM | 1861 | CA  | LEU | 400 | 56.327 | 46.374 | 25.445 | 1.00 | 35.86 |
| ATOM | 1862 | CB  | LEU | 400 | 56.314 | 46.385 | 23.914 | 1.00 | 31.49 |
| ATOM | 1863 | CG  | LEU | 400 | 56.181 | 45.017 | 23.227 | 1.00 | 30.73 |
| ATOM | 1864 | CD1 | LEU | 400 | 54.901 | 44.330 | 23.674 | 1.00 | 21.35 |
| ATOM | 1865 | CD2 | LEU | 400 | 56.197 | 45.183 | 21.720 | 1.00 | 25.42 |
| ATOM | 1866 | C   | LEU | 400 | 57.542 | 45.597 | 25.958 | 1.00 | 36.51 |
| ATOM | 1867 | O   | LEU | 490 | 57.458 | 44.392 | 26.219 | 1.00 | 37.47 |
| ATOM | 1868 | N   | PHE | 401 | 58.671 | 46.290 | 26.095 | 1.00 | 32.26 |
| ATOM | 1869 | CA  | PHE | 401 | 59.899 | 45.682 | 26.596 | 1.00 | 35.15 |
| ATOM | 1870 | CB  | PHE | 401 | 61.014 | 46.739 | 26.648 | 1.00 | 35.99 |
| ATOM | 1871 | CG  | PHE | 401 | 62.346 | 46.213 | 27.117 | 1.00 | 39.41 |
| ATOM | 1872 | CD1 | PHE | 401 | 62.845 | 45.003 | 26.639 | 1.00 | 35.94 |
| ATOM | 1873 | CD2 | PHE | 401 | 63.119 | 46.944 | 28.019 | 1.00 | 40.55 |
| ATOM | 1874 | CE1 | PHE | 401 | 64.088 | 44.531 | 27.055 | 1.00 | 30.16 |
| ATOM | 1875 | CE2 | PHE | 401 | 64.367 | 46.478 | 28.439 | 1.00 | 35.53 |
| ATOM | 1876 | CZ  | PHE | 401 | 64.849 | 45.271 | 27.952 | 1.00 | 36.39 |
| ATOM | 1877 | C   | PHE | 401 | 59.607 | 45.129 | 27.996 | 1.00 | 36.42 |
| ATOM | 1878 | O   | PHE | 401 | 59.957 | 43.995 | 28.317 | 1.00 | 36.71 |
| ATOM | 1879 | N   | LEU | 402 | 58.920 | 45.925 | 28.805 | 1.00 | 36.59 |
| ATOM | 1880 | CA  | LEU | 402 | 58.561 | 45.528 | 30.158 | 1.00 | 37.68 |
| ATOM | 1881 | CB  | LEU | 402 | 57.986 | 46.720 | 30.917 | 1.00 | 40.71 |
| ATOM | 1882 | CG  | LEU | 402 | 58.963 | 47.751 | 31.463 | 1.00 | 43.13 |
| ATOM | 1883 | CD1 | LEU | 402 | 58.180 | 48.926 | 32.031 | 1.00 | 39.88 |
| ATOM | 1884 | CD2 | LEU | 402 | 59.847 | 47.103 | 32.527 | 1.00 | 38.39 |
| ATOM | 1885 | C   | LEU | 402 | 57.521 | 44.420 | 30.164 | 1.00 | 38.02 |
| ATOM | 1886 | O   | LEU | 402 | 57.582 | 43.507 | 30.984 | 1.00 | 37.39 |

APPENDIX 5-continued

TR_IPBR2.PDB

| ATOM | 1887 | N | GLU | 403 | 56.558 | 44.522 | 29.251 | 1.00 | 39.74 |
|---|---|---|---|---|---|---|---|---|---|
| ATOM | 1888 | CA | GLU | 403 | 55.469 | 43.559 | 29.166 | 1.00 | 42.79 |
| ATOM | 1889 | CB | GLU | 403 | 54.445 | 44.022 | 28.129 | 1.00 | 46.21 |
| ATOM | 1890 | CG | GLU | 403 | 53.092 | 43.330 | 28.232 | 1.00 | 56.88 |
| ATOM | 1891 | CD | GLU | 403 | 52.090 | 43.833 | 27.202 | 1.00 | 65.21 |
| ATOM | 1892 | OE1 | GLU | 403 | 52.230 | 44.983 | 26.728 | 1.00 | 70.60 |
| ATOM | 1893 | OE2 | GLU | 403 | 51.154 | 43.073 | 26.870 | 1.00 | 70.53 |
| ATOM | 1894 | C | GLU | 403 | 55.890 | 42.121 | 28.886 | 1.00 | 40.14 |
| ATOM | 1895 | O | GLU | 403 | 55.368 | 41.200 | 29.506 | 1.00 | 40.57 |
| ATOM | 1896 | N | VAL | 404 | 56.835 | 41.932 | 27.966 | 1.00 | 39.43 |
| ATOM | 1897 | CA | VAL | 404 | 57.292 | 40.586 | 27.610 | 1.00 | 40.96 |
| ATOM | 1898 | CB | VAL | 404 | 57.851 | 40.516 | 26.159 | 1.00 | 35.50 |
| ATOM | 1899 | CG1 | VAL | 404 | 56.807 | 40.995 | 25.177 | 1.00 | 43.46 |
| ATOM | 1900 | CG2 | VAL | 404 | 59.132 | 41.321 | 26.030 | 1.00 | 25.74 |
| ATOM | 1901 | C | VAL | 404 | 58.317 | 39.946 | 28.536 | 1.00 | 41.94 |
| ATOM | 1902 | O | VAL | 404 | 58.468 | 38.722 | 28.533 | 1.00 | 43.82 |
| ATOM | 1903 | N | PHE | 405 | 59.026 | 40.759 | 29.310 | 1.00 | 39.84 |
| ATOM | 1904 | CA | PHE | 405 | 60.051 | 40.223 | 30.189 | 1.00 | 42.73 |
| ATOM | 1905 | CB | PHE | 405 | 61.401 | 40.897 | 29.913 | 1.00 | 36.85 |
| ATOM | 1906 | CG | PHE | 405 | 61.963 | 40.596 | 28.551 | 1.00 | 33.23 |
| ATOM | 1907 | CD1 | PHE | 405 | 62.283 | 41.625 | 27.672 | 1.00 | 33.90 |
| ATOM | 1908 | CD2 | PHE | 405 | 62.157 | 39.281 | 28.138 | 1.00 | 31.62 |
| ATOM | 1909 | CE1 | PHE | 405 | 62.786 | 41.351 | 26.399 | 1.00 | 39.16 |
| ATOM | 1910 | CE2 | PHE | 405 | 62.657 | 38.997 | 26.872 | 1.00 | 33.33 |
| ATOM | 1911 | CZ | PHE | 405 | 62.972 | 40.033 | 25.999 | 1.00 | 31.99 |
| ATOM | 1912 | C | PHE | 405 | 59.723 | 40.273 | 31.676 | 1.00 | 43.97 |
| ATOM | 1913 | O | PHE | 405 | 60.636 | 39.943 | 32.460 | 1.00 | 46.56 |
| ATOM | 1 | O1 | HOH | 501 | 67.928 | 36.755 | 11.188 | 1.00 | 33.04 |
| ATOM | 2 | O1 | HOH | 502 | 69.618 | 40.719 | 13.009 | 1.00 | 23.00 |
| ATOM | 3 | O1 | HOH | 503 | 64.885 | 40.168 | 12.340 | 1.00 | 23.00 |
| ATOM | 4 | O1 | HOH | 504 | 63.079 | 40.108 | 15.841 | 1.00 | 23.00 |
| ATOM | 5 | O1 | HOH | 505 | 63.404 | 46.536 | 15.354 | 1.00 | 36.41 |
| ATOM | 6 | O1 | HOH | 506 | 61.299 | 15.617 | −0.595 | 1.00 | 23.00 |
| ATOM | 7 | O1 | HOH | 507 | 67.359 | 15.375 | 0.551 | 1.00 | 23.00 |
| ATOM | 8 | O1 | HOH | 508 | 67.230 | 12.002 | −0.634 | 1.00 | 23.00 |
| ATOM | 9 | O1 | HOH | 509 | 66.906 | 12.467 | 3.855 | 1.00 | 23.00 |
| ATOM | 10 | O1 | HOH | 510 | 61.785 | 9.946 | 3.983 | 1.00 | 23.00 |
| ATOM | 11 | O1 | HOH | 511 | 57.670 | 11.385 | 9.909 | 1.00 | 23.00 |
| ATOM | 12 | O1 | HOH | 512 | 55.791 | 11.570 | 10.291 | 1.00 | 23.00 |
| ATOM | 13 | O1 | HOH | 513 | 54.637 | 14.058 | 9.201 | 1.00 | 23.00 |
| ATOM | 14 | O1 | HOH | 514 | 55.882 | 16.054 | 12.204 | 1.00 | 26.53 |
| ATOM | 15 | O1 | HOH | 515 | 53.685 | 15.842 | 18.209 | 1.00 | 23.00 |
| ATOM | 16 | O1 | HOH | 516 | 49.559 | 24.773 | 19.020 | 1.00 | 23.00 |
| ATOM | 17 | O1 | HOH | 517 | 51.258 | 25.512 | 13.384 | 1.00 | 37.74 |
| ATOM | 18 | O1 | HOH | 518 | 53.551 | 25.749 | 10.593 | 1.00 | 42.31 |
| ATOM | 19 | O1 | HOH | 519 | 50.338 | 23.299 | 7.662 | 1.00 | 41.19 |
| ATOM | 20 | O1 | HOH | 520 | 50.830 | 20.272 | 8.323 | 1.00 | 28.46 |
| ATOM | 21 | O1 | HOH | 521 | 48.630 | 20.291 | 6.429 | 1.00 | 23.00 |
| ATOM | 22 | O1 | HOH | 522 | 49.233 | 17.389 | 2.867 | 1.00 | 23.00 |
| ATOM | 23 | O1 | HOH | 523 | 52.076 | 22.770 | 1.260 | 1.00 | 23.00 |
| ATOM | 24 | O1 | HOH | 524 | 51.671 | 23.621 | −1.020 | 1.00 | 23.00 |
| ATOM | 25 | O1 | HOH | 525 | 58.294 | 31.509 | 2.147 | 1.00 | 31.83 |
| ATOM | 26 | O1 | HOH | 526 | 57.497 | 36.071 | 2.268 | 1.00 | 23.00 |
| ATOM | 27 | O1 | HOH | 527 | 65.373 | 36.025 | 6.809 | 1.00 | 23.00 |
| ATOM | 28 | O1 | HOH | 528 | 67.871 | 36.399 | 6.419 | 1.00 | 66.52 |
| ATOM | 29 | O1 | HOH | 529 | 67.189 | 33.811 | 9.409 | 1.00 | 23.00 |
| ATOM | 30 | O1 | HOH | 530 | 62.458 | 48.056 | 13.590 | 1.00 | 23.00 |
| ATOM | 31 | O1 | HOH | 531 | 63.943 | 46.824 | 10.638 | 1.00 | 39.26 |
| ATOM | 32 | O1 | HOH | 532 | 57.465 | 45.867 | 13.186 | 1.00 | 23.00 |
| ATOM | 33 | O1 | HOH | 533 | 55.223 | 40.774 | 10.959 | 1.00 | 23.00 |
| ATOM | 34 | O1 | HOH | 534 | 53.737 | 44.032 | 19.560 | 1.00 | 23.00 |
| ATOM | 35 | O1 | HOH | 535 | 55.982 | 49.757 | 24.168 | 1.00 | 23.00 |
| ATOM | 36 | O1 | HOH | 536 | 58.575 | 52.330 | 31.881 | 1.00 | 23.00 |
| ATOM | 37 | O1 | HOH | 537 | 62.563 | 49.327 | 37.804 | 1.00 | 23.00 |
| ATOM | 38 | O1 | HOH | 538 | 61.736 | 40.280 | 35.059 | 1.00 | 60.53 |
| ATOM | 39 | O1 | HOH | 539 | 63.271 | 38.155 | 34.156 | 1.00 | 52.21 |
| ATOM | 40 | O1 | HOH | 540 | 61.872 | 35.187 | 29.990 | 1.00 | 23.00 |
| ATOM | 41 | O1 | HOH | 541 | 63.701 | 36.808 | 28.720 | 1.00 | 23.00 |
| ATOM | 42 | O1 | HOH | 542 | 62.255 | 35.864 | 26.425 | 1.00 | 26.69 |
| ATOM | 43 | O1 | HOH | 543 | 63.567 | 33.453 | 25.308 | 1.00 | 44.90 |
| ATOM | 44 | O1 | HOH | 544 | 65.456 | 30.135 | 27.713 | 1.00 | 23.00 |
| ATOM | 45 | O1 | HOH | 545 | 61.997 | 26.566 | 24.157 | 1.00 | 23.00 |
| ATOM | 46 | O1 | HOH | 546 | 61.422 | 22.231 | 24.358 | 1.00 | 23.00 |
| ATOM | 47 | O1 | HOH | 547 | 59.636 | 21.462 | 25.378 | 1.00 | 23.00 |
| ATOM | 48 | O1 | HOH | 548 | 64.860 | 21.210 | 22.578 | 1.00 | 23.00 |
| ATOM | 49 | O1 | HOH | 549 | 63.316 | 14.964 | 15.508 | 1.00 | 52.55 |
| ATOM | 50 | O1 | HOH | 550 | 62.779 | 10.707 | 15.710 | 1.00 | 48.78 |

APPENDIX 5-continued

TR_IPBR2.PDB

| ATOM | 51 | O1 | HOH | 551 | 61.579 | 9.665 | 12.081 | 1.00 | 23.00 |
|---|---|---|---|---|---|---|---|---|---|
| ATOM | 52 | O1 | HOH | 552 | 65.916 | 11.929 | 11.639 | 1.00 | 23.00 |
| ATOM | 53 | O1 | HOH | 553 | 68.086 | 12.882 | 11.226 | 1.00 | 23.00 |
| ATOM | 54 | O1 | HOH | 554 | 69.504 | 11.968 | 14.083 | 1.00 | 23.00 |
| ATOM | 55 | O1 | HOH | 555 | 72.311 | 15.121 | 10.552 | 1.00 | 23.00 |
| ATOM | 56 | O1 | HOH | 556 | 74.716 | 15.172 | 10.253 | 1.00 | 23.00 |
| ATOM | 57 | O1 | HOH | 557 | 73.109 | 17.916 | 7.451 | 1.00 | 23.00 |
| ATOM | 58 | O1 | HOH | 558 | 71.316 | 15.446 | 7.652 | 1.00 | 23.00 |
| ATOM | 59 | O1 | HOH | 559 | 74.717 | 14.555 | 5.957 | 1.00 | 23.00 |
| ATOM | 60 | O1 | HOH | 560 | 73.523 | 22.311 | 2.467 | 1.00 | 23.00 |
| ATOM | 61 | O1 | HOH | 561 | 76.491 | 23.094 | 5.700 | 1.00 | 51.34 |
| ATOM | 62 | O1 | HOH | 562 | 73.961 | 29.841 | 10.035 | 1.00 | 33.87 |
| ATOM | 63 | O1 | HOH | 563 | 76.164 | 33.031 | 11.370 | 1.00 | 23.00 |
| ATOM | 64 | O1 | HOH | 564 | 77.193 | 34.039 | 9.712 | 1.00 | 37.14 |
| ATOM | 65 | O1 | HOH | 565 | 76.525 | 41.395 | 10.460 | 1.00 | 23.00 |
| ATOM | 66 | O1 | HOH | 566 | 79.358 | 49.535 | 15.048 | 1.00 | 53.78 |
| ATOM | 67 | O1 | HOH | 567 | 78.046 | 53.530 | 9.188 | 1.00 | 23.00 |
| ATOM | 68 | O1 | HOH | 568 | 68.058 | 52.158 | 15.548 | 1.00 | 23.00 |
| ATOM | 69 | O1 | HOH | 569 | 68.598 | 53.164 | 18.083 | 1.00 | 45.72 |
| ATOM | 70 | O1 | HOH | 570 | 73.482 | 58.914 | 21.552 | 1.00 | 58.99 |
| ATOM | 71 | O1 | HOH | 571 | 65.648 | 53.551 | 26.240 | 1.00 | 23.00 |
| ATOM | 72 | O1 | HOH | 572 | 75.776 | 46.207 | 30.367 | 1.00 | 33.32 |
| ATOM | 73 | O1 | HOH | 573 | 78.686 | 46.470 | 31.087 | 1.00 | 23.00 |
| ATOM | 74 | O1 | HOH | 574 | 77.580 | 41.209 | 31.884 | 1.00 | 23.00 |
| ATOM | 75 | O1 | HOH | 575 | 76.879 | 31.531 | 24.067 | 1.00 | 23.00 |
| ATOM | 76 | O1 | HOH | 576 | 77.927 | 29.163 | 20.647 | 1.00 | 23.00 |
| ATOM | 77 | O1 | HOH | 577 | 80.180 | 24.963 | 17.233 | 1.00 | 53.36 |
| ATOM | 78 | O1 | HOH | 578 | 80.631 | 25.802 | 15.508 | 1.00 | 23.00 |
| ATOM | 79 | O1 | HOH | 579 | 82.104 | 22.566 | 14.156 | 1.00 | 23.00 |
| ATOM | 80 | O1 | HOH | 580 | 76.954 | 22.077 | 18.425 | 1.00 | 46.50 |
| ATOM | 81 | O1 | HOH | 581 | 86.619 | 37.903 | 16.945 | 1.00 | 47.66 |
| ATOM | 82 | O1 | HOH | 582 | 83.586 | 42.305 | 18.576 | 1.00 | 23.00 |
| ATOM | 83 | O1 | HOH | 583 | 83.481 | 45.262 | 19.526 | 1.00 | 23.00 |
| ATOM | 84 | O1 | HOH | 584 | 66.787 | 32.864 | 33.796 | 1.00 | 23.00 |
| ATOM | 85 | O1 | HOH | 585 | 59.447 | 33.572 | 30.734 | 1.00 | 23.00 |
| ATOM | 86 | O1 | HOH | 586 | 57.013 | 32.278 | 31.125 | 1.00 | 23.00 |
| ATOM | 87 | O1 | HOH | 587 | 58.084 | 29.428 | 24.648 | 1.00 | 24.06 |
| ATOM | 88 | O1 | HOH | 588 | 52.774 | 25.054 | 32.650 | 1.00 | 57.81 |
| ATOM | 89 | O1 | HOH | 589 | 53.800 | 24.465 | 34.834 | 1.00 | 23.00 |
| ATOM | 90 | O1 | HOH | 590 | 47.195 | 30.205 | 30.414 | 1.00 | 23.00 |
| ATOM | 91 | O1 | HOH | 591 | 48.978 | 35.051 | 30.228 | 1.00 | 23.00 |
| ATOM | 92 | O1 | HOH | 592 | 49.280 | 39.962 | 31.041 | 1.00 | 23.00 |
| ATOM | 93 | O1 | HOH | 593 | 42.329 | 32.230 | 20.993 | 1.00 | 23.00 |
| ATOM | 94 | O1 | HOH | 594 | 44.199 | 32.910 | 19.088 | 1.00 | 23.00 |
| ATOM | 95 | O1 | HOH | 595 | 41.542 | 27.336 | 19.178 | 1.00 | 23.00 |
| ATOM | 96 | O1 | HOH | 596 | 48.971 | 31.296 | 14.022 | 1.00 | 23.00 |
| ATOM | 97 | O1 | HOH | 597 | 50.180 | 31.092 | 7.307 | 1.00 | 23.00 |
| ATOM | 98 | O1 | HOH | 598 | 64.465 | 28.209 | 3.208 | 1.00 | 45.35 |
| ATOM | 99 | O1 | HOH | 599 | 67.740 | 26.910 | 1.986 | 1.00 | 23.00 |
| ATOM | 100 | O1 | HOH | 600 | 67.958 | 31.203 | 3.532 | 1.00 | 23.00 |
| ATOM | 101 | O1 | HOH | 601 | 68.885 | 22.721 | 0.234 | 1.00 | 39.53 |
| ATOM | 102 | O1 | HOH | 602 | 46.735 | 20.335 | 25.877 | 1.00 | 44.92 |
| ATOM | 103 | O1 | HOH | 603 | 47.359 | 19.644 | 28.494 | 1.00 | 41.57 |
| ATOM | 2300 | C | ACY | 701 | 52.555 | 39.909 | 24.622 | 1.00 | 48.75 |
| ATOM | 2301 | O | ACY | 701 | 52.351 | 40.361 | 25.771 | 1.00 | 48.92 |
| ATOM | 2302 | OXT | ACY | 701 | 53.503 | 39.156 | 24.279 | 1.00 | 50.69 |
| ATOM | 2303 | CH3 | ACY | 701 | 51.543 | 40.314 | 23.527 | 1.00 | 41.32 |
| ATOM | 2304 | C1 | IBR | 1 | 67.309 | 42.207 | 18.510 | 1.00 | 32.20 |
| ATOM | 2305 | C2 | IBR | 1 | 68.795 | 43.194 | 23.237 | 1.00 | 29.59 |
| ATOM | 2306 | C3 | IBR | 1 | 67.192 | 43.467 | 19.068 | 1.00 | 25.49 |
| ATOM | 2307 | C4 | IBR | 1 | 69.096 | 44.270 | 24.011 | 1.00 | 25.67 |
| ATOM | 2308 | C5 | IBR | 1 | 67.884 | 43.772 | 20.218 | 1.00 | 35.08 |
| ATOM | 2309 | C6 | IBR | 1 | 68.489 | 44.345 | 25.356 | 1.00 | 30.87 |
| ATOM | 2310 | C7 | IBR | 1 | 68.673 | 42.828 | 20.790 | 1.00 | 30.76 |
| ATOM | 2311 | C8 | IBR | 1 | 67.681 | 43.327 | 25.704 | 1.00 | 29.18 |
| ATOM | 2312 | C9 | IBR | 1 | 68.811 | 41.580 | 20.269 | 1.00 | 32.19 |
| ATOM | 2313 | C10 | IBR | 1 | 67.383 | 42.244 | 24.921 | 1.00 | 26.78 |
| ATOM | 2314 | C11 | IBR | 1 | 68.122 | 41.241 | 19.099 | 1.00 | 25.50 |
| ATOM | 2315 | C12 | IBR | 1 | 67.979 | 42.171 | 23.609 | 1.00 | 24.47 |
| ATOM | 2316 | C13 | IBR | 1 | 66.529 | 41.932 | 17.285 | 1.00 | 17.69 |
| ATOM | 2317 | C14 | IBR | 1 | 68.730 | 45.450 | 26.287 | 1.00 | 30.43 |
| ATOM | 2318 | C15 | IBR | 1 | 67.011 | 40.785 | 16.271 | 1.00 | 21.37 |
| ATOM | 2319 | C16 | IBR | 1 | 67.939 | 46.867 | 25.912 | 1.00 | 23.75 |
| ATOM | 2320 | C17 | IBR | 1 | 65.946 | 40.598 | 15.151 | 1.00 | 23.91 |
| ATOM | 2321 | C18 | IBR | 1 | 70.126 | 46.087 | 26.069 | 1.00 | 26.02 |
| ATOM | 2322 | BR1 | IBR | 1 | 67.708 | 45.504 | 20.878 | 1.00 | 34.64 |
| ATOM | 2323 | BR2 | IBR | 1 | 69.927 | 40.301 | 21.039 | 1.00 | 32.01 |

APPENDIX 5-continued

TR_IPBR2.PDB

| ATOM | 2324 | N1 | IBR | 1 | 68.284 | 40.938 | 15.821 | 1.00 | 18.75 |
|---|---|---|---|---|---|---|---|---|---|
| ATOM | 2325 | O1 | IBR | 1 | 67.068 | 43.397 | 26.981 | 1.00 | 26.31 |
| ATOM | 2326 | O2 | IBR | 1 | 69.393 | 43.153 | 21.933 | 1.00 | 30.15 |
| ATOM | 2327 | O3 | IBR | 1 | 66.368 | 40.592 | 14.004 | 1.00 | 23.29 |
| ATOM | 2328 | O4 | IBR | 1 | 64.786 | 40.511 | 15.515 | 1.00 | 23.47 |
| END | | | | | | | | | |
| END | | | | | | | | | |

APPENDIX 6

TR_T3.PBD

REMARK rTR_t3 full length numbering
REMARK
REMARK Rfactor 0.221 Rfree 0.240
REMARK Resolution 5. 2.0 all reflections
REMARK conformation of MET 388 confirmed by SA_omit map
REMARK
REMARK Three cacodylate-modified cysteines (CYA)
REMARK Cya334, Cya380, Cya392
REMARK cacodylate modeled as single arsenic atom
REMARK
REMARK side chain of certain residues modeled as ALA due to poor density;
REMARK however, residue name reflects true residue for clarity
REMARK
REMARK clone obtained from Murray et. al.
REMARK deposited sequence confirmed,
REMARK differing from that reported by Thompson et. al.
REMARK in the following codons:
REMARK 281 Thr—Ala
REMARK 285 Lys—Glu
REMARK identical to that reported by Mitsuhashi et. al.
REMARK gb:RNTRAVI X07409
JRNL      AUTH    M. B. MURRAY, N. D. ZILZ, N. L. MCCREARY, M. J. MACDONALD
JRNL      AUTH 2 H. C. TOWLE
JRNL      TITL    ISOLATION AND CHARACTERIZATION OF RAT CDNA CLONES FOR TWO
JRNL      TITL 2 DISTINCT THYROID HORMONE RECPTORS
JRNL      REF    JBC          V. 263 25 1988
JRNL      AUTH    C. C. THOMPSON, C. WEINBERGER, R. LEBO, R. M. EVANS
JRNL      TITL    IDENTIFICATION OF A NOVEL THYROID HORMONE RECEPTOR EXPRESSED
JRNL      TITL 2 IN THE MAMMALIAN CENTRAL NERVOUS SYSTEM
JRNL      REF    SCIENCE          V. 237    1987
JRNL      AUTH    T. MITSUHASHI, G. TENNYSON, V. NIKODEM
JRNL      TITL    NUCLEOTIDE SEQUENCE OF NOVEL CDNAS GENERATED BY ALTERNATIVE
JRNL      TITL 2 SPLICING OF A RAT THYROID HORMONE RECEPTOR GENE TRANSCRIPT
JRNL      REF    NUC. ACIDS. RES.          V. 16 12 1988
REMARK

| ATOM | 1 | CB | ARG | 157 | 68.406 | 10.620 | 7.027 | 1.00 | 41.66 |
|---|---|---|---|---|---|---|---|---|---|
| ATOM | 2 | CG | ARG | 157 | 69.926 | 10.540 | 6.997 | 1.00 | 44.48 |
| ATOM | 3 | CD | ARG | 157 | 70.552 | 11.261 | 8.173 | 1.00 | 47.02 |
| ATOM | 4 | NE | ARG | 157 | 70.112 | 10.680 | 9.435 | 1.00 | 49.73 |
| ATOM | 5 | CZ | ARG | 157 | 70.917 | 10.392 | 10.450 | 1.00 | 51.21 |
| ATOM | 6 | NH1 | ARG | 157 | 72.223 | 10.629 | 10.361 | 1.00 | 51.79 |
| ATOM | 7 | NH2 | ARG | 157 | 70.405 | 9.871 | 11.556 | 1.00 | 51.92 |
| ATOM | 8 | C | ARG | 157 | 66.308 | 9.993 | 5.774 | 1.00 | 36.48 |
| ATOM | 9 | O | ARG | 157 | 66.047 | 10.318 | 4.622 | 1.00 | 38.84 |
| ATOM | 10 | N | ARG | 157 | 68.479 | 9.473 | 4.839 | 1.00 | 41.22 |
| ATOM | 11 | CA | ARG | 157 | 67.734 | 9.580 | 6.135 | 1.00 | 39.98 |
| ATOM | 12 | N | PRO | 158 | 65.366 | 9.953 | 6.728 | 1.00 | 33.85 |
| ATOM | 13 | CD | PRO | 158 | 65.494 | 9.553 | 8.139 | 1.00 | 34.72 |
| ATOM | 14 | CA | PRO | 158 | 63.981 | 10.336 | 6.407 | 1.00 | 31.89 |
| ATOM | 15 | CB | PRO | 158 | 63.219 | 10.015 | 7.694 | 1.00 | 31.87 |
| ATOM | 16 | CG | PRO | 158 | 64.260 | 10.158 | 8.759 | 1.00 | 33.55 |
| ATOM | 17 | C | PRO | 158 | 63.758 | 11.783 | 5.947 | 1.00 | 29.77 |
| ATOM | 18 | O | PRO | 158 | 64.221 | 12.739 | 6.575 | 1.00 | 27.93 |
| ATOM | 19 | N | GLU | 159 | 63.071 | 11.918 | 4.819 | 1.00 | 26.20 |
| ATOM | 20 | CA | GLU | 159 | 62.759 | 13.217 | 4.239 | 1.00 | 24.07 |
| ATOM | 21 | CB | GLU | 159 | 62.565 | 13.080 | 2.721 | 1.00 | 22.90 |
| ATOM | 22 | CG | GLU | 159 | 63.847 | 12.933 | 1.916 | 1.00 | 22.04 |
| ATOM | 23 | CD | GLU | 159 | 64.386 | 14.260 | 1.427 | 1.00 | 22.07 |

APPENDIX 6-continued

| | | | TR_T3.PBD | | | | |
|---|---|---|---|---|---|---|---|
| ATOM | 24 OE1 | GLU | 159 | 63.577 | 15.175 | 1.203 | 1.00 | 24.63 |
| ATOM | 25 OE2 | GLU | 159 | 65.612 | 14.389 | 1.240 | 1.00 | 23.54 |
| ATOM | 26 C | GLU | 159 | 61.463 | 13.717 | 4.855 | 1.00 | 21.56 |
| ATOM | 27 O | GLU | 159 | 60.747 | 12.958 | 5.516 | 1.00 | 21.03 |
| ATOM | 28 N | PRO | 160 | 61.176 | 15.022 | 4.713 | 1.00 | 19.69 |
| ATOM | 29 CD | PRO | 160 | 61.997 | 16.139 | 4.207 | 1.00 | 16.57 |
| ATOM | 30 CA | PRO | 160 | 59.923 | 15.500 | 5.292 | 1.00 | 18.12 |
| ATOM | 31 CB | PRO | 160 | 59.935 | 16.990 | 4.955 | 1.00 | 15.65 |
| ATOM | 32 CG | PRO | 160 | 61.390 | 17.328 | 4.905 | 1.00 | 14.83 |
| ATOM | 33 C | PRO | 160 | 58.741 | 14.782 | 4.626 | 1.00 | 19.79 |
| ATOM | 34 O | PRO | 160 | 58.793 | 14.431 | 3.445 | 1.00 | 20.20 |
| ATOM | 35 N | THR | 161 | 57.713 | 14.497 | 5.412 | 1.00 | 20.15 |
| ATOM | 36 CA | THR | 161 | 56.525 | 13.846 | 4.901 | 1.00 | 20.73 |
| ATOM | 37 CB | THR | 161 | 55.672 | 13.274 | 6.060 | 1.00 | 20.77 |
| ATOM | 38 OG1 | THR | 161 | 55.195 | 14.348 | 6.881 | 1.00 | 21.74 |
| ATOM | 39 OG2 | THR | 161 | 56.489 | 12.324 | 6.917 | 1.00 | 19.52 |
| ATOM | 40 C | THR | 161 | 55.724 | 14.954 | 4.219 | 1.00 | 21.64 |
| ATOM | 41 O | THR | 161 | 56.010 | 16.139 | 4.421 | 1.00 | 23.13 |
| ATOM | 42 N | PRO | 162 | 54.701 | 14.596 | 3.425 | 1.00 | 21.21 |
| ATOM | 43 CD | PRO | 162 | 54.309 | 13.235 | 3.012 | 1.00 | 19.57 |
| ATOM | 44 CA | PRO | 162 | 53.884 | 15.602 | 2.751 | 1.00 | 21.01 |
| ATOM | 45 CB | PRO | 162 | 52.722 | 14.776 | 2.223 | 1.00 | 19.74 |
| ATOM | 46 CG | PRO | 162 | 53.387 | 13.490 | 1.861 | 1.00 | 20.34 |
| ATOM | 47 C | PRO | 162 | 53.391 | 16.643 | 3.753 | 1.00 | 22.52 |
| ATOM | 48 O | PRO | 162 | 53.508 | 17.851 | 3.526 | 1.00 | 21.68 |
| ATOM | 49 N | GLU | 163 | 52.880 | 16.151 | 4.878 | 1.00 | 23.01 |
| ATOM | 50 CA | GLU | 163 | 52.349 | 16.996 | 5.941 | 1.00 | 25.97 |
| ATOM | 51 CB | GLU | 163 | 51.672 | 16.148 | 7.022 | 1.00 | 29.50 |
| ATOM | 52 CG | GLU | 163 | 50.476 | 15.312 | 6.543 | 1.00 | 37.07 |
| ATOM | 53 CD | GLU | 163 | 50.865 | 14.159 | 5.614 | 1.00 | 41.36 |
| ATOM | 54 OE1 | GLU | 163 | 51.937 | 13.544 | 5.828 | 1.00 | 40.11 |
| ATOM | 55 OE2 | GLU | 163 | 50.094 | 13.874 | 4.660 | 1.00 | 46.16 |
| ATOM | 56 C | GLU | 163 | 53.415 | 17.879 | 6.581 | 1.00 | 24.92 |
| ATOM | 57 O | GLU | 163 | 53.110 | 18.971 | 7.061 | 1.00 | 25.82 |
| ATOM | 58 N | GLU | 164 | 54.661 | 17.412 | 6.600 | 1.00 | 22.87 |
| ATOM | 59 CA | GLU | 164 | 55.724 | 18.209 | 7.187 | 1.00 | 21.46 |
| ATOM | 60 CB | GLU | 164 | 56.880 | 17.340 | 7.664 | 1.00 | 21.23 |
| ATOM | 61 CG | GLU | 164 | 56.509 | 16.508 | 8.886 | 1.00 | 20.30 |
| ATOM | 62 CD | GLU | 164 | 57.557 | 15.483 | 9.243 | 1.00 | 20.07 |
| ATOM | 63 OE1 | GLU | 164 | 58.409 | 15.186 | 8.385 | 1.00 | 19.80 |
| ATOM | 64 OE2 | GLU | 164 | 57.532 | 14.977 | 10.385 | 1.00 | 21.00 |
| ATOM | 65 C | GLU | 164 | 56.195 | 19.289 | 6.235 | 1.00 | 22.45 |
| ATOM | 66 O | GLU | 164 | 56.607 | 20.354 | 6.684 | 1.00 | 23.36 |
| ATOM | 67 N | TRP | 165 | 56.140 | 19.024 | 4.928 | 1.00 | 21.06 |
| ATOM | 68 CA | TRP | 165 | 56.518 | 20.031 | 3.936 | 1.00 | 19.57 |
| ATOM | 69 CB | TRP | 165 | 56.486 | 19.466 | 2.518 | 1.00 | 16.06 |
| ATOM | 70 CG | TRP | 165 | 57.775 | 18.839 | 2.120 | 1.00 | 14.01 |
| ATOM | 71 CD2 | TRP | 165 | 59.055 | 19.480 | 2.037 | 1.00 | 13.26 |
| ATOM | 72 CE2 | TRP | 165 | 59.976 | 18.515 | 1.588 | 1.00 | 12.91 |
| ATOM | 73 CE3 | TRP | 165 | 59.507 | 20.779 | 2.300 | 1.00 | 14.44 |
| ATOM | 74 CD1 | TRP | 165 | 57.972 | 17.544 | 1.738 | 1.00 | 12.89 |
| ATOM | 75 NE1 | TRP | 165 | 59.290 | 17.343 | 1.413 | 1.00 | 12.80 |
| ATOM | 76 CZ2 | TRP | 165 | 61.328 | 18.805 | 1.388 | 1.00 | 15.06 |
| ATOM | 77 CZ3 | TRP | 165 | 60.850 | 21.069 | 2.103 | 1.00 | 14.72 |
| ATOM | 78 CH2 | TRP | 165 | 61.747 | 20.084 | 1.649 | 1.00 | 16.82 |
| ATOM | 79 C | TRP | 165 | 55.553 | 21.210 | 4.056 | 1.00 | 18.93 |
| ATOM | 80 O | TRP | 165 | 55.960 | 22.359 | 3.926 | 1.00 | 21.12 |
| ATOM | 81 N | ASP | 166 | 54.279 | 20.922 | 4.307 | 1.00 | 19.33 |
| ATOM | 82 CA | ASP | 166 | 53.262 | 21.963 | 4.483 | 1.00 | 20.35 |
| ATOM | 83 CB | ASP | 166 | 51.864 | 21.353 | 4.672 | 1.00 | 20.22 |
| ATOM | 84 CG | ASP | 166 | 51.302 | 20.748 | 3.386 | 1.00 | 23.36 |
| ATOM | 85 OD1 | ASP | 166 | 51.746 | 21.153 | 2.296 | 1.00 | 23.42 |
| ATOM | 86 OD2 | ASP | 166 | 50.414 | 19.878 | 3.462 | 1.00 | 21.02 |
| ATOM | 87 C | ASP | 166 | 53.623 | 22.785 | 5.712 | 1.00 | 21.02 |
| ATOM | 88 O | ASP | 166 | 53.627 | 24.013 | 5.654 | 1.00 | 22.56 |
| ATOM | 89 N | LEU | 167 | 53.926 | 22.096 | 6.813 | 1.00 | 20.50 |
| ATOM | 90 CA | LEU | 167 | 54.312 | 22.726 | 8.071 | 1.00 | 21.37 |
| ATOM | 91 CB | LEU | 167 | 54.661 | 21.657 | 9.109 | 1.00 | 23.49 |
| ATOM | 92 CG | LEU | 167 | 54.223 | 21.846 | 10.565 | 1.00 | 27.19 |
| ATOM | 93 CD1 | LEU | 167 | 55.312 | 21.291 | 11.453 | 1.00 | 27.70 |
| ATOM | 94 CD2 | LEU | 167 | 53.940 | 23.314 | 10.906 | 1.00 | 27.71 |
| ATOM | 95 C | LEU | 167 | 55.541 | 23.602 | 7.839 | 1.00 | 20.72 |
| ATOM | 96 O | LEU | 167 | 55.601 | 24.748 | 8.294 | 1.00 | 22.98 |
| ATOM | 97 N | ILE | 168 | 56.505 | 23.051 | 7.114 | 1.00 | 18.54 |
| ATOM | 98 CA | ILE | 168 | 57.747 | 23.725 | 6.778 | 1.00 | 18.60 |
| ATOM | 99 CB | ILE | 168 | 58.671 | 22.771 | 5.995 | 1.00 | 17.54 |
| ATOM | 100 CG2 | ILE | 168 | 59.695 | 23.533 | 5.163 | 1.00 | 17.65 |

APPENDIX 6-continued

TR_T3.PBD

| ATOM | 101 | CG1 | ILE | 168 | 59.330 | 21.794 | 6.972 | 1.00 | 20.27 |
|---|---|---|---|---|---|---|---|---|---|
| ATOM | 102 | CD1 | ILE | 168 | 60.048 | 20.631 | 6.322 | 1.00 | 17.96 |
| ATOM | 103 | C | ILE | 168 | 57.486 | 25.002 | 5.979 | 1.00 | 21.96 |
| ATOM | 104 | O | ILE | 168 | 58.045 | 26.064 | 6.291 | 1.00 | 23.06 |
| ATOM | 105 | N | HIS | 169 | 56.591 | 24.925 | 4.996 | 1.00 | 22.04 |
| ATOM | 106 | CA | HIS | 169 | 56.285 | 26.092 | 4.164 | 1.00 | 21.21 |
| ATOM | 107 | CB | HIS | 169 | 55.413 | 25.702 | 2.969 | 1.00 | 20.12 |
| ATOM | 108 | CG | HIS | 169 | 56.101 | 24.799 | 2.001 | 1.00 | 19.18 |
| ATOM | 109 | CD2 | HIS | 169 | 57.398 | 24.733 | 1.619 | 1.00 | 18.62 |
| ATOM | 110 | ND1 | HIS | 169 | 55.457 | 23.764 | 1.357 | 1.00 | 17.90 |
| ATOM | 111 | CE1 | HIS | 169 | 56.327 | 23.096 | 0.625 | 1.00 | 18.43 |
| ATOM | 112 | NE2 | HIS | 169 | 57.513 | 23.660 | 0.772 | 1.00 | 20.10 |
| ATOM | 113 | C | HIS | 169 | 55.615 | 27.198 | 4.959 | 1.00 | 20.61 |
| ATOM | 114 | O | HIS | 169 | 55.979 | 28.370 | 4.836 | 1.00 | 20.08 |
| ATOM | 115 | N | VAL | 170 | 54.632 | 26.821 | 5.769 | 1.00 | 20.01 |
| ATOM | 116 | CA | VAL | 170 | 53.922 | 27.785 | 6.580 | 1.00 | 20.52 |
| ATOM | 117 | CB | VAL | 170 | 52.816 | 27.120 | 7.384 | 1.00 | 21.33 |
| ATOM | 118 | CG1 | VAL | 170 | 52.224 | 28.113 | 8.366 | 1.00 | 22.32 |
| ATOM | 119 | CG2 | VAL | 170 | 51.740 | 26.608 | 6.438 | 1.00 | 23.27 |
| ATOM | 120 | C | VAL | 170 | 54.891 | 28.477 | 7.521 | 1.00 | 20.58 |
| ATOM | 121 | O | VAL | 170 | 54.926 | 29.704 | 7.554 | 1.00 | 22.32 |
| ATOM | 122 | N | ALA | 171 | 55.712 | 27.696 | 8.230 | 1.00 | 18.83 |
| ATOM | 123 | CA | ALA | 171 | 56.692 | 28.234 | 9.182 | 1.00 | 18.34 |
| ATOM | 124 | CB | ALA | 171 | 57.375 | 27.102 | 9.946 | 1.00 | 17.05 |
| ATOM | 125 | C | ALA | 171 | 57.733 | 29.151 | 8.533 | 1.00 | 17.84 |
| ATOM | 126 | O | ALA | 171 | 58.084 | 30.200 | 9.091 | 1.00 | 18.67 |
| ATOM | 127 | N | THR | 172 | 58.231 | 28.756 | 7.367 | 1.00 | 17.81 |
| ATOM | 128 | CA | THR | 172 | 59.215 | 29.551 | 6.639 | 1.00 | 18.88 |
| ATOM | 129 | CB | THR | 172 | 59.726 | 28.794 | 5.380 | 1.00 | 20.47 |
| ATOM | 130 | OG1 | THR | 172 | 60.280 | 27.531 | 5.776 | 1.00 | 21.38 |
| ATOM | 131 | CG2 | THR | 172 | 60.806 | 29.599 | 4.648 | 1.00 | 20.22 |
| ATOM | 132 | C | THR | 172 | 58.655 | 30.932 | 6.251 | 1.00 | 19.42 |
| ATOM | 133 | O | THR | 172 | 59.320 | 31.957 | 6.435 | 1.00 | 17.98 |
| ATOM | 134 | N | GLU | 173 | 57.425 | 30.970 | 5.756 | 1.00 | 19.97 |
| ATOM | 135 | CA | GLU | 173 | 56.811 | 32.236 | 5.374 | 1.00 | 22.51 |
| ATOM | 136 | CB | GLU | 173 | 55.520 | 31.981 | 4.577 | 1.00 | 27.26 |
| ATOM | 137 | CG | GLU | 173 | 54.823 | 33.244 | 4.005 | 1.00 | 34.96 |
| ATOM | 138 | CD | GLU | 173 | 55.690 | 34.040 | 3.020 | 1.00 | 39.54 |
| ATOM | 139 | OE1 | GLU | 173 | 56.610 | 33.454 | 2.395 | 1.00 | 41.82 |
| ATOM | 140 | OE2 | GLU | 173 | 55.443 | 35.259 | 2.872 | 1.00 | 41.06 |
| ATOM | 141 | C | GLU | 173 | 56.538 | 33.099 | 6.622 | 1.00 | 21.60 |
| ATOM | 142 | O | GLU | 173 | 56.726 | 34.313 | 6.595 | 1.00 | 21.73 |
| ATOM | 143 | N | ALA | 174 | 56.123 | 32.461 | 7.716 | 1.00 | 19.69 |
| ATOM | 144 | CA | ALA | 174 | 55.844 | 33.155 | 8.968 | 1.00 | 18.07 |
| ATOM | 145 | CB | ALA | 174 | 55.423 | 32.169 | 10.037 | 1.00 | 16.90 |
| ATOM | 146 | C | ALA | 174 | 57.101 | 33.883 | 9.400 | 1.00 | 17.65 |
| ATOM | 147 | O | ALA | 174 | 57.052 | 35.031 | 9.829 | 1.00 | 19.80 |
| ATOM | 148 | N | HIS | 175 | 58.240 | 33.222 | 9.259 | 1.00 | 16.39 |
| ATOM | 149 | CA | HIS | 175 | 59.498 | 33.831 | 9.629 | 1.00 | 16.41 |
| ATOM | 150 | CB | HIS | 175 | 60.574 | 32.758 | 9.804 | 1.00 | 12.71 |
| ATOM | 151 | CG | HIS | 175 | 61.938 | 33.318 | 10.043 | 1.00 | 11.09 |
| ATOM | 152 | CD2 | HIS | 175 | 62.373 | 34.252 | 10.920 | 1.00 | 8.26 |
| ATOM | 153 | ND1 | HIS | 175 | 63.030 | 32.977 | 9.273 | 1.00 | 13.39 |
| ATOM | 154 | CE1 | HIS | 175 | 64.076 | 33.683 | 9.658 | 1.00 | 13.77 |
| ATOM | 155 | NE2 | HIS | 175 | 63.702 | 34.464 | 10.658 | 1.00 | 12.70 |
| ATOM | 156 | C | HIS | 175 | 59.959 | 34.903 | 8.624 | 1.00 | 19.55 |
| ATOM | 157 | O | HIS | 175 | 60.293 | 36.027 | 9.016 | 1.00 | 18.38 |
| ATOM | 158 | N | ARG | 176 | 59.987 | 34.555 | 7.339 | 1.00 | 20.77 |
| ATOM | 159 | CA | ARG | 176 | 60.424 | 35.494 | 6.307 | 1.00 | 21.30 |
| ATOM | 160 | CB | ARG | 176 | 60.315 | 34.876 | 4.917 | 1.00 | 24.87 |
| ATOM | 161 | CG | ARG | 176 | 61.361 | 33.827 | 4.609 | 1.00 | 30.22 |
| ATOM | 162 | CD | ARG | 176 | 61.429 | 33.603 | 3.116 | 1.00 | 36.29 |
| ATOM | 163 | NE | ARG | 176 | 62.256 | 32.457 | 2.758 | 1.00 | 44.72 |
| ATOM | 164 | CZ | ARG | 176 | 62.031 | 31.680 | 1.700 | 1.00 | 49.80 |
| ATOM | 165 | NH1 | ARG | 176 | 61.000 | 31.935 | 0.894 | 1.00 | 50.83 |
| ATOM | 166 | NH2 | ARG | 176 | 62.812 | 30.627 | 1.466 | 1.00 | 50.14 |
| ATOM | 167 | C | ARG | 176 | 59.658 | 36.807 | 6.337 | 1.00 | 20.67 |
| ATOM | 168 | O | ARG | 176 | 60.256 | 37.877 | 6.238 | 1.00 | 20.53 |
| ATOM | 169 | N | SER | 177 | 58.344 | 36.730 | 6.508 | 1.00 | 20.67 |
| ATOM | 170 | CA | SER | 177 | 57.526 | 37.934 | 6.551 | 1.00 | 21.86 |
| ATOM | 171 | CB | SER | 177 | 56.061 | 37.588 | 6.298 | 1.00 | 19.59 |
| ATOM | 172 | OG | SER | 177 | 55.541 | 36.774 | 7.329 | 1.00 | 21.85 |
| ATOM | 173 | C | SER | 177 | 57.659 | 38.733 | 7.857 | 1.00 | 23.27 |
| ATOM | 174 | O | SER | 177 | 57.073 | 39.807 | 7.989 | 1.00 | 24.40 |
| ATOM | 175 | N | THR | 178 | 58.383 | 38.202 | 8.837 | 1.00 | 22.16 |
| ATOM | 176 | CA | THR | 178 | 58.542 | 38.913 | 10.095 | 1.00 | 20.62 |
| ATOM | 177 | CB | THR | 178 | 57.853 | 38.162 | 11.265 | 1.00 | 19.93 |

APPENDIX 6-continued

TR_T3.PBD

| ATOM | 178 | OG1 | THR | 178 | 58.386 | 36.838 | 11.381 | 1.00 | 18.72 | |
| --- | --- | --- | --- | --- | --- | --- | --- | --- | --- | --- |
| ATOM | 179 | CG2 | THR | 178 | 56.359 | 38.057 | 11.033 | 1.00 | 16.95 | |
| ATOM | 180 | C | THR | 178 | 60.015 | 39.137 | 10.394 | 1.00 | 21.57 | |
| ATOM | 181 | O | THR | 178 | 60.368 | 39.649 | 11.449 | 1.00 | 23.91 | |
| ATOM | 182 | N | ASN | 179 | 60.870 | 38.769 | 9.445 | 1.00 | 22.22 | |
| ATOM | 183 | CA | ASN | 179 | 62.316 | 38.912 | 9.585 | 1.00 | 24.22 | |
| ATOM | 184 | CB | ASN | 179 | 63.013 | 37.690 | 8.970 | 1.00 | 22.49 | |
| ATOM | 185 | CG | ASN | 179 | 64.480 | 37.596 | 9.344 | 1.00 | 23.53 | |
| ATOM | 186 | OD1 | ASN | 179 | 64.866 | 37.912 | 10.464 | 1.00 | 22.32 | |
| ATOM | 187 | ND2 | ASN | 179 | 65.296 | 37.100 | 8.425 | 1.00 | 23.84 | |
| ATOM | 188 | C | ASN | 179 | 62.744 | 40.210 | 8.881 | 1.00 | 26.52 | |
| ATOM | 189 | O | ASN | 179 | 62.923 | 40.253 | 7.657 | 1.00 | 26.65 | |
| ATOM | 190 | N | ALA | 180 | 62.898 | 41.267 | 9.671 | 1.00 | 27.47 | |
| ATOM | 191 | CA | ALA | 180 | 63.255 | 42.582 | 9.166 | 1.00 | 30.30 | |
| ATOM | 192 | CB | ALA | 180 | 63.552 | 43.508 | 10.321 | 1.00 | 27.21 | |
| ATOM | 193 | C | ALA | 180 | 64.404 | 42.593 | 8.166 | 1.00 | 33.14 | |
| ATOM | 194 | O | ALA | 180 | 65.440 | 41.972 | 8.397 | 1.00 | 33.71 | |
| ATOM | 195 | N | GLN | 181 | 64.209 | 43.295 | 7.049 | 0.50 | 35.09 | ALTA |
| ATOM | 196 | CA | GLN | 181 | 65.212 | 43.423 | 5.980 | 0.50 | 37.44 | ALTA |
| ATOM | 197 | CB | GLN | 181 | 66.544 | 43.974 | 6.511 | 0.50 | 38.60 | ALTA |
| ATOM | 198 | CG | GLN | 181 | 66.728 | 45.462 | 6.299 | 0.50 | 40.53 | ALTA |
| ATOM | 199 | CD | GLN | 181 | 65.805 | 46.291 | 7.162 | 0.50 | 42.72 | ALTA |
| ATOM | 200 | OE1 | GLN | 181 | 64.639 | 46.512 | 6.828 | 0.50 | 42.05 | ALTA |
| ATOM | 201 | NE2 | GLN | 181 | 66.324 | 46.756 | 8.284 | 0.50 | 44.59 | ALTA |
| ATOM | 202 | C | GLN | 181 | 65.481 | 42.180 | 5.138 | 0.50 | 38.43 | ALTA |
| ATOM | 203 | O | GLN | 181 | 66.175 | 42.262 | 4.118 | 0.50 | 38.92 | ALTA |
| ATOM | 204 | N | GLY | 182 | 64.958 | 41.034 | 5.562 | 1.00 | 38.74 | |
| ATOM | 205 | CA | GLY | 182 | 65.166 | 39.808 | 4.805 | 1.00 | 40.07 | |
| ATOM | 206 | C | GLY | 182 | 66.634 | 39.554 | 4.486 | 1.00 | 42.06 | |
| ATOM | 207 | O | GLY | 182 | 67.504 | 39.684 | 5.346 | 1.00 | 43.28 | |
| ATOM | 208 | N | SER | 183 | 66.926 | 39.272 | 3.224 | 1.00 | 43.72 | |
| ATOM | 209 | CA | SER | 183 | 68.299 | 39.001 | 2.812 | 1.00 | 45.88 | |
| ATOM | 210 | CB | SER | 183 | 68.304 | 38.069 | 1.593 | 1.00 | 47.26 | |
| ATOM | 211 | OG | SER | 183 | 67.519 | 38.605 | 0.531 | 1.00 | 47.23 | |
| ATOM | 212 | C | SER | 183 | 69.095 | 40.268 | 2.497 | 1.00 | 46.24 | |
| ATOM | 213 | O | SER | 183 | 70.290 | 40.194 | 2.185 | 1.00 | 48.13 | |
| ATOM | 214 | N | HIS | 184 | 68.445 | 41.426 | 2.579 | 1.00 | 45.79 | |
| ATOM | 215 | CA | HIS | 184 | 69.111 | 42.690 | 2.276 | 1.00 | 45.00 | |
| ATOM | 216 | CB | HIS | 184 | 68.127 | 43.636 | 1.594 | 1.00 | 43.54 | |
| ATOM | 217 | C | HIS | 184 | 69.732 | 43.351 | 3.516 | 1.00 | 44.67 | |
| ATOM | 218 | O | HIS | 184 | 70.316 | 44.440 | 3.428 | 1.00 | 45.02 | |
| ATOM | 219 | N | TRP | 185 | 69.659 | 42.663 | 4.653 | 1.00 | 43.24 | |
| ATOM | 220 | CA | TRP | 185 | 70.190 | 43.172 | 5.919 | 1.00 | 40.98 | |
| ATOM | 221 | CB | TRP | 185 | 70.078 | 42.106 | 7.020 | 1.00 | 37.96 | |
| ATOM | 222 | CG | TRP | 185 | 70.889 | 40.874 | 6.775 | 1.00 | 34.14 | |
| ATOM | 223 | CD2 | TRP | 185 | 72.197 | 40.593 | 7.291 | 1.00 | 33.38 | |
| ATOM | 224 | CE2 | TRP | 185 | 72.572 | 39.321 | 6.807 | 1.00 | 31.68 | |
| ATOM | 225 | CE3 | TRP | 185 | 73.092 | 41.296 | 8.107 | 1.00 | 31.65 | |
| ATOM | 226 | CD1 | TRP | 185 | 70.530 | 39.790 | 6.028 | 1.00 | 34.27 | |
| ATOM | 227 | NE1 | TRP | 185 | 71.536 | 38.852 | 6.043 | 1.00 | 33.51 | |
| ATOM | 228 | CZ2 | TRP | 185 | 73.795 | 38.733 | 7.121 | 1.00 | 31.67 | |
| ATOM | 229 | CZ3 | TRP | 185 | 74.308 | 40.713 | 8.419 | 1.00 | 31.29 | |
| ATOM | 230 | CH2 | TRP | 185 | 74.651 | 39.444 | 7.923 | 1.00 | 31.06 | |
| ATOM | 231 | C | TRP | 185 | 71.618 | 43.720 | 5.856 | 1.00 | 41.52 | |
| ATOM | 232 | O | TRP | 185 | 71.893 | 44.817 | 6.335 | 1.00 | 40.52 | |
| ATOM | 233 | N | LYS | 186 | 72.520 | 42.976 | 5.234 | 1.00 | 42.94 | |
| ATOM | 234 | CA | LYS | 186 | 73.896 | 43.417 | 5.143 | 1.00 | 45.25 | |
| ATOM | 235 | CB | LYS | 186 | 74.764 | 42.328 | 4.508 | 1.00 | 45.96 | |
| ATOM | 236 | CG | LYS | 186 | 76.255 | 42.600 | 4.590 | 1.00 | 48.07 | |
| ATOM | 237 | CD | LYS | 186 | 77.053 | 41.307 | 4.504 | 1.00 | 51.20 | |
| ATOM | 238 | CE | LYS | 186 | 78.554 | 41.574 | 4.457 | 1.00 | 52.69 | |
| ATOM | 239 | NZ | LYS | 186 | 78.975 | 42.277 | 3.201 | 1.00 | 55.56 | |
| ATOM | 240 | C | LYS | 186 | 74.025 | 44.730 | 4.377 | 1.00 | 47.38 | |
| ATOM | 241 | O | LYS | 186 | 74.914 | 45.535 | 4.663 | 1.00 | 47.65 | |
| ATOM | 242 | N | GLN | 187 | 73.134 | 44.959 | 3.418 | 0.50 | 48.02 | ALTA |
| ATOM | 243 | CA | GLN | 187 | 73.193 | 46.183 | 2.623 | 0.50 | 48.69 | ALTA |
| ATOM | 244 | CB | GLN | 187 | 72.547 | 45.973 | 1.246 | 0.50 | 48.66 | ALTA |
| ATOM | 245 | CG | GLN | 187 | 73.104 | 44.771 | 0.453 | 0.50 | 49.05 | ALTA |
| ATOM | 246 | CD | GLN | 187 | 74.624 | 44.766 | 0.339 | 0.50 | 49.17 | ALTA |
| ATOM | 247 | OE1 | GLN | 187 | 75.225 | 45.691 | −0.209 | 0.50 | 49.71 | ALTA |
| ATOM | 248 | NE2 | GLN | 187 | 75.250 | 43.710 | 0.847 | 0.50 | 48.57 | ALTA |
| ATOM | 249 | C | GLN | 187 | 72.551 | 47.373 | 3.343 | 0.50 | 49.06 | ALTA |
| ATOM | 250 | O | GLN | 187 | 73.094 | 48.475 | 3.329 | 0.50 | 49.53 | ALTA |
| ATOM | 251 | N | ARG | 188 | 71.405 | 47.152 | 3.980 | 1.00 | 49.18 | |
| ATOM | 252 | CA | ARG | 188 | 70.723 | 48.221 | 4.695 | 1.00 | 49.90 | |
| ATOM | 253 | CB | ARG | 188 | 69.209 | 47.988 | 4.653 | 1.00 | 53.68 | |
| ATOM | 254 | CG | ARG | 188 | 68.617 | 47.798 | 3.251 | 1.00 | 57.22 | |

APPENDIX 6-continued

TR_T3.PBD

| ATOM | 255 | CD | ARG | 188 | 67.099 | 47.962 | 3.302 | 1.00 | 60.67 |
|---|---|---|---|---|---|---|---|---|---|
| ATOM | 256 | NE | ARG | 188 | 66.430 | 47.441 | 2.110 | 1.00 | 64.43 |
| ATOM | 257 | CZ | ARG | 188 | 65.931 | 46.208 | 2.009 | 1.00 | 66.13 |
| ATOM | 258 | NH1 | ARG | 188 | 66.027 | 45.362 | 3.031 | 1.00 | 66.69 |
| ATOM | 259 | NH2 | ARG | 188 | 65.318 | 45.823 | 0.893 | 1.00 | 66.10 |
| ATOM | 260 | C | ARG | 188 | 71.150 | 48.510 | 6.133 | 1.00 | 48.42 |
| ATOM | 261 | O | ARG | 188 | 70.544 | 49.368 | 6.784 | 1.00 | 48.86 |
| ATOM | 262 | N | ARG | 189 | 72.153 | 47.804 | 6.647 | 1.00 | 46.00 |
| ATOM | 263 | CA | ARG | 189 | 72.581 | 48.030 | 8.028 | 1.00 | 44.24 |
| ATOM | 264 | CB | ARG | 189 | 73.039 | 46.726 | 8.690 | 1.00 | 43.40 |
| ATOM | 265 | CG | ARG | 189 | 74.367 | 46.204 | 8.203 | 1.00 | 43.05 |
| ATOM | 266 | CD | ARG | 189 | 74.808 | 45.021 | 9.019 | 1.00 | 43.62 |
| ATOM | 267 | NE | ARG | 189 | 76.185 | 44.660 | 8.717 | 1.00 | 45.95 |
| ATOM | 268 | CZ | ARG | 189 | 76.981 | 43.976 | 9.536 | 1.00 | 48.56 |
| ATOM | 269 | NH1 | ARG | 189 | 76.548 | 43.560 | 10.724 | 1.00 | 46.34 |
| ATOM | 270 | NH2 | ARG | 189 | 78.233 | 43.735 | 9.174 | 1.00 | 50.12 |
| ATOM | 271 | C | ARG | 189 | 73.642 | 49.116 | 8.238 | 1.00 | 43.20 |
| ATOM | 272 | O | ARG | 189 | 74.629 | 49.210 | 7.500 | 1.00 | 43.07 |
| ATOM | 273 | N | LYS | 190 | 73.427 | 49.925 | 9.268 | 1.00 | 41.56 |
| ATOM | 274 | CA | LYS | 190 | 74.335 | 51.003 | 9.628 | 1.00 | 39.96 |
| ATOM | 275 | CB | LYS | 190 | 73.563 | 52.323 | 9.757 | 1.00 | 38.85 |
| ATOM | 276 | C | LYS | 190 | 74.983 | 50.631 | 10.956 | 1.00 | 38.91 |
| ATOM | 277 | O | LYS | 190 | 74.345 | 50.015 | 11.806 | 1.00 | 38.17 |
| ATOM | 278 | N | PHE | 191 | 76.261 | 50.959 | 11.104 | 1.00 | 38.49 |
| ATOM | 279 | CA | PHE | 191 | 76.998 | 50.673 | 12.326 | 1.00 | 38.42 |
| ATOM | 280 | CB | PHE | 191 | 78.500 | 50.762 | 12.073 | 1.00 | 38.37 |
| ATOM | 281 | CG | PHE | 191 | 79.056 | 49.608 | 11.308 | 1.00 | 39.05 |
| ATOM | 282 | CD1 | PHE | 191 | 78.712 | 49.408 | 9.976 | 1.00 | 40.02 |
| ATOM | 283 | CD2 | PHE | 191 | 79.942 | 48.727 | 11.917 | 1.00 | 39.19 |
| ATOM | 284 | CE1 | PHE | 191 | 79.245 | 48.344 | 9.256 | 1.00 | 40.57 |
| ATOM | 285 | CE2 | PHE | 191 | 80.482 | 47.661 | 11.213 | 1.00 | 40.32 |
| ATOM | 286 | CZ | PHE | 191 | 80.133 | 47.466 | 9.875 | 1.00 | 41.84 |
| ATOM | 287 | C | PHE | 191 | 76.650 | 51.673 | 13.416 | 1.00 | 37.96 |
| ATOM | 288 | O | PHE | 191 | 76.568 | 52.872 | 13.151 | 1.00 | 38.95 |
| ATOM | 289 | N | LEU | 192 | 76.433 | 51.184 | 14.634 | 1.00 | 37.05 |
| ATOM | 290 | CA | LEU | 192 | 76.138 | 52.063 | 15.759 | 1.00 | 35.99 |
| ATOM | 291 | CB | LEU | 192 | 75.833 | 51.247 | 17.014 | 1.00 | 33.04 |
| ATOM | 292 | CG | LEU | 192 | 75.503 | 52.074 | 18.260 | 1.00 | 31.38 |
| ATOM | 293 | CD1 | LEU | 192 | 74.116 | 52.651 | 18.102 | 1.00 | 29.02 |
| ATOM | 294 | CD2 | LEU | 192 | 75.592 | 51.229 | 19.536 | 1.00 | 30.32 |
| ATOM | 295 | C | LEU | 192 | 77.436 | 52.831 | 15.976 | 1.00 | 36.99 |
| ATOM | 296 | O | LEU | 192 | 78.500 | 52.218 | 16.112 | 1.00 | 37.66 |
| ATOM | 297 | N | PRO | 193 | 77.377 | 54.177 | 15.988 | 1.00 | 38.15 |
| ATOM | 298 | CD | PRO | 193 | 76.156 | 54.996 | 15.902 | 1.00 | 37.90 |
| ATOM | 299 | CA | PRO | 193 | 78.561 | 55.025 | 16.187 | 1.00 | 38.68 |
| ATOM | 300 | CB | PRO | 193 | 77.950 | 56.365 | 16.568 | 1.00 | 37.20 |
| ATOM | 301 | CG | PRO | 193 | 76.711 | 56.397 | 15.758 | 1.00 | 37.08 |
| ATOM | 302 | C | PRO | 193 | 79.475 | 54.503 | 17.294 | 1.00 | 41.12 |
| ATOM | 303 | O | PRO | 193 | 79.005 | 54.129 | 18.367 | 1.00 | 42.26 |
| ATOM | 304 | N | ASP | 194 | 80.782 | 54.509 | 17.052 | 1.00 | 43.62 |
| ATOM | 305 | CA | ASP | 194 | 81.731 | 54.012 | 18.050 | 1.00 | 46.71 |
| ATOM | 306 | CB | ASP | 194 | 83.131 | 53.938 | 17.470 | 1.00 | 49.32 |
| ATOM | 307 | CG | ASP | 194 | 83.237 | 52.904 | 16.397 | 1.00 | 52.34 |
| ATOM | 308 | OD1 | ASP | 194 | 83.539 | 51.726 | 16.719 | 1.00 | 53.18 |
| ATOM | 309 | OD2 | ASP | 194 | 82.981 | 53.268 | 15.227 | 1.00 | 55.10 |
| ATOM | 310 | C | ASP | 194 | 81.769 | 54.743 | 19.386 | 1.00 | 47.12 |
| ATOM | 311 | O | ASP | 194 | 82.158 | 54.163 | 20.403 | 1.00 | 48.16 |
| ATOM | 312 | N | ASP | 195 | 81.389 | 56.015 | 19.386 | 1.00 | 47.54 |
| ATOM | 313 | CA | ASP | 195 | 81.382 | 56.791 | 20.620 | 1.00 | 48.68 |
| ATOM | 314 | CB | ASP | 195 | 81.180 | 58.285 | 20.322 | 1.00 | 50.76 |
| ATOM | 315 | CG | ASP | 195 | 79.871 | 58.572 | 19.602 | 1.00 | 54.24 |
| ATOM | 316 | OD1 | ASP | 195 | 78.929 | 59.082 | 20.253 | 1.00 | 56.17 |
| ATOM | 317 | OD2 | ASP | 195 | 79.786 | 58.292 | 18.385 | 1.00 | 56.08 |
| ATOM | 318 | C | ASP | 195 | 80.304 | 56.274 | 21.580 | 1.00 | 47.63 |
| ATOM | 319 | O | ASP | 195 | 80.294 | 56.621 | 22.772 | 1.00 | 49.07 |
| ATOM | 320 | N | ILE | 196 | 79.400 | 55.444 | 21.065 | 1.00 | 44.87 |
| ATOM | 321 | CA | ILE | 196 | 78.330 | 54.890 | 21.888 | 1.00 | 42.53 |
| ATOM | 322 | CB | ILE | 196 | 76.983 | 54.813 | 21.121 | 1.00 | 42.19 |
| ATOM | 323 | CG2 | ILE | 196 | 75.870 | 54.357 | 22.060 | 1.00 | 40.29 |
| ATOM | 324 | CG1 | ILE | 196 | 76.635 | 56.191 | 20.535 | 1.00 | 41.32 |
| ATOM | 325 | CD1 | ILE | 196 | 75.344 | 56.219 | 19.732 | 1.00 | 41.32 |
| ATOM | 326 | C | ILE | 196 | 78.725 | 53.509 | 22.391 | 1.00 | 40.89 |
| ATOM | 327 | O | ILE | 196 | 79.358 | 52.722 | 21.679 | 1.00 | 40.08 |
| ATOM | 328 | N | GLY | 197 | 78.384 | 53.240 | 23.642 | 1.00 | 40.16 |
| ATOM | 329 | CA | GLY | 197 | 78.705 | 51.957 | 24.228 | 1.00 | 40.21 |
| ATOM | 330 | C | GLY | 197 | 80.066 | 51.907 | 24.879 | 1.00 | 40.18 |
| ATOM | 331 | O | GLY | 197 | 80.512 | 50.839 | 25.267 | 1.00 | 40.55 |

APPENDIX 6-continued

TR_T3.PBD

| ATOM | 332 | N | GLN | 198 | 80.718 | 53.057 | 25.029 | 1.00 | 41.25 |
|---|---|---|---|---|---|---|---|---|---|
| ATOM | 333 | CA | GLN | 198 | 82.038 | 53.111 | 25.664 | 1.00 | 40.94 |
| ATOM | 334 | CB | GLN | 198 | 83.041 | 53.823 | 24.738 | 1.00 | 39.51 |
| ATOM | 335 | C | GLN | 198 | 81.995 | 53.796 | 27.046 | 1.00 | 40.93 |
| ATOM | 336 | O | GLN | 198 | 83.036 | 54.197 | 27.571 | 1.00 | 41.83 |
| ATOM | 337 | N | SER | 199 | 80.806 | 53.859 | 27.654 | 1.00 | 39.68 |
| ATOM | 338 | CA | SER | 199 | 80.615 | 54.510 | 28.961 | 1.00 | 37.74 |
| ATOM | 339 | CB | SER | 199 | 79.995 | 55.905 | 28.768 | 1.00 | 38.50 |
| ATOM | 340 | OG | SER | 199 | 80.687 | 56.672 | 27.792 | 1.00 | 40.71 |
| ATOM | 341 | C | SER | 199 | 79.743 | 53.726 | 29.958 | 1.00 | 36.31 |
| ATOM | 342 | O | SER | 199 | 78.719 | 54.228 | 30.436 | 1.00 | 35.69 |
| ATOM | 343 | N | PRO | 200 | 80.123 | 52.484 | 30.280 | 1.00 | 35.05 |
| ATOM | 344 | CD | PRO | 200 | 81.246 | 51.684 | 29.760 | 1.00 | 33.97 |
| ATOM | 345 | CA | PRO | 200 | 79.313 | 51.715 | 31.228 | 1.00 | 35.89 |
| ATOM | 346 | CB | PRO | 200 | 79.872 | 50.304 | 31.075 | 1.00 | 33.94 |
| ATOM | 347 | CG | PRO | 200 | 81.297 | 50.532 | 30.708 | 1.00 | 33.31 |
| ATOM | 348 | C | PRO | 200 | 79.477 | 52.241 | 32.656 | 1.00 | 37.75 |
| ATOM | 349 | O | PRO | 200 | 80.484 | 51.959 | 33.299 | 1.00 | 38.78 |
| ATOM | 350 | N | ILE | 201 | 78.493 | 52.988 | 33.158 | 1.00 | 39.61 |
| ATOM | 351 | CA | ILE | 201 | 78.590 | 53.551 | 34.511 | 1.00 | 40.56 |
| ATOM | 352 | CB | ILE | 201 | 78.715 | 55.093 | 34.484 | 1.00 | 40.20 |
| ATOM | 353 | CG2 | ILE | 201 | 80.125 | 55.501 | 34.082 | 1.00 | 41.06 |
| ATOM | 354 | CG1 | ILE | 201 | 77.690 | 55.694 | 33.532 | 1.00 | 40.98 |
| ATOM | 355 | CD1 | ILE | 201 | 77.969 | 57.147 | 33.205 | 1.00 | 44.31 |
| ATOM | 356 | C | ILE | 201 | 77.535 | 53.160 | 35.546 | 1.00 | 41.40 |
| ATOM | 357 | O | ILE | 201 | 77.768 | 53.313 | 36.751 | 1.00 | 42.09 |
| ATOM | 358 | N | VAL | 202 | 76.365 | 52.701 | 35.104 | 1.00 | 41.42 |
| ATOM | 359 | CA | VAL | 202 | 75.325 | 52.293 | 36.053 | 1.00 | 40.70 |
| ATOM | 360 | CB | VAL | 202 | 73.913 | 52.292 | 35.422 | 1.00 | 38.44 |
| ATOM | 361 | CG1 | VAL | 202 | 72.881 | 51.826 | 36.435 | 1.00 | 35.91 |
| ATOM | 362 | CG2 | VAL | 202 | 73.560 | 53.692 | 34.934 | 1.00 | 36.42 |
| ATOM | 363 | C | VAL | 202 | 75.687 | 50.917 | 36.622 | 1.00 | 41.64 |
| ATOM | 364 | O | VAL | 202 | 76.094 | 50.008 | 35.894 | 1.00 | 42.05 |
| ATOM | 365 | N | SER | 203 | 75.596 | 50.800 | 37.938 | 1.00 | 43.06 |
| ATOM | 366 | CA | SER | 203 | 75.947 | 49.576 | 38.639 | 1.00 | 44.57 |
| ATOM | 367 | CB | SER | 203 | 75.916 | 49.842 | 40.154 | 1.00 | 46.82 |
| ATOM | 368 | OG | SER | 203 | 76.457 | 48.772 | 40.916 | 1.00 | 50.18 |
| ATOM | 369 | C | SER | 203 | 75.052 | 48.388 | 38.294 | 1.00 | 44.08 |
| ATOM | 370 | O | SER | 203 | 73.849 | 48.534 | 38.093 | 1.00 | 44.28 |
| ATOM | 371 | N | MET | 204 | 75.656 | 47.210 | 38.231 | 1.00 | 43.11 |
| ATOM | 372 | CA | MET | 204 | 74.930 | 45.980 | 37.963 | 1.00 | 43.12 |
| ATOM | 373 | CB | MET | 204 | 75.048 | 45.557 | 36.494 | 1.00 | 41.07 |
| ATOM | 374 | CG | MET | 204 | 74.126 | 46.320 | 35.554 | 1.00 | 36.96 |
| ATOM | 375 | SD | MET | 204 | 72.375 | 46.134 | 35.990 | 1.00 | 38.66 |
| ATOM | 376 | CE | MET | 204 | 71.970 | 44.592 | 35.098 | 1.00 | 37.26 |
| ATOM | 377 | C | MET | 204 | 75.561 | 44.943 | 38.866 | 1.00 | 43.68 |
| ATOM | 378 | O | MET | 204 | 76.784 | 44.817 | 38.912 | 1.00 | 44.32 |
| ATOM | 379 | N | PRO | 205 | 74.735 | 44.204 | 39.619 | 1.00 | 44.22 |
| ATOM | 380 | CD | PRO | 205 | 73.261 | 44.310 | 39.610 | 1.00 | 44.44 |
| ATOM | 381 | CA | PRO | 205 | 75.187 | 43.164 | 40.546 | 1.00 | 44.32 |
| ATOM | 382 | CB | PRO | 205 | 73.944 | 42.299 | 40.701 | 1.00 | 45.18 |
| ATOM | 383 | CG | PRO | 205 | 72.832 | 43.335 | 40.691 | 1.00 | 44.29 |
| ATOM | 384 | C | PRO | 205 | 76.417 | 42.354 | 40.122 | 1.00 | 44.31 |
| ATOM | 385 | O | PRO | 205 | 77.393 | 42.293 | 40.864 | 1.00 | 43.97 |
| ATOM | 386 | N | ASP | 206 | 76.404 | 41.802 | 38.912 | 1.00 | 44.30 |
| ATOM | 387 | CA | ASP | 206 | 77.524 | 40.984 | 38.433 | 1.00 | 44.77 |
| ATOM | 388 | CB | ASP | 206 | 77.073 | 40.106 | 37.270 | 1.00 | 47.12 |
| ATOM | 389 | CG | ASP | 206 | 76.503 | 40.912 | 36.120 | 1.00 | 49.73 |
| ATOM | 390 | OD1 | ASP | 206 | 76.992 | 42.039 | 35.863 | 1.00 | 49.65 |
| ATOM | 391 | OD2 | ASP | 206 | 75.553 | 40.416 | 35.478 | 1.00 | 51.96 |
| ATOM | 392 | C | ASP | 206 | 78.805 | 41.718 | 38.037 | 1.00 | 44.10 |
| ATOM | 393 | O | ASP | 206 | 79.754 | 41.099 | 37.549 | 1.00 | 43.60 |
| ATOM | 394 | N | GLY | 207 | 78.804 | 43.039 | 38.145 | 1.00 | 44.19 |
| ATOM | 395 | CA | GLY | 207 | 80.001 | 43.785 | 37.803 | 1.00 | 43.51 |
| ATOM | 396 | C | GLY | 207 | 80.041 | 44.425 | 36.433 | 1.00 | 43.29 |
| ATOM | 397 | O | GLY | 207 | 80.745 | 45.421 | 36.257 | 1.00 | 44.47 |
| ATOM | 398 | N | ASP | 208 | 79.363 | 43.845 | 35.446 | 1.00 | 42.45 |
| ATOM | 399 | CA | ASP | 208 | 79.347 | 44.436 | 34.106 | 1.00 | 41.51 |
| ATOM | 400 | CB | ASP | 208 | 78.915 | 43.402 | 33.070 | 1.00 | 42.91 |
| ATOM | 401 | CG | ASP | 208 | 80.001 | 42.379 | 32.785 | 1.00 | 43.57 |
| ATOM | 402 | OD1 | ASP | 208 | 79.675 | 41.218 | 32.468 | 1.00 | 44.55 |
| ATOM | 403 | OD2 | ASP | 208 | 81.191 | 42.742 | 32.868 | 1.00 | 47.14 |
| ATOM | 404 | C | ASP | 208 | 78.378 | 45.606 | 34.143 | 1.00 | 40.78 |
| ATOM | 405 | O | ASP | 208 | 77.176 | 45.403 | 34.277 | 1.00 | 42.50 |
| ATOM | 406 | N | LYS | 209 | 78.902 | 46.827 | 34.058 | 1.00 | 39.10 |
| ATOM | 407 | CA | LYS | 209 | 78.071 | 48.033 | 34.150 | 1.00 | 37.23 |
| ATOM | 408 | CB | LYS | 209 | 78.910 | 49.211 | 34.681 | 1.00 | 37.29 |

APPENDIX 6-continued

TR_T3.PBD

| ATOM | 409 | C | LYS | 209 | 77.326 | 48.423 | 32.871 | 1.00 | 34.47 |
|---|---|---|---|---|---|---|---|---|---|
| ATOM | 410 | O | LYS | 209 | 77.707 | 48.013 | 31.776 | 1.00 | 33.85 |
| ATOM | 411 | N | VAL | 210 | 76.275 | 49.228 | 33.028 | 1.00 | 33.30 |
| ATOM | 412 | CA | VAL | 210 | 75.448 | 49.684 | 31.907 | 1.00 | 31.78 |
| ATOM | 413 | CB | VAL | 210 | 73.929 | 49.618 | 32.235 | 1.00 | 29.51 |
| ATOM | 414 | CG1 | VAL | 210 | 73.102 | 50.012 | 31.010 | 1.00 | 29.24 |
| ATOM | 415 | CG2 | VAL | 210 | 73.541 | 48.237 | 32.698 | 1.00 | 29.84 |
| ATOM | 416 | C | VAL | 210 | 75.731 | 51.115 | 31.451 | 1.00 | 32.68 |
| ATOM | 417 | O | VAL | 210 | 75.845 | 52.033 | 32.264 | 1.00 | 32.69 |
| ATOM | 418 | N | ASP | 211 | 75.769 | 51.290 | 30.134 | 1.00 | 33.00 |
| ATOM | 419 | CA | ASP | 211 | 75.978 | 52.574 | 29.476 | 1.00 | 31.85 |
| ATOM | 420 | CB | ASP | 211 | 76.826 | 52.353 | 28.221 | 1.00 | 32.38 |
| ATOM | 421 | CG | ASP | 211 | 77.019 | 53.612 | 27.386 | 1.00 | 31.88 |
| ATOM | 422 | OD1 | ASP | 211 | 78.123 | 53.768 | 26.843 | 1.00 | 32.78 |
| ATOM | 423 | OD2 | ASP | 211 | 76.079 | 54.412 | 27.208 | 1.00 | 32.32 |
| ATOM | 424 | C | ASP | 211 | 74.562 | 53.023 | 29.101 | 1.00 | 33.39 |
| ATOM | 425 | O | ASP | 211 | 73.925 | 52.444 | 28.206 | 1.00 | 31.94 |
| ATOM | 426 | N | LEU | 212 | 74.078 | 54.063 | 29.770 | 1.00 | 32.50 |
| ATOM | 427 | CA | LEU | 212 | 72.731 | 54.568 | 29.532 | 1.00 | 32.29 |
| ATOM | 428 | CB | LEU | 212 | 72.440 | 55.736 | 30.470 | 1.00 | 32.41 |
| ATOM | 429 | CG | LEU | 212 | 72.311 | 55.336 | 31.936 | 1.00 | 32.11 |
| ATOM | 430 | CD1 | LEU | 212 | 72.447 | 56.555 | 32.830 | 1.00 | 32.35 |
| ATOM | 431 | CD2 | LEU | 212 | 70.979 | 54.650 | 32.148 | 1.00 | 30.87 |
| ATOM | 432 | C | LEU | 212 | 72.419 | 54.962 | 28.092 | 1.00 | 32.29 |
| ATOM | 433 | O | LEU | 212 | 71.326 | 54.695 | 27.609 | 1.00 | 32.13 |
| ATOM | 434 | N | GLU | 213 | 73.370 | 55.589 | 27.407 | 1.00 | 32.21 |
| ATOM | 435 | CA | GLU | 213 | 73.144 | 56.007 | 26.028 | 1.00 | 33.12 |
| ATOM | 436 | CB | GLU | 213 | 74.305 | 56.864 | 25.530 | 1.00 | 36.72 |
| ATOM | 437 | CG | GLU | 213 | 74.067 | 57.468 | 24.146 | 1.00 | 40.61 |
| ATOM | 438 | CD | GLU | 213 | 75.316 | 58.101 | 23.545 | 1.00 | 44.21 |
| ATOM | 439 | OE1 | GLU | 213 | 76.434 | 57.851 | 24.059 | 1.00 | 46.23 |
| ATOM | 440 | OE2 | GLU | 213 | 75.178 | 58.836 | 22.543 | 1.00 | 45.81 |
| ATOM | 441 | C | GLU | 213 | 72.966 | 54.801 | 25.111 | 1.00 | 31.91 |
| ATOM | 442 | O | GLU | 213 | 72.064 | 54.775 | 24.273 | 1.00 | 31.31 |
| ATOM | 443 | N | ALA | 214 | 73.827 | 53.803 | 25.285 | 1.00 | 30.66 |
| ATOM | 444 | CA | ALA | 214 | 73.769 | 52.585 | 24.482 | 1.00 | 30.43 |
| ATOM | 445 | CB | ALA | 214 | 74.971 | 51.690 | 24.783 | 1.00 | 29.77 |
| ATOM | 446 | C | ALA | 214 | 72.464 | 51.854 | 24.778 | 1.00 | 29.34 |
| ATOM | 447 | O | ALA | 214 | 71.772 | 51.421 | 23.862 | 1.00 | 28.33 |
| ATOM | 448 | N | PHE | 215 | 72.116 | 51.762 | 26.058 | 1.00 | 28.45 |
| ATOM | 449 | CA | PHE | 215 | 70.882 | 51.116 | 26.492 | 1.00 | 29.05 |
| ATOM | 450 | CB | PHE | 215 | 70.732 | 51.240 | 28.005 | 1.00 | 25.98 |
| ATOM | 451 | CG | PHE | 215 | 69.443 | 50.689 | 28.535 | 1.00 | 25.53 |
| ATOM | 452 | CD1 | PHE | 215 | 69.330 | 49.344 | 28.854 | 1.00 | 26.16 |
| ATOM | 453 | CD2 | PHE | 215 | 68.349 | 51.519 | 28.737 | 1.00 | 25.04 |
| ATOM | 454 | CE1 | PHE | 215 | 68.144 | 48.831 | 29.370 | 1.00 | 25.73 |
| ATOM | 455 | CE2 | PHE | 215 | 67.160 | 51.018 | 29.252 | 1.00 | 25.84 |
| ATOM | 456 | CZ | PHE | 215 | 67.058 | 49.669 | 29.570 | 1.00 | 25.25 |
| ATOM | 457 | C | PHE | 215 | 69.694 | 51.780 | 25.801 | 1.00 | 30.92 |
| ATOM | 458 | O | PHE | 215 | 68.773 | 51.107 | 25.316 | 1.00 | 30.38 |
| ATOM | 459 | N | SER | 246 | 69.714 | 53.108 | 25.776 | 1.00 | 31.41 |
| ATOM | 460 | CA | SER | 216 | 68.667 | 53.887 | 25.136 | 1.00 | 31.23 |
| ATOM | 461 | CB | SER | 216 | 68.976 | 55.375 | 25.256 | 1.00 | 32.50 |
| ATOM | 462 | OG | SER | 216 | 67.972 | 56.153 | 24.628 | 1.00 | 35.83 |
| ATOM | 463 | C | SER | 216 | 68.600 | 53.504 | 23.663 | 1.00 | 31.67 |
| ATOM | 464 | O | SER | 216 | 67.527 | 53.235 | 23.129 | 1.00 | 31.34 |
| ATOM | 465 | N | GLU | 217 | 69.756 | 53.475 | 23.014 | 1.00 | 31.72 |
| ATOM | 466 | CA | GLU | 217 | 69.823 | 53.121 | 21.609 | 1.00 | 33.06 |
| ATOM | 467 | CB | GLU | 217 | 71.269 | 53.153 | 21.110 | 1.00 | 34.93 |
| ATOM | 468 | CG | GLU | 217 | 71.824 | 54.557 | 20.921 | 1.00 | 38.98 |
| ATOM | 469 | CD | GLU | 217 | 70.986 | 55.399 | 19.963 | 1.00 | 41.92 |
| ATOM | 470 | OE1 | GLU | 217 | 70.177 | 56.221 | 20.444 | 1.00 | 44.02 |
| ATOM | 471 | OE2 | GLU | 217 | 71.139 | 55.246 | 18.731 | 1.00 | 44.46 |
| ATOM | 472 | C | GLU | 217 | 69.199 | 51.759 | 21.330 | 1.00 | 31.78 |
| ATOM | 473 | O | GLU | 217 | 68.447 | 51.607 | 20.369 | 1.00 | 32.51 |
| ATOM | 474 | N | PHE | 218 | 69.477 | 50.779 | 22.181 | 1.00 | 29.80 |
| ATOM | 475 | CA | PHE | 218 | 68.924 | 49.447 | 21.979 | 1.00 | 27.65 |
| ATOM | 476 | CB | PHE | 218 | 69.668 | 48.416 | 22.827 | 1.00 | 26.79 |
| ATOM | 477 | CG | PHE | 218 | 71.114 | 48.292 | 22.467 | 1.00 | 24.76 |
| ATOM | 478 | CD1 | PHE | 218 | 72.083 | 48.191 | 23.446 | 1.00 | 24.37 |
| ATOM | 479 | CD2 | PHE | 218 | 71.510 | 48.354 | 21.134 | 1.00 | 24.30 |
| ATOM | 480 | CE1 | PHE | 218 | 73.424 | 48.167 | 23.106 | 1.00 | 23.85 |
| ATOM | 481 | CE2 | PHE | 218 | 72.843 | 48.329 | 20.785 | 1.00 | 23.07 |
| ATOM | 482 | CZ | PHE | 218 | 73.804 | 48.236 | 21.772 | 1.00 | 24.45 |
| ATOM | 483 | C | PHE | 218 | 67.441 | 49.403 | 22.255 | 1.00 | 26.94 |
| ATOM | 484 | O | PHE | 218 | 66.658 | 48.985 | 21.409 | 1.00 | 27.98 |
| ATOM | 485 | N | THR | 219 | 67.032 | 49.906 | 23.405 | 1.00 | 26.97 |

APPENDIX 6-continued

| | | | TR_T3.PBD | | | | |
|---|---|---|---|---|---|---|---|
| ATOM | 486 CA | THR | 219 | 65.619 | 49.876 | 23.740 | 1.00 | 27.25 |
| ATOM | 487 CB | THR | 219 | 65.379 | 50.304 | 25.195 | 1.00 | 27.35 |
| ATOM | 488 OG1 | THR | 219 | 65.924 | 51.612 | 25.410 | 1.00 | 26.48 |
| ATOM | 489 CG2 | THR | 219 | 66.034 | 49.303 | 26.139 | 1.00 | 24.51 |
| ATOM | 490 C | THR | 219 | 64.747 | 50.689 | 22.782 | 1.00 | 27.21 |
| ATOM | 491 O | THR | 219 | 63.588 | 50.348 | 22.557 | 1.00 | 28.58 |
| ATOM | 492 N | LYS | 220 | 65.318 | 51.726 | 22.184 | 1.00 | 26.75 |
| ATOM | 493 CA | LYS | 220 | 64.576 | 52.569 | 21.254 | 1.00 | 27.81 |
| ATOM | 494 CB | LYS | 220 | 65.439 | 53.753 | 20.782 | 1.00 | 27.46 |
| ATOM | 495 C | LYS | 220 | 64.058 | 51.772 | 20.056 | 1.00 | 28.62 |
| ATOM | 496 O | LYS | 220 | 63.014 | 52.101 | 19.500 | 1.00 | 28.63 |
| ATOM | 497 N | ILE | 221 | 64.774 | 50.721 | 19.662 | 1.00 | 28.92 |
| ATOM | 498 CA | ILE | 221 | 64.331 | 49.907 | 18.527 | 1.00 | 28.19 |
| ATOM | 499 CB | ILE | 221 | 65.450 | 49.732 | 17.465 | 1.00 | 27.17 |
| ATOM | 500 CG2 | ILE | 221 | 65.866 | 51.095 | 16.911 | 1.00 | 26.61 |
| ATOM | 501 CG1 | ILE | 221 | 66.645 | 48.977 | 18.061 | 1.00 | 26.80 |
| ATOM | 502 CD1 | ILE | 221 | 67.621 | 48.417 | 17.029 | 1.00 | 24.91 |
| ATOM | 503 C | ILE | 221 | 63.840 | 48.512 | 18.937 | 1.00 | 28.82 |
| ATOM | 504 O | ILE | 221 | 63.552 | 47.678 | 18.076 | 1.00 | 28.59 |
| ATOM | 505 N | ILE | 222 | 63.690 | 48.263 | 20.236 | 1.00 | 27.09 |
| ATOM | 506 CA | ILE | 222 | 63.279 | 46.934 | 20.665 | 1.00 | 27.22 |
| ATOM | 507 CB | ILE | 222 | 63.777 | 46.591 | 22.101 | 1.00 | 26.58 |
| ATOM | 508 CG2 | ILE | 222 | 62.815 | 47.151 | 23.171 | 1.00 | 23.83 |
| ATOM | 509 CG1 | ILE | 222 | 63.949 | 45.065 | 22.230 | 1.00 | 24.15 |
| ATOM | 510 CD1 | ILE | 222 | 64.727 | 44.610 | 23.458 | 1.00 | 21.43 |
| ATOM | 511 C | ILE | 222 | 61.797 | 46.614 | 20.519 | 1.00 | 28.33 |
| ATOM | 512 O | ILE | 222 | 61.445 | 45.459 | 20.260 | 1.00 | 29.81 |
| ATOM | 513 N | THR | 223 | 60.929 | 47.618 | 20.622 | 1.00 | 27.63 |
| ATOM | 514 CA | THR | 223 | 59.494 | 47.366 | 20.505 | 1.00 | 26.83 |
| ATOM | 515 CB | THR | 223 | 58.667 | 48.631 | 20.797 | 1.00 | 29.85 |
| ATOM | 516 OG1 | THR | 223 | 58.839 | 48.983 | 22.180 | 1.00 | 30.67 |
| ATOM | 517 CG2 | THR | 223 | 57.183 | 48.390 | 20.525 | 1.00 | 26.50 |
| ATOM | 518 C | THR | 223 | 59.103 | 46.698 | 19.183 | 1.00 | 25.28 |
| ATOM | 519 O | THR | 223 | 58.390 | 45.691 | 19.196 | 1.00 | 24.87 |
| ATOM | 520 N | PRO | 224 | 59.535 | 47.256 | 18.031 | 1.00 | 23.96 |
| ATOM | 521 CD | PRO | 224 | 60.138 | 48.580 | 17.792 | 1.00 | 22.28 |
| ATOM | 522 CA | PRO | 224 | 59.181 | 46.612 | 16.759 | 1.00 | 23.13 |
| ATOM | 523 CB | PRO | 224 | 59.747 | 47.570 | 15.699 | 1.00 | 22.96 |
| ATOM | 524 CG | PRO | 224 | 60.762 | 48.406 | 16.443 | 1.00 | 24.53 |
| ATOM | 525 C | PRO | 224 | 59.790 | 45.204 | 16.634 | 1.00 | 22.56 |
| ATOM | 526 O | PRO | 224 | 59.198 | 44.332 | 15.994 | 1.00 | 22.77 |
| ATOM | 527 N | ALA | 225 | 60.960 | 44.989 | 17.240 | 1.00 | 19.17 |
| ATOM | 528 CA | ALA | 225 | 61.622 | 43.684 | 17.213 | 1.00 | 18.54 |
| ATOM | 529 CB | ALA | 225 | 63.009 | 43.773 | 17.806 | 1.00 | 16.79 |
| ATOM | 530 C | ALA | 225 | 60.862 | 42.643 | 17.969 | 1.00 | 19.08 |
| ATOM | 531 O | ALA | 225 | 60.681 | 41.502 | 17.523 | 1.00 | 21.30 |
| ATOM | 532 N | ILE | 226 | 60.253 | 43.033 | 19.117 | 1.00 | 18.30 |
| ATOM | 533 CA | ILE | 226 | 59.420 | 42.147 | 19.929 | 1.00 | 18.65 |
| ATOM | 534 CB | ILE | 226 | 59.092 | 42.779 | 21.288 | 1.00 | 17.30 |
| ATOM | 535 CG2 | ILE | 226 | 58.057 | 41.952 | 22.020 | 1.00 | 17.76 |
| ATOM | 536 CG1 | ILE | 226 | 60.361 | 42.915 | 22.123 | 1.00 | 17.07 |
| ATOM | 537 CD1 | ILE | 226 | 60.175 | 43.775 | 23.351 | 1.00 | 14.65 |
| ATOM | 538 C | ILE | 226 | 58.109 | 41.858 | 19.199 | 1.00 | 19.56 |
| ATOM | 539 O | ILE | 226 | 57.638 | 40.719 | 19.163 | 1.00 | 19.51 |
| ATOM | 540 N | THR | 227 | 57.521 | 42.903 | 18.627 | 1.00 | 20.26 |
| ATOM | 541 CA | THR | 227 | 56.278 | 42.782 | 17.881 | 1.00 | 21.19 |
| ATOM | 542 CB | THR | 227 | 55.856 | 44.150 | 17.326 | 1.00 | 22.41 |
| ATOM | 543 OG1 | THR | 227 | 55.670 | 45.053 | 18.420 | 1.00 | 25.09 |
| ATOM | 544 CG2 | THR | 227 | 54.558 | 44.041 | 16.560 | 1.00 | 24.29 |
| ATOM | 545 C | THR | 227 | 56.411 | 41.758 | 16.742 | 1.00 | 20.16 |
| ATOM | 546 O | THR | 227 | 55.487 | 40.978 | 16.496 | 1.00 | 21.18 |
| ATOM | 547 N | ARG | 228 | 57.558 | 41.744 | 16.069 | 1.00 | 18.42 |
| ATOM | 548 CA | ARG | 228 | 57.783 | 40.786 | 14.991 | 1.00 | 18.29 |
| ATOM | 549 CB | ARG | 228 | 59.032 | 41.136 | 14.191 | 1.00 | 19.95 |
| ATOM | 550 CG | ARG | 228 | 58.810 | 42.349 | 13.286 | 1.00 | 23.31 |
| ATOM | 551 CD | ARG | 228 | 60.001 | 42.646 | 12.405 | 1.00 | 25.64 |
| ATOM | 552 NE | ARG | 228 | 61.139 | 43.138 | 13.171 | 1.00 | 27.01 |
| ATOM | 553 CZ | ARG | 228 | 62.209 | 42.413 | 13.468 | 1.00 | 28.20 |
| ATOM | 554 NH1 | ARG | 228 | 62.280 | 41.155 | 13.067 | 1.00 | 28.99 |
| ATOM | 555 NH2 | ARG | 228 | 63.219 | 42.951 | 14.141 | 1.00 | 27.25 |
| ATOM | 556 C | ARG | 228 | 57.834 | 39.352 | 15.502 | 1.00 | 18.40 |
| ATOM | 557 O | ARG | 228 | 57.433 | 38.431 | 14.788 | 1.00 | 17.50 |
| ATOM | 558 N | VAL | 229 | 58.278 | 39.162 | 16.747 | 1.00 | 17.42 |
| ATOM | 559 CA | VAL | 229 | 58.316 | 37.822 | 17.334 | 1.00 | 16.40 |
| ATOM | 560 CB | VAL | 229 | 59.116 | 37.779 | 18.674 | 1.00 | 15.88 |
| ATOM | 561 CG1 | VAL | 229 | 58.955 | 36.422 | 19.334 | 1.00 | 16.19 |
| ATOM | 562 CG2 | VAL | 229 | 60.591 | 38.010 | 18.421 | 1.00 | 14.44 |

APPENDIX 6-continued

TR_T3.PBD

| ATOM | 563 | C | VAL | 229 | 56.852 | 37.408 | 17.552 | 1.00 | 16.75 |
|---|---|---|---|---|---|---|---|---|---|
| ATOM | 564 | O | VAL | 229 | 56.456 | 36.282 | 17.219 | 1.00 | 16.06 |
| ATOM | 565 | N | VAL | 230 | 56.039 | 38.343 | 18.046 | 1.00 | 16.09 |
| ATOM | 566 | CA | VAL | 230 | 54.612 | 38.097 | 18.266 | 1.00 | 16.97 |
| ATOM | 567 | CB | VAL | 230 | 53.896 | 39.327 | 18.897 | 1.00 | 18.60 |
| ATOM | 568 | CG1 | VAL | 230 | 52.401 | 39.084 | 18.972 | 1.00 | 17.19 |
| ATOM | 569 | CG2 | VAL | 230 | 54.445 | 39.629 | 20.299 | 1.00 | 17.82 |
| ATOM | 570 | C | VAL | 230 | 53.938 | 37.780 | 16.916 | 1.00 | 18.46 |
| ATOM | 571 | O | VAL | 230 | 53.115 | 36.863 | 16.828 | 1.00 | 18.46 |
| ATOM | 572 | N | ASP | 231 | 54.289 | 38.539 | 15.874 | 1.00 | 19.21 |
| ATOM | 573 | CA | ASP | 231 | 53.730 | 38.339 | 14.531 | 1.00 | 19.93 |
| ATOM | 574 | CB | ASP | 231 | 54.231 | 39.415 | 13.555 | 1.00 | 20.98 |
| ATOM | 575 | CG | ASP | 231 | 53.754 | 40.817 | 13.915 | 1.00 | 24.11 |
| ATOM | 576 | OD1 | ASP | 231 | 52.704 | 40.953 | 14.586 | 1.00 | 24.23 |
| ATOM | 577 | OD2 | ASP | 231 | 54.443 | 41.784 | 13.522 | 1.00 | 25.90 |
| ATOM | 578 | C | ASP | 231 | 54.097 | 36.962 | 13.982 | 1.00 | 19.27 |
| ATOM | 579 | O | ASP | 231 | 53.266 | 36.279 | 13.380 | 1.00 | 17.80 |
| ATOM | 580 | N | PHE | 232 | 55.357 | 36.582 | 14.163 | 1.00 | 18.91 |
| ATOM | 581 | CA | PHE | 232 | 55.841 | 35.288 | 13.712 | 1.00 | 19.65 |
| ATOM | 582 | CB | PHE | 232 | 57.308 | 35.078 | 14.104 | 1.00 | 18.14 |
| ATOM | 583 | CG | PHE | 232 | 57.752 | 33.639 | 14.027 | 1.00 | 19.70 |
| ATOM | 584 | CD1 | PHE | 232 | 57.895 | 33.005 | 12.799 | 1.00 | 19.18 |
| ATOM | 585 | CD2 | PHE | 232 | 57.987 | 32.904 | 15.188 | 1.00 | 17.61 |
| ATOM | 586 | CE1 | PHE | 232 | 58.259 | 31.660 | 12.723 | 1.00 | 19.86 |
| ATOM | 587 | CE2 | PHE | 232 | 58.350 | 31.560 | 15.126 | 1.00 | 18.98 |
| ATOM | 588 | CZ | PHE | 232 | 58.487 | 30.935 | 13.892 | 1.00 | 19.46 |
| ATOM | 589 | C | PHE | 232 | 54.996 | 34.179 | 14.320 | 1.00 | 21.02 |
| ATOM | 590 | O | PHE | 232 | 54.458 | 33.339 | 13.598 | 1.00 | 20.88 |
| ATOM | 591 | N | ALA | 233 | 54.863 | 34.202 | 15.645 | 1.00 | 21.64 |
| ATOM | 592 | CA | ALA | 233 | 54.106 | 33.187 | 16.378 | 1.00 | 21.43 |
| ATOM | 593 | CB | ALA | 233 | 54.223 | 33.443 | 17.868 | 1.00 | 18.72 |
| ATOM | 594 | C | ALA | 233 | 52.643 | 33.134 | 15.955 | 1.00 | 23.15 |
| ATOM | 595 | O | ALA | 233 | 52.043 | 32.062 | 15.857 | 1.00 | 21.76 |
| ATOM | 596 | N | LYS | 234 | 52.083 | 34.307 | 15.689 | 1.00 | 25.54 |
| ATOM | 597 | CA | LYS | 234 | 50.695 | 34.446 | 15.273 | 1.00 | 27.57 |
| ATOM | 598 | CB | LYS | 234 | 50.360 | 35.935 | 15.146 | 1.00 | 30.65 |
| ATOM | 599 | CG | LYS | 234 | 49.110 | 36.349 | 15.867 | 1.00 | 36.27 |
| ATOM | 600 | CD | LYS | 234 | 49.192 | 35.988 | 17.334 | 1.00 | 41.19 |
| ATOM | 601 | CE | LYS | 234 | 47.800 | 35.677 | 17.890 | 1.00 | 43.69 |
| ATOM | 602 | NZ | LYS | 234 | 47.119 | 34.565 | 17.147 | 1.00 | 44.98 |
| ATOM | 603 | C | LYS | 234 | 50.443 | 33.739 | 13.933 | 1.00 | 27.70 |
| ATOM | 604 | O | LYS | 234 | 49.355 | 33.200 | 13.693 | 1.00 | 28.42 |
| ATOM | 605 | N | LYS | 235 | 51.458 | 33.732 | 13.074 | 1.00 | 26.06 |
| ATOM | 606 | CA | LYS | 235 | 51.364 | 33.113 | 11.758 | 1.00 | 26.47 |
| ATOM | 607 | CB | LYS | 235 | 52.350 | 33.791 | 10.819 | 1.00 | 25.23 |
| ATOM | 608 | CG | LYS | 235 | 52.051 | 35.269 | 10.644 | 1.00 | 26.92 |
| ATOM | 609 | CD | LYS | 235 | 53.017 | 35.959 | 9.697 | 1.00 | 28.41 |
| ATOM | 610 | CE | LYS | 235 | 52.500 | 37.350 | 9.318 | 1.00 | 29.31 |
| ATOM | 611 | NZ | LYS | 235 | 53.400 | 38.026 | 8.347 | 1.00 | 30.37 |
| ATOM | 612 | C | LYS | 235 | 51.540 | 31.588 | 11.722 | 1.00 | 27.93 |
| ATOM | 613 | O | LYS | 235 | 51.540 | 30.984 | 10.649 | 1.00 | 29.04 |
| ATOM | 614 | N | LEU | 236 | 51.718 | 30.973 | 12.887 | 1.00 | 28.83 |
| ATOM | 615 | CA | LEU | 236 | 51.866 | 29.524 | 12.986 | 1.00 | 29.05 |
| ATOM | 616 | CB | LEU | 236 | 52.928 | 29.150 | 14.026 | 1.00 | 27.43 |
| ATOM | 617 | CG | LEU | 236 | 54.352 | 29.660 | 13.774 | 1.00 | 25.84 |
| ATOM | 618 | CD1 | LEU | 236 | 55.311 | 29.118 | 14.841 | 1.00 | 23.99 |
| ATOM | 619 | CD2 | LEU | 236 | 54.801 | 29.236 | 12.389 | 1.00 | 23.86 |
| ATOM | 620 | C | LEU | 236 | 50.513 | 28.948 | 13.392 | 1.00 | 31.19 |
| ATOM | 621 | O | LEU | 236 | 49.870 | 29.435 | 14.328 | 1.00 | 31.48 |
| ATOM | 622 | N | PRO | 237 | 50.078 | 27.875 | 12.717 | 1.00 | 34.60 |
| ATOM | 623 | CD | PRO | 237 | 50.829 | 27.156 | 11.668 | 1.00 | 35.04 |
| ATOM | 624 | CA | PRO | 237 | 48.789 | 27.223 | 13.002 | 1.00 | 36.52 |
| ATOM | 625 | CB | PRO | 237 | 48.751 | 26.081 | 11.981 | 1.00 | 37.48 |
| ATOM | 626 | CG | PRO | 237 | 50.229 | 25.776 | 11.718 | 1.00 | 36.60 |
| ATOM | 627 | C | PRO | 237 | 48.582 | 26.720 | 14.447 | 1.00 | 37.82 |
| ATOM | 628 | O | PRO | 237 | 47.629 | 27.102 | 15.125 | 1.00 | 37.08 |
| ATOM | 629 | N | MET | 238 | 49.495 | 25.893 | 14.935 | 1.00 | 40.42 |
| ATOM | 630 | CA | MET | 238 | 49.366 | 25.350 | 16.285 | 1.00 | 43.00 |
| ATOM | 631 | CB | MET | 238 | 50.453 | 24.298 | 16.549 | 1.00 | 45.20 |
| ATOM | 632 | CG | MET | 238 | 50.043 | 22.837 | 16.296 | 1.00 | 47.16 |
| ATOM | 633 | SD | MET | 238 | 50.598 | 22.117 | 14.725 | 1.00 | 52.25 |
| ATOM | 634 | CE | MET | 238 | 52.305 | 21.809 | 15.033 | 1.00 | 47.29 |
| ATOM | 635 | C | MET | 238 | 49.389 | 26.389 | 17.414 | 1.00 | 43.25 |
| ATOM | 636 | O | MET | 238 | 49.061 | 26.056 | 18.558 | 1.00 | 44.74 |
| ATOM | 637 | N | PHE | 239 | 49.720 | 27.642 | 17.088 | 1.00 | 41.55 |
| ATOM | 638 | CA | PHE | 239 | 49.825 | 28.716 | 18.091 | 1.00 | 37.31 |
| ATOM | 639 | CB | PHE | 239 | 51.031 | 29.615 | 17.765 | 1.00 | 32.40 |

APPENDIX 6-continued

TR_T3.PBD

| ATOM | 640 | CG  | PHE | 239 | 51.293 | 30.673 | 18.795 | 1.00 | 27.12 |
|------|-----|-----|-----|-----|--------|--------|--------|------|-------|
| ATOM | 641 | CD1 | PHE | 239 | 52.099 | 30.398 | 19.893 | 1.00 | 24.57 |
| ATOM | 642 | CD2 | PHE | 239 | 50.705 | 31.933 | 18.686 | 1.00 | 24.70 |
| ATOM | 643 | CE1 | PHE | 239 | 52.319 | 31.356 | 20.876 | 1.00 | 25.09 |
| ATOM | 644 | CE2 | PHE | 239 | 50.915 | 32.901 | 19.659 | 1.00 | 25.90 |
| ATOM | 645 | CZ  | PHE | 239 | 51.726 | 32.612 | 20.761 | 1.00 | 24.52 |
| ATOM | 646 | C   | PHE | 239 | 48.574 | 29.582 | 18.352 | 1.00 | 36.84 |
| ATOM | 647 | O   | PHE | 239 | 48.136 | 29.728 | 19.497 | 1.00 | 34.67 |
| ATOM | 648 | N   | SER | 240 | 48.027 | 30.180 | 17.299 | 1.00 | 36.92 |
| ATOM | 649 | CA  | SER | 240 | 46.857 | 31.038 | 17.433 | 1.00 | 37.16 |
| ATOM | 650 | CB  | SER | 240 | 46.534 | 31.706 | 16.094 | 1.00 | 38.34 |
| ATOM | 651 | C   | SER | 240 | 45.627 | 30.304 | 17.981 | 1.00 | 37.30 |
| ATOM | 652 | O   | SER | 240 | 44.680 | 30.941 | 18.433 | 1.00 | 36.95 |
| ATOM | 653 | N   | GLU | 241 | 45.639 | 28.974 | 17.917 | 1.00 | 37.73 |
| ATOM | 654 | CA  | GLU | 241 | 44.531 | 28.155 | 18.418 | 1.00 | 38.44 |
| ATOM | 655 | CB  | GLU | 241 | 44.644 | 26.705 | 17.912 | 1.00 | 42.18 |
| ATOM | 656 | CG  | GLU | 241 | 44.290 | 26.471 | 16.436 | 1.00 | 48.01 |
| ATOM | 657 | CD  | GLU | 241 | 44.559 | 25.028 | 15.973 | 1.00 | 50.12 |
| ATOM | 658 | OE1 | GLU | 241 | 44.375 | 24.088 | 16.779 | 1.00 | 51.14 |
| ATOM | 659 | OE2 | GLU | 241 | 44.957 | 24.838 | 14.799 | 1.00 | 50.68 |
| ATOM | 660 | C   | GLU | 241 | 44.571 | 28.122 | 19.937 | 1.00 | 35.85 |
| ATOM | 661 | O   | GLU | 241 | 43.561 | 27.868 | 20.598 | 1.00 | 36.01 |
| ATOM | 662 | N   | LEU | 242 | 45.762 | 28.329 | 20.480 | 1.00 | 33.28 |
| ATOM | 663 | CA  | LEU | 242 | 45.959 | 28.296 | 21.920 | 1.00 | 31.31 |
| ATOM | 664 | CB  | LEU | 242 | 47.452 | 28.382 | 22.244 | 1.00 | 29.28 |
| ATOM | 665 | CG  | LEU | 242 | 48.318 | 27.202 | 21.797 | 1.00 | 29.95 |
| ATOM | 666 | CD1 | LEU | 242 | 49.771 | 27.538 | 22.025 | 1.00 | 29.19 |
| ATOM | 667 | CD2 | LEU | 242 | 47.935 | 25.931 | 22.564 | 1.00 | 29.57 |
| ATOM | 668 | C   | LEU | 242 | 45.223 | 29.390 | 22.676 | 1.00 | 30.10 |
| ATOM | 669 | O   | LEU | 242 | 44.874 | 30.434 | 22.116 | 1.00 | 28.69 |
| ATOM | 670 | N   | PRO | 243 | 44.867 | 29.115 | 23.937 | 1.00 | 30.09 |
| ATOM | 671 | CD  | PRO | 243 | 44.783 | 27.843 | 24.674 | 1.00 | 28.53 |
| ATOM | 672 | CA  | PRO | 243 | 44.183 | 30.200 | 24.640 | 1.00 | 31.01 |
| ATOM | 673 | CB  | PRO | 243 | 43.829 | 29.577 | 26.005 | 1.00 | 30.34 |
| ATOM | 674 | CG  | PRO | 243 | 44.640 | 28.300 | 26.093 | 1.00 | 29.25 |
| ATOM | 675 | C   | PRO | 243 | 45.195 | 31.356 | 24.774 | 1.00 | 31.71 |
| ATOM | 676 | O   | PRO | 243 | 46.412 | 31.128 | 24.840 | 1.00 | 30.69 |
| ATOM | 677 | N   | CYS | 244 | 44.694 | 32.585 | 24.804 | 1.00 | 32.36 |
| ATOM | 678 | CA  | CYS | 244 | 45.539 | 33.763 | 24.920 | 1.00 | 33.57 |
| ATOM | 679 | CB  | CYS | 244 | 44.675 | 35.028 | 25.050 | 1.00 | 37.62 |
| ATOM | 680 | SG  | CYS | 244 | 45.262 | 36.418 | 24.022 | 1.00 | 51.95 |
| ATOM | 681 | C   | CYS | 244 | 46.536 | 33.660 | 26.081 | 1.00 | 31.12 |
| ATOM | 682 | O   | CYS | 244 | 47.677 | 34.087 | 25.942 | 1.00 | 30.37 |
| ATOM | 683 | N   | GLU | 245 | 46.124 | 33.045 | 27.194 | 1.00 | 30.00 |
| ATOM | 684 | CA  | GLU | 245 | 46.993 | 32.877 | 28.366 | 1.00 | 29.62 |
| ATOM | 685 | CB  | GLU | 245 | 46.270 | 32.159 | 29.514 | 1.00 | 33.10 |
| ATOM | 686 | CG  | GLU | 245 | 45.325 | 33.018 | 30.333 | 1.00 | 36.43 |
| ATOM | 687 | CD  | GLU | 245 | 43.882 | 32.940 | 29.860 | 1.00 | 37.87 |
| ATOM | 688 | OE1 | GLU | 245 | 42.989 | 33.006 | 30.730 | 1.00 | 37.36 |
| ATOM | 689 | OE2 | GLU | 245 | 43.639 | 32.813 | 28.634 | 1.00 | 39.63 |
| ATOM | 690 | C   | GLU | 245 | 48.239 | 32.077 | 28.030 | 1.00 | 28.34 |
| ATOM | 691 | O   | GLU | 245 | 49.322 | 32.343 | 28.557 | 1.00 | 27.88 |
| ATOM | 692 | N   | ASP | 246 | 48.063 | 31.043 | 27.213 | 1.00 | 26.10 |
| ATOM | 693 | CA  | ASP | 246 | 49.182 | 30.212 | 26.798 | 1.00 | 25.23 |
| ATOM | 694 | CB  | ASP | 246 | 48.685 | 28.923 | 26.135 | 1.00 | 26.98 |
| ATOM | 695 | CG  | ASP | 246 | 48.146 | 27.912 | 27.137 | 1.00 | 29.13 |
| ATOM | 696 | OD1 | ASP | 246 | 48.158 | 28.193 | 28.354 | 1.00 | 26.52 |
| ATOM | 697 | OD2 | ASP | 246 | 47.712 | 26.824 | 26.696 | 1.00 | 31.38 |
| ATOM | 698 | C   | ASP | 246 | 50.065 | 30.983 | 25.826 | 1.00 | 23.57 |
| ATOM | 699 | O   | ASP | 246 | 51.288 | 30.993 | 25.955 | 1.00 | 22.61 |
| ATOM | 700 | N   | GLN | 247 | 49.431 | 31.630 | 24.852 | 1.00 | 23.23 |
| ATOM | 701 | CA  | GLN | 247 | 50.144 | 32.408 | 23.855 | 1.00 | 22.20 |
| ATOM | 702 | CB  | GLN | 247 | 49.159 | 33.178 | 22.991 | 1.00 | 22.06 |
| ATOM | 703 | CG  | GLN | 247 | 48.329 | 32.307 | 22.066 | 1.00 | 22.74 |
| ATOM | 704 | CD  | GLN | 247 | 47.435 | 33.141 | 21.169 | 1.00 | 24.91 |
| ATOM | 705 | OE1 | GLN | 247 | 47.860 | 34.160 | 20.625 | 1.00 | 26.30 |
| ATOM | 706 | NE2 | GLN | 247 | 46.186 | 32.732 | 21.035 | 1.00 | 25.65 |
| ATOM | 707 | C   | GLN | 247 | 51.098 | 33.374 | 24.528 | 1.00 | 22.10 |
| ATOM | 708 | O   | GLN | 247 | 52.280 | 33.454 | 24.182 | 1.00 | 23.07 |
| ATOM | 709 | N   | ILE | 248 | 50.587 | 34.076 | 25.527 | 1.00 | 23.27 |
| ATOM | 710 | CA  | ILE | 248 | 51.379 | 35.042 | 26.276 | 1.00 | 23.21 |
| ATOM | 711 | CB  | ILE | 248 | 50.473 | 35.824 | 27.273 | 1.00 | 24.59 |
| ATOM | 712 | CG2 | ILE | 248 | 51.304 | 36.682 | 28.242 | 1.00 | 24.09 |
| ATOM | 713 | CG1 | ILE | 248 | 49.499 | 36.707 | 26.487 | 1.00 | 23.47 |
| ATOM | 714 | CD1 | ILE | 248 | 48.413 | 37.323 | 27.341 | 1.00 | 23.84 |
| ATOM | 715 | C   | ILE | 248 | 52.568 | 34.387 | 26.986 | 1.00 | 22.27 |
| ATOM | 716 | O   | ILE | 248 | 53.705 | 34.833 | 26.829 | 1.00 | 22.06 |

APPENDIX 6-continued

TR_T3.PBD

| | | | | | | | | |
|---|---|---|---|---|---|---|---|---|
| ATOM | 717 | N | ILE | 249 | 52.321 | 33.313 | 27.729 | 1.00 | 21.40 |
| ATOM | 718 | CA | ILE | 249 | 53.398 | 32.630 | 28.440 | 1.00 | 21.40 |
| ATOM | 719 | CB | ILE | 249 | 52.850 | 31.438 | 29.279 | 1.00 | 23.53 |
| ATOM | 720 | CG2 | ILE | 249 | 53.972 | 30.489 | 29.711 | 1.00 | 21.44 |
| ATOM | 721 | CG1 | ILE | 249 | 52.098 | 31.963 | 30.500 | 1.00 | 22.76 |
| ATOM | 722 | CD1 | ILE | 249 | 51.252 | 30.911 | 31.175 | 1.00 | 25.03 |
| ATOM | 723 | C | ILE | 249 | 54.481 | 32.148 | 27.470 | 1.00 | 22.24 |
| ATOM | 724 | O | ILE | 249 | 55.677 | 32.321 | 27.733 | 1.00 | 22.90 |
| ATOM | 725 | N | LEU | 250 | 54.072 | 31.582 | 26.334 | 1.00 | 22.65 |
| ATOM | 726 | CA | LEU | 250 | 55.028 | 31.079 | 25.345 | 1.00 | 21.40 |
| ATOM | 727 | CB | LEU | 250 | 54.319 | 30.290 | 24.239 | 1.00 | 20.06 |
| ATOM | 728 | CG | LEU | 250 | 53.566 | 29.038 | 24.677 | 1.00 | 20.22 |
| ATOM | 729 | CD1 | LEU | 250 | 52.952 | 28.406 | 23.453 | 1.00 | 19.19 |
| ATOM | 730 | CD2 | LEU | 250 | 54.494 | 28.050 | 25.386 | 1.00 | 18.52 |
| ATOM | 731 | C | LEU | 250 | 55.850 | 32.209 | 24.736 | 1.00 | 20.82 |
| ATOM | 732 | O | LEU | 250 | 57.069 | 32.094 | 24.603 | 1.00 | 20.27 |
| ATOM | 733 | N | LEU | 251 | 55.179 | 33.302 | 24.384 | 1.00 | 22.14 |
| ATOM | 734 | CA | LEU | 251 | 55.842 | 34.467 | 23.805 | 1.00 | 22.90 |
| ATOM | 735 | CB | LEU | 251 | 54.806 | 35.543 | 23.471 | 1.00 | 22.76 |
| ATOM | 736 | CG | LEU | 251 | 54.513 | 35.899 | 22.012 | 1.00 | 23.35 |
| ATOM | 737 | CD1 | LEU | 251 | 55.347 | 35.103 | 21.047 | 1.00 | 22.38 |
| ATOM | 738 | CD2 | LEU | 251 | 53.040 | 35.708 | 21.747 | 1.00 | 22.86 |
| ATOM | 739 | C | LEU | 251 | 56.891 | 35.030 | 24.776 | 1.00 | 23.67 |
| ATOM | 740 | O | LEU | 251 | 58.051 | 35.234 | 24.402 | 1.00 | 22.58 |
| ATOM | 741 | N | LYS | 252 | 56.491 | 35.236 | 26.029 | 1.00 | 24.64 |
| ATOM | 742 | CA | LYS | 252 | 57.395 | 35.754 | 27.057 | 1.00 | 26.22 |
| ATOM | 743 | CB | LYS | 252 | 56.617 | 36.037 | 28.350 | 1.00 | 27.79 |
| ATOM | 744 | CG | LYS | 252 | 55.351 | 36.838 | 28.093 | 1.00 | 32.69 |
| ATOM | 745 | CD | LYS | 252 | 55.185 | 38.023 | 29.003 | 1.00 | 35.85 |
| ATOM | 746 | CE | LYS | 252 | 54.773 | 37.626 | 30.397 | 1.00 | 39.34 |
| ATOM | 747 | NZ | LYS | 252 | 54.477 | 38.870 | 31.168 | 1.00 | 44.60 |
| ATOM | 748 | C | LYS | 252 | 58.566 | 34.793 | 27.312 | 1.00 | 25.26 |
| ATOM | 749 | O | LYS | 252 | 59.701 | 35.222 | 27.555 | 1.00 | 26.67 |
| ATOM | 750 | N | GLY | 253 | 58.306 | 33.497 | 27.195 | 1.00 | 23.97 |
| ATOM | 751 | CA | GLY | 253 | 59.356 | 32.521 | 27.404 | 1.00 | 22.00 |
| ATOM | 752 | C | GLY | 253 | 60.397 | 32.429 | 26.292 | 1.00 | 23.10 |
| ATOM | 753 | O | GLY | 253 | 61.568 | 32.165 | 26.585 | 1.00 | 25.12 |
| ATOM | 754 | N | CYS | 254 | 60.014 | 32.702 | 25.041 | 1.00 | 22.27 |
| ATOM | 755 | CA | CYS | 254 | 60.944 | 32.584 | 23.908 | 1.00 | 20.91 |
| ATOM | 756 | CB | CYS | 254 | 60.353 | 31.648 | 22.845 | 1.00 | 21.46 |
| ATOM | 757 | SG | CYS | 254 | 58.992 | 32.385 | 21.893 | 1.00 | 22.92 |
| ATOM | 758 | C | CYS | 254 | 61.354 | 33.869 | 23.201 | 1.00 | 19.77 |
| ATOM | 759 | O | CYS | 254 | 62.215 | 33.834 | 22.316 | 1.00 | 19.88 |
| ATOM | 760 | N | CYS | 255 | 60.731 | 34.984 | 23.561 | 1.00 | 19.56 |
| ATOM | 761 | CA | CYS | 255 | 61.018 | 36.264 | 22.917 | 1.00 | 21.16 |
| ATOM | 762 | CB | CYS | 255 | 60.292 | 37.407 | 23.634 | 1.00 | 21.21 |
| ATOM | 763 | SG | CYS | 255 | 60.404 | 38.957 | 22.735 | 1.00 | 22.22 |
| ATOM | 764 | C | CYS | 255 | 62.504 | 36.590 | 22.775 | 1.00 | 21.36 |
| ATOM | 765 | O | CYS | 255 | 62.986 | 36.847 | 21.667 | 1.00 | 20.58 |
| ATOM | 766 | N | MET | 256 | 63.232 | 36.574 | 23.887 | 1.00 | 20.52 |
| ATOM | 767 | CA | MET | 256 | 64.657 | 36.874 | 23.835 | 1.00 | 20.07 |
| ATOM | 768 | CB | MET | 256 | 65.255 | 36.967 | 25.253 | 1.00 | 20.39 |
| ATOM | 769 | CG | MET | 256 | 66.744 | 37.360 | 25.267 | 1.00 | 19.20 |
| ATOM | 770 | SD | MET | 256 | 67.066 | 38.952 | 24.447 | 1.00 | 20.26 |
| ATOM | 771 | CE | MET | 256 | 68.856 | 38.971 | 24.375 | 1.00 | 18.47 |
| ATOM | 772 | C | MET | 256 | 65.408 | 35.830 | 23.005 | 1.00 | 18.75 |
| ATOM | 773 | O | MET | 256 | 66.305 | 36.164 | 22.225 | 1.00 | 18.15 |
| ATOM | 774 | N | GLU | 257 | 65.035 | 34.568 | 23.170 | 1.00 | 19.00 |
| ATOM | 775 | CA | GLU | 257 | 65.685 | 33.480 | 22.443 | 1.00 | 19.71 |
| ATOM | 776 | CB | GLU | 257 | 65.104 | 32.145 | 22.882 | 1.00 | 21.15 |
| ATOM | 777 | CG | GLU | 257 | 65.451 | 31.821 | 24.319 | 1.00 | 26.39 |
| ATOM | 778 | CD | GLU | 257 | 64.513 | 30.820 | 24.929 | 1.00 | 30.75 |
| ATOM | 779 | OE1 | GLU | 257 | 63.875 | 30.069 | 24.162 | 1.00 | 32.36 |
| ATOM | 780 | OE2 | GLU | 257 | 64.415 | 30.783 | 26.172 | 1.00 | 33.70 |
| ATOM | 781 | C | GLU | 257 | 65.545 | 33.648 | 20.940 | 1.00 | 18.54 |
| ATOM | 782 | O | GLU | 257 | 66.521 | 33.506 | 20.197 | 1.00 | 17.58 |
| ATOM | 783 | N | ILE | 258 | 64.336 | 33.977 | 20.497 | 1.00 | 17.78 |
| ATOM | 784 | CA | ILE | 258 | 64.101 | 34.176 | 19.081 | 1.00 | 17.60 |
| ATOM | 785 | CB | ILE | 258 | 62.590 | 34.267 | 18.765 | 1.00 | 16.35 |
| ATOM | 786 | CG2 | ILE | 258 | 62.376 | 34.777 | 17.326 | 1.00 | 16.20 |
| ATOM | 787 | CG1 | ILE | 258 | 61.935 | 32.884 | 18.980 | 1.00 | 17.24 |
| ATOM | 788 | CD1 | ILE | 258 | 60.437 | 32.787 | 18.593 | 1.00 | 14.08 |
| ATOM | 789 | C | ILE | 258 | 64.872 | 35.408 | 18.595 | 1.00 | 19.11 |
| ATOM | 790 | O | ILE | 258 | 65.609 | 35.326 | 17.601 | 1.00 | 19.02 |
| ATOM | 791 | N | MET | 259 | 64.785 | 36.517 | 19.341 | 1.00 | 19.71 |
| ATOM | 792 | CA | MET | 259 | 65.486 | 37.744 | 18.956 | 1.00 | 18.43 |
| ATOM | 793 | CB | MET | 259 | 65.162 | 38.890 | 19.910 | 1.00 | 19.99 |

APPENDIX 6-continued

TR_T3.PBD

| ATOM | 794 | CG | MET | 259 | 63.700 | 39.278 | 19.962 | 1.00 | 21.15 |
|---|---|---|---|---|---|---|---|---|---|
| ATOM | 795 | SD | MET | 259 | 63.452 | 40.921 | 20.700 | 1.00 | 24.33 |
| ATOM | 796 | CE | MET | 259 | 63.769 | 40.595 | 22.415 | 1.00 | 22.50 |
| ATOM | 797 | C | MET | 259 | 66.993 | 37.540 | 18.888 | 1.00 | 18.64 |
| ATOM | 798 | O | MET | 259 | 67.638 | 37.993 | 17.941 | 1.00 | 19.96 |
| ATOM | 799 | N | SER | 260 | 67.556 | 36.858 | 19.884 | 1.00 | 17.37 |
| ATOM | 800 | CA | SER | 260 | 68.993 | 36.592 | 19.915 | 1.00 | 16.76 |
| ATOM | 801 | CB | SER | 260 | 69.387 | 35.840 | 21.195 | 1.00 | 17.25 |
| ATOM | 802 | OG | SER | 260 | 69.078 | 36.589 | 22.346 | 1.00 | 22.89 |
| ATOM | 803 | C | SER | 260 | 69.387 | 35.750 | 18.717 | 1.00 | 15.13 |
| ATOM | 804 | O | SER | 260 | 70.460 | 35.941 | 18.137 | 1.00 | 16.62 |
| ATOM | 805 | N | LEU | 261 | 68.539 | 34.781 | 18.385 | 1.00 | 15.15 |
| ATOM | 806 | CA | LEU | 261 | 68.802 | 33.900 | 17.262 | 1.00 | 15.31 |
| ATOM | 807 | CB | LEU | 261 | 67.708 | 32.834 | 17.153 | 1.00 | 15.43 |
| ATOM | 808 | CG | LEU | 261 | 67.652 | 32.014 | 15.858 | 1.00 | 15.82 |
| ATOM | 809 | CD1 | LEU | 261 | 68.963 | 31.251 | 15.621 | 1.00 | 16.35 |
| ATOM | 810 | CD2 | LEU | 261 | 66.470 | 31.060 | 15.937 | 1.00 | 13.72 |
| ATOM | 811 | C | LEU | 261 | 68.839 | 34.741 | 16.001 | 1.00 | 16.31 |
| ATOM | 812 | O | LEU | 261 | 69.766 | 34.619 | 15.194 | 1.00 | 16.68 |
| ATOM | 813 | N | ARG | 262 | 67.848 | 35.620 | 15.853 | 1.00 | 16.47 |
| ATOM | 814 | CA | ARG | 262 | 67.778 | 36.493 | 14.680 | 1.00 | 16.66 |
| ATOM | 815 | CB | ARG | 262 | 66.475 | 37.279 | 14.693 | 1.00 | 16.00 |
| ATOM | 816 | CG | ARG | 262 | 65.291 | 36.404 | 14.354 | 1.00 | 15.62 |
| ATOM | 817 | CD | ARG | 262 | 63.995 | 37.167 | 14.378 | 1.00 | 17.31 |
| ATOM | 818 | NE | ARG | 262 | 62.967 | 36.454 | 13.628 | 1.00 | 20.09 |
| ATOM | 819 | CZ | ARG | 262 | 61.755 | 36.932 | 13.361 | 1.00 | 21.06 |
| ATOM | 820 | NH1 | ARG | 262 | 61.390 | 38.136 | 13.787 | 1.00 | 19.02 |
| ATOM | 821 | NH2 | ARG | 262 | 60.909 | 36.207 | 12.640 | 1.00 | 22.63 |
| ATOM | 822 | C | ARG | 262 | 69.003 | 37.396 | 14.527 | 1.00 | 16.80 |
| ATOM | 823 | O | ARG | 262 | 69.440 | 37.664 | 13.412 | 1.00 | 16.82 |
| ATOM | 824 | N | ALA | 263 | 69.578 | 37.832 | 15.650 | 1.00 | 17.77 |
| ATOM | 825 | CA | ALA | 263 | 70.795 | 38.647 | 15.637 | 1.00 | 18.41 |
| ATOM | 826 | CB | ALA | 263 | 70.996 | 39.337 | 17.004 | 1.00 | 18.26 |
| ATOM | 827 | C | ALA | 263 | 71.998 | 37.740 | 15.327 | 1.00 | 19.15 |
| ATOM | 828 | O | ALA | 263 | 72.837 | 38.063 | 14.475 | 1.00 | 19.40 |
| ATOM | 829 | N | ALA | 264 | 72.056 | 36.587 | 15.996 | 1.00 | 19.84 |
| ATOM | 830 | CA | ALA | 264 | 73.155 | 35.633 | 15.818 | 1.00 | 20.35 |
| ATOM | 831 | CB | ALA | 264 | 73.045 | 34.483 | 16.832 | 1.00 | 18.09 |
| ATOM | 832 | C | ALA | 264 | 73.289 | 35.079 | 14.398 | 1.00 | 20.66 |
| ATOM | 833 | O | ALA | 264 | 74.406 | 34.870 | 13.922 | 1.00 | 21.04 |
| ATOM | 834 | N | VAL | 265 | 72.173 | 34.822 | 13.723 | 1.00 | 21.14 |
| ATOM | 835 | CA | VAL | 265 | 72.249 | 34.299 | 12.358 | 1.00 | 22.96 |
| ATOM | 836 | CB | VAL | 265 | 70.910 | 33.660 | 11.879 | 1.00 | 21.04 |
| ATOM | 837 | CG1 | VAL | 265 | 70.458 | 32.600 | 12.866 | 1.00 | 19.48 |
| ATOM | 838 | CG2 | VAL | 265 | 69.838 | 34.708 | 11.698 | 1.00 | 18.96 |
| ATOM | 839 | C | VAL | 265 | 72.718 | 35.387 | 11.382 | 1.00 | 24.66 |
| ATOM | 840 | O | VAL | 265 | 73.026 | 35.103 | 10.224 | 1.00 | 26.03 |
| ATOM | 841 | N | ARG | 266 | 72.777 | 36.628 | 11.858 | 1.00 | 25.11 |
| ATOM | 842 | CA | ARG | 266 | 73.233 | 37.729 | 11.031 | 1.00 | 25.60 |
| ATOM | 843 | CB | ARG | 266 | 72.187 | 38.819 | 10.964 | 1.00 | 24.09 |
| ATOM | 844 | CG | ARG | 266 | 71.035 | 38.427 | 10.088 | 1.00 | 23.37 |
| ATOM | 845 | CD | ARG | 266 | 69.998 | 39.492 | 10.098 | 1.00 | 24.80 |
| ATOM | 846 | NE | ARG | 266 | 68.961 | 39.253 | 9.109 | 1.00 | 24.01 |
| ATOM | 847 | CZ | ARG | 266 | 67.833 | 39.940 | 9.069 | 1.00 | 23.26 |
| ATOM | 848 | NH1 | ARG | 266 | 67.613 | 40.880 | 9.970 | 1.00 | 24.16 |
| ATOM | 849 | NH2 | ARG | 266 | 66.960 | 39.733 | 8.099 | 1.00 | 23.31 |
| ATOM | 850 | C | ARG | 266 | 74.543 | 38.273 | 11.543 | 1.00 | 28.07 |
| ATOM | 851 | O | ARG | 266 | 74.786 | 39.479 | 11.517 | 1.00 | 29.67 |
| ATOM | 852 | N | TYR | 267 | 75.367 | 37.366 | 12.053 | 1.00 | 28.90 |
| ATOM | 853 | CA | TYR | 267 | 76.679 | 37.714 | 12.558 | 1.00 | 30.23 |
| ATOM | 854 | CB | TYR | 267 | 77.223 | 36.584 | 13.434 | 1.00 | 29.98 |
| ATOM | 855 | CG | TYR | 267 | 78.699 | 36.702 | 13.727 | 1.00 | 31.75 |
| ATOM | 856 | CD1 | TYR | 267 | 79.179 | 37.577 | 14.712 | 1.00 | 31.21 |
| ATOM | 857 | CE1 | TYR | 267 | 80.544 | 37.705 | 14.950 | 1.00 | 31.29 |
| ATOM | 858 | CD2 | TYR | 267 | 79.625 | 35.958 | 12.994 | 1.00 | 31.84 |
| ATOM | 859 | CE2 | TYR | 267 | 80.986 | 36.078 | 13.222 | 1.00 | 32.15 |
| ATOM | 860 | CZ | TYR | 267 | 81.442 | 36.949 | 14.197 | 1.00 | 32.60 |
| ATOM | 861 | OH | TYR | 267 | 82.801 | 37.052 | 14.389 | 1.00 | 34.13 |
| ATOM | 862 | C | TYR | 267 | 77.570 | 37.900 | 11.343 | 1.00 | 31.17 |
| ATOM | 863 | O | TYR | 267 | 77.543 | 37.086 | 10.426 | 1.00 | 30.91 |
| ATOM | 864 | N | ASP | 268 | 78.361 | 38.966 | 11.336 | 1.00 | 33.09 |
| ATOM | 865 | CA | ASP | 268 | 79.252 | 39.233 | 10.216 | 1.00 | 35.57 |
| ATOM | 866 | CB | ASP | 268 | 79.085 | 40.679 | 9.747 | 1.00 | 39.39 |
| ATOM | 867 | CG | ASP | 268 | 79.796 | 40.954 | 8.432 | 1.00 | 42.22 |
| ATOM | 868 | OD1 | ASP | 268 | 79.426 | 40.331 | 7.412 | 1.00 | 46.07 |
| ATOM | 869 | OD2 | ASP | 268 | 80.718 | 41.798 | 8.415 | 1.00 | 44.30 |
| ATOM | 870 | C | ASP | 268 | 80.700 | 38.967 | 10.620 | 1.00 | 35.72 |

APPENDIX 6-continued

TR_T3.PBD

| ATOM | 871 | O   | ASP | 268 | 81.287 | 39.737 | 11.384 | 1.00 | 34.49 |
|------|-----|-----|-----|-----|--------|--------|--------|------|-------|
| ATOM | 872 | N   | PRO | 269 | 81.295 | 37.872 | 10.108 | 1.00 | 37.00 |
| ATOM | 873 | CD  | PRO | 269 | 80.712 | 36.887 | 9.182  | 1.00 | 36.77 |
| ATOM | 874 | CA  | PRO | 269 | 82.679 | 37.514 | 10.427 | 1.00 | 38.52 |
| ATOM | 875 | CB  | PRO | 269 | 82.905 | 36.239 | 9.611  | 1.00 | 37.06 |
| ATOM | 876 | CG  | PRO | 269 | 81.549 | 35.669 | 9.453  | 1.00 | 36.19 |
| ATOM | 877 | C   | PRO | 269 | 83.656 | 38.613 | 10.019 | 1.00 | 40.96 |
| ATOM | 878 | O   | PRO | 269 | 84.586 | 38.929 | 10.760 | 1.00 | 42.23 |
| ATOM | 879 | N   | ALA | 270 | 83.418 | 39.209 | 8.854  | 1.00 | 41.92 |
| ATOM | 880 | CA  | ALA | 270 | 84.277 | 40.272 | 8.342  | 1.00 | 42.08 |
| ATOM | 881 | CB  | ALA | 270 | 83.709 | 40.838 | 7.029  | 1.00 | 42.64 |
| ATOM | 882 | C   | ALA | 270 | 84.495 | 41.394 | 9.355  | 1.00 | 41.70 |
| ATOM | 883 | O   | ALA | 270 | 85.632 | 41.709 | 9.684  | 1.00 | 42.25 |
| ATOM | 884 | N   | SER | 271 | 83.408 | 41.970 | 9.865  | 1.00 | 41.87 |
| ATOM | 885 | CA  | SER | 271 | 83.495 | 43.073 | 10.830 | 1.00 | 40.75 |
| ATOM | 886 | CB  | SER | 271 | 82.454 | 44.143 | 10.500 | 1.00 | 40.60 |
| ATOM | 887 | OG  | SER | 271 | 81.150 | 43.590 | 10.464 | 1.00 | 40.31 |
| ATOM | 888 | C   | SER | 271 | 83.344 | 42.658 | 12.290 | 1.00 | 39.99 |
| ATOM | 889 | O   | SER | 271 | 83.484 | 43.487 | 13.194 | 1.00 | 38.77 |
| ATOM | 890 | N   | ASP | 272 | 83.042 | 41.381 | 12.508 | 1.00 | 38.94 |
| ATOM | 891 | CA  | ASP | 272 | 82.859 | 40.844 | 13.845 | 1.00 | 37.78 |
| ATOM | 892 | CB  | ASP | 272 | 84.182 | 40.904 | 14.625 | 1.00 | 38.86 |
| ATOM | 893 | CG  | ASP | 272 | 84.094 | 40.255 | 16.000 | 1.00 | 41.09 |
| ATOM | 894 | OD1 | ASP | 272 | 83.342 | 39.275 | 16.173 | 1.00 | 41.64 |
| ATOM | 895 | OD2 | ASP | 272 | 84.781 | 40.734 | 16.924 | 1.00 | 43.84 |
| ATOM | 896 | C   | ASP | 272 | 81.744 | 41.634 | 14.536 | 1.00 | 36.92 |
| ATOM | 897 | O   | ASP | 272 | 81.907 | 42.156 | 15.648 | 1.00 | 37.56 |
| ATOM | 898 | N   | THR | 273 | 80.603 | 41.723 | 13.865 | 1.00 | 33.65 |
| ATOM | 899 | CA  | THR | 273 | 79.469 | 42.443 | 14.425 | 1.00 | 31.57 |
| ATOM | 900 | CB  | THR | 273 | 79.246 | 43.790 | 13.695 | 1.00 | 31.69 |
| ATOM | 901 | OG1 | THR | 273 | 79.087 | 43.557 | 12.289 | 1.00 | 30.71 |
| ATOM | 902 | CG2 | THR | 273 | 80.426 | 44.730 | 13.922 | 1.00 | 31.53 |
| ATOM | 903 | C   | THR | 273 | 78.184 | 41.631 | 14.310 | 1.00 | 30.15 |
| ATOM | 904 | O   | THR | 273 | 78.104 | 40.697 | 13.504 | 1.00 | 30.10 |
| ATOM | 905 | N   | LEU | 274 | 77.213 | 41.942 | 15.164 | 1.00 | 27.09 |
| ATOM | 906 | CA  | LEU | 274 | 75.907 | 41.303 | 15.103 | 1.00 | 25.94 |
| ATOM | 907 | CB  | LEU | 274 | 75.396 | 40.936 | 16.496 | 1.00 | 24.47 |
| ATOM | 908 | CG  | LEU | 274 | 76.020 | 39.731 | 17.206 | 1.00 | 23.33 |
| ATOM | 909 | CD1 | LEU | 274 | 75.436 | 39.631 | 18.602 | 1.00 | 21.14 |
| ATOM | 910 | CD2 | LEU | 274 | 75.792 | 38.444 | 16.427 | 1.00 | 20.04 |
| ATOM | 911 | C   | LEU | 274 | 75.010 | 42.377 | 14.500 | 1.00 | 26.57 |
| ATOM | 912 | O   | LEU | 274 | 75.339 | 43.557 | 14.568 | 1.00 | 27.03 |
| ATOM | 913 | N   | THR | 275 | 73.914 | 41.987 | 13.865 | 1.00 | 26.60 |
| ATOM | 914 | CA  | THR | 275 | 73.009 | 42.966 | 13.285 | 1.00 | 26.48 |
| ATOM | 915 | CB  | THR | 275 | 72.786 | 42.717 | 11.781 | 1.00 | 26.52 |
| ATOM | 916 | OG1 | THR | 275 | 74.044 | 42.719 | 11.097 | 1.00 | 28.67 |
| ATOM | 917 | CG2 | THR | 275 | 71.919 | 43.799 | 11.198 | 1.00 | 27.35 |
| ATOM | 918 | C   | THR | 275 | 71.674 | 42.898 | 14.014 | 1.00 | 26.57 |
| ATOM | 919 | O   | THR | 275 | 71.069 | 41.825 | 14.121 | 1.00 | 28.50 |
| ATOM | 920 | N   | LEU | 276 | 71.236 | 44.026 | 14.564 | 1.00 | 25.18 |
| ATOM | 921 | CA  | LEU | 276 | 69.970 | 44.069 | 15.276 | 1.00 | 24.61 |
| ATOM | 922 | CB  | LEU | 276 | 70.057 | 44.987 | 16.506 | 1.00 | 23.61 |
| ATOM | 923 | CG  | LEU | 276 | 71.199 | 44.730 | 17.503 | 1.00 | 24.36 |
| ATOM | 924 | CD1 | LEU | 276 | 71.039 | 45.654 | 18.709 | 1.00 | 19.91 |
| ATOM | 925 | CD2 | LEU | 276 | 71.225 | 43.253 | 17.947 | 1.00 | 22.20 |
| ATOM | 926 | C   | LEU | 276 | 68.894 | 44.560 | 14.322 | 1.00 | 25.63 |
| ATOM | 927 | O   | LEU | 276 | 69.100 | 45.556 | 13.623 | 1.00 | 25.35 |
| ATOM | 928 | N   | SER | 277 | 67.787 | 43.814 | 14.249 | 1.00 | 25.94 |
| ATOM | 929 | CA  | SER | 277 | 66.634 | 44.141 | 13.403 | 1.00 | 24.61 |
| ATOM | 930 | CB  | SER | 277 | 65.874 | 45.335 | 13.987 | 1.00 | 21.96 |
| ATOM | 931 | OG  | SER | 277 | 65.368 | 45.029 | 15.273 | 1.00 | 19.68 |
| ATOM | 932 | C   | SER | 277 | 67.005 | 44.406 | 11.946 | 1.00 | 25.20 |
| ATOM | 933 | O   | SER | 277 | 66.350 | 45.199 | 11.267 | 1.00 | 25.21 |
| ATOM | 934 | N   | GLY | 278 | 68.067 | 43.747 | 11.489 | 1.00 | 27.08 |
| ATOM | 935 | CA  | GLY | 278 | 68.556 | 43.899 | 10.127 | 1.00 | 29.27 |
| ATOM | 936 | C   | GLY | 278 | 69.022 | 45.297 | 9.753  | 1.00 | 31.57 |
| ATOM | 937 | O   | GLY | 278 | 69.303 | 45.564 | 8.591  | 1.00 | 31.42 |
| ATOM | 938 | N   | GLU | 279 | 69.159 | 46.177 | 10.740 | 1.00 | 33.41 |
| ATOM | 939 | CA  | GLU | 279 | 69.558 | 47.560 | 10.484 | 1.00 | 34.84 |
| ATOM | 940 | CB  | GLU | 279 | 68.345 | 48.485 | 10.650 | 1.00 | 36.16 |
| ATOM | 941 | CG  | GLU | 279 | 67.843 | 48.606 | 12.090 | 1.00 | 38.08 |
| ATOM | 942 | CD  | GLU | 279 | 66.566 | 49.419 | 12.206 | 1.00 | 41.07 |
| ATOM | 943 | OE1 | GLU | 279 | 66.475 | 50.279 | 13.108 | 1.00 | 41.98 |
| ATOM | 944 | OE2 | GLU | 279 | 65.643 | 49.197 | 11.399 | 1.00 | 43.80 |
| ATOM | 945 | C   | GLU | 279 | 70.706 | 48.116 | 11.326 | 1.00 | 34.38 |
| ATOM | 946 | O   | GLU | 279 | 71.366 | 49.057 | 10.901 | 1.00 | 35.60 |
| ATOM | 947 | N   | MET | 280 | 70.944 | 47.565 | 12.511 | 1.00 | 33.43 |

APPENDIX 6-continued

TR_T3.PBD

| ATOM | 948 | CA | MET | 280 | 72.014 | 48.085 | 13.358 | 1.00 | 32.27 |
|------|-----|------|-----|-----|--------|--------|--------|------|-------|
| ATOM | 949 | CB | MET | 280 | 71.443 | 48.544 | 14.702 | 1.00 | 31.81 |
| ATOM | 950 | CG | MET | 280 | 72.471 | 49.181 | 15.637 | 1.00 | 29.76 |
| ATOM | 951 | SD | MET | 280 | 71.813 | 49.482 | 17.289 | 1.00 | 29.63 |
| ATOM | 952 | CE | MET | 280 | 70.592 | 50.735 | 16.989 | 1.00 | 24.91 |
| ATOM | 953 | C | MET | 280 | 73.161 | 47.119 | 13.603 | 1.00 | 32.51 |
| ATOM | 954 | O | MET | 280 | 72.995 | 46.117 | 14.303 | 1.00 | 32.78 |
| ATOM | 955 | N | ALA | 281 | 74.321 | 47.408 | 13.021 | 1.00 | 31.74 |
| ATOM | 956 | CA | ALA | 281 | 75.491 | 46.564 | 13.231 | 1.00 | 32.25 |
| ATOM | 957 | CB | ALA | 281 | 76.494 | 46.740 | 12.108 | 1.00 | 30.91 |
| ATOM | 958 | C | ALA | 281 | 76.091 | 47.006 | 14.563 | 1.00 | 33.09 |
| ATOM | 959 | O | ALA | 281 | 76.261 | 48.202 | 14.805 | 1.00 | 34.06 |
| ATOM | 960 | N | VAL | 282 | 76.358 | 46.053 | 15.447 | 1.00 | 33.78 |
| ATOM | 961 | CA | VAL | 282 | 76.913 | 46.366 | 16.755 | 1.00 | 33.45 |
| ATOM | 962 | CB | VAL | 282 | 75.858 | 46.208 | 17.885 | 1.00 | 34.92 |
| ATOM | 963 | CG1 | VAL | 282 | 74.775 | 47.269 | 17.744 | 1.00 | 34.90 |
| ATOM | 964 | CG2 | VAL | 282 | 75.246 | 44.806 | 17.860 | 1.00 | 34.39 |
| ATOM | 965 | C | VAL | 282 | 78.119 | 45.514 | 17.087 | 1.00 | 33.93 |
| ATOM | 966 | O | VAL | 282 | 78.202 | 44.347 | 16.702 | 1.00 | 35.11 |
| ATOM | 967 | N | LYS | 283 | 79.071 | 46.123 | 17.777 | 1.00 | 33.49 |
| ATOM | 968 | CA | LYS | 283 | 80.285 | 45.446 | 18.187 | 1.00 | 34.83 |
| ATOM | 969 | CB | LYS | 283 | 81.446 | 46.445 | 18.183 | 1.00 | 35.96 |
| ATOM | 970 | CG | LYS | 283 | 81.726 | 47.013 | 16.797 | 1.00 | 39.20 |
| ATOM | 971 | CD | LYS | 283 | 82.621 | 48.245 | 16.844 | 1.00 | 43.38 |
| ATOM | 972 | CE | LYS | 283 | 83.142 | 48.611 | 15.455 | 1.00 | 44.17 |
| ATOM | 973 | NZ | LYS | 283 | 84.077 | 47.563 | 14.922 | 1.00 | 47.27 |
| ATOM | 974 | C | LYS | 283 | 80.068 | 44.832 | 19.572 | 1.00 | 33.94 |
| ATOM | 975 | O | LYS | 283 | 79.134 | 45.215 | 20.290 | 1.00 | 33.85 |
| ATOM | 976 | N | ARG | 284 | 80.939 | 43.895 | 19.941 | 1.00 | 33.63 |
| ATOM | 977 | CA | ARG | 284 | 80.873 | 43.184 | 21.217 | 1.00 | 34.00 |
| ATOM | 978 | CB | ARG | 284 | 82.094 | 42.285 | 21.381 | 1.00 | 34.04 |
| ATOM | 979 | CG | ARG | 284 | 82.332 | 41.369 | 20.219 | 1.00 | 36.31 |
| ATOM | 980 | CD | ARG | 284 | 83.638 | 40.643 | 20.354 | 1.00 | 37.03 |
| ATOM | 981 | NE | ARG | 284 | 83.724 | 39.576 | 19.369 | 1.00 | 39.27 |
| ATOM | 982 | CZ | ARG | 284 | 83.323 | 38.326 | 19.583 | 1.00 | 40.07 |
| ATOM | 983 | NH1 | ARG | 284 | 82.804 | 37.973 | 20.759 | 1.00 | 39.78 |
| ATOM | 984 | NH2 | ARG | 284 | 83.434 | 37.428 | 18.613 | 1.00 | 40.16 |
| ATOM | 985 | C | ARG | 284 | 80.787 | 44.101 | 22.419 | 1.00 | 35.16 |
| ATOM | 986 | O | ARG | 284 | 79.884 | 43.977 | 23.249 | 1.00 | 35.87 |
| ATOM | 987 | N | GLU | 285 | 81.763 | 44.993 | 22.530 | 1.00 | 35.75 |
| ATOM | 988 | CA | GLU | 285 | 81.827 | 45.939 | 23.632 | 1.00 | 36.86 |
| ATOM | 989 | CB | GLU | 285 | 83.071 | 46.818 | 23.464 | 1.00 | 40.47 |
| ATOM | 990 | CG | GLU | 285 | 83.202 | 47.973 | 24.444 | 1.00 | 49.23 |
| ATOM | 991 | CD | GLU | 285 | 83.587 | 49.284 | 23.747 | 1.00 | 54.22 |
| ATOM | 992 | OE1 | GLU | 285 | 84.784 | 49.657 | 23.760 | 1.00 | 55.37 |
| ATOM | 993 | OE2 | GLU | 285 | 82.686 | 49.942 | 23.176 | 1.00 | 56.95 |
| ATOM | 994 | C | GLU | 285 | 80.552 | 46.785 | 23.684 | 1.00 | 34.45 |
| ATOM | 995 | O | GLU | 285 | 79.990 | 47.007 | 24.754 | 1.00 | 34.47 |
| ATOM | 996 | N | GLN | 286 | 80.046 | 47.166 | 22.515 | 1.00 | 32.27 |
| ATOM | 997 | CA | GLN | 286 | 78.853 | 47.991 | 22.438 | 1.00 | 30.35 |
| ATOM | 998 | CB | GLN | 286 | 78.615 | 48.472 | 21.006 | 1.00 | 33.34 |
| ATOM | 999 | CG | GLN | 286 | 79.632 | 49.497 | 20.500 | 1.00 | 35.09 |
| ATOM | 1000 | CD | GLN | 286 | 79.293 | 50.023 | 19.108 | 1.00 | 38.42 |
| ATOM | 1001 | OE1 | GLN | 286 | 79.161 | 49.248 | 18.158 | 1.00 | 39.03 |
| ATOM | 1002 | NE2 | GLN | 286 | 79.156 | 51.339 | 18.982 | 1.00 | 37.82 |
| ATOM | 1003 | C | GLN | 286 | 77.605 | 47.308 | 22.970 | 1.00 | 29.57 |
| ATOM | 1004 | O | GLN | 286 | 76.870 | 47.891 | 23.770 | 1.00 | 26.96 |
| ATOM | 1005 | N | LEU | 287 | 77.352 | 46.080 | 22.524 | 1.00 | 29.50 |
| ATOM | 1006 | CA | LEU | 287 | 76.164 | 45.350 | 22.979 | 1.00 | 28.93 |
| ATOM | 1007 | CB | LEU | 287 | 75.831 | 44.182 | 22.029 | 1.00 | 27.14 |
| ATOM | 1008 | CG | LEU | 287 | 74.474 | 43.484 | 22.227 | 1.00 | 24.66 |
| ATOM | 1009 | CD1 | LEU | 287 | 73.316 | 44.475 | 22.184 | 1.00 | 22.70 |
| ATOM | 1010 | CD2 | LEU | 287 | 74.297 | 42.413 | 21.163 | 1.00 | 25.17 |
| ATOM | 1011 | C | LEU | 287 | 76.303 | 44.874 | 24.433 | 1.00 | 28.10 |
| ATOM | 1012 | O | LEU | 287 | 75.301 | 44.748 | 25.155 | 1.00 | 28.58 |
| ATOM | 1013 | N | LYS | 288 | 77.541 | 44.652 | 24.868 | 1.00 | 27.97 |
| ATOM | 1014 | CA | LYS | 288 | 77.808 | 44.218 | 26.230 | 1.00 | 28.55 |
| ATOM | 1015 | CB | LYS | 288 | 79.270 | 43.800 | 26.376 | 1.00 | 28.93 |
| ATOM | 1016 | CG | LYS | 288 | 79.603 | 43.254 | 27.750 | 1.00 | 32.46 |
| ATOM | 1017 | CD | LYS | 288 | 81.015 | 42.725 | 27.826 | 1.00 | 33.48 |
| ATOM | 1018 | CE | LYS | 288 | 81.205 | 41.878 | 29.071 | 1.00 | 35.76 |
| ATOM | 1019 | NZ | LYS | 288 | 82.525 | 41.186 | 29.029 | 1.00 | 40.52 |
| ATOM | 1020 | C | LYS | 288 | 77.497 | 45.341 | 27.220 | 1.00 | 29.15 |
| ATOM | 1021 | O | LYS | 288 | 76.782 | 45.132 | 28.207 | 1.00 | 31.28 |
| ATOM | 1022 | N | ASN | 289 | 77.996 | 46.539 | 26.933 | 1.00 | 28.58 |
| ATOM | 1023 | CA | ASN | 289 | 77.794 | 47.692 | 27.811 | 1.00 | 28.40 |
| ATOM | 1024 | CB | ASN | 289 | 78.815 | 48.775 | 27.485 | 1.00 | 28.28 |

APPENDIX 6-continued

TR_T3.PBD

| ATOM | 1025 | CG  | ASN | 289 | 80.224 | 48.329 | 27.770 | 1.00 | 31.30 |
|------|------|-----|-----|-----|--------|--------|--------|------|-------|
| ATOM | 1026 | OD1 | ASN | 289 | 80.445 | 47.442 | 28.601 | 1.00 | 33.02 |
| ATOM | 1027 | ND2 | ASN | 289 | 81.190 | 48.928 | 27.087 | 1.00 | 30.49 |
| ATOM | 1028 | C   | ASN | 289 | 76.395 | 48.278 | 27.792 | 1.00 | 28.33 |
| ATOM | 1029 | O   | ASN | 289 | 76.005 | 48.977 | 28.724 | 1.00 | 28.36 |
| ATOM | 1030 | N   | GLY | 290 | 75.638 | 47.977 | 26.740 | 1.00 | 26.71 |
| ATOM | 1031 | CA  | GLY | 290 | 74.286 | 48.487 | 26.606 | 1.00 | 23.27 |
| ATOM | 1032 | C   | GLY | 290 | 73.233 | 47.852 | 27.484 | 1.00 | 22.93 |
| ATOM | 1033 | O   | GLY | 290 | 72.063 | 48.219 | 27.399 | 1.00 | 23.84 |
| ATOM | 1034 | N   | GLY | 291 | 73.620 | 46.905 | 28.330 | 1.00 | 21.30 |
| ATOM | 1035 | CA  | GLY | 291 | 72.637 | 46.290 | 29.199 | 1.00 | 20.38 |
| ATOM | 1036 | C   | GLY | 291 | 72.653 | 44.778 | 29.200 | 1.00 | 20.05 |
| ATOM | 1037 | O   | GLY | 291 | 72.190 | 44.165 | 30.147 | 1.00 | 21.91 |
| ATOM | 1038 | N   | LEU | 292 | 73.211 | 44.173 | 28.160 | 1.00 | 21.36 |
| ATOM | 1039 | CA  | LEU | 292 | 73.248 | 42.717 | 28.062 | 1.00 | 21.51 |
| ATOM | 1040 | CB  | LEU | 292 | 73.319 | 42.280 | 26.593 | 1.00 | 18.52 |
| ATOM | 1041 | CG  | LEU | 292 | 72.019 | 42.506 | 25.815 | 1.00 | 17.07 |
| ATOM | 1042 | CD1 | LEU | 292 | 72.103 | 41.818 | 24.479 | 1.00 | 18.09 |
| ATOM | 1043 | CD2 | LEU | 292 | 70.844 | 41.947 | 26.599 | 1.00 | 16.35 |
| ATOM | 1044 | C   | LEU | 292 | 74.347 | 42.046 | 28.872 | 1.00 | 22.17 |
| ATOM | 1045 | O   | LEU | 292 | 74.176 | 40.923 | 29.352 | 1.00 | 21.91 |
| ATOM | 1046 | N   | GLY | 293 | 75.479 | 42.724 | 29.011 | 1.00 | 23.76 |
| ATOM | 1047 | CA  | GLY | 293 | 76.588 | 42.169 | 29.760 | 1.00 | 23.92 |
| ATOM | 1048 | C   | GLY | 293 | 77.134 | 40.926 | 29.091 | 1.00 | 25.09 |
| ATOM | 1049 | O   | GLY | 293 | 77.362 | 49.919 | 27.883 | 1.00 | 26.51 |
| ATOM | 1050 | N   | VAL | 294 | 77.332 | 39.866 | 29.867 | 1.00 | 26.08 |
| ATOM | 1051 | CA  | VAL | 294 | 77.854 | 38.618 | 29.329 | 1.00 | 26.34 |
| ATOM | 1052 | CB  | VAL | 294 | 78.263 | 37.636 | 30.443 | 1.00 | 26.97 |
| ATOM | 1053 | CG1 | VAL | 294 | 79.440 | 38.199 | 31.209 | 1.00 | 28.20 |
| ATOM | 1054 | CG2 | VAL | 294 | 77.099 | 37.371 | 31.384 | 1.00 | 25.56 |
| ATOM | 1055 | C   | VAL | 294 | 76.891 | 37.937 | 28.360 | 1.00 | 26.41 |
| ATOM | 1056 | O   | VAL | 294 | 77.315 | 37.097 | 27.568 | 1.00 | 27.65 |
| ATOM | 1057 | N   | VAL | 295 | 75.608 | 38.304 | 28.408 | 1.00 | 26.09 |
| ATOM | 1058 | CA  | VAL | 295 | 74.606 | 37.740 | 27.499 | 1.00 | 26.65 |
| ATOM | 1059 | CB  | VAL | 295 | 73.186 | 38.312 | 27.777 | 1.00 | 28.39 |
| ATOM | 1060 | CG1 | VAL | 295 | 72.164 | 37.740 | 26.782 | 1.00 | 26.69 |
| ATOM | 1061 | CG2 | VAL | 295 | 72.763 | 38.005 | 29.206 | 1.00 | 26.23 |
| ATOM | 1062 | C   | VAL | 295 | 75.035 | 38.089 | 26.069 | 1.00 | 25.83 |
| ATOM | 1063 | O   | VAL | 295 | 74.903 | 37.286 | 25.151 | 1.00 | 27.12 |
| ATOM | 1064 | N   | SER | 296 | 75.609 | 39.275 | 25.908 | 1.00 | 24.95 |
| ATOM | 1065 | CA  | SER | 296 | 76.097 | 39.725 | 24.619 | 1.00 | 26.17 |
| ATOM | 1066 | CB  | SER | 296 | 76.665 | 41.132 | 24.742 | 1.00 | 25.82 |
| ATOM | 1067 | OG  | SER | 296 | 77.253 | 41.554 | 23.525 | 1.00 | 26.64 |
| ATOM | 1068 | C   | SER | 296 | 77.196 | 38.783 | 24.142 | 1.00 | 28.63 |
| ATOM | 1069 | O   | SER | 296 | 77.241 | 38.420 | 22.963 | 1.00 | 29.19 |
| ATOM | 1070 | N   | ASP | 297 | 78.118 | 38.443 | 25.046 | 1.00 | 29.69 |
| ATOM | 1071 | CA  | ASP | 297 | 79.211 | 37.531 | 24.731 | 1.00 | 28.96 |
| ATOM | 1072 | CB  | ASP | 297 | 80.058 | 37.234 | 25.973 | 1.00 | 31.82 |
| ATOM | 1073 | CG  | ASP | 297 | 80.768 | 38.454 | 26.506 | 1.00 | 35.23 |
| ATOM | 1074 | OD1 | ASP | 297 | 80.958 | 39.429 | 25.743 | 1.00 | 35.71 |
| ATOM | 1075 | OD2 | ASP | 297 | 81.140 | 38.430 | 27.698 | 1.00 | 37.68 |
| ATOM | 1076 | C   | ASP | 297 | 78.605 | 36.227 | 24.247 | 1.00 | 27.63 |
| ATOM | 1077 | O   | ASP | 297 | 79.048 | 35.666 | 23.248 | 1.00 | 29.88 |
| ATOM | 1078 | N   | ALA | 298 | 77.581 | 35.762 | 24.952 | 1.00 | 25.15 |
| ATOM | 1079 | CA  | ALA | 298 | 76.909 | 34.527 | 24.592 | 1.00 | 24.49 |
| ATOM | 1080 | CB  | ALA | 298 | 75.811 | 34.224 | 25.594 | 1.00 | 21.91 |
| ATOM | 1081 | C   | ALA | 298 | 76.343 | 34.569 | 23.158 | 1.00 | 24.93 |
| ATOM | 1082 | O   | ALA | 298 | 76.589 | 33.654 | 22.357 | 1.00 | 24.83 |
| ATOM | 1083 | N   | ILE | 299 | 75.632 | 35.647 | 22.814 | 1.00 | 24.70 |
| ATOM | 1084 | CA  | ILE | 299 | 75.041 | 35.756 | 21.480 | 1.00 | 22.49 |
| ATOM | 1085 | CB  | ILE | 299 | 74.057 | 36.950 | 21.351 | 1.00 | 21.96 |
| ATOM | 1086 | CG2 | ILE | 299 | 73.338 | 36.876 | 20.005 | 1.00 | 19.17 |
| ATOM | 1087 | CG1 | ILE | 299 | 72.994 | 36.876 | 22.459 | 1.00 | 21.16 |
| ATOM | 1088 | CD1 | ILE | 299 | 72.363 | 38.228 | 22.853 | 1.00 | 22.04 |
| ATOM | 1089 | C   | ILE | 299 | 76.127 | 35.829 | 20.428 | 1.00 | 22.33 |
| ATOM | 1090 | O   | ILE | 299 | 75.995 | 35.234 | 19.367 | 1.00 | 24.80 |
| ATOM | 1091 | N   | PHE | 300 | 77.209 | 36.538 | 20.724 | 1.00 | 21.92 |
| ATOM | 1092 | CA  | PHE | 300 | 78.322 | 36.641 | 19.785 | 1.00 | 23.08 |
| ATOM | 1093 | CB  | PHE | 300 | 79.385 | 37.636 | 20.278 | 1.00 | 24.08 |
| ATOM | 1094 | CG  | PHE | 300 | 79.249 | 39.017 | 19.686 | 1.00 | 24.18 |
| ATOM | 1095 | CD1 | PHE | 300 | 78.494 | 39.991 | 20.325 | 1.00 | 22.64 |
| ATOM | 1096 | CD2 | PHE | 300 | 79.857 | 39.331 | 18.471 | 1.00 | 23.76 |
| ATOM | 1097 | CE1 | PHE | 300 | 78.347 | 41.253 | 19.770 | 1.00 | 22.38 |
| ATOM | 1098 | CE2 | PHE | 300 | 79.715 | 40.596 | 17.904 | 1.00 | 23.21 |
| ATOM | 1099 | CZ  | PHE | 300 | 78.957 | 41.558 | 18.554 | 1.00 | 22.46 |
| ATOM | 1100 | C   | PHE | 300 | 78.948 | 35.274 | 19.561 | 1.00 | 23.06 |
| ATOM | 1101 | O   | PHE | 300 | 79.264 | 34.913 | 18.426 | 1.00 | 23.97 |

APPENDIX 6-continued

| | | | TR_T3.PBD | | | | | |
|---|---|---|---|---|---|---|---|---|
| ATOM | 1102 | N | GLU | 301 | 79.113 | 34.506 | 20.636 | 1.00 | 23.75 |
| ATOM | 1103 | CA | GLU | 301 | 79.694 | 33.169 | 20.525 | 1.00 | 24.16 |
| ATOM | 1104 | CB | GLU | 301 | 79.884 | 32.545 | 21.902 | 1.00 | 23.03 |
| ATOM | 1105 | C | GLU | 301 | 78.776 | 32.302 | 19.672 | 1.00 | 23.62 |
| ATOM | 1106 | O | GLU | 301 | 79.240 | 31.591 | 18.777 | 1.00 | 25.11 |
| ATOM | 1107 | N | LEU | 302 | 77.472 | 32.394 | 19.926 | 1.00 | 23.12 |
| ATOM | 1108 | CA | LEU | 302 | 76.495 | 31.624 | 19.166 | 1.00 | 23.56 |
| ATOM | 1109 | CB | LEU | 302 | 75.082 | 31.865 | 19.701 | 1.00 | 21.75 |
| ATOM | 1110 | CG | LEU | 302 | 73.953 | 31.120 | 18.979 | 1.00 | 22.61 |
| ATOM | 1111 | CD1 | LEU | 302 | 74.084 | 29.612 | 19.193 | 1.00 | 22.31 |
| ATOM | 1112 | CD2 | LEU | 302 | 72.611 | 31.604 | 19.485 | 1.00 | 19.27 |
| ATOM | 1113 | C | LEU | 302 | 76.588 | 32.011 | 17.687 | 1.00 | 24.41 |
| ATOM | 1114 | O | LEU | 302 | 76.670 | 31.140 | 16.814 | 1.00 | 24.63 |
| ATOM | 1115 | N | GLY | 303 | 76.651 | 33.316 | 17.425 | 1.00 | 25.69 |
| ATOM | 1116 | CA | GLY | 303 | 76.746 | 33.816 | 16.062 | 1.00 | 25.87 |
| ATOM | 1117 | C | GLY | 303 | 77.975 | 33.288 | 15.338 | 1.00 | 28.63 |
| ATOM | 1118 | O | GLY | 303 | 77.893 | 32.895 | 14.170 | 1.00 | 28.30 |
| ATOM | 1119 | N | LYS | 304 | 79.116 | 33.279 | 16.023 | 1.00 | 29.53 |
| ATOM | 1120 | CA | LYS | 304 | 80.360 | 32.791 | 15.437 | 1.00 | 31.18 |
| ATOM | 1121 | CB | LYS | 304 | 81.529 | 32.931 | 16.418 | 1.00 | 34.79 |
| ATOM | 1122 | CG | LYS | 304 | 82.157 | 34.307 | 16.506 | 1.00 | 40.28 |
| ATOM | 1123 | CD | LYS | 304 | 83.441 | 34.262 | 17.332 | 1.00 | 44.37 |
| ATOM | 1124 | CE | LYS | 304 | 83.174 | 33.814 | 18.775 | 1.00 | 47.63 |
| ATOM | 1125 | NZ | LYS | 304 | 82.459 | 34.847 | 19.592 | 1.00 | 48.83 |
| ATOM | 1126 | C | LYS | 304 | 80.245 | 31.328 | 15.042 | 1.00 | 30.87 |
| ATOM | 1127 | O | LYS | 304 | 80.632 | 30.944 | 13.932 | 1.00 | 29.53 |
| ATOM | 1128 | N | SER | 305 | 79.720 | 30.518 | 15.961 | 1.00 | 30.46 |
| ATOM | 1129 | CA | SER | 305 | 79.566 | 29.086 | 15.731 | 1.00 | 31.09 |
| ATOM | 1130 | CB | SER | 305 | 79.243 | 28.370 | 17.041 | 1.00 | 29.83 |
| ATOM | 1131 | OG | SER | 305 | 77.990 | 28.783 | 17.550 | 1.00 | 34.66 |
| ATOM | 1132 | C | SER | 305 | 78.532 | 28.732 | 14.653 | 1.00 | 31.06 |
| ATOM | 1133 | O | SER | 305 | 78.745 | 27.799 | 13.872 | 1.00 | 31.84 |
| ATOM | 1134 | N | LEU | 306 | 77.436 | 29.491 | 14.594 | 1.00 | 29.43 |
| ATOM | 1135 | CA | LEU | 306 | 76.378 | 29.258 | 13.611 | 1.00 | 28.39 |
| ATOM | 1136 | CB | LEU | 306 | 75.121 | 30.055 | 13.962 | 1.00 | 26.05 |
| ATOM | 1137 | CG | LEU | 306 | 74.306 | 29.573 | 15.157 | 1.00 | 26.33 |
| ATOM | 1138 | CD1 | LEU | 306 | 73.061 | 30.430 | 15.285 | 1.00 | 26.22 |
| ATOM | 1139 | CD2 | LEU | 306 | 73.924 | 28.110 | 14.985 | 1.00 | 25.86 |
| ATOM | 1140 | C | LEU | 306 | 76.754 | 29.529 | 12.157 | 1.00 | 28.66 |
| ATOM | 1141 | O | LEU | 306 | 76.116 | 29.001 | 11.253 | 1.00 | 28.58 |
| ATOM | 1142 | N | SER | 307 | 77.786 | 30.338 | 11.931 | 1.00 | 29.72 |
| ATOM | 1143 | CA | SER | 307 | 78.224 | 30.667 | 10.577 | 1.00 | 31.19 |
| ATOM | 1144 | CB | SER | 307 | 79.466 | 31.556 | 10.617 | 1.00 | 30.15 |
| ATOM | 1145 | OG | SER | 307 | 79.226 | 32.710 | 11.396 | 1.00 | 35.19 |
| ATOM | 1146 | C | SER | 307 | 78.531 | 29.412 | 9.777 | 1.00 | 32.75 |
| ATOM | 1147 | O | SER | 307 | 78.110 | 29.283 | 8.621 | 1.00 | 33.09 |
| ATOM | 1148 | N | ALA | 308 | 79.248 | 28.482 | 10.407 | 1.00 | 33.36 |
| ATOM | 1149 | CA | ALA | 308 | 79.626 | 27.223 | 9.769 | 1.00 | 34.50 |
| ATOM | 1150 | CB | ALA | 308 | 80.636 | 26.473 | 10.637 | 1.00 | 33.55 |
| ATOM | 1151 | C | ALA | 308 | 78.417 | 26.328 | 9.466 | 1.00 | 35.00 |
| ATOM | 1152 | O | ALA | 308 | 78.469 | 25.501 | 8.550 | 1.00 | 37.10 |
| ATOM | 1153 | N | PHE | 309 | 77.335 | 26.496 | 10.226 | 1.00 | 32.76 |
| ATOM | 1154 | CA | PHE | 309 | 76.134 | 25.698 | 10.028 | 1.00 | 31.73 |
| ATOM | 1155 | CB | PHE | 309 | 75.214 | 25.818 | 11.232 | 1.00 | 30.04 |
| ATOM | 1156 | CG | PHE | 309 | 75.705 | 25.091 | 12.438 | 1.00 | 31.19 |
| ATOM | 1157 | CD1 | PHE | 309 | 74.973 | 24.048 | 12.975 | 1.00 | 31.61 |
| ATOM | 1158 | CD2 | PHE | 309 | 76.884 | 25.459 | 13.054 | 1.00 | 31.92 |
| ATOM | 1159 | CE1 | PHE | 309 | 75.400 | 23.391 | 14.110 | 1.00 | 31.22 |
| ATOM | 1160 | CE2 | PHE | 309 | 77.320 | 24.807 | 14.194 | 1.00 | 31.01 |
| ATOM | 1161 | CZ | PHE | 309 | 76.577 | 23.771 | 14.720 | 1.00 | 30.47 |
| ATOM | 1162 | C | PHE | 309 | 75.364 | 26.050 | 8.753 | 1.00 | 31.53 |
| ATOM | 1163 | O | PHE | 309 | 74.516 | 25.269 | 8.310 | 1.00 | 31.28 |
| ATOM | 1164 | N | ASN | 310 | 75.661 | 27.220 | 8.181 | 1.00 | 31.12 |
| ATOM | 1165 | CA | ASN | 310 | 75.020 | 27.711 | 6.957 | 1.00 | 30.34 |
| ATOM | 1166 | CB | ASN | 310 | 75.636 | 27.036 | 5.719 | 1.00 | 31.63 |
| ATOM | 1167 | C | ASN | 310 | 73.511 | 27.492 | 7.003 | 1.00 | 29.40 |
| ATOM | 1168 | O | ASN | 310 | 72.939 | 26.791 | 6.156 | 1.00 | 29.15 |
| ATOM | 1169 | N | LEU | 311 | 72.875 | 28.055 | 8.026 | 1.00 | 27.60 |
| ATOM | 1170 | CA | LEU | 311 | 71.435 | 27.907 | 8.205 | 1.00 | 28.23 |
| ATOM | 1171 | CB | LEU | 311 | 71.021 | 28.313 | 9.621 | 1.00 | 27.41 |
| ATOM | 1172 | CG | LEU | 311 | 71.603 | 27.558 | 10.822 | 1.00 | 26.80 |
| ATOM | 1173 | CD1 | LEU | 311 | 70.949 | 28.078 | 12.112 | 1.00 | 25.05 |
| ATOM | 1174 | CD2 | LEU | 311 | 71.360 | 26.062 | 10.662 | 1.00 | 24.72 |
| ATOM | 1175 | C | LEU | 311 | 70.628 | 28.719 | 7.192 | 1.00 | 29.01 |
| ATOM | 1176 | O | LEU | 311 | 71.040 | 29.808 | 6.782 | 1.00 | 30.66 |
| ATOM | 1177 | N | ASP | 312 | 69.503 | 28.168 | 6.748 | 1.00 | 26.30 |
| ATOM | 1178 | CA | ASP | 312 | 68.675 | 28.894 | 5.817 | 1.00 | 25.13 |

APPENDIX 6-continued

TR_T3.PBD

| ATOM | 1179 | CB  | ASP | 312 | 68.391 | 28.067 | 4.539  | 1.00 | 23.90 |
| ATOM | 1180 | CG  | ASP | 312 | 67.438 | 26.890 | 4.754  | 1.00 | 21.34 |
| ATOM | 1181 | OD1 | ASP | 312 | 66.959 | 26.631 | 5.868  | 1.00 | 22.47 |
| ATOM | 1182 | OD2 | ASP | 312 | 67.154 | 26.206 | 3.758  | 1.00 | 22.18 |
| ATOM | 1183 | C   | ASP | 312 | 67.419 | 29.379 | 6.542  | 1.00 | 24.49 |
| ATOM | 1184 | O   | ASP | 312 | 67.221 | 29.056 | 7.725  | 1.00 | 24.01 |
| ATOM | 1185 | N   | ASP | 313 | 66.587 | 30.153 | 5.845  | 1.00 | 23.40 |
| ATOM | 1186 | CA  | ASP | 313 | 65.363 | 30.697 | 6.421  | 1.00 | 22.63 |
| ATOM | 1187 | CB  | ASP | 313 | 64.557 | 31.486 | 5.385  | 1.00 | 24.99 |
| ATOM | 1188 | CG  | ASP | 313 | 65.224 | 32.799 | 4.994  | 1.00 | 28.02 |
| ATOM | 1189 | OD1 | ASP | 313 | 66.036 | 33.334 | 5.778  | 1.00 | 30.34 |
| ATOM | 1190 | OD2 | ASP | 313 | 64.936 | 33.306 | 3.897  | 1.00 | 30.41 |
| ATOM | 1191 | C   | ASP | 313 | 64.480 | 29.650 | 7.053  | 1.00 | 21.47 |
| ATOM | 1192 | O   | ASP | 313 | 63.853 | 29.917 | 8.082  | 1.00 | 21.76 |
| ATOM | 1193 | N   | THR | 314 | 64.407 | 28.474 | 6.435  | 1.00 | 19.16 |
| ATOM | 1194 | CA  | THR | 314 | 63.580 | 27.386 | 6.966  | 1.00 | 18.79 |
| ATOM | 1195 | CB  | THR | 314 | 63.398 | 26.240 | 5.913  | 1.00 | 19.68 |
| ATOM | 1196 | OG1 | THR | 314 | 62.743 | 26.758 | 4.747  | 1.00 | 20.56 |
| ATOM | 1197 | CG2 | THR | 314 | 62.558 | 25.112 | 6.482  | 1.00 | 18.84 |
| ATOM | 1198 | C   | THR | 314 | 64.133 | 26.818 | 8.293  | 1.00 | 15.38 |
| ATOM | 1199 | O   | THR | 314 | 63.383 | 26.538 | 9.223  | 1.00 | 14.08 |
| ATOM | 1200 | N   | GLU | 315 | 65.445 | 26.656 | 8.376  | 1.00 | 15.16 |
| ATOM | 1201 | CA  | GLU | 315 | 66.051 | 26.126 | 9.593  | 1.00 | 16.78 |
| ATOM | 1202 | CW  | GLU | 315 | 67.513 | 25.785 | 9.340  | 1.00 | 14.29 |
| ATOM | 1203 | CG  | GLU | 315 | 67.611 | 24.483 | 8.579  | 1.00 | 15.13 |
| ATOM | 1204 | CD  | GLU | 315 | 68.910 | 24.291 | 7.872  | 1.00 | 15.90 |
| ATOM | 1205 | OE1 | GLU | 315 | 69.625 | 25.285 | 7.639  | 1.00 | 19.80 |
| ATOM | 1206 | OE2 | GLU | 315 | 69.211 | 23.129 | 7.527  | 1.00 | 19.34 |
| ATOM | 1207 | C   | GLU | 315 | 65.872 | 27.119 | 10.736 | 1.00 | 17.27 |
| ATOM | 1208 | O   | GLU | 315 | 65.457 | 26.742 | 11.836 | 1.00 | 17.46 |
| ATOM | 1209 | N   | VAL | 316 | 66.081 | 28.399 | 10.440 | 1.00 | 17.12 |
| ATOM | 1210 | CA  | VAL | 316 | 65.897 | 29.441 | 11.446 | 1.00 | 16.92 |
| ATOM | 1211 | CB  | VAL | 316 | 66.336 | 30.828 | 10.918 | 1.00 | 15.89 |
| ATOM | 1212 | CG1 | VAL | 316 | 66.062 | 31.921 | 11.962 | 1.00 | 14.60 |
| ATOM | 1213 | CG2 | VAL | 316 | 67.811 | 30.785 | 10.579 | 1.00 | 15.95 |
| ATOM | 1214 | C   | VAL | 316 | 64.430 | 29.472 | 11.869 | 1.00 | 17.32 |
| ATOM | 1215 | O   | VAL | 316 | 64.131 | 29.582 | 13.055 | 1.00 | 18.11 |
| ATOM | 1216 | N   | ALA | 317 | 63.515 | 29.324 | 10.905 | 1.00 | 17.42 |
| ATOM | 1217 | CA  | ALA | 317 | 62.076 | 29.342 | 11.195 | 1.00 | 16.21 |
| ATOM | 1218 | CB  | ALA | 317 | 61.262 | 29.321 | 9.910  | 1.00 | 14.63 |
| ATOM | 1219 | C   | ALA | 317 | 61.656 | 28.181 | 12.079 | 1.00 | 16.84 |
| ATOM | 1220 | O   | ALA | 317 | 60.904 | 28.359 | 13.036 | 1.00 | 16.08 |
| ATOM | 1221 | N   | LEU | 318 | 62.146 | 26.990 | 11.759 | 1.00 | 17.27 |
| ATOM | 1222 | CA  | LEU | 318 | 61.783 | 25.804 | 12.526 | 1.00 | 17.88 |
| ATOM | 1223 | CB  | LEU | 318 | 62.141 | 24.525 | 11.748 | 1.00 | 17.58 |
| ATOM | 1224 | CG  | LEU | 318 | 61.331 | 24.333 | 10.439 | 1.00 | 16.87 |
| ATOM | 1225 | CD1 | LEU | 318 | 61.837 | 23.155 | 9.658  | 1.00 | 15.79 |
| ATOM | 1226 | CD2 | LEU | 318 | 59.860 | 24.149 | 10.728 | 1.00 | 14.08 |
| ATOM | 1227 | C   | LEU | 318 | 62.394 | 25.852 | 13.932 | 1.00 | 18.20 |
| ATOM | 1228 | O   | LEU | 318 | 61.733 | 25.495 | 14.910 | 1.00 | 18.71 |
| ATOM | 1229 | N   | LEU | 319 | 63.614 | 26.380 | 14.034 | 1.00 | 17.73 |
| ATOM | 1230 | CA  | LEU | 319 | 64.288 | 26.531 | 15.321 | 1.00 | 16.57 |
| ATOM | 1231 | CB  | LEU | 319 | 65.689 | 27.105 | 15.107 | 1.00 | 18.81 |
| ATOM | 1232 | CG  | LEU | 319 | 66.733 | 27.223 | 16.224 | 1.00 | 21.77 |
| ATOM | 1233 | CD1 | LEU | 319 | 66.767 | 25.994 | 17.117 | 1.00 | 23.03 |
| ATOM | 1234 | CD2 | LEU | 319 | 68.076 | 27.421 | 15.554 | 1.00 | 20.86 |
| ATOM | 1235 | C   | LEU | 319 | 63.433 | 27.471 | 16.160 | 1.00 | 16.07 |
| ATOM | 1236 | O   | LEU | 319 | 63.134 | 27.183 | 17.319 | 1.00 | 16.40 |
| ATOM | 1237 | N   | GLN | 320 | 62.948 | 28.546 | 15.545 | 1.00 | 13.91 |
| ATOM | 1238 | CA  | GLN | 320 | 62.101 | 29.490 | 16.253 | 1.00 | 13.86 |
| ATOM | 1239 | CB  | GLN | 320 | 61.782 | 30.697 | 15.373 | 1.00 | 13.26 |
| ATOM | 1240 | CG  | GLN | 320 | 62.994 | 31.553 | 15.080 | 1.00 | 12.17 |
| ATOM | 1241 | CD  | GLN | 320 | 62.691 | 32.802 | 14.253 | 1.00 | 13.98 |
| ATOM | 1242 | OE1 | GLN | 320 | 63.597 | 33.568 | 13.950 | 1.00 | 15.61 |
| ATOM | 1243 | NE2 | GLN | 320 | 61.436 | 32.993 | 13.862 | 1.00 | 13.85 |
| ATOM | 1244 | C   | GLN | 320 | 60.813 | 28.832 | 16.746 | 1.00 | 14.52 |
| ATOM | 1245 | O   | GLN | 320 | 60.367 | 29.087 | 17.864 | 1.00 | 15.12 |
| ATOM | 1246 | N   | ALA | 321 | 60.211 | 27.982 | 15.924 | 1.00 | 14.21 |
| ATOM | 1247 | CA  | ALA | 321 | 58.976 | 27.298 | 16.309 | 1.00 | 15.04 |
| ATOM | 1248 | CB  | ALA | 321 | 58.408 | 26.519 | 15.115 | 1.00 | 13.84 |
| ATOM | 1249 | C   | ALA | 321 | 59.217 | 26.349 | 17.487 | 1.00 | 15.98 |
| ATOM | 1250 | O   | ALA | 321 | 58.358 | 26.197 | 18.355 | 1.00 | 15.12 |
| ATOM | 1251 | N   | VAL | 322 | 60.373 | 25.687 | 17.488 | 1.00 | 16.63 |
| ATOM | 1252 | CA  | VAL | 322 | 60.720 | 24.757 | 18.557 | 1.00 | 18.74 |
| ATOM | 1253 | CB  | VAL | 322 | 62.012 | 23.943 | 18.231 | 1.00 | 19.42 |
| ATOM | 1254 | CG1 | VAL | 322 | 62.493 | 23.154 | 19.455 | 1.00 | 19.45 |
| ATOM | 1255 | CG2 | VAL | 322 | 61.745 | 22.986 | 17.083 | 1.00 | 19.05 |

APPENDIX 6-continued

| | | | | | | | | |
|---|---|---|---|---|---|---|---|---|
| | | | TR_T3.PBD | | | | | |
| ATOM | 1256 | C | VAL | 322 | 60.910 | 25.556 | 19.833 | 1.00 | 18.42 |
| ATOM | 1257 | O | VAL | 322 | 60.421 | 25.164 | 20.886 | 1.00 | 19.46 |
| ATOM | 1258 | N | LEU | 323 | 61.607 | 26.685 | 19.735 | 1.00 | 18.65 |
| ATOM | 1259 | CA | LEU | 323 | 61.836 | 27.543 | 20.894 | 1.00 | 18.49 |
| ATOM | 1260 | CB | LEU | 323 | 62.710 | 28.740 | 20.508 | 1.00 | 18.36 |
| ATOM | 1261 | CG | LEU | 323 | 64.179 | 28.449 | 20.186 | 1.00 | 18.13 |
| ATOM | 1262 | CD1 | LEU | 323 | 64.829 | 29.669 | 19.585 | 1.00 | 17.37 |
| ATOM | 1263 | CD2 | LEU | 323 | 64.923 | 27.999 | 21.447 | 1.00 | 17.27 |
| ATOM | 1264 | C | LEU | 323 | 60.499 | 28.029 | 21.454 | 1.00 | 18.38 |
| ATOM | 1265 | O | LEU | 323 | 60.275 | 28.008 | 22.663 | 1.00 | 18.81 |
| ATOM | 1266 | N | LEU | 324 | 59.595 | 28.406 | 20.557 | 1.00 | 18.67 |
| ATOM | 1267 | CA | LEU | 324 | 58.275 | 28.897 | 20.924 | 1.00 | 19.02 |
| ATOM | 1268 | CB | LEU | 324 | 57.564 | 29.467 | 19.685 | 1.00 | 17.78 |
| ATOM | 1269 | CG | LEU | 324 | 56.095 | 29.891 | 19.838 | 1.00 | 17.59 |
| ATOM | 1270 | CD1 | LEU | 324 | 55.983 | 31.123 | 20.709 | 1.00 | 18.15 |
| ATOM | 1271 | CD2 | LEU | 324 | 55.489 | 30.180 | 18.476 | 1.00 | 16.43 |
| ATOM | 1272 | C | LEU | 324 | 57.354 | 27.884 | 21.610 | 1.00 | 19.62 |
| ATOM | 1273 | O | LEU | 324 | 56.735 | 28.185 | 22.633 | 1.00 | 19.40 |
| ATOM | 1274 | N | MET | 325 | 57.224 | 26.701 | 21.029 | 1.00 | 21.14 |
| ATOM | 1275 | CA | MET | 325 | 56.330 | 25.680 | 21.585 | 1.00 | 24.06 |
| ATOM | 1276 | CB | MET | 325 | 55.857 | 24.738 | 20.473 | 1.00 | 24.68 |
| ATOM | 1277 | CG | MET | 325 | 55.169 | 25.444 | 19.303 | 1.00 | 24.49 |
| ATOM | 1278 | SD | MET | 325 | 53.759 | 26.457 | 19.820 | 1.00 | 26.18 |
| ATOM | 1279 | CE | MET | 325 | 52.609 | 25.252 | 20.373 | 1.00 | 24.03 |
| ATOM | 1280 | C | MET | 325 | 56.996 | 24.887 | 22.705 | 1.00 | 26.15 |
| ATOM | 1281 | O | MET | 325 | 57.021 | 23.664 | 22.693 | 1.00 | 25.68 |
| ATOM | 1282 | N | SER | 326 | 57.555 | 25.593 | 23.671 | 1.00 | 29.34 |
| ATOM | 1283 | CA | SER | 326 | 58.232 | 24.938 | 24.774 | 1.00 | 32.40 |
| ATOM | 1284 | CB | SER | 326 | 59.512 | 25.701 | 25.112 | 1.00 | 32.12 |
| ATOM | 1285 | OG | SER | 326 | 60.127 | 25.173 | 26.272 | 1.00 | 36.86 |
| ATOM | 1286 | C | SER | 326 | 57.317 | 24.831 | 25.996 | 1.00 | 34.04 |
| ATOM | 1287 | O | SER | 326 | 56.532 | 25.741 | 26.280 | 1.00 | 33.24 |
| ATOM | 1288 | N | THR | 327 | 57.366 | 23.687 | 26.674 | 1.00 | 35.62 |
| ATOM | 1289 | CA | THR | 327 | 56.560 | 23.486 | 27.867 | 1.00 | 36.88 |
| ATOM | 1290 | CB | THR | 327 | 55.938 | 22.085 | 27.907 | 1.00 | 36.58 |
| ATOM | 1291 | OG1 | THR | 327 | 56.953 | 21.094 | 27.714 | 1.00 | 38.58 |
| ATOM | 1292 | CG2 | THR | 327 | 54.883 | 21.938 | 26.826 | 1.00 | 37.73 |
| ATOM | 1293 | C | THR | 327 | 57.378 | 23.733 | 29.135 | 1.00 | 38.77 |
| ATOM | 1294 | O | THR | 327 | 56.921 | 23.438 | 30.240 | 1.00 | 39.53 |
| ATOM | 1295 | N | ASP | 328 | 58.593 | 24.260 | 28.972 | 1.00 | 41.25 |
| ATOM | 1296 | CA | ASP | 328 | 59.473 | 24.573 | 30.099 | 1.00 | 43.20 |
| ATOM | 1297 | CB | ASP | 328 | 60.940 | 24.698 | 29.655 | 1.00 | 46.47 |
| ATOM | 1298 | CG | ASP | 328 | 61.618 | 23.346 | 29.439 | 1.00 | 51.94 |
| ATOM | 1299 | OD1 | ASP | 328 | 62.547 | 23.278 | 28.601 | 1.00 | 55.43 |
| ATOM | 1300 | OD2 | ASP | 328 | 61.251 | 22.354 | 30.111 | 1.00 | 54.77 |
| ATOM | 1301 | C | ASP | 328 | 59.001 | 25.905 | 30.653 | 1.00 | 43.79 |
| ATOM | 1302 | O | ASP | 328 | 59.755 | 26.877 | 30.709 | 1.00 | 45.91 |
| ATOM | 1303 | N | ARG | 329 | 57.724 | 25.967 | 30.995 | 1.00 | 43.55 |
| ATOM | 1304 | CA | ARG | 329 | 57.143 | 27.178 | 31.542 | 1.00 | 43.04 |
| ATOM | 1305 | CB | ARG | 329 | 56.398 | 27.997 | 30.482 | 1.00 | 43.87 |
| ATOM | 1306 | CG | ARG | 329 | 57.258 | 28.740 | 29.504 | 1.00 | 40.87 |
| ATOM | 1307 | CD | ARG | 329 | 57.545 | 27.886 | 28.314 | 1.00 | 39.52 |
| ATOM | 1308 | NE | ARG | 329 | 58.301 | 28.643 | 27.341 | 1.00 | 38.90 |
| ATOM | 1309 | CZ | ARG | 329 | 59.624 | 28.708 | 27.313 | 1.00 | 40.59 |
| ATOM | 1310 | NH1 | ARG | 329 | 60.359 | 28.052 | 28.196 | 1.00 | 42.41 |
| ATOM | 1311 | NH2 | ARG | 329 | 60.210 | 29.466 | 26.413 | 1.00 | 41.87 |
| ATOM | 1312 | C | ARG | 329 | 56.152 | 26.817 | 32.609 | 1.00 | 43.00 |
| ATOM | 1313 | O | ARG | 329 | 55.600 | 25.716 | 32.628 | 1.00 | 43.66 |
| ATOM | 1314 | N | SER | 330 | 55.886 | 27.797 | 33.456 | 1.00 | 41.58 |
| ATOM | 1315 | CA | SER | 330 | 54.953 | 27.641 | 34.538 | 1.00 | 40.11 |
| ATOM | 1316 | CB | SER | 330 | 55.491 | 28.362 | 35.777 | 1.00 | 40.38 |
| ATOM | 1317 | C | SER | 330 | 53.602 | 28.223 | 34.103 | 1.00 | 38.99 |
| ATOM | 1318 | O | SER | 330 | 53.553 | 29.172 | 33.320 | 1.00 | 39.22 |
| ATOM | 1319 | N | GLY | 331 | 52.517 | 27.581 | 34.529 | 1.00 | 37.52 |
| ATOM | 1320 | CA | GLY | 331 | 51.176 | 28.063 | 34.232 | 1.00 | 35.64 |
| ATOM | 1321 | C | GLY | 331 | 50.493 | 27.782 | 32.906 | 1.00 | 35.14 |
| ATOM | 1322 | O | GLY | 331 | 49.439 | 28.363 | 32.640 | 1.00 | 34.48 |
| ATOM | 1323 | N | LEU | 332 | 51.059 | 26.925 | 32.066 | 1.00 | 34.54 |
| ATOM | 1324 | CA | LEU | 332 | 50.424 | 26.637 | 30.780 | 1.00 | 34.59 |
| ATOM | 1325 | CB | LEU | 332 | 51.394 | 25.942 | 29.828 | 1.00 | 33.09 |
| ATOM | 1326 | CG | LEU | 332 | 52.532 | 26.765 | 29.236 | 1.00 | 32.72 |
| ATOM | 1327 | CD1 | LEU | 332 | 53.473 | 25.834 | 28.497 | 1.00 | 30.29 |
| ATOM | 1328 | CD2 | LEU | 332 | 51.987 | 27.844 | 28.313 | 1.00 | 29.20 |
| ATOM | 1329 | C | LEU | 332 | 49.191 | 25.763 | 30.969 | 1.00 | 35.14 |
| ATOM | 1330 | O | LEU | 332 | 49.178 | 24.874 | 31.811 | 1.00 | 35.96 |
| ATOM | 1331 | N | LEU | 333 | 48.153 | 26.076 | 30.204 | 1.00 | 35.65 |
| ATOM | 1332 | CA | LEU | 333 | 46.898 | 25.345 | 30.215 | 1.00 | 37.97 |

APPENDIX 6-continued

TR_T3.PBD

| | | | | | | | | |
|---|---|---|---|---|---|---|---|---|
| ATOM | 1333 | CB | LEU | 333 | 45.743 | 26.271 | 29.796 | 1.00 | 40.71 |
| ATOM | 1334 | CG | LEU | 333 | 45.389 | 27.483 | 30.670 | 1.00 | 43.46 |
| ATOM | 1335 | CD1 | LEU | 333 | 44.713 | 28.620 | 29.882 | 1.00 | 42.72 |
| ATOM | 1336 | CD2 | LEU | 333 | 44.487 | 27.021 | 31.806 | 1.00 | 45.25 |
| ATOM | 1337 | C | LEU | 333 | 46.952 | 24.115 | 29.300 | 1.00 | 37.78 |
| ATOM | 1338 | O | LEU | 333 | 46.695 | 22.991 | 29.720 | 1.00 | 37.65 |
| ATOM | 1339 | N | CYA | 334 | 47.361 | 24.323 | 28.060 | 1.00 | 38.65 |
| ATOM | 1340 | CA | CYA | 334 | 47.413 | 23.249 | 27.073 | 1.00 | 40.91 |
| ATOM | 1341 | CB | CYA | 334 | 46.936 | 23.788 | 25.721 | 1.00 | 47.35 |
| ATOM | 1342 | SG | CYA | 334 | 45.406 | 24.693 | 25.867 | 1.00 | 52.24 |
| ATOM | 1343 | AS | CYA | 334 | 44.066 | 22.890 | 25.562 | 1.00 | 70.72 |
| ATOM | 1344 | C | CYA | 334 | 48.778 | 22.588 | 26.901 | 1.00 | 39.85 |
| ATOM | 1345 | O | CYA | 334 | 49.287 | 22.473 | 25.775 | 1.00 | 39.54 |
| ATOM | 1346 | N | VAL | 335 | 49.329 | 22.078 | 27.997 | 1.00 | 37.67 |
| ATOM | 1347 | CA | VAL | 335 | 50.641 | 21.432 | 27.967 | 1.00 | 36.07 |
| ATOM | 1348 | CB | VAL | 335 | 51.019 | 20.905 | 29.384 | 1.00 | 33.70 |
| ATOM | 1349 | CG1 | VAL | 335 | 52.434 | 20.332 | 29.401 | 1.00 | 33.70 |
| ATOM | 1350 | CG2 | VAL | 335 | 50.913 | 22.028 | 30.387 | 1.00 | 31.84 |
| ATOM | 1351 | C | VAL | 335 | 50.734 | 20.334 | 26.885 | 1.00 | 36.09 |
| ATOM | 1352 | O | VAL | 335 | 51.662 | 20.335 | 26.064 | 1.00 | 34.41 |
| ATOM | 1353 | N | ASP | 336 | 49.747 | 19.444 | 26.833 | 1.00 | 35.95 |
| ATOM | 1354 | CA | ASP | 336 | 49.748 | 18.372 | 25.844 | 1.00 | 36.34 |
| ATOM | 1355 | CB | ASP | 336 | 48.591 | 17.394 | 26.091 | 1.00 | 41.36 |
| ATOM | 1356 | CG | ASP | 336 | 48.613 | 16.206 | 25.129 | 1.00 | 46.23 |
| ATOM | 1357 | OD1 | ASP | 336 | 47.615 | 16.021 | 24.392 | 1.00 | 49.55 |
| ATOM | 1358 | OD2 | ASP | 336 | 49.639 | 15.470 | 25.097 | 1.00 | 48.07 |
| ATOM | 1359 | C | ASP | 336 | 49.727 | 18.846 | 24.390 | 1.00 | 33.05 |
| ATOM | 1360 | O | ASP | 336 | 50.527 | 18.377 | 23.573 | 1.00 | 32.33 |
| ATOM | 1361 | N | LYS | 337 | 48.794 | 19.743 | 24.076 | 1.00 | 29.57 |
| ATOM | 1362 | CA | LYS | 337 | 48.661 | 20.286 | 22.723 | 1.00 | 27.76 |
| ATOM | 1363 | CB | LYS | 337 | 47.520 | 21.313 | 22.689 | 1.00 | 27.09 |
| ATOM | 1364 | C | LYS | 337 | 49.988 | 20.941 | 22.286 | 1.00 | 27.64 |
| ATOM | 1365 | O | LYS | 337 | 50.472 | 20.713 | 21.173 | 1.00 | 26.09 |
| ATOM | 1366 | N | ILE | 338 | 50.597 | 21.688 | 23.208 | 1.00 | 25.90 |
| ATOM | 1367 | CA | ILE | 338 | 51.852 | 22.394 | 22.971 | 1.00 | 24.21 |
| ATOM | 1368 | CB | ILE | 338 | 52.128 | 23.391 | 24.122 | 1.00 | 23.30 |
| ATOM | 1369 | CG2 | ILE | 338 | 53.500 | 24.048 | 23.958 | 1.00 | 21.75 |
| ATOM | 1370 | CG1 | ILE | 338 | 51.014 | 24.448 | 24.155 | 1.00 | 21.19 |
| ATOM | 1371 | CD1 | ILE | 338 | 51.055 | 25.393 | 25.361 | 1.00 | 21.39 |
| ATOM | 1372 | C | ILE | 338 | 53.041 | 21.451 | 22.782 | 1.00 | 25.55 |
| ATOM | 1373 | O | ILE | 338 | 53.861 | 21.640 | 21.875 | 1.00 | 24.74 |
| ATOM | 1374 | N | GLU | 339 | 53.124 | 20.421 | 23.622 | 1.00 | 27.43 |
| ATOM | 1375 | CA | GLU | 339 | 54.220 | 19.448 | 23.536 | 1.00 | 27.60 |
| ATOM | 1376 | CB | GLU | 339 | 54.201 | 18.512 | 24.755 | 1.00 | 27.21 |
| ATOM | 1377 | C | GLU | 339 | 54.112 | 18.650 | 22.236 | 1.00 | 26.85 |
| ATOM | 1378 | O | GLU | 339 | 55.119 | 18.385 | 21.581 | 1.00 | 26.71 |
| ATOM | 1379 | N | LYS | 340 | 52.888 | 18.276 | 21.872 | 1.00 | 27.04 |
| ATOM | 1380 | CA | LYS | 340 | 52.663 | 17.515 | 20.654 | 1.00 | 28.19 |
| ATOM | 1381 | CB | LYS | 340 | 51.210 | 17.008 | 20.609 | 1.00 | 28.67 |
| ATOM | 1382 | C | LYS | 340 | 53.002 | 18.402 | 19.439 | 1.00 | 27.96 |
| ATOM | 1383 | O | LYS | 340 | 53.558 | 17.934 | 18.436 | 1.00 | 27.48 |
| ATOM | 1384 | N | SER | 341 | 52.746 | 19.700 | 19.567 | 1.00 | 28.32 |
| ATOM | 1385 | CA | SER | 341 | 53.058 | 20.662 | 18.514 | 1.00 | 28.02 |
| ATOM | 1386 | CB | SER | 341 | 52.457 | 22.022 | 18.867 | 1.00 | 31.25 |
| ATOM | 1387 | OG | SER | 341 | 52.880 | 23.029 | 17.965 | 1.00 | 37.69 |
| ATOM | 1388 | C | SER | 341 | 54.578 | 20.773 | 18.350 | 1.00 | 26.01 |
| ATOM | 1389 | O | SER | 341 | 55.096 | 20.717 | 17.234 | 1.00 | 25.06 |
| ATOM | 1390 | N | GLN | 342 | 55.297 | 20.899 | 19.462 | 1.00 | 25.71 |
| ATOM | 1391 | CA | GLN | 342 | 56.750 | 20.993 | 19.398 | 1.00 | 26.39 |
| ATOM | 1392 | CB | GLN | 342 | 57.356 | 21.254 | 20.777 | 1.00 | 24.17 |
| ATOM | 1393 | CG | GLN | 342 | 58.834 | 21.590 | 20.703 | 1.00 | 25.09 |
| ATOM | 1394 | CD | GLN | 342 | 59.476 | 21.677 | 22.057 | 1.00 | 26.93 |
| ATOM | 1395 | OE1 | GLN | 342 | 59.479 | 20.704 | 22.810 | 1.00 | 27.77 |
| ATOM | 1396 | NE2 | GLN | 342 | 60.022 | 22.839 | 22.386 | 1.00 | 24.61 |
| ATOM | 1397 | C | GLN | 342 | 57.354 | 19.715 | 18.806 | 1.00 | 25.69 |
| ATOM | 1398 | O | GLN | 342 | 58.356 | 19.771 | 18.075 | 1.00 | 24.99 |
| ATOM | 1399 | N | GLU | 343 | 56.753 | 18.569 | 19.127 | 1.00 | 25.00 |
| ATOM | 1400 | CA | GLU | 343 | 57.222 | 17.280 | 18.610 | 1.00 | 25.34 |
| ATOM | 1401 | CB | GLU | 343 | 56.411 | 16.118 | 19.245 | 1.00 | 25.90 |
| ATOM | 1402 | C | GLU | 343 | 57.089 | 17.276 | 17.076 | 1.00 | 24.32 |
| ATOM | 1403 | O | GLU | 343 | 58.021 | 16.891 | 16.365 | 1.00 | 23.99 |
| ATOM | 1404 | N | ALA | 344 | 55.961 | 17.789 | 16.587 | 1.00 | 23.56 |
| ATOM | 1405 | CA | ALA | 344 | 55.701 | 17.875 | 15.153 | 1.00 | 22.85 |
| ATOM | 1406 | CB | ALA | 344 | 54.320 | 18.451 | 14.917 | 1.00 | 22.64 |
| ATOM | 1407 | C | ALA | 344 | 56.768 | 18.743 | 14.489 | 1.00 | 22.77 |
| ATOM | 1408 | O | ALA | 344 | 57.355 | 18.360 | 13.477 | 1.00 | 22.08 |
| ATOM | 1409 | N | TYR | 345 | 57.057 | 19.893 | 15.092 | 1.00 | 21.89 |

APPENDIX 6-continued

TR_T3.PBD

| | | | | | | | | |
|---|---|---|---|---|---|---|---|---|
| ATOM | 1410 | CA | TYR | 345 | 58.075 | 20.792 | 14.550 | 1.00 | 21.18 |
| ATOM | 1411 | CB | TYR | 345 | 58.108 | 22.119 | 15.313 | 1.00 | 20.27 |
| ATOM | 1412 | CG | TYR | 345 | 57.048 | 23.078 | 14.856 | 1.00 | 17.45 |
| ATOM | 1413 | CD1 | TYR | 345 | 56.001 | 23.431 | 15.698 | 1.00 | 17.99 |
| ATOM | 1414 | CE1 | TYR | 345 | 54.992 | 24.253 | 15.270 | 1.00 | 19.97 |
| ATOM | 1415 | CD2 | TYR | 345 | 57.063 | 23.589 | 13.562 | 1.00 | 19.11 |
| ATOM | 1416 | CE2 | TYR | 345 | 56.055 | 24.424 | 43.116 | 1.00 | 19.14 |
| ATOM | 1417 | CZ | TYR | 345 | 55.017 | 24.749 | 13.972 | 1.00 | 20.78 |
| ATOM | 1418 | OH | TYR | 345 | 53.983 | 25.539 | 13.530 | 1.00 | 20.70 |
| ATOM | 1419 | C | TYR | 345 | 59.454 | 20.167 | 14.583 | 1.00 | 20.96 |
| ATOM | 1420 | O | TYR | 345 | 60.221 | 20.314 | 13.632 | 1.00 | 22.29 |
| ATOM | 1421 | N | LEU | 346 | 59.778 | 19.480 | 15.677 | 1.00 | 20.82 |
| ATOM | 1422 | CA | LEU | 346 | 61.079 | 18.838 | 15.817 | 1.00 | 20.18 |
| ATOM | 1423 | CB | LEU | 346 | 61.216 | 18.203 | 17.205 | 1.00 | 21.04 |
| ATOM | 1424 | CG | LEU | 346 | 61.606 | 19.158 | 18.335 | 1.00 | 21.25 |
| ATOM | 1425 | CD1 | LEU | 346 | 61.226 | 18.595 | 19.685 | 1.00 | 20.95 |
| ATOM | 1426 | CD2 | LEU | 346 | 63.099 | 19.438 | 18.267 | 1.00 | 19.90 |
| ATOM | 1427 | C | LEU | 346 | 61.317 | 17.806 | 14.716 | 1.00 | 20.19 |
| ATOM | 1428 | O | LEU | 346 | 62.407 | 17.755 | 14.142 | 1.00 | 20.69 |
| ATOM | 1429 | N | LEU | 347 | 60.290 | 17.016 | 14.390 | 1.00 | 22.00 |
| ATOM | 1430 | CA | LEU | 347 | 60.406 | 15.994 | 13.344 | 1.00 | 21.81 |
| ATOM | 1431 | CB | LEU | 347 | 59.199 | 15.051 | 13.366 | 1.00 | 24.03 |
| ATOM | 1432 | CG | LEU | 347 | 59.301 | 13.805 | 14.250 | 1.00 | 26.28 |
| ATOM | 1433 | CD1 | LEU | 347 | 57.964 | 13.072 | 14.277 | 1.00 | 27.79 |
| ATOM | 1434 | CD2 | LEU | 347 | 60.409 | 12.889 | 13.728 | 1.00 | 24.78 |
| ATOM | 1435 | C | LEU | 347 | 60.544 | 16.623 | 11.966 | 1.00 | 20.50 |
| ATOM | 1436 | O | LEU | 347 | 61.351 | 16.179 | 11.143 | 1.00 | 21.39 |
| ATOM | 1437 | N | ALA | 348 | 59.767 | 17.674 | 11.727 | 1.00 | 20.84 |
| ATOM | 1438 | CA | ALA | 348 | 59.788 | 18.381 | 10.456 | 1.00 | 18.12 |
| ATOM | 1439 | CB | ALA | 348 | 58.729 | 19.480 | 10.457 | 1.00 | 18.49 |
| ATOM | 1440 | C | ALA | 348 | 61.168 | 18.963 | 10.269 | 1.00 | 17.53 |
| ATOM | 1441 | O | ALA | 348 | 61.785 | 18.781 | 9.228 | 1.00 | 18.78 |
| ATOM | 1442 | N | PHE | 349 | 61.677 | 19.569 | 11.338 | 1.00 | 19.55 |
| ATOM | 1443 | CA | PHE | 349 | 63.001 | 20.196 | 11.389 | 1.00 | 19.84 |
| ATOM | 1444 | CB | PHE | 349 | 63.188 | 20.823 | 12.786 | 1.00 | 18.68 |
| ATOM | 1445 | CG | PHE | 349 | 64.380 | 21.758 | 12.917 | 1.00 | 19.12 |
| ATOM | 1446 | CD1 | PHE | 349 | 65.234 | 22.008 | 11.851 | 1.00 | 19.95 |
| ATOM | 1447 | CD2 | PHE | 349 | 64.618 | 22.420 | 14.126 | 1.00 | 20.06 |
| ATOM | 1448 | CE1 | PHE | 349 | 66.294 | 22.905 | 11.971 | 1.00 | 18.99 |
| ATOM | 1449 | CE2 | PHE | 349 | 65.674 | 23.317 | 14.261 | 1.00 | 16.79 |
| ATOM | 1450 | CZ | PHE | 349 | 66.516 | 23.562 | 13.184 | 1.00 | 18.91 |
| ATOM | 1451 | C | PHE | 349 | 64.108 | 19.170 | 11.103 | 1.00 | 20.44 |
| ATOM | 1452 | O | PHE | 349 | 64.980 | 19.401 | 10.260 | 1.00 | 19.83 |
| ATOM | 1453 | N | GLU | 350 | 64.064 | 18.032 | 11.794 | 1.00 | 23.59 |
| ATOM | 1454 | CA | GLU | 350 | 65.077 | 16.995 | 11.610 | 1.00 | 23.46 |
| ATOM | 1455 | CB | GLU | 350 | 64.830 | 15.845 | 12.584 | 1.00 | 25.26 |
| ATOM | 1456 | CG | GLU | 350 | 65.694 | 14.644 | 12.288 | 1.00 | 31.98 |
| ATOM | 1457 | CD | GLU | 350 | 65.526 | 13.482 | 13.257 | 1.00 | 35.49 |
| ATOM | 1458 | OE1 | GLU | 350 | 66.560 | 12.853 | 13.555 | 1.00 | 40.26 |
| ATOM | 1459 | OE2 | GLU | 350 | 64.380 | 13.173 | 13.689 | 1.00 | 36.23 |
| ATOM | 1460 | C | GLU | 350 | 65.083 | 16.489 | 10.165 | 1.00 | 21.12 |
| ATOM | 1461 | O | GLU | 350 | 66.133 | 16.384 | 9.526 | 1.00 | 19.81 |
| ATOM | 1462 | N | HIS | 351 | 63.888 | 16.234 | 9.651 | 1.00 | 21.98 |
| ATOM | 1463 | CA | HIS | 351 | 63.694 | 15.751 | 8.292 | 1.00 | 21.31 |
| ATOM | 1464 | CB | HIS | 351 | 62.238 | 15.321 | 8.107 | 1.00 | 21.76 |
| ATOM | 1465 | CG | HIS | 351 | 61.839 | 14.160 | 8.967 | 1.00 | 22.08 |
| ATOM | 1466 | CD2 | HIS | 351 | 62.578 | 13.317 | 9.728 | 1.00 | 22.65 |
| ATOM | 1467 | ND1 | HIS | 351 | 60.532 | 13.751 | 9.115 | 1.00 | 22.37 |
| ATOM | 1468 | CE1 | HIS | 351 | 60.478 | 12.716 | 9.930 | 1.00 | 21.44 |
| ATOM | 1469 | NE2 | HIS | 351 | 61.705 | 12.429 | 10.314 | 1.00 | 20.85 |
| ATOM | 1470 | C | HIS | 351 | 64.117 | 16.815 | 7.275 | 1.00 | 21.18 |
| ATOM | 1471 | O | HIS | 351 | 64.683 | 16.489 | 6.231 | 1.00 | 22.65 |
| ATOM | 1472 | N | TYR | 352 | 63.915 | 18.088 | 7.602 | 1.00 | 19.79 |
| ATOM | 1473 | CA | TYR | 352 | 64.327 | 19.146 | 6.697 | 1.00 | 18.72 |
| ATOM | 1474 | CB | TYR | 352 | 63.768 | 20.502 | 7.122 | 1.00 | 19.55 |
| ATOM | 1475 | CG | TYR | 352 | 64.140 | 21.580 | 6.137 | 1.00 | 19.27 |
| ATOM | 1476 | CD1 | TYR | 352 | 63.556 | 21.623 | 4.867 | 1.00 | 19.29 |
| ATOM | 1477 | CE1 | TYR | 352 | 63.961 | 22.555 | 3.927 | 1.00 | 17.55 |
| ATOM | 1478 | CD2 | TYR | 352 | 65.132 | 22.507 | 6.438 | 1.00 | 18.91 |
| ATOM | 1479 | CE2 | TYR | 352 | 65.545 | 23.443 | 5.503 | 1.00 | 17.30 |
| ATOM | 1480 | CZ | TYR | 352 | 64.954 | 23.459 | 4.256 | 1.00 | 18.41 |
| ATOM | 1481 | OH | TYR | 352 | 65.355 | 24.384 | 3.334 | 1.00 | 19.40 |
| ATOM | 1482 | C | TYR | 352 | 65.849 | 19.182 | 6.687 | 1.00 | 19.31 |
| ATOM | 1483 | O | TYR | 352 | 66.479 | 19.333 | 5.639 | 1.00 | 20.25 |
| ATOM | 1484 | N | VAL | 353 | 66.446 | 19.017 | 7.858 | 1.00 | 21.25 |
| ATOM | 1485 | CA | VAL | 353 | 67.899 | 18.993 | 7.960 | 1.00 | 22.03 |
| ATOM | 1486 | CB | VAL | 353 | 68.348 | 18.880 | 9.450 | 1.00 | 22.60 |

APPENDIX 6-continued

TR_T3.PBD

| ATOM | 1487 | CG1 | VAL | 353 | 69.843 | 18.635 | 9.550 | 1.00 | 20.34 |
|---|---|---|---|---|---|---|---|---|---|
| ATOM | 1488 | CG2 | VAL | 353 | 67.997 | 20.167 | 10.183 | 1.00 | 22.61 |
| ATOM | 1489 | C | VAL | 353 | 68.442 | 17.827 | 7.108 | 1.00 | 22.74 |
| ATOM | 1490 | O | VAL | 353 | 69.448 | 17.985 | 6.398 | 1.00 | 23.44 |
| ATOM | 1491 | N | ASN | 354 | 67.773 | 16.674 | 7.165 | 1.00 | 22.30 |
| ATOM | 1492 | CA | ASN | 354 | 68.185 | 15.508 | 6.373 | 1.00 | 23.56 |
| ATOM | 1493 | CB | ASN | 354 | 67.241 | 14.320 | 6.603 | 1.00 | 22.26 |
| ATOM | 1494 | CG | ASN | 354 | 67.374 | 13.715 | 7.981 | 1.00 | 23.06 |
| ATOM | 1495 | OD1 | ASN | 354 | 68.406 | 13.843 | 8.628 | 1.00 | 25.79 |
| ATOM | 1496 | ND2 | ASN | 354 | 66.327 | 13.044 | 8.435 | 1.00 | 21.07 |
| ATOM | 1497 | C | ASN | 354 | 68.134 | 15.877 | 4.888 | 1.00 | 25.10 |
| ATOM | 1498 | O | ASN | 354 | 69.024 | 15.534 | 4.111 | 1.00 | 26.70 |
| ATOM | 1499 | N | HIS | 355 | 67.067 | 16.568 | 4.503 | 1.00 | 24.50 |
| ATOM | 1500 | CA | HIS | 355 | 66.881 | 16.986 | 3.123 | 1.00 | 24.46 |
| ATOM | 1501 | CB | HIS | 355 | 65.557 | 17.750 | 2.969 | 1.00 | 26.07 |
| ATOM | 1502 | CG | HIS | 355 | 65.365 | 18.337 | 1.604 | 1.00 | 28.28 |
| ATOM | 1503 | CD2 | HIS | 355 | 65.918 | 19.422 | 1.018 | 1.00 | 28.10 |
| ATOM | 1504 | ND1 | HIS | 355 | 64.600 | 17.724 | 0.632 | 1.00 | 26.32 |
| ATOM | 1505 | CE1 | HIS | 355 | 64.706 | 18.407 | −0.499 | 1.00 | 27.71 |
| ATOM | 1506 | NE2 | HIS | 355 | 65.502 | 19.435 | −0.288 | 1.00 | 27.79 |
| ATOM | 1507 | C | HIS | 355 | 68.022 | 17.857 | 2.624 | 1.00 | 24.07 |
| ATOM | 1508 | O | HIS | 355 | 68.460 | 17.729 | 1.484 | 1.00 | 23.54 |
| ATOM | 1509 | N | ARG | 356 | 68.463 | 18.774 | 3.471 | 1.00 | 25.31 |
| ATOM | 1510 | CA | ARG | 356 | 69.523 | 19.714 | 3.130 | 1.00 | 25.69 |
| ATOM | 1511 | CB | ARG | 356 | 69.561 | 20.820 | 4.168 | 1.00 | 24.06 |
| ATOM | 1512 | CG | ARG | 356 | 68.337 | 21.682 | 4.094 | 1.00 | 23.23 |
| ATOM | 1513 | CD | ARG | 356 | 68.670 | 22.973 | 3.424 | 1.00 | 25.91 |
| ATOM | 1514 | NE | ARG | 356 | 69.447 | 23.814 | 4.322 | 1.00 | 24.87 |
| ATOM | 1515 | CZ | ARG | 356 | 70.325 | 24.726 | 3.928 | 1.00 | 25.05 |
| ATOM | 1516 | NH1 | ARG | 356 | 70.546 | 24.920 | 2.640 | 1.00 | 24.97 |
| ATOM | 1517 | NH2 | ARG | 356 | 70.978 | 25.453 | 4.831 | 1.00 | 25.62 |
| ATOM | 1518 | C | ARG | 356 | 70.900 | 19.109 | 2.949 | 1.00 | 27.73 |
| ATOM | 1519 | O | ARG | 356 | 71.724 | 19.645 | 2.208 | 1.00 | 28.38 |
| ATOM | 1520 | N | LYS | 357 | 71.179 | 18.048 | 3.693 | 1.00 | 29.45 |
| ATOM | 1521 | CA | LYS | 357 | 72.457 | 17.355 | 3.588 | 1.00 | 31.35 |
| ATOM | 1522 | CB | LYS | 357 | 72.503 | 16.566 | 2.270 | 1.00 | 32.80 |
| ATOM | 1523 | CG | LYS | 357 | 71.290 | 15.650 | 2.103 | 1.00 | 35.78 |
| ATOM | 1524 | CD | LYS | 357 | 71.264 | 14.927 | 0.778 | 1.00 | 39.43 |
| ATOM | 1525 | CE | LYS | 357 | 70.121 | 13.918 | 0.739 | 1.00 | 42.93 |
| ATOM | 1526 | NZ | LYS | 357 | 70.162 | 13.074 | −0.498 | 1.00 | 45.97 |
| ATOM | 1527 | C | LYS | 357 | 73.692 | 18.247 | 3.743 | 1.00 | 31.34 |
| ATOM | 1528 | O | LYS | 357 | 74.489 | 18.390 | 2.818 | 1.00 | 32.65 |
| ATOM | 1529 | N | HIS | 358 | 73.837 | 18.861 | 4.913 | 1.00 | 30.72 |
| ATOM | 1530 | CA | HIS | 358 | 74.995 | 19.706 | 5.186 | 1.00 | 31.49 |
| ATOM | 1531 | CB | HIS | 358 | 74.895 | 20.322 | 6.579 | 1.00 | 29.13 |
| ATOM | 1532 | CG | HIS | 358 | 73.882 | 21.415 | 6.688 | 1.00 | 25.30 |
| ATOM | 1533 | CD2 | HIS | 358 | 74.026 | 22.760 | 6.646 | 1.00 | 24.90 |
| ATOM | 1534 | ND1 | HIS | 358 | 72.543 | 21.175 | 6.892 | 1.00 | 24.54 |
| ATOM | 1535 | CE1 | HIS | 358 | 71.901 | 22.324 | 6.975 | 1.00 | 23.68 |
| ATOM | 1536 | NE2 | HIS | 358 | 72.777 | 23.302 | 6.830 | 1.00 | 25.28 |
| ATOM | 1537 | C | HIS | 358 | 76.235 | 18.831 | 5.161 | 1.00 | 33.38 |
| ATOM | 1538 | O | HIS | 358 | 76.166 | 17.647 | 5.495 | 1.00 | 35.46 |
| ATOM | 1539 | N | ASN | 359 | 77.366 | 19.399 | 4.768 | 1.00 | 35.34 |
| ATOM | 1540 | CA | ASN | 359 | 78.606 | 18.636 | 4.746 | 1.00 | 38.17 |
| ATOM | 1541 | CB | ASN | 359 | 79.544 | 19.150 | 3.646 | 1.00 | 37.84 |
| ATOM | 1542 | C | ASN | 359 | 79.236 | 18.825 | 6.120 | 1.00 | 39.85 |
| ATOM | 1543 | O | ASN | 359 | 80.317 | 19.406 | 6.240 | 1.00 | 42.72 |
| ATOM | 1544 | N | ILE | 360 | 78.510 | 18.411 | 7.159 | 1.00 | 39.01 |
| ATOM | 1545 | CA | ILE | 360 | 78.968 | 18.526 | 8.549 | 1.00 | 36.72 |
| ATOM | 1546 | CB | ILE | 360 | 78.351 | 19.752 | 9.264 | 1.00 | 37.69 |
| ATOM | 1547 | CG2 | ILE | 360 | 78.802 | 19.793 | 10.722 | 1.00 | 37.56 |
| ATOM | 1548 | CG1 | ILE | 360 | 78.735 | 21.049 | 8.549 | 1.00 | 37.68 |
| ATOM | 1549 | CD1 | ILE | 360 | 77.970 | 22.253 | 9.041 | 1.00 | 38.40 |
| ATOM | 1550 | C | ILE | 360 | 78.524 | 17.278 | 9.303 | 1.00 | 35.15 |
| ATOM | 1551 | O | ILE | 360 | 77.343 | 16.931 | 9.314 | 1.00 | 33.75 |
| ATOM | 1552 | N | PRO | 361 | 79.475 | 16.564 | 9.912 | 1.00 | 34.64 |
| ATOM | 1553 | CD | PRO | 361 | 80.930 | 16.785 | 9.873 | 1.00 | 35.59 |
| ATOM | 1554 | CA | PRO | 361 | 79.138 | 15.349 | 10.660 | 1.00 | 33.92 |
| ATOM | 1555 | CB | PRO | 361 | 80.513 | 14.768 | 11.014 | 1.00 | 35.27 |
| ATOM | 1556 | CG | PRO | 361 | 81.412 | 15.972 | 11.048 | 1.00 | 35.97 |
| ATOM | 1557 | C | PRO | 364 | 78.292 | 15.618 | 11.909 | 1.00 | 30.95 |
| ATOM | 1558 | O | PRO | 361 | 78.555 | 16.554 | 12.653 | 1.00 | 31.50 |
| ATOM | 1559 | N | HIS | 362 | 77.269 | 14.793 | 12.112 | 1.00 | 28.75 |
| ATOM | 1560 | CA | HIS | 362 | 76.378 | 14.900 | 13.263 | 1.00 | 30.25 |
| ATOM | 1561 | CB | HIS | 362 | 77.152 | 14.612 | 14.548 | 1.00 | 31.20 |
| ATOM | 1562 | CG | HIS | 362 | 78.075 | 13.441 | 14.440 | 1.00 | 33.72 |
| ATOM | 1563 | CD2 | HIS | 362 | 77.826 | 12.122 | 14.275 | 1.00 | 34.55 |

APPENDIX 6-continued

| | | | | TR_T3.PBD | | | | |
|---|---|---|---|---|---|---|---|---|
| ATOM | 1564 | ND1 | HIS | 362 | 79.449 | 13.569 | 14.469 | 1.00 | 35.55 |
| ATOM | 1565 | CE1 | HIS | 362 | 80.006 | 12.377 | 14.322 | 1.00 | 35.28 |
| ATOM | 1566 | NE2 | HIS | 362 | 79.040 | 11.484 | 14.204 | 1.00 | 37.61 |
| ATOM | 1567 | C | HIS | 362 | 75.742 | 16.275 | 13.368 | 1.00 | 29.44 |
| ATOM | 1568 | O | HIS | 362 | 75.521 | 16.769 | 14.472 | 1.00 | 29.93 |
| ATOM | 1569 | N | PHE | 363 | 75.397 | 16.856 | 12.222 | 1.00 | 29.22 |
| ATOM | 1570 | CA | PHE | 363 | 74.803 | 18.188 | 12.160 | 1.00 | 27.72 |
| ATOM | 1571 | CB | PHE | 363 | 74.446 | 18.538 | 10.709 | 1.00 | 26.85 |
| ATOM | 1572 | CG | PHE | 363 | 73.901 | 19.931 | 10.532 | 1.00 | 27.48 |
| ATOM | 1573 | CD1 | PHE | 363 | 74.758 | 21.017 | 10.391 | 1.00 | 27.76 |
| ATOM | 1574 | CD2 | PHE | 363 | 72.523 | 20.157 | 10.513 | 1.00 | 27.45 |
| ATOM | 1575 | CE1 | PHE | 363 | 74.244 | 22.313 | 10.234 | 1.00 | 28.56 |
| ATOM | 1576 | CE2 | PHE | 363 | 72.001 | 21.446 | 10.357 | 1.00 | 25.15 |
| ATOM | 1577 | CZ | PHE | 363 | 72.860 | 22.521 | 10.219 | 1.00 | 24.41 |
| ATOM | 1578 | C | PHE | 363 | 73.597 | 18.385 | 13.075 | 1.00 | 27.45 |
| ATOM | 1579 | O | PHE | 363 | 73.577 | 19.324 | 13.880 | 1.00 | 27.73 |
| ATOM | 1580 | N | TRP | 364 | 72.616 | 17.489 | 12.983 | 1.00 | 25.89 |
| ATOM | 1581 | CA | TRP | 364 | 71.401 | 17.592 | 13.800 | 1.00 | 25.85 |
| ATOM | 1582 | CB | TRP | 364 | 70.444 | 16.426 | 13.506 | 1.00 | 24.27 |
| ATOM | 1583 | CG | TRP | 364 | 69.168 | 16.391 | 14.328 | 1.00 | 23.75 |
| ATOM | 1584 | CD2 | TRP | 364 | 68.152 | 17.407 | 14.397 | 1.00 | 24.87 |
| ATOM | 1585 | CE2 | TRP | 364 | 67.140 | 16.922 | 15.261 | 1.00 | 24.81 |
| ATOM | 1586 | CE3 | TRP | 364 | 67.989 | 18.674 | 13.820 | 1.00 | 25.47 |
| ATOM | 1587 | CD1 | TRP | 364 | 68.745 | 15.370 | 15.122 | 1.00 | 22.98 |
| ATOM | 1588 | NE1 | TRP | 364 | 67.530 | 15.679 | 15.684 | 1.00 | 25.99 |
| ATOM | 1589 | CZ2 | TRP | 364 | 65.987 | 17.661 | 15.560 | 1.00 | 25.14 |
| ATOM | 1590 | CZ3 | TRP | 364 | 66.844 | 19.405 | 14.116 | 1.00 | 25.29 |
| ATOM | 1591 | CH2 | TRP | 364 | 65.857 | 18.894 | 14.982 | 1.00 | 24.53 |
| ATOM | 1592 | C | TRP | 364 | 71.659 | 17.747 | 15.308 | 1.00 | 26.94 |
| ATOM | 1593 | O | TRP | 364 | 71.202 | 18.721 | 15.904 | 1.00 | 27.16 |
| ATOM | 1594 | N | PRO | 365 | 72.382 | 16.796 | 15.944 | 1.00 | 27.60 |
| ATOM | 1595 | CD | PRO | 365 | 72.912 | 15.522 | 15.411 | 1.00 | 27.55 |
| ATOM | 1596 | CA | PRO | 365 | 72.655 | 16.915 | 17.387 | 1.00 | 25.90 |
| ATOM | 1597 | CB | PRO | 365 | 73.565 | 15.717 | 17.668 | 1.00 | 26.00 |
| ATOM | 1598 | CG | PRO | 365 | 73.136 | 14.705 | 16.658 | 1.00 | 28.32 |
| ATOM | 1599 | C | PRO | 365 | 73.374 | 18.225 | 17.714 | 1.00 | 23.89 |
| ATOM | 1600 | O | PRO | 365 | 73.088 | 18.861 | 18.725 | 1.00 | 23.81 |
| ATOM | 1601 | N | LYS | 366 | 74.297 | 18.626 | 16.845 | 1.00 | 24.24 |
| ATOM | 1602 | CA | LYS | 366 | 75.058 | 19.862 | 17.027 | 1.00 | 26.24 |
| ATOM | 1603 | CB | LYS | 366 | 76.144 | 19.982 | 15.963 | 1.00 | 27.44 |
| ATOM | 1604 | CG | LYS | 366 | 77.310 | 19.022 | 16.138 | 1.00 | 28.76 |
| ATOM | 1605 | CD | LYS | 366 | 78.254 | 19.171 | 14.975 | 1.00 | 30.53 |
| ATOM | 1606 | CE | LYS | 366 | 79.527 | 18.387 | 15.167 | 1.00 | 34.25 |
| ATOM | 1607 | NZ | LYS | 366 | 80.388 | 18.463 | 13.947 | 1.00 | 37.89 |
| ATOM | 1608 | C | LYS | 366 | 74.181 | 21.107 | 16.993 | 1.00 | 26.73 |
| ATOM | 1609 | O | LYS | 366 | 74.385 | 22.042 | 17.762 | 1.00 | 27.36 |
| ATOM | 1610 | N | LEU | 367 | 73.216 | 21.124 | 16.086 | 1.00 | 27.98 |
| ATOM | 1611 | CA | LEU | 367 | 72.308 | 22.256 | 15.967 | 1.00 | 27.87 |
| ATOM | 1612 | CW | LEU | 367 | 71.559 | 22.192 | 14.632 | 1.00 | 27.29 |
| ATOM | 1613 | CG | LEU | 367 | 70.613 | 23.356 | 14.318 | 1.00 | 27.25 |
| ATOM | 1614 | CD1 | LEU | 367 | 71.334 | 24.707 | 14.510 | 1.00 | 22.90 |
| ATOM | 1615 | CD2 | LEU | 367 | 70.081 | 23.189 | 12.896 | 1.00 | 24.54 |
| ATOM | 1616 | C | LEU | 367 | 71.327 | 22.223 | 17.134 | 1.00 | 29.38 |
| ATOM | 1617 | O | LEU | 367 | 70.993 | 23.249 | 17.716 | 1.00 | 31.09 |
| ATOM | 1618 | N | LEU | 368 | 70.889 | 21.026 | 17.491 | 1.00 | 30.38 |
| ATOM | 1619 | CA | LEU | 368 | 69.962 | 20.843 | 18.594 | 1.00 | 31.14 |
| ATOM | 1620 | CB | LEU | 368 | 69.659 | 19.353 | 18.731 | 1.00 | 32.20 |
| ATOM | 1621 | CG | LEU | 368 | 68.247 | 18.852 | 19.014 | 1.00 | 33.52 |
| ATOM | 1622 | CD1 | LEU | 368 | 67.184 | 19.651 | 18.267 | 1.00 | 31.14 |
| ATOM | 1623 | CD2 | LEU | 368 | 68.210 | 17.379 | 18.632 | 1.00 | 33.99 |
| ATOM | 1624 | C | LEU | 368 | 70.601 | 21.395 | 19.876 | 1.00 | 32.36 |
| ATOM | 1625 | O | LEU | 368 | 69.917 | 21.963 | 20.730 | 1.00 | 32.58 |
| ATOM | 1626 | N | MET | 369 | 71.922 | 21.272 | 19.985 | 1.00 | 33.30 |
| ATOM | 1627 | CA | MET | 369 | 72.641 | 21.771 | 21.149 | 1.00 | 34.04 |
| ATOM | 1628 | CB | MET | 369 | 74.051 | 21.190 | 21.209 | 1.00 | 35.31 |
| ATOM | 1629 | CG | MET | 369 | 74.108 | 19.858 | 21.935 | 1.00 | 36.83 |
| ATOM | 1630 | SD | MET | 369 | 75.312 | 18.728 | 21.235 | 1.00 | 43.07 |
| ATOM | 1631 | CE | MET | 369 | 76.862 | 19.636 | 21.472 | 1.00 | 41.31 |
| ATOM | 1632 | C | MET | 369 | 72.675 | 23.297 | 21.212 | 1.00 | 34.30 |
| ATOM | 1633 | O | MET | 369 | 72.961 | 23.876 | 22.269 | 1.00 | 35.82 |
| ATOM | 1634 | N | LYS | 370 | 72.368 | 23.949 | 20.091 | 1.00 | 32.14 |
| ATOM | 1635 | CA | LYS | 370 | 72.325 | 25.405 | 20.044 | 1.00 | 29.17 |
| ATOM | 1636 | CB | LYS | 370 | 72.394 | 25.904 | 18.608 | 1.00 | 28.18 |
| ATOM | 1637 | CG | LYS | 370 | 73.662 | 25.518 | 17.900 | 1.00 | 27.72 |
| ATOM | 1638 | CD | LYS | 370 | 74.866 | 25.969 | 18.679 | 1.00 | 28.10 |
| ATOM | 1639 | CE | LYS | 370 | 76.127 | 25.650 | 17.930 | 1.00 | 27.79 |
| ATOM | 1640 | NZ | LYS | 370 | 77.298 | 25.941 | 18.777 | 1.00 | 30.78 |

APPENDIX 6-continued

| | | | TR_T3.PBD | | | | | |
|---|---|---|---|---|---|---|---|---|
| ATOM | 1641 | C | LYS | 370 | 71.033 | 25.875 | 20.705 | 1.00 | 29.27 |
| ATOM | 1642 | O | LYS | 370 | 70.950 | 26.999 | 21.200 | 1.00 | 29.43 |
| ATOM | 1643 | N | VAL | 371 | 70.018 | 25.014 | 20.714 | 1.00 | 29.40 |
| ATOM | 1644 | CA | VAL | 371 | 68.756 | 25.358 | 21.358 | 1.00 | 29.90 |
| ATOM | 1645 | CB | VAL | 371 | 67.687 | 24.237 | 21.218 | 1.00 | 28.75 |
| ATOM | 1646 | CG1 | VAL | 371 | 66.463 | 24.561 | 22.064 | 1.00 | 27.12 |
| ATOM | 1647 | CG2 | VAL | 371 | 67.275 | 24.080 | 19.762 | 1.00 | 29.23 |
| ATOM | 1648 | C | VAL | 371 | 69.075 | 25.573 | 22.832 | 1.00 | 31.39 |
| ATOM | 1649 | O | VAL | 371 | 68.543 | 26.481 | 23.462 | 1.00 | 31.20 |
| ATOM | 1650 | N | THR | 372 | 69.971 | 24.743 | 23.366 | 1.00 | 31.39 |
| ATOM | 1651 | CA | THR | 372 | 70.371 | 24.847 | 24.762 | 1.00 | 31.10 |
| ATOM | 1652 | CB | THR | 372 | 71.282 | 23.664 | 25.170 | 1.00 | 31.59 |
| ATOM | 1653 | OG1 | THR | 372 | 70.554 | 22.441 | 25.008 | 1.00 | 30.60 |
| ATOM | 1654 | CG2 | THR | 372 | 71.720 | 23.795 | 26.625 | 1.00 | 30.14 |
| ATOM | 1655 | C | THR | 372 | 71.071 | 26.186 | 24.994 | 1.00 | 30.76 |
| ATOM | 1656 | O | THR | 372 | 70.711 | 26.935 | 25.910 | 1.00 | 31.45 |
| ATOM | 1657 | N | ASP | 373 | 72.038 | 26.507 | 24.138 | 1.00 | 29.31 |
| ATOM | 1658 | CA | ASP | 373 | 72.744 | 27.772 | 24.252 | 1.00 | 27.32 |
| ATOM | 1659 | CB | ASP | 373 | 73.745 | 27.934 | 23.115 | 1.00 | 27.98 |
| ATOM | 1660 | CG | ASP | 373 | 74.886 | 26.933 | 23.190 | 1.00 | 28.94 |
| ATOM | 1661 | OD1 | ASP | 373 | 75.043 | 26.259 | 24.225 | 1.00 | 31.01 |
| ATOM | 1662 | OD2 | ASP | 373 | 75.639 | 26.825 | 22.205 | 1.00 | 31.38 |
| ATOM | 1663 | C | ASP | 373 | 71.742 | 28.926 | 24.247 | 1.00 | 26.50 |
| ATOM | 1664 | O | ASP | 373 | 71.872 | 29.861 | 25.040 | 1.00 | 27.35 |
| ATOM | 1665 | N | LEU | 374 | 70.711 | 28.826 | 23.412 | 1.00 | 24.17 |
| ATOM | 1666 | CA | LEU | 374 | 69.688 | 29.864 | 23.331 | 1.00 | 23.38 |
| ATOM | 1667 | CB | LEU | 374 | 68.795 | 29.660 | 22.107 | 1.00 | 22.98 |
| ATOM | 1668 | CG | LEU | 374 | 69.361 | 30.183 | 20.786 | 1.00 | 24.45 |
| ATOM | 1669 | CD1 | LEU | 374 | 68.668 | 29.520 | 19.589 | 1.00 | 24.72 |
| ATOM | 1670 | CD2 | LEU | 374 | 69.223 | 31.704 | 20.735 | 1.00 | 22.40 |
| ATOM | 1671 | C | LEU | 374 | 68.839 | 29.964 | 24.589 | 1.00 | 24.31 |
| ATOM | 1672 | O | LEU | 374 | 68.442 | 31.065 | 24.986 | 1.00 | 23.31 |
| ATOM | 1673 | N | ARG | 375 | 68.543 | 28.826 | 25.211 | 1.00 | 25.32 |
| ATOM | 1674 | CA | ARG | 375 | 67.748 | 28.821 | 26.438 | 1.00 | 27.76 |
| ATOM | 1675 | CB | ARG | 375 | 67.455 | 27.392 | 26.908 | 1.00 | 30.82 |
| ATOM | 1676 | CG | ARG | 375 | 66.901 | 26.439 | 25.854 | 1.00 | 38.79 |
| ATOM | 1677 | CD | ARG | 375 | 65.424 | 26.630 | 25.582 | 1.00 | 45.40 |
| ATOM | 1678 | NE | ARG | 375 | 64.709 | 25.360 | 25.620 | 1.00 | 52.61 |
| ATOM | 1679 | CZ | ARG | 375 | 63.800 | 24.967 | 24.726 | 1.00 | 56.89 |
| ATOM | 1680 | NH1 | ARG | 375 | 63.473 | 25.732 | 23.694 | 1.00 | 58.27 |
| ATOM | 1681 | NH2 | ARG | 375 | 63.201 | 23.793 | 24.855 | 1.00 | 58.46 |
| ATOM | 1682 | C | ARG | 375 | 68.563 | 29.542 | 27.512 | 1.00 | 26.98 |
| ATOM | 1683 | O | ARG | 375 | 68.025 | 30.336 | 28.282 | 1.00 | 26.18 |
| ATOM | 1684 | N | MET | 376 | 69.862 | 29.255 | 27.551 | 1.00 | 26.80 |
| ATOM | 1685 | CA | MET | 376 | 70.767 | 29.867 | 28.511 | 1.00 | 29.22 |
| ATOM | 1686 | CB | MET | 376 | 72.172 | 29.270 | 28.379 | 1.00 | 33.70 |
| ATOM | 1687 | CG | MET | 376 | 72.595 | 28.371 | 29.562 | 1.00 | 43.20 |
| ATOM | 1688 | SD | MET | 376 | 73.320 | 29.260 | 31.011 | 1.00 | 52.38 |
| ATOM | 1689 | CE | MET | 376 | 71.843 | 29.854 | 31.913 | 1.00 | 48.11 |
| ATOM | 1690 | C | MET | 376 | 70.804 | 31.384 | 28.339 | 1.00 | 27.54 |
| ATOM | 1691 | O | MET | 376 | 70.792 | 32.126 | 29.323 | 1.00 | 26.96 |
| ATOM | 1692 | N | ILE | 377 | 70.841 | 31.835 | 27.087 | 1.00 | 25.39 |
| ATOM | 1693 | CA | ILE | 377 | 70.847 | 33.264 | 26.767 | 1.00 | 23.26 |
| ATOM | 1694 | CB | ILE | 377 | 70.992 | 33.488 | 25.222 | 1.00 | 22.73 |
| ATOM | 1695 | CG2 | ILE | 377 | 70.560 | 34.909 | 24.819 | 1.00 | 21.81 |
| ATOM | 1696 | CG1 | ILE | 377 | 72.431 | 33.205 | 24.789 | 1.00 | 20.39 |
| ATOM | 1697 | CD1 | ILE | 377 | 72.644 | 33.148 | 23.300 | 1.00 | 18.85 |
| ATOM | 1698 | C | ILE | 377 | 69.558 | 33.900 | 27.309 | 1.00 | 22.91 |
| ATOM | 1699 | O | ILE | 377 | 69.597 | 34.925 | 27.989 | 1.00 | 22.02 |
| ATOM | 1700 | N | GLY | 378 | 68.427 | 33.244 | 27.069 | 1.00 | 22.29 |
| ATOM | 1701 | CA | GLY | 378 | 67.161 | 33.757 | 27.547 | 1.00 | 22.83 |
| ATOM | 1702 | C | GLY | 378 | 67.111 | 33.815 | 29.063 | 1.00 | 25.60 |
| ATOM | 1703 | O | GLY | 378 | 66.546 | 34.752 | 29.630 | 1.00 | 26.25 |
| ATOM | 1704 | N | ALA | 379 | 67.691 | 32.804 | 29.713 | 1.00 | 26.88 |
| ATOM | 1705 | CA | ALA | 379 | 67.744 | 32.707 | 31.175 | 1.00 | 27.19 |
| ATOM | 1706 | CB | ALA | 379 | 68.322 | 31.358 | 31.590 | 1.00 | 26.97 |
| ATOM | 1707 | C | ALA | 379 | 68.606 | 33.827 | 31.738 | 1.00 | 26.13 |
| ATOM | 1708 | O | ALA | 379 | 68.174 | 34.580 | 32.601 | 1.00 | 26.46 |
| ATOM | 1709 | N | CYA | 380 | 69.826 | 33.935 | 31.230 | 1.00 | 27.61 |
| ATOM | 1710 | CA | CYA | 380 | 70.742 | 34.973 | 31.667 | 1.00 | 29.74 |
| ATOM | 1711 | CB | CYA | 380 | 72.070 | 34.865 | 30.923 | 1.00 | 35.44 |
| ATOM | 1712 | SG | CYA | 380 | 73.081 | 33.458 | 31.417 | 1.00 | 42.61 |
| ATOM | 1713 | AS | CYA | 380 | 74.829 | 33.691 | 29.945 | 1.00 | 55.91 |
| ATOM | 1714 | C | CYA | 380 | 70.142 | 36.349 | 31.446 | 1.00 | 29.07 |
| ATOM | 1715 | O | CYA | 380 | 70.243 | 37.225 | 32.303 | 1.00 | 29.46 |
| ATOM | 1716 | N | HIS | 381 | 69.494 | 36.538 | 30.304 | 1.00 | 28.29 |
| ATOM | 1717 | CA | HIS | 381 | 68.885 | 37.824 | 30.002 | 1.00 | 26.84 |

APPENDIX 6-continued

TR_T3.PBD

| | | | | | | | | | |
|---|---|---|---|---|---|---|---|---|---|
| ATOM | 1718 | CB | HIS | 381 | 68.384 | 37.880 | 28.557 | 1.00 | 23.13 |
| ATOM | 1719 | CG | HIS | 38.1 | 67.597 | 39.113 | 28.259 | 1.00 | 19.84 |
| ATOM | 1720 | CD2 | HIS | 381 | 67.993 | 40.365 | 27.931 | 1.00 | 18.68 |
| ATOM | 1721 | ND1 | HIS | 381 | 66.229 | 39.169 | 28.403 | 1.00 | 19.47 |
| ATOM | 1722 | CE1 | HIS | 381 | 65.817 | 40.407 | 28.190 | 1.00 | 18.64 |
| ATOM | 1723 | NE2 | HIS | 381 | 66.868 | 41.149 | 27.900 | 1.00 | 18.29 |
| ATOM | 1724 | C | HIS | 381 | 67.747 | 38.157 | 30.967 | 1.00 | 26.78 |
| ATOM | 1725 | O | HIS | 381 | 67.560 | 39.314 | 31.337 | 1.00 | 26.39 |
| ATOM | 1726 | N | ALA | 382 | 66.964 | 37.158 | 31.347 | 1.00 | 27.78 |
| ATOM | 1727 | CA | ALA | 382 | 65.867 | 37.395 | 32.269 | 1.00 | 29.45 |
| ATOM | 1728 | CB | ALA | 382 | 65.077 | 36.125 | 32.471 | 1.00 | 29.51 |
| ATOM | 1729 | C | ALA | 382 | 66.425 | 37.904 | 33.604 | 1.00 | 31.74 |
| ATOM | 1730 | O | ALA | 382 | 65.932 | 38.882 | 34.159 | 1.00 | 32.60 |
| ATOM | 1731 | N | SER | 383 | 67.483 | 37.262 | 34.093 | 1.00 | 33.02 |
| ATOM | 1732 | CA | SER | 383 | 68.109 | 37.662 | 35.350 | 1.00 | 34.69 |
| ATOM | 1733 | CB | SER | 383 | 69.212 | 36.677 | 35.733 | 1.00 | 36.18 |
| ATOM | 1734 | OG | SER | 383 | 68.663 | 35.386 | 35.933 | 1.00 | 40.61 |
| ATOM | 1735 | C | SER | 383 | 68.689 | 39.064 | 35.242 | 1.00 | 33.49 |
| ATOM | 1736 | O | SER | 383 | 68.526 | 39.889 | 36.146 | 1.00 | 34.28 |
| ATOM | 1737 | N | ARG | 384 | 69.377 | 39.332 | 34.141 | 1.00 | 32.60 |
| ATOM | 1738 | CA | ARG | 384 | 69.955 | 40.642 | 33.938 | 1.00 | 32.60 |
| ATOM | 1739 | CB | ARG | 384 | 70.926 | 40.638 | 32.762 | 1.00 | 33.60 |
| ATOM | 1740 | CG | ARG | 384 | 71.429 | 42.013 | 32.409 | 1.00 | 36.33 |
| ATOM | 1741 | CD | ARG | 384 | 72.875 | 41.975 | 31.993 | 1.00 | 39.62 |
| ATOM | 1742 | NE | ARG | 384 | 73.760 | 42.260 | 33.114 | 1.00 | 41.76 |
| ATOM | 1743 | CZ | ARG | 384 | 74.587 | 43.301 | 33.179 | 1.00 | 41.92 |
| ATOM | 1744 | NH1 | ARG | 384 | 74.670 | 44.182 | 32.191 | 1.00 | 40.66 |
| ATOM | 1745 | NH2 | ARG | 384 | 75.319 | 43.471 | 34.260 | 1.00 | 44.88 |
| ATOM | 1746 | C | ARG | 384 | 68.862 | 41.694 | 33.758 | 1.00 | 32.28 |
| ATOM | 1747 | O | ARG | 384 | 69.014 | 42.831 | 34.213 | 1.00 | 33.27 |
| ATOM | 1748 | N | PHE | 385 | 67.739 | 41.311 | 33.159 | 1.00 | 29.13 |
| ATOM | 1749 | CA | PHE | 385 | 66.663 | 42.259 | 32.977 | 1.00 | 27.55 |
| ATOM | 1750 | CB | PHE | 385 | 65.552 | 41.687 | 32.105 | 1.00 | 26.89 |
| ATOM | 1751 | CG | PHE | 385 | 64.415 | 42.641 | 31.888 | 1.00 | 25.11 |
| ATOM | 1752 | CD1 | PHE | 385 | 64.495 | 43.630 | 30.918 | 1.00 | 24.94 |
| ATOM | 1753 | CD2 | PHE | 385 | 63.281 | 42.580 | 32.689 | 1.00 | 25.01 |
| ATOM | 1754 | CE1 | PHE | 385 | 63.466 | 44.547 | 30.753 | 1.00 | 25.50 |
| ATOM | 1755 | CE2 | PHE | 385 | 62.244 | 43.495 | 32.531 | 1.00 | 24.06 |
| ATOM | 1756 | CZ | PHE | 385 | 62.338 | 44.482 | 31.563 | 1.00 | 25.44 |
| ATOM | 1757 | C | PHE | 385 | 66.125 | 42.641 | 34.348 | 1.00 | 29.08 |
| ATOM | 1758 | O | PHE | 385 | 65.887 | 43.816 | 34.613 | 1.00 | 27.90 |
| ATOM | 1759 | N | LEU | 386 | 65.972 | 41.658 | 35.231 | 1.00 | 31.19 |
| ATOM | 1760 | CA | LEU | 386 | 65.465 | 41.929 | 36.577 | 1.00 | 33.22 |
| ATOM | 1761 | CB | LEU | 386 | 65.355 | 40.640 | 37.397 | 1.00 | 34.35 |
| ATOM | 1762 | C | LEU | 386 | 66.362 | 42.940 | 37.279 | 1.00 | 33.52 |
| ATOM | 1763 | O | LEU | 386 | 65.874 | 43.907 | 37.855 | 1.00 | 32.93 |
| ATOM | 1764 | N | HIS | 387 | 67.673 | 42.760 | 37.158 | 1.00 | 34.80 |
| ATOM | 1765 | CA | HIS | 387 | 68.628 | 43.674 | 37.775 | 1.00 | 37.88 |
| ATOM | 1766 | CB | HIS | 387 | 70.042 | 43.112 | 37.705 | 1.00 | 36.66 |
| ATOM | 1767 | CG | HIS | 387 | 70.206 | 41.832 | 38.456 | 1.00 | 39.14 |
| ATOM | 1768 | CD2 | HIS | 387 | 69.307 | 41.080 | 39.144 | 1.00 | 39.28 |
| ATOM | 1769 | ND1 | HIS | 387 | 71.408 | 41.161 | 38.543 | 1.00 | 40.97 |
| ATOM | 1770 | CE1 | HIS | 387 | 71.241 | 40.055 | 39.245 | 1.00 | 41.57 |
| ATOM | 1771 | NE2 | HIS | 387 | 69.980 | 39.984 | 39.618 | 1.00 | 41.45 |
| ATOM | 1772 | C | HIS | 387 | 68.589 | 45.071 | 37.164 | 1.00 | 40.38 |
| ATOM | 1773 | O | HIS | 387 | 68.673 | 46.054 | 37.888 | 1.00 | 40.87 |
| ATOM | 1774 | N | MET | 388 | 68.466 | 45.161 | 35.842 | 1.00 | 43.32 |
| ATOM | 1775 | CA | MET | 388 | 68.398 | 46.455 | 35.168 | 1.00 | 46.28 |
| ATOM | 1776 | CB | MET | 388 | 68.170 | 46.286 | 33.665 | 1.00 | 43.30 |
| ATOM | 1777 | CG | MET | 388 | 69.342 | 45.738 | 32.875 | 1.00 | 43.55 |
| ATOM | 1778 | SD | MET | 388 | 69.034 | 45.896 | 31.098 | 1.00 | 46.27 |
| ATOM | 1779 | CE | MET | 388 | 68.208 | 44.370 | 30.709 | 1.00 | 42.36 |
| ATOM | 1780 | C | MET | 388 | 67.256 | 47.289 | 35.737 | 1.00 | 50.25 |
| ATOM | 1781 | O | MET | 388 | 67.363 | 48.506 | 35.886 | 1.00 | 49.79 |
| ATOM | 1782 | N | LYS | 389 | 66.163 | 46.610 | 36.075 | 1.00 | 52.74 | ALTA |
| ATOM | 1783 | CA | LYS | 389 | 64.983 | 47.274 | 36.633 | 1.00 | 56.15 | ALTA |
| ATOM | 1784 | CB | LYS | 389 | 63.770 | 46.334 | 36.565 | 1.00 | 56.87 | ALTA |
| ATOM | 1785 | CG | LYS | 389 | 63.227 | 46.087 | 35.161 | 1.00 | 57.76 | ALTA |
| ATOM | 1786 | CD | LYS | 389 | 62.029 | 45.156 | 35.212 | 1.00 | 55.98 | ALTA |
| ATOM | 1787 | CE | LYS | 389 | 62.426 | 43.796 | 35.778 | 1.00 | 55.48 | ALTA |
| ATOM | 1788 | NZ | LYS | 389 | 61.267 | 43.040 | 36.311 | 1.00 | 55.55 | ALTA |
| ATOM | 1789 | C | LYS | 389 | 65.177 | 47.767 | 38.064 | 1.00 | 56.69 | ALTA |
| ATOM | 1790 | O | LYS | 389 | 64.623 | 48.814 | 38.453 | 1.00 | 58.54 | ALTA |
| ATOM | 1791 | N | VAL | 390 | 65.955 | 47.038 | 38.839 | 1.00 | 55.21 | |
| ATOM | 1792 | CA | VAL | 390 | 66.225 | 47.386 | 40.236 | 1.00 | 51.78 | |
| ATOM | 1793 | CB | VAL | 390 | 66.999 | 46.231 | 40.985 | 1.00 | 50.07 | |
| ATOM | 1794 | CG1 | VAL | 390 | 67.648 | 46.726 | 42.263 | 1.00 | 49.74 | |

APPENDIX 6-continued

TR_T3.PBD

| ATOM | 1795 | CG2 | VAL | 390 | 66.037 | 45.093 | 41.317 | 1.00 | 49.06 |
|------|------|-----|-----|-----|--------|--------|--------|------|-------|
| ATOM | 1796 | C   | VAL | 390 | 67.053 | 48.681 | 40.227 | 1.00 | 49.38 |
| ATOM | 1797 | O   | VAL | 390 | 66.785 | 49.605 | 40.992 | 1.00 | 48.71 |
| ATOM | 1798 | N   | GLU | 391 | 67.974 | 48.778 | 39.272 | 1.00 | 46.71 |
| ATOM | 1799 | CA  | GLU | 391 | 68.866 | 49.919 | 39.142 | 1.00 | 44.88 |
| ATOM | 1800 | CB  | GLU | 391 | 70.156 | 49.488 | 38.438 | 1.00 | 45.24 |
| ATOM | 1801 | CG  | GLU | 391 | 70.793 | 48.207 | 38.997 | 1.00 | 47.65 |
| ATOM | 1802 | CD  | GLU | 391 | 71.461 | 48.388 | 40.358 | 1.00 | 50.29 |
| ATOM | 1803 | OE1 | GLU | 391 | 71.141 | 49.373 | 41.063 | 1.00 | 50.68 |
| ATOM | 1804 | OE2 | GLU | 391 | 72.310 | 47.535 | 40.718 | 1.00 | 50.85 |
| ATOM | 1805 | C   | GLU | 391 | 68.324 | 51.174 | 38.458 | 1.00 | 45.28 |
| ATOM | 1806 | O   | GLU | 391 | 68.568 | 52.286 | 38.940 | 1.00 | 46.46 |
| ATOM | 1807 | N   | CYA | 392 | 67.568 | 51.024 | 37.372 | 1.00 | 43.33 |
| ATOM | 1808 | CA  | CYA | 392 | 67.071 | 52.192 | 36.643 | 1.00 | 42.28 |
| ATOM | 1809 | CB  | CYA | 392 | 67.519 | 52.096 | 35.197 | 1.00 | 42.45 |
| ATOM | 1810 | SG  | CYA | 392 | 69.280 | 52.182 | 35.127 | 1.00 | 43.69 |
| ATOM | 1811 | AS  | CYA | 392 | 69.908 | 51.044 | 33.336 | 1.00 | 48.17 |
| ATOM | 1812 | C   | CYA | 392 | 65.589 | 52.493 | 36.709 | 1.00 | 42.51 |
| ATOM | 1813 | O   | CYA | 392 | 64.792 | 51.634 | 37.070 | 1.00 | 43.30 |
| ATOM | 1814 | N   | PRO | 393 | 65.205 | 53.752 | 36.418 | 1.00 | 42.13 |
| ATOM | 1815 | CD  | PRO | 393 | 66.109 | 54.899 | 36.199 | 1.00 | 40.54 |
| ATOM | 1816 | CA  | PRO | 393 | 63.794 | 54.182 | 36.441 | 1.00 | 42.26 |
| ATOM | 1817 | CB  | PRO | 393 | 63.896 | 55.710 | 36.365 | 1.00 | 41.47 |
| ATOM | 1818 | CG  | PRO | 393 | 65.189 | 55.938 | 35.614 | 1.00 | 41.10 |
| ATOM | 1819 | C   | PRO | 393 | 62.954 | 53.606 | 35.281 | 1.00 | 43.20 |
| ATOM | 1820 | O   | PRO | 393 | 63.463 | 53.452 | 34.163 | 1.00 | 42.61 |
| ATOM | 1821 | N   | THR | 394 | 61.686 | 53.305 | 35.559 | 1.00 | 43.70 |
| ATOM | 1822 | CA  | THR | 394 | 60.764 | 52.755 | 34.564 | 1.00 | 45.50 |
| ATOM | 1823 | CB  | THR | 394 | 59.340 | 52.609 | 35.129 | 1.00 | 47.20 |
| ATOM | 1824 | OG1 | THR | 394 | 59.304 | 53.139 | 36.464 | 1.00 | 50.57 |
| ATOM | 1825 | CG2 | THR | 394 | 58.878 | 51.150 | 35.137 | 1.00 | 47.99 |
| ATOM | 1826 | C   | THR | 394 | 60.682 | 53.583 | 33.283 | 1.00 | 44.58 |
| ATOM | 1827 | O   | THR | 394 | 60.409 | 53.054 | 32.215 | 1.00 | 46.36 |
| ATOM | 1828 | N   | GLU | 395 | 60.899 | 54.888 | 33.396 | 1.00 | 42.88 |
| ATOM | 1829 | CA  | GLU | 395 | 60.842 | 55.790 | 32.246 | 1.00 | 40.54 |
| ATOM | 1830 | CB  | GLU | 395 | 61.096 | 57.234 | 32.699 | 1.00 | 40.69 |
| ATOM | 1831 | C   | GLU | 395 | 61.799 | 55.421 | 31.098 | 1.00 | 38.51 |
| ATOM | 1832 | O   | GLU | 395 | 61.628 | 55.877 | 29.968 | 1.00 | 39.41 |
| ATOM | 1833 | N   | LEU | 396 | 62.828 | 54.640 | 31.402 | 1.00 | 35.60 |
| ATOM | 1834 | CA  | LEU | 396 | 63.795 | 54.220 | 30.386 | 1.00 | 33.11 |
| ATOM | 1835 | CB  | LEU | 396 | 65.169 | 54.003 | 31.027 | 1.00 | 33.60 |
| ATOM | 1836 | CG  | LEU | 396 | 65.831 | 55.230 | 31.660 | 1.00 | 34.54 |
| ATOM | 1837 | CD1 | LEU | 396 | 67.160 | 54.835 | 32.282 | 1.00 | 32.83 |
| ATOM | 1838 | CD2 | LEU | 396 | 66.026 | 56.308 | 30.599 | 1.00 | 35.71 |
| ATOM | 1839 | C   | LEU | 396 | 63.388 | 52.940 | 29.660 | 1.00 | 30.95 |
| ATOM | 1840 | O   | LEU | 396 | 63.950 | 52.605 | 28.624 | 1.00 | 30.90 |
| ATOM | 1841 | N   | PHE | 397 | 62.422 | 52.227 | 30.223 | 1.00 | 30.18 |
| ATOM | 1842 | CA  | PHE | 397 | 61.961 | 50.970 | 29.654 | 1.00 | 28.80 |
| ATOM | 1843 | CB  | PHE | 397 | 61.712 | 49.946 | 30.777 | 1.00 | 28.10 |
| ATOM | 1844 | CG  | PHE | 397 | 62.938 | 49.604 | 31.592 | 1.00 | 28.96 |
| ATOM | 1845 | CD1 | PHE | 397 | 63.403 | 50.472 | 32.591 | 1.00 | 28.39 |
| ATOM | 1846 | CD2 | PHE | 397 | 63.636 | 48.422 | 31.359 | 1.00 | 26.28 |
| ATOM | 1847 | CE1 | PHE | 397 | 64.546 | 50.166 | 33.337 | 1.00 | 28.44 |
| ATOM | 1848 | CE2 | PHE | 397 | 64.784 | 48.107 | 32.103 | 1.00 | 29.21 |
| ATOM | 1849 | CZ  | PHE | 397 | 65.240 | 48.984 | 33.096 | 1.00 | 27.37 |
| ATOM | 1850 | C   | PHE | 397 | 60.683 | 51.093 | 28.836 | 1.00 | 27.54 |
| ATOM | 1851 | O   | PHE | 397 | 59.630 | 51.431 | 29.370 | 1.00 | 26.96 |
| ATOM | 1852 | N   | PRO | 398 | 60.753 | 50.836 | 27.501 | 1.00 | 27.41 |
| ATOM | 1853 | CD  | PRO | 398 | 61.968 | 50.600 | 26.686 | 1.00 | 25.42 |
| ATOM | 1854 | CA  | PRO | 398 | 59.560 | 50.920 | 26.654 | 1.00 | 25.90 |
| ATOM | 1855 | CB  | PRO | 398 | 60.068 | 50.383 | 25.320 | 1.00 | 25.26 |
| ATOM | 1856 | CG  | PRO | 398 | 61.490 | 50.893 | 25.290 | 1.00 | 23.99 |
| ATOM | 1857 | C   | PRO | 398 | 58.494 | 49.995 | 27.272 | 1.00 | 25.86 |
| ATOM | 1858 | O   | PRO | 398 | 58.839 | 48.962 | 27.843 | 1.00 | 25.82 |
| ATOM | 1859 | N   | PRO | 399 | 57.197 | 50.355 | 27.175 | 1.00 | 25.52 |
| ATOM | 1860 | CD  | PRO | 399 | 56.627 | 51.576 | 26.578 | 1.00 | 25.49 |
| ATOM | 1861 | CA  | PRO | 399 | 56.145 | 49.510 | 27.754 | 1.00 | 25.42 |
| ATOM | 1862 | CB  | PRO | 399 | 54.861 | 50.181 | 27.273 | 1.00 | 26.23 |
| ATOM | 1863 | CG  | PRO | 399 | 55.237 | 51.609 | 27.156 | 1.00 | 25.25 |
| ATOM | 1864 | C   | PRO | 399 | 56.198 | 48.043 | 27.317 | 1.00 | 26.08 |
| ATOM | 1865 | O   | PRO | 399 | 56.132 | 47.131 | 28.159 | 1.00 | 25.45 |
| ATOM | 1866 | N   | LEU | 400 | 56.350 | 47.810 | 26.019 | 1.00 | 25.57 |
| ATOM | 1867 | CA  | LEU | 400 | 56.406 | 46.440 | 25.509 | 1.00 | 26.27 |
| ATOM | 1868 | CB  | LEU | 400 | 56.404 | 46.418 | 23.980 | 1.00 | 25.03 |
| ATOM | 1869 | CG  | LEU | 400 | 56.117 | 45.042 | 23.363 | 1.00 | 24.51 |
| ATOM | 1870 | CD1 | LEU | 400 | 54.757 | 44.530 | 23.806 | 1.00 | 23.22 |
| ATOM | 1871 | CD2 | LEU | 400 | 56.173 | 45.149 | 21.862 | 1.00 | 23.70 |

APPENDIX 6-continued

TR_T3.PBD

| ATOM | 1872 | C | LEU | 400 | 57.602 | 45.657 | 26.067 | 1.00 | 27.06 | |
|------|------|------|------|-----|--------|--------|--------|------|-------|------|
| ATOM | 1873 | O | LEU | 400 | 57.484 | 44.465 | 26.363 | 1.00 | 27.41 | |
| ATOM | 1874 | N | PHE | 401 | 58.736 | 46.339 | 26.231 | 1.00 | 27.16 | |
| ATOM | 1875 | CA | PHE | 401 | 59.966 | 45.754 | 26.779 | 1.00 | 27.06 | |
| ATOM | 1876 | CB | PHE | 401 | 61.047 | 46.833 | 26.802 | 1.00 | 26.60 | |
| ATOM | 1877 | CG | PHE | 401 | 62.408 | 46.351 | 27.217 | 1.00 | 28.08 | |
| ATOM | 1878 | CD1 | PHE | 401 | 62.918 | 45.138 | 26.747 | 1.00 | 27.45 | |
| ATOM | 1879 | CD2 | PHE | 401 | 63.223 | 47.165 | 28.013 | 1.00 | 27.48 | |
| ATOM | 1880 | CE1 | PHE | 401 | 64.220 | 44.746 | 27.055 | 1.00 | 26.95 | |
| ATOM | 1881 | CE2 | PHE | 401 | 64.523 | 46.786 | 28.327 | 1.00 | 27.97 | |
| ATOM | 1882 | CZ | PHE | 401 | 65.028 | 45.575 | 27.846 | 1.00 | 28.46 | |
| ATOM | 1883 | C | PHE | 401 | 59.690 | 45.247 | 28.205 | 1.00 | 27.62 | |
| ATOM | 1884 | O | PHE | 401 | 60.046 | 44.125 | 28.570 | 1.00 | 26.24 | |
| ATOM | 1885 | N | LEU | 402 | 59.036 | 46.082 | 29.002 | 1.00 | 28.75 | |
| ATOM | 1886 | CA | LEU | 402 | 58.692 | 45.719 | 30.366 | 1.00 | 29.58 | |
| ATOM | 1887 | CB | LEU | 402 | 58.064 | 46.910 | 31.088 | 1.00 | 30.04 | |
| ATOM | 1888 | CG | LEU | 402 | 59.025 | 47.974 | 31.594 | 1.00 | 30.14 | |
| ATOM | 1889 | CD1 | LEU | 402 | 58.270 | 49.263 | 31.880 | 1.00 | 29.61 | |
| ATOM | 1890 | CD2 | LEU | 402 | 59.734 | 47.438 | 32.827 | 1.00 | 27.99 | |
| ATOM | 1891 | C | LEU | 402 | 57.693 | 44.583 | 30.368 | 1.00 | 30.10 | |
| ATOM | 1892 | O | LEU | 402 | 57.836 | 43.631 | 31.121 | 1.00 | 29.78 | |
| ATOM | 1893 | N | GLU | 403 | 56.688 | 44.683 | 29.510 | 1.00 | 30.49 | |
| ATOM | 1894 | CA | GLU | 403 | 55.646 | 43.671 | 29.453 | 1.00 | 32.60 | |
| ATOM | 1895 | CB | GLU | 403 | 54.562 | 44.094 | 28.469 | 1.00 | 37.01 | |
| ATOM | 1896 | CG | GLU | 403 | 53.329 | 43.218 | 28.520 | 1.00 | 44.01 | |
| ATOM | 1897 | CD | GLU | 403 | 52.263 | 43.632 | 27.523 | 1.00 | 48.50 | |
| ATOM | 1898 | OE1 | GLU | 403 | 52.516 | 44.525 | 26.677 | 1.00 | 49.66 | |
| ATOM | 1899 | OE2 | GLU | 403 | 51.157 | 43.050 | 27.594 | 1.00 | 53.06 | |
| ATOM | 1900 | C | GLU | 403 | 56.083 | 42.237 | 29.151 | 1.00 | 32.03 | |
| ATOM | 1901 | O | GLU | 403 | 55.627 | 41.304 | 29.816 | 1.00 | 32.58 | |
| ATOM | 1902 | N | VAL | 404 | 56.955 | 42.078 | 28.159 | 0.50 | 31.51 | ALTA |
| ATOM | 1903 | CA | VAL | 404 | 57.450 | 40.765 | 27.739 | 0.50 | 30.96 | ALTA |
| ATOM | 1904 | CB | VAL | 404 | 58.108 | 40.849 | 26.333 | 0.50 | 30.32 | ALTA |
| ATOM | 1905 | CG1 | VAL | 404 | 58.616 | 39.489 | 25.889 | 0.50 | 28.72 | ALTA |
| ATOM | 1906 | CG2 | VAL | 404 | 57.115 | 41.388 | 25.328 | 0.50 | 31.67 | ALTA |
| ATOM | 1907 | C | VAL | 404 | 58.465 | 40.149 | 28.696 | 0.50 | 30.45 | ALTA |
| ATOM | 1908 | O | VAL | 404 | 58.549 | 38.926 | 28.822 | 0.50 | 30.10 | ALTA |
| ATOM | 1909 | N | PHE | 405 | 59.224 | 41.002 | 29.369 | 1.00 | 30.16 | |
| ATOM | 1910 | CA | PHE | 405 | 60.266 | 40.549 | 30.263 | 1.00 | 30.65 | |
| ATOM | 1911 | CB | PHE | 405 | 61.577 | 41.221 | 29.863 | 1.00 | 28.92 | |
| ATOM | 1912 | CG | PHE | 405 | 62.062 | 40.834 | 28.493 | 1.00 | 26.31 | |
| ATOM | 1913 | CD1 | PHE | 405 | 62.342 | 41.804 | 27.543 | 1.00 | 25.72 | |
| ATOM | 1914 | CD2 | PHE | 405 | 62.269 | 39.500 | 28.166 | 1.00 | 25.92 | |
| ATOM | 1915 | CE1 | PHE | 405 | 62.827 | 41.456 | 26.278 | 1.00 | 26.78 | |
| ATOM | 1916 | CE2 | PHE | 405 | 62.752 | 39.139 | 26.910 | 1.00 | 25.39 | |
| ATOM | 1917 | CZ | PHE | 405 | 63.034 | 40.122 | 25.962 | 1.00 | 24.39 | |
| ATOM | 1918 | C | PHE | 405 | 60.011 | 40.674 | 31.771 | 1.00 | 32.10 | |
| ATOM | 1919 | O | PHE | 405 | 60.903 | 40.237 | 32.533 | 1.00 | 33.88 | |
| ATOM | 1920 | OXT | PHE | 405 | 58.936 | 41.169 | 32.188 | 1.00 | 34.95 | |
| ATOM | 1 | O1 | HOH | 501 | 67.542 | 37.066 | 11.311 | 1.00 | 26.83 | |
| ATOM | 3 | O1 | HOH | 502 | 68.713 | 41.227 | 12.821 | 1.00 | 23.42 | |
| ATOM | 2 | O1 | HOH | 503 | 64.446 | 40.325 | 12.123 | 1.00 | 22.84 | |
| ATOM | 4 | O1 | HOH | 504 | 62.236 | 39.752 | 15.941 | 1.00 | 17.97 | |
| ATOM | 5 | O1 | HOH | 505 | 48.732 | 20.137 | 5.515 | 1.00 | 50.48 | |
| ATOM | 6 | O1 | HOH | 506 | 47.365 | 21.522 | 3.716 | 1.00 | 53.40 | |
| ATOM | 7 | O1 | HOH | 507 | 50.211 | 23.203 | 7.900 | 1.00 | 32.66 | |
| ATOM | 8 | O1 | HOH | 508 | 51.043 | 20.258 | 8.253 | 1.00 | 21.81 | |
| ATOM | 9 | O1 | HOH | 509 | 48.225 | 18.176 | 7.905 | 1.00 | 38.96 | |
| ATOM | 10 | O1 | HOH | 510 | 49.569 | 20.871 | 11.586 | 1.00 | 32.97 | |
| ATOM | 11 | O1 | HOH | 511 | 53.732 | 17.159 | 10.856 | 1.00 | 47.20 | |
| ATOM | 12 | O1 | HOH | 512 | 56.201 | 16.223 | 12.164 | 1.00 | 18.50 | |
| ATOM | 13 | O1 | HOH | 513 | 56.653 | 12.298 | 10.528 | 1.00 | 27.71 | |
| ATOM | 14 | O1 | HOH | 514 | 58.661 | 10.694 | 9.014 | 1.00 | 46.73 | |
| ATOM | 15 | O1 | HOH | 515 | 62.950 | 10.692 | 11.952 | 1.00 | 43.05 | |
| ATOM | 16 | O1 | HOH | 516 | 66.411 | 11.552 | 10.897 | 1.00 | 37.36 | |
| ATOM | 17 | O1 | HOH | 517 | 68.949 | 13.188 | 12.029 | 1.00 | 39.28 | |
| ATOM | 18 | O1 | HOH | 518 | 71.997 | 15.171 | 8.362 | 1.00 | 49.69 | |
| ATOM | 19 | O1 | HOH | 519 | 71.946 | 17.928 | 6.743 | 1.00 | 24.50 | |
| ATOM | 20 | O1 | HOH | 520 | 75.117 | 15.684 | 9.377 | 1.00 | 35.98 | |
| ATOM | 21 | O1 | HOH | 521 | 76.677 | 12.815 | 10.294 | 1.00 | 49.33 | |
| ATOM | 22 | O1 | HOH | 522 | 81.421 | 15.415 | 15.139 | 1.00 | 46.74 | |
| ATOM | 23 | O1 | HOH | 523 | 78.784 | 21.696 | 17.564 | 1.00 | 49.01 | |
| ATOM | 24 | O1 | HOH | 524 | 79.954 | 24.822 | 17.152 | 1.00 | 42.91 | |
| ATOM | 25 | O1 | HOH | 525 | 82.199 | 30.253 | 18.821 | 1.00 | 40.27 | |
| ATOM | 26 | O1 | HOH | 526 | 82.862 | 33.444 | 21.988 | 1.00 | 46.81 | |
| ATOM | 27 | O1 | HOH | 527 | 76.608 | 30.793 | 23.452 | 1.00 | 46.22 | |
| ATOM | 28 | O1 | HOH | 528 | 74.726 | 30.483 | 25.469 | 1.00 | 43.76 | |

APPENDIX 6-continued

TR_T3.PBD

| ATOM | 29 | O1 | HOH | 529 | 77.059 | 28.762 | 20.900 | 1.00 | 33.67 |
|---|---|---|---|---|---|---|---|---|---|
| ATOM | 30 | O1 | HOH | 530 | 75.935 | 33.279 | 12.269 | 1.00 | 25.26 |
| ATOM | 31 | O1 | HOH | 531 | 77.402 | 34.447 | 10.087 | 1.00 | 37.04 |
| ATOM | 32 | O1 | HOH | 532 | 74.054 | 29.941 | 9.998 | 1.00 | 26.86 |
| ATOM | 33 | O1 | HOH | 533 | 69.544 | 32.658 | 7.572 | 1.00 | 40.34 |
| ATOM | 34 | O1 | HOH | 534 | 66.709 | 33.618 | 8.477 | 1.00 | 20.63 |
| ATOM | 35 | O1 | HOH | 535 | 68.073 | 35.828 | 8.931 | 1.00 | 23.99 |
| ATOM | 36 | O1 | HOH | 536 | 61.865 | 45.643 | 14.011 | 1.00 | 40.43 |
| ATOM | 37 | O1 | HOH | 537 | 63.662 | 46.881 | 15.670 | 1.00 | 28.04 |
| ATOM | 38 | O1 | HOH | 538 | 63.391 | 49.310 | 13.883 | 1.00 | 39.59 |
| ATOM | 39 | O1 | HOH | 539 | 63.491 | 50.570 | 10.631 | 1.00 | 52.34 |
| ATOM | 40 | O1 | HOH | 540 | 64.592 | 46.849 | 10.299 | 1.00 | 26.63 |
| ATOM | 41 | O1 | HOH | 541 | 55.575 | 41.632 | 10.980 | 1.00 | 38.06 |
| ATOM | 42 | O1 | HOH | 542 | 51.631 | 42.062 | 17.343 | 1.00 | 45.99 |
| ATOM | 43 | O1 | HOH | 543 | 52.755 | 43.156 | 20.209 | 1.00 | 34.17 |
| ATOM | 44 | O1 | HOH | 544 | 57.061 | 49.627 | 24.004 | 1.00 | 24.09 |
| ATOM | 45 | O1 | HOH | 545 | 61.040 | 50.561 | 21.351 | 1.00 | 30.91 |
| ATOM | 46 | O1 | HOH | 546 | 68.533 | 53.616 | 18.390 | 1.00 | 30.91 |
| ATOM | 47 | O1 | HOH | 547 | 63.371 | 58.813 | 29.014 | 1.00 | 59.25 |
| ATOM | 48 | O1 | HOH | 548 | 57.934 | 52.905 | 31.175 | 1.00 | 40.12 |
| ATOM | 49 | O1 | HOH | 549 | 62.364 | 50.496 | 37.543 | 1.00 | 52.28 |
| ATOM | 50 | O1 | HOH | 550 | 62.256 | 49.704 | 40.891 | 1.00 | 54.18 |
| ATOM | 51 | O1 | HOH | 551 | 61.994 | 46.430 | 40.384 | 1.00 | 43.84 |
| ATOM | 52 | O1 | HOH | 552 | 63.675 | 44.459 | 39.268 | 1.00 | 44.73 |
| ATOM | 53 | O1 | HOH | 553 | 58.405 | 43.920 | 33.936 | 1.00 | 42.88 |
| ATOM | 54 | O1 | HOH | 554 | 62.863 | 39.071 | 34.046 | 1.00 | 45.07 |
| ATOM | 55 | O1 | HOH | 555 | 64.426 | 36.925 | 28.676 | 1.00 | 25.36 |
| ATOM | 56 | O1 | HOH | 556 | 62.375 | 35.807 | 26.610 | 1.00 | 21.14 |
| ATOM | 57 | O1 | HOH | 557 | 63.684 | 33.760 | 25.609 | 1.00 | 33.03 |
| ATOM | 58 | O1 | HOH | 558 | 61.542 | 29.906 | 24.568 | 1.00 | 57.37 |
| ATOM | 59 | O1 | HOH | 559 | 62.353 | 27.540 | 24.855 | 1.00 | 39.63 |
| ATOM | 60 | O1 | HOH | 560 | 62.814 | 28.785 | 27.536 | 1.00 | 58.40 |
| ATOM | 61 | O1 | HOH | 561 | 65.531 | 30.642 | 28.821 | 1.00 | 54.44 |
| ATOM | 62 | O1 | HOH | 562 | 63.423 | 24.645 | 32.964 | 1.00 | 50.75 |
| ATOM | 63 | O1 | HOH | 563 | 64.697 | 21.149 | 28.711 | 1.00 | 51.41 |
| ATOM | 64 | O1 | HOH | 564 | 67.100 | 23.370 | 26.900 | 1.00 | 52.36 |
| ATOM | 65 | O1 | HOH | 565 | 65.582 | 20.422 | 23.303 | 1.00 | 40.32 |
| ATOM | 66 | O1 | HOH | 566 | 61.577 | 18.167 | 23.386 | 1.00 | 65.08 |
| ATOM | 67 | O1 | HOH | 567 | 61.022 | 22.649 | 25.573 | 1.00 | 48.85 |
| ATOM | 68 | O1 | HOH | 568 | 57.919 | 21.446 | 25.147 | 1.00 | 43.39 |
| ATOM | 69 | O1 | HOH | 569 | 59.435 | 20.179 | 28.543 | 1.00 | 51.41 |
| ATOM | 70 | O1 | HOH | 570 | 53.860 | 23.216 | 30.984 | 1.00 | 50.28 |
| ATOM | 71 | O1 | HOH | 571 | 52.825 | 24.880 | 32.696 | 1.00 | 43.96 |
| ATOM | 72 | O1 | HOH | 572 | 48.228 | 29.683 | 30.486 | 1.00 | 44.51 |
| ATOM | 73 | O1 | HOH | 573 | 48.925 | 34.467 | 30.521 | 1.00 | 36.28 |
| ATOM | 74 | O1 | HOH | 574 | 50.766 | 40.547 | 29.178 | 1.00 | 51.45 |
| ATOM | 75 | O1 | HOH | 575 | 57.058 | 32.490 | 30.420 | 1.00 | 31.03 |
| ATOM | 76 | O1 | HOH | 576 | 58.075 | 29.544 | 24.664 | 1.00 | 19.54 |
| ATOM | 77 | O1 | HOH | 577 | 47.451 | 19.292 | 28.703 | 1.00 | 33.04 |
| ATOM | 78 | O1 | HOH | 578 | 53.120 | 15.471 | 17.478 | 1.00 | 35.68 |
| ATOM | 79 | O1 | HOH | 579 | 55.101 | 14.146 | 16.095 | 1.00 | 50.46 |
| ATOM | 80 | O1 | HOH | 580 | 53.726 | 14.016 | 9.059 | 1.00 | 41.44 |
| ATOM | 81 | O1 | HOH | 581 | 57.223 | 13.820 | 1.435 | 1.00 | 48.31 |
| ATOM | 82 | O1 | HOH | 582 | 61.169 | 15.688 | 0.210 | 1.00 | 17.60 |
| ATOM | 83 | O1 | HOH | 583 | 67.411 | 16.019 | −0.314 | 1.00 | 23.93 |
| ATOM | 84 | O1 | HOH | 584 | 67.033 | 17.221 | −2.796 | 1.00 | 26.21 |
| ATOM | 85 | O1 | HOH | 585 | 69.893 | 19.520 | −1.582 | 1.00 | 59.67 |
| ATOM | 86 | O1 | HOH | 586 | 68.489 | 22.464 | 0.350 | 1.00 | 37.85 |
| ATOM | 87 | O1 | HOH | 587 | 65.794 | 23.354 | 0.823 | 1.00 | 27.38 |
| ATOM | 88 | O1 | HOH | 588 | 67.550 | 26.810 | 0.937 | 1.00 | 37.18 |
| ATOM | 89 | O1 | HOH | 589 | 64.646 | 28.208 | 3.323 | 1.00 | 36.74 |
| ATOM | 90 | O1 | HOH | 590 | 67.215 | 31.103 | 3.174 | 1.00 | 30.29 |
| ATOM | 91 | O1 | HOH | 591 | 64.164 | 35.667 | 6.220 | 1.00 | 39.72 |
| ATOM | 92 | O1 | HOH | 592 | 62.810 | 37.518 | 4.836 | 1.00 | 48.48 |
| ATOM | 93 | O1 | HOH | 593 | 68.105 | 36.898 | 6.110 | 1.00 | 58.00 |
| ATOM | 94 | O1 | HOH | 594 | 57.390 | 37.485 | 2.631 | 1.00 | 37.29 |
| ATOM | 95 | O1 | HOH | 595 | 53.088 | 36.068 | 3.949 | 1.00 | 50.10 |
| ATOM | 96 | O1 | HOH | 596 | 52.974 | 34.676 | 6.758 | 1.00 | 42.52 |
| ATOM | 97 | O1 | HOH | 597 | 58.581 | 31.465 | 2.076 | 1.00 | 32.18 |
| ATOM | 98 | O1 | HOH | 598 | 52.786 | 23.277 | 1.357 | 1.00 | 28.98 |
| ATOM | 99 | O1 | HOH | 599 | 47.501 | 26.551 | 7.672 | 1.00 | 47.83 |
| ATOM | 100 | O1 | HOH | 600 | 46.411 | 35.754 | 14.049 | 1.00 | 53.46 |
| ATOM | 101 | O1 | HOH | 601 | 63.514 | 14.944 | 15.842 | 1.00 | 55.02 |
| ATOM | 102 | O1 | HOH | 602 | 67.943 | 11.792 | 3.438 | 1.00 | 61.21 |
| ATOM | 103 | O1 | HOH | 603 | 62.232 | 9.378 | 3.311 | 1.00 | 35.65 |
| ATOM | 104 | O1 | HOH | 604 | 76.734 | 22.468 | 5.002 | 1.00 | 42.56 |
| ATOM | 105 | O1 | HOH | 605 | 83.589 | 28.967 | 9.626 | 1.00 | 50.64 |

APPENDIX 6-continued

TR_T3.PBD

| ATOM | 106 | O1 | HOH | | 606 | 82.807 | 43.437 | 17.940 | 1.00 | 39.28 |
|------|------|-----|-----|---|-----|--------|--------|--------|------|-------|
| ATOM | 107 | O1 | HOH | | 607 | 83.882 | 45.673 | 20.638 | 1.00 | 41.64 |
| ATOM | 108 | O1 | HOH | | 608 | 80.215 | 41.021 | 23.441 | 1.00 | 43.16 |
| ATOM | 109 | O1 | HOH | | 609 | 79.459 | 46.296 | 31.165 | 1.00 | 32.40 |
| ATOM | 110 | O1 | HOH | | 610 | 81.880 | 47.681 | 33.923 | 1.00 | 46.96 |
| ATOM | 111 | O1 | HOH | | 611 | 75.594 | 46.142 | 30.384 | 1.00 | 28.64 |
| ATOM | 112 | O1 | HOH | | 612 | 77.118 | 40.568 | 32.575 | 1.00 | 34.21 |
| ATOM | 113 | O1 | HOH | | 613 | 73.563 | 41.750 | 36.926 | 1.00 | 26.07 |
| ATOM | 114 | O1 | HOH | | 614 | 75.955 | 56.565 | 28.863 | 1.00 | 46.31 |
| ATOM | 115 | O1 | HOH | | 615 | 79.915 | 59.136 | 15.809 | 1.00 | 50.81 |
| ATOM | 116 | O1 | HOH | | 616 | 77.390 | 52.542 | 8.816 | 1.00 | 34.34 |
| ATOM | 117 | O1 | HOH | | 617 | 72.726 | 25.005 | 29.671 | 1.00 | 62.84 |
| ATOM | 2038 | C | ACY | | 701 | 52.664 | 40.106 | 24.800 | 1.00 | 46.39 |
| ATOM | 2039 | O | ACY | | 701 | 53.721 | 39.649 | 24.298 | 1.00 | 47.12 |
| ATOM | 2040 | OXT | ACY | | 701 | 51.652 | 40.521 | 24.172 | 1.00 | 46.96 |
| ATOM | 2041 | CH3 | ACY | | 701 | 52.600 | 40.162 | 26.329 | 1.00 | 45.99 |
| ATOM | 2050 | C1 | T3 | | 1 | 66.961 | 42.243 | 18.491 | 1.00 | 22.34 |
| ATOM | 2051 | C2 | T3 | | 1 | 68.748 | 43.593 | 23.015 | 1.00 | 21.84 |
| ATOM | 2052 | C3 | T3 | | 1 | 66.873 | 43.557 | 18.970 | 1.00 | 23.43 |
| ATOM | 2053 | C4 | T3 | | 1 | 69.252 | 44.540 | 23.871 | 1.00 | 22.31 |
| ATOM | 2054 | C5 | T3 | | 1 | 67.638 | 43.989 | 20.011 | 1.00 | 24.83 |
| ATOM | 2055 | C6 | T3 | | 1 | 68.851 | 44.553 | 25.178 | 1.00 | 25.16 |
| ATOM | 2056 | C7 | T3 | | 1 | 68.541 | 43.108 | 20.632 | 1.00 | 24.65 |
| ATOM | 2057 | C8 | T3 | | 1 | 67.895 | 43.567 | 25.639 | 1.00 | 21.93 |
| ATOM | 2058 | C9 | T3 | | 1 | 68.665 | 41.792 | 20.183 | 1.00 | 25.09 |
| ATOM | 2059 | C10 | T3 | | 1 | 67.427 | 42.654 | 24.733 | 1.00 | 23.66 |
| ATOM | 2060 | C11 | T3 | | 1 | 67.878 | 41.380 | 19.117 | 1.00 | 23.12 |
| ATOM | 2061 | C12 | T3 | | 1 | 67.829 | 42.624 | 23.384 | 1.00 | 19.67 |
| ATOM | 2062 | C13 | T3 | | 1 | 66.055 | 41.788 | 17.371 | 1.00 | 18.97 |
| ATOM | 2063 | C15 | T3 | | 1 | 66.721 | 40.956 | 16.295 | 1.00 | 19.32 |
| ATOM | 2064 | C17 | T3 | | 1 | 65.901 | 40.829 | 15.051 | 1.00 | 19.02 |
| ATOM | 2065 | I1 | T3 | | 1 | 67.393 | 45.986 | 20.621 | 1.00 | 25.29 |
| ATOM | 2066 | I2 | T3 | | 1 | 69.483 | 46.066 | 26.432 | 1.00 | 26.49 |
| ATOM | 2067 | I3 | T3 | | 1 | 70.019 | 40.450 | 20.975 | 1.00 | 25.67 |
| ATOM | 2068 | N1 | T3 | | 1 | 68.131 | 41.337 | 16.037 | 1.00 | 15.12 |
| ATOM | 2069 | O1 | T3 | | 1 | 67.542 | 43.587 | 26.966 | 1.00 | 21.79 |
| ATOM | 2070 | O2 | T3 | | 1 | 69.259 | 43.600 | 21.682 | 1.00 | 22.05 |
| ATOM | 2071 | O3 | T3 | | 1 | 66.504 | 40.852 | 13.963 | 1.00 | 20.38 |
| ATOM | 2072 | O4 | T3 | | 1 | 64.675 | 40.731 | 15.192 | 1.00 | 20.16 |
| END | | | | | | | | | | |

APPENDIX 7

TRBTRIAC.PDB

REMARK TR-beta Triac Full length numbering
REMARK refinement resolution: 100 – 2.9 A r = 0.273258 free_r = 0.333794
REMARK wa = 5.78307
REMARK target = mlf cycles = 1 steps = 25
REMARK a = 68.72 b = 68.72 c = 130.092 alpha = 90 beta = 90 gamma = 120
REMARK ncs = none
REMARK initial B-factor correction: "none"
REMARK ALA 199 to ALA 201 from His-tag
REMARK
RLMARK Four cacodylate-modified cysteines (CYA)
REMARK Cys294, Cys298, Cys388, Cys434
REMARK cacodylate modeled as single arsenic atom
REMARK
REMARK side chain of certain residues modeled as ALA due to poor density;
REMARK however, residue name reflects true residue for clarity
REMARK
REMARK amino acid sequence confirmed,
REMARK differing from that reported by Weinberger et. al.
REMARK in the following codons:
REMARK 243 Pro - Arg
REMARK 337 Ile - Thr
REMARK 451 Leu - Phe
REMARK as reported by Sakurai et. al.
REMARK note also correction of initiation codon,
REMARK yielding a polypeptide of 461 amino acids
JRNL AUTH A. SAKURAJ, A. NAKAI, L. J. DEGROOT
JRNL TITL STRUCTURAL ANALYSIS OF HUMAN THYROID HORMONE RECEPTOR
JRNL TITL2 BETA GENE
JRNL REF MOL. CELL. ENDO. V.71 1990

APPENDIX 7-continued

TRBTRIAC.PDB

JRNL AUTH C .WEINBERGER, C. C. THOMPSON, R. LEBO, D. J. GRUOL, R. M. EVANS
JRNL TITL THE C-ERB-A GENE ENCODES A THYROID HORMONE RECEPTOR
JRNL REF NATURE V.324 6098 1986

| ATOM | 1 | CB | ALA | 199 | 31.247 | 28.289 | 43.613 | 1.00 | 71.30 | PROT |
|---|---|---|---|---|---|---|---|---|---|---|
| ATOM | 2 | C | ALA | 199 | 32.916 | 26.485 | 44.170 | 1.00 | 68.99 | PROT |
| ATOM | 3 | O | ALA | 199 | 33.485 | 25.410 | 43.976 | 1.00 | 63.84 | PROT |
| ATOM | 4 | N | ALA | 199 | 30.462 | 25.993 | 44.096 | 1.00 | 75.00 | PROT |
| ATOM | 5 | CA | ALA | 199 | 31.571 | 26.795 | 43.497 | 1.00 | 73.24 | PROT |
| ATOM | 6 | N | ALA | 200 | 33.419 | 27.432 | 44.958 | 1.00 | 73.81 | PROT |
| ATOM | 7 | CA | ALA | 200 | 34.686 | 27.251 | 45.658 | 1.00 | 67.87 | PROT |
| ATOM | 8 | CB | ALA | 200 | 35.182 | 28.583 | 46.203 | 1.00 | 62.83 | PROT |
| ATOM | 9 | C | ALA | 200 | 34.539 | 26.239 | 46.791 | 1.00 | 63.23 | PROT |
| ATOM | 10 | O | ALA | 200 | 35.486 | 25.986 | 47.534 | 1.00 | 59.14 | PROT |
| ATOM | 11 | N | ALA | 201 | 33.345 | 25.670 | 46.932 | 1.00 | 56.98 | PROT |
| ATOM | 12 | CA | ALA | 201 | 33.117 | 24.664 | 47.957 | 1.00 | 51.46 | PROT |
| ATOM | 13 | CB | ALA | 201 | 31.776 | 23.992 | 47.744 | 1.00 | 40.35 | PROT |
| ATOM | 14 | C | ALA | 201 | 34.248 | 23.662 | 47.762 | 1.00 | 53.15 | PROT |
| ATOM | 15 | O | ALA | 201 | 34.624 | 22.938 | 48.679 | 1.00 | 54.90 | PROT |
| ATOM | 16 | N | GLU | 202 | 34.789 | 23.645 | 46.546 | 1.00 | 44.13 | PROT |
| ATOM | 17 | CA | GLU | 202 | 35.891 | 22.767 | 46.190 | 1.00 | 37.47 | PROT |
| ATOM | 18 | CB | GLU | 202 | 36.086 | 22.760 | 44.671 | 1.00 | 37.74 | PROT |
| ATOM | 19 | CG | GLU | 202 | 37.060 | 21.702 | 44.173 | 1.00 | 57.14 | PROT |
| ATOM | 20 | CD | GLU | 202 | 36.457 | 20.303 | 44.140 | 1.00 | 61.74 | PROT |
| ATOM | 21 | OE1 | GLU | 202 | 35.211 | 20.175 | 44.133 | 1.00 | 63.81 | PROT |
| ATOM | 22 | OE2 | GLU | 202 | 37.236 | 19.327 | 44.115 | 1.00 | 65.54 | PROT |
| ATOM | 23 | C | GLU | 202 | 37.156 | 23.266 | 46.878 | 1.00 | 35.54 | PROT |
| ATOM | 24 | O | GLU | 202 | 37.874 | 22.492 | 47.510 | 1.00 | 32.70 | PROT |
| ATOM | 25 | N | GLU | 203 | 37.415 | 24.566 | 46.755 | 1.00 | 31.79 | PROT |
| ATOM | 26 | CA | GLU | 203 | 38.588 | 25.188 | 47.366 | 1.00 | 33.63 | PROT |
| ATOM | 27 | CB | GLU | 203 | 38.603 | 26.683 | 47.079 | 1.00 | 28.28 | PROT |
| ATOM | 28 | C | GLU | 203 | 38.588 | 24.948 | 48.869 | 1.00 | 33.86 | PROT |
| ATOM | 29 | O | GLU | 203 | 39.644 | 24.818 | 49.485 | 1.00 | 33.10 | PROT |
| ATOM | 30 | N | LEU | 204 | 37.393 | 24.898 | 49.451 | 1.00 | 34.15 | PROT |
| ATOM | 31 | CA | LEU | 204 | 37.244 | 24.650 | 50.876 | 1.00 | 33.22 | PROT |
| ATOM | 32 | CB | LEU | 204 | 35.853 | 25.081 | 51.353 | 1.00 | 30.47 | PROT |
| ATOM | 33 | CG | LEU | 204 | 35.567 | 25.083 | 52.862 | 1.00 | 23.17 | PROT |
| ATOM | 34 | CD1 | LEU | 204 | 35.904 | 26.439 | 53.443 | 1.00 | 5.41 | PROT |
| ATOM | 35 | CD2 | LEU | 204 | 34.106 | 24.748 | 53.111 | 1.00 | 12.70 | PROT |
| ATOM | 36 | C | LEU | 204 | 37.424 | 23.156 | 51.100 | 1.00 | 40.17 | PROT |
| ATOM | 37 | O | LEU | 204 | 38.219 | 22.736 | 51.951 | 1.00 | 45.33 | PROT |
| ATOM | 38 | N | GLN | 205 | 36.682 | 22..360 | 50.329 | 1.00 | 43.86 | PROT |
| ATOM | 39 | CA | GLN | 205 | 36.754 | 20.899 | 50.415 | 1.00 | 43.96 | PROT |
| ATOM | 40 | CB | GLN | 205 | 36.089 | 20.261 | 49.184 | 1.00 | 45.56 | PROT |
| ATOM | 41 | CG | GLN | 205 | 34.562 | 20.195 | 49.245 | 1.00 | 42.39 | PROT |
| ATOM | 42 | CD | GLN | 205 | 34.022 | 18.775 | 49.159 | 1.00 | 46.79 | PROT |
| ATOM | 43 | OE1 | GLN | 205 | 33.258 | 18.444 | 48.252 | 1.00 | 38.84 | PROT |
| ATOM | 44 | NE2 | GLN | 205 | 34.412 | 17.932 | 50.109 | 1.00 | 37.95 | PROT |
| ATOM | 45 | C | GLN | 205 | 38.224 | 20.482 | 50.483 | 1.00 | 42.39 | PROT |
| ATOM | 46 | O | GLN | 205 | 38.630 | 19.702 | 51.355 | 1.00 | 36.27 | PROT |
| ATOM | 47 | N | LYS | 206 | 39.014 | 21.015 | 49.553 | 1.00 | 42.37 | PROT |
| ATOM | 48 | CA | LYS | 206 | 40.440 | 20.729 | 49.5O5 | 1.00 | 44.40 | PROT |
| ATOM | 49 | CB | LYS | 206 | 41.110 | 21.531 | 48.385 | 1.00 | 38.73 | PROT |
| ATOM | 50 | C | LYS | 206 | 41.024 | 21.118 | 50.853 | 1.00 | 42.36 | PROT |
| ATOM | 51 | O | LYS | 206 | 41.550 | 20.271 | 51.570 | 1.00 | 46.93 | PROT |
| ATOM | 52 | N | SER | 207 | 40.913 | 22.401 | 51.192 | 1.00 | 34.68 | PROT |
| ATOM | 53 | CA | SER | 207 | 41.415 | 22.933 | 52.455 | 1.00 | 29.43 | PROT |
| ATOM | 54 | CB | SER | 207 | 40.690 | 24.228 | 52.791 | 1.00 | 24.63 | PROT |
| ATOM | 55 | OG | SER | 207 | 41.327 | 25.332 | 52.173 | 1.00 | 36.56 | PROT |
| ATOM | 56 | C | SER | 207 | 41.254 | 21.958 | 53.614 | 1.00 | 29.20 | PROT |
| ATOM | 57 | O | SER | 207 | 42.223 | 21.623 | 54.293 | 1.00 | 31.01 | PROT |
| ATOM | 58 | N | ILE | 208 | 40.028 | 21.504 | 53.841 | 1.00 | 22.55 | PROT |
| ATOM | 59 | CA | ILE | 208 | 39.777 | 20.568 | 54.928 | 1.00 | 27.93 | PROT |
| ATOM | 60 | CB | ILE | 208 | 38.267 | 20.216 | 55.027 | 1.00 | 39.85 | PROT |
| ATOM | 61 | CG2 | ILE | 208 | 38.062 | 18.895 | 55.769 | 1.00 | 32.13 | PROT |
| ATOM | 62 | CG1 | ILE | 208 | 37.528 | 21.340 | 55.753 | 1.00 | 37.63 | PROT |
| ATOM | 63 | CD1 | ILE | 208 | 36.788 | 22.296 | 54.827 | 1.00 | 41.47 | PROT |
| ATOM | 64 | C | ILE | 208 | 40.591 | 19.291 | 54.725 | 1.00 | 29.61 | PROT |
| ATOM | 65 | O | ILE | 208 | 40.905 | 18.580 | 55.679 | 1.00 | 40.00 | PROT |
| ATOM | 66 | N | GLY | 209 | 40.928 | 19.002 | 53.475 | 1.00 | 35.05 | PROT |
| ATOM | 67 | CA | GLY | 209 | 41.698 | 17.809 | 53.4181 | 1.00 | 31.94 | PROT |
| ATOM | 68 | C | GLY | 209 | 40.826 | 16.695 | 52.643 | 1.00 | 28.66 | PROT |
| ATOM | 69 | O | GLY | 209 | 41.257 | 15.553 | 52.532 | 1.00 | 19.46 | PROT |
| ATOM | 70 | N | HIS | 210 | 39.586 | 17.021 | 52.313 | 1.00 | 20.47 | PROT |
| ATOM | 71 | CA | HIS | 210 | 38.684 | 16.018 | 51.774 | 1.00 | 26.99 | PROT |
| ATOM | 72 | CB | HIS | 210 | 37.240 | 16.451 | 52.012 | 1.00 | 37.16 | PROT |
| ATOM | 73 | C | HIS | 210 | 38.959 | 15.806 | 50.266 | 1.00 | 27.75 | PROT |

APPENDIX 7-continued

TRBTRIAC.PDB

| | | | | | | | | | |
|---|---|---|---|---|---|---|---|---|---|
| ATOM | 74 | O | HIS | 210 | 39.328 | 16.741 | 49.550 | 1.00 | 34.08 PROT |
| ATOM | 75 | N | LYS | 211 | 38.807 | 14.566 | 49.805 | 1.00 | 16.50 PROT |
| ATOM | 76 | CA | LYS | 211 | 39.019 | 14.206 | 48.403 | 1.00 | 5.57 PROT |
| ATOM | 77 | CB | LYS | 211 | 39.932 | 12.981 | 48.295 | 1.00 | 5.67 PROT |
| ATOM | 78 | CG | LYS | 211 | 41.370 | 13.208 | 48.742 | 1.00 | 7.30 PROT |
| ATOM | 79 | CD | LYS | 211 | 41.873 | 14.594 | 48.347 | 1.00 | 14.34 PROT |
| ATOM | 80 | CE | LYS | 211 | 43.339 | 14.556 | 47.897 | 1.00 | 29.48 PROT |
| ATOM | 81 | NZ | LYS | 211 | 43.777 | 15.851 | 47.262 | 1.00 | 33.43 PROT |
| ATOM | 82 | C | LYS | 211 | 37.642 | 13.861 | 47.876 | 1.00 | 2.73 PROT |
| ATOM | 83 | O | LYS | 211 | 37.176 | 12.741 | 48.039 | 1.00 | 6.57 PROT |
| ATOM | 84 | N | PRO | 212 | 36.983 | 14.813 | 47.208 | 1.00 | 2.00 PROT |
| ATOM | 85 | CD | PRO | 212 | 37.472 | 16.156 | 46.846 | 1.00 | 10.43 PROT |
| ATOM | 86 | CA | PRO | 212 | 35.642 | 14.542 | 46.689 | 1.00 | 2.05 PROT |
| ATOM | 87 | CB | PRO | 212 | 35.088 | 15.928 | 46.341 | 1.00 | 10.09 PROT |
| ATOM | 88 | CG | PRO | 212 | 36.240 | 16.888 | 46.422 | 1.00 | 8.43 PROT |
| ATOM | 89 | C | PRO | 212 | 35.523 | 13.578 | 45.520 | 1.00 | 2.00 PROT |
| ATOM | 90 | O | PRO | 212 | 36.344 | 13.554 | 44.611 | 1.00 | 6.04 PROT |
| ATOM | 91 | N | GLU | 213 | 34.476 | 12.773 | 45.577 | 1.00 | 2.68 PROT |
| ATOM | 92 | CA | GLU | 213 | 34.181 | 11.817 | 44.542 | 1.00 | 6.81 PROT |
| ATOM | 93 | CB | GLU | 213 | 33.539 | 10.594 | 45.173 | 1.00 | 7.20 PROT |
| ATOM | 94 | CG | GLU | 213 | 34.222 | 10.232 | 46.462 | 1.00 | 15.33 PROT |
| ATOM | 95 | CD | GLU | 213 | 34.293 | 8.743 | 46.689 | 1.00 | 21.36 PROT |
| ATOM | 96 | OE1 | GLU | 213 | 33.334 | 8.051 | 46.290 | 1.00 | 29.32 PROT |
| ATOM | 97 | OE2 | GLU | 213 | 35.301 | 8.265 | 47.268 | 1.00 | 28.50 PROT |
| ATOM | 98 | C | GLU | 213 | 33.229 | 12.543 | 43.584 | 1.00 | 12.00 PROT |
| ATOM | 99 | O | GLU | 213 | 32.693 | 13.599 | 43.926 | 1.00 | 19.02 PROT |
| ATOM | 100 | N | PRO | 214 | 33.011 | 11.985 | 42.375 | 1.00 | 25.74 PROT |
| ATOM | 101 | CD | PRO | 214 | 33.592 | 10.692 | 41.973 | 1.00 | 28.98 PROT |
| ATOM | 102 | CA | PRO | 214 | 32.145 | 12.536 | 41.322 | 1.00 | 23.38 PROT |
| ATOM | 103 | CB | PRO | 214 | 32.180 | 11.476 | 40.232 | 1.00 | 18.01 PROT |
| ATOM | 104 | CG | PRO | 214 | 33.376 | 10.665 | 40.514 | 1.00 | 27.50 PROT |
| ATOM | 105 | C | PRO | 214 | 30.715 | 12.828 | 41.734 | 1.00 | 25.02 PROT |
| ATOM | 106 | O | PRO | 214 | 30.069 | 11.986 | 42.355 | 1.00 | 31.17 PROT |
| ATOM | 107 | N | THR | 215 | 30.211 | 14.009 | 41.377 | 1.00 | 19.56 PROT |
| ATOM | 108 | CA | THR | 215 | 28.830 | 14.352 | 41.714 | 1.00 | 24.48 PROT |
| ATOM | 109 | CB | THR | 215 | 28.535 | 15.841 | 41.522 | 1.00 | 27.13 PROT |
| ATOM | 110 | OG1 | THR | 215 | 27.939 | 16.038 | 40.234 | 1.00 | 40.19 PROT |
| ATOM | 111 | CG2 | THR | 215 | 29.805 | 16.659 | 41.640 | 1.00 | 30.81 PROT |
| ATOM | 112 | C | THR | 215 | 27.899 | 13.562 | 40.805 | 1.00 | 22.14 PROT |
| ATOM | 113 | O | THR | 215 | 28.357 | 12.905 | 39.883 | 1.00 | 27.52 PROT |
| ATOM | 114 | N | ASP | 216 | 26.599 | 13.617 | 41.072 | 1.00 | 35.65 PROT |
| ATOM | 115 | CA | ASP | 216 | 25.631 | 12.890 | 40.258 | 1.00 | 41.16 PROT |
| ATOM | 116 | CB | ASP | 216 | 24.219 | 13.091 | 40.810 | 1.00 | 38.17 PROT |
| ATOM | 117 | C | ASP | 216 | 25.714 | 13.370 | 38.810 | 1.00 | 40.44 PROT |
| ATOM | 118 | O | ASP | 216 | 25.683 | 12.569 | 37.874 | 1.00 | 38.26 PROT |
| ATOM | 119 | N | GLU | 217 | 25.832 | 14.682 | 38.635 | 1.00 | 40.14 PROT |
| ATOM | 120 | CA | GLU | 217 | 25.932 | 15.275 | 37.305 | 1.00 | 38.89 PROT |
| ATOM | 121 | CB | GLU | 217 | 25.883 | 16.796 | 37.413 | 1.00 | 29.95 PROT |
| ATOM | 122 | C | GLU | 217 | 27.231 | 14.829 | 36.619 | 1.00 | 39.44 PROT |
| ATOM | 123 | O | GLU | 217 | 27.245 | 14.525 | 35.425 | 1.00 | 40.08 PROT |
| ATOM | 124 | N | GLU | 218 | 28.319 | 14.794 | 37.384 | 1.00 | 34.92 PROT |
| ATOM | 125 | CA | GLU | 218 | 29.615 | 14.370 | 36.871 | 1.00 | 23.70 PROT |
| ATOM | 126 | CB | GLU | 218 | 30.698 | 14.606 | 37.924 | 1.00 | 18.47 PROT |
| ATOM | 127 | CG | GLU | 218 | 30.990 | 16.067 | 38.198 | 1.00 | 15.66 PROT |
| ATOM | 128 | CD | GLU | 218 | 32.085 | 16.264 | 39.231 | 1.00 | 26.88 PROT |
| ATOM | 129 | OE1 | GLU | 218 | 32.164 | 15.458 | 40.191 | 1.00 | 25.07 PROT |
| ATOM | 130 | OE2 | GLU | 218 | 32.864 | 17.232 | 39.078 | 1.00 | 33.79 PROT |
| ATOM | 131 | C | GLU | 218 | 29.589 | 12.892 | 36.491 | 1.00 | 21.05 PROT |
| ATOM | 132 | O | GLU | 218 | 30.182 | 12.490 | 35.495 | 1.00 | 24.30 PROT |
| ATOM | 133 | N | TRP | 219 | 28.907 | 12.080 | 37.288 | 1.00 | 13.98 PROT |
| ATOM | 134 | CA | TRP | 219 | 28.829 | 10.660 | 37.000 | 1.00 | 17.30 PROT |
| ATOM | 135 | CB | TRP | 219 | 28.052 | 9.921 | 38.089 | 1.00 | 16.27 PROT |
| ATOM | 136 | CG | TRP | 219 | 28.890 | 9.520 | 39.277 | 1.00 | 31.14 PROT |
| ATOM | 137 | CD2 | TRP | 219 | 29.984 | 8.585 | 39.296 | 1.00 | 36.40 PROT |
| ATOM | 138 | CE2 | TRP | 219 | 30.476 | 8.547 | 40.621 | 1.00 | 29.24 PROT |
| ATOM | 139 | CE3 | TRP | 219 | 30.595 | 7.781 | 38.323 | 1.00 | 41.61 PROT |
| ATOM | 140 | CD1 | TRP | 219 | 28.771 | 9.988 | 40.551 | 1.00 | 28.69 PROT |
| ATOM | 141 | NE1 | TRP | 219 | 29.718 | 9.411 | 41.362 | 1.00 | 35.01 PROT |
| ATOM | 142 | CZ2 | TRP | 219 | 31.552 | 7.737 | 41.004 | 1.00 | 30.89 PROT |
| ATOM | 143 | CZ3 | TRP | 219 | 31.673 | 6.969 | 38.707 | 1.00 | 45.72 PROT |
| ATOM | 144 | CH2 | TRP | 219 | 32.137 | 6.958 | 40.038 | 1.00 | 35.17 PROT |
| ATOM | 145 | C | TRP | 219 | 28.125 | 10.500 | 35.660 | 1.00 | 20.83 PROT |
| ATOM | 146 | O | TRP | 219 | 28.467 | 9.616 | 34.865 | 1.00 | 31.36 PROT |
| ATOM | 147 | N | GLU | 220 | 27.143 | 11.364 | 35.412 | 1.00 | 30.53 PROT |
| ATOM | 148 | CA | GLU | 226 | 26.400 | 11.323 | 34.159 | 1.00 | 33.95 PROT |
| ATOM | 149 | CB | GLU | 220 | 25.237 | 12.318 | 34.201 | 1.00 | 22.17 PROT |
| ATOM | 150 | C | GLU | 220 | 27.356 | 11.658 | 33.013 | 1.00 | 34.66 PROT |

APPENDIX 7-continued

TRBTRIAC.PDB

| ATOM | 151 | O   | GLU | 220 | 27.233 | 11.134 | 31.900 | 1.00 | 43.86 | PROT |
|------|-----|-----|-----|-----|--------|--------|--------|------|-------|------|
| ATOM | 152 | N   | LEU | 221 | 28.320 | 12.528 | 33.297 | 1.00 | 22.60 | PROT |
| ATOM | 153 | CA  | LEU | 221 | 29.305 | 12.926 | 32.304 | 1.00 | 17.18 | PROT |
| ATOM | 154 | CB  | LEU | 221 | 29.995 | 14.219 | 32.743 | 1.00 | 11.03 | PROT |
| ATOM | 155 | CG  | LEU | 221 | 31.078 | 14.824 | 31.850 | 1.00 | 5.17  | PROT |
| ATOM | 156 | CD1 | LEU | 221 | 30.756 | 14.569 | 30.415 | 1.00 | 6.41  | PROT |
| ATOM | 157 | CD2 | LEU | 221 | 31.181 | 16.305 | 32.092 | 1.00 | 10.65 | PROT |
| ATOM | 158 | C   | LEU | 221 | 30.344 | 11.817 | 32.122 | 1.00 | 22.25 | PROT |
| ATOM | 159 | O   | LEU | 221 | 30.759 | 11.521 | 31.092 | 1.00 | 18.99 | PROT |
| ATOM | 160 | N   | ILE | 222 | 30.754 | 11.198 | 33.228 | 1.00 | 20.74 | PROT |
| ATOM | 161 | CA  | ILE | 222 | 31.744 | 10.136 | 33.177 | 1.00 | 12.88 | PROT |
| ATOM | 162 | CB  | ILE | 222 | 32.115 | 9.662  | 34.587 | 1.00 | 12.96 | PROT |
| ATOM | 163 | CG2 | ILE | 222 | 33.030 | 8.468  | 34.515 | 1.00 | 2.00  | PROT |
| ATOM | 164 | CG1 | ILE | 222 | 32.811 | 10.796 | 35.332 | 1.00 | 16.50 | PROT |
| ATOM | 165 | CD1 | ILE | 222 | 33.625 | 10.351 | 36.511 | 1.00 | 15.90 | PROT |
| ATOM | 166 | C   | ILE | 222 | 31.241 | 8.958  | 32.363 | 1.00 | 17.72 | PROT |
| ATOM | 167 | O   | ILE | 222 | 32.001 | 8.363  | 31.594 | 1.00 | 16.59 | PROT |
| ATOM | 168 | N   | LYS | 223 | 29.966 | 8.618  | 32.530 | 1.00 | 33.88 | PROT |
| ATOM | 169 | CA  | LYS | 223 | 29.371 | 7.503  | 31.795 | 1.00 | 39.02 | PROT |
| ATOM | 170 | CB  | LYS | 223 | 27.908 | 7.307  | 32.224 | 1.00 | 40.29 | PROT |
| ATOM | 171 | C   | LYS | 223 | 29.444 | 7.779  | 30.293 | 1.00 | 39.14 | PROT |
| ATOM | 172 | O   | LYS | 223 | 29.949 | 6.963  | 29.517 | 1.00 | 32.99 | PROT |
| ATOM | 173 | N   | THR | 224 | 28.936 | 8.942  | 29.897 | 1.00 | 27.19 | PROT |
| ATOM | 174 | CA  | THR | 224 | 28.929 | 9.363  | 28.498 | 1.00 | 25.75 | PROT |
| ATOM | 175 | CB  | THR | 224 | 28.440 | 10.817 | 28.407 | 1.00 | 22.51 | PROT |
| ATOM | 176 | OG1 | THR | 224 | 27.018 | 10.837 | 28.568 | 1.00 | 35.46 | PROT |
| ATOM | 177 | CG2 | THR | 224 | 28.799 | 11.436 | 27.083 | 1.00 | 15.53 | PROT |
| ATOM | 178 | C   | THR | 224 | 30.307 | 9.235  | 27.833 | 1.00 | 22.31 | PROT |
| ATOM | 179 | O   | THR | 224 | 30.480 | 8.517  | 26.843 | 1.00 | 27.13 | PROT |
| ATOM | 180 | N   | VAL | 225 | 31.287 | 9.936  | 28.386 | 1.00 | 17.87 | PROT |
| ATOM | 181 | CA  | VAL | 225 | 32.635 | 9.906  | 27.854 | 1.00 | 17.07 | PROT |
| ATOM | 182 | CB  | VAL | 225 | 33.559 | 10.759 | 28.720 | 1.00 | 16.86 | PROT |
| ATOM | 183 | CG1 | VAL | 225 | 34.845 | 11.064 | 27.973 | 1.00 | 26.54 | PROT |
| ATOM | 184 | CG2 | VAL | 225 | 32.854 | 12.057 | 29.075 | 1.00 | 24.46 | PROT |
| ATOM | 185 | C   | VAL | 225 | 33.169 | 8.486  | 27.793 | 1.00 | 16.11 | PROT |
| ATOM | 186 | O   | VAL | 225 | 33.683 | 8.042  | 26.763 | 1.00 | 12.75 | PROT |
| ATOM | 187 | N   | THR | 226 | 33.040 | 7.769  | 28.900 | 1.00 | 12.23 | PROT |
| ATOM | 188 | CA  | THR | 226 | 33.520 | 6.400  | 28.951 | 1.00 | 12.34 | PROT |
| ATOM | 189 | CB  | THR | 226 | 33.175 | 5.747  | 30.271 | 1.00 | 17.01 | PROT |
| ATOM | 190 | OG1 | THR | 226 | 33.715 | 6.536  | 31.342 | 1.00 | 6.78  | PROT |
| ATOM | 191 | CG2 | THR | 226 | 33.739 | 4.324  | 30.307 | 1.00 | 2.00  | PROT |
| ATOM | 192 | C   | THR | 226 | 32.909 | 5.581  | 27.837 | 1.00 | 14.82 | PROT |
| ATOM | 193 | O   | THR | 226 | 33.623 | 4.953  | 27.061 | 1.00 | 20.90 | PROT |
| ATOM | 194 | N   | GLU | 227 | 31.582 | 5.588  | 27.758 | 1.00 | 22.90 | PROT |
| ATOM | 195 | CA  | GLU | 227 | 30.886 | 4.849  | 26.714 | 1.00 | 22.63 | PROT |
| ATOM | 196 | CB  | GLU | 227 | 29.417 | 5.248  | 26.678 | 1.00 | 20.14 | PROT |
| ATOM | 197 | C   | GLU | 227 | 31.556 | 5.173  | 25.386 | 1.00 | 21.74 | PROT |
| ATOM | 198 | O   | GLU | 227 | 32.057 | 4.283  | 24.700 | 1.00 | 24.42 | PROT |
| ATOM | 199 | N   | ALA | 228 | 31.590 | 6.460  | 25.050 | 1.00 | 13.26 | PROT |
| ATOM | 200 | CA  | ALA | 228 | 32.196 | 6.928  | 23.800 | 1.00 | 22.76 | PROT |
| ATOM | 201 | CB  | ALA | 228 | 32.267 | 8.450  | 23.785 | 1.00 | 22.50 | PROT |
| ATOM | 202 | C   | ALA | 228 | 33.584 | 6.358  | 23.538 | 1.00 | 19.19 | PROT |
| ATOM | 203 | O   | ALA | 228 | 33.913 | 6.003  | 22.408 | 1.00 | 17.19 | PROT |
| ATOM | 204 | N   | HIS | 229 | 34.408 | 6.290  | 24.573 | 1.00 | 20.11 | PROT |
| ATOM | 205 | CA  | HIS | 229 | 35.741 | 5.756  | 24.389 | 1.00 | 18.68 | PROT |
| ATOM | 206 | CB  | HIS | 229 | 36.537 | 5.819  | 25.686 | 1.00 | 10.37 | PROT |
| ATOM | 207 | CG  | HIS | 229 | 37.894 | 5.201  | 25.586 | 1.00 | 2.00  | PROT |
| ATOM | 208 | CD2 | HIS | 229 | 38.524 | 4.299  | 26.376 | 1.00 | 7.61  | PROT |
| ATOM | 209 | ND1 | HIS | 229 | 38.780 | 5.517  | 24.582 | 1.00 | 3.78  | PROT |
| ATOM | 210 | CE1 | HIS | 229 | 39.900 | 4.837  | 24.758 | 1.00 | 15.67 | PROT |
| ATOM | 211 | NE2 | HIS | 229 | 39.771 | 4.090  | 25.840 | 1.00 | 7.10  | PROT |
| ATOM | 212 | C   | HIS | 229 | 35.637 | 4.316  | 23.940 | 1.00 | 21.45 | PROT |
| ATOM | 213 | O   | HIS | 229 | 36.127 | 3.950  | 22.866 | 1.00 | 22.42 | PROT |
| ATOM | 214 | N   | VAL | 230 | 34.983 | 3.505  | 24.762 | 1.00 | 21.64 | PROT |
| ATOM | 215 | CA  | VAL | 230 | 34.827 | 2.086  | 24.468 | 1.00 | 33.80 | PROT |
| ATOM | 216 | CB  | VAL | 230 | 33.960 | 1.388  | 25.528 | 1.00 | 33.11 | PROT |
| ATOM | 217 | CG1 | VAL | 230 | 34.251 | -0.106 | 25.515 | 1.00 | 33.80 | PROT |
| ATOM | 218 | CG2 | VAL | 230 | 34.228 | 1.985  | 26.896 | 1.00 | 26.54 | PROT |
| ATOM | 219 | C   | VAL | 230 | 34.224 | 1.781  | 23.100 | 1.00 | 33.12 | PROT |
| ATOM | 220 | O   | VAL | 230 | 34.703 | 0.897  | 22.385 | 1.00 | 40.80 | PROT |
| ATOM | 221 | N   | ALA | 231 | 33.170 | 2.507  | 22.746 | 1.00 | 36.22 | PROT |
| ATOM | 222 | CA  | ALA | 231 | 32.497 | 2.298  | 21.471 | 1.00 | 36.24 | PROT |
| ATOM | 223 | CB  | ALA | 231 | 31.318 | 3.255  | 21.343 | 1.00 | 18.90 | PROT |
| ATOM | 224 | C   | ALA | 231 | 33.445 | 2.501  | 20.303 | 1.00 | 37.54 | PROT |
| ATOM | 225 | O   | ALA | 231 | 33.342 | 1.816  | 19.285 | 1.00 | 35.93 | PROT |
| ATOM | 226 | N   | THR | 232 | 34.380 | 3.434  | 20.474 | 1.00 | 23.74 | PROT |
| ATOM | 227 | CA  | THR | 232 | 35.329 | 3.789  | 19.432 | 1.00 | 15.54 | PROT |

APPENDIX 7-continued

| | | | | TRBTRIAC.PDB | | | | | |
|---|---|---|---|---|---|---|---|---|---|
| ATOM | 228 | CB | THR | 232 | 35.335 | 5.321 | 19.238 | 1.00 | 9.70 PROT |
| ATOM | 229 | OG1 | THR | 232 | 35.733 | 5.949 | 20.460 | 1.00 | 16.73 PROT |
| ATOM | 230 | CG2 | THR | 232 | 33.942 | 5.828 | 18.891 | 1.00 | 2.00 PROT |
| ATOM | 231 | C | THR | 232 | 36.758 | 3.309 | 19.670 | 1.00 | 19.86 PROT |
| ATOM | 232 | O | THR | 232 | 37.695 | 3.854 | 19.094 | 1.00 | 15.31 PROT |
| ATOM | 233 | N | ASN | 233 | 36.938 | 2.305 | 20.523 | 1.00 | 28.26 PROT |
| ATOM | 234 | CA | ASN | 233 | 3&280 | 1.771 | 20.772 | 1.00 | 39.32 PROT |
| ATOM | 235 | CB | ASN | 233 | 38.435 | 1.343 | 22.234 | 1.00 | 47.14 PROT |
| ATOM | 236 | CG | ASN | 233 | 39.804 | 1.689 | 22.801 | 1.00 | 54.02 PROT |
| ATOM | 237 | OD1 | ASN | 233 | 40.633 | 2.303 | 22.128 | 1.00 | 60.36 PROT |
| ATOM | 238 | ND2 | ASN | 233 | 40.045 | 1.296 | 24.045 | 1.00 | 48.67 PROT |
| ATOM | 239 | C | ASN | 233 | 38.507 | 0.574 | 19.840 | 1.00 | 49.33 PROT |
| ATOM | 240 | O | ASN | 233 | 38.338 | 0.693 | 18.625 | 1.00 | 65.36 PROT |
| ATOM | 241 | N | ALA | 234 | 38.877 | −0.577 | 20.388 | 1.00 | 57.89 PROT |
| ATOM | 242 | CA | ALA | 234 | 39.090 | −1.752 | 19.552 | 1.00 | 57.22 PROT |
| ATOM | 243 | CB | ALA | 234 | 40.372 | −1.595 | 18.754 | 1.00 | 48.03 PROT |
| ATOM | 244 | C | ALA | 234 | 39.141 | −3.027 | 20.384 | 1.00 | 62.42 PROT |
| ATOM | 245 | O | ALA | 234 | 38.471 | −3.073 | 21.440 | 1.00 | 56.93 PROT |
| ATOM | 246 | OT | ALA | 234 | 39.853 | −3.968 | 19.965 | 1.00 | 76.16 PROT |
| ATOM | 247 | N | TRP | 239 | 41.987 | −7.449 | 22.970 | 1.00 | 58.82 PROT |
| ATOM | 248 | CA | TRP | 239 | 43.077 | −6.886 | 22.154 | 1.00 | 51.37 PROT |
| ATOM | 249 | CB | TRP | 239 | 43.325 | −5.406 | 22.534 | 1.00 | 45.12 PROT |
| ATOM | 250 | CG | TRP | 239 | 44.193 | −5.170 | 23.760 | 1.00 | 43.09 PROT |
| ATOM | 251 | CD2 | TRP | 239 | 45.617 | −5.037 | 23.793 | 1.00 | 32.36 PROT |
| ATOM | 252 | CE2 | TRP | 239 | 45.990 | −4.872 | 25.142 | 1.00 | 28.37 PROT |
| ATOM | 253 | CE3 | TRP | 239 | 46.615 | −5.049 | 22.813 | 1.00 | 40.79 PROT |
| ATOM | 254 | CD1 | TRP | 239 | 43.773 | −5.073 | 25.059 | 1.00 | 46.63 PROT |
| ATOM | 255 | NE1 | TRP | 239 | 44.847 | −4.896 | 25.893 | 1.00 | 27.08 PROT |
| ATOM | 256 | CZ2 | TRP | 239 | 47.315 | 4.717 | 25.535 | 1.00 | 35.48 PROT |
| ATOM | 257 | CZ3 | TRP | 239 | 47.936 | −4.896 | 23.204 | 1.00 | 40.18 PROT |
| ATOM | 258 | CH2 | TRP | 239 | 48.273 | 4.733 | 24.554 | 1.00 | 49.93 PROT |
| ATOM | 259 | C | TRP | 239 | 44.422 | −7.623 | 22.063 | 1.00 | 49.76 PROT |
| ATOM | 260 | O | TRP | 239 | 44.944 | −7.799 | 20.962 | 1.00 | 48.14 PROT |
| ATOM | 261 | N | LYS | 240 | 44.975 | −8.048 | 23.198 | 1.00 | 38.92 PROT |
| ATOM | 262 | CA | LYS | 240 | 46.263 | −8.735 | 23.232 | 1.00 | 37.29 PROT |
| ATOM | 263 | CB | LYS | 240 | 46.572 | −9.196 | 24.657 | 1.00 | 38.79 PROT |
| ATOM | 264 | CG | LYS | 240 | 47.106 | −8.099 | 25.571 | 1.00 | 38.43 PROT |
| ATOM | 265 | CD | LYS | 240 | 48.307 | −8.584 | 26.370 | 1.00 | 35.71 PROT |
| ATOM | 266 | CE | LYS | 240 | 48.631 | −7.646 | 27.523 | 1.00 | 37.87 PROT |
| ATOM | 267 | NZ | LYS | 240 | 49.058 | −8.377 | 28.750 | 1.00 | 28.85 PROT |
| ATOM | 268 | C | LYS | 240 | 46A04 | −9.914 | 22.269 | 1.00 | 42.18 PROT |
| ATOM | 269 | O | LYS | 240 | 47.491 | −10.132 | 21.732 | 1.00 | 45.89 PROT |
| ATOM | 270 | N | GLN | 241 | 45.331 | −10.679 | 22.058 | 1.00 | 46.08 PROT |
| ATOM | 271 | CA | GLN | 241 | 45.390 | −11.816 | 21.133 | 1.00 | 45.02 PROT |
| ATOM | 272 | CB | GLN | 241 | 44.575 | −13.011 | 21.638 | 1.00 | 46.30 PROT |
| ATOM | 273 | CG | GLN | 241 | 44.284 | −13.018 | 23.116 | 1.00 | 60.38 PROT |
| ATOM | 274 | CD | GLN | 241 | 42.828 | −13.312 | 23.408 | 1.00 | 63.76 PROT |
| ATOM | 275 | OE1 | GLN | 241 | 42.154 | −13.988 | 22.631 | 1.00 | 66.34 PROT |
| ATOM | 276 | NE2 | GLN | 241 | 42.333 | −12.801 | 24.531 | 1.00 | 69.18 PROT |
| ATOM | 277 | C | GLN | 241 | 44.866 | −11.405 | 19.764 | 1.00 | 45.77 PROT |
| ATOM | 278 | O | GLN | 241 | 45.107 | −12.085 | 18.765 | 1.00 | 51.18 PROT |
| ATOM | 279 | N | LYS | 242 | 44.132 | −10.300 | 19.723 | 1.00 | 42.04 PROT |
| ATOM | 280 | CA | LYS | 242 | 43.613 | −9.794 | 18.464 | 1.00 | 48.33 PROT |
| ATOM | 281 | CB | LYS | 242 | 42.498 | −8.786 | 18.727 | 1.00 | 40.17 PROT |
| ATOM | 282 | C | LYS | 242 | 44.796 | −9.123 | 17.742 | 1.00 | 53.04 PROT |
| ATOM | 283 | O | LYS | 242 | 44.709 | −8.753 | 16.565 | 1.00 | 48.21 PROT |
| ATOM | 284 | N | ARG | 243 | 45.906 | −8.992 | 18.470 | 1.00 | 45.44 PROT |
| ATOM | 285 | CA | ARG | 243 | 47.128 | −8.374 | 17.965 | 1.00 | 43.53 PROT |
| ATOM | 286 | CB | ARG | 243 | 48.108 | −8.135 | 19.118 | 1.00 | 40.21 PROT |
| ATOM | 287 | C | ARG | 243 | 47.795 | −9.220 | 16.892 | 1.00 | 45.96 PROT |
| ATOM | 288 | O | ARG | 243 | 47.684 | −10.443 | 16.894 | 1.00 | 50.22 PROT |
| ATOM | 289 | N | LYS | 244 | 48.498 | −8.551 | 15.982 | 1.00 | 52.12 PROT |
| ATOM | 290 | CA | LYS | 244 | 49.202 | −9.262 | 14.879 | 1.00 | 45.30 PROT |
| ATOM | 291 | CB | LYS | 244 | 48.466 | −8.950 | 13.558 | 1.00 | 48.24 PROT |
| ATOM | 292 | CG | LYS | 244 | 47.109 | −9.631 | 13.446 | 1.00 | 53.78 PROT |
| ATOM | 293 | CD | LYS | 244 | 46.835 | −10.078 | 12.011 | 1.00 | 60.50 PROT |
| ATOM | 294 | CE | LYS | 244 | 46.038 | −9.030 | 11.241 | 1.00 | 61.03 PROT |
| ATOM | 295 | NZ | LYS | 244 | 45.455 | −7.997 | 12.146 | 1.00 | 55.25 PROT |
| ATOM | 296 | C | LYS | 244 | 50.616 | −8.641 | 14.786 | 1.00 | 40.33 PROT |
| ATOM | 297 | O | LYS | 244 | 50.849 | −7.629 | 14.125 | 1.00 | 36.07 PROT |
| ATOM | 298 | N | PHE | 245 | 51.556 | −9.312 | 15.445 | 1.00 | 27.87 PROT |
| ATOM | 299 | CA | PHE | 245 | 52.949 | −8.885 | 15.461 | 1.00 | 30.61 PROT |
| ATOM | 300 | CB | PHE | 245 | 53.784 | −9.887 | 16.253 | 1.00 | 20.28 PROT |
| ATOM | 301 | CG | PHE | 245 | 53.454 | −9.922 | 17.713 | 1.00 | 37.23 PROT |
| ATOM | 302 | CD1 | PHE | 245 | 52.636 | −10.917 | 18.234 | 1.00 | 40.93 PROT |
| ATOM | 303 | CD2 | PHE | 245 | 53.958 | −8.959 | 18.577 | 1.00 | 41.60 PROT |
| ATOM | 304 | CE1 | PHE | 245 | 52.326 | −10.953 | 19.594 | 1.00 | 42.54 PROT |

APPENDIX 7-continued

TRBTRIAC.PDB

| ATOM | 305 | CE2 | PHE | 245 | 53.652 | −8.989 | 19.936 | 1.00 | 45.84 | PROT |
|---|---|---|---|---|---|---|---|---|---|---|
| ATOM | 306 | CZ | PHE | 245 | 52.835 | −9.988 | 20.443 | 1.00 | 33.72 | PROT |
| ATOM | 307 | C | PHE | 245 | 53.549 | −8.693 | 14.068 | 1.00 | 38.75 | PROT |
| ATOM | 308 | O | PHE | 245 | 53.794 | −9.660 | 13.337 | 1.00 | 48.93 | PROT |
| ATOM | 309 | N | LEU | 246 | 53.789 | −7.437 | 13.704 | 1.00 | 41.18 | PROT |
| ATOM | 310 | CA | LEU | 246 | 54.362 | −7.124 | 12.404 | 1.00 | 43.43 | PROT |
| ATOM | 311 | CB | LEU | 246 | 54.378 | −5.612 | 12.181 | 1.00 | 42.78 | PROT |
| ATOM | 312 | CG | LEU | 246 | 54.535 | −5.200 | 10.718 | 1.00 | 49.88 | PROT |
| ATOM | 313 | CD1 | LEU | 246 | 53.528 | 4.113 | 10.365 | 1.00 | 40.64 | PROT |
| ATOM | 314 | CD2 | LEU | 246 | 55.966 | 4.730 | 10.485 | 1.00 | 48.66 | PROT |
| ATOM | 315 | C | LEU | 246 | 55.777 | −7.692 | 12.250 | 1.00 | 42.60 | PROT |
| ATOM | 316 | O | LEU | 246 | 56.677 | −7.383 | 13.028 | 1.00 | 45.75 | PROT |
| ATOM | 317 | N | PRO | 247 | 55.977 | −8.540 | 11.233 | 1.00 | 50.03 | PROT |
| ATOM | 318 | CD | PRO | 247 | 54.914 | −8.924 | 10.286 | 1.00 | 60.17 | PROT |
| ATOM | 319 | CA | PRO | 247 | 57.237 | −9.199 | 10.894 | 1.00 | 49.90 | PROT |
| ATOM | 320 | CB | PRO | 247 | 57.181 | −9.282 | 9.369 | 1.00 | 59.51 | PROT |
| ATOM | 321 | CG | PRO | 247 | 55.678 | −9.244 | 9.023 | 1.00 | 52.86 | PROT |
| ATOM | 322 | C | PRO | 247 | 58.499 | −8.494 | 11.392 | 1.00 | 48.85 | PROT |
| ATOM | 323 | O | PRO | 247 | 58.675 | −7.295 | 11.186 | 1.00 | 49.28 | PROT |
| ATOM | 324 | N | GLU | 248 | 59.379 | −9.261 | 12.032 | 1.00 | 47.62 | PROT |
| ATOM | 325 | CA | GLU | 248 | 60.628 | −8.733 | 12.574 | 1.00 | 51.41 | PROT |
| ATOM | 326 | CB | GLU | 248 | 61.266 | −9.750 | 13.522 | 1.00 | 44.22 | PROT |
| ATOM | 327 | C | GLU | 248 | 61.623 | −8.354 | 11.490 | 1.00 | 53.28 | PROT |
| ATOM | 328 | O | GLU | 248 | 62.815 | −8.214 | 11.765 | 1.00 | 62.57 | PROT |
| ATOM | 329 | N | ASP | 249 | 61.146 | −8.200 | 10.258 | 1.00 | 56.20 | PROT |
| ATOM | 330 | CA | ASP | 249 | 62.030 | −7.818 | 9.164 | 1.00 | S5.88 | PROT |
| ATOM | 331 | CB | ASP | 249 | 62.231 | −8.981 | 8.173 | 1.00 | 53.88 | PROT |
| ATOM | 332 | CG | ASP | 249 | 60.928 | −9.637 | 7.739 | 1.00 | 54.39 | PROT |
| ATOM | 333 | OD1 | ASP | 249 | 60.578 | −10.693 | 8.310 | 1.00 | 57.70 | PROT |
| ATOM | 334 | OD2 | ASP | 249 | 60.264 | −9.112 | 6.819 | 1.00 | 45.76 | PROT |
| ATOM | 335 | C | ASP | 249 | 61.539 | −6.567 | 8.437 | 1.00 | 54.20 | PROT |
| ATOM | 336 | O | ASP | 249 | 62.119 | −6.154 | 7.429 | 1.00 | 55.31 | PROT |
| ATOM | 337 | N | ILE | 250 | 60.469 | −5.965 | 8.954 | 1.00 | 46.13 | PROT |
| ATOM | 338 | CA | ILE | 250 | 59.933 | 4.735 | 8.376 | 1.00 | 46.12 | PROT |
| ATOM | 339 | CB | ILE | 250 | 58.413 | −4.764 | 8.253 | 1.00 | 43.38 | PROT |
| ATOM | 340 | CG2 | ILE | 250 | 57.892 | −3.344 | 8.057 | 1.00 | 39.15 | PROT |
| ATOM | 341 | CG1 | ILE | 250 | 58.007 | −5.654 | 7.074 | 1.00 | 48.96 | PROT |
| ATOM | 342 | CD1 | ILE | 250 | 56.707 | −6.401 | 7.283 | 1.00 | 43.14 | PROT |
| ATOM | 343 | C | ILE | 250 | 60.311 | −3.590 | 9.294 | 1.00 | 45.32 | PROT |
| ATOM | 344 | O | ILE | 250 | 60.257 | −3.724 | 10.513 | 1.00 | 43.74 | PROT |
| ATOM | 345 | N | GLY | 251 | 60.680 | −2.459 | 8.711 | 1.00 | 36.80 | PROT |
| ATOM | 346 | CA | GLY | 251 | 61.091 | −1.329 | 9.521 | 1.00 | 39.28 | PROT |
| ATOM | 347 | C | GLY | 251 | 62.370 | −1.621 | 10.305 | 1.00 | 44.31 | PROT |
| ATOM | 348 | O | GLY | 251 | 62.538 | −1.145 | 11.428 | 1.00 | 51.39 | PROT |
| ATOM | 349 | N | GLN | 252 | 63.277 | −2.399 | 9.715 | 1.00 | 55.47 | PROT |
| ATOM | 350 | CA | GLN | 252 | 64.536 | −2.745 | 10.374 | 1.00 | 54.24 | PROT |
| ATOM | 351 | CB | GLN | 252 | 64.792 | −4.237 | 10.245 | 1.00 | 49.31 | PROT |
| ATOM | 352 | C | GLN | 252 | 65.720 | −1.959 | 9.812 | 1.00 | 54.86 | PROT |
| ATOM | 353 | O | GLN | 252 | 65.492 | −1.079 | 8.953 | 1.00 | 58.80 | PROT |
| ATOM | 354 | CB | VAL | 264 | 60.887 | 6.759 | 5.510 | 1.00 | 34.33 | PROT |
| ATOM | 355 | CG1 | VAL | 264 | 59.550 | 6.086 | 5.790 | 1.00 | 34.34 | PROT |
| ATOM | 356 | CG2 | VAL | 264 | 60.893 | 8.163 | 6.080 | 1.00 | 20.22 | PROT |
| ATOM | 357 | C | VAL | 264 | 62.053 | 4.557 | 5.439 | 1.00 | 34.08 | PROT |
| ATOM | 358 | O | VAL | 264 | 62.280 | 4.466 | 4.232 | 1.00 | 46.39 | PROT |
| ATOM | 359 | N | VAL | 264 | 63.361 | 6.605 | 5.966 | 1.00 | 21.27 | PROT |
| ATOM | 360 | CA | VAL | 264 | 62.041 | 5.920 | 6.122 | 1.00 | 29.68 | PROT |
| ATOM | 361 | N | ASP | 265 | 61.809 | 3.499 | 6.209 | 1.00 | 40.63 | PROT |
| ATOM | 362 | CA | ASP | 265 | 61.796 | 2.141 | 5.670 | 1.00 | 43.58 | PROT |
| ATOM | 363 | CB | ASP | 265 | 61.243 | 1.160 | 6.704 | 1.00 | 44.07 | PROT |
| ATOM | 364 | CG | ASP | 265 | 61.179 | −0.262 | 6.185 | 1.00 | 49.19 | PROT |
| ATOM | 365 | OD1 | ASP | 265 | 62.223 | −0.945 | 6.175 | 1.00 | 57.67 | PROT |
| ATOM | 366 | OD2 | ASP | 265 | 60.082 | −0.702 | 5.789 | 1.00 | 54.75 | PROT |
| ATOM | 367 | C | ASP | 265 | 60.956 | 2.071 | 4.401 | 1.00 | 48.03 | PROT |
| ATOM | 368 | O | ASP | 265 | 61.362 | 1.458 | 3.411 | 1.00 | 57.44 | PROT |
| ATOM | 369 | N | LEU | 266 | 59.793 | 2.711 | 4.436 | 1.00 | 40.55 | PROT |
| ATOM | 370 | CA | LEU | 266 | 58.879 | 2.741 | 3.295 | 1.00 | 45.78 | PROT |
| ATOM | 371 | CB | LEU | 266 | 59.638 | 2.962 | 1.977 | 1.00 | 45.92 | PROT |
| ATOM | 372 | CG | LEU | 266 | 59.881 | 4.407 | 1.506 | 1.00 | 48.41 | PROT |
| ATOM | 373 | CD1 | LEU | 266 | 59.934 | 4.432 | −0.007 | 1.00 | 32.83 | PROT |
| ATOM | 374 | CD2 | LEU | 266 | 58.787 | 5.344 | 2.012 | 1.00 | 45.08 | PROT |
| ATOM | 375 | C | LEU | 266 | 58.064 | 1.462 | 3.21 | 1.00 | 45.45 | PROT |
| ATOM | 376 | O | LEU | 266 | 56.862 | 1.503 | 2.949 | 1.00 | 42.92 | PROT |
| ATOM | 377 | N | GLU | 267 | 58.712 | 0.324 | 3.431 | 1.00 | 46.47 | PROT |
| ATOM | 378 | CA | GLU | 267 | 57.986 | −0.935 | 3.415 | 1.00 | 44.34 | PROT |
| ATOM | 379 | CB | GLU | 267 | 58.943 | −2.123 | 3.505 | 1.00 | 39.42 | PROT |
| ATOM | 380 | CG | GLU | 267 | 58.291 | −3.457 | 3.188 | 1.00 | 40.68 | PROT |
| ATOM | 381 | CD | GLU | 267 | 58.929 | −4.607 | 3.943 | 1.00 | 63.54 | PROT |

APPENDIX 7-continued

TRBTRIAC.PDB

| ATOM | 382 | OE1 | GLU | 267 | 60.103 | −4.470 | 4.361 | 1.00 | 68.92 | PROT |
|---|---|---|---|---|---|---|---|---|---|---|
| ATOM | 383 | OE2 | GLU | 267 | 58.258 | −5.650 | 4.120 | 1.00 | 66.66 | PROT |
| ATOM | 384 | C | GLU | 267 | 57.106 | −0.880 | 4.655 | 1.00 | 41.57 | PROT |
| ATOM | 385 | O | GLU | 267 | 55.991 | −1.398 | 4.673 | 1.00 | 48.68 | PROT |
| ATOM | 386 | N | ALA | 268 | 57.620 | −0.215 | 5.686 | 1.00 | 39.33 | PROT |
| ATOM | 387 | CA | ALA | 268 | 56.916 | −0.057 | 6.951 | 1.00 | 31.62 | PROT |
| ATOM | 388 | CB | ALA | 268 | 57.918 | 0.134 | 8.063 | 1.00 | 7.56 | PROT |
| ATOM | 389 | C | ALA | 268 | 55.960 | 1.135 | 6.888 | 1.00 | 25.96 | PROT |
| ATOM | 390 | O | ALA | 268 | 54.786 | 1.036 | 7.237 | 1.00 | 17.35 | PROT |
| ATOM | 391 | N | PHE | 269 | 56.464 | 2.274 | 6.446 | 1.00 | 11.34 | PROT |
| ATOM | 392 | CA | PHE | 269 | 55.615 | 3.453 | 6.335 | 1.00 | 15.72 | PROT |
| ATOM | 393 | CB | PHE | 269 | 56.274 | 4.474 | 5.405 | 1.00 | 20.08 | PROT |
| ATOM | 394 | CG | PHE | 269 | 55.552 | 5.788 | 5.334 | 1.00 | 24.67 | PROT |
| ATOM | 395 | CD1 | PHE | 269 | 55.661 | 6.713 | 6.369 | 1.00 | 15.69 | PROT |
| ATOM | 396 | CD2 | PHE | 269 | 54.772 | 6.111 | 4.222 | 1.00 | 20.64 | PROT |
| ATOM | 397 | CE1 | PHE | 269 | 55.003 | 7.942 | 6.300 | 1.00 | 22.55 | PROT |
| ATOM | 398 | CE2 | PHE | 269 | 54.108 | 7.342 | 4.143 | 1.00 | 19.77 | PROT |
| ATOM | 399 | CZ | PHE | 269 | 54.224 | 8.257 | 5.186 | 1.00 | 19.27 | PROT |
| ATOM | 400 | C | PHE | 269 | 54.277 | 3.010 | 5.754 | 1.00 | 19.45 | PROT |
| ATOM | 401 | O | PHE | 269 | 53.212 | 3.351 | 6.261 | 1.00 | 13.40 | PROT |
| ATOM | 402 | N | SER | 270 | 54.367 | 2.214 | 4.692 | 1.00 | 43.85 | PROT |
| ATOM | 403 | CA | SER | 270 | 53.217 | 1.686 | 3.967 | 1.00 | 46.67 | PROT |
| ATOM | 404 | CB | SER | 270 | 53.687 | 0.669 | 2.924 | 1.00 | 53.60 | PROT |
| ATOM | 405 | OG | SER | 270 | 52.662 | 0.382 | 1.988 | 1.00 | 68.82 | PROT |
| ATOM | 406 | C | SER | 270 | 52.181 | 1.039 | 4.865 | 1.00 | 43.32 | PROT |
| ATOM | 407 | O | SER | 270 | 51.024 | 1.459 | 4.893 | 1.00 | 43.87 | PROT |
| ATOM | 408 | N | HIS | 271 | 52.594 | 0.009 | 5.590 | 1.00 | 34.59 | PROT |
| ATOM | 409 | CA | HIS | 271 | 51.681 | −0.694 | 6.486 | 1.00 | 37.12 | PROT |
| ATOM | 410 | CB | HIS | 271 | 52.441 | −1.772 | 7.266 | 1.00 | 46.61 | PROT |
| ATOM | 411 | CG | HIS | 271 | 52.603 | −3.056 | 6.512 | 1.00 | 63.99 | PROT |
| ATOM | 412 | CD2 | HIS | 271 | 51.879 | 4.201 | 6.533 | 1.00 | 62.06 | PROT |
| ATOM | 413 | ND1 | HIS | 271 | 53.608 | −3.256 | 5.590 | 1.00 | 60.86 | PROT |
| ATOM | 414 | CE1 | HIS | 271 | 53.497 | 4.467 | 5.075 | 1.00 | 60.70 | PROT |
| ATOM | 415 | NE2 | HIS | 271 | 52.456 | −5.061 | 5.630 | 1.00 | 64.10 | PROT |
| ATOM | 416 | C | HIS | 271 | 50.973 | 0.261 | 7.459 | 1.00 | 36.53 | PROT |
| ATOM | 417 | O | HIS | 271 | 49.744 | 0.245 | 7.586 | 1.00 | 37.75 | PROT |
| ATOM | 418 | N | PHE | 272 | 51.752 | 1.099 | 8.133 | 1.00 | 32.81 | PROT |
| ATOM | 419 | CA | PHE | 272 | 51.190 | 2.038 | 9.085 | 1.00 | 27.77 | PROT |
| ATOM | 420 | CB | PHE | 272 | 52.302 | 2.886 | 9.714 | 1.00 | 10.49 | PROT |
| ATOM | 421 | CG | PHE | 272 | 53.338 | 2.086 | 10.459 | 1.00 | 6.98 | PROT |
| ATOM | 422 | CD1 | PHE | 272 | 54.671 | 2.478 | 10.449 | 1.00 | 4.13 | PROT |
| ATOM | 423 | CD2 | PHE | 272 | 52.978 | 0.961 | 11.193 | 1.00 | 6.95 | PROT |
| ATOM | 424 | CE1 | PHE | 272 | 55.634 | 1.764 | 11.163 | 1.00 | 7.86 | PROT |
| ATOM | 425 | CE2 | PHE | 272 | 53.930 | 0.242 | 11.909 | 1.00 | 6.13 | PROT |
| ATOM | 426 | CZ | PHE | 272 | 55.263 | 0.645 | 11.895 | 1.00 | 8.93 | PROT |
| ATOM | 427 | C | PHE | 272 | 50.168 | 2.939 | 8.405 | 1.00 | 30.96 | PROT |
| ATOM | 428 | O | PHE | 272 | 49.071 | 3.156 | 8.931 | 1.00 | 30.21 | PROT |
| ATOM | 429 | N | THR | 273 | 50.522 | 3.452 | 7.231 | 1.00 | 31.55 | PROT |
| ATOM | 430 | CA | THR | 273 | 49.633 | 4.343 | 6.487 | 1.00 | 33.39 | PROT |
| ATOM | 431 | CB | THR | 273 | 50.335 | 4.912 | 5.243 | 1.00 | 36.80 | PROT |
| ATOM | 432 | OG1 | THR | 273 | 50.649 | 3.847 | 4.332 | 1.00 | 27.42 | PROT |
| ATOM | 433 | CG2 | THR | 273 | 51.613 | 5.641 | 5.656 | 1.00 | 32.25 | PROT |
| ATOM | 434 | C | THR | 273 | 48.350 | 3.647 | 6.056 | 1.00 | 34.07 | PROT |
| ATOM | 435 | O | THR | 273 | 47.362 | 4.294 | 5.697 | 1.00 | 17.11 | PROT |
| ATOM | 436 | N | LYS | 274 | 48.372 | 2.321 | 6.088 | 1.00 | 34.47 | PROT |
| ATOM | 437 | CA | LYS | 274 | 47.196 | 1.555 | 5.726 | 1.00 | 42.17 | PROT |
| ATOM | 438 | CB | LYS | 274 | 47.544 | 0.069 | 5.615 | 1.00 | 40.02 | PROT |
| ATOM | 439 | C | LYS | 274 | 46.153 | 1.778 | 6.818 | 1.00 | 41.47 | PROT |
| ATOM | 440 | O | LYS | 274 | 45.115 | 2.402 | 6.584 | 1.00 | 47.37 | PROT |
| ATOM | 441 | N | ILE | 275 | 46.456 | 1.290 | 8.019 | 1.00 | 34.08 | PROT |
| ATOM | 442 | CA | ILE | 275 | 45.559 | 1.403 | 9.166 | 1.00 | 25.49 | PROT |
| ATOM | 443 | CB | ILE | 275 | 45.991 | 0.435 | 10.262 | 1.00 | 19.72 | PROT |
| ATOM | 444 | CG2 | ILE | 275 | 46.290 | −0.934 | 9.642 | 1.00 | 23.39 | PROT |
| ATOM | 445 | CG1 | ILE | 275 | 47.249 | 0.958 | 10.953 | 1.00 | 12.96 | PROT |
| ATOM | 446 | CD1 | ILE | 275 | 47.970 | −0.103 | 11.769 | 1.00 | 11.07 | PROT |
| ATOM | 447 | C | ILE | 275 | 45.440 | 2.805 | 9.762 | 1.00 | 20.03 | PROT |
| ATOM | 448 | O | ILE | 275 | 44.541 | 3.081 | 10.547 | 1.00 | 18.98 | PROT |
| ATOM | 449 | N | ILE | 276 | 46.347 | 3.694 | 9.402 | 1.00 | 8.88 | PROT |
| ATOM | 450 | CA | ILE | 276 | 46.268 | 5.043 | 9.924 | 1.00 | 6.62 | PROT |
| ATOM | 451 | CB | ILE | 276 | 47.298 | 5.972 | 9.261 | 1.00 | 21.77 | PROT |
| ATOM | 452 | CG2 | ILE | 276 | 46.894 | 6.267 | 7.831 | 1.00 | 27.28 | PROT |
| ATOM | 453 | CG1 | ILE | 276 | 47.374 | 7.288 | 10.028 | 1.00 | 6.75 | PROT |
| ATOM | 454 | CD1 | ILE | 276 | 48.349 | 7.255 | 11.153 | 1.00 | 15.44 | PROT |
| ATOM | 455 | C | ILE | 276 | 44.887 | 5.649 | 9.697 | 1.00 | 12.17 | PROT |
| ATOM | 456 | O | ILE | 276 | 44.349 | 6.331 | 10.565 | 1.00 | 29.36 | PROT |
| ATOM | 457 | N | THR | 277 | 44.303 | 5.411 | 8.535 | 1.00 | 22.12 | PROT |
| ATOM | 458 | CA | THR | 277 | 43.007 | 6.005 | 8.260 | 1.00 | 27.16 | PROT |

APPENDIX 7-continued

TRBTRIAC.PDB

| ATOM | 459 | CB  | THR | 277 | 42.532 | 5.675  | 6.834  | 1.00 | 27.11 | PROT |
|------|-----|-----|-----|-----|--------|--------|--------|------|-------|------|
| ATOM | 460 | OG1 | THR | 277 | 43.665 | 5.584  | 5.955  | 1.00 | 22.55 | PROT |
| ATOM | 461 | CG2 | ThR | 277 | 41.594 | 6.763  | 6.337  | 1.00 | 26.98 | PROT |
| ATOM | 462 | C   | THR | 277 | 41.944 | 5.591  | 9.270  | 1.00 | 25.23 | PROT |
| ATOM | 463 | O   | THR | 277 | 41.271 | 6.443  | 9.847  | 1.00 | 21.62 | PROT |
| ATOM | 464 | N   | PRO | 278 | 41.769 | 4.279  | 9.491  | 1.00 | 18.64 | PROT |
| ATOM | 465 | CD  | PRO | 278 | 42.472 | 3.167  | 8.832  | 1.00 | 9.52  | PROT |
| ATOM | 466 | CA  | PRO | 278 | 40.765 | 3.803  | 10.453 | 1.00 | 18.48 | PROT |
| ATOM | 467 | CB  | PRO | 278 | 40.907 | 2.280  | 10.415 | 1.00 | 14.77 | PROT |
| ATOM | 468 | CG  | PRO | 278 | 42.195 | 2.008  | 9.738  | 1.00 | 7.70  | PROT |
| ATOM | 469 | C   | PRO | 278 | 40.956 | 4.356  | 11.870 | 1.00 | 25.40 | PROT |
| ATOM | 470 | O   | PRO | 278 | 39.983 | 4.628  | 12.576 | 1.00 | 22.33 | PROT |
| ATOM | 471 | N   | ALA | 279 | 42.211 | 4.507  | 12.285 | 1.00 | 22.14 | PROT |
| ATOM | 472 | CA  | ALA | 279 | 42.519 | 5.038  | 13.607 | 1.00 | 20.26 | PROT |
| ATOM | 473 | CB  | ALA | 279 | 44.016 | 5.033  | 13.831 | 1.00 | 13.33 | PROT |
| ATOM | 474 | C   | ALA | 279 | 41.984 | 6.456  | 13.699 | 1.00 | 16.49 | PROT |
| ATOM | 475 | O   | ALA | 279 | 41.222 | 6.797  | 14.598 | 1.00 | 32.38 | PROT |
| ATOM | 476 | N   | ILE | 280 | 42.384 | 7.286  | 12.753 | 1.00 | 7.56  | PROT |
| ATOM | 477 | CA  | ILE | 280 | 41.935 | 8.666  | 12.734 | 1.00 | 9.96  | PROT |
| ATOM | 478 | CB  | ILE | 280 | 42.422 | 9.380  | 11.462 | 1.00 | 8.46  | PROT |
| ATOM | 479 | CG2 | ILE | 280 | 42.172 | 10.871 | 11.581 | 1.00 | 2.00  | PROT |
| ATOM | 480 | CG1 | ILE | 280 | 43.901 | 9.059  | 11.220 | 1.00 | 10.96 | PROT |
| ATOM | 481 | CD1 | ILE | 280 | 44.615 | 10.036 | 10.294 | 1.00 | 8.54  | PROT |
| ATOM | 482 | C   | ILE | 280 | 40.410 | 8.805  | 12.805 | 1.00 | 15.46 | PROT |
| ATOM | 483 | O   | ILE | 280 | 39.887 | 9.741  | 13.421 | 1.00 | 24.39 | PROT |
| ATOM | 484 | N   | THR | 281 | 39.692 | 7.883  | 12.172 | 1.00 | 24.18 | PROT |
| ATOM | 485 | CA  | THR | 281 | 38.238 | 7.962  | 12.153 | 1.00 | 24.77 | PROT |
| ATOM | 486 | CB  | THR | 281 | 37.650 | 6.952  | 11.145 | 1.00 | 33.90 | PROT |
| ATOM | 487 | OG1 | THR | 281 | 38.607 | 6.711  | 10.108 | 1.00 | 34.62 | PROT |
| ATOM | 488 | CG2 | THR | 281 | 36.379 | 7.506  | 10.513 | 1.00 | 39.80 | PROT |
| ATOM | 489 | C   | THR | 281 | 37.655 | 7.726  | 13.535 | 1.00 | 23.39 | PROT |
| ATOM | 490 | O   | THR | 281 | 36.733 | 8.422  | 13.960 | 1.00 | 19.51 | PROT |
| ATOM | 491 | N   | ARG | 282 | 38.213 | 6.743  | 14.234 | 1.00 | 16.90 | PROT |
| ATOM | 492 | CA  | ARG | 282 | 37.781 | 6.404  | 15.583 | 1.00 | 12.29 | PROT |
| ATOM | 493 | CB  | ARG | 282 | 38.641 | 5.260  | 16.115 | 1.00 | 5.36  | PROT |
| ATOM | 494 | CG  | ARG | 282 | 37.936 | 3.926  | 16.136 | 1.00 | 17.05 | PROT |
| ATOM | 495 | CD  | ARG | 282 | 38.296 | 3.095  | 14.942 | 1.00 | 18.41 | PROT |
| ATOM | 496 | NE  | ARG | 282 | 39.622 | 2.475  | 15.011 | 1.00 | 35.77 | PROT |
| ATOM | 497 | CZ  | ARG | 282 | 40.454 | 2.501  | 16.055 | 1.00 | 36.80 | PROT |
| ATOM | 498 | NH1 | ARG | 282 | 41.629 | 1.888  | 15.967 | 1.00 | 35.96 | PROT |
| ATOM | 499 | NH2 | ARG | 282 | 40.134 | 3.120  | 17.183 | 1.00 | 25.20 | PROT |
| ATOM | 500 | C   | ARG | 282 | 37.863 | 7.626  | 16.520 | 1.00 | 16.75 | PROT |
| ATOM | 501 | O   | ARG | 282 | 37.078 | 7.758  | 17.456 | 1.00 | 22.98 | PROT |
| ATOM | 502 | N   | VAL | 283 | 38.813 | 8.518  | 16.268 | 1.00 | 11.92 | PROT |
| ATOM | 503 | CA  | VAL | 283 | 38.937 | 9.719  | 17.083 | 1.00 | 14.68 | PROT |
| ATOM | 504 | CB  | VAL | 283 | 40.191 | 10.541 | 16.696 | 1.00 | 23.35 | PROT |
| ATOM | 505 | CG1 | VAL | 283 | 40.467 | 11.593 | 17.752 | 1.00 | 11.98 | PROT |
| ATOM | 506 | CG2 | VAL | 283 | 41.396 | 9.621  | 16.526 | 1.00 | 20.41 | PROT |
| ATOM | 507 | C   | VAL | 283 | 37.705 | 10.580 | 16.833 | 1.00 | 12.72 | PROT |
| ATOM | 508 | O   | VAL | 283 | 36.965 | 10.929 | 17.752 | 1.00 | 20.37 | PROT |
| ATOM | 509 | N   | VAL | 284 | 37.503 | 10.920 | 15.567 | 1.00 | 18.28 | PROT |
| ATOM | 510 | CA  | VAL | 284 | 36.369 | 11.727 | 15.150 | 1.00 | 16.98 | PROT |
| ATOM | 511 | CB  | VAL | 284 | 36.251 | 11.765 | 13.602 | 1.00 | 27.40 | PROT |
| ATOM | 512 | CG1 | VAL | 284 | 35.434 | 12.973 | 13.172 | 1.00 | 19.30 | PROT |
| ATOM | 513 | CG2 | VAL | 284 | 37.649 | 11.794 | 12.959 | 1.00 | 16.94 | PROT |
| ATOM | 514 | C   | VAL | 284 | 35.113 | 11.093 | 15.715 | 1.00 | 14.89 | PROT |
| ATOM | 515 | O   | VAL | 284 | 34.233 | 11.781 | 16.219 | 1.00 | 10.93 | PROT |
| ATOM | 516 | N   | ASP | 285 | 35.046 | 9.768  | 15.623 | 1.00 | 10.68 | PROT |
| ATOM | 517 | CA  | ASP | 285 | 33.898 | 9.022  | 16.114 | 1.00 | 20.76 | PROT |
| ATOM | 518 | CB  | ASP | 285 | 34.079 | 7.518  | 15.874 | 1.00 | 22.99 | PROT |
| ATOM | 519 | CG  | ASP | 285 | 33.985 | 7.130  | 14.397 | 1.00 | 30.01 | PROT |
| ATOM | 520 | OD1 | ASP | 285 | 33.185 | 7.735  | 13.648 | 1.00 | 18.56 | PROT |
| ATOM | 521 | OD2 | ASP | 285 | 34.720 | 6.202  | 13.993 | 1.00 | 27.74 | PROT |
| ATOM | 522 | C   | ASP | 285 | 33.734 | 9.274  | 17.604 | 1.00 | 26.87 | PROT |
| ATOM | 523 | O   | ASP | 285 | 32.609 | 9.349  | 18.103 | 1.00 | 39.89 | PROT |
| ATOM | 524 | N   | PHE | 286 | 34.861 | 9.405  | 18.308 | 1.00 | 25.45 | PROT |
| ATOM | 525 | CA  | PHE | 286 | 34.862 | 9.654  | 19.746 | 1.00 | 15.66 | PROT |
| ATOM | 526 | CB  | PHE | 286 | 36.284 | 9.533  | 20.305 | 1.00 | 7.30  | PROT |
| ATOM | 527 | CG  | PHE | 286 | 36.454 | 10.104 | 21.703 | 1.00 | 17.92 | PROT |
| ATOM | 528 | CD1 | PHE | 286 | 35.848 | 9.499  | 22.805 | 1.00 | 19.35 | PROT |
| ATOM | 529 | CD2 | PHE | 286 | 37.229 | 11.245 | 21.920 | 1.00 | 19.24 | PROT |
| ATOM | 530 | CE1 | PHE | 286 | 36.014 | 10.021 | 24.087 | 1.00 | 9.94  | PROT |
| ATOM | 531 | CE2 | PHE | 286 | 37.395 | 11.769 | 23.207 | 1.00 | 11.33 | PROT |
| ATOM | 532 | CZ  | PHE | 286 | 36.786 | 11.154 | 24.283 | 1.00 | 2.00  | PROT |
| ATOM | 533 | C   | PHE | 286 | 34.313 | 11.043 | 20.030 | 1.00 | 17.67 | PROT |
| ATOM | 534 | O   | PHE | 286 | 33.367 | 11.201 | 20.797 | 1.00 | 14.36 | PROT |
| ATOM | 535 | N   | ALA | 287 | 34.905 | 12.056 | 19.410 | 1.00 | 12.57 | PROT |

APPENDIX 7-continued

TRBTRIAC.PDB

| ATOM | 536 | CA  | ALA | 287 | 34.443 | 13.426 | 19.622 | 1.00 | 12.49 | PROT |
|------|-----|-----|-----|-----|--------|--------|--------|------|-------|------|
| ATOM | 537 | CB  | ALA | 287 | 35.250 | 14.386 | 18.759 | 1.00 | 23.54 | PROT |
| ATOM | 538 | C   | ALA | 287 | 32.954 | 13.559 | 19.307 | 1.00 | 9.21  | PROT |
| ATOM | 539 | O   | ALA | 287 | 32.209 | 14.205 | 20.043 | 1.00 | 11.68 | PROT |
| ATOM | 540 | N   | LYS | 288 | 32.540 | 12.929 | 18.209 | 1.00 | 16.43 | PROT |
| ATOM | 541 | CA  | LYS | 288 | 31.157 | 12.944 | 17.736 | 1.00 | 16.10 | PROT |
| ATOM | 542 | CB  | LYS | 288 | 31.003 | 11.977 | 16.569 | 1.00 | 13.15 | PROT |
| ATOM | 543 | CG  | LYS | 288 | 31.117 | 12.636 | 15.219 | 1.00 | 25.55 | PROT |
| ATOM | 544 | CD  | LYS | 288 | 30.480 | 11.779 | 14.136 | 1.00 | 32.95 | PROT |
| ATOM | 545 | CE  | LYS | 288 | 31.279 | 10.507 | 13.900 | 1.00 | 34.58 | PROT |
| ATOM | 546 | NZ  | LYS | 288 | 30.755 | 9.721  | 12.748 | 1.00 | 36.93 | PROT |
| ATOM | 547 | C   | LYS | 288 | 30.154 | 12.569 | 18.813 | 1.00 | 18.87 | PROT |
| ATOM | 548 | O   | LYS | 288 | 29.078 | 13.171 | 18.917 | 1.00 | 12.83 | PROT |
| ATOM | 549 | N   | LYS | 289 | 30.525 | 11.574 | 19.614 | 1.00 | 11.81 | PROT |
| ATOM | 550 | CA  | LYS | 289 | 29.674 | 11.067 | 20.681 | 1.00 | 15.53 | PROT |
| ATOM | 551 | CB  | LYS | 289 | 30.070 | 9.631  | 21.011 | 1.00 | 15.88 | PROT |
| ATOM | 552 | CG  | LYS | 289 | 29.767 | 8.645  | 19.911 | 1.00 | 20.93 | PROT |
| ATOM | 553 | CD  | LYS | 289 | 29.140 | 7.382  | 20.471 | 1.00 | 28.97 | PROT |
| ATOM | 554 | CE  | LYS | 289 | 29.951 | 6.167  | 20.071 | 1.00 | 25.06 | PROT |
| ATOM | 555 | NZ  | LYS | 289 | 30.043 | 6.060  | 18.590 | 1.00 | 39.19 | PROT |
| ATOM | 556 | C   | LYS | 289 | 29.660 | 11.884 | 21.969 | 1.00 | 15.95 | PROT |
| ATOM | 557 | O   | LYS | 289 | 29.205 | 11.398 | 23.001 | 1.00 | 28.53 | PROT |
| ATOM | 558 | N   | LEU | 290 | 30.151 | 13.116 | 21.919 | 1.00 | 10.13 | PROT |
| ATOM | 559 | CA  | LEU | 290 | 30.155 | 13.959 | 23.104 | 1.00 | 7.83  | PROT |
| ATOM | 560 | CB  | LEU | 290 | 31.588 | 14.300 | 23.532 | 1.00 | 14.46 | PROT |
| ATOM | 561 | CG  | LEU | 290 | 32.676 | 13.228 | 23.542 | 1.00 | 11.22 | PROT |
| ATOM | 562 | CD1 | LEU | 290 | 34.016 | 13.900 | 23.678 | 1.00 | 3.02  | PROT |
| ATOM | 563 | CD2 | LEU | 290 | 32.449 | 12.257 | 24.686 | 1.00 | 9.39  | PROT |
| ATOM | 564 | C   | LEU | 290 | 29.410 | 15.259 | 22.849 | 1.00 | 7.59  | PROT |
| ATOM | 565 | O   | LEU | 290 | 29.942 | 16.148 | 22.196 | 1.00 | 11.01 | PROT |
| ATOM | 566 | N   | PRO | 291 | 28.169 | 15.381 | 23.365 | 1.00 | 14.33 | PROT |
| ATOM | 567 | CD  | PRO | 291 | 27.515 | 14.291 | 24.109 | 1.00 | 18.52 | PROT |
| ATOM | 568 | CA  | PRO | 291 | 27.290 | 16.556 | 23.240 | 1.00 | 6.61  | PROT |
| ATOM | 569 | CB  | PRO | 291 | 26.296 | 16.400 | 24.384 | 1.00 | 11.95 | PROT |
| ATOM | 570 | CG  | PRO | 291 | 26.496 | 15.004 | 24.929 | 1.00 | 20.22 | PROT |
| ATOM | 571 | C   | PRO | 291 | 28.029 | 17.885 | 23.332 | 1.00 | 14.74 | PROT |
| ATOM | 572 | O   | PRO | 291 | 27.795 | 18.792 | 22.537 | 1.00 | 26.09 | PROT |
| ATOM | 573 | N   | MET | 292 | 28.917 | 18.002 | 24.315 | 1.00 | 24.06 | PROT |
| ATOM | 574 | CA  | MET | 292 | 29.697 | 19.225 | 24.494 | 1.00 | 25.33 | PROT |
| ATOM | 575 | CB  | MET | 292 | 30.706 | 19.046 | 25.628 | 1.00 | 26.65 | PROT |
| ATOM | 576 | CG  | MET | 292 | 30.222 | 19.581 | 26.962 | 1.00 | 26.97 | PROT |
| ATOM | 577 | SD  | MET | 292 | 31.153 | 18.943 | 28.362 | 1.00 | 29.01 | PROT |
| ATOM | 578 | CE  | MET | 292 | 30.315 | 17.438 | 28.685 | 1.00 | 17.91 | PROT |
| ATOM | 579 | C   | MET | 292 | 30.430 | 19.588 | 23.204 | 1.00 | 23.01 | PROT |
| ATOM | 580 | O   | MET | 292 | 30.478 | 20.747 | 22.813 | 1.00 | 31.98 | PROT |
| ATOM | 581 | N   | PHE | 293 | 31.007 | 18.591 | 22.547 | 1.00 | 23.44 | PROT |
| ATOM | 582 | CA  | PHE | 293 | 31.724 | 18.819 | 21.297 | 1.00 | 24.83 | PROT |
| ATOM | 583 | CB  | PHE | 293 | 32.389 | 17.529 | 20.830 | 1.00 | 15.05 | PROT |
| ATOM | 584 | CG  | PHE | 293 | 33.214 | 17.686 | 19.594 | 1.00 | 13.55 | PROT |
| ATOM | 585 | CD1 | PHE | 293 | 34.376 | 18.446 | 19.614 | 1.00 | 19.86 | PROT |
| ATOM | 586 | CD2 | PHE | 293 | 32.867 | 17.024 | 18.425 | 1.00 | 22.99 | PROT |
| ATOM | 587 | CE1 | PHE | 293 | 35.184 | 18.540 | 18.495 | 1.00 | 18.15 | PROT |
| ATOM | 588 | CE2 | PHE | 293 | 33.671 | 17.108 | 17.291 | 1.00 | 20.83 | PROT |
| ATOM | 589 | CZ  | PHE | 293 | 34.831 | 17.866 | 17.328 | 1.00 | 22.53 | PROT |
| ATOM | 590 | C   | PHE | 293 | 30.759 | 19.291 | 20.222 | 1.00 | 27.26 | PROT |
| ATOM | 591 | O   | PHE | 293 | 30.971 | 20.319 | 19.577 | 1.00 | 28.69 | PROT |
| ATOM | 592 | N   | CYS | 294 | 29.689 | 18.528 | 20.040 | 1.00 | 29.92 | PROT |
| ATOM | 593 | CA  | CYS | 294 | 28.700 | 18.855 | 19.037 | 1.00 | 35.54 | PROT |
| ATOM | 594 | CB  | CYS | 294 | 27.540 | 17.860 | 19.106 | 1.00 | 19.11 | PROT |
| ATOM | 595 | SG  | CYS | 294 | 27.843 | 16.358 | 18.132 | 1.00 | 35.66 | PROT |
| ATOM | 596 | C   | CYS | 294 | 28.203 | 20.291 | 19.171 | 1.00 | 38.84 | PROT |
| ATOM | 597 | O   | CYS | 294 | 28.072 | 20.995 | 18.169 | 1.00 | 45.94 | PROT |
| ATOM | 598 | N   | GLU | 295 | 27.959 | 20.739 | 20.401 | 1.00 | 27.34 | PROT |
| ATOM | 599 | CA  | GLU | 295 | 27.472 | 22.097 | 20.632 | 1.00 | 21.06 | PROT |
| ATOM | 600 | CB  | GLU | 295 | 27.178 | 22.306 | 22.121 | 1.00 | 29.78 | PROT |
| ATOM | 601 | C   | GLU | 295 | 28.458 | 23.158 | 20.128 | 1.00 | 23.67 | PROT |
| ATOM | 602 | O   | GLU | 295 | 28.228 | 24.357 | 20.272 | 1.00 | 29.89 | PROT |
| ATOM | 603 | N   | LEU | 296 | 29.551 | 22.715 | 19.522 | 1.00 | 21.46 | PROT |
| ATOM | 604 | CA  | LEU | 296 | 30.545 | 23.642 | 19.005 | 1.00 | 26.35 | PROT |
| ATOM | 605 | CB  | LEU | 296 | 31.947 | 23.128 | 19.330 | 1.00 | 25.17 | PROT |
| ATOM | 606 | CG  | LEU | 296 | 32.419 | 23.157 | 20.778 | 1.00 | 13.78 | PROT |
| ATOM | 607 | CD1 | LEU | 296 | 33.593 | 22.217 | 20.931 | 1.00 | 23.61 | PROT |
| ATOM | 608 | CD2 | LEU | 296 | 32.814 | 24.564 | 21.160 | 1.00 | 13.82 | PROT |
| ATOM | 609 | C   | LEU | 296 | 30.415 | 23.783 | 17.493 | 1.00 | 31.88 | PROT |
| ATOM | 610 | O   | LEU | 296 | 29.890 | 22.890 | 16.827 | 1.00 | 45.99 | PROT |
| ATOM | 611 | N   | PRO | 297 | 30.884 | 24.912 | 16.932 | 1.00 | 27.00 | PROT |
| ATOM | 612 | CD  | PRO | 297 | 31.423 | 26.037 | 17.708 | 1.00 | 36.12 | PROT |

APPENDIX 7-continued

TRBTRIAC.PDB

| ATOM | 613 | CA | PRO | 297 | 30.856 | 25.222 | 15.492 | 1.00 | 22.30 | PROT |
|---|---|---|---|---|---|---|---|---|---|---|
| ATOM | 614 | CB | PRO | 297 | 31.182 | 26.716 | 15.424 | 1.00 | 16.06 | PROT |
| ATOM | 615 | CG | PRO | 297 | 31.107 | 27.208 | 16.827 | 1.00 | 42.41 | PROT |
| ATOM | 616 | C | PRO | 297 | 31.838 | 24.413 | 14.642 | 1.00 | 28.19 | PROT |
| ATOM | 617 | O | PRO | 297 | 32.983 | 24.189 | 15.036 | 1.00 | 39.38 | PROT |
| ATOM | 618 | N | CYS | 298 | 31.371 | 24.014 | 13.457 | 1.00 | 35.37 | PROT |
| ATOM | 619 | CA | CYS | 298 | 32.134 | 23.233 | 12.481 | 1.00 | 32.41 | PROT |
| ATOM | 620 | CB | CYS | 298 | 31.416 | 23.289 | 11.112 | 1.00 | 40.85 | PROT |
| ATOM | 621 | SG | CYS | 298 | 32.431 | 23.615 | 9.614 | 1.00 | 61.24 | PROT |
| ATOM | 622 | C | CYS | 298 | 33.596 | 23.654 | 12.352 | 1.00 | 31.68 | PROT |
| ATOM | 623 | O | CYS | 298 | 34.474 | 22.804 | 12.225 | 1.00 | 28.49 | PROT |
| ATOM | 624 | N | GLU | 299 | 33.869 | 24.954 | 12.393 | 1.00 | 29.93 | PROT |
| ATOM | 625 | CA | GLU | 299 | 35.253 | 25.407 | 12.278 | 1.00 | 36.38 | PROT |
| ATOM | 626 | CB | GLU | 299 | 35.346 | 26.931 | 12.203 | 1.00 | 32.78 | PROT |
| ATOM | 627 | CG | GLU | 299 | 34.467 | 27.546 | 11.167 | 1.00 | 43.40 | PROT |
| ATOM | 628 | CD | GLU | 299 | 33.038 | 27.593 | 11.625 | 1.00 | 58.19 | PROT |
| ATOM | 629 | OE1 | GLU | 299 | 32.723 | 28.457 | 12.474 | 1.00 | 67.37 | PROT |
| ATOM | 630 | OE2 | GLU | 299 | 32.237 | 26.762 | 11.143 | 1.00 | 54.02 | PROT |
| ATOM | 631 | C | GLU | 299 | 36.057 | 24.932 | 13.475 | 1.00 | 38.89 | PROT |
| ATOM | 632 | O | GLU | 299 | 37.129 | 24.342 | 13.316 | 1.00 | 48.67 | PROT |
| ATOM | 633 | N | ASP | 300 | 35.528 | 25.186 | 14.671 | 1.00 | 36.49 | PROT |
| ATOM | 634 | CA | ASP | 300 | 36.201 | 24.805 | 15.906 | 1.00 | 29.96 | PROT |
| ATOM | 635 | CB | ASP | 300 | 35.455 | 25.391 | 17.111 | 1.00 | 5.33 | PROT |
| ATOM | 636 | CG | ASP | 300 | 35.830 | 26.853 | 17.378 | 1.00 | 19.10 | PROT |
| ATOM | 637 | OD1 | ASP | 300 | 36.491 | 27.473 | 16.518 | 1.00 | 27.28 | PROT |
| ATOM | 638 | OD2 | ASP | 300 | 35.470 | 27.396 | 18.444 | 1.00 | 23.55 | PROT |
| ATOM | 639 | C | ASP | 300 | 36.380 | 23.294 | 16.054 | 1.00 | 25.88 | PROT |
| ATOM | 640 | O | ASP | 300 | 37.441 | 22.845 | 16.484 | 1.00 | 19.03 | PROT |
| ATOM | 641 | N | GLN | 301 | 35.360 | 22.516 | 15.689 | 1.00 | 6.29 | PROT |
| ATOM | 642 | CA | GLN | 301 | 35.432 | 21.055 | 15.769 | 1.00 | 9.51 | PROT |
| ATOM | 643 | CB | GLN | 301 | 34.170 | 20.421 | 15.183 | 1.00 | 18.27 | PROT |
| ATOM | 644 | CG | GLN | 301 | 32.886 | 20.813 | 15.875 | 1.00 | 28.72 | PROT |
| ATOM | 645 | CD | GLN | 301 | 31.676 | 20.155 | 15.243 | 1.00 | 17.63 | PROT |
| ATOM | 646 | OE1 | GLN | 301 | 31.689 | 19.823 | 14.060 | 1.00 | 30.65 | PROT |
| ATOM | 647 | NE2 | GLN | 301 | 30.625 | 19.965 | 16.027 | 1.00 | 30.44 | PROT |
| ATOM | 648 | C | GLN | 301 | 36.646 | 20.491 | 15.020 | 1.00 | 15.48 | PROT |
| ATOM | 649 | O | GLN | 301 | 37.333 | 19.584 | 15.500 | 1.00 | 21.96 | PROT |
| ATOM | 650 | N | ILE | 302 | 36.891 | 21.014 | 13.825 | 1.00 | 24.00 | PROT |
| ATOM | 651 | CA | ILE | 302 | 38.011 | 20.555 | 13.026 | 1.00 | 28.84 | PROT |
| ATOM | 652 | CB | ILE | 302 | 37.930 | 21.112 | 11.607 | 1.00 | 33.13 | PROT |
| ATOM | 653 | CG2 | ILE | 302 | 39.147 | 20.690 | 10.813 | 1.00 | 37.90 | PROT |
| ATOM | 654 | CG1 | ILE | 302 | 36.656 | 20.610 | 10.941 | 1.00 | 29.63 | PROT |
| ATOM | 655 | CD1 | ILE | 302 | 36.296 | 21.356 | 9.698 | 1.00 | 32.99 | PROT |
| ATOM | 656 | C | ILE | 302 | 39.308 | 21.014 | 13.670 | 1.00 | 28.73 | PROT |
| ATOM | 657 | O | ILE | 302 | 40.219 | 20.219 | 13.895 | 1.00 | 36.02 | PROT |
| ATOM | 658 | N | ILE | 303 | 39.396 | 22.304 | 13.968 | 1.00 | 25.04 | PROT |
| ATOM | 659 | CA | ILE | 303 | 40.590 | 22.817 | 14.603 | 1.00 | 24.27 | PROT |
| ATOM | 660 | CB | ILE | 303 | 40.414 | 24.270 | 15.054 | 1.00 | 20.89 | PROT |
| ATOM | 661 | CG2 | ILE | 303 | 41.686 | 24.740 | 15.744 | 1.00 | 32.38 | PROT |
| ATOM | 662 | CG1 | ILE | 303 | 40.079 | 25.158 | 13.849 | 1.00 | 18.88 | PROT |
| ATOM | 663 | CD1 | ILE | 303 | 40.298 | 26.648 | 14.079 | 1.00 | 5.31 | PROT |
| ATOM | 664 | C | ILE | 303 | 40.861 | 21.948 | 15.825 | 1.00 | 26.92 | PROT |
| ATOM | 665 | O | ILE | 303 | 41.963 | 21.440 | 15.997 | 1.00 | 31.32 | PROT |
| ATOM | 666 | N | LEU | 304 | 39.843 | 21.763 | 16.659 | 1.00 | 11.00 | PROT |
| ATOM | 667 | CA | LEU | 304 | 39.983 | 20.953 | 17.854 | 1.00 | 7.21 | PROT |
| ATOM | 668 | CB | LEU | 304 | 38.663 | 20.886 | 18.613 | 1.00 | 2.00 | PROT |
| ATOM | 669 | CG | LEU | 304 | 38.633 | 21.511 | 20.012 | 1.00 | 8.04 | PROT |
| ATOM | 670 | CD1 | LEU | 304 | 39.383 | 22.812 | 19.997 | 1.00 | 2.00 | PROT |
| ATOM | 671 | CD2 | LEU | 304 | 37.188 | 21.729 | 20.472 | 1.00 | 4.99 | PROT |
| ATOM | 672 | C | LEU | 304 | 40.441 | 19.554 | 17.507 | 1.00 | 4.64 | PROT |
| ATOM | 673 | O | LEU | 304 | 41.368 | 19.032 | 18.119 | 1.00 | 14.88 | PROT |
| ATOM | 674 | N | LEU | 305 | 39.807 | 18.953 | 16.510 | 1.00 | 4.55 | PROT |
| ATOM | 675 | CA | LEU | 305 | 40.140 | 17.590 | 16.093 | 1.00 | 7.03 | PROT |
| ATOM | 676 | CB | LEU | 305 | 39.099 | 17.098 | 15.104 | 1.00 | 3.70 | PROT |
| ATOM | 677 | CG | LEU | 305 | 38464 | 16.054 | 15.691 | 1.00 | 10.31 | PROT |
| ATOM | 678 | CD1 | LEU | 305 | 36.744 | 16.340 | 15.245 | 1.00 | 2.00 | PROT |
| ATOM | 679 | CD2 | LEU | 305 | 38.629 | 14.665 | 15.260 | 1.00 | 9.42 | PROT |
| ATOM | 680 | C | LEU | 305 | 41.527 | 17.418 | 15.483 | 1.00 | 10.17 | PROT |
| ATOM | 681 | O | LEU | 305 | 42.174 | 16.374 | 15.651 | 1.00 | 7.58 | PROT |
| ATOM | 682 | N | LYS | 306 | 41.975 | 18.442 | 14.765 | 1.00 | 9.98 | PROT |
| ATOM | 683 | CA | LYS | 306 | 43.283 | 18.408 | 14.127 | 1.00 | 9.14 | PROT |
| ATOM | 684 | CB | LYS | 306 | 43.409 | 19.558 | 13.131 | 1.00 | 18.85 | PROT |
| ATOM | 685 | CG | LYS | 306 | 42.815 | 19.270 | 11.763 | 1.00 | 25.44 | PROT |
| ATOM | 686 | CD | LYS | 306 | 42.198 | 20.529 | 11.178 | 1.00 | 29.07 | PROT |
| ATOM | 687 | CE | LYS | 306 | 42.698 | 20.808 | 9.774 | 1.00 | 37.81 | PROT |
| ATOM | 688 | NZ | LYS | 306 | 43.867 | 19.964 | 9.403 | 1.00 | 30.48 | PROT |
| ATOM | 689 | C | LYS | 306 | 44.376 | 18.522 | 15.175 | 1.00 | 7.31 | PROT |

APPENDIX 7-continued

TRBTRIAC.PDB

| | | | | | | | | | |
|---|---|---|---|---|---|---|---|---|---|
| ATOM | 690 | O | LYS | 306 | 45.439 | 17.919 | 15.048 | 1.00 | 16.95 PROT |
| ATOM | 691 | N | GLY | 307 | 44.097 | 19.295 | 16.218 | 1.00 | 12.67 PROT |
| ATOM | 692 | CA | GLY | 307 | 45.062 | 19.484 | 17.279 | 1.00 | 7.25 PROT |
| ATOM | 693 | C | GLY | 307 | 45.297 | 18.269 | 18.150 | 1.00 | 15.08 PROT |
| ATOM | 694 | O | GLY | 307 | 46.441 | 17.972 | 18.488 | 1.00 | 20.11 PROT |
| ATOM | 695 | N | CYS | 308 | 44.225 | 17.552 | 18.481 | 1.00 | 8.29 PROT |
| ATOM | 696 | CA | CYS | 308 | 44.286 | 16.380 | 19.364 | 1.00 | 3.44 PROT |
| ATOM | 697 | CB | CYS | 308 | 43.097 | 16.402 | 20.326 | 1.00 | 14.26 PROT |
| ATOM | 698 | SG | CYS | 308 | 41.539 | 15.750 | 19.634 | 1.00 | 21.83 PROT |
| ATOM | 699 | C | CYS | 308 | 44.344 | 14.995 | 18.738 | 1.00 | 8.37 PROT |
| ATOM | 700 | O | CYS | 308 | 44.502 | 13.997 | 19.453 | 1.00 | 10.98 PROT |
| ATOM | 701 | N | CYS | 309 | 44.202 | 14.916 | 17.420 | 1.00 | 10.83 PROT |
| ATOM | 702 | CA | CYS | 309 | 44.236 | 13.625 | 16.752 | 1.00 | 3.22 PROT |
| ATOM | 703 | CB | CYS | 309 | 44.240 | 13.831 | 15.240 | 1.00 | 15.79 PROT |
| ATOM | 704 | SG | CYS | 309 | 43.683 | 12.402 | 14.319 | 1.00 | 25.54 PROT |
| ATOM | 705 | C | CYS | 309 | 45.439 | 12.767 | 17.193 | 1.00 | 2.00 PROT |
| ATOM | 706 | O | CYS | 309 | 45.251 | 11.722 | 17.807 | 1.00 | 12.28 PROT |
| ATOM | 707 | N | MET | 310 | 46.663 | 13.205 | 16.900 | 1.00 | 2.00 PROT |
| ATOM | 708 | CA | MET | 310 | 47.858 | 12.446 | 17.286 | 1.00 | 2.00 PROT |
| ATOM | 709 | CB | MET | 310 | 49.122 | 13.171 | 16.860 | 1.00 | 2.00 PROT |
| ATOM | 710 | CG | MET | 310 | 49.975 | 12.422 | 15.880 | 1.00 | 5.92 PROT |
| ATOM | 711 | SD | MET | 310 | 50.481 | 10.805 | 16.368 | 1.00 | 22.47 PROT |
| ATOM | 712 | CE | MET | 310 | 52.140 | 11.112 | 16.808 | 1.00 | 20.84 PROT |
| ATOM | 713 | C | MET | 310 | 47.941 | 12.239 | 18.793 | 1.00 | 11.95 PROT |
| ATOM | 714 | O | MET | 310 | 48.455 | 11.220 | 19.270 | 1.00 | 15.53 PROT |
| ATOM | 715 | N | GLU | 311 | 47.463 | 13.225 | 19.542 | 1.00 | 6.79 PROT |
| ATOM | 716 | CA | GLU | 311 | 47.493 | 13.139 | 20.979 | 1.00 | 2.00 PROT |
| ATOM | 717 | CB | GLU | 311 | 46.932 | 14.427 | 21.581 | 1.00 | 6.42 PROT |
| ATOM | 718 | CG | GLU | 311 | 47.880 | 15.619 | 21.436 | 1.00 | 8.40 PROT |
| ATOM | 719 | CD | GLU | 311 | 47.236 | 16.940 | 21.820 | 1.00 | 14.10 PROT |
| ATOM | 720 | OE1 | GLU | 311 | 46.157 | 16.895 | 22.434 | 1.00 | 16.54 PROT |
| ATOM | 721 | OE2 | GLU | 311 | 47.795 | 18.020 | 21.515 | 1.00 | 4.09 PROT |
| ATOM | 722 | C | GLU | 311 | 46.683 | 11.923 | 21.406 | 1.00 | 7.80 PROT |
| ATOM | 723 | O | GLU | 311 | 47.195 | 11.026 | 22.067 | 1.00 | 14.07 PROT |
| ATOM | 724 | N | ILE | 312 | 45.425 | 11.873 | 21.001 | 1.00 | 2.00 PROT |
| ATOM | 725 | CA | ILE | 312 | 44.574 | 10.752 | 21.371 | 1.00 | 3.60 PROT |
| ATOM | 726 | CB | ILE | 312 | 43.114 | 11.013 | 20.947 | 1.00 | 2.00 PROT |
| ATOM | 727 | CG2 | ILE | 312 | 42.277 | 9.769 | 21.145 | 1.00 | 2.00 PROT |
| ATOM | 728 | CG1 | ILE | 312 | 42.579 | 12.221 | 21.727 | 1.00 | 2.00 PROT |
| ATOM | 729 | CD1 | ILE | 312 | 41.118 | 12.555 | 21.495 | 1.00 | 2.00 PROT |
| ATOM | 730 | C | ILE | 312 | 45.049 | 9.437 | 20.760 | 1.00 | 8.32 PROT |
| ATOM | 731 | O | ILE | 312 | 44.918 | 8.373 | 21.370 | 1.00 | 5.58 PROT |
| ATOM | 732 | N | MET | 313 | 45.615 | 9.501 | 19.563 | 1.00 | 3.98 PROT |
| ATOM | 733 | CA | MET | 313 | 46.054 | 8.282 | 18.905 | 1.00 | 8.91 PROT |
| ATOM | 734 | CB | MET | 313 | 46.455 | 8.572 | 17.462 | 1.00 | 25.71 PROT |
| ATOM | 735 | CG | MET | 313 | 45.430 | 8.111 | 16.431 | 1.00 | 22.86 PROT |
| ATOM | 736 | SD | MET | 313 | 45.955 | 8.430 | 14.736 | 1.00 | 20.60 PROT |
| ATOM | 737 | CE | MET | 313 | 45.412 | 10.055 | 14.534 | 1.00 | 14.95 PROT |
| ATOM | 738 | C | MET | 313 | 47.211 | 7.634 | 19.635 | 1.00 | 12.95 PROT |
| ATOM | 739 | O | MET | 313 | 47.213 | 6.426 | 19.857 | 1.00 | 22.09 PROT |
| ATOM | 740 | N | SER | 314 | 48.190 | 8.442 | 20.021 | 1.00 | 10.79 PROT |
| ATOM | 741 | CA | SER | 314 | 49.354 | 7.935 | 20.719 | 1.00 | 2.00 PROT |
| ATOM | 742 | CB | SER | 314 | 50.399 | 9.042 | 20.816 | 1.00 | 7.24 PROT |
| ATOM | 743 | OG | SER | 314 | 50.453 | 9.815 | 19.619 | 1.00 | 10.89 PROT |
| ATOM | 744 | C | SER | 314 | 48.991 | 7.399 | 22.105 | 1.00 | 8.64 PROT |
| ATOM | 745 | O | SER | 314 | 49.559 | 6.392 | 22.558 | 1.00 | 5.72 PROT |
| ATOM | 746 | N | LEU | 315 | 48.050 | 8.062 | 22.782 | 1.00 | 2.00 PROT |
| ATOM | 747 | CA | LEU | 315 | 47.628 | 7.605 | 24.104 | 1.00 | 2.00 PROT |
| ATOM | 748 | CB | LEU | 315 | 46.521 | 8.502 | 24.671 | 1.00 | 2.95 PROT |
| ATOM | 749 | CG | LEU | 315 | 45.831 | 8.096 | 25.992 | 1.00 | 2.00 PROT |
| ATOM | 750 | CD1 | LEU | 315 | 46.876 | 7.845 | 27.072 | 1.00 | 2.54 PROT |
| ATOM | 751 | CD2 | LEU | 315 | 44.865 | 9.182 | 26.444 | 1.00 | 2.00 PROT |
| ATOM | 752 | C | LEU | 315 | 47.107 | 6.182 | 23.945 | 1.00 | 3.25 PROT |
| ATOM | 753 | O | LEU | 315 | 47.568 | 5.253 | 24.603 | 1.00 | 2.00 PROT |
| ATOM | 754 | N | ARG | 316 | 46.157 | 6.010 | 23.039 | 1.00 | 7.28 PROT |
| ATOM | 755 | CA | ARG | 316 | 45.588 | 4.691 | 22.808 | 1.00 | 13.31 PROT |
| ATOM | 756 | CB | ARG | 316 | 44.551 | 4.758 | 21.693 | 1.00 | 11.11 PROT |
| ATOM | 757 | CG | ARG | 316 | 43.545 | 5.872 | 21.887 | 1.00 | 10.55 PROT |
| ATOM | 758 | CD | ARG | 316 | 42.354 | 5.639 | 21.012 | 1.00 | 10.09 PROT |
| ATOM | 759 | NE | ARG | 316 | 41.131 | 6.149 | 21.605 | 1.00 | 12.29 PROT |
| ATOM | 760 | CZ | ARG | 316 | 39.955 | 6.127 | 20.994 | 1.00 | 6.99 PROT |
| ATOM | 761 | NH1 | ARG | 316 | 38.880 | 6.608 | 21.595 | 1.00 | 19.32 PROT |
| ATOM | 762 | NH2 | ARG | 316 | 39.853 | 5.619 | 19.778 | 1.00 | 17.16 PROT |
| ATOM | 763 | C | ARG | 316 | 46.666 | 3.686 | 22.458 | 1.00 | 10.10 PROT |
| ATOM | 764 | O | ARG | 316 | 46.549 | 2.508 | 22.753 | 1.00 | 14.94 PROT |
| ATOM | 765 | N | ALA | 317 | 47.723 | 4.148 | 21.819 | 1.00 | 6.51 PROT |
| ATOM | 766 | CA | ALA | 317 | 48.801 | 3.243 | 21.474 | 1.00 | 11.04 PROT |

APPENDIX 7-continued

TRBTRIAC.PDB

| | | | | | | | | | | |
|---|---|---|---|---|---|---|---|---|---|---|
| ATOM | 767 | CB | ALA | 317 | 49.749 | 3.902 | 20.487 | 1.00 | 16.13 | PROT |
| ATOM | 768 | C | ALA | 317 | 49.539 | 2.910 | 22.753 | 1.00 | 12.70 | PROT |
| ATOM | 769 | O | ALA | 317 | 49.822 | 1.755 | 23.033 | 1.00 | 23.09 | PROT |
| ATOM | 770 | N | ALA | 318 | 49.832 | 3.943 | 23.534 | 1.00 | 14.79 | PROT |
| ATOM | 771 | CA | ALA | 318 | 50.567 | 3.779 | 24.776 | 1.00 | 8.38 | PROT |
| ATOM | 772 | CB | ALA | 318 | 50.727 | 5.122 | 25.448 | 1.00 | 11.75 | PROT |
| ATOM | 773 | C | ALA | 318 | 49.941 | 2.786 | 25.741 | 1.00 | 10.30 | PROT |
| ATOM | 774 | O | ALA | 318 | 50.585 | 1.824 | 26.165 | 1.00 | 8.48 | PROT |
| ATOM | 775 | N | VAL | 319 | 48.680 | 3.011 | 26.083 | 1.00 | 7.87 | PROT |
| ATOM | 776 | CA | VAL | 319 | 48.002 | 2.131 | 27.027 | 1.00 | 9.64 | PROT |
| ATOM | 777 | CB | VAL | 319 | 46.579 | 2.622 | 27.334 | 1.00 | 2.57 | PROT |
| ATOM | 778 | CG1 | VAL | 319 | 46.644 | 3.929 | 28.127 | 1.00 | 5.09 | PROT |
| ATOM | 779 | CG2 | VAL | 319 | 45.807 | 2.823 | 26.043 | 1.00 | 5.15 | PROT |
| ATOM | 780 | C | VAL | 319 | 47.930 | 0.695 | 26.541 | 1.00 | 11.68 | PROT |
| ATOM | 781 | O | VAL | 319 | 47.440 | −0.171 | 27.254 | 1.00 | 16.32 | PROT |
| ATOM | 782 | N | ARG | 320 | 48.415 | 0.444 | 25.329 | 1.00 | 16.40 | PROT |
| ATOM | 783 | CA | ARG | 320 | 48.405 | −0.902 | 24.767 | 1.00 | 13.20 | PROT |
| ATOM | 784 | CB | ARG | 320 | 47.736 | −0.918 | 23.393 | 1.00 | 2.00 | PROT |
| ATOM | 785 | CG | ARG | 320 | 46.310 | −0.405 | 23.420 | 1.00 | 14.07 | PROT |
| ATOM | 786 | CD | ARG | 320 | 45.283 | −1.460 | 23.035 | 1.00 | 19.69 | PROT |
| ATOM | 787 | NE | ARG | 320 | 44.168 | −0.868 | 22.292 | 1.00 | 36.52 | PROT |
| ATOM | 788 | CZ | ARG | 320 | 42.912 | −1.313 | 22.322 | 1.00 | 47.43 | PROT |
| ATOM | 789 | NH1 | ARG | 320 | 41.966 | −0.705 | 21.609 | 1.00 | 43.57 | PROT |
| ATOM | 790 | NH2 | ARG | 320 | 42.596 | −2.367 | 23.061 | 1.00 | 49.93 | PROT |
| ATOM | 791 | C | ARG | 320 | 49.835 | −1.391 | 24.662 | 1.00 | 15.45 | PROT |
| ATOM | 792 | O | ARG | 320 | 50.167 | −2.218 | 23.809 | 1.00 | 24.78 | PROT |
| ATOM | 793 | N | TYR | 321 | 50.684 | −0.860 | 25.537 | 1.00 | 13.68 | PROT |
| ATOM | 794 | CA | TYR | 321 | 52.085 | −1.258 | 25.572 | 1.00 | 18.80 | PROT |
| ATOM | 795 | CB | TYR | 321 | 52.925 | −0.208 | 26.295 | 1.00 | 9.64 | PROT |
| ATOM | 796 | CG | TYR | 321 | 54.313 | −0.685 | 26.622 | 1.00 | 11.20 | PROT |
| ATOM | 797 | CD1 | TYR | 321 | 55.211 | −1.005 | 25.612 | 1.00 | 2.00 | PROT |
| ATOM | 798 | CE1 | TYR | 321 | 56.483 | −1.461 | 25.906 | 1.00 | 9.63 | PROT |
| ATOM | 799 | CD2 | TYR | 321 | 54.727 | −0.834 | 27.943 | 1.00 | 18.93 | PROT |
| ATOM | 800 | CE2 | TYR | 321 | .56.003 | −1.293 | 28.250 | 1.00 | 19.49 | PROT |
| ATOM | 801 | CZ | TYR | 321 | 56.874 | −1.604 | 27.225 | 1.00 | 14.75 | PROT |
| ATOM | 802 | OH | TYR | 321 | 58.137 | −2.053 | 27.518 | 1.00 | 22.96 | PROT |
| ATOM | 803 | C | TYR | 321 | 52.209 | −2.607 | 26.287 | 1.00 | 19.74 | PROT |
| ATOM | 804 | O | TYR | 321 | 51.483 | −2.889 | 27.242 | 1.00 | 31.56 | PROT |
| ATOM | 805 | N | ASP | 322 | 53.136 | −3.435 | 25.823 | 1.00 | 26.35 | PROT |
| ATOM | 806 | CA | ASP | 322 | 53.346 | −4.759 | 26.392 | 1.00 | 22.38 | PROT |
| ATOM | 807 | CB | ASP | 322 | 52.982 | −5.814 | 25.353 | 1.00 | 33.63 | PROT |
| ATOM | 808 | CG | ASP | 322 | ,52.601 | −7.128 | 25.970 | 1.00 | 40.70 | PROT |
| ATOM | 809 | OD1 | ASP | 322 | 51.539 | −7.658 | 25.591 | 1.00 | 48.18 | PROT |
| ATOM | 810 | OD2 | ASP | 322 | 53.358 | −7.628 | 26.826 | 1.00 | 38.91 | PROT |
| ATOM | 811 | C | ASP | 322 | 54.800 | 4.928 | 26.776 | 1.00 | 23.51 | PROT |
| ATOM | 812 | O | ASP | 322 | 55.683 | 4.844 | 25.924 | 1.00 | 37.80 | PROT |
| ATOM | 813 | N | PRO | 323 | 55.076 | −5.160 | 28.066 | 1.00 | 24.06 | PROT |
| ATOM | 814 | CD | PRO | 323 | 54.130 | −5.258 | 29.187 | 1.00 | 19.35 | PROT |
| ATOM | 815 | CA | PRO | 323 | 56.462 | −5.339 | 28.507 | 1.00 | 23.60 | PROT |
| ATOM | 816 | CB | PRO | 323 | 56.390 | −5.121 | 30.007 | 1.00 | 3.90 | PROT |
| ATOM | 817 | CG | PRO | 323 | 55.031 | −5.570 | 30.360 | 1.00 | 14.06 | PROT |
| ATOM | 818 | C | PRO | 323 | 56.949 | −6.736 | 28.151 | 1.00 | 21.79 | PROT |
| ATOM | 819 | O | PRO | 323 | 58.149 | −7.003 | 28.119 | 1.00 | 27.28 | PROT |
| ATOM | 820 | N | GLU | 324 | 56.009 | −7.633 | 27.889 | 1.00 | 37.63 | PROT |
| ATOM | 821 | CA | GLU | 324 | 56.366 | −8.993 | 27.524 | 1.00 | 42.63 | PROT |
| ATOM | 822 | CB | GLU | 324 | 55.133 | −9.885 | 27.551 | 1.00 | 37.58 | PROT |
| ATOM | 823 | C | GLU | 324 | 56.971 | −8.956 | 26.124 | 1.00 | 43.28 | PROT |
| ATOM | 824 | O | GLU | 324 | 58.154 | −9.239 | 25.938 | 1.00 | 43.14 | PROT |
| ATOM | 825 | N | SER | 325 | 56.153 | −8.586 | 25.142 | 1.00 | 31.72 | PROT |
| ATOM | 826 | CA | SER | 325 | 56.607 | −8.508 | 23.765 | 1.00 | 30.34 | PROT |
| ATOM | 827 | CB | SER | 325 | 55.413 | −8.522 | 22.814 | 1.00 | 17.63 | PROT |
| ATOM | 828 | OG | SER | 325 | 54.356 | −7.729 | 23.315 | 1.00 | 31.90 | PROT |
| ATOM | 829 | C | SER | 325 | 57.441 | −7.257 | 23.519 | 1.00 | 31.94 | PROT |
| ATOM | 830 | O | SER | 325 | 58.146 | −7.169 | 22.513 | 1.00 | 45.47 | PROT |
| ATOM | 831 | N | GLU | 326 | 57.359 | −6.289 | 24.429 | 1.00 | 31.10 | PROT |
| ATOM | 832 | CA | GLU | 326 | 58.119 | −5.050 | 24.281 | 1.00 | 31.43 | PROT |
| ATOM | 833 | CB | GLU | 326 | 59.598 | −5.382 | 24.091 | 1.00 | 30.39 | PROT |
| ATOM | 834 | CG | GLU | 326 | 60.552 | 4.342 | 24.612 | 1.00 | 35.00 | PROT |
| ATOM | 835 | CD | GLU | 326 | 61.738 | 4.965 | 25.304 | 1.00 | 29.12 | PROT |
| ATOM | 836 | OE1 | GLU | 326 | 61.525 | −5.579 | 26.370 | 1.00 | 39.21 | PROT |
| ATOM | 837 | OE2 | GLU | 326 | 62.872 | −4.844 | 24.788 | 1.00 | 29.11 | PROT |
| ATOM | 838 | C | GLU | 326 | 57.605 | −4.283 | 23.063 | 1.00 | 28.37 | PRbT |
| ATOM | 839 | O | GLU | 326 | 58.382 | −3.677 | 22.321 | 1.00 | 26.51 | PROT |
| ATOM | 840 | N | THR | 327 | 56.290 | −4.301 | 22.873 | 1.00 | 23.71 | PROT |
| ATOM | 841 | CA | THR | 327 | 55.674 | −3.648 | 21.720 | 1.00 | 22.11 | PROT |
| ATOM | 842 | CB | THR | 327 | 55.298 | 4.705 | 20.652 | 1.00 | 28.08 | PROT |
| ATOM | 843 | OG1 | THR | 327 | 54.226 | −5.524 | 21.145 | 1.00 | 16.87 | PROT |

APPENDIX 7-continued

TRBTRIAC.PDB

| ATOM | 844 | CG2 | THR | 327 | 56.494 | −5.597 | 20.340 | 1.00 | 24.03 | PROT |
|---|---|---|---|---|---|---|---|---|---|---|
| ATOM | 845 | C | THR | 327 | 54.420 | −2.824 | 22.046 | 1.00 | 22.42 | PROT |
| ATOM | 846 | O | THR | 327 | 53.928 | −2.830 | 23.172 | 1.00 | 17.50 | PROT |
| ATOM | 847 | N | LEU | 328 | 53.914 | −2.122 | 21.038 | 1.00 | 17.28 | PROT |
| ATOM | 848 | CA | LEU | 328 | 52.728 | −1.285 | 21.171 | 1.00 | 14.83 | PROT |
| ATOM | 849 | CB | LEU | 328 | 53.065 | 0.157 | 20.806 | 1.00 | 15.27 | PROT |
| ATOM | 850 | CG | LEU | 328 | 53.693 | 1.036 | 21.879 | 1.00 | 10.50 | PROT |
| ATOM | 851 | CD1 | LEU | 328 | 54.137 | 2.336 | 21.254 | 1.00 | 16.75 | PROT |
| ATOM | 852 | CD2 | LEU | 328 | 52.682 | 1.285 | 22.979 | 1.00 | 20.19 | PROT |
| ATOM | 853 | C | LEU | 328 | 51.687 | −1.804 | 20.198 | 1.00 | 18.16 | PROT |
| ATOM | 854 | O | LEU | 328 | 52.035 | −2.508 | 19.254 | 1.00 | 23.88 | PROT |
| ATOM | 855 | N | THR | 329 | 50.421 | −1.450 | 20.402 | 1.00 | 9.40 | PROT |
| ATOM | 856 | CA | THR | 329 | 49.389 | −1.920 | 19.495 | 1.00 | 8.26 | PROT |
| ATOM | 857 | CB | THR | 329 | 48.460 | −2.888 | 20.199 | 1.00 | 8.67 | PROT |
| ATOM | 858 | OG1 | THR | 329 | 49.213 | 4.052 | 20.577 | 1.00 | 13.23 | PROT |
| ATOM | 859 | CG2 | THR | 329 | 47.308 | −3.289 | 19.270 | 1.00 | 2.00 | PROT |
| ATOM | 860 | C | THR | 329 | 48.569 | −0.841 | 18.800 | 1.00 | 16.65 | PROT |
| ATOM | 861 | O | THR | 329 | 47.726 | −0.158 | 19.406 | 1.00 | 17.20 | PROT |
| ATOM | 862 | N | LEU | 330 | 48.808 | −0.725 | 17.495 | 1.00 | 21.56 | PROT |
| ATOM | 863 | CA | LEU | 330 | 48.138 | 0.258 | 16.655 | 1.00 | 20.95 | PROT |
| ATOM | 864 | CB | LEU | 330 | 49.106 | 0.676 | 15.539 | 1.00 | 17.36 | PROT |
| ATOM | 865 | CG | LEU | 330 | 50.570 | 0.797 | 16.028 | 1.00 | 12.86 | PROT |
| ATOM | 866 | CD1 | LEU | 330 | 51.531 | 0.521 | 14.898 | 1.00 | 10.10 | PROT |
| ATOM | 867 | CD2 | LEU | 330 | 50.830 | 2.180 | 16.600 | 1.00 | 2.00 | PROT |
| ATOM | 868 | C | LEU | 330 | 46.803 | −0.258 | 16.097 | 1.00 | 21.35 | PROT |
| ATOM | 869 | O | LEU | 330 | 46.655 | −1.444 | 15.791 | 1.00 | 21.93 | PROT |
| ATOM | 870 | N | ASN | 331 | 45.834 | 0.648 | 15.981 | 1.00 | 27.76 | PROT |
| ATOM | 871 | CA | ASN | 331 | 44.487 | 0.338 | 15.498 | 1.00 | 28.09 | PROT |
| ATOM | 872 | CB | ASN | 331 | 44.460 | 0.275 | 13.971 | 1.00 | 24.95 | PROT |
| ATOM | 873 | CG | ASN | 331 | 43.074 | 0.540 | 13.397 | 1.00 | 33.45 | PROT |
| ATOM | 874 | OD1 | ASN | 331 | 42.512 | −0.305 | 12.701 | 1.00 | 38.21 | PROT |
| ATOM | 875 | ND2 | ASN | 331 | 42.522 | 1.715 | 13.680 | 1.00 | 24.73 | PROT |
| ATOM | 876 | C | ASN | 331 | 43.946 | −0.967 | 16.075 | 1.00 | 32.03 | PROT |
| ATOM | 877 | O | ASN | 331 | 43.166 | −1.668 | 15.431 | 1.00 | 35.49 | PROT |
| ATOM | 878 | N | GLY | 332 | 44.357 | −1.282 | 17.299 | 1.00 | 40.24 | PROT |
| ATOM | 879 | CA | GLY | 332 | 43.894 | −2.495 | 17.941 | 1.00 | 38.04 | PROT |
| ATOM | 880 | C | GLY | 332 | 44.009 | −3.665 | 16.998 | 1.00 | 40.09 | PROT |
| ATOM | 881 | O | GLY | 332 | 43.001 | −4.225 | 16.563 | 1.00 | 45.79 | PROT |
| ATOM | 882 | N | GLU | 333 | 45.249 | −4.013 | 16.664 | 1.00 | 41.60 | PROT |
| ATOM | 883 | CA | GLU | 333 | 45.539 | −5.126 | 15.763 | 1.00 | 36.28 | PROT |
| ATOM | 884 | CB | GLU | 333 | 44.752 | −4.978 | 14.454 | 1.00 | 46.39 | PROT |
| ATOM | 885 | CG | GLU | 333 | 44.745 | −3.580 | 13.862 | 1.00 | 58.03 | PROT |
| ATOM | 886 | CD | GLU | 333 | 43.883 | −3.485 | 12.610 | 1.00 | 67.00 | PROT |
| ATOM | 887 | OE1 | GLU | 333 | 44.446 | −3.282 | 11.511 | 1.00 | 67.51 | PROT |
| ATOM | 888 | OE2 | GLU | 333 | 42.644 | −3.615 | 12.727 | 1.00 | 71.01 | PROT |
| ATOM | 889 | C | GLU | 333 | 47.027 | −5.266 | 15.446 | 1.00 | 33.13 | PROT |
| ATOM | 890 | O | GLU | 333 | 47.563 | −6.366 | 15.486 | 1.00 | 27.97 | PROT |
| ATOM | 891 | N | MET | 334 | 47.692 | −4.152 | 15.143 | 1.00 | 27.00 | PROT |
| ATOM | 892 | CA | MET | 334 | 49.111 | −4.188 | 14.798 | 1.00 | 29.83 | PROT |
| ATOM | 893 | CB | MET | 334 | 49.416 | −3.159 | 13.699 | 1.00 | 26.04 | PROT |
| ATOM | 894 | CG | MET | 334 | 50.561 | −3.588 | 12.765 | 1.00 | 28.06 | PROT |
| ATOM | 895 | SD | MET | 334 | 51.263 | −2.273 | 11.736 | 1.00 | 28.46 | PROT |
| ATOM | 896 | CE | MET | 334 | 50.021 | −2.123 | 10.497 | 1.00 | 22.48 | PROT |
| ATOM | 897 | C | MET | 334 | 50.087 | −3.995 | 15.959 | 1.00 | 33.52 | PROT |
| ATOM | 898 | O | MET | 334 | 50.071 | −2.962 | 16.631 | 1.00 | 35.81 | PROT |
| ATOM | 899 | N | ALA | 335 | 50.942 | 4.996 | 16.171 | 1.00 | 27.46 | PROT |
| ATOM | 900 | CA | ALA | 335 | 51.948 | −4.976 | 17.234 | 1.00 | 29.69 | PROT |
| ATOM | 901 | CB | ALA | 335 | 51.966 | −6.314 | 17.965 | 1.00 | 12.67 | PROT |
| ATOM | 902 | C | ALA | 335 | 53.336 | 4.682 | 16.662 | 1.00 | 31.74 | PROT |
| ATOM | 903 | O | ALA | 335 | 53.943 | −5.530 | 16.009 | 1.00 | 43.66 | PROT |
| ATOM | 904 | N | VAL | 336 | 53.848 | −3.489 | 16.923 | 1.00 | 23.98 | PROT |
| ATOM | 905 | CA | VAL | 336 | 55.151 | −3.118 | 16.405 | 1.00 | 21.32 | PROT |
| ATOM | 906 | CB | VAL | 336 | 55.028 | −1.873 | 15.504 | 1.00 | 17.37 | PROT |
| ATOM | 907 | CG1 | VAL | 336 | 53.945 | −2.104 | 14.462 | 1.00 | 14.88 | PROT |
| ATOM | 908 | CG2 | VAL | 336 | 54.686 | −0.648 | 16.339 | 1.00 | 15.53 | PROT |
| ATOM | 909 | C | VAL | 336 | 56.150 | −2.852 | 17.526 | 1.00 | 22.72 | PROT |
| ATOM | 910 | O | VAL | 336 | 55.763 | −2.540 | 18.651 | 1.00 | 25.15 | PROT |
| ATOM | 911 | N | THR | 337 | 57.435 | −3.001 | 17.220 | 1.00 | 19.21 | PROT |
| ATOM | 912 | CA | THR | 337 | 58.476 | −2.765 | 18.205 | 1.00 | 20.31 | PROT |
| ATOM | 913 | CB | THR | 337 | 59.752 | −3.578 | 17.884 | 1.00 | 14.76 | PROT |
| ATOM | 914 | OG1 | THR | 337 | 59.957 | −3.616 | 16.467 | 1.00 | 16.43 | PROT |
| ATOM | 915 | CG2 | THR | 337 | 59.615 | 4.995 | 18.393 | 1.00 | 7.08 | PROT |
| ATOM | 916 | C | THR | 337 | 58.785 | −1.272 | 18.157 | 1.00 | 24.20 | PROT |
| ATOM | 917 | O | THR | 337 | 58.322 | −0.591 | 17.245 | 1.00 | 28.05 | PROT |
| ATOM | 918 | N | ARG | 338 | 59.548 | −0.766 | 19.134 | 1.00 | 27.55 | PROT |
| ATOM | 919 | CA | ARG | 338 | 59.917 | 0.655 | 19.197 | 1.00 | 16.80 | PROT |
| ATOM | 920 | CB | ARG | 338 | 60.757 | 0.942 | 20.446 | 1.00 | 17.04 | PROT |

APPENDIX 7-continued

TRBTRIAC.PDB

| | | | | | | | | | | |
|---|---|---|---|---|---|---|---|---|---|---|
| ATOM | 921 | CG | ARG | 338 | 61.687 | 2.149 | 20.303 | 1.00 | 9.79 | PROT |
| ATOM | 922 | CD | ARG | 338 | 62.666 | 2.276 | 21.458 | 1.00 | 2.00 | PROT |
| ATOM | 923 | NE | ARG | 338 | 61.994 | 2.128 | 22.739 | 1.00 | 20.70 | PROT |
| ATOM | 924 | CZ | ARG | 338 | 61.897 | 3.083 | 23.657 | 1.00 | 12.04 | PROT |
| ATOM | 925 | NH1 | ARG | 338 | 61.261 | 2.840 | 24.784 | 1.00 | 27.11 | PROT |
| ATOM | 926 | NH2 | ARG | 338 | 62.436 | 4.272 | 23.459 | 1.00 | 22.23 | PROT |
| ATOM | 927 | C | ARG | 338 | 60.702 | 1.085 | 17.968 | 1.00 | 21.26 | PROT |
| ATOM | 928 | O | ARG | 338 | 60.338 | 2.049 | 17.295 | 1.00 | 16.40 | PROT |
| ATOM | 929 | N | GLY | 339 | 61.792 | 0.374 | 17.693 | 1.00 | 31.57 | PROT |
| ATOM | 930 | CA | GLY | 339 | 62.609 | 0.696 | 16.540 | 1.00 | 32.42 | PROT |
| ATOM | 931 | C | GLY | 339 | 61.816 | 0.534 | 15.254 | 1.00 | 30.08 | PROT |
| ATOM | 932 | O | GLY | 339 | 61.932 | 1.342 | 14.328 | 1.00 | 25.82 | PROT |
| ATOM | 933 | N | GLN | 340 | 61.008 | −0.520 | 15.192 | 1.00 | 16.60 | PROT |
| ATOM | 934 | CA | GLN | 340 | 60.191 | −0.768 | 14.012 | 1.00 | 14.08 | PROT |
| ATOM | 935 | CB | GLN | 340 | 59.199 | −1.884 | 14.301 | 1.00 | 5.73 | PROT |
| ATOM | 936 | CG | GLN | 340 | 58.849 | −2.697 | 13.100 | 1.00 | 16.15 | PROT |
| ATOM | 937 | CD | GLN | 340 | 58.577 | −4.141 | 13.442 | 1.00 | 22.46 | PROT |
| ATOM | 938 | OE1 | GLN | 340 | 57.767 | 4.450 | 14.316 | 1.00 | 30.45 | PROT |
| ATOM | 939 | NE2 | GLN | 340 | 59.254 | −5.040 | 12.749 | 1.00 | 34.19 | PROT |
| ATOM | 940 | C | GLN | 340 | 59.452 | 0.521 | 13.632 | 1.00 | 22.07 | PROT |
| ATOM | 941 | O | GLN | 340 | 59.707 | 1.103 | 12.576 | 1.00 | 21.13 | PROT |
| ATOM | 942 | N | LEU | 341 | 58.561 | 0.976 | 14.518 | 1.00 | 27.88 | PROT |
| ATOM | 943 | CA | LEU | 341 | 57.778 | 2.197 | 14.306 | 1.00 | 21.82 | PROT |
| ATOM | 944 | CB | LEU | 341 | 56.813 | 2.418 | 1S.483 | 1.00 | 10.20 | PROT |
| ATOM | 945 | CG | LEU | 341 | 55.930 | 3.682 | 15.534 | 1.00 | 16.27 | PROT |
| ATOM | 946 | CD1 | LEU | 341 | 54.777 | 3.618 | 14.518 | 1.00 | 13.27 | PROT |
| ATOM | 947 | CD2 | LEU | 341 | 55.370 | 3.822 | 16.935 | 1.00 | 10.68 | PROT |
| ATOM | 948 | C | LEU | 341 | 58.683 | 3.413 | 14.138 | 1.00 | 13.98 | PROT |
| ATOM | 949 | O | LEU | 341 | 58.315 | 4.386 | 13.486 | 1.00 | 7.94 | PROT |
| ATOM | 950 | N | LYS | 342 | 59.867 | 3.361 | 14.734 | 1.00 | 11.48 | PROT |
| ATOM | 951 | CA | LYS | 342 | 60.804 | 4.465 | 14.613 | 1.00 | 17.77 | PROT |
| ATOM | 952 | CB | LYS | 342 | 62.063 | 4.213 | 15.459 | 1.00 | 13.58 | PROT |
| ATOM | 953 | CG | LYS | 342 | 63.219 | 5.173 | 15.140 | 1.00 | 13.27 | PROT |
| ATOM | 954 | CD | LYS | 342 | 64.173 | 5.358 | 16.319 | 1.00 | 5.44 | PROT |
| ATOM | 955 | CE | LYS | 342 | 64.500 | 6.829 | 16.546 | 1.00 | 5.47 | PROT |
| ATOM | 956 | NZ | LYS | 342 | 65.721 | 7.019 | 17.388 | 1.00 | 4.98 | PROT |
| ATOM | 957 | C | LYS | 342 | 61.184 | 4.579 | 13.141 | 1.00 | 19.97 | PROT |
| ATOM | 958 | O | LYS | 342 | 60.939 | 5.595 | 12.501 | 1.00 | 20.34 | PROT |
| ATOM | 959 | N | ASN | 343 | 61.764 | 3.510 | 12.605 | 1.00 | 26.88 | PROT |
| ATOM | 960 | CA | ASN | 343 | 62.196 | 3.470 | 11.219 | 1.00 | 22.34 | PROT |
| ATOM | 961 | CB | ASN | 343 | 62.829 | 2.123 | 10.929 | 1.00 | 4.80 | PROT |
| ATOM | 962 | CG | ASN | 343 | 64.060 | 1.894 | 11.758 | 1.00 | 18.77 | PROT |
| ATOM | 963 | OD1 | ASN | 343 | 64.755 | 2.848 | 12.117 | 1.00 | 14.12 | PROT |
| ATOM | 964 | ND2 | ASN | 343 | 64.340 | 0.634 | 12.083 | 1.00 | 12.72 | PROT |
| ATOM | 965 | C | ASN | 343 | 61.091 | 3.736 | 10.224 | 1.00 | 20.40 | PROT |
| ATOM | 966 | O | ASN | 343 | 61.309 | 4.417 | 9.232 | 1.00 | 20.76 | PROT |
| ATOM | 967 | N | GLY | 344 | 59.908 | 3.200 | 10.494 | 1.00 | 12.62 | PROT |
| ATOM | 968 | CA | GLY | 344 | 58.775 | 3.382 | 9.603 | 1.00 | 6.27 | PROT |
| ATOM | 969 | C | GLY | 344 | 58.229 | 4.796 | 9.451 | 1.00 | 14.56 | PROT |
| ATOM | 970 | O | GLY | 344 | 57.177 | 4.972 | 8.826 | 1.00 | 13.30 | PROT |
| ATOM | 971 | N | GLY | 345 | 58.902 | 5.795 | 10.030 | 1.00 | 16.51 | PROT |
| ATOM | 972 | CA | GLY | 345 | 58.439 | 7.166 | 9.869 | 1.00 | 20.04 | PROT |
| ATOM | 973 | C | GLY | 345 | 58.248 | 8.112 | 11.046 | 1.00 | 25.64 | PROT |
| ATOM | 974 | O | GLY | 345 | 58.243 | 9.331 | 10.849 | 1.00 | 23.32 | PROT |
| ATOM | 975 | N | LEU | 346 | 58.099 | 7.588 | 12.260 | 1.00 | 22.22 | PROT |
| ATOM | 976 | CA | LEU | 346 | 57.874 | 8.449 | 13.415 | 1.00 | 14.94 | PROT |
| ATOM | 977 | CB | LEU | 346 | 57.070 | 7.700 | 14.474 | 1.00 | 3.92 | PROT |
| ATOM | 978 | CG | LEU | 346 | 55.566 | 7.538 | 14.193 | 1.00 | 5.92 | PROT |
| ATOM | 979 | CD1 | LEU | 346 | 54.938 | 6.796 | 15.355 | 1.00 | 2.00 | PROT |
| ATOM | 980 | CD2 | LEU | 346 | 54.884 | 8.885 | 13.973 | 1.00 | 2.00 | PROT |
| ATOM | 981 | C | LEU | 346 | 59.126 | 9.042 | 14.041 | 1.00 | 14.60 | PROT |
| ATOM | 982 | O | LEU | 346 | 59.102 | 10.153 | 14.554 | 1.00 | 17.36 | PROT |
| ATOM | 983 | N | GLY | 347 | 60.226 | 8.312 | 14.001 | 1.00 | 12.09 | PROT |
| ATOM | 984 | CA | GLY | 347 | 61.455 | 8.828 | 14.581 | 1.00 | 15.62 | PROT |
| ATOM | 985 | G | GLY | 347 | 61.439 | 8.963 | 16.090 | 1.00 | 6.31 | PROT |
| ATOM | 986 | O | GLY | 347 | 60.865 | 8.141 | 16.790 | 1.00 | 13.15 | PROT |
| ATOM | 987 | N | VAL | 348 | 62.076 | 10.011 | 16.592 | 1.00 | 13.74 | PROT |
| ATOM | 988 | CA | VAL | 348 | 62.141 | 10.259 | 18.030 | 1.00 | 10.13 | PROT |
| ATOM | 989 | CB | VAL | 348 | 62.757 | 11.646 | 18.342 | 1.00 | 9.26 | PROT |
| ATOM | 990 | CG1 | VAL | 348 | 61.867 | 12.752 | 17.794 | 1.00 | 2.00 | PROT |
| ATOM | 991 | CG2 | VAL | 348 | 62.942 | 11.802 | 19.836 | 1.00 | 2.00 | PROT |
| ATOM | 992 | C | VAL | 348 | 60.763 | 10.216 | 18.650 | 1.00 | 6.61 | PROT |
| ATOM | 993 | O | VAL | 348 | 60.619 | 10.066 | 19.862 | 1.00 | 3.12 | PROT |
| ATOM | 994 | N | VAL | 349 | 59.746 | 10.358 | 17.816 | 1.00 | 5.51 | PROT |
| ATOM | 995 | CA | VAL | 349 | 58.386 | 10.342 | 18.306 | 1.00 | 2.00 | PROT |
| ATOM | 996 | CB | VAL | 349 | 57.421 | 10.886 | 17.260 | 1.00 | 4.46 | PROT |
| ATOM | 997 | CG1 | VAL | 349 | 56.001 | 10.578 | 17.656 | 1.00 | 2.00 | PROT |

APPENDIX 7-continued

TRBTRIAC.PDB

| | | | | | | | | | | |
|---|---|---|---|---|---|---|---|---|---|---|
| ATOM | 998 | CG2 | VAL | 349 | 57.623 | 12.387 | 17.122 | 1.00 | 2.00 | PROT |
| ATOM | 999 | C | VAL | 349 | 57.995 | 8.933 | 18.687 | 1.00 | 9.15 | PROT |
| ATOM | 1000 | O | VAL | 349 | 57.284 | 8.726 | 19.664 | 1.00 | 15.02 | PROT |
| ATOM | 1001 | N | SER | 350 | 58.446 | 7.943 | 17.933 | 1.00 | 7.42 | PROT |
| ATOM | 1002 | CA | SER | 350 | 58.087 | 6.590 | 18.315 | 1.00 | 12.87 | PROT |
| ATOM | 1003 | CB | SER | 350 | 58.695 | 5.561 | 17.382 | 1.00 | 9.48 | PROT |
| ATOM | 1004 | OG | SER | 350 | 58.529 | 4.269 | 17.931 | 1.00 | 10.82 | PROT |
| ATOM | 1005 | C | SER | 350 | 58.628 | 6.364 | 19.717 | 1.00 | 15.55 | PROT |
| ATOM | 1006 | O | SER | 350 | 57.963 | 5.761 | 20.558 | 1.00 | 25.88 | PROT |
| ATOM | 1007 | N | ASP | 351 | 59.838 | 6.863 | 19.950 | 1.00 | 16.38 | PROT |
| ATOM | 1008 | CA | ASP | 351 | 60.522 | 6.743 | 21.230 | 1.00 | 9.58 | PROT |
| ATOM | 1009 | CB | ASP | 351 | 61.861 | 7.469 | 21.176 | 1.00 | 7.32 | PROT |
| ATOM | 1010 | CG | ASP | 351 | 62.989 | 6.576 | 20.742 | 1.00 | 24.16 | PROT |
| ATOM | 1011 | OD1 | ASP | 351 | 64.011 | 7.110 | 20.275 | 1.00 | 30.24 | PROT |
| ATOM | 1012 | OD2 | ASP | 351 | 62.866 | 5.343 | 20.869 | 1.00 | 33.85 | PROT |
| ATOM | 1013 | C | ASP | 351 | 59.695 | 7.360 | 22.334 | 1.00 | 17.01 | PROT |
| ATOM | 1014 | O | ASP | 351 | 59.605 | 6.822 | 23.435 | 1.00 | 26.28 | PROT |
| ATOM | 1015 | N | ALA | 352 | 59.100 | 8.508 | 22.032 | 1.00 | 13.51 | PROT |
| ATOM | 1016 | CA | ALA | 352 | 58.294 | 9.224 | 23.004 | 1.00 | 5.19 | PROT |
| ATOM | 1017 | CB | ALA | 352 | 57.914 | 10.593 | 22.452 | 1.00 | 2.00 | PROT |
| ATOM | 1018 | C | ALA | 352 | 57.055 | 8.432 | 23.374 | 1.00 | 2.00 | PROT |
| ATOM | 1019 | O | ALA | 352 | 56.701 | 8.360 | 24.535 | 1.00 | 7.20 | PROT |
| ATOM | 1020 | N | ILE | 353 | 56.396 | 7.832 | 22.393 | 1.00 | 2.00 | PROT |
| ATOM | 1021 | CA | ILE | 353 | 55.201 | 7.049 | 22.677 | 1.00 | 5.90 | PROT |
| ATOM | 1022 | CB | ILE | 353 | 54.468 | 6.626 | 21.381 | 1.00 | 5.87 | PROT |
| ATOM | 1023 | CG2 | ILE | 353 | 53.113 | 6.049 | 21.732 | 1.00 | 2.00 | PROT |
| ATOM | 1024 | CG1 | ILE | 353 | 54.349 | 7.831 | 20.428 | 1.00 | 3.91 | PROT |
| ATOM | 1025 | CD1 | ILE | 353 | 53.330 | 7.664 | 19.294 | 1.00 | 2.00 | PROT |
| ATOM | 1026 | C | ILE | 353 | 55.554 | 5.795 | 23.484 | 1.00 | 12.46 | PROT |
| ATOM | 1027 | O | ILE | 353 | 54.848 | 5.426 | 24.428 | 1.00 | 11.74 | PROT |
| ATOM | 1028 | N | PHE | 354 | 56.644 | 5.131 | 23.122 | 1.00 | 19.57 | PROT |
| ATOM | 1029 | CA | PHE | 354 | 57.034 | 3.944 | 23.862 | 1.00 | 14.42 | PROT |
| ATOM | 1030 | CB | PHE | 354 | 58.256 | 3.270 | 23.209 | 1.00 | 3.70 | PROT |
| ATOM | 1031 | CG | PHE | 354 | 57.890 | 2.141 | 22.284 | 1.00 | 9.42 | PROT |
| ATOM | 1032 | CD1 | PHE | 354 | 57.427 | 2.401 | 20.995 | 1.00 | 12.33 | PROT |
| ATOM | 1033 | CD2 | PHE | 354 | 57.912 | 0.822 | 22.727 | 1.00 | 15.63 | PROT |
| ATOM | 1034 | CE1 | PHE | 354 | 56.982 | 1.366 | 20.165 | 1.00 | 6.67 | PROT |
| ATOM | 1035 | CE2 | PHE | 354 | 57.468 | −0.224 | 21.900 | 1.00 | 16.53 | PROT |
| ATOM | 1036 | CZ | PHE | 354 | 57.002 | 0.053 | 20.620 | 1.00 | 11.61 | PROT |
| ATOM | 1037 | C | PHE | 354 | 57.322 | 4.346 | 25.307 | 1.00 | 18.55 | PROT |
| ATOM | 1038 | O | PHE | 354 | 56.796 | 3.740 | 26.233 | 1.00 | 16.67 | PROT |
| ATOM | 1039 | N | ASP | 355 | 58.125 | 5.392 | 25.491 | 1.00 | 12.83 | PROT |
| ATOM | 1040 | CA | ASP | 355 | 58.486 | 5.881 | 26.818 | 1.00 | 5.31 | PROT |
| ATOM | 1041 | CB | ASP | 355 | .59.351 | 7.132 | 26.697 | 1.00 | 9.38 | PROT |
| ATOM | 1042 | CG | ASP | 355 | 60.805 | 6.814 | 26.428 | 1.00 | 5.96 | PROT |
| ATOM | 1043 | OD1 | ASP | 355 | 61.112 | 5.683 | 26.016 | 1.00 | 8.53 | PROT |
| ATOM | 1044 | OD2 | ASP | 355 | 61.650 | 7.706 | 26.628 | 1.00 | 15.51 | PROT |
| ATOM | 1045 | C | ASP | 355 | 57.252 | 6.199 | 27.659 | 1.00 | 10.27 | PROT |
| ATOM | 1046 | O | ASP | 355 | 57.231 | 5.972 | 28.871 | 1.00 | 21.86 | PROT |
| ATOM | 1047 | N | LEU | 356 | 56.224 | 6.726 | 27.014 | 1.00 | 4.18 | PROT |
| ATOM | 1048 | CA | LEU | 356 | 54.988 | 7.061 | 27.697 | 1.00 | 2.07 | PROT |
| ATOM | 1049 | CB | LEU | 356 | 54.086 | 7.865 | 26.771 | 1.00 | 2.24 | PROT |
| ATOM | 1050 | CG | LEU | 356 | 52.694 | 8.229 | 27.266 | 1.00 | 3.11 | PROT |
| ATOM | 1051 | CD1 | LEU | 356 | 52.771 | 9.317 | 28.323 | 1.00 | 2.00 | PROT |
| ATOM | 1052 | CD2 | LEU | 356 | 51.877 | 8.709 | 26.086 | 1.00 | 2.00 | PROT |
| ATOM | 1053 | C | LEU | 356 | 54.281 | 5.786 | 28.091 | 1.00 | 9.17 | PROT |
| ATOM | 1054 | O | LEU | 356 | 53.831 | 5.644 | 29.221 | 1.00 | 14.77 | PROT |
| ATOM | 1055 | N | GLY | 357 | 54.183 | 4.856 | 27.147 | 1.00 | 13.10 | PROT |
| ATOM | 1056 | CA | GLY | 357 | 53.515 | 3.597 | 27.413 | 1.00 | 6.91 | PROT |
| ATOM | 1057 | C | GLY | 357 | 54.113 | 2.879 | 28.598 | 1.00 | 8.33 | PROT |
| ATOM | 1058 | O | GLY | 357 | 53.400 | 2.426 | 29.492 | 1.00 | 9.09 | PROT |
| ATOM | 1059 | N | MET | 358 | 55.435 | 2.768 | 28.607 | 1.00 | 12.61 | PROT |
| ATOM | 1060 | CA | MET | 358 | 56.112 | 2.091 | 29.692 | 1.00 | 10.53 | PROT |
| ATOM | 1061 | CB | MET | 358 | 57.626 | 2.153 | 29.498 | 1.00 | 5.45 | PROT |
| ATOM | 1062 | CG | MET | 358 | 58.138 | 1.507 | 28.210 | 1.00 | 15.15 | PROT |
| ATOM | 1063 | SD | MET | 358 | 59.971 | 1.352 | 28.113 | 1.00 | 17.63 | PROT |
| ATOM | 1064 | CE | MET | 358 | 60.445 | 3.023 | 27.774 | 1.00 | 20.56 | PROT |
| ATOM | 1065 | C | MET | 358 | 55.714 | 2.809 | 30.972 | 1.00 | 15.08 | PROT |
| ATOM | 1066 | O | MET | 358 | 55.241 | 2.191 | 31.920 | 1.00 | 27.69 | PROT |
| ATOM | 1067 | N | SER | 359 | 55.875 | 4.125 | 30.984 | 1.00 | 20.67 | PROT |
| ATOM | 1068 | CA | SER | 359 | 55.551 | 4.924 | 32.158 | 1.00 | 19.72 | PROT |
| ATOM | 1069 | CB | SER | 359 | 55.831 | 6.398 | 31.861 | 1.00 | 19.98 | PROT |
| ATOM | 1070 | OG | SER | 359 | 54.753 | 7.220 | 32.262 | 1.00 | 33.66 | PROT |
| ATOM | 1071 | C | SER | 359 | 54.115 | 4.757 | 32.656 | 1.00 | 22.67 | PROT |
| ATOM | 1072 | O | SER | 359 | 53.849 | 4.837 | 33.860 | 1.00 | 22.94 | PROT |
| ATOM | 1073 | N | LEU | 360 | 53.197 | 4.514 | 31.727 | 1.00 | 20.55 | PROT |
| ATOM | 1074 | CA | LEU | 360 | 51.785 | 4.360 | 32.054 | 1.00 | 17.01 | PROT |

APPENDIX 7-continued

TRBTRIAC.PDB

| | | | | | | | | | | |
|---|---|---|---|---|---|---|---|---|---|---|
| ATOM | 1075 | CB | LEU | 360 | 50.934 | 4.578 | 30.802 | 1.00 | 2.60 | PROT |
| ATOM | 1076 | CG | LEU | 360 | 50.674 | 5.988 | 30.291 | 1.00 | 6.99 | PROT |
| ATOM | 1077 | CD1 | LEU | 360 | 49.589 | 5.935 | 29.236 | 1.00 | 4.15 | PROT |
| ATOM | 1078 | CD2 | LEU | 360 | 50.247 | 6.892 | 31.432 | 1.00 | 18.93 | PROT |
| ATOM | 1079 | C | LEU | 360 | 51.437 | 3.001 | 32.638 | 1.00 | 19.29 | PROT |
| ATOM | 1080 | O | LEU | 360 | 50.319 | 2.802 | 33.102 | 1.00 | 27.53 | PROT |
| ATOM | 1081 | N | SER | 361 | 52.375 | 2.061 | 32.596 | 1.00 | 21.73 | PROT |
| ATOM | 1082 | CA | SER | 361 | 52.139 | 0.712 | 33.114 | 1.00 | 23.03 | PROT |
| ATOM | 1083 | CB | SER | 361 | 53L415 | −0.130 | 33.027 | 1.00 | 25.89 | PROT |
| ATOM | 1084 | OG | SER | 361 | 53.645 | −0.613 | 31.717 | 1.00 | 27.77 | PROT |
| ATOM | 1085 | C | SER | 361 | 51.681 | 0.730 | 34.563 | 1.00 | 23.26 | PROT |
| ATOM | 1086 | O | SER | 361 | S0.720 | 0.046 | 34.929 | 1.00 | 18.73 | PROT |
| ATOM | 1087 | N | SER | 362 | 52.388 | 1.524 | 35.367 | 1.00 | 29.84 | PROT |
| ATOM | 1088 | CA | SER | 362 | 52.141 | 1.668 | 36.799 | 1.00 | 24.49 | PROT |
| ATOM | 1089 | CB | SER | 362 | 53.435 | 2.089 | 37.491 | 1.00 | 26.14 | PROT |
| ATOM | 1090 | OG | SER | 362 | 53.917 | 3.305 | 36.949 | 1.00 | 25.03 | PROT |
| ATOM | 1091 | C | SER | 362 | 51.031 | 2.635 | 37.210 | 1.00 | 26.86 | PROT |
| ATOM | 1092 | O | SER | 362 | 50.797 | 2.831 | 38.404 | 1.00 | 39.63 | PROT |
| ATOM | 1093 | N | PHE | 363 | 50.361 | 3.251 | 36.240 | 1.00 | 20.94 | PROT |
| ATOM | 1094 | CA | PHE | 363 | 49.272 | 4.185 | 36.545 | 1.00 | 18.33 | PROT |
| ATOM | 1095 | CB | PHE | 363 | 49.191 | 5.294 | 35.486 | 1.00 | 17.03 | PROT |
| ATOM | 1096 | CG | PHE | 363 | 50.171 | 6.407 | 35.706 | 1.00 | 22.73 | PROT |
| ATOM | 1097 | CD1 | PHE | 363 | 49.733 | 7.689 | 35.990 | 1.00 | 9.72 | PROT |
| ATOM | 1098 | CD2 | PHE | 363 | 51.545 | 6.167 | 35.659 | 1.00 | 24.77 | PROT |
| ATOM | 1099 | CE1 | PHE | 363 | 50.645 | 8.712 | 36.225 | 1.00 | 16.85 | PROT |
| ATOM | 1100 | CE2 | PHE | 363 | 52.463 | 7.198 | 35.897 | 1.00 | 14.26 | PROT |
| ATOM | 1101 | CZ | PHE | 363 | 52.011 | 8.462 | 36.179 | 1.00 | 2.26 | PROT |
| ATOM | 1102 | C | PHE | 363 | 47.958 | 3.417 | 36.598 | 1.00 | 16.57 | PROT |
| ATOM | 1103 | O | PHE | 363 | 46.971 | 3.882 | 37.165 | 1.00 | 13.08 | PROT |
| ATOM | 1104 | N | ASN | 364 | .47.976 | 2.231 | 36.002 | 1.00 | 17.31 | PROT |
| ATOM | 1105 | CA | ASN | 364 | 46.819 | 1.349 | 35.949 | 1.00 | 26.11 | PROT |
| ATOM | 1106 | CB | ASN | 364 | 46.673 | 0.608 | 37.276 | 1.00 | 16.96 | PROT |
| ATOM | 1107 | CG | ASN | 364 | 47.402 | −0.715 | 37.267 | 1.00 | 31.34 | PROT |
| ATOM | 1108 | OD1 | ASN | 364 | 46.965 | −1.657 | 36.613 | 1.00 | 36.66 | PROT |
| ATOM | 1109 | ND2 | ASN | 364 | 48.527 | −0.794 | 37.985 | 1.00 | 31.61 | PROT |
| ATOM | 1110 | C | ASN | 364 | 45.527 | 2.060 | 35.594 | 1.00 | 18.22 | PROT |
| ATOM | 1111 | O | ASN | 364 | 44.522 | 1.923 | 36.286 | 1.00 | 23.17 | PROT |
| ATOM | 1112 | N | LEU | 365 | 45.567 | 2.803 | 34.491 | 1.00 | 13.10 | PROT |
| ATOM | 1113 | CA | LEU | 365 | 44.417 | 3.562 | 34.013 | 1.00 | 15.41 | PROT |
| ATOM | 1114 | CB | LEU | 365 | 44.833 | 4.483 | 32.861 | 1.00 | 16.55 | PROT |
| ATOM | 1115 | CG | LEU | 365 | 45.762 | 5.653 | 33.181 | 1.00 | 19.56 | PROT |
| ATOM | 1116 | CD1 | LEU | 365 | 46.146 | 6.373 | 31.897 | 1.00 | 6.69 | PROT |
| ATOM | 1117 | CD2 | LEU | 365 | 45.067 | 6.602 | 34.128 | 1.00 | 15.69 | PROT |
| ATOM | 1118 | C | LEU | 365 | 43.328 | 2.624 | 33.520 | 1.00 | 12.07 | PROT |
| ATOM | 1119 | O | LEU | 365 | 43.620 | 1.534 | 33.043 | 1.00 | 19.81 | PROT |
| ATOM | 1120 | N | ASP | 366 | 42.077 | 3.047 | 33.653 | 1.00 | 10.86 | PROT |
| ATOM | 1121 | CA | ASP | 366 | 40.942 | 2.263 | 33.180 | 1.00 | 8.96 | PROT |
| ATOM | 1122 | CB | ASP | 366 | 39.933 | 2.021 | 34.326 | 1.00 | 9.59 | PROT |
| ATOM | 1123 | CG | ASP | 366 | 39.300 | 3.306 | 34.859 | 1.00 | 21.78 | PROT |
| ATOM | 1124 | OD1 | ASP | 366 | 39.871 | 4.397 | 34.676 | 1.00 | 25.60 | PROT |
| ATOM | 1125 | OD2 | ASP | 366 | 38.217 | 3.222 | 31.474 | 1.00 | 19.16 | PROT |
| ATOM | 1126 | C | ASP | 366 | 40.288 | 3.005 | 32.002 | 1.00 | 8.82 | PROT |
| ATOM | 1127 | O | ASP | 366 | 40.666 | 4.132 | 31.681 | 1.00 | 17.66 | PROT |
| ATOM | 1128 | N | ASP | 367 | 39.321 | 2.379 | 31.346 | 1.00 | 9.45 | PROT |
| ATOM | 1129 | CA | ASP | 367 | 38.668 | 3.023 | 30.218 | 1.00 | 11.11 | PROT |
| ATOM | 1130 | CB | ASP | 367 | 37.457 | 2.205 | 29.769 | 1.00 | 20.67 | PROT |
| ATOM | 1131 | CG | ASP | 367 | 37.832 | 0.812 | 29.301 | 1.00 | 25.02 | PROT |
| ATOM | 1132 | OD1 | ASP | 367 | 39.040 | 0.525 | 29.158 | 1.00 | 21.06 | PROT |
| ATOM | 1133 | OD2 | ASP | 367 | 36.909 | 0.002 | 29.076 | 1.00 | 31.37 | PROT |
| ATOM | 1134 | C | ASP | 367 | 38.233 | 4.445 | 30.574 | 1.00 | 14.44 | PROT |
| ATOM | 1135 | O | ASP | 367 | 38.457 | 5.380 | 29.815 | 1.00 | 26.42 | PROT |
| ATOM | 1136 | N | THR | 368 | 37.619 | 4.612 | 31.735 | 1.00 | 13.62 | PROT |
| ATOM | 1137 | CA | THR | 368 | 37.157 | 5.926 | 32.160 | 1.00 | 13.14 | PROT |
| ATOM | 1138 | CB | THR | 368 | 36.510 | 5.853 | 33.547 | 1.00 | 16.53 | PROT |
| ATOM | 1139 | OG1 | THR | 368 | 35.482 | 4.856 | 33.550 | 1.00 | 10.44 | PROT |
| ATOM | 1140 | CG2 | THR | 368 | 35.928 | 7.188 | 33.925 | 1.00 | 5.20 | PROT |
| ATOM | 1141 | C | THR | 368 | 38.291 | 6.942 | 32.226 | 1.00 | 13.03 | PROT |
| ATOM | 1142 | O | THR | 368 | 38.114 | 8.108 | 31.878 | 1.00 | 12.90 | PROT |
| ATOM | 1143 | N | GLU | 369 | 39.455 | 6.492 | 32.686 | 1.00 | 9.96 | PROT |
| ATOM | 1144 | CA | GLU | 369 | 40.616 | 7.365 | 32.821 | 1.00 | 7.34 | PROT |
| ATOM | 1145 | CB | GLU | 369 | 41.673 | 6.687 | 33.708 | 1.00 | 10.25 | PROT |
| ATOM | 1146 | CG | GLU | 369 | 41.584 | 7.113 | 35.189 | 1.00 | 14.56 | PROT |
| ATOM | 1147 | CD | GLU | 369 | 41.599 | 5.945 | 36.167 | 1.00 | 19.39 | PROT |
| ATOM | 1148 | OE1 | GLU | 369 | 42.255 | 4.922 | 35.864 | 1.00 | 19.65 | PROT |
| ATOM | 1149 | OE2 | GLU | 369 | 40.954 | 6.054 | 37.233 | 1.00 | 7.98 | PROT |
| ATOM | 11S0 | C | GLU | 369 | 41.203 | 7.768 | 31.468 | 1.00 | 4.33 | PROT |
| ATOM | 1151 | O | GLU | 369 | 41.467 | 8.944 | 31.213 | 1.00 | 7.50 | PROT |

APPENDIX 7-continued

| | | | | TRBTRIAC.PDB | | | | | |
|---|---|---|---|---|---|---|---|---|---|
| ATOM | 1152 | N | VAL | 370 | 41.406 | 6.784 | 30.603 | 1.00 | 12.29 | PROT |
| ATOM | 1153 | CA | VAL | 370 | 41.927 | 7.040 | 29.267 | 1.00 | 19.01 | PROT |
| ATOM | 1154 | CB | VAL | 370 | 42.092 | 5.726 | 28.496 | 1.00 | 10.10 | PROT |
| ATOM | 1155 | CG1 | VAL | 370 | 42.431 | 6.011 | 27.049 | 1.00 | 8.57 | PROT |
| ATOM | 1156 | CG2 | VAL | 370 | 43.168 | 4.877 | 29.159 | 1.00 | 12.40 | PROT |
| ATOM | 1157 | C | VAL | 370 | 40.896 | 7.915 | 28.555 | 1.00 | 18.30 | PROT |
| ATOM | 1158 | O | VAL | 370 | 41.230 | 8.872 | 27.855 | 1.00 | 17.19 | PROT |
| ATOM | 1159 | N | ALA | 371 | 39.633 | 7.581 | 28.760 | 1.00 | 2.00 | PROT |
| ATOM | 1160 | CA | ALA | 371 | 38.549 | 8.321 | 28.157 | 1.00 | 3.53 | PROT |
| ATOM | 1161 | CB | ALA | 371 | 37.215 | 7.728 | 28.591 | 1.00 | 9.17 | PROT |
| ATOM | 1162 | C | ALA | 371 | 38.603 | 9.797 | 28.529 | 1.00 | 9.97 | PROT |
| ATOM | 1163 | O | ALA | 371 | 38.626 | 10.666 | 27.655 | 1.00 | 24.55 | PROT |
| ATOM | 1164 | N | LEU | 372 | 38.633 | 10.082 | 29.831 | 1.00 | 14.85 | PROT |
| ATOM | 1165 | CA | LEU | 372 | 38.636 | 11.463 | 30.307 | 1.00 | 9.24 | PROT |
| ATOM | 1166 | CB | LEU | 372 | 38.480 | 11.501 | 31.830 | 1.00 | 8.83 | PROT |
| ATOM | 1167 | CG | LEU | 372 | 37.043 | 11.288 | 32.364 | 1.00 | 5.50 | PROT |
| ATOM | 1168 | CD1 | LEU | 372 | 37.036 | 10.338 | 33.553 | 1.00 | 2.02 | PROT |
| ATOM | 1169 | CD2 | LEU | 372 | 36.455 | 12.626 | 32.770 | 1.00 | 2.00 | PROT |
| ATOM | 1170 | C | LEU | 372 | 39.867 | 12.218 | 29.870 | 1.00 | 10.17 | PROT |
| ATOM | 1171 | O | LEU | 372 | 39.791 | 13.413 | 29.568 | 1.00 | 7.23 | PROT |
| ATOM | 1172 | N | LEU | 373 | 40.996 | 11.510 | 29.825 | 1.00 | 13.10 | PROT |
| ATOM | 1173 | CA | LEU | 373 | 42.270 | 12.078 | 29.399 | 1.00 | 2.00 | PROT |
| ATOM | 1174 | CB | LEU | 373 | 43.325 | 10.981 | 29.381 | 1.00 | 2.00 | PROT |
| ATOM | 1175 | CG | LEU | 373 | 44.705 | 11.118 | 30.045 | 1.00 | 9.64 | PROT |
| ATOM | 1176 | CD1 | LEU | 373 | 44.817 | 12.382 | 30.875 | 1.00 | 2.00 | PROT |
| ATOM | 1177 | CD2 | LEU | 373 | 44.955 | 9.883 | 30.882 | 1.00 | 2.00 | PROT |
| ATOM | 1178 | C | LEU | 373 | 42.026 | 12.602 | 27.987 | 1.00 | 6.58 | PROT |
| ATOM | 1179 | O | LEU | 373 | 42.357 | 13.738 | 27.660 | 1.00 | 9.73 | PROT |
| ATOM | 1180 | N | GLN | 374 | 41.401 | 11.763 | 27.165 | 1.00 | 9.45 | PROT |
| ATOM | 1181 | CA | GLN | 374 | 41.076 | 12.097 | 25.785 | 1.00 | 2.00 | PROT |
| ATOM | 1182 | CB | GLN | 374 | 40.382 | 10.914 | 25.121 | 1.00 | 2.00 | PROT |
| ATOM | 1183 | CG | GLN | 374 | 41.332 | 9.896 | 24.537 | 1.00 | 2.00 | PROT |
| ATOM | 1184 | CD | GLN | 374 | 40.630 | 8.641 | 24.095 | 1.00 | 2.00 | PROT |
| ATOM | 1185 | OE1 | GLN | 374 | 41.261 | 7.622 | 23.855 | 1.00 | 8.01 | PROT |
| ATOM | 1186 | NE2 | GLN | 374 | 39.316 | 8.705 | 23.989 | 1.00 | 2.00 | PROT |
| ATOM | 1187 | C | GLN | 374 | 40.187 | 13.326 | 25.694 | 1.00 | 2.78 | PROT |
| ATOM | 1188 | O | GLN | 374 | 40.427 | 14.213 | 24.875 | 1.00 | 13.91 | PROT |
| ATOM | 1189 | N | ALA | 375 | 39.151 | 13.386 | 26.521 | 1.00 | 2.00 | PROT |
| ATOM | 1190 | CA | ALA | 375 | 38.261 | 14.546 | 26.505 | 1.00 | 2.00 | PROT |
| ATOM | 1191 | CB | ALA | 375 | 37.128 | 14.348 | 27.489 | 1.00 | 3.97 | PROT |
| ATOM | 1192 | C | ALA | 375 | 39.061 | 15.801 | 26.868 | 1.00 | 4.60 | PROT |
| ATOM | 1193 | O | ALA | 375 | 38.881 | 16.864 | 26.274 | 1.00 | 8.82 | PROT |
| ATOM | 1194 | N | VAL | 376, | 39.956 | 15.667 | 27.842 | 1.00 | 9.01 | PROT |
| ATOM | 1195 | CA | VAL | 376 | 40.772 | 16.790 | 28.267 | 1.00 | 7.36 | PROT |
| ATOM | 1196 | CB | VAL | 376 | 41.669 | 16.401 | 29.467 | 1.00 | 2.30 | PROT |
| ATOM | 1197 | CG1 | VAL | 376 | 42.597 | 17.532 | 29.839 | 1.00 | 2.00 | PROT |
| ATOM | 1198 | CG2 | VAL | 376 | 40.801 | 16.076 | 30.646 | 1.00 | 9.15 | PROT |
| ATOM | 1199 | C | VAL | 376 | 41.629 | 17.256 | 27.110 | 1.00 | 3.94 | PROT |
| ATOM | 1200 | O | VAL | 376 | 41.788 | 18.455 | 26.880 | 1.00 | 2.00 | PROT |
| ATOM | 1201 | N | LEU | 377 | 42.179 | 16.297 | 26.379 | 1.00 | 3.92 | PROT |
| ATOM | 1202 | CA | LEU | 377 | 43.020 | 16.618 | 25.239 | 1.00 | 5.65 | PROT |
| ATOM | 1203 | CB | LEU | 377 | 43.714 | 15.354 | 24.731 | 1.00 | 5.08 | PROT |
| ATOM | 1204 | CG | LEU | 377 | 45.052 | 15.005 | 25.386 | 1.00 | 2.00 | PROT |
| ATOM | 1205 | CD1 | LEU | 377 | 45.620 | 13.790 | 24.719 | 1.00 | 2.00 | PROT |
| ATOM | 1206 | CD2 | LEU | 377 | 46.016 | 16.157 | 25.264 | 1.00 | 4.14 | PROT |
| ATOM | 1207 | C | LEU | 377 | 42.173 | 17.271 | 24.137 | 1.00 | 11.35 | PROT |
| ATOM | 1208 | O | LEU | 377 | 42.607 | 18.240 | 23.515 | 1.00 | 8.78 | PROT |
| ATOM | 1209 | N | LEU | 378 | 40.959 | 16.766 | 23.912 | 1.00 | 5.62 | PROT |
| ATOM | 1210 | CA | LEU | 378 | 40.080 | 17.352 | 22.900 | 1.00 | 8.57 | PROT |
| ATOM | 1211 | CB | LEU | 378 | 38.784 | 16.553 | 22.788 | 1.00 | 5.98 | PROT |
| ATOM | 1212 | CG | LEU | 378 | 37.847 | 16.993 | 21.658 | 1.00 | 6.60 | PROT |
| ATOM | 1213 | CD1 | LEU | 378 | 38.550 | 16.826 | 20.329 | 1.00 | 2.00 | PROT |
| ATOM | 1214 | CD2 | LEU | 378 | 36.563 | 16.172 | 21.690 | 1.00 | 2.00 | PROT |
| ATOM | 1215 | C | LEU | 378 | 39.738 | 18.833 | 23.146 | 1.00 | 10.76 | PROT |
| ATOM | 1216 | O | LEU | 378 | 40.045 | 19.689 | 22.312 | 1.00 | 14.81 | PROT |
| ATOM | 1217 | N | MET | 379 | 39.106 | 19.139 | 24.278 | 1.00 | 13.15 | PROT |
| ATOM | 1218 | CA | MET | 379 | 38.735 | 20.521 | 24.591 | 1.00 | 13.60 | PROT |
| ATOM | 1219 | CB | MET | 379 | 37.698 | 20.543 | 25.709 | 1.00 | 12.57 | PROT |
| ATOM | 1220 | CG | MET | 379 | 36.425 | 19.782 | 25.395 | 1.00 | 21.12 | PROT |
| ATOM | 1221 | SD | MET | 379 | 35.533 | 20.396 | 23.927 | 1.00 | 15.79 | PROT |
| ATOM | 1222 | CE | MET | 319 | 34.397 | 19.099 | 23.756 | 1.00 | 13.95 | PROT |
| ATOM | 1223 | C | MET | 379 | 39.912 | 21.419 | 24.988 | 1.00 | 16.01 | PROT |
| ATOM | 1224 | O | MET | 379 | 39.981 | 21.897 | 26.121 | 1.00 | 16.95 | PROT |
| ATOM | 1225 | N | SER | 380 | 40.824 | 21.663 | 24.048 | 1.00 | 12.39 | PROT |
| ATOM | 1226 | CA | SER | 380 | 41.984 | 22.506 | 24.303 | 1.00 | 10.77 | PROT |
| ATOM | 1227 | CB | SER | 380 | 43.248 | 21.815 | 23.810 | 1.00 | 8.45 | PROT |
| ATOM | 1228 | OG | SER | 380 | 43.288 | 20.487 | 24.286 | 1.00 | 17.27 | PROT |

APPENDIX 7-continued

| TRBTRIAC.PDB | | | | | | | | | |
|---|---|---|---|---|---|---|---|---|---|
| ATOM | 1229 | C | SER | 380 | 41.825 | 23.859 | 23.621 | 1.00 | 15.58 | PROT |
| ATOM | 1230 | O | SER | 380 | 42.125 | 24.019 | 22.432 | 1.00 | 23.09 | PROT |
| ATOM | 1231 | N | SER | 381 | 41.368 | 24.837 | 24.396 | 1.00 | 23.65 | PROT |
| ATOM | 1232 | CA | SER | 381 | 41.123 | 26.187 | 23.904 | 1.00 | 25.18 | PROT |
| ATOM | 1233 | CB | SER | 381 | 40.449 | 27.018 | 25.003 | 1.00 | 34.78 | PROT |
| ATOM | 1234 | OG | SER | 381 | 41.250 | 27.073 | 26.170 | 1.00 | 37.79 | PROT |
| ATOM | 1235 | C | SER | 381 | 42.342 | 26.940 | 23.388 | 1.00 | 19.38 | PROT |
| ATOM | 1236 | O | SER | 381 | 42.216 | 28.032 | 22.850 | 1.00 | 28.81 | PROT |
| ATOM | 1237 | N | ASP | 382 | 43.519 | 26.361 | 23.523 | 1.00 | 11.80 | PROT |
| ATOM | 1238 | CA | ASP | 382 | 44.716 | 27.057 | 23.082 | 1.00 | 15.78 | PROT |
| ATOM | 1239 | CB | ASP | 382 | 45.908 | 26.595 | 23.909 | 1.00 | 33.97 | PROT |
| ATOM | 1240 | CG | ASP | 382 | 46.069 | 25.098 | 23.891 | 1.00 | 48.78 | PROT |
| ATOM | 1241 | OD1 | ASP | 382 | 45.169 | 24.401 | 24.406 | 1.00 | 45.58 | PROT |
| ATOM | 1242 | OD2 | ASP | 382 | 47.091 | 24.620 | 23.356 | 1.00 | 56.52 | PROT |
| ATOM | 1243 | C | ASP | 382 | 45.037 | 26.888 | 21.604 | 1.00 | 21.28 | PROT |
| ATOM | 1244 | O | ASP | 382 | 45.907 | 27.585 | 21.079 | 1.00 | 41.91 | PROT |
| ATOM | 1245 | N | ARG | 383 | 44.357 | 25.971 | 20.923 | 1.00 | 21.81 | PROT |
| ATOM | 1246 | CA | ARG | 383 | 44.636 | 25.773 | 19.503 | 1.00 | 18.95 | PROT |
| ATOM | 1247 | CB | ARG | 383 | 43.745 | 24.685 | 18.921 | 1.00 | 8.26 | PROT |
| ATOM | 1248 | CG | ARG | 383 | 43.580 | 23.491 | 19.821 | 1.00 | 18.07 | PROT |
| ATOM | 1249 | CD | ARG | 383 | 44.693 | 22.487 | 19.610 | 1.00 | 11.10 | PROT |
| ATOM | 1250 | NE | ARG | 383 | 44.480 | 21.261 | 20.378 | 1.00 | 20.54 | PROT |
| ATOM | 1251 | CZ | ARG | 383 | 45.460 | 20.462 | 20.786 | 1.00 | 18.25 | PROT |
| ATOM | 1252 | NH1 | ARG | 383 | 45.187 | 19.365 | 21.481 | 1.00 | 5.24 | PROT |
| ATOM | 1253 | NH2 | ARG | 383 | 46.717 | 20.765 | 20.495 | 1.00 | 19.21 | PROT |
| ATOM | 1254 | C | ARG | 383 | 44.420 | 27.064 | 18.728 | 1.00 | 19.64 | PROT |
| ATOM | 1255 | O | ARG | 383 | 43.493 | 27.828 | 19.001 | 1.00 | 17.46 | PROT |
| ATOM | 1256 | N | PRO | 384 | 45.298 | 27.342 | 17.762 | 1.00 | 25.37 | PROT |
| ATOM | 1257 | CD | PRO | 384 | 46.485 | 26.567 | 17.359 | 1.00 | 35.06 | PROT |
| ATOM | 1258 | CA | PRO | 384 | 45.124 | 28.569 | 16.983 | 1.00 | 27.53 | PROT |
| ATOM | 1259 | CB | PRO | 384 | 46.422 | 28.693 | 16.181 | 1.00 | 18.75 | PROT |
| ATOM | 1260 | CG | PRO | 384 | 47.041 | 27.338 | 16.190 | 1.00 | 27.78 | PROT |
| ATOM | 1261 | C | PRO | 384 | 43.895 | 28.476 | 16.081 | 1.00 | 28.76 | PROT |
| ATOM | 1262 | O | PRO | 384 | 43.562 | 27.402 | 15.560 | 1.00 | 31.18 | PROT |
| ATOM | 1263 | N | GLY | 385 | 43.215 | 29.606 | 15.917 | 1.00 | 27.37 | PROT |
| ATOM | 1264 | CA | GLY | 385 | 42.039 | 29.638 | 15.073 | 1.00 | 26.98 | PROT |
| ATOM | 1265 | C | GLY | 385 | 40.728 | 29.442 | 15.803 | 1.00 | 27.46 | PROT |
| ATOM | 1266 | O | GLY | 385 | 39.689 | 29.911 | 15.339 | 1.00 | 31.99 | PROT |
| ATOM | 1267 | N | LEU | 386 | 40.756 | 28.756 | 16.939 | 1.00 | 34.99 | PROT |
| ATOM | 1268 | CA | LEU | 386 | 39.524 | 28.515 | 17.673 | 1.00 | 37.24 | PROT |
| ATOM | 1269 | CB | LEU | 386 | 39.820 | 27.947 | 19.059 | 1.00 | 26.60 | PROT |
| ATOM | 1270 | CG | LEU | 386 | 40.233 | 26.472 | 18.988 | 1.00 | 32.45 | PROT |
| ATOM | 1271 | CD1 | LEU | 386 | 40.177 | 25.859 | 20.363 | 1.00 | 34.82 | PROT |
| ATOM | 1272 | CD2 | LEU | 386 | 39.314 | 25.719 | 18.030 | 1.00 | 29.64 | PROT |
| ATOM | 1273 | C | LEU | 386 | 38.733 | 29.795 | 17.778 | 1.00 | 36.93 | PROT |
| ATOM | 1274 | O | LEU | 386 | 39.291 | 30.881 | 17.674 | 1.00 | 37.60 | PROT |
| ATOM | 1275 | N | ALA | 387 | 37.427 | 29.665 | 17.962 | 1.00 | 31.47 | PROT |
| ATOM | 1276 | CA | ALA | 387 | 36.578 | 30.832 | 18.058 | 1.00 | 28.80 | PROT |
| ATOM | 1277 | CB | ALA | 387 | 35.553 | 30.814 | 16.950 | 1.00 | 41.01 | PROT |
| ATOM | 1278 | C | ALA | 387 | 35.890 | 30.864 | 19.400 | 1.00 | 28.89 | PROT |
| ATOM | 1279 | O | ALA | 387 | 35.998 | 31.842 | 20.133 | 1.00 | 30.62 | PROT |
| ATOM | 1280 | N | CYS | 388 | 35.167 | 29.797 | 19.710 | 1.00 | 25.92 | PROT |
| ATOM | 1281 | CA | CYS | 388 | 34.469 | 29.712 | 20.978 | 1.00 | 26.90 | PROT |
| ATOM | 1282 | CB | CYS | 388 | 33.224 | 28.823 | 20.826 | 1.00 | 21.38 | PROT |
| ATOM | 1283 | SG | CYS | 388 | 31.625 | 29.732 | 20.698 | 1.00 | 33.66 | PROT |
| ATOM | 1284 | C | CYS | 388 | 35.443 | 29.159 | 22.040 | 1.00 | 31.18 | PROT |
| ATOM | 1285 | O | CYS | 388 | 35.272 | 28.054 | 22.552 | 1.00 | 36.57 | PROT |
| ATOM | 1286 | N | vAL | 389 | 36.473 | 29.951 | 22.346 | 1.00 | 20.22 | PROT |
| ATOM | 1287 | CA | VAL | 389 | 37.511 | 29.622 | 23.327 | 1.00 | 16.02 | PROT |
| ATOM | 1288 | CB | VAL | 389 | 38.554 | 30.737 | 23.381 | 1.00 | 9.80 | PROT |
| ATOM | 1289 | CG1 | VAL | 389 | 39.526 | 30.480 | 24.498 | 1.00 | 16.03 | PROT |
| ATOM | 1290 | CG2 | VAL | 389 | 39.257 | 30.843 | 22.056 | 1.00 | 16.27 | PROT |
| ATOM | 1291 | C | VAL | 389 | 36.977 | 29.425 | 24.753 | 1.00 | 18.85 | PROT |
| ATOM | 1292 | O | VAL | 389 | 37.066 | 28.336 | 25.323 | 1.00 | 24.21 | PROT |
| ATOM | 1293 | N | GLU | 390 | 36.461 | 30.500 | 25.337 | 1.00 | 5.06 | PROT |
| ATOM | 1294 | CA | GLU | 390 | 35.908 | 30.434 | 26.660 | 1.00 | 2.00 | PROT |
| ATOM | 1295 | CB | GLU | 390 | 35.092 | 31.684 | 26.952 | 1.00 | 5.13 | PROT |
| ATOM | 1296 | C | GLU | 390 | 35.047 | 29.184 | 26.817 | 1.00 | 3.75 | PROT |
| ATOM | 1297 | O | GLU | 390 | 35.252 | 28.419 | 27.754 | 1.00 | 23.35 | PROT |
| ATOM | 1298 | N | ARG | 391 | 34.103 | 28.938 | 25.915 | 1.00 | 14.06 | PROT |
| ATOM | 1299 | CA | ARG | 391 | 33.248 | 27.754 | 26.093 | 1.00 | 26.18 | PROT |
| ATOM | 1300 | CB | ARG | 391 | 32.121 | 27.699 | 21.049 | 1.00 | 31.84 | PROT |
| ATOM | 1301 | CG | ARG | 391 | 30.843 | 27.040 | 25.601 | 1.00 | 47.73 | PROT |
| ATOM | 1302 | CD | ARG | 391 | 29.882 | 26.572 | 24.512 | 1.00 | 58.24 | PROT |
| ATOM | 1303 | NE | ARG | 391 | 29.879 | 27.487 | 23.378 | 1.00 | 66.80 | PROT |
| ATOM | 1304 | CZ | ARG | 391 | 29.001 | 28.470 | 23.211 | 1.00 | 69.56 | PROT |
| ATOM | 1305 | NH1 | ARG | 391 | 29.088 | 29.255 | 22.139 | 1.00 | 66.99 | PROT |

APPENDIX 7-continued

TRBTRIAC.PDB

| | | | | | | | | | |
|---|---|---|---|---|---|---|---|---|---|
| ATOM | 1306 | NH2 | ARG | 391 | 28.034 | 28.663 | 24.105 | 1.00 | 56.08 PROT |
| ATOM | 1307 | C | ARG | 391 | 33.979 | 26.415 | 26.110 | 1.00 | 23.65 PROT |
| ATOM | 1308 | O | ARG | 391 | 33.561 | 25.479 | 26.794 | 1.00 | 28.58 PROT |
| ATOM | 1309 | N | ILE | 392 | 35.064 | 26.316 | 25.359 | 1.00 | 15.05 PROT |
| ATOM | 1310 | CA | ILE | 392 | 35.812 | 25.077 | 25.335 | 1.00 | 19.03 PROT |
| ATOM | 1311 | CB | ILE | 392 | 36.804 | 25.063 | 24.165 | 1.00 | 22.30 PROT |
| ATOM | 1312 | CG2 | ILE | 392 | 37.971 | 24.130 | 24.467 | 1.00 | 21.71 PROT |
| ATOM | 1313 | CG1 | ILE | 392 | 36.074 | 24.614 | 22.892 | 1.00 | 23.47 PROT |
| ATOM | 1314 | CD1 | ILE | 392 | 36.245 | 25.551 | 21.707 | 1.00 | 4.13 PROT |
| ATOM | 1315 | C | ILE | 392 | 36.544 | 24.907 | 26.671 | 1.00 | 25.03 PROT |
| ATOM | 1316 | O | ILE | 392 | 36.728 | 23.783 | 27.153 | 1.00 | 26.11 PROT |
| ATOM | 1317 | N | GLU | 393 | 36.947 | 26.029 | 27.266 | 1.00 | 30.74 PROT |
| ATOM | 1318 | CA | GLU | 393 | 37.630 | 26.021 | 28.558 | 1.00 | 23.39 PROT |
| ATOM | 1319 | CB | GLU | 393 | 38.073 | 27.430 | 28.930 | 1.00 | 27.18 PROT |
| ATOM | 1320 | CG | GLU | 393 | 39.435 | 27.817 | 28.402 | 1.00 | 41.39 PROT |
| ATOM | 1321 | CD | GLU | 393 | 39.990 | 29.051 | 29.093 | 1.00 | 47.72 PROT |
| ATOM | 1322 | OE1 | GLU | 393 | 39.365 | 29.524 | 30.070 | 1.00 | 39.94 PROT |
| ATOM | 1323 | OE2 | GLU | 393 | 41.051 | 29.547 | 28.653 | 1.00 | 51.17 PROT |
| ATOM | 1324 | C | GLU | 393 | 36.655 | 25.516 | 29.610 | 1.00 | 21.72 PROT |
| ATOM | 1325 | O | GLU | 393 | 36.942 | 24.574 | 30.344 | 1.00 | 22.82 PROT |
| ATOM | 1326 | N | LYS | 394 | 35.497 | 26.163 | 29.676 | 1.00 | 9.64 PROT |
| ATOM | 1327 | CA | LYS | 394 | 34.462 | 25.779 | 30.618 | 1.00 | 11.56 PROT |
| ATOM | 1328 | CB | LYS | 394 | 33.177 | 26.557 | 30.338 | 1.00 | 7.52 PROT |
| ATOM | 1329 | C | LYS | 394 | 34.213 | 24.280 | 30.492 | 1.00 | 16.31 PROT |
| ATOM | 1330 | O | LYS | 394 | 34.000 | 23.594 | 31.498 | 1.00 | 24.52 PROT |
| ATOM | 1331 | N | TYR | 395 | 34.251 | 23.763 | 29.264 | 1.00 | 12.79 PROT |
| ATOM | 1332 | CA | TYR | 395 | 34.033 | 22.332 | 29.057 | 1.00 | 19.02 PROT |
| ATOM | 1333 | CB | TYR | 395 | 33.803 | 22.025 | 27.572 | 1.00 | 27.90 PROT |
| ATOM | 1334 | CG | TYR | 395 | 32.454 | 22.456 | 27.027 | 1.00 | 31.64 PROT |
| ATOM | 1335 | CD1 | TYR | 395 | 32.136 | 22.267 | 25.684 | 1.00 | 30.15 PROT |
| ATOM | 1336 | CE1 | TYR | 395 | 30.927 | 22.695 | 25.160 | 1.00 | 28.34 PROT |
| ATOM | 1337 | CD2 | TYR | 395 | 31.514 | 23.085 | 27.835 | 1.00 | 34.21 PROT |
| ATOM | 1338 | CE2 | TYR | 395 | 30.298 | 23.518 | 27.317 | 1.00 | 34.01 PROT |
| ATOM | 1339 | CZ | TYR | 395 | 30.014 | 23.322 | 25.979 | 1.00 | 33.73 PROT |
| ATOM | 1340 | OH | TYR | 395 | 28.824 | 23.785 | 25.453 | 1.00 | 44.99 PROT |
| ATOM | 1341 | C | TYR | 395 | 35.208 | 21.490 | 29.584 | 1.00 | 19.03 PROT |
| ATOM | 1342 | O | TYR | 395 | 35.003 | 20.494 | 30.277 | 1.00 | 25.23 PROT |
| ATOM | 1343 | N | GLN | 396 | 36.437 | 21.883 | 29.256 | 1.00 | 17.76 PROT |
| ATOM | 1344 | CA | GLN | 396 | 37.596 | 21.134 | 29.725 | 1.00 | 13.73 PROT |
| ATOM | 1345 | CB | GLN | 396 | 38.905 | 21.766 | 29.240 | 1.00 | 2.45 PROT |
| ATOM | 1346 | CG | GLN | 396 | 40.061 | 20.767 | 29.110 | 1.00 | 2.00 PROT |
| ATOM | 1347 | CD | GLN | 396 | 41.388 | 21.439 | 28.799 | 1.00 | 5.12 PROT |
| ATOM | 1348 | OE1 | GLN | 396 | 41.706 | 22.484 | 29.359 | 1.00 | 10.11 PROT |
| ATOM | 1349 | NE2 | GLN | 396 | 42.169 | 20.840 | 27.903 | 1.00 | 9.09 PROT |
| ATOM | 1350 | C | GLN | 396 | 37.562 | 21.149 | 31.238 | 1.00 | 17.65 PROT |
| ATOM | 1351 | O | GLN | 396 | 37.802 | 20.125 | 31.894 | 1.00 | 9.63 PROT |
| ATOM | 1352 | N | ASP | 397 | 37.250 | 22.319 | 31.787 | 1.00 | 6.69 PROT |
| ATOM | 1353 | CA | ASP | 397 | 37.178 | 22.476 | 33.226 | 1.00 | 9.36 PROT |
| ATOM | 1354 | CB | ASP | 397 | 36.732 | 23.893 | 33.570 | 1.00 | 11.44 PROT |
| ATOM | 1355 | CG | ASP | 397 | 37.867 | 24.891 | 33.446 | 1.00 | 18.32 PROT |
| ATOM | 1356 | OD1 | ASP | 397 | 39.033 | 24.438 | 33.397 | 1.00 | 24.00 PROT |
| ATOM | 1357 | OD2 | ASP | 397 | 37.615 | 26.114 | 33.395 | 1.00 | 20.67 PROT |
| ATOM | 1358 | C | ASP | 397 | 36.215 | 21.443 | 33.771 | 1.00 | 7.77 PROT |
| ATOM | 1359 | O | ASP | 397 | 36.497 | 20.771 | 34.761 | 1.00 | 7.66 PROT |
| ATOM | 1360 | N | SER | 398 | 35.087 | 21.293 | 33.093 | 1.00 | 9.19 PROT |
| ATOM | 1361 | CA | SER | 398 | 34.094 | 20.322 | 33.508 | 1.00 | 14.18 PROT |
| ATOM | 1362 | CB | SER | 398 | 32.916 | 20.334 | 32.542 | 1.00 | 12.11 PROT |
| ATOM | 1363 | OG | SER | 398 | 32.406 | 21.650 | 32.423 | 1.00 | 31.95 PROT |
| ATOM | 1364 | C | SER | 398 | 34.712 | 18.939 | 33.556 | 1.00 | 11.47 PROT |
| ATOM | 1365 | O | SER | 398 | 34.591 | 18.227 | 34.551 | 1.00 | 21.11 PROT |
| ATOM | 1366 | N | PHE | 399 | 35.394 | 18.565 | 32.485 | 1.00 | 18.68 PROT |
| ATOM | 1367 | CA | PHE | 399 | 36.017 | 17.252 | 32.417 | 1.00 | 24.93 PROT |
| ATOM | 1368 | CB | PHE | 399 | 36.587 | 17.012 | 31.014 | 1.00 | 23.38 PROT |
| ATOM | 1369 | CG | PHE | 399 | 35.543 | 16.705 | 29.981 | 1.00 | 20.19 PROT |
| ATOM | 1370 | CD1 | PHE | 399 | 35.224 | 17.638 | 28.997 | 1.00 | 22.94 PROT |
| ATOM | 1371 | CD2 | PHE | 399 | 34.878 | 15.486 | 29.988 | 1.00 | 8.62 PROT |
| ATOM | 1372 | CE1 | PHE | 399 | 34.257 | 17.361 | 28.029 | 1.00 | 12.53 PROT |
| ATOM | 1373 | CE2 | PHE | 399 | 33.914 | 15.201 | 29.027 | 1.00 | 19.25 PROT |
| ATOM | 1374 | CZ | PHE | 399 | 33.604 | 16.143 | 28.044 | 1.00 | 15.15 PROT |
| ATOM | 1375 | C | PHE | 399 | 37.113 | 17.097 | 33.463 | 1.00 | 23.06 PROT |
| ATOM | 1376 | O | PHE | 399 | 37.210 | 16.063 | 34.137 | 1.00 | 15.58 PROT |
| ATOM | 1377 | N | LEU | 400 | 37.932 | 18.131 | 33.604 | 1.00 | 22.12 PROT |
| ATOM | 1378 | CA | LEU | 400 | 39.017 | 18.095 | 34.567 | 1.00 | 18.27 PROT |
| ATOM | 1379 | CB | LEU | 400 | 39.846 | 19.372 | 34.461 | 1.00 | 10.06 PROT |
| ATOM | 1380 | CG | LEU | 400 | 41.021 | 19.248 | 33.491 | 1.00 | 8.13 PROT |
| ATOM | 1381 | CD1 | LEU | 400 | 41.616 | 20.594 | 33.195 | 1.00 | 2.00 PROT |
| ATOM | 1382 | CD2 | LEU | 400 | 42.055 | 18.333 | 4.095 | 1.00 | 13.73 PROT |

APPENDIX 7-continued

TRBTRIAC.PDB

| ATOM | 1383 | C | LEU | 400 | 38.527 | 17.892 | 36.002 | 1.00 | 24.79 | PROT |
|---|---|---|---|---|---|---|---|---|---|---|
| ATOM | 1384 | O | LEU | 400 | 39.189 | 17.228 | 36.787 | 1.00 | 26.46 | PROT |
| ATOM | 1385 | N | LEU | 401 | 37.371 | 18.447 | 36.354 | 1.00 | 21.93 | PROT |
| ATOM | 1386 | CA | LEU | 401 | 36.862 | 18.268 | 37.707 | 1.00 | 17.21 | PROT |
| ATOM | 1387 | CB | LEU | 401 | 35.766 | 19.285 | 38.022 | 1.00 | 19.27 | PROT |
| ATOM | 1388 | CG | LEU | 401 | 35.538 | 19.547 | 39.515 | 1.00 | 16.76 | PROT |
| ATOM | 1389 | CD1 | LEU | 401 | 36.652 | 20.403 | 40.085 | 1.00 | 2.00 | PROT |
| ATOM | 1390 | CD2 | LEU | 401 | 34.206 | 20.235 | 39.687 | 1.00 | 14.41 | PROT |
| ATOM | 1391 | C | LEU | 401 | 36.316 | 16.864 | 37.879 | 1.00 | 18.03 | PROT |
| ATOM | 1392 | O | LEU | 401 | 36.482 | 16.250 | 38.925 | 1.00 | 28.63 | PROT |
| ATOM | 1393 | N | ALA | 402 | 35.656 | 16.346 | 36.856 | 1.00 | 9.30 | PROT |
| ATOM | 1394 | CA | ALA | 402 | 35.124 | 15.000 | 36.951 | 1.00 | 7.03 | PROT |
| ATOM | 1395 | CB | ALA | 402 | 34.233 | 14.703 | 35.758 | 1.00 | 14.15 | PROT |
| ATOM | 1396 | C | ALA | 402 | 36.298 | 14.029 | 36.989 | 1.00 | 7.68 | PROT |
| ATOM | 1397 | O | ALA | 402 | 36.294 | 13.054 | 37.739 | 1.00 | 2.00 | PROT |
| ATOM | 1398 | N | PHE | 403 | 37.311 | 14.305 | 36.178 | 1.00 | 4.49 | PROT |
| ATOM | 1399 | CA | PHE | 403 | 38.477 | 13.439 | 36.140 | 1.00 | 9.18 | PROT |
| ATOM | 1400 | CB | PHE | 403 | 39.510 | 13.977 | 35.138 | 1.00 | 12.80 | PROT |
| ATOM | 1401 | CG | PHE | 403 | 40.545 | 12.957 | 34.693 | 1.00 | 5.42 | PROT |
| ATOM | 1402 | CD1 | PHE | 403 | 41.590 | 13.334 | 33.859 | 1.00 | 2.00 | PROT |
| ATOM | 1403 | CD2 | PHE | 403 | 40.480 | 11.634 | 35.103 | 1.00 | 2.00 | PROT |
| ATOM | 1404 | CE1 | PHE | 403 | 42.546 | 12.410 | 33.448 | 1.00 | 2.00 | PROT |
| ATOM | 1405 | CE2 | PHE | 403 | 41.440 | 10.711 | 34.688 | 1.00 | 2.00 | PROT |
| ATOM | 1406 | CZ | PHE | 403 | 42.468 | 11.100 | 33.863 | 1.00 | 2.00 | PROT |
| ATOM | 1407 | C | PHE | 403 | 39.080 | 13.366 | 37.539 | 1.00 | 10.08 | PROT |
| ATOM | 1408 | O | PHE | 403 | 39.207 | 12.279 | 38.097 | 1.00 | 8.23 | PROT |
| ATOM | 1409 | N | GLU | 404 | 39.451 | 14.514 | 38.103 | 1.00 | 12.64 | PROT |
| ATOM | 1410 | CA | GLU | 404 | 40.030 | 14.546 | 39.448 | 1.00 | 19.23 | PROT |
| ATOM | 1411 | CB | GLU | 404 | 40.227 | 15.989 | 39.942 | 1.00 | 19.80 | PROT |
| ATOM | 1412 | CG | GLU | 404 | 41.532 | 16.220 | 40.728 | 1.00 | 24.03 | PROT |
| ATOM | 1413 | CD | GLU | 404 | 41.474 | 17.429 | 41.655 | 1.00 | 29.60 | PROT |
| ATOM | 1414 | OE1 | GLU | 404 | 41.706 | 18.565 | 41.182 | 1.00 | 29.51 | PROT |
| ATOM | 1415 | OE2 | GLU | 404 | 41.197 | 17.247 | 42.861 | 1.00 | 30.42 | PROT |
| ATOM | 1416 | C | GLU | 404 | 39.112 | 13.806 | 40.416 | 1.00 | 24.36 | PROT |
| ATOM | 1417 | O | GLU | 404 | 39.571 | 12.963 | 41.200 | 1.00 | 28.04 | PROT |
| ATOM | 1418 | N | HIS | 405 | 37.815 | 14.108 | 40.358 | 1.00 | 10.26 | PROT |
| ATOM | 1419 | CA | HIS | 405. | 36.870 | 13.446 | 41.240 | 1.00 | 7.78 | PROT |
| ATOM | 1420 | CB | HIS | 405 | 35.473 | 14.023 | 41.054 | 1.00 | 3.47 | PROT |
| ATOM | 1421 | CG | HIS | 405 | 35.312 | 15.393 | 41.630 | 1.00 | 15.49 | PROT |
| ATOM | 1422 | CD2 | HIS | 405 | 36.223 | 16.260 | 42.134 | 1.00 | 17.97 | PROT |
| ATOM | 1423 | ND1 | HIS | 405 | 34.096 | 16.036 | 41.694 | 1.00 | 21.57 | PROT |
| ATOM | 1424 | CE1 | HIS | 405 | 34.265 | 17.242 | 42.210 | 1.00 | 27.50 | PROT |
| ATOM | 1425 | NE2 | HIS | 405 | 35.547 | 17.403 | 42.485 | 1.00 | 13.53 | PROT |
| ATOM | 1426 | C | HIS | 405 | 36.856 | 11.936 | 41.005 | 1.00 | 14.88 | PROT |
| ATOM | 1427 | O | HIS | 405 | 36.641 | 11.155 | 41.935 | 1.00 | 22.11 | PROT |
| ATOM | 1428 | N | TYR | 406 | 37.091 | 11.512 | 39.767 | 1.00 | 16.52 | PROT |
| ATOM | 1429 | CA | TYR | 406 | 37.085 | 10.083 | 39.491 | 1.00 | 14.35 | PROT |
| ATOM | 1430 | CB | TYR | 406 | 37.007 | 9.808 | 37.989 | 1.00 | 9.90 | PROT |
| ATOM | 1431 | CG | TYR | 406 | 36.840 | 8.346 | 37.657 | 1.00 | 2.00 | PROT |
| ATOM | 1432 | CD1 | TYR | 406 | 35.587 | 7.742 | 37.676 | 1.00 | 8.84 | PROT |
| ATOM | 1433 | CE1 | TYR | 406 | 35.433 | 6.382 | 37.386 | 1.00 | 8.78 | PROT |
| ATOM | 1434 | CD2 | TYR | 406 | 37.939 | 7.562 | 37.338 | 1.00 | 15.34 | PROT |
| ATOM | 1435 | CE2 | TYR | 406 | 37.801 | 6.204 | 37.044 | 1.00 | 13.48 | PROT |
| ATOM | 1436 | CZ | TYR | 406 | 36.548 | 5.624 | 37.073 | 1.00 | 15.64 | PROT |
| ATOM | 1437 | OH | TYR | 406 | 36.431 | 4.287 | 36.804 | 1.00 | 2.00 | PROT |
| ATOM | 1438 | C | TYR | 406 | 38.340 | 9.466 | 40.071 | 1.00 | 9.54 | PROT |
| ATOM | 1439 | O | TYR | 406 | 38.328 | 8.328 | 40.525 | 1.00 | 14.29 | PROT |
| ATOM | 1440 | N | ILE | 407 | 39.430 | 10.217 | 40.058 | 1.00 | 6.56 | PROT |
| ATOM | 1441 | CA | ILE | 407 | 40.671 | 9.708 | 40.617 | 1.00 | 13.87 | PROT |
| ATOM | 1442 | CB | ILE | 407 | 41.808 | 10.728 | 40.474 | 1.00 | 11.28 | PROT |
| ATOM | 1443 | CG2 | ILE | 407 | 42.902 | 10.413 | 41.461 | 1.00 | 6.25 | PROT |
| ATOM | 1444 | CG1 | ILE | 407 | 42.357 | 10.714 | 39.039 | 1.00 | 18.73 | PROT |
| ATOM | 1445 | CD1 | ILE | 407 | 41.863 | 9.579 | 38.169 | 1.00 | 13.14 | PROT |
| ATOM | 1446 | C | ILE | 407 | 40.438 | 9.426 | 42.091 | 1.00 | 11.44 | PROT |
| ATOM | 1447 | O | ILE | 407 | 40.691 | 8.325 | 42.571 | 1.00 | 4.46 | PROT |
| ATOM | 1448 | N | ASN | 408 | 39.953 | 10.448 | 42.792 | 1.00 | 12.35 | PROT |
| ATOM | 1449 | CA | ASN | 408 | 39.642 | 10.363 | 44.213 | 1.00 | 2.00 | PROT |
| ATOM | 1450 | CB | ASN | 408 | 38.758 | 11.535 | 44.629 | 1.00 | 2.00 | PROT |
| ATOM | 1451 | CG | ASN | 408 | 39.499 | 12.840 | 44.657 | 1.00 | 3.57 | PROT |
| ATOM | 1452 | OD1 | ASN | 408 | 40.733 | 12.859 | 44.656 | 1.00 | 14.35 | PROT |
| ATOM | 1453 | ND2 | ASN | 408 | 38.758 | 13.949 | 44.689 | 1.00 | 2.00 | PROT |
| ATOM | 1454 | C | ASN | 408 | 38.868 | 9.078 | 44.432 | 1.00 | 6.49 | PROT |
| ATOM | 1455 | O | ASN | 408 | 39.282 | 8.187 | 45.178 | 1.00 | 10.45 | PROT |
| ATOM | 1456 | N | TYR | 409 | 37.731 | 8.987 | 43.766 | 1.00 | 2.00 | PROT |
| ATOM | 1457 | CA | TYR | 409 | 36.900 | 7.816 | 43.893 | 1.00 | 9.20 | PROT |
| ATOM | 1458 | CB | TYR | 409 | 35.879 | 7.783 | 42.760 | 1.00 | 11.66 | PROT |
| ATOM | 1459 | CG | TYR | 409 | 35.121 | 6.489 | 42.683 | 1.00 | 12.54 | PROT |

APPENDIX 7-continued

| TRBTRIAC.PDB | | | | | | | | | |
|---|---|---|---|---|---|---|---|---|---|
| ATOM | 1460 | CD1 | TYR | 409 | 33.984 | 6.281 | 43.456 | 1.00 | 29.23 | PROT |
| ATOM | 1461 | CE1 | TYR | 409 | 33.285 | 5.077 | 43.403 | 1.00 | 25.45 | PROT |
| ATOM | 1462 | CD2 | TYR | 409 | 35.547 | 5.465 | 41.850 | 1.00 | 24.96 | PROT |
| ATOM | 1463 | CE2 | TYR | 409 | 34.860 | 4.259 | 41.788 | 1.00 | 33.40 | PROT |
| ATOM | 1464 | CZ | TYR | 409 | 33.733 | 4.074 | 42.567 | 1.00 | 24.27 | PROT |
| ATOM | 1465 | OH | TYR | 409 | 33.065 | 2.883 | 42.509 | 1.00 | 32.72 | PROT |
| ATOM | 1466 | C | TYR | 409 | 37.753 | 6.553 | 43.867 | 1.00 | 13.96 | PROT |
| ATOM | 1467 | O | TYR | 409 | 37.730 | 5.763 | 44.804 | 1.00 | 29.48 | PROT |
| ATOM | 1468 | N | ARG | 410 | 38.531 | 6.399 | 42.803 | 1.00 | 23.04 | PROT |
| ATOM | 1469 | CA | ARG | 410 | 39.377 | 5.230 | 42.588 | 1.00 | 22.09 | PROT |
| ATOM | 1470 | CB | ARG | 410 | 39.982 | 5.327 | 41.190 | 1.00 | 13.24 | PROT |
| ATOM | 1471 | CG | ARG | 410 | 38.947 | 5.399 | 40.090 | 1.00 | 14.01 | PROT |
| ATOM | 1472 | CD | ARG | 410 | 38.934 | 4.111 | 39.275 | 1.00 | 16.49 | PROT |
| ATOM | 1473 | NE | ARG | 410 | 40.227 | 3.848 | 38.651 | 1.00 | 9.77 | PROT |
| ATOM | 1474 | CZ | ARG | 410 | 40.617 | 2.651 | 38.239 | 1.00 | 11.38 | PROT |
| ATOM | 1475 | NH1 | ARG | 410 | 41.806 | 2.493 | 37.685 | 1.00 | 14.94 | PROT |
| ATOM | 1476 | NH2 | ARG | 410 | 39.810 | 1.613 | 38.375 | 1.00 | 12.78 | PROT |
| ATOM | 1477 | C | ARG | 410 | 40.486 | 4.914 | 43.604 | 1.00 | 24.49 | PROT |
| ATOM | 1478 | O | ARG | 410 | 40.860 | 3.753 | 43.780 | 1.00 | 12.85 | PROT |
| ATOM | 1479 | N | LYS | 411 | 41.023 | 5.931 | 44.262 | 1.00 | 24.16 | PROT |
| ATOM | 1480 | CA | LYS | 411 | 42.085 | 5.706 | 45.235 | 1.00 | 27.14 | PROT |
| ATOM | 1481 | CB | LYS | 411 | 41.525 | 5.069 | 46.516 | 1.00 | 37.40 | PROT |
| ATOM | 1482 | CG | LYS | 411 | 40.317 | 5.779 | 47.103 | 1.00 | 35.00 | PROT |
| ATOM | 1483 | CD | LYS | 411 | 39.406 | 4.788 | 47.804 | 1.00 | 40.83 | PROT |
| ATOM | 1484 | CE | LYS | 411 | 38.414 | 5.496 | 48.725 | 1.00 | 58.04 | PROT |
| ATOM | 1485 | NZ | LYS | 411 | 38.833 | 5.496 | 50.168 | 1.00 | 54.40 | PROT |
| ATOM | 1486 | C | LYS | 411 | 43.186 | 4.814 | 44.664 | 1.00 | 28.02 | PROT |
| ATOM | 1487 | O | LYS | 411 | 43.209 | 3.598 | 44.876 | 1.00 | 25.00 | PROT |
| ATOM | 1488 | N | HIS | 412 | 44.091 | 5.438 | 43.923 | 1.00 | 30.05 | PROT |
| ATOM | 1489 | CA | HIS | 412 | 45.223 | 4.738 | 43.332 | 4.00 | 26.70 | PROT |
| ATOM | 1490 | CB | HIS | 412 | 45.756 | 5.491 | 42.104 | 1.00 | 29.28 | PROT |
| ATOM | 1491 | CG | HIS | 412 | 44.953 | 5.289 | 40.857 | 1.00 | 18.44 | PROT |
| ATOM | 1492 | CD2 | HIS | 412 | 43.783 | 5.836 | 40.451 | 1.00 | 19.98 | PROT |
| ATOM | 1493 | ND1 | HIS | 42 | 45.366 | 4.465 | 39.833 | 1.00 | 16.33 | PROT |
| ATOM | 1494 | CE1 | HIS | 412 | 44.486 | 4.513 | 38.850 | 1.00 | 24.80 | PROT |
| ATOM | 1495 | NE2 | HIS | 412 | 43.516 | 5.338 | 39.200 | 1.00 | 23.01 | PROT |
| ATOM | 1496 | C | HIS | 412 | 46.281 | 4.788 | 44.406 | 1.00 | 20.73 | PROT |
| ATOM | 1497 | O | HIS | 412 | 46.335 | 5.740 | 45.171 | 1.00 | 24.69 | PROT |
| ATOM | 1498 | N | HIS | 413 | 47.138 | 3.784 | 44.461 | 1.00 | 28.17 | PROT |
| ATOM | 1499 | CA | HIS | 413 | 48.183 | 3.788 | 45.465 | 1.00 | 28.09 | PROT |
| ATOM | 1500 | CB | HIS | 413 | 48.219 | 2.426 | 46.144 | 1.00 | 21.71 | PROT |
| ATOM | 1501 | CG | HIS | 413 | 46.906 | 2.053 | 46.759 | 1.00 | 44.26 | PROT |
| ATOM | 1502 | CD2 | HIS | 413 | 46.140 | 0.941 | 46.632 | 1.00 | 43.48 | PROT |
| ATOM | 1503 | ND1 | HIS | 413 | 46.214 | 2.902 | 47.600 | 1.00 | 40.00 | PROT |
| ATOM | 1504 | CE1 | HIS | 413 | 45.080 | 2.328 | 47.962 | 1.00 | 47.35 | PROT |
| ATOM | 1505 | NE2 | HIS | 413 | 45.011 | 1.137 | 47.390 | 1.00 | 35.50 | PROT |
| ATOM | 1506 | C | HIS | 413 | 49.527 | 4.194 | 44.875 | 1.00 | 26.49 | PROT |
| ATOM | 1507 | O | HIS | 413 | 50.483 | 3.421 | 44.829 | 1.00 | 31.82 | PROT |
| ATOM | 1508 | N | VAL | 414 | 49.555 | 5.439 | 44.411 | 1.00 | 18.32 | PROT |
| ATOM | 1509 | CA | VAL | 414 | 50.726 | 6.069 | 43.820 | 1.00 | 22.60 | PROT |
| ATOM | 1510 | CB | VAL | 414 | 50.718 | 5.966 | 42.290 | 1.00 | 32.50 | PROT |
| ATOM | 1511 | CG1 | VAL | 414 | 51.636 | 7.026 | 41.694 | 1.00 | 33.83 | PROT |
| ATOM | 1512 | CG2 | VAL | 414 | 51.169 | 4.574 | 41.863 | 1.00 | 40.20 | PROT |
| ATOM | 1513 | C | VAL | 414 | 50.630 | 7.529 | 44.225 | 1.00 | 17.96 | PROT |
| ATOM | 1514 | O | VAL | 414 | 49.708 | 8.236 | 43.829 | 1.00 | 30.33 | PROT |
| ATOM | 1515 | N | THR | 415 | 51.586 | 7.969 | 45.028 | 1.00 | 32.51 | PROT |
| ATOM | 1516 | CA | THR | 415 | 51.601 | 9.332 | 45.531 | 1.00 | 35.31 | PROT |
| ATOM | 1517 | CB | THR | 415 | 52.779 | 9.529 | 46.511 | 1.00 | 49.75 | PROT |
| ATOM | 1518 | OG1 | THR | 415 | 53.023 | 10.930 | 46.702 | 1.00 | 60.64 | PROT |
| ATOM | 1519 | CG2 | THR | 415 | 54.038 | 8.850 | 45.974 | 1.00 | 50.83 | PROT |
| ATOM | 1520 | C | THR | 415 | 51.668 | 10.387 | 44.436 | 1.00 | 31.44 | PROT |
| ATOM | 1521 | O | THR | 415 | 52.423 | 10.251 | 43.475 | 1.00 | 22.01 | PROT |
| ATOM | 1522 | N | HIS | 416 | 50.865 | 11.437 | 44.607 | 1.00 | 24.94 | PROT |
| ATOM | 1523 | CA | HIS | 416 | 50.781 | 12.559 | 43.671 | 1.00 | 27.82 | PROT |
| ATOM | 1524 | CB | HIS | 416 | 52.163 | 13.164 | 43.440 | 1.00 | 32.98 | PROT |
| ATOM | 1525 | CG | HIS | 416 | 52.776 | 13.747 | 44.671 | 1.00 | 44.74 | PROT |
| ATOM | 1526 | CD2 | HIS | 416 | 53.982 | 13.539 | 45.251 | 1.00 | 44.91 | PROT |
| ATOM | 1527 | ND1 | HIS | 416 | 52.121 | 14.665 | 45.462 | 1.00 | 49.20 | PROT |
| ATOM | 1528 | CE1 | HIS | 416 | 52.899 | 15.000 | 46.477 | 1.00 | 53.14 | PROT |
| ATOM | 1529 | NE2 | HIS | 416 | 54.033 | 14.330 | 46.373 | 1.00 | 41.72 | PROT |
| ATOM | 1530 | C | HIS | 416 | 50.176 | 12.172 | 42.328 | 1.00 | 29.13 | PROT |
| ATOM | 1531 | O | HIS | 416 | 50.612 | 12.660 | 41.286 | 1.00 | 37.24 | PROT |
| ATOM | 1532 | N | PHE | 417 | 49.163 | 11.311 | 42.350 | 1.00 | 18.38 | PROT |
| ATOM | 1533 | CA | PHE | 417 | 48.528 | 10.867 | 41.115 | 1.00 | 16.08 | PROT |
| ATOM | 1534 | CB | PHE | 417 | 47.295 | 10.029 | 41.407 | 1.00 | 17.89 | PROT |
| ATOM | 1535 | CG | PHE | 417 | 47.021 | 8.997 | 40.364 | 1.00 | 16.15 | PROT |
| ATOM | 1536 | CD1 | PHE | 417 | 47.980 | 8.044 | 40.051 | 1.00 | 16.55 | PROT |

APPENDIX 7-continued

TRBTRIAC.PDB

| ATOM | 1537 | CD2 | PHE | 417 | 45.806 | 8.971 | 39.696 | 1.00 | 15.49 | PROT |
|---|---|---|---|---|---|---|---|---|---|---|
| ATOM | 1538 | CE1 | PHE | 417 | 47.727 | 7.081 | 39.087 | 1.00 | 19.81 | PROT |
| ATOM | 1539 | CE2 | PHE | 417 | 45.544 | 8.008 | 38.731 | 1.00 | 9.76 | PROT |
| ATOM | 1540 | CZ | PHE | 417 | 46.501 | 7.064 | 38.427 | 1.00 | 5.25 | PROT |
| ATOM | 1541 | C | PHE | 417 | 48.117 | 11.990 | 40.187 | 1.00 | 14.51 | PROT |
| ATOM | 1542 | O | PHE | 417 | 48.636 | 12.119 | 39.081 | 1.00 | 18.44 | PROT |
| ATOM | 1543 | N | TRP | 418 | 47.171 | 12.800 | 40.640 | 1.00 | 21.08 | PROT |
| ATOM | 1544 | CA | TRP | 418 | 46.688 | 13.900 | 39.828 | 1.00 | 16.28 | PROT |
| ATOM | 1545 | CB | TRP | 418 | 45.796 | 14.832 | 40.659 | 1.00 | 15.19 | PROT |
| ATOM | 1546 | CG | TRP | 418 | 45.002 | 15.746 | 39.802 | 1.00 | 16.60 | PROT |
| ATOM | 1547 | CD2 | TRP | 418 | 44.165 | 15.369 | 38.710 | 1.00 | 21.85 | PROT |
| ATOM | 1548 | CE2 | TRP | 418 | 43.690 | 16.557 | 38.118 | 1.00 | 22.53 | PROT |
| ATOM | 1549 | CE3 | TRP | 418 | 43.771 | 14.138 | 38.170 | 1.00 | 16.42 | PROT |
| ATOM | 1550 | CD1 | TRP | 418 | 44.999 | 17.107 | 39.836 | 1.00 | 21.01 | PROT |
| ATOM | 1551 | NE1 | TRP | 418 | 44.215 | 17.606 | 38.826 | 1.00 | 24.02 | PROT |
| ATOM | 1552 | CZ2 | TRP | 418 | 42.838 | 16.555 | 37.010 | 1.00 | 24.64 | PROT |
| ATOM | 1553 | CZ3 | TRP | 418 | 42.925 | 14.135 | 37.069 | 1.00 | 28.80 | PROT |
| ATOM | 1554 | CH2 | TRP | 418 | 42.467 | 15.337 | 36.500 | 1.00 | 21.25 | PROT |
| ATOM | 1555 | C | TRP | 418 | 47.834 | 14.676 | 39.192 | 1.00 | 16.17 | PROT |
| ATOM | 1556 | O | TRP | 418 | 47.928 | 14.764 | 37.977 | 1.00 | 19.51 | PROT |
| ATOM | 1557 | N | PRO | 419 | 48.723 | 15.250 | 40.007 | 1.00 | 19.59 | PROT |
| ATOM | 1558 | CD | PRO | 419 | 48.757 | 15.274 | 41.477 | 1.00 | 19.81 | PROT |
| ATOM | 1559 | CA | PRO | 419 | 49.837 | 16.002 | 39.429 | 1.00 | 17.87 | PROT |
| ATOM | 1560 | CB | PRO | 419 | S0.720 | 16.309 | 40.629 | 1.00 | 6.85 | PROT |
| ATOM | 1561 | CG | PRO | 419 | 49.785 | 16.326 | 41.764 | 1.00 | 25.11 | PROT |
| ATOM | 1562 | C | PRO | 419 | 50.578 | 15.202 | 38.373 | 1.00 | 15.44 | PROT |
| ATOM | 1563 | O | PRO | 419 | 50.922 | 15.720 | 37.315 | 1.00 | 24.75 | PROT |
| ATOM | 1564 | N | LYS | 420 | 50.811 | 13.932 | 38.664 | 1.00 | 15.10 | PROT |
| ATOM | 1565 | CA | LYS | 420 | 51.534 | 13.056 | 37.748 | 1.00 | 20.59 | PROT |
| ATOM | 1566 | CB | LYS | 420 | 51.900 | 11.746 | 38.471 | 1.00 | 28.85 | PROT |
| ATOM | 1567 | CG | LYS | 420 | 52.955 | 11.906 | 39.577 | 1.00 | 30.61 | PROT |
| ATOM | 1568 | CD | LYS | 420 | 52.907 | 10.759 | 40.580 | 1.00 | 24.41 | PROT |
| ATOM | 1569 | CE | LYS | 420 | 54.275 | 10.493 | 41.224 | 1.00 | 31.94 | PROT |
| ATOM | 1570 | NZ | LYS | 420 | 54.485 | 9.040 | 41.557 | 1.00 | 27.34 | PROT |
| ATOM | 1571 | C | LYS | 420 | 50.779 | 12.757 | 36.445 | 1.00 | 17.36 | PROT |
| ATOM | 1572 | O | LYS | 420 | 51.393 | 12.439 | 35.437 | 1.00 | 26.28 | PROT |
| ATOM | 1573 | N | LEU | 421 | 49.455 | 12.859 | 36.474 | 1.00 | 16.34 | PROT |
| ATOM | 1574 | CA | LEU | 421 | 48.627 | 12.614 | 35.297 | 1.00 | 9.38 | PROT |
| ATOM | 1575 | CB | LEU | 421 | 47.231 | 12.139 | 35.707 | 1.00 | 13.22 | PROT |
| ATOM | 1576 | CG | LEU | 421 | 46.739 | 10.818 | 35.107 | 1.00 | 15.75 | PROT |
| ATOM | 1577 | CD1 | LEU | 421 | 47.919 | 9.993 | 34.652 | 1.00 | 29.24 | PROT |
| ATOM | 1578 | CD2 | LEU | 421 | 45.949 | 10.049 | 36.135 | 1.00 | 12.19 | PROT |
| ATOM | 1579 | C | LEU | 421 | 48.511 | 13.866 | 34.441 | 1.00 | 12.61 | PROT |
| ATOM | 1580 | O | LEU | 421 | 48.458 | 13.777 | 33.223 | 1.00 | 17.85 | PROT |
| ATOM | 1581 | N | LEU | 422 | 4&451 | 15.036 | 35.063 | 1.00 | 8.47 | PROT |
| ATOM | 1582 | CA | LEU | 422 | 48.393 | 16.254 | 34.277 | 1.00 | 7.21 | PROT |
| ATOM | 1583 | CB | LEU | 422 | 48.160 | 17.468 | 35.164 | 1.00 | 2.00 | PROT |
| ATOM | 1584 | CG | LEU | 422 | 46.941 | 17.445 | 36.088 | 1.00 | 12.16 | PROT |
| ATOM | 1585 | CD1 | LEU | 422 | 47.024 | 18.660 | 36.982 | 1.00 | 6.96 | PROT |
| ATOM | 1586 | CD2 | LEU | 422 | 45.632 | 17.450 | 35.313 | 1.00 | 2.00 | PROT |
| ATOM | 1587 | C | LEU | 422 | 49.748 | 16.365 | 33.567 | 1.00 | 10.59 | PROT |
| ATOM | 1588 | O | LEU | 422 | 49.851 | 16.938 | 32.477 | 1.00 | 13.48 | PROT |
| ATOM | 1589 | N | MET | 423 | 50.786 | 15.804 | 34.185 | 1.00 | 2.29 | PROT |
| ATOM | 1590 | CA | MET | 423 | 52.109 | 15.821 | 33.579 | 1.00 | 6.50 | PROT |
| ATOM | 1591 | CB | MET | 423 | 53.158 | 15.215 | 34.514 | 1.00 | 2.13 | PROT |
| ATOM | 1592 | CG | MET | 423 | 53.361 | 15.968 | 35.803 | 1.00 | 16.33 | PROT |
| ATOM | 1593 | SD | MET | 423 | 55.075 | 16.415 | 36.070 | 1.00 | 26.66 | PROT |
| ATOM | 1594 | CE | MET | 423 | 55.751 | 14.880 | 36.623 | 1.00 | 20.24 | PROT |
| ATOM | 1595 | C | MET | 423 | 52.016 | 14.966 | 32.318 | 1.00 | 12.20 | PROT |
| ATOM | 1596 | O | MET | 423 | 52.741 | 15.183 | 31.345 | 1.00 | 18.67 | PROT |
| ATOM | 1597 | N | LYS | 424 | 51.114 | 13.988 | 32.352 | 1.00 | 7.89 | PROT |
| ATOM | 1598 | CA | LYS | 424 | 50.907 | 13.084 | 31.230 | 1.00 | 12.91 | PROT |
| ATOM | 1599 | CB | LYS | 424 | 49.990 | 11.924 | 31.645 | 1.00 | 5.14 | PROT |
| ATOM | 1600 | CG | LYS | 424 | 50.669 | 10.579 | 31.980 | 1.00 | 11.76 | PROT |
| ATOM | 1601 | CD | LYS | 424 | 52.187 | 10.590 | 31.866 | 1.00 | 3.70 | PROT |
| ATOM | 1602 | CE | LYS | 424 | 52.844 | 10.020 | 33.113 | 1.00 | 7.84 | PROT |
| ATOM | 1603 | NZ | LYS | 424 | 54.335 | 9.959 | 32.995 | 1.00 | 25.86 | PROT |
| ATOM | 1604 | C | LYS | 424 | 50.293 | 13.840 | 30.046 | 1.00 | 17.44 | PROT |
| ATOM | 1605 | O | LYS | 424 | 50.650 | 13.596 | 28.897 | 1.00 | 11.72 | PROT |
| ATOM | 1606 | N | VAL | 425 | 49.370 | 14.756 | 30.322 | 1.00 | 3.16 | PROT |
| ATOM | 1607 | CA | VAL | 425 | 48.768 | 15.515 | 29.249 | 1.00 | 2.00 | PROT |
| ATOM | 1608 | CB | VAL | 425 | 47.744 | 16.532 | 29.773 | 1.00 | 6.77 | PROT |
| ATOM | 1609 | CG1 | VAL | 425 | 47.653 | 17.716 | 28.815 | 1.00 | 2.00 | PROT |
| ATOM | 1610 | CG2 | VAL | 425 | 46.381 | 15.870 | 29.914 | 1.00 | 10.91 | PROT |
| ATOM | 1611 | C | VAL | 425 | 49.845 | 16.274 | 28.487 | 1.00 | 4.83 | PROT |
| ATOM | 1612 | O | VAL | 425 | 49.853 | 16.265 | 27.269 | 1.00 | 15.69 | PROT |
| ATOM | 1613 | N | THR | 426 | 50.753 | 16.924 | 29.208 | 1.00 | 14.38 | PROT |

APPENDIX 7-continued

TRBTRIAC.PDB

| ATOM | 1614 | CA  | THR | 426 | 51.824 | 17.707 | 28.593 | 1.00 | 12.41 | PROT |
|------|------|-----|-----|-----|--------|--------|--------|------|-------|------|
| ATOM | 1615 | CB  | THR | 426 | 52.713 | 18.372 | 29.667 | 1.00 | 12.49 | PROT |
| ATOM | 1616 | OG1 | THR | 426 | 51.890 | 19.138 | 30.552 | 1.00 | 11.06 | PROT |
| ATOM | 1617 | CG2 | THR | 426 | 53.763 | 19.283 | 29.015 | 1.00 | 2.93  | PROT |
| ATOM | 1618 | C   | THR | 426 | 52.734 | 16.928 | 27.653 | 1.00 | 15.72 | PROT |
| ATOM | 1619 | O   | THR | 426 | 53.198 | 17.463 | 26.651 | 1.00 | 14.40 | PROT |
| ATOM | 1620 | N   | ASP | 427 | 53.000 | 15.672 | 27.981 | 1.00 | 16.23 | PROT |
| ATOM | 1621 | CA  | ASP | 427 | 53.865 | 14.843 | 27.157 | 1.00 | 16.35 | PROT |
| ATOM | 1622 | CB  | ASP | 427 | 54.342 | 13.630 | 27.950 | 1.00 | 19.48 | PROT |
| ATOM | 1623 | CG  | ASP | 427 | 55.337 | 13.997 | 29.029 | 1.00 | 18.96 | PROT |
| ATOM | 1624 | OD1 | ASP | 427 | 55.874 | 15.125 | 29.010 | 1.00 | 8.75  | PROT |
| ATOM | 1625 | OD2 | ASP | 427 | 55.579 | 13.145 | 29.902 | 1.00 | 24.25 | PROT |
| ATOM | 1626 | C   | ASP | 427 | 53.155 | 14.381 | 25.891 | 1.00 | 20.52 | PROT |
| ATOM | 1627 | O   | ASP | 427 | 53.793 | 14.164 | 24.856 | 1.00 | 25.69 | PROT |
| ATOM | 1628 | N   | LEU | 428 | .51.838 | 14.218 | 25.986 | 1.00 | 5.49  | PROT |
| ATOM | 1629 | CA  | LEU | 428 | 51.040 | 13.815 | 24.849 | 1.00 | 2.00  | PROT |
| ATOM | 1630 | CB  | LEU | 428 | 49.634 | 13.470 | 25.301 | 1.00 | 2.00  | PROT |
| ATOM | 1631 | CG  | LEU | 428 | 49.579 | 12.127 | 26.028 | 1.00 | 2.00  | PROT |
| ATOM | 1632 | CD1 | LEU | 428 | 48.184 | 11.789 | 26.481 | 1.00 | 2.00  | PROT |
| ATOM | 1633 | CD2 | LEU | 428 | 50.088 | 11.080 | 25.108 | 1.00 | 2.00  | PROT |
| ATOM | 1634 | C   | LEU | 428 | 51.019 | 14.987 | 23.881 | 1.00 | 7.72  | PROT |
| ATOM | 1635 | O   | LEU | 428 | 51.072 | 14.800 | 22.666 | 1.00 | 9.22  | PROT |
| ATOM | 1636 | N   | ARG | 429 | 50.961 | 16.197 | 24.432 | 1.00 | 10.07 | PROT |
| ATOM | 1637 | CA  | ARG | 429 | 50.948 | 17.438 | 23.659 | 1.00 | 7.97  | PROT |
| ATOM | 1638 | CB  | ARG | 429 | 50.799 | 18.642 | 24.583 | 1.00 | 18.55 | PROT |
| ATOM | 1639 | CG  | ARG | 429 | 49.548 | 18.634 | 25.429 | 1.00 | 14.80 | PROT |
| ATOM | 1640 | CD  | ARG | 429 | 48.588 | 19.674 | 24.935 | 1.00 | 32.08 | PROT |
| ATOM | 1641 | NE  | ARG | 429 | 47.508 | 19.923 | 25.880 | 1.00 | 42.46 | PROT |
| ATOM | 1642 | CZ  | ARG | 429 | 46.226 | 19.673 | 25.631 | 1.00 | 48.51 | PROT |
| ATOM | 1643 | NH1 | ARG | 429 | 45.860 | 19.163 | 24.459 | 1.00 | 33.35 | PROT |
| ATOM | 1644 | NH2 | ARG | 429 | 45.307 | 19.955 | 26.549 | 1.00 | 46.08 | PROT |
| ATOM | 1645 | C   | ARG | 429 | 52.260 | 17.557 | 22.919 | 1.00 | 11.77 | PROT |
| ATOM | 1646 | O   | ARG | 429 | 52.298 | 17.904 | 21.737 | 1.00 | 28.66 | PROT |
| ATOM | 1647 | N   | MET | 430 | 53.343 | 17.270 | 23.629 | 1.00 | 20.26 | PROT |
| ATOM | 1648 | CA  | MET | 430 | 54.671 | 17.328 | 23.042 | 1.00 | 21.06 | PROT |
| ATOM | 1649 | CB  | MET | 430 | 55.738 | 17.015 | 24.100 | 1.00 | 30.24 | PROT |
| ATOM | 1650 | CG  | MET | 430 | 56.061 | 18.165 | 25.056 | 1.00 | 34.66 | PROT |
| ATOM | 1651 | SD  | MET | 430 | 55.727 | 19.795 | 24.373 | 1.00 | 35.91 | PROT |
| ATOM | 1652 | CE  | MET | 430 | 56.839 | 19.814 | 22.978 | 1.00 | 32.52 | PROT |
| ATOM | 1653 | C   | MET | 430 | 54.735 | 16.302 | 21.925 | 1.00 | 18.70 | PROT |
| ATOM | 1654 | O   | MET | 430 | 55.287 | 16.560 | 20.860 | 1.00 | 16.59 | PROT |
| ATOM | 1655 | N   | ILE | 431 | 54.161 | 15.133 | 22.182 | 1.00 | 15.38 | PROT |
| ATOM | 1656 | CA  | ILE | 431 | 54.144 | 14.069 | 21.196 | 1.00 | 15.85 | PROT |
| ATOM | 1657 | CB  | ILE | 431 | 53.326 | 12.859 | 21.705 | 1.00 | 13.76 | PROT |
| ATOM | 1658 | CG2 | ILE | 431 | 52.727 | 12.084 | 20.539 | 1.00 | 11.11 | PROT |
| ATOM | 1659 | CG1 | ILE | 431 | 54.239 | 11.924 | 22.489 | 1.00 | 11.72 | PROT |
| ATOM | 1660 | CD1 | ILE | 431 | 53.552 | 11.224 | 23.615 | 1.00 | 16.22 | PROT |
| ATOM | 1661 | C   | ILE | 431 | 53.538 | 14.609 | 19.904 | 1.00 | 18.49 | PROT |
| ATOM | 1662 | O   | ILE | 431 | 54.134 | 14.483 | 18.839 | 1.00 | 17.36 | PROT |
| ATOM | 1663 | N   | GLY | 432 | 52.361 | 15.220 | 20.003 | 1.00 | 2.00  | PROT |
| ATOM | 1664 | CA  | GLY | 432 | 51.721 | 15.772 | 18.831 | 1.00 | 2.00  | PROT |
| ATOM | 1665 | C   | GLY | 432 | 52.542 | 16.851 | 18.148 | 1.00 | 10.55 | PROT |
| ATOM | 1666 | O   | GLY | 432 | 52.707 | 16.834 | 16.936 | 1.00 | 9.60  | PROT |
| ATOM | 1667 | N   | ALA | 433 | 53.043 | 17.805 | 18.926 | 1.00 | 11.17 | PROT |
| ATOM | 1668 | CA  | ALA | 433 | 53.855 | 18.884 | 18.385 | 1.00 | 2.00  | PROT |
| ATOM | 1669 | CB  | ALA | 433 | 54.326 | 19.771 | 19.506 | 1.00 | 2.00  | PROT |
| ATOM | 1670 | C   | ALA | 433 | 55.050 | 18.285 | 17.646 | 1.00 | 6.43  | PROT |
| ATOM | 1671 | O   | ALA | 433 | 55.493 | 18.789 | 16.623 | 1.00 | 11.71 | PROT |
| ATOM | 1672 | N   | CYS | 434 | 55.579 | 17.197 | 18.179 | 1.00 | 15.71 | PROT |
| ATOM | 1673 | CA  | CYS | 434 | 56.715 | 16.534 | 17.573 | 1.00 | 13.44 | PROT |
| ATOM | 1674 | CB  | CYS | 434 | 57.228 | 15.464 | 18.518 | 1.00 | 14.76 | PROT |
| ATOM | 1675 | SG  | CYS | 434 | 58.910 | 15.703 | 18.985 | 1.00 | 20.82 | PROT |
| ATOM | 1676 | C   | CYS | 434 | 56.269 | 15.902 | 16.264 | 1.00 | 9.28  | PROT |
| ATOM | 1677 | O   | CYS | 434 | 56.969 | 15.948 | 15.256 | 1.00 | 8.50  | PROT |
| ATOM | 1678 | N   | HIS | 435 | 55.091 | 15.300 | 16.298 | 1.00 | 11.04 | PROT |
| ATOM | 1679 | CA  | HIS | 435 | 54.533 | 14.657 | 15.122 | 1.00 | 11.30 | PROT |
| ATOM | 1680 | CB  | HIS | 435 | 53.142 | 14.132 | 15.438 | 1.00 | 4.30  | PROT |
| ATOM | 1681 | CG  | HIS | 435 | 52.480 | 13.460 | 14.283 | 1.00 | 13.68 | PROT |
| ATOM | 1682 | CD2 | HIS | 435 | 52.751 | 12.288 | 13.662 | 1.00 | 4.72  | PROT |
| ATOM | 1683 | ND1 | HIS | 435 | 51.358 | 13.976 | 13.666 | 1.00 | 5.53  | PROT |
| ATOM | 1684 | CE1 | HIS | 435 | 50.966 | 13.147 | 12.717 | 1.00 | 12.84 | PROT |
| ATOM | 1685 | NE2 | HIS | 435 | 51.794 | 12.116 | 12.694 | 1.00 | 15.77 | PROT |
| ATOM | 1686 | C   | HIS | 435 | 54.482 | 15.661 | 13.973 | 1.00 | 8.50  | PROT |
| ATOM | 1687 | O   | HIS | 435 | 54.941 | 15.370 | 12.869 | 1.00 | 14.82 | PROT |
| ATOM | 1688 | N   | ALA | 436 | 53.938 | 16.844 | 14.245 | 1.00 | 5.74  | PROT |
| ATOM | 1689 | CA  | ALA | 436 | 53.843 | 17.905 | 13.252 | 1.00 | 2.00  | PROT |
| ATOM | 1690 | CB  | ALA | 436 | 53.632 | 19.2,41 | 13.942 | 1.00 | 2.00 | PROT |

APPENDIX 7-continued

TRBTRIAC.PDB

| ATOM | 1691 | C | ALA | 436 | 55.121 | 17.934 | 12.406 | 1.00 | 8.68 | PROT |
|---|---|---|---|---|---|---|---|---|---|---|
| ATOM | 1692 | O | ALA | 436 | 55.080 | 17.712 | 11.193 | 1.00 | 15.14 | PROT |
| ATOM | 1693 | N | SER | 437 | 56.256 | 18.189 | 13.047 | 1.00 | 6.82 | PROT |
| ATOM | 1694 | CA | SER | 437 | 57.522 | 18.226 | 12.337 | 1.00 | 9.05 | PROT |
| ATOM | 1695 | CB | SER | 437 | 58.671 | 18.511 | 13.295 | 1.00 | 2.00 | PROT |
| ATOM | 1696 | OG | SER | 437 | 59.593 | 19.406 | 12.699 | 1.00 | 21.18 | PROT |
| ATOM | 1697 | C | SER | 437 | 57.758 | 16.896 | 11.637 | 1.00 | 15.18 | PROT |
| ATOM | 1698 | O | SER | 437 | 58.076 | 16.849 | 10.445 | 1.00 | 19.33 | PROT |
| ATOM | 1699 | N | ARG | 438 | 57.607 | 15.805 | 12.373 | 1.00 | 16.98 | PROT |
| ATOM | 1700 | CA | ARG | 438 | 57.799 | 14.501 | 11.766 | 1.00 | 16.98 | PROT |
| ATOM | 1701 | CB | ARG | 438 | 57.294 | 13.409 | 12.702 | 1.00 | 24.77 | PROT |
| ATOM | 1702 | CG | ARG | 438 | 58.006 | 12.086 | 12.534 | 1.00 | 33.76 | PROT |
| ATOM | 1703 | CD | ARG | 438 | 59.506 | 12.280 | 12.614 | 1.00 | 30.64 | PROT |
| ATOM | 1704 | NE | ARG | 438 | 60.219 | 11.380 | 11.721 | 1.00 | 29.76 | PROT |
| ATOM | 1705 | CZ | ARG | 438 | 6.1.505 | 11.504 | 11.423 | 1.00 | 25.21 | PROT |
| ATOM | 1706 | NH1 | ARG | 438 | 62.077 | 10.641 | 10.603 | 1.00 | 39.58 | PROT |
| ATOM | 1707 | NH2 | ARG | 438 | 62.217 | 12.492 | 11.942 | 1.00 | 14.13 | PROT |
| ATOM | 1708 | C | ARG | 438 | 57.031 | 14.441 | 10.448 | 1.00 | 16.49 | PROT |
| ATOM | 1709 | O | ARG | 438 | 57.563 | 14.008 | 9.424 | 1.00 | 15.57 | PROT |
| ATOM | 1710 | N | PHE | 439 | 55.781 | 14.893 | 10.484 | 1.00 | 16.75 | PROT |
| ATOM | 1711 | CA | PHE | 439 | 54.933 | 14.878 | 9.303 | 1.00 | 21.63 | PROT |
| ATOM | 1712 | CB | PHE | 439 | 53.603 | 15.575 | 9.574 | 1.00 | 17.84 | PROT |
| ATOM | 1713 | CG | PHE | 439 | 52.597 | 15.364 | 8.490 | 1.00 | 20.60 | PROT |
| ATOM | 1714 | CD1 | PHE | 439 | 52.042 | 14.103 | 8.279 | 1.00 | 30.60 | PROT |
| ATOM | 1715 | CD2 | PHE | 439 | 52.265 | 16.394 | 7.622 | 1.00 | 14.95 | PROT |
| ATOM | 1716 | CE1 | PHE | 439 | 51.175 | 13.867 | 7.206 | 1.00 | 29.12 | PROT |
| ATOM | 1717 | CE2 | PHE | 439 | 51.404 | 16.173 | 6.552 | 1.00 | 25.18 | PROT |
| ATOM | 1718 | CZ | PHE | 439 | 50.860 | 14.905 | 6.341 | 1.00 | 27.82 | PROT |
| ATOM | 1719 | C | PHE | 439 | 55.620 | 15.548 | 8.130 | 1.00 | 28.17 | PROT |
| ATOM | 1720 | O | PHE | 439 | 55.512 | 15.095 | 6.987 | 1.00 | 28.83 | PROT |
| ATOM | 1721 | N | LEU | 440 | 56.328 | 16.633 | 8.427 | 1.00 | 26.77 | PROT |
| ATOM | 1722 | CA | LEU | 440 | 57.055 | 17.382 | 7.418 | 1.00 | 24.66 | PROT |
| ATOM | 1723 | CB | LEU | 440 | 57.555 | 18.696 | 8.005 | 1.00 | 10.80 | PROT |
| ATOM | 1724 | CG | LEU | 440 | 56.501 | 19.658 | 8.541 | 1.00 | 8.60 | PROT |
| ATOM | 1725 | CD1 | LEU | 440 | 57.152 | 20.985 | 8.855 | 1.00 | 17.69 | PROT |
| ATOM | 1726 | CD2 | LEU | 440 | 55.410 | 19.847 | 7.522 | 1.00 | 15.71 | PROT |
| ATOM | 1727 | C | LEU | 440 | 58.245 | 16.578 | 6.912 | 1.00 | 29.61 | PROT |
| ATOM | 1728 | O | LEU | 440 | 58.506 | 16.526 | 5.718 | 1.00 | 32.37 | PROT |
| ATOM | 1729 | N | HIS | 441 | 58.971 | 15.954 | 7.830 | 1.00 | 28.12 | PROT |
| ATOM | 1730 | CA | HIS | 441 | 60.140 | 15.172 | 7.460 | 1.00 | 28.51 | PROT |
| ATOM | 1731 | CB | HIS | 441 | 60.783 | 14.564 | 8.705 | 1.00 | 36.77 | PROT |
| ATOM | 1732 | C | HIS | 441 | 59.724 | 14.081 | 6.497 | 1.00 | 31.94 | PROT |
| ATOM | 1733 | O | HIS | 441 | 60.461 | 13.725 | 5.579 | 1.00 | 49.29 | PROT |
| ATOM | 1734 | N | MET | 442 | 58.533 | 13.545 | 6.711 | 1.00 | 41.16 | PROT |
| ATOM | 1735 | CA | MET | 442 | 58.033 | 12.487 | 5.854 | 1.00 | 39.99 | PROT |
| ATOM | 1736 | CB | MET | 442 | 56.871 | 11.776 | 6.551 | 1.00 | 38.32 | PROT |
| ATOM | 1737 | CG | MET | 442 | 57.263 | 11.122 | 7.860 | 1.00 | 19.20 | PROT |
| ATOM | 1738 | SD | MET | 442 | 55.859 | 10.350 | 8.675 | 1.00 | 38.06 | PROT |
| ATOM | 1739 | CE | MET | 442 | 54.906 | 11.767 | 9.073 | 1.00 | 21.45 | PROT |
| ATOM | 1740 | C | MET | 442 | 57.599 | 13.031 | 4.495 | 1.00 | 35.68 | PROT |
| ATOM | 1741 | O | MET | 442 | 57.887 | 12.431 | 3.461 | 1.00 | 27.43 | PROT |
| ATOM | 1742 | N | LYS | 443 | 56.920 | 14.175 | 4.503 | 1.00 | 34.17 | PROT |
| ATOM | 1743 | CA | LYS | 443 | 56.447 | 14.796 | 3.268 | 1.00 | 34.33 | PROT |
| ATOM | 1744 | CB | LYS | 443 | 55.767 | 16.129 | 3.574 | 1.00 | 21.68 | PROT |
| ATOM | 1745 | CG | LYS | 443 | 54.303 | 15.989 | 3.953 | 1.00 | 26.95 | PROT |
| ATOM | 1746 | CD | LYS | 443 | 53.497 | 17.231 | 3.602 | 1.00 | 30.78 | PROT |
| ATOM | 1747 | CE | LYS | 443 | 52.204 | 16.848 | 2.861 | 1.00 | 56.06 | PROT |
| ATOM | 1748 | NZ | LYS | 443 | 50.931 | 17.261 | 3.564 | 1.00 | 45.26 | PROT |
| ATOM | 1749 | C | LYS | 443 | 57.570 | 15.007 | 2.251 | 1.00 | 37.81 | PROT |
| ATOM | 1750 | O | LYS | 443 | 57.325 | 15.049 | 1.041 | 1.00 | 38.26 | PROT |
| ATOM | 1751 | N | VAL | 444 | 58.798 | 15.130 | 2.741 | 1.00 | 25.12 | PROT |
| ATOM | 1752 | CA | VAL | 444 | 59.942 | 15.318 | 1.867 | 1.00 | 25.43 | PROT |
| ATOM | 1753 | CB | VAL | 444 | 60.802 | 16.531 | 2.334 | 1.00 | 29.15 | PROT |
| ATOM | 1754 | CG1 | VAL | 444 | 59.893 | 17.621 | 2.861 | 1.00 | 29.48 | PROT |
| ATOM | 1755 | CG2 | VAL | 444 | 61.785 | 16.121 | 3.419 | 1.00 | 36.65 | PROT |
| ATOM | 1756 | C | VAL | 444 | 60.786 | 14.042 | 1.825 | 1.00 | 30.03 | PROT |
| ATOM | 1757 | O | VAL | 444 | 62.009 | 14.099 | 1.698 | 1.00 | 39.43 | PROT |
| ATOM | 1758 | N | GLU | 445 | 60.127 | 12.888 | 1.903 | 1.00 | 39.84 | PROT |
| ATOM | 1759 | CA | GLU | 445 | 60.842 | 11.612 | 1.896 | 1.00 | 43.07 | PROT |
| ATOM | 1760 | CB | GLU | 445 | 61.429 | 11.360 | 3.282 | 1.00 | 50.55 | PROT |
| ATOM | 1761 | CG | GLU | 445 | 62.399 | 10.203 | 3.351 | 1.00 | 77.00 | PROT |
| ATOM | 1762 | CD | GLU | 445 | 63.569 | 10.495 | 4.267 | 1.00 | 98.21 | PROT |
| ATOM | 1763 | OE1 | GLU | 445 | 64.251 | 9.538 | 4.701 | 1.00 | 100.00 | PROT |
| ATOM | 1764 | OE2 | GLU | 445 | 63.804 | 11.690 | 4.554 | 1.00 | 100.00 | PROT |
| ATOM | 1765 | C | GLU | 445 | 59.989 | 10.408 | 1.491 | 1.00 | 43.41 | PROT |
| ATOM | 1766 | O | GLU | 445 | 60.466 | 9.274 | 1.511 | 1.00 | 48.80 | PROT |
| ATOM | 1767 | N | CYS | 446 | 58.731 | 10.644 | 1.137 | 1.00 | 38.17 | PROT |

APPENDIX 7-continued

| | | | | TRBTRIAC.PDB | | | | | |
|---|---|---|---|---|---|---|---|---|---|
| ATOM | 1768 | CA | CYS | 446 | 57.852 | 9.548 | 0.743 | 1.00 | 41.38 PROT |
| ATOM | 1769 | CB | CYS | 446 | 57.066 | 9.035 | 1.965 | 1.00 | 40.61 PROT |
| ATOM | 1770 | SG | CYS | 446 | 58.062 | 8.276 | 3.320 | 1.00 | 44.73 PROT |
| ATOM | 1771 | C | CYS | 446 | 56.886 | 10.003 | −0.362 | 1.00 | 45.83 PROT |
| ATOM | 1772 | O | CYS | 446 | 56.466 | 11.184 | −0.323 | 1.00 | 44.17 PROT |
| ATOM | 1773 | OT | CYS | 446 | 56.570 | 9.180 | −1.259 | 1.00 | 40.79 PROT |
| ATOM | 1774 | CB | GLU | 449 | 52.635 | 12.140 | −2.649 | 1.00 | 28.60 PROT |
| ATOM | 1775 | C | GLU | 449 | 52.019 | 10.014 | −1.526 | 1.00 | 38.06 PROT |
| ATOM | 1776 | O | GLU | 449 | 50.873 | 10.220 | −1.935 | 1.00 | 43.52 PROT |
| ATOM | 1777 | N | GLU | 449 | 54.378 | 10.460 | −2.167 | 1.00 | 17.78 PROT |
| ATOM | 1778 | CA | GLU | 449 | 53.105 | 11.069 | −1.689 | 1.00 | 33.80 PROT |
| ATOM | 1779 | N | LEU | 450 | 52.387 | 8.880 | −0.936 | 1.00 | 46.88 PROT |
| ATOM | 1780 | CA | LEU | 450 | 51.432 | 7.808 | −0.696 | 1.00 | 52.62 PROT |
| ATOM | 1781 | CB | LEU | 450 | 52.101 | 6.436 | −0.850 | 1.00 | 57.50 PROT |
| ATOM | 1782 | CG | LEU | 450 | 53.338 | 6.066 | −0.028 | 1.00 | 59.81 PROT |
| ATOM | 1783 | CD1 | LEU | 450 | 53.613 | 4.573 | −0.198 | 1.00 | 51.33 PROT |
| ATOM | 1784 | CD2 | LEU | 450 | 54.544 | 6.890 | −0.473 | 1.00 | 57.03 PROT |
| ATOM | 1785 | C | LEU | 450 | 50.850 | 7.970 | 0.711 | 1.00 | 50.65 PROT |
| ATOM | 1786 | O | LEU | 450 | 50.965 | 7.091 | 1.569 | 1.00 | 38.49 PROT |
| ATOM | 1787 | N | PHE | 451 | 50.225 | 9.123 | 0.923 | 1.00 | 32.24 PROT |
| ATOM | 1788 | CA | PHE | 451 | 49.602 | 9.478 | 2.188 | 1.00 | 32.64 PROT |
| ATOM | 1789 | CB | PHE | 451 | 50.091 | 10.857 | 2.648 | 1.00 | 56.06 PROT |
| ATOM | 1790 | CG | PHE | 451 | 51.534 | 10.895 | 3.056 | 1.00 | 61.73 PROT |
| ATOM | 1791 | CD1 | PHE | 451 | 52.523 | 10.366 | 2.235 | 1.00 | 66.92 PROT |
| ATOM | 1792 | CD2 | PHE | 451 | 5.1.905 | 11.486 | 4.256 | 1.00 | 58.76 PROT |
| ATOM | 1793 | CE1 | PHE | 451 | 53.860 | 10.430 | 2.604 | 1.00 | 69.17 PROT |
| ATOM | 1794 | CE2 | PHE | 451 | 53.231 | 11.556 | 4.635 | 1.00 | 61.48 PROT |
| ATOM | 1795 | CZ | PHE | 451 | 54.214 | 11.028 | 3.809 | 1.00 | 71.95 PROT |
| ATOM | 1796 | C | PHE | 451 | 48.081 | 9.548 | 2.025 | 1.00 | 30.67 PROT |
| ATOM | 1797 | O | PHE | 451 | 47.571 | 10.429 | 1.324 | 1.00 | 38.49 PROT |
| ATOM | 1798 | N | PRO | 452 | 47.336 | 8.627 | 2.672 | 1.00 | 19.14 PROT |
| ATOM | 1799 | CD | PRO | 452 | 47.774 | 7.495 | 3.510 | 1.00 | 24.21 PROT |
| ATOM | 1800 | CA | PRO | 452 | 45.881 | 8.672 | 2.538 | 1.00 | 5.88 PROT |
| ATOM | 1801 | CB | PRO | 452 | 45.397 | 7.742 | 3.633 | 1.00 | 16.92 PROT |
| ATOM | 1802 | CG | PRO | 452 | 46.496 | 6.737 | 3.761 | 1.00 | 16.91 PROT |
| ATOM | 1803 | C | PRO | 452 | 45.354 | 10.090 | 2.687 | 1.00 | 15.15 PROT |
| ATOM | 1804 | O | PRO | 452 | 45.879 | 10.886 | 3.463 | 1.00 | 22.59 PROT |
| ATOM | 1805 | N | PRO | 453 | 44.315 | 10.429 | 1.920 | 1.00 | 18.37 PROT |
| ATOM | 1806 | CD | PRO | 453 | 43.653 | 9.540 | 0.951 | 1.00 | 3.83 PROT |
| ATOM | 1807 | CA | PRO | 453 | 43.710 | 11.766 | 1.960 | 1.00 | 14.00 PROT |
| ATOM | 1808 | CB | PRO | 453 | 42.502 | 11.649 | 1.032 | 1.00 | 20.04 PROT |
| ATOM | 1809 | CG | PRO | 453 | 42.316 | 10.163 | 0.807 | 1.00 | 19.43 PROT |
| ATOM | 1810 | C | PRO | 453 | 43.321 | 12.277 | 3.346 | 1.00 | 14.70 PROT |
| ATOM | 1811 | O | PRO | 453 | 43.609 | 13.422 | 3.682 | 1.00 | 9.70 PROT |
| ATOM | 1812 | N | LEU | 454 | 42.667 | 11.446 | 4.152 | 1.00 | 25.39 PROT |
| ATOM | 1813 | CA | LEU | 454 | 42.261 | 11.886 | 5.491 | 1.00 | 28.61 PROT |
| ATOM | 1814 | CB | LEU | 454 | 41.463 | 10.804 | 6.217 | 1.00 | 17.29 PROT |
| ATOM | 1815 | CG | LEU | 454 | 40.893 | 11.224 | 7.572 | 1.00 | 9.05 PROT |
| ATOM | 1816 | CD1 | LEU | 454 | 40.174 | 12.547 | 7.435 | 1.00 | 17.23 PROT |
| ATOM | 1817 | CD2 | LEU | 454 | 39.946 | 10.148 | 8.079 | 1.00 | 8.05 PROT |
| ATOM | 1818 | C | LEU | 454 | 43.479 | 12.234 | 6.316 | 1.00 | 23.36 PROT |
| ATOM | 1819 | O | LEU | 454 | 43.484 | 13.225 | 7.037 | 1.00 | 10.99 PROT |
| ATOM | 1820 | N | PHE | 455 | 44.503 | 11.394 | 6.205 | 1.00 | 14.26 PROT |
| ATOM | 1821 | CA | PHE | 455 | 45.769 | 11.595 | 6.902 | 1.00 | 15.33 PROT |
| ATOM | 1822 | CB | PHE | 455 | 46.761 | 10.496 | 6.501 | 1.00 | 26.32 PROT |
| ATOM | 1823 | CG | PHE | 455 | 48.138 | 10.644 | 7.108 | 1.00 | 43.03 PROT |
| ATOM | 1824 | CD1 | PHE | 455 | 48.305 | 11.094 | 8.414 | 1.00 | 43.52 PROT |
| ATOM | 1825 | CD2 | PHE | 455 | 49.270 | 10.282 | 6.380 | 1.00 | 41.44 PROT |
| ATOM | 1826 | CE1 | PHE | 455 | 49.576 | 11.176 | 8.987 | 1.00 | 37.77 PROT |
| ATOM | 1827 | CE2 | PHE | 455 | 50.536 | 10.363 | 6.947 | 1.00 | 49.43 PROT |
| ATOM | 1828 | CZ | PHE | 455 | 50.686 | 10.8U | 8.255 | 1.00 | 39.99 PROT |
| ATOM | 1829 | C | PHE | 455 | 46.313 | 12.956 | 6.500 | 1.00 | 19.37 PROT |
| ATOM | 1830 | O | PHE | 455 | 46.945 | 13.646 | 7.298 | 1.00 | 29.31 PROT |
| ATOM | 1831 | N | LEU | 456 | 46.048 | 13.345 | 5.257 | 1.00 | 17.16 PROT |
| ATOM | 1832 | CA | LEU | 456 | 46.527 | 14.625 | 4.750 | 1.00 | 20.15 PROT |
| ATOM | 1833 | CB | LEU | 456 | 46.572 | 14.603 | 3.218 | 1.00 | 35.14 PROT |
| ATOM | 1834 | CG | LEU | 456 | 47.593 | 13.660 | 2.568 | 1.00 | 40.45 PROT |
| ATOM | 1835 | CD1 | LEU | 456 | 47.233 | 13.456 | 1.116 | 1.00 | 44.38 PROT |
| ATOM | 1836 | CD2 | LEU | 456 | 48.990 | 14.234 | 2.680 | 1.00 | 34.88 PROT |
| ATOM | 1837 | C | LEU | 456 | 45.680 | 15.800 | 5.226 | 1.00 | 20.37 PROT |
| ATOM | 1838 | O | LEU | 456 | 46.207 | 16.866 | 5.548 | 1.00 | 29.61 PROT |
| ATOM | 1839 | N | GLU | 457 | 44.367 | 15.607 | 5.280 | 1.00 | 13.06 PROT |
| ATOM | 1840 | CA | GLU | 457 | 43.483 | 16.675 | 5.713 | 1.00 | 14.14 PROT |
| ATOM | 1841 | CB | GLU | 457 | 42.037 | 16.256 | 5.516 | 1.00 | 29.57 PROT |
| ATOM | 1842 | C | GLU | 457 | 43.731 | 17.058 | 7.173 | 1.00 | 14.95 PROT |
| ATOM | 1843 | O | GLU | 457 | 43.771 | 18.237 | 7.514 | 1.00 | 15.98 PROT |
| ATOM | 1844 | N | VAL | 458 | 43.901 | 16.051 | 8.026 | 1.00 | 26.34 PROT |

APPENDIX 7-continued

TRBTRIAC.PDB

| ATOM | 1845 | CA | VAL | 458 | 44.143 | 16.260 | 9.455 | 1.00 | 24.39 | PROT |
|---|---|---|---|---|---|---|---|---|---|---|
| ATOM | 1846 | CB | VAL | 458 | 44.219 | 14.910 | 10.208 | 1.00 | 20.14 | PROT |
| ATOM | 1847 | CG1 | VAL | 458 | 44.882 | 15.102 | 11.554 | 1.00 | 22.01 | PROT |
| ATOM | 1848 | CG2 | VAL | 458 | 42.831 | 14.341 | 10.400 | 1.00 | 28.11 | PROT |
| ATOM | 1849 | C | VAL | 458 | 45.417 | 17.039 | 9.778 | 1.00 | 21.50 | PROT |
| ATOM | 1850 | O | VAL | 458 | 45.364 | 18.062 | 10.439 | 1.00 | 18.85 | PROT |
| ATOM | 1851 | N | PHE | 459 | 46.557 | 16.546 | 9.308 | 1.00 | 16.05 | PROT |
| ATOM | 1852 | CA | PHE | 459 | 47.840 | 17.174 | 9.586 | 1.00 | 20.28 | PROT |
| ATOM | 1853 | CB | PHE | 459 | 48.862 | 16.072 | 9.846 | 1.00 | 20.26 | PROT |
| ATOM | 1854 | CG | PHE | 459 | 48.389 | 15.055 | 10.833 | 1.00 | 27.22 | PROT |
| ATOM | 1855 | CD1 | PHE | 459 | 47.917 | 13.822 | 10.408 | 1.00 | 28.01 | PROT |
| ATOM | 1856 | CD2 | PHE | 459 | 48.390 | 15.339 | 12.204 | 1.00 | 40.66 | PROT |
| ATOM | 1857 | CE1 | PHE | 459 | 47.447 | 12.876 | 11.334 | 1.00 | 21.78 | PROT |
| ATOM | 1858 | CE2 | PHE | 459 | 47.922 | 14.402 | 13.140 | 1.00 | 25.98 | PROT |
| ATOM | 1859 | CZ | PHE | 459 | 47.450 | 13.172 | 12.702 | 1.00 | 17.63 | PROT |
| ATOM | 1860 | C | PHE | 459 | 48.381 | 18.152 | 8.540 | 1.00 | 23.03 | PROT |
| ATOM | 1861 | O | PHE | 459 | 49.601 | 18.311 | 8.416 | 1.00 | 27.34 | PROT |
| ATOM | 1862 | N | GLU | 460 | 47.480 | 18.816 | 7.815 | 1.00 | 33.88 | PROT |
| ATOM | 1863 | CA | GLU | 460 | 47.846 | 19.774 | 6.767 | 1.00 | 36.60 | PROT |
| ATOM | 1864 | CB | GLU | 460 | 48.930 | 20.732 | 7.257 | 1.00 | 46.04 | PROT |
| ATOM | 1865 | CG | GLU | 460 | 48.406 | 21.899 | 8.054 | 1.00 | 67.27 | PROT |
| ATOM | 1866 | CD | GLU | 460 | 47.298 | 22.636 | 7.339 | 1.00 | 71.34 | PROT |
| ATOM | 1867 | OE1 | GLU | 460 | 47.448 | 23.859 | 7.121 | 1.00 | 71.99 | PROT |
| ATOM | 1868 | OE2 | GLU | 460 | 46.280 | 21.993 | 6.998 | 1.00 | 72.73 | PROT |
| ATOM | 1869 | C | GLU | 460 | 48.353 | 19.037 | 5.535 | 1.00 | 46.31 | PROT |
| ATOM | 1870 | O | GLU | 460 | 48.642 | 17.829 | 5.655 | 1.00 | 51.79 | PROT |
| ATOM | 1871 | OT | GLU | 460 | 48.461 | 19.669 | 4.462 | 1.00 | 60.92 | PROT |
| ATOM | 1872 | C1 | GC1 | 1 | 47.011 | 4.539 | 15.912 | 1.00 | 29.38 | LIGA |
| ATOM | 1873 | C2 | GC1 | 1 | 51.292 | 6.537 | 13.571 | 1.00 | 17.11 | LIGA |
| ATOM | 1874 | C3 | GC1 | 1 | 47.393 | 4.205 | 14.573 | 1.00 | 33.72 | LIGA |
| ATOM | 1875 | C4 | GC1 | 1 | 52.119 | 6.409 | 12.400 | 1.00 | 19.76 | LIGA |
| ATOM | 1876 | C5 | GC1 | 1 | 48.689 | 4.481 | 14.089 | 1.00 | 25.02 | LIGA |
| ATOM | 1877 | C6 | GC1 | 1 | 52.344 | 7.525 | 11.539 | 1.00 | 17.51 | LIGA |
| ATOM | 1878 | C7 | GC1 | 1 | 49.684 | 5.122 | 14.949 | 1.00 | 23.99 | LIGA |
| ATOM | 1879 | C8 | GC1 | 1 | 51.722 | 8.778 | 11.873 | 1.00 | 20.21 | LIGA |
| ATOM | 1880 | C9 | GC1 | 1 | 49.283 | 5.452 | 16.318 | 1.00 | 18.19 | LIGA |
| ATOM | 1881 | C10 | GC1 | 1 | 50.906 | 8.928 | 13.018 | 1.00 | 15.43 | LIGA |
| ATOM | 1882 | C11 | GC1 | 1 | 47.973 | 5.163 | 16.779 | 1.00 | 30.64 | UGA |
| ATOM | 1883 | C12 | GC1 | 1 | 50.696 | 7.827 | 13.850 | 1.00 | 25.06 | LIGA |
| ATOM | 1884 | O5 | GC1 | 1 | 45.700 | 4.254 | 16.325 | 1.00 | 28.60 | LIGA |
| ATOM | 1885 | C14 | GC1 | 1 | 53.198 | 7.459 | 10.291 | 1.00 | 20.30 | LIGA |
| ATOM | 1886 | C15 | GC1 | 1 | 45.305 | 3.866 | 17.666 | 1.00 | 18.51 | LIGA |
| ATOM | 1887 | C16 | GC1 | 1 | 52.423 | 6.824 | 9.131 | 1.00 | 17.21 | LIGA |
| ATOM | 1888 | C17 | GC1 | 1 | 43.816 | 4.078 | 17.872 | 1.00 | 21.43 | LIGA |
| ATOM | 1889 | C18 | GC1 | 1 | 54.514 | 6.689 | 10.543 | 1.00 | 24.97 | LIGA |
| ATOM | 1890 | C19 | GC1 | 1 | 48.994 | 4.093 | 12.664 | 1.00 | 33.46 | LIGA |
| ATOM | 1891 | C20 | GC1 | 1 | 50.243 | 6.110 | 17.278 | 1.00 | 27.69 | LIGA |
| ATOM | 1892 | O1 | GC1 | 1 | 51.902 | 9.861 | 11.086 | 1.00 | 23.34 | LIGA |
| ATOM | 1893 | C21 | GC1 | 1 | 51.026 | 5.430 | 14.458 | 1.00 | 22.49 | LIGA |
| ATOM | 1894 | O3 | GC1 | 1 | 43.147 | 3.117 | 18.247 | 1.00 | 18.06 | LIGA |
| ATOM | 1895 | O4 | GC1 | 1 | 43.331 | 5.204 | 17.665 | 1.00 | 28.27 | LIGA |
| END | | | | | | | | | | |

APPENDIX 8

TRBGC1.PDB

REMARK TR-beta GC-2 Full length numbering
REMARK refinement resolution:
100.00 - 2.40 A starting r = 0.2602 free_r = 0.2960
REMARK final r = 0.2532 free_r = 0.2894
REMARK sg = P3(1)21 a = 68.9 b = 68.9 c = 131.5 alpha = 90 beta = 90 gamma = 120
REMARK theoretical total number of refl. in resol. range: 14710 (100.0%)
REMARK number of unobserved reflections
(no entry or |F| =0): 336 (2.3%)
REMARK number of reflections rejected: 0 (0.0%)
REMARK total number of reflections used: 14374 (97.7%)
REMARK number of reflections in working set: 13656 (92.8%)
REMARK number of reflections in test set: 718 (4.9%)
REMARK
REMARK ALA 199 to ALA 201 from His-tag
REMARK

APPENDIX 8-continued

TRBGC1.PDB

REMARK Four cacodylate-modified cysteines (CYA)
REMARK Cys294, Cys298, Cys388, Cys434
REMARK cacodylate modeled as single arsenic atom
REMARK
REMARK side chain of certain residues modeled as
ALA due to poor density;
REMARK however; residue name reflects true residue for clarity
REMARK
REMARK amino acid sequence confirmed,
REMARK differing from that reported by Weinberger et. al.
REMARK in the following codons:
REMARK 243 Pro - Arg
REMARK 337 Ile - Thr
REMARK 451 Leu - Phe
REMARK as reported by Sakurai et. al;
REMARK note also correction of initiation codon,

APPENDIX 8-continued

TRBGC1.PDB

REMARK yielding a polypeptide of 461 amino acids
JRNL AUTH A. SAKURAI, A. NAKAI, L. J. DEGROOT
JRNL TITL STRUCTURAL ANALYSIS OF
HUMAN THYROID HORMONE RECEPTOR
JRNL TITL2 BETA GENE
JRNL REF MOL.CELL.ENDO. V.71 1990
JRNL AUTH C. WEINBERGER, C. C. THOMPSON,
R. LEBO, D. J. GRUOL, R. M. EVANS
JRNL TITL THE C-ERB-A GENE ENCODES A
THYROID HORMONE RECEPTOR
JRNL REF NATURE V.324 6098 1986

```
ATOM    1 CB  ALA    199 36.564 26.104 43.169 1.00 73.87
ATOM    2 C   ALA    199 34.723 26.996 44.613 1.00 78.22
ATOM    3 O   ALA    199 34.741 28.230 44.568 1.00 81.84
ATOM    4 N   ALA    199 34.389 26.744 42.166 1.00 77.76
ATOM    5 CA  ALA    199 35.048 26.165 43.375 1.00 77.98
ATOM    6 N   ALA    200 34.428 26.309 45.713 1.00 77.78
ATOM    7 CA  ALA    200 34.098 26.961 46.984 1.00 77.03
ATOM    8 CB  ALA    200 32.761 27.693 46.865 1.00 79.04
ATOM    9 C   ALA    200 34.028 25.897 48.084 1.00 75.79
ATOM   10 O   ALA    200 34.877 25.857 48.978 1.00 71.58
ATOM   11 N   ALA    201 33.005 25.050 48.010 1.00 73.70
ATOM   12 CA  ALA    201 32.838 23.968 48.972 1.00 70.15
ATOM   13 CB  ALA    201 31.468 23.328 48.809 1.00 71.16
ATOM   14 C   ALA    201 33.934 22.963 48.642 1.00 67.54
ATOM   15 O   ALA    201 34.218 22.044 49.413 1.00 67.14
ATOM   16 N   GLU    202 34.540 23.164 47.476 1.00 62.05
ATOM   17 CA  GLU    202 35.624 22.325 46.975 1.00 59.45
ATOM   18 CB  GLU    202 35.835 22.621 45.482 1.00 55.12
ATOM   19 CG  GLU    202 36.820 21.716 44.749 1.00 56.25
ATOM   20 CD  GLU    202 36.382 20.260 44.723 1.00 54.99
ATOM   21 OE1 GLU    202 35.216 19.990 44.361 1.00 53.83
ATOM   22 OE2 GLU    202 37.210 19.385 45.050 1.00 59.90
ATOM   23 C   GLU    202 36.885 22.674 47.770 1.00 55.96
ATOM   24 O   GLU    202 37.472 21.823 48.435 1.00 52.90
ATOM   25 N   GLU    203 37.282 23.943 47.698 1.00 54.95
ATOM   26 CA  GLU    203 38.464 24.434 48.390 1.00 55.59
ATOM   27 CB  GLU    203 38.632 25.924 48.126 1.00 53.21
ATOM   28 C   GLU    203 38.415 24.171 49.894 1.00 56.30
ATOM   29 O   GLU    203 39.445 23.948 50.526 1.00 58.70
ATOM   30 N   LEU    204 37.213 24.193 50.462 1.00 57.14
ATOM   31 CA  LEU    204 37.038 23.966 51.893 1.00 56.93
ATOM   32 CB  LEU    204 35.658 24.465 52.338 1.00 58.31
ATOM   33 CG  LEU    204 35.348 24.508 53.839 1.00 51.69
ATOM   34 CD1 LEU    204 36.314 25.446 54.549 1.00 44.38
ATOM   35 CD2 LEU    204 33.920 24.986 54.039 1.00 52.44
ATOM   36 C   LEU    204 37.198 22.489 52.246 1.00 58.20
ATOM   37 O   LEU    204 37.831 22.155 53.252 1.00 58.99
ATOM   38 N   GLN    205 36.620 21.607 51.431 1.00 58.26
ATOM   39 CA  GLN    205 36.736 20.167 51.657 1.00 55.38
ATOM   40 CB  GLN    205 35.993 19.377 50.584 1.00 54.52
ATOM   41 CG  GLN    205 34.498 19.324 50.741 1.00 53.33
ATOM   42 CD  GLN    205 33.854 18.520 49.629 1.00 53.40
ATOM   43 OE1 GLN    205 33.850 18.939 48.473 1.00 51.68
ATOM   44 NE2 GLN    205 33.325 17.352 49.968 1.00 51.34
ATOM   45 C   GLN    205 38.200 19.775 51.608 1.00 55.05
ATOM   46 O   GLN    205 38.665 18.964 52.407 1.00 53.63
ATOM   47 N   LYS    206 38.918 20.348 50.648 1.00 53.55
ATOM   48 CA  LYS    206 40.337 20.078 50.493 1.00 57.40
ATOM   49 CB  LYS    206 40.896 20.814 49.269 1.00 58.94
ATOM   50 CG  LYS    206 40.300 20.375 47.941 1.00 67.73
ATOM   51 CD  LYS    206 40.921 21.141 46.781 1.00 72.50
ATOM   52 CE  LYS    206 40.346 20.695 45.445 1.00 75.60
ATOM   53 NZ  LYS    206 40.945 21.445 44.304 1.00 77.08
ATOM   54 C   LYS    206 41.053 20.559 51.747 1.00 53.98
ATOM   55 O   LYS    206 41.905 19.866 52.300 1.00 53.49
ATOM   56 N   SER    207 40.680 21.757 52.184 1.00 53.61
ATOM   57 CA  SER    207 41.254 22.386 53.364 1.00 51.49
ATOM   58 CB  SER    207 40.546 23.715 53.619 1.00 51.01
ATOM   59 OG  SER    207 41.108 24.383 54.731 1.00 63.00
ATOM   60 C   SER    207 41.178 21.502 54.616 1.00 49.49
ATOM   61 O   SER    207 42.073 21.538 55.465 1.00 47.44
ATOM   62 N   ILE    208 40.117 20.707 54.725 1.00 44.39
ATOM   63 CA  ILE    208 39.938 19.829 55.874 1.00 45.99
ATOM   64 CB  ILE    208 38.421 19.627 56.174 1.00 44.50
ATOM   65 CG2 ILE    208 38.226 18.801 57.445 1.00 49.37
ATOM   66 CG1 ILE    208 37.766 20.993 56.385 1.00 42.73
ATOM   67 CD1 ILE    208 36.266 20.941 56.567 1.00 44.13
ATOM   68 C   ILE    208 40.614 18.477 55.643 1.00 47.80
ATOM   69 O   ILE    208 40.735 17.666 56.562 1.00 49.81
ATOM   70 N   GLY    209 41.059 18.238 54.412 1.00 51.31
ATOM   71 CA  GLY    209 41.728 16.983 54.107 1.00 46.85
ATOM   72 C   GLY    209 40.813 15.896 53.573 1.00 48.31
ATOM   73 O   GLY    209 41.203 14.730 53.485 1.00 47.75
ATOM   74 N   HIS    210 39.582 16.274 53.237 1.00 46.79
ATOM   75 CA  HIS    210 38.622 15.326 52.686 1.00 47.34
ATOM   76 CB  HIS    210 37.200 15.739 53.068 1.00 49.39
ATOM   77 C   HIS    210 38.796 15.350 51.162 1.00 45.47
ATOM   78 O   HIS    210 38.924 16.420 50.566 1.00 41.32
ATOM   79 N   LYS    211 38.829 14.176 50.545 1.00 45.76
ATOM   80 CA  LYS    211 38.991 14.095 49.090 1.00 43.42
ATOM   81 CB  LYS    211 39.892 12.910 48.715 1.00 46.72
ATOM   82 CG  LYS    211 41.210 12.815 49.497 1.00 56.48
ATOM   83 CD  LYS    211 42.068 14.089 49.486 1.00 60.93
ATOM   84 CE  LYS    211 42.562 14.496 48.103 1.00 61.95
ATOM   85 NZ  LYS    211 41.485 15.024 47.218 1.00 69.93
ATOM   86 C   LYS    211 37.609 13.917 48.473 1.00 35.68
ATOM   87 O   LYS    211 37.019 12.847 48.557 1.00 33.58
ATOM   88 N   PRO    212 37.077 14.972 47.828 1.00 35.64
ATOM   89 CD  PRO    212 37.654 16.304 47.584 1.00 38.60
ATOM   90 CA  PRO    212 35.748 14.896 47.211 1.00 38.35
ATOM   91 CB  PRO    212 35.537 16.318 46.682 1.00 38.95
ATOM   92 CG  PRO    212 36.409 17.156 47.604 1.00 42.00
ATOM   93 C   PRO    212 35.635 13.865 46.096 1.00 38.78
ATOM   94 O   PRO    212 36.546 13.714 45.280 1.00 34.64
ATOM   95 N   GLU    213 34.517 13.153 46.077 1.00 40.31
ATOM   96 CA  GLU    213 34.256 12.160 45.049 1.00 43.87
ATOM   97 CB  GLU    213 33.722 10.873 45.684 1.00 45.16
ATOM   98 CG  GLU    213 34.616 10.344 46.800 1.00 47.60
ATOM   99 CD  GLU    213 34.404  8.870 47.088 1.00 50.68
ATOM  100 OE1 GLU    213 33.240  8.416 47.072 1.00 59.18
ATOM  101 OE2 GLU    213 35.402  8.167 47.353 1.00 49.06
ATOM  102 C   GLU    213 33.234 12.796 44.083 1.00 45.96
ATOM  103 O   GLU    213 32.703 13.876 44.368 1.00 43.13
ATOM  104 N   PRO    214 32.953 12.154 42.933 1.00 46.52
ATOM  105 CD  PRO    214 33.459 10.884 42.391 1.00 46.44
ATOM  106 CA  PRO    214 31.995 12.737 41.982 1.00 47.52
ATOM  107 CB  PRO    214 32.040 11.750 40.813 1.00 45.40
ATOM  108 CG  PRO    214 33.445 11.181 40.913 1.00 49.89
ATOM  109 C   PRO    214 30.564 12.969 42.465 1.00 45.70
ATOM  110 O   PRO    214 29.972 12.112 43.121 1.00 44.49
ATOM  111 N   THR    215 30.013 14.136 42.129 1.00 45.24
ATOM  112 CA  THR    215 28.629 14.447 42.483 1.00 49.36
ATOM  113 CB  THR    215 28.312 15.949 42.330 1.00 44.86
ATOM  114 OG1 THR    215 28.253 16.285 40.942 1.00 52.26
ATOM  115 CG2 THR    215 29.387 16.793 42.992 1.00 39.43
ATOM  116 C   THR    215 27.791 13.673 41.464 1.00 52.51
ATOM  117 O   THR    215 28.326 13.192 40.465 1.00 53.48
ATOM  118 N   ASP    216 26.491 13.543 41.712 1.00 58.81
ATOM  119 CA  ASP    216 25.603 12.810 40.805 1.00 61.51
ATOM  120 CB  ASP    216 24.150 12.941 41.270 1.00 70.57
ATOM  121 CG  ASP    216 23.902 12.257 42.595 1.00 78.07
ATOM  122 OD1 ASP    216 24.042 11.018 42.660 1.00 82.31
ATOM  123 OD2 ASP    216 23.572 12.962 43.571 1.00 86.55
ATOM  124 C   ASP    216 25.706 13.277 39.356 1.00 58.42
ATOM  125 O   ASP    216 25.695 12.464 38.429 1.00 56.85
ATOM  126 N   GLU    217 25.798 14.587 39.167 1.00 54.92
ATOM  127 CA  GLU    217 25.905 15.156 37.833 1.00 53.37
ATOM  128 CB  GLU    217 25.861 16.682 37.906 1.00 51.02
ATOM  129 C   GLU    217 27.211 14.692 37.195 1.00 53.55
ATOM  130 O   GLU    217 27.239 14.301 36.027 1.00 54.33
ATOM  131 N   GLU    218 28.290 14.726 37.975 1.00 49.20
ATOM  132 CA  GLU    218 29.593 14.310 37.486 1.00 45.94
ATOM  133 CB  GLU    218 30.674 14.601 38.530 1.00 43.43
ATOM  134 CG  GLU    218 30.787 16.069 38.878 1.00 40.86
ATOM  135 CD  GLU    218 31.930 16.347 39.826 1.00 39.88
ATOM  136 OE1 GLU    218 32.000 15.667 40.875 1.00 37.61
ATOM  137 OE2 GLU    218 32.748 17.250 39.529 1.00 34.01
ATOM  138 C   GLU    218 29.624 12.838 37.101 1.00 44.71
ATOM  139 O   GLU    218 30.275 12.471 36.130 1.00 45.31
ATOM  140 N   TRP    219 28.935 11.991 37.863 1.00 44.02
ATOM  141 CA  TRP    219 28.892 10.572 37.539 1.00 46.97
ATOM  142 CB  TRP    219 28.183  9.762 38.630 1.00 48.42
ATOM  143 CG  TRP    219 29.034  9.473 39.823 1.00 54.61
```

APPENDIX 8-continued

TRBGC1.PDB

| ATOM | 144 CD2 TRP | 219 30.167 8.572 39.879 1.00 55.24 |
|---|---|---|
| ATOM | 145 CE2 TRP | 219 30.659 8.610 41.201 1.00 53.67 |
| ATOM | 146 CE3 TRP | 219 30.795 7.745 38.938 1.00 54.55 |
| ATOM | 147 CD1 TRP | 219 28.902 10.000 41.074 1.00 55.75 |
| ATOM | 148 NE1 TRP | 219 29.868 9.491 41.912 1.00 54.43 |
| ATOM | 149 CZ2 TRP | 219 31.771 7.846 41.622 1.00 52.54 |
| ATOM | 150 CZ3 TRP | 219 31.912 6.975 39.353 1.00 55.17 |
| ATOM | 151 CH2 TRP | 219 32.380 7.038 40.690 1.00 55.59 |
| ATOM | 152 C TRP | 219 28.167 10.356 36.216 1.00 47.32 |
| ATOM | 153 O TRP | 219 28.433 9.384 35.503 1.00 43.56 |
| ATOM | 154 N GLU | 220 27.247 11.259 35.898 1.00 49.91 |
| ATOM | 155 CA GLU | 220 26.497 11.155 34.655 1.00 53.57 |
| ATOM | 156 CB GLU | 220 25.274 12.075 34.694 1.00 58.18 |
| ATOM | 157 CG GLU | 220 24.323 11.876 33.526 1.00 73.13 |
| ATOM | 158 CD GLU | 220 23.082 12.742 33.630 1.00 80.06 |
| ATOM | 159 OE1 GLU | 220 22.348 12.619 34.636 1.00 82.12 |
| ATOM | 160 OE2 GLU | 220 22.839 13.545 32.701 1.00 82.78 |
| ATOM | 161 C GLU | 220 27.419 11.534 33.497 1.00 50.51 |
| ATOM | 162 O GLU | 220 27.399 10.899 32.443 1.00 49.94 |
| ATOM | 163 N LEU | 221 28.232 12.567 33.711 1.00 43.71 |
| ATOM | 164 CA LEU | 221 29.187 13.019 32.702 1.00 42.81 |
| ATOM | 165 CB LEU | 221 29.868 14.317 33.155 1.00 39.21 |
| ATOM | 166 CG LEU | 221 30.945 14.949 32.261 1.00 36.34 |
| ATOM | 167 CD1 LEU | 221 30.339 15.351 30.922 1.00 36.93 |
| ATOM | 168 CD2 LEU | 221 31.535 16.164 32.949 1.00 24.18 |
| ATOM | 169 C LEU | 221 30.234 11.928 32.505 1.00 43.46 |
| ATOM | 170 O LEU | 221 30.618 11.621 31.375 1.00 45.25 |
| ATOM | 171 N ILE | 222 30.683 11.342 33.614 1.00 39.09 |
| ATOM | 172 CA ILE | 222 31.677 10.273 33.586 1.00 35.47 |
| ATOM | 173 CB ILE | 222 32.031 9.811 35.037 1.00 33.74 |
| ATOM | 174 CG2 ILE | 222 32.822 8.505 35.018 1.00 28.86 |
| ATOM | 175 CG1 ILE | 222 32.813 10.918 35.745 1.00 33.33 |
| ATOM | 176 CD1 ILE | 222 33.111 10.646 37.199 1.00 34.85 |
| ATOM | 177 C ILE | 222 31.139 9.098 32.781 1.00 34.26 |
| ATOM | 178 O ILE | 222 31.877 8.427 32.070 1.00 31.90 |
| ATOM | 179 N LYS | 223 29.840 8.860 32.908 1.00 39.49 |
| ATOM | 180 CA LYS | 223 29.168 7.775 32.210 1.00 44.43 |
| ATOM | 181 CB LYS | 223 27.696 7.733 32.655 1.00 50.81 |
| ATOM | 182 CG LYS | 223 26.845 6.693 31.929 1.00 62.51 |
| ATOM | 183 CD LYS | 223 25.379 6.856 32.313 1.00 72.22 |
| ATOM | 184 CE LYS | 223 24.487 5.855 31.591 1.00 74.55 |
| ATOM | 185 NZ LYS | 223 23.045 6.057 31.925 1.00 75.78 |
| ATOM | 186 C LYS | 223 29.266 7.983 30.691 1.00 42.81 |
| ATOM | 187 O LYS | 223 29.640 7.078 29.946 1.00 40.36 |
| ATOM | 188 N THR | 224 28.924 9.194 30.257 1.00 39.89 |
| ATOM | 189 CA THR | 224 28.948 9.566 28.850 1.00 39.93 |
| ATOM | 190 CB THR | 224 28.466 11.021 28.680 1.00 40.57 |
| ATOM | 191 OG1 THR | 224 27.135 11.134 29.197 1.00 39.27 |
| ATOM | 192 CG2 THR | 224 28.480 11.437 27.214 1.00 38.11 |
| ATOM | 193 C THR | 224 30.333 9.433 28.234 1.00 39.96 |
| ATOM | 194 O THR | 224 30.515 8.714 27.248 1.00 36.23 |
| ATOM | 195 N VAL | 225 31.303 10.123 28.833 1.00 38.02 |
| ATOM | 196 CA VAL | 225 32.680 10.117 28.355 1.00 38.12 |
| ATOM | 197 CB VAL | 225 33.565 11.014 29.243 1.00 38.19 |
| ATOM | 198 CG1 VAL | 225 34.960 11.162 28.632 1.00 36.77 |
| ATOM | 199 CG2 VAL | 225 32.910 12.361 29.406 1.00 41.76 |
| ATOM | 200 C VAL | 225 33.291 8.724 28.302 1.00 37.52 |
| ATOM | 201 O VAL | 225 34.022 8.395 27.364 1.00 36.77 |
| ATOM | 202 N THR | 226 33.002 7.904 29.310 1.00 34.02 |
| ATOM | 203 CA THR | 226 33.542 6.552 29.350 1.00 34.61 |
| ATOM | 204 CB THR | 226 33.237 5.857 30.707 1.00 30.56 |
| ATOM | 205 OG1 THR | 226 33.858 6.598 31.768 1.00 32.20 |
| ATOM | 206 CG2 THR | 226 33.775 4.437 30.722 1.00 20.99 |
| ATOM | 207 C THR | 226 32.960 5.722 28.211 1.00 36.41 |
| ATOM | 208 O THR | 226 33.698 5.075 27.472 1.00 39.64 |
| ATOM | 209 N GLU | 227 31.636 5.758 28.073 1.00 39.20 |
| ATOM | 210 CA GLU | 227 30.935 5.020 27.027 1.00 36.93 |
| ATOM | 211 CB GLU | 227 29.434 5.296 27.111 1.00 38.06 |
| ATOM | 212 C GLU | 227 31.466 5.409 25.651 1.00 37.69 |
| ATOM | 213 O GLU | 227 31.713 4.544 24.805 1.00 40.94 |
| ATOM | 214 N ALA | 228 31.641 6.709 25.439 1.00 32.86 |
| ATOM | 215 CA ALA | 228 32.156 7.236 24.177 1.00 32.48 |
| ATOM | 216 CB ALA | 228 32.285 8.746 24.256 1.00 28.25 |
| ATOM | 217 C ALA | 228 33.508 6.612 23.861 1.00 36.12 |
| ATOM | 218 O ALA | 228 33.736 6.135 22.747 1.00 37.86 |
| ATOM | 219 N HIS | 229 34.404 6.611 24.843 1.00 33.58 |
| ATOM | 220 CA HIS | 229 35.724 6.029 24.669 1.00 32.97 |
| ATOM | 221 CB HIS | 229 36.579 6.263 25.921 1.00 33.69 |
| ATOM | 222 CG HIS | 229 37.857 5.489 25.934 1.00 28.39 |
| ATOM | 223 CD2 HIS | 229 38.338 4.576 26.811 1.00 28.83 |
| ATOM | 224 ND1 HIS | 229 38.804 5.593 24.937 1.00 30.47 |
| ATOM | 225 CE1 HIS | 229 39.812 4.779 25.193 1.00 26.95 |
| ATOM | 226 NE2 HIS | 229 39.556 4.147 26.332 1.00 31.27 |
| ATOM | 227 C HIS | 229 35.653 4.536 24.371 1.00 38.40 |
| ATOM | 228 O HIS | 229 36.227 4.071 23.383 1.00 41.49 |
| ATOM | 229 N VAL | 230 34.951 3.786 25.216 1.00 38.55 |
| ATOM | 230 CA VAL | 230 34.823 2.339 25.049 1.00 40.40 |
| ATOM | 231 CB VAL | 230 33.964 1.726 26.196 1.00 44.68 |
| ATOM | 232 CG1 VAL | 230 33.865 0.208 26.041 1.00 39.39 |
| ATOM | 233 CG2 VAL | 230 34.576 2.075 27.540 1.00 42.18 |
| ATOM | 234 C VAL | 230 34.219 1.934 23.700 1.00 44.28 |
| ATOM | 235 O VAL | 230 34.640 0.948 23.092 1.00 45.94 |
| ATOM | 236 N ALA | 231 33.236 2.698 23.230 1.00 45.59 |
| ATOM | 237 CA ALA | 231 32.580 2.403 21.961 1.00 47.84 |
| ATOM | 238 CB ALA | 231 31.297 3.227 21.832 1.00 45.08 |
| ATOM | 239 C ALA | 231 33.487 2.666 20.761 1.00 48.04 |
| ATOM | 240 O ALA | 231 33.364 2.012 19.727 1.00 49.95 |
| ATOM | 241 N THR | 232 34.403 3.619 20.907 1.00 47.26 |
| ATOM | 242 CA THR | 232 35.312 3.973 19.824 1.00 43.64 |
| ATOM | 243 CB THR | 232 35.379 5.502 19.629 1.00 41.93 |
| ATOM | 244 CG1 THR | 232 35.945 6.117 20.797 1.00 39.10 |
| ATOM | 245 CG2 THR | 232 33.985 6.065 19.382 1.00 29.80 |
| ATOM | 246 C THR | 232 36.720 3.458 20.046 1.00 43.97 |
| ATOM | 247 O THR | 232 37.629 3.791 19.292 1.00 40.55 |
| ATOM | 248 N ASN | 233 36.905 2.648 21.081 1.00 48.62 |
| ATOM | 249 CA ASN | 233 38.218 2.101 21.368 1.00 58.62 |
| ATOM | 250 CB ASN | 233 38.473 2.092 22.876 1.00 62.44 |
| ATOM | 251 CG ASN | 233 39.909 1.765 23.223 1.00 68.35 |
| ATOM | 252 OD1 ASN | 233 40.843 2.401 22.724 1.00 65.50 |
| ATOM | 253 ND2 ASN | 233 40.098 0.776 24.090 1.00 74.29 |
| ATOM | 254 C ASN | 233 38.282 0.690 20.802 1.00 65.06 |
| ATOM | 255 O ASN | 233 37.748 −0.257 21.382 1.00 69.47 |
| ATOM | 256 N ALA | 234 38.934 0.577 19.645 1.00 68.80 |
| ATOM | 257 CA ALA | 234 39.098 −0.672 18.909 1.00 70.98 |
| ATOM | 258 CB ALA | 234 40.215 −0.508 17.886 1.00 71.43 |
| ATOM | 259 C ALA | 234 39.353 −1.919 19.753 1.00 73.83 |
| ATOM | 260 O ALA | 234 40.193 −1.911 20.652 1.00 74.33 |
| ATOM | 261 N GLN | 235 38.615 −2.983 19.434 1.00 75.07 |
| ATOM | 262 CA GLN | 235 38.720 4.281 20.103 1.00 76.32 |
| ATOM | 263 CB GLN | 235 40.130 −4.856 19.912 1.00 76.98 |
| ATOM | 264 CG GLN | 235 40.429 −5.417 18.516 1.00 77.07 |
| ATOM | 265 CD GLN | 235 40.142 4.444 17.377 1.00 80.85 |
| ATOM | 266 OE1 GLN | 235 38.985 −4.144 17.072 1.00 82.01 |
| ATOM | 267 NE2 GLN | 235 41.201 −3.949 16.742 1.00 78.80 |
| ATOM | 268 C GLN | 235 38.351 −4.293 21.586 1.00 77.15 |
| ATOM | 269 O GLN | 235 38.217 −5.361 22.190 1.00 76.06 |
| ATOM | 270 N GLY | 236 38.188 −3.103 22.161 1.00 77.46 |
| ATOM | 271 CA GLY | 236 37.818 −2.974 23.562 1.00 78.37 |
| ATOM | 272 C GLY | 236 38.620 −3.783 24.566 1.00 79.43 |
| ATOM | 273 O GLY | 236 39.826 −3.575 24.736 1.00 79.47 |
| ATOM | 274 N SER | 237 37.937 −4.711 25.234 1.00 77.98 |
| ATOM | 275 CA SER | 237 38.544 −5.561 26.253 1.00 76.49 |
| ATOM | 276 CB SER | 237 37.475 −6.462 26.874 1.00 76.46 |
| ATOM | 277 C SER | 237 39.712 −6.412 25.765 1.00 75.35 |
| ATOM | 278 O SER | 237 40.858 −6.181 26.152 1.00 75.47 |
| ATOM | 279 N HIS | 238 39.421 −7.397 24.922 1.00 75.56 |
| ATOM | 280 CA HIS | 238 40.451 −8.294 24.409 1.00 75.46 |
| ATOM | 281 CB HIS | 238 39.837 −9.654 24.076 1.00 75.85 |
| ATOM | 282 C HIS | 238 41.185 −7.751 23.191 1.00 74.10 |
| ATOM | 283 O HIS | 238 40.610 −7.638 22.109 1.00 75.34 |
| ATOM | 284 N TRP | 239 42.459 −7.417 23.381 1.00 73.39 |
| ATOM | 285 CA TRP | 239 43.300 −6.907 22.302 1.00 74.02 |
| ATOM | 286 CB TRP | 239 43.556 −5.402 22.460 1.00 81.77 |
| ATOM | 287 CG TRP | 239 44.190 −5.023 23.761 1.00 89.67 |
| ATOM | 288 CD2 TRP | 239 45.597 −4.797 24.008 1.00 93.19 |
| ATOM | 289 CE2 TRP | 239 45.744 −4.527 25.384 1.00 95.46 |
| ATOM | 290 CE3 TRP | 239 46.732 −4.793 23.186 1.00 95.35 |
| ATOM | 291 CD1 TRP | 239 43.566 −4.888 24.972 1.00 94.16 |
| ATOM | 292 NE1 TRP | 239 44.483 −4.591 25.954 1.00 97.48 |
| ATOM | 293 CZ2 TRP | 239 46.993 −4.262 25.981 1.00 96.23 |
| ATOM | 294 CZ3 TRP | 239 47.992 −4.528 23.778 1.00 96.75 |
| ATOM | 295 CH2 TRP | 239 48.101 4.262 25.164 1.00 97.32 |
| ATOM | 296 C TRP | 239 44.633 −7.649 22.283 1.00 70.77 |
| ATOM | 297 O TRP | 239 45.339 −7.644 21.274 1.00 71.70 |

APPENDIX 8-continued

TRBGC1.PDB

| ATOM | 298 | N LYS | 240 | 44.978 | -8.276 | 23.405 | 1.00 | 67.10 |
|------|-----|-------|-----|--------|--------|--------|------|-------|
| ATOM | 299 | CA LYS | 240 | 46.219 | -9.040 | 23.519 | 1.00 | 65.63 |
| ATOM | 300 | CB LYS | 240 | 46.387 | -9.569 | 24.946 | 1.00 | 66.65 |
| ATOM | 301 | CG LYS | 240 | 46.379 | -8.504 | 26.030 | 1.00 | 69.83 |
| ATOM | 302 | CD LYS | 240 | 47.664 | -7.691 | 26.069 | 1.00 | 71.49 |
| ATOM | 303 | CE LYS | 240 | 48.839 | -8.515 | 26.573 | 1.00 | 71.31 |
| ATOM | 304 | NZ LYS | 240 | 50.071 | -7.684 | 26.691 | 1.00 | 72.23 |
| ATOM | 305 | C LYS | 240 | 46.143 | -10.222 | 22.555 | 1.00 | 66.19 |
| ATOM | 306 | O LYS | 240 | 47.075 | -10.493 | 21.797 | 1.00 | 65.20 |
| ATOM | 307 | N ASN | 241 | 45.010 | -10.923 | 22.598 | 1.00 | 66.69 |
| ATOM | 308 | CA ASN | 241 | 44.773 | -12.089 | 21.750 | 1.00 | 67.53 |
| ATOM | 309 | CB ASN | 241 | 43.503 | -12.813 | 22.213 | 1.00 | 67.98 |
| ATOM | 310 | CG ASN | 241 | 43.504 | -13.096 | 23.704 | 1.00 | 70.19 |
| ATOM | 311 | OD1 ASN | 241 | 44.410 | -13.744 | 24.227 | 1.00 | 71.37 |
| ATOM | 312 | ND2 ASN | 241 | 42.483 | -12.605 | 24.400 | 1.00 | 71.48 |
| ATOM | 313 | C ASN | 241 | 44.621 | -11.681 | 20.286 | 1.00 | 66.62 |
| ATOM | 314 | O ASN | 241 | 44.882 | -12.475 | 19.382 | 1.00 | 64.76 |
| ATOM | 315 | N LYS | 242 | 44.196 | -10.436 | 20.070 | 1.00 | 66.86 |
| ATOM | 316 | CA LYS | 242 | 43.989 | -9.882 | 18.732 | 1.00 | 67.46 |
| ATOM | 317 | CB LYS | 242 | 42.982 | -8.731 | 18.799 | 1.00 | 67.93 |
| ATOM | 318 | CG LYS | 242 | 41.601 | -9.138 | 19.279 | 1.00 | 71.52 |
| ATOM | 319 | CD LYS | 242 | 40.876 | -9.986 | 18.246 | 1.00 | 74.32 |
| ATOM | 320 | CE LYS | 242 | 40.449 | -9.160 | 17.043 | 1.00 | 74.41 |
| ATOM | 321 | NZ LYS | 242 | 39.455 | -8.120 | 17.436 | 1.00 | 74.44 |
| ATOM | 322 | C LYS | 242 | 45.281 | -9.367 | 18.097 | 1.00 | 66.28 |
| ATOM | 323 | O LYS | 242 | 45.414 | -9.334 | 16.874 | 1.00 | 67.61 |
| ATOM | 324 | N ARG | 243 | 46.225 | -8.961 | 18.938 | 1.00 | 64.19 |
| ATOM | 325 | CA ARG | 243 | 47.497 | -8.422 | 18.478 | 1.00 | 62.43 |
| ATOM | 326 | CB ARG | 243 | 48.376 | -8.070 | 19.685 | 1.00 | 60.12 |
| ATOM | 327 | C ARG | 243 | 48.261 | -9.348 | 17.538 | 1.00 | 62.97 |
| ATOM | 328 | O ARG | 243 | 48.585 | -10.484 | 17.891 | 1.00 | 63.96 |
| ATOM | 329 | N LYS | 244 | 48.531 | -8.853 | 16.334 | 1.00 | 62.41 |
| ATOM | 330 | CA LYS | 244 | 49.303 | -9.593 | 15.339 | 1.00 | 61.57 |
| ATOM | 331 | CB LYS | 244 | 48.601 | -9.607 | 13.972 | 1.00 | 63.68 |
| ATOM | 332 | CG LYS | 244 | 47.210 | -10.231 | 13.970 | 1.00 | 71.29 |
| ATOM | 333 | CD LYS | 244 | 46.666 | -10.441 | 12.549 | 1.00 | 73.83 |
| ATOM | 334 | CE LYS | 244 | 46.505 | -9.139 | 11.767 | 1.00 | 74.71 |
| ATOM | 335 | NZ LYS | 244 | 45.542 | -8.199 | 12.407 | 1.00 | 73.32 |
| ATOM | 336 | C LYS | 244 | 50.613 | -8.824 | 15.223 | 1.00 | 59.30 |
| ATOM | 337 | O LYS | 244 | 50.637 | -7.716 | 14.686 | 1.00 | 56.34 |
| ATOM | 338 | N PHE | 245 | 51.690 | -9.405 | 15.744 | 1.00 | 57.06 |
| ATOM | 339 | CA PHE | 245 | 52.996 | -8.757 | 15.704 | 1.00 | 59.01 |
| ATOM | 340 | CB PHE | 245 | 54.034 | -9.588 | 16.467 | 1.00 | 59.62 |
| ATOM | 341 | CG PHE | 245 | 53.704 | -9.783 | 17.934 | 1.00 | 66.60 |
| ATOM | 342 | CD1 PHE | 245 | 52.656 | -10.626 | 18.329 | 1.00 | 67.17 |
| ATOM | 343 | CD2 PHE | 245 | 54.427 | -9.096 | 18.918 | 1.00 | 69.25 |
| ATOM | 344 | CE1 PHE | 245 | 52.320 | -10.789 | 19.699 | 1.00 | 69.92 |
| ATOM | 345 | CE2 PHE | 245 | 54.111 | -9.240 | 20.294 | 1.00 | 70.50 |
| ATOM | 346 | CZ PHE | 245 | 53.051 | -10.091 | 20.686 | 1.00 | 70.89 |
| ATOM | 347 | C PHE | 245 | 53.463 | -8.537 | 14.272 | 1.00 | 60.68 |
| ATOM | 348 | O PHE | 245 | 53.433 | -9.455 | 13.447 | 1.00 | 62.37 |
| ATOM | 349 | N LEU | 246 | 53.880 | -7.311 | 13.976 | 1.00 | 60.10 |
| ATOM | 350 | CA LEU | 246 | 54.359 | -6.968 | 12.642 | 1.00 | 59.44 |
| ATOM | 351 | CB LEU | 246 | 54.654 | -5.464 | 12.560 | 1.00 | 57.43 |
| ATOM | 352 | CG LEU | 246 | 54.937 | -4.851 | 11.183 | 1.00 | 54.41 |
| ATOM | 353 | CD1 LEU | 246 | 53.681 | -4.931 | 10.320 | 1.00 | 52.43 |
| ATOM | 354 | CD2 LEU | 246 | 55.358 | -3.398 | 11.343 | 1.00 | 51.69 |
| ATOM | 355 | C LEU | 246 | 55.638 | -7.772 | 12.425 | 1.00 | 62.05 |
| ATOM | 356 | O LEU | 246 | 56.447 | -7.923 | 13.346 | 1.00 | 59.85 |
| ATOM | 357 | N PRO | 247 | 55.836 | -8.312 | 11.203 | 1.00 | 63.33 |
| ATOM | 358 | CD PRO | 247 | 54.990 | -8.230 | 10.001 | 1.00 | 64.44 |
| ATOM | 359 | CA PRO | 247 | 57.036 | -9.102 | 10.910 | 1.00 | 63.56 |
| ATOM | 360 | CB PRO | 247 | 56.917 | -9.327 | 9.404 | 1.00 | 64.42 |
| ATOM | 361 | CG PRO | 247 | 55.413 | -9.481 | 9.251 | 1.00 | 64.90 |
| ATOM | 362 | C PRO | 247 | 58.342 | -8.431 | 11.325 | 1.00 | 61.94 |
| ATOM | 363 | O PRO | 247 | 58.581 | -7.256 | 11.053 | 1.00 | 61.60 |
| ATOM | 364 | N ALA | 248 | 59.180 | -9.219 | 11.990 | 1.00 | 61.33 |
| ATOM | 365 | CA ALA | 248 | 60.468 | -8.785 | 12.511 | 1.00 | 63.50 |
| ATOM | 366 | CB ALA | 248 | 61.151 | -9.991 | 13.174 | 1.00 | 66.94 |
| ATOM | 370 | C ALA | 248 | 61.412 | -8.140 | 11.489 | 1.00 | 64.19 |
| ATOM | 371 | O ALA | 248 | 62.449 | -7.593 | 11.867 | 1.00 | 65.56 |
| ATOM | 372 | N ASP | 249 | 61.055 | -8.188 | 10.207 | 1.00 | 64.36 |
| ATOM | 373 | CA ASP | 249 | 61.900 | -7.610 | 9.163 | 1.00 | 63.33 |
| ATOM | 374 | CB ASP | 249 | 62.104 | -8.618 | 8.026 | 1.00 | 62.97 |
| ATOM | 375 | CG ASP | 249 | 60.798 | -9.051 | 7.395 | 1.00 | 64.63 |
| ATOM | 376 | OD1 ASP | 249 | 60.037 | -9.803 | 8.043 | 1.00 | 64.84 |
| ATOM | 377 | OD2 ASP | 249 | 60.526 | -8.626 | 6.253 | 1.00 | 66.52 |
| ATOM | 378 | C ASP | 249 | 61.388 | -6.293 | 8.572 | 1.00 | 64.31 |
| ATOM | 379 | O ASP | 249 | 62.112 | -5.624 | 7.830 | 1.00 | 64.73 |
| ATOM | 380 | N ILE | 250 | 60.148 | -5.927 | 8.885 | 1.00 | 63.09 |
| ATOM | 381 | CA ILE | 250 | 59.577 | -4.676 | 8.385 | 1.00 | 64.39 |
| ATOM | 382 | CB ILE | 250 | 58.035 | -4.741 | 8.349 | 1.00 | 65.79 |
| ATOM | 383 | CG2 ILE | 250 | 57.463 | -3.408 | 7.861 | 1.00 | 64.78 |
| ATOM | 384 | CG1 ILE | 250 | 57.594 | -5.893 | 7.439 | 1.00 | 65.28 |
| ATOM | 385 | CD1 ILE | 250 | 56.094 | -6.103 | 7.362 | 1.00 | 65.08 |
| ATOM | 386 | C ILE | 250 | 60.015 | -3.534 | 9.299 | 1.00 | 65.21 |
| ATOM | 387 | O ILE | 250 | 66.002 | -3.676 | 10.524 | 1.00 | 64.05 |
| ATOM | 388 | N GLY | 251 | 60.401 | -2.405 | 8.700 | 1.00 | 65.48 |
| ATOM | 389 | CA GLY | 251 | 60.864 | -1.263 | 9.472 | 1.00 | 67.32 |
| ATOM | 390 | C GLY | 251 | 62.069 | -1.711 | 10.271 | 1.00 | 68.52 |
| ATOM | 391 | O GLY | 251 | 62.099 | -1.610 | 11.497 | 1.00 | 65.49 |
| ATOM | 392 | N GLN | 252 | 63.080 | -2.194 | 9.555 | 1.00 | 72.26 |
| ATOM | 393 | CA GLN | 252 | 64.277 | -2.726 | 10.176 | 1.00 | 74.10 |
| ATOM | 394 | CB GLN | 252 | 64.598 | -4.068 | 9.515 | 1.00 | 75.82 |
| ATOM | 395 | CG GLN | 252 | 65.518 | -4.974 | 10.302 | 1.00 | 77.81 |
| ATOM | 396 | CD GLN | 252 | 65.686 | -6.319 | 9.630 | 1.00 | 79.38 |
| ATOM | 397 | OE1 GLN | 252 | 66.087 | -6.397 | 8.468 | 1.00 | 80.55 |
| ATOM | 398 | NE2 GLN | 252 | 65.384 | -7.391 | 10.357 | 1.00 | 78.12 |
| ATOM | 399 | C GLN | 252 | 65.496 | -1.817 | 10.138 | 1.00 | 77.17 |
| ATOM | 400 | O GLN | 252 | 65.553 | -0.826 | 9.399 | 1.00 | 76.50 |
| ATOM | 401 | N ALA | 253 | 66.470 | -2.187 | 10.966 | 1.00 | 80.78 |
| ATOM | 402 | CA ALA | 253 | 67.729 | -1.475 | 11.104 | 1.00 | 83.70 |
| ATOM | 403 | CB ALA | 253 | 68.402 | -1.903 | 12.401 | 1.00 | 83.23 |
| ATOM | 404 | C ALA | 253 | 68.639 | -1.774 | 9.913 | 1.00 | 85.59 |
| ATOM | 405 | O ALA | 253 | 68.294 | -2.673 | 9.117 | 1.00 | 85.69 |
| ATOM | 406 | OXT ALA | 253 | 69.694 | -1.115 | 9.802 | 1.00 | 88.37 |
| ATOM | 429 | CB LYS | 263 | 65.708 | 7.766 | 4.514 | 1.00 | 63.50 |
| ATOM | 430 | C LYS | 263 | 64.141 | 6.903 | 6.272 | 1.00 | 63.41 |
| ATOM | 431 | O LYS | 263 | 64.442 | 5.776 | 6.673 | 1.00 | 61.93 |
| ATOM | 432 | N LYS | 263 | 66.368 | 7.841 | 6.894 | 1.00 | 61.71 |
| ATOM | 433 | CA LYS | 263 | 65.218 | 7.942 | 5.950 | 1.00 | 64.36 |
| ATOM | 434 | N VAL | 264 | 62.886 | 7.305 | 6.090 | 1.00 | 61.15 |
| ATOM | 435 | CA VAL | 264 | 61.724 | 6.462 | 6.351 | 1.00 | 59.46 |
| ATOM | 436 | CB VAL | 264 | 60.429 | 7.221 | 5.962 | 1.00 | 59.03 |
| ATOM | 437 | CG1 VAL | 264 | 59.200 | 6.421 | 6.363 | 1.00 | 53.79 |
| ATOM | 438 | CG2 VAL | 264 | 60.422 | 8.593 | 6.623 | 1.00 | 55.32 |
| ATOM | 439 | C VAL | 264 | 61.790 | 5.129 | 5.595 | 1.00 | 60.96 |
| ATOM | 440 | O VAL | 264 | 62.071 | 5.098 | 4.395 | 1.00 | 62.13 |
| ATOM | 441 | N ASP | 265 | 61.522 | 4.034 | 6.304 | 1.00 | 62.59 |
| ATOM | 442 | CA ASP | 265 | 61.562 | 2.693 | 5.727 | 1.00 | 64.95 |
| ATOM | 443 | CB ASP | 265 | 61.322 | 1.644 | 6.810 | 1.00 | 64.32 |
| ATOM | 444 | CG ASP | 265 | 61.415 | 0.232 | 6.277 | 1.00 | 67.70 |
| ATOM | 445 | OD1 ASP | 265 | 62.514 | -0.158 | 5.831 | 1.00 | 72.59 |
| ATOM | 446 | OD2 ASP | 265 | 60.393 | -0.486 | 6.289 | 1.00 | 68.84 |
| ATOM | 447 | C ASP | 265 | 60.560 | 2.470 | 4.591 | 1.00 | 65.64 |
| ATOM | 448 | O ASP | 265 | 60.789 | 1.637 | 3.717 | 1.00 | 68.81 |
| ATOM | 449 | N LEU | 266 | 59.456 | 3.211 | 4.624 | 1.00 | 65.12 |
| ATOM | 450 | CA LEU | 266 | 58.394 | 3.138 | 3.615 | 1.00 | 63.40 |
| ATOM | 451 | CB LEU | 266 | 58.963 | 3.333 | 2.202 | 1.00 | 67.34 |
| ATOM | 452 | CG LEU | 266 | 59.665 | 4.662 | 1.894 | 1.00 | 69.35 |
| ATOM | 453 | CD1 LEU | 266 | 60.193 | 4.627 | 0.469 | 1.00 | 68.24 |
| ATOM | 454 | CD2 LEU | 266 | 58.705 | 5.831 | 2.075 | 1.00 | 70.47 |
| ATOM | 455 | C LEU | 266 | 57.562 | 1.854 | 3.658 | 1.00 | 59.67 |
| ATOM | 456 | O LEU | 266 | 56.342 | 1.903 | 3.486 | 1.00 | 53.35 |
| ATOM | 457 | N GLU | 267 | 58.205 | 0.713 | 3.872 | 1.00 | 58.01 |
| ATOM | 458 | CA GLU | 267 | 57.454 | -0.535 | 3.945 | 1.00 | 58.34 |
| ATOM | 459 | CB GLU | 267 | 58.387 | -1.750 | 3.921 | 1.00 | 59.21 |
| ATOM | 460 | CG GLU | 267 | 57.640 | -3.072 | 4.053 | 1.00 | 62.89 |
| ATOM | 461 | CD GLU | 267 | 58.548 | -4.285 | 3.979 | 1.00 | 67.66 |
| ATOM | 462 | OE1 GLU | 267 | 59.513 | -4.371 | 4.771 | 1.00 | 69.95 |
| ATOM | 463 | OE2 GLU | 267 | 58.285 | -5.162 | 3.129 | 1.00 | 69.40 |
| ATOM | 464 | C GLU | 267 | 56.666 | -0.515 | 5.243 | 1.00 | 57.67 |
| ATOM | 465 | O GLU | 267 | 55.488 | -0.877 | 5.276 | 1.00 | 58.34 |
| ATOM | 466 | N ALA | 268 | 57.327 | -0.077 | 6.317 | 1.00 | 53.43 |
| ATOM | 467 | CA ALA | 268 | 56.701 | 0.013 | 7.629 | 1.00 | 49.00 |
| ATOM | 468 | CB ALA | 268 | 57.766 | 0.244 | 8.695 | 1.00 | 45.72 |
| ATOM | 469 | C ALA | 268 | 55.701 | 1.166 | 7.611 | 1.00 | 45.76 |
| ATOM | 470 | O ALA | 268 | 54.598 | 1.057 | 8.144 | 1.00 | 41.50 |
| ATOM | 471 | N PHE | 269 | 56.106 | 2.267 | 6.983 | 1.00 | 41.43 |
| ATOM | 472 | CA PHE | 269 | 55.277 | 3.457 | 6.855 | 1.00 | 43.96 |
| ATOM | 473 | CB PHE | 269 | 56.016 | 4.511 | 6.022 | 1.00 | 40.10 |
| ATOM | 474 | CG PHE | 269 | 55.264 | 5.818 | 5.859 | 1.00 | 40.44 |
| ATOM | 475 | CD1 PHE | 269 | 55.102 | 6.690 | 6.949 | 1.00 | 38.98 |
| ATOM | 476 | CD2 PHE | 269 | 54.706 | 6.170 | 4.626 | 1.00 | 37.15 |

APPENDIX 8-continued

TRBGC1.PDB

| ATOM | 477 CE1 PHE | 269 54.401 7.920 6.807 1.00 32.12 |
|---|---|---|
| ATOM | 478 CE2 PHE | 269 53.999 7.389 4.457 1.00 38.41 |
| ATOM | 479 CZ PHE | 269 53.843 8.269 5.554 1.00 40.55 |
| ATOM | 480 C PHE | 269 53.976 3.081 6.151 1.00 49.76 |
| ATOM | 481 O PHE | 269 52.903 3.622 6.443 1.00 52.15 |
| ATOM | 482 N SER | 270 54.089 2.140 5.217 1.00 53.15 |
| ATOM | 483 CA SER | 270 52.957 1.669 4.432 1.00 52.29 |
| ATOM | 484 CB SER | 270 53.456 0.703 3.349 1.00 51.85 |
| ATOM | 485 OG SER | 270 52.400 0.297 2.499 1.00 53.42 |
| ATOM | 486 C SER | 270 51.901 0.992 5.303 1.00 49.38 |
| ATOM | 487 O SER | 270 50.713 1.284 5.185 1.00 48.74 |
| ATOM | 488 N HIS | 271 52.335 0.085 6.173 1.00 50.15 |
| ATOM | 489 CA HIS | 271 51.410 −0.614 7.061 1.00 51.67 |
| ATOM | 490 CB HIS | 271 52.150 −1.682 7.878 1.00 58.52 |
| ATOM | 491 CG HIS | 271 52.697 −2.808 7.059 1.00 68.97 |
| ATOM | 492 CD2 HIS | 271 52.425 −4.131 7.063 1.00 70.88 |
| ATOM | 493 ND1 HIS | 271 53.660 −2.621 6.080 1.00 71.98 |
| ATOM | 494 CE1 HIS | 271 53.951 −3.782 5.528 1.00 73.91 |
| ATOM | 495 NE2 HIS | 271 53.214 4.720 6.104 1.00 73.59 |
| ATOM | 496 C HIS | 271 50.711 0.365 8.008 1.00 48.33 |
| ATOM | 497 O HIS | 271 49.507 0.260 8.240 1.00 48.39 |
| ATOM | 498 N PHE | 272 51.472 1.321 8.537 1.00 41.34 |
| ATOM | 499 CA PHE | 272 50.946 2.316 9.462 1.00 39.44 |
| ATOM | 500 CB PHE | 272 52.076 3.215 9.976 1.00 36.67 |
| ATOM | 501 CG PHE | 272 53.167 2.475 10.749 1.00 33.39 |
| ATOM | 502 CD1 PHE | 272 54.421 3.065 10.915 1.00 33.14 |
| ATOM | 503 CD2 PHE | 272 52.934 1.216 11.311 1.00 38.28 |
| ATOM | 504 CE1 PHE | 272 55.454 2.418 11.633 1.00 38.26 |
| ATOM | 505 CE2 PHE | 272 53.961 0.538 12.047 1.00 43.28 |
| ATOM | 506 CZ PHE | 272 55.225 1.146 12.207 1.00 39.74 |
| ATOM | 507 C PHE | 272 49.857 3.183 8.822 1.00 40.75 |
| ATOM | 508 O PHE | 272 48.784 3.361 9.394 1.00 35.51 |
| ATOM | 509 N THR | 273 50.136 3.714 7.635 1.00 41.64 |
| ATOM | 510 CA THR | 273 49.170 4.561 6.938 1.00 45.97 |
| ATOM | 511 CB THR | 273 49.813 5.249 5.711 1.00 51.52 |
| ATOM | 512 OG1 THR | 273 50.339 4.257 4.815 1.00 45.74 |
| ATOM | 513 CG2 THR | 273 50.936 6.179 6.158 1.00 49.73 |
| ATOM | 514 C THR | 273 47.941 3.772 6.481 1.00 46.23 |
| ATOM | 515 O THR | 273 46.879 4.344 6.233 1.00 41.21 |
| ATOM | 516 N LYS | 274 48.096 2.455 6.380 1.00 46.21 |
| ATOM | 517 CA LYS | 274 46.984 1.608 5.955 1.00 54.53 |
| ATOM | 518 CB LYS | 274 47.482 0.180 5.708 1.00 54.36 |
| ATOM | 519 C LYS | 274 45.878 1.595 7.006 1.00 56.88 |
| ATOM | 520 O LYS | 274 44.695 1.486 6.675 1.00 57.98 |
| ATOM | 521 N ILE | 275 46.267 1.718 8.268 1.00 56.48 |
| ATOM | 522 CA ILE | 275 45.312 1.695 9.368 1.00 52.64 |
| ATOM | 523 CB ILE | 275 45.710 0.611 10.391 1.00 49.15 |
| ATOM | 524 CG2 ILE | 275 45.719 −0.758 9.701 1.00 47.42 |
| ATOM | 525 CG1 ILE | 275 47.101 0.921 10.971 1.00 45.31 |
| ATOM | 526 CD1 ILE | 275 47.565 −0.050 12.053 1.00 37.22 |
| ATOM | 527 C ILE | 275 45.175 3.032 10.086 1.00 51.78 |
| ATOM | 528 O ILE | 275 44.578 3.108 11.159 1.00 49.80 |
| ATOM | 529 N ILE | 276 45.710 4.088 9.481 1.00 51.76 |
| ATOM | 530 CA ILE | 276 45.657 5.416 10.084 1.00 52.58 |
| ATOM | 531 CB ILE | 276 46.733 6.364 9.464 1.00 55.04 |
| ATOM | 532 CG2 ILE | 276 46.395 6.696 8.020 1.00 53.28 |
| ATOM | 533 CG1 ILE | 276 46.823 7.663 10.270 1.00 57.31 |
| ATOM | 534 CD1 ILE | 276 47.364 7.485 11.664 1.00 60.32 |
| ATOM | 535 C ILE | 276 44.279 6.073 9.774 1.00 50.70 |
| ATOM | 536 O ILE | 276 43.858 6.775 10.895 1.00 55.55 |
| ATOM | 537 N THR | 277 43.576 5.849 8.866 1.00 47.33 |
| ATOM | 538 CA THR | 277 42.255 6.450 8.681 1.00 42.59 |
| ATOM | 539 CB THR | 277 41.695 6.190 7.254 1.00 44.97 |
| ATOM | 540 OG1 THR | 277 42.611 6.702 6.280 1.00 46.38 |
| ATOM | 541 CG2 THR | 277 40.349 6.892 7.065 1.00 37.17 |
| ATOM | 542 C THR | 277 41.252 5.954 9.718 1.00 39.84 |
| ATOM | 543 O THR | 277 40.570 6.759 10.351 1.00 40.55 |
| ATOM | 544 N PRO | 278 41.126 4.620 9.899 1.00 38.20 |
| ATOM | 545 CD PRO | 278 41.746 3.457 9.242 1.00 36.34 |
| ATOM | 546 CA PRO | 278 40.165 4.167 10.907 1.00 36.63 |
| ATOM | 547 CB PRO | 278 40.242 2.639 10.783 1.00 32.95 |
| ATOM | 548 CG PRO | 278 41.668 2.419 10.343 1.00 35.75 |
| ATOM | 549 C PRO | 278 40.532 4.681 12.306 1.00 38.60 |
| ATOM | 550 O PRO | 278 39.653 5.017 13.104 1.00 37.67 |
| ATOM | 551 N ALA | 279 41.831 4.758 12.586 1.00 37.05 |
| ATOM | 552 CA ALA | 279 42.315 5.248 13.877 1.00 33.18 |
| ATOM | 553 CB ALA | 279 43.836 5.135 13.949 1.00 30.56 |
| ATOM | 554 C ALA | 279 41.890 6.692 14.077 1.00 33.47 |
| ATOM | 555 O ALA | 279 41.403 7.060 15.151 1.00 33.74 |
| ATOM | 556 N ILE | 280 42.067 7.517 13.041 1.00 29.96 |
| ATOM | 557 CA ILE | 280 41.687 8.921 13.121 1.00 25.94 |
| ATOM | 558 CB ILE | 280 42.155 9.716 11.871 1.00 26.95 |
| ATOM | 559 CG2 ILE | 280 41.643 11.168 11.923 1.00 15.40 |
| ATOM | 560 CG1 ILE | 280 43.686 9.702 11.798 1.00 26.73 |
| ATOM | 561 CD1 ILE | 280 44.255 10.378 10.550 1.00 34.31 |
| ATOM | 562 C ILE | 280 40.181 9.074 13.251 1.00 31.39 |
| ATOM | 563 O ILE | 280 39.696 9.943 13.973 1.00 35.69 |
| ATOM | 564 N THR | 281 39.428 8.226 12.552 1.00 30.90 |
| ATOM | 565 CA THR | 281 37.982 8.318 12.592 1.00 33.49 |
| ATOM | 566 CB THR | 281 37.321 7.451 11.478 1.00 37.18 |
| ATOM | 567 OG1 THR | 281 37.760 6.091 11.592 1.00 46.48 |
| ATOM | 568 CG2 THR | 281 37.703 7.972 10.114 1.00 32.85 |
| ATOM | 569 C THR | 281 37.435 7.926 13.968 1.00 29.94 |
| ATOM | 570 O THR | 281 36.428 8.473 14.408 1.00 25.55 |
| ATOM | 571 N ARG | 282 38.103 6.997 14.641 1.00 32.70 |
| ATOM | 572 CA ARG | 282 37.676 6.585 15.975 1.00 34.27 |
| ATOM | 573 CB ARG | 282 38.511 5.411 16.479 1.00 33.78 |
| ATOM | 574 CG ARG | 282 38.259 4.111 15.743 1.00 45.15 |
| ATOM | 575 CD ARG | 282 39.017 2.976 16.404 1.00 58.24 |
| ATOM | 576 NE ARG | 282 38.763 1.679 15.776 1.00 68.41 |
| ATOM | 577 CZ ARG | 282 39.141 1.344 14.546 1.00 72.31 |
| ATOM | 578 NH1 ARG | 282 39.802 2.213 13.791 1.00 77.89 |
| ATOM | 579 NH2 ARG | 282 38.864 0.139 14.066 1.00 69.25 |
| ATOM | 580 C ARG | 282 37.789 7.764 16.942 1.00 34.81 |
| ATOM | 581 O ARG | 282 37.006 7.886 17.884 1.00 36.03 |
| ATOM | 582 N VAL | 283 38.761 8.640 16.696 1.00 31.71 |
| ATOM | 583 CA VAL | 283 38.952 9.815 17.532 1.00 30.16 |
| ATOM | 584 CB VAL | 283 40.298 10.524 17.224 1.00 29.00 |
| ATOM | 585 CG1 VAL | 283 40.448 11.777 18.076 1.00 28.64 |
| ATOM | 586 CG2 VAL | 283 41.448 9.577 17.487 1.00 28.28 |
| ATOM | 587 C VAL | 283 37.801 10.787 17.292 1.00 32.50 |
| ATOM | 588 O VAL | 283 37.284 11.388 18.236 1.00 33.48 |
| ATOM | 589 N VAL | 284 37.403 10.945 16.028 1.00 30.96 |
| ATOM | 590 CA VAL | 284 36.293 11.838 15.694 1.00 29.14 |
| ATOM | 591 CB VAL | 284 36.138 12.023 14.158 1.00 31.27 |
| ATOM | 592 CG1 VAL | 284 34.990 12.985 13.868 1.00 24.21 |
| ATOM | 593 CG2 VAL | 284 37.450 12.565 13.554 1.00 30.51 |
| ATOM | 594 C VAL | 284 34.995 11.260 16.258 1.00 28.89 |
| ATOM | 595 O VAL | 284 34.146 12.005 16.743 1.00 27.29 |
| ATOM | 596 N ASP | 285 34.845 9.937 16.208 1.00 28.76 |
| ATOM | 597 CA ASP | 285 33.639 9.307 16.738 1.00 35.32 |
| ATOM | 598 CB ASP | 285 33.627 7.792 16.459 1.00 33.29 |
| ATOM | 599 CG ASP | 285 33.523 7.471 14.971 1.00 38.15 |
| ATOM | 600 OD1 ASP | 285 32.729 8.139 14.276 1.00 34.70 |
| ATOM | 601 OD2 ASP | 285 34.209 6.532 14.504 1.00 34.43 |
| ATOM | 602 C ASP | 285 33.531 9.553 18.248 1.00 36.70 |
| ATOM | 603 O ASP | 285 32.431 9.685 18.786 1.00 37.96 |
| ATOM | 604 N PHE | 286 34.679 9.624 18.916 1.00 35.96 |
| ATOM | 605 CA PHE | 286 34.736 9.869 20.349 1.00 37.10 |
| ATOM | 606 CB PHE | 286 36.187 9.777 20.845 1.00 37.97 |
| ATOM | 607 CG PHE | 286 36.377 10.219 22.283 1.00 36.50 |
| ATOM | 608 CD1 PHE | 286 35.815 9.490 23.340 1.00 36.75 |
| ATOM | 609 CD2 PHE | 286 37.100 11.381 22.575 1.00 33.83 |
| ATOM | 610 CE1 PHE | 286 35.966 9.917 24.685 1.00 39.55 |
| ATOM | 611 CE2 PHE | 286 37.265 11.831 23.911 1.00 38.08 |
| ATOM | 612 CZ PHE | 286 36.696 11.092 24.972 1.00 34.44 |
| ATOM | 613 C PHE | 286 34.179 11.249 20.665 1.00 36.83 |
| ATOM | 614 O PHE | 286 33.292 11.401 21.518 1.00 35.61 |
| ATOM | 615 N ALA | 287 34.696 12.255 19.968 1.00 37.33 |
| ATOM | 616 CA ALA | 287 34.266 13.631 20.171 1.00 36.34 |
| ATOM | 617 CB ALA | 287 35.118 14.565 19.325 1.00 36.40 |
| ATOM | 618 C ALA | 287 32.785 13.840 19.861 1.00 38.76 |
| ATOM | 619 O ALA | 287 32.121 14.641 20.525 1.00 41.98 |
| ATOM | 620 N LYS | 288 32.267 13.130 18.862 1.00 38.28 |
| ATOM | 621 CA LYS | 288 30.856 13.268 18.499 1.00 45.26 |
| ATOM | 622 CB LYS | 288 30.541 12.534 17.188 1.00 48.35 |
| ATOM | 623 CG LYS | 288 31.159 13.158 15.951 1.00 51.43 |
| ATOM | 624 CD LYS | 288 30.556 12.589 14.665 1.00 60.23 |
| ATOM | 625 CE LYS | 288 30.848 11.107 14.479 1.00 62.81 |
| ATOM | 626 NZ LYS | 288 32.312 10.852 14.392 1.00 64.69 |
| ATOM | 627 C LYS | 288 29.913 12.763 19.586 1.00 43.31 |
| ATOM | 628 O LYS | 288 28.791 13.253 19.707 1.00 45.66 |
| ATOM | 629 N LYS | 289 30.367 11.789 20.371 1.00 41.70 |
| ATOM | 630 CA LYS | 289 29.548 11.235 21.443 1.00 40.67 |

APPENDIX 8-continued

TRBGC1.PDB

| ATOM | 631 | CB | LYS | 289 | 29.984 | 9.806 | 21.767 | 1.00 | 42.25 |
|---|---|---|---|---|---|---|---|---|---|
| ATOM | 632 | CG | LYS | 289 | 29.912 | 8.853 | 20.591 | 1.00 | 39.53 |
| ATOM | 633 | CD | LYS | 289 | 30.341 | 7.456 | 21.003 | 1.00 | 43.19 |
| ATOM | 634 | CE | LYS | 289 | 30.454 | 6.539 | 19.807 | 1.00 | 45.74 |
| ATOM | 635 | NZ | LYS | 289 | 29.175 | 6.457 | 19.049 | 1.00 | 52.49 |
| ATOM | 636 | C | LYS | 289 | 29.585 | 12.076 | 22.721 | 1.00 | 41.50 |
| ATOM | 637 | O | LYS | 289 | 29.030 | 11.676 | 23.742 | 1.00 | 39.77 |
| ATOM | 638 | N | LEU | 290 | 30.242 | 13.235 | 22.661 | 1.00 | 40.68 |
| ATOM | 639 | CA | LEU | 290 | 30.307 | 14.143 | 23.811 | 1.00 | 39.33 |
| ATOM | 640 | CB | LEU | 290 | 31.757 | 14.590 | 24.075 | 1.00 | 36.14 |
| ATOM | 641 | CG | LEU | 290 | 32.815 | 13.526 | 24.401 | 1.00 | 34.81 |
| ATOM | 642 | CD1 | LEU | 290 | 34.155 | 14.200 | 24.558 | 1.00 | 29.07 |
| ATOM | 643 | CD2 | LEU | 290 | 32.445 | 12.764 | 25.667 | 1.00 | 33.45 |
| ATOM | 644 | C | LEU | 290 | 29.448 | 15.368 | 23.481 | 1.00 | 40.08 |
| ATOM | 645 | O | LEU | 290 | 29.828 | 16.196 | 22.655 | 1.00 | 42.00 |
| ATOM | 646 | N | PRO | 291 | 28.279 | 15.500 | 24.137 | 1.00 | 40.27 |
| ATOM | 647 | CD | PRO | 291 | 27.716 | 14.625 | 25.185 | 1.00 | 39.65 |
| ATOM | 648 | CA | PRO | 291 | 27.372 | 16.628 | 23.899 | 1.00 | 38.28 |
| ATOM | 649 | CB | PRO | 291 | 26.327 | 16.447 | 24.997 | 1.00 | 35.88 |
| ATOM | 650 | CG | PRO | 291 | 26.230 | 14.932 | 25.071 | 1.00 | 34.19 |
| ATOM | 651 | C | PRO | 291 | 28.010 | 18.006 | 23.910 | 1.00 | 40.05 |
| ATOM | 652 | O | PRO | 291 | 27.663 | 18.857 | 23.089 | 1.00 | 41.33 |
| ATOM | 653 | N | MET | 292 | 28.933 | 18.235 | 24.837 | 1.00 | 40.59 |
| ATOM | 654 | CA | MET | 292 | 29.607 | 19.529 | 24.932 | 1.00 | 42.86 |
| ATOM | 655 | CB | MET | 292 | 30.635 | 19.521 | 26.059 | 1.00 | 43.28 |
| ATOM | 656 | CG | MET | 292 | 30.050 | 19.286 | 27.428 | 1.00 | 50.35 |
| ATOM | 657 | SD | MET | 292 | 31.329 | 19.157 | 28.679 | 1.00 | 51.17 |
| ATOM | 658 | CE | MET | 292 | 30.331 | 18.787 | 30.111 | 1.00 | 54.63 |
| ATOM | 659 | C | MET | 292 | 30.311 | 19.869 | 23.629 | 1.00 | 41.05 |
| ATOM | 660 | O | MET | 292 | 30.341 | 21.024 | 23.210 | 1.00 | 39;66 |
| ATOM | 661 | N | PHE | 293 | 30.882 | 18.854 | 22.992 | 1.00 | 39.30 |
| ATOM | 662 | CA | PHE | 293 | 31.594 | 19.057 | 21.747 | 1.00 | 40.92 |
| ATOM | 663 | CB | PHE | 293 | 32.300 | 17.772 | 21.335 | 1.00 | 40.98 |
| ATOM | 664 | CG | PHE | 293 | 33.117 | 17.902 | 20.070 | 1.00 | 42.78 |
| ATOM | 665 | CD1 | PHE | 293 | 34.272 | 18.692 | 20.046 | 1.00 | 44.40 |
| ATOM | 666 | CD2 | PHE | 293 | 32.727 | 17.235 | 18.902 | 1.00 | 43.66 |
| ATOM | 667 | CE1 | PHE | 293 | 35.051 | 18.823 | 18.865 | 1.00 | 39.83 |
| ATOM | 668 | CE2 | PHE | 293 | 33.483 | 17.348 | 17.710 | 1.00 | 46.21 |
| ATOM | 669 | CZ | PHE | 293 | 34.654 | 18.147 | 17.693 | 1.00 | 45.18 |
| ATOM | 670 | C | PHE | 293 | 30.653 | 19.492 | 20.624 | 1.00 | 45.54 |
| ATOM | 671 | O | PHE | 293 | 30.985 | 20.377 | 19.829 | 1.00 | 42.01 |
| ATOM | 672 | N | CYS | 294 | 29.468 | 18.895 | 20.579 | 1.00 | 47.05 |
| ATOM | 673 | CA | CYS | 294 | 28.545 | 19.200 | 19.512 | 1.00 | 50.15 |
| ATOM | 674 | CB | CYS | 294 | 27.320 | 18.329 | 19.584 | 1.00 | 45.90 |
| ATOM | 675 | SG | CYS | 294 | 27.680 | 16.529 | 19.352 | 1.00 | 51.50 |
| ATOM | 676 | C | CYS | 294 | 28.062 | 20.636 | 19.220 | 1.00 | 51.38 |
| ATOM | 677 | O | CYS | 294 | 27.682 | 21.199 | 18.543 | 1.00 | 53.83 |
| ATOM | 678 | N | GLU | 295 | 27.996 | 21.170 | 20.802 | 1.00 | 49.72 |
| ATOM | 679 | CA | GLU | 295 | 27.541 | 22.535 | 21.067 | 1.00 | 52.53 |
| ATOM | 680 | CB | GLU | 295 | 27.384 | 22.762 | 22.575 | 1.00 | 57.40 |
| ATOM | 681 | CG | GLU | 295 | 26.179 | 22.090 | 23.208 | 1.00 | 69.63 |
| ATOM | 682 | CD | GLU | 295 | 24.871 | 22.731 | 22.785 | 1.00 | 78.49 |
| ATOM | 683 | OE1 | GLU | 295 | 24.698 | 23.942 | 23.041 | 1.00 | 82.82 |
| ATOM | 684 | OE2 | GLU | 295 | 24.017 | 22.029 | 22.199 | 1.00 | 85.30 |
| ATOM | 685 | C | GLU | 295 | 28.484 | 23.589 | 20.515 | 1.00 | 48.54 |
| ATOM | 686 | O | GLU | 295 | 28.170 | 24.777 | 20.537 | 1.00 | 49.82 |
| ATOM | 687 | N | LEU | 296 | 29.637 | 23.149 | 20.030 | 1.00 | 43.79 |
| ATOM | 688 | CA | LEU | 296 | 30.629 | 24.066 | 19.476 | 1.00 | 45.42 |
| ATOM | 689 | CB | LEU | 296 | 32.040 | 23.541 | 19.771 | 1.00 | 41.04 |
| ATOM | 690 | CG | LEU | 296 | 32.416 | 23.394 | 21.252 | 1.00 | 42.74 |
| ATOM | 691 | CD1 | LEU | 296 | 33.789 | 22.753 | 21.352 | 1.00 | 40.99 |
| ATOM | 692 | CD2 | LEU | 296 | 32.406 | 24.755 | 21.945 | 1.00 | 39.44 |
| ATOM | 693 | C | LEU | 296 | 30.448 | 24.239 | 17.968 | 1.00 | 45.56 |
| ATOM | 694 | O | LEU | 296 | 29.966 | 23.333 | 17.278 | 1.00 | 43.07 |
| ATOM | 695 | N | PRO | 297 | 30.823 | 25.414 | 17.436 | 1.00 | 46.99 |
| ATOM | 696 | CD | PRO | 297 | 31.372 | 26.613 | 18.083 | 1.00 | 47.12 |
| ATOM | 697 | CA | PRO | 297 | 30.689 | 25.650 | 15.998 | 1.00 | 49.61 |
| ATOM | 698 | CB | PRO | 297 | 31.106 | 27.118 | 15.861 | 1.00 | 49.91 |
| ATOM | 699 | CG | PRO | 297 | 30.757 | 27.693 | 17.230 | 1.00 | 51.28 |
| ATOM | 700 | C | PRO | 297 | 31.600 | 24.717 | 15.202 | 1.00 | 49.59 |
| ATOM | 701 | O | PRO | 297 | 32.727 | 24.446 | 15.615 | 1.00 | 51.66 |
| ATOM | 702 | N | CYS | 298 | 31.093 | 24.227 | 14.075 | 1.00 | 51.02 |
| ATOM | 703 | CA | CYS | 298 | 31.817 | 23.322 | 13.158 | 1.00 | 52.86 |
| ATOM | 704 | CB | CYS | 298 | 31.100 | 23.260 | 11.804 | 1.00 | 54.57 |
| ATOM | 705 | SG | CYS | 298 | 31.935 | 24.249 | 10.470 | 1.00 | 67.87 |
| ATOM | 706 | C | CYS | 298 | 33.269 | 23.797 | 12.974 | 1.00 | 48.51 |
| ATOM | 707 | O | CYS | 298 | 34.197 | 22.991 | 12.819 | 1.00 | 49.58 |
| ATOM | 708 | N | GLU | 299 | 33.464 | 25.113 | 13.019 | 1.00 | 44.17 |
| ATOM | 709 | CA | GLU | 299 | 34.797 | 25.692 | 12.890 | 1.00 | 47.57 |
| ATOM | 710 | CB | GLU | 299 | 34.741 | 27.227 | 12.912 | 1.00 | 49.92 |
| ATOM | 711 | CG | GLU | 299 | 34.001 | 27.871 | 11.747 | 1.00 | 59.30 |
| ATOM | 712 | CD | GLU | 299 | 32.489 | 27.763 | 11.848 | 1.00 | 63.80 |
| ATOM | 713 | OE1 | GLU | 299 | 31.805 | 28.162 | 10.882 | 1.00 | 69.03 |
| ATOM | 714 | OE2 | GLU | 299 | 31.979 | 27.297 | 12.889 | 1.00 | 67.10 |
| ATOM | 715 | C | GLU | 299 | 35.698 | 25.213 | 14.031 | 1.00 | 46.57 |
| ATOM | 716 | O | GLU | 299 | 36.772 | 24.659 | 13.787 | 1.00 | 44.65 |
| ATOM | 717 | N | ASP | 300 | 35.263 | 25.432 | 15.274 | 1.00 | 45.17 |
| ATOM | 718 | CA | ASP | 300 | 36.046 | 25.008 | 16.433 | 1.00 | 43.32 |
| ATOM | 719 | CB | ASP | 300 | 35.442 | 25.517 | 17.747 | 1.00 | 37.38 |
| ATOM | 720 | CG | ASP | 300 | 35.567 | 27.016 | 17.910 | 1.00 | 36.23 |
| ATOM | 721 | OD1 | ASP | 300 | 36.486 | 27.613 | 17.313 | 1.00 | 35.87 |
| ATOM | 722 | OD2 | ASP | 300 | 34.769 | 27.601 | 18.669 | 1.00 | 40.14 |
| ATOM | 723 | C | ASP | 300 | 36.174 | 23.495 | 16.513 | 1.00 | 42.81 |
| ATOM | 724 | O | ASP | 300 | 37.193 | 22.979 | 16.974 | 1.00 | 46.02 |
| ATOM | 725 | N | GLN | 301 | 35.139 | 22.788 | 16.066 | 1.00 | 38.60 |
| ATOM | 726 | CA | GLN | 301 | 35.151 | 21.334 | 16.086 | 1.00 | 40.00 |
| ATOM | 727 | CB | GLN | 301 | 33.815 | 20.783 | 15.576 | 1.00 | 38.59 |
| ATOM | 728 | CG | GLN | 301 | 32.608 | 21.334 | 16.317 | 1.00 | 40.26 |
| ATOM | 729 | CD | GLN | 301 | 31.311 | 20.696 | 15.869 | 1.00 | 44.15 |
| ATOM | 730 | OE1 | GLN | 301 | 31.074 | 20.527 | 14.673 | 1.00 | 45.73 |
| ATOM | 731 | NE2 | GLN | 301 | 30.450 | 20.363 | 16.824 | 1.00 | 46.13 |
| ATOM | 732 | C | GLN | 301 | 36.298 | 20.807 | 15.227 | 1.00 | 41.64 |
| ATOM | 733 | O | GLN | 301 | 36.975 | 19.850 | I5.601 | 1.00 | 45.02 |
| ATOM | 734 | N | ILE | 302 | 36.523 | 21.441 | 14.077 | 1.00 | 41.01 |
| ATOM | 735 | CA | ILE | 302 | 37.607 | 21.029 | 13.189 | 1.00 | 40.23 |
| ATOM | 736 | CB | ILE | 302 | 37.580 | 21.798 | 11.825 | 1.00 | 39.52 |
| ATOM | 737 | CG2 | ILE | 302 | 38.724 | 21.308 | 10.931 | 1.00 | 31.98 |
| ATOM | 738 | CG1 | ILE | 302 | 36.230 | 21.607 | 11.119 | 1.00 | 40.77 |
| ATOM | 739 | CD1 | ILE | 302 | 35.895 | 20.166 | 10.733 | 1.00 | 45.43 |
| ATOM | 740 | C | ILE | 302 | 38.948 | 21.322 | 13.869 | 1.00 | 38.58 |
| ATOM | 741 | O | ILE | 302 | 39.811 | 20.452 | 13.938 | 1.00 | 40.81 |
| ATOM | 742 | N | ILE | 303 | 39.110 | 22.547 | 14.364 | 1.00 | 37.50 |
| ATOM | 743 | CA | ILE | 303 | 40.343 | 22.958 | 15.030 | 1.00 | 39.33 |
| ATOM | 744 | CB | ILE | 303 | 40.263 | 24.442 | 15.501 | 1.00 | 39.06 |
| ATOM | 745 | CG2 | ILE | 303 | 41.525 | 24.822 | 16.279 | 1.00 | 36.19 |
| ATOM | 746 | CG1 | ILE | 303 | 40.103 | 25.358 | 14.280 | 1.00 | 40.15 |
| ATOM | 747 | CD1 | ILE | 303 | 39.972 | 26.846 | 14.602 | 1.00 | 36.93 |
| ATOM | 748 | C | ILE | 303 | 40.676 | 22.061 | 16.222 | 1.00 | 36.49 |
| ATOM | 749 | O | ILE | 303 | 41.818 | 21.623 | 16.378 | 1.00 | 36.58 |
| ATOM | 750 | N | LEU | 304 | 39.674 | 21.788 | 17.057 | 1.00 | 32.91 |
| ATOM | 751 | CA | LEU | 304 | 39.851 | 20.940 | 18.234 | 1.00 | 27.55 |
| ATOM | 752 | CB | LEU | 304 | 38.546 | 20.875 | 19.026 | 1.00 | 22.35 |
| ATOM | 753 | CG | LEU | 304 | 38.472 | 21.629 | 20.361 | 1.00 | 26.88 |
| ATOM | 754 | CD1 | LEU | 304 | 39.096 | 22.998 | 20.275 | 1.00 | 24.82 |
| ATOM | 755 | CD2 | LEU | 304 | 37.024 | 21.728 | 20.787 | 1.00 | 23.69 |
| ATOM | 756 | C | LEU | 304 | 40.313 | 19.534 | 17.855 | 1.00 | 28.05 |
| ATOM | 757 | O | LEU | 304 | 41.277 | 19.013 | 18.429 | 1.00 | 24.68 |
| ATOM | 758 | N | LEU | 305 | 39.637 | 18.929 | 16.882 | 1.00 | 26.34 |
| ATOM | 759 | CA | LEU | 305 | 39.997 | 17.588 | 16.436 | 1.00 | 30.91 |
| ATOM | 760 | CB | LEU | 305 | 38.937 | 17.055 | 15.466 | 1.00 | 32.50 |
| ATOM | 761 | CG | LEU | 305 | 37.585 | 16.757 | 16.132 | 1.00 | 33.36 |
| ATOM | 762 | CD1 | LEU | 305 | 36.557 | 16.439 | 15.079 | 1.00 | 33.87 |
| ATOM | 763 | CD2 | LEU | 305 | 37.733 | 15.581 | 17.101 | 1.00 | 31.72 |
| ATOM | 764 | C | LEU | 305 | 41.381 | 17.523 | 15.796 | 1.00 | 29.76 |
| ATOM | 765 | O | LEU | 305 | 42.109 | 16.553 | 15.990 | 1.00 | 29.33 |
| ATOM | 766 | N | LYS | 306 | 41.754 | 18.554 | 15.048 | 1.00 | 29.72 |
| ATOM | 767 | CA | LYS | 306 | 43.065 | 18.569 | 14.409 | 1.00 | 34.28 |
| ATOM | 768 | CB | LYS | 306 | 43.122 | 19.673 | 13.345 | 1.00 | 35.98 |
| ATOM | 769 | CG | LYS | 306 | 42.140 | 19.465 | 12.206 | 1.00 | 43.35 |
| ATOM | 770 | CD | LYS | 306 | 42.195 | 20.583 | 11.170 | 1.00 | 51.50 |
| ATOM | 771 | CE | LYS | 306 | 43.532 | 20.639 | 10.446 | 1.00 | 53.26 |
| ATOM | 772 | NZ | LYS | 306 | 43.522 | 21.702 | 9.409 | 1.00 | 59.61 |
| ATOM | 773 | C | LYS | 306 | 44.183 | 18.777 | 15.434 | 1.00 | 35.25 |
| ATOM | 774 | O | LYS | 306 | 45.312 | 18.332 | 15.231 | 1.00 | 33.95 |
| ATOM | 775 | N | GLY | 307 | 43.853 | 19.446 | 16.536 | 1.00 | 35.79 |
| ATOM | 776 | CA | GLY | 307 | 44.836 | 19.700 | 17.576 | 1.00 | 34.59 |
| ATOM | 777 | C | GLY | 307 | 45.075 | 18.562 | 18.559 | 1.00 | 33.80 |
| ATOM | 778 | O | GLY | 307 | 46.200 | 18.360 | 19.008 | 1.00 | 31.59 |
| ATOM | 779 | N | CYS | 308 | 44.030 | 17.806 | 18.880 | 1.00 | 31.15 |
| ATOM | 780 | CA | CYS | 308 | 44.153 | 16.712 | 19.839 | 1.00 | 29.04 |
| ATOM | 781 | CB | CYS | 308 | 42.929 | 16.667 | 20.750 | 1.00 | 27.59 |
| ATOM | 782 | SG | CYS | 308 | 41.452 | 15.974 | 19.941 | 1.00 | 30.50 |
| ATOM | 783 | C | CYS | 308 | 44.289 | 15.339 | 19.208 | 1.00 | 30.59 |
| ATOM | 784 | O | CYS | 308 | 44.609 | 14.374 | 19.899 | 1.00 | 33.77 |

APPENDIX 8-continued

TRBGC1.PDB

| | | | | | | | | |
|---|---|---|---|---|---|---|---|---|
| ATOM | 785 | N CYS | 309 | 44.053 | 15.247 | 17.907 | 1.00 | 28.46 |
| ATOM | 786 | CA CYS | 309 | 44.099 | 13.961 | 17.219 | 1.00 | 30.10 |
| ATOM | 787 | CB CYS | 309 | 43.983 | 14.161 | 15.706 | 1.00 | 33.43 |
| ATOM | 788 | SG CYS | 309 | 43.761 | 12.613 | 14.819 | 1.00 | 35.20 |
| ATOM | 789 | C CYS | 309 | 45.301 | 13.071 | 17.524 | 1.00 | 27.72 |
| ATOM | 790 | O CYS | 309 | 45.135 | 11.907 | 17.913 | 1.00 | 27.69 |
| ATOM | 791 | N MET | 310 | 46.508 | 13.594 | 17.339 | 1.00 | 26.15 |
| ATOM | 792 | CA MET | 310 | 47.700 | 12.798 | 17.605 | 1.00 | 26.06 |
| ATOM | 793 | CB MET | 310 | 48.928 | 13.439 | 16.951 | 1.00 | 25.31 |
| ATOM | 794 | CG MET | 310 | 50.207 | 12.648 | 17.132 | 1.00 | 24.08 |
| ATOM | 795 | SD MET | 310 | 50.101 | 10.991 | 16.423 | 1.00 | 27.71 |
| ATOM | 796 | CE MET | 310 | 51.674 | 10.307 | 16.934 | 1.00 | 28.50 |
| ATOM | 797 | C MET | 310 | 47.941 | 12.612 | 19.113 | 1.00 | 25.94 |
| ATOM | 798 | O MET | 310 | 48.592 | 11.653 | 19.526 | 1.00 | 28.09 |
| ATOM | 799 | N GLU | 311 | 47.405 | 13.522 | 19.923 | 1.00 | 25.39 |
| ATOM | 800 | CA GLU | 311 | 47.560 | 13.445 | 21.370 | 1.00 | 27.03 |
| ATOM | 801 | CB GLU | 311 | 47.099 | 14.748 | 22.030 | 1.00 | 24.39 |
| ATOM | 802 | CG GLU | 311 | 47.610 | 15.999 | 21.331 | 1.00 | 26.00 |
| ATOM | 803 | CD GLU | 311 | 47.292 | 17.271 | 22.084 | 1.00 | 23.95 |
| ATOM | 804 | OE1 GLU | 311 | 46.182 | 17.379 | 22.640 | 1.00 | 19.72 |
| ATOM | 805 | OE2 GLU | 311 | 48.150 | 18.181 | 22.088 | 1.00 | 26.51 |
| ATOM | 806 | C GLU | 311 | 46.727 | 12.272 | 21.902 | 1.00 | 27.51 |
| ATOM | 807 | O GLU | 311 | 47.152 | 11.552 | 22.807 | 1.00 | 29.67 |
| ATOM | 808 | N ILE | 312 | 45.547 | 12.086 | 21.326 | 1.00 | 26.82 |
| ATOM | 809 | CA ILE | 312 | 44.661 | 11.001 | 21.724 | 1.00 | 25.71 |
| ATOM | 810 | CB ILE | 312 | 43.194 | 11.296 | 21.304 | 1.00 | 23.35 |
| ATOM | 811 | CG2 ILE | 312 | 42.301 | 10.068 | 21.583 | 1.00 | 20.27 |
| ATOM | 812 | CG1 ILE | 312 | 42.690 | 12.534 | 22.062 | 1.00 | 20.88 |
| ATOM | 813 | CD1 ILE | 312 | 41.244 | 12.961 | 21.755 | 1.00 | 18.15 |
| ATOM | 814 | C ILE | 312 | 45.116 | 9.665 | 21.132 | 1.00 | 27.91 |
| ATOM | 815 | O ILE | 312 | 45.064 | 8.628 | 21.804 | 1.00 | 28.96 |
| ATOM | 816 | N MET | 313 | 45.582 | 9.683 | 19.886 | 1.00 | 27.66 |
| ATOM | 817 | CA MET | 313 | 46.045 | 8.447 | 19.257 | 1.00 | 30.18 |
| ATOM | 818 | CB MET | 313 | 46.386 | 8.662 | 17.771 | 1.00 | 36.89 |
| ATOM | 819 | CG MET | 313 | 45.186 | 8.938 | 16.861 | 1.00 | 37.95 |
| ATOM | 820 | SD MET | 313 | 45.624 | 8.943 | 15.096 | 1.00 | 42.38 |
| ATOM | 821 | CE MET | 313 | 46.724 | 10.319 | 14.999 | 1.00 | 40.68 |
| ATOM | 822 | C MET | 313 | 47.264 | 7.897 | 19.975 | 1.00 | 27.43 |
| ATOM | 823 | O MET | 313 | 47.351 | 6.690 | 20.219 | 1.00 | 28.61 |
| ATOM | 824 | N SER | 314 | 48.202 | 8.776 | 20.318 | 1.00 | 24.88 |
| ATOM | 825 | CA SER | 314 | 49.416 | 8.352 | 21.011 | 1.00 | 27.98 |
| ATOM | 826 | CB SER | 314 | 50.420 | 9.511 | 21.118 | 1.00 | 29.64 |
| ATOM | 827 | OG SER | 314 | 49.912 | 10.560 | 21.911 | 1.00 | 43.44 |
| ATOM | 828 | C SER | 314 | 49.082 | 7.818 | 22.402 | 1.00 | 22.30 |
| ATOM | 829 | O SER | 314 | 49.737 | 6.895 | 22.892 | 1.00 | 24.18 |
| ATOM | 830 | N LEU | 315 | 48.070 | 8.395 | 23.039 | 1.00 | 23.99 |
| ATOM | 831 | CA LEU | 315 | 47.646 | 7.918 | 24.365 | 1.00 | 25.07 |
| ATOM | 832 | CB LEU | 315 | 46.580 | 8.842 | 24.965 | 1.00 | 19.11 |
| ATOM | 833 | CG LEU | 315 | 45.863 | 8.355 | 26.228 | 1.00 | 20.39 |
| ATOM | 834 | CD1 LEU | 315 | 46.872 | 8.076 | 27.362 | 1.00 | 18.92 |
| ATOM | 835 | CD2 LEU | 315 | 44.848 | 9.401 | 26.655 | 1.00 | 12.93 |
| ATOM | 836 | C LEU | 315 | 47.070 | 6.518 | 24.222 | 1.00 | 24.53 |
| ATOM | 837 | O LEU | 315 | 47.394 | 5.615 | 24.992 | 1.00 | 26.32 |
| ATOM | 838 | N ARG | 316 | 46.212 | 6.338 | 23.220 | 1.00 | 28.18 |
| ATOM | 839 | CA ARG | 316 | 45.595 | 5.041 | 22.978 | 1.00 | 27.54 |
| ATOM | 840 | CB ARG | 316 | 44.575 | 5.155 | 21.848 | 1.00 | 27.39 |
| ATOM | 841 | CG ARG | 316 | 43.340 | 5.929 | 22.253 | 1.00 | 22.00 |
| ATOM | 842 | CD ARG | 316 | 42.291 | 5.902 | 21.172 | 1.00 | 18.78 |
| ATOM | 843 | NE ARG | 316 | 40.975 | 6.205 | 21.719 | 1.00 | 26.57 |
| ATOM | 844 | CZ ARG | 316 | 39.852 | 6.224 | 21.014 | 1.00 | 30.81 |
| ATOM | 845 | NH1 ARG | 316 | 39.878 | 5.972 | 19.711 | 1.00 | 33.71 |
| ATOM | 846 | NH2 ARG | 316 | 38.692 | 6.471 | 21.613 | 1.00 | 33.13 |
| ATOM | 847 | C ARG | 316 | 46.612 | 3.949 | 22.682 | 1.00 | 28.09 |
| ATOM | 848 | O ARG | 316 | 46.399 | 2.790 | 23.027 | 1.00 | 32.41 |
| ATOM | 849 | N ALA | 317 | 47.718 | 4.317 | 22.047 | 1.00 | 28.36 |
| ATOM | 850 | CA ALA | 317 | 48.771 | 3.359 | 21.744 | 1.00 | 26.64 |
| ATOM | 851 | CB ALA | 317 | 49.674 | 3.904 | 20.643 | 1.00 | 22.93 |
| ATOM | 852 | C ALA | 317 | 49.591 | 3.115 | 23.002 | 1.00 | 28.35 |
| ATOM | 853 | O ALA | 317 | 49.968 | 1.979 | 23.312 | 1.00 | 32.10 |
| ATOM | 854 | N ALA | 318 | 49.863 | 4.197 | 23.727 | 1.00 | 29.12 |
| ATOM | 855 | CA ALA | 318 | 50.655 | 4.123 | 24.953 | 1.00 | 27.50 |
| ATOM | 856 | CB ALA | 318 | 50.854 | 5.518 | 25.522 | 1.00 | 28.39 |
| ATOM | 857 | C ALA | 318 | 50.053 | 3.215 | 26.013 | 1.00 | 28.10 |
| ATOM | 858 | O ALA | 318 | 50.783 | 2.491 | 26.684 | 1.00 | 28.18 |
| ATOM | 859 | N VAL | 319 | 48.730 | 3.245 | 26.165 | 1.00 | 29.16 |
| ATOM | 860 | CA VAL | 319 | 48.082 | 2.414 | 27.176 | 1.00 | 35.24 |
| ATOM | 861 | CB VAL | 319 | 46.663 | 2.933 | 27.541 | 1.00 | 27.34 |
| ATOM | 862 | CG1 VAL | 319 | 46.759 | 4.324 | 28.136 | 1.00 | 29.96 |
| ATOM | 863 | CG2 VAL | 319 | 45.773 | 2.936 | 26.322 | 1.00 | 31.70 |
| ATOM | 864 | C VAL | 319 | 47.970 | 0.955 | 26.764 | 1.00 | 40.01 |
| ATOM | 865 | G VAL | 319 | 47.448 | 0.129 | 27.515 | 1.00 | 42.70 |
| ATOM | 866 | N ARG | 320 | 48.460 | 0.644 | 25.565 | 1.00 | 38.64 |
| ATOM | 867 | CA ARG | 320 | 48.436 | −0.715 | 25.041 | 1.00 | 38.61 |
| ATOM | 868 | CB ARG | 320 | 47.764 | −0.751 | 23.674 | 1.00 | 37.26 |
| ATOM | 869 | CG ARG | 320 | 46.258 | −0.655 | 23.720 | 1.00 | 43.12 |
| ATOM | 870 | CD ARG | 320 | 45.712 | −0.368 | 22.339 | 1.00 | 50.79 |
| ATOM | 871 | NE ARG | 320 | 44.260 | −0.446 | 22.286 | 1.00 | 54.71 |
| ATOM | 872 | CZ ARG | 320 | 43.527 | 0.074 | 21.306 | 1.00 | 57.89 |
| ATOM | 873 | NH1 ARG | 320 | 44.119 | 0.713 | 20.300 | 1.00 | 49.08 |
| ATOM | 874 | NH2 ARG | 320 | 42.206 | −0.058 | 21.326 | 1.00 | 59.59 |
| ATOM | 875 | C ARG | 320 | 49.852 | −1.247 | 24.930 | 1.00 | 42.14 |
| ATOM | 876 | O ARG | 320 | 50.162 | −2.055 | 24.051 | 1.00 | 46.30 |
| ATOM | 877 | N TYR | 321 | 50.712 | −0.772 | 25.822 | 1.00 | 42.04 |
| ATOM | 878 | CA TYR | 321 | 52.098 | −1.202 | 25.852 | 1.00 | 42.70 |
| ATOM | 879 | CB TYR | 321 | 52.971 | −0.133 | 26.529 | 1.00 | 38.01 |
| ATOM | 880 | CG TYR | 321 | 54.416 | −0.579 | 26.734 | 1.00 | 37.94 |
| ATOM | 881 | CD1 TYR | 321 | 55.275 | −0.779 | 25.636 | 1.00 | 33.85 |
| ATOM | 882 | CE1 TYR | 321 | 56.581 | −1.297 | 25.813 | 1.00 | 34.49 |
| ATOM | 883 | CD2 TYR | 321 | 54.892 | −0.894 | 28.016 | 1.00 | 28.03 |
| ATOM | 884 | CE2 TYR | 321 | 56.194 | −1.411 | 28.207 | 1.00 | 32.69 |
| ATOM | 885 | CZ TYR | 321 | 57.026 | −1.614 | 27.103 | 1.00 | 35.18 |
| ATOM | 886 | OH TYR | 321 | 58.289 | −2.158 | 27.288 | 1.00 | 39.48 |
| ATOM | 887 | C TYR | 321 | 52.189 | −2.515 | 26.629 | 1.00 | 45.51 |
| ATOM | 888 | O TYR | 321 | 51.571 | −2.662 | 27.687 | 1.00 | 48.02 |
| ATOM | 889 | N ASP | 322 | 52.945 | −3.471 | 26.095 | 1.00 | 44.56 |
| ATOM | 890 | CA ASP | 322 | 53.129 | −4.764 | 26.753 | 1.00 | 45.86 |
| ATOM | 891 | CB ASP | 322 | 52.697 | −5.899 | 25.816 | 1.00 | 46.64 |
| ATOM | 892 | C ASP | 322 | 54.606 | −4.910 | 27.098 | 1.00 | 45.82 |
| ATOM | 893 | O ASP | 322 | 55.434 | −5.109 | 26.214 | 1.00 | 45.38 |
| ATOM | 894 | N PRO | 323 | 54.962 | 4.803 | 28.393 | 1.00 | 46.53 |
| ATOM | 895 | CD PRO | 323 | 54.123 | 4.541 | 29.572 | 1.00 | 47.16 |
| ATOM | 896 | CA PRO | 323 | 56.366 | −4.932 | 28.805 | 1.00 | 46.63 |
| ATOM | 897 | CB PRO | 323 | 56.293 | −4.667 | 30.308 | 1.00 | 43.95 |
| ATOM | 898 | CG PRO | 323 | 54.926 | −5.223 | 30.655 | 1.00 | 43.93 |
| ATOM | 899 | C PRO | 323 | 56.993 | −6.285 | 28.478 | 1.00 | 48.34 |
| ATOM | 900 | O PRO | 323 | 58.217 | −6.407 | 28.379 | 1.00 | 50.84 |
| ATOM | 901 | N GLU | 324 | 56.149 | −7.301 | 28.315 | 1.00 | 52.39 |
| ATOM | 902 | CA GLU | 324 | 56.621 | −8.646 | 28.005 | 1.00 | 55.85 |
| ATOM | 903 | CB GLU | 324 | 55.453 | −9.633 | 28.048 | 1.00 | 55.54 |
| ATOM | 904 | C GLU | 324 | 57.283 | −8.670 | 26.632 | 1.00 | 54.94 |
| ATOM | 905 | O GLU | 324 | 58.460 | −9.013 | 26.502 | 1.00 | 59.81 |
| ATOM | 906 | N SER | 325 | 56.522 | −8.299 | 25.611 | 1.00 | 52.95 |
| ATOM | 907 | CA SER | 325 | 57.021 | −8.269 | 24.244 | 1.00 | 50.10 |
| ATOM | 908 | CB SER | 325 | 55.889 | −8.613 | 23.279 | 1.00 | 48.23 |
| ATOM | 909 | OG SER | 325 | 54.788 | −7.749 | 23.471 | 1.00 | 48.71 |
| ATOM | 910 | C SER | 325 | 57.608 | −6.908 | 23.879 | 1.00 | 50.61 |
| ATOM | 911 | O SER | 325 | 58.194 | −6.743 | 22.808 | 1.00 | 52.19 |
| ATOM | 912 | N GLU | 326 | 57.450 | −5.939 | 24.786 | 1.00 | 45.64 |
| ATOM | 913 | CA GLU | 326 | 57.938 | 4.579 | 24.588 | 1.00 | 43.35 |
| ATOM | 914 | CB GLU | 326 | 59.469 | −4.562 | 24.587 | 1.00 | 42.74 |
| ATOM | 915 | CG GLU | 326 | 60.053 | −5.016 | 25.909 | 1.00 | 50.32 |
| ATOM | 916 | CD GLU | 326 | 61.565 | −5.067 | 25.907 | 1.00 | 56.34 |
| ATOM | 917 | OE1 GLU | 326 | 62.139 | −5.407 | 26.966 | 1.00 | 59.31 |
| ATOM | 918 | OE2 GLU | 326 | 62.178 | −4.774 | 24.856 | 1.00 | 55.74 |
| ATOM | 919 | C GLU | 326 | 57.397 | −3.993 | 23.291 | 1.00 | 40.23 |
| ATOM | 920 | O GLU | 326 | 58.145 | −3.474 | 22.465 | 1.00 | 40.44 |
| ATOM | 921 | N THR | 327 | 56.080 | −4.079 | 23.127 | 1.00 | 35.90 |
| ATOM | 922 | CA THR | 327 | 55.427 | −3.573 | 21.936 | 1.00 | 37.29 |
| ATOM | 923 | CB THR | 327 | 54.983 | 4.717 | 21.008 | 1.00 | 37.63 |
| ATOM | 924 | OG1 THR | 327 | 53.994 | −5.503 | 21.674 | 1.00 | 38.12 |
| ATOM | 925 | CG2 THR | 327 | 56.165 | −5.609 | 20.635 | 1.00 | 39.90 |
| ATOM | 926 | C THR | 327 | 54.170 | −2.780 | 22.282 | 1.00 | 39.49 |
| ATOM | 927 | O THR | 327 | 53.603 | −2.930 | 23.364 | 1.00 | 40.50 |
| ATOM | 928 | N LEU | 328 | 53.758 | −1.933 | 21.347 | 1.00 | 36.64 |
| ATOM | 929 | CN LEU | 328 | 52.544 | −1.136 | 21.480 | 1.00 | 37.73 |
| ATOM | 930 | CB LEU | 328 | 52.791 | 0.340 | 21.127 | 1.00 | 37.78 |
| ATOM | 931 | CG LEU | 328 | 53.667 | 1.257 | 21.982 | 1.00 | 36.26 |
| ATOM | 932 | CD1 LEU | 328 | 53.690 | 2.641 | 21.348 | 1.00 | 36.56 |
| ATOM | 933 | CD2 LEU | 328 | 53.101 | 1.351 | 23.396 | 1.00 | 39.85 |
| ATOM | 934 | C LEU | 328 | 51.617 | −1.722 | 20.431 | 1.00 | 37.27 |
| ATOM | 935 | O LEU | 328 | 52.083 | −2.233 | 19.410 | 1.00 | 34.96 |
| ATOM | 936 | N THR | 329 | 50.314 | −1.652 | 20.669 | 1.00 | 39.73 |
| ATOM | 937 | CA THR | 329 | 49.368 | −2.173 | 19.701 | 1.00 | 40.81 |
| ATOM | 938 | CB THR | 329 | 48.401 | −3.176 | 20.349 | 1.00 | 42.67 |

APPENDIX 8-continued

TRBGC1.PDB

| ATOM | 939 | OG1 | THR | 329 | 49.156 | 4.271 | 20.896 | 1.00 | 42.52 |
|---|---|---|---|---|---|---|---|---|---|
| ATOM | 940 | CG2 | THR | 329 | 47.425 | -3.722 | 19.315 | 1.00 | 43.52 |
| ATOM | 941 | C | THR | 329 | 48.591 | -1.034 | 19.058 | 1.00 | 44.31 |
| ATOM | 942 | O | THR | 329 | 47.825 | -0.325 | 19.712 | 1.00 | 43.72 |
| ATOM | 943 | N | LEU | 330 | 48.822 | -0.859 | 17.759 | 1.00 | 44.62 |
| ATOM | 944 | CA | LEU | 330 | 48.179 | 0.182 | 16.972 | 1.00 | 45.09 |
| ATOM | 945 | CB | LEU | 330 | 49.056 | 0.545 | 15.766 | 1.00 | 44.66 |
| ATOM | 946 | CG | LEU | 330 | 50.329 | 1.393 | 15.951 | 1.00 | 51.06 |
| ATOM | 947 | CD1 | LEU | 330 | 51.195 | 0.890 | 17.095 | 1.00 | 48.58 |
| ATOM | 948 | CD2 | LEU | 330 | 51.107 | 1.387 | 14.638 | 1.00 | 45.18 |
| ATOM | 949 | C | LEU | 330 | 46.802 | -0.264 | 16.501 | 1.00 | 48.06 |
| ATOM | 950 | O | LEU | 330 | 46.634 | -1.386 | 16.012 | 1.00 | 49.33 |
| ATOM | 951 | N | ASN | 331 | 45.826 | 0.618 | 16.663 | 1.00 | 52.20 |
| ATOM | 952 | CA | ASN | 331 | 44.450 | 0.363 | 16.257 | 1.00 | 54.41 |
| ATOM | 953 | CB | ASN | 331 | 44.370 | 0.353 | 14.731 | 1.00 | 54.94 |
| ATOM | 954 | CG | ASN | 331 | 42.970 | 0.603 | 14.219 | 1.00 | 60.35 |
| ATOM | 955 | OD1 | ASN | 331 | 42.375 | 1.642 | 14.521 | 1.00 | 61.84 |
| ATOM | 956 | ND2 | ASN | 331 | 42.438 | -0.344 | 13.459 | 1.00 | 65.92 |
| ATOM | 957 | C | ASN | 331 | 43.940 | -0.963 | 16.836 | 1.00 | 58.00 |
| ATOM | 958 | O | ASN | 331 | 42.985 | -1.557 | 16.328 | 1.00 | 60.17 |
| ATOM | 959 | N | GLY | 332 | 44.590 | -1.414 | 17.908 | 1.00 | 58.45 |
| ATOM | 960 | CA | GLY | 332 | 44.215 | -2.658 | 18.556 | 1.00 | 58.55 |
| ATOM | 961 | C | GLY | 332 | 44.408 | -3.880 | 17.680 | 1.00 | 59.79 |
| ATOM | 962 | O | GLY | 332 | 43.892 | -4.953 | 17.993 | 1.00 | 61.32 |
| ATOM | 963 | N | GLU | 333 | 45.165 | -3.725 | 16.597 | 1.00 | 60.28 |
| ATOM | 964 | CA | GLU | 333 | 45.408 | -4.821 | 15.659 | 1.00 | 59.13 |
| ATOM | 965 | CB | GLU | 333 | 44.817 | -4.478 | 14.296 | 1.00 | 62.40 |
| ATOM | 966 | CG | GLU | 333 | 43.345 | -4.129 | 14.296 | 1.00 | 75.69 |
| ATOM | 967 | CD | GLU | 333 | 42.851 | -3.731 | 12.917 | 1.00 | 80.41 |
| ATOM | 968 | OE1 | GLU | 333 | 43.374 | -2.740 | 12.359 | 1.00 | 79.98 |
| ATOM | 969 | OE2 | GLU | 333 | 41.942 | 4.412 | 12.392 | 1.00 | 83.81 |
| ATOM | 970 | C | GLU | 333 | 46.881 | -5.146 | 15.452 | 1.00 | 57.18 |
| ATOM | 971 | O | GLU | 333 | 47.291 | -6.301 | 15.545 | 1.00 | 57.50 |
| ATOM | 972 | N | MET | 334 | 47.663 | -4.112 | 15.166 | 1.00 | 55.20 |
| ATOM | 973 | CA | MET | 334 | 49.085 | 4.245 | 14.873 | 1.00 | 50.85 |
| ATOM | 974 | CB | MET | 334 | 49.416 | -3.334 | 13.687 | 1.00 | 48.70 |
| ATOM | 975 | CG | MET | 334 | 50.844 | -3.412 | 13.181 | 1.00 | 45.39 |
| ATOM | 976 | SD | MET | 334 | 51.159 | -2.124 | 11.959 | 1.00 | 44.56 |
| ATOM | 977 | CE | MET | 334 | 49.908 | -2.477 | 10.749 | 1.00 | 45.25 |
| ATOM | 978 | C | MET | 334 | 50.041 | -3.941 | 16.026 | 1.00 | 51.59 |
| ATOM | 979 | O | MET | 334 | 50.104 | -2.810 | 16.508 | 1.00 | 52.52 |
| ATOM | 980 | N | ALA | 335 | 50.796 | 4.946 | 16.109 | 1.00 | 51.00 |
| ATOM | 981 | CA | ALA | 335 | 51.769 | -4.787 | 17.527 | 1.00 | 48.98 |
| ATOM | 982 | CB | ALA | 335 | 51.850 | -6.062 | 18.347 | 1.00 | 47.86 |
| ATOM | 983 | C | ALA | 335 | 53.136 | -4.470 | 16.917 | 1.00 | 51.01 |
| ATOM | 984 | O | ALA | 335 | 53.655 | -5.242 | 16.109 | 1.00 | 51.61 |
| ATOM | 985 | N | VAL | 336 | 53.718 | -3.336 | 17.307 | 1.00 | 46.62 |
| ATOM | 986 | CA | VAL | 336 | 55.016 | -2.926 | 16.783 | 1.00 | 42.35 |
| ATOM | 987 | CB | VAL | 336 | 54.876 | -1.687 | 15.877 | 1.00 | 42.41 |
| ATOM | 988 | CG1 | VAL | 336 | 53.963 | -2.004 | 14.707 | 1.00 | 42.00 |
| ATOM | 989 | CG2 | VAL | 336 | 54.313 | -0.506 | 16.676 | 1.00 | 40.32 |
| ATOM | 990 | C | VAL | 336 | 56.023 | -2.608 | 17.883 | 1.00 | 45.33 |
| ATOM | 991 | O | VAL | 336 | 55.650 | -2.309 | 19.019 | 1.00 | 47.42 |
| ATOM | 992 | N | THR | 337 | 57.310 | -2.678 | 17.541 | 1.00 | 41.60 |
| ATOM | 993 | CA | THR | 337 | 58.357 | -2.381 | 18.508 | 1.00 | 39.69 |
| ATOM | 994 | CB | THR | 337 | 59.608 | -3.259 | 18.296 | 1.00 | 41.35 |
| ATOM | 995 | OG1 | THR | 337 | 60.168 | -2.985 | 17.007 | 1.00 | 49.35 |
| ATOM | 996 | CG2 | THR | 337 | 59.253 | 4.734 | 18.392 | 1.00 | 40.38 |
| ATOM | 997 | C | THR | 337 | 58.777 | -0.924 | 18.367 | 1.00 | 37.88 |
| ATOM | 998 | O | THR | 337 | 58.312 | -0.218 | 17.473 | 1.00 | 34.06 |
| ATOM | 999 | N | ARG | 338 | 59.655 | -0.489 | 19.268 | 1.00 | 37.61 |
| ATOM | 1000 | CA | ARG | 338 | 60.171 | 0.876 | 19.268 | 1.00 | 38.68 |
| ATOM | 1001 | CB | ARG | 338 | 61.177 | 1.041 | 20.424 | 1.00 | 35.95 |
| ATOM | 1002 | CG | ARG | 338 | 61.804 | 2.434 | 20.570 | 1.00 | 38.83 |
| ATOM | 1003 | CD | ARG | 338 | 62.791 | 2.462 | 21.749 | 1.00 | 35.88 |
| ATOM | 1004 | NE | ARG | 338 | 62.114 | 2.277 | 23.035 | 1.00 | 37.42 |
| ATOM | 1005 | CZ | ARG | 338 | 61.858 | 3.256 | 23.902 | 1.00 | 30.20 |
| ATOM | 1006 | NH1 | ARG | 338 | 62.224 | 4.501 | 23.636 | 1.00 | 27.98 |
| ATOM | 1007 | NH2 | ARG | 338 | 61.213 | 2.992 | 25.025 | 1.00 | 27.40 |
| ATOM | 1008 | C | ARG | 338 | 60.843 | 1.158 | 17.925 | 1.00 | 38.09 |
| ATOM | 1009 | O | ARG | 338 | 60.529 | 2.142 | 17.251 | 1.00 | 34.12 |
| ATOM | 1010 | N | GLY | 339 | 61.755 | 0.267 | 17.535 | 1.00 | 41.25 |
| ATOM | 1011 | CA | GLY | 339 | 62.475 | 0.416 | 16.282 | 1.00 | 41.35 |
| ATOM | 1012 | C | GLY | 339 | 61.594 | 0.463 | 15.046 | 1.00 | 41.23 |
| ATOM | 1013 | O | GLY | 339 | 61.811 | 1.288 | 14.159 | 1.00 | 38.30 |
| ATOM | 1014 | N | GLN | 340 | 60.594 | -0.414 | 14.982 | 1.00 | 38.58 |
| ATOM | 1015 | CA | GLN | 340 | 59.704 | -0.449 | 13.826 | 1.00 | 40.79 |
| ATOM | 1016 | CB | GLN | 340 | 58.757 | -1.651 | 13.911 | 1.00 | 40.82 |
| ATOM | 1017 | CG | GLN | 340 | 59.450 | -2.995 | 13.944 | 1.00 | 41.10 |
| ATOM | 1018 | CD | GLN | 340 | 58.468 | 14.144 | 13.890 | 1.00 | 48.84 |
| ATOM | 1019 | OE1 | GLN | 340 | 57.529 | -4.208 | 14.679 | 1.00 | 50.53 |
| ATOM | 1020 | NE2 | GLN | 340 | 58.685 | -5.068 | 12.959 | 1.00 | 54.25 |
| ATOM | 1021 | C | GLN | 340 | 58.884 | 0.822 | 13.679 | 1.00 | 41.50 |
| ATOM | 1022 | O | GLN | 340 | 58.725 | 1.342 | 12.576 | 1.00 | 42.72 |
| ATOM | 1023 | N | LEU | 341 | 58.360 | 1.324 | 14.795 | 1.00 | 42.00 |
| ATOM | 1024 | CA | LEU | 341 | 57.546 | 2.532 | 14.775 | 1.00 | 38.10 |
| ATOM | 1025 | CB | LEU | 341 | 56.868 | 2.740 | 16.133 | 1.00 | 36.66 |
| ATOM | 1026 | CG | LEU | 341 | 55.886 | 3.914 | 16.267 | 1.00 | 39.94 |
| ATOM | 1027 | CD1 | LEU | 341 | 54.711 | 3.741 | 15.311 | 1.00 | 34.98 |
| ATOM | 1028 | CD2 | LEU | 341 | 55.389 | 3.989 | 17.700 | 1.00 | 40.95 |
| ATOM | 1029 | C | LEU | 341 | 58.404 | 3.743 | 14.423 | 1.00 | 36.37 |
| ATOM | 1030 | O | LEU | 341 | 57.980 | 4.620 | 13.668 | 1.00 | 37.89 |
| ATOM | 1031 | N | LYS | 342 | 59.616 | 3.777 | 14.969 | 1.00 | 33.29 |
| ATOM | 1032 | CA | LYS | 342 | 60.542 | 4.872 | 14.723 | 1.00 | 35.17 |
| ATOM | 1033 | CB | LYS | 342 | 61.801 | 4.687 | 15.582 | 1.00 | 34.97 |
| ATOM | 1034 | CG | LYS | 342 | 62.764 | 5.863 | 15.519 | 1.00 | 40.00 |
| ATOM | 1035 | CD | LYS | 342 | 63.868 | 5.739 | 16.555 | 1.00 | 34.48 |
| ATOM | 1036 | CE | LYS | 342 | 64.709 | 7.001 | 16.596 | 1.00 | 37.54 |
| ATOM | 1037 | NZ | LYS | 342 | 65.716 | 6.972 | 17.689 | 1.00 | 42.32 |
| ATOM | 1038 | C | LYS | 342 | 60.928 | 4.970 | 13.235 | 1.00 | 38.29 |
| ATOM | 1039 | O | LYS | 342 | 60.621 | 5.963 | 12.569 | 1.00 | 36.23 |
| ATOM | 1040 | N | ASN | 343 | 61.585 | 3.932 | 12.721 | 1.00 | 39.25 |
| ATOM | 1041 | CA | ASN | 343 | 62.014 | 3.903 | 11.328 | 1.00 | 40.19 |
| ATOM | 1042 | CB | ASN | 343 | 62.808 | 2.627 | 11.050 | 1.00 | 37.96 |
| ATOM | 1043 | CG | ASN | 343 | 63.937 | 2.429 | 12.027 | 1.00 | 39.22 |
| ATOM | 1044 | OD1 | ASN | 343 | 64.648 | 3.376 | 12.374 | 1.00 | 42.37 |
| ATOM | 1045 | ND2 | ASN | 343 | 64.125 | 1.197 | 12.471 | 1.00 | 42.19 |
| ATOM | 1046 | C | ASN | 343 | 60.831 | 3.997 | 10.368 | 1.00 | 40.12 |
| ATOM | 1047 | O | ASN | 343 | 60.991 | 4.371 | 9.208 | 1.00 | 36.01 |
| ATOM | 1048 | N | GLY | 344 | 59.645 | 3.665 | 10.868 | 1.00 | 40.95 |
| ATOM | 1049 | CA | GLY | 344 | 58.439 | 3.721 | 10.057 | 1.00 | 39.25 |
| ATOM | 1050 | C | GLY | 344 | 57.947 | 5.131 | 9.772 | 1.00 | 38.26 |
| ATOM | 1051 | O | GLY | 344 | 56.971 | 5.308 | 9.044 | 1.00 | 35.69 |
| ATOM | 1052 | N | GLY | 345 | 58.604 | 6.135 | 10.359 | 1.00 | 35.89 |
| ATOM | 1053 | CA | GLY | 345 | 58.212 | 7.510 | 10.110 | 1.00 | 34.00 |
| ATOM | 1054 | C | GLY | 345 | 58.050 | 8.444 | 11.300 | 1.00 | 38.64 |
| ATOM | 1055 | O | GLY | 345 | 57.902 | 9.652 | 11.116 | 1.00 | 38.14 |
| ATOM | 1056 | N | LEU | 346 | 58.085 | 7.912 | 12.520 | 1.00 | 39.52 |
| ATOM | 1057 | CA | LEU | 346 | 57.904 | 8.761 | 13.692 | 1.00 | 36.05 |
| ATOM | 1058 | CB | LEU | 346 | 57.039 | 8.048 | 14.738 | 1.00 | 35.72 |
| ATOM | 1059 | CG | LEU | 346 | 55.561 | 7.864 | 14.371 | 1.00 | 34.89 |
| ATOM | 1060 | CD1 | LEU | 346 | 54.850 | 7.132 | 15.494 | 1.00 | 44.09 |
| ATOM | 1061 | CD2 | LEU | 346 | 54.903 | 9.213 | 14.146 | 1.00 | 34.84 |
| ATOM | 1062 | C | LEU | 346 | 59.189 | 9.264 | 14.339 | 1.00 | 33.52 |
| ATOM | 1063 | O | LEU | 346 | 59.171 | 10.257 | 15.066 | 1.00 | 35.58 |
| ATOM | 1064 | N | GLY | 347 | 60.299 | 8.595 | 14.067 | 1.00 | 30.47 |
| ATOM | 1065 | CA | GLY | 347 | 61.559 | 9.017 | 14.661 | 1.00 | 33.01 |
| ATOM | 1066 | C | GLY | 347 | 61.504 | 9.069 | 16.182 | 1.00 | 30.72 |
| ATOM | 1067 | O | GLY | 347 | 60.967 | 8.160 | 16.812 | 1.00 | 30.89 |
| ATOM | 1068 | N | VAL | 348 | 62.051 | 10.132 | 16.765 | 1.00 | 31.30 |
| ATOM | 1069 | CA | VAL | 348 | 62.084 | 10.291 | 18.221 | 1.00 | 31.27 |
| ATOM | 1070 | CB | VAL | 348 | 62.843 | 11.612 | 18.620 | 1.00 | 31.66 |
| ATOM | 1071 | CG1 | VAL | 348 | 62.071 | 12.841 | 18.146 | 1.00 | 20.19 |
| ATOM | 1072 | CG2 | VAL | 348 | 63.080 | 11.651 | 20.118 | 1.00 | 24.77 |
| ATOM | 1073 | C | VAL | 348 | 60.683 | 10.273 | 18.855 | 1.00 | 33.84 |
| ATOM | 1074 | O | VAL | 348 | 60.546 | 10.034 | 20.050 | 1.00 | 29.99 |
| ATOM | 1075 | N | VAL | 349 | 59.649 | 10.518 | 18.049 | 1.00 | 33.31 |
| ATOM | 1076 | CA | VAL | 349 | 58.270 | 10.495 | 18.538 | 1.00 | 32.23 |
| ATOM | 1077 | CB | VAL | 349 | 57.279 | 10.911 | 17.415 | 1.00 | 32.59 |
| ATOM | 1078 | CG1 | VAL | 349 | 55.837 | 10.678 | 17.838 | 1.00 | 33.68 |
| ATOM | 1079 | CG2 | VAL | 349 | 57.474 | 12.378 | 17.103 | 1.00 | 32.30 |
| ATOM | 1080 | C | VAL | 349 | 57.931 | 9.094 | 19.050 | 1.00 | 34.91 |
| ATOM | 1081 | O | VAL | 349 | 57.133 | 8.932 | 19.980 | 1.00 | 33.73 |
| ATOM | 1082 | N | SER | 350 | 58.551 | 8.081 | 18.444 | 1.00 | 32.81 |
| ATOM | 1083 | CA | SER | 350 | 58.335 | 6.704 | 18.853 | 1.00 | 30.10 |
| ATOM | 1084 | CB | SER | 350 | 59.041 | 5.746 | 17.904 | 1.00 | 24.95 |
| ATOM | 1085 | OG | SER | 350 | 58.943 | 4.417 | 18.387 | 1.00 | 23.16 |
| ATOM | 1086 | C | SER | 350 | 58.863 | 6.486 | 20.266 | 1.00 | 31.59 |
| ATOM | 1087 | O | SER | 350 | 58.207 | 5.845 | 21.086 | 1.00 | 37.62 |
| ATOM | 1088 | N | ASP | 351 | 66.655 | 7.007 | 20.546 | 1.00 | 28.60 |
| ATOM | 1089 | CA | ASP | 351 | 60.652 | 6.863 | 21.867 | 1.00 | 29.82 |
| ATOM | 1090 | CB | ASP | 351 | 62.048 | 7.491 | 21.919 | 1.00 | 27.49 |
| ATOM | 1091 | CG | ASP | 351 | 63.030 | 6.806 | 21.000 | 1.00 | 30.22 |
| ATOM | 1092 | OD1 | ASP | 351 | 63.411 | 7.412 | 19.974 | 1.00 | 32.61 |

APPENDIX 8-continued

TRBGC1.PDB

| ATOM | 1093 | OD2 ASP | 351 | 63.422 | 5.664 | 21.301 | 1.00 | 30.02 |
|------|------|---------|-----|--------|-------|--------|------|-------|
| ATOM | 1094 | C ASP | 351 | 59.785 | 7.548 | 22.913 | 1.00 | 30.63 |
| ATOM | 1095 | O ASP | 351 | 59.632 | 7.055 | 24.027 | 1.00 | 29.54 |
| ATOM | 1096 | N ALA | 352 | 59.222 | 8.692 | 22.537 | 1.00 | 25.33 |
| ATOM | 1097 | CA ALA | 352 | 58.390 | 9.464 | 23.432 | 1.00 | 28.59 |
| ATOM | 1098 | CB ALA | 352 | 58.011 | 10.798 | 22.788 | 1.00 | 20.95 |
| ATOM | 1099 | C ALA | 352 | 57.136 | 8.695 | 23.831 | 1.00 | 29.69 |
| ATOM | 1100 | O ALA | 352 | 56.711 | 8.753 | 24.982 | 1.00 | 30.36 |
| ATOM | 1101 | N ILE | 353 | 56.557 | 7.979 | 22.876 | 1.00 | 27.63 |
| ATOM | 1102 | CA ILE | 353 | 55.345 | 7.227 | 23.129 | 1.00 | 27.55 |
| ATOM | 1103 | CB ILE | 353 | 54.611 | 6.925 | 21.805 | 1.00 | 28.04 |
| ATOM | 1104 | CG2 ILE | 353 | 53.329 | 6.111 | 22.065 | 1.00 | 23.68 |
| ATOM | 1105 | CG1 ILE | 353 | 54.269 | 8.251 | 21.119 | 1.00 | 27.33 |
| ATOM | 1106 | CD1 ILE | 353 | 53.637 | 8.105 | 19.734 | 1.00 | 26.23 |
| ATOM | 1107 | C ILE | 353 | 55.631 | 5.943 | 23.901 | 1.00 | 30.88 |
| ATOM | 1108 | O ILE | 353 | 54.880 | 5.597 | 24.814 | 1.00 | 31.22 |
| ATOM | 1109 | N PHE | 354 | 56.710 | 5.240 | 23.549 | 1.00 | 29.86 |
| ATOM | 1110 | CA PHE | 354 | 57.056 | 4.022 | 24.275 | 1.00 | 31.08 |
| ATOM | 1111 | CB PHE | 354 | 58.227 | 3.274 | 23.619 | 1.00 | 28.80 |
| ATOM | 1112 | CG PHE | 354 | 57.799 | 2.322 | 22.523 | 1.00 | 28.80 |
| ATOM | 1113 | CD1 PHE | 354 | 57.330 | 2.804 | 21.292 | 1.00 | 30.96 |
| ATOM | 1114 | CD2 PHE | 354 | 57.811 | 0.939 | 22.749 | 1.00 | 29.45 |
| ATOM | 1115 | CE1 PHE | 354 | 56.864 | 1.909 | 20.281 | 1.00 | 27.12 |
| ATOM | 1116 | CE2 PHE | 354 | 57.354 | 0.026 | 21.761 | 1.00 | 25.19 |
| ATOM | 1117 | CZ PHE | 354 | 56.879 | 0.518 | 20.521 | 1.00 | 28.09 |
| ATOM | 1118 | C PHE | 354 | 57.398 | 4.349 | 25.721 | 1.00 | 29.17 |
| ATOM | 1119 | O PHE | 354 | 57.001 | 3.625 | 26.631 | 1.00 | 32.62 |
| ATOM | 1120 | N ASP | 355 | 58.133 | 5.438 | 25.925 | 1.00 | 23.86 |
| ATOM | 1121 | CA ASP | 355 | 58.508 | 5.873 | 27.262 | 1.00 | 25.34 |
| ATOM | 1122 | CB ASP | 355 | 59.434 | 7.083 | 27.180 | 1.00 | 21.41 |
| ATOM | 1123 | CG ASP | 355 | 60.846 | 6.708 | 26.769 | 1.00 | 32.08 |
| ATOM | 1124 | OD1 ASP | 355 | 61.051 | 5.595 | 26.226 | 1.00 | 33.58 |
| ATOM | 1125 | OD2 ASP | 355 | 61.756 | 7.534 | 26.970 | 1.00 | 33.20 |
| ATOM | 1126 | C ASP | 355 | 57.254 | 6.211 | 28.062 | 1.00 | 27.86 |
| ATOM | 1127 | O ASP | 355 | 57.167 | 5.916 | 29.252 | 1.00 | 32.42 |
| ATOM | 1128 | N LEU | 356 | 56.276 | 6.821 | 27.401 | 1.00 | 26.84 |
| ATOM | 1129 | CA LEU | 356 | 55.031 | 7.164 | 28.066 | 1.00 | 28.66 |
| ATOM | 1130 | CB LEU | 356 | 54.112 | 7.953 | 27.131 | 1.00 | 25.37 |
| ATOM | 1131 | CG LEU | 356 | 52.787 | 8.427 | 27.742 | 1.00 | 27.61 |
| ATOM | 1132 | CD1 LEU | 356 | 53.056 | 9.452 | 28.842 | 1.00 | 25.43 |
| ATOM | 1133 | CD2 LEU | 356 | 51.924 | 9.057 | 26.667 | 1.00 | 27.49 |
| ATOM | 1134 | C LEU | 356 | 54.334 | 5.875 | 28.473 | 1.00 | 30.44 |
| ATOM | 1135 | O LEU | 356 | 53.873 | 5.743 | 29.601 | 1.00 | 31.55 |
| ATOM | 1136 | N GLY | 357 | 54.266 | 4.928 | 27.536 | 1.00 | 32.69 |
| ATOM | 1137 | CA GLY | 357 | 53.621 | 3.652 | 27.787 | 1.00 | 29.87 |
| ATOM | 1138 | C GLY | 357 | 54.239 | 2.884 | 28.939 | 1.00 | 33.12 |
| ATOM | 1139 | O GLY | 357 | 53.524 | 2.268 | 29.732 | 1.00 | 29.41 |
| ATOM | 1140 | N MET | 358 | 55.570 | 2.911 | 29.026 | 1.00 | 33.31 |
| ATOM | 1141 | CA MET | 358 | 56.277 | 2.217 | 30.100 | 1.00 | 35.87 |
| ATOM | 1142 | CB MET | 358 | 57.794 | 2.265 | 29.871 | 1.00 | 34.56 |
| ATOM | 1143 | CG MET | 358 | 58.265 | 1.608 | 28.576 | 1.00 | 46.43 |
| ATOM | 1144 | SD MET | 358 | 60.073 | 1.600 | 28.351 | 1.00 | 42.13 |
| ATOM | 1145 | CE MET | 358 | 60.429 | 3.306 | 28.411 | 1.00 | 44.29 |
| ATOM | 1146 | C MET | 358 | 55.948 | 2.884 | 31.434 | 1.00 | 33.26 |
| ATOM | 1147 | O MET | 358 | 55.802 | 2.222 | 32.453 | 1.00 | 36.39 |
| ATOM | 1148 | N SER | 359 | 55.825 | 4.202 | 31.398 | 1.00 | 33.31 |
| ATOM | 1149 | CA SER | 359 | 55.533 | 4.998 | 32.580 | 1.00 | 34.39 |
| ATOM | 1150 | CB SER | 359 | 55.859 | 6.463 | 32.303 | 1.00 | 30.84 |
| ATOM | 1151 | OG SER | 359 | 55.487 | 7.265 | 33.404 | 1.00 | 47.14 |
| ATOM | 1152 | C SER | 359 | 54.094 | 4.897 | 33.072 | 1.00 | 36.43 |
| ATOM | 1153 | O SER | 359 | 53.833 | 5.073 | 34.260 | 1.00 | 35.46 |
| ATOM | 1154 | N LEU | 360 | 53.165 | 4.617 | 32.156 | 1.00 | 36.74 |
| ATOM | 1155 | CA LEU | 360 | 51.750 | 4.519 | 32.493 | 1.00 | 35.44 |
| ATOM | 1156 | CB LEU | 360 | 50.889 | 4.817 | 31.263 | 1.00 | 34.16 |
| ATOM | 1157 | CG LEU | 360 | 50.896 | 6.263 | 30.751 | 1.00 | 34.59 |
| ATOM | 1158 | CD1 LEU | 360 | 50.031 | 6.353 | 29.513 | 1.00 | 33.53 |
| ATOM | 1159 | CD2 LEU | 360 | 50.376 | 7.211 | 31.836 | 1.00 | 31.69 |
| ATOM | 1160 | C LEU | 360 | 51.324 | 3.192 | 33.088 | 1.00 | 38.72 |
| ATOM | 1161 | O LEU | 360 | 50.185 | 3.058 | 33.546 | 1.00 | 38.29 |
| ATOM | 1162 | N SER | 361 | 52.227 | 2.214 | 33.080 | 1.00 | 40.96 |
| ATOM | 1163 | CA SER | 361 | 51.938 | 0.897 | 33.636 | 1.00 | 45.67 |
| ATOM | 1164 | CB SER | 361 | 53.131 | -0.044 | 33.436 | 1.00 | 46.45 |
| ATOM | 1165 | OG SER | 361 | 53.362 | -0.296 | 32.061 | 1.00 | 51.81 |
| ATOM | 1166 | C SER | 361 | 51.628 | 1.004 | 35.124 | 1.00 | 44.49 |
| ATOM | 1167 | O SER | 361 | 50.724 | 0.337 | 35.630 | 1.00 | 46.67 |
| ATOM | 1168 | N SER | 362 | 52.385 | 1.858 | 35.809 | 1.00 | 41.44 |
| ATOM | 1169 | CA SER | 362 | 52.231 | 2.081 | 37.245 | 1.00 | 42.13 |
| ATOM | 1170 | CB SER | 362 | 53.431 | 2.876 | 37.779 | 1.00 | 42.61 |
| ATOM | 1171 | OG SER | 362 | 54.647 | 2.215 | 37.492 | 1.00 | 51.87 |
| ATOM | 1172 | C SER | 362 | 50.951 | 2.832 | 37.610 | 1.00 | 38.41 |
| ATOM | 1173 | O SER | 362 | 50.444 | 2.700 | 38.722 | 1.00 | 38.01 |
| ATOM | 1174 | N PHE | 363 | 50.443 | 3.631 | 36.672 | 1.00 | 34.55 |
| ATOM | 1175 | CA PHE | 363 | 49.232 | 4.404 | 36.906 | 1.00 | 32.96 |
| ATOM | 1176 | CB PHE | 363 | 49.109 | 5.518 | 35.859 | 1.00 | 31.99 |
| ATOM | 1177 | CG PHE | 363 | 50.093 | 6.659 | 36.058 | 1.00 | 29.97 |
| ATOM | 1178 | CD1 PHE | 363 | 49.667 | 7.872 | 36.594 | 1.00 | 30.61 |
| ATOM | 1179 | CD2 PHE | 363 | 51.445 | 6.501 | 35.731 | 1.00 | 32.02 |
| ATOM | 1180 | CE1 PHE | 363 | 50.579 | 8.940 | 36.803 | 1.00 | 33.67 |
| ATOM | 1181 | CE2 PHE | 363 | 52.376 | 7.552 | 35.934 | 1.00 | 30.91 |
| ATOM | 1182 | CZ PHE | 363 | 51.938 | 8.777 | 36.473 | 1.00 | 29.33 |
| ATOM | 1183 | C PHE | 363 | 47.973 | 3.554 | 36.916 | 1.00 | 30.52 |
| ATOM | 1184 | O PHE | 363 | 46.971 | 3.947 | 37.491 | 1.00 | 32.19 |
| ATOM | 1185 | N ASN | 364 | 48.036 | 2.384 | 36.283 | 1.00 | 33.51 |
| ATOM | 1186 | CA ASN | 364 | 46.894 | 1.471 | 36.216 | 1.00 | 38.03 |
| ATOM | 1187 | CB ASN | 364 | 46.754 | 0.711 | 37.539 | 1.00 | 42.32 |
| ATOM | 1188 | CG ASN | 364 | 47.824 | -0.361 | 37.713 | 1.00 | 53.11 |
| ATOM | 1189 | OD1 ASN | 364 | 47.815 | -1.370 | 37.012 | 1.00 | 59.51 |
| ATOM | 1190 | ND2 ASN | 364 | 48.751 | -0.138 | 38.639 | 1.00 | 55.95 |
| ATOM | 1191 | C ASN | 364 | 45.574 | 2.161 | 35.871 | 1.00 | 31.89 |
| ATOM | 1192 | O ASN | 364 | 44.587 | 2.027 | 36.588 | 1.00 | 30.28 |
| ATOM | 1193 | N LEU | 365 | 45.561 | 2.883 | 34.751 | 1.00 | 27.62 |
| ATOM | 1194 | CA LEU | 365 | 44.365 | 3.606 | 34.317 | 1.00 | 29.36 |
| ATOM | 1195 | CB LEU | 365 | 44.738 | 4.627 | 33.240 | 1.00 | 27.54 |
| ATOM | 1196 | CG LEU | 365 | 45.826 | 5.659 | 33.576 | 1.00 | 38.91 |
| ATOM | 1197 | CD1 LEU | 365 | 46.115 | 6.499 | 32.338 | 1.00 | 34.47 |
| ATOM | 1198 | CD2 LEU | 365 | 45.394 | 6.546 | 34.743 | 1.00 | 34.24 |
| ATOM | 1199 | C LEU | 365 | 43.264 | 2.691 | 33.774 | 1.00 | 26.23 |
| ATOM | 1200 | O LEU | 365 | 43.546 | 1.648 | 33.197 | 1.00 | 27.06 |
| ATOM | 1201 | N ASP | 366 | 42.011 | 3.074 | 33.991 | 1.00 | 25.23 |
| ATOM | 1202 | CA ASP | 366 | 40.892 | 2.307 | 33.462 | 1.00 | 26.07 |
| ATOM | 1203 | CB ASP | 366 | 39.832 | 2.008 | 34.538 | 1.00 | 29.68 |
| ATOM | 1204 | CG ASP | 366 | 39.337 | 3.253 | 35.261 | 1.00 | 35.74 |
| ATOM | 1205 | OD1 ASP | 366 | 39.438 | 4.371 | 34.717 | 1.00 | 36.78 |
| ATOM | 1206 | OD2 ASP | 366 | 38.803 | 3.100 | 36.378 | 1.00 | 41.23 |
| ATOM | 1207 | C ASP | 366 | 40.274 | 3.100 | 32.305 | 1.00 | 27.70 |
| ATOM | 1208 | O ASP | 366 | 40.748 | 4.191 | 31.975 | 1.00 | 31.94 |
| ATOM | 1209 | N ASP | 367 | 39.223 | 2.564 | 31.693 | 1.00 | 29.18 |
| ATOM | 1210 | CA ASP | 367 | 38.594 | 3.233 | 30.560 | 1.00 | 32.72 |
| ATOM | 1211 | CB ASP | 367 | 37.428 | 2.395 | 30.018 | 1.00 | 38.04 |
| ATOM | 1212 | CG ASP | 367 | 37.855 | 0.995 | 29.606 | 1.00 | 42.43 |
| ATOM | 1213 | OD1 ASP | 367 | 38.913 | 0.852 | 28.956 | 1.00 | 35.95 |
| ATOM | 1214 | OD2 ASP | 367 | 37.115 | 0.034 | 29.917 | 1.00 | 51.42 |
| ATOM | 1215 | C ASP | 367 | 38.093 | 4.631 | 30.881 | 1.00 | 33.71 |
| ATOM | 1216 | O ASP | 367 | 38.059 | 5.506 | 30.013 | 1.00 | 38.30 |
| ATOM | 1217 | N THR | 368 | 37.705 | 4.852 | 32.132 | 1.00 | 31.06 |
| ATOM | 1218 | CA THR | 368 | 37.199 | 6.155 | 32.543 | 1.00 | 26.28 |
| ATOM | 1219 | CB THR | 368 | 36.537 | 6.066 | 33.922 | 1.00 | 27.30 |
| ATOM | 1220 | OG1 THR | 368 | 35.461 | 5.127 | 33.861 | 1.00 | 33.42 |
| ATOM | 1221 | CG2 THR | 368 | 36.003 | 7.423 | 34.355 | 1.00 | 25.16 |
| ATOM | 1222 | C THR | 368 | 38.303 | 7.194 | 32.593 | 1.00 | 21.13 |
| ATOM | 1223 | O THR | 368 | 38.133 | 8.314 | 32.104 | 1.00 | 23.17 |
| ATOM | 1224 | N GLU | 369 | 39.431 | 6.816 | 33.179 | 1.00 | 21.32 |
| ATOM | 1225 | CA GLU | 369 | 40.565 | 7.720 | 33.317 | 1.00 | 28.00 |
| ATOM | 1226 | CB GLU | 369 | 41.582 | 7.107 | 34.277 | 1.00 | 32.79 |
| ATOM | 1227 | CG GLU | 369 | 40.944 | 6.804 | 35.619 | 1.00 | 36.29 |
| ATOM | 1228 | CD GLU | 369 | 41.834 | 6.026 | 36.546 | 1.00 | 41.03 |
| ATOM | 1229 | OE1 GLU | 369 | 42.361 | 4.967 | 36.123 | 1.00 | 42.05 |
| ATOM | 1230 | OE2 GLU | 369 | 41.986 | 6.458 | 37.705 | 1.00 | 42.03 |
| ATOM | 1231 | C GLU | 369 | 41.201 | 8.047 | 31.970 | 1.00 | 25.57 |
| ATOM | 1232 | O GLU | 369 | 41.626 | 9.175 | 31.741 | 1.00 | 20.56 |
| ATOM | 1233 | N VAL | 370 | 41.249 | 7.055 | 31.080 | 1.00 | 25.39 |
| ATOM | 1234 | CA VAL | 370 | 41.794 | 7.278 | 29.745 | 1.00 | 25.99 |
| ATOM | 1235 | CB VAL | 370 | 42.005 | 5.936 | 28.977 | 1.00 | 26.15 |
| ATOM | 1236 | CG1 VAL | 370 | 42.450 | 6.216 | 27.539 | 1.00 | 27.65 |
| ATOM | 1237 | CG2 VAL | 370 | 43.056 | 5.086 | 29.685 | 1.00 | 17.70 |
| ATOM | 1238 | C VAL | 370 | 40.814 | 8.164 | 28.966 | 1.00 | 26.49 |
| ATOM | 1239 | O VAL | 370 | 41.226 | 9.038 | 28.202 | 1.00 | 28.16 |
| ATOM | 1240 | N ALA | 371 | 39.514 | 7.950 | 29.184 | 1.00 | 21.01 |
| ATOM | 1241 | CA ALA | 371 | 38.486 | 8.730 | 28.510 | 1.00 | 19.57 |
| ATOM | 1242 | CB ALA | 371 | 37.116 | 8.136 | 28.783 | 1.00 | 18.62 |
| ATOM | 1243 | C ALA | 371 | 38.512 | 10.191 | 28.947 | 1.00 | 23.48 |
| ATOM | 1244 | O ALA | 371 | 38.500 | 11.103 | 28.111 | 1.00 | 32.67 |
| ATOM | 1245 | N LEU | 372 | 38.540 | 10.414 | 30.256 | 1.00 | 22.89 |
| ATOM | 1246 | CA LEU | 372 | 38.560 | 11.772 | 30.806 | 1.00 | 23.28 |

APPENDIX 8-continued

TRBGC1.PDB

| ATOM | 1247 | CB LEU | 372 | 38.517 | 11.709 | 32.343 | 1.00 | 27.76 |
| --- | --- | --- | --- | --- | --- | --- | --- | --- |
| ATOM | 1248 | CG LEU | 372 | 37.155 | 11.306 | 32.924 | 1.00 | 21.18 |
| ATOM | 1249 | CD1 LEU | 372 | 37.289 | 10.891 | 34.381 | 1.00 | 27.64 |
| ATOM | 1250 | CD2 LEU | 372 | 36.197 | 12.480 | 32.763 | 1.00 | 20.90 |
| ATOM | 1251 | C LEU | 372 | 39.804 | 12.505 | 30.357 | 1.00 | 21.34 |
| ATOM | 1252 | O LEU | 372 | 39.779 | 13.708 | 30.086 | 1.00 | 23.16 |
| ATOM | 1253 | N LEU | 373 | 40.896 | 11.761 | 30.276 | 1.00 | 24.42 |
| ATOM | 1254 | CA LEU | 373 | 42.177 | 12.302 | 29.855 | 1.00 | 23.78 |
| ATOM | 1255 | CB LEU | 373 | 43.222 | 11.205 | 30.007 | 1.00 | 22.18 |
| ATOM | 1256 | CG LEU | 373 | 44.724 | 11.456 | 30.036 | 1.00 | 31.52 |
| ATOM | 1257 | CD1 LEU | 373 | 45.099 | 12.565 | 31.001 | 1.00 | 31.93 |
| ATOM | 1258 | CD2 LEU | 373 | 45.382 | 10.152 | 30.460 | 1.00 | 30.24 |
| ATOM | 1259 | C LEU | 373 | 42.025 | 12.757 | 28.399 | 1.00 | 25.69 |
| ATOM | 1260 | O LEU | 373 | 42.469 | 13.842 | 28.025 | 1.00 | 30.13 |
| ATOM | 1261 | N GLN | 374 | 41.370 | 11.934 | 27.587 | 1.00 | 26.24 |
| ATOM | 1262 | CA GLN | 374 | 41.151 | 12.269 | 26.184 | 1.00 | 21.60 |
| ATOM | 1263 | CB GLN | 374 | 40.501 | 11.091 | 25.444 | 1.00 | 24.57 |
| ATOM | 1264 | CG GLN | 374 | 41.428 | 9.900 | 25.234 | 1.00 | 21.02 |
| ATOM | 1265 | CD GLN | 374 | 40.762 | 8.744 | 24.501 | 1.00 | 22.86 |
| ATOM | 1266 | OE1 GLN | 374 | 41.407 | 7.754 | 24.174 | 1.00 | 24.07 |
| ATOM | 1267 | NE2 GLN | 374 | 39.466 | 8.865 | 24.249 | 1.00 | 25.59 |
| ATOM | 1268 | C GLN | 374 | 40.267 | 13.498 | 26.070 | 1.00 | 20.66 |
| ATOM | 1269 | O GLN | 374 | 40.518 | 14.366 | 25.242 | 1.00 | 24.47 |
| ATOM | 1270 | N ALA | 375 | 39.237 | 13.579 | 26.902 | 1.00 | 16.26 |
| ATOM | 1271 | CA ALA | 375 | 38.337 | 14.727 | 26.870 | 1.00 | 17.16 |
| ATOM | 1272 | CB ALA | 375 | 37.156 | 14.491 | 27.803 | 1.00 | 19.53 |
| ATOM | 1273 | C ALA | 375 | 39.056 | 16.024 | 27.252 | 1.00 | 25.13 |
| ATOM | 1274 | O ALA | 375 | 38.722 | 17.100 | 26.750 | 1.00 | 23.81 |
| ATOM | 1275 | N VAL | 376 | 40.036 | 15.926 | 28.156 | 1.00 | 24.57 |
| ATOM | 1276 | CA VAL | 376 | 40.796 | 17.101 | 28.568 | 1.00 | 25.80 |
| ATOM | 1277 | CB VAL | 376 | 41.711 | 16.792 | 29.814 | 1.00 | 26.48 |
| ATOM | 1278 | CG1 VAL | 376 | 42.625 | 17.971 | 30.102 | 1.00 | 23.20 |
| ATOM | 1279 | CG2 VAL | 376 | 40.845 | 16.521 | 31.044 | 1.00 | 19.08 |
| ATOM | 1280 | C VAL | 376 | 41.653 | 17.580 | 27.396 | 1.00 | 25.69 |
| ATOM | 1281 | O VAL | 376 | 41.775 | 18.780 | 27.151 | 1.00 | 27.87 |
| ATOM | 1282 | N LEU | 377 | 42.249 | 16.637 | 26.666 | 1.00 | 23.09 |
| ATOM | 1283 | CA LEU | 377 | 43.071 | 16.982 | 25.513 | 1.00 | 22.86 |
| ATOM | 1284 | CB LEU | 377 | 43.748 | 15.730 | 24.962 | 1.00 | 18.50 |
| ATOM | 1285 | CG LEU | 377 | 44.814 | 15.096 | 25.867 | 1.00 | 22.65 |
| ATOM | 1286 | CD1 LEU | 377 | 45.144 | 13.708 | 25.374 | 1.00 | 16.70 |
| ATOM | 1287 | CD2 LEU | 377 | 46.070 | 15.987 | 25.901 | 1.00 | 19.58 |
| ATOM | 1288 | C LEU | 377 | 42.197 | 17.634 | 24.430 | 1.00 | 26.14 |
| ATOM | 1289 | O LEU | 377 | 42.579 | 18.638 | 23.830 | 1.00 | 20.62 |
| ATOM | 1290 | N LEU | 378 | 41.016 | 17.057 | 24.208 | 1.00 | 28.99 |
| ATOM | 1291 | CA LEU | 378 | 40.076 | 17.578 | 23.218 | 1.00 | 28.87 |
| ATOM | 1292 | CB LEU | 378 | 38.814 | 16.710 | 23.182 | 1.00 | 26.89 |
| ATOM | 1293 | CG LEU | 378 | 37.637 | 17.167 | 22.311 | 1.00 | 28.83 |
| ATOM | 1294 | CD1 LEU | 378 | 38.053 | 17.273 | 20.840 | 1.00 | 27.97 |
| ATOM | 1295 | CD2 LEU | 378 | 36.496 | 16.175 | 22.478 | 1.00 | 27.69 |
| ATOM | 1296 | C LEU | 378 | 39.693 | 19.025 | 23.504 | 1.00 | 31.09 |
| ATOM | 1297 | O LEU | 378 | 39.812 | 19.883 | 22.629 | 1.00 | 31.77 |
| ATOM | 1298 | N MET | 379 | 39.247 | 19.297 | 24.729 | 1.00 | 31.44 |
| ATOM | 1299 | CA MET | 379 | 38.841 | 20.649 | 25.104 | 1.00 | 32.62 |
| ATOM | 1300 | CB MET | 379 | 37.876 | 20.603 | 26.293 | 1.00 | 31.45 |
| ATOM | 1301 | CG MET | 379 | 36.586 | 19.855 | 26.010 | 1.00 | 38.75 |
| ATOM | 1302 | SD MET | 379 | 35.646 | 20.541 | 24.601 | 1.00 | 41.27 |
| ATOM | 1303 | CE MET | 379 | 34.231 | 19.443 | 24.609 | 1.00 | 35.68 |
| ATOM | 1304 | C MET | 379 | 39.980 | 21.613 | 25.421 | 1.00 | 33.72 |
| ATOM | 1305 | O MET | 379 | 39.940 | 22.297 | 26.446 | 1.00 | 36.29 |
| ATOM | 1306 | N SER | 380 | 40.981 | 21.676 | 24.543 | 1.00 | 34.49 |
| ATOM | 1307 | CA SER | 380 | 42.116 | 22.585 | 24.721 | 1.00 | 33.97 |
| ATOM | 1308 | CB SER | 380 | 43.371 | 22.025 | 24.061 | 1.00 | 31.24 |
| ATOM | 1309 | OG SER | 380 | 43.771 | 20.814 | 24.674 | 1.00 | 39.42 |
| ATOM | 1310 | C SER | 380 | 41.772 | 23.926 | 24.088 | 1.00 | 39.69 |
| ATOM | 1311 | O SER | 380 | 41.787 | 24.069 | 22.864 | 1.00 | 44.64 |
| ATOM | 1312 | N SER | 381 | 41.472 | 24.907 | 24.927 | 1.00 | 41.04 |
| ATOM | 1313 | CA SER | 381 | 41.090 | 26.234 | 24.462 | 1.00 | 44.91 |
| ATOM | 1314 | CB SER | 381 | 40.406 | 27.004 | 25.594 | 1.00 | 44.50 |
| ATOM | 1315 | OG SER | 381 | 41.294 | 27.177 | 26.678 | 1.00 | 45.42 |
| ATOM | 1316 | C SER | 381 | 42.231 | 27.084 | 23.921 | 1.00 | 44.59 |
| ATOM | 1317 | O SER | 381 | 42.012 | 28.227 | 23.516 | 1.00 | 49.32 |
| ATOM | 1318 | N ASP | 382 | 43.440 | 26.541 | 23.896 | 1.00 | 43.75 |
| ATOM | 1319 | CA ASP | 382 | 44.571 | 27.315 | 23.407 | 1.00 | 43.93 |
| ATOM | 1320 | CB ASP | 382 | 45.817 | 27.047 | 24.257 | 1.00 | 48.39 |
| ATOM | 1321 | CG ASP | 382 | 46.319 | 25.632 | 24.113 | 1.00 | 53.23 |
| ATOM | 1322 | OD1 ASP | 382 | 45.590 | 24.702 | 24.517 | 1.00 | 56.97 |
| ATOM | 1323 | OD2 ASP | 382 | 47.440 | 25.449 | 23.584 | 1.00 | 58.91 |
| ATOM | 1324 | C ASP | 382 | 44.900 | 27.026 | 21.955 | 1.00 | 41.09 |
| ATOM | 1325 | O ASP | 382 | 45.912 | 27.502 | 21.446 | 1.00 | 40.93 |
| ATOM | 1326 | N ARG | 383 | 44.068 | 26.236 | 21.287 | 1.00 | 42.63 |
| ATOM | 1327 | CA ARG | 383 | 44.316 | 25.937 | 19.876 | 1.00 | 43.32 |
| ATOM | 1328 | CB ARG | 383 | 43.289 | 24.935 | 19.331 | 1.00 | 42.31 |
| ATOM | 1329 | CG ARG | 383 | 43.174 | 23.619 | 20.095 | 1.00 | 40.83 |
| ATOM | 1330 | CD ARG | 383 | 44.478 | 22.835 | 20.139 | 1.00 | 38.09 |
| ATOM | 1331 | NE ARG | 383 | 44.271 | 21.542 | 20.787 | 1.00 | 37.33 |
| ATOM | 1332 | CZ ARG | 383 | 45.235 | 20.690 | 21.115 | 1.00 | 38.35 |
| ATOM | 1333 | NH1 ARG | 383 | 46.505 | 20.972 | 20.850 | 1.00 | 33.70 |
| ATOM | 1334 | NH2 ARG | 383 | 44.922 | 19.545 | 21.704 | 1.00 | 35.46 |
| ATOM | 1335 | C ARG | 383 | 44.166 | 27.256 | 19.127 | 1.00 | 44.96 |
| ATOM | 1336 | O ARG | 383 | 43.214 | 28.006 | 19.361 | 1.00 | 45.60 |
| ATOM | 1337 | N PRO | 384 | 45.112 | 27.574 | 18.230 | 1.00 | 45.33 |
| ATOM | 1338 | CD PRO | 384 | 46.330 | 26.852 | 17.836 | 1.00 | 46.85 |
| ATOM | 1339 | CA PRO | 384 | 45.024 | 28.830 | 17.484 | 1.00 | 47.37 |
| ATOM | 1340 | CB PRO | 384 | 46.323 | 28.823 | 16.672 | 1.00 | 46.90 |
| ATOM | 1341 | CG PRO | 384 | 47.257 | 27.998 | 17.552 | 1.00 | 46.41 |
| ATOM | 1342 | C PRO | 384 | 43.788 | 28.910 | 16.590 | 1.00 | 48.29 |
| ATOM | 1343 | O PRO | 384 | 43.394 | 27.927 | 15.960 | 1.00 | 48.34 |
| ATOM | 1344 | N GLY | 385 | 43.176 | 30.090 | 16.552 | 1.00 | 49.88 |
| ATOM | 1345 | CA GLY | 385 | 42.013 | 30.290 | 15.712 | 1.00 | 50.35 |
| ATOM | 1346 | C GLY | 385 | 40.669 | 29.958 | 16.324 | 1.00 | 50.70 |
| ATOM | 1347 | O GLY | 385 | 39.639 | 30.201 | 15.697 | 1.00 | 53.48 |
| ATOM | 1348 | N LEU | 386 | 40.663 | 29.404 | 17.529 | 1.00 | 49.04 |
| ATOM | 1349 | CA LEU | 386 | 39.405 | 29.057 | 18.182 | 1.00 | 50.53 |
| ATOM | 1350 | CB LEU | 386 | 39.655 | 28.433 | 19.558 | 1.00 | 45.17 |
| ATOM | 1351 | CG LEU | 386 | 40.245 | 27.019 | 19.544 | 1.00 | 48.26 |
| ATOM | 1352 | CD1 LEU | 386 | 40.502 | 26.564 | 20.970 | 1.00 | 41.68 |
| ATOM | 1353 | CD2 LEU | 386 | 39.285 | 26.065 | 18.836 | 1.00 | 38.40 |
| ATOM | 1354 | C LEU | 386 | 38.495 | 30.268 | 18.319 | 1.00 | 52.13 |
| ATOM | 1355 | O LEU | 386 | 38.955 | 31.395 | 18.476 | 1.00 | 53.67 |
| ATOM | 1356 | N ALA | 387 | 37.193 | 30.020 | 18.261 | 1.00 | 53.42 |
| ATOM | 1357 | CA ALA | 387 | 36.225 | 31.093 | 18.354 | 1.00 | 56.01 |
| ATOM | 1358 | CB ALA | 387 | 35.221 | 30.976 | 17.202 | 1.00 | 56.47 |
| ATOM | 1359 | C ALA | 387 | 35.482 | 31.144 | 19.681 | 1.00 | 55.52 |
| ATOM | 1360 | O ALA | 387 | 35.491 | 32.171 | 20.358 | 1.00 | 53.75 |
| ATOM | 1361 | N CYS | 388 | 34.854 | 30.038 | 20.065 | 1.00 | 56.03 |
| ATOM | 1362 | CA CYS | 388 | 34.072 | 30.036 | 21.312 | 1.00 | 59.57 |
| ATOM | 1363 | CB CYS | 388 | 32.724 | 29.351 | 21.089 | 1.00 | 59.23 |
| ATOM | 1364 | SG CYS | 388 | 31.314 | 30.363 | 21.641 | 1.00 | 58.64 |
| ATOM | 1365 | C CYS | 388 | 34.846 | 29.289 | 22.398 | 1.00 | 62.18 |
| ATOM | 1366 | O CYS | 388 | 34.458 | 28.190 | 22.790 | 1.00 | 67.88 |
| ATOM | 1367 | N VAL | 389 | 35.955 | 29.950 | 22.760 | 1.00 | 60.78 |
| ATOM | 1368 | CA VAL | 389 | 37.005 | 29.583 | 23.713 | 1.00 | 57.70 |
| ATOM | 1369 | CB VAL | 389 | 38.202 | 30.580 | 23.565 | 1.00 | 57.09 |
| ATOM | 1370 | CG1 VAL | 389 | 39.351 | 30.194 | 24.494 | 1.00 | 59.03 |
| ATOM | 1371 | CG2 VAL | 389 | 38.671 | 30.618 | 22.124 | 1.00 | 53.98 |
| ATOM | 1372 | C VAL | 389 | 36.661 | 29.515 | 25.195 | 1.00 | 57.77 |
| ATOM | 1373 | O VAL | 389 | 36.943 | 28.513 | 25.851 | 1.00 | 60.94 |
| ATOM | 1374 | N GLU | 390 | 36.102 | 30.594 | 25.732 | 1.00 | 52.68 |
| ATOM | 1375 | CA GLU | 390 | 35.738 | 30.636 | 27.138 | 1.00 | 48.41 |
| ATOM | 1376 | CB GLU | 390 | 35.001 | 31.928 | 27.451 | 1.00 | 45.19 |
| ATOM | 1377 | C GLU | 390 | 34.868 | 29.439 | 27.459 | 1.00 | 47.63 |
| ATOM | 1378 | O GLU | 390 | 34.986 | 28.837 | 28.529 | 1.00 | 51.95 |
| ATOM | 1379 | N ARG | 391 | 34.002 | 29.082 | 26.517 | 1.00 | 47.11 |
| ATOM | 1380 | CA ARG | 391 | 33.099 | 27.950 | 26.699 | 1.00 | 51.64 |
| ATOM | 1381 | CB ARG | 391 | 32.050 | 27.930 | 25.588 | 1.00 | 54.22 |
| ATOM | 1382 | CG ARG | 391 | 30.830 | 27.094 | 25.915 | 1.00 | 64.20 |
| ATOM | 1383 | CD ARG | 391 | 29.867 | 27.074 | 24.748 | 1.00 | 73.80 |
| ATOM | 1384 | NE ARG | 391 | 28.533 | 26.622 | 25.128 | 1.00 | 79.76 |
| ATOM | 1385 | CZ ARG | 391 | 27.714 | 27.298 | 25.929 | 1.00 | 84.27 |
| ATOM | 1386 | NH1 ARG | 391 | 28.090 | 28.465 | 26.439 | 1.00 | 85.28 |
| ATOM | 1387 | NH2 ARG | 391 | 26.515 | 26.809 | 26.217 | 1.00 | 86.84 |
| ATOM | 1388 | C ARG | 391 | 33.890 | 26.644 | 26.684 | 1.00 | 48.18 |
| ATOM | 1389 | O ARG | 391 | 33.504 | 25.671 | 27.330 | 1.00 | 49.57 |
| ATOM | 1390 | N ILE | 392 | 34.987 | 26.625 | 25.936 | 1.00 | 45.01 |
| ATOM | 1391 | CA ILE | 392 | 35.835 | 25.440 | 25.858 | 1.00 | 48.77 |
| ATOM | 1392 | CB ILE | 392 | 36.854 | 25.565 | 24.692 | 1.00 | 46.45 |
| ATOM | 1393 | CG2 ILE | 392 | 37.798 | 24.370 | 24.679 | 1.00 | 42.35 |
| ATOM | 1394 | CG1 ILE | 392 | 36.086 | 25.664 | 23.367 | 1.00 | 49.69 |
| ATOM | 1395 | CD1 ILE | 392 | 36.950 | 25.897 | 22.136 | 1.00 | 51.09 |
| ATOM | 1396 | C ILE | 392 | 36.570 | 25.246 | 27.192 | 1.00 | 50.90 |
| ATOM | 1397 | O ILE | 392 | 36.731 | 24.118 | 27.657 | 1.00 | 52.21 |
| ATOM | 1398 | N GLU | 393 | 36.999 | 26.346 | 27.811 | 1.00 | 50.43 |
| ATOM | 1399 | CA GLU | 393 | 37.673 | 26.267 | 29.101 | 1.00 | 50.30 |
| ATOM | 1400 | CB GLU | 393 | 38.202 | 27.638 | 29.531 | 1.00 | 53.97 |

APPENDIX 8-continued

TRBGC1.PDB

| ATOM | 1401 | CG GLU | 393 | 39.322 | 28.168 | 28.658 | 1.00 | 62.18 |
|------|------|--------|-----|--------|--------|--------|------|-------|
| ATOM | 1402 | CD GLU | 393 | 39.911 | 29.478 | 29.168 | 1.00 | 67.69 |
| ATOM | 1403 | OE1 GLU | 393 | 40.869 | 29.977 | 28.537 | 1.00 | 66.42 |
| ATOM | 1404 | OE2 GLU | 393 | 39.423 | 30.009 | 30.191 | 1.00 | 70.64 |
| ATOM | 1405 | C GLU | 393 | 36.686 | 25.765 | 30.145 | 1.00 | 49.31 |
| ATOM | 1406 | O GLU | 393 | 37.018 | 24.923 | 30.980 | 1.00 | 49.53 |
| ATOM | 1407 | N LYS | 394 | 35.468 | 26.286 | 30.090 | 1.00 | 46.07 |
| ATOM | 1408 | CA LYS | 394 | 34.428 | 25.893 | 31.022 | 1.00 | 45.76 |
| ATOM | 1409 | CB LYS | 394 | 33.147 | 26.666 | 30.727 | 1.00 | 43.85 |
| ATOM | 1410 | C LYS | 394 | 34.188 | 24.391 | 30.909 | 1.00 | 46.69 |
| ATOM | 1411 | O LYS | 394 | 33.982 | 23.699 | 31.911 | 1.00 | 49.13 |
| ATOM | 1412 | N TYR | 395 | 34.223 | 23.887 | 29.679 | 1.00 | 46.57 |
| ATOM | 1413 | CA TYR | 395 | 34.014 | 22.467 | 29.427 | 1.00 | 43.33 |
| ATOM | 1414 | CB TYR | 395 | 33.818 | 22.211 | 27.929 | 1.00 | 48.44 |
| ATOM | 1415 | CG TYR | 395 | 32.493 | 22.710 | 27.335 | 1.00 | 53.83 |
| ATOM | 1416 | CD1 TYR | 395 | 32.302 | 22.727 | 25.947 | 1.00 | 56.43 |
| ATOM | 1417 | CE1 TYR | 395 | 31.078 | 23.148 | 25.374 | 1.00 | 59.73 |
| ATOM | 1418 | CD2 TYR | 395 | 31.434 | 23.132 | 28.153 | 1.00 | 56.47 |
| ATOM | 1419 | CE2 TYR | 395 | 30.198 | 23.559 | 27.592 | 1.00 | 62.60 |
| ATOM | 1420 | CZ TYR | 395 | 30.037 | 23.562 | 26.200 | 1.00 | 63.18 |
| ATOM | 1421 | OH TYR | 395 | 28.834 | 23.962 | 25.635 | 1.00 | 64.46 |
| ATOM | 1422 | C TYR | 395 | 35.189 | 21.635 | 29.938 | 1.00 | 37.30 |
| ATOM | 1423 | O TYR | 395 | 34.993 | 20.599 | 30.564 | 1.00 | 34.10 |
| ATOM | 1424 | N GLN | 396 | 36.408 | 22.091 | 29.671 | 1.00 | 31.92 |
| ATOM | 1425 | CA GLN | 396 | 37.584 | 21.363 | 30.120 | 1.00 | 34.81 |
| ATOM | 1426 | CB GLN | 396 | 38.861 | 21.987 | 29.560 | 1.00 | 32.64 |
| ATOM | 1427 | CG GLN | 396 | 40.114 | 21.183 | 29.882 | 1.00 | 29.57 |
| ATOM | 1428 | CD GLN | 396 | 41.370 | 21.827 | 29.352 | 1.00 | 29.46 |
| ATOM | 1429 | OE1 GLN | 396 | 41.648 | 22.982 | 29.649 | 1.00 | 34.65 |
| ATOM | 1430 | NE2 GLN | 396 | 42.139 | 21.088 | 28.570 | 1.00 | 27.21 |
| ATOM | 1431 | C GLN | 396 | 37.647 | 21.342 | 31.647 | 1.00 | 37.13 |
| ATOM | 1432 | O GLN | 396 | 37.939 | 20.302 | 32.236 | 1.00 | 37.36 |
| ATOM | 1433 | N ASP | 397 | 37.371 | 22.484 | 32.284 | 1.00 | 38.61 |
| ATOM | 1434 | CA ASP | 397 | 37.393 | 22.555 | 33.742 | 1.00 | 40.37 |
| ATOM | 1435 | CB ASP | 397 | 37.099 | 23.973 | 34.240 | 1.00 | 40.51 |
| ATOM | 1436 | CG ASP | 397 | 38.130 | 24.974 | 33.772 | 1.00 | 43.77 |
| ATOM | 1437 | OD1 ASP | 397 | 39.330 | 24.632 | 33.775 | 1.00 | 46.50 |
| ATOM | 1438 | OD2 ASP | 397 | 37.750 | 26.109 | 33.422 | 1.00 | 51.34 |
| ATOM | 1439 | C ASP | 397 | 36.352 | 21.601 | 34.295 | 1.00 | 38.62 |
| ATOM | 1440 | O ASP | 397 | 36.515 | 21.034 | 35.372 | 1.00 | 39.20 |
| ATOM | 1441 | N SER | 398 | 35.282 | 21.423 | 33.540 | 1.00 | 37.84 |
| ATOM | 1442 | CA SER | 398 | 34.221 | 20.524 | 33.942 | 1.00 | 37.80 |
| ATOM | 1443 | CB SER | 398 | 33.039 | 20.669 | 32.984 | 1.00 | 34.28 |
| ATOM | 1444 | OG SER | 398 | 31.981 | 19.815 | 33.360 | 1.00 | 46.60 |
| ATOM | 1445 | C SER | 398 | 34.752 | 19.082 | 33.939 | 1.00 | 38.41 |
| ATOM | 1446 | O SER | 398 | 34.372 | 18.274 | 34.787 | 1.00 | 39.98 |
| ATOM | 1447 | N PHE | 399 | 35.630 | 18.772 | 32.987 | 1.00 | 34.82 |
| ATOM | 1448 | CA PHE | 399 | 36.213 | 17.433 | 32.885 | 1.00 | 35.96 |
| ATOM | 1449 | CB PHE | 399 | 36.809 | 17.181 | 31.493 | 1.00 | 35.75 |
| ATOM | 1450 | CG PHE | 399 | 35.775 | 16.936 | 30.419 | 1.00 | 39.30 |
| ATOM | 1451 | CD1 PHE | 399 | 35.640 | 17.826 | 29.344 | 1.00 | 39.86 |
| ATOM | 1452 | CD2 PHE | 399 | 34.936 | 15.819 | 30.487 | 1.00 | 36.81 |
| ATOM | 1453 | CE1 PHE | 399 | 34.674 | 17.607 | 28.330 | 1.00 | 41.25 |
| ATOM | 1454 | CE2 PHE | 399 | 33.962 | 15.577 | 29.488 | 1.00 | 43.61 |
| ATOM | 1455 | CZ PHE | 399 | 33.829 | 16.480 | 28.402 | 1.00 | 40.34 |
| ATOM | 1456 | C PHE | 399 | 37.306 | 17.217 | 33.921 | 1.00 | 33.48 |
| ATOM | 1457 | O PHE | 399 | 37.406 | 16.139 | 34.512 | 1.00 | 26.86 |
| ATOM | 1458 | N LEU | 400 | 38.132 | 18.239 | 34.118 | 1.00 | 31.47 |
| ATOM | 1459 | CA LEU | 400 | 39.213 | 18.162 | 35.086 | 1.00 | 37.41 |
| ATOM | 1460 | CB LEU | 400 | 40.051 | 19.441 | 35.038 | 1.00 | 34.24 |
| ATOM | 1461 | CG LEU | 400 | 40.934 | 19.574 | 33.788 | 1.00 | 35.10 |
| ATOM | 1462 | CD1 LEU | 400 | 41.469 | 20.991 | 33.651 | 1.00 | 26.60 |
| ATOM | 1463 | CD2 LEU | 400 | 42.077 | 18.569 | 33.684 | 1.00 | 29.44 |
| ATOM | 1464 | C LEU | 400 | 38.666 | 17.931 | 36.491 | 1.00 | 38.84 |
| ATOM | 1465 | O LEU | 400 | 39.137 | 17.049 | 37.205 | 1.00 | 40.38 |
| ATOM | 1466 | N LEU | 401 | 37.654 | 18.703 | 36.870 | 1.00 | 42.79 |
| ATOM | 1467 | CA LEU | 401 | 37.056 | 18.584 | 38.197 | 1.00 | 43.48 |
| ATOM | 1468 | CB LEU | 401 | 35.997 | 19.675 | 38.406 | 1.00 | 44.73 |
| ATOM | 1469 | CG LEU | 401 | 35.322 | 19.737 | 39.779 | 1.00 | 51.39 |
| ATOM | 1470 | CD1 LEU | 401 | 36.359 | 20.002 | 40.866 | 1.00 | 50.11 |
| ATOM | 1471 | CD2 LEU | 401 | 34.273 | 20.834 | 39.778 | 1.00 | 49.30 |
| ATOM | 1472 | C LEU | 401 | 36.433 | 17.215 | 38.409 | 1.00 | 41.62 |
| ATOM | 1473 | O LEU | 401 | 36.563 | 16.622 | 39.482 | 1.00 | 45.14 |
| ATOM | 1474 | N ALA | 402 | 35.744 | 16.712 | 37.389 | 1.00 | 37.92 |
| ATOM | 1475 | CA ALA | 402 | 35.115 | 15.402 | 37.484 | 1.00 | 29.90 |
| ATOM | 1476 | CB ALA | 402 | 34.196 | 15.187 | 36.297 | 1.00 | 30.70 |
| ATOM | 1477 | C ALA | 402 | 36.203 | 14.336 | 37.508 | 1.00 | 28.88 |
| ATOM | 1478 | O ALA | 402 | 36.083 | 13.322 | 38.188 | 1.00 | 32.14 |
| ATOM | 1479 | N PHE | 403 | 37.274 | 14.588 | 36.764 | 1.00 | 31.07 |
| ATOM | 1480 | CA PHE | 403 | 38.402 | 13.656 | 36.661 | 1.00 | 29.90 |
| ATOM | 1481 | CB PHE | 403 | 39.396 | 14.178 | 35.605 | 1.00 | 27.03 |
| ATOM | 1482 | CG PHE | 403 | 40.434 | 13.146 | 35.140 | 1.00 | 26.97 |
| ATOM | 1483 | CD1 PHE | 403 | 41.362 | 13.509 | 34.149 | 1.00 | 25.55 |
| ATOM | 1484 | CD2 PHE | 403 | 40.475 | 11.841 | 35.664 | 1.00 | 19.75 |
| ATOM | 1485 | CE1 PHE | 403 | 42.331 | 12.588 | 33.679 | 1.00 | 27.90 |
| ATOM | 1486 | CE2 PHE | 403 | 41.441 | 10.899 | 35.206 | 1.00 | 22.56 |
| ATOM | 1487 | CZ PHE | 403 | 42.371 | 11.273 | 34.210 | 1.00 | 22.24 |
| ATOM | 1488 | C PHE | 403 | 39.081 | 13.523 | 38.023 | 1.00 | 28.82 |
| ATOM | 1489 | O PHE | 403 | 39.313 | 12.413 | 38.495 | 1.00 | 26.00 |
| ATOM | 1490 | N GLU | 404 | 39.405 | 14.652 | 38.652 | 1.00 | 30.25 |
| ATOM | 1491 | CA GLU | 404 | 40.039 | 14.627 | 39.966 | 1.00 | 34.03 |
| ATOM | 1492 | CB GLU | 404 | 40.264 | 16.046 | 40.497 | 1.00 | 39.45 |
| ATOM | 1493 | CG GLU | 404 | 40.987 | 16.076 | 41.839 | 1.00 | 47.68 |
| ATOM | 1494 | CD GLU | 404 | 41.062 | 17.465 | 42.446 | 1.00 | 54.02 |
| ATOM | 1495 | OE1 GLU | 404 | 41.607 | 18.380 | 41.796 | 1.00 | 57.27 |
| ATOM | 1496 | OE2 GLU | 404 | 40.573 | 17.638 | 43.585 | 1.00 | 63.85 |
| ATOM | 1497 | C GLU | 404 | 39.164 | 13.860 | 40.960 | 1.00 | 36.01 |
| ATOM | 1498 | O GLU | 404 | 39.661 | 12.997 | 41.701 | 1.00 | 38.64 |
| ATOM | 1499 | N HIS | 405 | 37.870 | 14.168 | 40.975 | 1.00 | 29.56 |
| ATOM | 1500 | CA HIS | 405 | 36.949 | 13.508 | 41.892 | 1.00 | 31.69 |
| ATOM | 1501 | CB HIS | 405 | 35.534 | 14.077 | 41.757 | 1.00 | 33.75 |
| ATOM | 1502 | CG HIS | 405 | 35.401 | 15.498 | 42.213 | 1.00 | 34.75 |
| ATOM | 1503 | CD2 HIS | 405 | 36.308 | 16.361 | 42.730 | 1.00 | 34.58 |
| ATOM | 1504 | ND1 HIS | 405 | 34.207 | 16.187 | 42.146 | 1.00 | 32.43 |
| ATOM | 1505 | CE1 HIS | 405 | 34.385 | 17.414 | 42.598 | 1.00 | 36.15 |
| ATOM | 1506 | NE2 HIS | 405 | 35.650 | 17.549 | 42.960 | 1.00 | 39.84 |
| ATOM | 1507 | C HIS | 405 | 36.904 | 12.013 | 41.673 | 1.00 | 34.21 |
| ATOM | 1508 | O HIS | 405 | 36.700 | 11.247 | 42.624 | 1.00 | 37.06 |
| ATOM | 1509 | N TYR | 406 | 37.081 | 11.594 | 40.419 | 1.00 | 30.83 |
| ATOM | 1510 | CA TYR | 406 | 37.059 | 10.173 | 40.093 | 1.00 | 28.85 |
| ATOM | 1511 | CB TYR | 406 | 37.018 | 9.959 | 38.575 | 1.00 | 31.48 |
| ATOM | 1512 | CG TYR | 406 | 36.879 | 8.490 | 38.181 | 1.00 | 23.49 |
| ATOM | 1513 | CD1 TYR | 406 | 35.683 | 7.798 | 38.397 | 1.00 | 19.42 |
| ATOM | 1514 | CE1 TYR | 406 | 35.556 | 6.427 | 38.059 | 1.00 | 23.80 |
| ATOM | 1515 | CD2 TYR | 406 | 37.950 | 7.794 | 37.624 | 1.00 | 21.81 |
| ATOM | 1516 | CE2 TYR | 406 | 37.838 | 6.421 | 37.278 | 1.00 | 24.64 |
| ATOM | 1517 | CZ TYR | 406 | 36.639 | 5.753 | 37.503 | 1.00 | 21.56 |
| ATOM | 1518 | OH TYR | 406 | 36.537 | 4.404 | 37.186 | 1.00 | 24.96 |
| ATOM | 1519 | C TYR | 406 | 38.318 | 9.526 | 40.638 | 1.00 | 24.24 |
| ATOM | 1520 | O TYR | 406 | 38.308 | 8.375 | 41.050 | 1.00 | 27.08 |
| ATOM | 1521 | N ILE | 407 | 39.407 | 10.278 | 40.617 | 1.00 | 25.76 |
| ATOM | 1522 | CA ILE | 407 | 40.688 | 9.799 | 41.105 | 1.00 | 33.75 |
| ATOM | 1523 | CB ILE | 407 | 41.815 | 10.822 | 40.796 | 1.00 | 34.23 |
| ATOM | 1524 | CG2 ILE | 407 | 43.121 | 10.400 | 41.435 | 1.00 | 32.46 |
| ATOM | 1525 | CG1 ILE | 407 | 41.959 | 10.972 | 39.275 | 1.00 | 43.30 |
| ATOM | 1526 | CD1 ILE | 407 | 42.267 | 9.677 | 38.523 | 1.00 | 40.40 |
| ATOM | 1527 | C ILE | 407 | 40.620 | 9.556 | 42.613 | 1.00 | 39.03 |
| ATOM | 1528 | O ILE | 407 | 41.192 | 8.583 | 43.107 | 1.00 | 35.18 |
| ATOM | 1529 | N ASN | 408 | 39.916 | 10.440 | 43.335 | 1.00 | 37.25 |
| ATOM | 1530 | CA ASN | 408 | 39.778 | 10.292 | 44.777 | 1.00 | 37.01 |
| ATOM | 1531 | CB ASN | 408 | 39.099 | 11.514 | 45.400 | 1.00 | 32.27 |
| ATOM | 1532 | CG ASN | 408 | 39.887 | 12.790 | 45.181 | 1.00 | 33.56 |
| ATOM | 1533 | OD1 ASN | 408 | 41.118 | 12.785 | 45.225 | 1.00 | 31.99 |
| ATOM | 1534 | ND2 ASN | 408 | 39.182 | 13.903 | 44.996 | 1.00 | 31.23 |
| ATOM | 1535 | C ASN | 408 | 38.961 | 9.046 | 45.055 | 1.00 | 38.14 |
| ATOM | 1536 | O ASN | 408 | 39.303 | 8.243 | 45.920 | 1.00 | 42.16 |
| ATOM | 1537 | N TYR | 409 | 37.874 | 8.894 | 44.303 | 1.00 | 35.62 |
| ATOM | 1538 | CA TYR | 409 | 37.002 | 7.733 | 44.412 | 1.00 | 35.91 |
| ATOM | 1539 | CB TYR | 409 | 35.929 | 7.804 | 43.323 | 1.00 | 34.41 |
| ATOM | 1540 | CG TYR | 409 | 35.196 | 6.495 | 43.066 | 1.00 | 38.73 |
| ATOM | 1541 | CD1 TYR | 409 | 34.266 | 5.982 | 43.980 | 1.00 | 41.34 |
| ATOM | 1542 | CE1 TYR | 409 | 33.600 | 4.745 | 43.741 | 1.00 | 47.16 |
| ATOM | 1543 | CD2 TYR | 409 | 35.461 | 5.752 | 41.907 | 1.00 | 46.20 |
| ATOM | 1544 | CE2 TYR | 409 | 34.814 | 4.518 | 41.651 | 1.00 | 50.74 |
| ATOM | 1545 | CZ TYR | 409 | 33.891 | 4.023 | 42.573 | 1.00 | 50.88 |
| ATOM | 1546 | OH TYR | 409 | 33.262 | 2.816 | 42.302 | 1.00 | 53.14 |
| ATOM | 1547 | C TYR | 409 | 37.827 | 6.459 | 44.240 | 1.00 | 38.16 |
| ATOM | 1548 | O TYR | 409 | 37.806 | 5.561 | 45.082 | 1.00 | 41.83 |
| ATOM | 1549 | N ARG | 410 | 38.551 | 6.399 | 43.125 | 1.00 | 42.25 |
| ATOM | 1550 | CA ARG | 410 | 39.410 | 5.272 | 42.765 | 1.00 | 42.83 |
| ATOM | 1551 | CB ARG | 410 | 40.029 | 5.540 | 41.392 | 1.00 | 36.83 |
| ATOM | 1552 | CG ARG | 410 | 39.055 | 5.397 | 40.249 | 1.00 | 34.32 |
| ATOM | 1553 | CD ARG | 410 | 39.134 | 3.996 | 39.681 | 1.00 | 36.62 |
| ATOM | 1554 | NE ARG | 410 | 40.420 | 3.787 | 39.013 | 1.00 | 38.64 |

APPENDIX 8-continued

TRBGC1.PDB

| ATOM | 1555 | CZ ARG | 410 | 40.832 | 2.625 | 38.517 | 1.00 | 35.73 |
|---|---|---|---|---|---|---|---|---|
| ATOM | 1556 | NH1 ARG | 410 | 40.068 | 1.548 | 38.617 | 1.00 | 33.17 |
| ATOM | 1557 | NH2 ARG | 410 | 42.006 | 2.544 | 37.916 | 1.00 | 32.70 |
| ATOM | 1558 | C ARG | 410 | 40.520 | 5.039 | 43.780 | 1.00 | 46.67 |
| ATOM | 1559 | O ARG | 410 | 40.900 | 3.901 | 44.053 | 1.00 | 41.78 |
| ATOM | 1560 | N LYS | 411 | 41.026 | 6.140 | 44.325 | 1.00 | 52.99 |
| ATOM | 1561 | CA LYS | 411 | 42.109 | 6.141 | 45.298 | 1.00 | 58.32 |
| ATOM | 1562 | CB LYS | 411 | 41.565 | 5.956 | 46.731 | 1.00 | 64.99 |
| ATOM | 1563 | CG LYS | 411 | 40.660 | 4.763 | 46.977 | 1.00 | 70.48 |
| ATOM | 1564 | CD LYS | 411 | 40.034 | 4.866 | 48.364 | 1.00 | 77.18 |
| ATOM | 1565 | CE LYS | 411 | 39.053 | 3.732 | 48.625 | 1.00 | 84.30 |
| ATOM | 1566 | NZ LYS | 411 | 38.392 | 3.865 | 49.958 | 1.00 | 86.48 |
| ATOM | 1567 | C LYS | 411 | 43.238 | 5.163 | 45.000 | 1.00 | 56.66 |
| ATOM | 1568 | O LYS | 411 | 43.329 | 4.075 | 45.575 | 1.00 | 55.47 |
| ATOM | 1569 | N HIS | 412 | 44.091 | 5.582 | 44.070 | 1.00 | 54.67 |
| ATOM | 1570 | CA HIS | 412 | 45.266 | 4.823 | 43.657 | 1.00 | 48.67 |
| ATOM | 1571 | CB HIS | 412 | 45.878 | 5.442 | 42.393 | 1.00 | 43.14 |
| ATOM | 1572 | CG HIS | 412 | 45.073 | 5.218 | 41.156 | 1.00 | 41.36 |
| ATOM | 1573 | CD2 HIS | 412 | 44.084 | 5.952 | 40.584 | 1.00 | 35.44 |
| ATOM | 1574 | ND1 HIS | 412 | 45.220 | 4.093 | 40.364 | 1.00 | 38.19 |
| ATOM | 1575 | CE1 HIS | 412 | 44.357 | 4.150 | 39.363 | 1.00 | 34.75 |
| ATOM | 1576 | NE2 HIS | 412 | 43.659 | 5.263 | 39.474 | 1.00 | 35.52 |
| ATOM | 1577 | C HIS | 412 | 46.264 | 4.932 | 44.793 | 1.00 | 46.35 |
| ATOM | 1578 | O HIS | 412 | 46.326 | 5.951 | 45.479 | 1.00 | 42.73 |
| ATOM | 1579 | N HIS | 413 | 47.049 | 3.883 | 44.993 | 1.00 | 48.92 |
| ATOM | 1580 | CA HIS | 413 | 48.040 | 3.903 | 46.052 | 1.00 | 53.15 |
| ATOM | 1581 | CB HIS | 413 | 48.148 | 2.515 | 46.688 | 1.00 | 55.27 |
| ATOM | 1582 | CG HIS | 413 | 46.843 | 2.015 | 47.238 | 1.00 | 58.77 |
| ATOM | 1583 | CD2 HIS | 413 | 46.138 | 0.892 | 46.977 | 1.00 | 61.65 |
| ATOM | 1584 | ND1 HIS | 413 | 46.108 | 2.726 | 48.161 | 1.00 | 60.31 |
| ATOM | 1585 | CE1 HIS | 413 | 45.003 | 2.061 | 48.445 | 1.00 | 63.01 |
| ATOM | 1586 | NE2 HIS | 413 | 44.993 | 0.942 | 47.743 | 1.00 | 62.93 |
| ATOM | 1587 | C HIS | 413 | 49.359 | 4.364 | 45.456 | 1.00 | 53.19 |
| ATOM | 1588 | O HIS | 413 | 50.335 | 3.617 | 45.300 | 1.00 | 54.93 |
| ATOM | 1589 | N VAL | 414 | 49.343 | 5.612 | 44.999 | 1.00 | 53.77 |
| ATOM | 1590 | CA VAL | 414 | 50.487 | 6.282 | 44.389 | 1.00 | 51.06 |
| ATOM | 1591 | CB VAL | 414 | 50.374 | 6.305 | 42.838 | 1.00 | 51.49 |
| ATOM | 1592 | CG1 VAL | 414 | 51.603 | 6.958 | 42.231 | 1.00 | 45.22 |
| ATOM | 1593 | CG2 VAL | 414 | 50.210 | 4.891 | 42.304 | 1.00 | 52.67 |
| ATOM | 1594 | C VAL | 414 | 50.444 | 7.724 | 44.894 | 1.00 | 54.28 |
| ATOM | 1595 | O VAL | 414 | 49.418 | 8.401 | 44.774 | 1.00 | 55.49 |
| ATOM | 1596 | N THR | 415 | 51.547 | 8.190 | 45.467 | 1.00 | 56.28 |
| ATOM | 1597 | CA THR | 415 | 51.610 | 9.550 | 45.986 | 1.00 | 57.83 |
| ATOM | 1598 | CB THR | 415 | 52.874 | 9.756 | 46.858 | 1.00 | 59.64 |
| ATOM | 1599 | OG1 THR | 415 | 52.922 | 11.115 | 47.311 | 1.00 | 66.69 |
| ATOM | 1600 | CG2 THR | 415 | 54.137 | 9.436 | 46.067 | 1.00 | 59.42 |
| ATOM | 1601 | C THR | 415 | 51.599 | 10.577 | 44.855 | 1.00 | 56.98 |
| ATOM | 1602 | O THR | 415 | 52.176 | 10.345 | 43.789 | 1.00 | 55.70 |
| ATOM | 1603 | N HIS | 416 | 50.936 | 11.707 | 45.093 | 1.00 | 57.44 |
| ATOM | 1604 | CA HIS | 416 | 50.835 | 12.786 | 44.108 | 1.00 | 57.34 |
| ATOM | 1605 | CB HIS | 416 | 52.207 | 13.425 | 43.875 | 1.00 | 61.35 |
| ATOM | 1606 | CG HIS | 416 | 52.860 | 13.940 | 45.123 | 1.00 | 69.78 |
| ATOM | 1607 | CD2 HIS | 416 | 54.049 | 13.633 | 45.695 | 1.00 | 71.42 |
| ATOM | 1608 | ND1 HIS | 416 | 52.283 | 14.901 | 45.922 | 1.00 | 72.49 |
| ATOM | 1609 | CE1 HIS | 416 | 53.087 | 15.165 | 46.938 | 1.00 | 75.50 |
| ATOM | 1610 | NE2 HIS | 416 | 54.165 | 14.410 | 46.819 | 1.00 | 73.91 |
| ATOM | 1611 | C HIS | 416 | 50.301 | 12.260 | 42.773 | 1.00 | 53.79 |
| ATOM | 1612 | O HIS | 416 | 50.769 | 12.667 | 41.710 | 1.00 | 52.81 |
| ATOM | 1613 | N PHE | 417 | 49.318 | 11.366 | 42.824 | 1.00 | 48.05 |
| ATOM | 1614 | CA PHE | 417 | 48.769 | 10.784 | 41.610 | 1.00 | 47.99 |
| ATOM | 1615 | CB PHE | 417 | 47.652 | 9.799 | 41.940 | 1.00 | 46.11 |
| ATOM | 1616 | CG PHE | 417 | 47.314 | 8.868 | 40.791 | 1.00 | 44.27 |
| ATOM | 1617 | CD1 PHE | 417 | 48.155 | 7.796 | 40.481 | 1.00 | 41.79 |
| ATOM | 1618 | CD2 PHE | 417 | 46.179 | 9.091 | 40.003 | 1.00 | 40.23 |
| ATOM | 1619 | CE1 PHE | 417 | 47.872 | 6.936 | 39.386 | 1.00 | 44.30 |
| ATOM | 1620 | CE2 PHE | 417 | 45.874 | 8.248 | 38.907 | 1.00 | 36.80 |
| ATOM | 1621 | CZ PHE | 417 | 46.725 | 7.167 | 38.595 | 1.00 | 40.69 |
| ATOM | 1622 | C PHE | 417 | 48.227 | 11.824 | 40.625 | 1.00 | 46.69 |
| ATOM | 1623 | O PHE | 417 | 48.551 | 11.787 | 39.436 | 1.00 | 43.35 |
| ATOM | 1624 | N TRP | 418 | 47.410 | 12.746 | 41.124 | 1.00 | 45.14 |
| ATOM | 1625 | CA TRP | 418 | 46.821 | 13.775 | 40.276 | 1.00 | 44.89 |
| ATOM | 1626 | CB TRP | 418 | 45.808 | 14.604 | 41.077 | 1.00 | 42.24 |
| ATOM | 1627 | CG TRP | 418 | 45.096 | 15.646 | 40.259 | 1.00 | 47.11 |
| ATOM | 1628 | CD2 TRP | 418 | 44.186 | 15.417 | 39.159 | 1.00 | 46.98 |
| ATOM | 1629 | CE2 TRP | 418 | 43.786 | 16.678 | 38.676 | 1.00 | 48.94 |
| ATOM | 1630 | CE3 TRP | 418 | 43.676 | 14.261 | 38.548 | 1.00 | 45.23 |
| ATOM | 1631 | CD1 TRP | 418 | 45.204 | 17.003 | 40.387 | 1.00 | 46.24 |
| ATOM | 1632 | NE1 TRP | 418 | 44.425 | 17.637 | 39.448 | 1.00 | 50.63 |
| ATOM | 1633 | CZ2 TRP | 418 | 42.891 | 16.839 | 37.598 | 1.00 | 45.46 |
| ATOM | 1634 | CZ3 TRP | 418 | 42.780 | 14.411 | 37.468 | 1.00 | 44.50 |
| ATOM | 1635 | CH2 TRP | 418 | 42.403 | 15.696 | 37.009 | 1.00 | 47.55 |
| ATOM | 1636 | C TRP | 418 | 47.862 | 14.676 | 39.598 | 1.00 | 43.88 |
| ATOM | 1637 | O TRP | 418 | 47.834 | 14.842 | 38.383 | 1.00 | 43.17 |
| ATOM | 1638 | N PRO | 419 | 48.788 | 15.281 | 40.369 | 1.00 | 43.55 |
| ATOM | 1639 | CD PRO | 419 | 49.006 | 15.290 | 41.826 | 1.00 | 41.52 |
| ATOM | 1640 | CA PRO | 419 | 49.787 | 16.135 | 39.725 | 1.00 | 41.48 |
| ATOM | 1641 | CB PRO | 419 | 50.626 | 16.627 | 40.912 | 1.00 | 39.21 |
| ATOM | 1642 | CG PRO | 419 | 49.593 | 16.667 | 42.017 | 1.00 | 39.25 |
| ATOM | 1643 | C PRO | 419 | 50.616 | 15.363 | 38.701 | 1.00 | 36.28 |
| ATOM | 1644 | O PRO | 419 | 50.940 | 15.882 | 37.638 | 1.00 | 37.08 |
| ATOM | 1645 | N LYS | 420 | 50.959 | 14.124 | 39.033 | 1.00 | 35.96 |
| ATOM | 1646 | CA LYS | 420 | 51.742 | 13.281 | 38.132 | 1.00 | 40.82 |
| ATOM | 1647 | CB LYS | 420 | 52.094 | 11.945 | 38.792 | 1.00 | 40.78 |
| ATOM | 1648 | CG LYS | 420 | 53.086 | 12.046 | 39.933 | 1.00 | 48.62 |
| ATOM | 1649 | CD LYS | 420 | 53.391 | 10.668 | 40.497 | 1.00 | 55.12 |
| ATOM | 1650 | CE LYS | 420 | 54.395 | 10.741 | 41.635 | 1.00 | 53.26 |
| ATOM | 1651 | NZ LYS | 420 | 54.719 | 9.388 | 42.152 | 1.00 | 52.69 |
| ATOM | 1652 | C LYS | 420 | 50.957 | 13.005 | 36.860 | 1.00 | 40.29 |
| ATOM | 1653 | O LYS | 420 | 51.516 | 12.989 | 35.764 | 1.00 | 39.66 |
| ATOM | 1654 | N LEU | 421 | 49.658 | 12.786 | 37.023 | 1.00 | 38.33 |
| ATOM | 1655 | CA LEU | 421 | 48.784 | 12.507 | 35.903 | 1.00 | 37.60 |
| ATOM | 1656 | CB LEU | 421 | 47.417 | 12.074 | 36.428 | 1.00 | 43.66 |
| ATOM | 1657 | CG LEU | 421 | 46.386 | 11.479 | 35.474 | 1.00 | 46.50 |
| ATOM | 1658 | CD1 LEU | 421 | 46.946 | 10.253 | 34.770 | 1.00 | 45.15 |
| ATOM | 1659 | CD2 LEU | 421 | 45.154 | 11.107 | 36.279 | 1.00 | 51.31 |
| ATOM | 1660 | C LEU | 421 | 48.661 | 13.747 | 35.014 | 1.00 | 39.59 |
| ATOM | 1661 | O LEU | 421 | 48.599 | 13.638 | 33.791 | 1.00 | 40.66 |
| ATOM | 1662 | N LEU | 422 | 48.642 | 14.928 | 35.623 | 1.00 | 39.57 |
| ATOM | 1663 | CA LEU | 422 | 48.545 | 16.170 | 34.867 | 1.00 | 38.63 |
| ATOM | 1664 | CB LEU | 422 | 48.313 | 17.357 | 35.802 | 1.00 | 41.79 |
| ATOM | 1665 | CG LEU | 422 | 46.996 | 17.407 | 36.581 | 1.00 | 42.74 |
| ATOM | 1666 | CD1 LEU | 422 | 47.010 | 18.606 | 37.515 | 1.00 | 42.89 |
| ATOM | 1667 | CD2 LEU | 422 | 45.823 | 17.494 | 35.628 | 1.00 | 39.27 |
| ATOM | 1668 | C LEU | 422 | 49.808 | 16.410 | 34.039 | 1.00 | 40.47 |
| ATOM | 1669 | O LEU | 422 | 49.747 | 17.029 | 32.979 | 1.00 | 47.83 |
| ATOM | 1670 | N MET | 423 | 50.949 | 15.936 | 34.519 | 1.00 | 34.27 |
| ATOM | 1671 | CA MET | 423 | 52.187 | 16.103 | 33.774 | 1.00 | 35.25 |
| ATOM | 1672 | CB MET | 423 | 53.403 | 15.716 | 34.622 | 1.00 | 32.56 |
| ATOM | 1673 | CG MET | 423 | 53.675 | 16.654 | 35.774 | 1.00 | 40.70 |
| ATOM | 1674 | SD MET | 423 | 55.226 | 16.278 | 36.597 | 1.00 | 47.65 |
| ATOM | 1675 | CE MET | 423 | 54.920 | 14.601 | 37.163 | 1.00 | 47.16 |
| ATOM | 1676 | C MET | 423 | 52.164 | 15.254 | 32.502 | 1.00 | 35.13 |
| ATOM | 1677 | O MET | 423 | 52.934 | 15.499 | 31.570 | 1.00 | 29.85 |
| ATOM | 1678 | N LYS | 424 | 51.285 | 14.252 | 32.482 | 1.00 | 31.56 |
| ATOM | 1679 | CA LYS | 424 | 51.152 | 13.384 | 31.316 | 1.00 | 32.29 |
| ATOM | 1680 | CB LYS | 424 | 50.373 | 12.115 | 31.681 | 1.00 | 30.56 |
| ATOM | 1681 | CG LYS | 424 | 51.106 | 11.178 | 32.631 | 1.00 | 30.07 |
| ATOM | 1682 | CD LYS | 424 | 52.248 | 10.482 | 31.938 | 1.00 | 33.22 |
| ATOM | 1683 | CE LYS | 424 | 53.059 | 9.593 | 32.875 | 1.00 | 28.75 |
| ATOM | 1684 | NZ LYS | 424 | 53.868 | 10.383 | 33.833 | 1.00 | 31.01 |
| ATOM | 1685 | C LYS | 424 | 50.435 | 14.150 | 30.197 | 1.00 | 29.26 |
| ATOM | 1686 | O LYS | 424 | 50.719 | 13.944 | 29.030 | 1.00 | 30.22 |
| ATOM | 1687 | N VAL | 425 | 49.514 | 15.036 | 30.573 | 1.00 | 23.53 |
| ATOM | 1688 | CA VAL | 425 | 48.792 | 15.849 | 29.601 | 1.00 | 28.91 |
| ATOM | 1689 | CB VAL | 425 | 47.808 | 16.829 | 30.295 | 1.00 | 29.44 |
| ATOM | 1690 | CG1 VAL | 425 | 47.148 | 17.737 | 29.273 | 1.00 | 28.81 |
| ATOM | 1691 | CG2 VAL | 425 | 46.744 | 16.049 | 31.057 | 1.00 | 31.22 |
| ATOM | 1692 | C VAL | 425 | 49.822 | 16.669 | 28.831 | 1.00 | 32.03 |
| ATOM | 1693 | O VAL | 425 | 49.771 | 16.769 | 27.605 | 1.00 | 31.95 |
| ATOM | 1694 | N THR | 426 | 50.763 | 17.247 | 29.570 | 1.00 | 33.61 |
| ATOM | 1695 | CA THR | 426 | 51.821 | 18.057 | 28.995 | 1.00 | 30.76 |
| ATOM | 1696 | CB THR | 426 | 52.678 | 18.695 | 30.105 | 1.00 | 32.34 |
| ATOM | 1697 | OG1 THR | 426 | 51.842 | 19.535 | 30.912 | 1.00 | 33.07 |
| ATOM | 1698 | CG2 THR | 426 | 53.812 | 19.533 | 29.514 | 1.00 | 25.40 |
| ATOM | 1699 | C THR | 426 | 52.712 | 17.225 | 28.086 | 1.00 | 32.53 |
| ATOM | 1700 | O THR | 426 | 53.113 | 17.686 | 27.014 | 1.00 | 35.19 |
| ATOM | 1701 | N ASP | 427 | 53.022 | 16.003 | 28.507 | 1.00 | 28.83 |
| ATOM | 1702 | CA ASP | 427 | 53.858 | 15.130 | 27.695 | 1.00 | 35.12 |
| ATOM | 1703 | CB ASP | 427 | 54.273 | 13.880 | 28.476 | 1.00 | 39.14 |
| ATOM | 1704 | CG ASP | 427 | 55.122 | 14.212 | 29.693 | 1.00 | 45.80 |
| ATOM | 1705 | OD1 ASP | 427 | 56.052 | 15.034 | 29.556 | 1.00 | 41.97 |
| ATOM | 1706 | OD2 ASP | 427 | 54.869 | 13.642 | 30.775 | 1.00 | 50.06 |
| ATOM | 1707 | C ASP | 427 | 53.124 | 14.726 | 26.422 | 1.00 | 33.94 |
| ATOM | 1708 | O ASP | 427 | 53.737 | 14.617 | 25.362 | 1.00 | 38.02 |

APPENDIX 8-continued

TRBGC1.PDB

| ATOM | 1709 | N LEU | 428 51.818 14.512 26.529 1.00 27.15 |
| ATOM | 1710 | CA LEU | 428 51.013 14.148 25.373 1.00 29.99 |
| ATOM | 1711 | CB LEU | 428 49.602 13.719 25.802 1.00 22.49 |
| ATOM | 1712 | CG LEU | 428 49.541 12.285 26.359 1.00 25.54 |
| ATOM | 1713 | CD1 LEU | 428 48.210 12.021 27.037 1.00 20.60 |
| ATOM | 1714 | CD2 LEU | 428 49.785 11.303 25.224 1.00 17.24 |
| ATOM | 1715 | C LEU | 428 50.947 15.305 24.381 1.00 28.94 |
| ATOM | 1716 | O LEU | 428 50.941 15.088 23.174 1.00 31.26 |
| ATOM | 1717 | N ARG | 429 50.910 16.531 24.887 1.00 27.64 |
| ATOM | 1718 | CA ARG | 429 50.877 17.694 24.011 1.00 28.13 |
| ATOM | 1719 | CB ARG | 429 50.584 18.969 24.800 1.00 29.59 |
| ATOM | 1720 | CG ARG | 429 49.224 18.980 25.455 1.00 34.85 |
| ATOM | 1721 | CD ARG | 429 48.951 20.314 26.118 1.00 47.18 |
| ATOM | 1722 | NE ARG | 429 47.657 20.358 26.797 1.00 57.93 |
| ATOM | 1723 | CZ ARG | 429 46.473 20.193 26.200 1.00 63.62 |
| ATOM | 1724 | NH1 ARG | 429 46.402 19.972 24.889 1.00 60.71 |
| ATOM | 1725 | NH2 ARG | 429 45.356 20.257 26.919 1.00 62.38 |
| ATOM | 1726 | C ARG | 429 52.229 17.819 23.304 1.00 29.81 |
| ATOM | 1727 | O ARG | 429 52.294 18.209 22.143 1.00 30.81 |
| ATOM | 1728 | N MET | 430 53.305 17.482 24.008 1.00 29.64 |
| ATOM | 1729 | CA MET | 430 54.639 17.545 23.422 1.00 34.72 |
| ATOM | 1730 | CB MET | 430 55.716 17.323 24.485 1.00 34.97 |
| ATOM | 1731 | CG MET | 430 55.864 18.480 25.451 1.00 45.34 |
| ATOM | 1732 | SD MET | 430 56.162 20.050 24.596 1.00 52.55 |
| ATOM | 1733 | CE MET | 430 57.598 19.639 23.589 1.00 55.56 |
| ATOM | 1734 | C MET | 430 54.778 16.500 22.325 1.00 34.01 |
| ATOM | 1735 | O MET | 430 55.440 16.733 21.318 1.00 37.29 |
| ATOM | 1736 | N ILE | 431 54.161 15.340 22.533 1.00 29.99 |
| ATOM | 1737 | CA ILE | 431 54.197 14.279 21.545 1.00 28.82 |
| ATOM | 1738 | CB ILE | 431 53.523 12.984 22.095 1.00 27.39 |
| ATOM | 1739 | CG2 ILE | 431 53.260 11.989 20.956 1.00 23.87 |
| ATOM | 1740 | CG1 ILE | 431 54.414 12.386 23.201 1.00 25.56 |
| ATOM | 1741 | CD1 ILE | 431 53.850 11.155 23.896 1.00 17.29 |
| ATOM | 1742 | C ILE | 431 53.450 14.785 20.301 1.00 29.49 |
| ATOM | 1743 | O ILE | 431 53.908 14.603 19.174 1.00 24.19 |
| ATOM | 1744 | N GLY | 432 52.311 15.435 20.524 1.00 25.25 |
| ATOM | 1745 | CA GLY | 432 51.542 15.971 19.419 1.00 30.38 |
| ATOM | 1746 | C GLY | 432 52.334 16.997 18.614 1.00 32.75 |
| ATOM | 1747 | O GLY | 432 52.410 16.895 17.387 1.00 36.38 |
| ATOM | 1748 | N ALA | 433 52.930 17.974 19.294 1.00 26.77 |
| ATOM | 1749 | CA ALA | 433 53.711 19.012 18.625 1.00 26.48 |
| ATOM | 1750 | CB ALA | 433 54.182 20.047 19.631 1.00 19.90 |
| ATOM | 1751 | C ALA | 433 54.902 18.407 17.890 1.00 30.73 |
| ATOM | 1752 | O ALA | 433 55.207 18.787 16.760 1.00 31.60 |
| ATOM | 1753 | N CYS | 434 55.582 17.467 18.537 1.00 33.22 |
| ATOM | 1754 | CA CYS | 434 56.728 16.801 17.914 1.00 34.34 |
| ATOM | 1755 | CB CYS | 434 57.339 15.808 18.895 1.00 35.20 |
| ATOM | 1756 | SG CYS | 434 59.191 15.745 18.798 1.00 54.48 |
| ATOM | 1757 | C CYS | 434 56.313 16.052 16.636 1.00 34.09 |
| ATOM | 1758 | O CYS | 434 57.095 15.937 15.679 1.00 34.89 |
| ATOM | 1759 | N HIS | 435 55.588 15.545 16.642 1.00 34.30 |
| ATOM | 1760 | CA HIS | 435 54.570 14.818 15.501 1.00 35.44 |
| ATOM | 1761 | CB HIS | 435 53.296 14.061 15.886 1.00 31.76 |
| ATOM | 1762 | CG HIS | 435 52.587 13.469 14.715 1.00 32.03 |
| ATOM | 1763 | CD2 HIS | 435 52.735 12.277 14.092 1.00 28.61 |
| ATOM | 1764 | ND1 HIS | 435 51.665 14.177 13.970 1.00 28.48 |
| ATOM | 1765 | CE1 HIS | 435 51.284 13.453 12.941 1.00 33.27 |
| ATOM | 1766 | NE2 HIS | 435 51.920 12.284 12.985 1.00 31.57 |
| ATOM | 1767 | C HIS | 435 54.311 15.750 14.319 1.00 32.74 |
| ATOM | 1768 | O HIS | 435 54.504 15.363 13.175 1.00 32.87 |
| ATOM | 1769 | N ALA | 436 53.881 16.975 14.608 1.00 31.01 |
| ATOM | 1770 | CA ALA | 436 53.628 17.966 13.571 1.00 29.91 |
| ATOM | 1771 | CB ALA | 436 53.221 19.290 14.197 1.00 21.23 |
| ATOM | 1772 | C ALA | 436 54.911 18.135 12.769 1.00 33.86 |
| ATOM | 1773 | O ALA | 436 54.892 18.128 11.541 1.00 36.10 |
| ATOM | 1774 | N SER | 437 56.030 18.266 13.483 1.00 35.19 |
| ATOM | 1775 | CA SER | 437 57.344 18.426 12.871 1.00 33.03 |
| ATOM | 1776 | CB SER | 437 58.389 18.720 13.941 1.00 35.31 |
| ATOM | 1777 | OG SER | 437 59.681 18.782 13.373 1.00 44.99 |
| ATOM | 1778 | C SER | 437 57.758 17.178 12.100 1.00 38.39 |
| ATOM | 1779 | O SER | 437 58.374 17.269 11.034 1.00 37.54 |
| ATOM | 1780 | N ARG | 438 57.427 16.012 12.642 1.00 37.32 |
| ATOM | 1781 | CA ARG | 438 57.762 14.754 11.992 1.00 39.30 |
| ATOM | 1782 | CB ARG | 438 57.517 13.572 12.941 1.00 42.97 |
| ATOM | 1783 | CG ARG | 438 58.542 13.436 14.059 1.00 41.72 |
| ATOM | 1784 | CD ARG | 438 59.926 13.212 13.484 1.00 45.23 |
| ATOM | 1785 | NE ARG | 438 59.961 12.050 12.601 1.00 45.66 |
| ATOM | 1786 | CZ ARG | 438 60.935 11.804 11.731 1.00 49.71 |
| ATOM | 1787 | NH1 ARG | 438 61.961 12.641 11.627 1.00 50.91 |
| ATOM | 1788 | NH2 ARG | 438 60.885 10.727 10.960 1.00 46.86 |
| ATOM | 1789 | C ARG | 438 56.939 14.565 10.725 1.00 42.37 |
| ATOM | 1790 | O ARG | 438 57.311 13.794 9.841 1.00 40.58 |
| ATOM | 1791 | N PHE | 439 55.816 15.269 10.645 1.00 42.25 |
| ATOM | 1792 | CA PHE | 439 54.957 15.170 9.479 1.00 42.81 |
| ATOM | 1793 | CB PHE | 439 53.593 15.790 9.771 1.00 42.18 |
| ATOM | 1794 | CG PHE | 439 52.594 15.597 8.656 1.00 42.48 |
| ATOM | 1795 | CD1 PHE | 439 52.173 14.312 8.295 1.00 47.09 |
| ATOM | 1796 | CD2 PHE | 439 52.086 16.696 7.961 1.00 39.76 |
| ATOM | 1797 | CE1 PHE | 439 51.256 14.110 7.234 1.00 49.17 |
| ATOM | 1798 | CE2 PHE | 439 51.174 16.524 6.896 1.00 45.10 |
| ATOM | 1799 | CZ PHE | 439 50.751 15.225 6.532 1.00 46.36 |
| ATOM | 1800 | C PHE | 439 55.626 15.905 8.322 1.00 44.79 |
| ATOM | 1801 | O PHE | 439 55.596 15.444 7.181 1.00 40.26 |
| ATOM | 1802 | N LEU | 440 56.236 17.049 8.629 1.00 42.77 |
| ATOM | 1803 | CA LEU | 440 56.927 17.839 7.621 1.00 42.96 |
| ATOM | 1804 | CB LEU | 440 57.421 19.156 8.216 1.00 37.19 |
| ATOM | 1805 | CG LEU | 440 56.348 20.117 8.725 1.00 36.97 |
| ATOM | 1806 | CD1 LEU | 440 57.020 21.338 9.321 1.00 33.65 |
| ATOM | 1807 | CD2 LEU | 440 55.411 20.519 7.572 1.00 35.42 |
| ATOM | 1808 | C LEU | 440 58.106 17.063 7.053 1.00 45.47 |
| ATOM | 1809 | O LEU | 440 58.421 17.191 5.876 1.00 52.48 |
| ATOM | 1810 | N HIS | 441 58.760 16.266 7.890 1.00 49.15 |
| ATOM | 1811 | CA HIS | 441 59.893 15.473 7.435 1.00 54.76 |
| ATOM | 1812 | CB HIS | 441 60.723 14.964 8.624 1.00 56.68 |
| ATOM | 1813 | CG HIS | 441 61.515 16.026 9.323 1.00 62.73 |
| ATOM | 1814 | CD2 HIS | 441 62.851 16.166 9.508 1.00 65.73 |
| ATOM | 1815 | ND1 HIS | 441 60.929 17.098 9.966 1.00 66.01 |
| ATOM | 1816 | CE1 HIS | 441 61.871 17.845 10.518 1.00 65.55 |
| ATOM | 1817 | NE2 HIS | 441 63.044 17.306 10.258 1.00 60.09 |
| ATOM | 1818 | C HIS | 441 59.417 14.292 6.589 1.00 55.93 |
| ATOM | 1819 | O HIS | 441 60.084 13.908 5.630 1.00 57.33 |
| ATOM | 1820 | N MET | 442 58.271 13.716 6.948 1.00 57.81 |
| ATOM | 1821 | CA MET | 442 57.712 12.585 6.203 1.00 59.11 |
| ATOM | 1822 | CB MET | 442 56.562 11.924 6.978 1.00 55.93 |
| ATOM | 1823 | CG MET | 442 56.961 11.246 8.276 1.00 58.52 |
| ATOM | 1824 | SD MET | 442 55.564 10.420 9.105 1.00 60.99 |
| ATOM | 1825 | CE MET | 442 54.430 11.779 9.350 1.00 52.61 |
| ATOM | 1826 | C MET | 442 57.178 13.065 4.854 1.00 60.31 |
| ATOM | 1827 | O MET | 442 57.279 12.369 3.846 1.00 58.18 |
| ATOM | 1828 | N LYS | 443 56.608 14.266 4.863 1.00 61.45 |
| ATOM | 1829 | CA LYS | 443 56.038 14.871 3.669 1.00 64.90 |
| ATOM | 1830 | CB LYS | 443 55.434 16.232 4.035 1.00 64.40 |
| ATOM | 1831 | CG LYS | 443 54.589 16.872 2.945 1.00 69.12 |
| ATOM | 1832 | CD LYS | 443 54.064 18.250 3.363 1.00 71.14 |
| ATOM | 1833 | CE LYS | 443 53.138 18.183 4.575 1.00 73.43 |
| ATOM | 1834 | NZ LYS | 443 52.668 19.534 5.015 1.00 67.97 |
| ATOM | 1835 | C LYS | 443 57.112 15.030 2.585 1.00 67.29 |
| ATOM | 1836 | O LYS | 443 56.800 15.218 1.406 1.00 67.90 |
| ATOM | 1837 | N VAL | 444 58.373 14.941 2.996 1.00 66.57 |
| ATOM | 1838 | CA VAL | 444 59.501 15.064 2.078 1.00 64.76 |
| ATOM | 1839 | CB VAL | 444 60.618 15.940 2.693 1.00 62.76 |
| ATOM | 1840 | CG1 VAL | 444 61.767 16.092 1.712 1.00 64.00 |
| ATOM | 1841 | CG2 VAL | 444 60.062 17.301 3.072 1.00 59.27 |
| ATOM | 1842 | C VAL | 444 60.091 13.693 1.744 1.00 68.61 |
| ATOM | 1843 | O VAL | 444 60.145 13.294 0.577 1.00 70.60 |
| ATOM | 1844 | N GLU | 445 60.520 12.972 2.775 1.00 70.71 |
| ATOM | 1845 | CA GLU | 445 61.129 11.653 2.609 1.00 71.45 |
| ATOM | 1846 | CB GLU | 445 61.808 11.233 3.916 1.00 72.36 |
| ATOM | 1847 | C GLU | 445 60.181 10.547 2.148 1.00 71.46 |
| ATOM | 1848 | O GLU | 445 60.588 9.390 2.042 1.00 73.02 |
| ATOM | 1849 | N CYS | 446 58.925 10.895 1.871 1.00 71.12 |
| ATOM | 1850 | CA CYS | 446 57.945 9.901 1.419 1.00 70.83 |
| ATOM | 1851 | CB CYS | 446 57.031 9.485 2.581 1.00 71.05 |
| ATOM | 1852 | SG CYS | 446 57.845 8.593 3.925 1.00 72.83 |
| ATOM | 1853 | C CYS | 446 57.081 10.390 0.261 1.00 71.91 |
| ATOM | 1854 | O CYS | 446 56.776 11.582 0.155 1.00 72.06 |
| ATOM | 1855 | N PRO | 447 56.673 9.470 −0.635 1.00 73.12 |
| ATOM | 1856 | CD PRO | 447 56.967 8.026 −0.671 1.00 72.88 |
| ATOM | 1857 | CA PRO | 447 55.837 9.825 −1.784 1.00 74.22 |
| ATOM | 1858 | CB PRO | 447 55.717 8.500 −2.537 1.00 72.98 |
| ATOM | 1859 | CG PRO | 447 57.015 7.790 −2.161 1.00 74.77 |
| ATOM | 1860 | C PRO | 447 54.479 10.343 −1.330 1.00 75.94 |
| ATOM | 1861 | O PRO | 447 53.754 9.652 −0.616 1.00 76.67 |
| ATOM | 1862 | N THR | 448 54.145 11.558 −1.755 1.00 76.91 |

APPENDIX 8-continued

TRBGC1.PDB

| ATOM | 1863 | CA  | THR | 448 | 52.879 | 12.197 | -1.403 | 1.00 | 78.24 |
| ---- | ---- | --- | --- | --- | ------ | ------ | ------ | ---- | ----- |
| ATOM | 1864 | CB  | THR | 448 | 52.647 | 13.459 | -2.261 | 1.00 | 81.33 |
| ATOM | 1865 | OG1 | THR | 448 | 52.552 | 13.087 | -3.643 | 1.00 | 84.46 |
| ATOM | 1866 | CG2 | THR | 448 | 53.802 | 14.444 | -2.089 | 1.00 | 83.51 |
| ATOM | 1867 | C   | THR | 448 | 51.676 | 11.270 | -1.580 | 1.00 | 77.42 |
| ATOM | 1868 | O   | THR | 448 | 50.662 | 11.413 | -0.894 | 1.00 | 77.65 |
| ATOM | 1869 | N   | GLU | 449 | 51.795 | 10.319 | -2.502 | 1.00 | 76.29 |
| ATOM | 1870 | CA  | GLU | 449 | 50.720 | 9.375  | -2.783 | 1.00 | 75.03 |
| ATOM | 1871 | CB  | GLU | 449 | 51.048 | 8.572  | -4.043 | 1.00 | 74.62 |
| ATOM | 1872 | C   | GLU | 449 | 50.445 | 8.421  | -1.622 | 1.00 | 73.49 |
| ATOM | 1873 | O   | GLU | 449 | 49.310 | 7.973  | -1.442 | 1.00 | 70.24 |
| ATOM | 1874 | N   | LEU | 450 | 51.477 | 8.113  | -0.840 | 1.00 | 70.80 |
| ATOM | 1875 | CA  | LEU | 450 | 51.327 | 7.194  | 0.285  | 1.00 | 68.82 |
| ATOM | 1876 | CB  | LEU | 450 | 52.693 | 6.644  | 0.705  | 1.00 | 71.91 |
| ATOM | 1877 | CG  | LEU | 450 | 53.428 | 5.795  | -0.336 | 1.00 | 76.62 |
| ATOM | 1878 | CD1 | LEU | 450 | 54.799 | 5.414  | 0.195  | 1.00 | 77.95 |
| ATOM | 1879 | CD2 | LEU | 450 | 52.617 | 4.546  | -0.662 | 1.00 | 76.46 |
| ATOM | 1880 | C   | LEU | 450 | 50.636 | 7.818  | 1.492  | 1.00 | 66.22 |
| ATOM | 1881 | O   | LEU | 450 | 50.501 | 7.181  | 2.540  | 1.00 | 66.01 |
| ATOM | 1882 | N   | PHE | 451 | 50.189 | 9.060  | 1.342  | 1.00 | 61.96 |
| ATOM | 1883 | CA  | PHE | 451 | 49.513 | 9.750  | 2.428  | 1.00 | 58.44 |
| ATOM | 1884 | CB  | PHE | 451 | 50.006 | 11.204 | 2.528  | 1.00 | 61.34 |
| ATOM | 1885 | CG  | PHE | 451 | 51.466 | 11.343 | 2.923  | 1.00 | 63.02 |
| ATOM | 1886 | CD1 | PHE | 451 | 52.488 | 10.888 | 2.077  | 1.00 | 62.92 |
| ATOM | 1887 | CD2 | PHE | 451 | 51.812 | 11.932 | 4.146  | 1.00 | 63.07 |
| ATOM | 1888 | CE1 | PHE | 451 | 53.855 | 11.029 | 2.437  | 1.00 | 65.12 |
| ATOM | 1889 | CE2 | PHE | 451 | 53.167 | 12.085 | 4.531  | 1.00 | 64.66 |
| ATOM | 1890 | CZ  | PHE | 451 | 54.195 | 11.628 | 3.673  | 1.00 | 67.12 |
| ATOM | 1891 | C   | PHE | 451 | 48.005 | 9.756  | 2.219  | 1.00 | 56.41 |
| ATOM | 1892 | O   | PHE | 451 | 47.501 | 10.471 | 1.350  | 1.00 | 56.56 |
| ATOM | 1893 | N   | PRO | 452 | 47.260 | 8.954  | 3.009  | 1.00 | 53.28 |
| ATOM | 1894 | CD  | PRO | 452 | 47.678 | 8.027  | 4.076  | 1.00 | 50.46 |
| ATOM | 1895 | CA  | PRO | 452 | 45.797 | 8.910  | 2.866  | 1.00 | 50.26 |
| ATOM | 1896 | CB  | PRO | 452 | 45.388 | 7.976  | 4.000  | 1.00 | 49.19 |
| ATOM | 1897 | CG  | PRO | 452 | 46.558 | 7.010  | 4.039  | 1.00 | 45.89 |
| ATOM | 1898 | C   | PRO | 452 | 45.183 | 10.305 | 2.974  | 1.00 | 49.62 |
| ATOM | 1899 | O   | PRO | 452 | 45.727 | 11.176 | 3.644  | 1.00 | 52.35 |
| ATOM | 1900 | N   | PRO | 453 | 44.034 | 10.530 | 2.313  | 1.00 | 51.50 |
| ATOM | 1901 | CD  | PRO | 453 | 43.257 | 9.585  | 1.494  | 1.00 | 49.66 |
| ATOM | 1902 | CA  | PRO | 453 | 43.354 | 11.830 | 2.335  | 1.00 | 50.89 |
| ATOM | 1903 | CB  | PRO | 453 | 42.101 | 11.559 | 1.506  | 1.00 | 51.49 |
| ATOM | 1904 | CG  | PRO | 453 | 42.600 | 10.524 | 0.521  | 1.00 | 50.82 |
| ATOM | 1905 | C   | PRO | 453 | 43.030 | 12.405 | 3.706  | 1.00 | 50.99 |
| ATOM | 1906 | O   | PRO | 453 | 43.264 | 13.588 | 3.953  | 1.00 | 54.17 |
| ATOM | 1907 | N   | LEU | 454 | 42.479 | 11.576 | 4.592  | 1.00 | 51.21 |
| ATOM | 1908 | CA  | LEU | 454 | 42.112 | 12.034 | 5.936  | 1.00 | 47.17 |
| ATOM | 1909 | CB  | LEU | 454 | 41.305 | 10.951 | 6.660  | 1.00 | 44.44 |
| ATOM | 1910 | CG  | LEU | 454 | 40.748 | 11.283 | 8.050  | 1.00 | 41.33 |
| ATOM | 1911 | CD1 | LEU | 454 | 39.838 | 12.504 | 7.978  | 1.00 | 35.93 |
| ATOM | 1912 | CD2 | LEU | 454 | 39.986 | 10.072 | 8.587  | 1.00 | 34.79 |
| ATOM | 1913 | C   | LEU | 454 | 43.363 | 12.380 | 6.733  | 1.00 | 42.25 |
| ATOM | 1914 | O   | LEU | 454 | 43.387 | 13.357 | 7.475  | 1.00 | 40.82 |
| ATOM | 1915 | N   | PHE | 455 | 44.399 | 11.567 | 6.565  | 1.00 | 39.29 |
| ATOM | 1916 | CA  | PHE | 455 | 45.674 | 11.774 | 7.240  | 1.00 | 41.81 |
| ATOM | 1917 | CB  | PHE | 455 | 46.655 | 10.679 | 6.802  | 1.00 | 47.22 |
| ATOM | 1918 | CG  | PHE | 455 | 48.045 | 10.800 | 7.407  | 1.00 | 56.97 |
| ATOM | 1919 | CD1 | PHE | 455 | 48.220 | 10.990 | 8.785  | 1.00 | 57.23 |
| ATOM | 1920 | CD2 | PHE | 455 | 49.180 | 10.645 | 6.597  | 1.00 | 59.40 |
| ATOM | 1921 | CE1 | PHE | 455 | 49.522 | 11.030 | 9.302  | 1.00 | 56.58 |
| ATOM | 1922 | CE2 | PHE | 455 | 50.487 | 10.682 | 7.149  | 1.00 | 61.80 |
| ATOM | 1923 | CZ  | PHE | 455 | 50.656 | 10.870 | 8.541  | 1.00 | 59.94 |
| ATOM | 1924 | C   | PHE | 455 | 46.203 | 13.161 | 6.892  | 1.00 | 45.12 |
| ATOM | 1925 | O   | PHE | 455 | 46.558 | 13.944 | 7.773  | 1.00 | 39.95 |
| ATOM | 1926 | N   | LEU | 456 | 46.236 | 13.471 | 5.592  | 1.00 | 43.92 |
| ATOM | 1927 | CA  | LEU | 456 | 46.704 | 14.767 | 5.123  | 1.00 | 44.08 |
| ATOM | 1928 | CB  | LEU | 456 | 46.748 | 14.795 | 3.593  | 1.00 | 50.20 |
| ATOM | 1929 | CG  | LEU | 456 | 47.796 | 13.921 | 2.903  | 1.00 | 55.79 |
| ATOM | 1930 | CD1 | LEU | 456 | 47.527 | 13.869 | 1.408  | 1.00 | 54.70 |
| ATOM | 1931 | CD2 | LEU | 456 | 49.187 | 14.473 | 3.193  | 1.00 | 53.01 |
| ATOM | 1932 | C   | LEU | 456 | 45.782 | 15.871 | 5.616  | 1.00 | 44.65 |
| ATOM | 1933 | O   | LEU | 456 | 46.219 | 16.987 | 5.887  | 1.00 | 45.93 |
| ATOM | 1934 | N   | GLU | 457 | 44.500 | 15.549 | 5.726  | 1.00 | 44.56 |
| ATOM | 1935 | CA  | GLU | 457 | 43.498 | 16.504 | 6.175  | 1.00 | 46.37 |
| ATOM | 1936 | CB  | GLU | 457 | 42.138 | 15.854 | 6.133  | 1.00 | 50.16 |
| ATOM | 1937 | C   | GLU | 457 | 43.759 | 17.039 | 7.579  | 1.00 | 43.60 |
| ATOM | 1938 | O   | GLU | 457 | 43.867 | 18.245 | 7.795  | 1.00 | 42.69 |
| ATOM | 1939 | N   | VAL | 458 | 43.847 | 16.117 | 8.528  | 1.00 | 43.21 |
| ATOM | 1940 | CA  | VAL | 458 | 44.064 | 16.446 | 9.930  | 1.00 | 44.98 |
| ATOM | 1941 | CB  | VAL | 458 | 44.020 | 15.159 | 10.802 | 1.00 | 44.83 |
| ATOM | 1942 | CG1 | VAL | 458 | 44.180 | 15.510 | 12.277 | 1.00 | 49.72 |
| ATOM | 1943 | CG2 | VAL | 458 | 42.708 | 14.427 | 10.567 | 1.00 | 40.89 |
| ATOM | 1944 | C   | VAL | 458 | 45.368 | 17.178 | 10.209 | 1.00 | 42.72 |
| ATOM | 1945 | O   | VAL | 458 | 45.393 | 18.139 | 10.974 | 1.00 | 42.88 |
| ATOM | 1946 | N   | PHE | 459 | 46.451 | 16.743 | 9.574  | 1.00 | 44.53 |
| ATOM | 1947 | CA  | PHE | 459 | 47.741 | 17.366 | 9.823  | 1.00 | 48.18 |
| ATOM | 1948 | CB  | PHE | 459 | 48.784 | 16.269 | 10.064 | 1.00 | 43.60 |
| ATOM | 1949 | CG  | PHE | 459 | 48.374 | 15.276 | 11.133 | 1.00 | 40.79 |
| ATOM | 1950 | CD1 | PHE | 459 | 47.835 | 14.032 | 10.783 | 1.00 | 41.01 |
| ATOM | 1951 | CD2 | PHE | 459 | 48.471 | 15.613 | 12.492 | 1.00 | 39.48 |
| ATOM | 1952 | CE1 | PHE | 459 | 47.387 | 13.118 | 11.776 | 1.00 | 40.62 |
| ATOM | 1953 | CE2 | PHE | 459 | 48.032 | 14.715 | 13.506 | 1.00 | 36.87 |
| ATOM | 1954 | CZ  | PHE | 459 | 47.489 | 13.463 | 13.146 | 1.00 | 36.39 |
| ATOM | 1955 | C   | PHE | 459 | 48.234 | 18.348 | 8.763  | 1.00 | 52.71 |
| ATOM | 1956 | O   | PHE | 459 | 49.336 | 18.878 | 8.877  | 1.00 | 51.34 |
| ATOM | 1957 | N   | GLU | 460 | 47.397 | 18.594 | 7.752  | 1.00 | 59.56 |
| ATOM | 1958 | CA  | GLU | 460 | 47.695 | 19.509 | 6.647  | 1.00 | 66.14 |
| ATOM | 1959 | CB  | GLU | 460 | 47.818 | 20.944 | 7.158  | 1.00 | 67.76 |
| ATOM | 1960 | CG  | GLU | 460 | 46.536 | 21.511 | 7.724  | 1.00 | 78.99 |
| ATOM | 1961 | CD  | GLU | 460 | 46.680 | 22.965 | 8.116  | 1.00 | 86.08 |
| ATOM | 1962 | OE1 | GLU | 460 | 47.014 | 23.786 | 7.237  | 1.00 | 87.62 |
| ATOM | 1963 | OE2 | GLU | 460 | 46.460 | 23.289 | 9.301  | 1.00 | 91.63 |
| ATOM | 1964 | C   | GLU | 460 | 48.940 | 19.163 | 5.836  | 1.00 | 69.17 |
| ATOM | 1965 | O   | GLU | 460 | 48.784 | 18.759 | 4.660  | 1.00 | 69.49 |
| ATOM | 1966 | OXT | GLU | 460 | 50.057 | 19.298 | 6.379  | 1.00 | 76.70 |
| ATOM | 1967 | C1  | TRI | 1   | 47.283 | 4.313  | 16.972 | 1.00 | 44.70 |
| ATOM | 1968 | C2  | TRI | 1   | 51.052 | 6.807  | 13.814 | 1.00 | 34.01 |
| ATOM | 1969 | C3  | TRI | 1   | 47.289 | 4.043  | 15.500 | 1.00 | 37.90 |
| ATOM | 1970 | C4  | TRI | 1   | 51.936 | 6.615  | 12.728 | 1.00 | 33.38 |
| ATOM | 1971 | C5  | TRI | 1   | 48.462 | 4.501  | 14.746 | 1.00 | 46.53 |
| ATOM | 1972 | C6  | TRI | 1   | 52.294 | 7.653  | 11.847 | 1.00 | 42.90 |
| ATOM | 1973 | C7  | TRI | 1   | 49.577 | 5.179  | 15.334 | 1.00 | 34.63 |
| ATOM | 1974 | C8  | TRI | 1   | 51.717 | 9.015  | 12.071 | 1.00 | 38.34 |
| ATOM | 1975 | C9  | TRI | 1   | 49.492 | 5.383  | 16.723 | 1.00 | 43.89 |
| ATOM | 1976 | C10 | TRI | 1   | 50.779 | 9.237  | 13.172 | 1.00 | 40.43 |
| ATOM | 1977 | C11 | TRI | 1   | 48.354 | 4.960  | 17.533 | 1.00 | 41.82 |
| ATOM | 1978 | C12 | TRI | 1   | 50.449 | 8.116  | 14.055 | 1.00 | 35.64 |
| ATOM | 1979 | C13 | TRI | 1   | 46.287 | 3.725  | 17.959 | 1.00 | 36.78 |
| ATOM | 1980 | C15 | TRI | 1   | 44.825 | 4.150  | 17.865 | 1.00 | 40.69 |
| ATOM | 1981 | I1  | TRI | 1   | 48.684 | 4.002  | 12.609 | 1.00 | 40.26 |
| ATOM | 1982 | I2  | TRI | 1   | 53.597 | 7.174  | 10.336 | 1.00 | 46.70 |
| ATOM | 1983 | I3  | TRI | 1   | 51.362 | 6.218  | 17.644 | 1.00 | 36.54 |
| ATOM | 1984 | O3  | TRI | 1   | 44.546 | 5.255  | 17.329 | 1.00 | 54.78 |
| ATOM | 1985 | O2  | TRI | 1   | 50.831 | 5.617  | 14.667 | 1.00 | 28.44 |
| ATOM | 1986 | O1  | TRI | 1   | 52.207 | 10.160 | 11.342 | 1.00 | 43.65 |
| ATOM | 1987 | O4  | TRI | 1   | 44.021 | 3.333  | 18.352 | 1.00 | 42.95 |
| ATOM | 1    | AS  | CAC | 501 | 60.548 | 16.977 | 16.916 | 1.00 | 65.97 | AS  |
| ATOM | 2    | AS  | CAC | 502 | 27.863 | 16.627 | 16.796 | 1.00 | 89.34 | AS  |
| ATOM | 3    | AS  | CAC | 503 | 29.889 | 28.698 | 21.811 | 1.00 | 100.00 | AS |
| ATOM | 4    | AS  | CAC | 504 | 33.547 | 24.203 | 8.880  | 1.00 | 100.00 | AS |
| ATOM | 5    | O   | HOH | 505 | 42.365 | 8.872  | 4.597  | 1.00 | 53.88 | HOH |
| ATOM | 6    | O   | HOH | 506 | 33.545 | 30.973 | 24.585 | 1.00 | 40.33 | HOH |
| ATOM | 7    | O   | HOH | 507 | 37.040 | 1.824  | 12.671 | 1.00 | 61.87 | HOH |
| ATOM | 8    | O   | HOH | 508 | 44.105 | 4.635  | 6.023  | 1.00 | 40.68 | HOH |
| ATOM | 9    | O   | HOH | 509 | 52.686 | 13.817 | -6.263 | 1.00 | 54.00 | HOH |
| ATOM | 10   | O   | HOH | 510 | 50.186 | 12.691 | -5.997 | 1.00 | 55.36 | HOH |
| ATOM | 11   | O   | HOH | 511 | 49.278 | 18.540 | 14.006 | 1.00 | 34.79 | HOH |
| ATOM | 12   | O   | HOH | 512 | 25.541 | 28.885 | 21.206 | 1.00 | 55.42 | HOH |
| ATOM | 13   | O   | HOH | 513 | 27.346 | 31.063 | 27.398 | 1.00 | 58.30 | HOH |
| ATOM | 14   | O   | HOH | 514 | 40.790 | 19.192 | 39.234 | 1.00 | 50.35 | HOH |
| ATOM | 15   | O   | HOH | 515 | 37.467 | 0.637  | 37.293 | 1.00 | 37.46 | HOH |
| ATOM | 16   | O   | HOH | 516 | 36.155 | 3.879  | 47.189 | 1.00 | 61.37 | HOH |
| ATOM | 17   | O   | HOH | 517 | 35.410 | 5.865  | 50.995 | 1.00 | 63.46 | HOH |
| ATOM | 18   | O   | HOH | 518 | 33.622 | 5.440  | 47.570 | 1.00 | 53.87 | HOH |
| ATOM | 19   | O   | HOH | 519 | 64.787 | 6.888  | 11.882 | 1.00 | 51.15 | HOH |
| ATOM | 20   | O   | HOH | 520 | 61.109 | -8.688 | 27.722 | 1.00 | 61.70 | HOH |
| ATOM | 21   | O   | HOH | 521 | 49.869 | -5.472 | 30.343 | 1.00 | 40.50 | HOH |
| ATOM | 22   | O   | HOH | 522 | 43.786 | -0.987 | 26.878 | 1.00 | 52.16 | HOH |
| ATOM | 23   | O   | HOH | 523 | 41.604 | 2.361  | 26.985 | 1.00 | 47.90 | HOH |
| ATOM | 24   | O   | HOH | 524 | 54.405 | 6.361  | 39.795 | 1.00 | 56.56 | HOH |
| ATOM | 25   | O   | HOH | 525 | 46.088 | 0.770  | 33.095 | 1.00 | 74.24 | HOH |
| ATOM | 26   | O   | HOH | 526 | 50.481 | 16.245 | 15.314 | 1.00 | 28.99 | HOH |
| ATOM | 27   | O   | HOH | 527 | 59.788 | 14.863 | 21.416 | 1.00 | 50.02 | HOH |
| ATOM | 28   | O   | HOH | 528 | 49.282 | 19.490 | 32.191 | 1.00 | 41.61 | HOH |
| ATOM | 29   | O   | HOH | 529 | 56.683 | 10.961 | 26.733 | 1.00 | 34.20 | HOH |

APPENDIX 8-continued

TRBGC1.PDB

| ATOM | 30 | O | HOH | 530 | 56.701 | 9.852 | 30.561 | 1.00 | 51.24 | HOH |
| ATOM | 31 | O | HOH | 531 | 26.487 | 13.273 | 30.591 | 1.00 | 43.94 | HOH |
| ATOM | 32 | O | HOH | 532 | 27.019 | 25.052 | 28.330 | 1.00 | 54.97 | HOH |
| ATOM | 33 | O | HOH | 533 | 50.689 | 1.918 | 29.551 | 1.00 | 39.63 | HOH |
| ATOM | 34 | O | HOH | 534 | 47.867 | 0.200 | 31.330 | 1.00 | 43.14 | HOH |
| ATOM | 35 | O | HOH | 535 | 61.434 | −0.721 | 23.218 | 1.00 | 49.83 | HOH |
| ATOM | 36 | O | HOH | 536 | 41.969 | 20.017 | 20.894 | 1.00 | 27.00 | HOH |
| ATOM | 37 | O | HOH | 537 | 46.897 | 16.244 | 15.992 | 1.00 | 31.50 | HOH |
| ATOM | 38 | O | HOH | 538 | 29.796 | 16.276 | 27.000 | 1.00 | 38.52 | HOH |
| ATOM | 39 | O | HOH | 539 | 47.853 | 23.205 | 20.217 | 1.00 | 44.39 | HOH |
| ATOM | 40 | O | HOH | 540 | 40.956 | 24.775 | 31.717 | 1.00 | 50.36 | HOH |
| ATOM | 41 | O | HOH | 541 | 43.310 | 1.560 | 41.912 | 1.00 | 43.56 | HOH |
| END | | | | | | | | | | |

What is claimed is:

1. A method for identifying a compound capable of selectively modulating the activity of a thyroid hormone receptor (TR) isoform, said method comprising:

modeling test compounds that fit spatially and preferentially into a TR ligand binding domain (TR LBD) isoform of interest using an atomic structural model of a TR LBD isoform bound to a test compound, wherein said atomic structural model is generated utilizing data from Appendix 3, 4, 5, 6, 7 or 8, screening said test compounds in a biological assay for TR isoform activity characterized by binding of a test compound to a TR LBD isoform, and identifying a test compound that selectively modulates the activity of a TR isoform.

2. The method of claim 1, wherein said compound is of the formula:

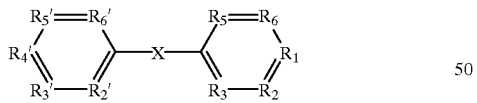

which comprises the following substituents:

(i) an $R_1$-substituent comprising an anionic group that interacts with a first side chain atom, wherein said first side chain atom is a nitrogen atom of an arginine corresponding to a residue selected from the group consisting of Arg228, Arg262, and Arg266 of human TR-α (SEQ ID NO: 2), and Arg282, Arg316 and Arg320 of human TR-β (SEQ ID NO: 3), and wherein the anionic group is 1.7–4.0 Å from the first side chain atom;

(ii) an $R_2$-substituent comprising a hydrophobic or hydrophilic group that fits spatially into the TR LBD;

(iii) an $R_3$-substituent comprising a hydrophobic or hydrophilic group that interacts with a second side chain atom, wherein said second side chain atom is an atom of a serine, alanine or isoleucine corresponding to a residue selected from the group consisting of Ser260, Ala263 and Ile299 of human TR-α (SEQ ID NO: 2), and Ser314, Ala317 and Ile352 of human TR-β (SEQ ID NO: 3), and wherein the hydrophobic or hydrophilic group is 1.7–4.0 Å from the second side chain atom;

(iv) an $R_5$-substituent comprising a hydrophobic or hydrophilic group that interacts with a third side chain atom, wherein said third side chain atom is an atom of a phenylalanine or isoleucine corresponding to a residue selected from the group consisting of Phe218, Ile221 and Ile222 of human TR-α (SEQ ID NO: 2, and Phe272, Ile275 and Ile276 of human TR-β (SEQ ID NO: 3), and wherein the hydrophobic or hydrophilic group is 1.7–4.0 Å from the third side chain atom;

(v) an $R_6$-substituent comprising a hydrophobic or hydrophilic group that fits spatially into the TR LBD;

(vi) an X-substituent comprising a hydrophobic or hydrophilic group that interacts with a fourth side chain atom, wherein said fourth side chain atom is an atom of a leucine corresponding to a residue selected from the group consisting of Leu276 and Leu292 of human TR-α (SEQ ID NO: 2), and Leu330 and Leu346 of human TR-β (SEQ ID NO: 3), and wherein the hydrophobic or hydrophilic group is 1.7–4.0 Å from the fourth side chain atom;

(vii) an $R_2'$-substituent comprising a hydrophobic or hydrophilic group that fits spatially into the TR LBD;

(viii) an $R_3'$-substituent comprising a hydrophobic group that interacts with a fifth side chain atom, wherein said fifth side chain atom is an atom of a phenylalanine, glycine or methionine corresponding to a residue selected from the group consisting of Phe215, Gly290, and Met388 of human TR-α (SEQ ID NO: 2), and Phe269, Gly344, Met442 of human TR-β (SEQ ID NO: 3), and wherein the hydrophobic group is 1.7–4.0 Å from the fifth side chain atom;

(ix) an $R_4'$-substituent comprising an hydrogen bond donor or acceptor group that interacts with a sixth side chain atom, wherein said sixth side chain atom is a carbon or nitrogen atom of a histidine corresponding to a residue selected from the group consisting of His381 of human TR-α (SEQ ID NO: 2) and His435 of human TR-β (SEQ ID NO: 3), and wherein the hydrogen bond donor or acceptor group is 1.7–4.0 Å from the sixth side chain atom;

(x) an $R_5'$-substituent comprising a hydrophobic or hydrophilic group that fits spatially into the TR LBD; and (xi) and $R_6'$-substituent comprising a hydrophobic or hydrophilic group that fits spatially into the TR LBD.

3. The method according to claim 2, wherein $R_1$ is
—O—CH$_2$CO$_2$H, —NHCH$_2$CO$_2$H, —CO$_2$H, —CH$_2$CO$_2$H, —CH$_2$CH$_2$CO$_2$H, —CH$_2$CH$_2$CH$_2$CO$_2$H, —CH$_2$CH(NH$_2$)CO$_2$H, —CH$_2$CH[NHCOCHφ$_2$]CO$_2$H, —CH$_2$CH[NHCO(CH$_2$)$_{15}$CH$_3$]CO$_2$H, —CH$_2$CH[NH-FMOC]CO$_2$H, —CH$_2$CH[NH-tBOC]CO$_2$H, or a carboxylate connected to the ring with a 0 to 3 carbon linker, —PO$_3$H$_2$, —CH$_2$PO$_3$H$_2$, —CH$_2$CH$_2$PO$_3$H$_2$, —CH$_2$CHNH$_2$PO$_3$H$_2$, —CH$_2$CH[NHCOCHφ$_2$]PO$_3$H$_2$, —CH$_2$CH[NHCO(CH$_2$)$_{15}$CH$_3$]PO$_3$H$_2$, —CH$_2$CH[NH-FMOC]PO$_3$H$_2$, —CH$_2$CH[NH-tBOC]PO$_3$H$_2$, or a phosphate or phosphonate connected to the ring with a 0 to 3 carbon linker, —SO$_3$H, —CH$_2$SO$_3$H, —CH$_2$CH$_2$SO$_3$H, —CH$_2$CHNH$_2$SO$_3$H, —CH$_2$CH[NHCOCHφ$_2$]SO$_3$H, —CH$_2$CH[NHCO(CH$_2$)$_{15}$CH$_3$]SO$_3$H, —CH$_2$CH[NH-FMOC]SO$_3$H, —CH$_2$CH[NH-tBOC]SO3H, or a sulfate or sulfite connected to the ring with a 0 to 3 carbon linker, or acts as the functional equivalent of CH$_2$CH(NH$_2$)CO$_2$H of T3 in the molecular recognition domain when bound to a TR, wherein $R_2$ is H, halogen, CF$_3$, OH, NH$_2$, SH, CH$_3$, —Et, or acts as the functional equivalent of H in the molecular recognition domain when bound to a TR, wherein $R_3$ is —H, halogen, —CF$_3$, —OH, —NH$_2$, —N$_3$, —SH, —CH$_3$, —Et, or acts as the functional equivalent of I in the molecular recognition domain when bound to a TR, wherein $R_5$ is —H, halogen, —CF$_3$, —OH, —NH$_2$, —N$_3$, —SH, —CH$_3$, —Et, or acts as the functional equivalent of I in the molecular recognition domain when bound to a TR, and $R_3$ can be identical to $R_5$, wherein $R_6$ is —H, halogen, —CF$_3$, —OH, —NH$_2$, —SH, —CH$_3$, or acts as the functional equivalent of H in the molecular recognition domain when bound to a TR, and $R_2$ can be identical to $R_6$, wherein $R_2'$ is —H, halogen, —CF$_3$, —OH, —NH$_2$, —N$_3$, —SH, —CH$_3$, —Et, or acts as the functional equivalent of H in the molecular recognition domain when bound to a TR, wherein $R_3'$ is any hydrophobic group, including
halogen, —CF$_3$, —SH, alkyl, aryl, 5- or 6-membered heterocyclic, cyano, or acts as the functional equivalent of I in the molecular recognition domain when bound to a TR, wherein $R_4'$ is —H, halogen, —CF$_3$, —OH, —NH$_2$, NH$_3$, —N(CH$_3$)$_3$, carboxylate, phosphonate, phosphate or sulfate, —SH, —CH$_3$, —Et, or alkyl, aryl or 5- or 6-membered heterocyclic aromatic attached through urea or carbamate linkages to O or N or S at the $R_4'$ position, or acts as the functional equivalent of OH in the molecular recognition domain when bound to a TR, wherein $R_5'$ is —H, —OH, —NH$_2$, —N(CH$_3$)$_2$—SH—NH$_3$, —N(CH$_3$)$_3$, carboxylate, phosphonate, phosphate, sulfate, branched or straight chain alkyl having 1 to 9 carbons, substituted or unsubstituted aryl, wherein said substituted aryl is substituted with halogen or 1 to 5 carbon alkyl and wherein said aryl is optionally connected to the ring by a —CH$_2$—, substituted or unsubstituted aromatic heterocycle having 5 to 6 atoms, wherein said substituted heterocycle is substituted with one or more groups selected from —OH, —NH$_2$, —SH, —NH$_3$, —N(CH$_3$)$_3$, carboxylate, phosphonate, phosphate or sulfate, heteroalkyl, arylalkyl, heteroaryl alkyl, polyaromatic, or polyheteroaromatic, wherein $R_6'$ is —H, halogen, —CF$_3$, —OH, —NH$_2$, —SH, —CH$_3$, —Et, or acts as the functional equivalent of H in the molecular recognition domain when bound to a TR, wherein X is O, S, SO$_2$, NH, NR$_7$, CH$_2$, CHR$_7$, CR$_7$R$_7$, wherein R$_7$ is alkyl, aryl or 5- or 6-membered heterocyclic aromatic, and wherein said TR LBD ligand has an apparent Kd for binding TR LBD of 1 TM or less.

4. The method of claim 3 wherein $R_1$ is carboxylate, phosphonate, phosphate or sulfite and is connected to the ring with a 0 to 3 carbon linker, $R_2$ is H, $R_3$ is —I, —Br, or —CH$_3$, $R_5$ is —I, —Br, or —CH$_3$, $R_6$ is H, $R_2'$ is H, $R_3'$ is —I, —Br, —CH$_3$, -iPr, -phenyl, benzyl, or 5- or 6-membered ring heterocycle, $R_4'$ is —OH, —NH$_2$, and —SH, $R_5'$ is —H, —OH, —NH$_2$, —N(CH$_3$)$_2$—SH—NH$_3$, —N(CH$_3$)$_3$, carboxylate, phosphonate, phosphate, sulfate, branched or straight chain alkyl having 1 to 9 carbons, substituted or unsubstituted aryl, wherein said substituted aryl is substituted with halogen or 1 to 5 carbon alkyl and wherein said aryl is optionally connected to the ring by a —CH$_2$—, substituted or unsubstituted aromatic heterocycle having 5 to 6 atoms, wherein said substituted heterocycle is substituted with one or more groups selected from —OH, —NH$_2$, —SH, —NH$_3$, —N(CH$_3$)$_3$, carboxylate, phosphonate, phosphate or sulfate, heteroalkyl, arylalkyl, heteroaryl alkyl, polyaromatic, or polyheteroaromatic, and $R_6'$ is H.

5. The method of claim 1, wherein said compound fits spatially and preferentially into TR LBD isoform α (TR-α).

6. The method of claim 5, wherein said compound comprises an anionic group that interacts with a side chain atom, wherein said side chain atom is an oxygen or carbon atom of a serine residue corresponding to Ser277 of human TR-α (SEQ ID NO: 2), and wherein the anionic group is 1.7–4.0 Å from the side chain atom.

7. The method of claim 1, wherein said compound fits spatially and preferentially into TR LBD isoform β (TR-β).

8. The method of claim 7, wherein said compound comprises an anionic group that interacts with a side chain atom, wherein said side chain atom is a nitrogen atom of an arginine corresponding to Asn331 of human TR-β (SEQ ID NO: 3), and the anionic group is 1.7–4.0 Å from the side chain atom.

9. The method of claim 1, wherein said compound binds to a TR LBD isoform with greater affinity than thyronine or triiodothyronine.

10. A method for identifying a thyroid hormone receptor (TR) agonist or antagonist ligand, said method comprising the steps of:

providing the atomic coordinates of a TR ligand binding domain (TR LBD) to a computerized modeling system, wherein said atomic coordinates are generated utilizing data from Appendix 3, 4, 5, 6, 7 or 8;

modeling ligands which fit spatially into the TR LBD; and identifying in a biological assay for TR activity a ligand which increases or decreases the activity of said TR, whereby a TR agonist or antagonist is identified.

11. A method of identifying a compound that selectively modulates the activity of a thyroid hormone receptor (TR) compared to other nuclear hormone receptors, said method comprising:

modeling compounds which fit spatially into a TR ligand binding domain (TR LBD) using an atomic structural model of a TR LBD, wherein said atomic structural model is generated utilizing data from Appendix 3, 4, 5, 6, 7 or 8, selecting a compound comprising conformationally constrained structural features that interact with conformationally constrained residues of a TR LBD, identifying in a biological assay for TR activity a compound that selectively binds to a TR LBD compared to other nuclear receptors, whereby a compound that selectively modulates a TR is identified.

12. The method of claim 11, wherein said conformationally constrained residues of a TR LBD correspond to residues Met259, Leu276, Leu292, His381, Gly290, Ile221, and Phe401 of human TR-α (SEQ ID NO: 2), and residues Met313, Leu330, Leu346, His435, Gly344, Ile275 and Phe455 of human TR-β (SEQ ID NO: 3).

13. The method of claim 11, wherein said compounds are of the formula:

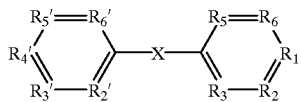

which comprises the following substituents:

(i) an $R_1$-substituent comprising an anionic group that interacts with a first side chain atom, wherein said first side chain atom is a nitrogen atom of an arginine corresponding to a residue selected from the group consisting of Arg228, Arg262, and Arg266 of human TR-α (SEQ ID NO: 2), and Arg282, Arg316 and Arg320 of human TR-β (SEQ ID NO: 3), and wherein the anionic group is 1.7–4.0 Å from the first side chain atom;

(ii) an $R_2$-substituent comprising a hydrophobic or hydrophilic group that fits spatially into the TR LBD;

(iii) an $R_3$-substituent comprising a hydrophobic or hydrophilic group that interacts with a second side chain atom, wherein said second side chain atom is an atom of a serine, alanine or isoleucine corresponding to a residue selected from the group consisting of Ser260, Ala263 and Ile299 of human TR-α (SEQ ID NO: 2), and Ser314, Ala317 and Ile352 of human TR-β (SEQ ID NO: 3), and wherein the hydrophobic or hydrophilic group is 1.7–4.0 Å from the second side chain atom;

(iv) an $R_5$-substituent comprising a hydrophobic or hydrophilic group that interacts with a third side chain atom, wherein said third side chain atom is an atom of a phenylalanine or isoleucine corresponding to a residue selected from the group consisting of Phe218, Ile221 and Ile222 of human TR-α (SEQ ID NO: 2), and Phe272, Ile275 and Ile276 of human TR-β (SEQ ID NO: 3, and wherein the hydrophobic or hydrophilic group is 1.7–4.0 Å from the third side chain atom;

(v) an $R_6$-substituent comprising a hydrophobic or hydrophilic group that fits spatially into the TR LBD;

(vi) an X-substituent comprising a hydrophobic or hydrophilic group that interacts with a fourth side chain atom, wherein said fourth side chain atom is an atom of a leucine corresponding to a residue selected from the group consisting of Leu276 and Leu292 of human TR-α (SEQ ID NO: 2), and Leu330 and Leu346 of human TR-β (SEQ ID NO: 3), and wherein the hydrophobic or hydrophilic group is 1.7–4.0 Å from the fourth side chain atom;

(vii) an $R_2'$-substituent comprising a hydrophobic or hydrophilic group that fits spatially into the TR LBD;

(viii) an $R_3'$-substituent comprising a hydrophobic group that interacts with a fifth side chain atom, wherein said fifth side chain atom is an atom of a phenylalanine, glycine or methionine corresponding to a residue selected from the group consisting of Phe215, Gly290, and Met388 of human TR-α (SEQ ID NO: 2), and Phe269, Gly344, Met442 of human TR-β (SEQ ID NO: 3), and wherein the hydrophobic group is 1.7–4.0 Å from the fifth side chain atom;

(ix) an $R_4'$-substituent comprising an hydrogen bond donor or acceptor group that interacts with a sixth side chain atom, wherein said sixth side chain atom is a carbon or nitrogen atom of a histidine corresponding to residue His381 of human TR-α (SEQ ID NO: 2, and His435 of human TR-β (SEQ ID NO: 3), and wherein the hydrogen bond donor or acceptor group is 1.7–4.0 Å from the sixth side chain atom;

(x) an $R_5'$-substituent comprising a hydrophobic or hydrophilic group that fits spatially into the TR LBD; and (xi) and $R_6'$-substituent comprising a hydrophobic or hydrophilic group that fits spatially into the TR LBD.

14. The method of claim 11, wherein said compound comprises:

(i) a cyclic carbon atom that interacts with a carbon and oxygen atom of a methionine residue corresponding to Met259 of human TR-α (SEQ ID NO: 2), and Met313 of human TR-β (SEQ ID NO: 3, wherein the cyclic carbon is about 3.0 to 4.0 Å from the carbon and oxygen atom of the methionine;

(ii) a cyclic carbon atom that interacts with a carbon atom of a leucine residue corresponding to Leu276 of human TR-α (SEQ ID NO: 2, and Leu330 of human TR-β (SEQ ID NO: 3), wherein the cyclic carbon is about 3.0 to 4.0 Å from the carbon atom of the leucine;

(iii) a cyclic carbon atom that interacts with a carbon atom of a leucine residue corresponding to Leu292 of human TR-α (SEQ ID NO: 2, and Leu346 of human TR-β

(SEQ ID NO: 3), wherein the cyclic carbon is about 3.0 to 4.0 Å from the carbon atom of the leucine;

(iv) a $R_3$-substituent comprising an atom that interacts with a carbon atom of an isoleucine residue corresponding to Ile221 of human TR-α (SEQ ID NO: 2), and Ile275 of human TR-β (SEQ ID NO: 3, wherein the R3-substituent atom is about 3.0 to 4.0 Å from the carbon atom of the isoleucine;

(v) a $R_3'$-substituent comprising an atom that interacts with an oxygen atom of a glycine residue corresponding to Gly290 of human TR-α (SEQ ID NO: 2), and Gly344 of human TR-β (SEQ ID NO: 3), wherein the R3'-substituent atom is about 3.0 to 4.0 Å from the carbon atom of the glycine; and (vi) a $R_4'$-substituent comprising an atom selected from the group consisting of oxygen and carbon that interacts with (a) a carbon and nitrogen atom of a histidine residue corresponding to His381 of human TR-α (SEQ ID NO: 2), and His435 of human TR-β (SEQ ID NO: 3, wherein the R4'-substituent atom is about 2.0 to 4.0 Å from the carbon atom of the histidine, and (b) a carbon atom of a phenylalanine residue corresponding to Phe401 of human TR-α (SEQ ID NO: 2), and Phe455 of TR-β (SEQ ID NO: 3), wherein said atom is about 3.0 to 4.0 Å from the carbon atom of the phenylalanine.

15. The method according to claim 13, wherein $R_1$ is

—O—$CH_2CO_2H$, —$NHCH_2CO_2H$, —$CO_2H$, —$CH_2CO_2H$, —$CH_2CH_2CO_2H$, —$CH_2CH_2CH_2CO_2H$, —$CH_2CH(NH_2)CO_2H$, —$CH_2CH[NHCOCH\phi_2]CO_2H$, —$CH_2CH[NHCO(CH_2)_{15}CH_3]CO_2H$, —$CH_2CH[NH-FMOC]CO_2H$, —$CH_2CH[NH-tBOC]CO_2H$, or a carboxylate connected to the ring with a 0 to 3 carbon linker, —$PO_3H_2$, —$CH_2PO_3H_2$, —$CH_2CH_2PO_3H_2$, —$CH_2CHNH_2PO_3H_2$, —$CH_2CH[NHCOCH\phi_2]PO_3H_2$, —$CH_2CH[NHCO(CH_2)_{15}CH_3]PO_3H_2$, —$CH_2CH[NH-FMOC]PO_3H_2$, —$CH_2CH[NH-tBOC]PO_3H_2$, or a phosphate or phosphonate connected to the ring with a 0 to 3 carbon linker, —$SO_3H$, —$CH_2SO_3H$, —$CH_2CH_2SO_3H$, —$CH_2CHNH_2SO_3H$, —$CH_2CH[NHCOCH\phi_2]SO_3H$, —$CH_2CH[NHCO(CH_2)_{15}CH_3]SO_3H$, —$CH_2CH[NH-FMOC]SO_3H$, —$CH_2CH[NH-tBOC]SO_3H$, or a sulfate or sulfite connected to the ring with a 0 to 3 carbon linker, or acts as the functional equivalent of $CH_2CH(NH_2)CO_2H$ of T3 in the molecular recognition domain when bound to a TR, wherein $R_2$ is H, halogen, $CF_3$, OH, $NH_2$, SH, $CH_3$, —Et, or acts as the functional equivalent of H in the molecular recognition domain when bound to a TR, wherein $R_3$ is —H, halogen, —$CF_3$, —OH, —$NH_2$, —$N_3$, —SH, —$CH_3$, —Et, or acts as the functional equivalent of I in the molecular recognition domain when bound to a TR, wherein $R_5$ is —H, halogen, —$CF_3$, —OH, —$NH_2$, —$N_3$, —SH, —$CH_3$, —Et, or acts as the functional equivalent of I in the molecular recognition domain when bound to a TR, and $R_3$ can be identical to $R_5$, wherein $R_6$ is —H, halogen, —$CF_3$, —OH, —$NH_2$, —SH, —$CH_3$, or acts as the functional equivalent of H in the molecular recognition domain when bound to a TR, and $R_2$ can be identical to $R_6$, wherein $R_2'$ is —H, halogen, —$CF_3$, —OH, —$NH_2$, —$N_3$, —SH, —$CH_3$, —Et, or acts as the functional equivalent of H in the molecular recognition domain when bound to a TR, wherein $R_3'$ is any hydrophobic group, including halogen, —$CF_3$, —SH, alkyl, aryl, 5- or 6-membered heterocycle, cyano, or acts as the functional equivalent of I in the molecular recognition domain when bound to a TR, wherein $R_4'$ is —H, halogen, —$CF_3$, —OH, —$NH_2$, $NH_3$, —$N(CH_3)_3$, carboxylate, phosphonate, phosphate or sulfate, —SH, —$CH_3$, —Et, or alkyl, aryl or 5- or 6-membered heterocyclic aromatic attached through urea or carbamate linkages to O or N or S at the $R_4'$ position, or acts as the functional equivalent of OH in the molecular recognition domain when bound to a TR, wherein $R_5'$ is —H, —OH, —$NH_2$, —$N(CH_3)_2$—SH—$NH_3$, —$N(CH_3)_3$, carboxylate, phosphonate, phosphate, sulfate, branched or straight chain alkyl having 1 to 9 carbons, substituted or unsubstituted aryl, wherein said substituted aryl is substituted with halogen or 1 to 5 carbon alkyl and wherein said aryl is optionally connected to the ring by a —$CH_2$—, substituted or unsubstituted aromatic heterocycle having 5 to 6 atoms, wherein said substituted heterocycle is substituted with one or more groups selected from —OH, —$NH_2$, —SH, —$NH_3$, —$N(CH_3)_3$, carboxylate, phosphonate, phosphate or sulfate, heteroalkyl, arylalkyl, heteroaryl alkyl, polyaromatic, or polyheteroaromatic, wherein $R_6'$ is —H, halogen, —$CF_3$, —OH, —$NH_2$, —SH, —$CH_3$, —Et, or acts as the functional equivalent of H in the molecular recognition domain when bound to a TR, wherein X is O, S, $SO_2$, NH, $NR_7$, $CH_2$, $CHR_7$, $CR_7R_7$, wherein $R_7$ is alkyl, aryl or 5- or 6-membered heterocyclic aromatic, and wherein said TR LBD ligand has an apparent Kd for binding TR LBD of 1 TM or less.

16. The method of claim 15, wherein $R_1$ is carboxylate, phosphonate, phosphate or sulfite and is connected to the ring with a 0 to 3 carbon linker, $R_2$ is H, $R_3$ is —I, —Br, or —$CH_3$, $R_5$ is —I, —Br, or —$CH_3$, $R_6$ is H, $R_2'$ is H, $R_3'$ is —I, —Br, —$CH_3$, -iPr, -phenyl, benzyl, or 5- or 6-membered ring heterocycles, $R_4'$ is —OH, —$NH_2$, and —SH, $R_5'$ is —H, —OH, —$NH_2$, —$N(CH_3)_2$—SH—$NH_3$, —$N(CH_3)_3$, carboxylate, phosphonate, phosphate, sulfate, branched or straight chain alkyl having 1 to 9 carbons, substituted or unsubstituted aryl, wherein said substituted aryl is substituted with halogen or 1 to 5 carbon alkyl and wherein said aryl is optionally connected to the ring by a substituted or unsubstituted aromatic heterocycle having 5 to 6 atoms, wherein said substituted heterocycle is substituted with one or more groups selected from —OH, —$NH_2$, —SH, —$NH_3$, —N(CH$_3$)$_3$, carboxylate, phosphonate, phosphate or sulfate, heteroalkyl, arylalkyl, heteroaryl alkyl, polyaromatic, or polyheteroaromatic, and R$_6$' is H.

17. The method of claim 11, wherein said compound fits spatially and preferentially into TR LBD isoform α (TR-α).

18. The method of claim 17, wherein said compound comprises an anionic group that interacts with the side chain oxygen or carbon of a serine residue corresponding to Ser277 of human TR-α (SEQ ID NO: 2), and wherein the anionic group is 1.7–4.0 Å from the side chain atom.

19. The method of claim 11, wherein said compound fits spatially and preferentially into TR LBD isoform β (TR-β).

20. The method of claim 19, wherein said compound comprises an anionic group that interacts with a side chain atom, wherein said side chain atom is a nitrogen atom of an arginine corresponding to Asn331 of human TR-β (SEQ ID NO: 3), and the anionic group is 1.7–4.0 Å from the side chain atom.

21. The method of claim 11, wherein said compound binds to a TR LBD isoform with greater affinity than thyronine or triiodothyronine.

22. A method for identifying a thyroid hormone receptor (TR) agonist or antagonist ligand that selectively modulates the activity of a TR compared to other nuclear receptors, said method comprising the steps of:

providing the atomic coordinates of a TR ligand binding domain (TR LBD) to a computerized modeling system, wherein said atomic coordinates are generated utilizing data from Appendix 3, 4, 5, 6, 7 or 8;

modeling ligands which fit spatially into the TR LBD and which interact with conformationally constrained residues of a TR LBD conserved among TR isoforms; and identifying in a biological assay for TR activity a ligand which selectively binds to said TR and increases or decreases the activity of said TR, whereby a TR agonist or antagonist that selectively modulates the activity of a TR is identified.

23. The method of claim 3 wherein said R$_1$ is substituted with an amine.

24. The method of claim 3 wherein said R$_5$' is substituted with polar or charged groups.

25. The method of claim 4, wherein said R$_5$' is substituted with polar or charged groups.

26. The method of claim 15, wherein said R$_1$ is substituted with an amine.

27. The method of claim 15, wherein said R$_5$' is substituted with polar or charged groups.

28. The method of claim 16, wherein said R$_5$' may be substituted with polar or charged groups.

* * * * *

SEQUENCE LISTING

<160> NUMBER OF SEQ ID NOS: 17

<210> SEQ ID NO 1
<211> LENGTH: 410
<212> TYPE: PRT
<213> ORGANISM: Rattus sp.
<220> FEATURE:
<221> NAME/KEY: DOMAIN
<222> LOCATION: (157)..(410)
<223> OTHER INFORMATION: minimal ligand binding domain
<220> FEATURE:
<221> NAME/KEY: DOMAIN
<222> LOCATION: (393)..(405)
<223> OTHER INFORMATION: activation domain

<400> SEQUENCE: 1

```
Met Glu Gln Lys Pro Ser Lys Val Glu Cys Gly Ser Asp Pro Glu Glu
 1               5                  10                  15

Asn Ser Ala Arg Ser Pro Asp Gly Lys Arg Lys Arg Lys Asn Gly Gln
            20                  25                  30

Cys Pro Leu Lys Ser Ser Met Ser Gly Tyr Ile Pro Ser Tyr Leu Asp
        35                  40                  45

Lys Asp Glu Gln Cys Val Val Cys Gly Asp Lys Ala Thr Gly Tyr His
    50                  55                  60

Tyr Arg Cys Ile Thr Cys Glu Gly Cys Lys Gly Phe Phe Arg Arg Thr
65                  70                  75                  80

Ile Gln Lys Asn Leu His Pro Thr Tyr Ser Cys Lys Tyr Asp Ser Cys
                85                  90                  95

Cys Val Ile Asp Lys Ile Thr Arg Asn Gln Cys Gln Leu Cys Arg Phe
            100                 105                 110

Lys Lys Cys Ile Ala Val Gly Met Ala Met Asp Leu Val Leu Asp Asp
        115                 120                 125

Ser Lys Arg Val Ala Lys Arg Lys Leu Ile Glu Gln Asn Arg Glu Arg
    130                 135                 140

Arg Arg Lys Glu Glu Met Ile Arg Ser Leu Gln Gln Arg Pro Glu Pro
145                 150                 155                 160

Thr Pro Glu Glu Trp Asp Leu Ile His Val Ala Thr Glu Ala His Arg
                165                 170                 175

Ser Thr Asn Ala Gln Gly Ser His Trp Lys Gln Arg Arg Lys Phe Leu
            180                 185                 190

Pro Asp Asp Ile Gly Gln Ser Pro Ile Val Ser Met Pro Asp Gly Asp
        195                 200                 205

Lys Val Asp Leu Glu Ala Phe Ser Glu Phe Thr Lys Ile Ile Thr Pro
    210                 215                 220
```

```
Ala Ile Thr Arg Val Val Asp Phe Ala Lys Lys Leu Pro Met Phe Ser
225                 230                 235                 240

Glu Leu Pro Cys Glu Asp Gln Ile Ile Leu Leu Lys Gly Cys Cys Met
            245                 250                 255

Glu Ile Met Ser Leu Arg Ala Ala Val Arg Tyr Asp Pro Glu Ser Asp
        260                 265                 270

Thr Leu Thr Leu Ser Gly Glu Met Thr Val Lys Arg Lys Gln Leu Lys
    275                 280                 285

Asn Gly Gly Leu Gly Val Val Ser Asp Ala Ile Phe Glu Leu Gly Lys
290                 295                 300

Ser Leu Ser Ala Phe Asn Leu Asp Asp Thr Glu Val Ala Leu Leu Gln
305                 310                 315                 320

Ala Val Leu Leu Met Ser Thr Asp Arg Ser Gly Leu Leu Cys Val Asp
                325                 330                 335

Lys Ile Glu Lys Ser Gln Glu Ala Tyr Leu Leu Ala Phe Glu His Tyr
            340                 345                 350

Val Asn His Arg Lys His Asn Ile Pro His Phe Trp Pro Lys Leu Leu
        355                 360                 365

Met Lys Val Thr Asp Leu Arg Met Ile Gly Ala Cys His Ala Ser Arg
370                 375                 380

Phe Leu His Met Lys Val Glu Cys Pro Thr Glu Leu Phe Pro Pro Leu
385                 390                 395                 400

Phe Leu Glu Val Phe Glu Asp Gln Glu Val
                405                 410

<210> SEQ ID NO 2
<211> LENGTH: 410
<212> TYPE: PRT
<213> ORGANISM: Homo sapiens
<220> FEATURE:
<221> NAME/KEY: DOMAIN
<222> LOCATION: (157)..(410)
<223> OTHER INFORMATION: minimal ligand binding domain

<400> SEQUENCE: 2

Met Glu Gln Lys Pro Ser Lys Val Glu Cys Gly Ser Asp Pro Glu Glu
1               5                   10                  15

Asn Ser Ala Arg Ser Pro Asp Gly Lys Arg Lys Arg Lys Asn Gly Gln
            20                  25                  30

Cys Ser Leu Lys Thr Ser Met Ser Gly Tyr Ile Pro Ser Tyr Leu Asp
        35                  40                  45

Lys Asp Glu Gln Cys Val Val Cys Gly Asp Lys Ala Thr Gly Tyr His
    50                  55                  60

Tyr Arg Cys Ile Thr Cys Glu Gly Cys Lys Gly Phe Phe Arg Arg Thr
65                  70                  75                  80

Ile Gln Lys Asn Leu His Pro Thr Tyr Ser Cys Lys Tyr Asp Ser Cys
                85                  90                  95

Cys Val Ile Asp Lys Ile Thr Arg Asn Gln Cys Gln Leu Cys Arg Phe
            100                 105                 110

Lys Lys Cys Ile Ala Val Gly Met Ala Met Asp Leu Val Leu Asp Asp
        115                 120                 125

Ser Lys Arg Val Ala Lys Arg Lys Leu Ile Glu Gln Asn Arg Glu Arg
    130                 135                 140

Arg Arg Lys Glu Glu Met Ile Arg Ser Leu Gln Gln Arg Pro Glu Pro
145                 150                 155                 160
```

-continued

```
Thr Pro Glu Glu Trp Asp Leu Ile His Ile Ala Thr Glu Ala His Arg
                165                 170                 175
Ser Thr Asn Ala Gln Gly Ser His Trp Lys Gln Arg Arg Lys Phe Leu
            180                 185                 190
Pro Asp Ile Gly Gln Ser Pro Ile Val Ser Met Pro Asp Gly Asp
        195                 200                 205
Lys Val Asp Leu Glu Ala Phe Ser Glu Phe Thr Lys Ile Ile Thr Pro
    210                 215                 220
Ala Ile Thr Arg Val Val Asp Phe Ala Lys Lys Leu Pro Met Phe Ser
225                 230                 235                 240
Glu Leu Pro Cys Glu Asp Gln Ile Ile Leu Leu Lys Gly Cys Cys Met
                245                 250                 255
Glu Ile Met Ser Leu Arg Ala Ala Val Arg Tyr Asp Pro Glu Ser Asp
            260                 265                 270
Thr Leu Thr Leu Ser Gly Glu Met Ala Val Lys Arg Glu Gln Leu Lys
        275                 280                 285
Asn Gly Gly Leu Gly Val Val Ser Asp Ala Ile Phe Glu Leu Gly Lys
    290                 295                 300
Ser Leu Ser Ala Phe Asn Leu Asp Asp Thr Glu Val Ala Leu Leu Gln
305                 310                 315                 320
Ala Val Leu Leu Met Ser Thr Asp Arg Ser Gly Leu Leu Cys Val Asp
                325                 330                 335
Lys Ile Glu Lys Ser Gln Glu Ala Tyr Leu Leu Ala Phe Glu His Tyr
            340                 345                 350
Val Asn His Arg Lys His Asn Ile Pro His Phe Trp Pro Lys Leu Leu
        355                 360                 365
Met Lys Val Thr Asp Leu Arg Met Ile Gly Ala Cys His Ala Ser Arg
    370                 375                 380
Phe Leu His Met Lys Val Glu Cys Pro Thr Glu Leu Phe Pro Pro Leu
385                 390                 395                 400
Phe Leu Glu Val Phe Glu Asp Gln Glu Val
                405                 410

<210> SEQ ID NO 3
<211> LENGTH: 461
<212> TYPE: PRT
<213> ORGANISM: Homo sapiens
<220> FEATURE:
<221> NAME/KEY: DOMAIN
<222> LOCATION: (211)..(461)
<223> OTHER INFORMATION: minimal ligand binding domain

<400> SEQUENCE: 3

Met Thr Pro Asn Ser Met Thr Glu Asn Gly Leu Thr Ala Trp Asp Lys
  1               5                  10                  15
Pro Lys His Cys Pro Asp Arg Glu His Asp Trp Lys Leu Val Gly Met
                 20                  25                  30
Ser Glu Ala Cys Leu His Arg Lys Ser His Ser Glu Arg Arg Ser Thr
             35                  40                  45
Leu Lys Asn Glu Gln Ser Ser Pro His Leu Ile Gln Thr Thr Trp Thr
         50                  55                  60
Ser Ser Ile Phe His Leu Asp His Asp Val Asn Asp Gln Ser Val
 65                  70                  75                  80
Ser Ser Ala Gln Thr Phe Gln Thr Glu Glu Lys Lys Cys Lys Gly Tyr
                 85                  90                  95
```

```
Ile Pro Ser Tyr Leu Asp Lys Asp Glu Leu Cys Val Cys Gly Asp
            100                 105                 110
Lys Ala Thr Gly Tyr His Tyr Arg Cys Ile Thr Cys Glu Gly Cys
        115                 120                 125
Lys Gly Phe Phe Arg Arg Thr Ile Gln Lys Asn Leu His Pro Ser Tyr Ser
            130                 135                 140
Cys Lys Tyr Glu Gly Lys Cys Val Ile Asp Lys Val Thr Arg Asn Gln
145                 150                 155                 160
Cys Gln Glu Cys Arg Phe Lys Lys Cys Ile Tyr Val Gly Met Ala Thr
                165                 170                 175
Asp Leu Val Leu Asp Asp Ser Lys Arg Leu Ala Lys Arg Lys Leu Ile
            180                 185                 190
Glu Glu Asn Arg Glu Lys Arg Arg Arg Glu Glu Leu Gln Lys Ser Ile
            195                 200                 205
Gly His Lys Pro Glu Pro Thr Asp Glu Glu Trp Glu Leu Ile Lys Thr
        210                 215                 220
Val Thr Glu Ala His Val Ala Thr Asn Ala Gln Gly Ser His Trp Lys
225                 230                 235                 240
Gln Lys Pro Lys Phe Leu Pro Glu Asp Ile Gly Gln Ala Pro Ile Val
                245                 250                 255
Asn Ala Pro Glu Gly Gly Lys Val Asp Leu Glu Ala Phe Ser His Phe
            260                 265                 270
Thr Lys Ile Ile Thr Pro Ala Ile Thr Arg Val Val Asp Phe Ala Lys
        275                 280                 285
Lys Leu Pro Met Phe Cys Glu Leu Pro Cys Glu Asp Gln Ile Ile Leu
    290                 295                 300
Leu Lys Gly Cys Cys Met Glu Ile Met Ser Leu Arg Ala Ala Val Arg
305                 310                 315                 320
Tyr Asp Pro Glu Ser Glu Thr Leu Thr Leu Asn Gly Glu Met Ala Val
                325                 330                 335
Ile Arg Gly Gln Leu Lys Asn Gly Gly Leu Gly Val Val Ser Asp Ala
            340                 345                 350
Ile Phe Asp Leu Gly Met Ser Leu Ser Ser Phe Asn Leu Asp Asp Thr
        355                 360                 365
Glu Val Ala Leu Leu Gln Ala Val Leu Leu Met Ser Ser Asp Arg Pro
    370                 375                 380
Gly Leu Ala Cys Val Glu Arg Ile Glu Lys Tyr Gln Asp Ser Phe Leu
385                 390                 395                 400
Leu Ala Phe Glu His Tyr Ile Asn Tyr Arg Lys His His Val Thr His
                405                 410                 415
Phe Trp Pro Lys Leu Leu Met Lys Val Thr Asp Leu Arg Met Ile Gly
            420                 425                 430
Ala Cys His Ala Ser Arg Phe Leu His Met Lys Val Glu Cys Pro Thr
        435                 440                 445
Glu Leu Leu Pro Pro Leu Phe Leu Glu Val Phe Glu Asp
    450                 455                 460

<210> SEQ ID NO 4
<211> LENGTH: 416
<212> TYPE: PRT
<213> ORGANISM: Homo sapiens
<220> FEATURE:
<221> NAME/KEY: DOMAIN
<222> LOCATION: (131)..(373)
<223> OTHER INFORMATION: minimal ligand binding domain
```

-continued

```
<400> SEQUENCE: 4

Pro Asn Ser Asn His Val Ala Ser Gly Ala Gly Glu Ala Ala Ile Glu
  1               5                  10                  15

Thr Gln Ser Ser Ser Glu Glu Ile Val Pro Ser Pro Pro Ser Pro
             20                  25                  30

Pro Pro Leu Pro Arg Ile Tyr Lys Pro Cys Phe Val Cys Gln Asp Lys
             35                  40                  45

Ser Ser Gly Tyr His Tyr Gly Val Ser Ala Cys Glu Gly Cys Lys Gly
         50                  55                  60

Phe Phe Arg Arg Ser Ile Gln Lys Asn Met Val Tyr Thr Cys His Arg
 65                  70                  75                  80

Asp Lys Asn Cys Ile Ile Asn Lys Val Thr Arg Asn Arg Cys Gln Tyr
                 85                  90                  95

Cys Arg Leu Gln Lys Cys Phe Glu Val Gly Met Ser Lys Glu Ser Val
            100                 105                 110

Arg Asn Asp Arg Asn Lys Lys Lys Glu Val Pro Lys Pro Glu Cys
            115                 120                 125

Ser Glu Ser Tyr Thr Leu Thr Pro Glu Val Gly Glu Leu Ile Glu Lys
130                 135                 140

Val Arg Lys Ala His Gln Glu Thr Phe Pro Ala Leu Cys Gln Leu Gly
145                 150                 155                 160

Lys Tyr Thr Thr Asn Ser Ser Glu Gln Arg Val Ser Leu Asp Ile
                165                 170                 175

Asp Leu Trp Asp Lys Phe Ser Glu Leu Ser Thr Lys Cys Ile Ile Lys
            180                 185                 190

Thr Val Glu Phe Ala Lys Gln Leu Pro Gly Phe Thr Thr Leu Thr Ile
            195                 200                 205

Ala Asp Gln Ile Thr Leu Leu Lys Ala Ala Cys Leu Asp Ile Leu Ile
210                 215                 220

Leu Arg Ile Cys Thr Arg Tyr Thr Pro Glu Gln Asp Thr Met Thr Phe
225                 230                 235                 240

Ser Asp Gly Leu Thr Leu Asn Arg Thr Gln Met His Asn Ala Gly Phe
                245                 250                 255

Gly Pro Leu Thr Asp Leu Val Phe Ala Phe Ala Asn Gln Leu Leu Pro
            260                 265                 270

Leu Glu Met Asp Asp Ala Glu Thr Gly Ile Leu Ser Ala Ile Cys Leu
            275                 280                 285

Ile Cys Gly Asp Arg Gln Asp Leu Glu Gln Pro Asp Arg Val Asp Met
290                 295                 300

Leu Gln Glu Pro Leu Leu Glu Ala Leu Lys Val Tyr Val Arg Lys Arg
305                 310                 315                 320

Arg Pro Ser Arg Pro His Met Phe Pro Lys Met Leu Met Lys Ile Thr
                325                 330                 335

Asp Leu Arg Ser Ile Ser Ala Lys Gly Ala Glu Arg Val Ile Thr Leu
            340                 345                 350

Lys Met Glu Ile Pro Gly Ser Met Pro Pro Leu Ile Gln Glu Met Leu
            355                 360                 365

Glu Asn Ser Glu Gly Leu Asp Thr Leu Ser Gly Gln Pro Gly Gly Gly
            370                 375                 380

Gly Arg Asp Gly Gly Gly Leu Ala Pro Pro Gly Ser Cys Ser Pro
385                 390                 395                 400

Ser Leu Ser Pro Ser Ser Asn Arg Ser Ser Pro Ala Thr His Ser Pro
                405                 410                 415
```

-continued

```
<210> SEQ ID NO 5
<211> LENGTH: 454
<212> TYPE: PRT
<213> ORGANISM: Homo sapiens
<220> FEATURE:
<221> NAME/KEY: DOMAIN
<222> LOCATION: (179)..(421)
<223> OTHER INFORMATION: minimal ligand binding domain

<400> SEQUENCE: 5

Met Ala Thr Asn Lys Glu Arg Leu Phe Ala Gly Ala Leu Gly Pro
  1               5                  10                 15

Gly Ser Gly Tyr Pro Gly Ala Gly Phe Pro Phe Ala Phe Pro Gly Ala
                 20                  25                 30

Leu Arg Gly Ser Pro Pro Phe Glu Met Leu Ser Pro Ser Phe Arg Gly
             35                  40                  45

Leu Gly Gln Pro Asp Leu Pro Lys Glu Met Ala Ser Leu Ser Val Glu
 50                  55                  60

Thr Gln Ser Thr Ser Ser Glu Glu Met Val Pro Ser Ser Pro Ser Pro
 65                  70                  75                  80

Pro Pro Pro Pro Arg Val Tyr Lys Pro Cys Phe Val Cys Asn Asp Lys
                 85                  90                  95

Ser Ser Gly Tyr His Tyr Gly Val Ser Ser Cys Glu Gly Cys Lys Gly
                100                 105                 110

Phe Phe Arg Arg Ser Ile Gln Lys Asn Met Val Tyr Thr Cys His Arg
            115                 120                 125

Asp Lys Asn Cys Ile Ile Asn Lys Val Thr Arg Asn Arg Cys Gln Tyr
130                 135                 140

Cys Arg Leu Gln Lys Cys Phe Glu Val Gly Met Ser Lys Glu Ala Val
145                 150                 155                 160

Arg Asn Asp Arg Asn Lys Lys Lys Lys Glu Val Lys Glu Glu Gly Ser
                165                 170                 175

Pro Asp Ser Tyr Glu Leu Ser Pro Gln Leu Glu Glu Leu Ile Thr Lys
            180                 185                 190

Val Ser Lys Ala His Gln Glu Thr Phe Pro Ser Leu Cys Gln Leu Gly
            195                 200                 205

Lys Tyr Thr Thr Asn Ser Ser Ala Asp His Arg Val Gln Leu Asp Leu
210                 215                 220

Gly Leu Trp Asp Lys Phe Ser Glu Leu Ala Thr Lys Cys Ile Ile Lys
225                 230                 235                 240

Ile Val Glu Phe Ala Lys Arg Leu Pro Gly Phe Thr Gly Leu Ser Ile
                245                 250                 255

Ala Asp Gln Ile Thr Leu Leu Lys Ala Ala Cys Leu Asp Ile Leu Met
            260                 265                 270

Leu Arg Ile Cys Thr Arg Tyr Thr Pro Glu Gln Asp Thr Met Thr Phe
            275                 280                 285

Ser Asp Gly Leu Thr Leu Asn Arg Thr Gln Met His Asn Ala Gly Phe
290                 295                 300

Gly Pro Leu Thr Asp Leu Val Phe Ala Phe Ala Gly Gln Leu Leu Pro
305                 310                 315                 320

Leu Glu Met Asp Asp Thr Glu Thr Gly Leu Leu Ser Ala Ile Cys Leu
                325                 330                 335

Ile Cys Gly Asp Arg Met Asp Leu Glu Glu Pro Glu Lys Val Asp Lys
            340                 345                 350

Leu Gln Glu Pro Leu Leu Glu Ala Leu Arg Leu Tyr Ala Arg Arg Arg
            355                 360                 365
```

-continued

```
Arg Pro Ser Gln Pro Tyr Met Phe Pro Arg Met Leu Met Lys Ile Thr
    370                 375                 380
Asp Leu Arg Gly Ile Ser Thr Lys Gly Ala Glu Arg Ala Ile Thr Leu
385                 390                 395                 400
Lys Met Glu Ile Pro Gly Pro Met Pro Leu Ile Arg Glu Met Leu
                405                 410                 415
Glu Asn Pro Glu Met Phe Glu Asp Asp Ser Ser Gln Pro Gly Pro His
                420                 425                 430
Pro Asn Ala Ser Ser Glu Asp Glu Val Pro Gly Gly Gln Gly Lys Gly
            435                 440                 445
Gly Leu Lys Ser Pro Ala
    450

<210> SEQ ID NO 6
<211> LENGTH: 462
<212> TYPE: PRT
<213> ORGANISM: Homo sapiens
<220> FEATURE:
<221> NAME/KEY: DOMAIN
<222> LOCATION: (231)..(460)
<223> OTHER INFORMATION: minimal ligand binding domain

<400> SEQUENCE: 6

Met Asp Thr Lys His Phe Leu Pro Leu Asp Phe Ser Thr Gln Val Asn
 1               5                  10                  15
Ser Ser Leu Thr Ser Pro Thr Gly Arg Gly Ser Met Ala Ala Pro Ser
                20                  25                  30
Leu His Pro Ser Leu Gly Pro Gly Ile Gly Ser Pro Gly Gln Leu His
            35                  40                  45
Ser Pro Ile Ser Thr Leu Ser Ser Pro Ile Asn Gly Met Gly Pro Pro
        50                  55                  60
Phe Ser Val Ile Ser Ser Pro Met Gly Pro His Ser Met Ser Val Pro
 65                 70                  75                  80
Thr Thr Pro Thr Leu Gly Phe Ser Thr Gly Ser Pro Gln Leu Ser Ser
                85                  90                  95
Pro Met Asn Pro Val Ser Ser Glu Asp Ile Lys Pro Pro Leu Gly
                100                 105                 110
Leu Asn Gly Val Leu Lys Val Pro Ala His Pro Ser Gly Asn Met Ala
            115                 120                 125
Ser Phe Thr Lys His Ile Cys Ala Ile Cys Gly Asp Arg Ser Ser Gly
        130                 135                 140
Lys His Tyr Gly Val Tyr Ser Cys Glu Gly Cys Lys Gly Phe Phe Lys
145                 150                 155                 160
Arg Thr Val Arg Lys Asp Leu Thr Tyr Thr Cys Arg Asp Asn Lys Asp
                165                 170                 175
Cys Leu Ile Asp Lys Arg Gln Arg Asn Arg Cys Gln Tyr Cys Arg Tyr
            180                 185                 190
Gln Lys Cys Leu Ala Met Gly Met Lys Arg Glu Ala Val Gln Glu Glu
        195                 200                 205
Arg Gln Arg Gly Lys Asp Arg Asn Glu Asn Glu Val Glu Ser Thr Ser
    210                 215                 220
Ser Ala Asn Glu Asp Met Pro Val Glu Arg Ile Leu Glu Ala Glu Leu
225                 230                 235                 240
Ala Val Glu Pro Lys Thr Glu Thr Tyr Val Glu Ala Asn Met Gly Leu
                245                 250                 255
```

```
Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350

Leu Val Ser Lys Met Arg Asp Met Gln Met Asp Lys Thr Glu Leu Gly
        355                 360                 365

Cys Leu Arg Ala Ile Val Leu Phe Asn Pro Asp Ser Lys Gly Leu Ser
    370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
            420                 425                 430

Leu Glu His Leu Phe Phe Phe Lys Leu Ile Gly Asp Thr Pro Ile Asp
        435                 440                 445

Thr Phe Leu Met Glu Met Leu Glu Ala Pro His Gln Met Thr
    450                 455                 460

<210> SEQ ID NO 7
<211> LENGTH: 525
<212> TYPE: PRT
<213> ORGANISM: Homo sapiens
<220> FEATURE:
<221> NAME/KEY: DOMAIN
<222> LOCATION: (292)..(523)
<223> OTHER INFORMATION: minimal ligand binding domain

<400> SEQUENCE: 7

Met Ser Trp Ala Ala Arg Pro Pro Phe Leu Pro Gln Arg His Ala Glu
  1               5                  10                  15

Gly Ser Val Gly Arg Trp Gly Ala Lys Glu Cys Ile Val Gly Ser Ala
                 20                  25                  30

Thr Ala Leu Ala Gly Ser Arg Ser Gly Gly Gly Gly Gly Gly Gly Arg
             35                  40                  45

Arg Arg Thr Thr Asn Pro Gly Ala Gly Ala Arg Gly Trp Thr Gly Arg
     50                  55                  60

Asp Gly Arg His Gly Arg Asp Ser Arg Ser Pro Asp Ser Ser Ser Pro
 65                  70                  75                  80

Asn Pro Leu Pro Gln Gly Val Pro Pro Ser Pro Gly Pro Pro
                 85                  90                  95

Leu Pro Pro Ser Thr Ala Pro Thr Leu Gly Gly Ser Gly Ala Pro Pro
                100                 105                 110

Pro Pro Pro Met Pro Pro Pro Leu Gly Ser Pro Phe Pro Val Ile
             115                 120                 125

Ser Ser Ser Met Gly Ser Pro Gly Leu Pro Pro Pro Ala Pro Pro Gly
        130                 135                 140
```

```
Phe Ser Gly Pro Val Ser Ser Pro Gln Ile Asn Ser Thr Val Ser Leu
145                 150                 155                 160

Pro Gly Gly Gly Ser Gly Pro Pro Glu Asp Val Lys Pro Pro Val Leu
            165                 170                 175

Gly Val Arg Gly Leu His Cys Pro Pro Pro Gly Pro Gly Ala
            180                 185                 190

Gly Lys Arg Leu Cys Ala Ile Cys Gly Asp Arg Ser Ser Gly Lys His
            195                 200                 205

Tyr Gly Val Tyr Ser Cys Glu Gly Cys Lys Gly Phe Phe Lys Arg Thr
210                 215                 220

Ile Arg Lys Asp Leu Thr Tyr Ser Cys Arg Asp Asn Lys Asp Cys Thr
225                 230                 235                 240

Val Asp Lys Arg Gln Arg Asn Arg Cys Gln Tyr Cys Arg Tyr Gln Lys
            245                 250                 255

Cys Leu Ala Thr Gly Met Lys Arg Glu Ala Val Gln Glu Glu Arg Gln
            260                 265                 270

Arg Gly Lys Asp Lys Asp Gly Asp Gly Glu Cys Ala Gly Gly Ala Pro
            275                 280                 285

Glu Glu Met Pro Val Asp Arg Ile Leu Glu Ala Glu Leu Ala Val Glu
290                 295                 300

Gln Lys Ser Asp Gln Gly Val Glu Gly Pro Gly Gly Thr Gly Gly Ser
305                 310                 315                 320

Gly Ser Ser Pro Asn Asp Pro Val Thr Asn Ile Cys Gln Ala Ala Asp
            325                 330                 335

Lys Gln Leu Phe Thr Leu Val Glu Trp Ala Lys Arg Ile Pro His Phe
            340                 345                 350

Ser Ser Leu Pro Leu Asp Asp Gln Val Ile Leu Leu Arg Ala Gly Trp
            355                 360                 365

Asn Glu Leu Leu Ile Ala Ser Phe Ser His Arg Ser Ile Asp Val Arg
370                 375                 380

Asp Gly Ile Leu Leu Ala Thr Gly Leu His Val His Arg Asn Ser Ala
385                 390                 395                 400

His Ser Ala Gly Val Gly Ala Ile Phe Asp Arg Val Leu Thr Glu Leu
            405                 410                 415

Val Ser Lys Met Arg Asp Met Arg Met Asp Lys Thr Glu Leu Gly Cys
            420                 425                 430

Leu Arg Ala Ile Ile Leu Phe Asn Pro Asp Ala Lys Gly Leu Ser Asn
            435                 440                 445

Pro Ser Glu Val Glu Val Leu Arg Glu Lys Val Tyr Ala Ser Leu Glu
450                 455                 460

Thr Tyr Cys Lys Gln Lys Tyr Pro Glu Gln Gln Gly Arg Phe Ala Lys
465                 470                 475                 480

Leu Leu Leu Arg Leu Pro Ala Leu Arg Ser Ile Gly Leu Lys Cys Leu
            485                 490                 495

Glu His Leu Phe Phe Phe Lys Leu Ile Gly Asp Thr Pro Ile Asp Thr
            500                 505                 510

Phe Leu Met Glu Met Leu Glu Ala Pro His Gln Leu Ala
            515                 520                 525

<210> SEQ ID NO 8
<211> LENGTH: 468
<212> TYPE: PRT
<213> ORGANISM: Homo sapiens
<220> FEATURE:
<221> NAME/KEY: DOMAIN
```

```
<222> LOCATION: (196)..(468)
<223> OTHER INFORMATION: minimal ligand binding domain

<400> SEQUENCE: 8
```

| | | | | | | | | | | | | | | |
|---|---|---|---|---|---|---|---|---|---|---|---|---|---|---|
| Met | Val | Asp | Thr | Glu | Ser | Pro | Leu | Cys | Pro | Leu | Ser | Pro | Leu | Glu | Ala |
| 1 | | | | 5 | | | | 10 | | | | 15 | | |

Gly Asp Leu Glu Ser Pro Leu Ser Glu Glu Phe Leu Gln Glu Met Gly
          20                  25                  30

Asn Ile Gln Glu Ile Ser Gln Ser Ile Gly Glu Asp Ser Ser Gly Ser
          35                  40                  45

Phe Gly Phe Thr Glu Tyr Gln Tyr Leu Gly Ser Cys Pro Gly Ser Asp
 50                  55                  60

Gly Ser Val Ile Thr Asp Thr Leu Ser Pro Ala Ser Ser Pro Ser Ser
 65                  70                  75                  80

Val Thr Tyr Pro Val Pro Gly Ser Val Asp Glu Ser Pro Ser Gly
                 85                  90                  95

Ala Leu Asn Ile Glu Cys Arg Ile Cys Gly Asp Lys Ala Ser Gly Tyr
                100                 105                 110

His Tyr Gly Val His Ala Cys Glu Gly Cys Lys Gly Phe Phe Arg Arg
             115                 120                 125

Thr Ile Arg Leu Lys Leu Val Tyr Asp Lys Cys Asp Arg Ser Cys Lys
130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Ile Glu Asp Ser Glu Thr Ala Asp Leu Lys Ser Leu Ala Lys
            195                 200                 205

Arg Ile Tyr Glu Ala Tyr Leu Lys Asn Phe Asn Met Asn Lys Val Lys
        210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255

Lys Leu Val Ala Asn Gly Ile Gln Asn Lys Glu Val Glu Val Arg Ile
            260                 265                 270

Phe His Cys Cys Gln Cys Thr Ser Val Glu Thr Val Thr Glu Leu Thr
        275                 280                 285

Glu Phe Ala Lys Ala Ile Pro Ala Phe Ala Asn Leu Asp Leu Asn Asp
    290                 295                 300

Gln Val Thr Leu Leu Lys Tyr Gly Val Tyr Glu Ala Ile Phe Ala Met
305                 310                 315                 320

Leu Ser Ser Val Met Asn Lys Asp Gly Met Leu Val Ala Tyr Gly Asn
                325                 330                 335

Gly Phe Ile Thr Arg Glu Phe Leu Lys Ser Leu Arg Lys Pro Phe Cys
            340                 345                 350

Asp Ile Met Glu Pro Lys Phe Asp Phe Ala Met Lys Phe Asn Ala Leu
        355                 360                 365

Glu Leu Asp Asp Ser Asp Ile Ser Leu Phe Val Ala Ala Ile Ile Cys
        370                 375                 380

Cys Gly Asp Arg Pro Gly Leu Leu Asn Val Gly His Ile Glu Lys Met
385                 390                 395                 400

-continued

```
Gln Glu Gly Ile Val His Val Leu Arg Leu His Leu Gln Ser Asn His
                405                 410                 415

Pro Asp Asp Ile Phe Leu Phe Pro Lys Leu Leu Gln Lys Met Ala Asp
            420                 425                 430

Leu Arg Gln Leu Val Thr Glu His Ala Gln Leu Val Gln Ile Ile Lys
        435                 440                 445

Lys Thr Glu Ser Asp Ala Ala Leu His Pro Leu Leu Gln Glu Ile Tyr
450                 455                 460

Arg Asp Met Tyr
465

<210> SEQ ID NO 9
<211> LENGTH: 441
<212> TYPE: PRT
<213> ORGANISM: Homo sapiens
<220> FEATURE:
<221> NAME/KEY: DOMAIN
<222> LOCATION: (168)..(441)
<223> OTHER INFORMATION: minimal ligand binding domain

<400> SEQUENCE: 9

Met Glu Gln Pro Gln Glu Glu Ala Pro Glu Val Arg Glu Glu Glu Glu
1               5                   10                  15

Lys Glu Glu Val Ala Glu Ala Glu Gly Ala Pro Glu Leu Asn Gly Gly
            20                  25                  30

Pro Gln His Ala Leu Pro Ser Ser Ser Tyr Thr Asp Leu Ser Arg Ser
        35                  40                  45

Ser Ser Pro Pro Ser Leu Leu Asp Gln Leu Gln Met Gly Cys Asp Gly
    50                  55                  60

Ala Ser Cys Gly Ser Leu Asn Met Glu Cys Arg Val Cys Gly Asp Lys
65                  70                  75                  80

Ala Ser Gly Phe His Tyr Gly Val His Ala Cys Glu Gly Cys Lys Gly
                85                  90                  95

Phe Phe Arg Arg Thr Ile Arg Met Lys Leu Glu Tyr Glu Lys Cys Glu
            100                 105                 110

Arg Ser Cys Lys Ile Gln Lys Lys Asn Arg Asn Lys Cys Gln Tyr Cys
        115                 120                 125

Arg Phe Gln Lys Cys Leu Ala Leu Gly Met Ser His Asn Ala Ile Arg
    130                 135                 140

Phe Gly Arg Met Pro Glu Ala Glu Lys Arg Lys Leu Val Ala Gly Leu
145                 150                 155                 160

Thr Ala Asn Glu Gly Ser Gln Tyr Asn Pro Gln Val Ala Asp Leu Lys
                165                 170                 175

Ala Phe Ser Lys His Ile Tyr Asn Ala Tyr Leu Lys Asn Phe Asn Met
            180                 185                 190

Thr Lys Lys Lys Ala Arg Ser Ile Leu Thr Gly Lys Ala Ser His Thr
        195                 200                 205

Ala Pro Phe Val Ile His Asp Ile Glu Thr Leu Trp Gln Ala Glu Lys
    210                 215                 220

Gly Leu Val Trp Lys Gln Leu Val Asn Gly Leu Pro Pro Tyr Lys Glu
225                 230                 235                 240

Ile Ser Val His Val Phe Tyr Arg Cys Gln Cys Thr Thr Val Glu Thr
                245                 250                 255

Val Arg Glu Leu Thr Glu Phe Ala Lys Ser Ile Pro Ser Phe Ser Ser
            260                 265                 270
```

-continued

```
Leu Phe Leu Asn Asp Gln Val Thr Leu Leu Lys Tyr Gly Val His Glu
        275                 280                 285

Ala Ile Phe Ala Met Leu Ala Ser Ile Val Asn Lys Asp Gly Leu Leu
        290                 295                 300

Val Ala Asn Gly Ser Gly Phe Val Thr Arg Glu Phe Leu Arg Ser Leu
305                 310                 315                 320

Arg Lys Pro Phe Ser Asp Ile Ile Glu Pro Lys Phe Glu Phe Ala Val
                325                 330                 335

Lys Phe Asn Ala Leu Glu Leu Asp Asp Ser Asp Leu Ala Leu Phe Ile
            340                 345                 350

Ala Ala Ile Ile Leu Cys Gly Asp Arg Pro Gly Leu Met Asn Val Pro
        355                 360                 365

Arg Val Glu Ala Ile Gln Asp Thr Ile Leu Arg Ala Leu Glu Phe His
        370                 375                 380

Leu Gln Ala Asn His Pro Asp Ala Gln Tyr Leu Phe Pro Lys Leu Leu
385                 390                 395                 400

Gln Lys Met Ala Asp Leu Arg Gln Leu Val Thr Glu His Ala Gln Met
                405                 410                 415

Met Gln Arg Ile Lys Lys Thr Glu Thr Glu Thr Ser Leu His Pro Leu
            420                 425                 430

Leu Gln Glu Ile Tyr Lys Asp Met Tyr
        435                 440

<210> SEQ ID NO 10
<211> LENGTH: 475
<212> TYPE: PRT
<213> ORGANISM: Homo sapiens
<220> FEATURE:
<221> NAME/KEY: DOMAIN
<222> LOCATION: (202)..(475)
<223> OTHER INFORMATION: minimal ligand binding domain

<400> SEQUENCE: 10

Met Val Asp Thr Glu Met Pro Phe Trp Pro Thr Asn Phe Gly Ile Ser
1               5                   10                  15

Ser Val Asp Leu Ser Met Met Asp His Ser His Ser Phe Asp Ile
            20                  25                  30

Lys Pro Phe Thr Thr Val Asp Phe Ser Ser Ile Ser Ala Pro His Tyr
        35                  40                  45

Glu Asp Ile Pro Phe Thr Arg Ala Asp Pro Met Val Ala Asp Tyr Lys
    50                  55                  60

Tyr Asp Leu Lys Leu Gln Glu Tyr Gln Ser Ala Ile Lys Val Glu Pro
65                  70                  75                  80

Ala Ser Pro Pro Tyr Tyr Ser Glu Lys Ala Gln Leu Tyr Asn Arg Pro
                85                  90                  95

His Glu Glu Pro Ser Asn Ser Leu Met Ala Ile Glu Cys Arg Val Cys
            100                 105                 110

Gly Asp Lys Ala Ser Gly Phe His Tyr Gly Val His Ala Cys Glu Gly
        115                 120                 125

Cys Lys Gly Phe Phe Arg Arg Thr Ile Arg Leu Lys Leu Ile Tyr Asp
        130                 135                 140

Arg Cys Asp Leu Asn Cys Arg Ile His Lys Lys Ser Arg Asn Lys Cys
145                 150                 155                 160

Gln Tyr Cys Arg Phe Gln Lys Cys Leu Ala Val Gly Met Ser His Asn
                165                 170                 175
```

-continued

Ala Ile Arg Phe Gly Arg Met Pro Gln Ala Glu Lys Glu Lys Leu Leu
            180                 185                 190

Ala Glu Ile Ser Ser Asp Ile Asp Gln Leu Asn Pro Glu Ser Ala Asp
            195                 200                 205

Leu Arg Ala Leu Ala Lys His Leu Tyr Asp Ser Tyr Ile Lys Ser Phe
            210                 215                 220

Pro Leu Thr Lys Ala Lys Ala Arg Ala Ile Leu Thr Gly Lys Thr Thr
225                 230                 235                 240

Asp Lys Ser Pro Phe Val Ile Tyr Asp Met Asn Ser Leu Met Met Gly
                245                 250                 255

Glu Asp Lys Ile Lys Phe Lys His Ile Thr Pro Leu Gln Glu Gln Ser
            260                 265                 270

Lys Glu Val Ala Ile Arg Ile Phe Gln Gly Cys Gln Phe Arg Ser Val
            275                 280                 285

Glu Ala Val Gln Glu Ile Thr Glu Tyr Ala Lys Asn Ile Pro Gly Phe
            290                 295                 300

Ile Asn Leu Asp Leu Asn Asp Gln Val Thr Leu Leu Lys Tyr Gly Val
305                 310                 315                 320

His Glu Ile Ile Tyr Thr Met Leu Ala Ser Leu Met Asn Lys Asp Gly
                325                 330                 335

Val Leu Ile Ser Glu Gly Gln Gly Phe Met Thr Arg Glu Phe Leu Lys
            340                 345                 350

Ser Leu Arg Lys Pro Phe Gly Asp Phe Met Glu Pro Lys Phe Glu Phe
            355                 360                 365

Ala Val Lys Phe Asn Ala Leu Glu Leu Asp Asp Ser Asp Leu Ala Ile
            370                 375                 380

Phe Ile Ala Val Ile Ile Leu Ser Gly Asp Arg Pro Gly Leu Leu Asn
385                 390                 395                 400

Val Lys Pro Ile Glu Asp Ile Gln Asp Asn Leu Leu Gln Ala Leu Glu
                405                 410                 415

Leu Gln Leu Lys Leu Asn His Pro Glu Ser Ser Gln Leu Phe Ala Lys
            420                 425                 430

Val Leu Gln Lys Met Thr Asp Leu Arg Gln Ile Val Thr Glu His Val
            435                 440                 445

Gln Leu Leu His Val Ile Lys Lys Thr Glu Thr Asp Met Ser Leu His
            450                 455                 460

Pro Leu Leu Gln Glu Ile Tyr Lys Asp Leu Tyr
465                 470                 475

<210> SEQ ID NO 11
<211> LENGTH: 609
<212> TYPE: PRT
<213> ORGANISM: Homo sapiens
<220> FEATURE:
<221> NAME/KEY: DOMAIN
<222> LOCATION: (295)..(585)
<223> OTHER INFORMATION: minimal ligand binding domain

<400> SEQUENCE: 11

Met Asp Thr Glu Asp Leu Pro Ala Asn Asn Ala Pro Leu Thr Val Asn
1               5                   10                  15

Glu Gln Leu Leu Gly Ser Cys Thr Leu Lys Phe Pro Ala Gln Asp Ala
            20                  25                  30

Gln Val Ile Val Met Ser Gly Gln Glu Thr Ile Arg Val Leu Glu Val
            35                  40                  45

-continued

```
Glu Val Asp Thr Ala Leu Ser Ser Ala Gly Ala Ala Glu Ser Gly Gly
 50                  55                  60

Asp Glu Glu Gly Ser Gly Gln Ser Leu Glu Ala Thr Glu Glu Ala Gln
 65                  70                  75                  80

Leu Asp Gly Pro Val Thr Thr Ser Ser Thr Thr Ala Val Thr Val Glu
                 85                  90                  95

Val Ser Ala Pro Val Val Gln Thr Val Val Ser Lys Ala Ala Ile Ser
                100                 105                 110

Val Ser Pro Ala Gln Gln Thr Ser Val Pro Ile Thr Val Gln Ala Cys
            115                 120                 125

Pro Gln Val Leu Thr Gln Asp Gly Leu Ala Ser Leu Met Thr Gly Met
        130                 135                 140

Leu Ala Gln Gln Ser Ser Leu Gly Gln Pro Leu Leu Ile Pro Leu Ser
145                 150                 155                 160

Met Ala Gly Ser Val Gly Gly Gln Gly Gly Leu Ala Val Leu Thr Leu
                165                 170                 175

Pro Thr Ala Thr Val Ala Thr Leu Pro Gly Leu Ala Ala Ser Pro
                180                 185                 190

Ala Gly Gly Leu Leu Lys Leu Pro Phe Ala Gly Leu Gln Ala Ala Thr
        195                 200                 205

Val Leu Asn Ser Val Gln Thr Gln Leu Gln Ala Pro Ala Gln Ala Val
    210                 215                 220

Leu Gln Pro Gln Met Ser Ala Leu Ala Met Gln Gln Thr Gln Thr Thr
225                 230                 235                 240

Ala Ala Thr Thr Ala Ser Ile Val Gln Lys Ala Ser Glu Pro Ser Val
                245                 250                 255

Ser Val Ala Thr Leu Gln Thr Ala Gly Leu Ser Ile Asn Pro Ala Ile
                260                 265                 270

Ile Ser Ala Ala Ser Leu Gly Ala Gln Pro Gln Phe Ile Ser Ser Leu
        275                 280                 285

Thr Thr Thr Pro Ile Ile Thr Ser Ala Met Ser Asn Val Ala Gly Leu
    290                 295                 300

Thr Ser Gln Leu Ile Thr Asn Ala Gln Gly Gln Val Ile Gly Thr Leu
305                 310                 315                 320

Pro Leu Leu Val Asn Pro Ala Ser Leu Ala Gly Ala Ala Ala Ala Ser
                325                 330                 335

Ala Leu Pro Ala Gln Gly Leu Gln Val Gln Thr Val Ala Pro Gln Leu
            340                 345                 350

Leu Leu Asn Ser Gln Gly Gln Ile Ile Ala Thr Ile Gly Asn Gly Pro
        355                 360                 365

Thr Ala Ala Ile Pro Ser Thr Ala Ser Val Leu Pro Lys Ala Thr Val
    370                 375                 380

Pro Leu Thr Leu Thr Lys Thr Thr Thr Gln Gly Pro Val Gly Lys Val
385                 390                 395                 400

Ala Pro Ser Lys Val Ile Ile Ala Pro Gln Pro Ser Val Val Lys Pro
                405                 410                 415

Val Thr Ser Leu Thr Ala Ala Gly Val Ile Ala Cys Gly Glu Met Pro
            420                 425                 430

Thr Val Gly Gln Leu Val Asn Lys Pro Ser Ala Val Lys Asp Glu Glu
        435                 440                 445

Ala Ile Asn Leu Glu Glu Ile Arg Glu Phe Ala Lys Asn Phe Lys Ile
    450                 455                 460
```

```
Arg Arg Leu Ser Leu Gly Leu Thr Gln Thr Gln Val Gly Gln Ala Leu
465                 470                 475                 480

Thr Ala Thr Glu Gly Pro Ala Tyr Ser Gln Ser Ala Ile Cys Arg Phe
                485                 490                 495

Glu Lys Leu Asp Ile Thr Pro Lys Ser Ala Gln Lys Leu Lys Pro Val
            500                 505                 510

Leu Glu Arg Trp Leu Ala Glu Ala Glu Leu Trp Asn Gln Lys Gly Gln
        515                 520                 525

Gln Asn Leu Met Glu Phe Val Gly Gly Glu Pro Ser Lys Lys Arg Lys
    530                 535                 540

Arg Arg Thr Ser Phe Thr Pro Gln Ala Ile Glu Val Leu Asn Thr Tyr
545                 550                 555                 560

Phe Glu Lys Asn Ser Leu Pro Thr Gly Gln Glu Ile Thr Glu Ile Ala
                565                 570                 575

Lys Glu Leu Asn Tyr Asp Arg Glu Val Val Arg Val Trp Phe Cys Asn
            580                 585                 590

Arg Arg Gln Thr Leu Lys Asn Thr Ser Lys Ile Asn Val Phe Gln Ser
        595                 600                 605

Gln

<210> SEQ ID NO 12
<211> LENGTH: 595
<212> TYPE: PRT
<213> ORGANISM: Homo sapiens
<220> FEATURE:
<221> NAME/KEY: DOMAIN
<222> LOCATION: (287)..(549)
<223> OTHER INFORMATION: minimal ligand binding domain

<400> SEQUENCE: 12

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205
```

```
Phe Lys Arg Ser Ile Gln Gly His Asn Asp Tyr Met Cys Pro Ala Thr
    210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                245                 250                 255
Lys Asp Arg Arg Gly Gly Arg Met Leu Lys His Lys Arg Gln Arg Asp
            260                 265                 270
Asp Gly Glu Gly Arg Gly Glu Val Gly Ser Ala Gly Asp Met Arg Ala
        275                 280                 285
Ala Asn Leu Trp Pro Ser Pro Leu Met Ile Lys Arg Ser Lys Lys Asn
    290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
        355                 360                 365
Asp Leu Thr Leu His Asp Gln Val His Leu Leu Glu Cys Ala Trp Leu
    370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
Lys Cys Lys Asn Val Val Pro Leu Tyr Asp Leu Leu Leu Glu Met Leu
    530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595

<210> SEQ ID NO 13
<211> LENGTH: 777
<212> TYPE: PRT
```

-continued

```
<213> ORGANISM: Homo sapiens
<220> FEATURE:
<221> NAME/KEY: DOMAIN
<222> LOCATION: (506)..(762)
<223> OTHER INFORMATION: minimal ligand binding domain

<400> SEQUENCE: 13
```

| | | | | | | | | | | | | | | |
|---|---|---|---|---|---|---|---|---|---|---|---|---|---|---|
| Met | Asp | Ser | Lys | Glu | Ser | Leu | Thr | Pro | Gly | Arg | Glu | Asn | Pro | Ser |
| 1 | | | | 5 | | | | | 10 | | | | | 15 |
| Ser | Val | Leu | Ala | Gln | Glu | Arg | Gly | Asp | Val | Met | Asp | Phe | Tyr | Lys | Thr |
| | | | 20 | | | | | 25 | | | | | 30 | | |
| Leu | Arg | Gly | Gly | Ala | Thr | Val | Lys | Val | Ser | Ala | Ser | Ser | Pro | Ser | Leu |
| | | 35 | | | | | 40 | | | | | 45 | | | |
| Ala | Val | Ala | Ser | Gln | Ser | Asp | Ser | Lys | Gln | Arg | Arg | Leu | Leu | Val | Asp |
| 50 | | | | | 55 | | | | | 60 | | | | | |
| Phe | Pro | Lys | Gly | Ser | Val | Ser | Asn | Ala | Gln | Gln | Pro | Asp | Leu | Ser | Lys |
| 65 | | | | | 70 | | | | | 75 | | | | | 80 |
| Ala | Val | Ser | Leu | Ser | Met | Gly | Leu | Tyr | Met | Gly | Glu | Thr | Glu | Thr | Lys |
| | | | | 85 | | | | | 90 | | | | | 95 | |
| Val | Met | Gly | Asn | Asp | Leu | Gly | Phe | Pro | Gln | Gln | Gly | Gln | Ile | Ser | Leu |
| | | | 100 | | | | | 105 | | | | | 110 | | |
| Ser | Ser | Gly | Glu | Thr | Asp | Leu | Lys | Leu | Leu | Glu | Glu | Ser | Ile | Ala | Asn |
| | | 115 | | | | | 120 | | | | | 125 | | | |
| Leu | Asn | Arg | Ser | Thr | Ser | Val | Pro | Glu | Asn | Pro | Lys | Ser | Ser | Ala | Ser |
| 130 | | | | | 135 | | | | | 140 | | | | | |
| Thr | Ala | Val | Ser | Ala | Ala | Pro | Thr | Glu | Lys | Glu | Phe | Pro | Lys | Thr | His |
| 145 | | | | | 150 | | | | | 155 | | | | | 160 |
| Ser | Asp | Val | Ser | Ser | Glu | Gln | Gln | His | Leu | Lys | Gly | Gln | Thr | Gly | Thr |
| | | | | 165 | | | | | 170 | | | | | 175 | |
| Asn | Gly | Gly | Asn | Val | Lys | Leu | Tyr | Thr | Thr | Asp | Gln | Ser | Thr | Phe | Asp |
| | | | 180 | | | | | 185 | | | | | 190 | | |
| Ile | Leu | Gln | Asp | Leu | Glu | Phe | Ser | Ser | Gly | Ser | Pro | Gly | Lys | Glu | Thr |
| | | | 195 | | | | | 200 | | | | | 205 | | |
| Asn | Glu | Ser | Pro | Trp | Arg | Ser | Asp | Leu | Leu | Ile | Asp | Glu | Asn | Cys | Leu |
| | | 210 | | | | | 215 | | | | | 220 | | | |
| Leu | Ser | Pro | Leu | Ala | Gly | Glu | Asp | Asp | Ser | Phe | Leu | Leu | Glu | Gly | Asn |
| 225 | | | | | 230 | | | | | 235 | | | | | 240 |
| Ser | Asn | Glu | Asp | Cys | Lys | Pro | Leu | Ile | Leu | Pro | Asp | Thr | Lys | Pro | Lys |
| | | | | 245 | | | | | 250 | | | | | 255 | |
| Ile | Lys | Asp | Asn | Gly | Asp | Leu | Val | Leu | Ser | Ser | Pro | Ser | Asn | Val | Thr |
| | | | 260 | | | | | 265 | | | | | 270 | | |
| Leu | Pro | Gln | Val | Lys | Thr | Glu | Lys | Glu | Asp | Phe | Ile | Glu | Leu | Cys | Thr |
| | | | 275 | | | | | 280 | | | | | 285 | | |
| Pro | Gly | Val | Ile | Lys | Gln | Glu | Lys | Leu | Gly | Thr | Val | Tyr | Cys | Gln | Ala |
| | | 290 | | | | | 295 | | | | | 300 | | | |
| Ser | Phe | Pro | Gly | Ala | Asn | Ile | Ile | Gly | Asn | Lys | Met | Ser | Ala | Ile | Ser |
| 305 | | | | | 310 | | | | | 315 | | | | | 320 |
| Val | His | Gly | Val | Ser | Thr | Ser | Gly | Gly | Gln | Met | Tyr | His | Tyr | Asp | Met |
| | | | | 325 | | | | | 330 | | | | | 335 | |
| Asn | Thr | Ala | Ser | Leu | Ser | Gln | Gln | Gln | Asp | Gln | Lys | Pro | Ile | Phe | Asn |
| | | | 340 | | | | | 345 | | | | | 350 | | |
| Val | Ile | Pro | Pro | Ile | Pro | Val | Gly | Ser | Glu | Asn | Trp | Asn | Arg | Cys | Gln |
| | | 355 | | | | | 360 | | | | | 365 | | | |
| Gly | Ser | Gly | Asp | Asp | Asn | Leu | Thr | Ser | Leu | Gly | Thr | Leu | Asn | Phe | Pro |
| | | 370 | | | | | 375 | | | | | 380 | | | |

```
Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
        405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
770                 775

<210> SEQ ID NO 14
<211> LENGTH: 933
<212> TYPE: PRT
```

```
<213> ORGANISM: Homo sapiens
<220> FEATURE:
<221> NAME/KEY: DOMAIN
<222> LOCATION: (659)..(918)
<223> OTHER INFORMATION: minimal ligand binding domain

<400> SEQUENCE: 14
```

Met Thr Glu Leu Lys Ala Lys Gly Pro Arg Ala Pro His Val Ala Gly
 1               5                  10                  15

Gly Pro Pro Ser Pro Glu Val Gly Ser Pro Leu Leu Cys Arg Pro Ala
             20                  25                  30

Ala Gly Pro Phe Pro Gly Ser Gln Thr Ser Asp Thr Leu Pro Glu Val
         35                  40                  45

Ser Ala Ile Pro Ile Ser Leu Asp Gly Leu Leu Phe Pro Arg Pro Cys
 50                  55                  60

Gln Gly Gln Asp Pro Ser Asp Glu Lys Thr Gln Asp Gln Gln Ser Leu
 65                  70                  75                  80

Ser Asp Val Glu Gly Ala Tyr Ser Arg Ala Glu Ala Thr Arg Gly Ala
                 85                  90                  95

Gly Gly Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
210                 215                 220

Asp Ser Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Cys
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Thr Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
370                 375                 380

-continued

```
Leu Lys Ile Lys Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
            405                 410                 415

Phe Pro Leu Gly Pro Pro Pro Leu Pro Pro Arg Ala Thr Pro Ser
                420                 425                 430

Arg Pro Gly Glu Ala Ala Val Thr Ala Ala Pro Ala Ser Ala Ser Val
            435                 440                 445

Ser Ser Ala Ser Ser Ser Gly Ser Thr Leu Glu Cys Ile Leu Tyr Lys
450                 455                 460

Ala Glu Gly Ala Pro Pro Gln Gln Gly Pro Phe Ala Pro Pro Cys
465                 470                 475                 480

Lys Ala Pro Gly Ala Ser Gly Cys Leu Leu Pro Arg Asp Gly Leu Pro
                485                 490                 495

Ser Thr Ser Ala Ser Ala Ala Ala Gly Ala Ala Pro Ala Leu Tyr
            500                 505                 510

Pro Ala Leu Gly Leu Asn Gly Leu Pro Gln Leu Gly Tyr Gln Ala Ala
            515                 520                 525

Val Leu Lys Glu Gly Leu Pro Gln Val Tyr Pro Pro Tyr Leu Asn Tyr
530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
            580                 585                 590

Arg Ala Met Glu Gly Gln His Asn Tyr Leu Cys Ala Gly Arg Asn Asp
            595                 600                 605

Cys Ile Val Asp Lys Ile Arg Arg Lys Asn Cys Pro Ala Cys Arg Leu
610                 615                 620

Arg Lys Cys Cys Gln Ala Gly Met Val Leu Gly Gly Arg Lys Phe Lys
625                 630                 635                 640

Lys Phe Asn Lys Val Arg Val Val Arg Ala Leu Asp Ala Val Ala Leu
                645                 650                 655

Pro Gln Pro Leu Gly Val Pro Asn Glu Ser Gln Ala Leu Ser Gln Arg
            660                 665                 670

Phe Thr Phe Ser Pro Gly Gln Asp Ile Gln Leu Ile Pro Pro Leu Ile
            675                 680                 685

Asn Leu Leu Met Ser Ile Glu Pro Asp Val Ile Tyr Ala Gly His Asp
690                 695                 700

Asn Thr Lys Pro Asp Thr Ser Ser Leu Leu Thr Ser Leu Asn Gln
705                 710                 715                 720

Leu Gly Glu Arg Gln Leu Leu Ser Val Val Lys Trp Ser Lys Ser Leu
            725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
            755                 760                 765

Lys His Val Ser Gly Gln Met Leu Tyr Phe Ala Pro Asp Leu Ile Leu
    770                 775                 780

Asn Glu Gln Arg Met Lys Glu Ser Ser Phe Tyr Ser Leu Cys Leu Thr
785                 790                 795                 800
```

-continued

Met Trp Gln Ile Pro Gln Glu Phe Val Lys Leu Gln Val Ser Gln Glu
                805                 810                 815

Glu Phe Leu Cys Met Lys Val Leu Leu Leu Asn Thr Ile Pro Leu
            820                 825                 830

Glu Gly Leu Arg Ser Gln Thr Gln Phe Glu Glu Met Arg Ser Ser Tyr
            835                 840                 845

Ile Arg Glu Leu Ile Lys Ala Ile Gly Leu Arg Gln Lys Gly Val Val
    850                 855                 860

Ser Ser Ser Gln Arg Phe Tyr Gln Leu Thr Lys Leu Leu Asp Asn Leu
865                 870                 875                 880

His Asp Leu Val Lys Gln Leu His Leu Tyr Cys Leu Asn Thr Phe Ile
                885                 890                 895

Gln Ser Arg Ala Leu Ser Val Glu Phe Pro Glu Met Met Ser Glu Val
            900                 905                 910

Ile Ala Ala Gln Leu Pro Lys Ile Leu Ala Gly Met Val Lys Pro Leu
            915                 920                 925

Leu Phe His Lys Lys
    930

<210> SEQ ID NO 15
<211> LENGTH: 984
<212> TYPE: PRT
<213> ORGANISM: Homo sapiens
<220> FEATURE:
<221> NAME/KEY: DOMAIN
<222> LOCATION: (695)..(969)
<223> OTHER INFORMATION: minimal ligand binding domain

<400> SEQUENCE: 15

Met Glu Thr Lys Gly Tyr His Ser Leu Pro Glu Gly Leu Asp Met Glu
1               5                   10                  15

Arg Arg Trp Gly Gln Val Ser Gln Ala Val Glu Arg Ser Ser Leu Gly
            20                  25                  30

Pro Thr Glu Arg Thr Asp Glu Asn Asn Tyr Met Glu Ile Val Asn Val
        35                  40                  45

Ser Cys Val Ser Gly Ala Ile Pro Asn Asn Ser Thr Gln Gly Ser Ser
    50                  55                  60

Lys Glu Lys Gln Glu Leu Leu Pro Cys Leu Gln Gln Asp Asn Asn Arg
65                  70                  75                  80

Pro Gly Ile Leu Thr Ser Asp Ile Lys Thr Glu Leu Glu Ser Lys Glu
                85                  90                  95

Leu Ser Ala Thr Val Ala Glu Ser Met Gly Leu Tyr Met Asp Ser Val
            100                 105                 110

Arg Asp Ala Asp Tyr Ser Tyr Glu Gln Gln Asn Gln Gln Gly Ser Met
        115                 120                 125

Ser Pro Ala Lys Ile Tyr Gln Asn Val Glu Gln Leu Val Lys Phe Tyr
    130                 135                 140

Lys Gly Asn Gly His Arg Pro Ser Thr Leu Ser Cys Val Asn Thr Pro
145                 150                 155                 160

Leu Arg Ser Phe Met Ser Asp Ser Gly Ser Ser Val Asn Gly Gly Val
                165                 170                 175

Met Arg Ala Ile Val Lys Ser Pro Ile Met Cys His Glu Lys Ser Pro
            180                 185                 190

Ser Val Cys Ser Pro Leu Asn Met Thr Ser Ser Val Cys Ser Pro Ala
        195                 200                 205

-continued

```
Gly Ile Asn Ser Val Ser Ser Thr Thr Ala Ser Phe Gly Ser Phe Pro
    210                 215                 220

Val His Ser Pro Ile Thr Gln Gly Thr Pro Leu Thr Cys Ser Pro Asn
225                 230                 235                 240

Ala Glu Asn Arg Gly Ser Arg Ser His Ser Pro Ala His Ala Ser Asn
                245                 250                 255

Val Gly Ser Pro Leu Ser Ser Pro Leu Ser Ser Met Lys Ser Ser Ile
            260                 265                 270

Ser Ser Pro Pro Ser His Cys Ser Val Lys Ser Pro Val Ser Ser Pro
        275                 280                 285

Asn Asn Val Thr Leu Arg Ser Ser Val Ser Ser Pro Ala Asn Ile Asn
290                 295                 300

Asn Ser Arg Cys Ser Val Ser Ser Pro Ser Asn Thr Asn Asn Arg Ser
305                 310                 315                 320

Thr Leu Ser Ser Pro Ala Ala Ser Thr Val Gly Ser Ile Cys Ser Pro
                325                 330                 335

Val Asn Asn Ala Phe Ser Tyr Thr Ala Ser Gly Thr Ser Ala Gly Ser
            340                 345                 350

Ser Thr Leu Arg Asp Val Val Pro Ser Pro Asp Thr Gln Glu Lys Gly
        355                 360                 365

Ala Gln Glu Val Pro Phe Pro Lys Thr Glu Val Glu Ser Ala Ile
370                 375                 380

Ser Asn Gly Val Thr Gly Gln Leu Asn Ile Val Gln Tyr Ile Lys Pro
385                 390                 395                 400

Glu Pro Asp Gly Ala Phe Ser Ser Cys Leu Gly Gly Asn Ser Lys
                405                 410                 415

Ile Asn Ser Asp Ser Ser Phe Ser Val Pro Ile Lys Gln Glu Ser Thr
            420                 425                 430

Lys His Ser Cys Ser Gly Thr Ser Phe Lys Gly Asn Pro Thr Val Asn
        435                 440                 445

Pro Phe Pro Phe Met Asp Gly Ser Tyr Phe Ser Phe Met Asp Asp Lys
450                 455                 460

Asp Tyr Tyr Ser Leu Ser Gly Ile Leu Gly Pro Pro Val Pro Gly Phe
465                 470                 475                 480

Asp Gly Asn Cys Glu Gly Ser Gly Phe Pro Val Gly Ile Lys Gln Glu
                485                 490                 495

Pro Asp Asp Gly Ser Tyr Tyr Pro Glu Ala Ser Ile Pro Ser Ser Ala
            500                 505                 510

Ile Val Gly Val Asn Ser Gly Gly Gln Ser Phe His Tyr Arg Ile Gly
        515                 520                 525

Ala Gln Gly Thr Ile Ser Leu Ser Arg Ser Ala Arg Asp Gln Ser Phe
530                 535                 540

Gln His Leu Ser Ser Phe Pro Pro Val Asn Thr Leu Val Glu Ser Trp
545                 550                 555                 560

Lys Ser His Gly Asp Leu Ser Ser Arg Arg Ser Asp Gly Tyr Pro Val
                565                 570                 575

Leu Glu Tyr Ile Pro Glu Asn Val Ser Ser Thr Leu Arg Ser Val
            580                 585                 590

Ser Thr Gly Ser Ser Arg Pro Ser Lys Ile Cys Leu Val Cys Gly Asp
        595                 600                 605

Glu Ala Ser Gly Cys His Tyr Gly Val Val Thr Cys Gly Ser Cys Lys
610                 615                 620
```

```
Val Phe Lys Arg Ala Val Glu Gly Gln His Asn Tyr Leu Cys Ala
625                 630                 635                 640

Gly Arg Asn Asp Cys Ile Ile Asp Lys Ile Arg Arg Lys Asn Cys Pro
            645                 650                 655

Ala Cys Arg Leu Gln Lys Cys Leu Gln Ala Gly Met Asn Leu Gly Ala
            660                 665                 670

Arg Lys Ser Lys Lys Leu Gly Lys Leu Lys Gly Ile His Glu Glu Gln
            675                 680                 685

Pro Gln Gln Gln Gln Pro Pro Pro Pro Pro Pro Pro Pro Gln Ser Pro
690                 695                 700

Glu Glu Gly Thr Thr Tyr Ile Ala Pro Ala Lys Glu Pro Ser Val Asn
705                 710                 715                 720

Thr Ala Leu Val Pro Gln Leu Ser Thr Ile Ser Arg Ala Leu Thr Pro
                725                 730                 735

Ser Pro Val Met Val Leu Glu Asn Ile Glu Pro Glu Ile Val Tyr Ala
                740                 745                 750

Gly Tyr Asp Ser Ser Lys Pro Asp Thr Ala Glu Asn Leu Leu Ser Thr
                755                 760                 765

Leu Asn Arg Leu Ala Gly Lys Gln Met Ile Gln Val Val Lys Trp Ala
770                 775                 780

Lys Val Leu Pro Gly Phe Lys Asn Leu Pro Leu Glu Asp Gln Ile Thr
785                 790                 795                 800

Leu Ile Gln Tyr Ser Trp Met Cys Leu Ser Ser Phe Ala Leu Ser Trp
                805                 810                 815

Arg Ser Tyr Lys His Thr Asn Ser Gln Phe Leu Tyr Phe Ala Pro Asp
                820                 825                 830

Leu Val Phe Asn Glu Glu Lys Met His Gln Ser Ala Met Tyr Glu Leu
                835                 840                 845

Cys Gln Gly Met His Gln Ile Ser Leu Gln Phe Val Arg Leu Gln Leu
                850                 855                 860

Thr Phe Glu Glu Tyr Thr Ile Met Lys Val Leu Leu Leu Leu Ser Thr
865                 870                 875                 880

Ile Pro Lys Asp Gly Leu Lys Ser Gln Ala Ala Phe Glu Glu Met Arg
                885                 890                 895

Thr Asn Tyr Ile Lys Glu Leu Arg Lys Met Val Thr Lys Cys Pro Asn
                900                 905                 910

Asn Ser Gly Gln Ser Trp Gln Arg Phe Tyr Gln Leu Thr Lys Leu Leu
                915                 920                 925

Asp Ser Met His Asp Leu Val Ser Asp Leu Leu Glu Phe Cys Phe Tyr
930                 935                 940

Thr Phe Arg Glu Ser His Ala Leu Lys Val Glu Phe Pro Ala Met Leu
945                 950                 955                 960

Val Glu Ile Ile Ser Asp Gln Leu Pro Lys Val Glu Ser Gly Asn Ala
                965                 970                 975

Lys Pro Leu Tyr Phe His Arg Lys
                980

<210> SEQ ID NO 16
<211> LENGTH: 452
<212> TYPE: PRT
<213> ORGANISM: Homo sapiens
<220> FEATURE:
<221> NAME/KEY: DOMAIN
<222> LOCATION: (184)..(437)
<223> OTHER INFORMATION: minimal ligand binding domain
```

-continued

```
<400> SEQUENCE: 16

Gly Gly Gly Gly Glu Ala Gly Ala Val Ala Pro Tyr Gly Tyr Thr
 1               5                  10                  15

Arg Pro Pro Gln Gly Leu Ala Gly Gln Glu Ser Asp Phe Thr Ala Pro
             20                  25                  30

Asp Val Trp Tyr Pro Gly Gly Met Val Ser Arg Val Pro Tyr Pro Ser
         35                  40                  45

Pro Thr Cys Val Lys Ser Glu Met Gly Pro Trp Met Asp Ser Tyr Ser
     50                  55                  60

Gly Pro Tyr Gly Asp Met Arg Leu Glu Thr Ala Arg Asp His Val Leu
 65                  70                  75                  80

Pro Ile Asp Tyr Tyr Phe Pro Pro Gln Lys Thr Cys Leu Ile Cys Gly
                 85                  90                  95

Asp Lys Ala Ser Gly Cys His Tyr Gly Ala Leu Thr Cys Gly Ser Cys
            100                 105                 110

Lys Val Phe Phe Lys Arg Ala Ala Glu Gly Lys Gln Lys Tyr Leu Cys
            115                 120                 125

Ala Ser Arg Asn Asp Cys Thr Ile Asp Lys Phe Arg Arg Lys Asn Cys
130                 135                 140

Pro Ser Cys Arg Leu Arg Lys Cys Tyr Glu Ala Gly Met Thr Leu Gly
145                 150                 155                 160

Ala Arg Lys Leu Lys Lys Leu Gly Asn Leu Lys Leu Gln Glu Glu Gly
                165                 170                 175

Glu Ala Ser Ser Thr Thr Ser Pro Thr Glu Thr Thr Gln Lys Leu
            180                 185                 190

Thr Val Ser His Ile Glu Gly Tyr Glu Cys Gln Pro Ile Phe Leu Asn
            195                 200                 205

Val Leu Glu Ala Ile Glu Pro Gly Val Val Cys Ala Gly His Asp Asn
210                 215                 220

Asn Gln Pro Asp Ser Phe Ala Ala Leu Leu Ser Ser Leu Asn Glu Leu
225                 230                 235                 240

Gly Glu Arg Gln Leu Val His Val Val Lys Trp Ala Lys Ala Leu Pro
                245                 250                 255

Gly Phe Arg Asn Leu His Val Asp Asp Gln Met Ala Val Ile Gln Tyr
            260                 265                 270

Ser Trp Met Gly Leu Met Val Phe Ala Met Gly Trp Arg Ser Phe Thr
            275                 280                 285

Asn Val Asn Ser Arg Met Leu Tyr Phe Ala Pro Asp Leu Val Phe Asn
290                 295                 300

Glu Tyr Arg Met His Lys Ser Arg Met Tyr Ser Gln Cys Val Arg Met
305                 310                 315                 320

Arg His Leu Ser Gln Glu Phe Gly Trp Leu Gln Ile Thr Pro Gln Glu
                325                 330                 335

Phe Leu Cys Met Lys Ala Leu Leu Leu Phe Ser Ile Ile Pro Val Asp
            340                 345                 350

Gly Leu Lys Asn Gln Lys Phe Phe Asp Glu Leu Arg Met Asn Tyr Ile
            355                 360                 365

Lys Glu Leu Asp Arg Ile Ile Ala Cys Lys Arg Lys Asn Pro Thr Ser
370                 375                 380

Cys Ser Arg Arg Phe Tyr Gln Leu Thr Lys Leu Leu Asp Ser Val Gln
385                 390                 395                 400

Pro Ile Ala Arg Glu Leu His Gln Phe Thr Phe Asp Leu Leu Ile Lys
                405                 410                 415
```

```
Ser His Met Val Ser Val Asp Phe Pro Glu Met Met Ala Glu Ile Ile
            420                 425                 430

Ser Val Gln Val Pro Lys Ile Leu Ser Gly Lys Val Lys Pro Ile Tyr
            435                 440                 445

Phe His Thr Gln
    450

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: two copies
      of T3 response element
<220> FEATURE:
<221> NAME/KEY: protein_bind
<222> LOCATION: (1)..(6)
<223> OTHER INFORMATION: T3 response element
<220> FEATURE:
<221> NAME/KEY: protein_bind
<222> LOCATION: (11)..(16)
<223> OTHER INFORMATION: T3 response element

<400> SEQUENCE: 17
aggtcacagg aggtca                                                  16
```